US011897921B2

(12) United States Patent
Ichtchenko et al.

(10) Patent No.: US 11,897,921 B2
(45) Date of Patent: Feb. 13, 2024

(54) PROPEPTIDE FUSION COMPRISING A MUTATED CLOSTRIDIUM BOTULINUM NEUROTOXIN AND A VHH DOMAIN

(71) Applicant: New York University, New York, NY (US)

(72) Inventors: Konstantin Ichtchenko, Brooklyn, NY (US); Edwin Vazquez-Cintron, New York, NY (US); Philip A. Band, West Orange, NJ (US); Timothy J. Cardozo, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/964,146

(22) Filed: Dec. 9, 2015

(65) Prior Publication Data

US 2016/0159866 A1 Jun. 9, 2016

Related U.S. Application Data

(60) Provisional application No. 62/118,970, filed on Feb. 20, 2015, provisional application No. 62/089,646, filed on Dec. 9, 2014.

(51) Int. Cl.

| | |
|---|---|
| ***C07K 14/47*** | (2006.01) |
| ***C07K 16/00*** | (2006.01) |
| ***C07K 14/00*** | (2006.01) |
| ***A61K 38/00*** | (2006.01) |
| ***A61K 39/395*** | (2006.01) |
| ***A61K 39/00*** | (2006.01) |
| ***A61K 49/00*** | (2006.01) |
| ***G01N 33/53*** | (2006.01) |
| ***A61K 38/17*** | (2006.01) |
| ***C07K 14/33*** | (2006.01) |
| ***C07K 16/12*** | (2006.01) |

(52) U.S. Cl.

CPC .......... *C07K 14/33* (2013.01); *C07K 16/1282* (2013.01); *A61K 2039/505* (2013.01); *C07K 2317/622* (2013.01); *C07K 2319/00* (2013.01); *C07K 2319/21* (2013.01); *C07K 2319/22* (2013.01); *C07K 2319/41* (2013.01); *C07K 2319/50* (2013.01)

(58) Field of Classification Search

CPC ............ C07K 2317/21; C07K 2317/22; C07K 16/1282; C07K 2317/92; C07K 2319/00; C07K 2317/76; C07K 2317/565; C07K 16/2863; C07K 2317/626; C07K 2317/77; C07K 2319/02; C07K 14/33; C07K 2319/50; C07K 14/001; C07K 14/435; C07K 2319/55; C07K 2317/24; C07K 16/40; C07K 2317/51; C07K 2317/515; C07K 2319/74; C07K 2319/20; C07K 2319/23; C07K 2317/705; C07K 2317/75; C07K 2317/20; C07K 2317/569; C07K 2319/06; C07K 2319/22; A61K 38/00; A61K 2039/505; A61K 47/48538; A61K 2039/507; A61K 39/08; A61K 39/00; A61K 47/48261; A61K 47/4833; A61K 48/00; C12N 9/52; C12N 9/50; C12N 9/96; G01N 2333/33; G01N 2333/952; C12Q 1/37; C12Y 304/24069

See application file for complete search history.

(56) References Cited

U.S. PATENT DOCUMENTS

| | | | |
|---|---|---|---|
| 5,750,383 | A | 5/1998 | Blissard et al. |
| 5,846,929 | A | 12/1998 | Johnson et al. |
| 5,919,665 | A | 7/1999 | Williams |
| 5,939,070 | A | 8/1999 | Johnson et al. |
| 6,001,806 | A | 12/1999 | Hilbert et al. |
| 6,022,950 | A | 2/2000 | Murphy |
| 6,037,150 | A | 3/2000 | Iatrou et al. |
| 6,051,239 | A | 4/2000 | Simpson et al. |
| 6,203,794 | B1 | 3/2001 | Dolly et al. |
| 6,261,561 | B1 | 7/2001 | Stewart et al. |
| 6,323,023 | B1 | 11/2001 | Shoseyov et al. |
| 6,461,617 | B1 | 10/2002 | Shone et al. |
| 6,787,517 | B1 | 9/2004 | Gil et al. |
| 6,831,059 | B2 | 12/2004 | Donovan |
| 6,852,510 | B2 | 2/2005 | Bremel et al. |

(Continued)

FOREIGN PATENT DOCUMENTS

| | | |
|---|---|---|
| EP | 0209281 | 1/1987 |
| JP | 23-2011527193 A | 10/2011 |

(Continued)

OTHER PUBLICATIONS

Thanongsaksrikul et al. Toxins, 2011; 3:469-488.*

(Continued)

*Primary Examiner* — Chang-Yu Wang

(74) *Attorney, Agent, or Firm* — Troutman Pepper Hamilton Sanders LLP (Rochester)

(57) ABSTRACT

The present invention is directed to a fusion protein comprising a light chain region of a Clostridial neurotoxin and a heavy chain region of a Clostridial neurotoxin, where the light and heavy chain regions are linked by a disulfide bond. The fusion protein also has a single chain antibody positioned upstream of the light chain region, where the single chain antibody possesses antigen-binding activity. Also disclosed are therapeutic agents, treatment methods, propeptide fusions, isolated nucleic acid molecules, expression systems, host cells, and methods of expressing fusion proteins.

1 Claim, 327 Drawing Sheets

Specification includes a Sequence Listing.

(56) References Cited

U.S. PATENT DOCUMENTS 6,881,411 B2 4/2005 Stewart et al.
6,967,088 B1 11/2005 Williams et al.
7,132,259 B1 11/2006 Dolly et al.
7,172,764 B2 2/2007 Li et al.
7,223,577 B2 5/2007 Steward et al.
7,227,010 B2 6/2007 Smith
7,273,722 B2 9/2007 Lin et al.
7,419,676 B2 * 9/2008 Dolly ........................ C12N 9/52 424/235.1
7,422,877 B2 9/2008 Dolly et al.
7,456,272 B2 11/2008 Lin et al.
7,632,251 B2 12/2009 Lin et al.
7,658,933 B2 2/2010 Foster et al.
7,709,228 B2 * 5/2010 Dolly ........................ C12N 9/52 424/236.1
7,740,868 B2 * 6/2010 Steward ................... C07K 1/22 424/236.1
7,749,514 B2 * 7/2010 Steward ................... C12N 9/52 424/236.1
7,785,606 B2 8/2010 Ichtchenko et al.
7,888,469 B2 2/2011 Steward et al.
7,893,202 B1 2/2011 Steward et al.
7,897,157 B2 * 3/2011 Steward ................... C12N 9/52 424/236.1
8,044,188 B2 10/2011 Ichtchenko et al.
8,119,767 B2 2/2012 Steward et al.
8,187,834 B2 5/2012 Foster et al.
8,454,976 B2 * 6/2013 Shone .................... A61K 39/08 424/164.1
8,753,831 B2 * 6/2014 Kalkum ............... C07K 14/705 435/4
8,865,186 B2 10/2014 Ichtchenko et al.
8,980,284 B2 * 3/2015 Ichtchenko ................ 424/234.1
9,000,131 B2 * 4/2015 Marks ................ C07K 16/1282 424/130.1
9,243,057 B2 * 1/2016 Marks ................ C07K 16/1282
9,315,549 B2 * 4/2016 Vazquez-Cintron ........................ C07K 14/001
2001/0016199 A1 8/2001 Johnston et al.
2002/0107199 A1 8/2002 Walker
2002/0137886 A1 9/2002 Lin et al.
2002/0168727 A1 11/2002 Smith et al.
2002/0177545 A1 11/2002 Donovan
2003/0027752 A1 2/2003 Steward et al.
2003/0049264 A1 3/2003 Foster et al.
2003/0100071 A1 5/2003 Apicella et al.
2003/0143651 A1 7/2003 Steward et al.
2003/0166238 A1 9/2003 Shone et al.
2003/0215468 A1 11/2003 Williams et al.
2003/0219402 A1 11/2003 Rutter
2003/0229454 A1 12/2003 Reinherz et al.
2004/0013687 A1 1/2004 Simpson et al.
2004/0018589 A1 1/2004 Zhong
2004/0052819 A1 3/2004 Kingsley et al.
2004/0071736 A1 4/2004 Quinn et al.
2004/0101531 A1 5/2004 Curtiss, III et al.
2004/0115215 A1 6/2004 Williams
2004/0115727 A1 6/2004 Steward et al.
2004/0220386 A1 11/2004 Steward et al.
2004/0235118 A1 11/2004 Williams
2005/0060762 A1 3/2005 Bleck
2005/0106182 A1 5/2005 Li et al.
2005/0158323 A1 7/2005 Evans et al.
2005/0260230 A1 11/2005 Steward et al.
2006/0024331 A1 2/2006 Fernandez-Salas et al.
2006/0024794 A1 2/2006 Li et al.
2006/0039929 A1 2/2006 Fernandez-Salas et al.
2006/0099672 A1 * 5/2006 Dolly ........................ C12N 9/52 435/68.1
2006/0204524 A1 9/2006 Ichtchenko et al.
2007/0104737 A1 5/2007 Smith
2008/0057575 A1 3/2008 Fernandez-Salas et al.
2008/0081355 A1 * 4/2008 Dolly ........................ C12N 9/52 435/69.1
2008/0161226 A1 * 7/2008 Steward ................... C12N 9/52 424/239.1
2008/0182294 A1 * 7/2008 Dolly ........................ C12N 9/52 435/69.1
2008/0221012 A1 * 9/2008 Steward ................... C12N 9/52 514/1.1
2008/0317782 A1 * 12/2008 Donovan ......... A61K 47/48261 424/239.1
2009/0004224 A1 * 1/2009 Steward ................... C12N 9/52 424/239.1
2009/0069238 A1 * 3/2009 Steward ................... C12N 9/52 514/10.3
2009/0081730 A1 * 3/2009 Dolly ........................ C12N 9/52 435/69.1
2009/0087458 A1 * 4/2009 Dolly ........................ C12N 9/52 424/239.1
2009/0087478 A1 4/2009 Hansen et al.
2009/0136465 A1 * 5/2009 Merenick ........... A61K 31/7088 424/93.21
2009/0246827 A1 * 10/2009 Shone .................... A61K 39/08 435/68.1
2009/0274708 A1 11/2009 Shone et al.
2010/0196421 A1 8/2010 Ichtchenko et al.
2010/0278826 A1 11/2010 Shoemaker et al.
2011/0200615 A1 * 8/2011 Marks ................ C07K 16/1282 424/167.1
2011/0206616 A1 * 8/2011 Ichtchenko ............ C07K 14/33 424/9.6
2012/0021002 A1 1/2012 Ichtchenko et al.
2012/0207735 A1 8/2012 Foster et al.
2012/0269822 A1 * 10/2012 Marks ................ C07K 16/1282 424/167.1
2012/0276132 A1 11/2012 Feng et al.
2013/0065259 A1 * 3/2013 Kalkum ............... C07K 14/705 435/8
2014/0212456 A1 * 7/2014 Vazquez-Cintron ........................ C07K 14/001 424/239.1
2014/0235490 A1 * 8/2014 Kalkum ............... C07K 14/705 506/9
2014/0377248 A1 * 12/2014 Grein ...................... C12P 21/06 424/94.67
2015/0030600 A1 * 1/2015 Marks ................ C07K 16/1282 424/139.1
2015/0197559 A1 * 7/2015 Marks ................ C07K 16/1282 424/167.1
2015/0283261 A1 * 10/2015 Chapman ......... A61K 47/48484 424/179.1
2015/0322118 A1 * 11/2015 Groer ..................... C07K 14/33 514/17.7
2016/0114059 A1 * 4/2016 Merenick ........... A61K 31/7088 514/44 R

FOREIGN PATENT DOCUMENTS

WO WO 98/07864 2/1998
WO WO 01/14570 3/2001
WO WO 01/18038 3/2001
WO 2006/071877 A2 7/2006
WO 2011/091419 A2 7/2011
WO 2014/034127 A1 3/2014

OTHER PUBLICATIONS

Heng et al. Medical Hypothesis, 2005: 64:1105-1108.*
Edupuganti FEBS J. 2012, 279: 2555-2567.*
Andrea et al., mAbs, 2011; 3: 3-16.*
Thanongsaksrikul et al. J. Biol. Chem. 2010; 285:9657-9666.*
Bakherad et al. Mol. Biotechnol. 2013; 55:159-167.*
Barth et al. J. Biol. Chem. 2002; 277:5074-5081.*
Cheng et al. Expert Opin. Drug Deliv. 2010; 7:461-478.*
The Product Information of the Thermo Scientific aLICator Ligation Independent Cloning and Expression System, retrieved from the Thermo Scientific website: assets.thermofisher.com/TFS-Assets/LSG/manuals/MAN0013755_aLICator_lic_clon_exp_kit4_NHisWQ_ug.pdf on Mar. 11, 2019.*

(56) References Cited

OTHER PUBLICATIONS

The Product Information of the Thermo Scientific WELQut Protease#EO0861, retrieved from the Thermo Scientific website: assets.thermofisher.com/TFS-Assets/LSG/manuals/MAN0014319_EO0861_WELQut_Pl.pdf on Mar. 11, 2019.*
Kuo et al., PLoS One, 6(5):e2352, doi:10.1371/journal.pone.0020352, published May 24, 2011.*
International Search Report for corresponding PCT Application No. PCT/US15/64787 (dated Mar. 17, 2016).
European Search Report For Corresponding European Application No. 15867414.3 (dated Apr. 11, 2018).
Mah et al., "Recombinant Anti-Botulinum Neurotoxin a Single-Chain Variable Fragment Antibody Generated Using a Phage Display System" Hybridoma and Hybridomics 22(5):277-283 (2003).
Band et al., "Recombinant Derivatives of Botulinum Neurotoxin A Engineered for Trafficking Studies and Neuronal Delivery" Protein Expression and Purification 71:62-73 (2010).
European Patent Application Serial No. 15867414.3 Communication Pursuant to Article 94(3) EPC (Office Action) (dated Feb. 5, 2019).
Notice of Reasons for Rejection for Japanese Patent Application No. 2017-530748 (dated Nov. 18, 2019).
Bowie et al., "Deciphering the Message in Sequences: Tolerance to Amino Acid Substitutions," Science 247:1306-1310 (1990).
Burgess et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," J. Cell Biol. 111:2129-2138 (1990).
Lazar et al., "Transforming Growth Factor °α: Mutation of Aspartic Acid 47 and Leucine 48 Results in Different Biological Activities," Mol. Cell. Biol. 8:1247-1252 (1998).
National Institute of Allergy and Infectious Diseases, "NIAID Biodefense Research Agenda for CDC Category A Agents. Progress Report," NIH Publication #03-5432, pp. 1-37 (2003).
Abrams, P., "The Role of Neuromodulation in the Management of Urinary Urge Incontinence," BJU Int. 93(7):1116 (2004).
Achem, S.R., "Treatment of Spastic Esophageal Motility Disorders," Gastroenterol Clin. North Am. 33(1):107-124 (2004).
Adler et al., "Botulinum Toxin Type A for Treating Voice Tremor," Arch. Neurol. 61(9):1416-1420 (2004).
Agarwal et al., "Structural Analysis of Botulinum Neurotoxin Type E Catalytic Domain and Its Mutant Glu212.fwdarw.Gln Reveals the Pivotal Role of the Glu212 Carboxylate in the Catalytic Pathway," Biochemistry 43(21):6637-6644 (2004).
Ahn et al., "Botulinum Toxin for Masseter Reduction in Asian Patients," Arch. Facial Plast. Surg. 6(3):188-191 (2004).
Aoki, K.R., "Evidence for Antinociceptive Activity of Botulinum Toxin Type A in Pain Management," Headache 43(Suppl 1):S9-S15 (2003).
Aquilina et al., "Reduction of a Chronic Bilateral Temporomandibular Joint Dislocation with Intel-maxillary Fixation and Botulinum Toxin A," Br J. Oral Maxillolac. Surg. 42(3):272-273 (2004).
Bach-Rojecky & Lackovi , "Antinociceptive Effect of Botulinum Toxin Type A in Rat Model of Carrageenan and Capsaicin Induced Pain," Croat. Med. J. 46(2):201-208 (2005).
Bade et al., "Botulinum Neurotoxin Type D Enables Cytosolic Delivery of Enzymatically Active Cargo Proteins to Neurons via Unfolded Translocation Intermediates," J. Neurochem. 91(6):1461-1472 (2004).
Bakheit, A.M., "Optimizing the Methods of Evaluation of the Effectiveness of Botulinum Toxin Treatment of Post-Stroke Muscle Spasticity," J. Neurol. Neurosurg. Psychiatry 75:665-666 (2004).
Balkrishnan et al., "Longitudinal Examination of Health Outcomes Associated with Botulinum Toxin Use in Children with Cerebral Palsy," J. Surg. Orthop. Adv. 13:76-80 (2004).
Bayles & Deschler, "Operative Prevention and Management of Voice-Limiting Pharyngoesophageal Spasm," Otolaryngol Clin. North Am. 37(3):547-558 (2004).
Bender et al., "Speech Intelligibility in Severe Adductor Spasmodic Dysphonia," J. Speech Lang. Hear. Res. 47(1):21-32 (2004).
Bentsianov et al., "Noncosmetic Uses of Botulinum Toxin," Clin. Dermatol. 22(1):82-88 (2004).
Berweck & Heinen, "Use of Botulinum Toxin in Pediatric Spasticity (Cerebral Palsy)," Mov. Disord. 19(Suppl 8)S162-S167 (2004).
Blersch et al., "Botulinum Toxin A and the Cutaneous Nociception in Humans: A Prospective, Double-Blind, Placebo-Controlled, Randomized Study," J. Neurol. Sci. 205(1):59-63 (2002).
Blumenfeld et al., "Botulinum Neurotoxin for the Treatment of Migraine and Other Primary Headache Disorders," Dermatol. Clin. 22(2):167-175 (2004).
Brandt & Boker, "Botulinum Toxin for the Treatment of Neck Lines and Neck Bands," Dermatol. Clin. 22(2):159-166 (2004).
Brisinda et al., "Botulinum Neurotoxin to Treat Chronic Anal Fissure: Results of a Randomized 'Botox vs. Dysport' Controlled Trial," Aliment Pharmacol. Ther., 19(6):695-701 (2004).
Byrne et al., "Purification, Potency, and Efficacy of the Botulinum Neurotoxin Type A Binding Domain from Pichia pastoris as a Recombinant Vaccine Candidate," Infect. Immun. 66(10):4817-4822 (1998).
Caccin et al., "VAMP/Synaptobrevin Cleavage by Tetanus and Botulinum Neurotoxins is Strongly Enhanced by Acidic Liposomes," FEBS Lett. 542(1-3):132-136 (2003).
Capaccio et al., "Dianosis and Therapeutic Management of Tatrogenic Parotid Sialocele," Ann. Otol. Rhinol. Laryngol. 113(7):562-564 (2004).
Carruthers & Carruthers,"Botox: Beyond Wrinkles," Clin. Dermatol. 22(1):89-93 (2004).
Carruthers & Carruthers, "Botulinum Toxin A in the Mid and Lower Face and Neck," Dermatol. Clin. 22(2):151-158 (2004).
Carruthers & Carruthers, "Botulinum Toxin Type A for the Treatment of Glabellar Rhytides," Dermatol. Clin. 22(2):137-144 (2004).
Chaddock et al., "Expression and Purification of Catalytically Active, Non-Toxic Endopeptidase Derivatives of Clostridium botulinum Toxin Type A," Protein Expr. Purif. 25(2):219-228 (2002).
Chaddock et al., "Retargeted Clostridial Endopeptidases. Inhibition of Nociceptive Neurotransmitter Release In Vitro, and Antinociceptive Activity in In Vivo Models of Pain," Mov. Disord. 19(Suppl 8):S42-S47 (2004).
Chao et al., "Management of Pharyngoesophageal Spasm with Botox," Otolaryngol Clin. North Am. 37(3):559-566 (2004).
Chen et al., "Altering Brow Contour with Botulinum Toxin," Facial Plast. Surg. Clin. N. Am. 11:457-464 (2003).
Cruz, F., "Mechanisms Involved in New Therapies for Overactive Bladder," Urology 63(Suppl 3A):65-73 (2004).
Cui et al., "Subcutaneous Administration of Botulinum Toxin A Reduces Formalin-Induced Pain," Pain 107:(1-2):125-133 (2004).
Defazio & Livrea, "Primary Blepharospasm: Diagnosis and Management," Drugs 64(3):237-244 (2004).
Dekleva & DasGupta, "Nicking of Single Chain Clostridium Botulinum Type A Neurotoxin by an Endogenous Protease," Biochem. Biophys. Res. Commun. 162(2):767-772 (1989).
Derman et al., "Mutations That Allow Disulfide Bond Formation in the Cytoplasm of *Escherichia coli*," Science 262(5140):1744-1747 (1993).
Dolly et al., "Acceptors for Botulinum Neurotoxin Reside on Motor Nerve Terminals and Mediate Its Internalization," Nature 307(5950):457-460 (1984).
Dong et al., "Synaptotagmins I and II Mediate Entry of Botulinum Neurotoxin B Into Cells," J. Cell. Biol. 162(7):1293-1303 (2003).
Eleopra et al., "Different Types of Botulinum Toxin in Humans," Mov. Disord. 19(Suppl 8)S53- S59 (2004).
Emonard et al., "Regulation of Matrix Metalloproteinase (MMP) Activity by the Low-Density Lipoprotein Receptor-Related Protein (LRP). A New Function for an 'Old Friend'," Biochimie 87(3-4):369-376 (2005).
Finn, J.C., "Botulinum Toxin Type A: Fine-Tuning Treatment of Facial Nerve Injury," J. Drugs Dermatol. 3(2):133-137 (2004).
Flynn, T.C., "Myobloc," Dermatol. Clin. 22(2):207-211 (2004).
Giannantoni et al., "Intravesical Resiniferatoxin Versus Botulinum-A Toxin Injections for Neurogenic Detrusor Overactivity: A Prospective Randomized Study," J. Urol. 172(1):240-243 (2004).

(56) References Cited

OTHER PUBLICATIONS

Glogau, R.G., "Treatment of Hyperhidrosis with Botulinum Toxin," Dermatol. Clin. 22(2):177- 185 (2004).
Goodnough et al., "Development of a Delivery Vehicle for Intracellular Transport of Botulinum Neurotoxin Antagonists," FEBS Lett. 513(2-3):163-168 (2002).
Haussermann et al., "Long-Term Follow-Up of Cervical Dystonia Patients Treated with Botulinum Toxin A," Mov. Disord. 19(3):303-308 (2004).
Hayden et al., "Discovery and Design of Novel Inhibitors of Botulinus Neurotoxin A: Targeted 'Hinge' Peptide Libraries," J. Appl. Toxicol. 23(1):1-7 (2003).
Hoch et al., "Channels Formed by Botulinum, Tetanus, and Diphtheria Toxins in Planar Lipid Bilayers: Relevance to Translocation of Proteins Across Membranes," Proc. Natl. Acad. Sci. USA 82(6):1692-1696 (1985).
Hojilla et al., "Matrix Metalloproteinases and Their Tissue Inhibitors Direct Cell Fate During Cancer Development," Br. J. Cancer 89(10):1817-1821 (2003).
Hyman et al., "Botulinum Toxin (Dysport.RTM.) Treatment of Hip Adductor Spasticity in Multiple Sclerosis: A Prospective, Randomised, Double Blind, Placebo Controlled, Dose Ranging Study," J Neurol. Neurosurg. Psychiatry 68(6):707-712 (2000).
Jankovic, J., "Botulinum Toxin in Clinical Practice," J Neurol. Neurosurg. Psychiatry 75(7):951- 957 (2004).
Johnson, E.A., "Clostridial Toxins as Therapeutic Agents: Benefits of Nature's Most Toxic Proteins," Annu. Rev. Microbiol. 53:551-575 (1999).
Jost & Aoki, "Botulinum Toxin A in Anal Fissure: Why Does It Work?" Dis. Colon Rectum. 47(2):257-258 (2004).
Kadkhodayan et al., "Cloning, Expression, and One-Step Purification of the Minimal Essential Domain of the Light Chain of Botulinum Neurotoxin Type A," Protein Expr. Purif. 19(1):125- 130 (2000).
Kern et al., "Effects of Botulinum Toxin Type B on Stump Pain and Involuntary Movements of the Stump," Am. J. Phys. Med. Rehabil. 83(5):396-399 (2004).
Kiyatkin et al., "Induction of an Immune Response by Oral Administration of Recombinant Botulinum Toxin," Infect. Immun. 65(11):4586-4591 (1997).
Klein, A.W., "The Therapeutic Potential of Botulinum Toxin," Dermatol. Surg. 30(3):452-455 (2004).
Koriazova & Montal., "Translocation of Botulinum Neurotoxin Light Chain Protease Through the Heavy Chain Channel," Nat. Struct. Biol. 10(1):13-18 (2003).
Kramer et al., "Botulinum Toxin A Reduces Neurogenic Flare But Has Almost No Effect on Pain and Ilyperalgesia in human Skin," J. Neurol. 250(2):188-193 (2003).
Kurazono et al., "Minimal Essential Domains Specifying Toxicity of the Light Chains of Tetanus Toxin and Botulinum Neurotoxin Type A," J Biol. Chem. 267(21):14721-14729 (1992).
Kyrmizakis et al., "The Use of Botulinum Toxin Type A in the Treatment of Frey and Crocodile Tears Syndromes," J. Oral Maxillofac. Surg. 62(7):840-844 (2004).
Lacy et al., "Crystal Structure of Botulinum Neurotoxin Type A and Implications for Toxicity," Nat. Struct. Biol. 5(10):898-902 (1998).
Lacy & Stevens, "Recombinant Expression and Purification of the Botulinum Neurotoxin Type A Translocation Domain," Protein Expr. Purif. 11(2):195-200 (1997).
Lalli et al., "Functional Characterisation of Tetanus and Botulinum Neurotoxins Binding Domains," J. Cell Sci. 112(Pt 16):2715-2724 (1999).
Lang, A., "History and Uses of Botox (Botulinum Toxin Type A)," Lippincott's Case Manag. 9(2):109-112 (2004).
Layeeque et al., "Botulinum Toxin Infiltration for Pain Control After Mastectomy and Expander Reconstruction," Ann, Surg. 240(4):608-614 (2004).
Lee et al., "A Case of Foul Genital Odor Treated with Botulinum Toxin A," Dermatol. Surg. 30(9):1233-1235 (2004).
Leippold et al., "Botulinum Toxin as a New Therapy Option for Voiding Disorders: Current State of the Art," Eur. Urol. 44(2):165-174 (2003).
Levy et al., "Botulinum Toxin A: A 9-Month Clinical and 3D In Vivo Profilometric Crow's Feet Wrinkle Formation Study," J Cosmet. Laser Ther. 6(1):16-20 (2004).
Li et al., "Recombinant Forms of Tetanus Toxin Engineered for Examining and Exploiting Neuronal Trafficking Pathways," J. Biol. Chem. 276(33):31394-31401 (2001).
Lozsadi et al., "Botulinum Toxin A Improves Involuntary Limb Movements in Rasmussen Syndrome," Neurology 62(7):1233-1234 (2004).
MacKinnon et al., "Corticospinal Excitability Accompanying Ballistic Wrist Movements in Primary Dystonia," Mov. Disord. 19(3):273-284 (2004).
Mahowald et al., "Long Term Effects of Mira-Articular Botulinum Toxin A for Refractory Joint Pain," Annual Meeting of the American College of Rheumatology (Oct. 19, 2004).
Mannello et al., "Matrix Metalloproteinase Inhibitors as Anticancer Therapeutics," Curr. Cancer Drug Targets 5:285-298 (2005).
Maskos, K., "Crystal Structures of MMPs in Complex with Physiological and Pharmacological Inhibitors," Biochimie 87(3-4):249-263 (2005).
Mazo et al., "Botulinic Toxin in Patients with Neurogenic Dysfunction of the Lower Urinary Tracts," Urologia Jul.-Aug.:44-48 (2004).
Mattcoli ct al., "Synaptic Vesicle Endocytosis Mediates the Entry of Tetanus Neurotoxin Into Hippocampal Neurons," Proc. Natl. Acad. Sci. USA 93(23):13310-13315 (1996).
Montecucco, C., "How Do Tetanus and Botulinum Toxins Bind to Neuronal Membranes?" Trends Biochem. Sci. 11(8):314-317 (1986).
Montecucco et al., "SNARE Complexes and Neuroexocytosis: How Many, How Close?" Trends Biochem. Sci. 30(7):367-372 (2005).
Montecucco et al., "Structure and Function of Tetanus and Botulinum Neurotoxins," Q. Rev. Biophys. 28(4):423-472 (1995).
Mukherjee et al., "Endocytosis," Physiol. Rev. 77(3):759-803 (1997).
Namazi & Majd, "Botulinum Toxin as a Novel Addition to Anti-Arthritis Armamentarium," Am. J. Immun. 1(2):92-93 (2005).
Naumann & Jankovic, "Safety of Botulinum Toxin Type A: A Systematic Review and Meta- Analysis," Curr. Med. Res. Opin. 20(7):981-990 (2004).
Nishiki et al., "The High-Affinity Binding of Clostridium botulinum Type B Neurotoxin to Synaptotagmin II Associated with Gangliosides G.sub.T1b/G.sub.1a," FEBS Lett. 378(3):253- 257 (1996).
Oost et al., "Design and Synthesis of Substrate-Based Inhibitors of Botulinum Neurotoxin Type B Metalloprotease," Biopolymers 71(6):602-619 (2003).
Ozsoy et al., "Two-Plane Injection of Botulinum Exotoxin A in Glabellar Frown Lines," Aesth. Plast. Surg. 28(2):114-115 (2004).
Park & Simpson, "Inhalational Poisoning by Botulinum Toxin and inhalation Vaccination with Its Ilavy-Chain Component," Infect. Immun. 71(3):1147-1154 (2003).
Pidcock, F.S., "The Emerging Role of Therapeutic Botulinum Toxin in the Treatment of Cerebral Palsy," J. Pediatr. 145(2 Suppl):S33-S35 (2004).
Pless et al., "Iligh-Affinity, Protective Antibodies to the Binding Domain of Botulinum Neurotoxin Type A," Infect. Immun. 69(1):570-574 (2001).
Porta et al., "Treatment of Phonic Tics in Patients with Tourette's Syndrome Using Botulinum Toxin Type A," Neurol. Sci. 24(6):420-423 (2003).
Prinz et al., "The Role of the Thioredoxin and Glutaredoxin Pathways in Reducing Protein Disulfide Bonds in the *Escherichia coli* Cytoplasm," J. Biol. Chem. 272(25):15661- 15667(1997).
Pucinelli et al., "Botulinic Toxin for the Rehabilitation of Osteoarthritis Fixed-Flexion Knee Deformity," Annual Meeting of the Osteoarthritis Research Society International, pp. S143, Abstract P346 (2004).
Rajkumar & Conn, "Botulinum Toxin: A New Dimension in the Treatment of Lower Urinary Tract Dysfunction," Urology 64(1):2-8 (2004).
Reitz & Schurch, "Intravesical Therapy Options for Neurogenic Detrusor Overactivity," Spinal Cord 42(5):267-272 (2004).

(56) References Cited

OTHER PUBLICATIONS

Rigoni et al., "Site-Directed Mutagenesis Identifies Active-Site Residues of the Light Chain of Botulinum Neurotoxin Type A," Biochem. Biophys. Res. Commun. 288(5):1231-1237 (2001).
Rossetto et al., "SNARE Motif and Neurotoxins," Nature 372(6505):415-416 (1994).
Rummel et al., "The H.sub.cc-Domain of Botulinum Neurotoxins A and B Exhibits a Singular Ganglioside Binding Site Displaying Serotype Specific Carbohydrate Interaction," Mol. Microbiol. 51(3):631-643 (2004).
Rummel et al., "Synaptotagmins I and II Act as Nerve Cell Receptors for Botulinum Neurotoxin G," J. Biol. Chem. 279(29):30865-30870 (2004).
Russman et al., "Cerebral Palsy: A Rational Approach to a Treatment Protocol, and the Role of Botulinum Toxin in Treatment," Muscle Nerve 20(Suppl 6):S181-S193 (1997).
Sadick & Matarasso, "Comparison of Botulinum Toxins A and B in the Treatment of Facial Rhytidcs," Dermatol. Clin. 22(2):221-226 (2004).
Salmanpoor & Rahmanian, "Treatment of Axillary Hyperhidrosis with Botulinum-A Toxin," Int. J. Dermatol. 41(7):428-430 (2002).
Sampaio et al., "Clinical Comparability of Marketed Formulations of Botulinum Toxin," Mov. Disord. 19(Suppl 8):S129-S136 (2004).
Schmulson & Valdovinos, "Current and Future Treatment of Chest Pain of Presumed Esophageal Origin," Gastroenierol Clin, North Am, 33(1):93-105 (2004).
Schurch, "The Role of Botulinum Toxin in Neurology," Drugs of Today 40(3):205-212 (2004).
Segelke et al., "Crystal Structure of Clostridium botulinum Neurotoxin Protease in a Product- Bound State: Evidence for Noncanonical Zinc Protease Activity," Proc. Natl. Acad. Sci. USA 101(18):6888-6893 (2004).
Shapiro et al., "Identification of a Ganglioside Recognition Domain of Tetanus Toxin Using a Novel Ganglioside Photoaffinity Ligand," J. Biol. Chem. 272(48):30380-30386 (1997).
Simpson, L.L., "Identification of the Major Steps in Botulinum Toxin Action," Annu. Rev. Pharmacol. Toxicol. 44:167-193 (2004).
Sukonpan et al., "Synthesis of Substrates and Inhibitors of Botulinum Neurotoxin Type A Metalloprolease," J. Pept. Res. 63(2):181-193 (2004).
Sutton et al., "Crystal Structure of a SNARE Complex Involved in Synaptic Exocytosis at 2.4 ANG.Resolution," Nature 395(6700):347-353 (1998).
Swaminathan & Eswaramoorthy, "Structural Analysis of the Catalytic and Binding Sites of Clostridium botulinum Neurotoxin B," Nat. Struct. Biol. 7(8):693-699 (2000).
Van Heyningen & Miller, "The Fixation of Tetanus Toxin by Ganglioside," J. Gen. Microbiol. 24:107-119 (1961).
Vartanian & Dayan, "Facial Rejuvenation Using Botulinum Toxin A: Review and Updates," Facial Plast. Surg. 20(1):11-19 (2004).
Wissel & Entner, "Botulinum Toxin Typ A in der Behandlung der Adduktorenspastizitat (Botulinum Toxin Treatment of Hip Adductor Spasticity in Multiple Sclerosis)," Wien. Klin. Wochesnchr. 113[Suppl 4]:20-24 (2001).
No Author, "Botulinum Toxin (Botox) for Axillary Hyperhidrosis," Med. Lett. Drugs Ther. 46(1191):76 (2004).
Marvaud et al., "Le Botulisme: Agent, Mode D'action des Neurotoxines Botuliques, Formes D'Acquisition, Traitement et Prevention," C.R. Biologies 325:863-878 (2002) (with English abstract).
Baldwin et al., "The C-Terminus of Botulinum Neurotoxin Type A Light Chain Contributes to Solubility, Catalysis, and Stability," Protein Expression and Purification 37:187-195 (2004).
Prabakaran et al., "Botulinum Neurotoxin Types B and E: Purification, Limited Proteolysis by Endoproteinase Glu-C and Pepsin, and Comparison of their Identified Cleaved Sites Relative to the Three-Dimensional Structure of Type A Neurotoxin," Toxicon 39:1515-1531 (2001).
Shone et al., "Inactivation of Clostridum Botulinum Type A Neurotoxin by Trypsin and Purification of Two Tryptic Fragments," European J. of Biochem. 151:75-82 (1985).
Allet et al., "A Bacterial Signal Peptide Directs Efficient Secretion of Eukaryotic Proteins in the Baculovirus Expression System," Pro. Exp. Pur. 9:61-68 (1997).
Cooke et al., "A Modified *Escherichia coli* Protein Production Strain Expressing Staphylococcal Nuclease, Capable of Auto-Hydrolysing Host Nucleic Acid," J. Biotech. 101:229-239 (2003).
Agarwal et al., Cloning, High Level Expression, Purification, and Crystallization of the Full Length Clostridium botulinum Neurotoxin Type E Light Chain, Pro. Exp. Pur. 34:95-102 (2004).
Pellet et al., "Neuronal Targeting, Internalization, and Biological Activity of a Recombinant Atoxic Derivative of Botulinum Neurotoxin A.," BBRC 405(4):673-677 (2011).
Gunnar Von Heijne, "Signals for Protein targeting into and Across Membranes," Subcell. Biochem. 22:1-19 (1994).
Band et al., "Recombinant Derivatives of Botulinum Neurotoxin A Engineered to Dissect Toxin Uptake and Trafficking Pathways," Abstract, 46th Annual Meeting of the Interagency Botulism Research Coordinating Committee (Oct. 18-21, 2009).
Fischer et al., "Single Molecule Detection of Intermediates During Botulinum Neurotoxin Translocation Across Membranes," PNAS 104(25):10447-10452 (2007).
Fischer et al., "Crucial Role of the Disulfide Bridge between Botulinum Neurotoxin and Heavy Chains in Protease Translocation across Membranes," The Journal of Biological Chemistry 282(40):29604-29611 (2007).
Ichtchenko, "Recombinant Derivatives of Botulinum Neurotoxin A Engineered for Trafficking Studies and Neuronal Delivery," Presentation, 46th Annual Meeting of the Interagency Botulism Research Coordinating Committee (Oct. 21, 2009).
International Search Report and Written Opinion for PCT/US2011/022408 (dated Dec. 26, 2011).
International Search Report for PCT/US05/43307 (dated Oct. 5, 2006).
Vazquez-Cintron et al., "Atoxic Derivative of Botulinum Neurotoxin A as a Prototype Molecular Vehicle for Targeted Delivery to the Neuronal Cytoplasm," PLoS ONE 9(1):e85517 (2014).
Vazquez-Cintron et al., Abstracts Toxins 2011 / Toxicon 68 (2013): 77 Abstract only.
Zhou et al., ACS Chemical Biology 2(5):337-346 (2007).
Pre-Appeal Examination Report for JP2017-530748 and partial English translation (dated Apr. 15, 2021).
Office Action for Canadian Patent Application No. 2969463 (dated Dec. 7, 2021).
Appeal Decision for Japan Patent Application No. 2017-530748 and translation (Jan. 5, 2022).

* cited by examiner

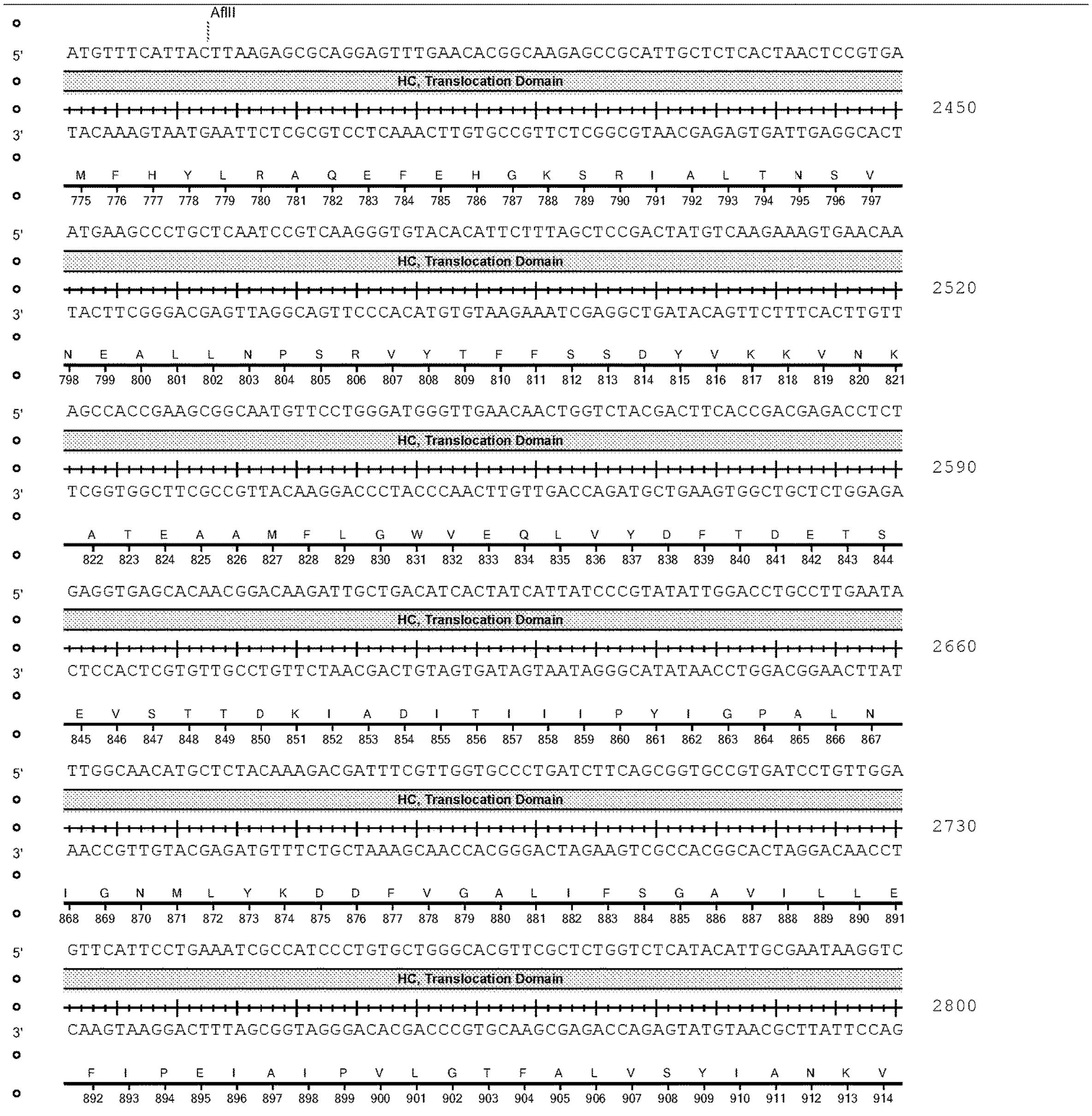

FIG. 9G

```
                    AflII
5'  ATGTTTCATTACTTAAGAGCGCAGGAGTTTGAACACGGCAAGAGCCGCATTGCTCTCACTAACTCCGTGA
                         HC, Translocation Domain
    ++++++++++++++++++++++++++++++++++++++++++++++++++++++++++++++++++++  2450
3'  TACAAAGTAATGAATTCTCGCGTCCTCAAACTTGTGCCGTTCTCGGCGTAACGAGAGTGATTGAGGCACT

    M   F   H   Y   L   R   A   Q   E   F   E   H   G   K   S   R   I   A   L   T   N   S   V
    775 776 777 778 779 780 781 782 783 784 785 786 787 788 789 790 791 792 793 794 795 796 797

5'  ATGAAGCCCTGCTCAATCCGTCAAGGGTGTACACATTCTTTAGCTCCGACTATGTCAAGAAAGTGAACAA
                         HC, Translocation Domain
    ++++++++++++++++++++++++++++++++++++++++++++++++++++++++++++++++++++  2520
3'  TACTTCGGGACGAGTTAGGCAGTTCCCACATGTGTAAGAAATCGAGGCTGATACAGTTCTTTCACTTGTT

    N   E   A   L   L   N   P   S   R   V   Y   T   F   F   S   S   D   Y   V   K   K   V   N   K
    798 799 800 801 802 803 804 805 806 807 808 809 810 811 812 813 814 815 816 817 818 819 820 821

5'  AGCCACCGAAGCGGCAATGTTCCTGGGATGGGTTGAACAACTGGTCTACGACTTCACCGACGAGACCTCT
                         HC, Translocation Domain
    ++++++++++++++++++++++++++++++++++++++++++++++++++++++++++++++++++++  2590
3'  TCGGTGGCTTCGCCGTTACAAGGACCCTACCCAACTTGTTGACCAGATGCTGAAGTGGCTGCTCTGGAGA

    A   T   E   A   A   M   F   L   G   W   V   E   Q   L   V   Y   D   F   T   D   E   T   S
    822 823 824 825 826 827 828 829 830 831 832 833 834 835 836 837 838 839 840 841 842 843 844

5'  GAGGTGAGCACAACGGACAAGATTGCTGACATCACTATCATTATCCCGTATATTGGACCTGCCTTGAATA
                         HC, Translocation Domain
    ++++++++++++++++++++++++++++++++++++++++++++++++++++++++++++++++++++  2660
3'  CTCCACTCGTGTTGCCTGTTCTAACGACTGTAGTGATAGTAATAGGGCATATAACCTGGACGGAACTTAT

    E   V   S   T   T   D   K   I   A   D   I   T   I   I   I   P   Y   I   G   P   A   L   N
    845 846 847 848 849 850 851 852 853 854 855 856 857 858 859 860 861 862 863 864 865 866 867

5'  TTGGCAACATGCTCTACAAAGACGATTTCGTTGGTGCCCTGATCTTCAGCGGTGCCGTGATCCTGTTGGA
                         HC, Translocation Domain
    ++++++++++++++++++++++++++++++++++++++++++++++++++++++++++++++++++++  2730
3'  AACCGTTGTACGAGATGTTTCTGCTAAAGCAACCACGGGACTAGAAGTCGCCACGGCACTAGGACAACCT

    I   G   N   M   L   Y   K   D   D   F   V   G   A   L   I   F   S   G   A   V   I   L   L   E
    868 869 870 871 872 873 874 875 876 877 878 879 880 881 882 883 884 885 886 887 888 889 890 891

5'  GTTCATTCCTGAAATCGCCATCCCTGTGCTGGGCACGTTCGCTCTGGTCTCATACATTGCGAATAAGGTC
                         HC, Translocation Domain
    ++++++++++++++++++++++++++++++++++++++++++++++++++++++++++++++++++++  2800
3'  CAAGTAAGGACTTTAGCGGTAGGGACACGACCCGTGCAAGCGAGACCAGAGTATGTAACGCTTATTCCAG

    F   I   P   E   I   A   I   P   V   L   G   T   F   A   L   V   S   Y   I   A   N   K   V
    892 893 894 895 896 897 898 899 900 901 902 903 904 905 906 907 908 909 910 911 912 913 914
```

```
                 TstI'                              TstI
5'  AACAACTCGGGATGGAAGGTGTCCCTCAACTACGGCGAGATCATCTGGACTTTGCAGGACACACAAGAAA
                         HC, Receptor-Binding Domain
                                                                              3710
3'  TTGTTGAGCCCTACCTTCCACAGGGAGTTGATGCCGCTCTAGTAGACCTGAAACGTCCTGTGTGTTCTTT

     N   N   S   G   W   K   V   S   L   N   Y   G   E   I   I   W   T   L   Q   D   T   Q   E
    1195 1196 1197 1198 1199 1200 1201 1202 1203 1204 1205 1206 1207 1208 1209 1210 1211 1212 1213 1214 1215 1216 1217

5'  TCAAGCAGAGGGTCGTGTTCAAGTACAGCCAAATGATCAACATCAGCGATTACATCAACCGTTGGATCTT
                         HC, Receptor-Binding Domain
                                                                              3780
3'  AGTTCGTCTCCCAGCACAAGTTCATGTCGGTTTACTAGTTGTAGTCGCTAATGTAGTTGGCAACCTAGAA

     I   K   Q   R   V   V   F   K   Y   S   Q   M   I   N   I   S   D   Y   I   N   R   W   I   F
    1218 1219 1220 1221 1222 1223 1224 1225 1226 1227 1228 1229 1230 1231 1232 1233 1234 1235 1236 1237 1238 1239 1240 1241

                                                                    NmeAIII
5'  CGTCACAATCACCAACAACCGCCTGAACAACTCCAAGATTTACATCAACGGTAGACTGATCGACCAGAAG
                         HC, Receptor-Binding Domain
                                                                              3850
3'  GCAGTGTTAGTGGTTGTTGGCGGACTTGTTGAGGTTCTAAATGTAGTTGCCATCTGACTAGCTGGTCTTC

     V   T   I   T   N   N   R   L   N   N   S   K   I   Y   I   N   G   R   L   I   D   Q   K
    1242 1243 1244 1245 1246 1247 1248 1249 1250 1251 1252 1253 1254 1255 1256 1257 1258 1259 1260 1261 1262 1263 1264

5'  CCAATCAGCAACCTCGGCAACATCCACGCCTCAAACAACATCATGTTCAAGTTGGACGGCTGTAGGGATA
                         HC, Receptor-Binding Domain
                                                                              3920
3'  GGTTAGTCGTTGGAGCCGTTGTAGGTGCGGAGTTTGTTGTAGTACAAGTTCAACCTGCCGACATCCCTAT

     P   I   S   N   L   G   N   I   H   A   S   N   N   I   M   F   K   L   D   G   C   R   D
    1265 1266 1267 1268 1269 1270 1271 1272 1273 1274 1275 1276 1277 1278 1279 1280 1281 1282 1283 1284 1285 1286 1287

                                                             EcoICRI
                                                             SacI
5'  CACACAGATACATCTGGATCAAATACTTCAACCTGTTCGACAAGGAGCTCAACGAGAAGGAAATCAAGGA
                         HC, Receptor-Binding Domain
                                                                              3990
3'  GTGTGTCTATGTAGACCTAGTTTATGAAGTTGGACAAGCTGTTCCTCGAGTTGCTCTTCCTTTAGTTCCT

     T   H   R   Y   I   W   I   K   Y   F   N   L   F   D   K   E   L   N   E   K   E   I   K   D
    1288 1289 1290 1291 1292 1293 1294 1295 1296 1297 1298 1299 1300 1301 1302 1303 1304 1305 1306 1307 1308 1309 1310 1311

5'  CCTCTACGATAACCAGTCCAACTCTGGTATCTTGAAGGACTTCTGGGGCGATTACCTGCAATACGACAAG
                         HC, Receptor-Binding Domain
                                                                              4060
3'  GGAGATGCTATTGGTCAGGTTGAGACCATAGAACTTCCTGAAGACCCCGCTAATGGACGTTATGCTGTTC

     L   Y   D   N   Q   S   N   S   G   I   L   K   D   F   W   G   D   Y   L   Q   Y   D   K
    1312 1313 1314 1315 1316 1317 1318 1319 1320 1321 1322 1323 1324 1325 1326 1327 1328 1329 1330 1331 1332 1333 1334

                                  FIG. 9J
```

5' CCCTACTACATGTTGAACCTGTACGACCCTAACAAGTACGTTGATGTGAACAACGTCGGTATCAGGGGCT
HC, Receptor-Binding Domain
4130
3' GGGATGATGTACAACTTGGACATGCTGGGATTGTTCATGCAACTACACTTGTTGCAGCCATAGTCCCCGA
P Y Y M L N L Y D P N K Y V D V N N V G I R G
1335 1336 1337 1338 1339 1340 1341 1342 1343 1344 1345 1346 1347 1348 1349 1350 1351 1352 1353 1354 1355 1356 1357

PmlI
5' ACATGTACCTGAAGGGACCACGTGGTTCTGTTATGACCACTAACATCTACCTCAACAGCTCATTGTACCG
HC, Receptor-Binding Domain
4200
3' TGTACATGGACTTCCCTGGTGCACCAAGACAATACTGGTGATTGTAGATGGAGTTGTCGAGTAACATGGC
Y M Y L K G P R G S V M T T N I Y L N S S L Y R
1358 1359 1360 1361 1362 1363 1364 1365 1366 1367 1368 1369 1370 1371 1372 1373 1374 1375 1376 1377 1378 1379 1380 1381

BspEI DrdI PvuI
5' TGGCACAAAGTTCATCATCAAGAAGTACGCCTCCGGAAACAAGGACAACATCGTCCGTAACAACGATCGC
HC, Receptor-Binding Domain
4270
3' ACCGTGTTTCAAGTAGTAGTTCTTCATGCGGAGGCCTTTGTTCCTGTTGTAGCAGGCATTGTTGCTAGCG
G T K F I I K K Y A S G N K D N I V R N N D R
1382 1383 1384 1385 1386 1387 1388 1389 1390 1391 1392 1393 1394 1395 1396 1397 1398 1399 1400 1401 1402 1403 1404

5' GTTTACATCAACGTTGTGGTCAAGAACAAGGAGTACAGACTGGCTACCAACGCTTCGCAGGCTGGAGTTG
HC, Receptor-Binding Domain
4340
3' CAAATGTAGTTGCAACACCAGTTCTTGTTCCTCATGTCTGACCGATGGTTGCGAAGCGTCCGACCTCAAC
V Y I N V V V K N K E Y R L A T N A S Q A G V
1405 1406 1407 1408 1409 1410 1411 1412 1413 1414 1415 1416 1417 1418 1419 1420 1421 1422 1423 1424 1425 1426 1427

BspHI
5' AGAAGATCCTGTCTGCTCTGGAAATCCCTGACGTGGGCAACCTCTCACAGGTTGTGGTCATGAAGTCGAA
HC, Receptor-Binding Domain
4410
3' TCTTCTAGGACAGACGAGACCTTTAGGGACTGCACCCGTTGGAGAGTGTCCAACACCAGTACTTCAGCTT
E K I L S A L E I P D V G N L S Q V V V M K S K
1428 1429 1430 1431 1432 1433 1434 1435 1436 1437 1438 1439 1440 1441 1442 1443 1444 1445 1446 1447 1448 1449 1450 1451

5' GAACGATCAAGGCATCACTAACAAGTGCAAGATGAACTTGCAGGACAACAACGGAAACGACATCGGCTTC
HC, Receptor-Binding Domain
4480
3' CTTGCTAGTTCCGTAGTGATTGTTCACGTTCTACTTGAACGTCCTGTTGTTGCCTTTGCTGTAGCCGAAG
N D Q G I T N K C K M N L Q D N N G N D I G F
1452 1453 1454 1455 1456 1457 1458 1459 1460 1461 1462 1463 1464 1465 1466 1467 1468 1469 1470 1471 1472 1473 1474

FIG. 9K

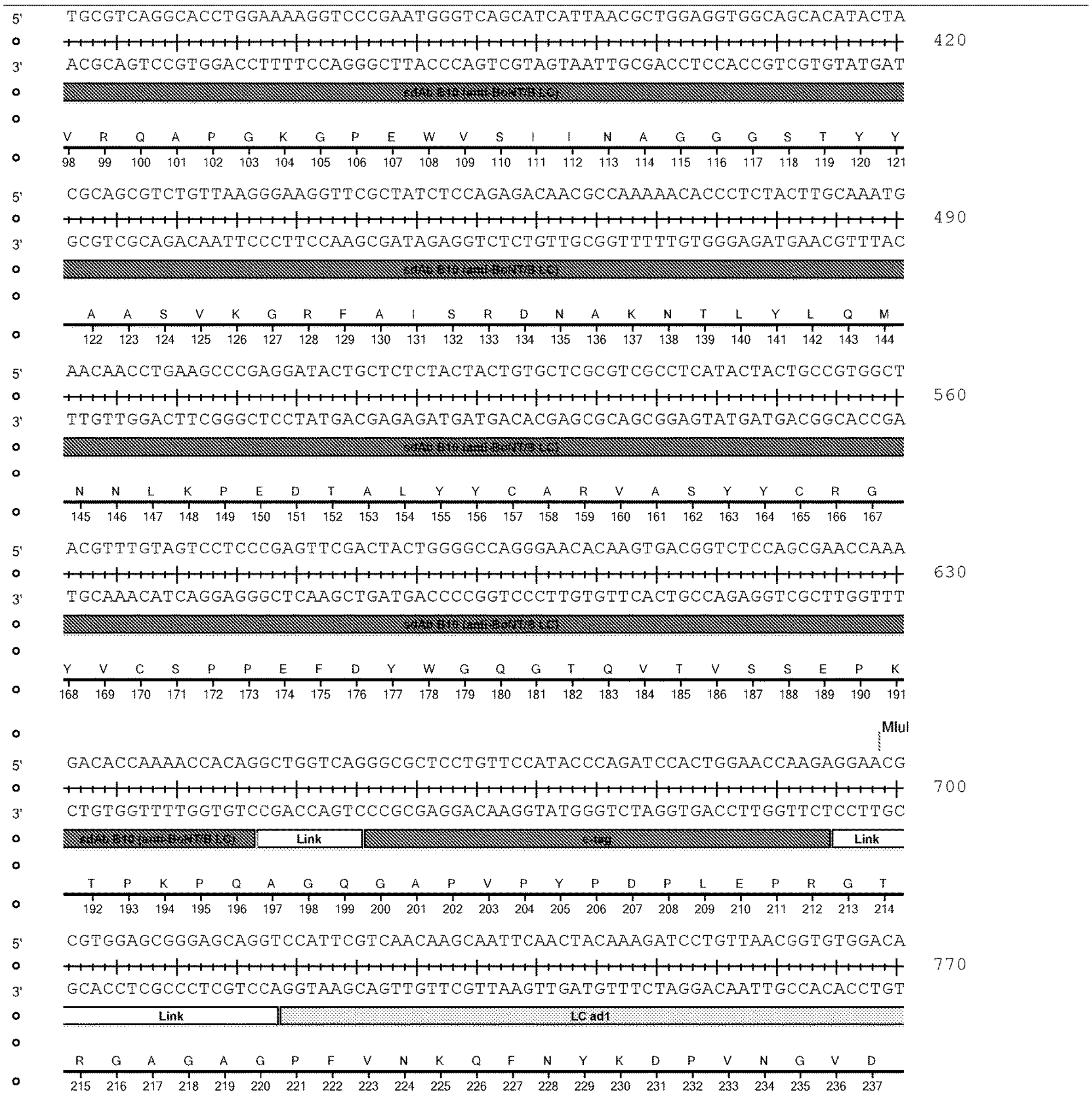

FIG. 10B

```
5'  TGCGTCAGGCACCTGGAAAAGGTCCCGAATGGGTCAGCATCATTAACGCTGGAGGTGGCAGCACATACTA
                                                                                        420
3'  ACGCAGTCCGTGGACCTTTTCCAGGGCTTACCCAGTCGTAGTAATTGCGACCTCCACCGTCGTGTATGAT

    V   R   Q   A   P   G   K   G   P   E   W   V   S   I   I   N   A   G   G   G   S   T   Y   Y
    98  99  100 101 102 103 104 105 106 107 108 109 110 111 112 113 114 115 116 117 118 119 120 121

5'  CGCAGCGTCTGTTAAGGGAAGGTTCGCTATCTCCAGAGACAACGCCAAAAACACCCTCTACTTGCAAATG
                                                                                        490
3'  GCGTCGCAGACAATTCCCTTCCAAGCGATAGAGGTCTCTGTTGCGGTTTTTGTGGGAGATGAACGTTTAC

    A   A   S   V   K   G   R   F   A   I   S   R   D   N   A   K   N   T   L   Y   L   Q   M
    122 123 124 125 126 127 128 129 130 131 132 133 134 135 136 137 138 139 140 141 142 143 144

5'  AACAACCTGAAGCCCGAGGATACTGCTCTCTACTACTGTGCTCGCGTCGCCTCATACTACTGCCGTGGCT
                                                                                        560
3'  TTGTTGGACTTCGGGCTCCTATGACGAGAGATGATGACACGAGCGCAGCGGAGTATGATGACGGCACCGA

    N   N   L   K   P   E   D   T   A   L   Y   Y   C   A   R   V   A   S   Y   Y   C   R   G
    145 146 147 148 149 150 151 152 153 154 155 156 157 158 159 160 161 162 163 164 165 166 167

5'  ACGTTTGTAGTCCTCCCGAGTTCGACTACTGGGGCCAGGGAACACAAGTGACGGTCTCCAGCGAACCAAA
                                                                                        630
3'  TGCAAACATCAGGAGGGCTCAAGCTGATGACCCCGGTCCCTTGTGTTCACTGCCAGAGGTCGCTTGGTTT

    Y   V   C   S   P   P   E   F   D   Y   W   G   Q   G   T   Q   V   T   V   S   S   E   P   K
    168 169 170 171 172 173 174 175 176 177 178 179 180 181 182 183 184 185 186 187 188 189 190 191

                                                                                      MluI
5'  GACACCAAAACCACAGGCTGGTCAGGGCGCTCCTGTTCCATACCCAGATCCACTGGAACCAAGAGGAACG
                                                                                        700
3'  CTGTGGTTTTGGTGTCCGACCAGTCCCGCGAGGACAAGGTATGGGTCTAGGTGACCTTGGTTCTCCTTGC

    T   P   K   P   Q   A   G   Q   G   A   P   V   P   Y   P   D   P   L   E   P   R   G   T
    192 193 194 195 196 197 198 199 200 201 202 203 204 205 206 207 208 209 210 211 212 213 214

5'  CGTGGAGCGGGAGCAGGTCCATTCGTCAACAAGCAATTCAACTACAAAGATCCTGTTAACGGTGTGGACA
                                                                                        770
3'  GCACCTCGCCCTCGTCCAGGTAAGCAGTTGTTCGTTAAGTTGATGTTTCTAGGACAATTGCCACACCTGT

    R   G   A   G   A   G   P   F   V   N   K   Q   F   N   Y   K   D   P   V   N   G   V   D
    215 216 217 218 219 220 221 222 223 224 225 226 227 228 229 230 231 232 233 234 235 236 237
```

BglII

5' TCGCCTACATCAAGATTCCGAACGCAGGCCAGATGCAACCTGTGAAGGCTTTCAAAATCCACAACAAGAT 840
3' AGCGGATGTAGTTCTAAGGCTTGCGTCCGGTCTACGTTGGACACTTCCGAAAGTTTTAGGTGTTGTTCTA

LC ad1

I A Y I K I P N A G Q M Q P V K A F K I H N K I
238 239 240 241 242 243 244 245 246 247 248 249 250 251 252 253 254 255 256 257 258 259 260 261

AarI

5' CTGGGTCATTCCCGAGAGAGACACATTCACGAACCCAGAGGAAGGTGATCTGAACCCTCCCCCAGAAGCC 910
3' GACCCAGTAAGGGCTCTCTCTGTGTAAGTGCTTGGGTCTCCTTCCACTAGACTTGGGAGGGGGTCTTCGG

LC ad1

W V I P E R D T F T N P E E G D L N P P P E A
262 263 264 265 266 267 268 269 270 271 272 273 274 275 276 277 278 279 280 281 282 283 284

ScaI

5' AAGCAGGTGCCGGTCTCTTACTACGATTCAACCTACCTCAGTACTGACAACGAGAAGGATAACTACCTGA 980
3' TTCGTCCACGGCCAGAGAATGATGCTAAGTTGGATGGAGTCATGACTGTTGCTCTTCCTATTGATGGACT

LC ad1

K Q V P V S Y Y D S T Y L S T D N E K D N Y L
285 286 287 288 289 290 291 292 293 294 295 296 297 298 299 300 301 302 303 304 305 306 307

5' AGGGCGTTACTAAACTCTTCGAGCGCATCTACTCGACAGACTTGGGCCGTATGCTGCTCACGTCCATCGT 1050
3' TCCCGCAATGATTTGAGAAGCTCGCGTAGATGAGCTGTCTGAACCCGGCATACGACGAGTGCAGGTAGCA

LC ad1

K G V T K L F E R I Y S T D L G R M L L T S I V
308 309 310 311 312 313 314 315 316 317 318 319 320 321 322 323 324 325 326 327 328 329 330 331

5' CAGGGGTATTCCTTTCTGGGGTGGCTCAACCATCGACACTGAGCTGAAGGTCATTGATACAAACTGCATC 1120
3' GTCCCCATAAGGAAAGACCCCACCGAGTTGGTAGCTGTGACTCGACTTCCAGTAACTATGTTTGACGTAG

LC ad1

R G I P F W G G S T I D T E L K V I D T N C I
332 333 334 335 336 337 338 339 340 341 342 343 344 345 346 347 348 349 350 351 352 353 354

5' AACGTTATTCAACCCGACGGCTCCTACCGCAGCGAGGAATTGAACCTGGTGATCATTGGACCAAGCGCCG 1190
3' TTGCAATAAGTTGGGCTGCCGAGGATGGCGTCGCTCCTTAACTTGGACCACTAGTAACCTGGTTCGCGGC

AgeI

5' CTCAAAAACTTCACCGGTTTGTTCGAGTTCTACAAGCTGCTCTGCGTGCGTGGTGGAGGCACATCTCACA 2030
3' GAGTTTTTGAAGTGGCCAAACAAGCTCAAGATGTTCGACGAGACGCACGCACCACCTCCGTGTAGAGTGT

LC ad1 | D>G | D>G | LC ad1 | K>H | J

L K N F T G L F E F Y K L L C V R G G G T S H
635 636 637 638 639 640 641 642 643 644 645 646 647 648 649 650 651 652 653 654 655 656 657

5' CGCAATCTGAGAACCTGTACTTCCAAGGTGGTGGCCAGGGTGGAGCTCTGAACGATCTGTGTATCAAGGT 2100
3' GCGTTAGACTCTTGGACATGAAGGTTCCACCACCGGTCCCACCTCGAGACTTGCTAGACACATAGTTCCA

J | K>Q | J | TEV site | linker | HC, Translocation Domain

T Q S E N L Y F Q G G G Q G G A L N D L C I K V
658 659 660 661 662 663 664 665 666 667 668 669 670 671 672 673 674 675 676 677 678 679 680 681

5' GAATAACTGGGATCTGTTCTTTAGCCCAAGCGAGGATAACTTCACGAACGATCTCAACAAAGGTGAAGAG 2170
3' CTTATTGACCCTAGACAAGAAATCGGGTTCGCTCCTATTGAAGTGCTTGCTAGAGTTGTTTCCACTTCTC

HC, Translocation Domain

N N W D L F F S P S E D N F T N D L N K G E E
682 683 684 685 686 687 688 689 690 691 692 693 694 695 696 697 698 699 700 701 702 703 704

5' ATCACGTCTGATACCAATATCGAAGCGGCTGAAGAGAATATCTCCTTGGATCTCATCCAGCAATATTACC 2240
3' TAGTGCAGACTATGGTTATAGCTTCGCCGACTTCTCTTATAGAGGAACCTAGAGTAGGTCGTTATAATGG

HC, Translocation Domain

I T S D T N I E A A E E N I S L D L I Q Q Y Y
705 706 707 708 709 710 711 712 713 714 715 716 717 718 719 720 721 722 723 724 725 726 727

Bpu10I
BbvCI

5' TGACCTTTAACTTCGATAACGAGCCCGAAAACATCTCCATCGAGAACCTCAGCTCAGACATCATTGGTCA 2310
3' ACTGGAAATTGAAGCTATTGCTCGGGCTTTTGTAGAGGTAGCTCTTGGAGTCGAGTCTGTAGTAACCAGT

HC, Translocation Domain

L T F N F D N E P E N I S I E N L S S D I I G Q
728 729 730 731 732 733 734 735 736 737 738 739 740 741 742 743 744 745 746 747 748 749 750 751

5' GTTGGAGCTGATGCCAAACATTGAACGCTTCCCCAACGGCAAGAAATACGAACTCGACAAGTATACGATG 2380
3' CAACCTCGACTACGGTTTGTAACTTGCGAAGGGGTTGCCGTTCTTTATGCTTGAGCTGTTCATATGCTAC

HC, Translocation Domain

```
                AflII
5'  TTTCATTACTTAAGAGCGCAGGAGTTTGAACACGGCAAGAGCCGCATTGCTCTCACTAACTCCGTGAATG
                                                                              2450
3'  AAAGTAATGAATTCTCGCGTCCTCAAACTTGTGCCGTTCTCGGCGTAACGAGAGTGATTGAGGCACTTAC
                                HC, Translocation Domain

    F   H   Y   L   R   A   Q   E   F   E   H   G   K   S   R   I   A   L   T   N   S   V   N
    775 776 777 778 779 780 781 782 783 784 785 786 787 788 789 790 791 792 793 794 795 796 797

5'  AAGCCCTGCTCAATCCGTCAAGGGTGTACACATTCTTTAGCTCCGACTATGTCAAGAAAGTGAACAAAGC
                                                                              2520
3'  TTCGGGACGAGTTAGGCAGTTCCCACATGTGTAAGAAATCGAGGCTGATACAGTTCTTTCACTTGTTTCG
                                HC, Translocation Domain

    E   A   L   L   N   P   S   R   V   Y   T   F   F   S   S   D   Y   V   K   K   V   N   K   A
    798 799 800 801 802 803 804 805 806 807 808 809 810 811 812 813 814 815 816 817 818 819 820 821

5'  CACCGAAGCGGCAATGTTCCTGGGATGGGTTGAACAACTGGTCTACGACTTCACCGACGAGACCTCTGAG
                                                                              2590
3'  GTGGCTTCGCCGTTACAAGGACCCTACCCAACTTGTTGACCAGATGCTGAAGTGGCTGCTCTGGAGACTC
                                HC, Translocation Domain

    T   E   A   A   M   F   L   G   W   V   E   Q   L   V   Y   D   F   T   D   E   T   S   E
    822 823 824 825 826 827 828 829 830 831 832 833 834 835 836 837 838 839 840 841 842 843 844

5'  GTGAGCACAACGGACAAGATTGCTGACATCACTATCATTATCCCGTATATTGGACCTGCCTTGAATATTG
                                                                              2660
3'  CACTCGTGTTGCCTGTTCTAACGACTGTAGTGATAGTAATAGGGCATATAACCTGGACGGAACTTATAAC
                                HC, Translocation Domain

    V   S   T   T   D   K   I   A   D   I   T   I   I   I   P   Y   I   G   P   A   L   N   I
    845 846 847 848 849 850 851 852 853 854 855 856 857 858 859 860 861 862 863 864 865 866 867

5'  GCAACATGCTCTACAAAGACGATTTCGTTGGTGCCCTGATCTTCAGCGGTGCCGTGATCCTGTTGGAGTT
                                                                              2730
3'  CGTTGTACGAGATGTTTCTGCTAAAGCAACCACGGGACTAGAAGTCGCCACGGCACTAGGACAACCTCAA
                                HC, Translocation Domain

    G   N   M   L   Y   K   D   D   F   V   G   A   L   I   F   S   G   A   V   I   L   L   E   F
    868 869 870 871 872 873 874 875 876 877 878 879 880 881 882 883 884 885 886 887 888 889 890 891

5'  CATTCCTGAAATCGCCATCCCTGTGCTGGGCACGTTCGCTCTGGTCTCATACATTGCGAATAAGGTCTTG
                                                                              2800
3'  GTAAGGACTTTAGCGGTAGGGACACGACCCGTGCAAGCGAGACCAGAGTATGTAACGCTTATTCCAGAAC
                                HC, Translocation Domain

    I   P   E   I   A   I   P   V   L   G   T   F   A   L   V   S   Y   I   A   N   K   V   L
    892 893 894 895 896 897 898 899 900 901 902 903 904 905 906 907 908 909 910 911 912 913 914
```

FIG. 10G

5' ACCGTGCAGACAATCGATAATGCCCTCTCCAAACGTAACGAAAAATGGGACGAGGTCTACAAATACATCG 2870
3' TGGCACGTCTGTTAGCTATTACGGGAGAGGTTTGCATTGCTTTTTACCCTGCTCCAGATGTTTATGTAGC

HC, Translocation Domain

T V Q T I D N A L S K R N E K W D E V Y K Y I
915 916 917 918 919 920 921 922 923 924 925 926 927 928 929 930 931 932 933 934 935 936 937

5' TGACCAACTGGCTGGCAAAGGTTAACACCCAAATTGATCTGATCCGTAAGAAAATGAAGGAGGCTTTGGA 2940
3' ACTGGTTGACCGACCGTTTCCAATTGTGGGTTTAACTAGACTAGGCATTCTTTTACTTCCTCCGAAACCT

HC, Translocation Domain

V T N W L A K V N T Q I D L I R K K M K E A L E
938 939 940 941 942 943 944 945 946 947 948 949 950 951 952 953 954 955 956 957 958 959 960 961

5' GAACCAGGCTGAAGCTACTAAAGCCATTATCAACTACCAGTATAATCAGTATACAGAAGAGGAAAAGAAT 3010
3' CTTGGTCCGACTTCGATGATTTCGGTAATAGTTGATGGTCATATTAGTCATATGTCTTCTCCTTTTCTTA

HC, Translocation Domain

N Q A E A T K A I I N Y Q Y N Q Y T E E E K N
962 963 964 965 966 967 968 969 970 971 972 973 974 975 976 977 978 979 980 981 982 983 984

5' AACATCAATTTCAACATCGATGACTTGTCCTCAAAGCTGAACGAGTCCATCAACAAAGCTATGATCAACA 3080
3' TTGTAGTTAAAGTTGTAGCTACTGAACAGGAGTTTCGACTTGCTCAGGTAGTTGTTTCGATACTAGTTGT

HC, Translocation Domain

N I N F N I D D L S S K L N E S I N K A M I N
985 986 987 988 989 990 991 992 993 994 995 996 997 998 999 1000 1001 1002 1003 1004 1005 1006 1007

5' TCAACAAATTCCTGAATCAGTGCTCCGTGTCTTACCTGATGAACTCTATGATCCCATACGGTGTGAAGCG 3150
3' AGTTGTTTAAGGACTTAGTCACGAGGCACAGAATGGACTACTTGAGATACTAGGGTATGCCACACTTCGC

HC, Translocation Domain

I N K F L N Q C S V S Y L M N S M I P Y G V K R
1008 1009 1010 1011 1012 1013 1014 1015 1016 1017 1018 1019 1020 1021 1022 1023 1024 1025 1026 1027 1028 1029 1030 1031

5' CCTGGAGGACTTCGATGCCAGCCTGAAAGACGCACTGCTCAAATACATTTACGATAATCGCGGCACTTTG 3220
3' GGACCTCCTGAAGCTACGGTCGGACTTTCTGCGTGACGAGTTTATGTAAATGCTATTAGCGCCGTGAAAC

HC, Translocation Domain

EcoRV

5' ATTGGCCAAGTTGACCGTCTGAAGGACAAGGTTAACAATACCTTGTCAACCGATATCCCCTTCCAACTCT 3290

3' TAACCGGTTCAACTGGCAGACTTCCTGTTCCAATTGTTATGGAACAGTTGGCTATAGGGGAAGGTTGAGA

HC, Translocation Domain

I G Q V D R L K D K V N N T L S T D I P F Q L 1055 1056 1057 1058 1059 1060 1061 1062 1063 1064 1065 1066 1067 1068 1069 1070 1071 1072 1073 1074 1075 1076 1077

AfeI BlpI

5' CTAAGTACGTCGATAACCAGCGCTTGCTGAGCACCTTCACAGAATACATCAACAACATCATCAACACCTC 3360

3' GATTCATGCAGCTATTGGTCGCGAACGACTCGTGGAAGTGTCTTATGTAGTTGTTGTAGTAGTTGTGGAG

HC, Translocation Domain | K>N | HC, Receptor-Binding Domain

S K Y V D N Q R L L S T F T E Y I N N I I N T S 1078 1079 1080 1081 1082 1083 1084 1085 1086 1087 1088 1089 1090 1091 1092 1093 1094 1095 1096 1097 1098 1099 1100 1101

NheI BmtI BpuEI

5' CATCCTGAACCTCCGTTACGAGTCTAACCACCTCATCGACTTGAGCAGATACGCTAGCAAGATCAACATC 3430

3' GTAGGACTTGGAGGCAATGCTCAGATTGGTGGAGTAGCTGAACTCGTCTATGCGATCGTTCTAGTTGTAG

HC, Receptor-Binding Domain

I L N L R Y E S N H L I D L S R Y A S K I N I 1102 1103 1104 1105 1106 1107 1108 1109 1110 1111 1112 1113 1114 1115 1116 1117 1118 1119 1120 1121 1122 1123 1124

5' GGTTCCAAGGTGAACTTCGACCCAATCGATAAGAACCAGATCCAACTGTTCAACCTCGAATCCTCTAAGA 3500

3' CCAAGGTTCCACTTGAAGCTGGGTTAGCTATTCTTGGTCTAGGTTGACAAGTTGGAGCTTAGGAGATTCT

HC, Receptor-Binding Domain

G S K V N F D P I D K N Q I Q L F N L E S S K 1125 1126 1127 1128 1129 1130 1131 1132 1133 1134 1135 1136 1137 1138 1139 1140 1141 1142 1143 1144 1145 1146 1147

5' TCGAAGTGATCCTGAAGAACGCTATCGTCTACAACTCCATGTACGAAAACTTCTCTACCAGCTTCTGGAT 3570

3' AGCTTCACTAGGACTTCTTGCGATAGCAGATGTTGAGGTACATGCTTTTGAAGAGATGGTCGAAGACCTA

HC, Receptor-Binding Domain

I E V I L K N A I V Y N S M Y E N F S T S F W I 1148 1149 1150 1151 1152 1153 1154 1155 1156 1157 1158 1159 1160 1161 1162 1163 1164 1165 1166 1167 1168 1169 1170 1171

5' CAGGATTCCGAAATACTTCAACTCAATCTCGCTCAACAACGAGTACACTATCATCAACTGCATGGAAAAC 3640

3' GTCCTAAGGCTTTATGAAGTTGAGTTAGAGCGAGTTGTTGCTCATGTGATAGTAGTTGACGTACCTTTTG

HC, Receptor-Binding Domain

```
5'  AACTCGGGATGGAAGGTGTCCCTCAACTACGGCGAGATCATCTGGACTTTGCAGGACACACAAGAAATCA
                                                                              3710
3'  TTGAGCCCTACCTTCCACAGGGAGTTGATGCCGCTCTAGTAGACCTGAAACGTCCTGTGTGTTCTTTAGT
                            HC, Receptor-Binding Domain

    N   S   G   W   K   V   S   L   N   Y   G   E   I   I   W   T   L   Q   D   T   Q   E   I
   1195 1196 1197 1198 1199 1200 1201 1202 1203 1204 1205 1206 1207 1208 1209 1210 1211 1212 1213 1214 1215 1216 1217

5'  AGCAGAGGGTCGTGTTCAAGTACAGCCAAATGATCAACATCAGCGATTACATCAACCGTTGGATCTTCGT
                                                                              3780
3'  TCGTCTCCCAGCACAAGTTCATGTCGGTTTACTAGTTGTAGTCGCTAATGTAGTTGGCAACCTAGAAGCA
                            HC, Receptor-Binding Domain

    K   Q   R   V   V   F   K   Y   S   Q   M   I   N   I   S   D   Y   I   N   R   W   I   F   V
   1218 1219 1220 1221 1222 1223 1224 1225 1226 1227 1228 1229 1230 1231 1232 1233 1234 1235 1236 1237 1238 1239 1240 1241

                                                                                    NmeAIII
5'  CACAATCACCAACAACCGCCTGAACAACTCCAAGATTTACATCAACGGTAGACTGATCGACCAGAAGCCA
                                                                              3850
3'  GTGTTAGTGGTTGTTGGCGGACTTGTTGAGGTTCTAAATGTAGTTGCCATCTGACTAGCTGGTCTTCGGT
                            HC, Receptor-Binding Domain

    T   I   T   N   N   R   L   N   N   S   K   I   Y   I   N   G   R   L   I   D   Q   K   P
   1242 1243 1244 1245 1246 1247 1248 1249 1250 1251 1252 1253 1254 1255 1256 1257 1258 1259 1260 1261 1262 1263 1264

5'  ATCAGCAACCTCGGCAACATCCACGCCTCAAACAACATCATGTTCAAGTTGGACGGCTGTAGGGATACAC
                                                                              3920
3'  TAGTCGTTGGAGCCGTTGTAGGTGCGGAGTTTGTTGTAGTACAAGTTCAACCTGCCGACATCCCTATGTG
                            HC, Receptor-Binding Domain

    I   S   N   L   G   N   I   H   A   S   N   N   I   M   F   K   L   D   G   C   R   D   T
   1265 1266 1267 1268 1269 1270 1271 1272 1273 1274 1275 1276 1277 1278 1279 1280 1281 1282 1283 1284 1285 1286 1287

5'  ACAGATACATCTGGATCAAATACTTCAACCTGTTCGACAAGGAGCTCAACGAGAAGGAAATCAAGGACCT
                                                                              3990
3'  TGTCTATGTAGACCTAGTTTATGAAGTTGGACAAGCTGTTCCTCGAGTTGCTCTTCCTTTAGTTCCTGGA
                            HC, Receptor-Binding Domain

    H   R   Y   I   W   I   K   Y   F   N   L   F   D   K   E   L   N   E   K   E   I   K   D   L
   1288 1289 1290 1291 1292 1293 1294 1295 1296 1297 1298 1299 1300 1301 1302 1303 1304 1305 1306 1307 1308 1309 1310 1311

5'  CTACGATAACCAGTCCAACTCTGGTATCTTGAAGGACTTCTGGGGCGATTACCTGCAATACGACAAGCCC
                                                                              4060
3'  GATGCTATTGGTCAGGTTGAGACCATAGAACTTCCTGAAGACCCCGCTAATGGACGTTATGCTGTTCGGG
                            HC, Receptor-Binding Domain

    Y   D   N   Q   S   N   S   G   I   L   K   D   F   W   G   D   Y   L   Q   Y   D   K   P
   1312 1313 1314 1315 1316 1317 1318 1319 1320 1321 1322 1323 1324 1325 1326 1327 1328 1329 1330 1331 1332 1333 1334
```

FIG. 10J

5' TACTACATGTTGAACCTGTACGACCCTAACAAGTACGTTGATGTGAACAACGTCGGTATCAGGGGCTACA 4130
3' ATGATGTACAACTTGGACATGCTGGGATTGTTCATGCAACTACACTTGTTGCAGCCATAGTCCCCGATGT
HC, Receptor-Binding Domain
Y Y M L N L Y D P N K Y V D V N N V G I R G Y
1335 1336 1337 1338 1339 1340 1341 1342 1343 1344 1345 1346 1347 1348 1349 1350 1351 1352 1353 1354 1355 1356 1357

PmlI
5' TGTACCTGAAGGGACCACGTGGTTCTGTTATGACCACTAACATCTACCTCAACAGCTCATTGTACCGTGG 4200
3' ACATGGACTTCCCTGGTGCACCAAGACAATACTGGTGATTGTAGATGGAGTTGTCGAGTAACATGGCACC
HC, Receptor-Binding Domain
M Y L K G P R G S V M T T N I Y L N S S L Y R G
1358 1359 1360 1361 1362 1363 1364 1365 1366 1367 1368 1369 1370 1371 1372 1373 1374 1375 1376 1377 1378 1379 1380 1381

BspEI DrdI PvuI
5' CACAAAGTTCATCATCAAGAAGTACGCCTCCGGAAACAAGGACAACATCGTCCGTAACAACGATCGCGTT 4270
3' GTGTTTCAAGTAGTAGTTCTTCATGCGGAGGCCTTTGTTCCTGTTGTAGCAGGCATTGTTGCTAGCGCAA
HC, Receptor-Binding Domain
T K F I I K K Y A S G N K D N I V R N N D R V
1382 1383 1384 1385 1386 1387 1388 1389 1390 1391 1392 1393 1394 1395 1396 1397 1398 1399 1400 1401 1402 1403 1404

5' TACATCAACGTTGTGGTCAAGAACAAGGAGTACAGACTGGCTACCAACGCTTCGCAGGCTGGAGTTGAGA 4340
3' ATGTAGTTGCAACACCAGTTCTTGTTCCTCATGTCTGACCGATGGTTGCGAAGCGTCCGACCTCAACTCT
HC, Receptor-Binding Domain
Y I N V V V K N K E Y R L A T N A S Q A G V E
1405 1406 1407 1408 1409 1410 1411 1412 1413 1414 1415 1416 1417 1418 1419 1420 1421 1422 1423 1424 1425 1426 1427

BspHI
5' AGATCCTGTCTGCTCTGGAAATCCCTGACGTGGGCAACCTCTCACAGGTTGTGGTCATGAAGTCGAAGAA 4410
3' TCTAGGACAGACGAGACCTTTAGGGACTGCACCCGTTGGAGAGTGTCCAACACCAGTACTTCAGCTTCTT
HC, Receptor-Binding Domain
K I L S A L E I P D V G N L S Q V V V M K S K N
1428 1429 1430 1431 1432 1433 1434 1435 1436 1437 1438 1439 1440 1441 1442 1443 1444 1445 1446 1447 1448 1449 1450 1451

5' CGATCAAGGCATCACTAACAAGTGCAAGATGAACTTGCAGGACAACAACGGAAACGACATCGGCTTCATC 4480
3' GCTAGTTCCGTAGTGATTGTTCACGTTCTACTTGAACGTCCTGTTGTTGCCTTTGCTGTAGCCGAAGTAG
HC, Receptor-Binding Domain
D Q G I T N K C K M N L Q D N N G N D I G F I
1452 1453 1454 1455 1456 1457 1458 1459 1460 1461 1462 1463 1464 1465 1466 1467 1468 1469 1470 1471 1472 1473 1474

FIG. 10K

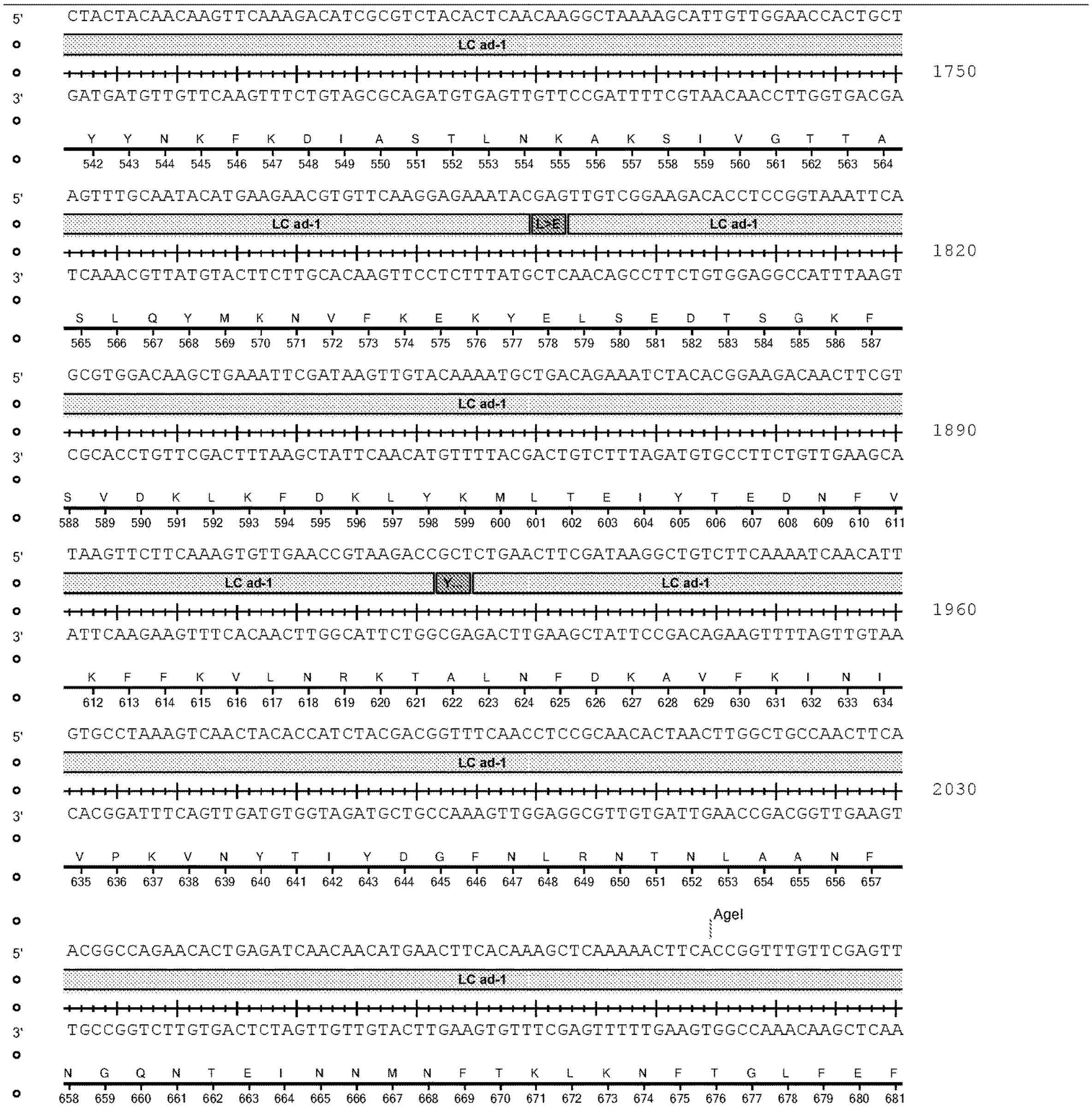

FIG. 11E

```
5'  CTACTACAACAAGTTCAAAGACATCGCGTCTACACTCAACAAGGCTAAAAGCATTGTTGGAACCACTGCT
                              LC ad-1
    ++++|++++|++++|++++|++++|++++|++++|++++|++++|++++|++++|++++|++++|++++|  1750
3'  GATGATGTTGTTCAAGTTTCTGTAGCGCAGATGTGAGTTGTTCCGATTTTCGTAACAACCTTGGTGACGA

      Y   Y   N   K   F   K   D   I   A   S   T   L   N   K   A   K   S   I   V   G   T   T   A
     542 543 544 545 546 547 548 549 550 551 552 553 554 555 556 557 558 559 560 561 562 563 564

5'  AGTTTGCAATACATGAAGAACGTGTTCAAGGAGAAATACGAGTTGTCGGAAGACACCTCCGGTAAATTCA
                      LC ad-1                                          LC ad-1
    ++++|++++|++++|++++|++++|++++|++++|++++|++++|++++|++++|++++|++++|++++|  1820
3'  TCAAACGTTATGTACTTCTTGCACAAGTTCCTCTTTATGCTCAACAGCCTTCTGTGGAGGCCATTTAAGT

      S   L   Q   Y   M   K   N   V   F   K   E   K   Y   E   L   S   E   D   T   S   G   K   F
     565 566 567 568 569 570 571 572 573 574 575 576 577 578 579 580 581 582 583 584 585 586 587

5'  GCGTGGACAAGCTGAAATTCGATAAGTTGTACAAAATGCTGACAGAAATCTACACGGAAGACAACTTCGT
                                     LC ad-1
    ++++|++++|++++|++++|++++|++++|++++|++++|++++|++++|++++|++++|++++|++++|  1890
3'  CGCACCTGTTCGACTTTAAGCTATTCAACATGTTTTACGACTGTCTTTAGATGTGCCTTCTGTTGAAGCA

      S   V   D   K   L   K   F   D   K   L   Y   K   M   L   T   E   I   Y   T   E   D   N   F   V
     588 589 590 591 592 593 594 595 596 597 598 599 600 601 602 603 604 605 606 607 608 609 610 611

5'  TAAGTTCTTCAAAGTGTTGAACCGTAAGACCGCTCTGAACTTCGATAAGGCTGTCTTCAAAATCAACATT
                    LC ad-1                                    LC ad-1
    ++++|++++|++++|++++|++++|++++|++++|++++|++++|++++|++++|++++|++++|++++|  1960
3'  ATTCAAGAAGTTTCACAACTTGGCATTCTGGCGAGACTTGAAGCTATTCCGACAGAAGTTTTAGTTGTAA

      K   F   F   K   V   L   N   R   K   T   A   L   N   F   D   K   A   V   F   K   I   N   I
     612 613 614 615 616 617 618 619 620 621 622 623 624 625 626 627 628 629 630 631 632 633 634

5'  GTGCCTAAAGTCAACTACACCATCTACGACGGTTTCAACCTCCGCAACACTAACTTGGCTGCCAACTTCA
                                     LC ad-1
    ++++|++++|++++|++++|++++|++++|++++|++++|++++|++++|++++|++++|++++|++++|  2030
3'  CACGGATTTCAGTTGATGTGGTAGATGCTGCCAAAGTTGGAGGCGTTGTGATTGAACCGACGGTTGAAGT

      V   P   K   V   N   Y   T   I   Y   D   G   F   N   L   R   N   T   N   L   A   A   N   F
     635 636 637 638 639 640 641 642 643 644 645 646 647 648 649 650 651 652 653 654 655 656 657

                                                                          AgeI
5'  ACGGCCAGAACACTGAGATCAACAACATGAACTTCACAAAGCTCAAAAACTTCACCGGTTTGTTCGAGTT
                                     LC ad-1
    ++++|++++|++++|++++|++++|++++|++++|++++|++++|++++|++++|++++|++++|++++|
3'  TGCCGGTCTTGTGACTCTAGTTGTTGTACTTGAAGTGTTTCGAGTTTTTGAAGTGGCCAAACAAGCTCAA

      N   G   Q   N   T   E   I   N   N   M   N   F   T   K   L   K   N   F   T   G   L   F   E   F
     658 659 660 661 662 663 664 665 666 667 668 669 670 671 672 673 674 675 676 677 678 679 680 681
```

5' ACACGGCAAGAGCCGCATTGCTCTCACTAACTCCGTGAATGAAGCCCTGCTCAATCCGTCAAGGGTGTAC
HC, Translocation Domain
2590
3' TGTGCCGTTCTCGGCGTAACGAGAGTGATTGAGGCACTTACTTCGGGACGAGTTAGGCAGTTCCCACATG
H G K S R I A L T N S V N E A L L N P S R V Y
822 823 824 825 826 827 828 829 830 831 832 833 834 835 836 837 838 839 840 841 842 843 844

5' ACATTCTTTAGCTCCGACTATGTCAAGAAAGTGAACAAAGCCACCGAAGCGGCAATGTTCCTGGGATGGG
HC, Translocation Domain
2660
3' TGTAAGAAATCGAGGCTGATACAGTTCTTTCACTTGTTTCGGTGGCTTCGCCGTTACAAGGACCCTACCC
T F F S S D Y V K K V N K A T E A A M F L G W
845 846 847 848 849 850 851 852 853 854 855 856 857 858 859 860 861 862 863 864 865 866 867

5' TTGAACAACTGGTCTACGACTTCACCGACGAGACCTCTGAGGTGAGCACAACGGACAAGATTGCTGACAT
HC, Translocation Domain
2730
3' AACTTGTTGACCAGATGCTGAAGTGGCTGCTCTGGAGACTCCACTCGTGTTGCCTGTTCTAACGACTGTA
V E Q L V Y D F T D E T S E V S T T D K I A D I
868 869 870 871 872 873 874 875 876 877 878 879 880 881 882 883 884 885 886 887 888 889 890 891

5' CACTATCATTATCCCGTATATTGGACCTGCCTTGAATATTGGCAACATGCTCTACAAAGACGATTTCGTT
HC, Translocation Domain
2800
3' GTGATAGTAATAGGGCATATAACCTGGACGGAACTTATAACCGTTGTACGAGATGTTTCTGCTAAAGCAA
T I I I P Y I G P A L N I G N M L Y K D D F V
892 893 894 895 896 897 898 899 900 901 902 903 904 905 906 907 908 909 910 911 912 913 914

5' GGTGCCCTGATCTTCAGCGGTGCCGTGATCCTGTTGGAGTTCATTCCTGAAATCGCCATCCCTGTGCTGG
HC, Translocation Domain
2870
3' CCACGGGACTAGAAGTCGCCACGGCACTAGGACAACCTCAAGTAAGGACTTTAGCGGTAGGGACACGACC
G A L I F S G A V I L L E F I P E I A I P V L
915 916 917 918 919 920 921 922 923 924 925 926 927 928 929 930 931 932 933 934 935 936 937

5' GCACGTTCGCTCTGGTCTCATACATTGCGAATAAGGTCTTGACCGTGCAGACAATCGATAATGCCCTCTC
HC, Translocation Domain
3' CGTGCAAGCGAGACCAGAGTATGTAACGCTTATTCCAGAACTGGCACGTCTGTTAGCTATTACGGGAGAG
G T F A L V S Y I A N K V L T V Q T I D N A L S
938 939 940 941 942 943 944 945 946 947 948 949 950 951 952 953 954 955 956 957 958 959 960 961

FIG. 11G

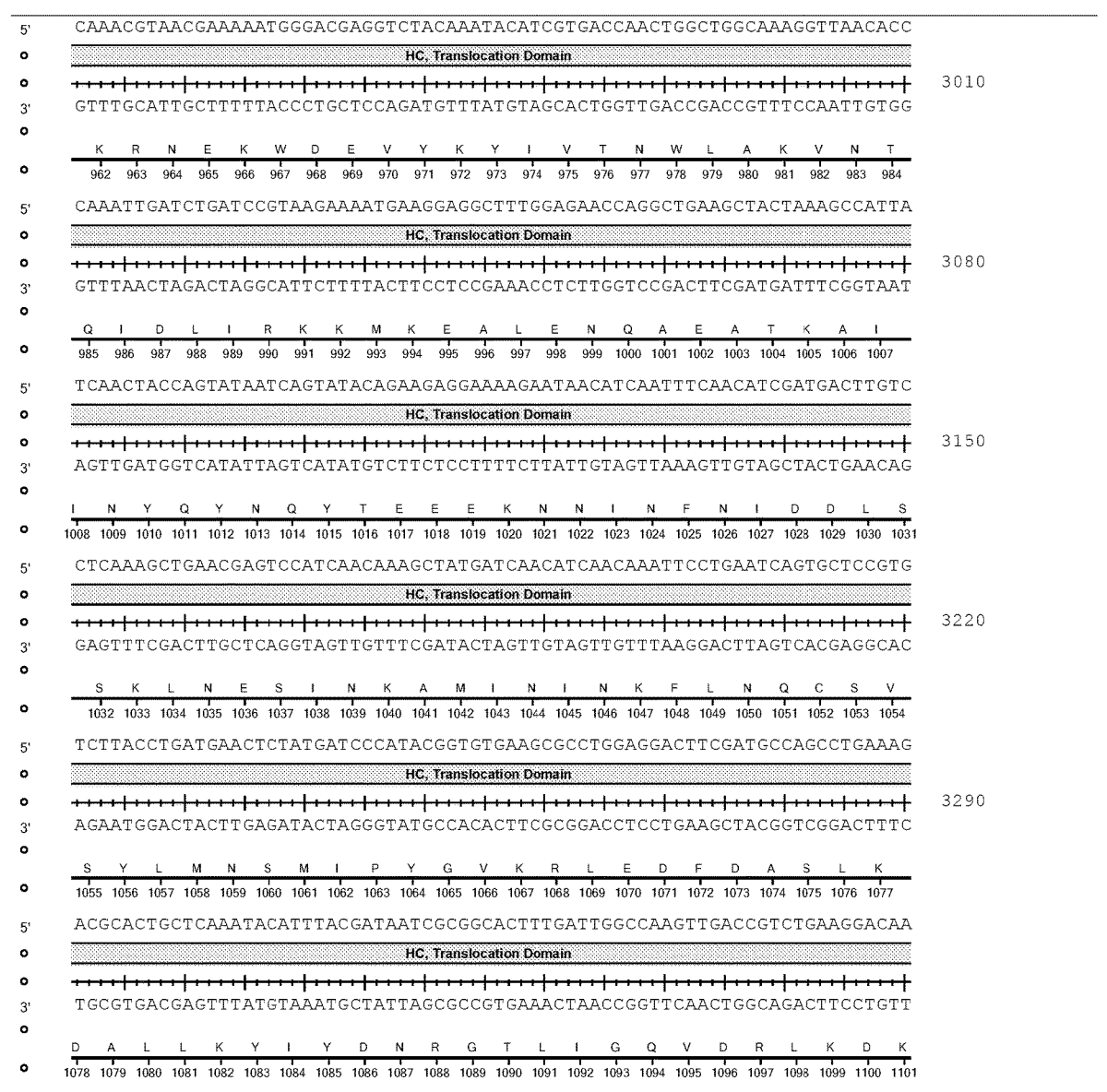

5' CAAACGTAACGAAAAATGGGACGAGGTCTACAAATACATCGTGACCAACTGGCTGGCAAAGGTTAACACC
HC, Translocation Domain
3010
3' GTTTGCATTGCTTTTTACCCTGCTCCAGATGTTTATGTAGCACTGGTTGACCGACCGTTTCCAATTGTGG
K R N E K W D E V Y K Y I V T N W L A K V N T
962 963 964 965 966 967 968 969 970 971 972 973 974 975 976 977 978 979 980 981 982 983 984

5' CAAATTGATCTGATCCGTAAGAAAATGAAGGAGGCTTTGGAGAACCAGGCTGAAGCTACTAAAGCCATTA
HC, Translocation Domain
3080
3' GTTTAACTAGACTAGGCATTCTTTTACTTCCTCCGAAACCTCTTGGTCCGACTTCGATGATTTCGGTAAT
Q I D L I R K K M K E A L E N Q A E A T K A I
985 986 987 988 989 990 991 992 993 994 995 996 997 998 999 1000 1001 1002 1003 1004 1005 1006 1007

5' TCAACTACCAGTATAATCAGTATACAGAAGAGGAAAAGAATAACATCAATTTCAACATCGATGACTTGTC
HC, Translocation Domain
3150
3' AGTTGATGGTCATATTAGTCATATGTCTTCTCCTTTTCTTATTGTAGTTAAAGTTGTAGCTACTGAACAG
I N Y Q Y N Q Y T E E E K N N I N F N I D D L S
1008 1009 1010 1011 1012 1013 1014 1015 1016 1017 1018 1019 1020 1021 1022 1023 1024 1025 1026 1027 1028 1029 1030 1031

5' CTCAAAGCTGAACGAGTCCATCAACAAAGCTATGATCAACATCAACAAATTCCTGAATCAGTGCTCCGTG
HC, Translocation Domain
3220
3' GAGTTTCGACTTGCTCAGGTAGTTGTTTCGATACTAGTTGTAGTTGTTTAAGGACTTAGTCACGAGGCAC
S K L N E S I N K A M I N I N K F L N Q C S V
1032 1033 1034 1035 1036 1037 1038 1039 1040 1041 1042 1043 1044 1045 1046 1047 1048 1049 1050 1051 1052 1053 1054

5' TCTTACCTGATGAACTCTATGATCCCATACGGTGTGAAGCGCCTGGAGGACTTCGATGCCAGCCTGAAAG
HC, Translocation Domain
3290
3' AGAATGGACTACTTGAGATACTAGGGTATGCCACACTTCGCGGACCTCCTGAAGCTACGGTCGGACTTTC
S Y L M N S M I P Y G V K R L E D F D A S L K
1055 1056 1057 1058 1059 1060 1061 1062 1063 1064 1065 1066 1067 1068 1069 1070 1071 1072 1073 1074 1075 1076 1077

5' ACGCACTGCTCAAATACATTTACGATAATCGCGGCACTTTGATTGGCCAAGTTGACCGTCTGAAGGACAA
HC, Translocation Domain
3' TGCGTGACGAGTTTATGTAAATGCTATTAGCGCCGTGAAACTAACCGGTTCAACTGGCAGACTTCCTGTT
D A L L K Y I Y D N R G T L I G Q V D R L K D K
1078 1079 1080 1081 1082 1083 1084 1085 1086 1087 1088 1089 1090 1091 1092 1093 1094 1095 1096 1097 1098 1099 1100 1101

FIG. 11H

AfeI BlpI

5' GGTTAACAATACCTTGTCAACCGATATCCCCTTCCAACTCTCTAAGTACGTCGATAACCAGCGCTTGCTG

HC, Translocation Domain

3430

3' CCAATTGTTATGGAACAGTTGGCTATAGGGGAAGGTTGAGAGATTCATGCAGCTATTGGTCGCGAACGAC

V N N T L S T D I P F Q L S K Y V D N Q R L L 1102 1103 1104 1105 1106 1107 1108 1109 1110 1111 1112 1113 1114 1115 1116 1117 1118 1119 1120 1121 1122 1123 1124

5' AGCACCTTCACAGAATACATCAACAACATCATCAACACCTCCATCCTGAACCTCCGTTACGAGTCTAACC

HC, Translocation Domain | K | HC, Receptor-Binding Domain

3500

3' TCGTGGAAGTGTCTTATGTAGTTGTTGTAGTAGTTGTGGAGGTAGGACTTGGAGGCAATGCTCAGATTGG

S T F T E Y I N N I I N T S I L N L R Y E S N 1125 1126 1127 1128 1129 1130 1131 1132 1133 1134 1135 1136 1137 1138 1139 1140 1141 1142 1143 1144 1145 1146 1147

NheI BmtI

5' ACCTCATCGACTTGAGCAGATACGCTAGCAAGATCAACATCGGTTCCAAGGTGAACTTCGACCCAATCGA

HC, Receptor-Binding Domain

3570

3' TGGAGTAGCTGAACTCGTCTATGCGATCGTTCTAGTTGTAGCCAAGGTTCCACTTGAAGCTGGGTTAGCT

H L I D L S R Y A S K I N I G S K V N F D P I D 1148 1149 1150 1151 1152 1153 1154 1155 1156 1157 1158 1159 1160 1161 1162 1163 1164 1165 1166 1167 1168 1169 1170 1171

5' TAAGAACCAGATCCAACTGTTCAACCTCGAATCCTCTAAGATCGAAGTGATCCTGAAGAACGCTATCGTC

HC, Receptor-Binding Domain

3640

3' ATTCTTGGTCTAGGTTGACAAGTTGGAGCTTAGGAGATTCTAGCTTCACTAGGACTTCTTGCGATAGCAG

K N Q I Q L F N L E S S K I E V I L K N A I V 1172 1173 1174 1175 1176 1177 1178 1179 1180 1181 1182 1183 1184 1185 1186 1187 1188 1189 1190 1191 1192 1193 1194

5' TACAACTCCATGTACGAAAACTTCTCTACCAGCTTCTGGATCAGGATTCCGAAATACTTCAACTCAATCT

HC, Receptor-Binding Domain

3710

3' ATGTTGAGGTACATGCTTTTGAAGAGATGGTCGAAGACCTAGTCCTAAGGCTTTATGAAGTTGAGTTAGA

Y N S M Y E N F S T S F W I R I P K Y F N S I 1195 1196 1197 1198 1199 1200 1201 1202 1203 1204 1205 1206 1207 1208 1209 1210 1211 1212 1213 1214 1215 1216 1217

TstI'

5' CGCTCAACAACGAGTACACTATCATCAACTGCATGGAAAACAACTCGGGATGGAAGGTGTCCCTCAACTA

HC, Receptor-Binding Domain

3' GCGAGTTGTTGCTCATGTGATAGTAGTTGACGTACCTTTTGTTGAGCCCTACCTTCCACAGGGAGTTGAT

PmlI

5' CAAGTACGTTGATGTGAACAACGTCGGTATCAGGGGCTACATGTACCTGAAGGGACCACGTGGTTCTGTT

HC, Receptor-Binding Domain

4270

3' GTTCATGCAACTACACTTGTTGCAGCCATAGTCCCCGATGTACATGGACTTCCCTGGTGCACCAAGACAA

K Y V D V N N V G I R G Y M Y L K G P R G S V 1382 1383 1384 1385 1386 1387 1388 1389 1390 1391 1392 1393 1394 1395 1396 1397 1398 1399 1400 1401 1402 1403 1404

5' ATGACCACTAACATCTACCTCAACAGCTCATTGTACCGTGGCACAAAGTTCATCATCAAGAAGTACGCCT

HC, Receptor-Binding Domain

4340

3' TACTGGTGATTGTAGATGGAGTTGTCGAGTAACATGGCACCGTGTTTCAAGTAGTAGTTCTTCATGCGGA

M T T N I Y L N S S L Y R G T K F I I K K Y A 1405 1406 1407 1408 1409 1410 1411 1412 1413 1414 1415 1416 1417 1418 1419 1420 1421 1422 1423 1424 1425 1426 1427

5' CCGGAAACAAGGACAACATCGTCCGTAACAACGATCGCGTTTACATCAACGTTGTGGTCAAGAACAAGGA

HC, Receptor-Binding Domain

4410

3' GGCCTTTGTTCCTGTTGTAGCAGGCATTGTTGCTAGCGCAAATGTAGTTGCAACACCAGTTCTTGTTCCT

S G N K D N I V R N N D R V Y I N V V V K N K E 1428 1429 1430 1431 1432 1433 1434 1435 1436 1437 1438 1439 1440 1441 1442 1443 1444 1445 1446 1447 1448 1449 1450 1451

5' GTACAGACTGGCTACCAACGCTTCGCAGGCTGGAGTTGAGAAGATCCTGTCTGCTCTGGAAATCCCTGAC

HC, Receptor-Binding Domain

4480

3' CATGTCTGACCGATGGTTGCGAAGCGTCCGACCTCAACTCTTCTAGGACAGACGAGACCTTTAGGGACTG

Y R L A T N A S Q A G V E K I L S A L E I P D 1452 1453 1454 1455 1456 1457 1458 1459 1460 1461 1462 1463 1464 1465 1466 1467 1468 1469 1470 1471 1472 1473 1474

5' GTGGGCAACCTCTCACAGGTTGTGGTCATGAAGTCGAAGAACGATCAAGGCATCACTAACAAGTGCAAGA

HC, Receptor-Binding Domain

4550

3' CACCCGTTGGAGAGTGTCCAACACCAGTACTTCAGCTTCTTGCTAGTTCCGTAGTGATTGTTCACGTTCT

V G N L S Q V V V M K S K N D Q G I T N K C K 1475 1476 1477 1478 1479 1480 1481 1482 1483 1484 1485 1486 1487 1488 1489 1490 1491 1492 1493 1494 1495 1496 1497

5' TGAACTTGCAGGACAACAACGGAAACGACATCGGCTTCATCGGATTCCACCAATTCAACAACATCGCCAA

HC, Receptor-Binding Domain

3' ACTTGAACGTCCTGTTGTTGCCTTTGCTGTAGCCGAAGTAGCCTAAGGTGGTTAAGTTGTTGTAGCGGTT

```
                    Bpu10I
                    BbvCI
5' AACATCTCCATCGAGAACCTCAGCTCAGACATCATTGGTCAGTTGGAGCTGATGCCAAACATTGAACGCT
                                                                              2450
3' TTGTAGAGGTAGCTCTTGGAGTCGAGTCTGTAGTAACCAGTCAACCTCGACTACGGTTTGTAACTTGCGA
                        HC, Translocation Domain

   N   I   S   I   E   N   L   S   S   D   I   I   G   Q   L   E   L   M   P   N   I   E   R
   794 795 796 797 798 799 800 801 802 803 804 805 806 807 808 809 810 811 812 813 814 815 816

                                                          AflII
5' TCCCCAACGGCAAGAAATACGAACTCGACAAGTATACGATGTTTCATTACTTAAGAGCGCAGGAGTTTGA
                                                                              2520
3' AGGGGTTGCCGTTCTTTATGCTTGAGCTGTTCATATGCTACAAAGTAATGAATTCTCGCGTCCTCAAACT
                        HC, Translocation Domain

   F   P   N   G   K   K   Y   E   L   D   K   Y   T   M   F   H   Y   L   R   A   Q   E   F   E
   817 818 819 820 821 822 823 824 825 826 827 828 829 830 831 832 833 834 835 836 837 838 839 840

5' ACACGGCAAGAGCCGCATTGCTCTCACTAACTCCGTGAATGAAGCCCTGCTCAATCCGTCAAGGGTGTAC
                                                                              2590
3' TGTGCCGTTCTCGGCGTAACGAGAGTGATTGAGGCACTTACTTCGGGACGAGTTAGGCAGTTCCCACATG
                        HC, Translocation Domain

   H   G   K   S   R   I   A   L   T   N   S   V   N   E   A   L   L   N   P   S   R   V   Y
   841 842 843 844 845 846 847 848 849 850 851 852 853 854 855 856 857 858 859 860 861 862 863

5' ACATTCTTTAGCTCCGACTATGTCAAGAAAGTGAACAAAGCCACCGAAGCGGCAATGTTCCTGGGATGGG
                                                                              2660
3' TGTAAGAAATCGAGGCTGATACAGTTCTTTCACTTGTTTCGGTGGCTTCGCCGTTACAAGGACCCTACCC
                        HC, Translocation Domain

   T   F   F   S   S   D   Y   V   K   K   V   N   K   A   T   E   A   A   M   F   L   G   W
   864 865 866 867 868 869 870 871 872 873 874 875 876 877 878 879 880 881 882 883 884 885 886

5' TTGAACAACTGGTCTACGACTTCACCGACGAGACCTCTGAGGTGAGCACAACGGACAAGATTGCTGACAT
                                                                              2730
3' AACTTGTTGACCAGATGCTGAAGTGGCTGCTCTGGAGACTCCACTCGTGTTGCCTGTTCTAACGACTGTA
                        HC, Translocation Domain

   V   E   Q   L   V   Y   D   F   T   D   E   T   S   E   V   S   T   T   D   K   I   A   D   I
   887 888 889 890 891 892 893 894 895 896 897 898 899 900 901 902 903 904 905 906 907 908 909 910

5' CACTATCATTATCCCGTATATTGGACCTGCCTTGAATATTGGCAACATGCTCTACAAAGACGATTTCGTT
                                                                              2800
3' GTGATAGTAATAGGGCATATAACCTGGACGGAACTTATAACCGTTGTACGAGATGTTTCTGCTAAAGCAA
                        HC, Translocation Domain

   T   I   I   I   P   Y   I   G   P   A   L   N   I   G   N   M   L   Y   K   D   D   F   V
   911 912 913 914 915 916 917 918 919 920 921 922 923 924 925 926 927 928 929 930 931 932 933
```

FIG. 12G

```
5' GGTGCCCTGATCTTCAGCGGTGCCGTGATCCTGTTGGAGTTCATTCCTGAAATCGCCATCCCTGTGCTGG
                                                                                    2870
3' CCACGGGACTAGAAGTCGCCACGGCACTAGGACAACCTCAAGTAAGGACTTTAGCGGTAGGGACACGACC
                              HC, Translocation Domain

   G  A  L  I  F  S  G  A  V  I  L  L  E  F  I  P  E  I  A  I  P  V  L
  934 935 936 937 938 939 940 941 942 943 944 945 946 947 948 949 950 951 952 953 954 955 956

5' GCACGTTCGCTCTGGTCTCATACATTGCGAATAAGGTCTTGACCGTGCAGACAATCGATAATGCCCTCTC
                                                                                    2940
3' CGTGCAAGCGAGACCAGAGTATGTAACGCTTATTCCAGAACTGGCACGTCTGTTAGCTATTACGGGAGAG
                              HC, Translocation Domain

   G  T  F  A  L  V  S  Y  I  A  N  K  V  L  T  V  Q  T  I  D  N  A  L  S
  957 958 959 960 961 962 963 964 965 966 967 968 969 970 971 972 973 974 975 976 977 978 979 980

5' CAAACGTAACGAAAAATGGGACGAGGTCTACAAATACATCGTGACCAACTGGCTGGCAAAGGTTAACACC
                                                                                    3010
3' GTTTGCATTGCTTTTTACCCTGCTCCAGATGTTTATGTAGCACTGGTTGACCGACCGTTTCCAATTGTGG
                              HC, Translocation Domain

   K  R  N  E  K  W  D  E  V  Y  K  Y  I  V  T  N  W  L  A  K  V  N  T
  981 982 983 984 985 986 987 988 989 990 991 992 993 994 995 996 997 998 999 1000 1001 1002 1003

5' CAAATTGATCTGATCCGTAAGAAAATGAAGGAGGCTTTGGAGAACCAGGCTGAAGCTACTAAAGCCATTA
                                                                                    3080
3' GTTTAACTAGACTAGGCATTCTTTTACTTCCTCCGAAACCTCTTGGTCCGACTTCGATGATTTCGGTAAT
                              HC, Translocation Domain

   Q  I  D  L  I  R  K  K  M  K  E  A  L  E  N  Q  A  E  A  T  K  A  I
  1004 1005 1006 1007 1008 1009 1010 1011 1012 1013 1014 1015 1016 1017 1018 1019 1020 1021 1022 1023 1024 1025 1026

5' TCAACTACCAGTATAATCAGTATACAGAAGAGGAAAAGAATAACATCAATTTCAACATCGATGACTTGTC
                                                                                    3150
3' AGTTGATGGTCATATTAGTCATATGTCTTCTCCTTTTCTTATTGTAGTTAAAGTTGTAGCTACTGAACAG
                              HC, Translocation Domain

   I  N  Y  Q  Y  N  Q  Y  T  E  E  E  K  N  N  I  N  F  N  I  D  D  L  S
  1027 1028 1029 1030 1031 1032 1033 1034 1035 1036 1037 1038 1039 1040 1041 1042 1043 1044 1045 1046 1047 1048 1049 1050

5' CTCAAAGCTGAACGAGTCCATCAACAAAGCTATGATCAACATCAACAAATTCCTGAATCAGTGCTCCGTG
                                                                                    3220
3' GAGTTTCGACTTGCTCAGGTAGTTGTTTCGATACTAGTTGTAGTTGTTTAAGGACTTAGTCACGAGGCAC
                              HC, Translocation Domain

   S  K  L  N  E  S  I  N  K  A  M  I  N  I  N  K  F  L  N  Q  C  S  V
  1051 1052 1053 1054 1055 1056 1057 1058 1059 1060 1061 1062 1063 1064 1065 1066 1067 1068 1069 1070 1071 1072 1073
```

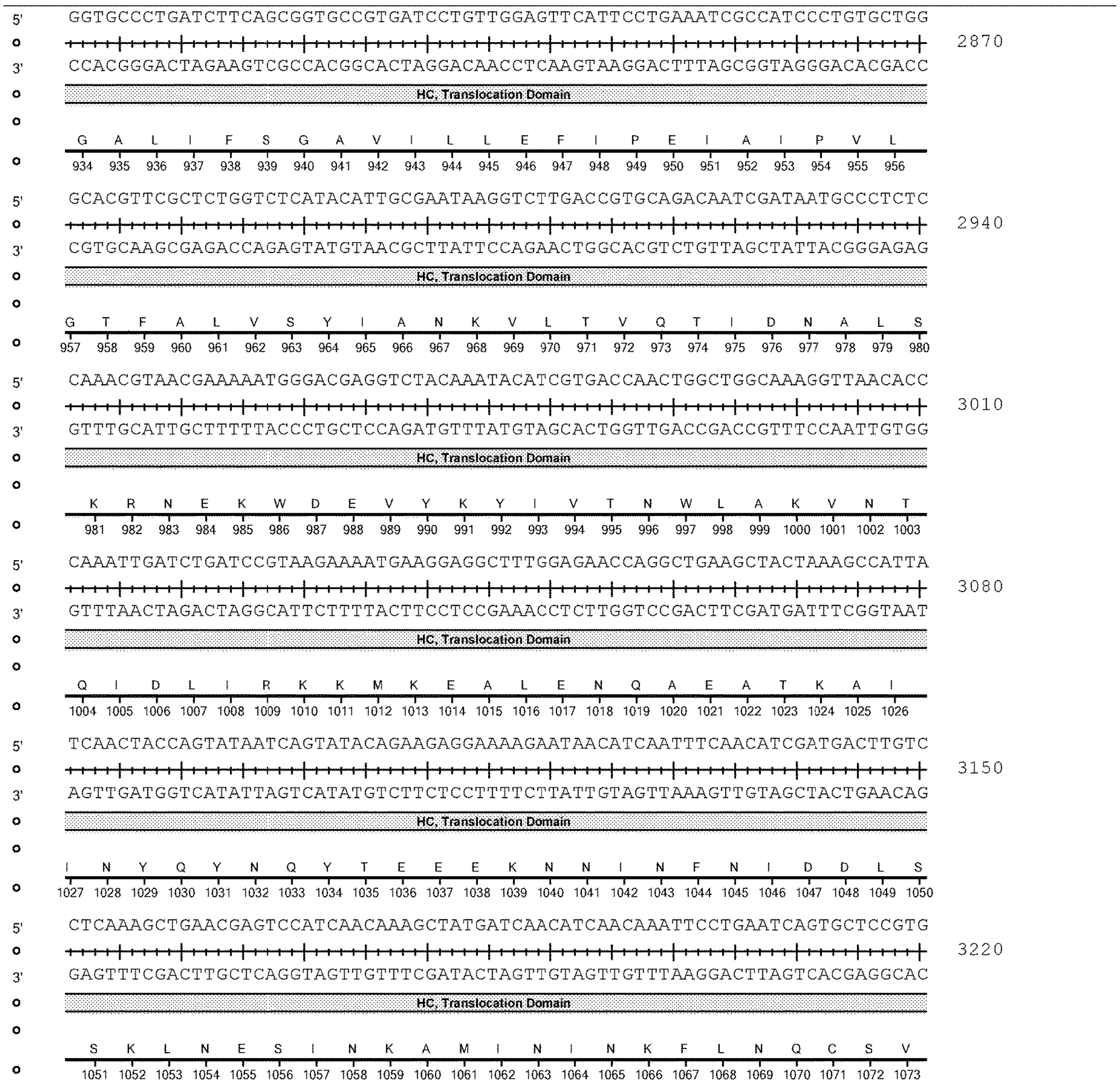

FIG. 12H

5' TCTTACCTGATGAACTCTATGATCCCATACGGTGTGAAGCGCCTGGAGGACTTCGATGCCAGCCTGAAAG 3290
3' AGAATGGACTACTTGAGATACTAGGGTATGCCACACTTCGCGGACCTCCTGAAGCTACGGTCGGACTTTC
HC, Translocation Domain
S Y L M N S M I P Y G V K R L E D F D A S L K
1074 1075 1076 1077 1078 1079 1080 1081 1082 1083 1084 1085 1086 1087 1088 1089 1090 1091 1092 1093 1094 1095 1096

5' ACGCACTGCTCAAATACATTTACGATAATCGCGGCACTTTGATTGGCCAAGTTGACCGTCTGAAGGACAA 3360
3' TGCGTGACGAGTTTATGTAAATGCTATTAGCGCCGTGAAACTAACCGGTTCAACTGGCAGACTTCCTGTT
HC, Translocation Domain
D A L L K Y I Y D N R G T L I G Q V D R L K D K
1097 1098 1099 1100 1101 1102 1103 1104 1105 1106 1107 1108 1109 1110 1111 1112 1113 1114 1115 1116 1117 1118 1119 1120

EcoRV AfeI BlpI
5' GGTTAACAATACCTTGTCAACCGATATCCCCTTCCAACTCTCTAAGTACGTCGATAACCAGCGCTTGCTG 3430
3' CCAATTGTTATGGAACAGTTGGCTATAGGGGAAGGTTGAGAGATTCATGCAGCTATTGGTCGCGAACGAC
HC, Translocation Domain
V N N T L S T D I P F Q L S K Y V D N Q R L L
1121 1122 1123 1124 1125 1126 1127 1128 1129 1130 1131 1132 1133 1134 1135 1136 1137 1138 1139 1140 1141 1142 1143

5' AGCACCTTCACAGAATACATCAACAACATCATCAACACCTCCATCCTGAACCTCCGTTACGAGTCTAACC 3500
3' TCGTGGAAGTGTCTTATGTAGTTGTTGTAGTAGTTGTGGAGGTAGGACTTGGAGGCAATGCTCAGATTGG
HC, Translocation Domain | K>N | HC, Receptor-Binding Domain
S T F T E Y I N N I I N T S I L N L R Y E S N
1144 1145 1146 1147 1148 1149 1150 1151 1152 1153 1154 1155 1156 1157 1158 1159 1160 1161 1162 1163 1164 1165 1166

NheI BmtI BpuEI
5' ACCTCATCGACTTGAGCAGATACGCTAGCAAGATCAACATCGGTTCCAAGGTGAACTTCGACCCAATCGA 3570
3' TGGAGTAGCTGAACTCGTCTATGCGATCGTTCTAGTTGTAGCCAAGGTTCCACTTGAAGCTGGGTTAGCT
HC, Receptor-Binding Domain
H L I D L S R Y A S K I N I G S K V N F D P I D
1167 1168 1169 1170 1171 1172 1173 1174 1175 1176 1177 1178 1179 1180 1181 1182 1183 1184 1185 1186 1187 1188 1189 1190

5' TAAGAACCAGATCCAACTGTTCAACCTCGAATCCTCTAAGATCGAAGTGATCCTGAAGAACGCTATCGTC 3640
3' ATTCTTGGTCTAGGTTGACAAGTTGGAGCTTAGGAGATTCTAGCTTCACTAGGACTTCTTGCGATAGCAG
HC, Receptor-Binding Domain
K N Q I Q L F N L E S S K I E V I L K N A I V
1191 1192 1193 1194 1195 1196 1197 1198 1199 1200 1201 1202 1203 1204 1205 1206 1207 1208 1209 1210 1211 1212 1213

FIG. 12I

```
5'  TACAACTCCATGTACGAAAACTTCTCTACCAGCTTCTGGATCAGGATTCCGAAATACTTCAACTCAATCT
                                                                                3710
3'  ATGTTGAGGTACATGCTTTTGAAGAGATGGTCGAAGACCTAGTCCTAAGGCTTTATGAAGTTGAGTTAGA
                              HC, Receptor-Binding Domain

    Y   N   S   M   Y   E   N   F   S   T   S   F   W   I   R   I   P   K   Y   F   N   S   I
    1214 1215 1216 1217 1218 1219 1220 1221 1222 1223 1224 1225 1226 1227 1228 1229 1230 1231 1232 1233 1234 1235 1236

5'  CGCTCAACAACGAGTACACTATCATCAACTGCATGGAAAACAACTCGGGATGGAAGGTGTCCCTCAACTA
                                                                                3780
3'  GCGAGTTGTTGCTCATGTGATAGTAGTTGACGTACCTTTTGTTGAGCCCTACCTTCCACAGGGAGTTGAT
                              HC, Receptor-Binding Domain

    S   L   N   N   E   Y   T   I   I   N   C   M   E   N   N   S   G   W   K   V   S   L   N   Y
    1237 1238 1239 1240 1241 1242 1243 1244 1245 1246 1247 1248 1249 1250 1251 1252 1253 1254 1255 1256 1257 1258 1259 1260

5'  CGGCGAGATCATCTGGACTTTGCAGGACACACAAGAAATCAAGCAGAGGGTCGTGTTCAAGTACAGCCAA
                                                                                3850
3'  GCCGCTCTAGTAGACCTGAAACGTCCTGTGTGTTCTTTAGTTCGTCTCCCAGCACAAGTTCATGTCGGTT
                              HC, Receptor-Binding Domain

    G   E   I   I   W   T   L   Q   D   T   Q   E   I   K   Q   R   V   V   F   K   Y   S   Q
    1261 1262 1263 1264 1265 1266 1267 1268 1269 1270 1271 1272 1273 1274 1275 1276 1277 1278 1279 1280 1281 1282 1283

5'  ATGATCAACATCAGCGATTACATCAACCGTTGGATCTTCGTCACAATCACCAACAACCGCCTGAACAACT
                                                                                3920
3'  TACTAGTTGTAGTCGCTAATGTAGTTGGCAACCTAGAAGCAGTGTTAGTGGTTGTTGGCGGACTTGTTGA
                              HC, Receptor-Binding Domain

    M   I   N   I   S   D   Y   I   N   R   W   I   F   V   T   I   T   N   N   R   L   N   N
    1284 1285 1286 1287 1288 1289 1290 1291 1292 1293 1294 1295 1296 1297 1298 1299 1300 1301 1302 1303 1304 1305 1306

                                              NmeAIII
5'  CCAAGATTTACATCAACGGTAGACTGATCGACCAGAAGCCAATCAGCAACCTCGGCAACATCCACGCCTC
                                                                                3990
3'  GGTTCTAAATGTAGTTGCCATCTGACTAGCTGGTCTTCGGTTAGTCGTTGGAGCCGTTGTAGGTGCGGAG
                              HC, Receptor-Binding Domain

    S   K   I   Y   I   N   G   R   L   I   D   Q   K   P   I   S   N   L   G   N   I   H   A   S
    1307 1308 1309 1310 1311 1312 1313 1314 1315 1316 1317 1318 1319 1320 1321 1322 1323 1324 1325 1326 1327 1328 1329 1330

5'  AAACAACATCATGTTCAAGTTGGACGGCTGTAGGGATACACACAGATACATCTGGATCAAATACTTCAAC
                                                                                4060
3'  TTTGTTGTAGTACAAGTTCAACCTGCCGACATCCCTATGTGTGTCTATGTAGACCTAGTTTATGAAGTTG
                              HC, Receptor-Binding Domain

    N   N   I   M   F   K   L   D   G   C   R   D   T   H   R   Y   I   W   I   K   Y   F   N
    1331 1332 1333 1334 1335 1336 1337 1338 1339 1340 1341 1342 1343 1344 1345 1346 1347 1348 1349 1350 1351 1352 1353
```

FIG. 12J

5' CTGTTCGACAAGGAGCTCAACGAGAAGGAAATCAAGGACCTCTACGATAACCAGTCCAACTCTGGTATCT 4130
3' GACAAGCTGTTCCTCGAGTTGCTCTTCCTTTAGTTCCTGGAGATGCTATTGGTCAGGTTGAGACCATAGA
HC, Receptor-Binding Domain
L F D K E L N E K E I K D L Y D N Q S N S G I
1354 1355 1356 1357 1358 1359 1360 1361 1362 1363 1364 1365 1366 1367 1368 1369 1370 1371 1372 1373 1374 1375 1376

5' TGAAGGACTTCTGGGGCGATTACCTGCAATACGACAAGCCCTACTACATGTTGAACCTGTACGACCCTAA 4200
3' ACTTCCTGAAGACCCCGCTAATGGACGTTATGCTGTTCGGGATGATGTACAACTTGGACATGCTGGGATT
HC, Receptor-Binding Domain
L K D F W G D Y L Q Y D K P Y Y M L N L Y D P N
1377 1378 1379 1380 1381 1382 1383 1384 1385 1386 1387 1388 1389 1390 1391 1392 1393 1394 1395 1396 1397 1398 1399 1400

PmlI
5' CAAGTACGTTGATGTGAACAACGTCGGTATCAGGGGCTACATGTACCTGAAGGGACCACGTGGTTCTGTT 4270
3' GTTCATGCAACTACACTTGTTGCAGCCATAGTCCCCGATGTACATGGACTTCCCTGGTGCACCAAGACAA
HC, Receptor-Binding Domain
K Y V D V N N V G I R G Y M Y L K G P R G S V
1401 1402 1403 1404 1405 1406 1407 1408 1409 1410 1411 1412 1413 1414 1415 1416 1417 1418 1419 1420 1421 1422 1423

5' ATGACCACTAACATCTACCTCAACAGCTCATTGTACCGTGGCACAAAGTTCATCATCAAGAAGTACGCCT 4340
3' TACTGGTGATTGTAGATGGAGTTGTCGAGTAACATGGCACCGTGTTTCAAGTAGTAGTTCTTCATGCGGA
HC, Receptor-Binding Domain
M T T N I Y L N S S L Y R G T K F I I K K Y A
1424 1425 1426 1427 1428 1429 1430 1431 1432 1433 1434 1435 1436 1437 1438 1439 1440 1441 1442 1443 1444 1445 1446

BspEI DrdI PvuI
5' CCGGAAACAAGGACAACATCGTCCGTAACAACGATCGCGTTTACATCAACGTTGTGGTCAAGAACAAGGA 4410
3' GGCCTTTGTTCCTGTTGTAGCAGGCATTGTTGCTAGCGCAAATGTAGTTGCAACACCAGTTCTTGTTCCT
HC, Receptor-Binding Domain
S G N K D N I V R N N D R V Y I N V V V K N K E
1447 1448 1449 1450 1451 1452 1453 1454 1455 1456 1457 1458 1459 1460 1461 1462 1463 1464 1465 1466 1467 1468 1469 1470

5' GTACAGACTGGCTACCAACGCTTCGCAGGCTGGAGTTGAGAAGATCCTGTCTGCTCTGGAAATCCCTGAC 4480
3' CATGTCTGACCGATGGTTGCGAAGCGTCCGACCTCAACTCTTCTAGGACAGACGAGACCTTTAGGGACTG
HC, Receptor-Binding Domain
Y R L A T N A S Q A G V E K I L S A L E I P D
1471 1472 1473 1474 1475 1476 1477 1478 1479 1480 1481 1482 1483 1484 1485 1486 1487 1488 1489 1490 1491 1492 1493

FIG. 12K

BspHI
5' GTGGGCAACCTCTCACAGGTTGTGGTCATGAAGTCGAAGAACGATCAAGGCATCACTAACAAGTGCAAGA 4550
3' CACCCGTTGGAGAGTGTCCAACACCAGTACTTCAGCTTCTTGCTAGTTCCGTAGTGATTGTTCACGTTCT
HC, Receptor-Binding Domain
V G N L S Q V V V M K S K N D Q G I T N K C K
1494 1495 1496 1497 1498 1499 1500 1501 1502 1503 1504 1505 1506 1507 1508 1509 1510 1511 1512 1513 1514 1515 1516

5' TGAACTTGCAGGACAACAACGGAAACGACATCGGCTTCATCGGATTCCACCAATTCAACAACATCGCCAA 4620
3' ACTTGAACGTCCTGTTGTTGCCTTTGCTGTAGCCGAAGTAGCCTAAGGTGGTTAAGTTGTTGTAGCGGTT
HC, Receptor-Binding Domain
M N L Q D N N G N D I G F I G F H Q F N N I A K
1517 1518 1519 1520 1521 1522 1523 1524 1525 1526 1527 1528 1529 1530 1531 1532 1533 1534 1535 1536 1537 1538 1539 1540

Bsu36I BssSI
5' GTTGGTGGCCAGCAACTGGTACAACCGTCAGATCGAGCGTTCGTCCCGCACCTTAGGATGCTCGTGGGAG 4690
3' CAACCACCGGTCGTTGACCATGTTGGCAGTCTAGCTCGCAAGCAGGGCGTGGAATCCTACGAGCACCCTC
HC, Receptor-Binding Domain
L V A S N W Y N R Q I E R S S R T L G C S W E
1541 1542 1543 1544 1545 1546 1547 1548 1549 1550 1551 1552 1553 1554 1555 1556 1557 1558 1559 1560 1561 1562 1563

5' TTCATTCCAGTCGATGACGGATGGGGAGAGAGACCTTTGGGCGCAGGATACCCCTACGATGTCCCTGACT 4760
3' AAGTAAGGTCAGCTACTGCCTACCCCTCTCTCTGGAAACCCGCGTCCTATGGGGATGCTACAGGGACTGA
HC, Receptor-Binding Domain | linker | HA Tag
F I P V D D G W G E R P L G A G Y P Y D V P D
1564 1565 1566 1567 1568 1569 1570 1571 1572 1573 1574 1575 1576 1577 1578 1579 1580 1581 1582 1583 1584 1585 1586

5' ACGCTGGAGAGAACCTGTACTTCCAGGGTGCAGGATGGTCCCACCCACAATTCGAGAAGGGTGCAGGATG 4830
3' TGCGACCTCTCTTGGACATGAAGGTCCCACGTCCTACCAGGGTGGGTGTTAAGCTCTTCCCACGTCCTAC
HA Tag | li...r | TEV site | linker | Strep Tag II | linker
Y A G E N L Y F Q G A G W S H P Q F E K G A G W
1587 1588 1589 1590 1591 1592 1593 1594 1595 1596 1597 1598 1599 1600 1601 1602 1603 1604 1605 1606 1607 1608 1609 1610

5' GAGTCACCCACAGTTCGAGAAGGGCGCTGGATGGTCCCACCCACAGTTCGAGAAATAATTAGTTGATGCA 4900
3' CTCAGTGGGTGTCAAGCTCTTCCCGCGACCTACCAGGGTGGGTGTCAAGCTCTTTATTAATCAACTACGT
Strep Tag II | linker | Strep Tag II
S H P Q F E K G A G W S H P Q F E K
1611 1612 1613 1614 1615 1616 1617 1618 1619 1620 1621 1622 1623 1624 1625 1626 1627 1628

FIG. 12L

NsiI XhoI

5' TAGTTAATTAGATAGCTCGAG

4921

3' ATCAATTAATCTATCGAGCTC

FIG. 12M

5' TGGGCTGGTACAGGCAGGCTCCTGGCAAGCAACGTGAACTGGTTGCTGCCATCTCCAGCTACGGTAGTAC 420
3' ACCCGACCATGTCCGTCCGAGGACCGTTCGTTGCACTTGACCAACGACGGTAGAGGTCGATGCCATCATG
sd-Ab B8, anti-BoNT A LC
M G W Y R Q A P G K Q R E L V A A I S S Y G S T
98 99 100 101 102 103 104 105 106 107 108 109 110 111 112 113 114 115 116 117 118 119 120 121

5' CAACTACGCTGATTCGGTCAAGGGCAGGTTCACCATCTCCCGCGACAATGCCAAGAATACCGTCTATTTG 490
3' GTTGATGCGACTAAGCCAGTTCCCGTCCAAGTGGTAGAGGGCGCTGTTACGGTTCTTATGGCAGATAAAC
sd-Ab B8, anti-BoNT A LC
N Y A D S V K G R F T I S R D N A K N T V Y L
122 123 124 125 126 127 128 129 130 131 132 133 134 135 136 137 138 139 140 141 142 143 144

Bsu36I
5' CAAATGAACTCTCTGAAACCTGAGGATACGGCCGTCTACTACTGCAACGCTGACATTGCTACTATGACCG 560
3' GTTTACTTGAGAGACTTTGGACTCCTATGCCGGCAGATGATGACGTTGCGACTGTAACGATGATACTGGC
sd-Ab B8, anti-BoNT A LC
Q M N S L K P E D T A V Y Y C N A D I A T M T
145 146 147 148 149 150 151 152 153 154 155 156 157 158 159 160 161 162 163 164 165 166 167

5' CGGTAGGCGGATTCGACTACTGGGGACAGGGAACTCAGGTGACGGTCTCTTCCGAACCTAAGACCCCTAA 630
3' GCCATCCGCCTAAGCTGATGACCCCTGTCCCTTGAGTCCACTGCCAGAGAAGGCTTGGATTCTGGGGATT
sd-Ab B8, anti-BoNT A LC
A V G G F D Y W G Q G T Q V T V S S E P K T P K
168 169 170 171 172 173 174 175 176 177 178 179 180 181 182 183 184 185 186 187 188 189 190 191

PasI MluI
5' ACCCCAAGCGGGCCAAGGCGCTCCAGTCCCATACCCAGACCCACTCGAACCCAGGGGCACGCGTGGAGCG 700
3' TGGGGTTCGCCCGGTTCCGCGAGGTCAGGGTATGGGTCTGGGTGAGCTTGGGTCCCCGTGCGCACCTCGC
sd-A...A LC | linker | c-tag | linker
P Q A G Q G A P V P Y P D P L E P R G T R G A
192 193 194 195 196 197 198 199 200 201 202 203 204 205 206 207 208 209 210 211 212 213 214

5' GGAGCTGGACCGATCACCATCAACAACTTCAATTACAGCGACCCGGTGGATAACAAGAACATCCTCTACT
3' CCTCGACCTGGCTAGTGGTAGTTGTTGAAGTTAATGTCGCTGGGCCACCTATTGTTCTTGTAGGAGATGA
linker | BoNT C atoxic light chain, triple mut.
G A G P I T I N N F N Y S D P V D N K N I L Y
215 216 217 218 219 220 221 222 223 224 225 226 227 228 229 230 231 232 233 234 235 236 237

FIG. 17B

5' TGGACACACACTTGAACACGCTGGCTAACGAGCCTGAAAAAGCTTTCAGGATCACCGGCAACATTTGGGT 840
3' ACCTGTGTGTGAACTTGTGCGACCGATTGCTCGGACTTTTTCGAAAGTCCTAGTGGCCGTTGTAAACCCA
BoNT C atoxic light chain, triple mut.
L D T H L N T L A N E P E K A F R I T G N I W V
238 239 240 241 242 243 244 245 246 247 248 249 250 251 252 253 254 255 256 257 258 259 260 261

5' CATTCCGGATAGGTTCAGCAGAAACTCTAACCCTAACTTGAACAAACCTCCCAGAGTGACCTCACCTAAG 910
3' GTAAGGCCTATCCAAGTCGTCTTTGAGATTGGGATTGAACTTGTTTGGAGGGTCTCACTGGAGTGGATTC
BoNT C atoxic light chain, triple mut.
I P D R F S R N S N P N L N K P P R V T S P K
262 263 264 265 266 267 268 269 270 271 272 273 274 275 276 277 278 279 280 281 282 283 284

5' AGTGGATACTACGACCCCAACTACCTCTCGACTGACTCCGATAAAGACCCCTTCCTGAAGGAGATCATTA 980
3' TCACCTATGATGCTGGGGTTGATGGAGAGCTGACTGAGGCTATTTCTGGGGAAGGACTTCCTCTAGTAAT
BoNT C atoxic light chain, triple mut.
S G Y Y D P N Y L S T D S D K D P F L K E I I
285 286 287 288 289 290 291 292 293 294 295 296 297 298 299 300 301 302 303 304 305 306 307

5' AACTCTTCAAGCGCATCAACTCTCGTGAAATTGGCGAGGAATTGATCTACCGCCTGAGTACAGACATCCC 1050
3' TTGAGAAGTTCGCGTAGTTGAGAGCACTTTAACCGCTCCTTAACTAGATGGCGGACTCATGTCTGTAGGG
BoNT C atoxic light chain, triple mut.
K L F K R I N S R E I G E E L I Y R L S T D I P
308 309 310 311 312 313 314 315 316 317 318 319 320 321 322 323 324 325 326 327 328 329 330 331

XmaI
SmaI
5' ATTCCCGGGTAACAACAACACCCCAATCAACACTTTCGATTTCGATGTCGATTTCAACTCAGTGGATGTC 1120
3' TAAGGGCCCATTGTTGTTGTGGGGTTAGTTGTGAAAGCTAAAGCTACAGCTAAAGTTGAGTCACCTACAG
BoNT C atoxic light chain, triple mut.
F P G N N N T P I N T F D F D V D F N S V D V
332 333 334 335 336 337 338 339 340 341 342 343 344 345 346 347 348 349 350 351 352 353 354

5' AAAACCAGGCAGGGAAACAACTGGGTGAAGACTGGTAGCATCAACCCATCTGTCATCATTACTGGCCCGA
3' TTTTGGTCCGTCCCTTTGTTGACCCACTTCTGACCATCGTAGTTGGGTAGACAGTAGTAATGACCGGGCT
BoNT C atoxic light chain, triple mut.
K T R Q G N N W V K T G S I N P S V I I T G P
355 356 357 358 359 360 361 362 363 364 365 366 367 368 369 370 371 372 373 374 375 376 377

FIG. 17C

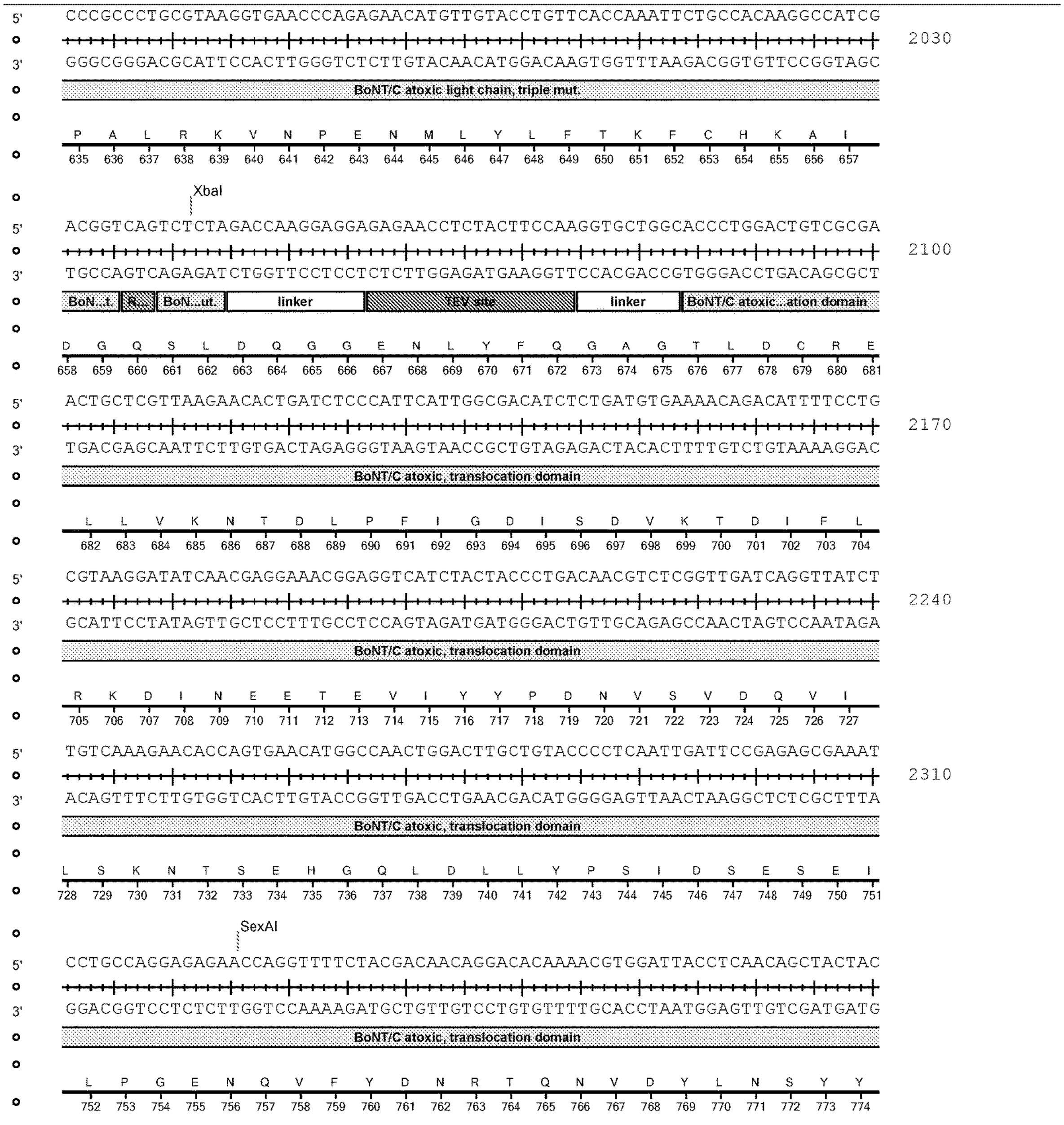

FIG. 17F

```
5'  CCCGCCCTGCGTAAGGTGAACCCAGAGAACATGTTGTACCTGTTCACCAAATTCTGCCACAAGGCCATCG
    ++++|++++|++++|++++|++++|++++|++++|++++|++++|++++|++++|++++|++++|++++|  2030
3'  GGGCGGGACGCATTCCACTTGGGTCTCTTGTACAACATGGACAAGTGGTTTAAGACGGTGTTCCGGTAGC
```
[BoNT/C atoxic light chain, triple mut.]

```
    P   A   L   R   K   V   N   P   E   N   M   L   Y   L   F   T   K   F   C   H   K   A   I
    635 636 637 638 639 640 641 642 643 644 645 646 647 648 649 650 651 652 653 654 655 656 657
```

XbaI
```
5'  ACGGTCAGTCTCTAGACCAAGGAGGAGAGAACCTCTACTTCCAAGGTGCTGGCACCCTGGACTGTCGCGA
    ++++|++++|++++|++++|++++|++++|++++|++++|++++|++++|++++|++++|++++|++++|  2100
3'  TGCCAGTCAGAGATCTGGTTCCTCCTCTCTTGGAGATGAAGGTTCCACGACCGTGGGACCTGACAGCGCT
```
[BoN...t.] [R...] [BoN...ut.] [linker] [TEV site] [linker] [BoNT/C atoxic...ation domain]

```
    D   G   Q   S   L   D   Q   G   G   E   N   L   Y   F   Q   G   A   G   T   L   D   C   R   E
    658 659 660 661 662 663 664 665 666 667 668 669 670 671 672 673 674 675 676 677 678 679 680 681
```

```
5'  ACTGCTCGTTAAGAACACTGATCTCCCATTCATTGGCGACATCTCTGATGTGAAAACAGACATTTTCCTG
    ++++|++++|++++|++++|++++|++++|++++|++++|++++|++++|++++|++++|++++|++++|  2170
3'  TGACGAGCAATTCTTGTGACTAGAGGGTAAGTAACCGCTGTAGAGACTACACTTTTGTCTGTAAAAGGAC
```
[BoNT/C atoxic, translocation domain]

```
    L   L   V   K   N   T   D   L   P   F   I   G   D   I   S   D   V   K   T   D   I   F   L
    682 683 684 685 686 687 688 689 690 691 692 693 694 695 696 697 698 699 700 701 702 703 704
```

```
5'  CGTAAGGATATCAACGAGGAAACGGAGGTCATCTACTACCCTGACAACGTCTCGGTTGATCAGGTTATCT
    ++++|++++|++++|++++|++++|++++|++++|++++|++++|++++|++++|++++|++++|++++|  2240
3'  GCATTCCTATAGTTGCTCCTTTGCCTCCAGTAGATGATGGGACTGTTGCAGAGCCAACTAGTCCAATAGA
```
[BoNT/C atoxic, translocation domain]

```
    R   K   D   I   N   E   E   T   E   V   I   Y   Y   P   D   N   V   S   V   D   Q   V   I
    705 706 707 708 709 710 711 712 713 714 715 716 717 718 719 720 721 722 723 724 725 726 727
```

```
5'  TGTCAAAGAACACCAGTGAACATGGCCAACTGGACTTGCTGTACCCCTCAATTGATTCCGAGAGCGAAAT
    ++++|++++|++++|++++|++++|++++|++++|++++|++++|++++|++++|++++|++++|++++|  2310
3'  ACAGTTTCTTGTGGTCACTTGTACCGGTTGACCTGAACGACATGGGGAGTTAACTAAGGCTCTCGCTTTA
```
[BoNT/C atoxic, translocation domain]

```
    L   S   K   N   T   S   E   H   G   Q   L   D   L   L   Y   P   S   I   D   S   E   S   E   I
    728 729 730 731 732 733 734 735 736 737 738 739 740 741 742 743 744 745 746 747 748 749 750 751
```

SexAI
```
5'  CCTGCCAGGAGAGAACCAGGTTTTCTACGACAACAGGACACAAAACGTGGATTACCTCAACAGCTACTAC
    ++++|++++|++++|++++|++++|++++|++++|++++|++++|++++|++++|++++|++++|++++|
3'  GGACGGTCCTCTCTTGGTCCAAAAGATGCTGTTGTCCTGTGTTTTGCACCTAATGGAGTTGTCGATGATG
```
[BoNT/C atoxic, translocation domain]

```
    L   P   G   E   N   Q   V   F   Y   D   N   R   T   Q   N   V   D   Y   L   N   S   Y   Y
    752 753 754 755 756 757 758 759 760 761 762 763 764 765 766 767 768 769 770 771 772 773 774
```

5' TACCTGGAGTCGCAGAAGCTCTCCGACAACGTCGAAGATTTCACATTTACGAGATCAATCGAGGAGGCTT 2450
3' ATGGACCTCAGCGTCTTCGAGAGGCTGTTGCAGCTTCTAAAGTGTAAATGCTCTAGTTAGCTCCTCCGAA
BoNT/C atoxic, translocation domain
Y L E S Q K L S D N V E D F T F T R S I E E A
775 776 777 778 779 780 781 782 783 784 785 786 787 788 789 790 791 792 793 794 795 796 797

5' TGGACAACAGTGCCAAAGTCTACACCTACTTCCCTACTCTGGCAAACAAGGTGAACGCGGGTGTCCAAGG 2520
3' ACCTGTTGTCACGGTTTCAGATGTGGATGAAGGGATGAGACCGTTTGTTCCACTTGCGCCCACAGGTTCC
BoNT/C atoxic, translocation domain
L D N S A K V Y T Y F P T L A N K V N A G V Q G
798 799 800 801 802 803 804 805 806 807 808 809 810 811 812 813 814 815 816 817 818 819 820 821

5' CGGACTCTTCTTGATGTGGGCTAACGACGTTGTGGAAGATTTCACAACGAACATCTTGCGCAAAGACACC 2590
3' GCCTGAGAAGAACTACACCCGATTGCTGCAACACCTTCTAAAGTGTTGCTTGTAGAACGCGTTTCTGTGG
BoNT/C atoxic, translocation domain
G L F L M W A N D V V E D F T T N I L R K D T
822 823 824 825 826 827 828 829 830 831 832 833 834 835 836 837 838 839 840 841 842 843 844

5' CTGGATAAGATCAGCGATGTCTCTGCCATCATTCCATACATTGGCCCGGCACTGAACATCTCTAACTCAG 2660
3' GACCTATTCTAGTCGCTACAGAGACGGTAGTAAGGTATGTAACCGGGCCGTGACTTGTAGAGATTGAGTC
BoNT/C atoxic, translocation domain
L D K I S D V S A I I P Y I G P A L N I S N S
845 846 847 848 849 850 851 852 853 854 855 856 857 858 859 860 861 862 863 864 865 866 867

PfoI
5' TTCGCCGTGGCAACTTCACTGAGGCATTCGCGGTCACAGGAGTTACGATCCTCTTGGAGGCTTTCCCGGA 2730
3' AAGCGGCACCGTTGAAGTGACTCCGTAAGCGCCAGTGTCCTCAATGCTAGGAGAACCTCCGAAAGGGCCT
BoNT/C atoxic, translocation domain
V R R G N F T E A F A V T G V T I L L E A F P E
868 869 870 871 872 873 874 875 876 877 878 879 880 881 882 883 884 885 886 887 888 889 890 891

5' GTTCACAATCCCCGCACTGGGCGCGTTCGTTATCTACTCCAAAGTGCAGGAGCGCAACGAAATCATTAAG
3' CAAGTGTTAGGGGCGTGACCCGCGCAAGCAATAGATGAGGTTTCACGTCCTCGCGTTGCTTTAGTAATTC
BoNT/C atoxic, translocation domain
F T I P A L G A F V I Y S K V Q E R N E I I K
892 893 894 895 896 897 898 899 900 901 902 903 904 905 906 907 908 909 910 911 912 913 914

FIG. 17G

```
                                                BsiWI
5' ACTATCGACAACTGCCTGGAGCAAAGGATCAAAAGATGGAAGGATTCGTACGAATGGATGATGGGTACCT  2870
3' TGATAGCTGTTGACGGACCTCGTTTCCTAGTTTTCTACCTTCCTAAGCATGCTTACCTACTACCCATGGA
   BoNT/C atoxic, translocation domain
   T   I   D   N   C   L   E   Q   R   I   K   R   W   K   D   S   Y   E   W   M   M   G   T
   915 916 917 918 919 920 921 922 923 924 925 926 927 928 929 930 931 932 933 934 935 936 937

5' GGCTCTCCCGTATCATTACGCAGTTCAACAACATCAGCTACCAAATGTACGACTCTCTCAACTACCAGGC  2940
3' CCGAGAGGGCATAGTAATGCGTCAAGTTGTTGTAGTCGATGGTTTACATGCTGAGAGAGTTGATGGTCCG
   BoNT/C atoxic, translocation domain
   W   L   S   R   I   I   T   Q   F   N   N   I   S   Y   Q   M   Y   D   S   L   N   Y   Q   A
   938 939 940 941 942 943 944 945 946 947 948 949 950 951 952 953 954 955 956 957 958 959 960 961

                          XcmI
5' TGGTGCCATCAAGGCCAAAATTGACTTGGAGTACAAGAAATACAGTGGCTCGGATAAAGAGAACATCAAG  3010
3' ACCACGGTAGTTCCGGTTTTAACTGAACCTCATGTTCTTTATGTCACCGAGCCTATTTCTCTTGTAGTTC
   BoNT/C atoxic, translocation domain
   G   A   I   K   A   K   I   D   L   E   Y   K   K   Y   S   G   S   D   K   E   N   I   K
   962 963 964 965 966 967 968 969 970 971 972 973 974 975 976 977 978 979 980 981 982 983 984

5' AGTCAAGTCGAAAACCTGAAAAACTCACTCGACGTTAAGATCAGTGAGGCAATGAACAACATCAACAAGT  3080
3' TCAGTTCAGCTTTTGGACTTTTTGAGTGAGCTGCAATTCTAGTCACTCCGTTACTTGTTGTAGTTGTTCA
   BoNT/C atoxic, translocation domain
   S   Q   V   E   N   L   K   N   S   L   D   V   K   I   S   E   A   M   N   N   I   N   K
   985 986 987 988 989 990 991 992 993 994 995 996 997 998 999 1000 1001 1002 1003 1004 1005 1006 1007

5' TCATTCGCGAATGTTCCGTTACCTACCTCTTCAAAAACATGTTGCCAAAGGTCATCGACGAGCTGAACGA  3150
3' AGTAAGCGCTTACAAGGCAATGGATGGAGAAGTTTTTGTACAACGGTTTCCAGTAGCTGCTCGACTTGCT
   BoNT/C atoxic, translocation domain
   F    I    R    E    C    S    V    T    Y    L    F    K    N    M    L    P    K    V    I    D    E    L    N    E
   1008 1009 1010 1011 1012 1013 1014 1015 1016 1017 1018 1019 1020 1021 1022 1023 1024 1025 1026 1027 1028 1029 1030 1031

5' ATTTGATCGTAACACTAAGGCGAAACTGATTAACCTCATCGACTCACACAACATCATTTTGGTGGGCGAA
3' TAAACTAGCATTGTGATTCCGCTTTGACTAATTGGAGTAGCTGAGTGTGTTGTAGTAAAACCACCCGCTT
   BoNT/C atoxic, translocation domain
   F    D    R    N    T    K    A    K    L    I    N    L    I    D    S    H    N    I    I    L    V    G    E
   1032 1033 1034 1035 1036 1037 1038 1039 1040 1041 1042 1043 1044 1045 1046 1047 1048 1049 1050 1051 1052 1053 1054
```

FIG. 17H

5' GTCGATAAGCTGAAAGCCAAGGTGAACAACAGTTTCCAGAACACAATCCCTTTCAACATTTTCTCATACA 3290
3' CAGCTATTCGACTTTCGGTTCCACTTGTTGTCAAAGGTCTTGTGTTAGGGAAAGTTGTAAAAGAGTATGT
BoNT/C atoxic, translocation domain
V D K L K A K V N N S F Q N T I P F N I F S Y
1055 1056 1057 1058 1059 1060 1061 1062 1063 1064 1065 1066 1067 1068 1069 1070 1071 1072 1073 1074 1075 1076 1077

5' CGAACAACAGTCTGCTCAAGGACATCATTAACGAGTACTTCAACAACATTAACGATAGCAAAATCCTGTC 3360
3' GCTTGTTGTCAGACGAGTTCCTGTAGTAATTGCTCATGAAGTTGTTGTAATTGCTATCGTTTTAGGACAG
BoNT/C atoxic, translocation domain | BoNT/C atoxic, receptor binding domain
T N N S L L K D I I N E Y F N N I N D S K I L S
1078 1079 1080 1081 1082 1083 1084 1085 1086 1087 1088 1089 1090 1091 1092 1093 1094 1095 1096 1097 1098 1099 1100 1101

SpeI
5' ACTGCAGAACCGTAAGAACACACTGGTCGATACTAGTGGATACAACGCCGAAGTCTCTGAGGAAGGTGAC 3430
3' TGACGTCTTGGCATTCTTGTGTGACCAGCTATGATCACCTATGTTGCGGCTTCAGAGACTCCTTCCACTG
BoNT/C atoxic, receptor binding domain
L Q N R K N T L V D T S G Y N A E V S E E G D
1102 1103 1104 1105 1106 1107 1108 1109 1110 1111 1112 1113 1114 1115 1116 1117 1118 1119 1120 1121 1122 1123 1124

PvuII
5' GTGCAGCTGAACCCTATCTTCCCCTTCGACTTCAAATTGGGCTCCAGCGGAGAGGATAGGGGCAAGGTCA 3500
3' CACGTCGACTTGGGATAGAAGGGGAAGCTGAAGTTTAACCCGAGGTCGCCTCTCCTATCCCCGTTCCAGT
BoNT/C atoxic, receptor binding domain
V Q L N P I F P F D F K L G S S G E D R G K V
1125 1126 1127 1128 1129 1130 1131 1132 1133 1134 1135 1136 1137 1138 1139 1140 1141 1142 1143 1144 1145 1146 1147

5' TCGTCACCCAGAACGAGAACATCGTCTACAACTCAATGTACGAATCCTTCAGCATCTCTTTCTGGATCAG 3570
3' AGCAGTGGGTCTTGCTCTTGTAGCAGATGTTGAGTTACATGCTTAGGAAGTCGTAGAGAAAGACCTAGTC
BoNT/C atoxic, receptor binding domain
I V T Q N E N I V Y N S M Y E S F S I S F W I R
1148 1149 1150 1151 1152 1153 1154 1155 1156 1157 1158 1159 1160 1161 1162 1163 1164 1165 1166 1167 1168 1169 1170 1171

5' GATTAACAAGTGGGTGAGCAACCTGCCCGGTTACACAATCATTGACTCTGTCAAGAACAACTCAGGTTGG
3' CTAATTGTTCACCCACTCGTTGGACGGGCCAATGTGTTAGTAACTGAGACAGTTCTTGTTGAGTCCAACC
BoNT/C atoxic, receptor binding domain
I N K W V S N L P G Y T I I D S V K N N S G W
1172 1173 1174 1175 1176 1177 1178 1179 1180 1181 1182 1183 1184 1185 1186 1187 1188 1189 1190 1191 1192 1193 1194

FIG. 17I

5' AGTATCGGCATCATTTCTAACTTCTTGGTCTTCACCCTGAAGCAGAACGAGGACTCGGAACAATCCATTA 3710
3' TCATAGCCGTAGTAAAGATTGAAGAACCAGAAGTGGGACTTCGTCTTGCTCCTGAGCCTTGTTAGGTAAT
BoNT/C atoxic, receptor binding domain
S I G I I S N F L V F T L K Q N E D S E Q S I
1195 1196 1197 1198 1199 1200 1201 1202 1203 1204 1205 1206 1207 1208 1209 1210 1211 1212 1213 1214 1215 1216 1217

5' ACTTCTCATACGATATCAGTAACAACGCTCCAGGTTACAACAAGTGGTTCTTCGTTACCGTGACTAACAA 3780
3' TGAAGAGTATGCTATAGTCATTGTTGCGAGGTCCAATGTTGTTCACCAAGAAGCAATGGCACTGATTGTT
BoNT/C atoxic, receptor binding domain
N F S Y D I S N N A P G Y N K W F F V T V T N N
1218 1219 1220 1221 1222 1223 1224 1225 1226 1227 1228 1229 1230 1231 1232 1233 1234 1235 1236 1237 1238 1239 1240 1241

5' CATGATGGGTAACATGAAAATTTACATCAACGGCAAGCTCATTGACACCATCAAAGTGAAGGAGTTGACT 3850
3' GTACTACCCATTGTACTTTTAAATGTAGTTGCCGTTCGAGTAACTGTGGTAGTTTCACTTCCTCAACTGA
BoNT/C atoxic, receptor binding domain
M M G N M K I Y I N G K L I D T I K V K E L T
1242 1243 1244 1245 1246 1247 1248 1249 1250 1251 1252 1253 1254 1255 1256 1257 1258 1259 1260 1261 1262 1263 1264

5' GGTATTAACTTCTCCAAAACAATCACGTTTGAAATTAACAAGATCCCTGACACCGGCCTGATCACTTCAG 3920
3' CCATAATTGAAGAGGTTTTGTTAGTGCAAACTTTAATTGTTCTAGGGACTGTGGCCGGACTAGTGAAGTC
BoNT/C atoxic, receptor binding domain
G I N F S K T I T F E I N K I P D T G L I T S
1265 1266 1267 1268 1269 1270 1271 1272 1273 1274 1275 1276 1277 1278 1279 1280 1281 1282 1283 1284 1285 1286 1287

EcoICRI
SacI
5' ACAGTGATAACATCAACATGTGGATTAGGGATTTCTACATCTTCGCCAAGGAGCTCGACGGAAAGGATAT 3990
3' TGTCACTATTGTAGTTGTACACCTAATCCCTAAAGATGTAGAAGCGGTTCCTCGAGCTGCCTTTCCTATA
BoNT/C atoxic, receptor binding domain
D S D N I N M W I R D F Y I F A K E L D G K D I
1288 1289 1290 1291 1292 1293 1294 1295 1296 1297 1298 1299 1300 1301 1302 1303 1304 1305 1306 1307 1308 1309 1310 1311

5' TAACATCCTCTTCAACAGCTTGCAGTACACCAACGTCGTTAAAGACTACTGGGGTAACGATTTGAGATAC
3' ATTGTAGGAGAAGTTGTCGAACGTCATGTGGTTGCAGCAATTTCTGATGACCCCATTGCTAAACTCTATG
BoNT/C atoxic, receptor binding domain
N I L F N S L Q Y T N V V K D Y W G N D L R Y
1312 1313 1314 1315 1316 1317 1318 1319 1320 1321 1322 1323 1324 1325 1326 1327 1328 1329 1330 1331 1332 1333 1334

FIG. 17J

5' AACAAGGAGTACTACATGGTCAACATCGACTACCTGAACAGGTACATGTACGCTAACTCCCGCCAAATCG 4130
3' TTGTTCCTCATGATGTACCAGTTGTAGCTGATGGACTTGTCCATGTACATGCGATTGAGGGCGGTTTAGC
BoNT/C atoxic, receptor binding domain
N K E Y Y M V N I D Y L N R Y M Y A N S R Q I
1335 1336 1337 1338 1339 1340 1341 1342 1343 1344 1345 1346 1347 1348 1349 1350 1351 1352 1353 1354 1355 1356 1357

5' TGTTCAACACCAGGAGAAACAACAACGACTTCAACGAGGGTTACAAAATCATTATCAAGCGCATCCGTGG 4200
3' ACAAGTTGTGGTCCTCTTTGTTGTTGCTGAAGTTGCTCCCAATGTTTTAGTAATAGTTCGCGTAGGCACC
BoNT/C atoxic, receptor binding domain
V F N T R R N N N D F N E G Y K I I I K R I R G
1358 1359 1360 1361 1362 1363 1364 1365 1366 1367 1368 1369 1370 1371 1372 1373 1374 1375 1376 1377 1378 1379 1380 1381

5' CAACACCAACGATACTAGGGTGAGAGGTGGCGACATTCTGTACTTCGATATGACTATCAACAACAAAGCC 4270
3' GTTGTGGTTGCTATGATCCCACTCTCCACCGCTGTAAGACATGAAGCTATACTGATAGTTGTTGTTTCGG
BoNT/C atoxic, receptor binding domain
N T N D T R V R G G D I L Y F D M T I N N K A
1382 1383 1384 1385 1386 1387 1388 1389 1390 1391 1392 1393 1394 1395 1396 1397 1398 1399 1400 1401 1402 1403 1404

5' TACAACTTGTTCATGAAAAACGAGACAATGTACGCCGACAACCATAGCACGGAGGATATTTACGCAATCG 4340
3' ATGTTGAACAAGTACTTTTTGCTCTGTTACATGCGGCTGTTGGTATCGTGCCTCCTATAAATGCGTTAGC
BoNT/C atoxic, receptor binding domain
Y N L F M K N E T M Y A D N H S T E D I Y A I
1405 1406 1407 1408 1409 1410 1411 1412 1413 1414 1415 1416 1417 1418 1419 1420 1421 1422 1423 1424 1425 1426 1427

5' GACTGAGGGAACAGACAAAGGACATCAACGATAACATTATCTTCCAGATCCAACCTATGAACAACACGTA 4410
3' CTGACTCCCTTGTCTGTTTCCTGTAGTTGCTATTGTAATAGAAGGTCTAGGTTGGATACTTGTTGTGCAT
BoNT/C atoxic, receptor binding domain
G L R E Q T K D I N D N I I F Q I Q P M N N T Y
1428 1429 1430 1431 1432 1433 1434 1435 1436 1437 1438 1439 1440 1441 1442 1443 1444 1445 1446 1447 1448 1449 1450 1451

5' CTACTACGCTTCGCAAATCTTCAAGTCCAACTTCAACGGAGAAAACATTTCGGGTATCTGTTCCATTGGC
3' GATGATGCGAAGCGTTTAGAAGTTCAGGTTGAAGTTGCCTCTTTTGTAAAGCCCATAGACAAGGTAACCG
BoNT/C atoxic, receptor binding domain
Y Y A S Q I F K S N F N G E N I S G I C S I G
1452 1453 1454 1455 1456 1457 1458 1459 1460 1461 1462 1463 1464 1465 1466 1467 1468 1469 1470 1471 1472 1473 1474

FIG. 17K

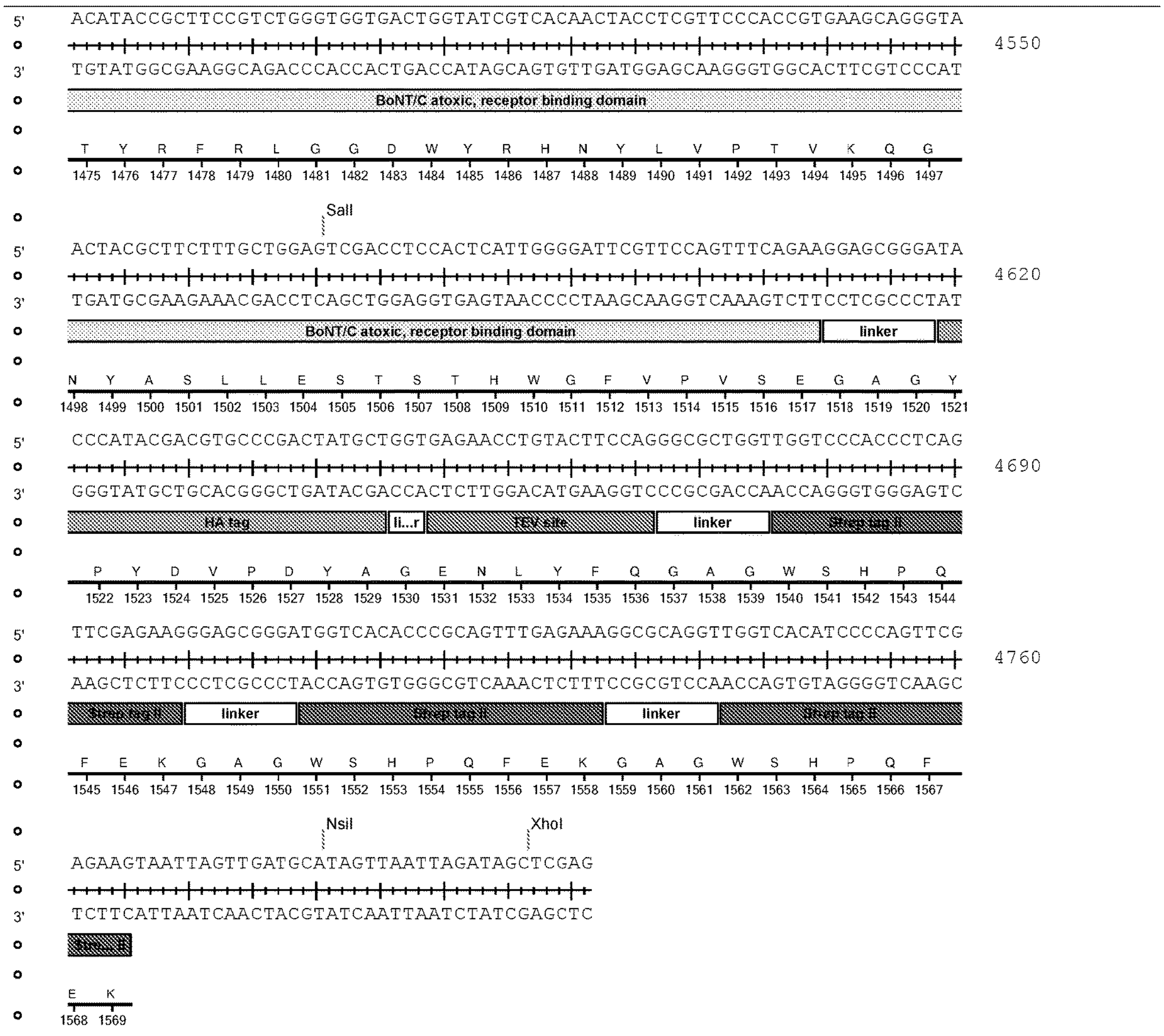

FIG. 17L

```
5'  ACATACCGCTTCCGTCTGGGTGGTGACTGGTATCGTCACAACTACCTCGTTCCCACCGTGAAGCAGGGTA
    ++++++++++++++++++++++++++++++++++++++++++++++++++++++++++++++++++++  4550
3'  TGTATGGCGAAGGCAGACCCACCACTGACCATAGCAGTGTTGATGGAGCAAGGGTGGCACTTCGTCCCAT
```
BoNT/C atoxic, receptor binding domain T  Y  R  F  R  L  G  G  D  W  Y  R  H  N  Y  L  V  P  T  V  K  Q  G
1475 1476 1477 1478 1479 1480 1481 1482 1483 1484 1485 1486 1487 1488 1489 1490 1491 1492 1493 1494 1495 1496 1497

SalI

```
5'  ACTACGCTTCTTTGCTGGAGTCGACCTCCACTCATTGGGGATTCGTTCCAGTTTCAGAAGGAGCGGGATA
    ++++++++++++++++++++++++++++++++++++++++++++++++++++++++++++++++++++  4620
3'  TGATGCGAAGAAACGACCTCAGCTGGAGGTGAGTAACCCCTAAGCAAGGTCAAAGTCTTCCTCGCCCTAT
```
BoNT/C atoxic, receptor binding domain | linker N  Y  A  S  L  L  E  S  T  S  T  H  W  G  F  V  P  V  S  E  G  A  G  Y
1498 1499 1500 1501 1502 1503 1504 1505 1506 1507 1508 1509 1510 1511 1512 1513 1514 1515 1516 1517 1518 1519 1520 1521

```
5'  CCCATACGACGTGCCCGACTATGCTGGTGAGAACCTGTACTTCCAGGGCGCTGGTTGGTCCCACCCTCAG
    ++++++++++++++++++++++++++++++++++++++++++++++++++++++++++++++++++++  4690
3'  GGGTATGCTGCACGGGCTGATACGACCACTCTTGGACATGAAGGTCCCGCGACCAACCAGGGTGGGAGTC
```
HA tag | li...r | TEV site | linker | Strep tag II P  Y  D  V  P  D  Y  A  G  E  N  L  Y  F  Q  G  A  G  W  S  H  P  Q
1522 1523 1524 1525 1526 1527 1528 1529 1530 1531 1532 1533 1534 1535 1536 1537 1538 1539 1540 1541 1542 1543 1544

```
5'  TTCGAGAAGGGAGCGGGATGGTCACACCCGCAGTTTGAGAAAGGCGCAGGTTGGTCACATCCCCAGTTCG
    ++++++++++++++++++++++++++++++++++++++++++++++++++++++++++++++++++++  4760
3'  AAGCTCTTCCCTCGCCCTACCAGTGTGGGCGTCAAACTCTTTCCGCGTCCAACCAGTGTAGGGGTCAAGC
```
Strep tag II | linker | Strep tag II | linker | Strep tag II F  E  K  G  A  G  W  S  H  P  Q  F  E  K  G  A  G  W  S  H  P  Q  F
1545 1546 1547 1548 1549 1550 1551 1552 1553 1554 1555 1556 1557 1558 1559 1560 1561 1562 1563 1564 1565 1566 1567

NsiI                    XhoI
```
5'  AGAAGTAATTAGTTGATGCATAGTTAATTAGATAGCTCGAG
    +++++++++++++++++++++++++++++++++++++++++
3'  TCTTCATTAATCAACTACGTATCAATTAATCTATCGAGCTC
```

E  K
1568 1569

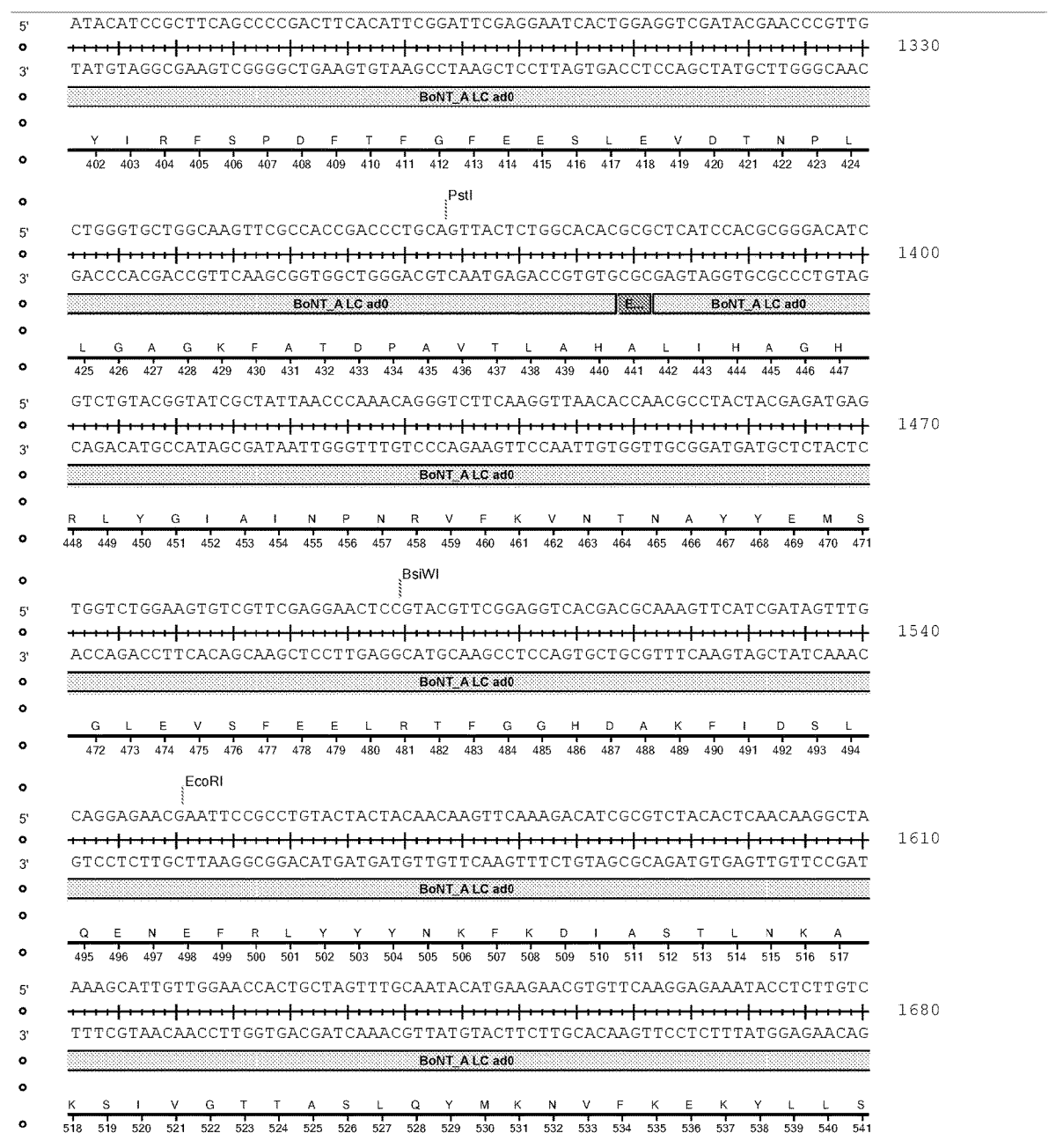

5' ATACATCCGCTTCAGCCCCGACTTCACATTCGGATTCGAGGAATCACTGGAGGTCGATACGAACCCGTTG 1330
3' TATGTAGGCGAAGTCGGGGCTGAAGTGTAAGCCTAAGCTCCTTAGTGACCTCCAGCTATGCTTGGGCAAC
BoNT_A LC ad0
Y I R F S P D F T F G F E E S L E V D T N P L
402 403 404 405 406 407 408 409 410 411 412 413 414 415 416 417 418 419 420 421 422 423 424

PstI
5' CTGGGTGCTGGCAAGTTCGCCACCGACCCTGCAGTTACTCTGGCACACGCGCTCATCCACGCGGGACATC 1400
3' GACCCACGACCGTTCAAGCGGTGGCTGGGACGTCAATGAGACCGTGTGCGCGAGTAGGTGCGCCCTGTAG
BoNT_A LC ad0 E... BoNT_A LC ad0
L G A G K F A T D P A V T L A H A L I H A G H
425 426 427 428 429 430 431 432 433 434 435 436 437 438 439 440 441 442 443 444 445 446 447

5' GTCTGTACGGTATCGCTATTAACCCAAACAGGGTCTTCAAGGTTAACACCAACGCCTACTACGAGATGAG 1470
3' CAGACATGCCATAGCGATAATTGGGTTTGTCCCAGAAGTTCCAATTGTGGTTGCGGATGATGCTCTACTC
BoNT_A LC ad0
R L Y G I A I N P N R V F K V N T N A Y Y E M S
448 449 450 451 452 453 454 455 456 457 458 459 460 461 462 463 464 465 466 467 468 469 470 471

BsiWI
5' TGGTCTGGAAGTGTCGTTCGAGGAACTCCGTACGTTCGGAGGTCACGACGCAAAGTTCATCGATAGTTTG 1540
3' ACCAGACCTTCACAGCAAGCTCCTTGAGGCATGCAAGCCTCCAGTGCTGCGTTTCAAGTAGCTATCAAAC
BoNT_A LC ad0
G L E V S F E E L R T F G G H D A K F I D S L
472 473 474 475 476 477 478 479 480 481 482 483 484 485 486 487 488 489 490 491 492 493 494

EcoRI
5' CAGGAGAACGAATTCCGCCTGTACTACTACAACAAGTTCAAAGACATCGCGTCTACACTCAACAAGGCTA 1610
3' GTCCTCTTGCTTAAGGCGGACATGATGATGTTGTTCAAGTTTCTGTAGCGCAGATGTGAGTTGTTCCGAT
BoNT_A LC ad0
Q E N E F R L Y Y Y N K F K D I A S T L N K A
495 496 497 498 499 500 501 502 503 504 505 506 507 508 509 510 511 512 513 514 515 516 517

5' AAAGCATTGTTGGAACCACTGCTAGTTTGCAATACATGAAGAACGTGTTCAAGGAGAAATACCTCTTGTC 1680
3' TTTCGTAACAACCTTGGTGACGATCAAACGTTATGTACTTCTTGCACAAGTTCCTCTTTATGGAGAACAG
BoNT_A LC ad0
K S I V G T T A S L Q Y M K N V F K E K Y L L S
518 519 520 521 522 523 524 525 526 527 528 529 530 531 532 533 534 535 536 537 538 539 540 541

FIG. 19D

```
5'  CTGGGATCTGTTCTTTAGCCCAAGCGAGGATAACTTCACGAACGATCTCAACAAAGGTGAAGAGATCACG
                                                                                    2170
3'  GACCCTAGACAAGAAATCGGGTTCGCTCCTATTGAAGTGCTTGCTAGAGTTGTTTCCACTTCTCTAGTGC
                                       Translocation Domain

    W   D   L   F   F   S   P   S   E   D   N   F   T   N   D   L   N   K   G   E   E   I   T
    682 683 684 685 686 687 688 689 690 691 692 693 694 695 696 697 698 699 700 701 702 703 704

5'  TCTGATACCAATATCGAAGCGGCTGAAGAGAATATCTCCTTGGATCTCATCCAGCAATATTACCTGACCT
                                                                                    2240
3'  AGACTATGGTTATAGCTTCGCCGACTTCTCTTATAGAGGAACCTAGAGTAGGTCGTTATAATGGACTGGA
                                       Translocation Domain

    S   D   T   N   I   E   A   A   E   E   N   I   S   L   D   L   I   Q   Q   Y   Y   L   T
    705 706 707 708 709 710 711 712 713 714 715 716 717 718 719 720 721 722 723 724 725 726 727

                                                                Bpu10I
                                                                BbvCI
5'  TTAACTTCGATAACGAGCCCGAAAACATCTCCATCGAGAACCTCAGCTCAGACATCATTGGTCAGTTGGA
                                                                                    2310
3'  AATTGAAGCTATTGCTCGGGCTTTTGTAGAGGTAGCTCTTGGAGTCGAGTCTGTAGTAACCAGTCAACCT
                                       Translocation Domain

    F   N   F   D   N   E   P   E   N   I   S   I   E   N   L   S   S   D   I   I   G   Q   L   E
    728 729 730 731 732 733 734 735 736 737 738 739 740 741 742 743 744 745 746 747 748 749 750 751

5'  GCTGATGCCAAACATTGAACGCTTCCCCAACGGCAAGAAATACGAACTCGACAAGTATACGATGTTTCAT
                                                                                    2380
3'  CGACTACGGTTTGTAACTTGCGAAGGGGTTGCCGTTCTTTATGCTTGAGCTGTTCATATGCTACAAAGTA
                                       Translocation Domain

    L   M   P   N   I   E   R   F   P   N   G   K   K   Y   E   L   D   K   Y   T   M   F   H
    752 753 754 755 756 757 758 759 760 761 762 763 764 765 766 767 768 769 770 771 772 773 774

        AflII
5'  TACTTAAGAGCGCAGGAGTTTGAACACGGCAAGAGCCGCATTGCTCTCACTAACTCCGTGAATGAAGCCC
                                                                                    2450
3'  ATGAATTCTCGCGTCCTCAAACTTGTGCCGTTCTCGGCGTAACGAGAGTGATTGAGGCACTTACTTCGGG
                                       Translocation Domain

    Y   L   R   A   Q   E   F   E   H   G   K   S   R   I   A   L   T   N   S   V   N   E   A
    775 776 777 778 779 780 781 782 783 784 785 786 787 788 789 790 791 792 793 794 795 796 797

5'  TGCTCAATCCGTCAAGGGTGTACACATTCTTTAGCTCCGACTATGTCAAGAAAGTGAACAAAGCCACCGA
                                                                                    2520
3'  ACGAGTTAGGCAGTTCCCACATGTGTAAGAAATCGAGGCTGATACAGTTCTTTCACTTGTTTCGGTGGCT
                                       Translocation Domain

    L   L   N   P   S   R   V   Y   T   F   F   S   S   D   Y   V   K   K   V   N   K   A   T   E
    798 799 800 801 802 803 804 805 806 807 808 809 810 811 812 813 814 815 816 817 818 819 820 821
```

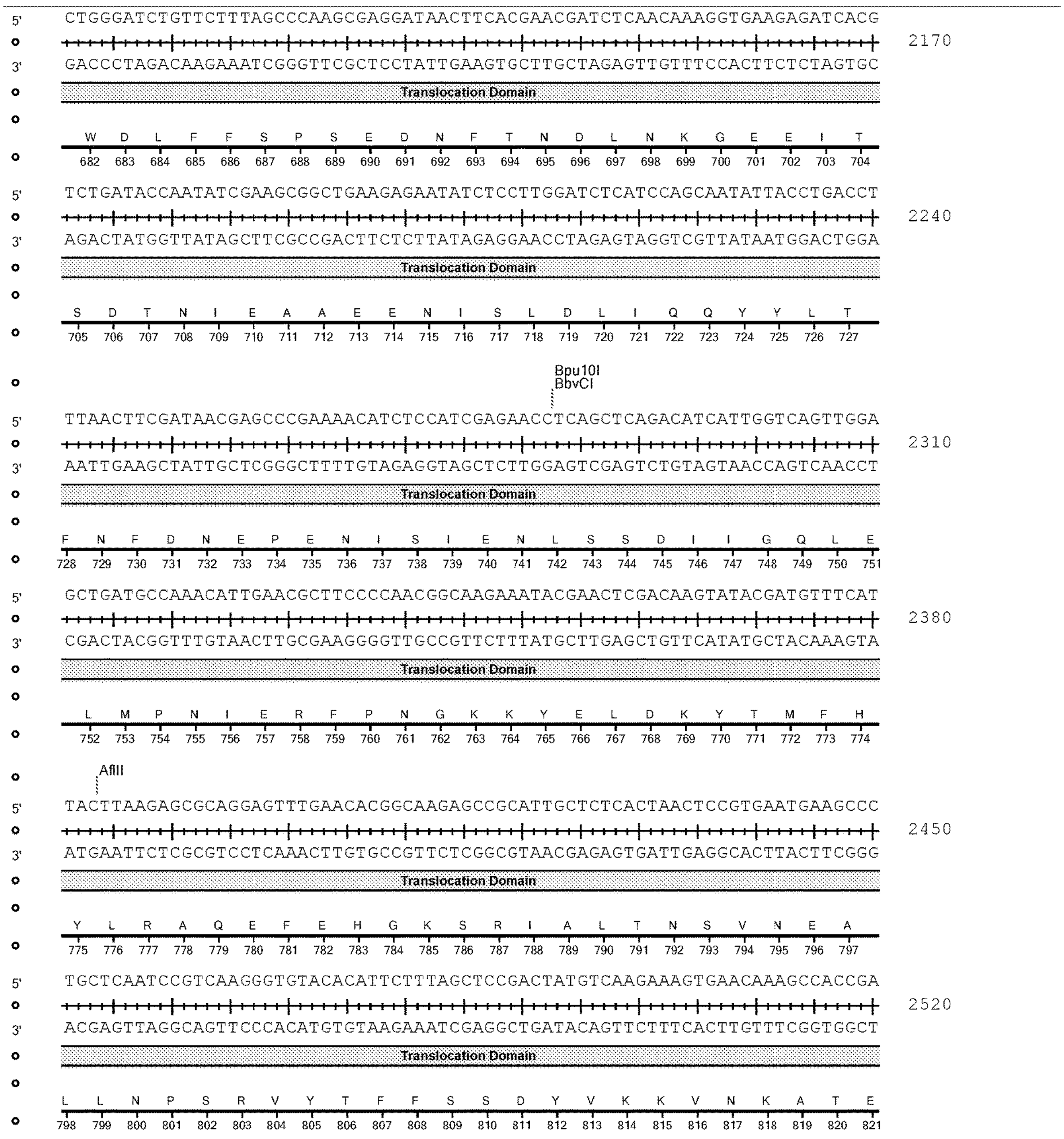

FIG. 19F

5' AGCGGCAATGTTCCTGGGATGGGTTGAACAACTGGTCTACGACTTCACCGACGAGACCTCTGAGGTGAGC 2590
3' TCGCCGTTACAAGGACCCTACCCAACTTGTTGACCAGATGCTGAAGTGGCTGCTCTGGAGACTCCACTCG
Translocation Domain
A A M F L G W V E Q L V Y D F T D E T S E V S
822 823 824 825 826 827 828 829 830 831 832 833 834 835 836 837 838 839 840 841 842 843 844

5' ACAACGGACAAGATTGCTGACATCACTATCATTATCCCGTATATTGGACCTGCCTTGAATATTGGCAACA 2660
3' TGTTGCCTGTTCTAACGACTGTAGTGATAGTAATAGGGCATATAACCTGGACGGAACTTATAACCGTTGT
Translocation Domain
T T D K I A D I T I I I P Y I G P A L N I G N
845 846 847 848 849 850 851 852 853 854 855 856 857 858 859 860 861 862 863 864 865 866 867

5' TGCTCTACAAAGACGATTTCGTTGGTGCCCTGATCTTCAGCGGTGCCGTGATCCTGTTGGAGTTCATTCC 2730
3' ACGAGATGTTTCTGCTAAAGCAACCACGGGACTAGAAGTCGCCACGGCACTAGGACAACCTCAAGTAAGG
Translocation Domain
M L Y K D D F V G A L I F S G A V I L L E F I P
868 869 870 871 872 873 874 875 876 877 878 879 880 881 882 883 884 885 886 887 888 889 890 891

5' TGAAATCGCCATCCCTGTGCTGGGCACGTTCGCTCTGGTCTCATACATTGCGAATAAGGTCTTGACCGTG 2800
3' ACTTTAGCGGTAGGGACACGACCCGTGCAAGCGAGACCAGAGTATGTAACGCTTATTCCAGAACTGGCAC
Translocation Domain
E I A I P V L G T F A L V S Y I A N K V L T V
892 893 894 895 896 897 898 899 900 901 902 903 904 905 906 907 908 909 910 911 912 913 914

5' CAGACAATCGATAATGCCCTCTCCAAACGTAACGAAAAATGGGACGAGGTCTACAAATACATCGTGACCA 2870
3' GTCTGTTAGCTATTACGGGAGAGGTTTGCATTGCTTTTTACCCTGCTCCAGATGTTTATGTAGCACTGGT
Translocation Domain
Q T I D N A L S K R N E K W D E V Y K Y I V T
915 916 917 918 919 920 921 922 923 924 925 926 927 928 929 930 931 932 933 934 935 936 937

5' ACTGGCTGGCAAAGGTTAACACCCAAATTGATCTGATCCGTAAGAAAATGAAGGAGGCTTTGGAGAACCA 2940
3' TGACCGACCGTTTCCAATTGTGGGTTTAACTAGACTAGGCATTCTTTTACTTCCTCCGAAACCTCTTGGT
Translocation Domain
N W L A K V N T Q I D L I R K K M K E A L E N Q
938 939 940 941 942 943 944 945 946 947 948 949 950 951 952 953 954 955 956 957 958 959 960 961

FIG. 19G

NheI
BmtI

5' GAACCTCCGTTACGAGTCTAACCACCTCATCGACTTGAGCAGATACGCTAGCAAGATCAACATCGGTTCC 3430
3' CTTGGAGGCAATGCTCAGATTGGTGGAGTAGCTGAACTCGTCTATGCGATCGTTCTAGTTGTAGCCAAGG
Receptor-Binding Domain
N L R Y E S N H L I D L S R Y A S K I N I G S
1102 1103 1104 1105 1106 1107 1108 1109 1110 1111 1112 1113 1114 1115 1116 1117 1118 1119 1120 1121 1122 1123 1124

5' AAGGTGAACTTCGACCCAATCGATAAGAACCAGATCCAACTGTTCAACCTCGAATCCTCTAAGATCGAAG 3500
3' TTCCACTTGAAGCTGGGTTAGCTATTCTTGGTCTAGGTTGACAAGTTGGAGCTTAGGAGATTCTAGCTTC
Receptor-Binding Domain
K V N F D P I D K N Q I Q L F N L E S S K I E
1125 1126 1127 1128 1129 1130 1131 1132 1133 1134 1135 1136 1137 1138 1139 1140 1141 1142 1143 1144 1145 1146 1147

5' TGATCCTGAAGAACGCTATCGTCTACAACTCCATGTACGAAAACTTCTCTACCAGCTTCTGGATCAGGAT 3570
3' ACTAGGACTTCTTGCGATAGCAGATGTTGAGGTACATGCTTTTGAAGAGATGGTCGAAGACCTAGTCCTA
Receptor-Binding Domain
V I L K N A I V Y N S M Y E N F S T S F W I R I
1148 1149 1150 1151 1152 1153 1154 1155 1156 1157 1158 1159 1160 1161 1162 1163 1164 1165 1166 1167 1168 1169 1170 1171

5' TCCGAAATACTTCAACTCAATCTCGCTCAACAACGAGTACACTATCATCAACTGCATGGAAAACAACTCG 3640
3' AGGCTTTATGAAGTTGAGTTAGAGCGAGTTGTTGCTCATGTGATAGTAGTTGACGTACCTTTTGTTGAGC
Receptor-Binding Domain
P K Y F N S I S L N N E Y T I I N C M E N N S
1172 1173 1174 1175 1176 1177 1178 1179 1180 1181 1182 1183 1184 1185 1186 1187 1188 1189 1190 1191 1192 1193 1194

5' GGATGGAAGGTGTCCCTCAACTACGGCGAGATCATCTGGACTTTGCAGGACACACAAGAAATCAAGCAGA 3710
3' CCTACCTTCCACAGGGAGTTGATGCCGCTCTAGTAGACCTGAAACGTCCTGTGTGTTCTTTAGTTCGTCT
Receptor-Binding Domain
G W K V S L N Y G E I I W T L Q D T Q E I K Q
1195 1196 1197 1198 1199 1200 1201 1202 1203 1204 1205 1206 1207 1208 1209 1210 1211 1212 1213 1214 1215 1216 1217

5' GGGTCGTGTTCAAGTACAGCCAAATGATCAACATCAGCGATTACATCAACCGTTGGATCTTCGTCACAAT 3780
3' CCCAGCACAAGTTCATGTCGGTTTACTAGTTGTAGTCGCTAATGTAGTTGGCAACCTAGAAGCAGTGTTA
Receptor-Binding Domain
R V V F K Y S Q M I N I S D Y I N R W I F V T I
1218 1219 1220 1221 1222 1223 1224 1225 1226 1227 1228 1229 1230 1231 1232 1233 1234 1235 1236 1237 1238 1239 1240 1241

FIG. 19I

```
5'  CACCAACAACCGCCTGAACAACTCCAAGATTTACATCAACGGTAGACTGATCGACCAGAAGCCAATCAGC
                                                                              3850
3'  GTGGTTGTTGGCGGACTTGTTGAGGTTCTAAATGTAGTTGCCATCTGACTAGCTGGTCTTCGGTTAGTCG
                              Receptor-Binding Domain

     T   N   N   R   L   N   N   S   K   I   Y   I   N   G   R   L   I   D   Q   K   P   I   S
    1242 1243 1244 1245 1246 1247 1248 1249 1250 1251 1252 1253 1254 1255 1256 1257 1258 1259 1260 1261 1262 1263 1264

5'  AACCTCGGCAACATCCACGCCTCAAACAACATCATGTTCAAGTTGGACGGCTGTAGGGATACACACAGAT
                                                                              3920
3'  TTGGAGCCGTTGTAGGTGCGGAGTTTGTTGTAGTACAAGTTCAACCTGCCGACATCCCTATGTGTGTCTA
                              Receptor-Binding Domain

     N   L   G   N   I   H   A   S   N   N   I   M   F   K   L   D   G   C   R   D   T   H   R
    1265 1266 1267 1268 1269 1270 1271 1272 1273 1274 1275 1276 1277 1278 1279 1280 1281 1282 1283 1284 1285 1286 1287

                                                   EcoICRI
                                                   SacI
5'  ACATCTGGATCAAATACTTCAACCTGTTCGACAAGGAGCTCAACGAGAAGGAAATCAAGGACCTCTACGA
                                                                              3990
3'  TGTAGACCTAGTTTATGAAGTTGGACAAGCTGTTCCTCGAGTTGCTCTTCCTTTAGTTCCTGGAGATGCT
                              Receptor-Binding Domain

     Y   I   W   I   K   Y   F   N   L   F   D   K   E   L   N   E   K   E   I   K   D   L   Y   D
    1288 1289 1290 1291 1292 1293 1294 1295 1296 1297 1298 1299 1300 1301 1302 1303 1304 1305 1306 1307 1308 1309 1310 1311

5'  TAACCAGTCCAACTCTGGTATCTTGAAGGACTTCTGGGGCGATTACCTGCAATACGACAAGCCCTACTAC
                                                                              4060
3'  ATTGGTCAGGTTGAGACCATAGAACTTCCTGAAGACCCCGCTAATGGACGTTATGCTGTTCGGGATGATG
                              Receptor-Binding Domain

     N   Q   S   N   S   G   I   L   K   D   F   W   G   D   Y   L   Q   Y   D   K   P   Y   Y
    1312 1313 1314 1315 1316 1317 1318 1319 1320 1321 1322 1323 1324 1325 1326 1327 1328 1329 1330 1331 1332 1333 1334

5'  ATGTTGAACCTGTACGACCCTAACAAGTACGTTGATGTGAACAACGTCGGTATCAGGGGCTACATGTACC
                                                                              4130
3'  TACAACTTGGACATGCTGGGATTGTTCATGCAACTACACTTGTTGCAGCCATAGTCCCCGATGTACATGG
                              Receptor-Binding Domain

     M   L   N   L   Y   D   P   N   K   Y   V   D   V   N   N   V   G   I   R   G   Y   M   Y
    1335 1336 1337 1338 1339 1340 1341 1342 1343 1344 1345 1346 1347 1348 1349 1350 1351 1352 1353 1354 1355 1356 1357

             PmlI
5'  TGAAGGGACCACGTGGTTCTGTTATGACCACTAACATCTACCTCAACAGCTCATTGTACCGTGGCACAAA
                                                                              4200
3'  ACTTCCCTGGTGCACCAAGACAATACTGGTGATTGTAGATGGAGTTGTCGAGTAACATGGCACCGTGTTT
                              Receptor-Binding Domain

     L   K   G   P   R   G   S   V   M   T   T   N   I   Y   L   N   S   S   L   Y   R   G   T   K
    1358 1359 1360 1361 1362 1363 1364 1365 1366 1367 1368 1369 1370 1371 1372 1373 1374 1375 1376 1377 1378 1379 1380 1381
```

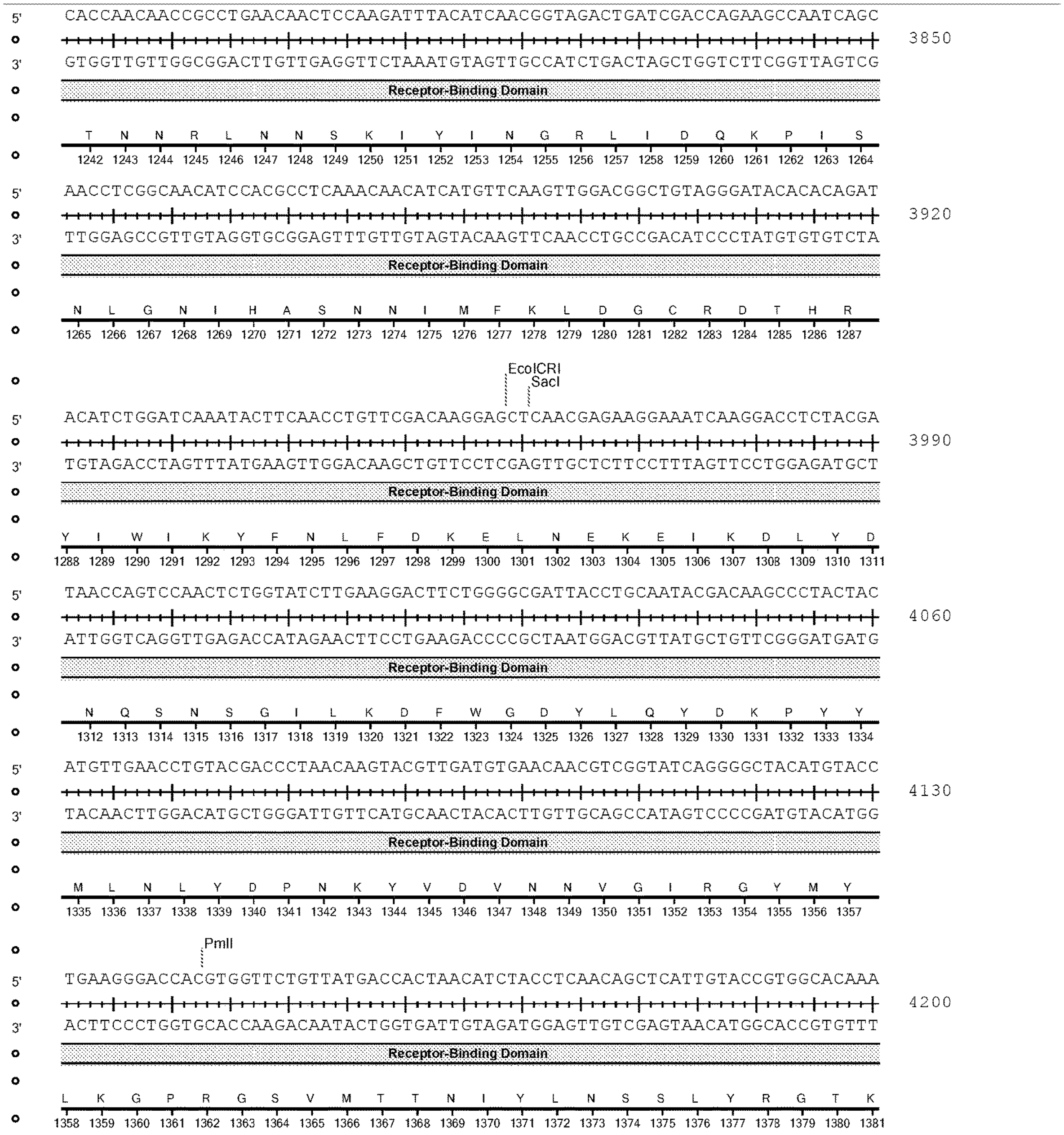

FIG. 19J

```
5'  GTTCATCATCAAGAAGTACGCCTCCGGAAACAAGGACAACATCGTCCGTAACAACGATCGCGTTTACATC
                                                                              4270
3'  CAAGTAGTAGTTCTTCATGCGGAGGCCTTTGTTCCTGTTGTAGCAGGCATTGTTGCTAGCGCAAATGTAG
                              Receptor-Binding Domain

     F   I   I   K   K   Y   A   S   G   N   K   D   N   I   V   R   N   N   D   R   V   Y   I
    1382 1383 1384 1385 1386 1387 1388 1389 1390 1391 1392 1393 1394 1395 1396 1397 1398 1399 1400 1401 1402 1403 1404

5'  AACGTTGTGGTCAAGAACAAGGAGTACAGACTGGCTACCAACGCTTCGCAGGCTGGAGTTGAGAAGATCC
                                                                              4340
3'  TTGCAACACCAGTTCTTGTTCCTCATGTCTGACCGATGGTTGCGAAGCGTCCGACCTCAACTCTTCTAGG
                              Receptor-Binding Domain

     N   V   V   V   K   N   K   E   Y   R   L   A   T   N   A   S   Q   A   G   V   E   K   I
    1405 1406 1407 1408 1409 1410 1411 1412 1413 1414 1415 1416 1417 1418 1419 1420 1421 1422 1423 1424 1425 1426 1427

5'  TGTCTGCTCTGGAAATCCCTGACGTGGGCAACCTCTCACAGGTTGTGGTCATGAAGTCGAAGAACGATCA
                                                                              4410
3'  ACAGACGAGACCTTTAGGGACTGCACCCGTTGGAGAGTGTCCAACACCAGTACTTCAGCTTCTTGCTAGT
                              Receptor-Binding Domain

     L   S   A   L   E   I   P   D   V   G   N   L   S   Q   V   V   V   M   K   S   K   N   D   Q
    1428 1429 1430 1431 1432 1433 1434 1435 1436 1437 1438 1439 1440 1441 1442 1443 1444 1445 1446 1447 1448 1449 1450 1451

5'  AGGCATCACTAACAAGTGCAAGATGAACTTGCAGGACAACAACGGAAACGACATCGGCTTCATCGGATTC
                                                                              4480
3'  TCCGTAGTGATTGTTCACGTTCTACTTGAACGTCCTGTTGTTGCCTTTGCTGTAGCCGAAGTAGCCTAAG
                              Receptor-Binding Domain

     G   I   T   N   K   C   K   M   N   L   Q   D   N   N   G   N   D   I   G   F   I   G   F
    1452 1453 1454 1455 1456 1457 1458 1459 1460 1461 1462 1463 1464 1465 1466 1467 1468 1469 1470 1471 1472 1473 1474

5'  CACCAATTCAACAACATCGCCAAGTTGGTGGCCAGCAACTGGTACAACCGTCAGATCGAGCGTTCGTCCC
                                                                              4550
3'  GTGGTTAAGTTGTTGTAGCGGTTCAACCACCGGTCGTTGACCATGTTGGCAGTCTAGCTCGCAAGCAGGG
                              Receptor-Binding Domain

     H   Q   F   N   N   I   A   K   L   V   A   S   N   W   Y   N   R   Q   I   E   R   S   S
    1475 1476 1477 1478 1479 1480 1481 1482 1483 1484 1485 1486 1487 1488 1489 1490 1491 1492 1493 1494 1495 1496 1497

            Bsu36I
5'  GCACCTTAGGATGCTCGTGGGAGTTCATTCCAGTCGATGACGGATGGGGAGAGAGACCTTTGGGCGCAGG
                                                                              4620
3'  CGTGGAATCCTACGAGCACCCTCAAGTAAGGTCAGCTACTGCCTACCCCTCTCTCTGGAAACCCGCGTCC
                        Receptor-Binding Domain              | linker

     R   T   L   G   C   S   W   E   F   I   P   V   D   D   G   W   G   E   R   P   L   G   A   G
    1498 1499 1500 1501 1502 1503 1504 1505 1506 1507 1508 1509 1510 1511 1512 1513 1514 1515 1516 1517 1518 1519 1520 1521
```

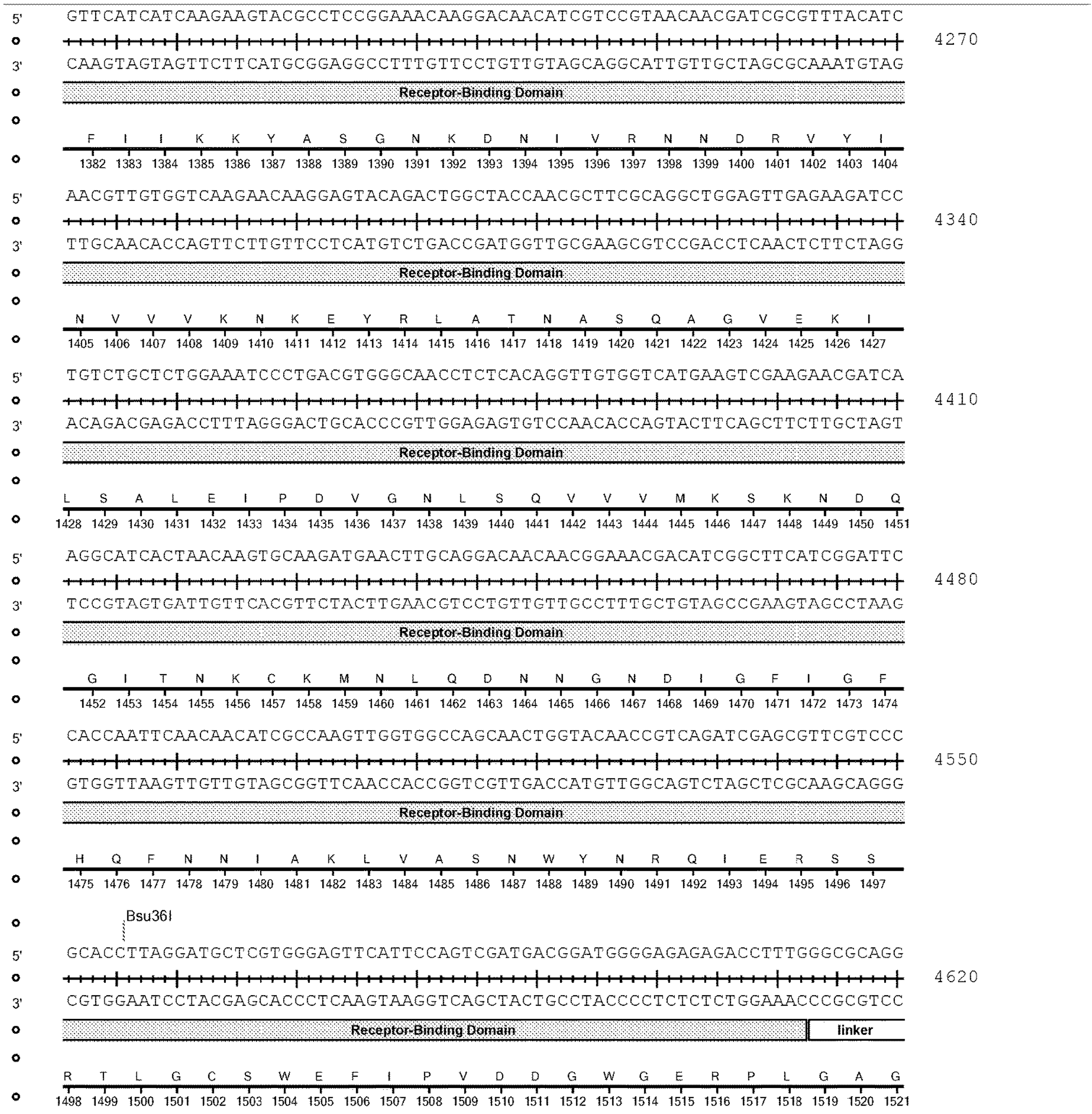

FIG. 19K

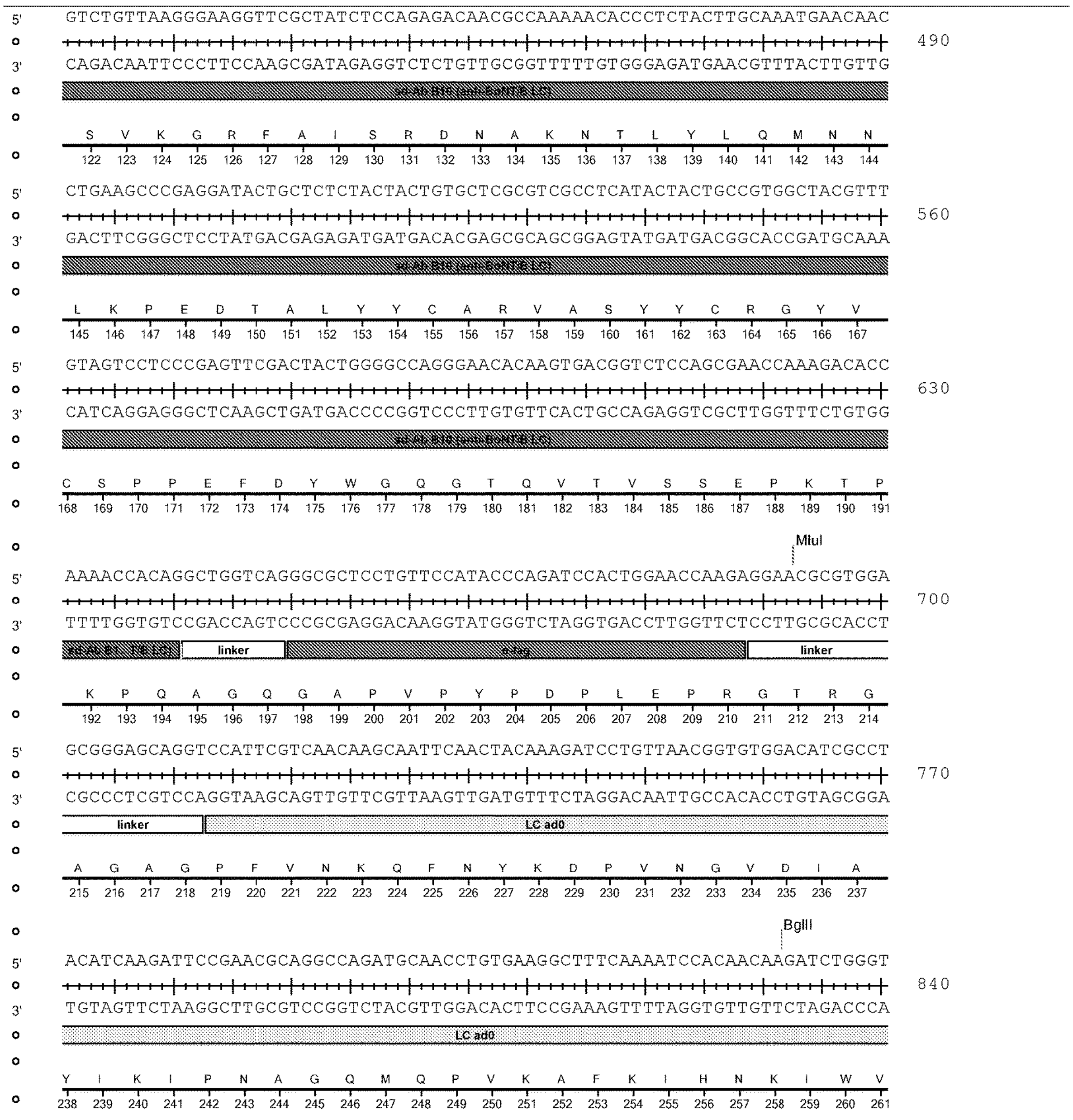

FIG. 20B

```
5'  GTCTGTTAAGGGAAGGTTCGCTATCTCCAGAGACAACGCCAAAAACACCCTCTACTTGCAAATGAACAAC
                                                                              490
3'  CAGACAATTCCCTTCCAAGCGATAGAGGTCTCTGTTGCGGTTTTTGTGGGAGATGAACGTTTACTTGTTG
```

S   V   K   G   R   F   A   I   S   R   D   N   A   K   N   T   L   Y   L   Q   M   N   N
    122 123 124 125 126 127 128 129 130 131 132 133 134 135 136 137 138 139 140 141 142 143 144

```
5'  CTGAAGCCCGAGGATACTGCTCTCTACTACTGTGCTCGCGTCGCCTCATACTACTGCCGTGGCTACGTTT
                                                                              560
3'  GACTTCGGGCTCCTATGACGAGAGATGATGACACGAGCGCAGCGGAGTATGATGACGGCACCGATGCAAA
```

L   K   P   E   D   T   A   L   Y   Y   C   A   R   V   A   S   Y   Y   C   R   G   Y   V
    145 146 147 148 149 150 151 152 153 154 155 156 157 158 159 160 161 162 163 164 165 166 167

```
5'  GTAGTCCTCCCGAGTTCGACTACTGGGGCCAGGGAACACAAGTGACGGTCTCCAGCGAACCAAAGACACC
                                                                              630
3'  CATCAGGAGGGCTCAAGCTGATGACCCCGGTCCCTTGTGTTCACTGCCAGAGGTCGCTTGGTTTCTGTGG
```

C   S   P   P   E   F   D   Y   W   G   Q   G   T   Q   V   T   V   S   S   E   P   K   T   P
    168 169 170 171 172 173 174 175 176 177 178 179 180 181 182 183 184 185 186 187 188 189 190 191

MluI
```
5'  AAAACCACAGGCTGGTCAGGGCGCTCCTGTTCCATACCCAGATCCACTGGAACCAAGAGGAACGCGTGGA
                                                                              700
3'  TTTTGGTGTCCGACCAGTCCCGCGAGGACAAGGTATGGGTCTAGGTGACCTTGGTTCTCCTTGCGCACCT
```

K   P   Q   A   G   Q   G   A   P   V   P   Y   P   D   P   L   E   P   R   G   T   R   G
    192 193 194 195 196 197 198 199 200 201 202 203 204 205 206 207 208 209 210 211 212 213 214

```
5'  GCGGGAGCAGGTCCATTCGTCAACAAGCAATTCAACTACAAAGATCCTGTTAACGGTGTGGACATCGCCT
                                                                              770
3'  CGCCCTCGTCCAGGTAAGCAGTTGTTCGTTAAGTTGATGTTTCTAGGACAATTGCCACACCTGTAGCGGA
```

A   G   A   G   P   F   V   N   K   Q   F   N   Y   K   D   P   V   N   G   V   D   I   A
    215 216 217 218 219 220 221 222 223 224 225 226 227 228 229 230 231 232 233 234 235 236 237

BglII
```
5'  ACATCAAGATTCCGAACGCAGGCCAGATGCAACCTGTGAAGGCTTTCAAAATCCACAACAAGATCTGGGT
                                                                              840
3'  TGTAGTTCTAAGGCTTGCGTCCGGTCTACGTTGGACACTTCCGAAAGTTTTAGGTGTTGTTCTAGACCCA
```

Y   I   K   I   P   N   A   G   Q   M   Q   P   V   K   A   F   K   I   H   N   K   I   W   V
    238 239 240 241 242 243 244 245 246 247 248 249 250 251 252 253 254 255 256 257 258 259 260 261

AarI

5' CATTCCCGAGAGAGACACATTCACGAACCCAGAGGAAGGTGATCTGAACCCTCCCCCAGAAGCCAAGCAG 910

3' GTAAGGGCTCTCTCTGTGTAAGTGCTTGGGTCTCCTTCCACTAGACTTGGGAGGGGGTCTTCGGTTCGTC

LC ad0

I P E R D T F T N P E E G D L N P P P E A K Q 262 263 264 265 266 267 268 269 270 271 272 273 274 275 276 277 278 279 280 281 282 283 284

ScaI

5' GTGCCGGTCTCTTACTACGATTCAACCTACCTCAGTACTGACAACGAGAAGGATAACTACCTGAAGGGCG 980

3' CACGGCCAGAGAATGATGCTAAGTTGGATGGAGTCATGACTGTTGCTCTTCCTATTGATGGACTTCCCGC

LC ad0

V P V S Y Y D S T Y L S T D N E K D N Y L K G 285 286 287 288 289 290 291 292 293 294 295 296 297 298 299 300 301 302 303 304 305 306 307

5' TTACTAAACTCTTCGAGCGCATCTACTCGACAGACTTGGGCCGTATGCTGCTCACGTCCATCGTCAGGGG 1050

3' AATGATTTGAGAAGCTCGCGTAGATGAGCTGTCTGAACCCGGCATACGACGAGTGCAGGTAGCAGTCCCC

LC ad0

V T K L F E R I Y S T D L G R M L L T S I V R G 308 309 310 311 312 313 314 315 316 317 318 319 320 321 322 323 324 325 326 327 328 329 330 331

5' TATTCCTTTCTGGGGTGGCTCAACCATCGACACTGAGCTGAAGGTCATTGATACAAACTGCATCAACGTT 1120

3' ATAAGGAAAGACCCCACCGAGTTGGTAGCTGTGACTCGACTTCCAGTAACTATGTTTGACGTAGTTGCAA

LC ad0

I P F W G G S T I D T E L K V I D T N C I N V 332 333 334 335 336 337 338 339 340 341 342 343 344 345 346 347 348 349 350 351 352 353 354

5' ATTCAACCCGACGGCTCCTACCGCAGCGAGGAATTGAACCTGGTGATCATTGGACCAAGCGCCGACATCA 1190

3' TAAGTTGGGCTGCCGAGGATGGCGTCGCTCCTTAACTTGGACCACTAGTAACCTGGTTCGCGGCTGTAGT

LC ad0

I Q P D G S Y R S E E L N L V I I G P S A D I 355 356 357 358 359 360 361 362 363 364 365 366 367 368 369 370 371 372 373 374 375 376 377

5' TTCAGTTCGAGTGTAAGTCTTTCGGCCATGAAGTCCTCAACTTGACCAGAAACGGCTACGGCTCCACTCA 1260

3' AAGTCAAGCTCACATTCAGAAAGCCGGTACTTCAGGAGTTGAACTGGTCTTTGCCGATGCCGAGGTGAGT

5' CTGAGAACCTGTACTTCCAAGGTGGTGGCCAGGGTGGAGCTCTGAACGATCTGTGTATCAAGGTGAATAA 2100
3' GACTCTTGGACATGAAGGTTCCACCACCGGTCCCACCTCGAGACTTGCTAGACACATAGTTCCACTTATT

J | TEV site | linker | HC, Translocation Domain

S E N L Y F Q G G G Q G G A L N D L C I K V N N
658 659 660 661 662 663 664 665 666 667 668 669 670 671 672 673 674 675 676 677 678 679 680 681

5' CTGGGATCTGTTCTTTAGCCCAAGCGAGGATAACTTCACGAACGATCTCAACAAAGGTGAAGAGATCACG 2170
3' GACCCTAGACAAGAAATCGGGTTCGCTCCTATTGAAGTGCTTGCTAGAGTTGTTTCCACTTCTCTAGTGC

HC, Translocation Domain

W D L F F S P S E D N F T N D L N K G E E I T
682 683 684 685 686 687 688 689 690 691 692 693 694 695 696 697 698 699 700 701 702 703 704

5' TCTGATACCAATATCGAAGCGGCTGAAGAGAATATCTCCTTGGATCTCATCCAGCAATATTACCTGACCT 2240
3' AGACTATGGTTATAGCTTCGCCGACTTCTCTTATAGAGGAACCTAGAGTAGGTCGTTATAATGGACTGGA

HC, Translocation Domain

S D T N I E A A E E N I S L D L I Q Q Y Y L T
705 706 707 708 709 710 711 712 713 714 715 716 717 718 719 720 721 722 723 724 725 726 727

Bpu10I
BbvCI

5' TTAACTTCGATAACGAGCCCGAAAACATCTCCATCGAGAACCTCAGCTCAGACATCATTGGTCAGTTGGA 2310
3' AATTGAAGCTATTGCTCGGGCTTTTGTAGAGGTAGCTCTTGGAGTCGAGTCTGTAGTAACCAGTCAACCT

HC, Translocation Domain

F N F D N E P E N I S I E N L S S D I I G Q L E
728 729 730 731 732 733 734 735 736 737 738 739 740 741 742 743 744 745 746 747 748 749 750 751

5' GCTGATGCCAAACATTGAACGCTTCCCCAACGGCAAGAAATACGAACTCGACAAGTATACGATGTTTCAT 2380
3' CGACTACGGTTTGTAACTTGCGAAGGGGTTGCCGTTCTTTATGCTTGAGCTGTTCATATGCTACAAAGTA

HC, Translocation Domain

L M P N I E R F P N G K K Y E L D K Y T M F H
752 753 754 755 756 757 758 759 760 761 762 763 764 765 766 767 768 769 770 771 772 773 774

AflII

5' TACTTAAGAGCGCAGGAGTTTGAACACGGCAAGAGCCGCATTGCTCTCACTAACTCCGTGAATGAAGCCC 2450
3' ATGAATTCTCGCGTCCTCAAACTTGTGCCGTTCTCGGCGTAACGAGAGTGATTGAGGCACTTACTTCGGG

HC, Translocation Domain

```
5'  TGCTCAATCCGTCAAGGGTGTACACATTCTTTAGCTCCGACTATGTCAAGAAAGTGAACAAAGCCACCGA
                                                                            2520
3'  ACGAGTTAGGCAGTTCCCACATGTGTAAGAAATCGAGGCTGATACAGTTCTTTCACTTGTTTCGGTGGCT
                              HC, Translocation Domain

    L   L   N   P   S   R   V   Y   T   F   F   S   S   D   Y   V   K   K   V   N   K   A   T   E
    798 799 800 801 802 803 804 805 806 807 808 809 810 811 812 813 814 815 816 817 818 819 820 821

5'  AGCGGCAATGTTCCTGGGATGGGTTGAACAACTGGTCTACGACTTCACCGACGAGACCTCTGAGGTGAGC
                                                                            2590
3'  TCGCCGTTACAAGGACCCTACCCAACTTGTTGACCAGATGCTGAAGTGGCTGCTCTGGAGACTCCACTCG
                              HC, Translocation Domain

    A   A   M   F   L   G   W   V   E   Q   L   V   Y   D   F   T   D   E   T   S   E   V   S
    822 823 824 825 826 827 828 829 830 831 832 833 834 835 836 837 838 839 840 841 842 843 844

5'  ACAACGGACAAGATTGCTGACATCACTATCATTATCCCGTATATTGGACCTGCCTTGAATATTGGCAACA
                                                                            2660
3'  TGTTGCCTGTTCTAACGACTGTAGTGATAGTAATAGGGCATATAACCTGGACGGAACTTATAACCGTTGT
                              HC, Translocation Domain

    T   T   D   K   I   A   D   I   T   I   I   P   Y   I   G   P   A   L   N   I   G   N
    845 846 847 848 849 850 851 852 853 854 855 856 857 858 859 860 861 862 863 864 865 866 867

5'  TGCTCTACAAAGACGATTTCGTTGGTGCCCTGATCTTCAGCGGTGCCGTGATCCTGTTGGAGTTCATTCC
                                                                            2730
3'  ACGAGATGTTTCTGCTAAAGCAACCACGGGACTAGAAGTCGCCACGGCACTAGGACAACCTCAAGTAAGG
                              HC, Translocation Domain

    M   L   Y   K   D   D   F   V   G   A   L   I   F   S   G   A   V   I   L   E   F   I   P
    868 869 870 871 872 873 874 875 876 877 878 879 880 881 882 883 884 885 886 887 888 889 890 891

5'  TGAAATCGCCATCCCTGTGCTGGGCACGTTCGCTCTGGTCTCATACATTGCGAATAAGGTCTTGACCGTG
                                                                            2800
3'  ACTTTAGCGGTAGGGACACGACCCGTGCAAGCGAGACCAGAGTATGTAACGCTTATTCCAGAACTGGCAC
                              HC, Translocation Domain

    E   I   A   I   P   V   L   G   T   F   A   L   V   S   Y   I   A   N   K   V   L   T   V
    892 893 894 895 896 897 898 899 900 901 902 903 904 905 906 907 908 909 910 911 912 913 914

5'  CAGACAATCGATAATGCCCTCTCCAAACGTAACGAAAAATGGGACGAGGTCTACAAATACATCGTGACCA
                                                                            2870
3'  GTCTGTTAGCTATTACGGGAGAGGTTTGCATTGCTTTTTACCCTGCTCCAGATGTTTATGTAGCACTGGT
                              HC, Translocation Domain

    Q   T   I   D   N   A   L   S   K   R   N   E   K   W   D   E   V   Y   K   Y   I   V   T
    915 916 917 918 919 920 921 922 923 924 925 926 927 928 929 930 931 932 933 934 935 936 937
```

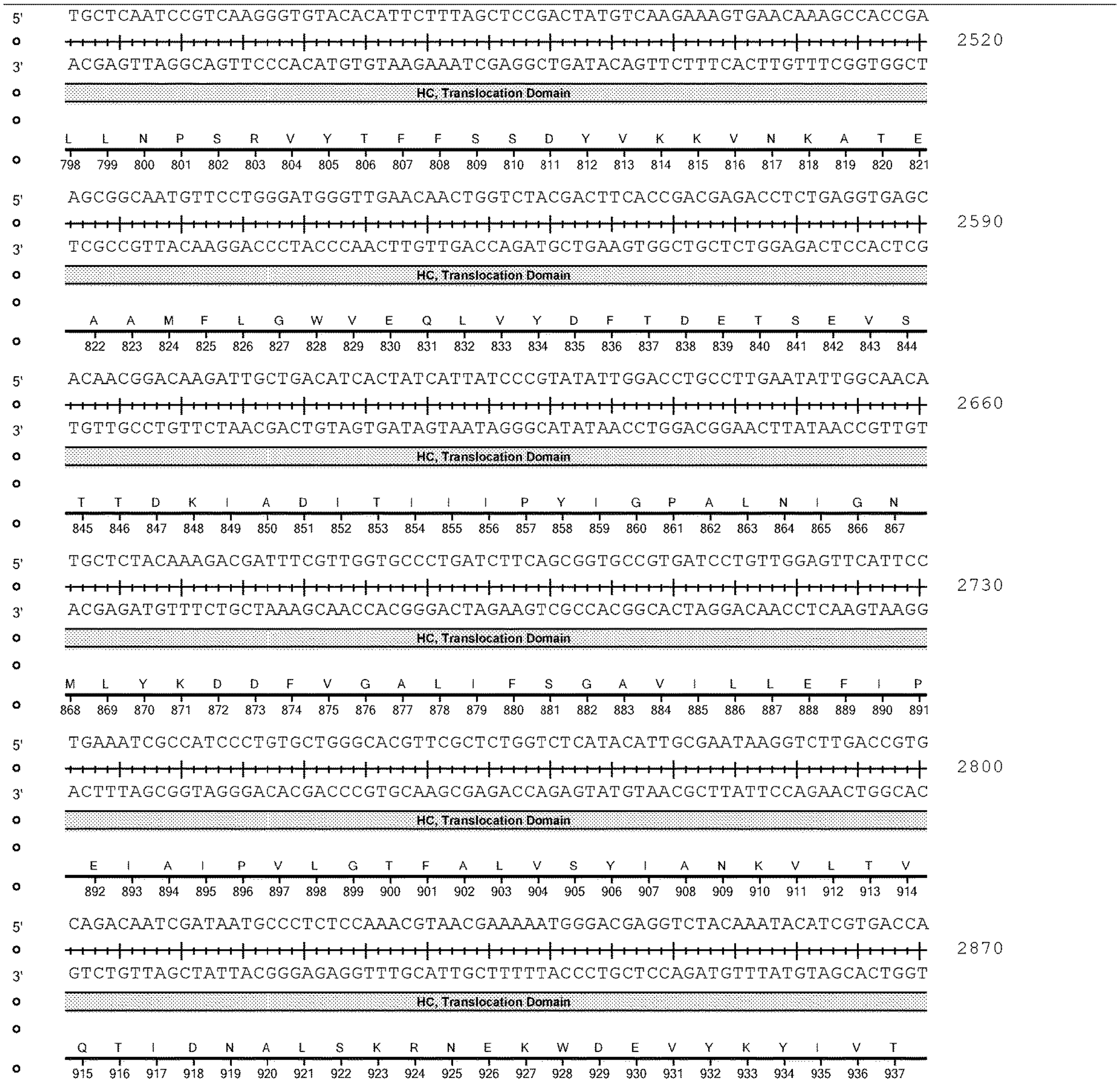

FIG. 20G

5' ACTGGCTGGCAAAGGTTAACACCCAAATTGATCTGATCCGTAAGAAAATGAAGGAGGCTTTGGAGAACCA 2940
3' TGACCGACCGTTTCCAATTGTGGGTTTAACTAGACTAGGCATTCTTTTACTTCCTCCGAAACCTCTTGGT

HC, Translocation Domain

N W L A K V N T Q I D L I R K K M K E A L E N Q
938 939 940 941 942 943 944 945 946 947 948 949 950 951 952 953 954 955 956 957 958 959 960 961

5' GGCTGAAGCTACTAAAGCCATTATCAACTACCAGTATAATCAGTATACAGAAGAGGAAAAGAATAACATC 3010
3' CCGACTTCGATGATTTCGGTAATAGTTGATGGTCATATTAGTCATATGTCTTCTCCTTTTCTTATTGTAG

HC, Translocation Domain

A E A T K A I I N Y Q Y N Q Y T E E E K N N I
962 963 964 965 966 967 968 969 970 971 972 973 974 975 976 977 978 979 980 981 982 983 984

5' AATTTCAACATCGATGACTTGTCCTCAAAGCTGAACGAGTCCATCAACAAAGCTATGATCAACATCAACA 3080
3' TTAAAGTTGTAGCTACTGAACAGGAGTTTCGACTTGCTCAGGTAGTTGTTTCGATACTAGTTGTAGTTGT

HC, Translocation Domain

N F N I D D L S S K L N E S I N K A M I N I N
985 986 987 988 989 990 991 992 993 994 995 996 997 998 999 1000 1001 1002 1003 1004 1005 1006 1007

5' AATTCCTGAATCAGTGCTCCGTGTCTTACCTGATGAACTCTATGATCCCATACGGTGTGAAGCGCCTGGA 3150
3' TTAAGGACTTAGTCACGAGGCACAGAATGGACTACTTGAGATACTAGGGTATGCCACACTTCGCGGACCT

HC, Translocation Domain

K F L N Q C S V S Y L M N S M I P Y G V K R L E
1008 1009 1010 1011 1012 1013 1014 1015 1016 1017 1018 1019 1020 1021 1022 1023 1024 1025 1026 1027 1028 1029 1030 1031

5' GGACTTCGATGCCAGCCTGAAAGACGCACTGCTCAAATACATTTACGATAATCGCGGCACTTTGATTGGC 3220
3' CCTGAAGCTACGGTCGGACTTTCTGCGTGACGAGTTTATGTAAATGCTATTAGCGCCGTGAAACTAACCG

HC, Translocation Domain

D F D A S L K D A L L K Y I Y D N R G T L I G
1032 1033 1034 1035 1036 1037 1038 1039 1040 1041 1042 1043 1044 1045 1046 1047 1048 1049 1050 1051 1052 1053 1054

EcoRV

5' CAAGTTGACCGTCTGAAGGACAAGGTTAACAATACCTTGTCAACCGATATCCCCTTCCAACTCTCTAAGT 3290
3' GTTCAACTGGCAGACTTCCTGTTCCAATTGTTATGGAACAGTTGGCTATAGGGGAAGGTTGAGAGATTCA

HC, Translocation Domain

AfeI BlpI

5' ACGTCGATAACCAGCGCTTGCTGAGCACCTTCACAGAATACATCAACAACATCATCAACACCTCCATCCT 3360
3' TGCAGCTATTGGTCGCGAACGACTCGTGGAAGTGTCTTATGTAGTTGTTGTAGTAGTTGTGGAGGTAGGA

HC, Translocation Domain | K>N | HC, Receptor-Binding Domain

Y V D N Q R L L S T F T E Y I N N I I N T S I L
1078 1079 1080 1081 1082 1083 1084 1085 1086 1087 1088 1089 1090 1091 1092 1093 1094 1095 1096 1097 1098 1099 1100 1101

NheI BmtI BpuEI

5' GAACCTCCGTTACGAGTCTAACCACCTCATCGACTTGAGCAGATACGCTAGCAAGATCAACATCGGTTCC 3430
3' CTTGGAGGCAATGCTCAGATTGGTGGAGTAGCTGAACTCGTCTATGCGATCGTTCTAGTTGTAGCCAAGG

HC, Receptor-Binding Domain

N L R Y E S N H L I D L S R Y A S K I N I G S
1102 1103 1104 1105 1106 1107 1108 1109 1110 1111 1112 1113 1114 1115 1116 1117 1118 1119 1120 1121 1122 1123 1124

5' AAGGTGAACTTCGACCCAATCGATAAGAACCAGATCCAACTGTTCAACCTCGAATCCTCTAAGATCGAAG 3500
3' TTCCACTTGAAGCTGGGTTAGCTATTCTTGGTCTAGGTTGACAAGTTGGAGCTTAGGAGATTCTAGCTTC

HC, Receptor-Binding Domain

K V N F D P I D K N Q I Q L F N L E S S K I E
1125 1126 1127 1128 1129 1130 1131 1132 1133 1134 1135 1136 1137 1138 1139 1140 1141 1142 1143 1144 1145 1146 1147

5' TGATCCTGAAGAACGCTATCGTCTACAACTCCATGTACGAAAACTTCTCTACCAGCTTCTGGATCAGGAT 3570
3' ACTAGGACTTCTTGCGATAGCAGATGTTGAGGTACATGCTTTTGAAGAGATGGTCGAAGACCTAGTCCTA

HC, Receptor-Binding Domain

V I L K N A I V Y N S M Y E N F S T S F W I R I
1148 1149 1150 1151 1152 1153 1154 1155 1156 1157 1158 1159 1160 1161 1162 1163 1164 1165 1166 1167 1168 1169 1170 1171

5' TCCGAAATACTTCAACTCAATCTCGCTCAACAACGAGTACACTATCATCAACTGCATGGAAAACAACTCG 3640
3' AGGCTTTATGAAGTTGAGTTAGAGCGAGTTGTTGCTCATGTGATAGTAGTTGACGTACCTTTTGTTGAGC

HC, Receptor-Binding Domain

P K Y F N S I S L N N E Y T I I N C M E N N S
1172 1173 1174 1175 1176 1177 1178 1179 1180 1181 1182 1183 1184 1185 1186 1187 1188 1189 1190 1191 1192 1193 1194

5' GGATGGAAGGTGTCCCTCAACTACGGCGAGATCATCTGGACTTTGCAGGACACACAAGAAATCAAGCAGA 3710
3' CCTACCTTCCACAGGGAGTTGATGCCGCTCTAGTAGACCTGAAACGTCCTGTGTGTTCTTTAGTTCGTCT

HC, Receptor-Binding Domain

5' GGGTCGTGTTCAAGTACAGCCAAATGATCAACATCAGCGATTACATCAACCGTTGGATCTTCGTCACAAT 3780
3' CCCAGCACAAGTTCATGTCGGTTTACTAGTTGTAGTCGCTAATGTAGTTGGCAACCTAGAAGCAGTGTTA
HC, Receptor-Binding Domain
R V V F K Y S Q M I N I S D Y I N R W I F V T I
1218 1219 1220 1221 1222 1223 1224 1225 1226 1227 1228 1229 1230 1231 1232 1233 1234 1235 1236 1237 1238 1239 1240 1241

NmeAIII
5' CACCAACAACCGCCTGAACAACTCCAAGATTTACATCAACGGTAGACTGATCGACCAGAAGCCAATCAGC 3850
3' GTGGTTGTTGGCGGACTTGTTGAGGTTCTAAATGTAGTTGCCATCTGACTAGCTGGTCTTCGGTTAGTCG
HC, Receptor-Binding Domain
T N N R L N N S K I Y I N G R L I D Q K P I S
1242 1243 1244 1245 1246 1247 1248 1249 1250 1251 1252 1253 1254 1255 1256 1257 1258 1259 1260 1261 1262 1263 1264

5' AACCTCGGCAACATCCACGCCTCAAACAACATCATGTTCAAGTTGGACGGCTGTAGGGATACACACAGAT 3920
3' TTGGAGCCGTTGTAGGTGCGGAGTTTGTTGTAGTACAAGTTCAACCTGCCGACATCCCTATGTGTGTCTA
HC, Receptor-Binding Domain
N L G N I H A S N N I M F K L D G C R D T H R
1265 1266 1267 1268 1269 1270 1271 1272 1273 1274 1275 1276 1277 1278 1279 1280 1281 1282 1283 1284 1285 1286 1287

5' ACATCTGGATCAAATACTTCAACCTGTTCGACAAGGAGCTCAACGAGAAGGAAATCAAGGACCTCTACGA 3990
3' TGTAGACCTAGTTTATGAAGTTGGACAAGCTGTTCCTCGAGTTGCTCTTCCTTTAGTTCCTGGAGATGCT
HC, Receptor-Binding Domain
Y I W I K Y F N L F D K E L N E K E I K D L Y D
1288 1289 1290 1291 1292 1293 1294 1295 1296 1297 1298 1299 1300 1301 1302 1303 1304 1305 1306 1307 1308 1309 1310 1311

5' TAACCAGTCCAACTCTGGTATCTTGAAGGACTTCTGGGGCGATTACCTGCAATACGACAAGCCCTACTAC 4060
3' ATTGGTCAGGTTGAGACCATAGAACTTCCTGAAGACCCCGCTAATGGACGTTATGCTGTTCGGGATGATG
HC, Receptor-Binding Domain
N Q S N S G I L K D F W G D Y L Q Y D K P Y Y
1312 1313 1314 1315 1316 1317 1318 1319 1320 1321 1322 1323 1324 1325 1326 1327 1328 1329 1330 1331 1332 1333 1334

5' ATGTTGAACCTGTACGACCCTAACAAGTACGTTGATGTGAACAACGTCGGTATCAGGGGCTACATGTACC 4130
3' TACAACTTGGACATGCTGGGATTGTTCATGCAACTACACTTGTTGCAGCCATAGTCCCCGATGTACATGG
HC, Receptor-Binding Domain
M L N L Y D P N K Y V D V N N V G I R G Y M Y
1335 1336 1337 1338 1339 1340 1341 1342 1343 1344 1345 1346 1347 1348 1349 1350 1351 1352 1353 1354 1355 1356 1357

FIG. 20J

PmlI

5' TGAAGGGACCACGTGGTTCTGTTATGACCACTAACATCTACCTCAACAGCTCATTGTACCGTGGCACAAA 4200
3' ACTTCCCTGGTGCACCAAGACAATACTGGTGATTGTAGATGGAGTTGTCGAGTAACATGGCACCGTGTTT

HC, Receptor-Binding Domain

L K G P R G S V M T T N I Y L N S S L Y R G T K
1358 1359 1360 1361 1362 1363 1364 1365 1366 1367 1368 1369 1370 1371 1372 1373 1374 1375 1376 1377 1378 1379 1380 1381

BspEI DrdI PvuI

5' GTTCATCATCAAGAAGTACGCCTCCGGAAACAAGGACAACATCGTCCGTAACAACGATCGCGTTTACATC 4270
3' CAAGTAGTAGTTCTTCATGCGGAGGCCTTTGTTCCTGTTGTAGCAGGCATTGTTGCTAGCGCAAATGTAG

HC, Receptor-Binding Domain

F I I K K Y A S G N K D N I V R N N D R V Y I
1382 1383 1384 1385 1386 1387 1388 1389 1390 1391 1392 1393 1394 1395 1396 1397 1398 1399 1400 1401 1402 1403 1404

5' AACGTTGTGGTCAAGAACAAGGAGTACAGACTGGCTACCAACGCTTCGCAGGCTGGAGTTGAGAAGATCC 4340
3' TTGCAACACCAGTTCTTGTTCCTCATGTCTGACCGATGGTTGCGAAGCGTCCGACCTCAACTCTTCTAGG

HC, Receptor-Binding Domain

N V V V K N K E Y R L A T N A S Q A G V E K I
1405 1406 1407 1408 1409 1410 1411 1412 1413 1414 1415 1416 1417 1418 1419 1420 1421 1422 1423 1424 1425 1426 1427

BspHI

5' TGTCTGCTCTGGAAATCCCTGACGTGGGCAACCTCTCACAGGTTGTGGTCATGAAGTCGAAGAACGATCA 4410
3' ACAGACGAGACCTTTAGGGACTGCACCCGTTGGAGAGTGTCCAACACCAGTACTTCAGCTTCTTGCTAGT

HC, Receptor-Binding Domain

L S A L E I P D V G N L S Q V V V M K S K N D Q
1428 1429 1430 1431 1432 1433 1434 1435 1436 1437 1438 1439 1440 1441 1442 1443 1444 1445 1446 1447 1448 1449 1450 1451

5' AGGCATCACTAACAAGTGCAAGATGAACTTGCAGGACAACAACGGAAACGACATCGGCTTCATCGGATTC 4480
3' TCCGTAGTGATTGTTCACGTTCTACTTGAACGTCCTGTTGTTGCCTTTGCTGTAGCCGAAGTAGCCTAAG

HC, Receptor-Binding Domain

G I T N K C K M N L Q D N N G N D I G F I G F
1452 1453 1454 1455 1456 1457 1458 1459 1460 1461 1462 1463 1464 1465 1466 1467 1468 1469 1470 1471 1472 1473 1474

5' CACCAATTCAACAACATCGCCAAGTTGGTGGCCAGCAACTGGTACAACCGTCAGATCGAGCGTTCGTCCC 4550
3' GTGGTTAAGTTGTTGTAGCGGTTCAACCACCGGTCGTTGACCATGTTGGCAGTCTAGCTCGCAAGCAGGG

HC, Receptor-Binding Domain

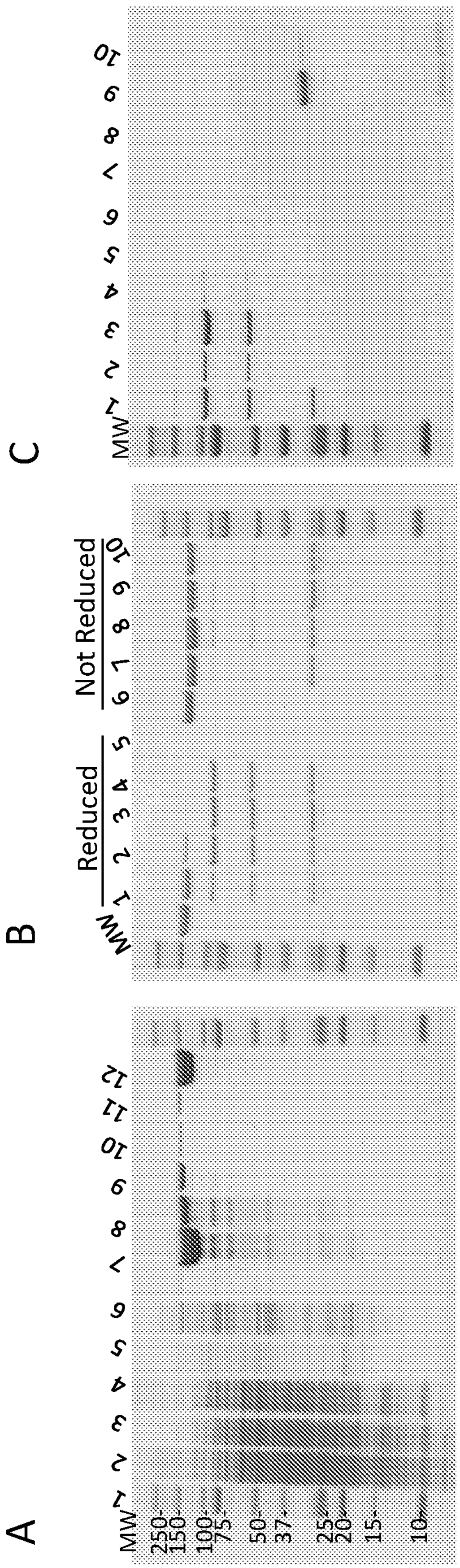
FIGs. 21A-C

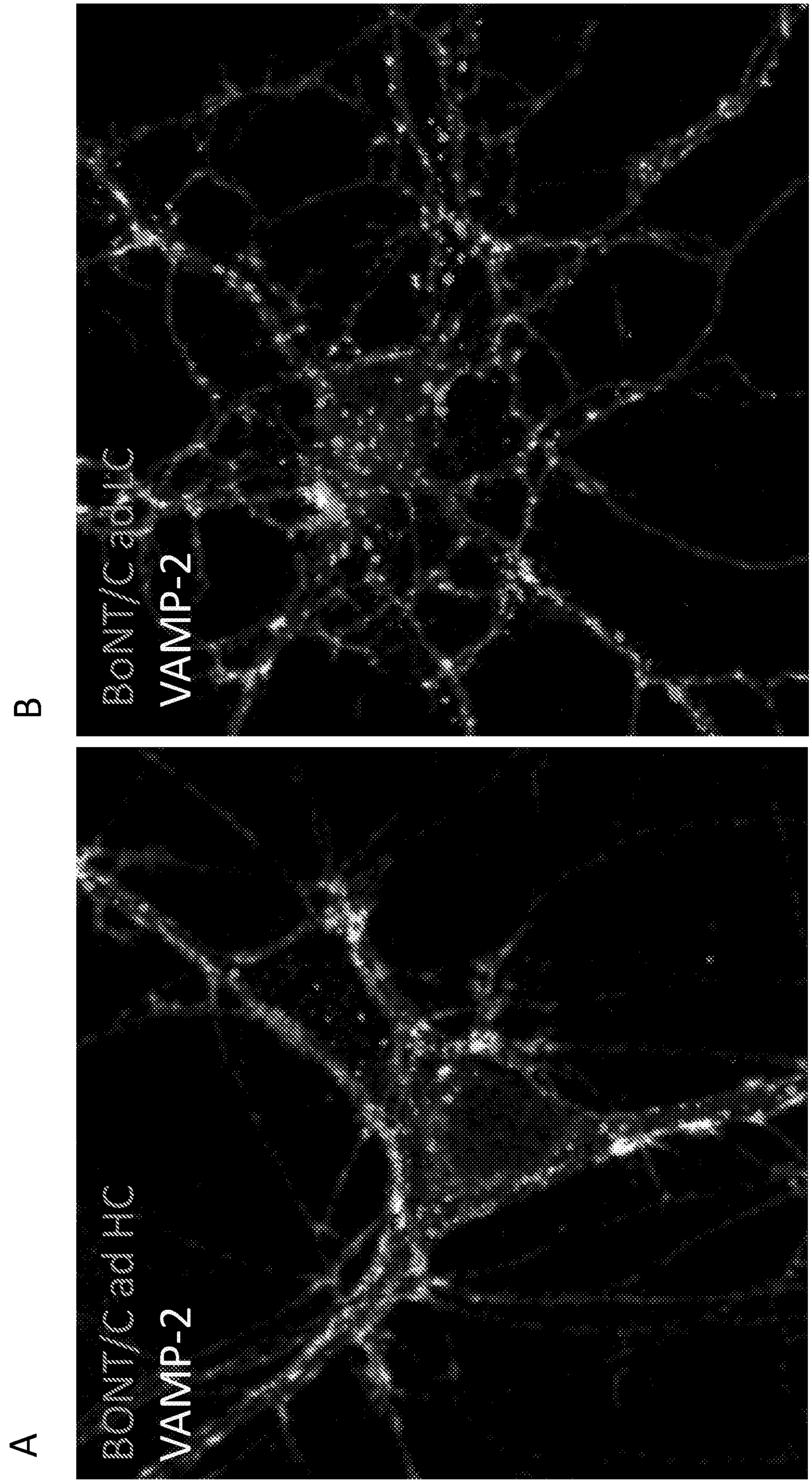
FIGs. 23A-B

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

5' CTTGATTAGGGTGATGGTTCACGTAGTGGGCCATCGCCCTGATAGACGGTTTTTCGCCCTTTGACGTTGG 280

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

5' TGCGGCCAACTTACTTCTGACAACGATCGGAGGACCGAAGGAGCTAACCGCTTTTTTGCACAACATGGGG 1050

5' GATCATGTAACTCGCCTTGATCGTTGGGAACCGGAGCTGAATGAAGCCATACCAAACGACGAGCGTGACA 1120

FIG. 33A

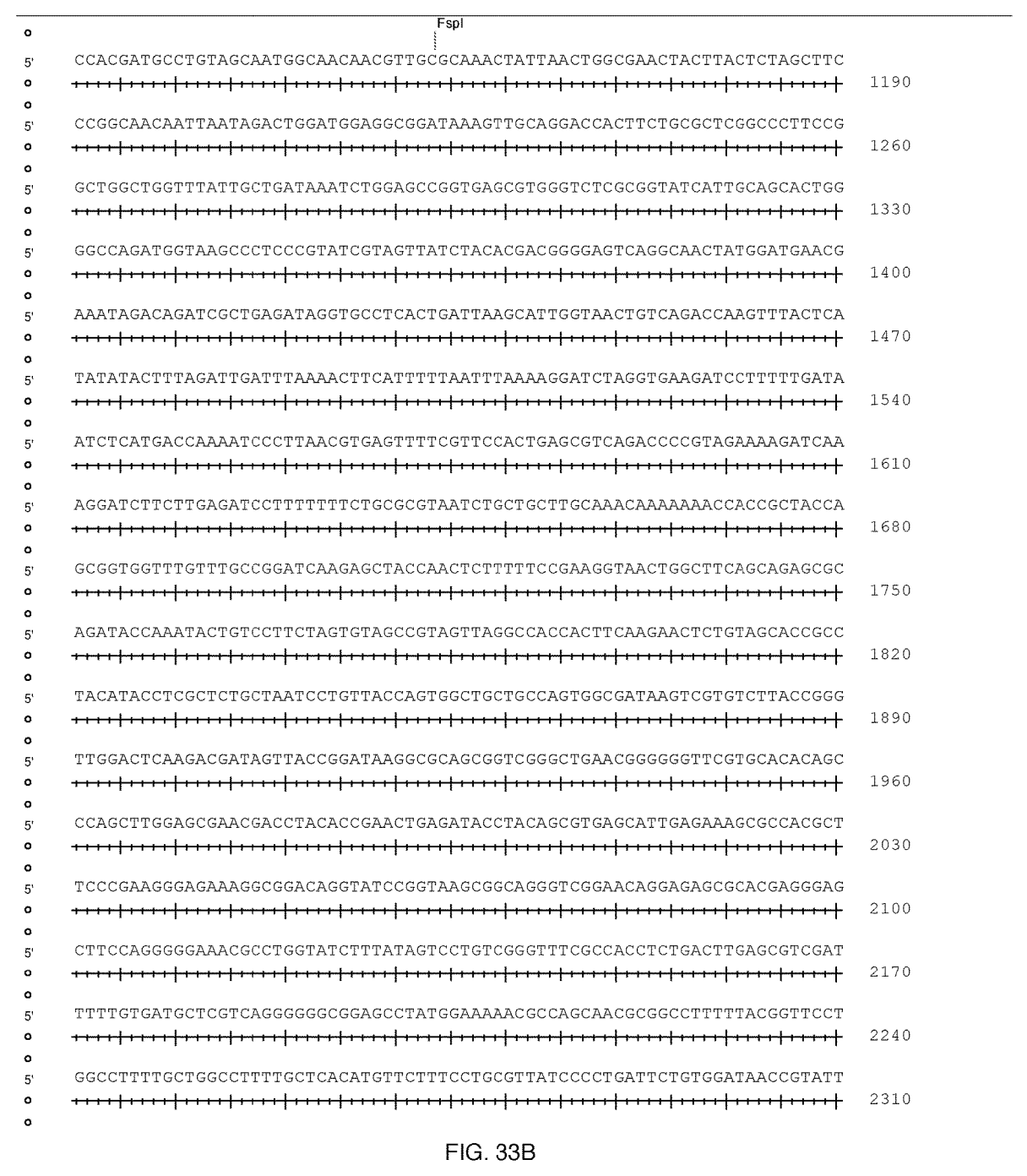

FspI

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

5' GGCCTTTTGCTGGCCTTTTGCTCACATGTTCTTTCCTGCGTTATCCCCTGATTCTGTGGATAACCGTATT 2310

FIG. 33B

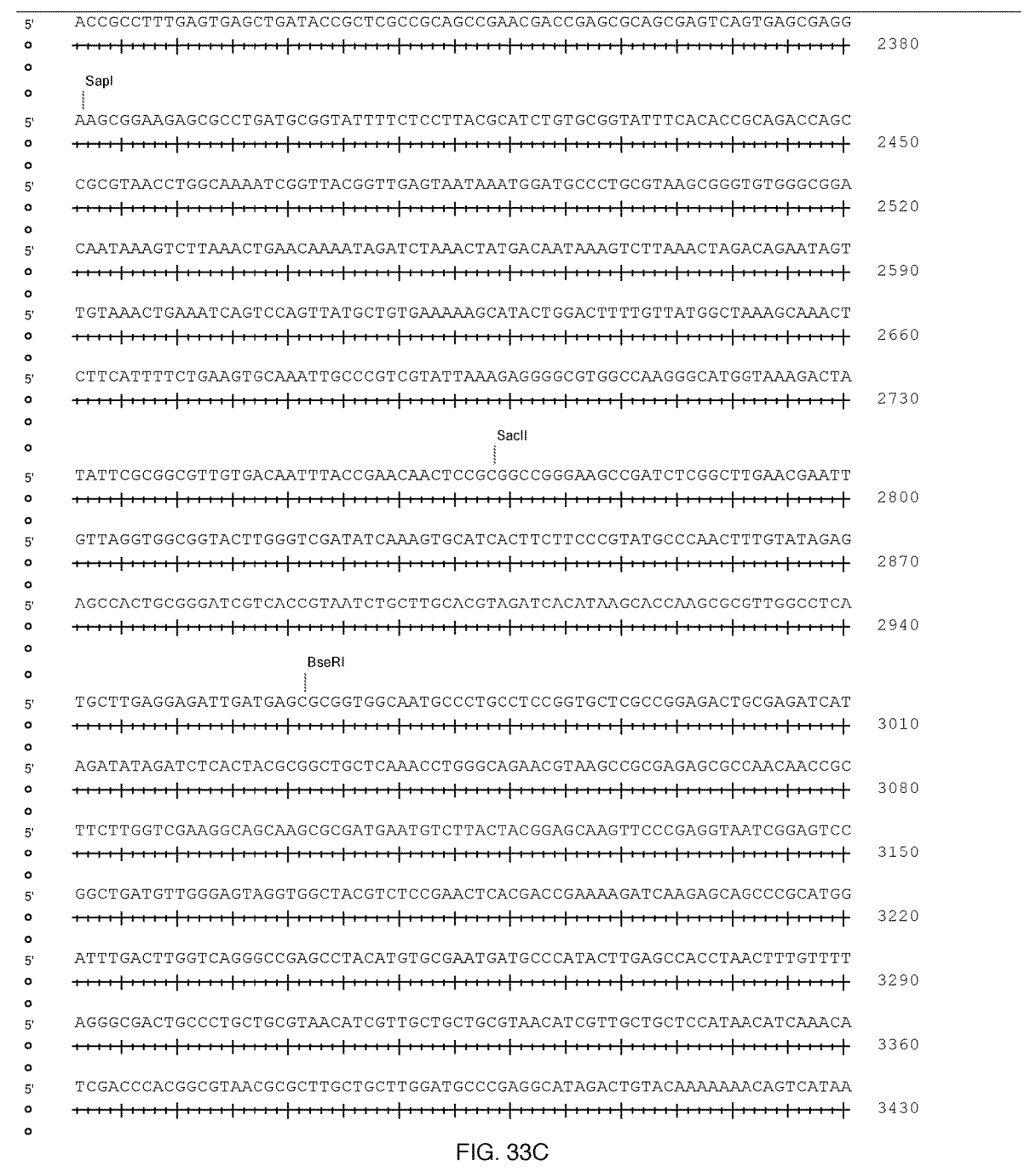

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

BseRI

5' TGCTTGAGGAGATTGATGAGCGCGGTGGCAATGCCCTGCCTCCGGTGCTCGCCGGAGACTGCGAGATCAT 3010

5' AGATATAGATCTCACTACGCGGCTGCTCAAACCTGGGCAGAACGTAAGCCGCGAGAGCGCCAACAACCGC 3080

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

FIG. 33C

```
5'  CAAGCCATGAAAACCGCCACTGCGCCGTTACCACCGCTGCGTTCGGTCAAGGTTCTGGACCAGTTGCGTG
                                                                              3500

5'  AGCGCATACGCTACTTGCATTACAGTTTACGAACCGAACAGGCTTATGTCAACTGGGTTCGTGCCTTCAT
                                                                              3570

5'  CCGTTTCCACGGTGTGCGTCACCCGGCAACCTTGGGCAGCAGCGAAGTCGAGGCATTTCTGTCCTGGCTG
                                                                              3640

5'  GCGAACGAGCGCAAGGTTTCGGTCTCCACGCATCGTCAGGCATTGGCGGCCTTGCTGTTCTTCTACGGCA
                                                                              3710

5'  AGGTGCTGTGCACGGATCTGCCCTGGCTTCAGGAGATCGGAAGACCTCGGCCGTCGCGGCGCTTGCCGGT
                                                                              3780

5'  GGTGCTGACCCCGGATGAAGTGGTTCGCATCCTCGGTTTTCTGGAAGGCGAGCATCGTTTGTTCGCCCAG
                                                                              3850
                                    SnaBI
5'  GACTCTAGCTATAGTTCTAGTGGTTGGCTACGTATACTCCGGAATATTAATAGATCATGGAGATAATTAA
                                                                              3920

5'  AATGATAACCATCTCGCAAATAAATAAGTATTTTACTGTTTTCGTAACAGTTTTGTAATAAAAAAACCTA
                                                                              3990
                                           BamHI   RsrII    BstBI
5'  TAAATATTCCGGATTATTCATACCGTCCCACCATCGGGCGCGGATCCCGGTCCGTTCGAACCAGAACTCT
                                                                              4060

5'  GGAAGCTTAACTCCTAAAAAACCGCCACCATGAAATTCTTAGTCAACGTTGCCCTTGTTTTTATGGTCGT
                                                                              4130
    [Lob. TMO cDNA Lead Seq]              [Signal Peptide
                                    M  K  F  L  V  N  V  A  L  V  F  M  V  V
                                    1  2  3  4  5  6  7  8  9  10 11 12 13 14

                                                                    ZraI
                                                                     AatII
5'  ATACATTTCTTACATCTATGCGGCCGGACACCACCACCACCACCACCACCACCACCACGACGTCTCG
                                                                              4200
    Signal Peptide]           [11 His tag]                        [linker][O..]
    Y  I  S  Y  I  Y  A  A  G  H  H  H  H  H  H  H  H  H  H  H  D  V  S
    15 16 17 18 19 20 21 22 23 24 25 26 27 28 29 30 31 32 33 34 35 36 37
```

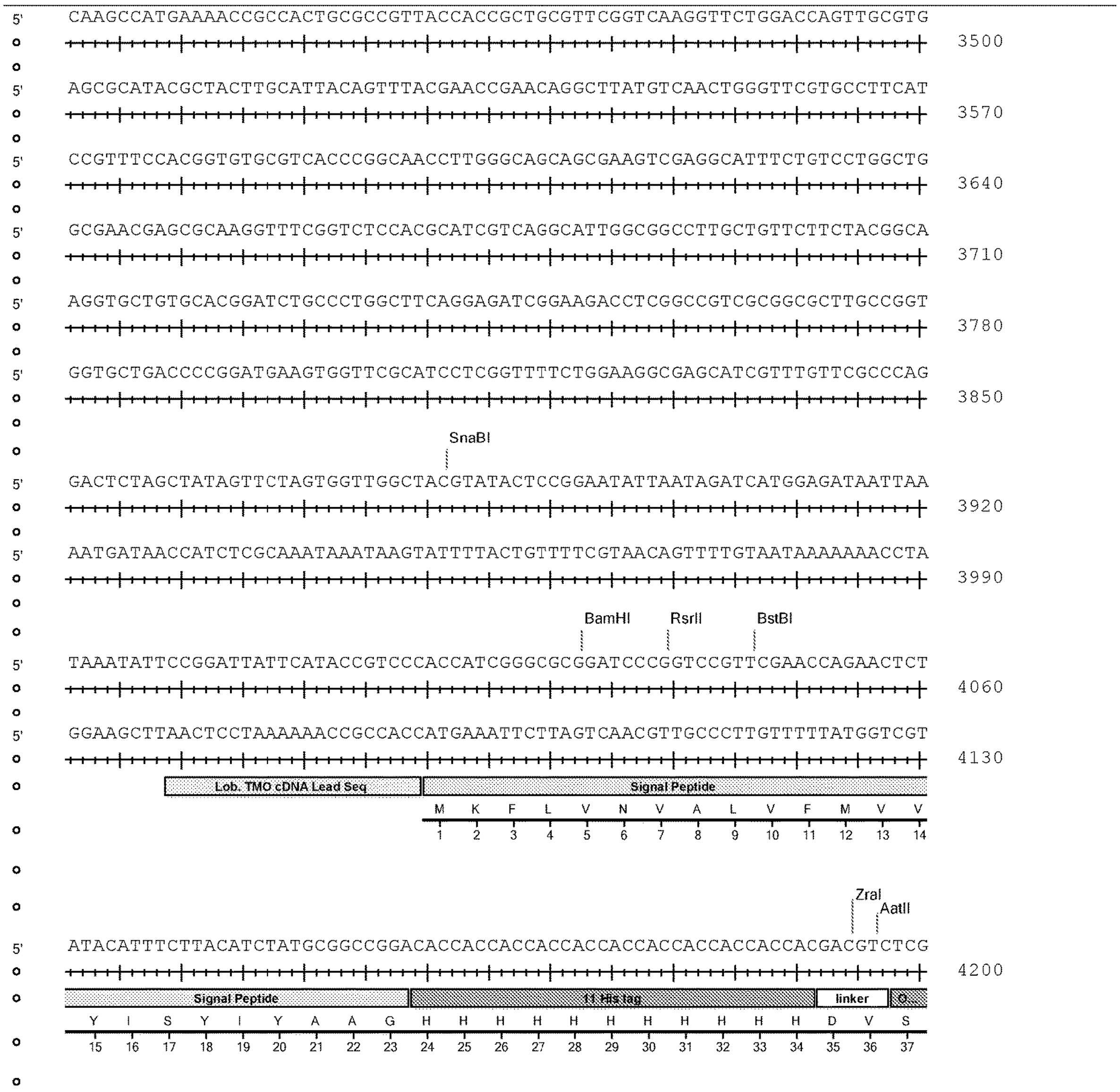

FIG. 33D

```
                                                                                    MluI
5'  GGCTTCGCTAACGAGCTGGGACCACGCCTGATGGGAAAAGGTGCAGGATGGGAACTCCAGCAAGCCACGC
                                                                                          4270
        [OLLAS tag]                          [linker]    [SpI B site]   [linker]
    G   F   A   N   E   L   G   P   R   L   M   G   K   G   A   G   W   E   L   Q   Q   A   T
    38  39  40  41  42  43  44  45  46  47  48  49  50  51  52  53  54  55  56  57  58  59  60

5'  GTGGAGCGGGAGCAGGTCCATTCGTCAACAAGCAATTCAACTACAAAGATCCTGTTAACGGTGTGGACAT
                                                                                          4340
        [linker]                       [BoNT/A ad0 LC]
    R   G   A   G   A   G   P   F   V   N   K   Q   F   N   Y   K   D   P   V   N   G   V   D   I
    61  62  63  64  65  66  67  68  69  70  71  72  73  74  75  76  77  78  79  80  81  82  83  84

5'  CGCCTACATCAaGATTCCGAACGCAGGCCAGATGCAACCTGTGAAGGCTTTCAAAATCCACAACAAGATC
                                                                                          4410
                                    [BoNT/A ad0 LC]
    A   Y   I   K   I   P   N   A   G   Q   M   Q   P   V   K   A   F   K   I   H   N   K   I
    85  86  87  88  89  90  91  92  93  94  95  96  97  98  99  100 101 102 103 104 105 106 107

                                                                                    AarI
5'  TGGGTCATTCCCGAGAGAGACACATTCACGAACCCAGAGGAAGGTGATCTGAACCCTCCCCCAGAAGCCA
                                                                                          4480
                                    [BoNT/A ad0 LC]
    W   V   I   P   E   R   D   T   F   T   N   P   E   E   G   D   L   N   P   P   P   E   A
    108 109 110 111 112 113 114 115 116 117 118 119 120 121 122 123 124 125 126 127 128 129 130

5'  AGCAGGTGCCGGTCTCTTACTACGATTCAACCTACCTCAGTACTGACAACGAGAAGGATAACTACCTGAA
                                                                                          4550
                                    [BoNT/A ad0 LC]
    K   Q   V   P   V   S   Y   Y   D   S   T   Y   L   S   T   D   N   E   K   D   N   Y   L   K
    131 132 133 134 135 136 137 138 139 140 141 142 143 144 145 146 147 148 149 150 151 152 153 154

5'  GGGCGTTACTAAACTCTTCGAGCGCATCTACTCGACAGACTTGGGCCGTATGCTGCTCACGTCCATCGTC
                                                                                          4620
                                    [BoNT/A ad0 LC]
    G   V   T   K   L   F   E   R   I   Y   S   T   D   L   G   R   M   L   L   T   S   I   V
    155 156 157 158 159 160 161 162 163 164 165 166 167 168 169 170 171 172 173 174 175 176 177

5'  AGGGGTATTCCTTTCTGGGGTGGCTCAACCATCGACACTGAGCTGAAGGTCATTGATACAAACTGCATCA
                                                                                          4690
                                    [BoNT/A ad0 LC]
    R   G   I   P   F   W   G   G   S   T   I   D   T   E   L   K   V   I   D   T   N   C   I
    178 179 180 181 182 183 184 185 186 187 188 189 190 191 192 193 194 195 196 197 198 199 200
```

FIG. 33E

```
5'  GAAGCGGCAATGTTCCTGGGATGGGTTGAACAACTGGTCTACGACTTCACCGACGAGACCTCTGAGGTGA
                                                                                    6160
                        BoNT/A Translocation Domain
     E   A   A   M   F   L   G   W   V   E   Q   L   V   Y   D   F   T   D   E   T   S   E   V
    668 669 670 671 672 673 674 675 676 677 678 679 680 681 682 683 684 685 686 687 688 689 690

5'  GCACAACGGACAAGATTGCTGACATCACTATCATTATCCCGTATATTGGACCTGCCTTGAATATTGGCAA
                                                                                    6230
                        BoNT/A Translocation Domain
     S   T   T   D   K   I   A   D   I   T   I   I   I   P   Y   I   G   P   A   L   N   I   G   N
    691 692 693 694 695 696 697 698 699 700 701 702 703 704 705 706 707 708 709 710 711 712 713 714

5'  CATGCTCTACAAAGACGATTTCGTTGGTGCCCTGATCTTCAGCGGTGCCGTGATCCTGTTGGAGTTCATT
                                                                                    6300
                        BoNT/A Translocation Domain
     M   L   Y   K   D   D   F   V   G   A   L   I   F   S   G   A   V   I   L   L   E   F   I
    715 716 717 718 719 720 721 722 723 724 725 726 727 728 729 730 731 732 733 734 735 736 737

5'  CCTGAAATCGCCATCCCTGTGCTGGGCACGTTCGCTCTGGTCTCATACATTGCGAATAARGTCTTGACCG
                                                                                    6370
                        BoNT/A Translocation Domain
     P   E   I   A   I   P   V   L   G   T   F   A   L   V   S   Y   I   A   N   K   V   L   T
    738 739 740 741 742 743 744 745 746 747 748 749 750 751 752 753 754 755 756 757 758 759 760

5'  TGCAGACAATCGATAATGCCCTCTCCAAACGTAACGAAAAATGGGACGAGGTCTACAAATACATCGTGAC
                                                                                    6440
                        BoNT/A Translocation Domain
     V   Q   T   I   D   N   A   L   S   K   R   N   E   K   W   D   E   V   Y   K   Y   I   V   T
    761 762 763 764 765 766 767 768 769 770 771 772 773 774 775 776 777 778 779 780 781 782 783 784

5'  CAAcTGGCTGGCAAAGGTTaACACCCAAATTGATCTGATCCGTAAGAAAATGAAGGAGGCTTTGGAGAAC
                                                                                    6510
                        BoNT/A Translocation Domain
     N   W   L   A   K   V   N   T   Q   I   D   L   I   R   K   K   M   K   E   A   L   E   N
    785 786 787 788 789 790 791 792 793 794 795 796 797 798 799 800 801 802 803 804 805 806 807

5'  CAGGCTGAAGCTACTAAAGCCATTATCAACTACCAGTATAATCAGTATACAGAAGAGGAAAAGAATAACA
                                                                                    6580
                        BoNT/A Translocation Domain
     Q   A   E   A   T   K   A   I   I   N   Y   Q   Y   N   Q   Y   T   E   E   E   K   N   N
    808 809 810 811 812 813 814 815 816 817 818 819 820 821 822 823 824 825 826 827 828 829 830
```

FIG. 33I

```
5'  TCAATTTCAACATCGATGACTTGTCCTCAAAGCTGAACGAGTCCATCAACAAAGCTATGATCAACATCAA
                                                                              6650
         BoNT/A Translocation Domain
      I  N  F  N  I  D  D  L  S  S  K  L  N  E  S  I  N  K  A  M  I  N  I  N
     831 832 833 834 835 836 837 838 839 840 841 842 843 844 845 846 847 848 849 850 851 852 853 854

5'  CAAATTCCTGAATCAGTGCTCCGTGTCTTACCTGATGAACTCTATGATCCCATACGGTGTGAAGCGCCTG
                                                                              6720
         BoNT/A Translocation Domain
      K  F  L  N  Q  C  S  V  S  Y  L  M  N  S  M  I  P  Y  G  V  K  R  L
     855 856 857 858 859 860 861 862 863 864 865 866 867 868 869 870 871 872 873 874 875 876 877

5'  GAGGACTTCGATGCCAGCCTGAAAGACGCACTGCTCAAATACATTTACGATAATCGCGGCACTTTGATTG
                                                                              6790
         BoNT/A Translocation Domain
      E  D  F  D  A  S  L  K  D  A  L  L  K  Y  I  Y  D  N  R  G  T  L  I
     878 879 880 881 882 883 884 885 886 887 888 889 890 891 892 893 894 895 896 897 898 899 900

5'  GCCAAGTTGACCGTCTGAAGGACAAGGTTAACAATACCTTGTCAACCGATATCCCCTTCCAACTCTCTAA
                                                                              6860
         BoNT/A Translocation Domain
      G  Q  V  D  R  L  K  D  K  V  N  N  T  L  S  T  D  I  P  F  Q  L  S  K
     901 902 903 904 905 906 907 908 909 910 911 912 913 914 915 916 917 918 919 920 921 922 923 924

                  AfeI    BlpI
5'  GTACGTCGATAACCAGCGCTTGCTGAGCACCTTCACAGAATACATCAACAACATCATCAACACCTCCATC
                                                                              6930
         BoNT/A Translocation Domain              BoNT/A Receptor-Binding Domain
      Y  V  D  N  Q  R  L  L  S  T  F  T  E  Y  I  N  N  I  I  N  T  S  I
     925 926 927 928 929 930 931 932 933 934 935 936 937 938 939 940 941 942 943 944 945 946 947

                                              NheI
                                                 BmtI
5'  CTGAACCTCCGTTACGAGTCTAACCACCTCATCGACTTGAGCAGATACGCTAGCAAGATCAACATCGGTT
                                                                              7000
         BoNT/A Receptor-Binding Domain
      L  N  L  R  Y  E  S  N  H  L  I  D  L  S  R  Y  A  S  K  I  N  I  G
     948 949 950 951 952 953 954 955 956 957 958 959 960 961 962 963 964 965 966 967 968 969 970

5'  CCAAGGTGAACTTCGACCCAATCGATAAGAACCAGATCCAACTGTTCAACCTCGAATCCTCTAAGATCGA
                                                                              7070
         BoNT/A Receptor-Binding Domain
      S  K  V  N  F  D  P  I  D  K  N  Q  I  Q  L  F  N  L  E  S  S  K  I  E
     971 972 973 974 975 976 977 978 979 980 981 982 983 984 985 986 987 988 989 990 991 992 993 994
```

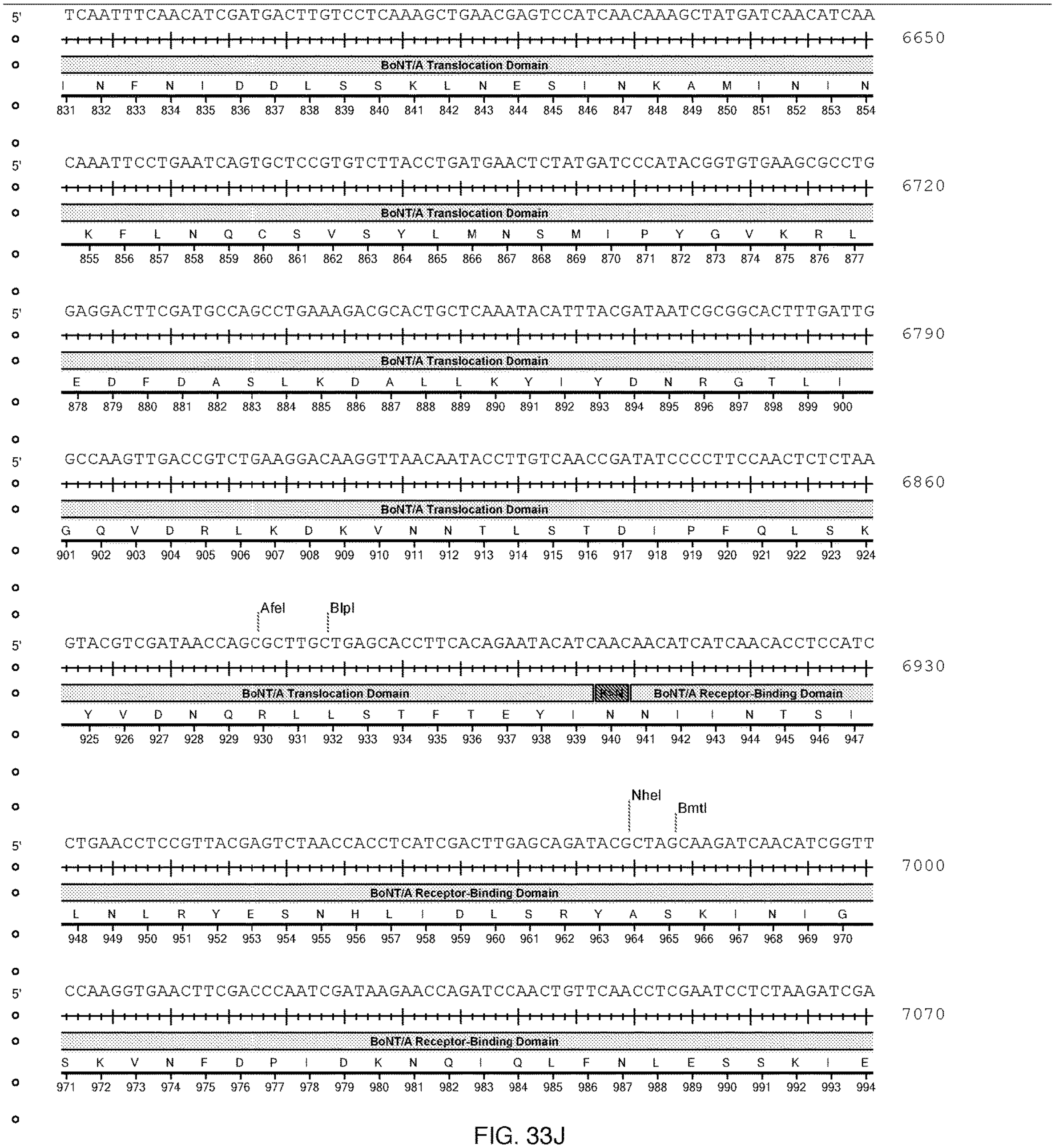

FIG. 33J

```
5'  AGTGATCCTGAAGAACGCTATCGTCTACAACTCCATGTACGAAAACTTCTCTACCAGCTTCTGGATCAGG
                                                                                    7140
                        BoNT/A Receptor-Binding Domain
     V   I   L   K   N   A   I   V   Y   N   S   M   Y   E   N   F   S   T   S   F   W   I   R
    995 996 997 998 999 1000 1001 1002 1003 1004 1005 1006 1007 1008 1009 1010 1011 1012 1013 1014 1015 1016 1017

                                                                              Tstl'
5'  ATTCCGAAATACTTCAACTCAATCTCGCTCAAcaACGAGTACACTATCATCAACTGCATGGAAAACAACT
                                                                                    7210
                        BoNT/A Receptor-Binding Domain
     I   P   K   Y   F   N   S   I   S   L   N   N   E   Y   T   I   I   N   C   M   E   N   N
    1018 1019 1020 1021 1022 1023 1024 1025 1026 1027 1028 1029 1030 1031 1032 1033 1034 1035 1036 1037 1038 1039 1040

                                    Tstl
5'  CGGGATGGAAGGTGTCCCTCAACTACGGCGAGATCATCTGGACTTTGCAGGACACACAAGAAATCAAGCA
                                                                                    7280
                        BoNT/A Receptor-Binding Domain
     S   G   W   K   V   S   L   N   Y   G   E   I   I   W   T   L   Q   D   T   Q   E   I   K   Q
    1041 1042 1043 1044 1045 1046 1047 1048 1049 1050 1051 1052 1053 1054 1055 1056 1057 1058 1059 1060 1061 1062 1063 1064

5'  GAGGGTCGTGTTCAAGTACAGCCAAATGATCAACATCAGCGATTACATCAACCGTTGGATCTTCGTCACA
                                                                                    7350
                        BoNT/A Receptor-Binding Domain
     R   V   V   F   K   Y   S   Q   M   I   N   I   S   D   Y   I   N   R   W   I   F   V   T
    1065 1066 1067 1068 1069 1070 1071 1072 1073 1074 1075 1076 1077 1078 1079 1080 1081 1082 1083 1084 1085 1086 1087

5'  ATCACCAACAACCGCCTGAACAaCTCCaAGATTTACATCAAcGGTAGACTGATCGACCAGAAGCCAATCA
                                                                                    7420
                        BoNT/A Receptor-Binding Domain
     I   T   N   N   R   L   N   N   S   K   I   Y   I   N   G   R   L   I   D   Q   K   P   I
    1088 1089 1090 1091 1092 1093 1094 1095 1096 1097 1098 1099 1100 1101 1102 1103 1104 1105 1106 1107 1108 1109 1110

5'  GCAACCTCGGCAACATCCACGCCTCAAACAACATCATGTTCAAGTTGGACGGCTGTAGGGATACACACAG
                                                                                    7490
                        BoNT/A Receptor-Binding Domain
     S   N   L   G   N   I   H   A   S   N   N   I   M   F   K   L   D   G   C   R   D   T   H   R
    1111 1112 1113 1114 1115 1116 1117 1118 1119 1120 1121 1122 1123 1124 1125 1126 1127 1128 1129 1130 1131 1132 1133 1134

                                                                              PpuMI
                                                                              EcoO109I
5'  ATACATCTGGATCAAATACTTCAACCTGTTCGACAAGGAGCTCAACGAGAAGGAAATCAAGGACCTCTAC
                                                                                    7560
                        BoNT/A Receptor-Binding Domain
     Y   I   W   I   K   Y   F   N   L   F   D   K   E   L   N   E   K   E   I   K   D   L   Y
    1135 1136 1137 1138 1139 1140 1141 1142 1143 1144 1145 1146 1147 1148 1149 1150 1151 1152 1153 1154 1155 1156 1157
```

FIG. 33K

```
5'  GATAACCAGTCCAACTCTGGTATCTTGAAGGACTTCTGGGGCGATTACCTGCAATACGACAAGCCCTACT
                                                                              7630
                          BoNT/A Receptor-Binding Domain
     D   N   Q   S   N   S   G   I   L   K   D   F   W   G   D   Y   L   Q   Y   D   K   P   Y
    1158 1159 1160 1161 1162 1163 1164 1165 1166 1167 1168 1169 1170 1171 1172 1173 1174 1175 1176 1177 1178 1179 1180

5'  ACATGTTGAACCTGTACGACCCTAACAAGTACGTTGATGTGAACAACGTCGGTATCAGGGGCTACATGTA
                                                                              7700
                          BoNT/A Receptor-Binding Domain
     Y   M   L   N   L   Y   D   P   N   K   Y   V   D   V   N   N   V   G   I   R   G   Y   M   Y
    1181 1182 1183 1184 1185 1186 1187 1188 1189 1190 1191 1192 1193 1194 1195 1196 1197 1198 1199 1200 1201 1202 1203 1204

                             PmlI
5'  cCTGAAGGGACCACGTGGTTCTGTTATGACCACTAACATCTACCTCAACAGCTCATTGTACCGTGGCACA
                                                                              7770
                          BoNT/A Receptor-Binding Domain
     L   K   G   P   R   G   S   V   M   T   T   N   I   Y   L   N   S   S   L   Y   R   G   T
    1205 1206 1207 1208 1209 1210 1211 1212 1213 1214 1215 1216 1217 1218 1219 1220 1221 1222 1223 1224 1225 1226 1227

5'  AAGTTCATCATCAAGAAGTACGCCTCCGGAAACAAGGACAACATCGTCCGTAACAACGATCGCGTTTACA
                                                                              7840
                          BoNT/A Receptor-Binding Domain
     K   F   I   I   K   K   Y   A   S   G   N   K   D   N   I   V   R   N   N   D   R   V   Y
    1228 1229 1230 1231 1232 1233 1234 1235 1236 1237 1238 1239 1240 1241 1242 1243 1244 1245 1246 1247 1248 1249 1250

5'  TCAACGTTGTGGTCAAGAACAAGGAGTACAGACTGGCTACCAACGCTTCGCAGGCTGGAGTTGAGAAGAT
                                                                              7910
                          BoNT/A Receptor-Binding Domain
     I   N   V   V   V   K   N   K   E   Y   R   L   A   T   N   A   S   Q   A   G   V   E   K   I
    1251 1252 1253 1254 1255 1256 1257 1258 1259 1260 1261 1262 1263 1264 1265 1266 1267 1268 1269 1270 1271 1272 1273 1274

                                                     EcoNI
5'  CCTGTCTGCTCTGGAAATCCCTGACGTGGGCAACCTCTCACAGGTTGTGGTCATGaAGTCGaAGaACGAT
                                                                              7980
                          BoNT/A Receptor-Binding Domain
     L   S   A   L   E   I   P   D   V   G   N   L   S   Q   V   V   M   K   S   K   N   D
    1275 1276 1277 1278 1279 1280 1281 1282 1283 1284 1285 1286 1287 1288 1289 1290 1291 1292 1293 1294 1295 1296 1297

5'  CAAGGCATCACTAACAAGTGCAAGATGAACTTGCAGGACAACAACGGAAACGACATCGGCTTCATCGGAT
                                                                              8050
                          BoNT/A Receptor-Binding Domain
     Q   G   I   T   N   K   C   K   M   N   L   Q   D   N   N   G   N   D   I   G   F   I   G
    1298 1299 1300 1301 1302 1303 1304 1305 1306 1307 1308 1309 1310 1311 1312 1313 1314 1315 1316 1317 1318 1319 1320
```

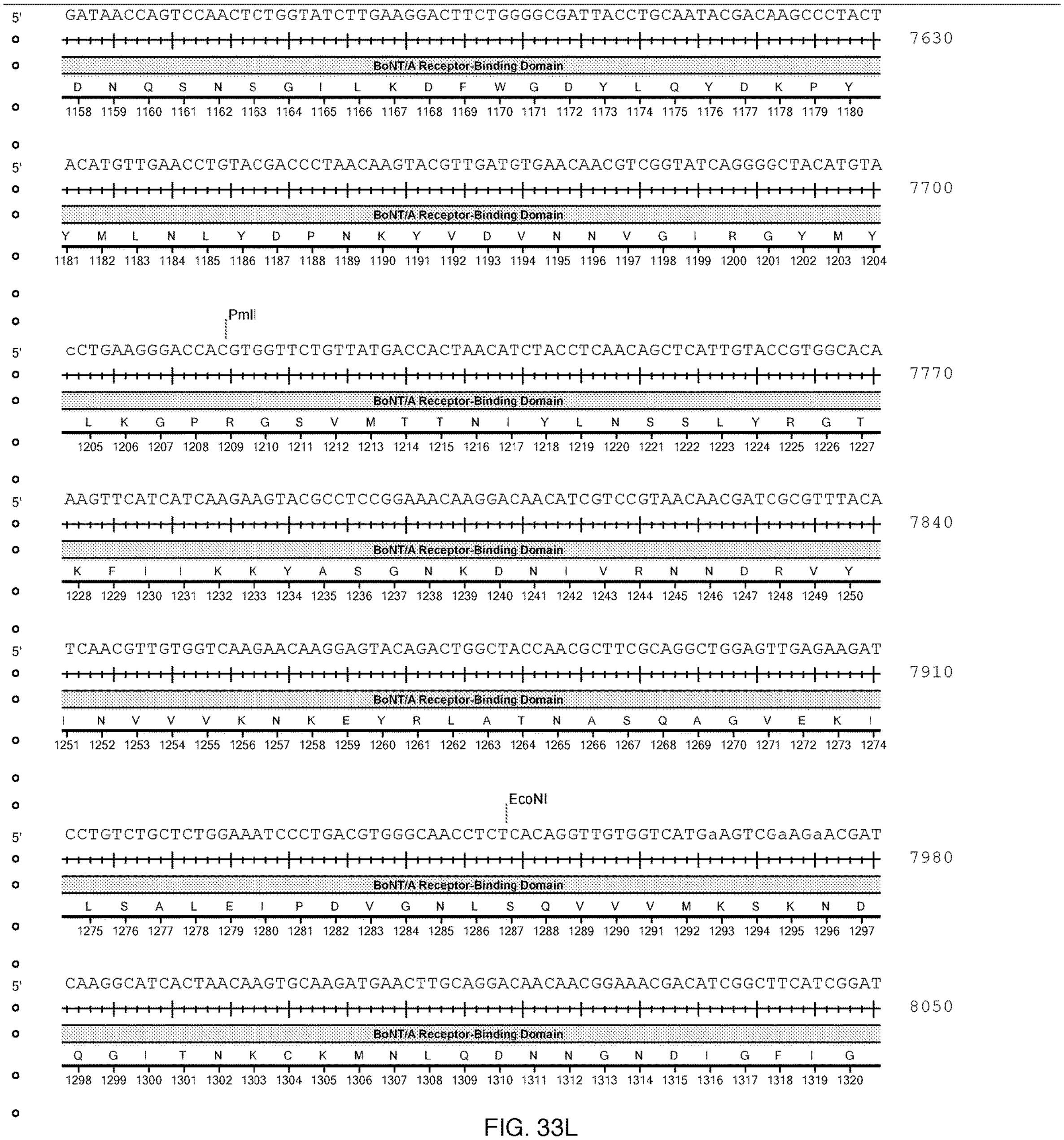

FIG. 33L

5' TCCACCAATTCAACAACATCGCCAAGTTGGTGGCCAGCAACTGGTACAACCGTCAGATCGAGCGTTCGTC 8120

BoNT/A Receptor-Binding Domain

F H Q F N N I A K L V A S N W Y N R Q I E R S S 1321 1322 1323 1324 1325 1326 1327 1328 1329 1330 1331 1332 1333 1334 1335 1336 1337 1338 1339 1340 1341 1342 1343 1344

Bsu36I

5' CCGCACCTTAGGATGCTCGTGGGAGTTCATTCCAGTCGATGACGGATGGGGAGAGAGACCTTTGGGCGCA 8190

BoNT/A Receptor-Binding Domain | linker

R T L G C S W E F I P V D D G W G E R P L G A 1345 1346 1347 1348 1349 1350 1351 1352 1353 1354 1355 1356 1357 1358 1359 1360 1361 1362 1363 1364 1365 1366 1367

BstEII

5' GGAGGATGGGAACTCCAGCAAGGTTACCCCTACGATGTCCCTGACTACGCTGGTGCAGGATGGTCCCACC 8260 linker | Spl B site | linker | HA tag | linker | Strep tag II

G G W E L Q Q G Y P Y D V P D Y A G A G W S H 1368 1369 1370 1371 1372 1373 1374 1375 1376 1377 1378 1379 1380 1381 1382 1383 1384 1385 1386 1387 1388 1389 1390

5' CACAATTCGAGAAGGGTGCAGGATGGAGTCACCCACAGTTCGAGAAGGGCGCTGGATGGTCCCACCCACA 8330

Strep tag II | linker | Strep tag II | linker | Strep tag II

P Q F E K G A G W S H P Q F E K G A G W S H P Q 1391 1392 1393 1394 1395 1396 1397 1398 1399 1400 1401 1402 1403 1404 1405 1406 1407 1408 1409 1410 1411 1412 1413 1414

NsiI PspXI XhoI SphI Acc65I KpnI

5' GTTCGAGAAATAATTAGTTGATGCATAGTTAATTAGATAGCTCGAGGCATGCGGTACCAAGCTTGTCGAG 8400

Strep tag II

F E K 1415 1416 1417

5' AAGTACTAGAGGATCATAATCAGCCATACCACATTTGTAGAGGTTTTACTTGCTTTAAAAAACCTCCCAC 8470

MfeI

5' ACCTCCCCCTGAACCTGAAACATAAAATGAATGCAATTGTTGTTGTTAACTTGTTTATTGCAGCTTATAA 8540

5' TGGTTACAAATAAAGCAATAGCATCACAAATTTCACAAATAAAGCATTTTTTTCACTGCATTCTAGTTGT 8610

FIG. 33M

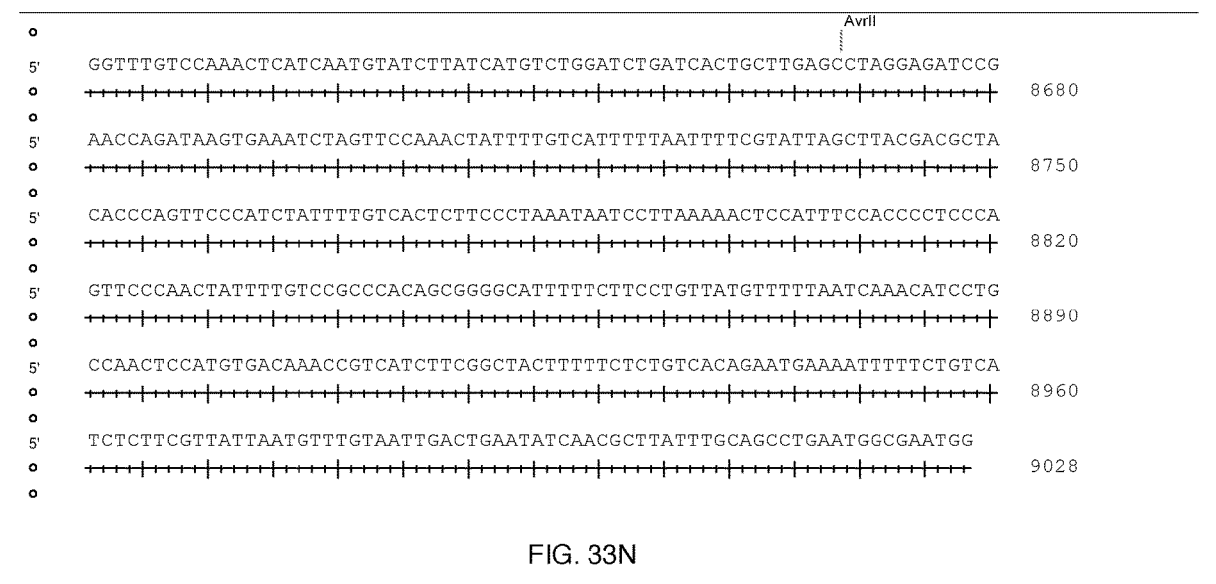

AvrII

5' GGTTTGTCCAAACTCATCAATGTATCTTATCATGTCTGGATCTGATCACTGCTTGAGCCTAGGAGATCCG 8680

5' AACCAGATAAGTGAAATCTAGTTCCAAACTATTTTGTCATTTTTAATTTTCGTATTAGCTTACGACGCTA 8750

5' CACCCAGTTCCCATCTATTTTGTCACTCTTCCCTAAATAATCCTTAAAAACTCCATTTCCACCCCTCCCA 8820

5' GTTCCCAACTATTTTGTCCGCCCACAGCGGGGCATTTTTCTTCCTGTTATGTTTTTAATCAAACATCCTG 8890

5' CCAACTCCATGTGACAAACCGTCATCTTCGGCTACTTTTTCTCTGTCACAGAATGAAAATTTTTCTGTCA 8960

5' TCTCTTCGTTATTAATGTTTGTAATTGACTGAATATCAACGCTTATTTGCAGCCTGAATGGCGAATGG 9028

FIG. 33N

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 34A

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 34B

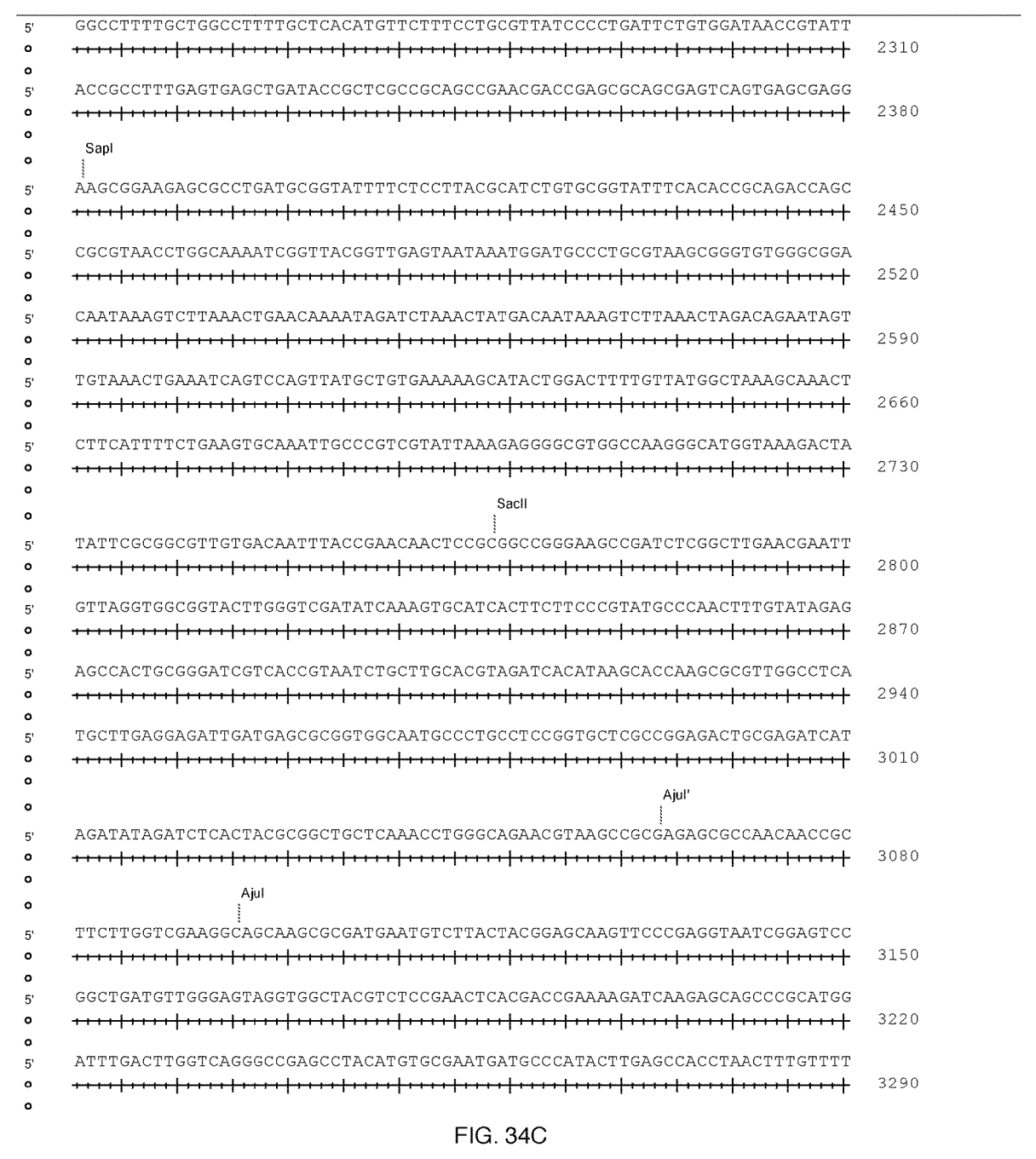

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 34C

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

BamHI RsrII

5' TAAATATTCCGGATTATTCATACCGTCCCACCATCGGGCGCGGATCCCGGTCCGTTCGAACCAGAACTCT 4060

5' GGAAGCTTAACTCCTAAAAAACCGCCACCATGAAATTCTTAGTCAACGTTGCCCTTGTTTTTATGGTCGT 4130

Lob. TMO cDNA Lead Seq | Signal Peptide

M K F L V N V A L V F M V V 1 2 3 4 5 6 7 8 9 10 11 12 13 14

BstZ17I ZraI AatII

5' ATACATTTCTTACATCTATGCGGCCGGACACCACCACCACCACCACCACCACCACCACCACGACGTCTCG 4200

Signal Peptide | 11 His tag | linker | Q...

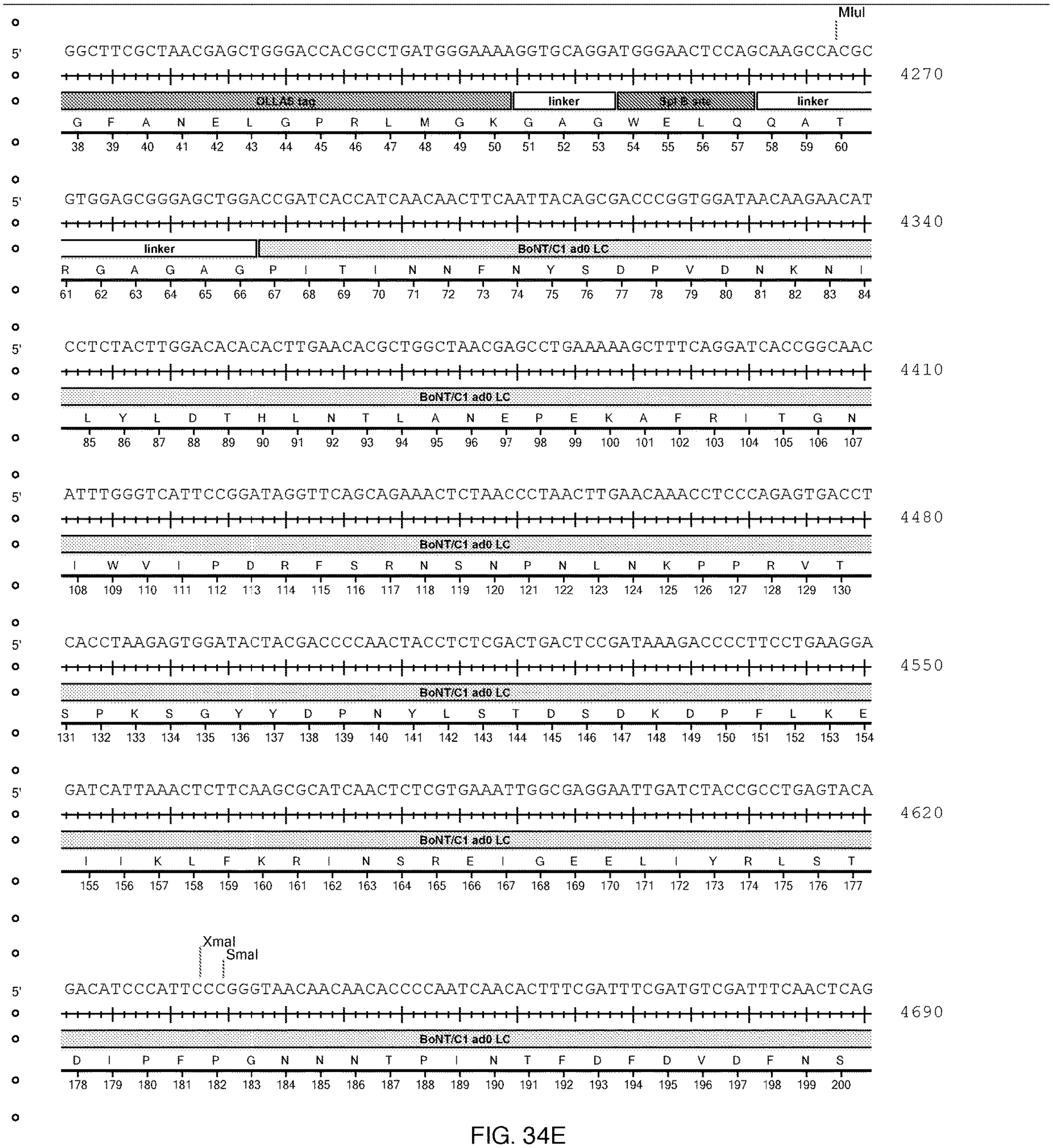

FIG. 34E

```
                                                                        MluI
5' GGCTTCGCTAACGAGCTGGGACCACGCCTGATGGGAAAAGGTGCAGGATGGGAACTCCAGCAAGCCACGC
   +++++++++++++++++++++++++++++++++++++++++++++++++++++++++++++++++++++  4270
           OLLAS tag                    linker         SpR site    linker
    G  F  A  N  E  L  G  P  R  L  M  G  K  G  A  G  W  E  L  Q  Q  A  T
    38 39 40 41 42 43 44 45 46 47 48 49 50 51 52 53 54 55 56 57 58 59 60

5' GTGGAGCGGGAGCTGGACCGATCACCATCAACAACTTCAATTACAGCGACCCGGTGGATAACAAGAACAT
   +++++++++++++++++++++++++++++++++++++++++++++++++++++++++++++++++++++  4340
           linker                       BoNT/C1 ad0 LC
    R  G  A  G  A  G  P  I  T  I  N  N  F  N  Y  S  D  P  V  D  N  K  N  I
    61 62 63 64 65 66 67 68 69 70 71 72 73 74 75 76 77 78 79 80 81 82 83 84

5' CCTCTACTTGGACACACACTTGAACACGCTGGCTAACGAGCCTGAAAAAGCTTTCAGGATCACCGGCAAC
   +++++++++++++++++++++++++++++++++++++++++++++++++++++++++++++++++++++  4410
                              BoNT/C1 ad0 LC
    L  Y  L  D  T  H  L  N  T  L  A  N  E  P  E  K  A  F  R  I  T  G  N
    85 86 87 88 89 90 91 92 93 94 95 96 97 98 99 100 101 102 103 104 105 106 107

5' ATTTGGGTCATTCCGGATAGGTTCAGCAGAAACTCTAACCCTAACTTGAACAAACCTCCCAGAGTGACCT
   +++++++++++++++++++++++++++++++++++++++++++++++++++++++++++++++++++++  4480
                              BoNT/C1 ad0 LC
    I  W  V  I  P  D  R  F  S  R  N  S  N  P  N  L  N  K  P  P  R  V  T
    108 109 110 111 112 113 114 115 116 117 118 119 120 121 122 123 124 125 126 127 128 129 130

5' CACCTAAGAGTGGATACTACGACCCCAACTACCTCTCGACTGACTCCGATAAAGACCCCTTCCTGAAGGA
   +++++++++++++++++++++++++++++++++++++++++++++++++++++++++++++++++++++  4550
                              BoNT/C1 ad0 LC
    S  P  K  S  G  Y  Y  D  P  N  Y  L  S  T  D  S  D  K  D  P  F  L  K  E
    131 132 133 134 135 136 137 138 139 140 141 142 143 144 145 146 147 148 149 150 151 152 153 154

5' GATCATTAAACTCTTCAAGCGCATCAACTCTCGTGAAATTGGCGAGGAATTGATCTACCGCCTGAGTACA
   +++++++++++++++++++++++++++++++++++++++++++++++++++++++++++++++++++++  4620
                              BoNT/C1 ad0 LC
    I  I  K  L  F  K  R  I  N  S  R  E  I  G  E  E  L  I  Y  R  L  S  T
    155 156 157 158 159 160 161 162 163 164 165 166 167 168 169 170 171 172 173 174 175 176 177

                  XmaI
                  SmaI
5' GACATCCCATTCCCGGGTAACAACAACACCCCAATCAACACTTTCGATTTCGATGTCGATTTCAACTCAG
   +++++++++++++++++++++++++++++++++++++++++++++++++++++++++++++++++++++  4690
                              BoNT/C1 ad0 LC
    D  I  P  F  P  G  N  N  N  T  P  I  N  T  F  D  F  D  V  D  F  N  S
    178 179 180 181 182 183 184 185 186 187 188 189 190 191 192 193 194 195 196 197 198 199 200
```

5' GGCCATCGACGGTCAGTCTCTAGACCAAGGAGGATGGGAACTCCAGCAAGGTGGCCAGGGTGGAGGTGCT 5670
BoNT/C1 ad0 LC | LC/HC spacer | Spl B site | LC/HC spacer
A I D G Q S L D Q G G W E L Q Q G G Q G G G A
505 506 507 508 509 510 511 512 513 514 515 516 517 518 519 520 521 522 523 524 525 526 527

5' GGCACCCTGGACTGTCGCGAACTGCTCGTTAAGAACACTGATCTCCCATTCATTGGCGACATCTCTGATG 5740
L...r | BoNT/C1 Translocation Domain
G T L D C R E L L V K N T D L P F I G D I S D
528 529 530 531 532 533 534 535 536 537 538 539 540 541 542 543 544 545 546 547 548 549 550

5' TGAAAACAGACATTTTCCTGCGTAAGGATATCAACGAGGAAACGGAGGTCATCTACTACCCTGACAACGT 5810
BoNT/C1 Translocation Domain
V K T D I F L R K D I N E E T E V I Y Y P D N V
551 552 553 554 555 556 557 558 559 560 561 562 563 564 565 566 567 568 569 570 571 572 573 574

5' CTCGGTTGATCAGGTTATCTTGTCAAAGAACACCAGTGAACATGGCCAACTGGACTTGCTGTACCCCTCA 5880
BoNT/C1 Translocation Domain
S V D Q V I L S K N T S E H G Q L D L L Y P S
575 576 577 578 579 580 581 582 583 584 585 586 587 588 589 590 591 592 593 594 595 596 597

SexAI
5' ATTGATTCCGAGAGCGAAATCCTGCCAGGAGAGAACCAGGTTTTCTACGACAACAGGACACAAAACGTGG 5950
BoNT/C1 Translocation Domain
I D S E S E I L P G E N Q V F Y D N R T Q N V
598 599 600 601 602 603 604 605 606 607 608 609 610 611 612 613 614 615 616 617 618 619 620

5' ATTACCTCAACAGCTACTACTACCTGGAGTCGCAGAAGCTCTCCGACAACGTCGAAGATTTCACATTTAC 6020
BoNT/C1 Translocation Domain
D Y L N S Y Y Y L E S Q K L S D N V E D F T F T
621 622 623 624 625 626 627 628 629 630 631 632 633 634 635 636 637 638 639 640 641 642 643 644

5' GAGATCAATCGAGGAGGCTTTGGACAACAGTGCCAAAGTCTACACCTACTTCCCTACTCTGGCAAACAAG 6090
BoNT/C1 Translocation Domain
R S I E E A L D N S A K V Y T Y F P T L A N K
645 646 647 648 649 650 651 652 653 654 655 656 657 658 659 660 661 662 663 664 665 666 667

FIG. 34H

```
5'  GTGAACGCGGGTGTCCAAGGCGGACTCTTCTTGATGTGGGCTAACGACGTTGTGGAAGATTTCACAACGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6160
                        BoNT/C1 Translocation Domain
     V   N   A   G   V   Q   G   G   L   F   L   M   W   A   N   D   V   V   E   D   F   T   T
    668 669 670 671 672 673 674 675 676 677 678 679 680 681 682 683 684 685 686 687 688 689 690

5'  ACATCTTGCGCAAAGACACCCTGGATAAGATCAGCGATGTCTCTGCCATCATTCCATACATTGGCCCGGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6230
                        BoNT/C1 Translocation Domain
     N   I   L   R   K   D   T   L   D   K   I   S   D   V   S   A   I   I   P   Y   I   G   P   A
    691 692 693 694 695 696 697 698 699 700 701 702 703 704 705 706 707 708 709 710 711 712 713 714

5'  ACTGAACATCTCTAACTCAGTTCGCCGTGGCAACTTCACTGAGGCATTCGCGGTCACAGGAGTTACGATC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6300
                        BoNT/C1 Translocation Domain
     L   N   I   S   N   S   V   R   R   G   N   F   T   E   A   F   A   V   T   G   V   T   I
    715 716 717 718 719 720 721 722 723 724 725 726 727 728 729 730 731 732 733 734 735 736 737

                    PfoI
5'  CTCTTGGAGGCTTTCCCGGAGTTCACAATCCCCGCACTGGGCGCGTTCGTTATCTACTCCAAAGTGCAGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6370
                        BoNT/C1 Translocation Domain
     L   L   E   A   F   P   E   F   T   I   P   A   L   G   A   F   V   I   Y   S   K   V   Q
    738 739 740 741 742 743 744 745 746 747 748 749 750 751 752 753 754 755 756 757 758 759 760

                                                                                    BsiWI
5'  AGCGCAACGAAATCATTAAGACTATCGACAACTGCCTGGAGCAAAGGATCAAAAGATGGAAGGATTCGTA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6440
                        BoNT/C1 Translocation Domain
     E   R   N   E   I   I   K   T   I   D   N   C   L   E   Q   R   I   K   R   W   K   D   S   Y
    761 762 763 764 765 766 767 768 769 770 771 772 773 774 775 776 777 778 779 780 781 782 783 784

5'  CGAATGGATGATGGGTACCTGGCTCTCCCGTATCATTACGCAGTTCAACAACATCAGCTACCAAATGTAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6510
                        BoNT/C1 Translocation Domain
     E   W   M   M   G   T   W   L   S   R   I   I   T   Q   F   N   N   I   S   Y   Q   M   Y
    785 786 787 788 789 790 791 792 793 794 795 796 797 798 799 800 801 802 803 804 805 806 807

                                                XcmI
5'  GACTCTCTCAACTACCAGGCTGGTGCCATCAAGGCCAAAATTGACTTGGAGTACAAGAAATACAGTGGCT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6580
                        BoNT/C1 Translocation Domain
     D   S   L   N   Y   Q   A   G   A   I   K   A   K   I   D   L   E   Y   K   K   Y   S   G
    808 809 810 811 812 813 814 815 816 817 818 819 820 821 822 823 824 825 826 827 828 829 830
```

FIG. 34I

5' CGGATAAAGAGAACATCAAGAGTCAAGTCGAAAaCCTGAAAAACTCACTCGACGTTAAGATCAGTGAGGC 6650
BoNT/C1 Translocation Domain
S D K E N I K S Q V E N L K N S L D V K I S E A
831 832 833 834 835 836 837 838 839 840 841 842 843 844 845 846 847 848 849 850 851 852 853 854

5' AATGAACAACATCAACAAGTTCATTCGCGAATGTTCCGTTACCTACCTCTTCAAAAACATGTTGCCAAAG 6720
BoNT/C1 Translocation Domain
M N N I N K F I R E C S V T Y L F K N M L P K
855 856 857 858 859 860 861 862 863 864 865 866 867 868 869 870 871 872 873 874 875 876 877

5' GTCATCGACGAGCTGAACGAATTTGATCGTAACACTAAGGCGAAACTGATTAACCTCATCGACTCACACA 6790
BoNT/C1 Translocation Domain
V I D E L N E F D R N T K A K L I N L I D S H
878 879 880 881 882 883 884 885 886 887 888 889 890 891 892 893 894 895 896 897 898 899 900

5' ACATCATTTTGGTGGGCGAAGTCGATAAGCTGAAAGCCAAGGtGAACAACAGTTTCCAGAACACAATCCC 6860
BoNT/C1 Translocation Domain
N I I L V G E V D K L K A K V N N S F Q N T I P
901 902 903 904 905 906 907 908 909 910 911 912 913 914 915 916 917 918 919 920 921 922 923 924

5' TTTCAAcATTTTCTCATACACGAACAACAGTCTGCTCAAGGACATCATTAACGAGTACTTCAACAACATT 6930
BoNT/C1 Translocation Domain | BoNT/C...omain
F N I F S Y T N N S L L K D I I N E Y F N N I
925 926 927 928 929 930 931 932 933 934 935 936 937 938 939 940 941 942 943 944 945 946 947

PstI SpeI
5' AACGATAGCAAAATCCTGTCACTGCAGAACCGTAAGAACACACTGGTCGATACTAGTGGATACAACGCCG 7000
BoNT/C1 Receptor Binding Domain
N D S K I L S L Q N R K N T L V D T S G Y N A
948 949 950 951 952 953 954 955 956 957 958 959 960 961 962 963 964 965 966 967 968 969 970

PvuII
5' AAGTCTCTGAGGAAGGTGACGTGCAGCTGAACCCTATCTTCCCCTTCGACTTCAAATTGGGCTCCAGCGG 7070
BoNT/C1 Receptor Binding Domain
E V S E E G D V Q L N P I F P F D F K L G S S G
971 972 973 974 975 976 977 978 979 980 981 982 983 984 985 986 987 988 989 990 991 992 993 994

FIG. 34J

```
5'  AGAGGATAGGGGCAAGGTCATCGTCACCCAGAACGAGAACATCGTCTACAACTCAATGTACGAATCCTTC
    ++++++++++++++++++++++++++++++++++++++++++++++++++++++++++++++++++++++  7140
                           BoNT/C1 Receptor Binding Domain
       E   D   R   G   K   V   I   V   T   Q   N   E   N   I   V   Y   N   S   M   Y   E   S   F
      995 996 997 998 999 1000 1001 1002 1003 1004 1005 1006 1007 1008 1009 1010 1011 1012 1013 1014 1015 1016 1017
```

BspMI

```
5'  AGCATCTCTTTCTGGATCAGGATTAACAAGTGGGTGAGCAACCTGCCCGGTTACACAATCATTGACTCTG
    ++++++++++++++++++++++++++++++++++++++++++++++++++++++++++++++++++++++  7210
                           BoNT/C1 Receptor Binding Domain
       S   I   S   F   W   I   R   I   N   K   W   V   S   N   L   P   G   Y   T   I   I   D   S
      1018 1019 1020 1021 1022 1023 1024 1025 1026 1027 1028 1029 1030 1031 1032 1033 1034 1035 1036 1037 1038 1039 1040

5'  TCAAGAACAACTCAGGTTGGAGTATCGGCATCATTTCTAACTTCTTGGTCTTCACCCTGAAGCAGAACGA
    ++++++++++++++++++++++++++++++++++++++++++++++++++++++++++++++++++++++  7280
                           BoNT/C1 Receptor Binding Domain
       V   K   N   N   S   G   W   S   I   G   I   I   S   N   F   L   V   F   T   L   K   Q   N   E
      1041 1042 1043 1044 1045 1046 1047 1048 1049 1050 1051 1052 1053 1054 1055 1056 1057 1058 1059 1060 1061 1062 1063 1064

5'  GGACTCGGAACAATCCATTAACTTCTCATACGATATCAGTAACAACGCTCCAGGTTACAACAAGTGGTTC
    ++++++++++++++++++++++++++++++++++++++++++++++++++++++++++++++++++++++  7350
                           BoNT/C1 Receptor Binding Domain
       D   S   E   Q   S   I   N   F   S   Y   D   I   S   N   N   A   P   G   Y   N   K   W   F
      1065 1066 1067 1068 1069 1070 1071 1072 1073 1074 1075 1076 1077 1078 1079 1080 1081 1082 1083 1084 1085 1086 1087

5'  TTCGTTACCGTGACTAACAACATGATGGGTAACATGAAAATTTACATCAACGGCAAGCTCATTGACACCA
    ++++++++++++++++++++++++++++++++++++++++++++++++++++++++++++++++++++++  7420
                           BoNT/C1 Receptor Binding Domain
       F   V   T   V   T   N   N   M   M   G   N   M   K   I   Y   I   N   G   K   L   I   D   T
      1088 1089 1090 1091 1092 1093 1094 1095 1096 1097 1098 1099 1100 1101 1102 1103 1104 1105 1106 1107 1108 1109 1110

5'  TCAAAGTGAAGGAGTTGACTGGTATTAACTTCTCCAAAACAATCACGTTTGAAATTAaCaAGATCCCTGA
    ++++++++++++++++++++++++++++++++++++++++++++++++++++++++++++++++++++++  7490
                           BoNT/C1 Receptor Binding Domain
       I   K   V   K   E   L   T   G   I   N   F   S   K   T   I   T   F   E   I   N   K   I   P   D
      1111 1112 1113 1114 1115 1116 1117 1118 1119 1120 1121 1122 1123 1124 1125 1126 1127 1128 1129 1130 1131 1132 1133 1134

5'  CACCGGCCTGATCACTTCAGACAGTGATAACATCAACATGTGGATTAGGGATTTCTACATCTTCGCCAAG
    ++++++++++++++++++++++++++++++++++++++++++++++++++++++++++++++++++++++  7560
                           BoNT/C1 Receptor Binding Domain
       T   G   L   I   T   S   D   S   D   N   I   N   M   W   I   R   D   F   Y   I   F   A   K
      1135 1136 1137 1138 1139 1140 1141 1142 1143 1144 1145 1146 1147 1148 1149 1150 1151 1152 1153 1154 1155 1156 1157
```

FIG. 34K

```
                EcoICRI
                  SacI
5'   GAGCTCGACGGAAAGGATATTAACATCCTCTTCAACAGCTTGCAGTACACCAACGTCGTTAAAGACTACT
                                                                              7630
                        BoNT/C1 Receptor Binding Domain
      E   L   D   G   K   D   I   N   I   L   F   N   S   L   Q   Y   T   N   V   V   K   D   Y
     1158 1159 1160 1161 1162 1163 1164 1165 1166 1167 1168 1169 1170 1171 1172 1173 1174 1175 1176 1177 1178 1179 1180

5'   GGGGTAACGATTTGAGATACAACAAGGAGTACTACATGGTCAACATCGACTACCTGAACAGGTACATGTA
                                                                              7700
                        BoNT/C1 Receptor Binding Domain
      W   G   N   D   L   R   Y   N   K   E   Y   Y   M   V   N   I   D   Y   L   N   R   Y   M   Y
     1181 1182 1183 1184 1185 1186 1187 1188 1189 1190 1191 1192 1193 1194 1195 1196 1197 1198 1199 1200 1201 1202 1203 1204

5'   CGCTAACTCCCGCCAAATCGTGTTCAACACCAGGAGAAACAACAACGACTTCAACGAGGGTTACAAAATC
                                                                              7770
                        BoNT/C1 Receptor Binding Domain
      A   N   S   R   Q   I   V   F   N   T   R   R   N   N   N   D   F   N   E   G   Y   K   I
     1205 1206 1207 1208 1209 1210 1211 1212 1213 1214 1215 1216 1217 1218 1219 1220 1221 1222 1223 1224 1225 1226 1227

5'   ATTATCAAGCGCATCCGTGGCAACACCAACGATACTAGGGTGAGAGGTGGCGACATTCTGTACTTCGATA
                                                                              7840
                        BoNT/C1 Receptor Binding Domain
      I   I   K   R   I   R   G   N   T   N   D   T   R   V   R   G   G   D   I   L   Y   F   D
     1228 1229 1230 1231 1232 1233 1234 1235 1236 1237 1238 1239 1240 1241 1242 1243 1244 1245 1246 1247 1248 1249 1250

5'   TGACTATCAACAACAAAGCCTACAACTTGTTCATGAAAAACGAGACAATGTACGCCGACAAcCATAGCAC
                                                                              7910
                        BoNT/C1 Receptor Binding Domain
      M   T   I   N   N   K   A   Y   N   L   F   M   K   N   E   T   M   Y   A   D   N   H   S   T
     1251 1252 1253 1254 1255 1256 1257 1258 1259 1260 1261 1262 1263 1264 1265 1266 1267 1268 1269 1270 1271 1272 1273 1274

5'   GGAGGATATTTACGCAATCGGACTGAGGGAACAGACAAAGGACATCAACGATAACATTATCTTCCAGATC
                                                                              7980
                        BoNT/C1 Receptor Binding Domain
      E   D   I   Y   A   I   G   L   R   E   Q   T   K   D   I   N   D   N   I   I   F   Q   I
     1275 1276 1277 1278 1279 1280 1281 1282 1283 1284 1285 1286 1287 1288 1289 1290 1291 1292 1293 1294 1295 1296 1297

5'   CAACCTATGAACAACACGTACTACTACGCTTCGCAAATCTTCAAGTCCAACTTCAACGGAGAAAACATTT
                                                                              8050
                        BoNT/C1 Receptor Binding Domain
      Q   P   M   N   N   T   Y   Y   Y   A   S   Q   I   F   K   S   N   F   N   G   E   N   I
     1298 1299 1300 1301 1302 1303 1304 1305 1306 1307 1308 1309 1310 1311 1312 1313 1314 1315 1316 1317 1318 1319 1320
```

FIG. 34L

```
5'  CGGGTATCTGTTCCATTGGCACATACCGCTTCCGTCTGGGTGGTGACTGGTATCGTCACAACTACCTCGT
                                                                              8120
                        BoNT/C1 Receptor Binding Domain
     S  G  I  C  S  I  G  T  Y  R  F  R  L  G  G  D  W  Y  R  H  N  Y  L  V
    1321 1322 1323 1324 1325 1326 1327 1328 1329 1330 1331 1332 1333 1334 1335 1336 1337 1338 1339 1340 1341 1342 1343 1344

                                              SalI
5'  TCCCACCGTGAAGCAGGGTAACTACGCTTCTTTGCTGGAGTCGACTTCCACGCACTGGGGATTCGTTCCT
                                                                              8190
                        BoNT/C1 Receptor Binding Domain
     P  T  V  K  Q  G  N  Y  A  S  L  L  E  S  T  S  T  H  W  G  F  V  P
    1345 1346 1347 1348 1349 1350 1351 1352 1353 1354 1355 1356 1357 1358 1359 1360 1361 1362 1363 1364 1365 1366 1367

5'  GTGTCAGAGGGCGCTGGCTACCCTTACGATGTTCCCGACTACGCTGGTTGGGAACTCCAGCAAGGTGCAG
                                                                              8260
    BoNT/C...omain | linker |        HA tag        | li...r |  SpH site  | linker
     V  S  E  A  G  Y  P  Y  D  V  P  D  Y  A  G  W  E  L  Q  Q  G  A
    1368 1369 1370 1371 1372 1373 1374 1375 1376 1377 1378 1379 1380 1381 1382 1383 1384 1385 1386 1387 1388 1389 1390

5'  GATGGTCCCACCCTCAATTCGAGAAGGGTGCCGGATGGAGTCACCCACAGTTCGAGAAAGGCGCTGGATG
                                                                              8330
    |..|        Strep tag II        | linker |        Strep tag II        | linker |
     G  W  S  H  P  Q  F  E  K  G  A  G  W  S  H  P  Q  F  E  K  G  A  G  W
    1391 1392 1393 1394 1395 1396 1397 1398 1399 1400 1401 1402 1403 1404 1405 1406 1407 1408 1409 1410 1411 1412 1413 1414

                                      NsiI              XhoI
5'  GAGTCACCCACAGTTCGAGAAATAATTAGTTGATGCATAGTTAATTAGATAGCTCGAGGCATGCGGTACC
                                                                              8400
    |   Strep tag II   |
     S  H  P  Q  F  E  K
    1415 1416 1417 1418 1419 1420 1421

                    NsiI              XhoI
5'  AAGATTGGATCTAGATGCATAGTTAATTAGATAGCTCGAGGCATGCGGTACCAAGCTTGTCGAGAAGTAC
                                                                              8470

5'  TAGAGGATCATAATCAGCCATACCACATTTGTAGAGGTTTTACTTGCTTTAAAAAACCTCCCACACCTCC
                                                                              8540
                                          HpaI
5'  CCCTGAACCTGAAACATAAAATGAATGCAATTGTTGTTGTTAACTTGTTTATTGCAGCTTATAATGGTTA
                                                                              8610

5'  CAAATAAAGCAATAGCATCACAAATTTCACAAATAAAGCATTTTTTTCACTGCATTCTAGTTGTGGTTTG
                                                                              8680
```

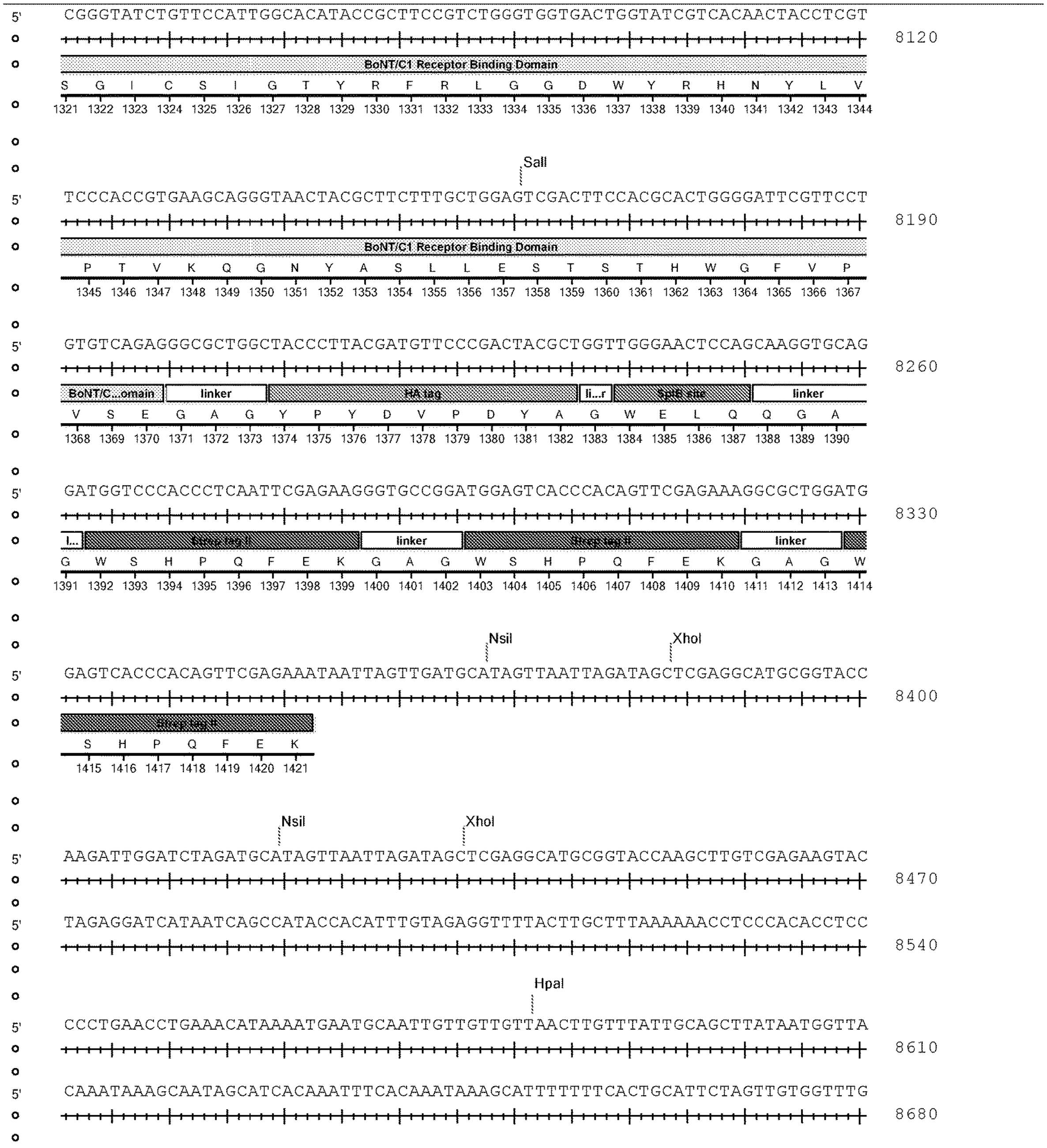

FIG. 34M

AvrII

5' TCCAAACTCATCAATGTATCTTATCATGTCTGGATCTGATCACTGCTTGAGCCTAGGAGATCCGAACCAG 8750

5' ATAAGTGAAATCTAGTTCCAAACTATTTTGTCATTTTTAATTTTCGTATTAGCTTACGACGCTACACCCA 8820

5' GTTCCCATCTATTTTGTCACTCTTCCCTAAATAATCCTTAAAAACTCCATTTCCACCCCTCCCAGTTCCC 8890

5' AACTATTTTGTCCGCCCACAGCGGGGCATTTTTCTTCCTGTTATGTTTTTAATCAAACATCCTGCCAACT 8960

5' CCATGTGACAAACCGTCATCTTCGGCTACTTTTTCTCTGTCACAGAATGAAAATTTTTCTGTCATCTCTT 9030

5' CGTTATTAATGTTTGTAATTGACTGAATATCAACGCTTATTTGCAGCCTGAATGGCGAATGG 9092

FIG. 34N

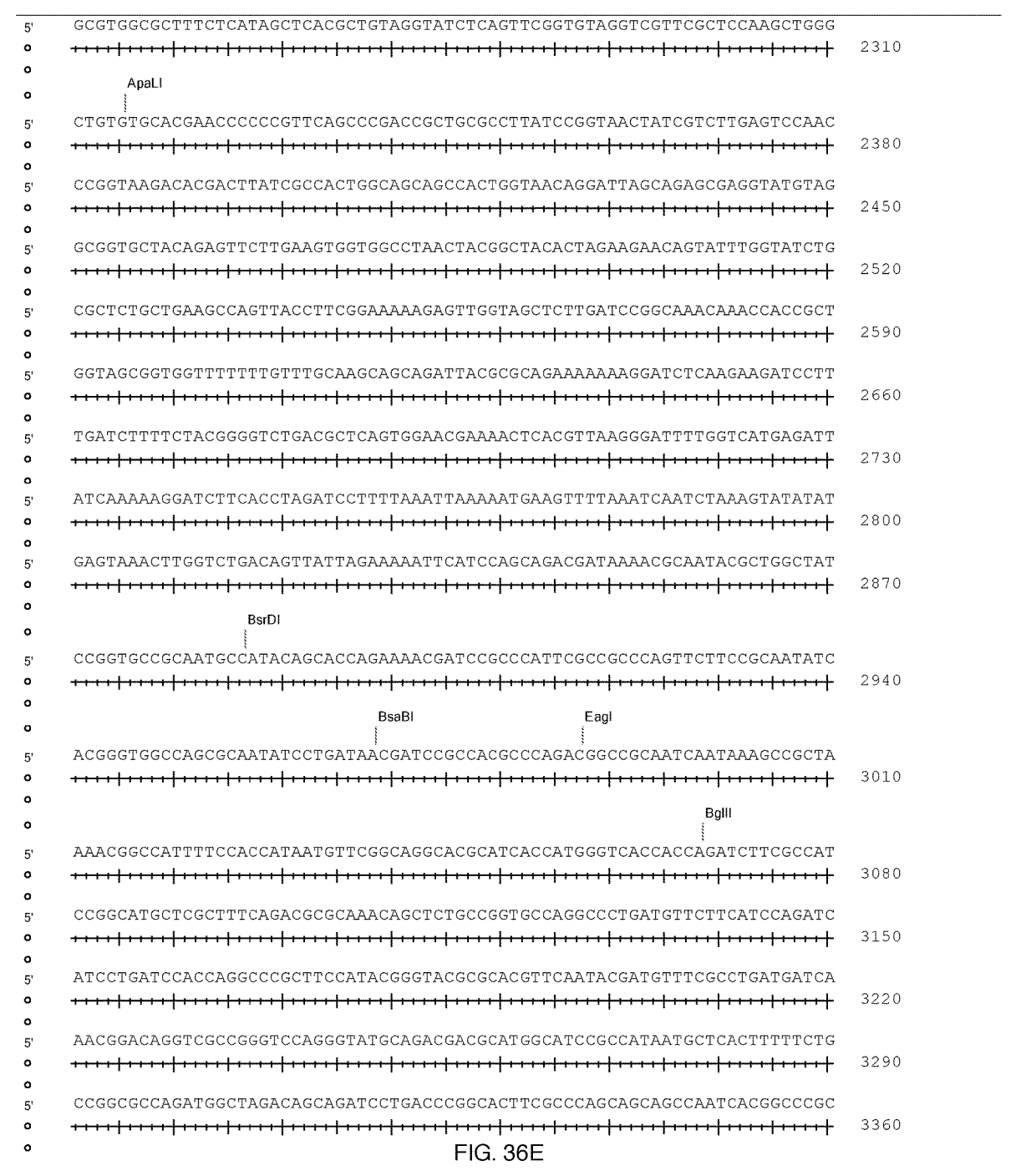

5' GCGTGGCGCTTTCTCATAGCTCACGCTGTAGGTATCTCAGTTCGGTGTAGGTCGTTCGCTCCAAGCTGGG 2310

ApaLI
5' CTGTGTGCACGAACCCCCCGTTCAGCCCGACCGCTGCGCCTTATCCGGTAACTATCGTCTTGAGTCCAAC 2380

5' CCGGTAAGACACGACTTATCGCCACTGGCAGCAGCCACTGGTAACAGGATTAGCAGAGCGAGGTATGTAG 2450

5' GCGGTGCTACAGAGTTCTTGAAGTGGTGGCCTAACTACGGCTACACTAGAAGAACAGTATTTGGTATCTG 2520

5' CGCTCTGCTGAAGCCAGTTACCTTCGGAAAAAGAGTTGGTAGCTCTTGATCCGGCAAACAAACCACCGCT 2590

5' GGTAGCGGTGGTTTTTTTGTTTGCAAGCAGCAGATTACGCGCAGAAAAAAAGGATCTCAAGAAGATCCTT 2660

5' TGATCTTTTCTACGGGGTCTGACGCTCAGTGGAACGAAAACTCACGTTAAGGGATTTTGGTCATGAGATT 2730

5' ATCAAAAAGGATCTTCACCTAGATCCTTTTAAATTAAAAATGAAGTTTTAAATCAATCTAAAGTATATAT 2800

5' GAGTAAACTTGGTCTGACAGTTATTAGAAAAATTCATCCAGCAGACGATAAAACGCAATACGCTGGCTAT 2870

BsrDI
5' CCGGTGCCGCAATGCCATACAGCACCAGAAAACGATCCGCCCATTCGCCGCCCAGTTCTTCCGCAATATC 2940

BsaBI EagI
5' ACGGGTGGCCAGCGCAATATCCTGATAACGATCCGCCACGCCCAGACGGCCGCAATCAATAAAGCCGCTA 3010

BglII
5' AAACGGCCATTTTCCACCATAATGTTCGGCAGGCACGCATCACCATGGGTCACCACCAGATCTTCGCCAT 3080

5' CCGGCATGCTCGCTTTCAGACGCGCAAACAGCTCTGCCGGTGCCAGGCCCTGATGTTCTTCATCCAGATC 3150

5' ATCCTGATCCACCAGGCCCGCTTCCATACGGGTACGCGCACGTTCAATACGATGTTTCGCCTGATGATCA 3220

5' AACGGACAGGTCGCCGGGTCCAGGGTATGCAGACGACGCATGGCATCCGCCATAATGCTCACTTTTTCTG 3290

5' CCGGCGCCAGATGGCTAGACAGCAGATCCTGACCCGGCACTTCGCCCAGCAGCAGCCAATCACGGCCCGC 3360

FIG. 36E

SgrAI
TstI' AgeI TstI
5' TTCGGTCACCACATCCAGCACCGCCGCACACGGAACACCGGTGGTGGCCAGCCAGCTCAGACGCGCCGCT 3430

PstI BssHII
5' TCATCCTGCAGCTCGTTCAGCGCACCGCTCAGATCGGTTTTCACAAACAGCACCGGACGACCCTGCGCGC 3500

AjuI'
5' TCAGACGAAACACCGCCGCATCAGAGCAGCCAATGGTCTGCTGCGCCCAATCATAGCCAAACAGACGTTC 3570

AjuI
5' CACCCACGCTGCCGGGCTACCCGCATGCAGGCCATCCTGTTCAATCATACTCTTCCTTTTTCAATATTAT 3640

5' TGAAGCATTTATCAGGGTTATTGTCTCATGAGCGGATACATATTTGAATGTATTTAGAAAAATAAACAAA 3710

5' TAGGGGTTCCGCGCACATTTCCCCGAAAAGTGCCAC 3746

FIG. 36F

5' CATAGCTGTTTCCTTGCGTATTGGGCGCTCTCCGCTTCCTCGCTCACTGACTCGCTGCGCTCGGTCGTTC 1680

5' GGGTAAAGCCTGGGGTGCCTAATGAGCAAAAGGCCAGCAAAAGGCCAGGAACCGTAAAAAGGCCGCGTTG 1750

DrdI

5' CTGGCGTTTTTCCATAGGCTCCGCCCCCCTGACGAGCATCACAAAAATCGACGCTCAAGTCAGAGGTGGC 1820

5' GAAACCCGACAGGACTATAAAGATACCAGGCGTTTCCCCCTGGAAGCTCCCTCGTGCGCTCTCCTGTTCC 1890

5' GACCCTGCCGCTTACCGGATACCTGTCCGCCTTTCTCCCTTCGGGAAGCGTGGCGCTTTCTCATAGCTCA 1960

ApaLI

5' CGCTGTAGGTATCTCAGTTCGGTGTAGGTCGTTCGCTCCAAGCTGGGCTGTGTGCACGAACCCCCCGTTC 2030

5' AGCCCGACCGCTGCGCCTTATCCGGTAACTATCGTCTTGAGTCCAACCCGGTAAGACACGACTTATCGCC 2100

5' ACTGGCAGCAGCCACTGGTAACAGGATTAGCAGAGCGAGGTATGTAGGCGGTGCTACAGAGTTCTTGAAG 2170

5' TGGTGGCCTAACTACGGCTACACTAGAAGAACAGTATTTGGTATCTGCGCTCTGCTGAAGCCAGTTACCT 2240

5' TCGGAAAAAGAGTTGGTAGCTCTTGATCCGGCAAACAAACCACCGCTGGTAGCGGTGGTTTTTTTGTTTG 2310

5' CAAGCAGCAGATTACGCGCAGAAAAAAAGGATCTCAAGAAGATCCTTTGATCTTTTCTACGGGGTCTGAC 2380

5' GCTCAGTGGAACGAAAACTCACGTTAAGGGATTTTGGTCATGAGATTATCAAAAAGGATCTTCACCTAGA 2450

5' TCCTTTTAAATTAAAAATGAAGTTTTAAATCAATCTAAAGTATATATGAGTAAACTTGGTCTGACAGTTA 2520

BsrDI

5' TTAGAAAAATTCATCCAGCAGACGATAAAACGCAATACGCTGGCTATCCGGTGCCGCAATGCCATACAGC 2590

5' ACCAGAAAACGATCCGCCCATTCGCCGCCCAGTTCTTCCGCAATATCACGGGTGGCCAGCGCAATATCCT 2660

FIG. 37D

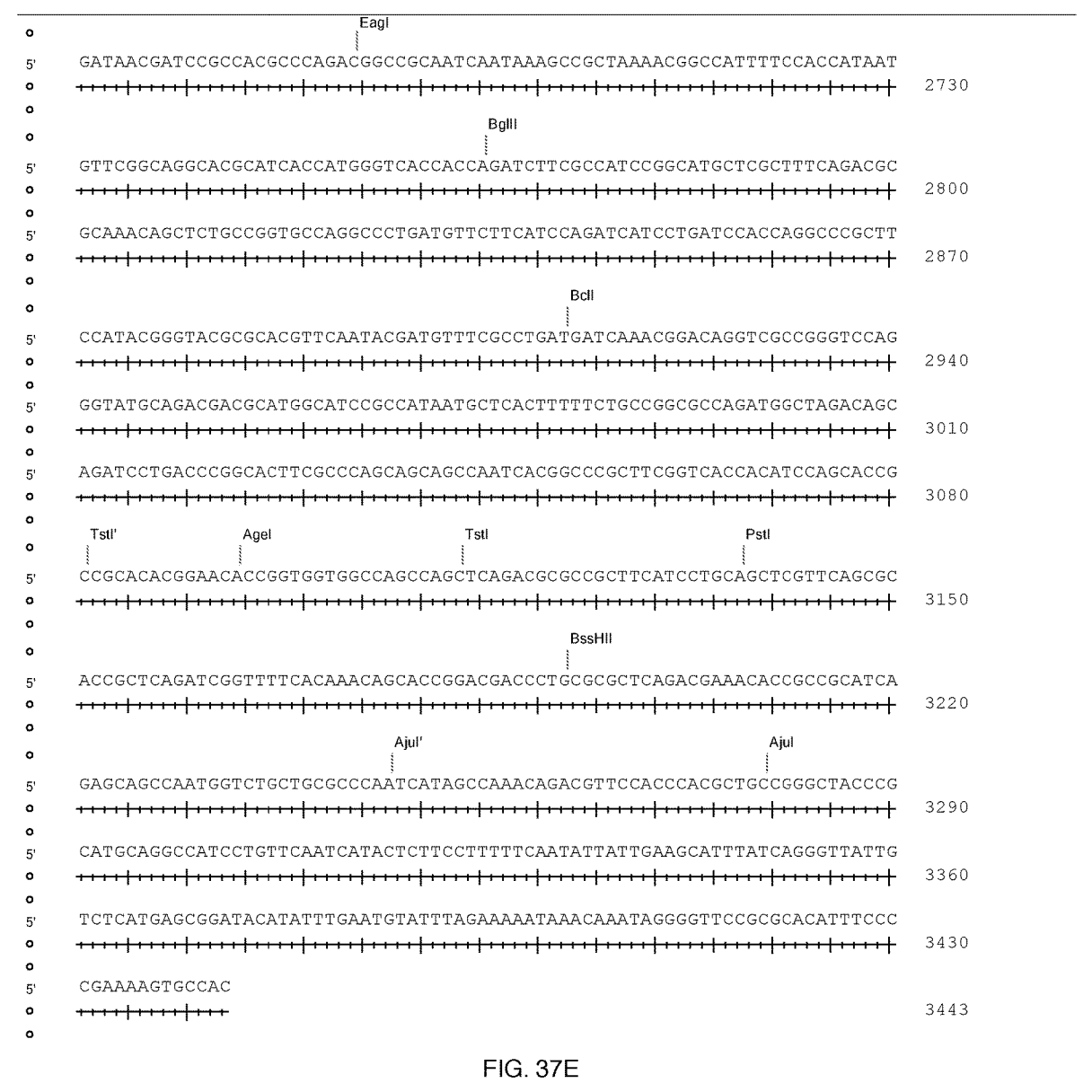

EagI

5' GATAACGATCCGCCACGCCCAGACGGCCGCAATCAATAAAGCCGCTAAAACGGCCATTTTCCACCATAAT 2730

BglII

5' GTTCGGCAGGCACGCATCACCATGGGTCACCACCAGATCTTCGCCATCCGGCATGCTCGCTTTCAGACGC 2800

5' GCAAACAGCTCTGCCGGTGCCAGGCCCTGATGTTCTTCATCCAGATCATCCTGATCCACCAGGCCCGCTT 2870

BclI

5' CCATACGGGTACGCGCACGTTCAATACGATGTTTCGCCTGATGATCAAACGGACAGGTCGCCGGGTCCAG 2940

5' GGTATGCAGACGACGCATGGCATCCGCCATAATGCTCACTTTTTCTGCCGGCGCCAGATGGCTAGACAGC 3010

5' AGATCCTGACCCGGCACTTCGCCCAGCAGCAGCCAATCACGGCCCGCTTCGGTCACCACATCCAGCACCG 3080

TstI' AgeI TstI PstI

5' CCGCACACGGAACACCGGTGGTGGCCAGCCAGCTCAGACGCGCCGCTTCATCCTGCAGCTCGTTCAGCGC 3150

BssHII

5' ACCGCTCAGATCGGTTTTCACAAACAGCACCGGACGACCCTGCGCGCTCAGACGAAACACCGCCGCATCA 3220

AjuI' AjuI

5' GAGCAGCCAATGGTCTGCTGCGCCCAATCATAGCCAAACAGACGTTCCACCCACGCTGCCGGGCTACCCG 3290

5' CATGCAGGCCATCCTGTTCAATCATACTCTTCCTTTTTCAATATTATTGAAGCATTTATCAGGGTTATTG 3360

5' TCTCATGAGCGGATACATATTTGAATGTATTTAGAAAAATAAACAAATAGGGGTTCCGCGCACATTTCCC 3430

5' CGAAAAGTGCCAC 3443

FIG. 37E

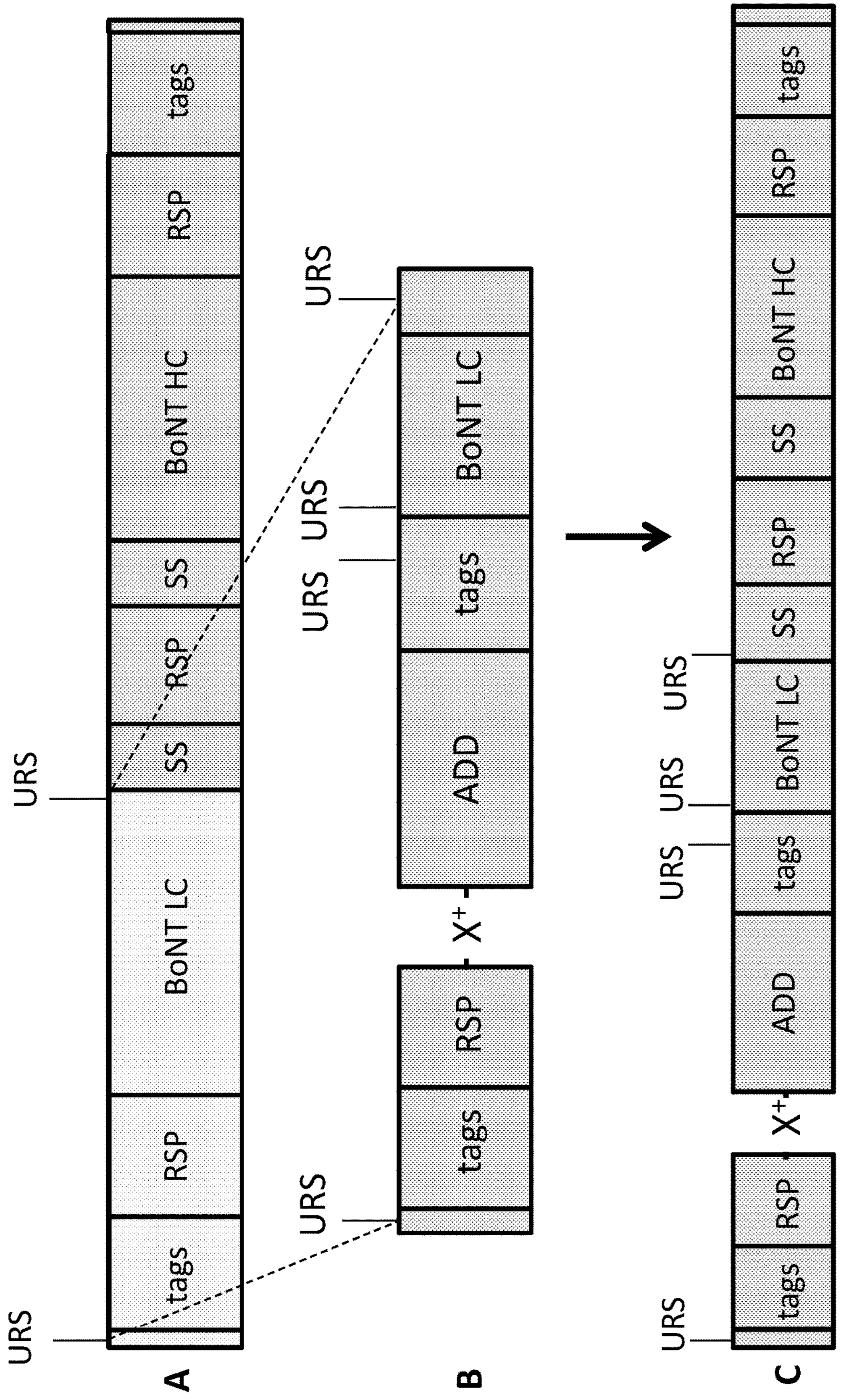
FIGS. 38A-C

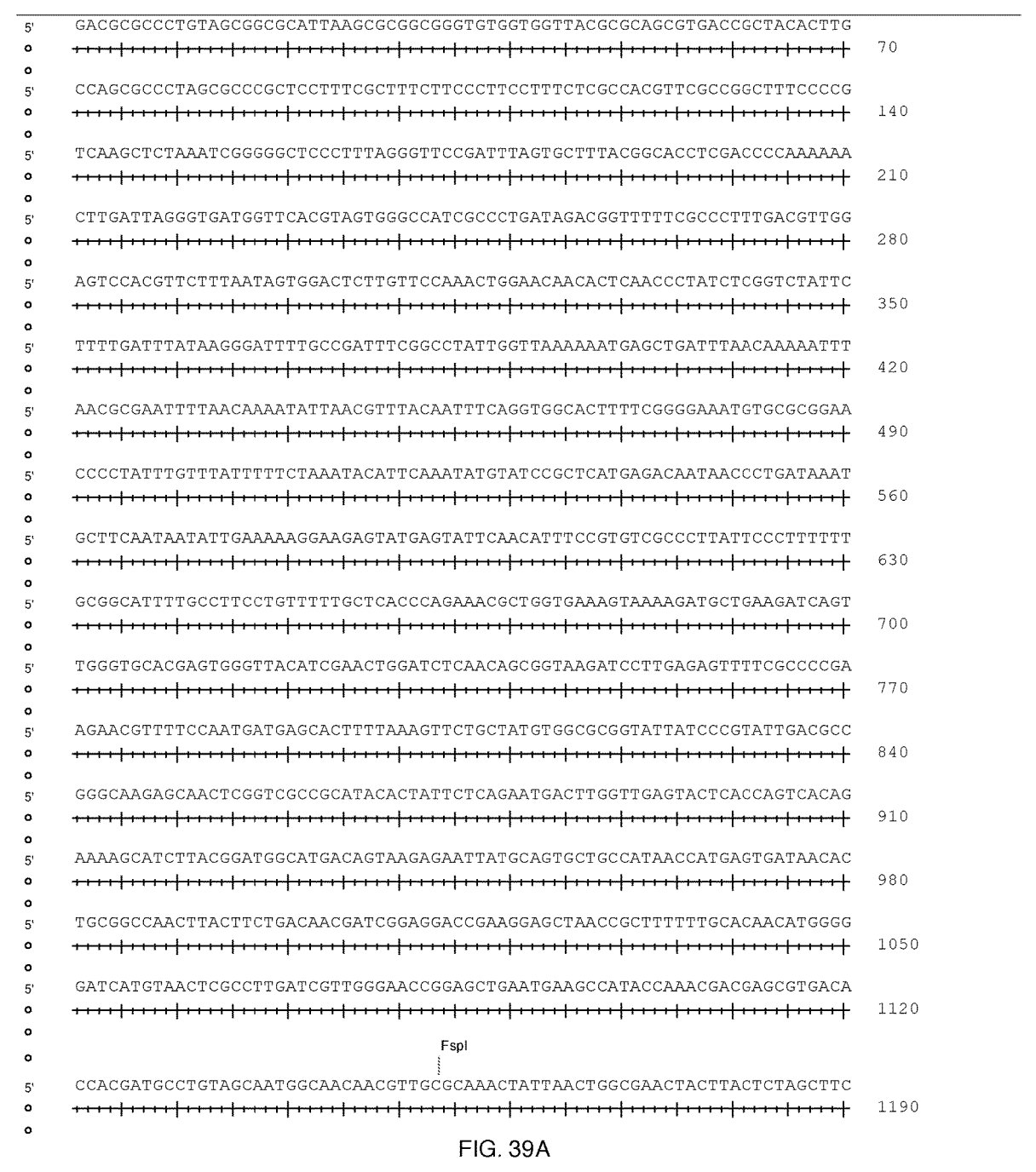

5' GACGCGCCCTGTAGCGGCGCATTAAGCGCGGCGGGTGTGGTGGTTACGCGCAGCGTGACCGCTACACTTG 70

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

5' CTTGATTAGGGTGATGGTTCACGTAGTGGGCCATCGCCCTGATAGACGGTTTTTCGCCCTTTGACGTTGG 280

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

5' TGCGGCCAACTTACTTCTGACAACGATCGGAGGACCGAAGGAGCTAACCGCTTTTTTGCACAACATGGGG 1050

5' GATCATGTAACTCGCCTTGATCGTTGGGAACCGGAGCTGAATGAAGCCATACCAAACGACGAGCGTGACA 1120

FspI

5' CCACGATGCCTGTAGCAATGGCAACAACGTTGCGCAAACTATTAACTGGCGAACTACTTACTCTAGCTTC 1190

FIG. 39A

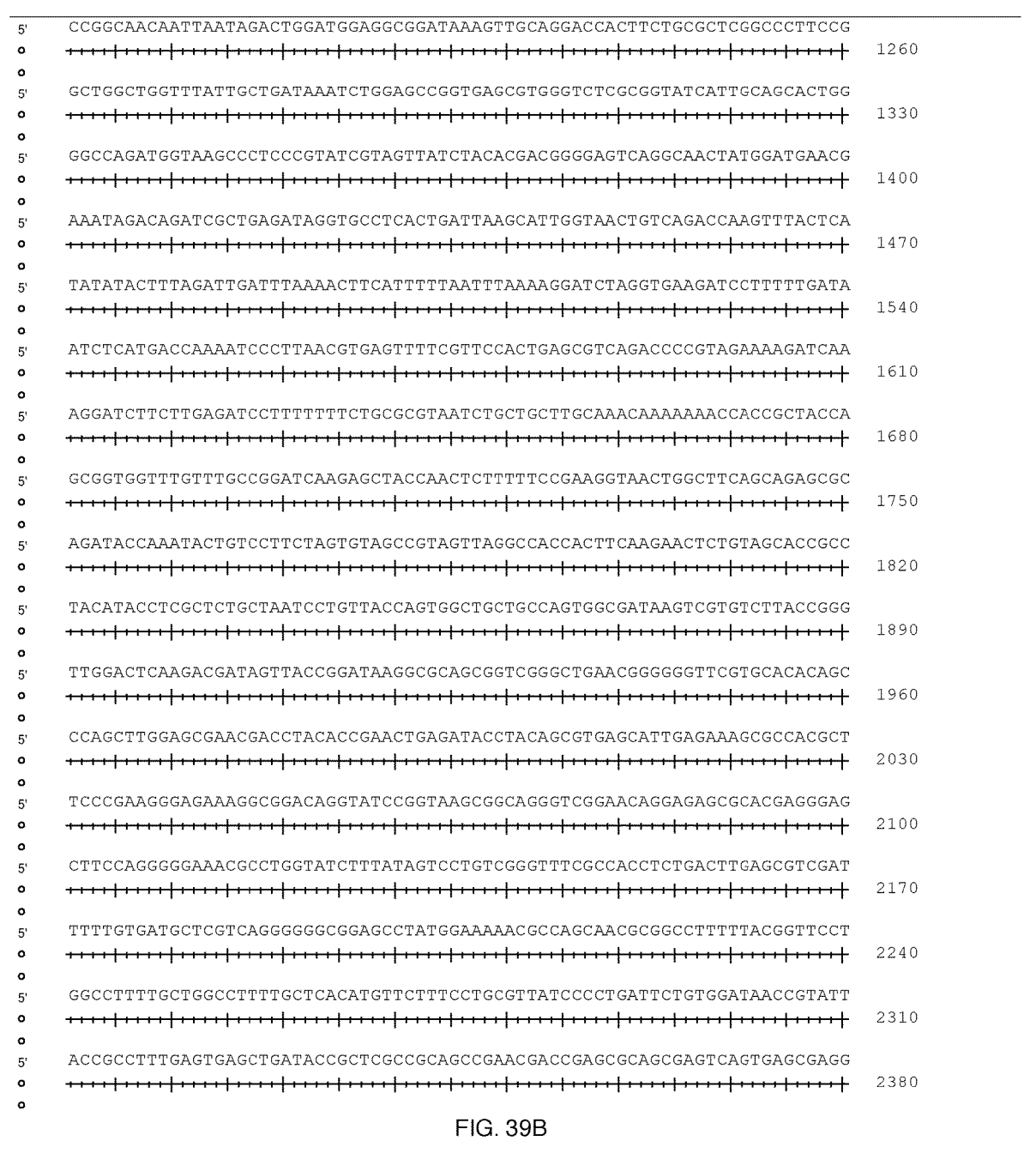

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

FIG. 39B

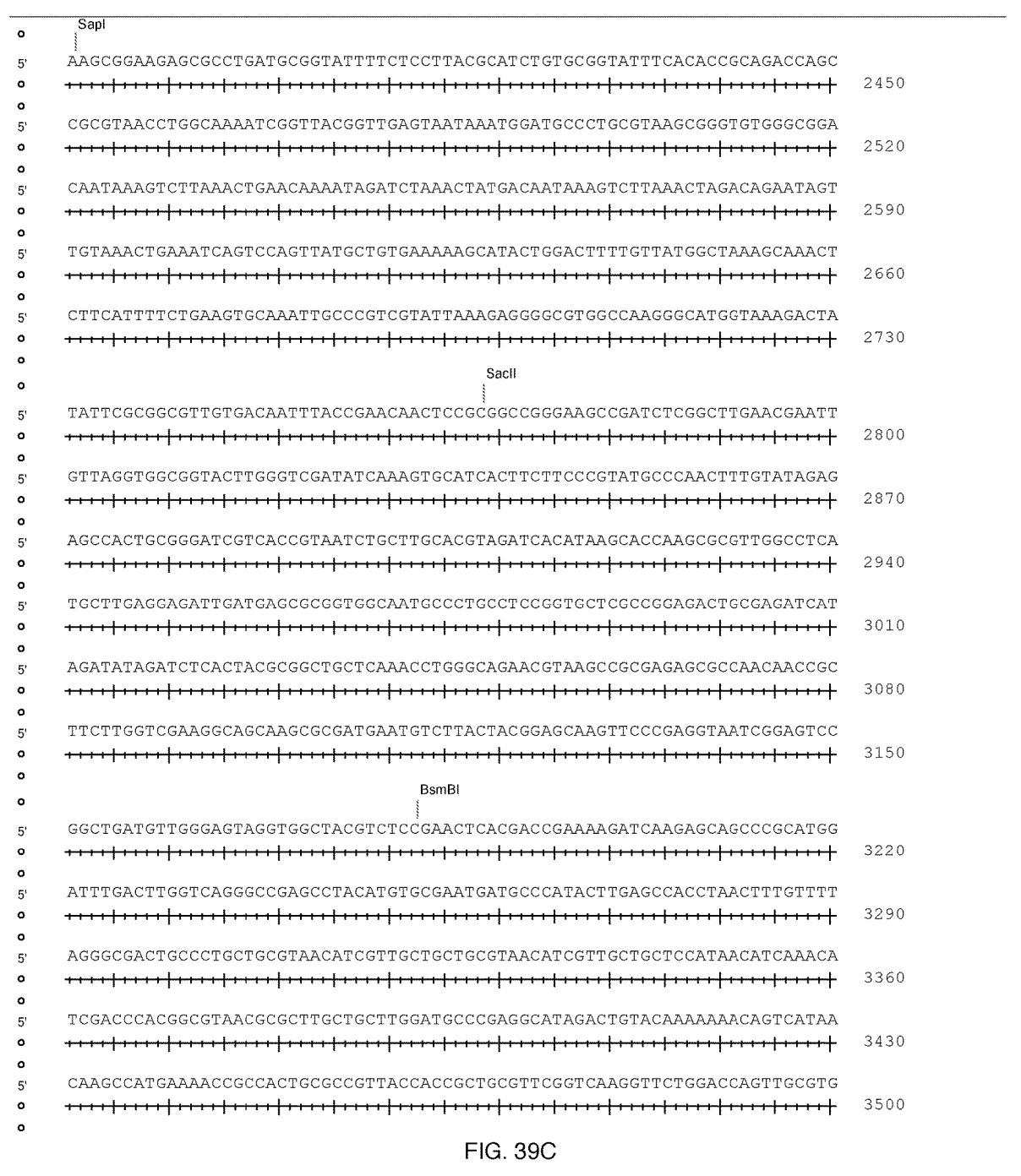

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

5' AGATATAGATCTCACTACGCGGCTGCTCAAACCTGGGCAGAACGTAAGCCGCGAGAGCGCCAACAACCGC 3080

5' TTCTTGGTCGAAGGCAGCAAGCGCGATGAATGTCTTACTACGGAGCAAGTTCCCGAGGTAATCGGAGTCC 3150

BsmBI

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

FIG. 39C

```
5'  AGCGCATACGCTACTTGCATTACAGTTTACGAACCGAACAGGCTTATGTCAACTGGGTTCGTGCCTTCAT
                                                                                        3570

5'  CCGTTTCCACGGTGTGCGTCACCCGGCAACCTTGGGCAGCAGCGAAGTCGAGGCATTTCTGTCCTGGCTG
                                                                                        3640

5'  GCGAACGAGCGCAAGGTTTCGGTCTCCACGCATCGTCAGGCATTGGCGGCCTTGCTGTTCTTCTACGGCA
                                                                                        3710

5'  AGGTGCTGTGCACGGATCTGCCCTGGCTTCAGGAGATCGGAAGACCTCGGCCGTCGCGGCGCTTGCCGGT
                                                                                        3780

5'  GGTGCTGACCCCGGATGAAGTGGTTCGCATCCTCGGTTTTCTGGAAGGCGAGCATCGTTTGTTCGCCCAG
                                                                                        3850

                                        SnaBI
5'  GACTCTAGCTATAGTTCTAGTGGTTGGCTACGTATACTCCGGAATATTAATAGATCATGGAGATAATTAA
                                                                                        3920

5'  AATGATAACCATCTCGCAAATAAATAAGTATTTTACTGTTTTCGTAACAGTTTTGTAATAAAAAAACCTA
                                                                                        3990

                                                        RsrII      BstBI
5'  TAAATATTCCGGATTATTCATACCGTCCCACCATCGGGCGCGGATCTCGGTCCGTTCGAACCAGAACTCT
                                                                                        4060
                                          [mut ...mHI]

5'  GGAAGCTTAACTCCTAAAAAACCGCCACCATGAAATTCTTAGTCAACGTTGCCCTTGTTTTTATGGTCGT
                                                                                        4130
         Lob. TMO cDNA Lead Seq                     Signal peptide
                                      M   K   F   L   V   N   V   A   L   V   F   M   V   V
                                      1   2   3   4   5   6   7   8   9   10  11  12  13  14

                                                                                   ZraI
                                                                                   ,AatII
5'  ATACATTTCTTACATCTATGCGGCCGGACATCATCATCATCATCACCATCACCACCACCACGACGTCGGC
                                                                                        4200
              Signal peptide                    11 His tag                    linker
         Y   I   S   Y   I   Y   A   A   G   H   H   H   H   H   H   H   H   H   D   V   G
         15  16  17  18  19  20  21  22  23  24  25  26  27  28  29  30  31  32  33  34  35  36  37

5'  TGGGAGCTGCAACGTCGTCCCCTGAACTGCATCGTGGCTGTGTCCCAGAACATGGGTATCGGCAAGAACG
                                                                                        4270
         Spl. B site                Mouse DHFR mutated
         W   E   L   Q   R   R   P   L   N   C   I   V   A   V   S   Q   N   M   G   I   G   K   N
         38  39  40  41  42  43  44  45  46  47  48  49  50  51  52  53  54  55  56  57  58  59  60
```

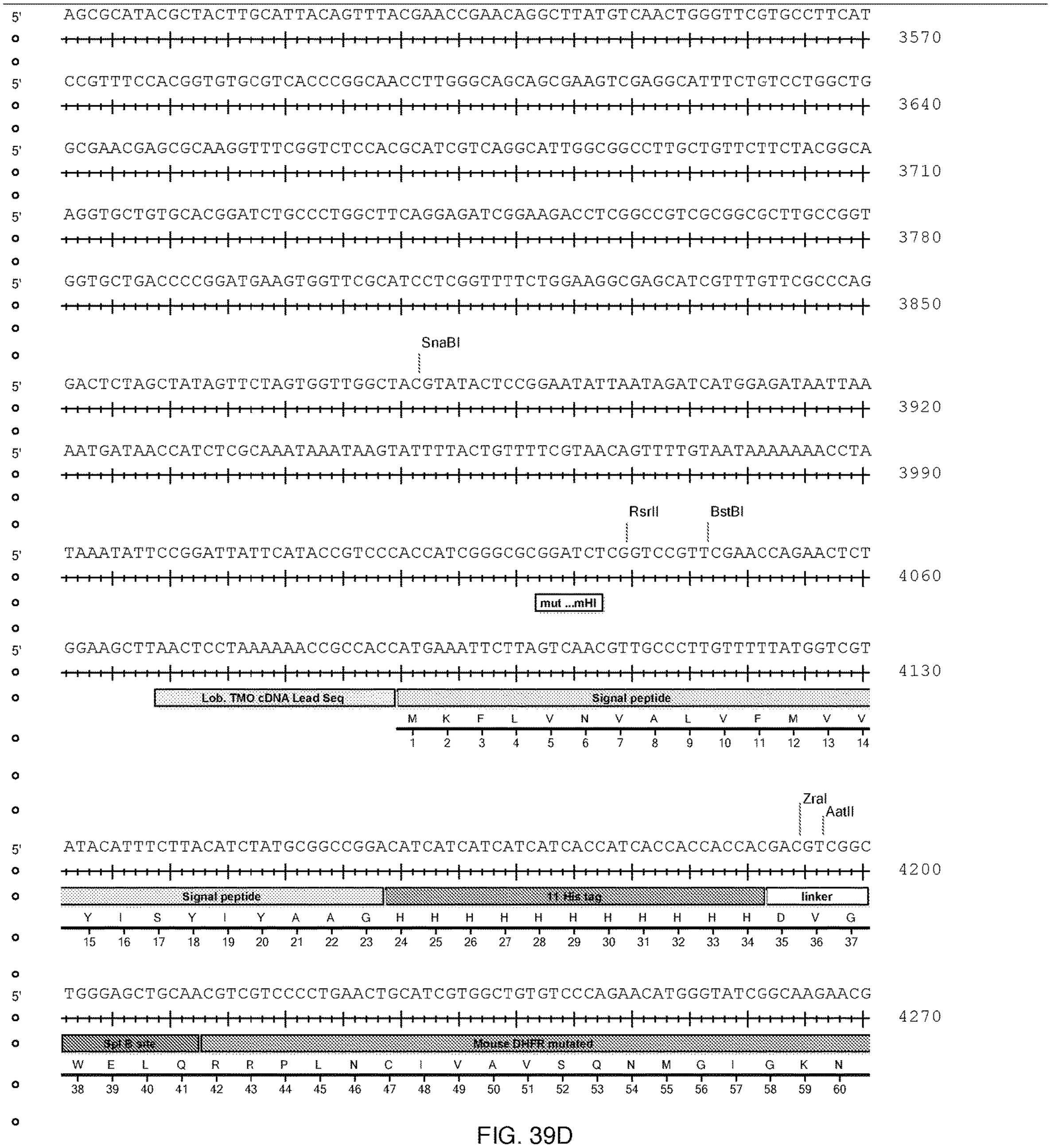

FIG. 39D

5' GCGACCTGCCCTGGCCTCCTCTGCGTAACGAGTTCAAGTACTTCCAGCGTATGACCACCACCTCCTCCGT 4340
Mouse DHFR mutated
G D L P W P P L R N E F K Y F Q R M T T T S S V
61 62 63 64 65 66 67 68 69 70 71 72 73 74 75 76 77 78 79 80 81 82 83 84

5' CGAGGGCAAGCAGAACCTGGTCATCATGGGTCGCAAGACCTGGTTCTCCATCCCCGAGAAGAACCGTCTG 4410
Mouse DHFR mutated
E G K Q N L V I M G R K T W F S I P E K N R L
85 86 87 88 89 90 91 92 93 94 95 96 97 98 99 100 101 102 103 104 105 106 107

5' CTGAAGGACCGTATCAACATCGTGCTGTCCCGCGAGCTGAAGGAACCCCCTCGTGGTGCTCACTTCCTGG 4480
Mouse DHFR mutated
L K D R I N I V L S R E L K E P P R G A H F L
108 109 110 111 112 113 114 115 116 117 118 119 120 121 122 123 124 125 126 127 128 129 130

5' CTAAGTCCCTGGACGACGCTCTGCGTCTGATCGAGCAGCCTGAGCTGGCTTCCAAGGTGGACATGGTCTG 4550
Mouse DHFR mutated
A K S L D D A L R L I E Q P E L A S K V D M V W
131 132 133 134 135 136 137 138 139 140 141 142 143 144 145 146 147 148 149 150 151 152 153 154

5' GATCGTGGGCGGTTCCTCCGTGTACCAAGAGGCTATGAACCAGCCCGGTCACTTGCGTCTGTTCGTGACC 4620
Mouse DHFR mutated
I V G G S S V Y Q E A M N Q P G H L R L F V T
155 156 157 158 159 160 161 162 163 164 165 166 167 168 169 170 171 172 173 174 175 176 177

5' CGTATCATGCAAGAGTTCGAGTCCGACACCTTCTTCCCCGAAATCGACCTGGGCAAGTACAAGCTGCTGC 4690
Mouse DHFR mutated
R I M Q E F E S D T F F P E I D L G K Y K L L
178 179 180 181 182 183 184 185 186 187 188 189 190 191 192 193 194 195 196 197 198 199 200

5' CCGAGTACCCCGGTGTCCTGTCCGAGGTGCAAGAGGAAAAGGGTATCAAGTACAAGTTCGAGGTGTACGA 4760
Mouse DHFR mutated
P E Y P G V L S E V Q E E K G I K Y K F E V Y E
201 202 203 204 205 206 207 208 209 210 211 212 213 214 215 216 217 218 219 220 221 222 223 224

FIG. 39E

5' GGGTATTCCTTTCTGGGGTGGCTCAACCATCGACACTGAGCTGAAGGTCATTGATACAAACTGCATCAAC 5250
BoNT/A ad0 LC
G I P F W G G S T I D T E L K V I D T N C I N
365 366 367 368 369 370 371 372 373 374 375 376 377 378 379 380 381 382 383 384 385 386 387

5' GTTATTCAACCCGACGGCTCCTACCGCAGCGAGGAATTGAACCTGGTGATCATTGGACCAAGCGCCGACA 5320
BoNT/A ad0 LC
V I Q P D G S Y R S E E L N L V I I G P S A D
388 389 390 391 392 393 394 395 396 397 398 399 400 401 402 403 404 405 406 407 408 409 410

5' TCATTCAGTTCGAGTGTAAGTCTTTCGGCCATGAAGTCCTCAACTTGACCAGAAACGGCTACGGCTCCAC 5390
BoNT/A ad0 LC
I I Q F E C K S F G H E V L N L T R N G Y G S T
411 412 413 414 415 416 417 418 419 420 421 422 423 424 425 426 427 428 429 430 431 432 433 434

5' TCAATACATCCGCTTCAGCCCCGACTTCACATTCGGATTCGAGGAATCACTGGAGGTCGATACGAACCCG 5460
BoNT/A ad0 LC
Q Y I R F S P D F T F G F E E S L E V D T N P
435 436 437 438 439 440 441 442 443 444 445 446 447 448 449 450 451 452 453 454 455 456 457

PstI
5' TTGCTGGGTGCTGGCAAGTTCGCCACCGACCCTGCAGTTACTCTGGCACACGCGCTCATCCACGCGGGAC 5530
BoNT/A ad0 LC BoNT/A LC ad0
L L G A G K F A T D P A V T L A H A L I H A G
458 459 460 461 462 463 464 465 466 467 468 469 470 471 472 473 474 475 476 477 478 479 480

5' ATCGTCTGTACGGTATCGCTATTAACCCAAACAGGGTCTTCAAGGTTAACACCAACGCCTACTACGAGAT 5600
BoNT/A LC ad0
H R L Y G I A I N P N R V F K V N T N A Y Y E M
481 482 483 484 485 486 487 488 489 490 491 492 493 494 495 496 497 498 499 500 501 502 503 504

BsiWI
5' GAGTGGTCTGGAAGTGTCGTTCGAGGAACTCCGTACGTTCGGAGGTCACGACGCAAAGTTCATCGATAGT 5670
BoNT/A LC ad0
S G L E V S F E E L R T F G G H D A K F I D S
505 506 507 508 509 510 511 512 513 514 515 516 517 518 519 520 521 522 523 524 525 526 527

FIG. 39G

EcoRI
5' TTGCAGGAGAACGAATTCCGCCTGTACTACTACAACAAGTTCAAAGACATCGCGTCTACACTCAACAAGG 5740
BoNT/A LC ad0
L Q E N E F R L Y Y Y N K F K D I A S T L N K
528 529 530 531 532 533 534 535 536 537 538 539 540 541 542 543 544 545 546 547 548 549 550

5' CTAAAAGCATTGTTGGAACCACTGCTAGTTTGCAATACATGAAGAACGTGTTCAAGGAGAAATACCTCTT 5810
BoNT/A LC ad0
A K S I V G T T A S L Q Y M K N V F K E K Y L L
551 552 553 554 555 556 557 558 559 560 561 562 563 564 565 566 567 568 569 570 571 572 573 574

5' GTCGGAAGACACCTCCGGTAAATTCAGCGTGGACAAGCTGAAATTCGATAAGTTGTACAAAATGCTGACA 5880
BoNT/A LC ad0
S E D T S G K F S V D K L K F D K L Y K M L T
575 576 577 578 579 580 581 582 583 584 585 586 587 588 589 590 591 592 593 594 595 596 597

5' GAAATCTACACGGAAGACAACTTCGTTAAGTTCTTCAAAGTGTTGAACCGTAAGACCGCTCTGAACTTCG 5950
BoNT/A LC ad0 | Y>A | BoNT/A ad0 LC
E I Y T E D N F V K F F K V L N R K T A L N F
598 599 600 601 602 603 604 605 606 607 608 609 610 611 612 613 614 615 616 617 618 619 620

5' ATAAGGCTGTCTTCAAAATCAACATTGTGCCTAAAGTCAACTACACCATCTACGACGGTTTCAACCTCCG 6020
BoNT/A ad0 LC
D K A V F K I N I V P K V N Y T I Y D G F N L R
621 622 623 624 625 626 627 628 629 630 631 632 633 634 635 636 637 638 639 640 641 642 643 644

5' CAACACTAACTTGGCTGCCAACTTCAACGGCCAGAACACTGAGATCaACAACATGAACTTCACAAAGCTC 6090
BoNT/A ad0 LC
N T N L A A N F N G Q N T E I N N M N F T K L
645 646 647 648 649 650 651 652 653 654 655 656 657 658 659 660 661 662 663 664 665 666 667

AgeI
5' AAAAACTTCACCGGTTTGTTCGAGTTCTACAAGCTGCTCTGCGTGCGTGGTGGAGGCACATCTCACACGC 6160
BoNT/A ad0 LC | LC/HC...acer
K N F T G L F E F Y K L L C V R G G G T S H T
668 669 670 671 672 673 674 675 676 677 678 679 680 681 682 683 684 685 686 687 688 689 690

FIG. 39H

5' AATCTGGCTGGGAaCTCCAGCAAGGTGGCCAGGGTGGAGCTCTGAACGATCTGTGTATCAAGGTGAATAA 6230

LC/HC spacer | Epl B site | LC/HC spacer | BoNT/A Translocation Domain

Q S G W E L Q Q G G Q G G A L N D L C I K V N N 691 692 693 694 695 696 697 698 699 700 701 702 703 704 705 706 707 708 709 710 711 712 713 714

5' CTGGGATCTGTTCTTTAGCCCAAGCGAGGATAACTTCACGAACGATCTCAACAAAGGTGAAGAGATCACG 6300

BoNT/A Translocation Domain

W D L F F S P S E D N F T N D L N K G E E I T 715 716 717 718 719 720 721 722 723 724 725 726 727 728 729 730 731 732 733 734 735 736 737

5' TCTGATACCAATATCGAAGCGGCTGAAGAGAATATCTCCTTGGATCTCATCCAGCAATATTACCTGACCT 6370

BoNT/A Translocation Domain

S D T N I E A A E E N I S L D L I Q Q Y Y L T 738 739 740 741 742 743 744 745 746 747 748 749 750 751 752 753 754 755 756 757 758 759 760

BbvCI

5' TTAACTTCGATAACGAGCCCGAAAACATCTCCATCGAGAACCTCAGCTCAGACATCATTGGTCAGTTGGA 6440

BoNT/A Translocation Domain

F N F D N E P E N I S I E N L S S D I I G Q L E 761 762 763 764 765 766 767 768 769 770 771 772 773 774 775 776 777 778 779 780 781 782 783 784

5' GCTGATGCCAAACATTGAACGCTTCCCCAACGGCAAGAAATACGAACTCGACAAGTATACGATGTTTCAT 6510

BoNT/A Translocation Domain

L M P N I E R F P N G K K Y E L D K Y T M F H 785 786 787 788 789 790 791 792 793 794 795 796 797 798 799 800 801 802 803 804 805 806 807

AflII

5' TACTTAAGAGCGCAGGAGTTTGAACACGGCAAGAGCCGCATTGCTCTCACTAACTCCGTGAATGAAGCCC 6580

BoNT/A Translocation Domain

Y L R A Q E F E H G K S R I A L T N S V N E A 808 809 810 811 812 813 814 815 816 817 818 819 820 821 822 823 824 825 826 827 828 829 830

5' TGCTCAATCCGTCAAGGGTGTACACATTCTTTAGCTCCGACTATGTCAAGAAAGTGAACAAAGCCACCGA 6650

BoNT/A Translocation Domain

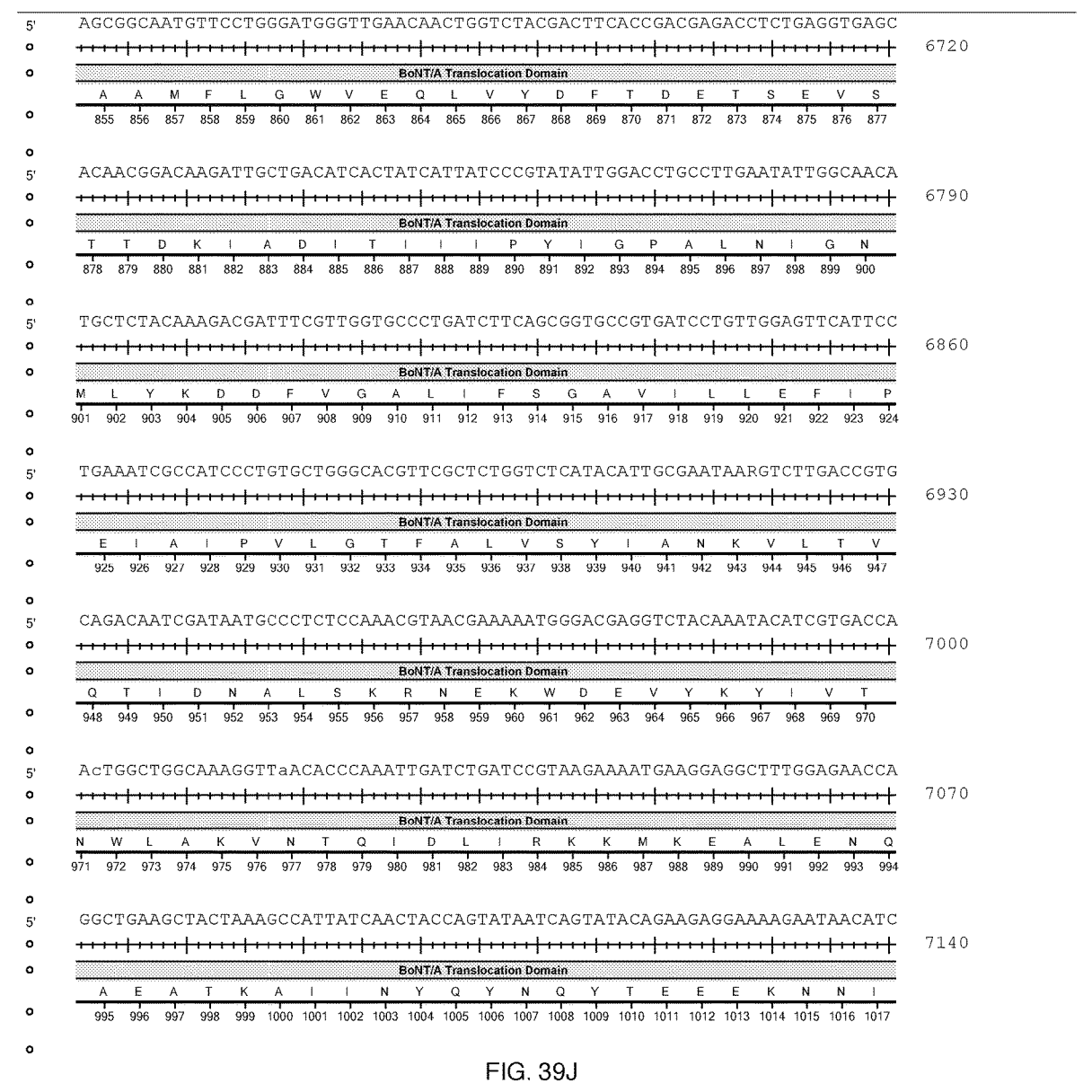

5' AGCGGCAATGTTCCTGGGATGGGTTGAACAACTGGTCTACGACTTCACCGACGAGACCTCTGAGGTGAGC 6720
BoNT/A Translocation Domain
A A M F L G W V E Q L V Y D F T D E T S E V S
855 856 857 858 859 860 861 862 863 864 865 866 867 868 869 870 871 872 873 874 875 876 877

5' ACAACGGACAAGATTGCTGACATCACTATCATTATCCCGTATATTGGACCTGCCTTGAATATTGGCAACA 6790
BoNT/A Translocation Domain
T T D K I A D I T I I I P Y I G P A L N I G N
878 879 880 881 882 883 884 885 886 887 888 889 890 891 892 893 894 895 896 897 898 899 900

5' TGCTCTACAAAGACGATTTCGTTGGTGCCCTGATCTTCAGCGGTGCCGTGATCCTGTTGGAGTTCATTCC 6860
BoNT/A Translocation Domain
M L Y K D D F V G A L I F S G A V I L L E F I P
901 902 903 904 905 906 907 908 909 910 911 912 913 914 915 916 917 918 919 920 921 922 923 924

5' TGAAATCGCCATCCCTGTGCTGGGCACGTTCGCTCTGGTCTCATACATTGCGAATAARGTCTTGACCGTG 6930
BoNT/A Translocation Domain
E I A I P V L G T F A L V S Y I A N K V L T V
925 926 927 928 929 930 931 932 933 934 935 936 937 938 939 940 941 942 943 944 945 946 947

5' CAGACAATCGATAATGCCCTCTCCAAACGTAACGAAAAATGGGACGAGGTCTACAAATACATCGTGACCA 7000
BoNT/A Translocation Domain
Q T I D N A L S K R N E K W D E V Y K Y I V T
948 949 950 951 952 953 954 955 956 957 958 959 960 961 962 963 964 965 966 967 968 969 970

5' AcTGGCTGGCAAAGGTTaACACCCAAATTGATCTGATCCGTAAGAAAATGAAGGAGGCTTTGGAGAACCA 7070
BoNT/A Translocation Domain
N W L A K V N T Q I D L I R K K M K E A L E N Q
971 972 973 974 975 976 977 978 979 980 981 982 983 984 985 986 987 988 989 990 991 992 993 994

5' GGCTGAAGCTACTAAAGCCATTATCAACTACCAGTATAATCAGTATACAGAAGAGGAAAAGAATAACATC 7140
BoNT/A Translocation Domain
A E A T K A I I N Y Q Y N Q Y T E E E K N N I
995 996 997 998 999 1000 1001 1002 1003 1004 1005 1006 1007 1008 1009 1010 1011 1012 1013 1014 1015 1016 1017

FIG. 39J

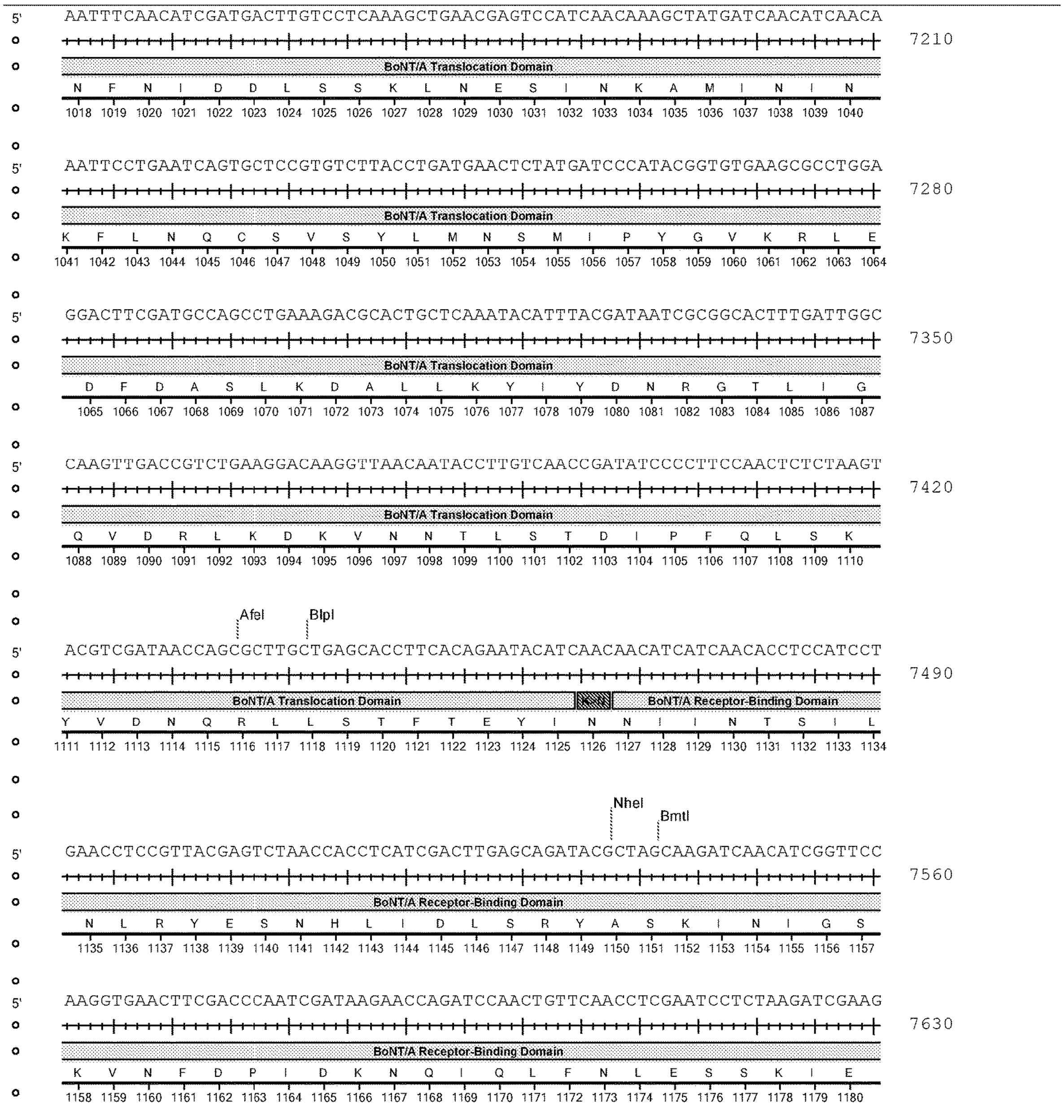

FIG. 39K

5' AATTTCAACATCGATGACTTGTCCTCAAAGCTGAACGAGTCCATCAACAAAGCTATGATCAACATCAACA
7210

BoNT/A Translocation Domain

N F N I D D L S S K L N E S I N K A M I N I N
1018 1019 1020 1021 1022 1023 1024 1025 1026 1027 1028 1029 1030 1031 1032 1033 1034 1035 1036 1037 1038 1039 1040

5' AATTCCTGAATCAGTGCTCCGTGTCTTACCTGATGAACTCTATGATCCCATACGGTGTGAAGCGCCTGGA
7280

BoNT/A Translocation Domain

K F L N Q C S V S Y L M N S M I P Y G V K R L E
1041 1042 1043 1044 1045 1046 1047 1048 1049 1050 1051 1052 1053 1054 1055 1056 1057 1058 1059 1060 1061 1062 1063 1064

5' GGACTTCGATGCCAGCCTGAAAGACGCACTGCTCAAATACATTTACGATAATCGCGGCACTTTGATTGGC
7350

BoNT/A Translocation Domain

D F D A S L K D A L L K Y I Y D N R G T L I G
1065 1066 1067 1068 1069 1070 1071 1072 1073 1074 1075 1076 1077 1078 1079 1080 1081 1082 1083 1084 1085 1086 1087

5' CAAGTTGACCGTCTGAAGGACAAGGTTAACAATACCTTGTCAACCGATATCCCCTTCCAACTCTCTAAGT
7420

BoNT/A Translocation Domain

Q V D R L K D K V N N T L S T D I P F Q L S K
1088 1089 1090 1091 1092 1093 1094 1095 1096 1097 1098 1099 1100 1101 1102 1103 1104 1105 1106 1107 1108 1109 1110

Afel   Blpl

5' ACGTCGATAACCAGCGCTTGCTGAGCACCTTCACAGAATACATCAACAACATCATCAACACCTCCATCCT
7490

BoNT/A Translocation Domain | BoNT/A Receptor-Binding Domain

Y V D N Q R L L S T F T E Y I N N I I N T S I L
1111 1112 1113 1114 1115 1116 1117 1118 1119 1120 1121 1122 1123 1124 1125 1126 1127 1128 1129 1130 1131 1132 1133 1134

Nhel   Bmtl

5' GAACCTCCGTTACGAGTCTAACCACCTCATCGACTTGAGCAGATACGCTAGCAAGATCAACATCGGTTCC
7560

BoNT/A Receptor-Binding Domain

N L R Y E S N H L I D L S R Y A S K I N I G S
1135 1136 1137 1138 1139 1140 1141 1142 1143 1144 1145 1146 1147 1148 1149 1150 1151 1152 1153 1154 1155 1156 1157

5' AAGGTGAACTTCGACCCAATCGATAAGAACCAGATCCAACTGTTCAACCTCGAATCCTCTAAGATCGAAG
7630

BoNT/A Receptor-Binding Domain

K V N F D P I D K N Q I Q L F N L E S S K I E
1158 1159 1160 1161 1162 1163 1164 1165 1166 1167 1168 1169 1170 1171 1172 1173 1174 1175 1176 1177 1178 1179 1180

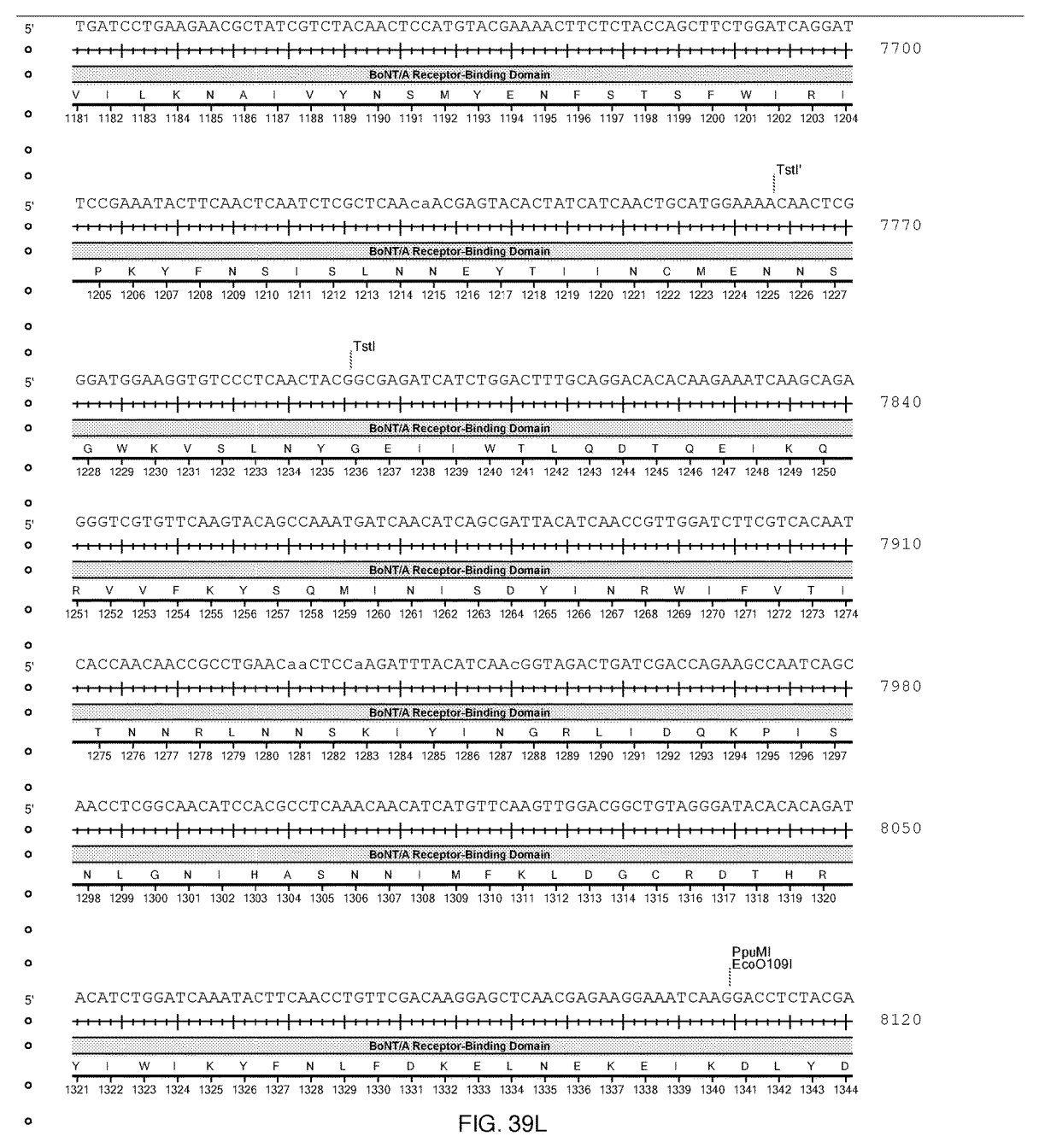

```
5'  TGATCCTGAAGAACGCTATCGTCTACAACTCCATGTACGAAAACTTCTCTACCAGCTTCTGGATCAGGAT
                                                                              7700
                        BoNT/A Receptor-Binding Domain
     V   I   L   K   N   A   I   V   Y   N   S   M   Y   E   N   F   S   T   S   F   W   I   R   I
    1181 1182 1183 1184 1185 1186 1187 1188 1189 1190 1191 1192 1193 1194 1195 1196 1197 1198 1199 1200 1201 1202 1203 1204
```

```
                                                                        TstI'
5'  TCCGAAATACTTCAACTCAATCTCGCTCAAcaACGAGTACACTATCATCAACTGCATGGAAAACAACTCG
                                                                              7770
                        BoNT/A Receptor-Binding Domain
     P   K   Y   F   N   S   I   S   L   N   N   E   Y   T   I   I   N   C   M   E   N   N   S
    1205 1206 1207 1208 1209 1210 1211 1212 1213 1214 1215 1216 1217 1218 1219 1220 1221 1222 1223 1224 1225 1226 1227
```

```
                    TstI
5'  GGATGGAAGGTGTCCCTCAACTACGGCGAGATCATCTGGACTTTGCAGGACACACAAGAAATCAAGCAGA
                                                                              7840
                        BoNT/A Receptor-Binding Domain
     G   W   K   V   S   L   N   Y   G   E   I   I   W   T   L   Q   D   T   Q   E   I   K   Q
    1228 1229 1230 1231 1232 1233 1234 1235 1236 1237 1238 1239 1240 1241 1242 1243 1244 1245 1246 1247 1248 1249 1250
```

```
5'  GGGTCGTGTTCAAGTACAGCCAAATGATCAACATCAGCGATTACATCAACCGTTGGATCTTCGTCACAAT
                                                                              7910
                        BoNT/A Receptor-Binding Domain
     R   V   V   F   K   Y   S   Q   M   I   N   I   S   D   Y   I   N   R   W   I   F   V   T   I
    1251 1252 1253 1254 1255 1256 1257 1258 1259 1260 1261 1262 1263 1264 1265 1266 1267 1268 1269 1270 1271 1272 1273 1274
```

```
5'  CACCAACAACCGCCTGAACaaCTCCaAGATTTACATCAAcGGTAGACTGATCGACCAGAAGCCAATCAGC
                                                                              7980
                        BoNT/A Receptor-Binding Domain
     T   N   N   R   L   N   N   S   K   I   Y   I   N   G   R   L   I   D   Q   K   P   I   S
    1275 1276 1277 1278 1279 1280 1281 1282 1283 1284 1285 1286 1287 1288 1289 1290 1291 1292 1293 1294 1295 1296 1297
```

```
5'  AACCTCGGCAACATCCACGCCTCAAACAACATCATGTTCAAGTTGGACGGCTGTAGGGATACACACAGAT
                                                                              8050
                        BoNT/A Receptor-Binding Domain
     N   L   G   N   I   H   A   S   N   N   I   M   F   K   L   D   G   C   R   D   T   H   R
    1298 1299 1300 1301 1302 1303 1304 1305 1306 1307 1308 1309 1310 1311 1312 1313 1314 1315 1316 1317 1318 1319 1320
```

```
                                                                        PpuMI
                                                                        EcoO109I
5'  ACATCTGGATCAAATACTTCAACCTGTTCGACAAGGAGCTCAACGAGAAGGAAATCAAGGACCTCTACGA
                                                                              8120
                        BoNT/A Receptor-Binding Domain
     Y   I   W   I   K   Y   F   N   L   F   D   K   E   L   N   E   K   E   I   K   D   L   Y   D
    1321 1322 1323 1324 1325 1326 1327 1328 1329 1330 1331 1332 1333 1334 1335 1336 1337 1338 1339 1340 1341 1342 1343 1344
```

FIG. 39L

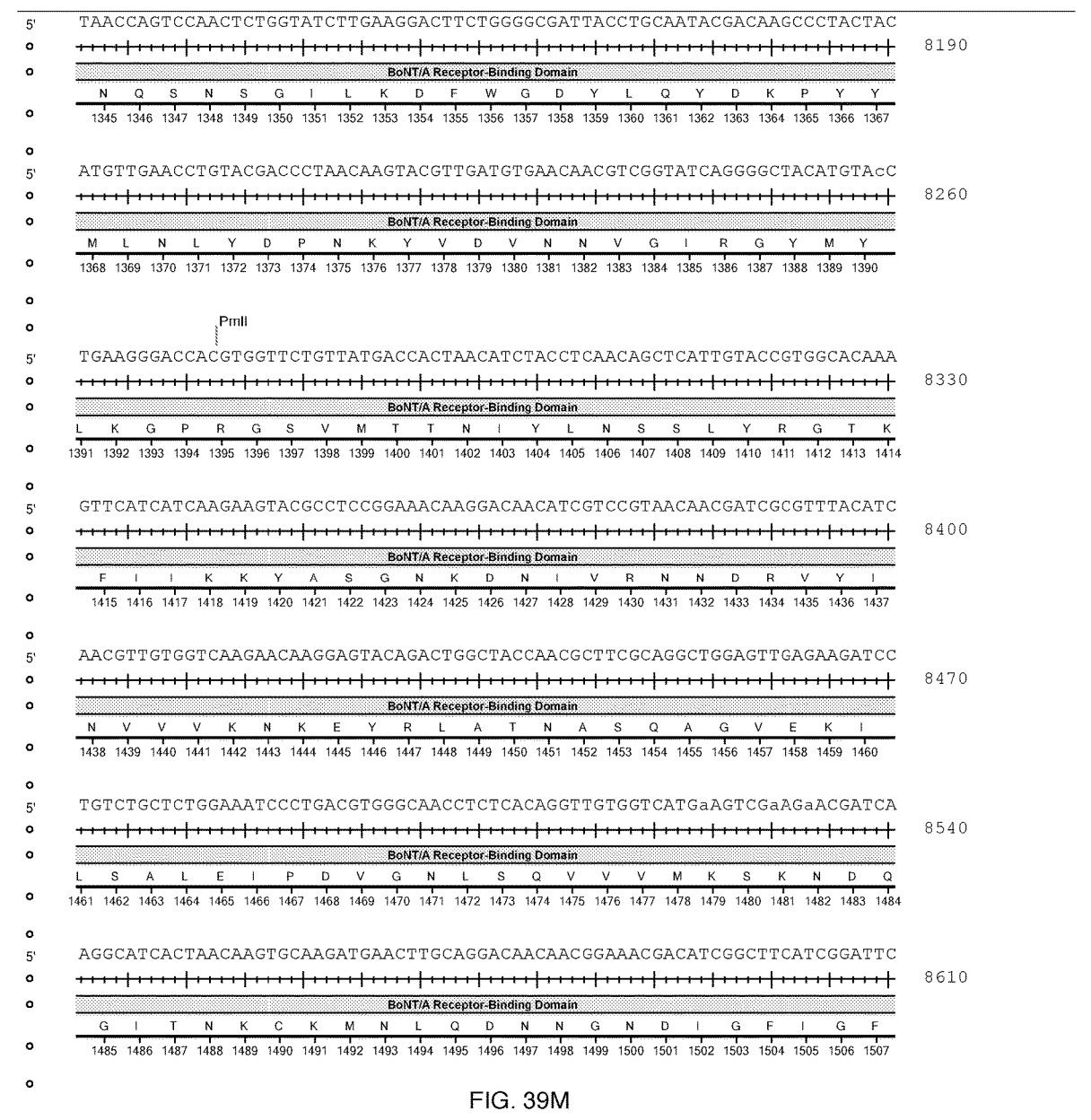

```
5'  TAACCAGTCCAACTCTGGTATCTTGAAGGACTTCTGGGGCGATTACCTGCAATACGACAAGCCCTACTAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8190
                              BoNT/A Receptor-Binding Domain
      N   Q   S   N   S   G   I   L   K   D   F   W   G   D   Y   L   Q   Y   D   K   P   Y   Y
     1345 1346 1347 1348 1349 1350 1351 1352 1353 1354 1355 1356 1357 1358 1359 1360 1361 1362 1363 1364 1365 1366 1367

5'  ATGTTGAACCTGTACGACCCTAACAAGTACGTTGATGTGAACAACGTCGGTATCAGGGGCTACATGTAcC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8260
                              BoNT/A Receptor-Binding Domain
      M   L   N   L   Y   D   P   N   K   Y   V   D   V   N   N   V   G   I   R   G   Y   M   Y
     1368 1369 1370 1371 1372 1373 1374 1375 1376 1377 1378 1379 1380 1381 1382 1383 1384 1385 1386 1387 1388 1389 1390

                    Pmll
5'  TGAAGGGACCACGTGGTTCTGTTATGACCACTAACATCTACCTCAACAGCTCATTGTACCGTGGCACAAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8330
                              BoNT/A Receptor-Binding Domain
      L   K   G   P   R   G   S   V   M   T   T   N   I   Y   L   N   S   S   L   Y   R   G   T   K
     1391 1392 1393 1394 1395 1396 1397 1398 1399 1400 1401 1402 1403 1404 1405 1406 1407 1408 1409 1410 1411 1412 1413 1414

5'  GTTCATCATCAAGAAGTACGCCTCCGGAAACAAGGACAACATCGTCCGTAACAACGATCGCGTTTACATC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8400
                              BoNT/A Receptor-Binding Domain
      F   I   I   K   K   Y   A   S   G   N   K   D   N   I   V   R   N   N   D   R   V   Y   I
     1415 1416 1417 1418 1419 1420 1421 1422 1423 1424 1425 1426 1427 1428 1429 1430 1431 1432 1433 1434 1435 1436 1437

5'  AACGTTGTGGTCAAGAACAAGGAGTACAGACTGGCTACCAACGCTTCGCAGGCTGGAGTTGAGAAGATCC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8470
                              BoNT/A Receptor-Binding Domain
      N   V   V   V   K   N   K   E   Y   R   L   A   T   N   A   S   Q   A   G   V   E   K   I
     1438 1439 1440 1441 1442 1443 1444 1445 1446 1447 1448 1449 1450 1451 1452 1453 1454 1455 1456 1457 1458 1459 1460

5'  TGTCTGCTCTGGAAATCCCTGACGTGGGCAACCTCTCACAGGTTGTGGTCATGaAGTCGaAGaACGATCA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8540
                              BoNT/A Receptor-Binding Domain
      L   S   A   L   E   I   P   D   V   G   N   L   S   Q   V   V   V   M   K   S   K   N   D   Q
     1461 1462 1463 1464 1465 1466 1467 1468 1469 1470 1471 1472 1473 1474 1475 1476 1477 1478 1479 1480 1481 1482 1483 1484

5'  AGGCATCACTAACAAGTGCAAGATGAACTTGCAGGACAACAACGGAAACGACATCGGCTTCATCGGATTC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8610
                              BoNT/A Receptor-Binding Domain
      G   I   T   N   K   C   K   M   N   L   Q   D   N   N   G   N   D   I   G   F   I   G   F
     1485 1486 1487 1488 1489 1490 1491 1492 1493 1494 1495 1496 1497 1498 1499 1500 1501 1502 1503 1504 1505 1506 1507
```

FIG. 39M

```
5'  CACCAATTCAACAACATCGCCAAGTTGGTGGCCAGCAACTGGTACAACCGTCAGATCGAGCGTTCGTCCC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8680
                         BoNT/A Receptor-Binding Domain
     H   Q   F   N   N   I   A   K   L   V   A   S   N   W   Y   N   R   Q   I   E   R   S   S
    1508 1509 1510 1511 1512 1513 1514 1515 1516 1517 1518 1519 1520 1521 1522 1523 1524 1525 1526 1527 1528 1529 1530

            Bsu36I
5'  GCACCTTAGGATGCTCGTGGGAGTTCATTCCAGTCGATGACGGATGGGGAGAGAGACCTTTGGGCGCAGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8750
                        BoNT/A Receptor-Binding Domain          | linker
     R   T   L   G   C   S   W   E   F   I   P   V   D   D   G   W   G   E   R   P   L   G   A   G
    1531 1532 1533 1534 1535 1536 1537 1538 1539 1540 1541 1542 1543 1544 1545 1546 1547 1548 1549 1550 1551 1552 1553 1554

                        BstEII
5'  AGGATGGGAACTCCAGCAAGGTTACCCCTACGATGTCCCTGACTACGCTGGTGCAGGATGGTCCCACCCA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8820
    linker | BoNT B site | linker |      HA tag      | linker |  Strep tag
     G   W   E   L   Q   Q   G   Y   P   Y   D   V   P   D   Y   A   G   A   G   W   S   H   P
    1555 1556 1557 1558 1559 1560 1561 1562 1563 1564 1565 1566 1567 1568 1569 1570 1571 1572 1573 1574 1575 1576 1577

5'  CAATTCGAGAAGGGTGCAGGATGGAGTCACCCACAGTTCGAGAAGGGCGCTGGATGGTCCCACCCACAGT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8890
     Strep tag  | linker |  Strep tag  | linker |  Strep tag
     Q   F   E   K   G   A   G   W   S   H   P   Q   F   E   K   G   A   G   W   S   H   P   Q
    1578 1579 1580 1581 1582 1583 1584 1585 1586 1587 1588 1589 1590 1591 1592 1593 1594 1595 1596 1597 1598 1599 1600

                                          PspXI         Acc65I
                              Nsil        Xhol     SphI    KpnI
5'  TCGAGAAATAATTAGTTGATGCATAGTTAATTAGATAGCTCGAGGCATGCGGTACCAAGCTTGTCGAGAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8960
    Strep tag
     F   E   K
    1601 1602 1603

5'  GTACTAGAGGATCATAATCAGCCATACCACATTTGTAGAGGTTTTACTTGCTTTAAAAAACCTCCCACAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  9030

                                    MfeI
5'  CTCCCCCTGAACCTGAAACATAAAATGAATGCAATTGTTGTTGTTAACTTGTTTATTGCAGCTTATAATG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  9100
5'  GTTACAAATAAAGCAATAGCATCACAAATTTCACAAATAAAGCATTTTTTTCACTGCATTCTAGTTGTGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  9170
```

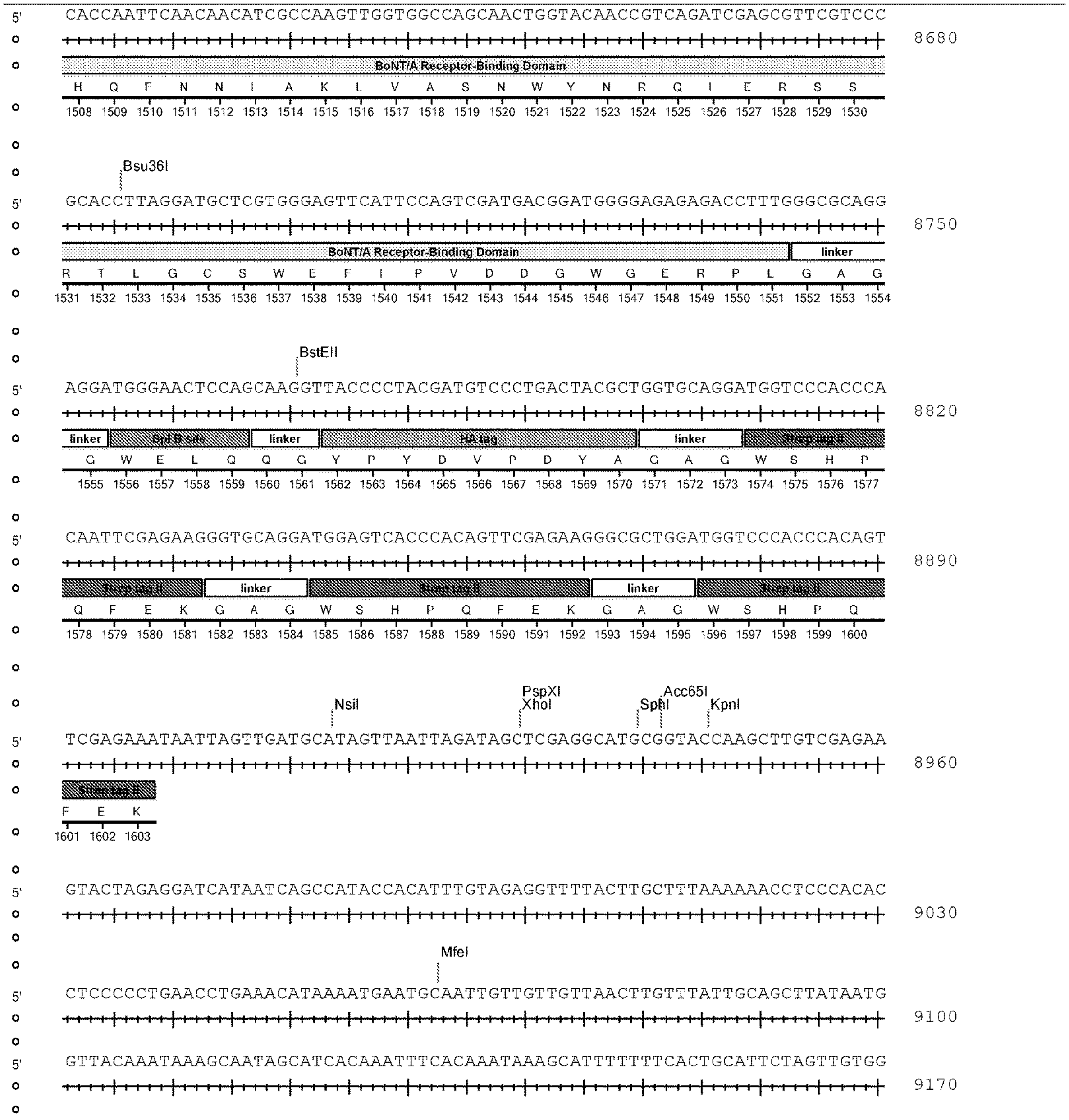

FIG. 39N

AvrII

5' TTTGTCCAAACTCATCAATGTATCTTATCATGTCTGGATCTGATCACTGCTTGAGCCTAGGAGATCCGAA 9240

5' CCAGATAAGTGAAATCTAGTTCCAAACTATTTTGTCATTTTTAATTTTCGTATTAGCTTACGACGCTACA 9310

5' CCCAGTTCCCATCTATTTTGTCACTCTTCCCTAAATAATCCTTAAAAACTCCATTTCCACCCCTCCCAGT 9380

5' TCCCAACTATTTTGTCCGCCCACAGCGGGGCATTTTTCTTCCTGTTATGTTTTTAATCAAACATCCTGCC 9450

5' AACTCCATGTGACAAACCGTCATCTTCGGCTACTTTTTCTCTGTCACAGAATGAAAATTTTTCTGTCATC 9520

5' TCTTCGTTATTAATGTTTGTAATTGACTGAATATCAACGCTTATTTGCAGCCTGAATGGCGAATGG 9586

FIG. 39O

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 40A

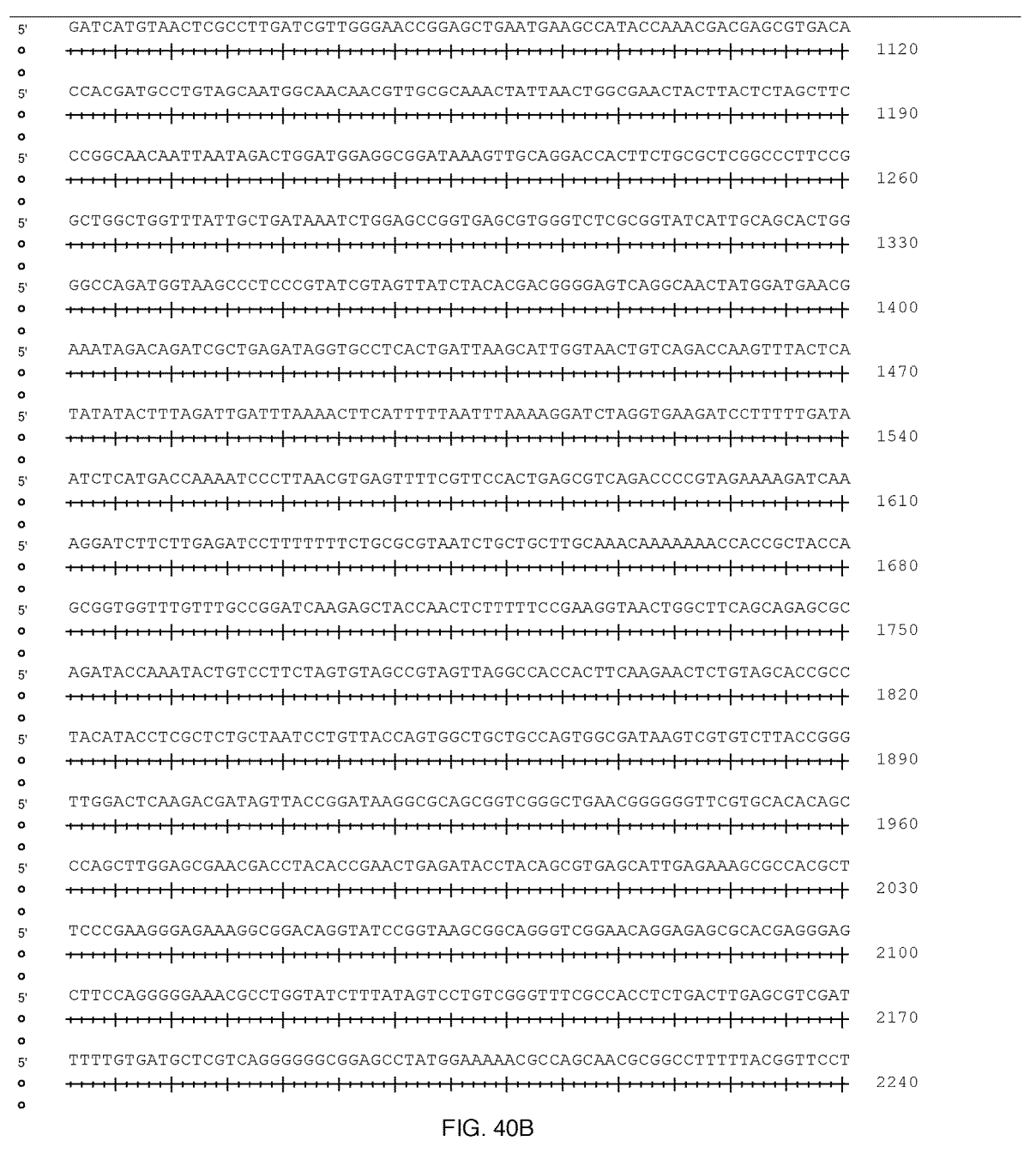

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 40B

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 40C

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI
BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

RsrII

5' TAAATATTCCGGATTATTCATACCGTCCCACCATCGGGCGCGGATCTCGGTCCGTTCGAACCAGAACTCT 4060 mut....mHI

5' GGAAGCTTAACTCCTAAAAAACCGCCACCATGAAATTCTTAGTCAACGTTGCCCTTGTTTTTATGGTCGT 4130

Lob. TMO cDNA Lead Seq | Signal Peptide

5' TTGGGTCATTCCGGATAGGTTCAGCAGAAACTCTAACCCTAACTTGAACAAACCTCCCAGAGTGACCTCA 5040

BoNT/C1 ad0 LC

W V I P D R F S R N S N P N L N K P P R V T S 295 296 297 298 299 300 301 302 303 304 305 306 307 308 309 310 311 312 313 314 315 316 317

5' CCTAAGAGTGGATACTACGACCCCAACTACCTCTCGACTGACTCCGATAAAGACCCCTTCCTGAAGGAGA 5110

BoNT/C1 ad0 LC

P K S G Y Y D P N Y L S T D S D K D P F L K E 318 319 320 321 322 323 324 325 326 327 328 329 330 331 332 333 334 335 336 337 338 339 340

5' TCATTAAACTCTTCAAGCGCATCAACTCTCGTGAAATTGGCGAGGAATTGATCTACCGCCTGAGTACAGA 5180

BoNT/C1 ad0 LC

I I K L F K R I N S R E I G E E L I Y R L S T D 341 342 343 344 345 346 347 348 349 350 351 352 353 354 355 356 357 358 359 360 361 362 363 364

XmaI

SmaI

5' CATCCCATTCCCGGGTAACAACAACACCCCAATCAACACTTTCGATTTCGATGTCGATTTCAACTCAGTG 5250

BoNT/C1 ad0 LC

I P F P G N N N T P I N T F D F D V D F N S V 365 366 367 368 369 370 371 372 373 374 375 376 377 378 379 380 381 382 383 384 385 386 387

5' GATGTCAAAACCAGGCAGGGAAACAACTGGGTGAAGACTGGTAGCATCAACCCATCTGTCATCATTACTG 5320

BoNT/C1 ad0 LC

D V K T R Q G N N W V K T G S I N P S V I I T 388 389 390 391 392 393 394 395 396 397 398 399 400 401 402 403 404 405 406 407 408 409 410

Bpu10I

5' GCCCGAGAGAGAACATCATTGACCCTGAAACCTCCACTTTCAaGCTGACaAACAACACGTTCGCTGCTCA 5390

BoNT/C1 ad0 LC

G P R E N I I D P E T S T F K L T N N T F A A Q 411 412 413 414 415 416 417 418 419 420 421 422 423 424 425 426 427 428 429 430 431 432 433 434

5' GGAAGGCTTCGGAGCGTTGAGCATCATTTCTATCTCACCTCGCTTCATGCTGACATACTCTAACGCTACG 5460

BoNT/C1 ad0 LC

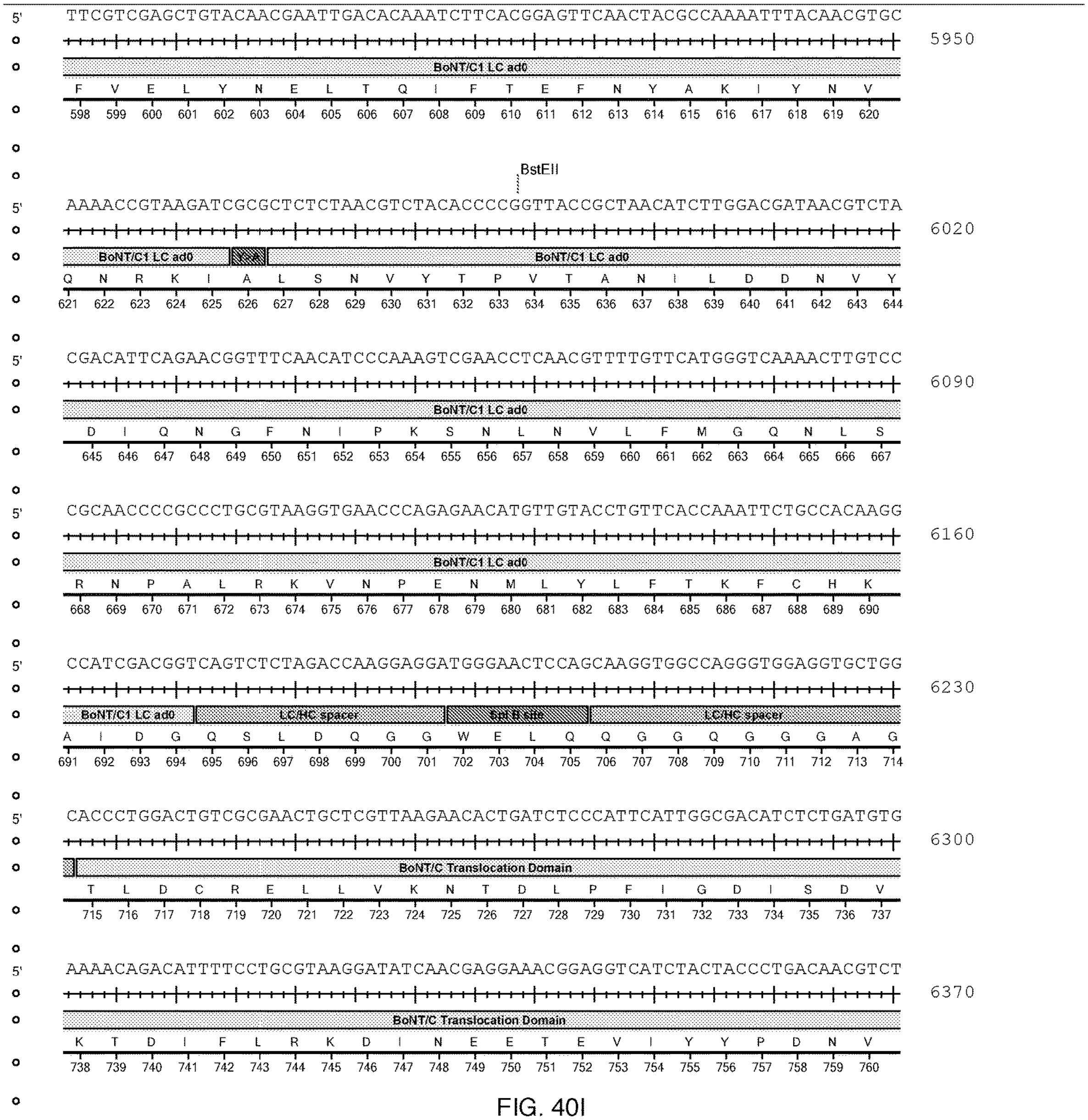

FIG. 40I

```
5'  TTCGTCGAGCTGTACAACGAATTGACACAAATCTTCACGGAGTTCAACTACGCCAAAATTTACAACGTGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   5950
                              BoNT/C1 LC ad0
     F   V   E   L   Y   N   E   L   T   Q   I   F   T   E   F   N   Y   A   K   I   Y   N   V
    598 599 600 601 602 603 604 605 606 607 608 609 610 611 612 613 614 615 616 617 618 619 620

                                                    BstEII

5'  AAAACCGTAAGATCGCGCTCTCTAACGTCTACACCCCGGTTACCGCTAACATCTTGGACGATAACGTCTA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6020
        BoNT/C1 LC ad0                        BoNT/C1 LC ad0
     Q   N   R   K   I   A   L   S   N   V   Y   T   P   V   T   A   N   I   L   D   D   N   V   Y
    621 622 623 624 625 626 627 628 629 630 631 632 633 634 635 636 637 638 639 640 641 642 643 644

5'  CGACATTCAGAACGGTTTCAACATCCCAAAGTCGAACCTCAACGTTTTGTTCATGGGTCAAAACTTGTCC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6090
                              BoNT/C1 LC ad0
     D   I   Q   N   G   F   N   I   P   K   S   N   L   N   V   L   F   M   G   Q   N   L   S
    645 646 647 648 649 650 651 652 653 654 655 656 657 658 659 660 661 662 663 664 665 666 667

5'  CGCAACCCCGCCCTGCGTAAGGTGAACCCAGAGAACATGTTGTACCTGTTCACCAAATTCTGCCACAAGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6160
                              BoNT/C1 LC ad0
     R   N   P   A   L   R   K   V   N   P   E   N   M   L   Y   L   F   T   K   F   C   H   K
    668 669 670 671 672 673 674 675 676 677 678 679 680 681 682 683 684 685 686 687 688 689 690

5'  CCATCGACGGTCAGTCTCTAGACCAAGGAGGATGGGAACTCCAGCAAGGTGGCCAGGGTGGAGGTGCTGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6230
      BoNT/C1 LC ad0    LC/HC spacer      BgI II site         LC/HC spacer
     A   I   D   G   Q   S   L   D   Q   G   G   W   E   L   Q   Q   G   G   Q   G   G   A   G
    691 692 693 694 695 696 697 698 699 700 701 702 703 704 705 706 707 708 709 710 711 712 713 714

5'  CACCCTGGACTGTCGCGAACTGCTCGTTAAGAACACTGATCTCCCATTCATTGGCGACATCTCTGATGTG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6300
                           BoNT/C Translocation Domain
     T   L   D   C   R   E   L   L   V   K   N   T   D   L   P   F   I   G   D   I   S   D   V
    715 716 717 718 719 720 721 722 723 724 725 726 727 728 729 730 731 732 733 734 735 736 737

5'  AAAACAGACATTTTCCTGCGTAAGGATATCAACGAGGAAACGGAGGTCATCTACTACCCTGACAACGTCT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼   6370
                           BoNT/C Translocation Domain
     K   T   D   I   F   L   R   K   D   I   N   E   E   T   E   V   I   Y   Y   P   D   N   V
    738 739 740 741 742 743 744 745 746 747 748 749 750 751 752 753 754 755 756 757 758 759 760
```

Figure 40J:
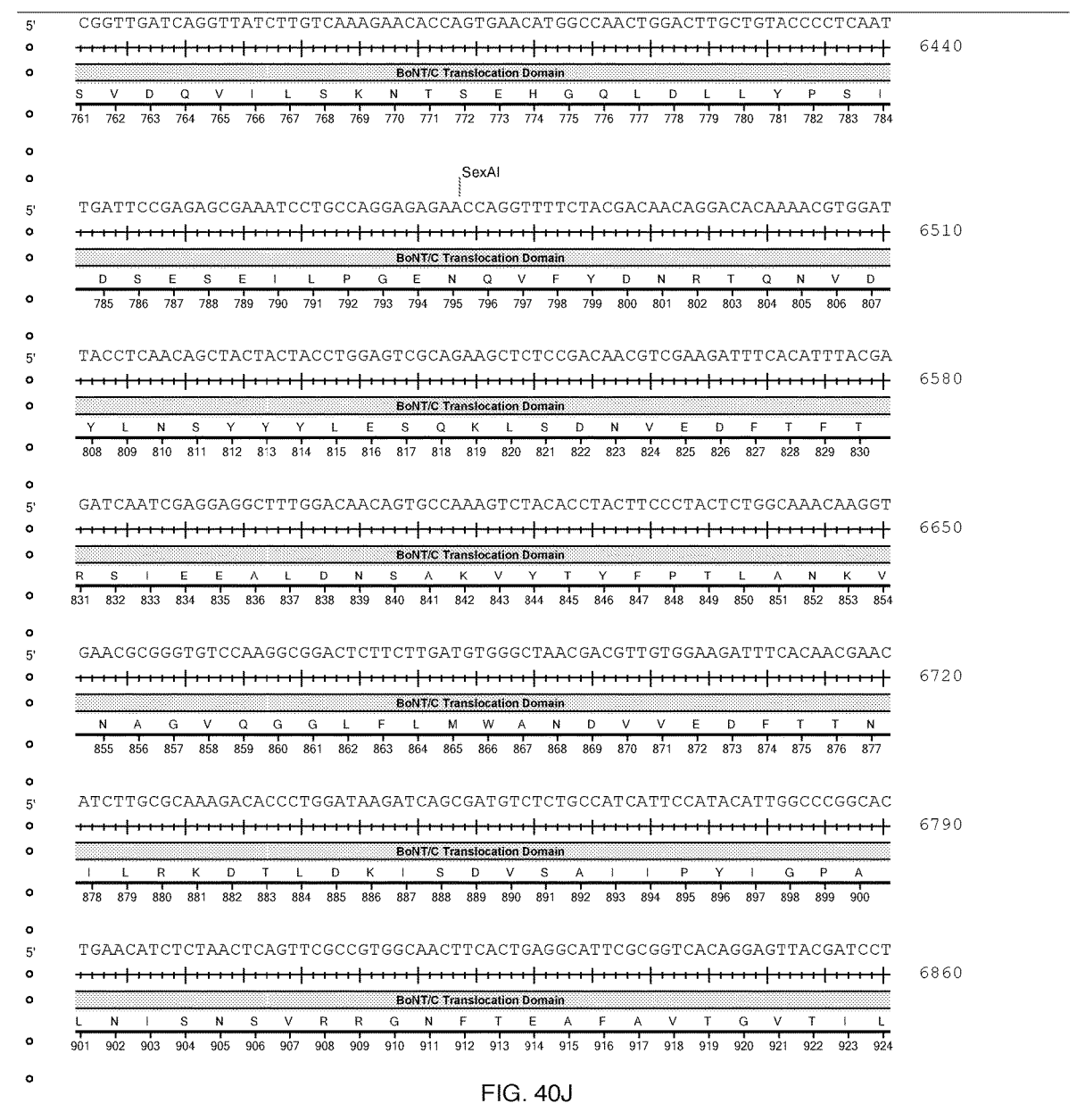

5' CGGTTGATCAGGTTATCTTGTCAAAGAACACCAGTGAACATGGCCAACTGGACTTGCTGTACCCCTCAAT 6440

BoNT/C Translocation Domain

S V D Q V I L S K N T S E H G Q L D L L Y P S I 761 762 763 764 765 766 767 768 769 770 771 772 773 774 775 776 777 778 779 780 781 782 783 784

SexAI

5' TGATTCCGAGAGCGAAATCCTGCCAGGAGAGAACCAGGTTTTCTACGACAACAGGACACAAAACGTGGAT 6510

BoNT/C Translocation Domain

D S E S E I L P G E N Q V F Y D N R T Q N V D 785 786 787 788 789 790 791 792 793 794 795 796 797 798 799 800 801 802 803 804 805 806 807

5' TACCTCAACAGCTACTACTACCTGGAGTCGCAGAAGCTCTCCGACAACGTCGAAGATTTCACATTTACGA 6580

BoNT/C Translocation Domain

Y L N S Y Y Y L E S Q K L S D N V E D F T F T 808 809 810 811 812 813 814 815 816 817 818 819 820 821 822 823 824 825 826 827 828 829 830

5' GATCAATCGAGGAGGCTTTGGACAACAGTGCCAAAGTCTACACCTACTTCCCTACTCTGGCAAACAAGGT 6650

BoNT/C Translocation Domain

R S I E E A L D N S A K V Y T Y F P T L A N K V 831 832 833 834 835 836 837 838 839 840 841 842 843 844 845 846 847 848 849 850 851 852 853 854

5' GAACGCGGGTGTCCAAGGCGGACTCTTCTTGATGTGGGCTAACGACGTTGTGGAAGATTTCACAACGAAC 6720

BoNT/C Translocation Domain

N A G V Q G G L F L M W A N D V V E D F T T N 855 856 857 858 859 860 861 862 863 864 865 866 867 868 869 870 871 872 873 874 875 876 877

5' ATCTTGCGCAAAGACACCCTGGATAAGATCAGCGATGTCTCTGCCATCATTCCATACATTGGCCCGGCAC 6790

BoNT/C Translocation Domain

I L R K D T L D K I S D V S A I I P Y I G P A 878 879 880 881 882 883 884 885 886 887 888 889 890 891 892 893 894 895 896 897 898 899 900

5' TGAACATCTCTAACTCAGTTCGCCGTGGCAACTTCACTGAGGCATTCGCGGTCACAGGAGTTACGATCCT 6860

BoNT/C Translocation Domain

PfoI

5' CTTGGAGGCTTTCCCGGAGTTCACAATCCCCGCACTGGGCGCGTTCGTTATCTACTCCAAAGTGCAGGAG 6930

BoNT/C Translocation Domain

L E A F P E F T I P A L G A F V I Y S K V Q E 925 926 927 928 929 930 931 932 933 934 935 936 937 938 939 940 941 942 943 944 945 946 947

BsiWI

5' CGCAACGAAATCATTAAGACTATCGACAACTGCCTGGAGCAAAGGATCAAAAGATGGAAGGATTCGTACG 7000

BoNT/C Translocation Domain

R N E I I K T I D N C L E Q R I K R W K D S Y 948 949 950 951 952 953 954 955 956 957 958 959 960 961 962 963 964 965 966 967 968 969 970

5' AATGGATGATGGGTACCTGGCTCTCCCGTATCATTACGCAGTTCAACAACATCAGCTACCAAATGTACGA 7070

BoNT/C Translocation Domain

E W M M G T W L S R I I T Q F N N I S Y Q M Y D 971 972 973 974 975 976 977 978 979 980 981 982 983 984 985 986 987 988 989 990 991 992 993 994

XcmI

5' CTCTCTCAACTACCAGGCTGGTGCCATCAAGGCCAAAATTGACTTGGAGTACAAGAAATACAGTGGCTCG 7140

BoNT/C Translocation Domain

S L N Y Q A G A I K A K I D L E Y K K Y S G S 995 996 997 998 999 1000 1001 1002 1003 1004 1005 1006 1007 1008 1009 1010 1011 1012 1013 1014 1015 1016 1017

5' GATAAAGAGAACATCAAGAGTCAAGTCGAAAaCCTGAAAAACTCACTCGACGTTAAGATCAGTGAGGCAA 7210

BoNT/C Translocation Domain

D K E N I K S Q V E N L K N S L D V K I S E A 1018 1019 1020 1021 1022 1023 1024 1025 1026 1027 1028 1029 1030 1031 1032 1033 1034 1035 1036 1037 1038 1039 1040

5' TGAACAACATCAACAAGTTCATTCGCGAATGTTCCGTTACCTACCTCTTCAAAAACATGTTGCCAAAGGT 7280

BoNT/C Translocation Domain

M N N I N K F I R E C S V T Y L F K N M L P K V 1041 1042 1043 1044 1045 1046 1047 1048 1049 1050 1051 1052 1053 1054 1055 1056 1057 1058 1059 1060 1061 1062 1063 1064

5' CATCGACGAGCTGAACGAATTTGATCGTAACACTAAGGCGAAACTGATTAACCTCATCGACTCACACAAC 7350

BoNT/C Translocation Domain

```
5'  ATCATTTTGGTGGGCGAAGTCGATAAGCTGAAAGCCAAGGtGAACAACAGTTTCCAGAACACAATCCCTT
                                                                                    7420
           BoNT/C Translocation Domain
     I  I  L  V  G  E  V  D  K  L  K  A  K  V  N  N  S  F  Q  N  T  I  P
    1088 1089 1090 1091 1092 1093 1094 1095 1096 1097 1098 1099 1100 1101 1102 1103 1104 1105 1106 1107 1108 1109 1110

5'  TCAAcATTTTCTCATACACGAACAACAGTCTGCTCAAGGACATCATTAACGAGTACTTCAACAACATTAA
                                                                                    7490
           BoNT/C Translocation Domain                          BoNT/C R... Domain
     F  N  I  F  S  Y  T  N  N  S  L  L  K  D  I  I  N  E  Y  F  N  N  I  N
    1111 1112 1113 1114 1115 1116 1117 1118 1119 1120 1121 1122 1123 1124 1125 1126 1127 1128 1129 1130 1131 1132 1133 1134

                           PstI                              SpeI
5'  CGATAGCAAAATCCTGTCACTGCAGAACCGTAAGAACACACTGGTCGATACTAGTGGATACAACGCCGAA
                                                                                    7560
           BoNT/C Receptor Binding Domain
     D  S  K  I  L  S  L  Q  N  R  K  N  T  L  V  D  T  S  G  Y  N  A  E
    1135 1136 1137 1138 1139 1140 1141 1142 1143 1144 1145 1146 1147 1148 1149 1150 1151 1152 1153 1154 1155 1156 1157

                           PvuII
5'  GTCTCTGAGGAAGGTGACGTGCAGCTGAACCCTATCTTCCCCTTCGACTTCAAATTGGGCTCCAGCGGAG
                                                                                    7630
           BoNT/C Receptor Binding Domain
     V  S  E  E  G  D  V  Q  L  N  P  I  F  P  F  D  F  K  L  G  S  S  G
    1158 1159 1160 1161 1162 1163 1164 1165 1166 1167 1168 1169 1170 1171 1172 1173 1174 1175 1176 1177 1178 1179 1180

5'  AGGATAGGGGCAAGGTCATCGTCACCCAGAACGAGAACATCGTCTACAACTCAATGTACGAATCCTTCAG
                                                                                    7700
           BoNT/C Receptor Binding Domain
     E  D  R  G  K  V  I  V  T  Q  N  E  N  I  V  Y  N  S  M  Y  E  S  F  S
    1181 1182 1183 1184 1185 1186 1187 1188 1189 1190 1191 1192 1193 1194 1195 1196 1197 1198 1199 1200 1201 1202 1203 1204

                                                     BspMI
5'  CATCTCTTTCTGGATCAGGATTAACAAGTGGGTGAGCAACCTGCCCGGTTACACAATCATTGACTCTGTC
                                                                                    7770
           BoNT/C Receptor Binding Domain
     I  S  F  W  I  R  I  N  K  W  V  S  N  L  P  G  Y  T  I  I  D  S  V
    1205 1206 1207 1208 1209 1210 1211 1212 1213 1214 1215 1216 1217 1218 1219 1220 1221 1222 1223 1224 1225 1226 1227

5'  AAGAACAACTCAGGTTGGAGTATCGGCATCATTTCTAACTTCTTGGTCTTCACCCTGAAGCAGAACGAGG
                                                                                    7840
           BoNT/C Receptor Binding Domain
     K  N  N  S  G  W  S  I  G  I  I  S  N  F  L  V  F  T  L  K  Q  N  E
    1228 1229 1230 1231 1232 1233 1234 1235 1236 1237 1238 1239 1240 1241 1242 1243 1244 1245 1246 1247 1248 1249 1250
```

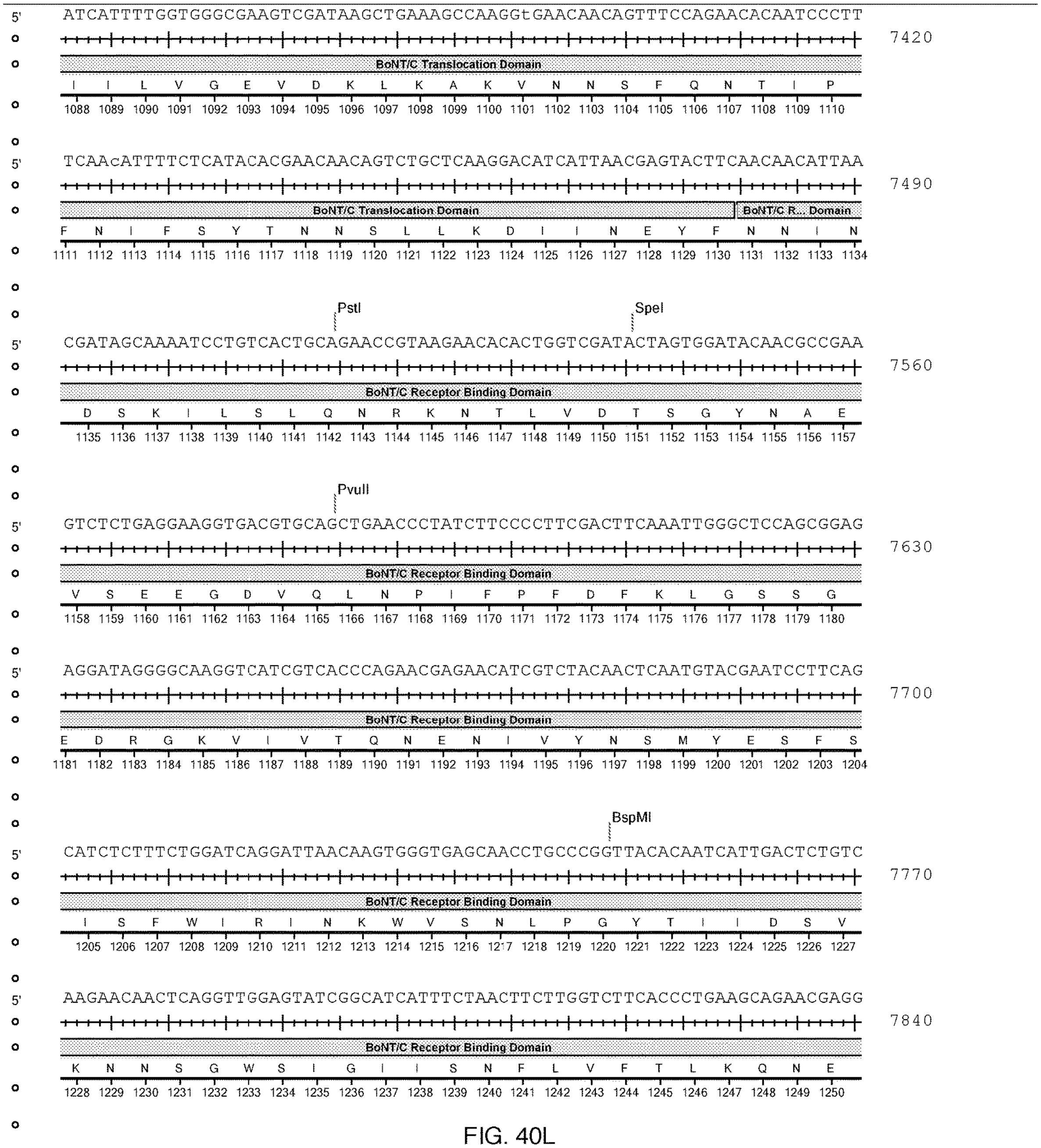

FIG. 40L

5' ACTCGGAACAATCCATTAACTTCTCATACGATATCAGTAACAACGCTCCAGGTTACAACAAGTGGTTCTT 7910
BoNT/C Receptor Binding Domain
D S E Q S I N F S Y D I S N N A P G Y N K W F F
1251 1252 1253 1254 1255 1256 1257 1258 1259 1260 1261 1262 1263 1264 1265 1266 1267 1268 1269 1270 1271 1272 1273 1274

5' CGTTACCGTGACTAACAACATGATGGGTAACATGAAAATTTACATCAACGGCAAGCTCATTGACACCATC 7980
BoNT/C Receptor Binding Domain
V T V T N N M M G N M K I Y I N G K L I D T I
1275 1276 1277 1278 1279 1280 1281 1282 1283 1284 1285 1286 1287 1288 1289 1290 1291 1292 1293 1294 1295 1296 1297

5' AAAGTGAAGGAGTTGACTGGTATTAACTTCTCCAAAACAATCACGTTTGAAATTAaCaAGATCCCTGACA 8050
BoNT/C Receptor Binding Domain
K V K E L T G I N F S K T I T F E I N K I P D
1298 1299 1300 1301 1302 1303 1304 1305 1306 1307 1308 1309 1310 1311 1312 1313 1314 1315 1316 1317 1318 1319 1320

5' CCGGCCTGATCACTTCAGACAGTGATAACATCAACATGTGGATTAGGGATTTCTACATCTTCGCCAAGGA 8120
BoNT/C Receptor Binding Domain
T G L I T S D S D N I N M W I R D F Y I F A K E
1321 1322 1323 1324 1325 1326 1327 1328 1329 1330 1331 1332 1333 1334 1335 1336 1337 1338 1339 1340 1341 1342 1343 1344

EcoICRI
SacI
5' GCTCGACGGAAAGGATATTAACATCCTCTTCAACAGCTTGCAGTACACCAACGTCGTTAAAGACTACTGG 8190
BoNT/C Receptor Binding Domain
L D G K D I N I L F N S L Q Y T N V V K D Y W
1345 1346 1347 1348 1349 1350 1351 1352 1353 1354 1355 1356 1357 1358 1359 1360 1361 1362 1363 1364 1365 1366 1367

5' GGTAACGATTTGAGATACAACAAGGAGTACTACATGGTCAACATCGACTACCTGAACAGGTACATGTACG 8260
BoNT/C Receptor Binding Domain
G N D L R Y N K E Y Y M V N I D Y L N R Y M Y
1368 1369 1370 1371 1372 1373 1374 1375 1376 1377 1378 1379 1380 1381 1382 1383 1384 1385 1386 1387 1388 1389 1390

5' CTAACTCCCGCCAAATCGTGTTCAACACCAGGAGAAACAACAACGACTTCAACGAGGGTTACAAAATCAT 8330
BoNT/C Receptor Binding Domain
A N S R Q I V F N T R R N N N D F N E G Y K I I
1391 1392 1393 1394 1395 1396 1397 1398 1399 1400 1401 1402 1403 1404 1405 1406 1407 1408 1409 1410 1411 1412 1413 1414

FIG. 40M

```
5' TATCAAGCGCATCCGTGGCAACACCAACGATACTAGGGTGAGAGGTGGCGACATTCTGTACTTCGATATG
                                    BoNT/C Receptor Binding Domain                          8400
    I    K    R    I    R    G    N    T    N    D    T    R    V    R    G    G    D    I    L    Y    F    D    M
   1415 1416 1417 1418 1419 1420 1421 1422 1423 1424 1425 1426 1427 1428 1429 1430 1431 1432 1433 1434 1435 1436 1437

5' ACTATCAACAACAAAGCCTACAACTTGTTCATGAAAAACGAGACAATGTACGCCGACAAcCATAGCACGG
                                    BoNT/C Receptor Binding Domain                          8470
    T    I    N    N    K    A    Y    N    L    F    M    K    N    E    T    M    Y    A    D    N    H    S    T
   1438 1439 1440 1441 1442 1443 1444 1445 1446 1447 1448 1449 1450 1451 1452 1453 1454 1455 1456 1457 1458 1459 1460

5' AGGATATTTACGCAATCGGACTGAGGGAACAGACAAAGGACATCAACGATAACATTATCTTCCAGATCCA
                                    BoNT/C Receptor Binding Domain                          8540
    E    D    I    Y    A    I    G    L    R    E    Q    T    K    D    I    N    D    N    I    I    F    Q    I    Q
   1461 1462 1463 1464 1465 1466 1467 1468 1469 1470 1471 1472 1473 1474 1475 1476 1477 1478 1479 1480 1481 1482 1483 1484

5' ACCTATGAACAACACGTACTACTACGCTTCGCAAATCTTCAAGTCCAACTTCAACGGAGAAAACATTTCG
                                    BoNT/C Receptor Binding Domain                          8610
    P    M    N    N    T    Y    Y    Y    A    S    Q    I    F    K    S    N    F    N    G    E    N    I    S
   1485 1486 1487 1488 1489 1490 1491 1492 1493 1494 1495 1496 1497 1498 1499 1500 1501 1502 1503 1504 1505 1506 1507

5' GGTATCTGTTCCATTGGCACATACCGCTTCCGTCTGGGTGGTGACTGGTATCGTCACAACTACCTCGTTC
                                    BoNT/C Receptor Binding Domain                          8680
    G    I    C    S    I    G    T    Y    R    F    R    L    G    G    D    W    Y    R    H    N    Y    L    V
   1508 1509 1510 1511 1512 1513 1514 1515 1516 1517 1518 1519 1520 1521 1522 1523 1524 1525 1526 1527 1528 1529 1530

                                                              SalI
5' CCACCGTGAAGCAGGGTAACTACGCTTCTTTGCTGGAGTCGACTTCCACGCACTGGGGATTCGTTCCTGT
                                    BoNT/C Receptor Binding Domain                          8750
    P    T    V    K    Q    G    N    Y    A    S    L    L    E    S    T    S    T    H    W    G    F    V    P    V
   1531 1532 1533 1534 1535 1536 1537 1538 1539 1540 1541 1542 1543 1544 1545 1546 1547 1548 1549 1550 1551 1552 1553 1554

5' GTCAGAGGGCGCTGGCTACCCTTACGATGTTCCCGACTACGCTGGTTGGGAACTCCAGCAAGGTGCAGGA
                                                                                            8820
   BoNT..main | linker |        HA tag         | li..r |            | linker
    S    E    G    A    G    Y    P    Y    D    V    P    D    Y    A    G    W    E    L    Q    Q    G    A    G
   1555 1556 1557 1558 1559 1560 1561 1562 1563 1564 1565 1566 1567 1568 1569 1570 1571 1572 1573 1574 1575 1576 1577
```

FIG. 40N

5' TGGTCCCACCCTCAATTCGAGAAGGGTGCCGGATGGAGTCACCCACAGTTCGAGAAAGGCGCTGGATGGA 8890

Strep tag II | linker | Strep tag II | linker | Str... II

W S H P Q F E K G A G W S H P Q F E K G A G W 1578 1579 1580 1581 1582 1583 1584 1585 1586 1587 1588 1589 1590 1591 1592 1593 1594 1595 1596 1597 1598 1599 1600

NsiI XhoI

5' GTCACCCACAGTTCGAGAAATAATTAGTTGATGCATAGTTAATTAGATAGCTCGAGGCATGCGGTACCAA 8960

Strep tag II

S H P Q F E K 1601 1602 1603 1604 1605 1606 1607

NsiI XhoI

5' GATTGGATCTAGATGCATAGTTAATTAGATAGCTCGAGGCATGCGGTACCAAGCTTGTCGAGAAGTACTA 9030

5' GAGGATCATAATCAGCCATACCACATTTGTAGAGGTTTTACTTGCTTTAAAAAACCTCCCACACCTCCCC 9100

HpaI

5' CTGAACCTGAAACATAAAATGAATGCAATTGTTGTTGTTAACTTGTTTATTGCAGCTTATAATGGTTACA 9170

5' AATAAAGCAATAGCATCACAAATTTCACAAATAAAGCATTTTTTTCACTGCATTCTAGTTGTGGTTTGTC 9240

AvrII

5' CAAACTCATCAATGTATCTTATCATGTCTGGATCTGATCACTGCTTGAGCCTAGGAGATCCGAACCAGAT 9310

5' AAGTGAAATCTAGTTCCAAACTATTTTGTCATTTTTAATTTTCGTATTAGCTTACGACGCTACACCCAGT 9380

5' TCCCATCTATTTTGTCACTCTTCCCTAAATAATCCTTAAAAACTCCATTTCCACCCCTCCCAGTTCCCAA 9450

5' CTATTTTGTCCGCCCACAGCGGGGCATTTTTCTTCCTGTTATGTTTTTAATCAAACATCCTGCCAACTCC 9520

5' ATGTGACAAACCGTCATCTTCGGCTACTTTTTCTCTGTCACAGAATGAAAATTTTTCTGTCATCTCTTCG 9590

5' TTATTAATGTTTGTAATTGACTGAATATCAACGCTTATTTGCAGCCTGAATGGCGAATGG 9650

FIG. 40O

```
                                    KasI
                                    NarI
                                    SfoI
                                    SgrAI
         ZraI    BseYI               MreI
           AatII    GsaI             PluTI                              NotI        Bpu10I
5'  GACGTCGGCTGGGAGCTGCAAGGCGCCGGCGAGCAGAAACTCATCAGCGAAGAAGATTTGGGTGCGGCCGCTGGCTCAGG
                                                                                            80
    |linker|   SpI B site  |linker|           cMyc tag           |       VHH spacer        |
     D  V  G  W  E  L  Q  G  A  G  E  Q  K  L  I  S  E  E  D  L  G  A  A  G  S  G

                       PmlI      PstI                              EcoP15I
                                 BsaXI'              BseRI           BsaXI
5'  AGGTGGCAGTCAGGCGCACGTGCAACTGCAGCAGTCTGGAGGAGGCTTGGTGCAGCCTGGGGGTTCCCTGCGCCTGTCAT
                                                                                            160
    |VHH spacer|              sd Ab B8 VHH - anti-BoNT/A LC
     G  G  S  Q  A  H  V  Q  L  Q  Q  S  G  G  G  L  V  Q  P  G  G  S  L  R  L  S

       AcuI
           AlwNI
5'  GTGCAGCCTCTGGAAGCATCTTCAGTATTTACGCTATGGGCTGGTACAGGCAGGCTCCTGGCAAGCAACGTGAACTGGTT
                                                                                            240
                        sd Ab B8 VHH - anti-BoNT/A LC
     C  A  A  S  G  S  I  F  S  I  Y  A  M  G  W  Y  R  Q  A  P  G  K  Q  R  E  L  V

                                          BspMI
5'  GCTGCCATCTCCAGCTACGGTAGTACCAACTACGCTGATTCGGTCAAGGGCAGGTTCACCATCTCCCGCGACAATGCCAA
                                                                                            320
                        sd Ab B8 VHH - anti-BoNT/A LC
     A  A  I  S  S  Y  G  S  T  N  Y  A  D  S  V  K  G  R  F  T  I  S  R  D  N  A  K

                                 BciVI
                                  Bsu36I                            BsrDI
5'  GAATACCGTCTATTTGCAAATGAACTCTCTGAAACCTGAGGATACGGCCGTCTACTACTGCAACGCTGACATTGCTACTA
                                                                                            400
                        sd Ab B8 VHH - anti-BoNT/A LC
     N  T  V  Y  L  Q  M  N  S  L  K  P  E  D  T  A  V  Y  Y  C  N  A  D  I  A  T

        SacII               EciI    BmrI                 BsaI
                                                            EarI
5'  TGACCGCGGTAGGCGGATTCGACTACTGGGGACAGGGAACTCAGGTGACGGTCTCTTCCGAACCTAAGACCCCTAAACCC
                                                                                            480
                        sd Ab B8 VHH - anti-BoNT/A LC
     M  T  A  V  G  G  F  D  Y  W  G  Q  G  T  Q  V  T  V  S  S  E  P  K  T  P  K  P

         FseI    BstXI            BsaBI               BamHI
5'  CAAGGGGCCGGCCAGGGTGCTGGTGCTGGACCGATCACCATCAACAACTTCAATTACTCGGATCCG
                                                                                            546
    |s|       linker        |         BoNT/C1 ad0 LC         |
     Q  G  A  G  Q  G  A  G  A  G  P  I  T  I  N  N  F  N  Y  S  D  P
```

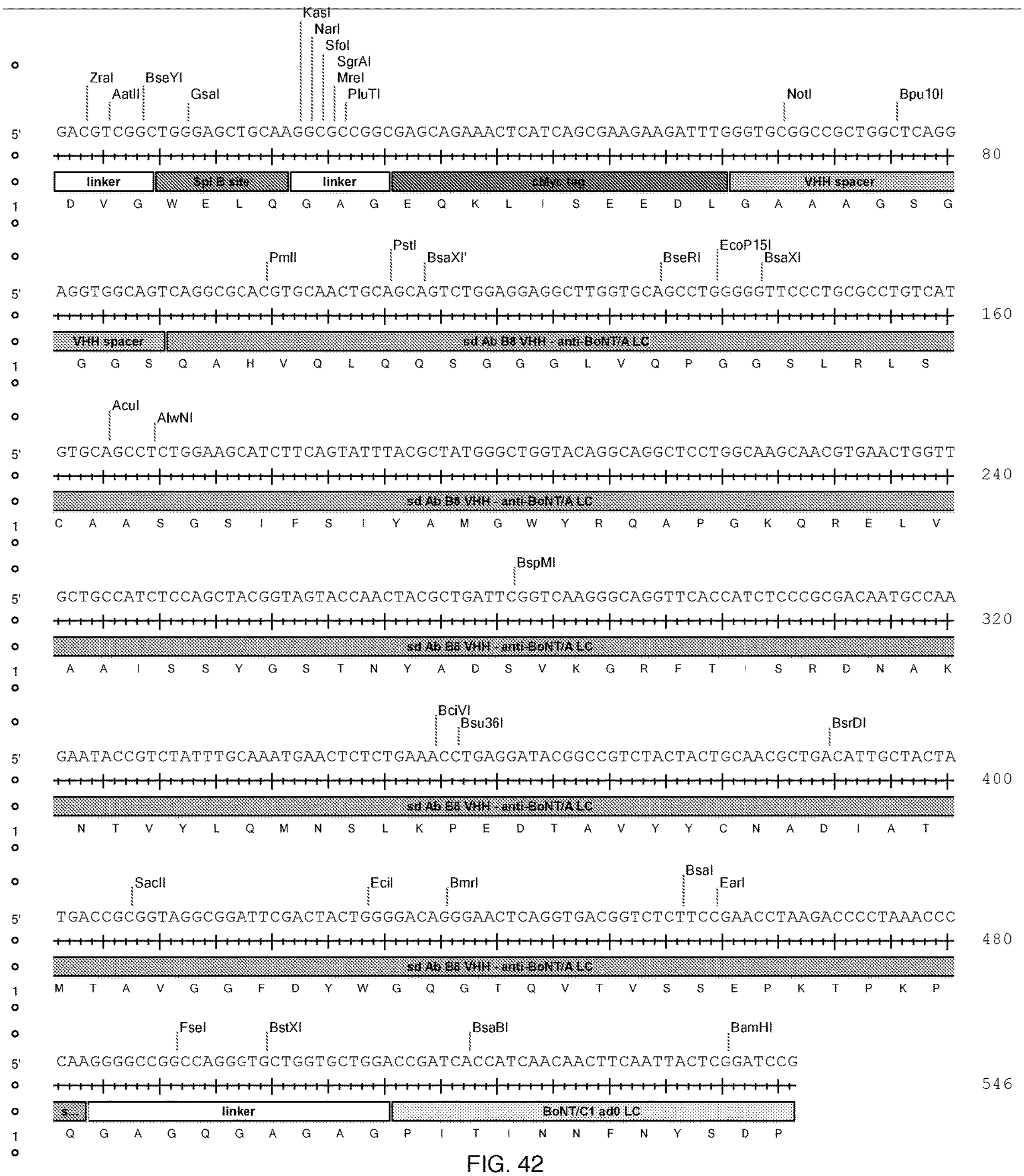

FIG. 42

```
                                    SexAI
5' CAACTCCAGCTCGTTGAGTCCGGTGGCGGAATGGTGCAACCTGGTGGCTCTTTGAGGCTGTCATGCGCTGCCAGTGGATT
   ++++++++++++++++++++++++++++++++++++++++++++++++++++++++++++++++++++++++++++++++   570
   [sd Ab B10 VHH - anti-BoNT/B LC]
   S  T  P  A  R  .  V  R  W  R  N  G  A  T  W  W  L  F  E  A  V  M  R  C  Q  W  I

              Pcil                              EcoNI
5' CACCTTCTCGACTTACGACATGTCCTGGGTGCGTCAGGCACCTGGAAAAGGTCCCGAATGGGTCAGCATCATTAACGCTG
   ++++++++++++++++++++++++++++++++++++++++++++++++++++++++++++++++++++++++++++++++   650
   [sd Ab B10 VHH - anti-BoNT/B LC]
   H  L  L  D  L  R  H  V  L  G  A  S  G  T  W  K  R  S  R  M  G  Q  H  H  .  R  W

                        AlwNI
5' GAGGTGGCAGCACATACTACGCAGCGTCTGTTAAGGGAAGGTTCGCTATCTCCAGAGACAACGCCAAAAACACCCTCTAC
   ++++++++++++++++++++++++++++++++++++++++++++++++++++++++++++++++++++++++++++++++   730
   [sd Ab B10 VHH - anti-BoNT/B LC]
   R  W  Q  H  I  L  R  S  V  C  .  G  K  V  R  Y  L  Q  R  Q  R  Q  K  H  P  L

          Bcgl                                  Bcgl'
5' TTGCAAATGAACAACCTGAAGCCCGAGGATACTGCTCTCTACTACTGTGCTCGCGTCGCCTCATACTACTGCCGTGGCTA
   ++++++++++++++++++++++++++++++++++++++++++++++++++++++++++++++++++++++++++++++++   810
   [sd Ab B10 VHH - anti-BoNT/B LC]
   L  A  N  E  Q  P  E  A  R  G  Y  C  S  L  L  L  C  S  R  R  L  I  L  L  P  W  L

                              Bmrl
5' CGTTTGTAGTCCTCCCGAGTTCGACTACTGGGGCCAGGGAACACAAGTGACGGTCTCCAGCGAACCAAAGACACCAAAAC
   ++++++++++++++++++++++++++++++++++++++++++++++++++++++++++++++++++++++++++++++++   890
   [sd Ab B10 VHH - anti-BoNT/B LC]
   R  L  .  S  S  R  V  R  L  L  G  P  G  N  T  S  D  G  L  Q  R  T  K  D  T  K  T

            Fsel                        BsaBI                    BamHI
5' CACAGGGGGCCGGCCAGGGTGCTGGTGCTGGACCGATCACCATCAACAACTTCAATTACTCGGATCCG
   +++++++++++++++++++++++++++++++++++++++++++++++++++++++++++++++++++   958
   [sd...LC][   linker        ][        BoNT/C1 ad0 LC           ]
   T  G  G  R  P  G  C  W  C  W  T  D  H  H  Q  Q  L  Q  L  L  G  S
```

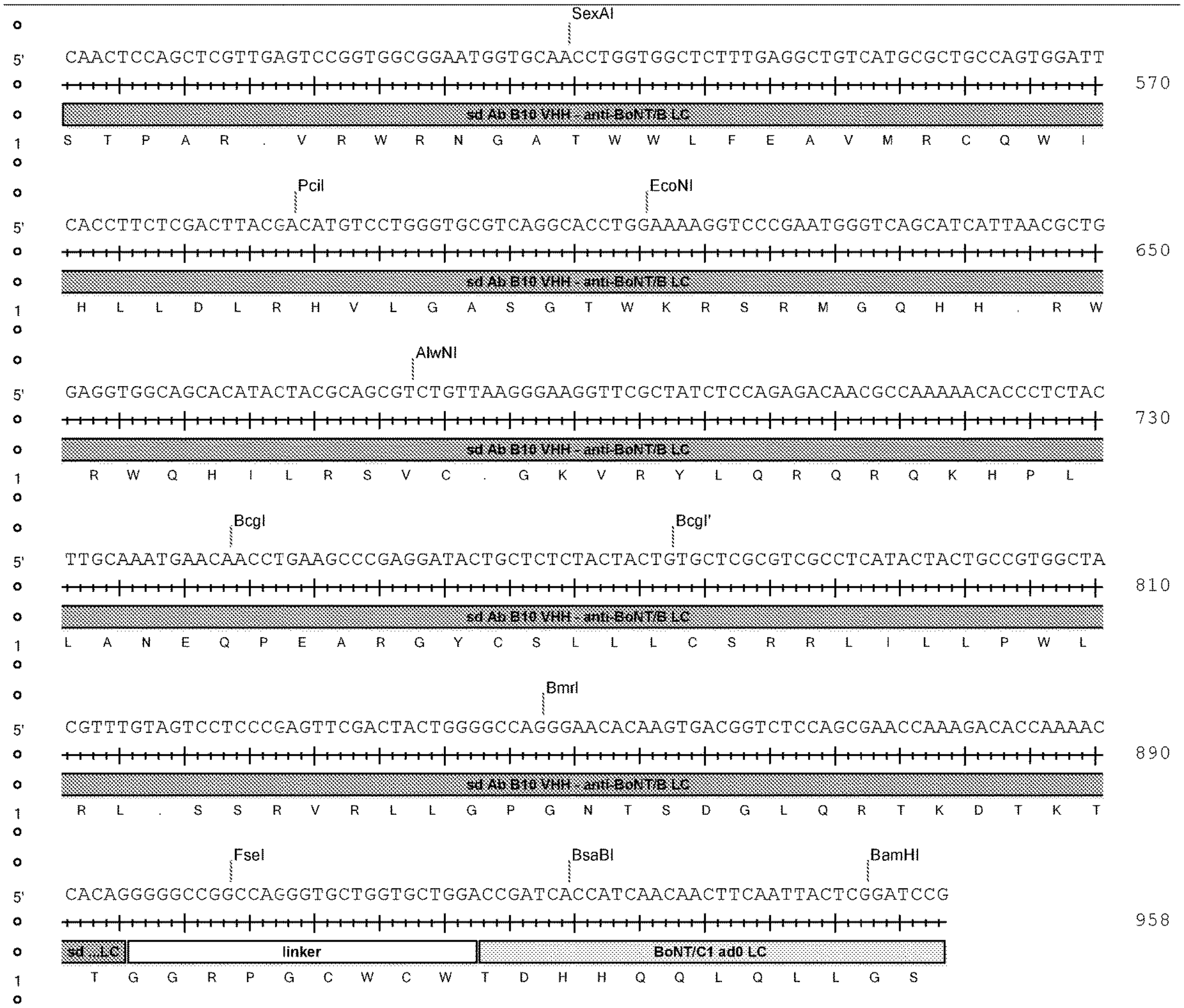

FIG. 43B

```
                                         Fspl                        Ahdl
5' TCCAAGCAGGAGGTAGCCTGCGCCTCTCTTGCGCAGCGTCAGGTATCGACAGTTCGTCCTACTGTATGGGCTGGTTCAGG
                                                                                      570
   [EPEA alpha-synuclein VHH 2]
    V  Q  A  G  G  S  L  R  L  S  C  A  A  S  G  I  D  S  S  S  Y  C  M  G  W  F  R

                          NmeAlll  BsaAl            Bsal       BsaXl              Pcsl
5' CAGCGTCCTGGCAAGGAGAGGGAAGGAGTGGCACGTATCAACGGTCTCGGCGGAGTCAAGACAGCTTACGCCGACTCCGT
                                                                                      650
   [EPEA alpha-synuclein VHH 2]
    Q  R  P  G  K  E  R  E  G  V  A  R  I  N  G  L  G  G  V  K  T  A  Y  A  D  S  V

      BsaXl'
5' TAAAGATAGGTTCACCATTAGCCGCGACAACGCTGAGAACACTGTCTACCTCCAAATGAACAGTTTGAAGCCGGAAGATA
                                                                                      730
   [EPEA alpha-synuclein VHH 2]
    K  D  R  F  T  I  S  R  D  N  A  E  N  T  V  Y  L  Q  M  N  S  L  K  P  E  D

                                                                              BpuEl
5' CTGCCATTTACTACTGTGCTGCCAAATTCTCACCGGGCTACTGTGGAGGAAGCTGGTCTAACTTCGGCTACTGGGGACAA
                                                                                      810
   [EPEA alpha-synuclein VHH 2]
    T  A  I  Y  Y  C  A  A  K  F  S  P  G  Y  C  G  G  S  W  S  N  F  G  Y  W  G  Q

   Smll           Fsel                                                      BstYl
      BsmFl       BsaJl  BstXl      Avall      BsaBl      Taqll       Alwl  BamHl
5' GGAACTCAAGTCACCGTTGGGGCCGGCCAGGGTGCTGGTGCTGGACCGATCACCATCAACAACTTCAATTACTCGGATCC
                                                                                      890
   [EPEA alpha-synuclein VHH 2][  linker          ][        BoNT/C1 ad0 LC           ]
    G  T  Q  V  T  V  G  A  G  Q  G  A  G  A  G  P  I  T  I  N  N  F  N  Y  S  D  P

5' G
                                                                                      891
```

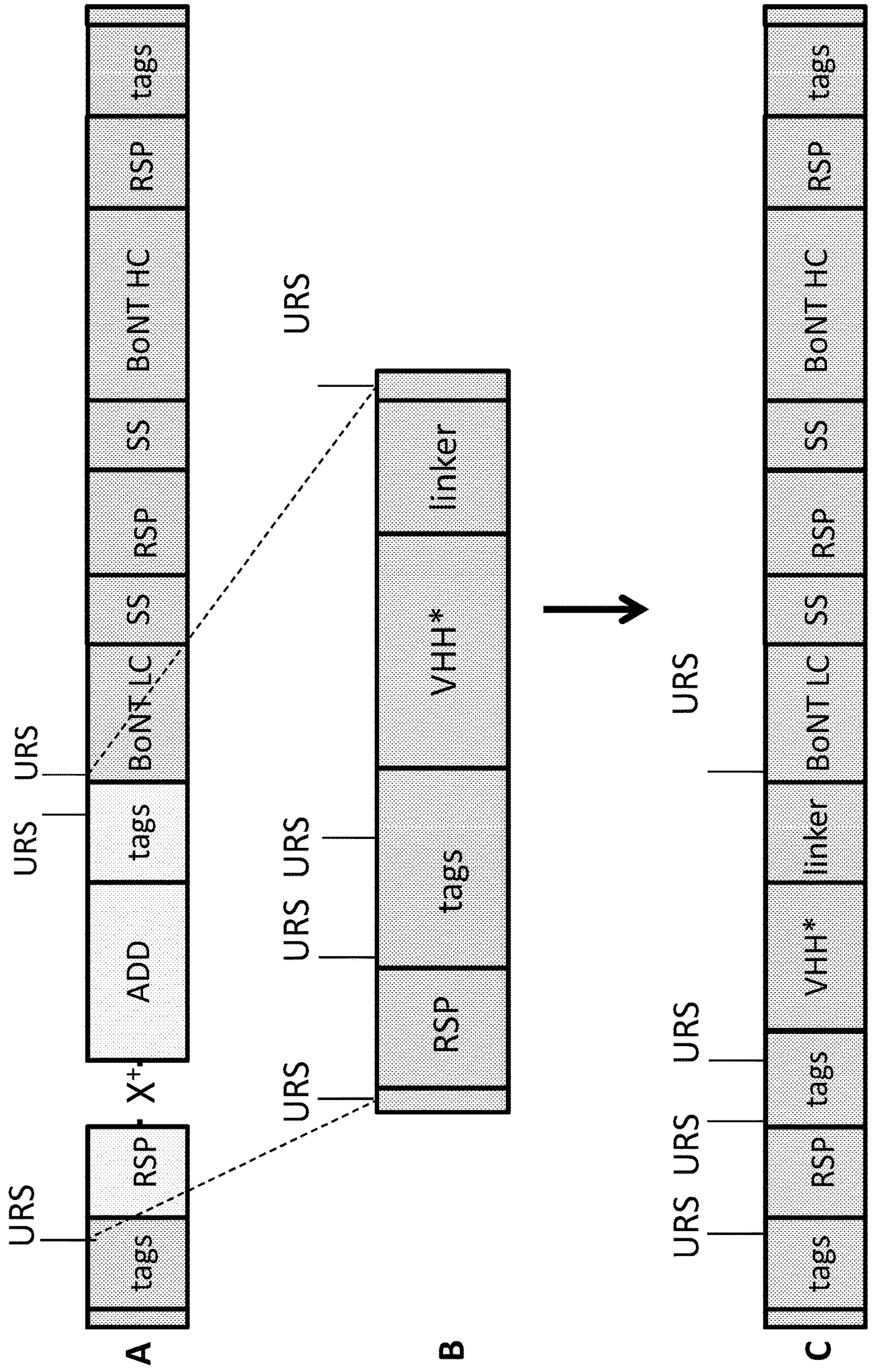
FIGS. 46A-C

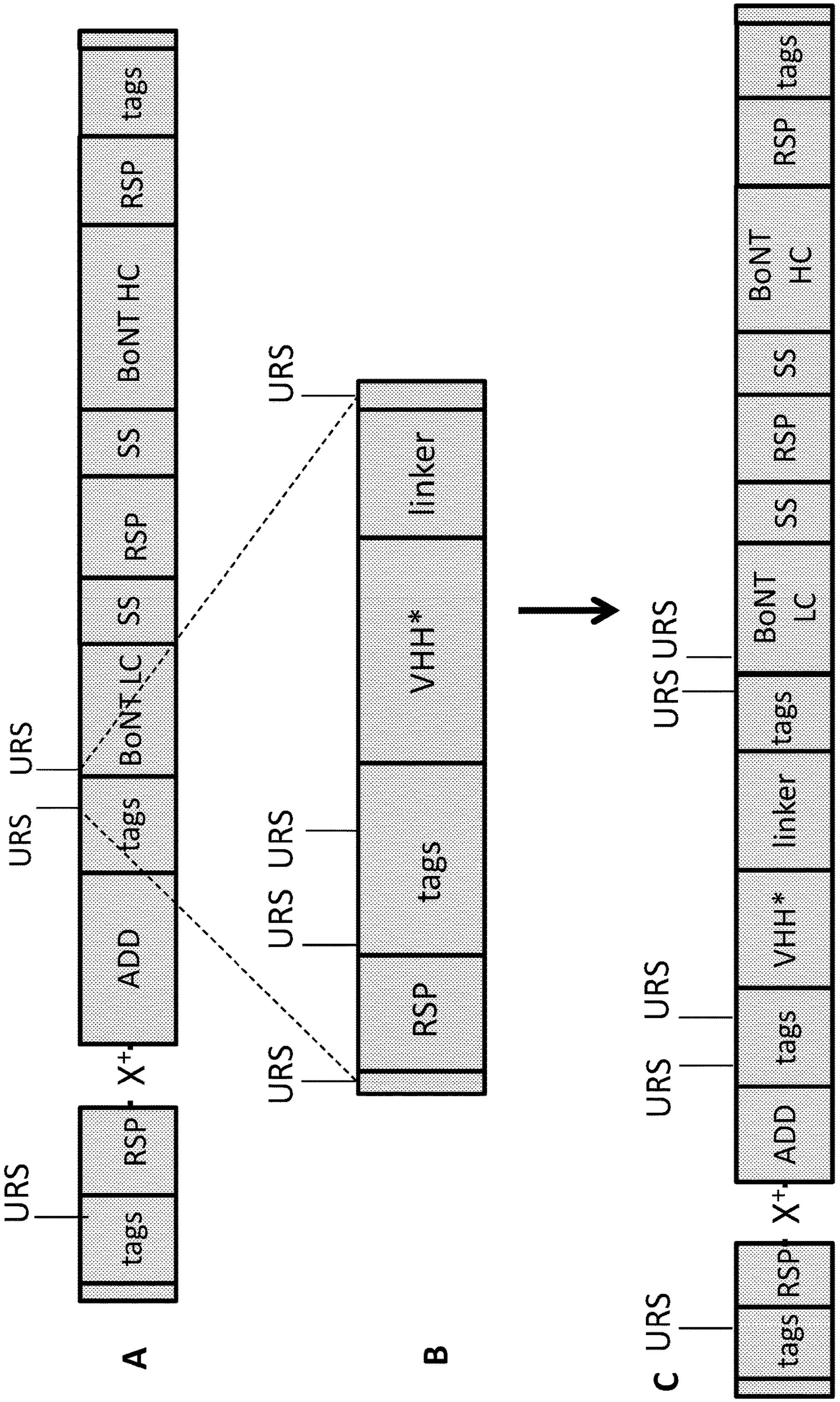
FIGS. 47A-C

NgoMIV
NaeI
AloI'
AloI
PvuI

5' GACGCGCCCTGTAGCGGCGCATTAAGCGCGGCGGGTGTGGTGGTTACGCGCAGCGTGACCGCTACACTTG 70

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

5' CTTGATTAGGGTGATGGTTCACGTAGTGGGCCATCGCCCTGATAGACGGTTTTTCGCCCTTTGACGTTGG 280

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

5' TGCGGCCAACTTACTTCTGACAACGATCGGAGGACCGAAGGAGCTAACCGCTTTTTTGCACAACATGGGG 1050

5' GATCATGTAACTCGCCTTGATCGTTGGGAACCGGAGCTGAATGAAGCCATACCAAACGACGAGCGTGACA 1120

FIG. 48A

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

FIG. 48B

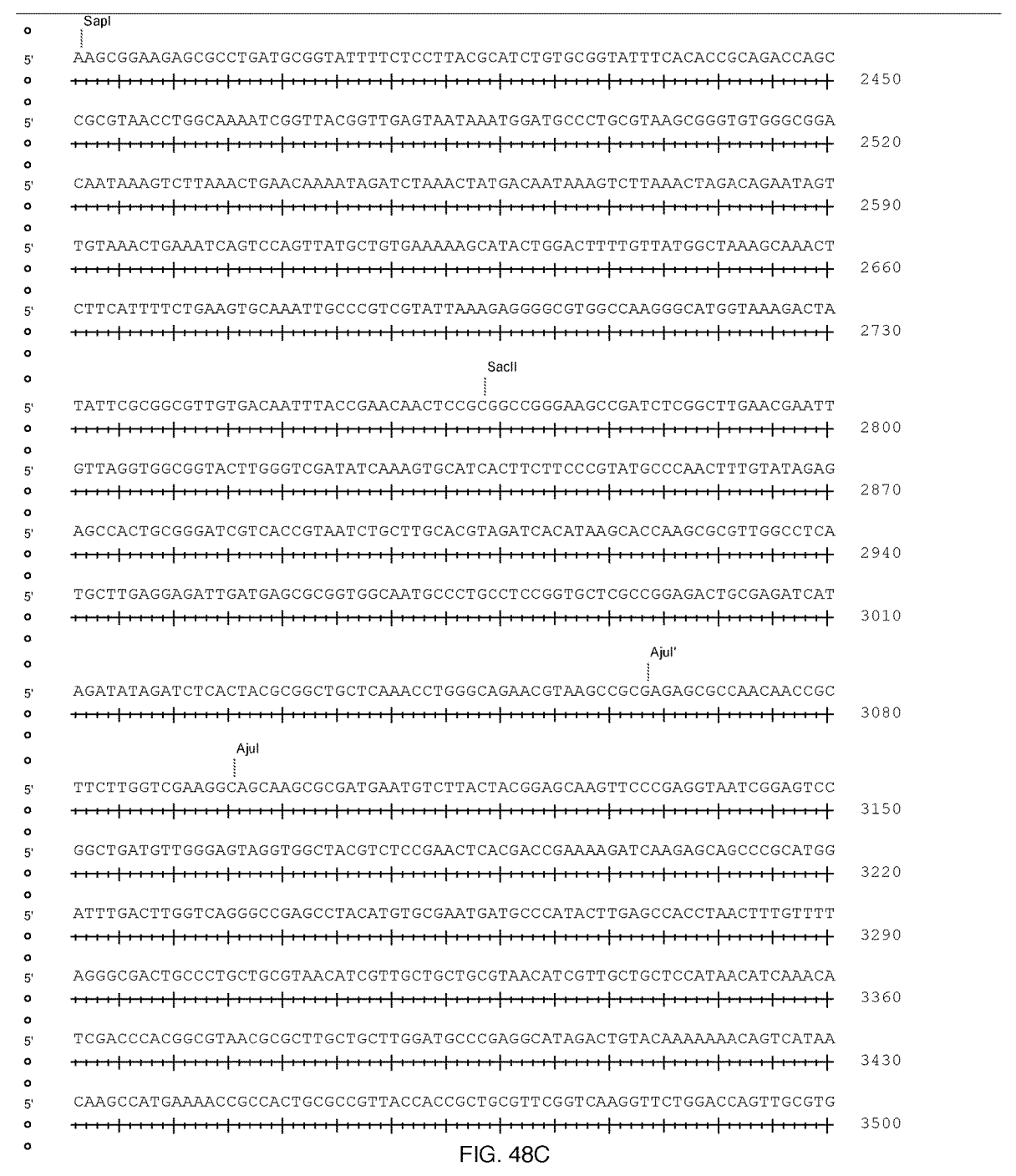

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

FIG. 48C

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI
BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

RsrII

5' TAAATATTCCGGATTATTCATACCGTCCCACCATCGGGCGCGGATCTCGGTCCGTTCGAACCAGAACTCT 4060 mut....mHI

5' GGAAGCTTAACTCCTAAAAAACCGCCACCATGAAATTCTTAGTCAACGTTGCCCTTGTTTTTATGGTCGT 4130

Lob. TMO cDNA Lead Seq | Signal Peptide

M K F L V N V A L V F M V V
1 2 3 4 5 6 7 8 9 10 11 12 13 14

BstZ17I
ZraI
AatII

5' ATACATTTCTTACATCTATGCGGCCGGACACCACCACCACCACCACCACCACCACCACCACGACGTCGGC 4200

Signal Peptide | 11 His tag | linker

```
                    Narl
                    Sfol
                    SgrAl
                    Mrel
                    NgoMIV
                    PluTI
              Kasl  Nael                                          Notl          Bpu10I
5' TGGGAGCTGCAAGGCGCCGGCGAGCAGAAACTCATCAGCGAAGAAGATTTGGGTGCGGCCGCTGGCTCAG
   ++++++++++++++++++++++++++++++++++++++++++++++++++++++++++++++++++++++  4270
   [sd B site]  [linker]              [Myc tag]                [VHH spacer]
    W   E   L   Q   G   A   G   E   Q   K   L   I   S   E   E   D   L   G   A   A   A   G   S
    38  39  40  41  42  43  44  45  46  47  48  49  50  51  52  53  54  55  56  57  58  59  60

                         Pmll         Pstl
                                      TstI'                               TstI
5' GAGGTGGCAGTCAGGCGCACGTGCAACTGCAGCAGTCTGGAGGAGGCTTGGTGCAGCCTGGGGGTTCCCT
   ++++++++++++++++++++++++++++++++++++++++++++++++++++++++++++++++++++++  4340
   [VHH spacer]           [sd Ab B8 VHH - anti-BoNT/A LC]
    G   G   G   S   Q   A   H   V   Q   L   Q   Q   S   G   G   G   L   V   Q   P   G   G   S   L
    61  62  63  64  65  66  67  68  69  70  71  72  73  74  75  76  77  78  79  80  81  82  83  84

5' GCGCCTGTCATGTGCAGCCTCTGGAAGCATCTTCAGTATTTACGCTATGGGCTGGTACAGGCAGGCTCCT
   ++++++++++++++++++++++++++++++++++++++++++++++++++++++++++++++++++++++  4410
   [sd Ab B8 VHH - anti-BoNT/A LC]
    R   L   S   C   A   A   S   G   S   I   F   S   I   Y   A   M   G   W   Y   R   Q   A   P
    85  86  87  88  89  90  91  92  93  94  95  96  97  98  99  100 101 102 103 104 105 106 107

                                                                       BspMI
5' GGCAAGCAACGTGAACTGGTTGCTGCCATCTCCAGCTACGGTAGTACCAACTACGCTGATTCGGTCAAGG
   ++++++++++++++++++++++++++++++++++++++++++++++++++++++++++++++++++++++  4480
   [sd Ab B8 VHH - anti-BoNT/A LC]
    G   K   Q   R   E   L   V   A   A   I   S   S   Y   G   S   T   N   Y   A   D   S   V   K
    108 109 110 111 112 113 114 115 116 117 118 119 120 121 122 123 124 125 126 127 128 129 130

                                                                          Bsu36I
5' GCAGGTTCACCATCTCCCGCGACAATGCCAAGAATACCGTCTATTTGCAAATGAACTCTCTGAAACCTGA
   ++++++++++++++++++++++++++++++++++++++++++++++++++++++++++++++++++++++  4550
   [sd Ab B8 VHH - anti-BoNT/A LC]
    G   R   F   T   I   S   R   D   N   A   K   N   T   V   Y   L   Q   M   N   S   L   K   P   E
    131 132 133 134 135 136 137 138 139 140 141 142 143 144 145 146 147 148 149 150 151 152 153 154

                                                      SacII                    TstI'
5' GGATACGGCCGTCTACTACTGCAACGCTGACATTGCTACTATGACCGCGGTAGGCGGATTCGACTACTGG
   ++++++++++++++++++++++++++++++++++++++++++++++++++++++++++++++++++++++  4620
   [sd Ab B8 VHH - anti-BoNT/A LC]
    D   T   A   V   Y   Y   C   N   A   D   I   A   T   M   T   A   V   G   G   F   D   Y   W
    155 156 157 158 159 160 161 162 163 164 165 166 167 168 169 170 171 172 173 174 175 176 177
```

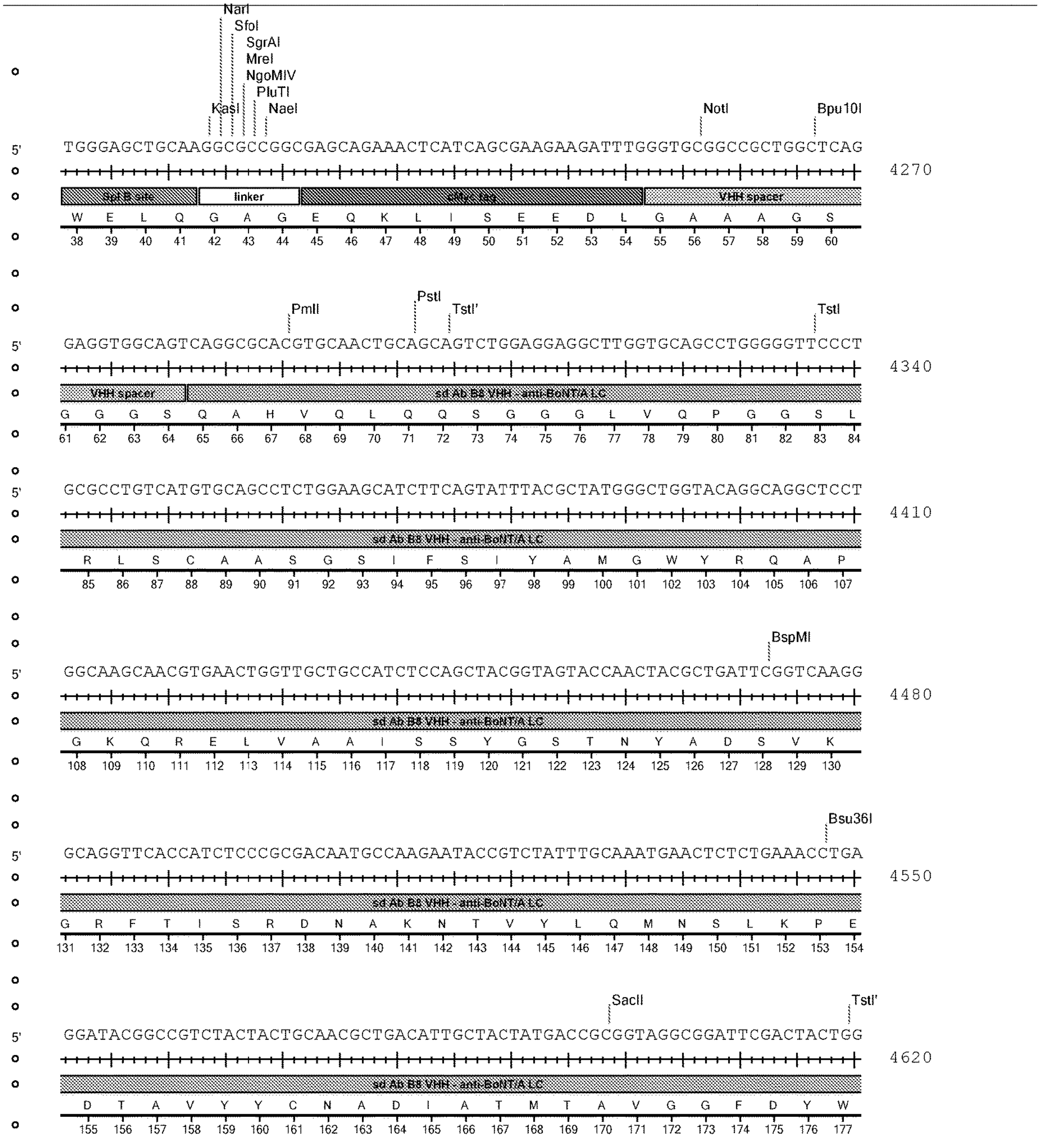

FIG. 48E

NgoMIV
NaeI
FseI
TstI
5' GGACAGGGAACTCAGGTGACGGTCTCTTCCGAACCTAAGACCCCTAAACCCCAAGGGGCCGGCCAGGGTG 4690
sd Ab B8 VHH - anti-BoNT/A LC | linker
G Q G T Q V T V S S E P K T P K P Q G A G Q G
178 179 180 181 182 183 184 185 186 187 188 189 190 191 192 193 194 195 196 197 198 199 200

BamHI
5' CTGGTGCTGGACCGATCACCATCAACAACTTCAATTACTCGGATCCGGTGGATAACAAGAACATCCTCTA 4760
linker | BoNT/C1 ad0 LC
A G A G P I T I N N F N Y S D P V D N K N I L Y
201 202 203 204 205 206 207 208 209 210 211 212 213 214 215 216 217 218 219 220 221 222 223 224

5' CTTGGACACACACTTGAACACGCTGGCTAACGAGCCTGAAAAAGCTTTCAGGATCACCGGCAACATTTGG 4830
BoNT/C1 ad0 LC
L D T H L N T L A N E P E K A F R I T G N I W
225 226 227 228 229 230 231 232 233 234 235 236 237 238 239 240 241 242 243 244 245 246 247

5' GTCATTCCGGATAGGTTCAGCAGAAACTCTAACCCTAACTTGAACAAACCTCCCAGAGTGACCTCACCTA 4900
BoNT/C1 ad0 LC
V I P D R F S R N S N P N L N K P P R V T S P
248 249 250 251 252 253 254 255 256 257 258 259 260 261 262 263 264 265 266 267 268 269 270

5' AGAGTGGATACTACGACCCCAACTACCTCTCGACTGACTCCGATAAAGACCCCTTCCTGAAGGAGATCAT 4970
BoNT/C1 ad0 LC
K S G Y Y D P N Y L S T D S D K D P F L K E I I
271 272 273 274 275 276 277 278 279 280 281 282 283 284 285 286 287 288 289 290 291 292 293 294

5' TAAACTCTTCAAGCGCATCAACTCTCGTGAAATTGGCGAGGAATTGATCTACCGCCTGAGTACAGACATC 5040
BoNT/C1 ad0 LC
K L F K R I N S R E I G E E L I Y R L S T D I
295 296 297 298 299 300 301 302 303 304 305 306 307 308 309 310 311 312 313 314 315 316 317

XmaI
SmaI
5' CCATTCCCGGGTAACAACAACACCCCAATCAACACTTTCGATTTCGATGTCGATTTCAACTCAGTGGATG 5110
BoNT/C1 ad0 LC
P F P G N N N T P I N T F D F D V D F N S V D
318 319 320 321 322 323 324 325 326 327 328 329 330 331 332 333 334 335 336 337 338 339 340

FIG. 48F

```
5'  AAGAGAACATCAAGAGTCAAGTCGAAAaCCTGAAAAACTCACTCGACGTTAAGATCAGTGAGGCAATGAA
                                                                                              7070
         BoNT/C Translocation Domain
     K   E   N   I   K   S   Q   V   E   N   L   K   N   S   L   D   V   K   I   S   E   A   M   N
    971 972 973 974 975 976 977 978 979 980 981 982 983 984 985 986 987 988 989 990 991 992 993 994

5'  CAACATCAACAAGTTCATTCGCGAATGTTCCGTTACCTACCTCTTCAAAAACATGTTGCCAAAGGTCATC
                                                                                              7140
         BoNT/C Translocation Domain
     N   I   N   K   F   I   R   E   C   S   V   T   Y   L   F   K   N   M   L   P   K   V   I
    995 996 997 998 999 1000 1001 1002 1003 1004 1005 1006 1007 1008 1009 1010 1011 1012 1013 1014 1015 1016 1017

5'  GACGAGCTGAACGAATTTGATCGTAACACTAAGGCGAAACTGATTAACCTCATCGACTCACACAACATCA
                                                                                              7210
         BoNT/C Translocation Domain
     D   E   L   N   E   F   D   R   N   T   K   A   K   L   I   N   L   I   D   S   H   N   I
    1018 1019 1020 1021 1022 1023 1024 1025 1026 1027 1028 1029 1030 1031 1032 1033 1034 1035 1036 1037 1038 1039 1040

5'  TTTTGGTGGGCGAAGTCGATAAGCTGAAAGCCAAGGtGAACAACAGTTTCCAGAACACAATCCCTTTCAA
                                                                                              7280
         BoNT/C Translocation Domain
     I   L   V   G   E   V   D   K   L   K   A   K   V   N   N   S   F   Q   N   T   I   P   F   N
    1041 1042 1043 1044 1045 1046 1047 1048 1049 1050 1051 1052 1053 1054 1055 1056 1057 1058 1059 1060 1061 1062 1063 1064

5'  cATTTTCTCATACACGAACAACAGTCTGCTCAAGGACATCATTAACGAGTACTTCAACAACATTAACGAT
                                                                                              7350
         BoNT/C Translocation Domain                          BoNT/C Rece...ding Domain
     I   F   S   Y   T   N   N   S   L   L   K   D   I   I   N   E   Y   F   N   N   I   N   D
    1065 1066 1067 1068 1069 1070 1071 1072 1073 1074 1075 1076 1077 1078 1079 1080 1081 1082 1083 1084 1085 1086 1087

                         PstI                                    SpeI
5'  AGCAAAATCCTGTCACTGCAGAACCGTAAGAACACACTGGTCGATACTAGTGGATACAACGCCGAAGTCT
                                                                                              7420
         BoNT/C Receptor Binding Domain
     S   K   I   L   S   L   Q   N   R   K   N   T   L   V   D   T   S   G   Y   N   A   E   V
    1088 1089 1090 1091 1092 1093 1094 1095 1096 1097 1098 1099 1100 1101 1102 1103 1104 1105 1106 1107 1108 1109 1110

                         PvuII
5'  CTGAGGAAGGTGACGTGCAGCTGAACCCTATCTTCCCCTTCGACTTCAAATTGGGCTCCAGCGGAGAGGA
                                                                                              7490
         BoNT/C Receptor Binding Domain
     S   E   E   G   D   V   Q   L   N   P   I   F   P   F   D   F   K   L   G   S   S   G   E   D
    1111 1112 1113 1114 1115 1116 1117 1118 1119 1120 1121 1122 1123 1124 1125 1126 1127 1128 1129 1130 1131 1132 1133 1134
```

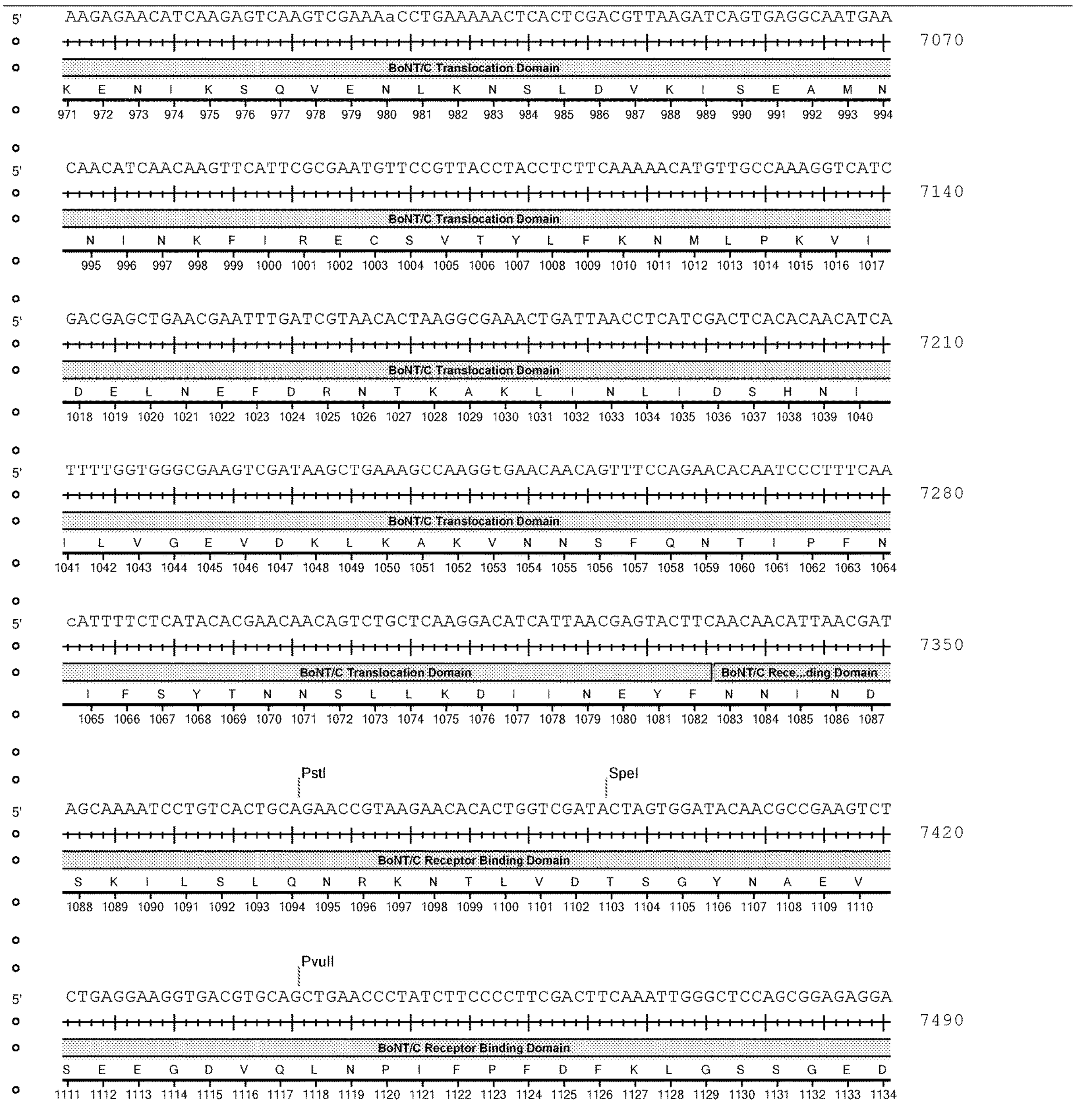

FIG. 48K

```
5'  TAGGGGCAAGGTCATCGTCACCCAGAACGAGAACATCGTCTACAACTCAATGTACGAATCCTTCAGCATC
    ++++++++++++++++++++++++++++++++++++++++++++++++++++++++++++++++++++++  7560
                         BoNT/C Receptor Binding Domain
         R   G   K   V   I   V   T   Q   N   E   N   I   V   Y   N   S   M   Y   E   S   F   S   I
        1135 1136 1137 1138 1139 1140 1141 1142 1143 1144 1145 1146 1147 1148 1149 1150 1151 1152 1153 1154 1155 1156 1157
```

BspMI

```
5'  TCTTTCTGGATCAGGATTAACAAGTGGGTGAGCAACCTGCCCGGTTACACAATCATTGACTCTGTCAAGA
    ++++++++++++++++++++++++++++++++++++++++++++++++++++++++++++++++++++++  7630
                         BoNT/C Receptor Binding Domain
         S   F   W   I   R   N   K   W   V   S   N   L   P   G   Y   T   I   I   D   S   V   K
        1158 1159 1160 1161 1162 1163 1164 1165 1166 1167 1168 1169 1170 1171 1172 1173 1174 1175 1176 1177 1178 1179 1180

5'  ACAACTCAGGTTGGAGTATCGGCATCATTTCTAACTTCTTGGTCTTCACCCTGAAGCAGAACGAGGACTC
    ++++++++++++++++++++++++++++++++++++++++++++++++++++++++++++++++++++++  7700
                         BoNT/C Receptor Binding Domain
         N   N   S   G   W   S   I   G   I   I   S   N   F   L   V   F   T   L   K   Q   N   E   D   S
        1181 1182 1183 1184 1185 1186 1187 1188 1189 1190 1191 1192 1193 1194 1195 1196 1197 1198 1199 1200 1201 1202 1203 1204

5'  GGAACAATCCATTAACTTCTCATACGATATCAGTAACAACGCTCCAGGTTACAACAAGTGGTTCTTCGTT
    ++++++++++++++++++++++++++++++++++++++++++++++++++++++++++++++++++++++  7770
                         BoNT/C Receptor Binding Domain
         E   Q   S   I   N   F   S   Y   D   I   S   N   N   A   P   G   Y   N   K   W   F   F   V
        1205 1206 1207 1208 1209 1210 1211 1212 1213 1214 1215 1216 1217 1218 1219 1220 1221 1222 1223 1224 1225 1226 1227

5'  ACCGTGACTAACAACATGATGGGTAACATGAAAATTTACATCAACGGCAAGCTCATTGACACCATCAAAG
    ++++++++++++++++++++++++++++++++++++++++++++++++++++++++++++++++++++++  7840
                         BoNT/C Receptor Binding Domain
         T   V   T   N   N   M   M   G   N   M   K   I   Y   I   N   G   K   L   I   D   T   I   K
        1228 1229 1230 1231 1232 1233 1234 1235 1236 1237 1238 1239 1240 1241 1242 1243 1244 1245 1246 1247 1248 1249 1250

5'  TGAAGGAGTTGACTGGTATTAACTTCTCCAAAACAATCACGTTTGAAATTAaCaAGATCCCTGACACCGG
    ++++++++++++++++++++++++++++++++++++++++++++++++++++++++++++++++++++++  7910
                         BoNT/C Receptor Binding Domain
         V   K   E   L   T   G   I   N   F   S   K   T   I   T   F   E   I   N   K   I   P   D   T   G
        1251 1252 1253 1254 1255 1256 1257 1258 1259 1260 1261 1262 1263 1264 1265 1266 1267 1268 1269 1270 1271 1272 1273 1274
```

EcoICRI
SacI

```
5'  CCTGATCACTTCAGACAGTGATAACATCAACATGTGGATTAGGGATTTCTACATCTTCGCCAAGGAGCTC
    ++++++++++++++++++++++++++++++++++++++++++++++++++++++++++++++++++++++  7980
                         BoNT/C Receptor Binding Domain
         L   I   T   S   D   S   D   N   I   N   M   W   I   R   D   F   Y   I   F   A   K   E   L
        1275 1276 1277 1278 1279 1280 1281 1282 1283 1284 1285 1286 1287 1288 1289 1290 1291 1292 1293 1294 1295 1296 1297
```

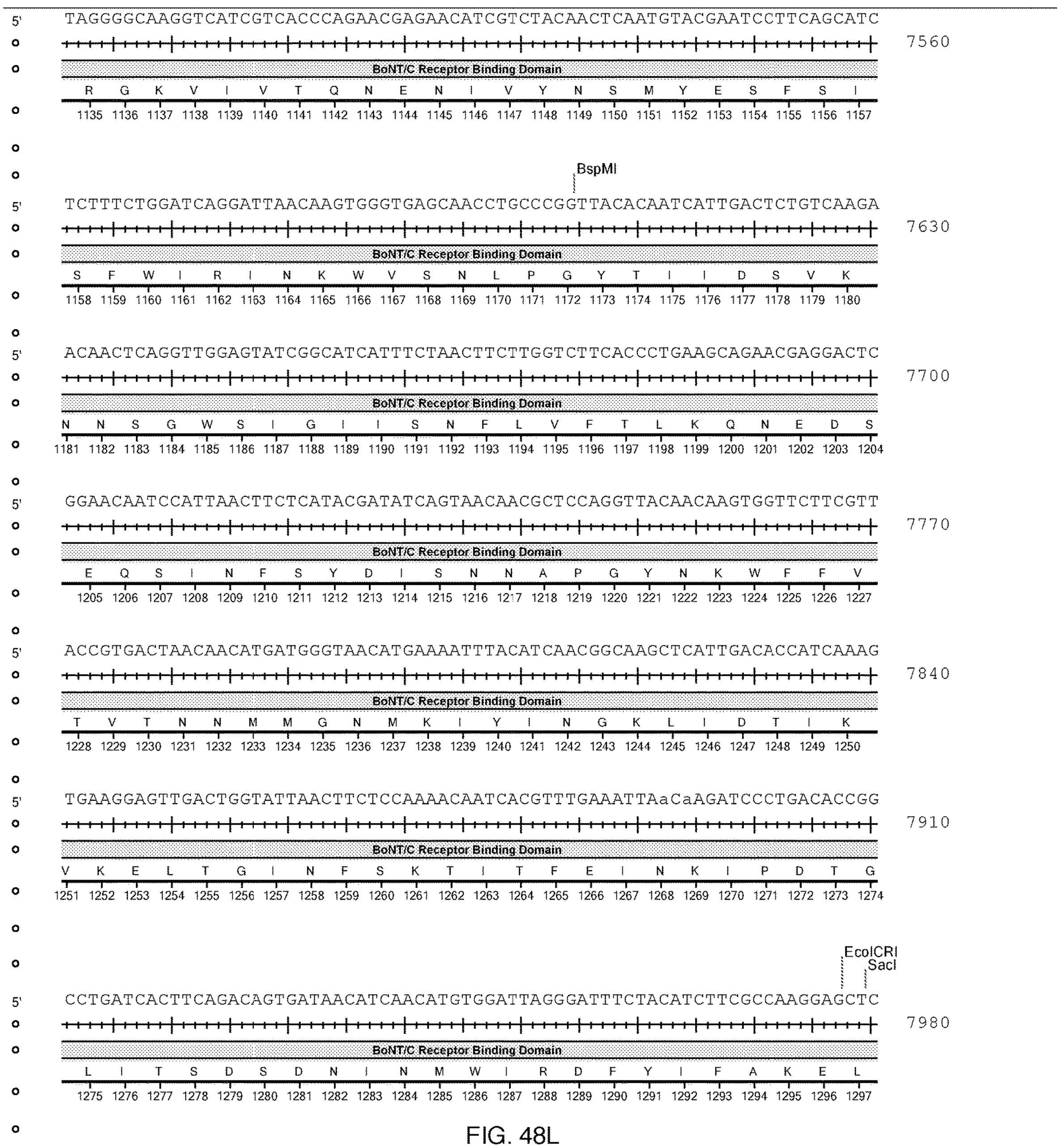

FIG. 48L

5' GACGGAAAGGATATTAACATCCTCTTCAACAGCTTGCAGTACACCAACGTCGTTAAAGACTACTGGGGTA 8050
BoNT/C Receptor Binding Domain
D G K D I N I L F N S L Q Y T N V V K D Y W G
1298 1299 1300 1301 1302 1303 1304 1305 1306 1307 1308 1309 1310 1311 1312 1313 1314 1315 1316 1317 1318 1319 1320

5' ACGATTTGAGATACAACAAGGAGTACTACATGGTCAACATCGACTACCTGAACAGGTACATGTACGCTAA 8120
BoNT/C Receptor Binding Domain
N D L R Y N K E Y Y M V N I D Y L N R Y M Y A N
1321 1322 1323 1324 1325 1326 1327 1328 1329 1330 1331 1332 1333 1334 1335 1336 1337 1338 1339 1340 1341 1342 1343 1344

5' CTCCCGCCAAATCGTGTTCAACACCAGGAGAAACAACAACGACTTCAACGAGGGTTACAAAATCATTATC 8190
BoNT/C Receptor Binding Domain
S R Q I V F N T R R N N N D F N E G Y K I I I
1345 1346 1347 1348 1349 1350 1351 1352 1353 1354 1355 1356 1357 1358 1359 1360 1361 1362 1363 1364 1365 1366 1367

5' AAGCGCATCCGTGGCAACACCAACGATACTAGGGTGAGAGGTGGCGACATTCTGTACTTCGATATGACTA 8260
BoNT/C Receptor Binding Domain
K R I R G N T N D T R V R G G D I L Y F D M T
1368 1369 1370 1371 1372 1373 1374 1375 1376 1377 1378 1379 1380 1381 1382 1383 1384 1385 1386 1387 1388 1389 1390

5' TCAACAACAAAGCCTACAACTTGTTCATGAAAAACGAGACAATGTACGCCGACAAcCATAGCACGGAGGA 8330
BoNT/C Receptor Binding Domain
I N N K A Y N L F M K N E T M Y A D N H S T E D
1391 1392 1393 1394 1395 1396 1397 1398 1399 1400 1401 1402 1403 1404 1405 1406 1407 1408 1409 1410 1411 1412 1413 1414

5' TATTTACGCAATCGGACTGAGGGAACAGACAAAGGACATCAACGATAACATTATCTTCCAGATCCAACCT 8400
BoNT/C Receptor Binding Domain
I Y A I G L R E Q T K D I N D N I I F Q I Q P
1415 1416 1417 1418 1419 1420 1421 1422 1423 1424 1425 1426 1427 1428 1429 1430 1431 1432 1433 1434 1435 1436 1437

5' ATGAACAACACGTACTACTACGCTTCGCAAATCTTCAAGTCCAACTTCAACGGAGAAAACATTTCGGGTA 8470
BoNT/C Receptor Binding Domain
M N N T Y Y Y A S Q I F K S N F N G E N I S G
1438 1439 1440 1441 1442 1443 1444 1445 1446 1447 1448 1449 1450 1451 1452 1453 1454 1455 1456 1457 1458 1459 1460

5' TCTGTTCCATTGGCACATACCGCTTCCGTCTGGGTGGTGACTGGTATCGTCACAACTACCTCGTTCCCAC 8540
BoNT/C Receptor Binding Domain
I C S I G T Y R F R L G G D W Y R H N Y L V P T
1461 1462 1463 1464 1465 1466 1467 1468 1469 1470 1471 1472 1473 1474 1475 1476 1477 1478 1479 1480 1481 1482 1483 1484

FIG. 48M

SalI

5' CGTGAAGCAGGGTAACTACGCTTCTTTGCTGGAGTCGACTTCCACGCACTGGGGATTCGTTCCTGTGTCA 8610

BoNT/C Receptor Binding Domain

V K Q G N Y A S L L E S T S T H W G F V P V S 1485 1486 1487 1488 1489 1490 1491 1492 1493 1494 1495 1496 1497 1498 1499 1500 1501 1502 1503 1504 1505 1506 1507

5' GAGGGCGCTGGCTACCCTTACGATGTTCCCGACTACGCTGGTTGGGAACTCCAGCAAGGTGCAGGATGGT 8680

B... linker HA tag li...r SpyB site linker Str...II

E G A G Y P Y D V P D Y A G W E L Q Q G A G W 1508 1509 1510 1511 1512 1513 1514 1515 1516 1517 1518 1519 1520 1521 1522 1523 1524 1525 1526 1527 1528 1529 1530

5' CCCACCCTCAATTCGAGAAGGGTGCCGGATGGAGTCACCCACAGTTCGAGAAAGGCGCTGGATGGAGTCA 8750

Strep tag II linker Strep tag II linker Strep tag II

S H P Q F E K G A G W S H P Q F E K G A G W S H 1531 1532 1533 1534 1535 1536 1537 1538 1539 1540 1541 1542 1543 1544 1545 1546 1547 1548 1549 1550 1551 1552 1553 1554

NsiI XhoI

5' CCCACAGTTCGAGAAATAATTAGTTGATGCATAGTTAATTAGATAGCTCGAGGCATGCGGTACCAAGATT 8820

Strep tag II

P Q F E K 1555 1556 1557 1558 1559

NsiI XhoI

5' GGATCTAGATGCATAGTTAATTAGATAGCTCGAGGCATGCGGTACCAAGCTTGTCGAGAAGTACTAGAGG 8890

5' ATCATAATCAGCCATACCACATTTGTAGAGGTTTTACTTGCTTTAAAAAACCTCCCACACCTCCCCCTGA 8960

HpaI

5' ACCTGAAACATAAAATGAATGCAATTGTTGTTGTTAACTTGTTTATTGCAGCTTATAATGGTTACAAATA 9030

5' AAGCAATAGCATCACAAATTTCACAAATAAAGCATTTTTTTCACTGCATTCTAGTTGTGGTTTGTCCAAA 9100

AvrII

5' CTCATCAATGTATCTTATCATGTCTGGATCTGATCACTGCTTGAGCCTAGGAGATCCGAACCAGATAAGT 9170

5' GAAATCTAGTTCCAAACTATTTTGTCATTTTTAATTTTCGTATTAGCTTACGACGCTACACCCAGTTCCC 9240

FIG. 48N

5' ATCTATTTTGTCACTCTTCCCTAAATAATCCTTAAAAACTCCATTTCCACCCCTCCCAGTTCCCAACTAT 9310

5' TTTGTCCGCCCACAGCGGGGCATTTTTCTTCCTGTTATGTTTTTAATCAAACATCCTGCCAACTCCATGT 9380

5' GACAAACCGTCATCTTCGGCTACTTTTTCTCTGTCACAGAATGAAAATTTTTCTGTCATCTCTTCGTTAT 9450

5' TAATGTTTGTAATTGACTGAATATCAACGCTTATTTGCAGCCTGAATGGCGAATGG 9506

FIG. 48O

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 49A

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 49B

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 49C

```
5'  AAGCATCTTCAGTATTTACGCTATGGGCTGGTACAGGCAGGCTCCTGGCAAGCAACGTGAACTGGTTGCT
    +---+---+---+---+---+---+---+---+---+---+---+---+---+---+---+---+---+---+---+---+---+  5040
    ░░░░░░░░░░░░░░░░░░░░sd Ab B8 VHH - anti-BoNT/A LC░░░░░░░░░░░░░░░░░░░░
     S   I   F   S   I   Y   A   M   G   W   Y   R   Q   A   P   G   K   Q   R   E   L   V   A
    295 296 297 298 299 300 301 302 303 304 305 306 307 308 309 310 311 312 313 314 315 316 317
```

```
                                                    ,BspMI
5'  GCCATCTCCAGCTACGGTAGTACCAACTACGCTGATTCGGTCAAGGGCAGGTTCACCATCTCCCGCGACA
    +---+---+---+---+---+---+---+---+---+---+---+---+---+---+---+---+---+---+---+---+---+  5110
    ░░░░░░░░░░░░░░░░░░░░sd Ab B8 VHH - anti-BoNT/A LC░░░░░░░░░░░░░░░░░░░░
     A   I   S   S   Y   G   S   T   N   Y   A   D   S   V   K   G   R   F   T   I   S   R   D
    318 319 320 321 322 323 324 325 326 327 328 329 330 331 332 333 334 335 336 337 338 339 340
```

```
                                                    ,Bsu36I
5'  ATGCCAAGAATACCGTCTATTTGCAAATGAACTCTCTGAAACCTGAGGATACGGCCGTCTACTACTGCAA
    +---+---+---+---+---+---+---+---+---+---+---+---+---+---+---+---+---+---+---+---+---+  5180
    ░░░░░░░░░░░░░░░░░░░░sd Ab B8 VHH - anti-BoNT/A LC░░░░░░░░░░░░░░░░░░░░
     N   A   K   N   T   V   Y   L   Q   M   N   S   L   K   P   E   D   T   A   V   Y   Y   C   N
    341 342 343 344 345 346 347 348 349 350 351 352 353 354 355 356 357 358 359 360 361 362 363 364
```

```
                              ,SacII                     ,TstI'
5'  CGCTGACATTGCTACTATGACCGCGGTAGGCGGATTCGACTACTGGGGACAGGGAACTCAGGTGACGGTC
    +---+---+---+---+---+---+---+---+---+---+---+---+---+---+---+---+---+---+---+---+---+  5250
    ░░░░░░░░░░░░░░░░░░░░sd Ab B8 VHH - anti-BoNT/A LC░░░░░░░░░░░░░░░░░░░░
     A   D   I   A   T   M   T   A   V   G   G   F   D   Y   W   G   Q   G   T   Q   V   T   V
    365 366 367 368 369 370 371 372 373 374 375 376 377 378 379 380 381 382 383 384 385 386 387
```

```
                                        ,NgoMIV
                                        ,NaeI
          ,TstI                         ,FseI
5'  TCTTCCGAACCTAAGACCCCTAAACCCCAAGGGGCCGGCCAGGGTGCTGGTGCTGGACCGATCACCATCA
    +---+---+---+---+---+---+---+---+---+---+---+---+---+---+---+---+---+---+---+---+---+  5320
    ░░░sd Ab B8 VHH - anti-BoNT/A LC░░░│       linker        │░BoNT/C1 ad0 LC░
     S   S   E   P   K   T   P   K   P   Q   G   A   G   Q   G   A   G   P   I   T   I
    388 389 390 391 392 393 394 395 396 397 398 399 400 401 402 403 404 405 406 407 408 409 410
```

```
                    ,BamHI
5'  ACAACTTCAATTACTCGGATCCGGTGGATAACAAGAACATCCTCTACTTGGACACACACTTGAACACGCT
    +---+---+---+---+---+---+---+---+---+---+---+---+---+---+---+---+---+---+---+---+---+  5390
    ░░░░░░░░░░░░░░░░░░░░░░░░░BoNT/C1 ad0 LC░░░░░░░░░░░░░░░░░░░░░░░░░
     N   N   F   N   Y   S   D   P   V   D   N   K   N   I   L   Y   L   D   T   H   L   N   T   L
    411 412 413 414 415 416 417 418 419 420 421 422 423 424 425 426 427 428 429 430 431 432 433 434
```

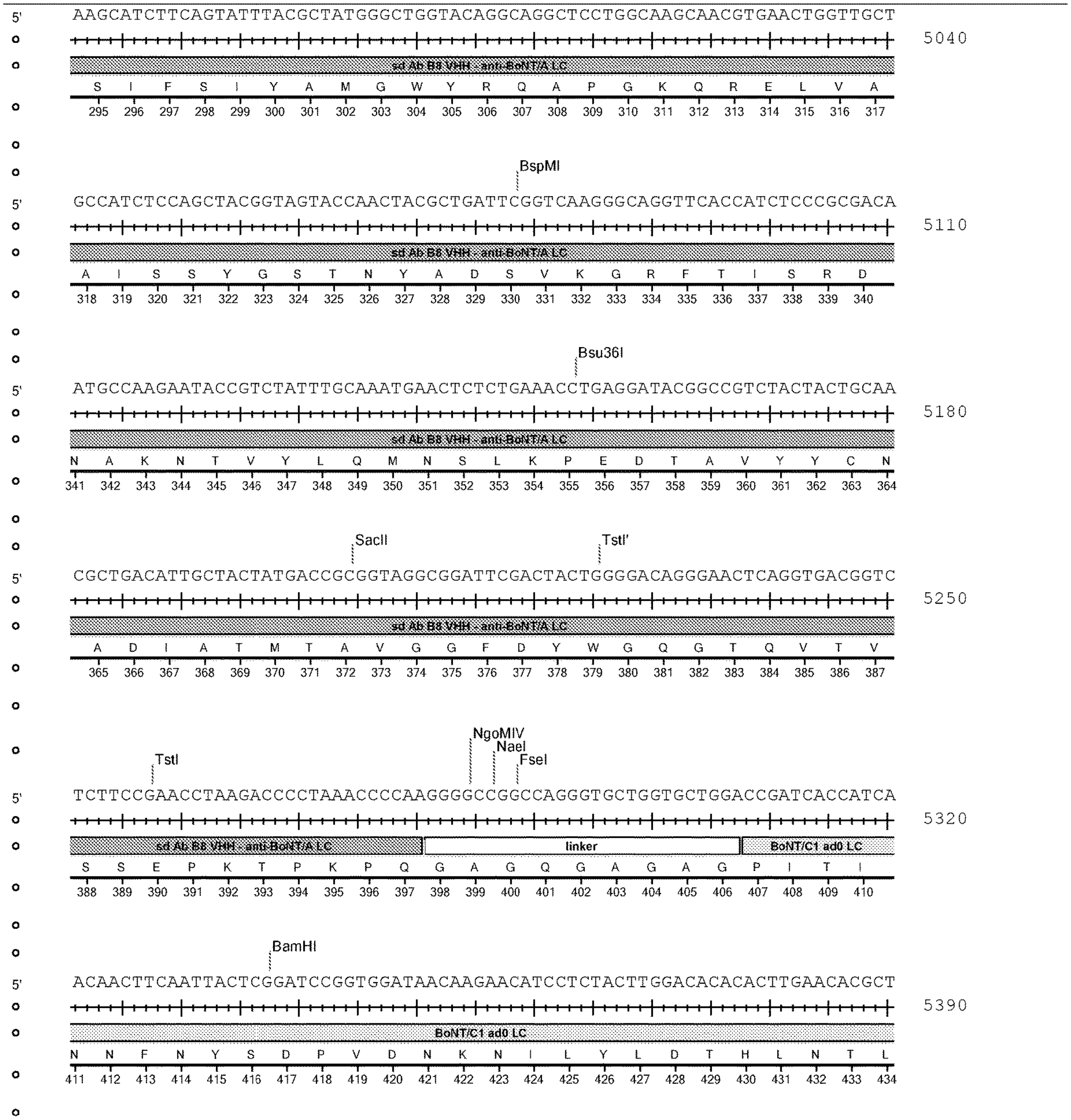

FIG. 49G

5' GGCTAACGAGCCTGAAAAAGCTTTCAGGATCACCGGCAACATTTGGGTCATTCCGGATAGGTTCAGCAGA 5460

BoNT/C1 ad0 LC

A N E P E K A F R I T G N I W V I P D R F S R 435 436 437 438 439 440 441 442 443 444 445 446 447 448 449 450 451 452 453 454 455 456 457

5' AACTCTAACCCTAACTTGAACAAACCTCCCAGAGTGACCTCACCTAAGAGTGGATACTACGACCCCAACT 5530

BoNT/C1 ad0 LC

N S N P N L N K P P R V T S P K S G Y Y D P N 458 459 460 461 462 463 464 465 466 467 468 469 470 471 472 473 474 475 476 477 478 479 480

5' ACCTCTCGACTGACTCCGATAAAGACCCCTTCCTGAAGGAGATCATTAAACTCTTCAAGCGCATCAACTC 5600

BoNT/C1 ad0 LC

Y L S T D S D K D P F L K E I I K L F K R I N S 481 482 483 484 485 486 487 488 489 490 491 492 493 494 495 496 497 498 499 500 501 502 503 504

XmaI

SmaI

5' TCGTGAAATTGGCGAGGAATTGATCTACCGCCTGAGTACAGACATCCCATTCCCGGGTAACAACAACACC 5670

BoNT/C1 ad0 LC

R E I G E E L I Y R L S T D I P F P G N N N T 505 506 507 508 509 510 511 512 513 514 515 516 517 518 519 520 521 522 523 524 525 526 527

5' CCAATCAACACTTTCGATTTCGATGTCGATTTCAACTCAGTGGATGTCAAAACCAGGCAGGGAAACAACT 5740

BoNT/C1 ad0 LC

P I N T F D F D V D F N S V D V K T R Q G N N 528 529 530 531 532 533 534 535 536 537 538 539 540 541 542 543 544 545 546 547 548 549 550

5' GGGTGAAGACTGGTAGCATCAACCCATCTGTCATCATTACTGGCCCGAGAGAGAACATCATTGACCCTGA 5810

BoNT/C1 ad0 LC

W V K T G S I N P S V I I T G P R E N I I D P E 551 552 553 554 555 556 557 558 559 560 561 562 563 564 565 566 567 568 569 570 571 572 573 574

Bpu10I

5' AACCTCCACTTTCAaGCTGACaAACAACACGTTCGCTGCTCAGGAAGGCTTCGGAGCGTTGAGCATCATT 5880

BoNT/C1 ad0 LC

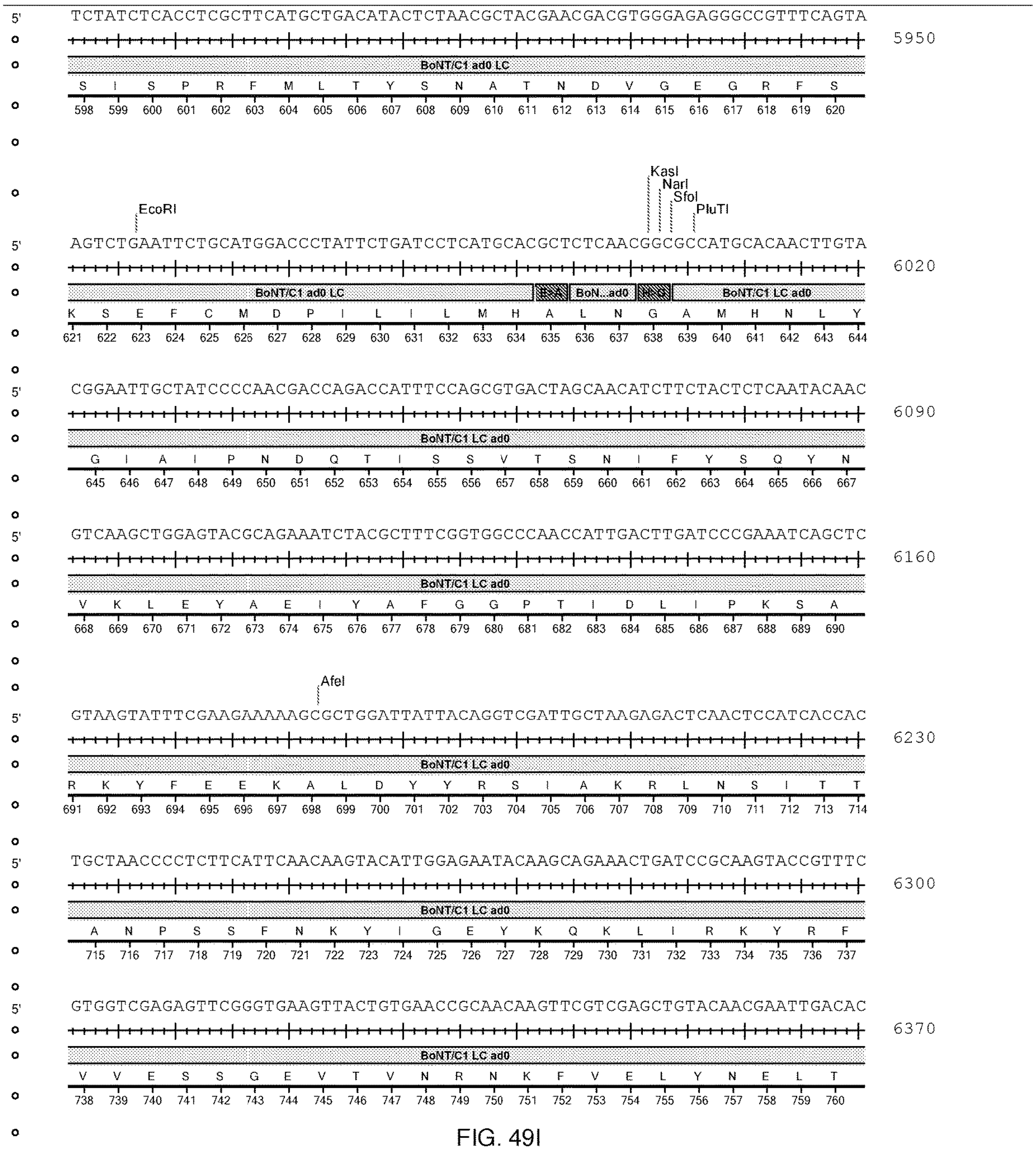

FIG. 49I

5' TCTATCTCACCTCGCTTCATGCTGACATACTCTAACGCTACGAACGACGTGGGAGAGGGCCGTTTCAGTA 5950

BoNT/C1 ad0 LC

S I S P R F M L T Y S N A T N D V G E G R F S 598 599 600 601 602 603 604 605 606 607 608 609 610 611 612 613 614 615 616 617 618 619 620

EcoRI KasI NarI SfoI PluTI

5' AGTCTGAATTCTGCATGGACCCTATTCTGATCCTCATGCACGCTCTCAACGGCGCCATGCACAACTTGTA 6020

BoNT/C1 ad0 LC BoN...ad0 BoNT/C1 LC ad0

K S E F C M D P I L I L M H A L N G A M H N L Y 621 622 623 624 625 626 627 628 629 630 631 632 633 634 635 636 637 638 639 640 641 642 643 644

5' CGGAATTGCTATCCCCAACGACCAGACCATTTCCAGCGTGACTAGCAACATCTTCTACTCTCAATACAAC 6090

BoNT/C1 LC ad0

G I A I P N D Q T I S S V T S N I F Y S Q Y N 645 646 647 648 649 650 651 652 653 654 655 656 657 658 659 660 661 662 663 664 665 666 667

5' GTCAAGCTGGAGTACGCAGAAATCTACGCTTTCGGTGGCCCAACCATTGACTTGATCCCGAAATCAGCTC 6160

BoNT/C1 LC ad0

V K L E Y A E I Y A F G G P T I D L I P K S A 668 669 670 671 672 673 674 675 676 677 678 679 680 681 682 683 684 685 686 687 688 689 690

AfeI

5' GTAAGTATTTCGAAGAAAAAGCGCTGGATTATTACAGGTCGATTGCTAAGAGACTCAACTCCATCACCAC 6230

BoNT/C1 LC ad0

R K Y F E E K A L D Y Y R S I A K R L N S I T T 691 692 693 694 695 696 697 698 699 700 701 702 703 704 705 706 707 708 709 710 711 712 713 714

5' TGCTAACCCCTCTTCATTCAACAAGTACATTGGAGAATACAAGCAGAAACTGATCCGCAAGTACCGTTTC 6300

BoNT/C1 LC ad0

A N P S S F N K Y I G E Y K Q K L I R K Y R F 715 716 717 718 719 720 721 722 723 724 725 726 727 728 729 730 731 732 733 734 735 736 737

5' GTGGTCGAGAGTTCGGGTGAAGTTACTGTGAACCGCAACAAGTTCGTCGAGCTGTACAACGAATTGACAC 6370

BoNT/C1 LC ad0

5' AAATCTTCACGGAGTTCAACTACGCCAAAATTTACAACGTGCAAAACCGTAAGATCGCGCTCTCTAACGT 6440

BoNT/C1 LC ad0 | Y>A | BoNT/C1 LC ad0

Q I F T E F N Y A K I Y N V Q N R K I A L S N V 761 762 763 764 765 766 767 768 769 770 771 772 773 774 775 776 777 778 779 780 781 782 783 784

BstEII

5' CTACACCCCGGTTACCGCTAACATCTTGGACGATAACGTCTACGACATTCAGAACGGTTTCAACATCCCA 6510

BoNT/C1 LC ad0

Y T P V T A N I L D D N V Y D I Q N G F N I P 785 786 787 788 789 790 791 792 793 794 795 796 797 798 799 800 801 802 803 804 805 806 807

5' AAGTCGAACCTCAACGTTTTGTTCATGGGTCAAAACTTGTCCCGCAACCCCGCCCTGCGTAAGGTGAACC 6580

BoNT/C1 LC ad0

K S N L N V L F M G Q N L S R N P A L R K V N 808 809 810 811 812 813 814 815 816 817 818 819 820 821 822 823 824 825 826 827 828 829 830

5' CAGAGAACATGTTGTACCTGTTCACCAAATTCTGCCACAAGGCCATCGACGGTCAGTCTCTAGACCAAGG 6650

BoNT/C1 LC ad0 | LC/HC spacer

P E N M L Y L F T K F C H K A I D G Q S L D Q G 831 832 833 834 835 836 837 838 839 840 841 842 843 844 845 846 847 848 849 850 851 852 853 854

5' AGGATGGGAACTCCAGCAAGGTGGCCAGGGTGGAGGTGCTGGCACCCTGGACTGTCGCGAACTGCTCGTT 6720

LC...er | Spl E site | LC/HC spacer | BoNT/C Translocation Domain

G W E L Q Q G G Q G G G A G T L D C R E L L V 855 856 857 858 859 860 861 862 863 864 865 866 867 868 869 870 871 872 873 874 875 876 877

5' AAGAACACTGATCTCCCATTCATTGGCGACATCTCTGATGTGAAAACAGACATTTTCCTGCGTAAGGATA 6790

BoNT/C Translocation Domain

K N T D L P F I G D I S D V K T D I F L R K D 878 879 880 881 882 883 884 885 886 887 888 889 890 891 892 893 894 895 896 897 898 899 900

5' TCAACGAGGAAACGGAGGTCATCTACTACCCTGACAACGTCTCGGTTGATCAGGTTATCTTGTCAAAGAA 6860

BoNT/C Translocation Domain

5' CACCAGTGAACATGGCCAACTGGACTTGCTGTACCCCTCAATTGATTCCGAGAGCGAAATCCTGCCAGGA 6930
BoNT/C Translocation Domain
T S E H G Q L D L L Y P S I D S E S E I L P G
925 926 927 928 929 930 931 932 933 934 935 936 937 938 939 940 941 942 943 944 945 946 947

SexAI
5' GAGAACCAGGTTTTCTACGACAACAGGACACAAAACGTGGATTACCTCAACAGCTACTACTACCTGGAGT 7000
BoNT/C Translocation Domain
E N Q V F Y D N R T Q N V D Y L N S Y Y Y L E
948 949 950 951 952 953 954 955 956 957 958 959 960 961 962 963 964 965 966 967 968 969 970

5' CGCAGAAGCTCTCCGACAACGTCGAAGATTTCACATTTACGAGATCAATCGAGGAGGCTTTGGACAACAG 7070
BoNT/C Translocation Domain
S Q K L S D N V E D F T F T R S I E E A L D N S
971 972 973 974 975 976 977 978 979 980 981 982 983 984 985 986 987 988 989 990 991 992 993 994

5' TGCCAAAGTCTACACCTACTTCCCTACTCTGGCAAACAAGGTGAACGCGGGTGTCCAAGGCGGACTCTTC 7140
BoNT/C Translocation Domain
A K V Y T Y F P T L A N K V N A G V Q G G L F
995 996 997 998 999 1000 1001 1002 1003 1004 1005 1006 1007 1008 1009 1010 1011 1012 1013 1014 1015 1016 1017

5' TTGATGTGGGCTAACGACGTTGTGGAAGATTTCACAACGAACATCTTGCGCAAAGACACCCTGGATAAGA 7210
BoNT/C Translocation Domain
L M W A N D V V E D F T T N I L R K D T L D K
1018 1019 1020 1021 1022 1023 1024 1025 1026 1027 1028 1029 1030 1031 1032 1033 1034 1035 1036 1037 1038 1039 1040

5' TCAGCGATGTCTCTGCCATCATTCCATACATTGGCCCGGCACTGAACATCTCTAACTCAGTTCGCCGTGG 7280
BoNT/C Translocation Domain
I S D V S A I I P Y I G P A L N I S N S V R R G
1041 1042 1043 1044 1045 1046 1047 1048 1049 1050 1051 1052 1053 1054 1055 1056 1057 1058 1059 1060 1061 1062 1063 1064

PfoI
5' CAACTTCACTGAGGCATTCGCGGTCACAGGAGTTACGATCCTCTTGGAGGCTTTCCCGGAGTTCACAATC 7350
BoNT/C Translocation Domain
N F T E A F A V T G V T I L L E A F P E F T I
1065 1066 1067 1068 1069 1070 1071 1072 1073 1074 1075 1076 1077 1078 1079 1080 1081 1082 1083 1084 1085 1086 1087

FIG. 49K

5' CCCGCACTGGGCGCGTTCGTTATCTACTCCAAAGTGCAGGAGCGCAACGAAATCATTAAGACTATCGACA 7420

BoNT/C Translocation Domain

P A L G A F V I Y S K V Q E R N E I I K T I D 1088 1089 1090 1091 1092 1093 1094 1095 1096 1097 1098 1099 1100 1101 1102 1103 1104 1105 1106 1107 1108 1109 1110

BsiWI

5' ACTGCCTGGAGCAAAGGATCAAAAGATGGAAGGATTCGTACGAATGGATGATGGGTACCTGGCTCTCCCG 7490

BoNT/C Translocation Domain

N C L E Q R I K R W K D S Y E W M M G T W L S R 1111 1112 1113 1114 1115 1116 1117 1118 1119 1120 1121 1122 1123 1124 1125 1126 1127 1128 1129 1130 1131 1132 1133 1134

5' TATCATTACGCAGTTCAACAACATCAGCTACCAAATGTACGACTCTCTCAACTACCAGGCTGGTGCCATC 7560

BoNT/C Translocation Domain

I I T Q F N N I S Y Q M Y D S L N Y Q A G A I 1135 1136 1137 1138 1139 1140 1141 1142 1143 1144 1145 1146 1147 1148 1149 1150 1151 1152 1153 1154 1155 1156 1157

XcmI

5' AAGGCCAAAATTGACTTGGAGTACAAGAAATACAGTGGCTCGGATAAAGAGAACATCAAGAGTCAAGTCG 7630

BoNT/C Translocation Domain

K A K I D L E Y K K Y S G S D K E N I K S Q V 1158 1159 1160 1161 1162 1163 1164 1165 1166 1167 1168 1169 1170 1171 1172 1173 1174 1175 1176 1177 1178 1179 1180

5' AAAaCCTGAAAAACTCACTCGACGTTAAGATCAGTGAGGCAATGAACAACATCAACAAGTTCATTCGCGA 7700

BoNT/C Translocation Domain

E N L K N S L D V K I S E A M N N I N K F I R E 1181 1182 1183 1184 1185 1186 1187 1188 1189 1190 1191 1192 1193 1194 1195 1196 1197 1198 1199 1200 1201 1202 1203 1204

5' ATGTTCCGTTACCTACCTCTTCAAAAACATGTTGCCAAAGGTCATCGACGAGCTGAACGAATTTGATCGT 7770

BoNT/C Translocation Domain

C S V T Y L F K N M L P K V I D E L N E F D R 1205 1206 1207 1208 1209 1210 1211 1212 1213 1214 1215 1216 1217 1218 1219 1220 1221 1222 1223 1224 1225 1226 1227

5' AACACTAAGGCGAAACTGATTAACCTCATCGACTCACACAACATCATTTTGGTGGGCGAAGTCGATAAGC 7840

BoNT/C Translocation Domain

```
5'  TGAAAGCCAAGGtGAACAACAGTTTCCAGAACACAATCCCTTTCAAcATTTTCTCATACACGAACAACAG
                                                                              7910
                         BoNT/C Translocation Domain
     L   K   A   K   V   N   N   S   F   Q   N   T   I   P   F   N   I   F   S   Y   T   N   N   S
    1251 1252 1253 1254 1255 1256 1257 1258 1259 1260 1261 1262 1263 1264 1265 1266 1267 1268 1269 1270 1271 1272 1273 1274

                                                                         PstI
5'  TCTGCTCAAGGACATCATTAACGAGTACTTCAACAACATTAACGATAGCAAAATCCTGTCACTGCAGAAC
                                                                              7980
          BoNT/C Translocation Domain          |        BoNT/C Receptor Binding Domain
     L   L   K   D   I   I   N   E   Y   F   N   N   I   N   D   S   K   I   L   S   L   Q   N
    1275 1276 1277 1278 1279 1280 1281 1282 1283 1284 1285 1286 1287 1288 1289 1290 1291 1292 1293 1294 1295 1296 1297

                       SpeI                                              PvuII
5'  CGTAAGAACACACTGGTCGATACTAGTGGATACAACGCCGAAGTCTCTGAGGAAGGTGACGTGCAGCTGA
                                                                              8050
                         BoNT/C Receptor Binding Domain
     R   K   N   T   L   V   D   T   S   G   Y   N   A   E   V   S   E   E   G   D   V   Q   L
    1298 1299 1300 1301 1302 1303 1304 1305 1306 1307 1308 1309 1310 1311 1312 1313 1314 1315 1316 1317 1318 1319 1320

5'  ACCCTATCTTCCCCTTCGACTTCAAATTGGGCTCCAGCGGAGAGGATAGGGGCAAGGTCATCGTCACCCA
                                                                              8120
                         BoNT/C Receptor Binding Domain
     N   P   I   F   P   F   D   F   K   L   G   S   S   G   E   D   R   G   K   V   I   V   T   Q
    1321 1322 1323 1324 1325 1326 1327 1328 1329 1330 1331 1332 1333 1334 1335 1336 1337 1338 1339 1340 1341 1342 1343 1344

5'  GAACGAGAACATCGTCTACAACTCAATGTACGAATCCTTCAGCATCTCTTTCTGGATCAGGATTAACAAG
                                                                              8190
                         BoNT/C Receptor Binding Domain
     N   E   N   I   V   Y   N   S   M   Y   E   S   F   S   I   S   F   W   I   R   I   N   K
    1345 1346 1347 1348 1349 1350 1351 1352 1353 1354 1355 1356 1357 1358 1359 1360 1361 1362 1363 1364 1365 1366 1367

                    BspMI
5'  TGGGTGAGCAACCTGCCCGGTTACACAATCATTGACTCTGTCAAGAACAACTCAGGTTGGAGTATCGGCA
                                                                              8260
                         BoNT/C Receptor Binding Domain
     W   V   S   N   L   P   G   Y   T   I   I   D   S   V   K   N   N   S   G   W   S   I   G
    1368 1369 1370 1371 1372 1373 1374 1375 1376 1377 1378 1379 1380 1381 1382 1383 1384 1385 1386 1387 1388 1389 1390

5'  TCATTTCTAACTTCTTGGTCTTCACCCTGAAGCAGAACGAGGACTCGGAACAATCCATTAACTTCTCATA
                                                                              8330
                         BoNT/C Receptor Binding Domain
     I   I   S   N   F   L   V   F   T   L   K   Q   N   E   D   S   E   Q   S   I   N   F   S   Y
    1391 1392 1393 1394 1395 1396 1397 1398 1399 1400 1401 1402 1403 1404 1405 1406 1407 1408 1409 1410 1411 1412 1413 1414
```

FIG. 49M

5' CGATATCAGTAACAACGCTCCAGGTTACAACAAGTGGTTCTTCGTTACCGTGACTAACAACATGATGGGT 8400

BoNT/C Receptor Binding Domain

D I S N N A P G Y N K W F F V T V T N N M M G 1415 1416 1417 1418 1419 1420 1421 1422 1423 1424 1425 1426 1427 1428 1429 1430 1431 1432 1433 1434 1435 1436 1437

5' AACATGAAAATTTACATCAACGGCAAGCTCATTGACACCATCAAAGTGAAGGAGTTGACTGGTATTAACT 8470

BoNT/C Receptor Binding Domain

N M K I Y I N G K L I D T I K V K E L T G I N 1438 1439 1440 1441 1442 1443 1444 1445 1446 1447 1448 1449 1450 1451 1452 1453 1454 1455 1456 1457 1458 1459 1460

5' TCTCCAAAACAATCACGTTTGAAATTAaCaAGATCCCTGACACCGGCCTGATCACTTCAGACAGTGATAA 8540

BoNT/C Receptor Binding Domain

F S K T I T F E I N K I P D T G L I T S D S D N 1461 1462 1463 1464 1465 1466 1467 1468 1469 1470 1471 1472 1473 1474 1475 1476 1477 1478 1479 1480 1481 1482 1483 1484

EcoICRI

SacI

5' CATCAACATGTGGATTAGGGATTTCTACATCTTCGCCAAGGAGCTCGACGGAAAGGATATTAACATCCTC 8610

BoNT/C Receptor Binding Domain

I N M W I R D F Y I F A K E L D G K D I N I L 1485 1486 1487 1488 1489 1490 1491 1492 1493 1494 1495 1496 1497 1498 1499 1500 1501 1502 1503 1504 1505 1506 1507

5' TTCAACAGCTTGCAGTACACCAACGTCGTTAAAGACTACTGGGGTAACGATTTGAGATACAACAAGGAGT 8680

BoNT/C Receptor Binding Domain

F N S L Q Y T N V V K D Y W G N D L R Y N K E 1508 1509 1510 1511 1512 1513 1514 1515 1516 1517 1518 1519 1520 1521 1522 1523 1524 1525 1526 1527 1528 1529 1530

5' ACTACATGGTCAACATCGACTACCTGAACAGGTACATGTACGCTAACTCCCGCCAAATCGTGTTCAACAC 8750

BoNT/C Receptor Binding Domain

Y Y M V N I D Y L N R Y M Y A N S R Q I V F N T 1531 1532 1533 1534 1535 1536 1537 1538 1539 1540 1541 1542 1543 1544 1545 1546 1547 1548 1549 1550 1551 1552 1553 1554

5' CAGGAGAAACAACAACGACTTCAACGAGGGTTACAAAATCATTATCAAGCGCATCCGTGGCAACACCAAC 8820

BoNT/C Receptor Binding Domain

5' GATACTAGGGTGAGAGGTGGCGACATTCTGTACTTCGATATGACTATCAACAACAAAGCCTACAACTTGT 8890
BoNT/C Receptor Binding Domain
D T R V R G G D I L Y F D M T I N N K A Y N L
1578 1579 1580 1581 1582 1583 1584 1585 1586 1587 1588 1589 1590 1591 1592 1593 1594 1595 1596 1597 1598 1599 1600

5' TCATGAAAAACGAGACAATGTACGCCGACAAcCATAGCACGGAGGATATTTACGCAATCGGACTGAGGGA 8960
BoNT/C Receptor Binding Domain
F M K N E T M Y A D N H S T E D I Y A I G L R E
1601 1602 1603 1604 1605 1606 1607 1608 1609 1610 1611 1612 1613 1614 1615 1616 1617 1618 1619 1620 1621 1622 1623 1624

5' ACAGACAAAGGACATCAACGATAACATTATCTTCCAGATCCAACCTATGAACAACACGTACTACTACGCT 9030
BoNT/C Receptor Binding Domain
Q T K D I N D N I I F Q I Q P M N N T Y Y Y A
1625 1626 1627 1628 1629 1630 1631 1632 1633 1634 1635 1636 1637 1638 1639 1640 1641 1642 1643 1644 1645 1646 1647

5' TCGCAAATCTTCAAGTCCAACTTCAACGGAGAAAACATTTCGGGTATCTGTTCCATTGGCACATACCGCT 9100
BoNT/C Receptor Binding Domain
S Q I F K S N F N G E N I S G I C S I G T Y R
1648 1649 1650 1651 1652 1653 1654 1655 1656 1657 1658 1659 1660 1661 1662 1663 1664 1665 1666 1667 1668 1669 1670

5' TCCGTCTGGGTGGTGACTGGTATCGTCACAACTACCTCGTTCCCACCGTGAAGCAGGGTAACTACGCTTC 9170
BoNT/C Receptor Binding Domain
F R L G G D W Y R H N Y L V P T V K Q G N Y A S
1671 1672 1673 1674 1675 1676 1677 1678 1679 1680 1681 1682 1683 1684 1685 1686 1687 1688 1689 1690 1691 1692 1693 1694

SalI
5' TTTGCTGGAGTCGACTTCCACGCACTGGGGATTCGTTCCTGTGTCAGAGGGCGCTGGCTACCCTTACGAT 9240
BoNT/C Receptor Binding Domain | linker | HA tag
L L E S T S T H W G F V P V S E G A G Y P Y D
1695 1696 1697 1698 1699 1700 1701 1702 1703 1704 1705 1706 1707 1708 1709 1710 1711 1712 1713 1714 1715 1716 1717

5' GTTCCCGACTACGCTGGTTGGGAACTCCAGCAAGGTGCAGGATGGTCCCACCCTCAATTCGAGAAGGGTG 9310
HA tag | li...r | SplB site | linker | Strep tag II | linker
V P D Y A G W E L Q Q G A G W S H P Q F E K G
1718 1719 1720 1721 1722 1723 1724 1725 1726 1727 1728 1729 1730 1731 1732 1733 1734 1735 1736 1737 1738 1739 1740

FIG. 49O

5' CCGGATGGAGTCACCCACAGTTCGAGAAAGGCGCTGGATGGAGTCACCCACAGTTCGAGAAATAATTAGT 9380

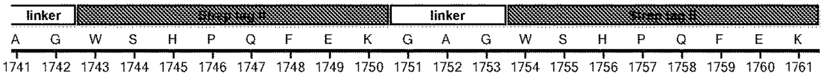

NsiI XhoI NsiI

5' TGATGCATAGTTAATTAGATAGCTCGAGGCATGCGGTACCAAGATTGGATCTAGATGCATAGTTAATTAG 9450

XhoI

5' ATAGCTCGAGGCATGCGGTACCAAGCTTGTCGAGAAGTACTAGAGGATCATAATCAGCCATACCACATTT 9520

5' GTAGAGGTTTTACTTGCTTTAAAAAACCTCCCACACCTCCCCCTGAACCTGAAACATAAAATGAATGCAA 9590

HpaI

5' TTGTTGTTGTTAACTTGTTTATTGCAGCTTATAATGGTTACAAATAAAGCAATAGCATCACAAATTTCAC 9660

5' AAATAAAGCATTTTTTTCACTGCATTCTAGTTGTGGTTTGTCCAAACTCATCAATGTATCTTATCATGTC 9730

AvrII

5' TGGATCTGATCACTGCTTGAGCCTAGGAGATCCGAACCAGATAAGTGAAATCTAGTTCCAAACTATTTTG 9800

5' TCATTTTTAATTTTCGTATTAGCTTACGACGCTACACCCAGTTCCCATCTATTTTGTCACTCTTCCCTAA 9870

5' ATAATCCTTAAAAACTCCATTTCCACCCCTCCCAGTTCCCAACTATTTTGTCCGCCCACAGCGGGGCATT 9940

5' TTTCTTCCTGTTATGTTTTTAATCAAACATCCTGCCAACTCCATGTGACAAACCGTCATCTTCGGCTACT 10010

5' TTTTCTCTGTCACAGAATGAAAATTTTTCTGTCATCTCTTCGTTATTAATGTTTGTAATTGACTGAATAT 10080

5' CAACGCTTATTTGCAGCCTGAATGGCGAATGG 10112

FIG. 49P

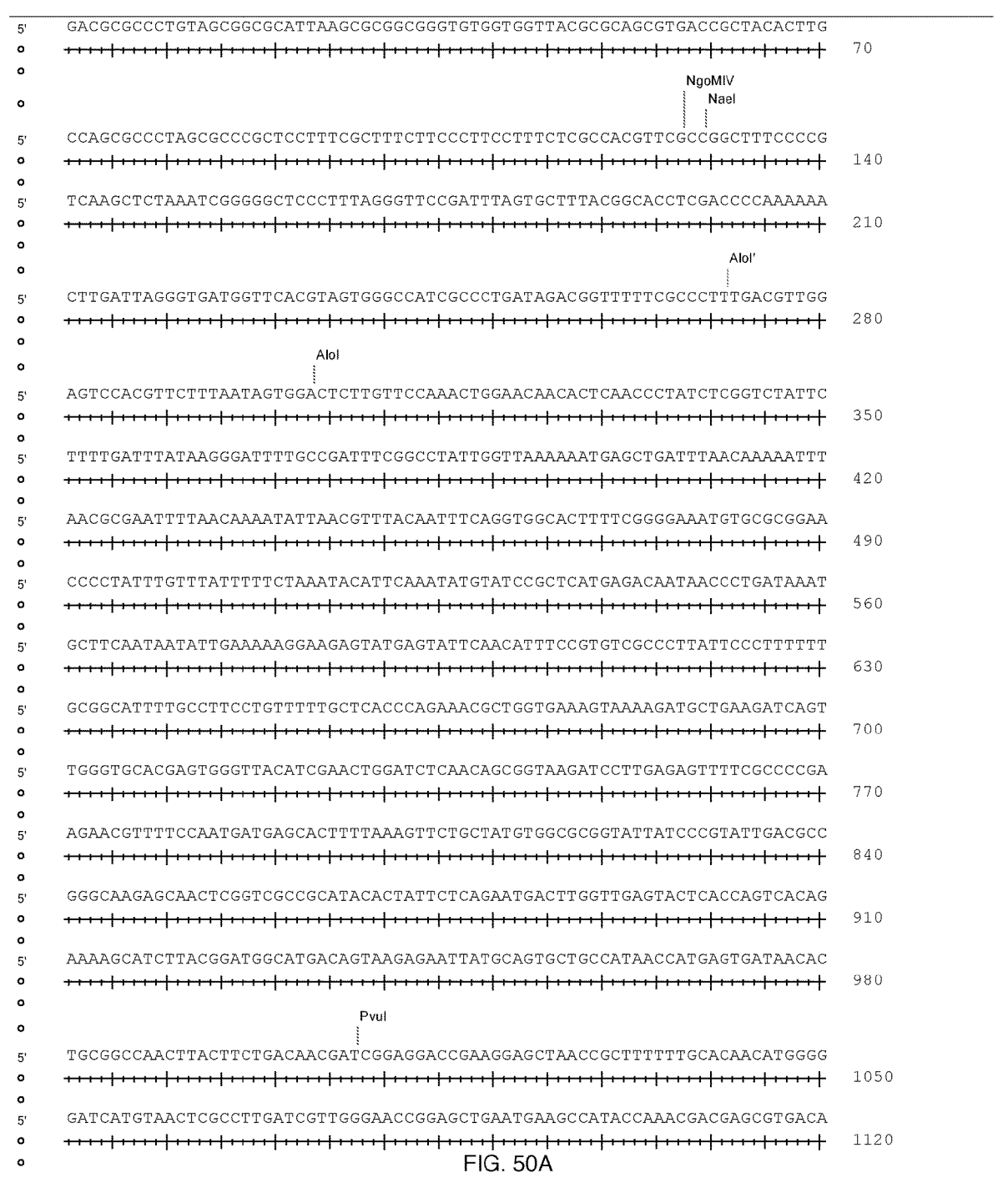

5' GACGCGCCCTGTAGCGGCGCATTAAGCGCGGCGGGTGTGGTGGTTACGCGCAGCGTGACCGCTACACTTG 70

NgoMIV NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

5' GATCATGTAACTCGCCTTGATCGTTGGGAACCGGAGCTGAATGAAGCCATACCAAACGACGAGCGTGACA 1120

FIG. 50A

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

FIG. 50B

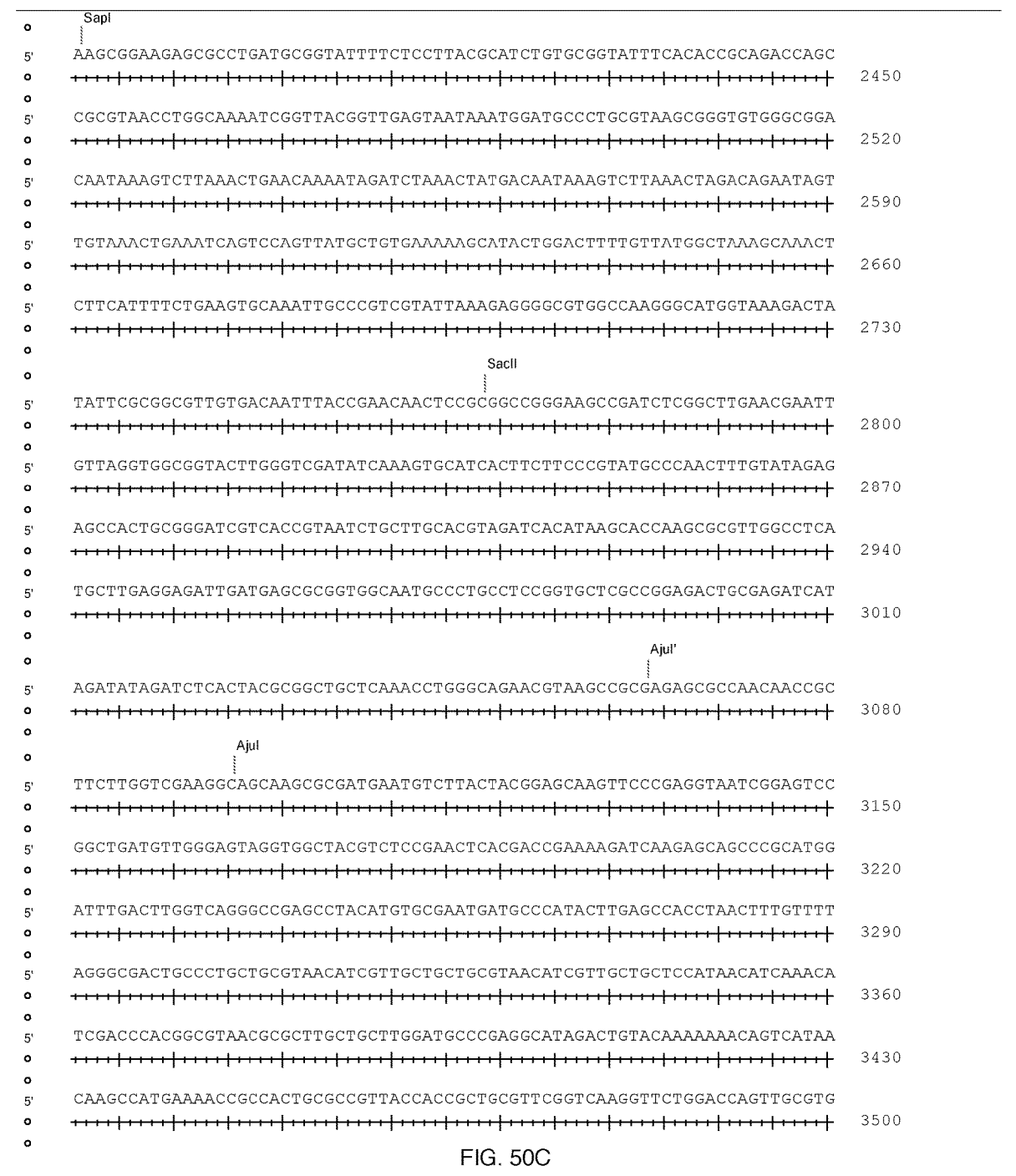

SapI
5' AAGCGGAAGAGCGCCTGATGCGGTATTTTCTCCTTACGCATCTGTGCGGTATTTCACACCGCAGACCAGC 2450
5' CGCGTAACCTGGCAAAATCGGTTACGGTTGAGTAATAAATGGATGCCCTGCGTAAGCGGGTGTGGGCGGA 2520
5' CAATAAAGTCTTAAACTGAACAAAATAGATCTAAACTATGACAATAAAGTCTTAAACTAGACAGAATAGT 2590
5' TGTAAACTGAAATCAGTCCAGTTATGCTGTGAAAAAGCATACTGGACTTTTGTTATGGCTAAAGCAAACT 2660
5' CTTCATTTTCTGAAGTGCAAATTGCCCGTCGTATTAAAGAGGGGCGTGGCCAAGGGCATGGTAAAGACTA 2730
SacII
5' TATTCGCGGCGTTGTGACAATTTACCGAACAACTCCGCGGCCGGGAAGCCGATCTCGGCTTGAACGAATT 2800
5' GTTAGGTGGCGGTACTTGGGTCGATATCAAAGTGCATCACTTCTTCCCGTATGCCCAACTTTGTATAGAG 2870
5' AGCCACTGCGGGATCGTCACCGTAATCTGCTTGCACGTAGATCACATAAGCACCAAGCGCGTTGGCCTCA 2940
5' TGCTTGAGGAGATTGATGAGCGCGGTGGCAATGCCCTGCCTCCGGTGCTCGCCGGAGACTGCGAGATCAT 3010
AjuI'
5' AGATATAGATCTCACTACGCGGCTGCTCAAACCTGGGCAGAACGTAAGCCGCGAGAGCGCCAACAACCGC 3080
AjuI
5' TTCTTGGTCGAAGGCAGCAAGCGCGATGAATGTCTTACTACGGAGCAAGTTCCCGAGGTAATCGGAGTCC 3150
5' GGCTGATGTTGGGAGTAGGTGGCTACGTCTCCGAACTCACGACCGAAAAGATCAAGAGCAGCCCGCATGG 3220
5' ATTTGACTTGGTCAGGGCCGAGCCTACATGTGCGAATGATGCCCATACTTGAGCCACCTAACTTTGTTTT 3290
5' AGGGCGACTGCCCTGCTGCGTAACATCGTTGCTGCTGCGTAACATCGTTGCTGCTCCATAACATCAAACA 3360
5' TCGACCCACGGCGTAACGCGCTTGCTGCTTGGATGCCCGAGGCATAGACTGTACAAAAAAACAGTCATAA 3430
5' CAAGCCATGAAAACCGCCACTGCGCCGTTACCACCGCTGCGTTCGGTCAAGGTTCTGGACCAGTTGCGTG 3500

FIG. 50C

NgoMIV
NaeI
FseI

5' AAGACCCCCAAGCCTCAAGGGGCCGGCCAGGGTGCTGGTGCTGGACCGATCACCATCAACAACTTCAATT 5110 sd Ab JNE-B10 V... anti-BoNT/B LC | linker | BoNT/C1 ad0 LC

K T P K P Q G A G Q G A G A G P I T I N N F N
318 319 320 321 322 323 324 325 326 327 328 329 330 331 332 333 334 335 336 337 338 339 340

BamHI

5' ACTCGGATCCGGTGGATAACAAGAACATCCTCTACTTGGACACACACTTGAACACGCTGGCTAACGAGCC 5180

BoNT/C1 ad0 LC

Y S D P V D N K N I L Y L D T H L N T L A N E P
341 342 343 344 345 346 347 348 349 350 351 352 353 354 355 356 357 358 359 360 361 362 363 364

5' TGAAAAAGCTTTCAGGATCACCGGCAACATTTGGGTCATTCCGGATAGGTTCAGCAGAAACTCTAACCCT 5250

BoNT/C1 ad0 LC

E K A F R I T G N I W V I P D R F S R N S N P
365 366 367 368 369 370 371 372 373 374 375 376 377 378 379 380 381 382 383 384 385 386 387

5' AACTTGAACAAACCTCCCAGAGTGACCTCACCTAAGAGTGGATACTACGACCCCAACTACCTCTCGACTG 5320

BoNT/C1 ad0 LC

N L N K P P R V T S P K S G Y Y D P N Y L S T
388 389 390 391 392 393 394 395 396 397 398 399 400 401 402 403 404 405 406 407 408 409 410

5' ACTCCGATAAAGACCCCTTCCTGAAGGAGATCATTAAACTCTTCAAGCGCATCAACTCTCGTGAAATTGG 5390

BoNT/C1 ad0 LC

D S D K D P F L K E I I K L F K R I N S R E I G
411 412 413 414 415 416 417 418 419 420 421 422 423 424 425 426 427 428 429 430 431 432 433 434

XmaI
SmaI

5' CGAGGAATTGATCTACCGCCTGAGTACAGACATCCCATTCCCGGGTAACAACAACACCCCAATCAACACT 5460

BoNT/C1 ad0 LC

E E L I Y R L S T D I P F P G N N N T P I N T
435 436 437 438 439 440 441 442 443 444 445 446 447 448 449 450 451 452 453 454 455 456 457

5' TTCGATTTCGATGTCGATTTCAACTCAGTGGATGTCAAAACCAGGCAGGGAAACAACTGGGTGAAGACTG 5530

BoNT/C1 ad0 LC

5' GTAGCATCAACCCATCTGTCATCATTACTGGCCCGAGAGAGAACATCATTGACCCTGAAACCTCCACTTT 5600
BoNT/C1 ad0 LC
G S I N P S V I I T G P R E N I I D P E T S T F
481 482 483 484 485 486 487 488 489 490 491 492 493 494 495 496 497 498 499 500 501 502 503 504

Bpu10I
5' CAaGCTGACaAACAACACGTTCGCTGCTCAGGAAGGCTTCGGAGCGTTGAGCATCATTTCTATCTCACCT 5670
BoNT/C1 ad0 LC
K L T N N T F A A Q E G F G A L S I I S I S P
505 506 507 508 509 510 511 512 513 514 515 516 517 518 519 520 521 522 523 524 525 526 527

EcoRI
5' CGCTTCATGCTGACATACTCTAACGCTACGAACGACGTGGGAGAGGGCCGTTTCAGTAAGTCTGAATTCT 5740
BoNT/C1 ad0 LC
R F M L T Y S N A T N D V G E G R F S K S E F
528 529 530 531 532 533 534 535 536 537 538 539 540 541 542 543 544 545 546 547 548 549 550

KasI
NarI
SfoI
PluTI
5' GCATGGACCCTATTCTGATCCTCATGCACGCTCTCAACGGCGCCATGCACAACTTGTACGGAATTGCTAT 5810
BoNT/C1 ad0 LC | E-A | BoN...ad0 | N-G | BoNT/C1 LC ad0
C M D P I L I L M H A L N G A M H N L Y G I A I
551 552 553 554 555 556 557 558 559 560 561 562 563 564 565 566 567 568 569 570 571 572 573 574

5' CCCCAACGACCAGACCATTTCCAGCGTGACTAGCAACATCTTCTACTCTCAATACAACGTCAAGCTGGAG 5880
BoNT/C1 LC ad0
P N D Q T I S S V T S N I F Y S Q Y N V K L E
575 576 577 578 579 580 581 582 583 584 585 586 587 588 589 590 591 592 593 594 595 596 597

5' TACGCAGAAATCTACGCTTTCGGTGGCCCAACCATTGACTTGATCCCGAAATCAGCTCGTAAGTATTTCG 5950
BoNT/C1 LC ad0
Y A E I Y A F G G P T I D L I P K S A R K Y F
598 599 600 601 602 603 604 605 606 607 608 609 610 611 612 613 614 615 616 617 618 619 620

FIG. 50H

AfeI

5' AAGAAAAAGCGCTGGATTATTACAGGTCGATTGCTAAGAGACTCAACTCCATCACCACTGCTAACCCCTC 6020

BoNT/C1 LC ad0

E E K A L D Y Y R S I A K R L N S I T T A N P S 621 622 623 624 625 626 627 628 629 630 631 632 633 634 635 636 637 638 639 640 641 642 643 644

5' TTCATTCAACAAGTACATTGGAGAATACAAGCAGAAACTGATCCGCAAGTACCGTTTCGTGGTCGAGAGT 6090

BoNT/C1 LC ad0

S F N K Y I G E Y K Q K L I R K Y R F V V E S 645 646 647 648 649 650 651 652 653 654 655 656 657 658 659 660 661 662 663 664 665 666 667

5' TCGGGTGAAGTTACTGTGAACCGCAACAAGTTCGTCGAGCTGTACAACGAATTGACACAAATCTTCACGG 6160

BoNT/C1 LC ad0

S G E V T V N R N K F V E L Y N E L T Q I F T 668 669 670 671 672 673 674 675 676 677 678 679 680 681 682 683 684 685 686 687 688 689 690

BstEII

5' AGTTCAACTACGCCAAAATTTACAACGTGCAAAACCGTAAGATCGCGCTCTCTAACGTCTACACCCCGGT 6230

BoNT/C1 LC ad0 | Y>A | BoNT/C1 LC ad0

E F N Y A K I Y N V Q N R K I A L S N V Y T P V 691 692 693 694 695 696 697 698 699 700 701 702 703 704 705 706 707 708 709 710 711 712 713 714

5' TACCGCTAACATCTTGGACGATAACGTCTACGACATTCAGAACGGTTTCAACATCCCAAAGTCGAACCTC 6300

BoNT/C1 LC ad0

T A N I L D D N V Y D I Q N G F N I P K S N L 715 716 717 718 719 720 721 722 723 724 725 726 727 728 729 730 731 732 733 734 735 736 737

5' AACGTTTTGTTCATGGGTCAAAACTTGTCCCGCAACCCCGCCCTGCGTAAGGTGAACCCAGAGAACATGT 6370

BoNT/C1 LC ad0

N V L F M G Q N L S R N P A L R K V N P E N M 738 739 740 741 742 743 744 745 746 747 748 749 750 751 752 753 754 755 756 757 758 759 760

5' TGTACCTGTTCACCAAATTCTGCCACAAGGCCATCGACGGTCAGTCTCTAGACCAAGGAGGATGGGAACT 6440

BoNT/C1 LC ad0 | LC/HC spacer | Spl B site

5' CCAGCAAGGTGGCCAGGGTGGAGGTGCTGGCACCCTGGACTGTCGCGAACTGCTCGTTAAGAACACTGAT 6510

Sp...te | LC/HC spacer | BoNT/C Translocation Domain

Q Q G G Q G G G A G T L D C R E L L V K N T D 785 786 787 788 789 790 791 792 793 794 795 796 797 798 799 800 801 802 803 804 805 806 807

5' CTCCCATTCATTGGCGACATCTCTGATGTGAAAACAGACATTTTCCTGCGTAAGGATATCAACGAGGAAA 6580

BoNT/C Translocation Domain

L P F I G D I S D V K T D I F L R K D I N E E 808 809 810 811 812 813 814 815 816 817 818 819 820 821 822 823 824 825 826 827 828 829 830

5' CGGAGGTCATCTACTACCCTGACAACGTCTCGGTTGATCAGGTTATCTTGTCAAAGAACACCAGTGAACA 6650

BoNT/C Translocation Domain

T E V I Y Y P D N V S V D Q V I L S K N T S E H 831 832 833 834 835 836 837 838 839 840 841 842 843 844 845 846 847 848 849 850 851 852 853 854

SexAI

5' TGGCCAACTGGACTTGCTGTACCCCTCAATTGATTCCGAGAGCGAAATCCTGCCAGGAGAGAACCAGGTT 6720

BoNT/C Translocation Domain

G Q L D L L Y P S I D S E S E I L P G E N Q V 855 856 857 858 859 860 861 862 863 864 865 866 867 868 869 870 871 872 873 874 875 876 877

5' TTCTACGACAACAGGACACAAAACGTGGATTACCTCAACAGCTACTACTACCTGGAGTCGCAGAAGCTCT 6790

BoNT/C Translocation Domain

F Y D N R T Q N V D Y L N S Y Y Y L E S Q K L 878 879 880 881 882 883 884 885 886 887 888 889 890 891 892 893 894 895 896 897 898 899 900

5' CCGACAACGTCGAAGATTTCACATTTACGAGATCAATCGAGGAGGCTTTGGACAACAGTGCCAAAGTCTA 6860

BoNT/C Translocation Domain

S D N V E D F T F T R S I E E A L D N S A K V Y 901 902 903 904 905 906 907 908 909 910 911 912 913 914 915 916 917 918 919 920 921 922 923 924

5' CACCTACTTCCCTACTCTGGCAAACAAGGTGAACGCGGGTGTCCAAGGCGGACTCTTCTTGATGTGGGCT 6930

BoNT/C Translocation Domain

5' AACGACGTTGTGGAAGATTTCACAACGAACATCTTGCGCAAAGACACCCTGGATAAGATCAGCGATGTCT 7000

BoNT/C Translocation Domain

N D V V E D F T T N I L R K D T L D K I S D V 948 949 950 951 952 953 954 955 956 957 958 959 960 961 962 963 964 965 966 967 968 969 970

5' CTGCCATCATTCCATACATTGGCCCGGCACTGAACATCTCTAACTCAGTTCGCCGTGGCAACTTCACTGA 7070

BoNT/C Translocation Domain

S A I I P Y I G P A L N I S N S V R R G N F T E 971 972 973 974 975 976 977 978 979 980 981 982 983 984 985 986 987 988 989 990 991 992 993 994

PfoI

5' GGCATTCGCGGTCACAGGAGTTACGATCCTCTTGGAGGCTTTCCCGGAGTTCACAATCCCCGCACTGGGC 7140

BoNT/C Translocation Domain

A F A V T G V T I L L E A F P E F T I P A L G 995 996 997 998 999 1000 1001 1002 1003 1004 1005 1006 1007 1008 1009 1010 1011 1012 1013 1014 1015 1016 1017

5' GCGTTCGTTATCTACTCCAAAGTGCAGGAGCGCAACGAAATCATTAAGACTATCGACAACTGCCTGGAGC 7210

BoNT/C Translocation Domain

A F V I Y S K V Q E R N E I I K T I D N C L E 1018 1019 1020 1021 1022 1023 1024 1025 1026 1027 1028 1029 1030 1031 1032 1033 1034 1035 1036 1037 1038 1039 1040

BsiWI

5' AAAGGATCAAAAGATGGAAGGATTCGTACGAATGGATGATGGGTACCTGGCTCTCCCGTATCATTACGCA 7280

BoNT/C Translocation Domain

Q R I K R W K D S Y E W M M G T W L S R I I T Q 1041 1042 1043 1044 1045 1046 1047 1048 1049 1050 1051 1052 1053 1054 1055 1056 1057 1058 1059 1060 1061 1062 1063 1064

5' GTTCAACAACATCAGCTACCAAATGTACGACTCTCTCAACTACCAGGCTGGTGCCATCAAGGCCAAAATT 7350

BoNT/C Translocation Domain

F N N I S Y Q M Y D S L N Y Q A G A I K A K I 1065 1066 1067 1068 1069 1070 1071 1072 1073 1074 1075 1076 1077 1078 1079 1080 1081 1082 1083 1084 1085 1086 1087

XcmI

5' GACTTGGAGTACAAGAAATACAGTGGCTCGGATAAAGAGAACATCAAGAGTCAAGTCGAAAaCCTGAAAA 7420

BoNT/C Translocation Domain

Figure 50M:
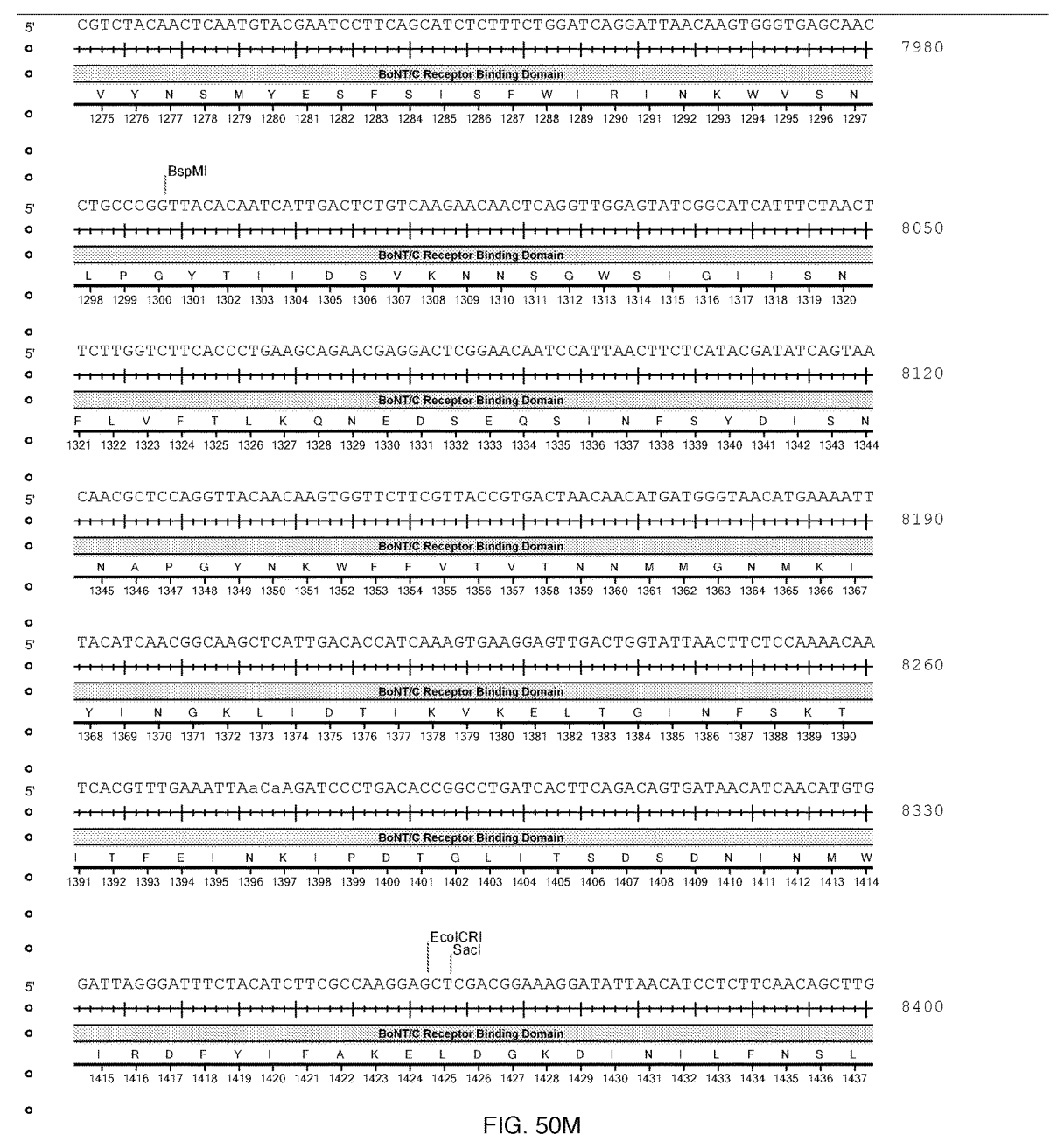

5' CGTCTACAACTCAATGTACGAATCCTTCAGCATCTCTTTCTGGATCAGGATTAACAAGTGGGTGAGCAAC 7980

BoNT/C Receptor Binding Domain

V Y N S M Y E S F S I S F W I R I N K W V S N 1275 1276 1277 1278 1279 1280 1281 1282 1283 1284 1285 1286 1287 1288 1289 1290 1291 1292 1293 1294 1295 1296 1297

BspMI

5' CTGCCCGGTTACACAATCATTGACTCTGTCAAGAACAACTCAGGTTGGAGTATCGGCATCATTTCTAACT 8050

BoNT/C Receptor Binding Domain

L P G Y T I I D S V K N N S G W S I G I I S N 1298 1299 1300 1301 1302 1303 1304 1305 1306 1307 1308 1309 1310 1311 1312 1313 1314 1315 1316 1317 1318 1319 1320

5' TCTTGGTCTTCACCCTGAAGCAGAACGAGGACTCGGAACAATCCATTAACTTCTCATACGATATCAGTAA 8120

BoNT/C Receptor Binding Domain

F L V F T L K Q N E D S E Q S I N F S Y D I S N 1321 1322 1323 1324 1325 1326 1327 1328 1329 1330 1331 1332 1333 1334 1335 1336 1337 1338 1339 1340 1341 1342 1343 1344

5' CAACGCTCCAGGTTACAACAAGTGGTTCTTCGTTACCGTGACTAACAACATGATGGGTAACATGAAAATT 8190

BoNT/C Receptor Binding Domain

N A P G Y N K W F F V T V T N N M M G N M K I 1345 1346 1347 1348 1349 1350 1351 1352 1353 1354 1355 1356 1357 1358 1359 1360 1361 1362 1363 1364 1365 1366 1367

5' TACATCAACGGCAAGCTCATTGACACCATCAAAGTGAAGGAGTTGACTGGTATTAACTTCTCCAAAACAA 8260

BoNT/C Receptor Binding Domain

Y I N G K L I D T I K V K E L T G I N F S K T 1368 1369 1370 1371 1372 1373 1374 1375 1376 1377 1378 1379 1380 1381 1382 1383 1384 1385 1386 1387 1388 1389 1390

5' TCACGTTTGAAATTAaCaAGATCCCTGACACCGGCCTGATCACTTCAGACAGTGATAACATCAACATGTG 8330

BoNT/C Receptor Binding Domain

I T F E I N K I P D T G L I T S D S D N I N M W 1391 1392 1393 1394 1395 1396 1397 1398 1399 1400 1401 1402 1403 1404 1405 1406 1407 1408 1409 1410 1411 1412 1413 1414

EcoICRI

SacI

5' GATTAGGGATTTCTACATCTTCGCCAAGGAGCTCGACGGAAAGGATATTAACATCCTCTTCAACAGCTTG 8400

BoNT/C Receptor Binding Domain

5' CAGTACACCAACGTCGTTAAAGACTACTGGGGTAACGATTTGAGATACAACAAGGAGTACTACATGGTCA 8470
BoNT/C Receptor Binding Domain
Q Y T N V V K D Y W G N D L R Y N K E Y Y M V
1438 1439 1440 1441 1442 1443 1444 1445 1446 1447 1448 1449 1450 1451 1452 1453 1454 1455 1456 1457 1458 1459 1460

5' ACATCGACTACCTGAACAGGTACATGTACGCTAACTCCCGCCAAATCGTGTTCAACACCAGGAGAAACAA 8540
BoNT/C Receptor Binding Domain
N I D Y L N R Y M Y A N S R Q I V F N T R R N N
1461 1462 1463 1464 1465 1466 1467 1468 1469 1470 1471 1472 1473 1474 1475 1476 1477 1478 1479 1480 1481 1482 1483 1484

5' CAACGACTTCAACGAGGGTTACAAAATCATTATCAAGCGCATCCGTGGCAACACCAACGATACTAGGGTG 8610
BoNT/C Receptor Binding Domain
N D F N E G Y K I I I K R I R G N T N D T R V
1485 1486 1487 1488 1489 1490 1491 1492 1493 1494 1495 1496 1497 1498 1499 1500 1501 1502 1503 1504 1505 1506 1507

5' AGAGGTGGCGACATTCTGTACTTCGATATGACTATCAACAACAAAGCCTACAACTTGTTCATGAAAAACG 8680
BoNT/C Receptor Binding Domain
R G G D I L Y F D M T I N N K A Y N L F M K N
1508 1509 1510 1511 1512 1513 1514 1515 1516 1517 1518 1519 1520 1521 1522 1523 1524 1525 1526 1527 1528 1529 1530

5' AGACAATGTACGCCGACAAcCATAGCACGGAGGATATTTACGCAATCGGACTGAGGGAACAGACAAAGGA 8750
BoNT/C Receptor Binding Domain
E T M Y A D N H S T E D I Y A I G L R E Q T K D
1531 1532 1533 1534 1535 1536 1537 1538 1539 1540 1541 1542 1543 1544 1545 1546 1547 1548 1549 1550 1551 1552 1553 1554

5' CATCAACGATAACATTATCTTCCAGATCCAACCTATGAACAACACGTACTACTACGCTTCGCAAATCTTC 8820
BoNT/C Receptor Binding Domain
I N D N I I F Q I Q P M N N T Y Y Y A S Q I F
1555 1556 1557 1558 1559 1560 1561 1562 1563 1564 1565 1566 1567 1568 1569 1570 1571 1572 1573 1574 1575 1576 1577

5' AAGTCCAACTTCAACGGAGAAAACATTTCGGGTATCTGTTCCATTGGCACATACCGCTTCCGTCTGGGTG 8890
BoNT/C Receptor Binding Domain
K S N F N G E N I S G I C S I G T Y R F R L G
1578 1579 1580 1581 1582 1583 1584 1585 1586 1587 1588 1589 1590 1591 1592 1593 1594 1595 1596 1597 1598 1599 1600

FIG. 50N

SalI
5' GTGACTGGTATCGTCACAACTACCTCGTTCCCACCGTGAAGCAGGGTAACTACGCTTCTTTGCTGGAGTC 8960
BoNT/C Receptor Binding Domain
G D W Y R H N Y L V P T V K Q G N Y A S L L E S
1601 1602 1603 1604 1605 1606 1607 1608 1609 1610 1611 1612 1613 1614 1615 1616 1617 1618 1619 1620 1621 1622 1623 1624

5' GACTTCCACGCACTGGGGATTCGTTCCTGTGTCAGAGGGCGCTGGCTACCCTTACGATGTTCCCGACTAC 9030
BoNT/C Receptor Binding Domain | linker | HA tag
T S T H W G F V P V S E G A G Y P Y D V P D Y
1625 1626 1627 1628 1629 1630 1631 1632 1633 1634 1635 1636 1637 1638 1639 1640 1641 1642 1643 1644 1645 1646 1647

5' GCTGGTTGGGAACTCCAGCAAGGTGCAGGATGGTCCCACCCTCAATTCGAGAAGGGTGCCGGATGGAGTC 9100
H... | li...r | SpllB site | linker | Strep tag II | linker | Strep tag II
A G W E L Q Q G A G W S H P Q F E K G A G W S
1648 1649 1650 1651 1652 1653 1654 1655 1656 1657 1658 1659 1660 1661 1662 1663 1664 1665 1666 1667 1668 1669 1670

NsiI
5' ACCCACAGTTCGAGAAAGGCGCTGGATGGAGTCACCCACAGTTCGAGAAATAATTAGTTGATGCATAGTT 9170
Strep tag II | linker | Strep tag II
H P Q F E K G A G W S H P Q F E K
1671 1672 1673 1674 1675 1676 1677 1678 1679 1680 1681 1682 1683 1684 1685 1686 1687

XhoI NsiI XhoI
5' AATTAGATAGCTCGAGGCATGCGGTACCAAGATTGGATCTAGATGCATAGTTAATTAGATAGCTCGAGGC 9240

5' ATGCGGTACCAAGCTTGTCGAGAAGTACTAGAGGATCATAATCAGCCATACCACATTTGTAGAGGTTTTA 9310

HpaI
5' CTTGCTTTAAAAAACCTCCCACACCTCCCCCTGAACCTGAAACATAAAATGAATGCAATTGTTGTTGTTA 9380

5' ACTTGTTTATTGCAGCTTATAATGGTTACAAATAAAGCAATAGCATCACAAATTTCACAAATAAAGCATT 9450

5' TTTTTCACTGCATTCTAGTTGTGGTTTGTCCAAACTCATCAATGTATCTTATCATGTCTGGATCTGATCA 9520

AvrII
5' CTGCTTGAGCCTAGGAGATCCGAACCAGATAAGTGAAATCTAGTTCCAAACTATTTTGTCATTTTTAATT 9590

FIG. 50O

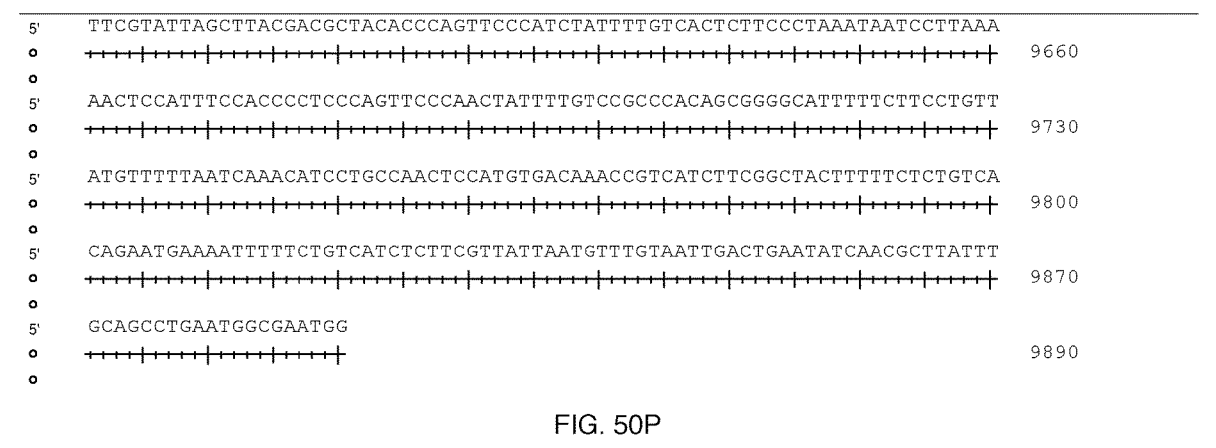

5' TTCGTATTAGCTTACGACGCTACACCCAGTTCCCATCTATTTTGTCACTCTTCCCTAAATAATCCTTAAA 9660

5' AACTCCATTTCCACCCCTCCCAGTTCCCAACTATTTTGTCCGCCCACAGCGGGGCATTTTTCTTCCTGTT 9730

5' ATGTTTTTAATCAAACATCCTGCCAACTCCATGTGACAAACCGTCATCTTCGGCTACTTTTTCTCTGTCA 9800

5' CAGAATGAAAATTTTTCTGTCATCTCTTCGTTATTAATGTTTGTAATTGACTGAATATCAACGCTTATTT 9870

5' GCAGCCTGAATGGCGAATGG 9890

FIG. 50P

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 51A

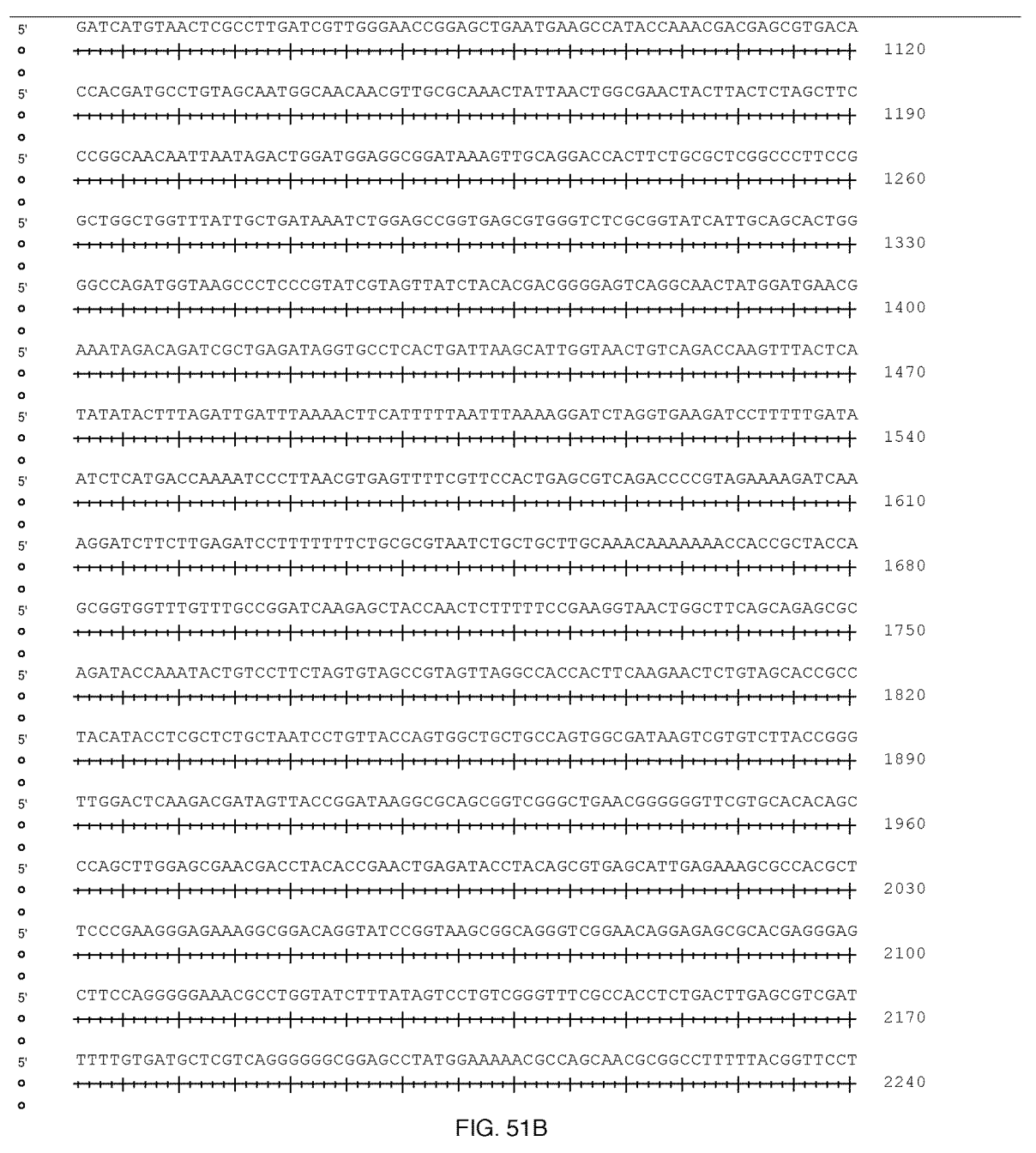

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 51B

```
5' GGCCTTTTGCTGGCCTTTTGCTCACATGTTCTTTCCTGCGTTATCCCCTGATTCTGTGGATAACCGTATT 2310
5' ACCGCCTTTGAGTGAGCTGATACCGCTCGCCGCAGCCGAACGACCGAGCGCAGCGAGTCAGTGAGCGAGG 2380
   SapI
5' AAGCGGAAGAGCGCCTGATGCGGTATTTTCTCCTTACGCATCTGTGCGGTATTTCACACCGCAGACCAGC 2450
5' CGCGTAACCTGGCAAAATCGGTTACGGTTGAGTAATAAATGGATGCCCTGCGTAAGCGGGTGTGGGCGGA 2520
5' CAATAAAGTCTTAAACTGAACAAAATAGATCTAAACTATGACAATAAAGTCTTAAACTAGACAGAATAGT 2590
5' TGTAAACTGAAATCAGTCCAGTTATGCTGTGAAAAAGCATACTGGACTTTTGTTATGGCTAAAGCAAACT 2660
5' CTTCATTTTCTGAAGTGCAAATTGCCCGTCGTATTAAAGAGGGGCGTGGCCAAGGGCATGGTAAAGACTA 2730
                                                     SacII
5' TATTCGCGGCGTTGTGACAATTTACCGAACAACTCCGCGGCCGGGAAGCCGATCTCGGCTTGAACGAATT 2800
5' GTTAGGTGGCGGTACTTGGGTCGATATCAAAGTGCATCACTTCTTCCCGTATGCCCAACTTTGTATAGAG 2870
5' AGCCACTGCGGGATCGTCACCGTAATCTGCTTGCACGTAGATCACATAAGCACCAAGCGCGTTGGCCTCA 2940
5' TGCTTGAGGAGATTGATGAGCGCGGTGGCAATGCCCTGCCTCCGGTGCTCGCCGGAGACTGCGAGATCAT 3010
                                                                  AjuI'
5' AGATATAGATCTCACTACGCGGCTGCTCAAACCTGGGCAGAACGTAAGCCGCGAGAGCGCCAACAACCGC 3080
                AjuI
5' TTCTTGGTCGAAGGCAGCAAGCGCGATGAATGTCTTACTACGGAGCAAGTTCCCGAGGTAATCGGAGTCC 3150
5' GGCTGATGTTGGGAGTAGGTGGCTACGTCTCCGAACTCACGACCGAAAAGATCAAGAGCAGCCCGCATGG 3220
5' ATTTGACTTGGTCAGGGCCGAGCCTACATGTGCGAATGATGCCCATACTTGAGCCACCTAACTTTGTTTT 3290
```

FIG. 51C

```
5'  AGGGCGACTGCCCTGCTGCGTAACATCGTTGCTGCTGCGTAACATCGTTGCTGCTCCATAACATCAAACA
                                                                              3360

5'  TCGACCCACGGCGTAACGCGCTTGCTGCTTGGATGCCCGAGGCATAGACTGTACAAAAAAACAGTCATAA
                                                                              3430

5'  CAAGCCATGAAAACCGCCACTGCGCCGTTACCACCGCTGCGTTCGGTCAAGGTTCTGGACCAGTTGCGTG
                                                                              3500

5'  AGCGCATACGCTACTTGCATTACAGTTTACGAACCGAACAGGCTTATGTCAACTGGGTTCGTGCCTTCAT
                                                                              3570

5'  CCGTTTCCACGGTGTGCGTCACCCGGCAACCTTGGGCAGCAGCGAAGTCGAGGCATTTCTGTCCTGGCTG
                                                                              3640

5'  GCGAACGAGCGCAAGGTTTCGGTCTCCACGCATCGTCAGGCATTGGCGGCCTTGCTGTTCTTCTACGGCA
                                                                              3710

5'  AGGTGCTGTGCACGGATCTGCCCTGGCTTCAGGAGATCGGAAGACCTCGGCCGTCGCGGCGCTTGCCGGT
                                                                              3780

5'  GGTGCTGACCCCGGATGAAGTGGTTCGCATCCTCGGTTTTCTGGAAGGCGAGCATCGTTTGTTCGCCCAG
                                                                              3850

                                            SnaBI
                                            │ BstZ17I
                                            │ │
5'  GACTCTAGCTATAGTTCTAGTGGTTGGCTACGTATACTCCGGAATATTAATAGATCATGGAGATAATTAA
                                                                              3920

5'  AATGATAACCATCTCGCAAATAAATAAGTATTTTACTGTTTTCGTAACAGTTTTGTAATAAAAAAACCTA
                                                                              3990

                                                        RsrII
                                                        │
5'  TAAATATTCCGGATTATTCATACCGTCCCACCATCGGGCGCGGATCTCGGTCCGTTCGAACCAGAACTCT
                                                                              4060
                                            [mut....mHI]

5'  GGAAGCTTAACTCCTAAAAAACCGCCACCATGAAATTCTTAGTCAACGTTGCCCTTGTTTTTATGGTCGT
                                                                              4130
    [Lob. TMO cDNA Lead Seq]  [Signal Peptide]
                              M  K  F  L  V  N  V  A  L  V  F  M  V  V
                              1  2  3  4  5  6  7  8  9 10 11 12 13 14
```

FIG. 51D

CspCI
5' GGGTTGGTACAGGCAGGCTCCCGGCAAGGAGAGGGAACTCGTCGCCAGAGTTCAAGACGGAGGTAGTACA 5040
sd Ab JLJG3 VHH - anti-BoNT/B LC
G W Y R Q A P G K E R E L V A R V Q D G G S T
295 296 297 298 299 300 301 302 303 304 305 306 307 308 309 310 311 312 313 314 315 316 317

PshAI
5' GCATACAAGGATTCGGTCAAAGGTCGCTTCACCATTTCTCGCGACTTCAGTCGTTCGACTATGTACTTGC 5110
sd Ab JLJG3 VHH - anti-BoNT/B LC
A Y K D S V K G R F T I S R D F S R S T M Y L
318 319 320 321 322 323 324 325 326 327 328 329 330 331 332 333 334 335 336 337 338 339 340

Bsu36I
5' AGATGAACTCACTGAAGCCTGAGGATACAGCCATCTACTACTGTGCAGCGAAATCTACCATTTCAACTCC 5180
sd Ab JLJG3 VHH - anti-BoNT/B LC
Q M N S L K P E D T A I Y Y C A A K S T I S T P
341 342 343 344 345 346 347 348 349 350 351 352 353 354 355 356 357 358 359 360 361 362 363 364

TstI' TstI
5' ACTGTCTTGGGGCCAGGGAACACAAGTGACGGTCTCCAGCGAACCGAAGACGCCTAAACCCCAATCTTCA 5250
sd Ab JLJG3 VHH - anti-BoNT/B LC | VHH ...cer
L S W G Q G T Q V T V S S E P K T P K P Q S S
365 366 367 368 369 370 371 372 373 374 375 376 377 378 379 380 381 382 383 384 385 386 387

NotI Bpu10I PvuII
5' GGCGGAGGTGCGGCCGCTGGCTCAGGAGGTGGCAGTCAGGTGCAGCTGGTGGAATCCGGTGGTGGACTGG 5320
VHH spacer | sd Ab JNE-B10 VHH - anti-BoNT/B LC
G G G A A A G S G G G S Q V Q L V E S G G G L
388 389 390 391 392 393 394 395 396 397 398 399 400 401 402 403 404 405 406 407 408 409 410

5' TCCAGCCTGGTGGTTCCCTGCGTCTGTCCTGCGCTGCTTCCGGTTTCCCCTTCCACGCTTACTACATGTC 5390
sd Ab JNE-B10 VHH - anti-BoNT/B LC
V Q P G G S L R L S C A A S G F P F H A Y Y M S
411 412 413 414 415 416 417 418 419 420 421 422 423 424 425 426 427 428 429 430 431 432 433 434

FIG. 51G

5' CAACATTTGGGTCATTCCGGATAGGTTCAGCAGAAACTCTAACCCTAACTTGAACAAACCTCCCAGAGTG 5880

BoNT/C1 ad0 LC

N I W V I P D R F S R N S N P N L N K P P R V 575 576 577 578 579 580 581 582 583 584 585 586 587 588 589 590 591 592 593 594 595 596 597

5' ACCTCACCTAAGAGTGGATACTACGACCCCAACTACCTCTCGACTGACTCCGATAAAGACCCCTTCCTGA 5950

BoNT/C1 ad0 LC

T S P K S G Y Y D P N Y L S T D S D K D P F L 598 599 600 601 602 603 604 605 606 607 608 609 610 611 612 613 614 615 616 617 618 619 620

5' AGGAGATCATTAAACTCTTCAAGCGCATCAACTCTCGTGAAATTGGCGAGGAATTGATCTACCGCCTGAG 6020

BoNT/C1 ad0 LC

K E I I K L F K R I N S R E I G E E L I Y R L S 621 622 623 624 625 626 627 628 629 630 631 632 633 634 635 636 637 638 639 640 641 642 643 644

XmaI
SmaI

5' TACAGACATCCCATTCCCGGGTAACAACAACACCCCAATCAACACTTTCGATTTCGATGTCGATTTCAAC 6090

BoNT/C1 ad0 LC

T D I P F P G N N N T P I N T F D F D V D F N 645 646 647 648 649 650 651 652 653 654 655 656 657 658 659 660 661 662 663 664 665 666 667

5' TCAGTGGATGTCAAAACCAGGCAGGGAAACAACTGGGTGAAGACTGGTAGCATCAACCCATCTGTCATCA 6160

BoNT/C1 ad0 LC

S V D V K T R Q G N N W V K T G S I N P S V I 668 669 670 671 672 673 674 675 676 677 678 679 680 681 682 683 684 685 686 687 688 689 690

5' TTACTGGCCCGAGAGAGAACATCATTGACCCTGAAACCTCCACTTTCAaGCTGACaAACAACACGTTCGC 6230

BoNT/C1 ad0 LC

I T G P R E N I I D P E T S T F K L T N N T F A 691 692 693 694 695 696 697 698 699 700 701 702 703 704 705 706 707 708 709 710 711 712 713 714

Bpu10I

5' TGCTCAGGAAGGCTTCGGAGCGTTGAGCATCATTTCTATCTCACCTCGCTTCATGCTGACATACTCTAAC 6300

BoNT/C1 ad0 LC

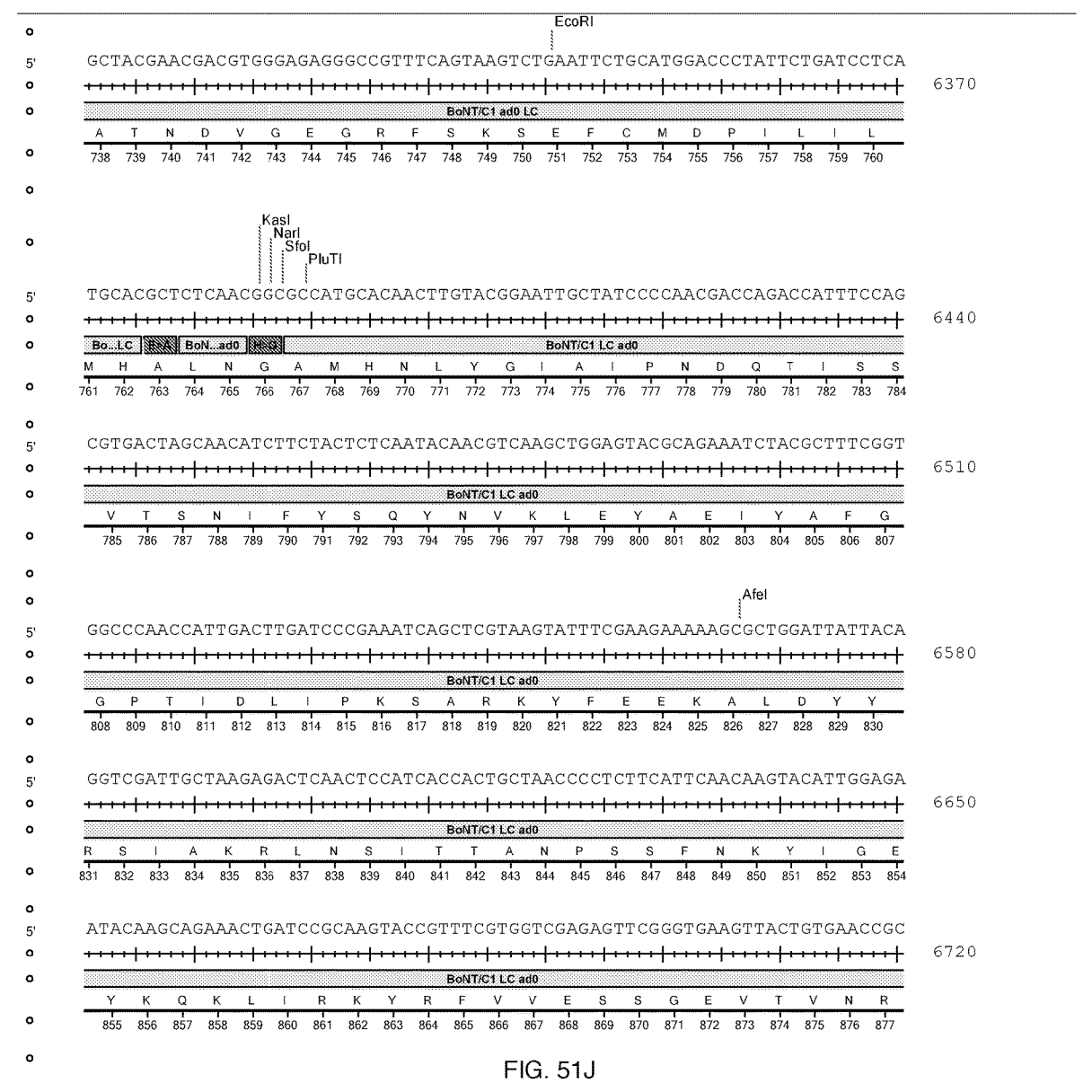

```
                                            EcoRI
5'  GCTACGAACGACGTGGGAGAGGGCCGTTTCAGTAAGTCTGAATTCTGCATGGACCCTATTCTGATCCTCA
    +---+---+---+---+---+---+---+---+---+---+---+---+---+---+---+---+---+---+---+---+---+   6370
                              BoNT/C1 ad0 LC
     A   T   N   D   V   G   E   G   R   F   S   K   S   E   F   C   M   D   P   I   L   I   L
    738 739 740 741 742 743 744 745 746 747 748 749 750 751 752 753 754 755 756 757 758 759 760

                       KasI
                       NarI
                       SfoI
                        PluTI
5'  TGCACGCTCTCAACGGCGCCATGCACAACTTGTACGGAATTGCTATCCCCAACGACCAGACCATTTCCAG
    +---+---+---+---+---+---+---+---+---+---+---+---+---+---+---+---+---+---+---+---+---+   6440
     Bo..LC    BoN...ad0              BoNT/C1 LC ad0
     M   H   A   L   N   G   A   M   H   N   L   Y   G   I   A   I   P   N   D   Q   T   I   S   S
    761 762 763 764 765 766 767 768 769 770 771 772 773 774 775 776 777 778 779 780 781 782 783 784

5'  CGTGACTAGCAACATCTTCTACTCTCAATACAACGTCAAGCTGGAGTACGCAGAAATCTACGCTTTCGGT
    +---+---+---+---+---+---+---+---+---+---+---+---+---+---+---+---+---+---+---+---+---+   6510
                              BoNT/C1 LC ad0
     V   T   S   N   I   F   Y   S   Q   Y   N   V   K   L   E   Y   A   E   I   Y   A   F   G
    785 786 787 788 789 790 791 792 793 794 795 796 797 798 799 800 801 802 803 804 805 806 807

                                                                    AfeI
5'  GGCCCAACCATTGACTTGATCCCGAAATCAGCTCGTAAGTATTTCGAAGAAAAAGCGCTGGATTATTACA
    +---+---+---+---+---+---+---+---+---+---+---+---+---+---+---+---+---+---+---+---+---+   6580
                              BoNT/C1 LC ad0
     G   P   T   I   D   L   I   P   K   S   A   R   K   Y   F   E   E   K   A   L   D   Y   Y
    808 809 810 811 812 813 814 815 816 817 818 819 820 821 822 823 824 825 826 827 828 829 830

5'  GGTCGATTGCTAAGAGACTCAACTCCATCACCACTGCTAACCCCTCTTCATTCAACAAGTACATTGGAGA
    +---+---+---+---+---+---+---+---+---+---+---+---+---+---+---+---+---+---+---+---+---+   6650
                              BoNT/C1 LC ad0
     R   S   I   A   K   R   L   N   S   I   T   T   A   N   P   S   S   F   N   K   Y   I   G   E
    831 832 833 834 835 836 837 838 839 840 841 842 843 844 845 846 847 848 849 850 851 852 853 854

5'  ATACAAGCAGAAACTGATCCGCAAGTACCGTTTCGTGGTCGAGAGTTCGGGTGAAGTTACTGTGAACCGC
    +---+---+---+---+---+---+---+---+---+---+---+---+---+---+---+---+---+---+---+---+---+   6720
                              BoNT/C1 LC ad0
     Y   K   Q   K   L   I   R   K   Y   R   F   V   V   E   S   S   G   E   V   T   V   N   R
    855 856 857 858 859 860 861 862 863 864 865 866 867 868 869 870 871 872 873 874 875 876 877
```

FIG. 51J

```
5'  AACAAGTTCGTCGAGCTGTACAACGAATTGACACAAATCTTCACGGAGTTCAACTACGCCAAAATTTACA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6790
                              BoNT/C1 LC ad0
     N  K  F  V  E  L  Y  N  E  L  T  Q  I  F  T  E  F  N  Y  A  K  I  Y
    878 879 880 881 882 883 884 885 886 887 888 889 890 891 892 893 894 895 896 897 898 899 900

                                                           BstEII
5'  ACGTGCAAAACCGTAAGATCGCGCTCTCTAACGTCTACACCCCGGTTACCGCTAACATCTTGGACGATAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6860
         BoNT/C1 LC ad0                        BoNT/C1 LC ad0
     N  V  Q  N  R  K  I  A  L  S  N  V  Y  T  P  V  T  A  N  I  L  D  D  N
    901 902 903 904 905 906 907 908 909 910 911 912 913 914 915 916 917 918 919 920 921 922 923 924

5'  CGTCTACGACATTCAGAACGGTTTCAACATCCCAAAGTCGAACCTCAACGTTTTGTTCATGGGTCAAAAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  6930
                              BoNT/C1 LC ad0
     V  Y  D  I  Q  N  G  F  N  I  P  K  S  N  L  N  V  L  F  M  G  Q  N
    925 926 927 928 929 930 931 932 933 934 935 936 937 938 939 940 941 942 943 944 945 946 947

5'  TTGTCCCGCAACCCCGCCCTGCGTAAGGTGAACCCAGAGAACATGTTGTACCTGTTCACCAAATTCTGCC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7000
                              BoNT/C1 LC ad0
     L  S  R  N  P  A  L  R  K  V  N  P  E  N  M  L  Y  L  F  T  K  F  C
    948 949 950 951 952 953 954 955 956 957 958 959 960 961 962 963 964 965 966 967 968 969 970

5'  ACAAGGCCATCGACGGTCAGTCTCTAGACCAAGGAGGATGGGAACTCCAGCAAGGTGGCCAGGGTGGAGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7070
         BoNT/C1 LC ad0       LC/HC spacer      Spl B site        LC/HC spacer
     H  K  A  I  D  G  Q  S  L  D  Q  G  G  W  E  L  Q  Q  G  G  Q  G  G  G
    971 972 973 974 975 976 977 978 979 980 981 982 983 984 985 986 987 988 989 990 991 992 993 994

5'  TGCTGGCACCCTGGACTGTCGCGAACTGCTCGTTAAGAACACTGATCTCCCATTCATTGGCGACATCTCT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7140
    LC/HC acer              BoNT/C Translocation Domain
     A  G  T  L  D  C  R  E  L  L  V  K  N  T  D  L  P  F  I  G  D  I  S
    995 996 997 998 999 1000 1001 1002 1003 1004 1005 1006 1007 1008 1009 1010 1011 1012 1013 1014 1015 1016 1017

5'  GATGTGAAAACAGACATTTTCCTGCGTAAGGATATCAACGAGGAAACGGAGGTCATCTACTACCCTGACA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7210
                          BoNT/C Translocation Domain
     D  V  K  T  D  I  F  L  R  K  D  I  N  E  E  T  E  V  I  Y  Y  P  D
    1018 1019 1020 1021 1022 1023 1024 1025 1026 1027 1028 1029 1030 1031 1032 1033 1034 1035 1036 1037 1038 1039 1040
```

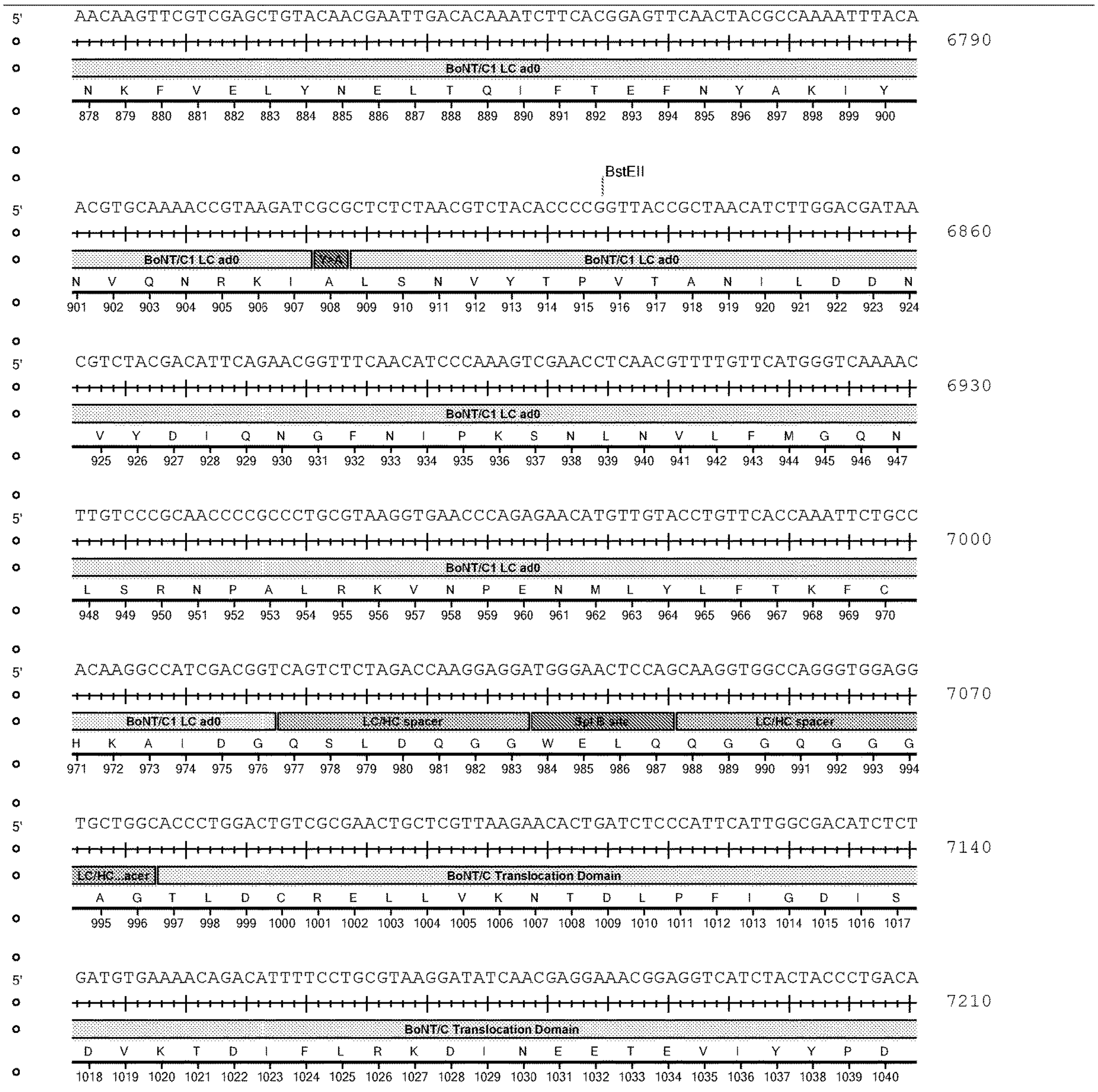

FIG. 51K

5' ACGTCTCGGTTGATCAGGTTATCTTGTCAAAGAACACCAGTGAACATGGCCAACTGGACTTGCTGTACCC 7280
BoNT/C Translocation Domain
N V S V D Q V I L S K N T S E H G Q L D L L Y P
1041 1042 1043 1044 1045 1046 1047 1048 1049 1050 1051 1052 1053 1054 1055 1056 1057 1058 1059 1060 1061 1062 1063 1064

SexAI
5' CTCAATTGATTCCGAGAGCGAAATCCTGCCAGGAGAGAACCAGGTTTTCTACGACAACAGGACACAAAAC 7350
BoNT/C Translocation Domain
S I D S E S E I L P G E N Q V F Y D N R T Q N
1065 1066 1067 1068 1069 1070 1071 1072 1073 1074 1075 1076 1077 1078 1079 1080 1081 1082 1083 1084 1085 1086 1087

5' GTGGATTACCTCAACAGCTACTACTACCTGGAGTCGCAGAAGCTCTCCGACAACGTCGAAGATTTCACAT 7420
BoNT/C Translocation Domain
V D Y L N S Y Y Y L E S Q K L S D N V E D F T
1088 1089 1090 1091 1092 1093 1094 1095 1096 1097 1098 1099 1100 1101 1102 1103 1104 1105 1106 1107 1108 1109 1110

5' TTACGAGATCAATCGAGGAGGCTTTGGACAACAGTGCCAAAGTCTACACCTACTTCCCTACTCTGGCAAA 7490
BoNT/C Translocation Domain
F T R S I E E A L D N S A K V Y T Y F P T L A N
1111 1112 1113 1114 1115 1116 1117 1118 1119 1120 1121 1122 1123 1124 1125 1126 1127 1128 1129 1130 1131 1132 1133 1134

5' CAAGGTGAACGCGGGTGTCCAAGGCGGACTCTTCTTGATGTGGGCTAACGACGTTGTGGAAGATTTCACA 7560
BoNT/C Translocation Domain
K V N A G V Q G G L F L M W A N D V V E D F T
1135 1136 1137 1138 1139 1140 1141 1142 1143 1144 1145 1146 1147 1148 1149 1150 1151 1152 1153 1154 1155 1156 1157

5' ACGAACATCTTGCGCAAAGACACCCTGGATAAGATCAGCGATGTCTCTGCCATCATTCCATACATTGGCC 7630
BoNT/C Translocation Domain
T N I L R K D T L D K I S D V S A I I P Y I G
1158 1159 1160 1161 1162 1163 1164 1165 1166 1167 1168 1169 1170 1171 1172 1173 1174 1175 1176 1177 1178 1179 1180

5' CGGCACTGAACATCTCTAACTCAGTTCGCCGTGGCAACTTCACTGAGGCATTCGCGGTCACAGGAGTTAC 7700
BoNT/C Translocation Domain
P A L N I S N S V R R G N F T E A F A V T G V T
1181 1182 1183 1184 1185 1186 1187 1188 1189 1190 1191 1192 1193 1194 1195 1196 1197 1198 1199 1200 1201 1202 1203 1204

FIG. 51L

PfoI
5' GATCCTCTTGGAGGCTTTCCCGGAGTTCACAATCCCCGCACTGGGCGCGTTCGTTATCTACTCCAAAGTG 7770
BoNT/C Translocation Domain
I L L E A F P E F T I P A L G A F V I Y S K V
1205 1206 1207 1208 1209 1210 1211 1212 1213 1214 1215 1216 1217 1218 1219 1220 1221 1222 1223 1224 1225 1226 1227

5' CAGGAGCGCAACGAAATCATTAAGACTATCGACAACTGCCTGGAGCAAAGGATCAAAAGATGGAAGGATT 7840
BoNT/C Translocation Domain
Q E R N E I I K T I D N C L E Q R I K R W K D
1228 1229 1230 1231 1232 1233 1234 1235 1236 1237 1238 1239 1240 1241 1242 1243 1244 1245 1246 1247 1248 1249 1250

BsiWI
5' CGTACGAATGGATGATGGGTACCTGGCTCTCCCGTATCATTACGCAGTTCAACAACATCAGCTACCAAAT 7910
BoNT/C Translocation Domain
S Y E W M M G T W L S R I I T Q F N N I S Y Q M
1251 1252 1253 1254 1255 1256 1257 1258 1259 1260 1261 1262 1263 1264 1265 1266 1267 1268 1269 1270 1271 1272 1273 1274

XcmI
5' GTACGACTCTCTCAACTACCAGGCTGGTGCCATCAAGGCCAAAATTGACTTGGAGTACAAGAAATACAGT 7980
BoNT/C Translocation Domain
Y D S L N Y Q A G A I K A K I D L E Y K K Y S
1275 1276 1277 1278 1279 1280 1281 1282 1283 1284 1285 1286 1287 1288 1289 1290 1291 1292 1293 1294 1295 1296 1297

5' GGCTCGGATAAAGAGAACATCAAGAGTCAAGTCGAAAaCCTGAAAAACTCACTCGACGTTAAGATCAGTG 8050
BoNT/C Translocation Domain
G S D K E N I K S Q V E N L K N S L D V K I S
1298 1299 1300 1301 1302 1303 1304 1305 1306 1307 1308 1309 1310 1311 1312 1313 1314 1315 1316 1317 1318 1319 1320

5' AGGCAATGAACAACATCAACAAGTTCATTCGCGAATGTTCCGTTACCTACCTCTTCAAAAACATGTTGCC 8120
BoNT/C Translocation Domain
E A M N N I N K F I R E C S V T Y L F K N M L P
1321 1322 1323 1324 1325 1326 1327 1328 1329 1330 1331 1332 1333 1334 1335 1336 1337 1338 1339 1340 1341 1342 1343 1344

5' AAAGGTCATCGACGAGCTGAACGAATTTGATCGTAACACTAAGGCGAAACTGATTAACCTCATCGACTCA 8190
BoNT/C Translocation Domain
K V I D E L N E F D R N T K A K L I N L I D S
1345 1346 1347 1348 1349 1350 1351 1352 1353 1354 1355 1356 1357 1358 1359 1360 1361 1362 1363 1364 1365 1366 1367

FIG. 51M

5' CACAACATCATTTTGGTGGGCGAAGTCGATAAGCTGAAAGCCAAGGtGAACAACAGTTTCCAGAACACAA 8260

BoNT/C Translocation Domain

H N I I L V G E V D K L K A K V N N S F Q N T 1368 1369 1370 1371 1372 1373 1374 1375 1376 1377 1378 1379 1380 1381 1382 1383 1384 1385 1386 1387 1388 1389 1390

5' TCCCTTTCAAcATTTTCTCATACACGAACAACAGTCTGCTCAAGGACATCATTAACGAGTACTTCAACAA 8330

BoNT/C Translocation Domain | BoN...in

I P F N I F S Y T N N S L L K D I I N E Y F N N 1391 1392 1393 1394 1395 1396 1397 1398 1399 1400 1401 1402 1403 1404 1405 1406 1407 1408 1409 1410 1411 1412 1413 1414

PstI SpeI

5' CATTAACGATAGCAAAATCCTGTCACTGCAGAACCGTAAGAACACACTGGTCGATACTAGTGGATACAAC 8400

BoNT/C Receptor Binding Domain

I N D S K I L S L Q N R K N T L V D T S G Y N 1415 1416 1417 1418 1419 1420 1421 1422 1423 1424 1425 1426 1427 1428 1429 1430 1431 1432 1433 1434 1435 1436 1437

PvuII

5' GCCGAAGTCTCTGAGGAAGGTGACGTGCAGCTGAACCCTATCTTCCCCTTCGACTTCAAATTGGGCTCCA 8470

BoNT/C Receptor Binding Domain

A E V S E E G D V Q L N P I F P F D F K L G S 1438 1439 1440 1441 1442 1443 1444 1445 1446 1447 1448 1449 1450 1451 1452 1453 1454 1455 1456 1457 1458 1459 1460

5' GCGGAGAGGATAGGGGCAAGGTCATCGTCACCCAGAACGAGAACATCGTCTACAACTCAATGTACGAATC 8540

BoNT/C Receptor Binding Domain

S G E D R G K V I V T Q N E N I V Y N S M Y E S 1461 1462 1463 1464 1465 1466 1467 1468 1469 1470 1471 1472 1473 1474 1475 1476 1477 1478 1479 1480 1481 1482 1483 1484

BspMI

5' CTTCAGCATCTCTTTCTGGATCAGGATTAACAAGTGGGTGAGCAACCTGCCCGGTTACACAATCATTGAC 8610

BoNT/C Receptor Binding Domain

F S I S F W I R I N K W V S N L P G Y T I I D 1485 1486 1487 1488 1489 1490 1491 1492 1493 1494 1495 1496 1497 1498 1499 1500 1501 1502 1503 1504 1505 1506 1507

5' TCTGTCAAGAACAACTCAGGTTGGAGTATCGGCATCATTTCTAACTTCTTGGTCTTCACCCTGAAGCAGA 8680

BoNT/C Receptor Binding Domain

```
5'  ACGAGGACTCGGAACAATCCATTAACTTCTCATACGATATCAGTAACAACGCTCCAGGTTACAACAAGTG
                                                                                              8750
         BoNT/C Receptor Binding Domain
     N   E   D   S   E   Q   S   I   N   F   S   Y   D   I   S   N   N   A   P   G   Y   N   K   W
    1531 1532 1533 1534 1535 1536 1537 1538 1539 1540 1541 1542 1543 1544 1545 1546 1547 1548 1549 1550 1551 1552 1553 1554

5'  GTTCTTCGTTACCGTGACTAACAACATGATGGGTAACATGAAAATTTACATCAACGGCAAGCTCATTGAC
                                                                                              8820
         BoNT/C Receptor Binding Domain
     F   F   V   T   V   T   N   N   M   M   G   N   M   K   I   Y   I   N   G   K   L   I   D
    1555 1556 1557 1558 1559 1560 1561 1562 1563 1564 1565 1566 1567 1568 1569 1570 1571 1572 1573 1574 1575 1576 1577

5'  ACCATCAAAGTGAAGGAGTTGACTGGTATTAACTTCTCCAAAACAATCACGTTTGAAATTAaCaAGATCC
                                                                                              8890
         BoNT/C Receptor Binding Domain
     T   I   K   V   K   E   L   T   G   I   N   F   S   K   T   I   T   F   E   I   N   K   I
    1578 1579 1580 1581 1582 1583 1584 1585 1586 1587 1588 1589 1590 1591 1592 1593 1594 1595 1596 1597 1598 1599 1600

5'  CTGACACCGGCCTGATCACTTCAGACAGTGATAACATCAACATGTGGATTAGGGATTTCTACATCTTCGC
                                                                                              8960
         BoNT/C Receptor Binding Domain
     P   D   T   G   L   I   T   S   D   S   D   N   I   N   M   W   I   R   D   F   Y   I   F   A
    1601 1602 1603 1604 1605 1606 1607 1608 1609 1610 1611 1612 1613 1614 1615 1616 1617 1618 1619 1620 1621 1622 1623 1624

         EcolCRI
         SacI
5'  CAAGGAGCTCGACGGAAAGGATATTAACATCCTCTTCAACAGCTTGCAGTACACCAACGTCGTTAAAGAC
                                                                                              9030
         BoNT/C Receptor Binding Domain
     K   E   L   D   G   K   D   I   N   I   L   F   N   S   L   Q   Y   T   N   V   V   K   D
    1625 1626 1627 1628 1629 1630 1631 1632 1633 1634 1635 1636 1637 1638 1639 1640 1641 1642 1643 1644 1645 1646 1647

5'  TACTGGGGTAACGATTTGAGATACAACAAGGAGTACTACATGGTCAACATCGACTACCTGAACAGGTACA
                                                                                              9100
         BoNT/C Receptor Binding Domain
     Y   W   G   N   D   L   R   Y   N   K   E   Y   Y   M   V   N   I   D   Y   L   N   R   Y
    1648 1649 1650 1651 1652 1653 1654 1655 1656 1657 1658 1659 1660 1661 1662 1663 1664 1665 1666 1667 1668 1669 1670

5'  TGTACGCTAACTCCCGCCAAATCGTGTTCAACACCAGGAGAAACAACAACGACTTCAACGAGGGTTACAA
                                                                                              9170
         BoNT/C Receptor Binding Domain
     M   Y   A   N   S   R   Q   I   V   F   N   T   R   R   N   N   N   D   F   N   E   G   Y   K
    1671 1672 1673 1674 1675 1676 1677 1678 1679 1680 1681 1682 1683 1684 1685 1686 1687 1688 1689 1690 1691 1692 1693 1694
```

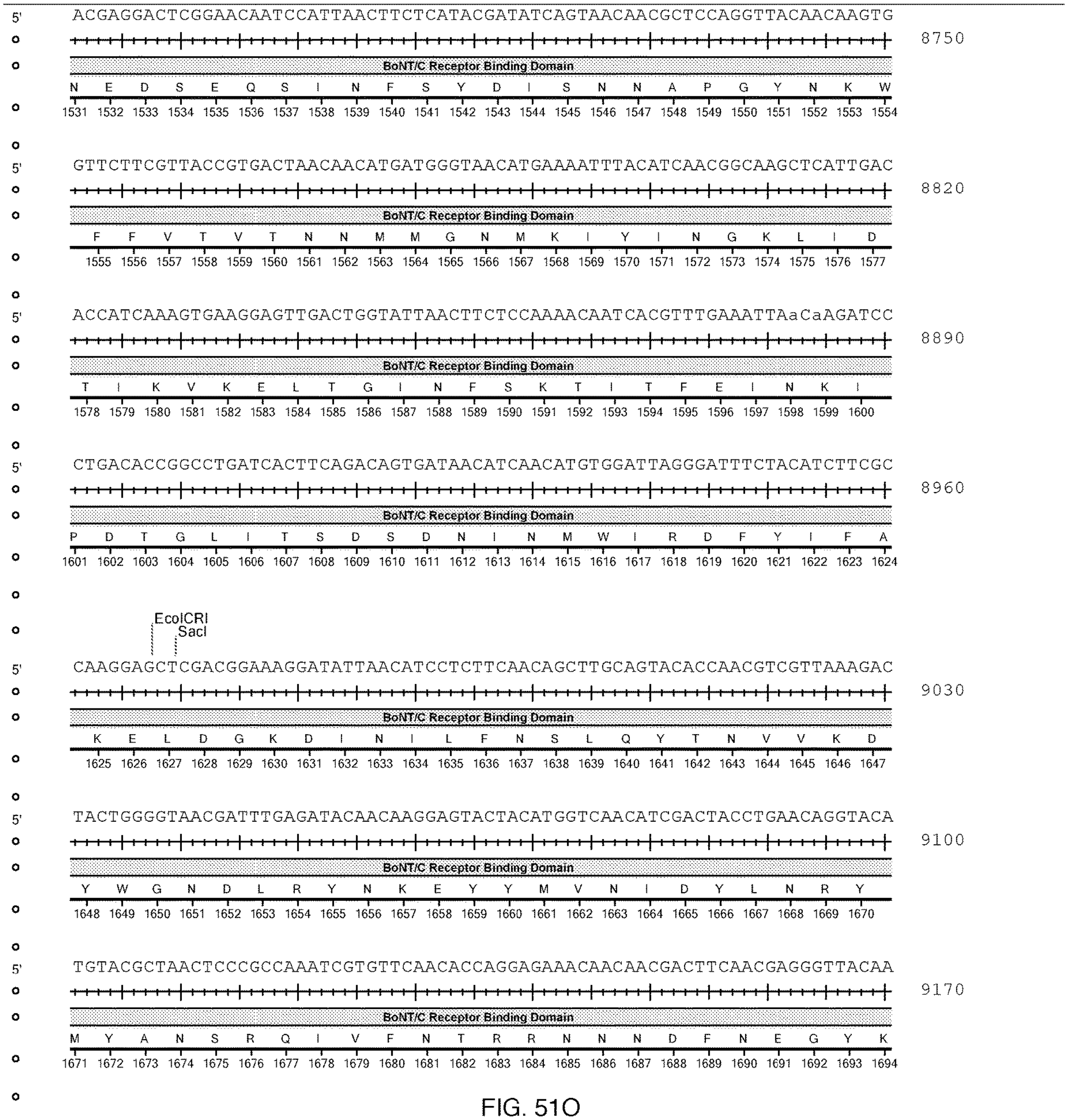

FIG. 51O

```
5'  AATCATTATCAAGCGCATCCGTGGCAACACCAACGATACTAGGGTGAGAGGTGGCGACATTCTGTACTTC
                                                                                          9240
                         BoNT/C Receptor Binding Domain
         I    I    I    K    R    I    R    G    N    T    N    D    T    R    V    R    G    G    D    I    L    Y    F
        1695 1696 1697 1698 1699 1700 1701 1702 1703 1704 1705 1706 1707 1708 1709 1710 1711 1712 1713 1714 1715 1716 1717

5'  GATATGACTATCAACAACAAAGCCTACAACTTGTTCATGAAAAACGAGACAATGTACGCCGACAAcCATA
                                                                                          9310
                         BoNT/C Receptor Binding Domain
         D    M    T    I    N    N    K    A    Y    N    L    F    M    K    N    E    T    M    Y    A    D    N    H
        1718 1719 1720 1721 1722 1723 1724 1725 1726 1727 1728 1729 1730 1731 1732 1733 1734 1735 1736 1737 1738 1739 1740

5'  GCACGGAGGATATTTACGCAATCGGACTGAGGGAACAGACAAAGGACATCAACGATAACATTATCTTCCA
                                                                                          9380
                         BoNT/C Receptor Binding Domain
         S    T    E    D    I    Y    A    I    G    L    R    E    Q    T    K    D    I    N    D    N    I    I    F    Q
        1741 1742 1743 1744 1745 1746 1747 1748 1749 1750 1751 1752 1753 1754 1755 1756 1757 1758 1759 1760 1761 1762 1763 1764

5'  GATCCAACCTATGAACAACACGTACTACTACGCTTCGCAAATCTTCAAGTCCAACTTCAACGGAGAAAAC
                                                                                          9450
                         BoNT/C Receptor Binding Domain
         I    Q    P    M    N    N    T    Y    Y    Y    A    S    Q    I    F    K    S    N    F    N    G    E    N
        1765 1766 1767 1768 1769 1770 1771 1772 1773 1774 1775 1776 1777 1778 1779 1780 1781 1782 1783 1784 1785 1786 1787

5'  ATTTCGGGTATCTGTTCCATTGGCACATACCGCTTCCGTCTGGGTGGTGACTGGTATCGTCACAACTACC
                                                                                          9520
                         BoNT/C Receptor Binding Domain
         I    S    G    I    C    S    I    G    T    Y    R    F    R    L    G    G    D    W    Y    R    H    N    Y
        1788 1789 1790 1791 1792 1793 1794 1795 1796 1797 1798 1799 1800 1801 1802 1803 1804 1805 1806 1807 1808 1809 1810

                                                                   Sall
5'  TCGTTCCCACCGTGAAGCAGGGTAACTACGCTTCTTTGCTGGAGTCGACTTCCACGCACTGGGGATTCGT
                                                                                          9590
                         BoNT/C Receptor Binding Domain
         L    V    P    T    V    K    Q    G    N    Y    A    S    L    L    E    S    T    S    T    H    W    G    F    V
        1811 1812 1813 1814 1815 1816 1817 1818 1819 1820 1821 1822 1823 1824 1825 1826 1827 1828 1829 1830 1831 1832 1833 1834

5'  TCCTGTGTCAGAGGGCGCTGGCTACCCTTACGATGTTCCCGACTACGCTGGTTGGGAACTCCAGCAAGGT
                                                                                          9660
     BoNT/C Rec...ng Domain | linker |           HA tag            | li...r |  EphB site  | linker
         P    V    S    E    G    A    G    Y    P    Y    D    V    P    D    Y    A    G    W    E    L    Q    Q    G
        1835 1836 1837 1838 1839 1840 1841 1842 1843 1844 1845 1846 1847 1848 1849 1850 1851 1852 1853 1854 1855 1856 1857
```

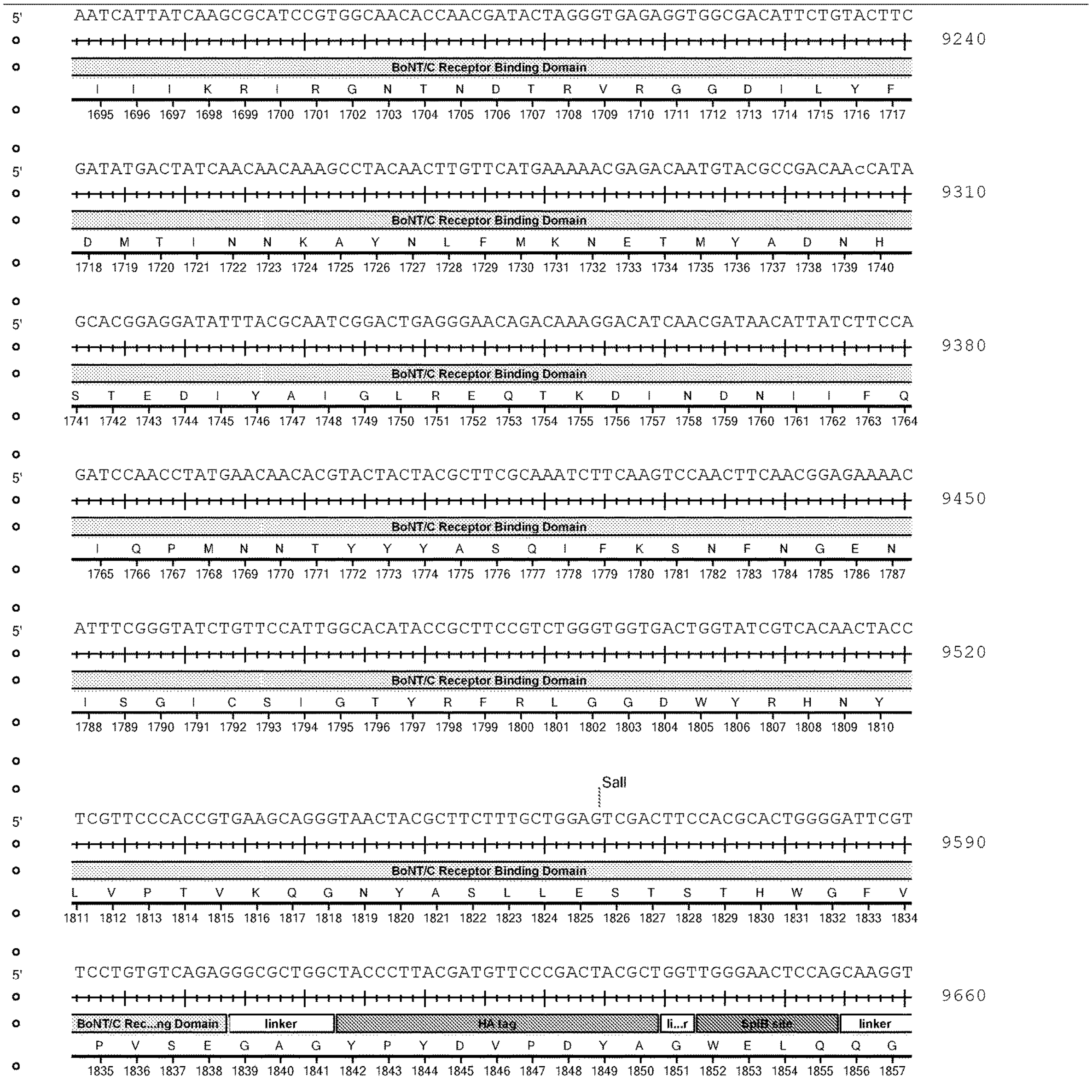

FIG. 51P

5' GCAGGATGGTCCCACCCTCAATTCGAGAAGGGTGCCGGATGGAGTCACCCACAGTTCGAGAAAGGCGCTG 9730 linker | Strep tag II | linker | Strep tag II | linker

A G W S H P Q F E K G A G W S H P Q F E K G A 1858 1859 1860 1861 1862 1863 1864 1865 1866 1867 1868 1869 1870 1871 1872 1873 1874 1875 1876 1877 1878 1879 1880

NsiI XhoI

5' GATGGAGTCACCCACAGTTCGAGAAATAATTAGTTGATGCATAGTTAATTAGATAGCTCGAGGCATGCGG 9800 l... | Strep tag II

G W S H P Q F E K 1881 1882 1883 1884 1885 1886 1887 1888 1889

NsiI XhoI

5' TACCAAGATTGGATCTAGATGCATAGTTAATTAGATAGCTCGAGGCATGCGGTACCAAGCTTGTCGAGAA 9870

5' GTACTAGAGGATCATAATCAGCCATACCACATTTGTAGAGGTTTTACTTGCTTTAAAAAACCTCCCACAC 9940

HpaI

5' CTCCCCCTGAACCTGAAACATAAAATGAATGCAATTGTTGTTGTTAACTTGTTTATTGCAGCTTATAATG 10010

5' GTTACAAATAAAGCAATAGCATCACAAATTTCACAAATAAAGCATTTTTTTCACTGCATTCTAGTTGTGG 10080

AvrII

5' TTTGTCCAAACTCATCAATGTATCTTATCATGTCTGGATCTGATCACTGCTTGAGCCTAGGAGATCCGAA 10150

5' CCAGATAAGTGAAATCTAGTTCCAAACTATTTTGTCATTTTTAATTTTCGTATTAGCTTACGACGCTACA 10220

5' CCCAGTTCCCATCTATTTTGTCACTCTTCCCTAAATAATCCTTAAAAACTCCATTTCCACCCCTCCCAGT 10290

5' TCCCAACTATTTTGTCCGCCCACAGCGGGGCATTTTTCTTCCTGTTATGTTTTTAATCAAACATCCTGCC 10360

5' AACTCCATGTGACAAACCGTCATCTTCGGCTACTTTTTCTCTGTCACAGAATGAAAATTTTTCTGTCATC 10430

5' TCTTCGTTATTAATGTTTGTAATTGACTGAATATCAACGCTTATTTGCAGCCTGAATGGCGAATGG 10496

FIG. 51Q

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 52A

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 52B

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 52C

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI
BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

RsrII

5' TAAATATTCCGGATTATTCATACCGTCCCACCATCGGGCGCGGATCTCGGTCCGTTCGAACCAGAACTCT 4060 mut....mHI

5' GGAAGCTTAACTCCTAAAAAACCGCCACCATGAAATTCTTAGTCAACGTTGCCCTTGTTTTTATGGTCGT 4130

Lob. TMO cDNA Lead Seq
Signal Peptide

Figure 52H:
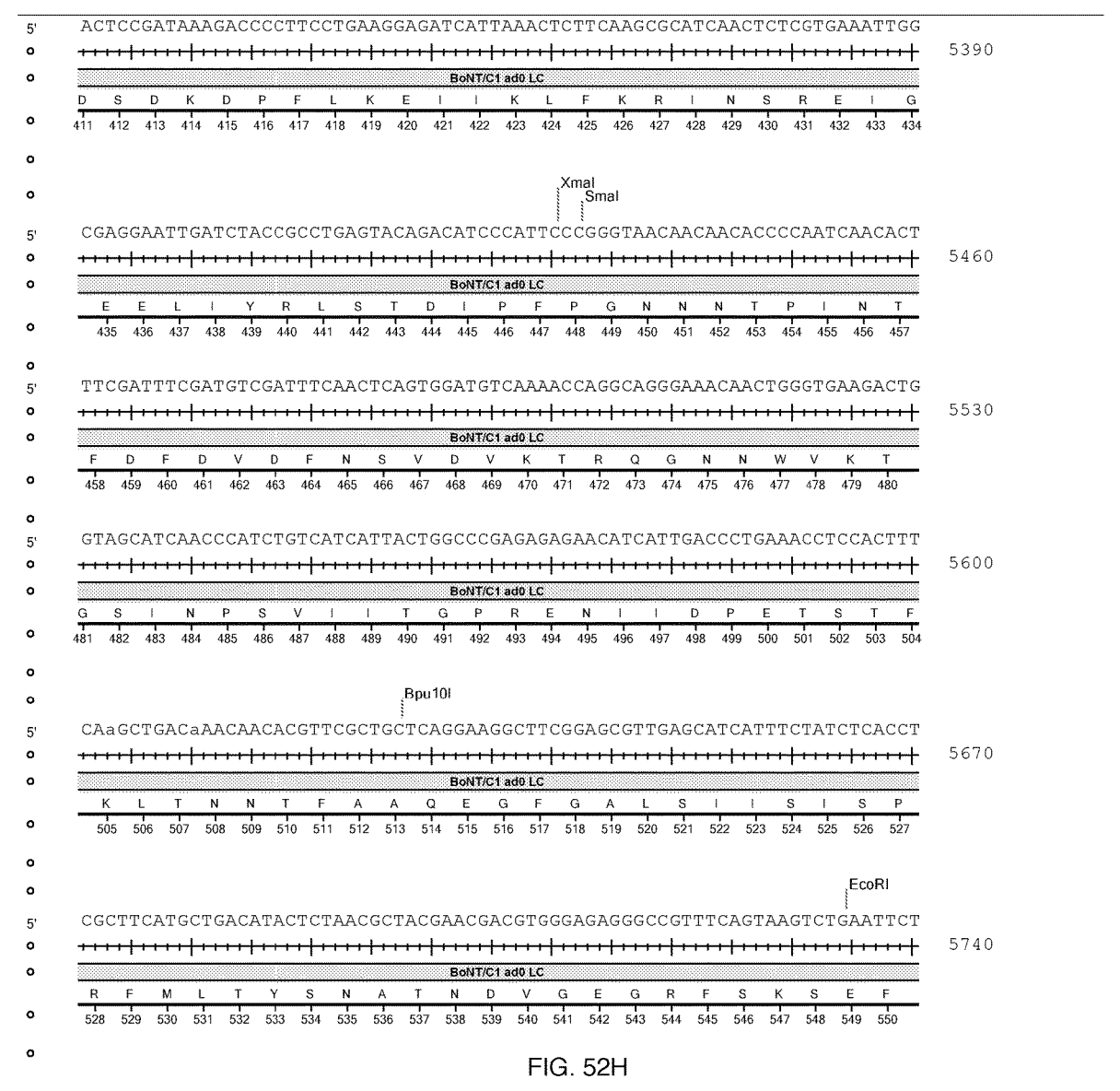

5' ACTCCGATAAAGACCCCTTCCTGAAGGAGATCATTAAACTCTTCAAGCGCATCAACTCTCGTGAAATTGG 5390

BoNT/C1 ad0 LC

D S D K D P F L K E I I K L F K R I N S R E I G 411 412 413 414 415 416 417 418 419 420 421 422 423 424 425 426 427 428 429 430 431 432 433 434

XmaI
SmaI

5' CGAGGAATTGATCTACCGCCTGAGTACAGACATCCCATTCCCGGGTAACAACAACACCCCAATCAACACT 5460

BoNT/C1 ad0 LC

E E L I Y R L S T D I P F P G N N N T P I N T 435 436 437 438 439 440 441 442 443 444 445 446 447 448 449 450 451 452 453 454 455 456 457

5' TTCGATTTCGATGTCGATTTCAACTCAGTGGATGTCAAAACCAGGCAGGGAAACAACTGGGTGAAGACTG 5530

BoNT/C1 ad0 LC

F D F D V D F N S V D V K T R Q G N N W V K T 458 459 460 461 462 463 464 465 466 467 468 469 470 471 472 473 474 475 476 477 478 479 480

5' GTAGCATCAACCCATCTGTCATCATTACTGGCCCGAGAGAGAACATCATTGACCCTGAAACCTCCACTTT 5600

BoNT/C1 ad0 LC

G S I N P S V I I T G P R E N I I D P E T S T F 481 482 483 484 485 486 487 488 489 490 491 492 493 494 495 496 497 498 499 500 501 502 503 504

Bpu10I

5' CAaGCTGACaAACAACACGTTCGCTGCTCAGGAAGGCTTCGGAGCGTTGAGCATCATTTCTATCTCACCT 5670

BoNT/C1 ad0 LC

K L T N N T F A A Q E G F G A L S I I S I S P 505 506 507 508 509 510 511 512 513 514 515 516 517 518 519 520 521 522 523 524 525 526 527

EcoRI

5' CGCTTCATGCTGACATACTCTAACGCTACGAACGACGTGGGAGAGGGCCGTTTCAGTAAGTCTGAATTCT 5740

BoNT/C1 ad0 LC

```
                                                                              BstEII
5'  AGTTCAACTACGCCAAAATTTACAACGTGCAAAACCGTAAGATCGCGCTCTCTAACGTCTACACCCCGGT
                                                                                     6230
              BoNT/C1 LC ad0                              BoNT/C1 LC ad0
    E   F   N   Y   A   K   I   Y   N   V   Q   N   R   K   I   A   L   S   N   V   Y   T   P   V
    691 692 693 694 695 696 697 698 699 700 701 702 703 704 705 706 707 708 709 710 711 712 713 714

5'  TACCGCTAACATCTTGGACGATAACGTCTACGACATTCAGAACGGTTTCAACATCCCAAAGTCGAACCTC
                                                                                     6300
                            BoNT/C1 LC ad0
    T   A   N   I   L   D   D   N   V   Y   D   I   Q   N   G   F   N   I   P   K   S   N   L
    715 716 717 718 719 720 721 722 723 724 725 726 727 728 729 730 731 732 733 734 735 736 737

5'  AACGTTTTGTTCATGGGTCAAAACTTGTCCCGCAACCCCGCCCTGCGTAAGGTGAACCCAGAGAACATGT
                                                                                     6370
                            BoNT/C1 LC ad0
    N   V   L   F   M   G   Q   N   L   S   R   N   P   A   L   R   K   V   N   P   E   N   M
    738 739 740 741 742 743 744 745 746 747 748 749 750 751 752 753 754 755 756 757 758 759 760

5'  TGTACCTGTTCACCAAATTCTGCCACAAGGCCATCGACGGTCAGTCTCTAGACCAAGGAGGATGGGAACT
                                                                                     6440
              BoNT/C1 LC ad0                       LC/HC spacer
    L   Y   L   F   T   K   F   C   H   K   A   I   D   G   Q   S   L   D   Q   G   G   W   E   L
    761 762 763 764 765 766 767 768 769 770 771 772 773 774 775 776 777 778 779 780 781 782 783 784

5'  CCAGCAAGGTGGCCAGGGTGGAGGTGCTGGCACCCTGGACTGTCGCGAACTGCTCGTTAAGAACACTGAT
                                                                                     6510
              LC/HC spacer                    BoNT/C Translocation Domain
    Q   Q   G   G   Q   G   G   A   G   T   L   D   C   R   E   L   L   V   K   N   T   D
    785 786 787 788 789 790 791 792 793 794 795 796 797 798 799 800 801 802 803 804 805 806 807

5'  CTCCCATTCATTGGCGACATCTCTGATGTGAAAACAGACATTTTCCTGCGTAAGGATATCAACGAGGAAA
                                                                                     6580
                            BoNT/C Translocation Domain
    L   P   F   I   G   D   I   S   D   V   K   T   D   I   F   L   R   K   D   I   N   E   E
    808 809 810 811 812 813 814 815 816 817 818 819 820 821 822 823 824 825 826 827 828 829 830

5'  CGGAGGTCATCTACTACCCTGACAACGTCTCGGTTGATCAGGTTATCTTGTCAAAGAACACCAGTGAACA
                                                                                     6650
                            BoNT/C Translocation Domain
    T   E   V   I   Y   Y   P   D   N   V   S   V   D   Q   V   I   L   S   K   N   T   S   E   H
    831 832 833 834 835 836 837 838 839 840 841 842 843 844 845 846 847 848 849 850 851 852 853 854
```

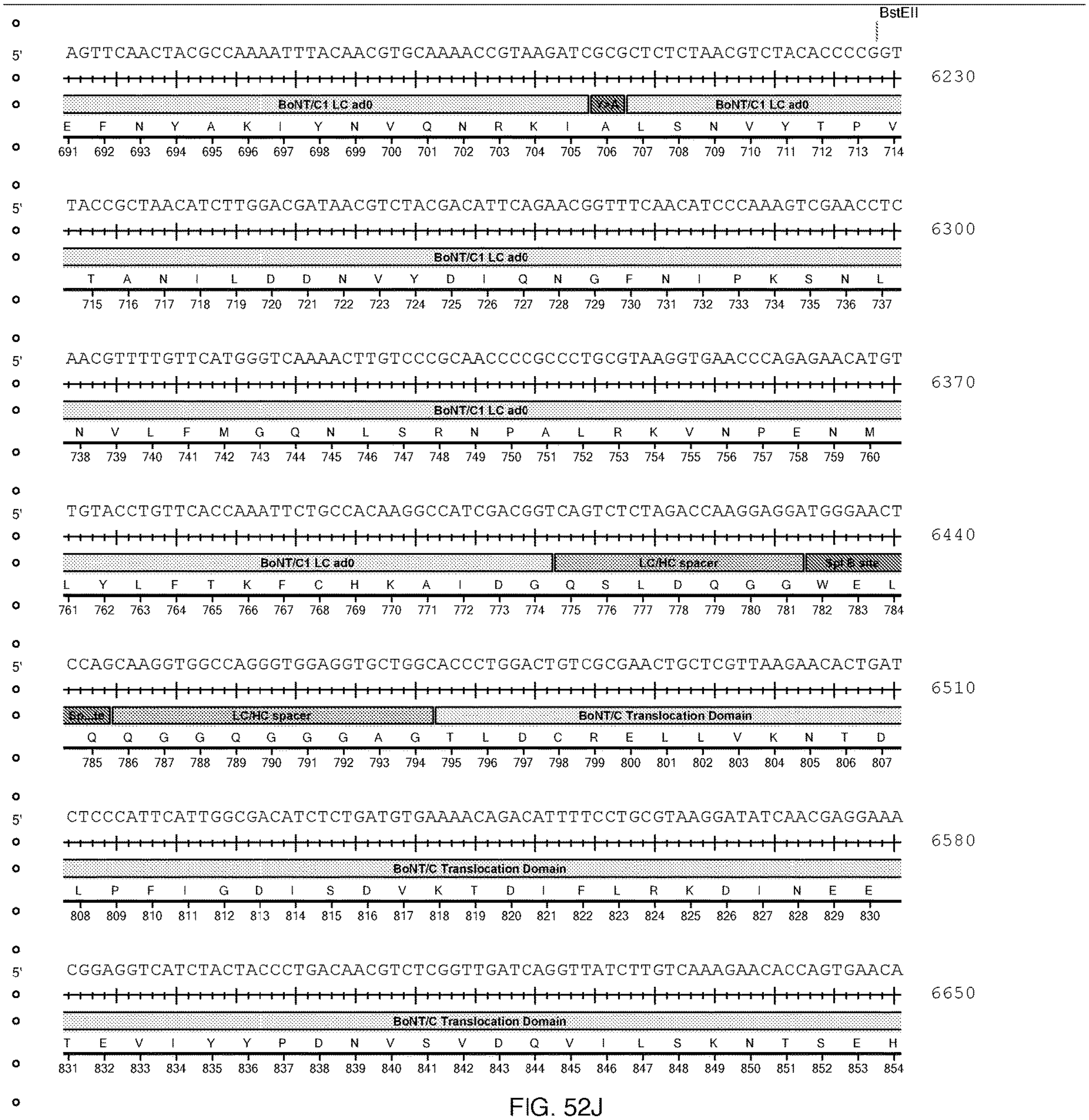

FIG. 52J

SexAI

5' TGGCCAACTGGACTTGCTGTACCCCTCAATTGATTCCGAGAGCGAAATCCTGCCAGGAGAGAACCAGGTT 6720

BoNT/C Translocation Domain

G Q L D L L Y P S I D S E S E I L P G E N Q V 855 856 857 858 859 860 861 862 863 864 865 866 867 868 869 870 871 872 873 874 875 876 877

5' TTCTACGACAACAGGACACAAAACGTGGATTACCTCAACAGCTACTACTACCTGGAGTCGCAGAAGCTCT 6790

BoNT/C Translocation Domain

F Y D N R T Q N V D Y L N S Y Y Y L E S Q K L 878 879 880 881 882 883 884 885 886 887 888 889 890 891 892 893 894 895 896 897 898 899 900

5' CCGACAACGTCGAAGATTTCACATTTACGAGATCAATCGAGGAGGCTTTGGACAACAGTGCCAAAGTCTA 6860

BoNT/C Translocation Domain

S D N V E D F T F T R S I E E A L D N S A K V Y 901 902 903 904 905 906 907 908 909 910 911 912 913 914 915 916 917 918 919 920 921 922 923 924

5' CACCTACTTCCCTACTCTGGCAAACAAGGTGAACGCGGGTGTCCAAGGCGGACTCTTCTTGATGTGGGCT 6930

BoNT/C Translocation Domain

T Y F P T L A N K V N A G V Q G G L F L M W A 925 926 927 928 929 930 931 932 933 934 935 936 937 938 939 940 941 942 943 944 945 946 947

5' AACGACGTTGTGGAAGATTTCACAACGAACATCTTGCGCAAAGACACCCTGGATAAGATCAGCGATGTCT 7000

BoNT/C Translocation Domain

N D V V E D F T T N I L R K D T L D K I S D V 948 949 950 951 952 953 954 955 956 957 958 959 960 961 962 963 964 965 966 967 968 969 970

5' CTGCCATCATTCCATACATTGGCCCGGCACTGAACATCTCTAACTCAGTTCGCCGTGGCAACTTCACTGA 7070

BoNT/C Translocation Domain

S A I I P Y I G P A L N I S N S V R R G N F T E 971 972 973 974 975 976 977 978 979 980 981 982 983 984 985 986 987 988 989 990 991 992 993 994

PfoI

5' GGCATTCGCGGTCACAGGAGTTACGATCCTCTTGGAGGCTTTCCCGGAGTTCACAATCCCCGCACTGGGC 7140

BoNT/C Translocation Domain

Figure 52L:
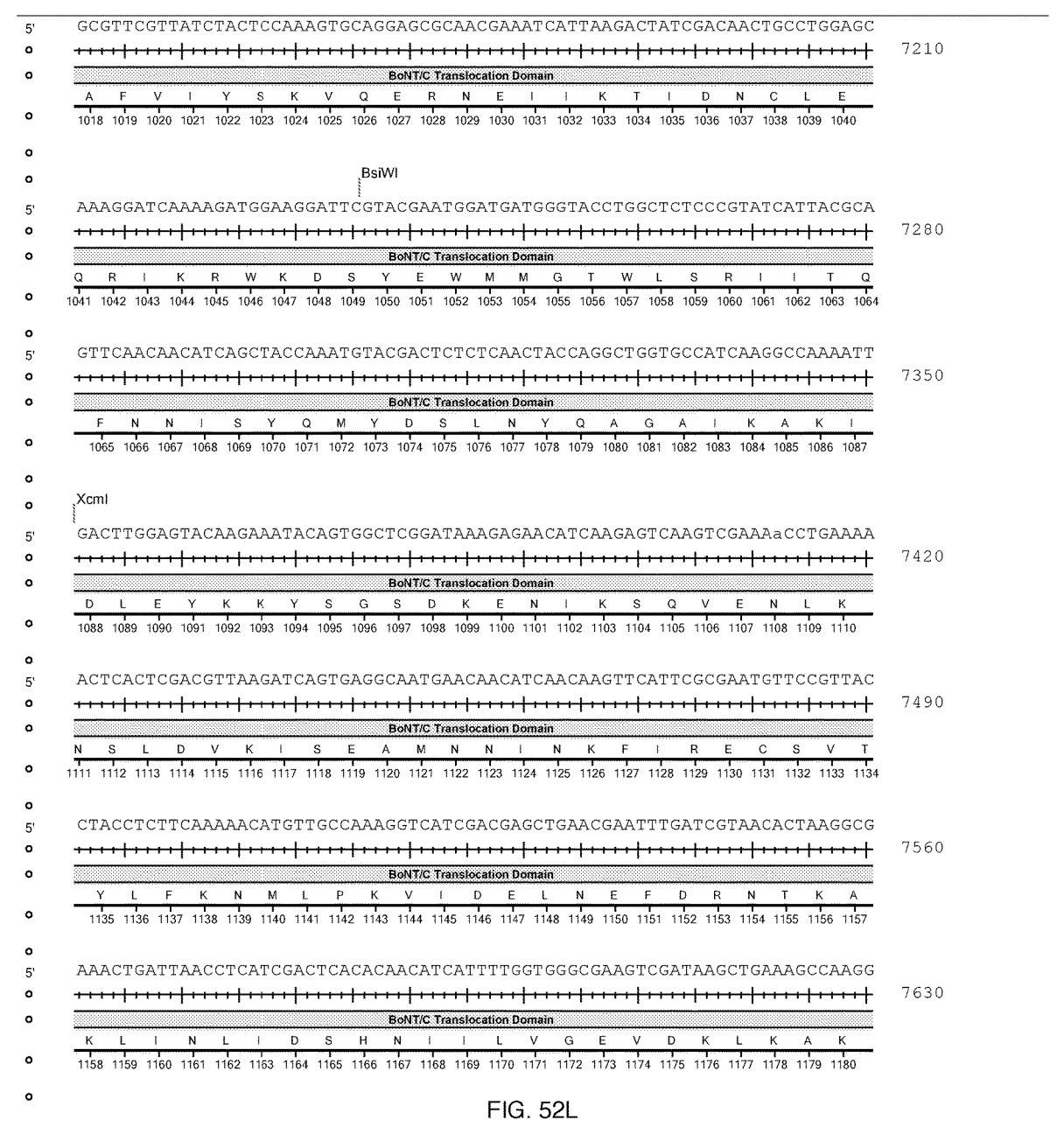

5' GCGTTCGTTATCTACTCCAAAGTGCAGGAGCGCAACGAAATCATTAAGACTATCGACAACTGCCTGGAGC 7210

BoNT/C Translocation Domain

A F V I Y S K V Q E R N E I I K T I D N C L E 1018 1019 1020 1021 1022 1023 1024 1025 1026 1027 1028 1029 1030 1031 1032 1033 1034 1035 1036 1037 1038 1039 1040

BsiWI

5' AAAGGATCAAAAGATGGAAGGATTCGTACGAATGGATGATGGGTACCTGGCTCTCCCGTATCATTACGCA 7280

BoNT/C Translocation Domain

Q R I K R W K D S Y E W M M G T W L S R I I T Q 1041 1042 1043 1044 1045 1046 1047 1048 1049 1050 1051 1052 1053 1054 1055 1056 1057 1058 1059 1060 1061 1062 1063 1064

5' GTTCAACAACATCAGCTACCAAATGTACGACTCTCTCAACTACCAGGCTGGTGCCATCAAGGCCAAAATT 7350

BoNT/C Translocation Domain

F N N I S Y Q M Y D S L N Y Q A G A I K A K I 1065 1066 1067 1068 1069 1070 1071 1072 1073 1074 1075 1076 1077 1078 1079 1080 1081 1082 1083 1084 1085 1086 1087

XcmI

5' GACTTGGAGTACAAGAAATACAGTGGCTCGGATAAAGAGAACATCAAGAGTCAAGTCGAAAaCCTGAAAA 7420

BoNT/C Translocation Domain

D L E Y K K Y S G S D K E N I K S Q V E N L K 1088 1089 1090 1091 1092 1093 1094 1095 1096 1097 1098 1099 1100 1101 1102 1103 1104 1105 1106 1107 1108 1109 1110

5' ACTCACTCGACGTTAAGATCAGTGAGGCAATGAACAACATCAACAAGTTCATTCGCGAATGTTCCGTTAC 7490

BoNT/C Translocation Domain

N S L D V K I S E A M N N I N K F I R E C S V T 1111 1112 1113 1114 1115 1116 1117 1118 1119 1120 1121 1122 1123 1124 1125 1126 1127 1128 1129 1130 1131 1132 1133 1134

5' CTACCTCTTCAAAAACATGTTGCCAAAGGTCATCGACGAGCTGAACGAATTTGATCGTAACACTAAGGCG 7560

BoNT/C Translocation Domain

Y L F K N M L P K V I D E L N E F D R N T K A 1135 1136 1137 1138 1139 1140 1141 1142 1143 1144 1145 1146 1147 1148 1149 1150 1151 1152 1153 1154 1155 1156 1157

5' AAACTGATTAACCTCATCGACTCACACAACATCATTTTGGTGGGCGAAGTCGATAAGCTGAAAGCCAAGG 7630

BoNT/C Translocation Domain

5' tGAACAACAGTTTCCAGAACACAATCCCTTTCAAcATTTTCTCATACACGAACAACAGTCTGCTCAAGGA 7700

BoNT/C Translocation Domain

V N N S F Q N T I P F N I F S Y T N N S L L K D 1181 1182 1183 1184 1185 1186 1187 1188 1189 1190 1191 1192 1193 1194 1195 1196 1197 1198 1199 1200 1201 1202 1203 1204

PstI

5' CATCATTAACGAGTACTTCAACAACATTAACGATAGCAAAATCCTGTCACTGCAGAACCGTAAGAACACA 7770

BoNT/C Translocation Domain | BoNT/C Receptor Binding Domain

I I N E Y F N N I N D S K I L S L Q N R K N T 1205 1206 1207 1208 1209 1210 1211 1212 1213 1214 1215 1216 1217 1218 1219 1220 1221 1222 1223 1224 1225 1226 1227

SpeI PvuII

5' CTGGTCGATACTAGTGGATACAACGCCGAAGTCTCTGAGGAAGGTGACGTGCAGCTGAACCCTATCTTCC 7840

BoNT/C Receptor Binding Domain

L V D T S G Y N A E V S E E G D V Q L N P I F 1228 1229 1230 1231 1232 1233 1234 1235 1236 1237 1238 1239 1240 1241 1242 1243 1244 1245 1246 1247 1248 1249 1250

5' CCTTCGACTTCAAATTGGGCTCCAGCGGAGAGGATAGGGGCAAGGTCATCGTCACCCAGAACGAGAACAT 7910

BoNT/C Receptor Binding Domain

P F D F K L G S S G E D R G K V I V T Q N E N I 1251 1252 1253 1254 1255 1256 1257 1258 1259 1260 1261 1262 1263 1264 1265 1266 1267 1268 1269 1270 1271 1272 1273 1274

5' CGTCTACAACTCAATGTACGAATCCTTCAGCATCTCTTTCTGGATCAGGATTAACAAGTGGGTGAGCAAC 7980

BoNT/C Receptor Binding Domain

V Y N S M Y E S F S I S F W I R I N K W V S N 1275 1276 1277 1278 1279 1280 1281 1282 1283 1284 1285 1286 1287 1288 1289 1290 1291 1292 1293 1294 1295 1296 1297

BspMI

5' CTGCCCGGTTACACAATCATTGACTCTGTCAAGAACAACTCAGGTTGGAGTATCGGCATCATTTCTAACT 8050

BoNT/C Receptor Binding Domain

L P G Y T I I D S V K N N S G W S I G I I S N 1298 1299 1300 1301 1302 1303 1304 1305 1306 1307 1308 1309 1310 1311 1312 1313 1314 1315 1316 1317 1318 1319 1320

5' TCTTGGTCTTCACCCTGAAGCAGAACGAGGACTCGGAACAATCCATTAACTTCTCATACGATATCAGTAA 8120

BoNT/C Receptor Binding Domain

5' CAACGCTCCAGGTTACAACAAGTGGTTCTTCGTTACCGTGACTAACAACATGATGGGTAACATGAAAATT 8190

BoNT/C Receptor Binding Domain

N A P G Y N K W F F V T V T N N M M G N M K I 1345 1346 1347 1348 1349 1350 1351 1352 1353 1354 1355 1356 1357 1358 1359 1360 1361 1362 1363 1364 1365 1366 1367

5' TACATCAACGGCAAGCTCATTGACACCATCAAAGTGAAGGAGTTGACTGGTATTAACTTCTCCAAAACAA 8260

BoNT/C Receptor Binding Domain

Y I N G K L I D T I K V K E L T G I N F S K T 1368 1369 1370 1371 1372 1373 1374 1375 1376 1377 1378 1379 1380 1381 1382 1383 1384 1385 1386 1387 1388 1389 1390

5' TCACGTTTGAAATTAaCaAGATCCCTGACACCGGCCTGATCACTTCAGACAGTGATAACATCAACATGTG 8330

BoNT/C Receptor Binding Domain

I T F E I N K I P D T G L I T S D S D N I N M W 1391 1392 1393 1394 1395 1396 1397 1398 1399 1400 1401 1402 1403 1404 1405 1406 1407 1408 1409 1410 1411 1412 1413 1414

EcoICRI
SacI

5' GATTAGGGATTTCTACATCTTCGCCAAGGAGCTCGACGGAAAGGATATTAACATCCTCTTCAACAGCTTG 8400

BoNT/C Receptor Binding Domain

I R D F Y I F A K E L D G K D I N I L F N S L 1415 1416 1417 1418 1419 1420 1421 1422 1423 1424 1425 1426 1427 1428 1429 1430 1431 1432 1433 1434 1435 1436 1437

5' CAGTACACCAACGTCGTTAAAGACTACTGGGGTAACGATTTGAGATACAACAAGGAGTACTACATGGTCA 8470

BoNT/C Receptor Binding Domain

Q Y T N V V K D Y W G N D L R Y N K E Y Y M V 1438 1439 1440 1441 1442 1443 1444 1445 1446 1447 1448 1449 1450 1451 1452 1453 1454 1455 1456 1457 1458 1459 1460

5' ACATCGACTACCTGAACAGGTACATGTACGCTAACTCCCGCCAAATCGTGTTCAACACCAGGAGAAACAA 8540

BoNT/C Receptor Binding Domain

N I D Y L N R Y M Y A N S R Q I V F N T R R N N 1461 1462 1463 1464 1465 1466 1467 1468 1469 1470 1471 1472 1473 1474 1475 1476 1477 1478 1479 1480 1481 1482 1483 1484

5' CAACGACTTCAACGAGGGTTACAAAATCATTATCAAGCGCATCCGTGGCAACACCAACGATACTAGGGTG 8610

BoNT/C Receptor Binding Domain

```
5'  AGAGGTGGCGACATTCTGTACTTCGATATGACTATCAACAACAAAGCCTACAACTTGTTCATGAAAAACG
                                                                              8680
                         BoNT/C Receptor Binding Domain
     R   G   G   D   I   L   Y   F   D   M   T   I   N   N   K   A   Y   N   L   F   M   K   N
    1508 1509 1510 1511 1512 1513 1514 1515 1516 1517 1518 1519 1520 1521 1522 1523 1524 1525 1526 1527 1528 1529 1530

5'  AGACAATGTACGCCGACAAcCATAGCACGGAGGATATTTACGCAATCGGACTGAGGGAACAGACAAAGGA
                                                                              8750
                         BoNT/C Receptor Binding Domain
     E   T   M   Y   A   D   N   H   S   T   E   D   I   Y   A   I   G   L   R   E   Q   T   K   D
    1531 1532 1533 1534 1535 1536 1537 1538 1539 1540 1541 1542 1543 1544 1545 1546 1547 1548 1549 1550 1551 1552 1553 1554

5'  CATCAACGATAACATTATCTTCCAGATCCAACCTATGAACAACACGTACTACTACGCTTCGCAAATCTTC
                                                                              8820
                         BoNT/C Receptor Binding Domain
     I   N   D   N   I   I   F   Q   I   Q   P   M   N   N   T   Y   Y   Y   A   S   Q   I   F
    1555 1556 1557 1558 1559 1560 1561 1562 1563 1564 1565 1566 1567 1568 1569 1570 1571 1572 1573 1574 1575 1576 1577

5'  AAGTCCAACTTCAACGGAGAAAACATTTCGGGTATCTGTTCCATTGGCACATACCGCTTCCGTCTGGGTG
                                                                              8890
                         BoNT/C Receptor Binding Domain
     K   S   N   F   N   G   E   N   I   S   G   I   C   S   I   G   T   Y   R   F   R   L   G
    1578 1579 1580 1581 1582 1583 1584 1585 1586 1587 1588 1589 1590 1591 1592 1593 1594 1595 1596 1597 1598 1599 1600

                                                                          SalI
5'  GTGACTGGTATCGTCACAACTACCTCGTTCCCACCGTGAAGCAGGGTAACTACGCTTCTTTGCTGGAGTC
                                                                              8960
                         BoNT/C Receptor Binding Domain
     G   D   W   Y   R   H   N   Y   L   V   P   T   V   K   Q   G   N   Y   A   S   L   L   E   S
    1601 1602 1603 1604 1605 1606 1607 1608 1609 1610 1611 1612 1613 1614 1615 1616 1617 1618 1619 1620 1621 1622 1623 1624

5'  GACTTCCACGCACTGGGGATTCGTTCCTGTGTCAGAGGGCGCTGGCTACCCTTACGATGTTCCCGACTAC
                                                                              9030
              BoNT/C Receptor Binding Domain           linker           HA tag
     T   S   T   H   W   G   F   V   P   V   S   E   G   A   G   Y   P   Y   D   V   P   D   Y
    1625 1626 1627 1628 1629 1630 1631 1632 1633 1634 1635 1636 1637 1638 1639 1640 1641 1642 1643 1644 1645 1646 1647

5'  GCTGGTTGGGAACTCCAGCAAGGTGCAGGATGGTCCCACCCTCAATTCGAGAAGGGTGCCGGATGGAGTC
                                                                              9100
      H.. li..r    SpyB site    linker              Strep-tag II          linker   Strep-tag II
     A   G   W   E   L   Q   Q   G   A   G   W   S   H   P   Q   F   E   K   G   A   G   W   S
    1648 1649 1650 1651 1652 1653 1654 1655 1656 1657 1658 1659 1660 1661 1662 1663 1664 1665 1666 1667 1668 1669 1670
```

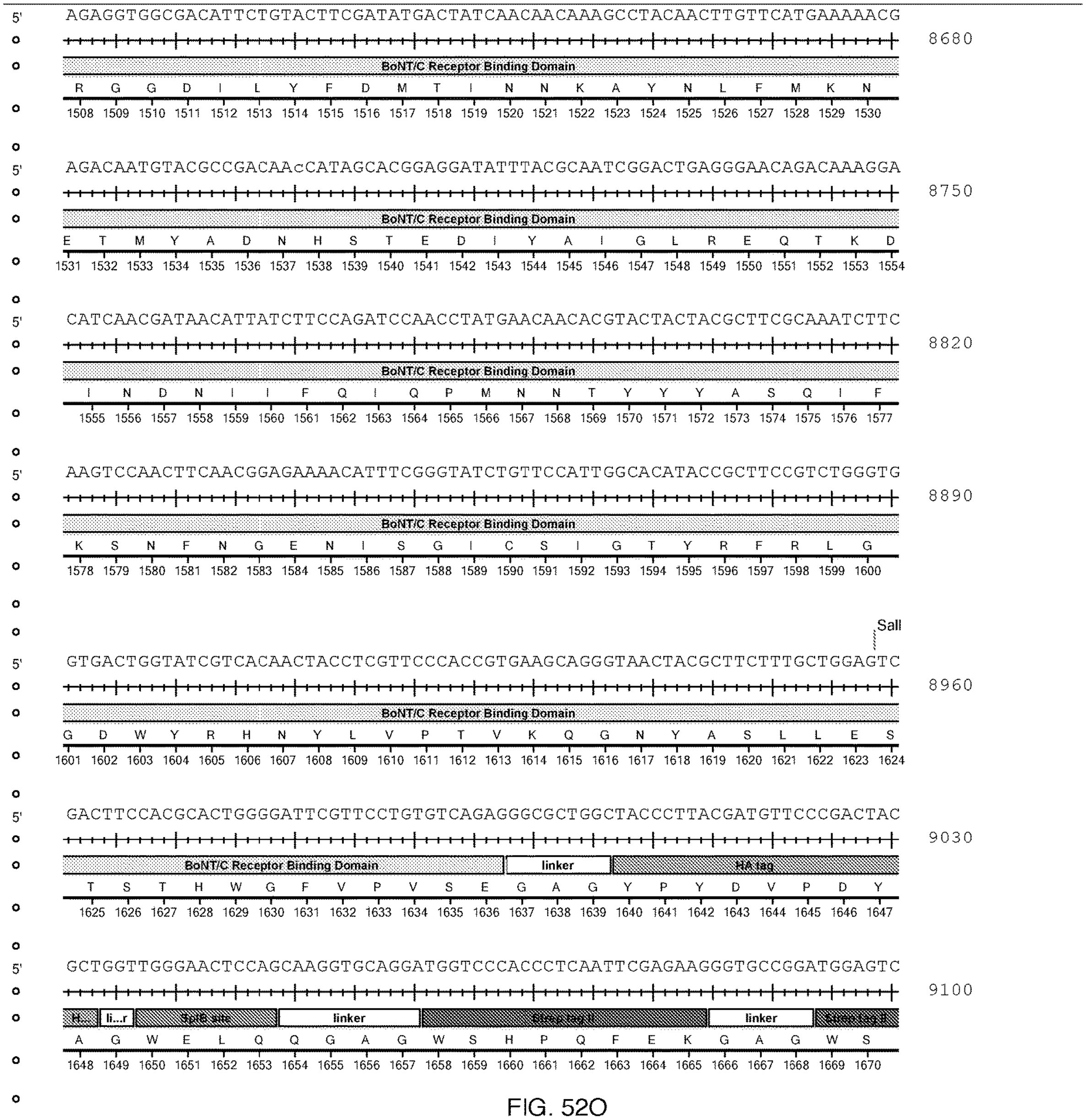

FIG. 52O

NsiI

5' ACCCACAGTTCGAGAAAGGCGCTGGATGGAGTCACCCACAGTTCGAGAAATAATTAGTTGATGCATAGTT 9170

Strep tag II | linker | Strep tag II

H P Q F E K G A G W S H P Q F E K 1671 1672 1673 1674 1675 1676 1677 1678 1679 1680 1681 1682 1683 1684 1685 1686 1687

XhoI NsiI XhoI

5' AATTAGATAGCTCGAGGCATGCGGTACCAAGATTGGATCTAGATGCATAGTTAATTAGATAGCTCGAGGC 9240

5' ATGCGGTACCAAGCTTGTCGAGAAGTACTAGAGGATCATAATCAGCCATACCACATTTGTAGAGGTTTTA 9310

HpaI

5' CTTGCTTTAAAAAACCTCCCACACCTCCCCCTGAACCTGAAACATAAAATGAATGCAATTGTTGTTGTTA 9380

5' ACTTGTTTATTGCAGCTTATAATGGTTACAAATAAAGCAATAGCATCACAAATTTCACAAATAAAGCATT 9450

5' TTTTTCACTGCATTCTAGTTGTGGTTTGTCCAAACTCATCAATGTATCTTATCATGTCTGGATCTGATCA 9520

AvrII

5' CTGCTTGAGCCTAGGAGATCCGAACCAGATAAGTGAAATCTAGTTCCAAACTATTTTGTCATTTTTAATT 9590

5' TTCGTATTAGCTTACGACGCTACACCCAGTTCCCATCTATTTTGTCACTCTTCCCTAAATAATCCTTAAA 9660

5' AACTCCATTTCCACCCCTCCCAGTTCCCAACTATTTTGTCCGCCCACAGCGGGGCATTTTTCTTCCTGTT 9730

5' ATGTTTTTAATCAAACATCCTGCCAACTCCATGTGACAAACCGTCATCTTCGGCTACTTTTTCTCTGTCA 9800

5' CAGAATGAAAATTTTTCTGTCATCTCTTCGTTATTAATGTTTGTAATTGACTGAATATCAACGCTTATTT 9870

5' GCAGCCTGAATGGCGAATGG 9890

FIG. 52P

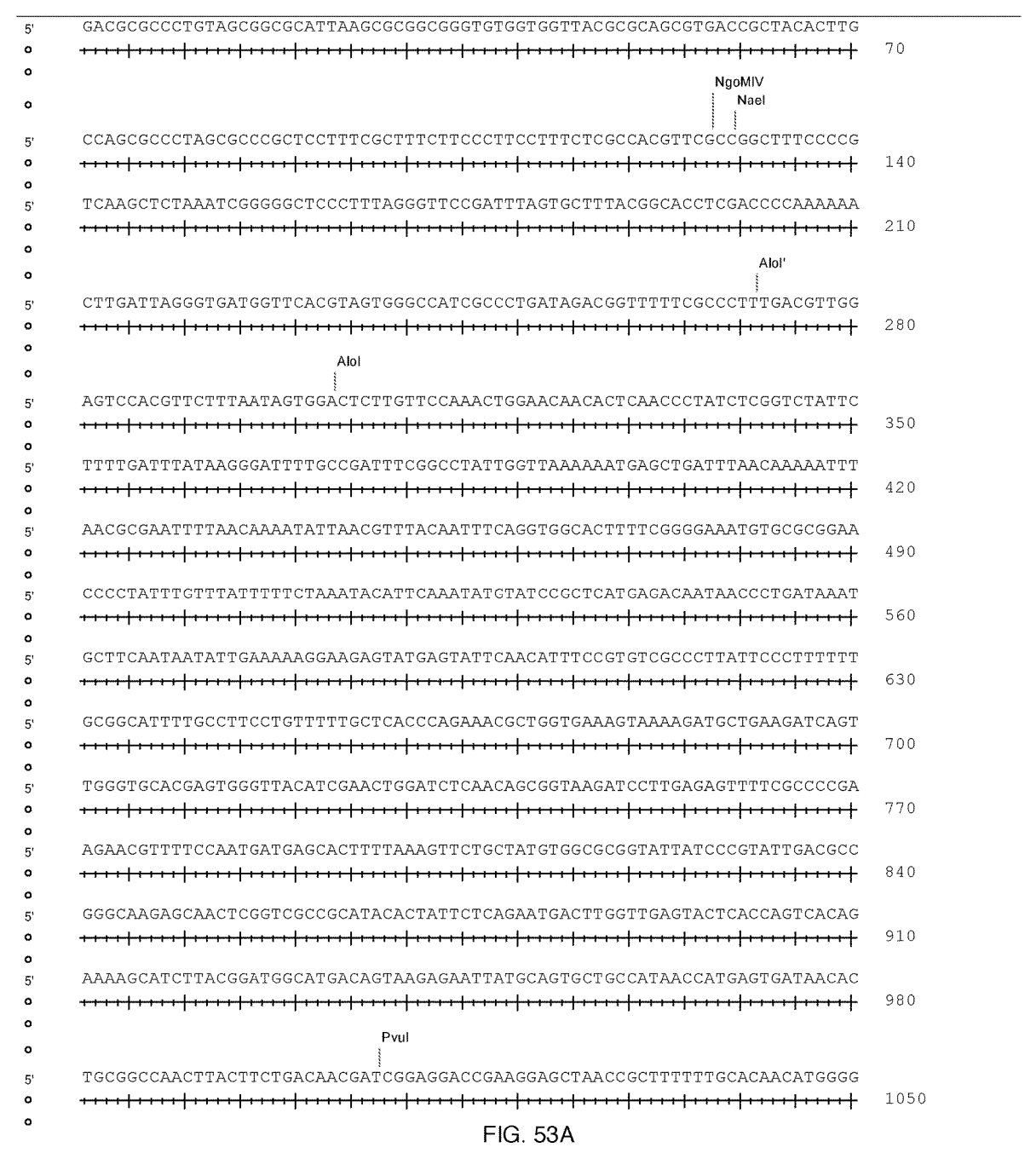

5' GACGCGCCCTGTAGCGGCGCATTAAGCGCGGCGGGTGTGGTGGTTACGCGCAGCGTGACCGCTACACTTG 70

NgoMIV
NaeI
5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'
5' CTTGATTAGGGTGATGGTTCACGTAGTGGGCCATCGCCCTGATAGACGGTTTTTCGCCCTTTGACGTTGG 280

AloI
5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI
5' TGCGGCCAACTTACTTCTGACAACGATCGGAGGACCGAAGGAGCTAACCGCTTTTTTGCACAACATGGGG 1050

FIG. 53A

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 53B

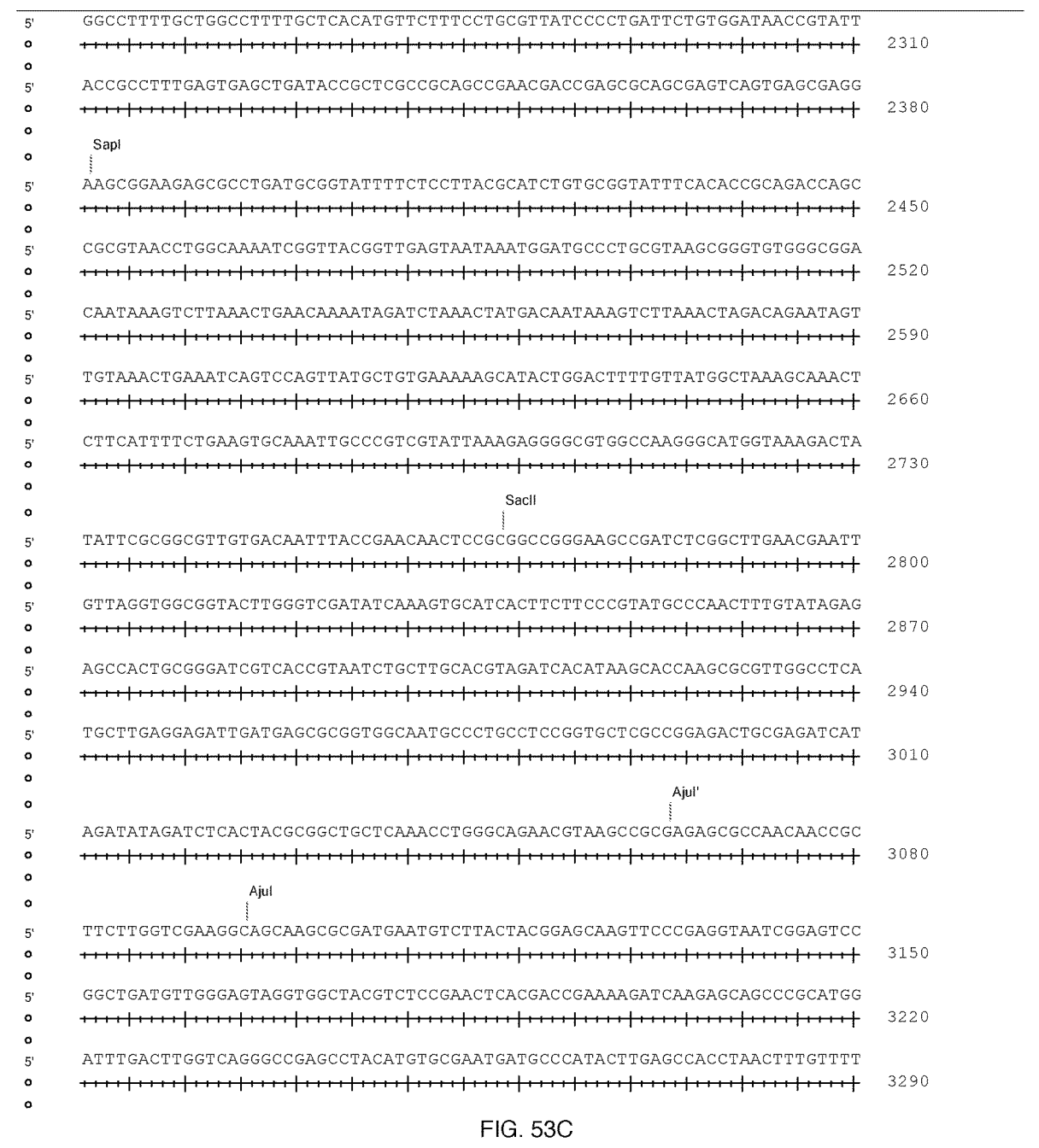

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 53C

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI

BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

RsrII

5' TAAATATTCCGGATTATTCATACCGTCCCACCATCGGGCGCGGATCTCGGTCCGTTCGAACCAGAACTCT 4060 mut....mHI

5' GGAAGCTTAACTCCTAAAAAACCGCCACCATGAAATTCTTAGTCAACGTTGCCCTTGTTTTTATGGTCGT 4130

Lob. TMO cDNA Lead Seq

Signal Peptide

5' CAACATTTGGGTCATTCCGGATAGGTTCAGCAGAAACTCTAACCCTAACTTGAACAAACCTCCCAGAGTG 5880

BoNT/C1 ad0 LC

N I W V I P D R F S R N S N P N L N K P P R V 575 576 577 578 579 580 581 582 583 584 585 586 587 588 589 590 591 592 593 594 595 596 597

5' ACCTCACCTAAGAGTGGATACTACGACCCCAACTACCTCTCGACTGACTCCGATAAAGACCCCTTCCTGA 5950

BoNT/C1 ad0 LC

T S P K S G Y Y D P N Y L S T D S D K D P F L 598 599 600 601 602 603 604 605 606 607 608 609 610 611 612 613 614 615 616 617 618 619 620

5' AGGAGATCATTAAACTCTTCAAGCGCATCAACTCTCGTGAAATTGGCGAGGAATTGATCTACCGCCTGAG 6020

BoNT/C1 ad0 LC

K E I I K L F K R I N S R E I G E E L I Y R L S 621 622 623 624 625 626 627 628 629 630 631 632 633 634 635 636 637 638 639 640 641 642 643 644

XmaI

SmaI

5' TACAGACATCCCATTCCCGGGTAACAACAACACCCCAATCAACACTTTCGATTTCGATGTCGATTTCAAC 6090

BoNT/C1 ad0 LC

T D I P F P G N N N T P I N T F D F D V D F N 645 646 647 648 649 650 651 652 653 654 655 656 657 658 659 660 661 662 663 664 665 666 667

5' TCAGTGGATGTCAAAACCAGGCAGGGAAACAACTGGGTGAAGACTGGTAGCATCAACCCATCTGTCATCA 6160

BoNT/C1 ad0 LC

S V D V K T R Q G N N W V K T G S I N P S V I 668 669 670 671 672 673 674 675 676 677 678 679 680 681 682 683 684 685 686 687 688 689 690

5' TTACTGGCCCGAGAGAGAACATCATTGACCCTGAAACCTCCACTTTCAaGCTGACaAACAACACGTTCGC 6230

BoNT/C1 ad0 LC

I T G P R E N I I D P E T S T F K L T N N T F A 691 692 693 694 695 696 697 698 699 700 701 702 703 704 705 706 707 708 709 710 711 712 713 714

Bpu10I

5' TGCTCAGGAAGGCTTCGGAGCGTTGAGCATCATTTCTATCTCACCTCGCTTCATGCTGACATACTCTAAC 6300

BoNT/C1 ad0 LC

5' AACAAGTTCGTCGAGCTGTACAACGAATTGACACAAATCTTCACGGAGTTCAACTACGCCAAAATTTACA 6790

BoNT/C1 LC ad0

N K F V E L Y N E L T Q I F T E F N Y A K I Y 878 879 880 881 882 883 884 885 886 887 888 889 890 891 892 893 894 895 896 897 898 899 900

BstEII

5' ACGTGCAAAACCGTAAGATCGCGCTCTCTAACGTCTACACCCCGGTTACCGCTAACATCTTGGACGATAA 6860

BoNT/C1 LC ad0 | Y>A | BoNT/C1 LC ad0

N V Q N R K I A L S N V Y T P V T A N I L D D N 901 902 903 904 905 906 907 908 909 910 911 912 913 914 915 916 917 918 919 920 921 922 923 924

5' CGTCTACGACATTCAGAACGGTTTCAACATCCCAAAGTCGAACCTCAACGTTTTGTTCATGGGTCAAAAC 6930

BoNT/C1 LC ad0

V Y D I Q N G F N I P K S N L N V L F M G Q N 925 926 927 928 929 930 931 932 933 934 935 936 937 938 939 940 941 942 943 944 945 946 947

5' TTGTCCCGCAACCCCGCCCTGCGTAAGGTGAACCCAGAGAACATGTTGTACCTGTTCACCAAATTCTGCC 7000

BoNT/C1 LC ad0

L S R N P A L R K V N P E N M L Y L F T K F C 948 949 950 951 952 953 954 955 956 957 958 959 960 961 962 963 964 965 966 967 968 969 970

5' ACAAGGCCATCGACGGTCAGTCTCTAGACCAAGGAGGATGGGAACTCCAGCAAGGTGGCCAGGGTGGAGG 7070

BoNT/C1 LC ad0 | LC/HC spacer | 3pl B site | LC/HC spacer

H K A I D G Q S L D Q G G W E L Q Q G G Q G G G 971 972 973 974 975 976 977 978 979 980 981 982 983 984 985 986 987 988 989 990 991 992 993 994

5' TGCTGGCACCCTGGACTGTCGCGAACTGCTCGTTAAGAACACTGATCTCCCATTCATTGGCGACATCTCT 7140

LC/HC...acer | BoNT/C Translocation Domain

A G T L D C R E L L V K N T D L P F I G D I S 995 996 997 998 999 1000 1001 1002 1003 1004 1005 1006 1007 1008 1009 1010 1011 1012 1013 1014 1015 1016 1017

5' GATGTGAAAACAGACATTTTCCTGCGTAAGGATATCAACGAGGAAACGGAGGTCATCTACTACCCTGACA 7210

BoNT/C Translocation Domain

Figure 53L:
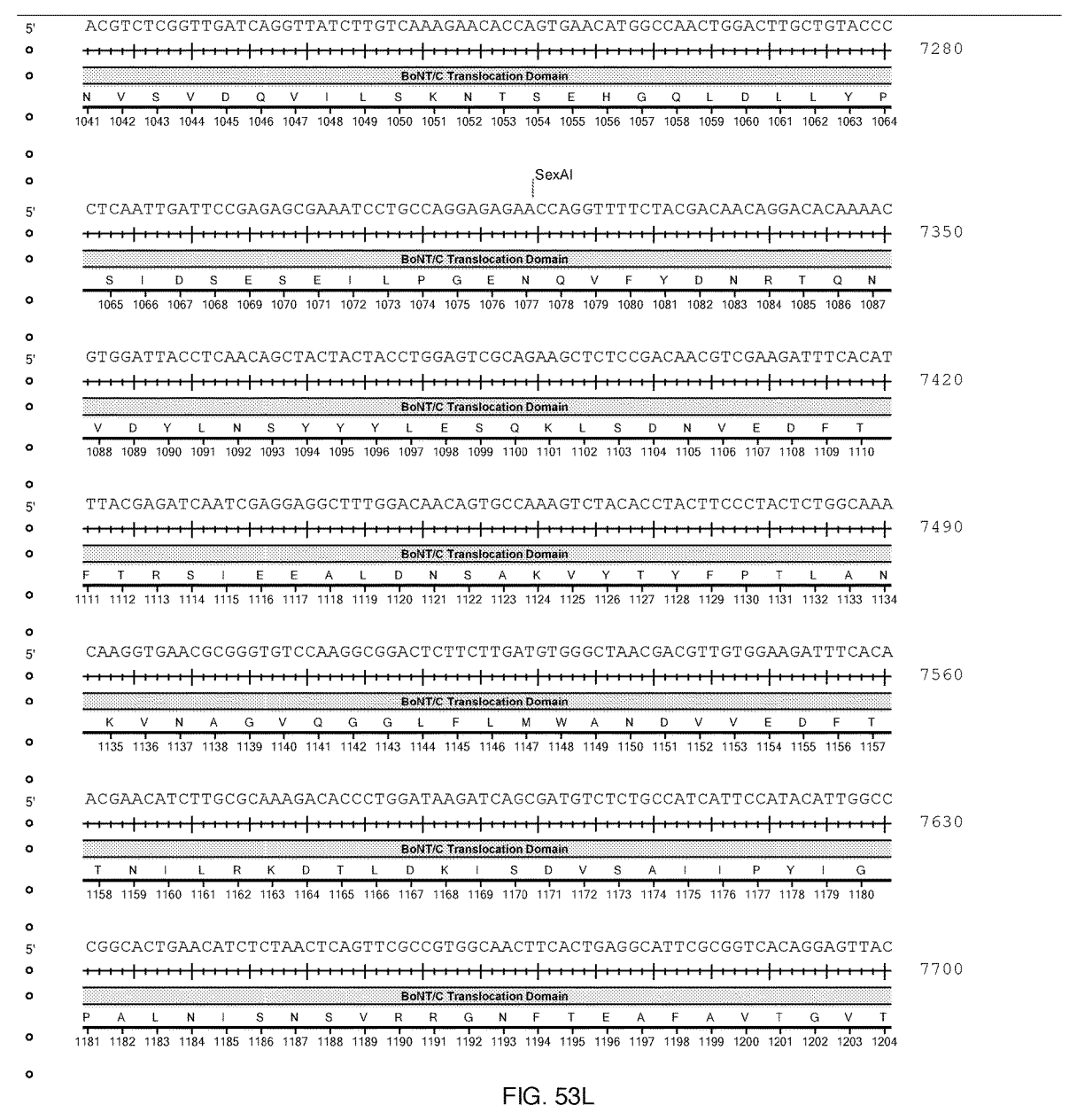

5' ACGTCTCGGTTGATCAGGTTATCTTGTCAAAGAACACCAGTGAACATGGCCAACTGGACTTGCTGTACCC 7280

BoNT/C Translocation Domain

N V S V D Q V I L S K N T S E H G Q L D L L Y P 1041 1042 1043 1044 1045 1046 1047 1048 1049 1050 1051 1052 1053 1054 1055 1056 1057 1058 1059 1060 1061 1062 1063 1064

SexAI

5' CTCAATTGATTCCGAGAGCGAAATCCTGCCAGGAGAGAACCAGGTTTTCTACGACAACAGGACACAAAAC 7350

BoNT/C Translocation Domain

S I D S E S E I L P G E N Q V F Y D N R T Q N 1065 1066 1067 1068 1069 1070 1071 1072 1073 1074 1075 1076 1077 1078 1079 1080 1081 1082 1083 1084 1085 1086 1087

5' GTGGATTACCTCAACAGCTACTACTACCTGGAGTCGCAGAAGCTCTCCGACAACGTCGAAGATTTCACAT 7420

BoNT/C Translocation Domain

V D Y L N S Y Y Y L E S Q K L S D N V E D F T 1088 1089 1090 1091 1092 1093 1094 1095 1096 1097 1098 1099 1100 1101 1102 1103 1104 1105 1106 1107 1108 1109 1110

5' TTACGAGATCAATCGAGGAGGCTTTGGACAACAGTGCCAAAGTCTACACCTACTTCCCTACTCTGGCAAA 7490

BoNT/C Translocation Domain

F T R S I E E A L D N S A K V Y T Y F P T L A N 1111 1112 1113 1114 1115 1116 1117 1118 1119 1120 1121 1122 1123 1124 1125 1126 1127 1128 1129 1130 1131 1132 1133 1134

5' CAAGGTGAACGCGGGTGTCCAAGGCGGACTCTTCTTGATGTGGGCTAACGACGTTGTGGAAGATTTCACA 7560

BoNT/C Translocation Domain

K V N A G V Q G G L F L M W A N D V V E D F T 1135 1136 1137 1138 1139 1140 1141 1142 1143 1144 1145 1146 1147 1148 1149 1150 1151 1152 1153 1154 1155 1156 1157

5' ACGAACATCTTGCGCAAAGACACCCTGGATAAGATCAGCGATGTCTCTGCCATCATTCCATACATTGGCC 7630

BoNT/C Translocation Domain

T N I L R K D T L D K I S D V S A I I P Y I G 1158 1159 1160 1161 1162 1163 1164 1165 1166 1167 1168 1169 1170 1171 1172 1173 1174 1175 1176 1177 1178 1179 1180

5' CGGCACTGAACATCTCTAACTCAGTTCGCCGTGGCAACTTCACTGAGGCATTCGCGGTCACAGGAGTTAC 7700

BoNT/C Translocation Domain

PfoI

5' GATCCTCTTGGAGGCTTTCCCGGAGTTCACAATCCCCGCACTGGGCGCGTTCGTTATCTACTCCAAAGTG 7770

BoNT/C Translocation Domain

I L L E A F P E F T I P A L G A F V I Y S K V 1205 1206 1207 1208 1209 1210 1211 1212 1213 1214 1215 1216 1217 1218 1219 1220 1221 1222 1223 1224 1225 1226 1227

5' CAGGAGCGCAACGAAATCATTAAGACTATCGACAACTGCCTGGAGCAAAGGATCAAAAGATGGAAGGATT 7840

BoNT/C Translocation Domain

Q E R N E I I K T I D N C L E Q R I K R W K D 1228 1229 1230 1231 1232 1233 1234 1235 1236 1237 1238 1239 1240 1241 1242 1243 1244 1245 1246 1247 1248 1249 1250

BsiWI

5' CGTACGAATGGATGATGGGTACCTGGCTCTCCCGTATCATTACGCAGTTCAACAACATCAGCTACCAAAT 7910

BoNT/C Translocation Domain

S Y E W M M G T W L S R I I T Q F N N I S Y Q M 1251 1252 1253 1254 1255 1256 1257 1258 1259 1260 1261 1262 1263 1264 1265 1266 1267 1268 1269 1270 1271 1272 1273 1274

XcmI

5' GTACGACTCTCTCAACTACCAGGCTGGTGCCATCAAGGCCAAAATTGACTTGGAGTACAAGAAATACAGT 7980

BoNT/C Translocation Domain

Y D S L N Y Q A G A I K A K I D L E Y K K Y S 1275 1276 1277 1278 1279 1280 1281 1282 1283 1284 1285 1286 1287 1288 1289 1290 1291 1292 1293 1294 1295 1296 1297

5' GGCTCGGATAAAGAGAACATCAAGAGTCAAGTCGAAAaCCTGAAAAACTCACTCGACGTTAAGATCAGTG 8050

BoNT/C Translocation Domain

G S D K E N I K S Q V E N L K N S L D V K I S 1298 1299 1300 1301 1302 1303 1304 1305 1306 1307 1308 1309 1310 1311 1312 1313 1314 1315 1316 1317 1318 1319 1320

5' AGGCAATGAACAACATCAACAAGTTCATTCGCGAATGTTCCGTTACCTACCTCTTCAAAAACATGTTGCC 8120

BoNT/C Translocation Domain

E A M N N I N K F I R E C S V T Y L F K N M L P 1321 1322 1323 1324 1325 1326 1327 1328 1329 1330 1331 1332 1333 1334 1335 1336 1337 1338 1339 1340 1341 1342 1343 1344

5' AAAGGTCATCGACGAGCTGAACGAATTTGATCGTAACACTAAGGCGAAACTGATTAACCTCATCGACTCA 8190

BoNT/C Translocation Domain

5' CACAACATCATTTTGGTGGGCGAAGTCGATAAGCTGAAAGCCAAGGtGAACAACAGTTTCCAGAACACAA 8260

BoNT/C Translocation Domain

H N I I L V G E V D K L K A K V N N S F Q N T 1368 1369 1370 1371 1372 1373 1374 1375 1376 1377 1378 1379 1380 1381 1382 1383 1384 1385 1386 1387 1388 1389 1390

5' TCCCTTTCAAcATTTTCTCATACACGAACAACAGTCTGCTCAAGGACATCATTAACGAGTACTTCAACAA 8330

BoNT/C Translocation Domain | BoN...in

I P F N I F S Y T N N S L L K D I I N E Y F N N 1391 1392 1393 1394 1395 1396 1397 1398 1399 1400 1401 1402 1403 1404 1405 1406 1407 1408 1409 1410 1411 1412 1413 1414

PstI SpeI

5' CATTAACGATAGCAAAATCCTGTCACTGCAGAACCGTAAGAACACACTGGTCGATACTAGTGGATACAAC 8400

BoNT/C Receptor Binding Domain

I N D S K I L S L Q N R K N T L V D T S G Y N 1415 1416 1417 1418 1419 1420 1421 1422 1423 1424 1425 1426 1427 1428 1429 1430 1431 1432 1433 1434 1435 1436 1437

PvuII

5' GCCGAAGTCTCTGAGGAAGGTGACGTGCAGCTGAACCCTATCTTCCCCTTCGACTTCAAATTGGGCTCCA 8470

BoNT/C Receptor Binding Domain

A E V S E E G D V Q L N P I F P F D F K L G S 1438 1439 1440 1441 1442 1443 1444 1445 1446 1447 1448 1449 1450 1451 1452 1453 1454 1455 1456 1457 1458 1459 1460

5' GCGGAGAGGATAGGGGCAAGGTCATCGTCACCCAGAACGAGAACATCGTCTACAACTCAATGTACGAATC 8540

BoNT/C Receptor Binding Domain

S G E D R G K V I V T Q N E N I V Y N S M Y E S 1461 1462 1463 1464 1465 1466 1467 1468 1469 1470 1471 1472 1473 1474 1475 1476 1477 1478 1479 1480 1481 1482 1483 1484

BspMI

5' CTTCAGCATCTCTTTCTGGATCAGGATTAACAAGTGGGTGAGCAACCTGCCCGGTTACACAATCATTGAC 8610

BoNT/C Receptor Binding Domain

F S I S F W I R I N K W V S N L P G Y T I I D 1485 1486 1487 1488 1489 1490 1491 1492 1493 1494 1495 1496 1497 1498 1499 1500 1501 1502 1503 1504 1505 1506 1507

5' TCTGTCAAGAACAACTCAGGTTGGAGTATCGGCATCATTTCTAACTTCTTGGTCTTCACCCTGAAGCAGA 8680

BoNT/C Receptor Binding Domain

```
5'  ACGAGGACTCGGAACAATCCATTAACTTCTCATACGATATCAGTAACAACGCTCCAGGTTACAACAAGTG
                                                                              8750
                          BoNT/C Receptor Binding Domain
     N   E   D   S   E   Q   S   I   N   F   S   Y   D   I   S   N   N   A   P   G   Y   N   K   W
    1531 1532 1533 1534 1535 1536 1537 1538 1539 1540 1541 1542 1543 1544 1545 1546 1547 1548 1549 1550 1551 1552 1553 1554

5'  GTTCTTCGTTACCGTGACTAACAACATGATGGGTAACATGAAAATTTACATCAACGGCAAGCTCATTGAC
                                                                              8820
                          BoNT/C Receptor Binding Domain
     F   F   V   T   V   T   N   N   M   M   G   N   M   K   I   Y   I   N   G   K   L   I   D
    1555 1556 1557 1558 1559 1560 1561 1562 1563 1564 1565 1566 1567 1568 1569 1570 1571 1572 1573 1574 1575 1576 1577

5'  ACCATCAAAGTGAAGGAGTTGACTGGTATTAACTTCTCCAAAACAATCACGTTTGAAATTAaCaAGATCC
                                                                              8890
                          BoNT/C Receptor Binding Domain
     T   I   K   V   K   E   L   T   G   I   N   F   S   K   T   I   T   F   E   I   N   K   I
    1578 1579 1580 1581 1582 1583 1584 1585 1586 1587 1588 1589 1590 1591 1592 1593 1594 1595 1596 1597 1598 1599 1600

5'  CTGACACCGGCCTGATCACTTCAGACAGTGATAACATCAACATGTGGATTAGGGATTTCTACATCTTCGC
                                                                              8960
                          BoNT/C Receptor Binding Domain
     P   D   T   G   L   I   T   S   D   S   D   N   I   N   M   W   I   R   D   F   Y   I   F   A
    1601 1602 1603 1604 1605 1606 1607 1608 1609 1610 1611 1612 1613 1614 1615 1616 1617 1618 1619 1620 1621 1622 1623 1624

         EcoICRI
         SacI
5'  CAAGGAGCTCGACGGAAAGGATATTAACATCCTCTTCAACAGCTTGCAGTACACCAACGTCGTTAAAGAC
                                                                              9030
                          BoNT/C Receptor Binding Domain
     K   E   L   D   G   K   D   I   N   I   L   F   N   S   L   Q   Y   T   N   V   V   K   D
    1625 1626 1627 1628 1629 1630 1631 1632 1633 1634 1635 1636 1637 1638 1639 1640 1641 1642 1643 1644 1645 1646 1647

5'  TACTGGGGTAACGATTTGAGATACAACAAGGAGTACTACATGGTCAACATCGACTACCTGAACAGGTACA
                                                                              9100
                          BoNT/C Receptor Binding Domain
     Y   W   G   N   D   L   R   Y   N   K   E   Y   Y   M   V   N   I   D   Y   L   N   R   Y
    1648 1649 1650 1651 1652 1653 1654 1655 1656 1657 1658 1659 1660 1661 1662 1663 1664 1665 1666 1667 1668 1669 1670

5'  TGTACGCTAACTCCCGCCAAATCGTGTTCAACACCAGGAGAAACAACAACGACTTCAACGAGGGTTACAA
                                                                              9170
                          BoNT/C Receptor Binding Domain
     M   Y   A   N   S   R   Q   I   V   F   N   T   R   R   N   N   N   D   F   N   E   G   Y   K
    1671 1672 1673 1674 1675 1676 1677 1678 1679 1680 1681 1682 1683 1684 1685 1686 1687 1688 1689 1690 1691 1692 1693 1694
```

FIG. 53O

```
5'  AATCATTATCAAGCGCATCCGTGGCAACACCAACGATACTAGGGTGAGAGGTGGCGACATTCTGTACTTC
                                                                              9240
              BoNT/C Receptor Binding Domain
        I   I   K   R   I   R   G   N   T   N   D   T   R   V   R   G   G   D   I   L   Y   F
      1695 1696 1697 1698 1699 1700 1701 1702 1703 1704 1705 1706 1707 1708 1709 1710 1711 1712 1713 1714 1715 1716 1717

5'  GATATGACTATCAACAACAAAGCCTACAACTTGTTCATGAAAAACGAGACAATGTACGCCGACAAcCATA
                                                                              9310
              BoNT/C Receptor Binding Domain
      D   M   T   I   N   N   K   A   Y   N   L   F   M   K   N   E   T   M   Y   A   D   N   H
     1718 1719 1720 1721 1722 1723 1724 1725 1726 1727 1728 1729 1730 1731 1732 1733 1734 1735 1736 1737 1738 1739 1740

5'  GCACGGAGGATATTTACGCAATCGGACTGAGGGAACAGACAAAGGACATCAACGATAACATTATCTTCCA
                                                                              9380
              BoNT/C Receptor Binding Domain
      S   T   E   D   I   Y   A   I   G   L   R   E   Q   T   K   D   I   N   D   N   I   I   F   Q
     1741 1742 1743 1744 1745 1746 1747 1748 1749 1750 1751 1752 1753 1754 1755 1756 1757 1758 1759 1760 1761 1762 1763 1764

5'  GATCCAACCTATGAACAACACGTACTACTACGCTTCGCAAATCTTCAAGTCCAACTTCAACGGAGAAAAC
                                                                              9450
              BoNT/C Receptor Binding Domain
      I   Q   P   M   N   N   T   Y   Y   Y   A   S   Q   I   F   K   S   N   F   N   G   E   N
     1765 1766 1767 1768 1769 1770 1771 1772 1773 1774 1775 1776 1777 1778 1779 1780 1781 1782 1783 1784 1785 1786 1787

5'  ATTTCGGGTATCTGTTCCATTGGCACATACCGCTTCCGTCTGGGTGGTGACTGGTATCGTCACAACTACC
                                                                              9520
              BoNT/C Receptor Binding Domain
      I   S   G   I   C   S   I   G   T   Y   R   F   R   L   G   G   D   W   Y   R   H   N   Y
     1788 1789 1790 1791 1792 1793 1794 1795 1796 1797 1798 1799 1800 1801 1802 1803 1804 1805 1806 1807 1808 1809 1810

                                                              SalI
5'  TCGTTCCCACCGTGAAGCAGGGTAACTACGCTTCTTTGCTGGAGTCGACTTCCACGCACTGGGGATTCGT
                                                                              9590
              BoNT/C Receptor Binding Domain
      L   V   P   T   V   K   Q   G   N   Y   A   S   L   L   E   S   T   S   T   H   W   G   F   V
     1811 1812 1813 1814 1815 1816 1817 1818 1819 1820 1821 1822 1823 1824 1825 1826 1827 1828 1829 1830 1831 1832 1833 1834

5'  TCCTGTGTCAGAGGGCGCTGGCTACCCTTACGATGTTCCCGACTACGCTGGTTGGGAACTCCAGCAAGGT
                                                                              9660
     BoNT/C Rec...ng Domain | linker |     HA tag     | li...r |  SpeI site  | linker
      P   V   S   E   G   A   Y   P   Y   D   V   P   D   Y   A   G   W   E   L   Q   Q   G
     1835 1836 1837 1838 1839 1840 1841 1842 1843 1844 1845 1846 1847 1848 1849 1850 1851 1852 1853 1854 1855 1856 1857
```

FIG. 53P

5' GCAGGATGGTCCCACCCTCAATTCGAGAAGGGTGCCGGATGGAGTCACCCACAGTTCGAGAAAGGCGCTG 9730 linker | Strep tag II | linker | Strep tag II | linker

A G W S H P Q F E K G A G W S H P Q F E K G A 1858 1859 1860 1861 1862 1863 1864 1865 1866 1867 1868 1869 1870 1871 1872 1873 1874 1875 1876 1877 1878 1879 1880

NsiI XhoI

5' GATGGAGTCACCCACAGTTCGAGAAATAATTAGTTGATGCATAGTTAATTAGATAGCTCGAGGCATGCGG 9800 l... | Strep tag II

G W S H P Q F E K 1881 1882 1883 1884 1885 1886 1887 1888 1889

NsiI XhoI

5' TACCAAGATTGGATCTAGATGCATAGTTAATTAGATAGCTCGAGGCATGCGGTACCAAGCTTGTCGAGAA 9870

5' GTACTAGAGGATCATAATCAGCCATACCACATTTGTAGAGGTTTTACTTGCTTTAAAAAACCTCCCACAC 9940

HpaI

5' CTCCCCCTGAACCTGAAACATAAAATGAATGCAATTGTTGTTGTTAACTTGTTTATTGCAGCTTATAATG 10010

5' GTTACAAATAAAGCAATAGCATCACAAATTTCACAAATAAAGCATTTTTTTCACTGCATTCTAGTTGTGG 10080

AvrII

5' TTTGTCCAAACTCATCAATGTATCTTATCATGTCTGGATCTGATCACTGCTTGAGCCTAGGAGATCCGAA 10150

5' CCAGATAAGTGAAATCTAGTTCCAAACTATTTTGTCATTTTTAATTTTCGTATTAGCTTACGACGCTACA 10220

5' CCCAGTTCCCATCTATTTTGTCACTCTTCCCTAAATAATCCTTAAAAACTCCATTTCCACCCCTCCCAGT 10290

5' TCCCAACTATTTTGTCCGCCCACAGCGGGGCATTTTTCTTCCTGTTATGTTTTTAATCAAACATCCTGCC 10360

5' AACTCCATGTGACAAACCGTCATCTTCGGCTACTTTTTCTCTGTCACAGAATGAAAATTTTTCTGTCATC 10430

5' TCTTCGTTATTAATGTTTGTAATTGACTGAATATCAACGCTTATTTGCAGCCTGAATGGCGAATGG 10496

FIG. 53Q

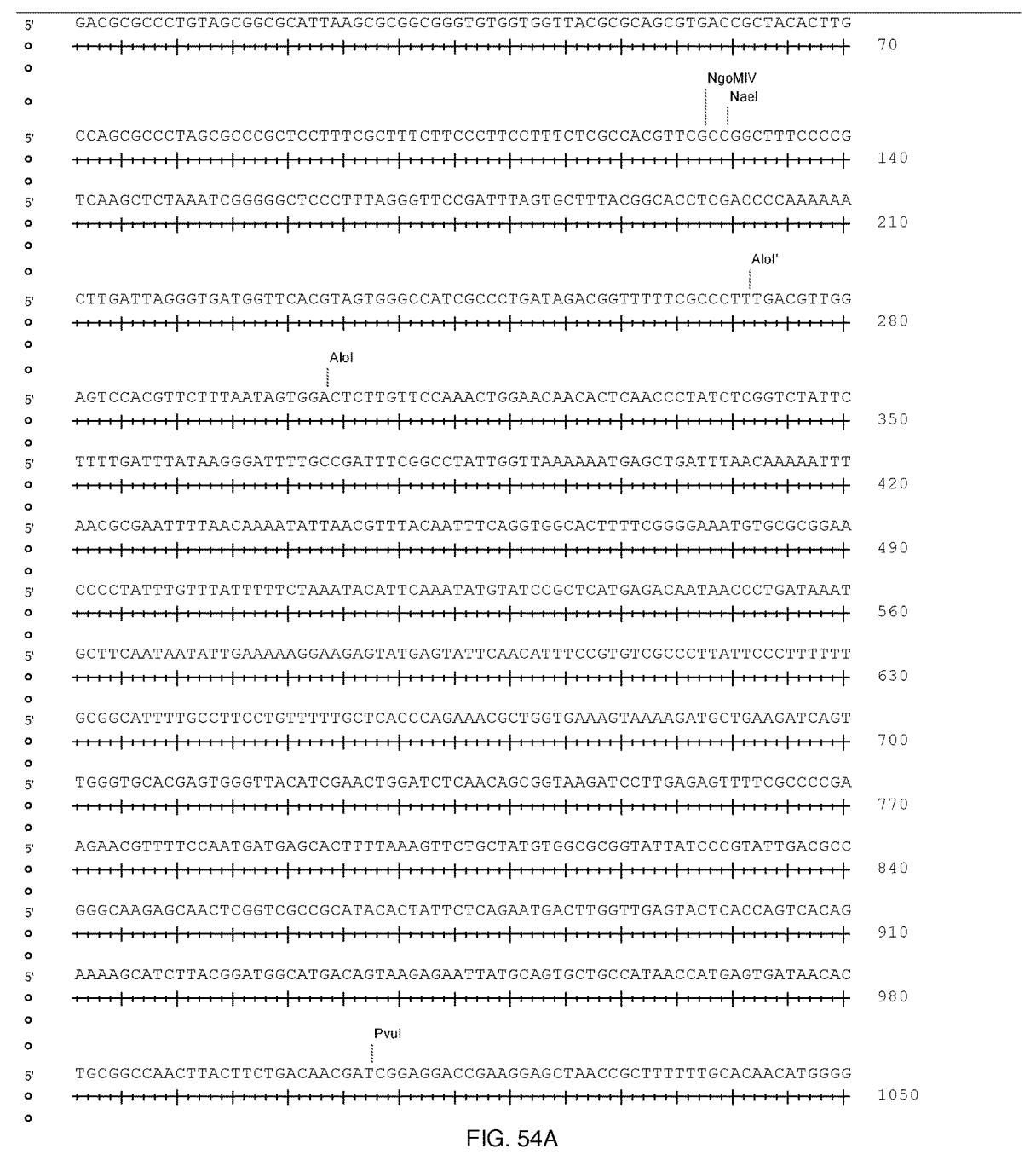

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 54A

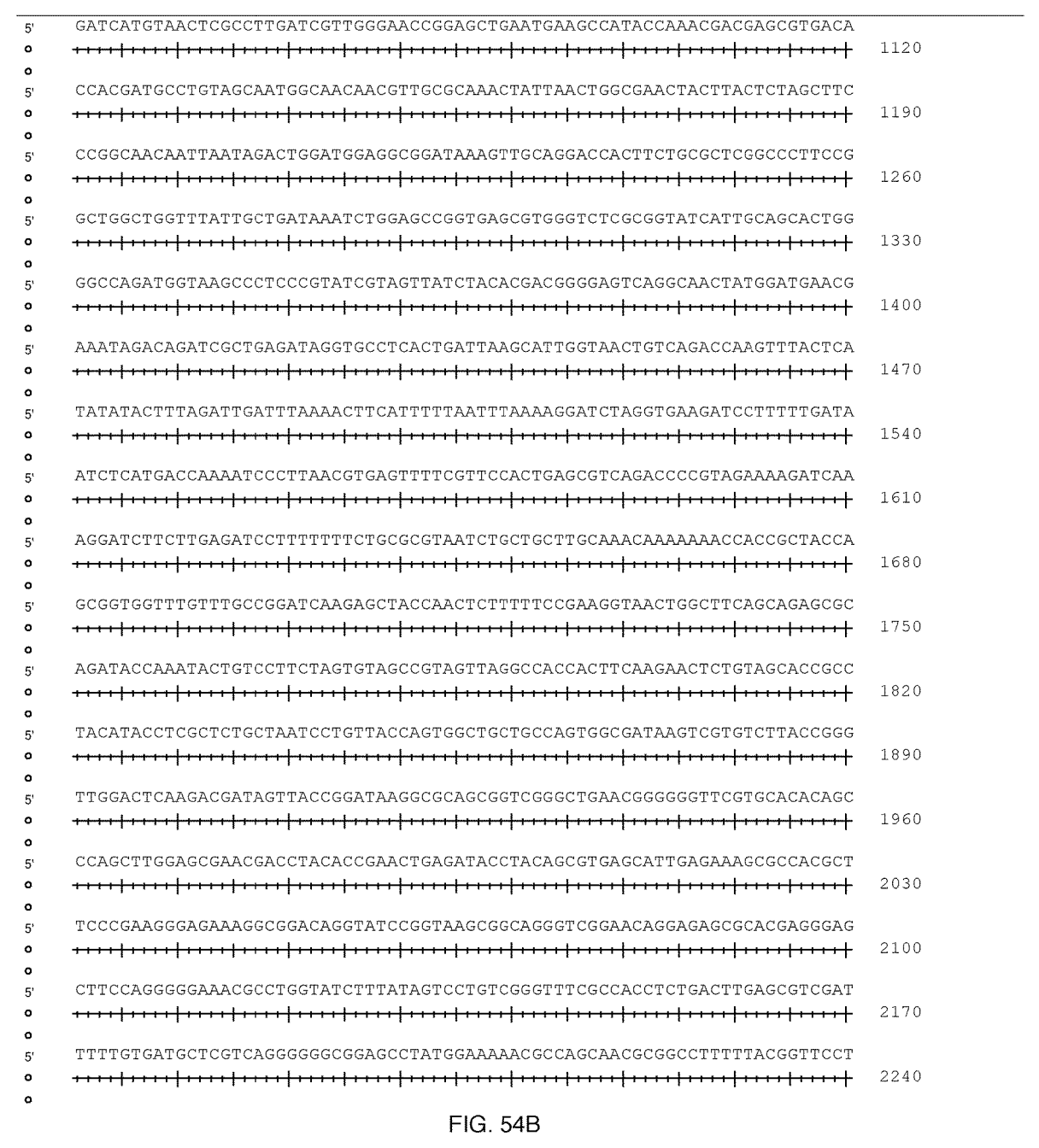

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 54B

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 54C

```
5'  AGGGCGACTGCCCTGCTGCGTAACATCGTTGCTGCTGCGTAACATCGTTGCTGCTCCATAACATCAAACA
                                                                              3360

5'  TCGACCCACGGCGTAACGCGCTTGCTGCTTGGATGCCCGAGGCATAGACTGTACAAAAAAACAGTCATAA
                                                                              3430

5'  CAAGCCATGAAAACCGCCACTGCGCCGTTACCACCGCTGCGTTCGGTCAAGGTTCTGGACCAGTTGCGTG
                                                                              3500

5'  AGCGCATACGCTACTTGCATTACAGTTTACGAACCGAACAGGCTTATGTCAACTGGGTTCGTGCCTTCAT
                                                                              3570

5'  CCGTTTCCACGGTGTGCGTCACCCGGCAACCTTGGGCAGCAGCGAAGTCGAGGCATTTCTGTCCTGGCTG
                                                                              3640

5'  GCGAACGAGCGCAAGGTTTCGGTCTCCACGCATCGTCAGGCATTGGCGGCCTTGCTGTTCTTCTACGGCA
                                                                              3710

5'  AGGTGCTGTGCACGGATCTGCCCTGGCTTCAGGAGATCGGAAGACCTCGGCCGTCGCGGCGCTTGCCGGT
                                                                              3780

5'  GGTGCTGACCCCGGATGAAGTGGTTCGCATCCTCGGTTTTCTGGAAGGCGAGCATCGTTTGTTCGCCCAG
                                                                              3850

                                       SnaBI
                                         BstZ17I
5'  GACTCTAGCTATAGTTCTAGTGGTTGGCTACGTATACTCCGGAATATTAATAGATCATGGAGATAATTAA
                                                                              3920

5'  AATGATAACCATCTCGCAAATAAATAAGTATTTTACTGTTTTCGTAACAGTTTTGTAATAAAAAAACCTA
                                                                              3990

                                                      RsrII
5'  TAAATATTCCGGATTATTCATACCGTCCCACCATCGGGCGCGGATCTCGGTCCGTTCGAACCAGAACTCT
                                                                              4060
                                             [mut....mHI]
5'  GGAAGCTTAACTCCTAAAAAACCGCCACCATGAAATTCTTAGTCAACGTTGCCCTTGTTTTTATGGTCGT
                                                                              4130
    | Lob. TMO cDNA Lead Seq |            Signal Peptide
                              M  K  F  L  V  N  V  A  L  V  F  M  V  V
                              1  2  3  4  5  6  7  8  9  10 11 12 13 14
```

FIG. 54D

```
                                                          AleI
5' TGGAGGTAGCTGGTCTAACTTCGGTTACTGGGGTCAAGGCACCCAAGTGACTGTCTCTTCAGGCGGAGGT
   ++++|++++|++++|++++|++++|++++|++++|++++|++++|++++|++++|++++|++++|++++|   4620
        EPEA alpha-synuclein VHH 1                              VHH spacer
    G   G   S   W   S   N   F   G   Y   W   G   Q   G   T   Q   V   T   V   S   S   G   G   G
   155 156 157 158 159 160 161 162 163 164 165 166 167 168 169 170 171 172 173 174 175 176 177

    NotI      Bpu10I                              PvuII PstI
5' GCGGCCGCTGGCTCAGGAGGTGGCAGTCAGGTGCAGCTGCAGGAGTCGGGAGGTGGCTCCGTCCAAGCAG
   ++++|++++|++++|++++|++++|++++|++++|++++|++++|++++|++++|++++|++++|++++|   4690
            VHH spacer                      EPEA alpha-synuclein VHH 2
    A   A   A   G   S   G   G   G   S   Q   V   Q   L   Q   E   S   G   G   G   S   V   Q   A
   178 179 180 181 182 183 184 185 186 187 188 189 190 191 192 193 194 195 196 197 198 199 200

5' GAGGTAGCCTGCGCCTCTCTTGCGCAGCGTCAGGTATCGACAGTTCGTCCTACTGTATGGGCTGGTTCAG
   ++++|++++|++++|++++|++++|++++|++++|++++|++++|++++|++++|++++|++++|++++|   4760
                         EPEA alpha-synuclein VHH 2
    G   G   S   L   R   L   S   C   A   A   S   G   I   D   S   S   S   Y   C   M   G   W   F   R
   201 202 203 204 205 206 207 208 209 210 211 212 213 214 215 216 217 218 219 220 221 222 223 224

5' GCAGCGTCCTGGCAAGGAGAGGGAAGGAGTGGCACGTATCAACGGTCTCGGCGGAGTCAAGACAGCTTAC
   ++++|++++|++++|++++|++++|++++|++++|++++|++++|++++|++++|++++|++++|++++|   4830
                         EPEA alpha-synuclein VHH 2
    Q   R   P   G   K   E   R   E   G   V   A   R   I   N   G   L   G   G   V   K   T   A   Y
   225 226 227 228 229 230 231 232 233 234 235 236 237 238 239 240 241 242 243 244 245 246 247

5' GCCGACTCCGTTAAAGATAGGTTCACCATTAGCCGCGACAACGCTGAGAACACTGTCTACCTCCAAATGA
   ++++|++++|++++|++++|++++|++++|++++|++++|++++|++++|++++|++++|++++|++++|   4900
                         EPEA alpha-synuclein VHH 2
    A   D   S   V   K   D   R   F   T   I   S   R   D   N   A   E   N   T   V   Y   L   Q   M
   248 249 250 251 252 253 254 255 256 257 258 259 260 261 262 263 264 265 266 267 268 269 270

5' ACAGTTTGAAGCCGGAAGATACTGCCATTTACTACTGTGCTGCCAAATTCTCACCGGGCTACTGTGGAGG
   ++++|++++|++++|++++|++++|++++|++++|++++|++++|++++|++++|++++|++++|++++|   4970
                         EPEA alpha-synuclein VHH 2
    N   S   L   K   P   E   D   T   A   I   Y   Y   C   A   A   K   F   S   P   G   Y   C   G   G
   271 272 273 274 275 276 277 278 279 280 281 282 283 284 285 286 287 288 289 290 291 292 293 294
```

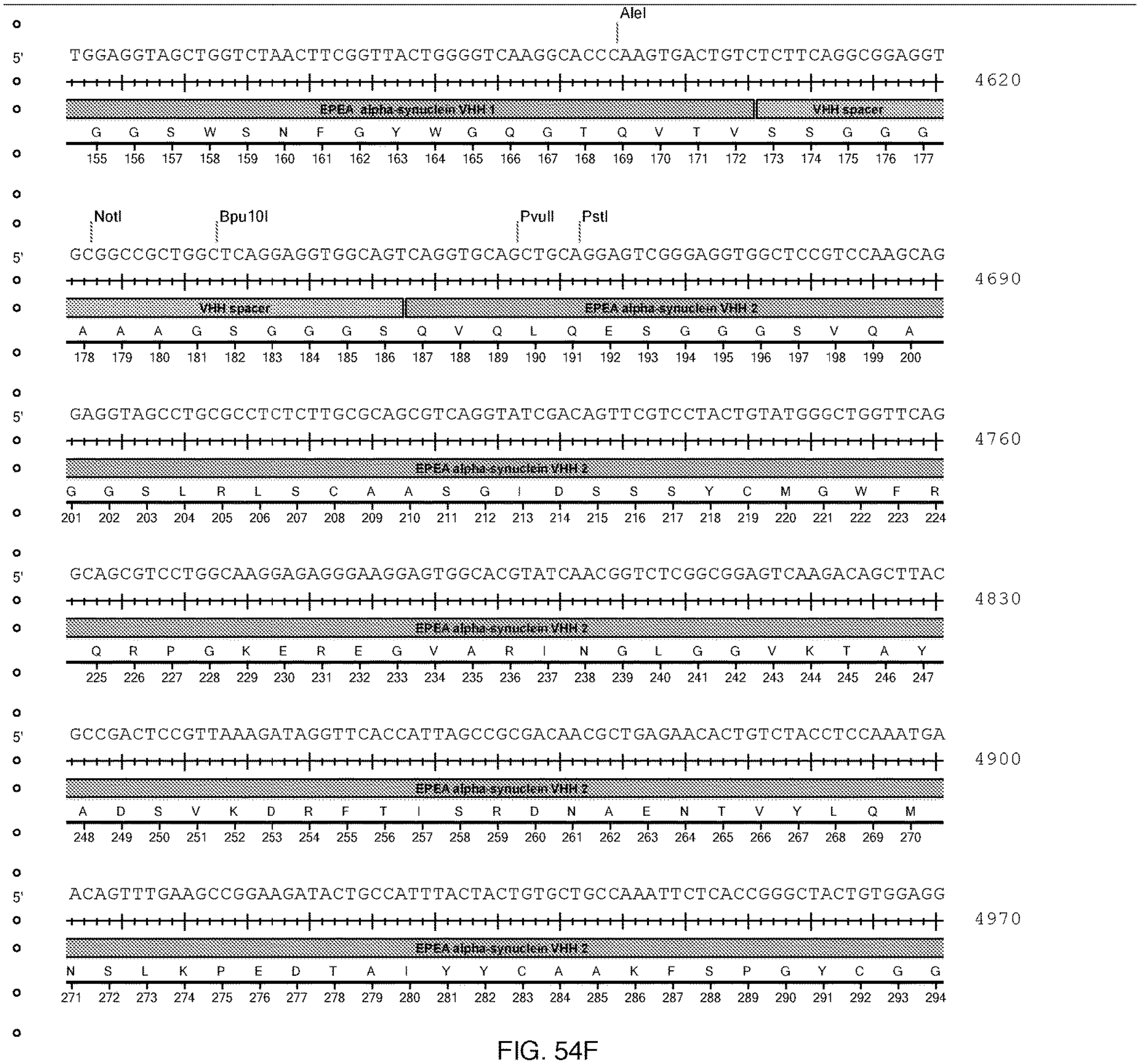

FIG. 54F

```
                                                        NgoMIV
                                                        | Nael
                                                        | | Fsel
5'  AAGCTGGTCTAACTTCGGCTACTGGGGACAAGGAACTCAAGTCACCGTTGGGGCCGGCCAGGGTGCTGGT
                                                                                    5040
    |EPEA alpha-synuclein VHH 2                         |linker
    S   W   S   N   F   G   Y   W   G   Q   G   T   Q   V   T   V   G   A   G   Q   G   A   G
    295 296 297 298 299 300 301 302 303 304 305 306 307 308 309 310 311 312 313 314 315 316 317

                                    BamHI
5'  GCTGGACCGATCACCATCAACAACTTCAATTACTCGGATCCGGTGGATAACAAGAACATCCTCTACTTGG
                                                                                    5110
    |linker |                 BoNT/C1 ad0 LC
    A   G   P   I   T   I   N   N   F   N   Y   S   D   P   V   D   N   K   N   I   L   Y   L
    318 319 320 321 322 323 324 325 326 327 328 329 330 331 332 333 334 335 336 337 338 339 340

5'  ACACACACTTGAACACGCTGGCTAACGAGCCTGAAAAAGCTTTCAGGATCACCGGCAACATTTGGGTCAT
                                                                                    5180
                              BoNT/C1 ad0 LC
    D   T   H   L   N   T   L   A   N   E   P   E   K   A   F   R   I   T   G   N   I   W   V   I
    341 342 343 344 345 346 347 348 349 350 351 352 353 354 355 356 357 358 359 360 361 362 363 364

5'  TCCGGATAGGTTCAGCAGAAACTCTAACCCTAACTTGAACAAACCTCCCAGAGTGACCTCACCTAAGAGT
                                                                                    5250
                              BoNT/C1 ad0 LC
    P   D   R   F   S   R   N   S   N   P   N   L   N   K   P   P   R   V   T   S   P   K   S
    365 366 367 368 369 370 371 372 373 374 375 376 377 378 379 380 381 382 383 384 385 386 387

5'  GGATACTACGACCCCAACTACCTCTCGACTGACTCCGATAAAGACCCCTTCCTGAAGGAGATCATTAAAC
                                                                                    5320
                              BoNT/C1 ad0 LC
    G   Y   Y   D   P   N   Y   L   S   T   D   S   D   K   D   P   F   L   K   E   I   I   K
    388 389 390 391 392 393 394 395 396 397 398 399 400 401 402 403 404 405 406 407 408 409 410

5'  TCTTCAAGCGCATCAACTCTCGTGAAATTGGCGAGGAATTGATCTACCGCCTGAGTACAGACATCCCATT
                                                                                    5390
                              BoNT/C1 ad0 LC
    L   F   K   R   I   N   S   R   E   I   G   E   E   L   I   Y   R   L   S   T   D   I   P   F
    411 412 413 414 415 416 417 418 419 420 421 422 423 424 425 426 427 428 429 430 431 432 433 434
```

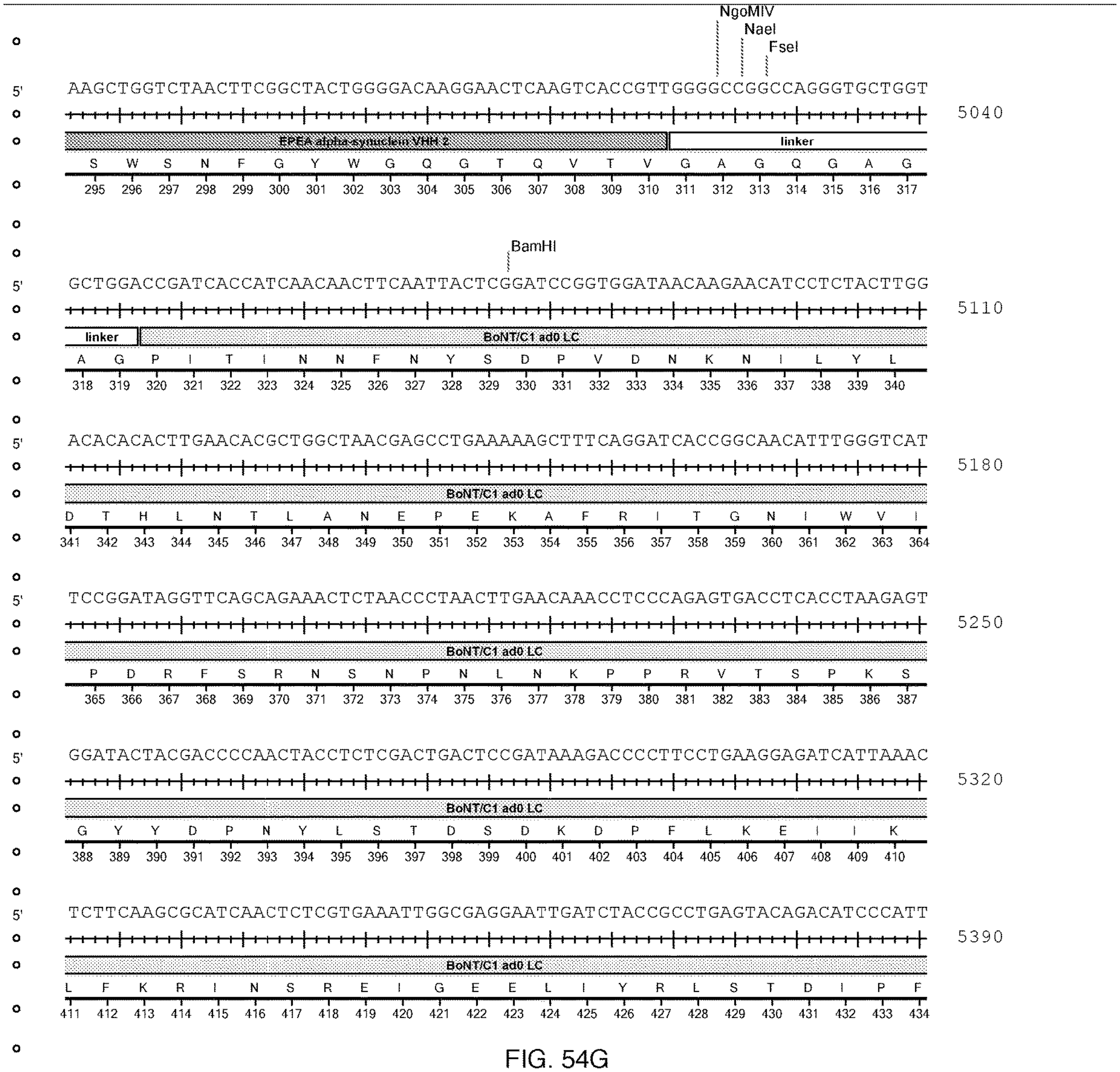

FIG. 54G

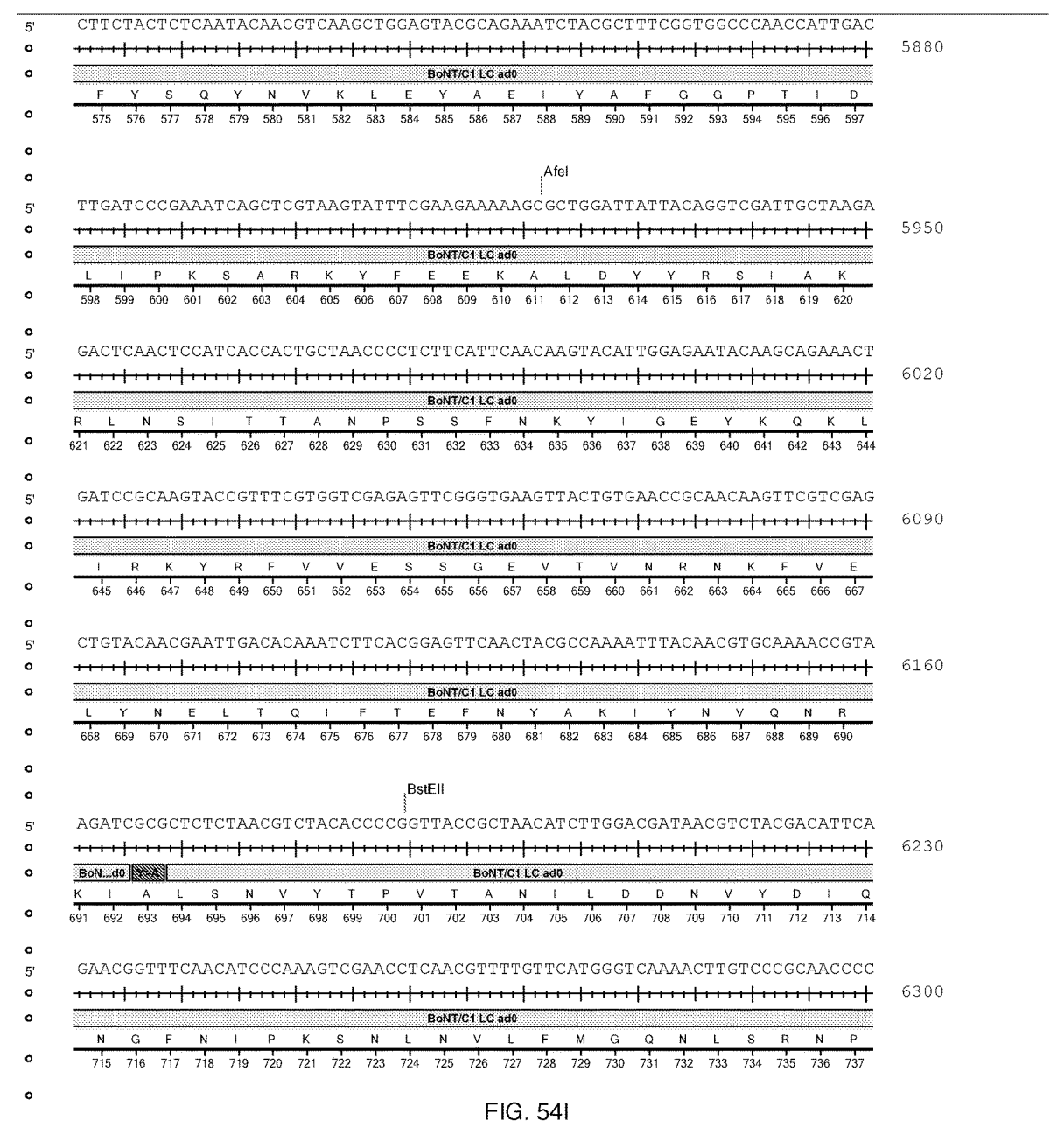

5' CTTCTACTCTCAATACAACGTCAAGCTGGAGTACGCAGAAATCTACGCTTTCGGTGGCCCAACCATTGAC 5880
BoNT/C1 LC ad0
F Y S Q Y N V K L E Y A E I Y A F G G P T I D
575 576 577 578 579 580 581 582 583 584 585 586 587 588 589 590 591 592 593 594 595 596 597

AfeI
5' TTGATCCCGAAATCAGCTCGTAAGTATTTCGAAGAAAAAGCGCTGGATTATTACAGGTCGATTGCTAAGA 5950
BoNT/C1 LC ad0
L I P K S A R K Y F E E K A L D Y Y R S I A K
598 599 600 601 602 603 604 605 606 607 608 609 610 611 612 613 614 615 616 617 618 619 620

5' GACTCAACTCCATCACCACTGCTAACCCCTCTTCATTCAACAAGTACATTGGAGAATACAAGCAGAAACT 6020
BoNT/C1 LC ad0
R L N S I T T A N P S S F N K Y I G E Y K Q K L
621 622 623 624 625 626 627 628 629 630 631 632 633 634 635 636 637 638 639 640 641 642 643 644

5' GATCCGCAAGTACCGTTTCGTGGTCGAGAGTTCGGGTGAAGTTACTGTGAACCGCAACAAGTTCGTCGAG 6090
BoNT/C1 LC ad0
I R K Y R F V V E S S G E V T V N R N K F V E
645 646 647 648 649 650 651 652 653 654 655 656 657 658 659 660 661 662 663 664 665 666 667

5' CTGTACAACGAATTGACACAAATCTTCACGGAGTTCAACTACGCCAAAATTTACAACGTGCAAAACCGTA 6160
BoNT/C1 LC ad0
L Y N E L T Q I F T E F N Y A K I Y N V Q N R
668 669 670 671 672 673 674 675 676 677 678 679 680 681 682 683 684 685 686 687 688 689 690

BstEII
5' AGATCGCGCTCTCTAACGTCTACACCCCGGTTACCGCTAACATCTTGGACGATAACGTCTACGACATTCA 6230
BoN...d0 BoNT/C1 LC ad0
K I A L S N V Y T P V T A N I L D D N V Y D I Q
691 692 693 694 695 696 697 698 699 700 701 702 703 704 705 706 707 708 709 710 711 712 713 714

5' GAACGGTTTCAACATCCCAAAGTCGAACCTCAACGTTTTGTTCATGGGTCAAAACTTGTCCCGCAACCCC 6300
BoNT/C1 LC ad0
N G F N I P K S N L N V L F M G Q N L S R N P
715 716 717 718 719 720 721 722 723 724 725 726 727 728 729 730 731 732 733 734 735 736 737

FIG. 54I

5' GCCCTGCGTAAGGTGAACCCAGAGAACATGTTGTACCTGTTCACCAAATTCTGCCACAAGGCCATCGACG 6370

BoNT/C1 LC ad0

A L R K V N P E N M L Y L F T K F C H K A I D 738 739 740 741 742 743 744 745 746 747 748 749 750 751 752 753 754 755 756 757 758 759 760

5' GTCAGTCTCTAGACCAAGGAGGATGGGAACTCCAGCAAGGTGGCCAGGGTGGAGGTGCTGGCACCCTGGA 6440

LC/HC spacer | SpI B site | LC/HC spacer | BoNT/...omain

G Q S L D Q G G W E L Q Q G G Q G G G A G T L D 761 762 763 764 765 766 767 768 769 770 771 772 773 774 775 776 777 778 779 780 781 782 783 784

5' CTGTCGCGAACTGCTCGTTAAGAACACTGATCTCCCATTCATTGGCGACATCTCTGATGTGAAAACAGAC 6510

BoNT/C Translocation Domain

C R E L L V K N T D L P F I G D I S D V K T D 785 786 787 788 789 790 791 792 793 794 795 796 797 798 799 800 801 802 803 804 805 806 807

5' ATTTTCCTGCGTAAGGATATCAACGAGGAAACGGAGGTCATCTACTACCCTGACAACGTCTCGGTTGATC 6580

BoNT/C Translocation Domain

I F L R K D I N E E T E V I Y Y P D N V S V D 808 809 810 811 812 813 814 815 816 817 818 819 820 821 822 823 824 825 826 827 828 829 830

5' AGGTTATCTTGTCAAAGAACACCAGTGAACATGGCCAACTGGACTTGCTGTACCCCTCAATTGATTCCGA 6650

BoNT/C Translocation Domain

Q V I L S K N T S E H G Q L D L L Y P S I D S E 831 832 833 834 835 836 837 838 839 840 841 842 843 844 845 846 847 848 849 850 851 852 853 854

SexAI

5' GAGCGAAATCCTGCCAGGAGAGAACCAGGTTTTCTACGACAACAGGACACAAAACGTGGATTACCTCAAC 6720

BoNT/C Translocation Domain

S E I L P G E N Q V F Y D N R T Q N V D Y L N 855 856 857 858 859 860 861 862 863 864 865 866 867 868 869 870 871 872 873 874 875 876 877

5' AGCTACTACTACCTGGAGTCGCAGAAGCTCTCCGACAACGTCGAAGATTTCACATTTACGAGATCAATCG 6790

BoNT/C Translocation Domain

5' AGGAGGCTTTGGACAACAGTGCCAAAGTCTACACCTACTTCCCTACTCTGGCAAACAAGGTGAACGCGGG 6860
BoNT/C Translocation Domain
E E A L D N S A K V Y T Y F P T L A N K V N A G
901 902 903 904 905 906 907 908 909 910 911 912 913 914 915 916 917 918 919 920 921 922 923 924

5' TGTCCAAGGCGGACTCTTCTTGATGTGGGCTAACGACGTTGTGGAAGATTTCACAACGAACATCTTGCGC 6930
BoNT/C Translocation Domain
V Q G G L F L M W A N D V V E D F T T N I L R
925 926 927 928 929 930 931 932 933 934 935 936 937 938 939 940 941 942 943 944 945 946 947

5' AAAGACACCCTGGATAAGATCAGCGATGTCTCTGCCATCATTCCATACATTGGCCCGGCACTGAACATCT 7000
BoNT/C Translocation Domain
K D T L D K I S D V S A I I P Y I G P A L N I
948 949 950 951 952 953 954 955 956 957 958 959 960 961 962 963 964 965 966 967 968 969 970

5' CTAACTCAGTTCGCCGTGGCAACTTCACTGAGGCATTCGCGGTCACAGGAGTTACGATCCTCTTGGAGGC 7070
BoNT/C Translocation Domain
S N S V R R G N F T E A F A V T G V T I L L E A
971 972 973 974 975 976 977 978 979 980 981 982 983 984 985 986 987 988 989 990 991 992 993 994

PfoI
5' TTTCCCGGAGTTCACAATCCCCGCACTGGGCGCGTTCGTTATCTACTCCAAAGTGCAGGAGCGCAACGAA 7140
BoNT/C Translocation Domain
F P E F T I P A L G A F V I Y S K V Q E R N E
995 996 997 998 999 1000 1001 1002 1003 1004 1005 1006 1007 1008 1009 1010 1011 1012 1013 1014 1015 1016 1017

BsiWI
5' ATCATTAAGACTATCGACAACTGCCTGGAGCAAAGGATCAAAAGATGGAAGGATTCGTACGAATGGATGA 7210
BoNT/C Translocation Domain
I I K T I D N C L E Q R I K R W K D S Y E W M
1018 1019 1020 1021 1022 1023 1024 1025 1026 1027 1028 1029 1030 1031 1032 1033 1034 1035 1036 1037 1038 1039 1040

5' TGGGTACCTGGCTCTCCCGTATCATTACGCAGTTCAACAACATCAGCTACCAAATGTACGACTCTCTCAA 7280
BoNT/C Translocation Domain
M G T W L S R I I T Q F N N I S Y Q M Y D S L N
1041 1042 1043 1044 1045 1046 1047 1048 1049 1050 1051 1052 1053 1054 1055 1056 1057 1058 1059 1060 1061 1062 1063 1064

FIG. 54K

XcmI

5' CTACCAGGCTGGTGCCATCAAGGCCAAAATTGACTTGGAGTACAAGAAATACAGTGGCTCGGATAAAGAG 7350

BoNT/C Translocation Domain

Y Q A G A I K A K I D L E Y K K Y S G S D K E 1065 1066 1067 1068 1069 1070 1071 1072 1073 1074 1075 1076 1077 1078 1079 1080 1081 1082 1083 1084 1085 1086 1087

5' AACATCAAGAGTCAAGTCGAAAaCCTGAAAAACTCACTCGACGTTAAGATCAGTGAGGCAATGAACAACA 7420

BoNT/C Translocation Domain

N I K S Q V E N L K N S L D V K I S E A M N N 1088 1089 1090 1091 1092 1093 1094 1095 1096 1097 1098 1099 1100 1101 1102 1103 1104 1105 1106 1107 1108 1109 1110

5' TCAACAAGTTCATTCGCGAATGTTCCGTTACCTACCTCTTCAAAAACATGTTGCCAAAGGTCATCGACGA 7490

BoNT/C Translocation Domain

I N K F I R E C S V T Y L F K N M L P K V I D E 1111 1112 1113 1114 1115 1116 1117 1118 1119 1120 1121 1122 1123 1124 1125 1126 1127 1128 1129 1130 1131 1132 1133 1134

5' GCTGAACGAATTTGATCGTAACACTAAGGCGAAACTGATTAACCTCATCGACTCACACAACATCATTTTG 7560

BoNT/C Translocation Domain

L N E F D R N T K A K L I N L I D S H N I I L 1135 1136 1137 1138 1139 1140 1141 1142 1143 1144 1145 1146 1147 1148 1149 1150 1151 1152 1153 1154 1155 1156 1157

5' GTGGGCGAAGTCGATAAGCTGAAAGCCAAGGtGAACAACAGTTTCCAGAACACAATCCCTTTCAAcATTT 7630

BoNT/C Translocation Domain

V G E V D K L K A K V N N S F Q N T I P F N I 1158 1159 1160 1161 1162 1163 1164 1165 1166 1167 1168 1169 1170 1171 1172 1173 1174 1175 1176 1177 1178 1179 1180

5' TCTCATACACGAACAACAGTCTGCTCAAGGACATCATTAACGAGTACTTCAACAACATTAACGATAGCAA 7700

BoNT/C Translocation Domain | BoNT/C Receptor Binding Domain

F S Y T N N S L L K D I I N E Y F N N I N D S K 1181 1182 1183 1184 1185 1186 1187 1188 1189 1190 1191 1192 1193 1194 1195 1196 1197 1198 1199 1200 1201 1202 1203 1204

PstI SpeI

5' AATCCTGTCACTGCAGAACCGTAAGAACACACTGGTCGATACTAGTGGATACAACGCCGAAGTCTCTGAG 7770

BoNT/C Receptor Binding Domain

```
                          PvuII
5'  GAAGGTGACGTGCAGCTGAACCCTATCTTCCCCTTCGACTTCAAATTGGGCTCCAGCGGAGAGGATAGGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7840
                          BoNT/C Receptor Binding Domain
     E   G   D   V   Q   L   N   P   I   F   P   F   D   F   K   L   G   S   S   G   E   D   R
    1228 1229 1230 1231 1232 1233 1234 1235 1236 1237 1238 1239 1240 1241 1242 1243 1244 1245 1246 1247 1248 1249 1250

5'  GCAAGGTCATCGTCACCCAGAACGAGAACATCGTCTACAACTCAATGTACGAATCCTTCAGCATCTCTTT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7910
                          BoNT/C Receptor Binding Domain
     G   K   V   I   V   T   Q   N   E   N   I   V   Y   N   S   M   Y   E   S   F   S   I   S   F
    1251 1252 1253 1254 1255 1256 1257 1258 1259 1260 1261 1262 1263 1264 1265 1266 1267 1268 1269 1270 1271 1272 1273 1274

                                                    BspMI
5'  CTGGATCAGGATTAACAAGTGGGTGAGCAACCTGCCCGGTTACACAATCATTGACTCTGTCAAGAACAAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  7980
                          BoNT/C Receptor Binding Domain
     W   I   R   I   N   K   W   V   S   N   L   P   G   Y   T   I   I   D   S   V   K   N   N
    1275 1276 1277 1278 1279 1280 1281 1282 1283 1284 1285 1286 1287 1288 1289 1290 1291 1292 1293 1294 1295 1296 1297

5'  TCAGGTTGGAGTATCGGCATCATTTCTAACTTCTTGGTCTTCACCCTGAAGCAGAACGAGGACTCGGAAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8050
                          BoNT/C Receptor Binding Domain
     S   G   W   S   I   G   I   I   S   N   F   L   V   F   T   L   K   Q   N   E   D   S   E
    1298 1299 1300 1301 1302 1303 1304 1305 1306 1307 1308 1309 1310 1311 1312 1313 1314 1315 1316 1317 1318 1319 1320

5'  AATCCATTAACTTCTCATACGATATCAGTAACAACGCTCCAGGTTACAACAAGTGGTTCTTCGTTACCGT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8120
                          BoNT/C Receptor Binding Domain
     Q   S   I   N   F   S   Y   D   I   S   N   N   A   P   G   Y   N   K   W   F   F   V   T   V
    1321 1322 1323 1324 1325 1326 1327 1328 1329 1330 1331 1332 1333 1334 1335 1336 1337 1338 1339 1340 1341 1342 1343 1344

5'  GACTAACAACATGATGGGTAACATGAAAATTTACATCAACGGCAAGCTCATTGACACCATCAAAGTGAAG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8190
                          BoNT/C Receptor Binding Domain
     T   N   N   M   M   G   N   M   K   I   Y   I   N   G   K   L   I   D   T   I   K   V   K
    1345 1346 1347 1348 1349 1350 1351 1352 1353 1354 1355 1356 1357 1358 1359 1360 1361 1362 1363 1364 1365 1366 1367

5'  GAGTTGACTGGTATTAACTTCTCCAAAACAATCACGTTTGAAATTAaCaAGATCCCTGACACCGGCCTGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  8260
                          BoNT/C Receptor Binding Domain
     E   L   T   G   I   N   F   S   K   T   I   T   F   E   I   N   K   I   P   D   T   G   L
    1368 1369 1370 1371 1372 1373 1374 1375 1376 1377 1378 1379 1380 1381 1382 1383 1384 1385 1386 1387 1388 1389 1390
```

FIG. 54M

EcoICRI
SacI

5' TCACTTCAGACAGTGATAACATCAACATGTGGATTAGGGATTTCTACATCTTCGCCAAGGAGCTCGACGG 8330

BoNT/C Receptor Binding Domain

I T S D S D N I N M W I R D F Y I F A K E L D G 1391 1392 1393 1394 1395 1396 1397 1398 1399 1400 1401 1402 1403 1404 1405 1406 1407 1408 1409 1410 1411 1412 1413 1414

5' AAAGGATATTAACATCCTCTTCAACAGCTTGCAGTACACCAACGTCGTTAAAGACTACTGGGGTAACGAT 8400

BoNT/C Receptor Binding Domain

K D I N I L F N S L Q Y T N V V K D Y W G N D 1415 1416 1417 1418 1419 1420 1421 1422 1423 1424 1425 1426 1427 1428 1429 1430 1431 1432 1433 1434 1435 1436 1437

5' TTGAGATACAACAAGGAGTACTACATGGTCAACATCGACTACCTGAACAGGTACATGTACGCTAACTCCC 8470

BoNT/C Receptor Binding Domain

L R Y N K E Y Y M V N I D Y L N R Y M Y A N S 1438 1439 1440 1441 1442 1443 1444 1445 1446 1447 1448 1449 1450 1451 1452 1453 1454 1455 1456 1457 1458 1459 1460

5' GCCAAATCGTGTTCAACACCAGGAGAAACAACAACGACTTCAACGAGGGTTACAAAATCATTATCAAGCG 8540

BoNT/C Receptor Binding Domain

R Q I V F N T R R N N N D F N E G Y K I I I K R 1461 1462 1463 1464 1465 1466 1467 1468 1469 1470 1471 1472 1473 1474 1475 1476 1477 1478 1479 1480 1481 1482 1483 1484

5' CATCCGTGGCAACACCAACGATACTAGGGTGAGAGGTGGCGACATTCTGTACTTCGATATGACTATCAAC 8610

BoNT/C Receptor Binding Domain

I R G N T N D T R V R G G D I L Y F D M T I N 1485 1486 1487 1488 1489 1490 1491 1492 1493 1494 1495 1496 1497 1498 1499 1500 1501 1502 1503 1504 1505 1506 1507

5' AACAAAGCCTACAACTTGTTCATGAAAAACGAGACAATGTACGCCGACAAcCATAGCACGGAGGATATTT 8680

BoNT/C Receptor Binding Domain

N K A Y N L F M K N E T M Y A D N H S T E D I 1508 1509 1510 1511 1512 1513 1514 1515 1516 1517 1518 1519 1520 1521 1522 1523 1524 1525 1526 1527 1528 1529 1530

5' ACGCAATCGGACTGAGGGAACAGACAAAGGACATCAACGATAACATTATCTTCCAGATCCAACCTATGAA 8750

BoNT/C Receptor Binding Domain

```
5'  CAACACGTACTACTACGCTTCGCAAATCTTCAAGTCCAACTTCAACGGAGAAAACATTTCGGGTATCTGT
                                                                               8820
                      BoNT/C Receptor Binding Domain
       N   T   Y   Y   Y   A   S   Q   I   F   K   S   N   F   N   G   E   N   I   S   G   I   C
      1555 1556 1557 1558 1559 1560 1561 1562 1563 1564 1565 1566 1567 1568 1569 1570 1571 1572 1573 1574 1575 1576 1577

5'  TCCATTGGCACATACCGCTTCCGTCTGGGTGGTGACTGGTATCGTCACAACTACCTCGTTCCCACCGTGA
                                                                               8890
                      BoNT/C Receptor Binding Domain
       S   I   G   T   Y   R   F   R   L   G   G   D   W   Y   R   H   N   Y   L   V   P   T   V
      1578 1579 1580 1581 1582 1583 1584 1585 1586 1587 1588 1589 1590 1591 1592 1593 1594 1595 1596 1597 1598 1599 1600

                                          SalI
5'  AGCAGGGTAACTACGCTTCTTTGCTGGAGTCGACTTCCACGCACTGGGGATTCGTTCCTGTGTCAGAGGG
                                                                               8960
                      BoNT/C Receptor Binding Domain                         L...
       K   Q   G   N   Y   A   S   L   L   E   S   T   S   T   H   W   G   F   V   P   V   S   E   G
      1601 1602 1603 1604 1605 1606 1607 1608 1609 1610 1611 1612 1613 1614 1615 1616 1617 1618 1619 1620 1621 1622 1623 1624

5'  CGCTGGCTACCCTTACGATGTTCCCGACTACGCTGGTTGGGAACTCCAGCAAGGTGCAGGATGGTCCCAC
                                                                               9030
      linker        HA tag          li...r    SpIc site        linker
       A   G   Y   P   Y   D   V   P   D   Y   A   G   W   E   L   Q   Q   G   A   G   W   S   H
      1625 1626 1627 1628 1629 1630 1631 1632 1633 1634 1635 1636 1637 1638 1639 1640 1641 1642 1643 1644 1645 1646 1647

5'  CCTCAATTCGAGAAGGGTGCCGGATGGAGTCACCCACAGTTCGAGAAGGCGCTGGATGGAGTCACCCAC
                                                                               9100
                          linker                              linker
       P   Q   F   E   K   G   A   G   W   S   H   P   Q   F   E   K   G   A   G   W   S   H   P
      1648 1649 1650 1651 1652 1653 1654 1655 1656 1657 1658 1659 1660 1661 1662 1663 1664 1665 1666 1667 1668 1669 1670

                          NsiI                  XhoI
5'  AGTTCGAGAAATAATTAGTTGATGCATAGTTAATTAGATAGCTCGAGGCATGCGGTACCAAGATTGGATC
                                                                               9170
       Q   F   E   K
      1671 1672 1673 1674

                   NsiI              XhoI
5'  TAGATGCATAGTTAATTAGATAGCTCGAGGCATGCGGTACCAAGCTTGTCGAGAAGTACTAGAGGATCAT
                                                                               9240

5'  AATCAGCCATACCACATTTGTAGAGGTTTTACTTGCTTTAAAAAACCTCCCACACCTCCCCCTGAACCTG
                                                                               9310
```

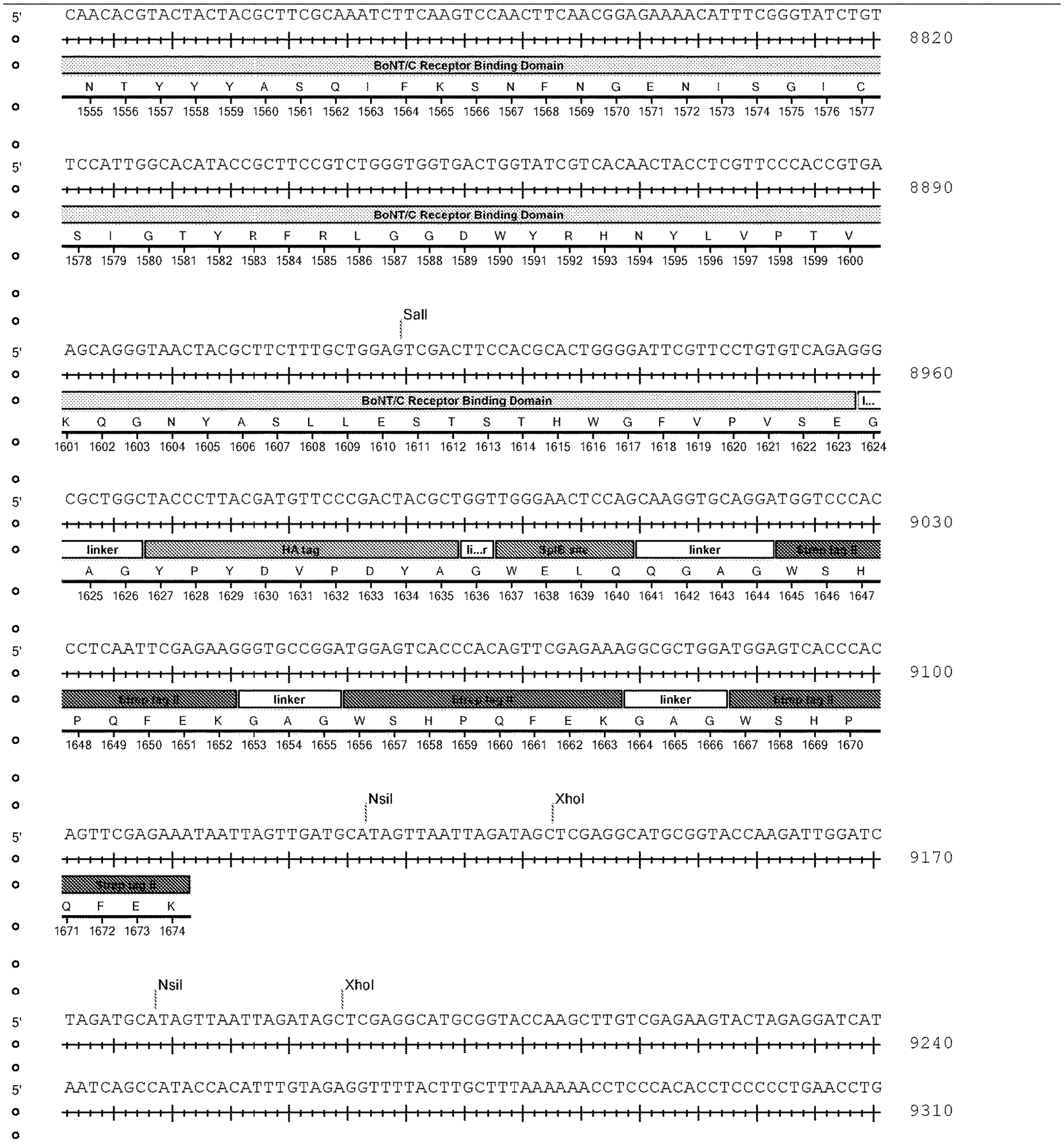

FIG. 54O

HpaI

5' AAACATAAAATGAATGCAATTGTTGTTGTTAACTTGTTTATTGCAGCTTATAATGGTTACAAATAAAGCA 9380

5' ATAGCATCACAAATTTCACAAATAAAGCATTTTTTTCACTGCATTCTAGTTGTGGTTTGTCCAAACTCAT 9450

AvrII

5' CAATGTATCTTATCATGTCTGGATCTGATCACTGCTTGAGCCTAGGAGATCCGAACCAGATAAGTGAAAT 9520

5' CTAGTTCCAAACTATTTTGTCATTTTTAATTTTCGTATTAGCTTACGACGCTACACCCAGTTCCCATCTA 9590

5' TTTTGTCACTCTTCCCTAAATAATCCTTAAAAACTCCATTTCCACCCCTCCCAGTTCCCAACTATTTTGT 9660

5' CCGCCCACAGCGGGGCATTTTTCTTCCTGTTATGTTTTTAATCAAACATCCTGCCAACTCCATGTGACAA 9730

5' ACCGTCATCTTCGGCTACTTTTTCTCTGTCACAGAATGAAAATTTTTCTGTCATCTCTTCGTTATTAATG 9800

5' TTTGTAATTGACTGAATATCAACGCTTATTTGCAGCCTGAATGGCGAATGG 9851

FIG. 54P

5' GACGCGCCCTGTAGCGGCGCATTAAGCGCGGCGGGTGTGGTGGTTACGCGCAGCGTGACCGCTACACTTG 70

NgoMIV
NaeI

5' CCAGCGCCCTAGCGCCCGCTCCTTTCGCTTTCTTCCCTTCCTTTCTCGCCACGTTCGCCGGCTTTCCCCG 140

5' TCAAGCTCTAAATCGGGGGCTCCCTTTAGGGTTCCGATTTAGTGCTTTACGGCACCTCGACCCCAAAAAA 210

AloI'

5' CTTGATTAGGGTGATGGTTCACGTAGTGGGCCATCGCCCTGATAGACGGTTTTTCGCCCTTTGACGTTGG 280

AloI

5' AGTCCACGTTCTTTAATAGTGGACTCTTGTTCCAAACTGGAACAACACTCAACCCTATCTCGGTCTATTC 350

5' TTTTGATTTATAAGGGATTTTGCCGATTTCGGCCTATTGGTTAAAAAATGAGCTGATTTAACAAAAATTT 420

5' AACGCGAATTTTAACAAAATATTAACGTTTACAATTTCAGGTGGCACTTTTCGGGGAAATGTGCGCGGAA 490

5' CCCCTATTTGTTTATTTTTCTAAATACATTCAAATATGTATCCGCTCATGAGACAATAACCCTGATAAAT 560

5' GCTTCAATAATATTGAAAAAGGAAGAGTATGAGTATTCAACATTTCCGTGTCGCCCTTATTCCCTTTTTT 630

5' GCGGCATTTTGCCTTCCTGTTTTTGCTCACCCAGAAACGCTGGTGAAAGTAAAAGATGCTGAAGATCAGT 700

5' TGGGTGCACGAGTGGGTTACATCGAACTGGATCTCAACAGCGGTAAGATCCTTGAGAGTTTTCGCCCCGA 770

5' AGAACGTTTTCCAATGATGAGCACTTTTAAAGTTCTGCTATGTGGCGCGGTATTATCCCGTATTGACGCC 840

5' GGGCAAGAGCAACTCGGTCGCCGCATACACTATTCTCAGAATGACTTGGTTGAGTACTCACCAGTCACAG 910

5' AAAAGCATCTTACGGATGGCATGACAGTAAGAGAATTATGCAGTGCTGCCATAACCATGAGTGATAACAC 980

PvuI

5' TGCGGCCAACTTACTTCTGACAACGATCGGAGGACCGAAGGAGCTAACCGCTTTTTTGCACAACATGGGG 1050

FIG. 55A

5' GATCATGTAACTCGCCTTGATCGTTGGGAACCGGAGCTGAATGAAGCCATACCAAACGACGAGCGTGACA 1120

5' CCACGATGCCTGTAGCAATGGCAACAACGTTGCGCAAACTATTAACTGGCGAACTACTTACTCTAGCTTC 1190

5' CCGGCAACAATTAATAGACTGGATGGAGGCGGATAAAGTTGCAGGACCACTTCTGCGCTCGGCCCTTCCG 1260

5' GCTGGCTGGTTTATTGCTGATAAATCTGGAGCCGGTGAGCGTGGGTCTCGCGGTATCATTGCAGCACTGG 1330

5' GGCCAGATGGTAAGCCCTCCCGTATCGTAGTTATCTACACGACGGGGAGTCAGGCAACTATGGATGAACG 1400

5' AAATAGACAGATCGCTGAGATAGGTGCCTCACTGATTAAGCATTGGTAACTGTCAGACCAAGTTTACTCA 1470

5' TATATACTTTAGATTGATTTAAAACTTCATTTTTAATTTAAAAGGATCTAGGTGAAGATCCTTTTTGATA 1540

5' ATCTCATGACCAAAATCCCTTAACGTGAGTTTTCGTTCCACTGAGCGTCAGACCCCGTAGAAAAGATCAA 1610

5' AGGATCTTCTTGAGATCCTTTTTTTCTGCGCGTAATCTGCTGCTTGCAAACAAAAAAACCACCGCTACCA 1680

5' GCGGTGGTTTGTTTGCCGGATCAAGAGCTACCAACTCTTTTTCCGAAGGTAACTGGCTTCAGCAGAGCGC 1750

5' AGATACCAAATACTGTCCTTCTAGTGTAGCCGTAGTTAGGCCACCACTTCAAGAACTCTGTAGCACCGCC 1820

5' TACATACCTCGCTCTGCTAATCCTGTTACCAGTGGCTGCTGCCAGTGGCGATAAGTCGTGTCTTACCGGG 1890

5' TTGGACTCAAGACGATAGTTACCGGATAAGGCGCAGCGGTCGGGCTGAACGGGGGGTTCGTGCACACAGC 1960

5' CCAGCTTGGAGCGAACGACCTACACCGAACTGAGATACCTACAGCGTGAGCATTGAGAAAGCGCCACGCT 2030

5' TCCCGAAGGGAGAAAGGCGGACAGGTATCCGGTAAGCGGCAGGGTCGGAACAGGAGAGCGCACGAGGGAG 2100

5' CTTCCAGGGGGAAACGCCTGGTATCTTTATAGTCCTGTCGGGTTTCGCCACCTCTGACTTGAGCGTCGAT 2170

5' TTTTGTGATGCTCGTCAGGGGGGCGGAGCCTATGGAAAAACGCCAGCAACGCGGCCTTTTTACGGTTCCT 2240

FIG. 55B

5' GGCCTTTTGCTGGCCTTTTGCTCACATGTTCTTTCCTGCGTTATCCCCTGATTCTGTGGATAACCGTATT 2310

5' ACCGCCTTTGAGTGAGCTGATACCGCTCGCCGCAGCCGAACGACCGAGCGCAGCGAGTCAGTGAGCGAGG 2380

SapI

5' AAGCGGAAGAGCGCCTGATGCGGTATTTTCTCCTTACGCATCTGTGCGGTATTTCACACCGCAGACCAGC 2450

5' CGCGTAACCTGGCAAAATCGGTTACGGTTGAGTAATAAATGGATGCCCTGCGTAAGCGGGTGTGGGCGGA 2520

5' CAATAAAGTCTTAAACTGAACAAAATAGATCTAAACTATGACAATAAAGTCTTAAACTAGACAGAATAGT 2590

5' TGTAAACTGAAATCAGTCCAGTTATGCTGTGAAAAAGCATACTGGACTTTTGTTATGGCTAAAGCAAACT 2660

5' CTTCATTTTCTGAAGTGCAAATTGCCCGTCGTATTAAAGAGGGGCGTGGCCAAGGGCATGGTAAAGACTA 2730

SacII

5' TATTCGCGGCGTTGTGACAATTTACCGAACAACTCCGCGGCCGGGAAGCCGATCTCGGCTTGAACGAATT 2800

5' GTTAGGTGGCGGTACTTGGGTCGATATCAAAGTGCATCACTTCTTCCCGTATGCCCAACTTTGTATAGAG 2870

5' AGCCACTGCGGGATCGTCACCGTAATCTGCTTGCACGTAGATCACATAAGCACCAAGCGCGTTGGCCTCA 2940

5' TGCTTGAGGAGATTGATGAGCGCGGTGGCAATGCCCTGCCTCCGGTGCTCGCCGGAGACTGCGAGATCAT 3010

AjuI'

5' AGATATAGATCTCACTACGCGGCTGCTCAAACCTGGGCAGAACGTAAGCCGCGAGAGCGCCAACAACCGC 3080

AjuI

5' TTCTTGGTCGAAGGCAGCAAGCGCGATGAATGTCTTACTACGGAGCAAGTTCCCGAGGTAATCGGAGTCC 3150

5' GGCTGATGTTGGGAGTAGGTGGCTACGTCTCCGAACTCACGACCGAAAAGATCAAGAGCAGCCCGCATGG 3220

5' ATTTGACTTGGTCAGGGCCGAGCCTACATGTGCGAATGATGCCCATACTTGAGCCACCTAACTTTGTTTT 3290

FIG. 55C

5' AGGGCGACTGCCCTGCTGCGTAACATCGTTGCTGCTGCGTAACATCGTTGCTGCTCCATAACATCAAACA 3360

5' TCGACCCACGGCGTAACGCGCTTGCTGCTTGGATGCCCGAGGCATAGACTGTACAAAAAAACAGTCATAA 3430

5' CAAGCCATGAAAACCGCCACTGCGCCGTTACCACCGCTGCGTTCGGTCAAGGTTCTGGACCAGTTGCGTG 3500

5' AGCGCATACGCTACTTGCATTACAGTTTACGAACCGAACAGGCTTATGTCAACTGGGTTCGTGCCTTCAT 3570

5' CCGTTTCCACGGTGTGCGTCACCCGGCAACCTTGGGCAGCAGCGAAGTCGAGGCATTTCTGTCCTGGCTG 3640

5' GCGAACGAGCGCAAGGTTTCGGTCTCCACGCATCGTCAGGCATTGGCGGCCTTGCTGTTCTTCTACGGCA 3710

5' AGGTGCTGTGCACGGATCTGCCCTGGCTTCAGGAGATCGGAAGACCTCGGCCGTCGCGGCGCTTGCCGGT 3780

5' GGTGCTGACCCCGGATGAAGTGGTTCGCATCCTCGGTTTTCTGGAAGGCGAGCATCGTTTGTTCGCCCAG 3850

SnaBI
BstZ17I

5' GACTCTAGCTATAGTTCTAGTGGTTGGCTACGTATACTCCGGAATATTAATAGATCATGGAGATAATTAA 3920

5' AATGATAACCATCTCGCAAATAAATAAGTATTTTACTGTTTTCGTAACAGTTTTGTAATAAAAAAACCTA 3990

RsrII

5' TAAATATTCCGGATTATTCATACCGTCCCACCATCGGGCGCGGATCTCGGTCCGTTCGAACCAGAACTCT 4060 mut....mHI

5' GGAAGCTTAACTCCTAAAAAACCGCCACCATGAAATTCTTAGTCAACGTTGCCCTTGTTTTTATGGTCGT 4130

Lob. TMO cDNA Lead Seq

Signal Peptide

```
5'  GATCGTGGGCGGTTCCTCCGTGTACCAAGAGGCTATGAACCAGCCCGGTCACTTGCGTCTGTTCGTGACC
                                                                              4620
                          Mouse DHFR, mutated
     I   V   G   S   S   V   Y   Q   E   A   M   N   Q   P   G   H   L   R   L   F   V   T
    155 156 157 158 159 160 161 162 163 164 165 166 167 168 169 170 171 172 173 174 175 176 177

5'  CGTATCATGCAAGAGTTCGAGTCCGACACCTTCTTCCCCGAAATCGACCTGGGCAAGTACAAGCTGCTGC
                                                                              4690
                          Mouse DHFR, mutated
     R   I   M   Q   E   F   E   S   D   T   F   F   P   E   I   D   L   G   K   Y   K   L   L
    178 179 180 181 182 183 184 185 186 187 188 189 190 191 192 193 194 195 196 197 198 199 200

5'  CCGAGTACCCCGGTGTCCTGTCCGAGGTGCAAGAGGAAAAGGGTATCAAGTACAAGTTCGAGGTGTACGA
                                                                              4760
                          Mouse DHFR, mutated
     P   E   Y   P   G   V   L   S   E   V   Q   E   E   K   G   I   K   Y   K   F   E   V   Y   E
    201 202 203 204 205 206 207 208 209 210 211 212 213 214 215 216 217 218 219 220 221 222 223 224

                                                                        Narl
                                                                        Sfol
                                                                        SgrAl
                                                                        Mrel
                                          EcoICRI                       NgoMIV
                                          SacI                          PluTI
                                                                     KasI  NaeI
5'  GAAGAAGGACGGCGCTTCCGGTTTCGCTAACGAGCTCGGTCCTCGTCTGATGGGAAAGGGCGCCGGCGGT
                                                                              4830
    Mouse D...mutated  linker                OLLAS tag                      linker
     K   K   D   G   A   S   G   F   A   N   E   L   G   P   R   L   M   G   K   G   A   G   G
    225 226 227 228 229 230 231 232 233 234 235 236 237 238 239 240 241 242 243 244 245 246 247

    NotI      Bpu10I
5'  GCGGCCGCTCAGGTTCAGTTGGTGGAATCAGGCGGCGGCTCAGTTCAAGCAGGCGGTTCACTCAGGCTCT
                                                                              4900
    linker                    EPEA alpha-synuclein VHH 1
     A   A   A   Q   V   Q   L   V   E   S   G   G   G   S   V   Q   A   G   G   S   L   R   L
    248 249 250 251 252 253 254 255 256 257 258 259 260 261 262 263 264 265 266 267 268 269 270

                                          XcmI
5'  CGTGTGCGGCAAGCGGTATCGACTCGTCCAGCTACTGCATGGGATGGTTCAGGCAAAGGCCAGGAAAGGA
                                                                              4970
                          EPEA alpha-synuclein VHH 1
     S   C   A   A   S   G   I   D   S   S   S   Y   C   M   G   W   F   R   Q   R   P   G   K   E
    271 272 273 274 275 276 277 278 279 280 281 282 283 284 285 286 287 288 289 290 291 292 293 294
```

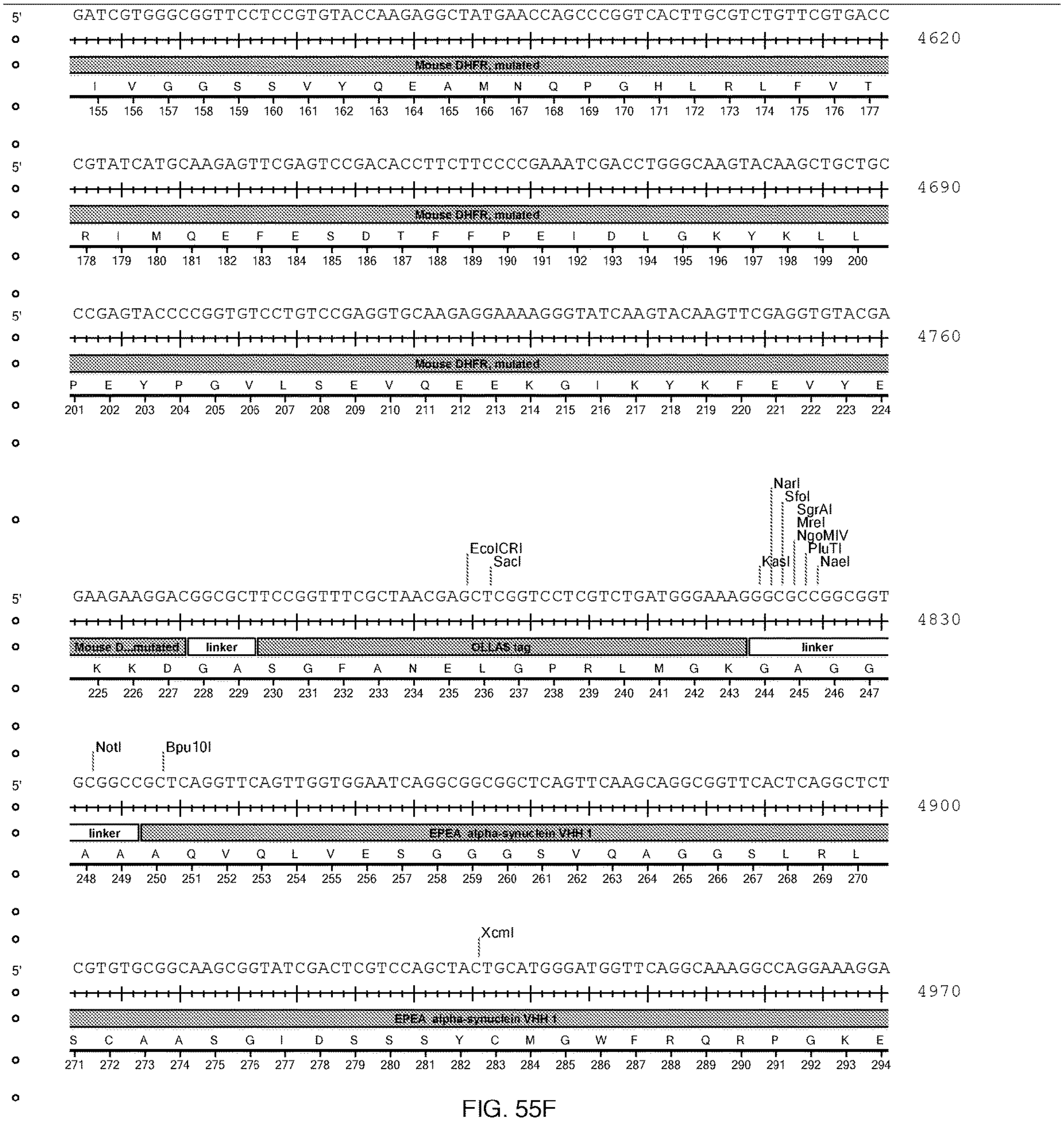

FIG. 55F

5' GAGGGAAGGTGTTGCTCGTATCAACGGACTGGGTGGCGTTAAGACAGCATACGCGGACAGTGTGAAAGAT 5040

EPEA alpha-synuclein VHH 1

R E G V A R I N G L G G V K T A Y A D S V K D 295 296 297 298 299 300 301 302 303 304 305 306 307 308 309 310 311 312 313 314 315 316 317

5' AGGTTCACAATTTCGAGAGACAACGCAGAGAACACGGTCTACTTGCAGATGAACTCTCTGAAGCCCGAAG 5110

EPEA alpha-synuclein VHH 1

R F T I S R D N A E N T V Y L Q M N S L K P E 318 319 320 321 322 323 324 325 326 327 328 329 330 331 332 333 334 335 336 337 338 339 340

5' ATACGGCGATCTACTACTGCGCTGCCAAATTCTCACCCGGATACTGTGGAGGTAGCTGGTCTAACTTCGG 5180

EPEA alpha-synuclein VHH 1

D T A I Y Y C A A K F S P G Y C G G S W S N F G 341 342 343 344 345 346 347 348 349 350 351 352 353 354 355 356 357 358 359 360 361 362 363 364

AleI NotI Bpu10I

5' TTACTGGGGTCAAGGCACCCAAGTGACTGTCTCTTCAGGCGGAGGTGCGGCCGCTGGCTCAGGAGGTGGC 5250

EPEA alpha-synuclein VHH 1 | VHH spacer

Y W G Q G T Q V T V S S G G G A A A G S G G G 365 366 367 368 369 370 371 372 373 374 375 376 377 378 379 380 381 382 383 384 385 386 387

PvuII PstI

5' AGTCAGGTGCAGCTGCAGGAGTCGGGAGGTGGCTCCGTCCAAGCAGGAGGTAGCCTGCGCCTCTCTTGCG 5320

V...r | EPEA alpha-synuclein VHH 2

S Q V Q L Q E S G G G S V Q A G G S L R L S C 388 389 390 391 392 393 394 395 396 397 398 399 400 401 402 403 404 405 406 407 408 409 410

5' CAGCGTCAGGTATCGACAGTTCGTCCTACTGTATGGGCTGGTTCAGGCAGCGTCCTGGCAAGGAGAGGGA 5390

EPEA alpha-synuclein VHH 2

A A S G I D S S S Y C M G W F R Q R P G K E R E 411 412 413 414 415 416 417 418 419 420 421 422 423 424 425 426 427 428 429 430 431 432 433 434

5' AGGAGTGGCACGTATCAACGGTCTCGGCGGAGTCAAGACAGCTTACGCCGACTCCGTTAAAGATAGGTTC 5460

EPEA alpha-synuclein VHH 2

```
5'  ACCATTAGCCGCGACAACGCTGAGAACACTGTCTACCTCCAAATGAACAGTTTGAAGCCGGAAGATACTG
                                                                              5530
         EPEA alpha-synuclein VHH 2
     T  I  S  R  D  N  A  E  N  T  V  Y  L  Q  M  N  S  L  K  P  E  D  T
     458 459 460 461 462 463 464 465 466 467 468 469 470 471 472 473 474 475 476 477 478 479 480

5'  CCATTTACTACTGTGCTGCCAAATTCTCACCGGGCTACTGTGGAGGAAGCTGGTCTAACTTCGGCTACTG
                                                                              5600
         EPEA alpha-synuclein VHH 2
     A  I  Y  Y  C  A  A  K  F  S  P  G  Y  C  G  G  S  W  S  N  F  G  Y  W
     481 482 483 484 485 486 487 488 489 490 491 492 493 494 495 496 497 498 499 500 501 502 503 504

                                         NgoMIV
                                         Nael
                                         FseI
5'  GGGACAAGGAACTCAAGTCACCGTTGGGGCCGGCCAGGGTGCTGGTGCTGGACCGATCACCATCAACAAC
                                                                              5670
      EPEA alpha-synuclein VHH 2         linker              BoNT/C1 ad0 LC
     G  Q  G  T  Q  V  T  V  G  A  G  Q  G  A  G  A  G  P  I  T  I  N  N
     505 506 507 508 509 510 511 512 513 514 515 516 517 518 519 520 521 522 523 524 525 526 527

                 BamHI
5'  TTCAATTACTCGGATCCGGTGGATAACAAGAACATCCTCTACTTGGACACACACTTGAACACGCTGGCTA
                                                                              5740
                              BoNT/C1 ad0 LC
     F  N  Y  S  D  P  V  D  N  K  N  I  L  Y  L  D  T  H  L  N  T  L  A
     528 529 530 531 532 533 534 535 536 537 538 539 540 541 542 543 544 545 546 547 548 549 550

5'  ACGAGCCTGAAAAAGCTTTCAGGATCACCGGCAACATTTGGGTCATTCCGGATAGGTTCAGCAGAAACTC
                                                                              5810
                              BoNT/C1 ad0 LC
     N  E  P  E  K  A  F  R  I  T  G  N  I  W  V  I  P  D  R  F  S  R  N  S
     551 552 553 554 555 556 557 558 559 560 561 562 563 564 565 566 567 568 569 570 571 572 573 574

5'  TAACCCTAACTTGAACAAACCTCCCAGAGTGACCTCACCTAAGAGTGGATACTACGACCCCAACTACCTC
                                                                              5880
                              BoNT/C1 ad0 LC
     N  P  N  L  N  K  P  P  R  V  T  S  P  K  S  G  Y  Y  D  P  N  Y  L
     575 576 577 578 579 580 581 582 583 584 585 586 587 588 589 590 591 592 593 594 595 596 597

5'  TCGACTGACTCCGATAAAGACCCCTTCCTGAAGGAGATCATTAAACTCTTCAAGCGCATCAACTCTCGTG
                                                                              5950
                              BoNT/C1 ad0 LC
     S  T  D  S  D  K  D  P  F  L  K  E  I  I  K  L  F  K  R  I  N  S  R
     598 599 600 601 602 603 604 605 606 607 608 609 610 611 612 613 614 615 616 617 618 619 620
```

FIG. 55H

```
5'  GAACCTCAACGTTTTGTTCATGGGTCAAAACTTGTCCCGCAACCCCGCCCTGCGTAAGGTGAACCCAGAG
                                                                                6930
         BoNT/C1 LC ad0
     N   L   N   V   L   F   M   G   Q   N   L   S   R   N   P   A   L   R   K   V   N   P   E
    925 926 927 928 929 930 931 932 933 934 935 936 937 938 939 940 941 942 943 944 945 946 947

5'  AACATGTTGTACCTGTTCACCAAATTCTGCCACAAGGCCATCGACGGTCAGTCTCTAGACCAAGGAGGAT
                                                                                7000
         BoNT/C1 LC ad0                                            LC/HC spacer
     N   M   L   Y   L   F   T   K   F   C   H   K   A   I   D   G   Q   S   L   D   Q   G   G
    948 949 950 951 952 953 954 955 956 957 958 959 960 961 962 963 964 965 966 967 968 969 970

5'  GGGAACTCCAGCAAGGTGGCCAGGGTGGAGGTGCTGGCACCCTGGACTGTCGCGAACTGCTCGTTAAGAA
                                                                                7070
         BptB site      LC/HC spacer              BoNT/C Translocation Domain
     W   E   L   Q   Q   G   G   Q   G   G   G   A   G   T   L   D   C   R   E   L   L   V   K   N
    971 972 973 974 975 976 977 978 979 980 981 982 983 984 985 986 987 988 989 990 991 992 993 994

5'  CACTGATCTCCCATTCATTGGCGACATCTCTGATGTGAAAACAGACATTTTCCTGCGTAAGGATATCAAC
                                                                                7140
                              BoNT/C Translocation Domain
     T   D   L   P   F   I   G   D   I   S   D   V   K   T   D   I   F   L   R   K   D   I   N
    995 996 997 998 999 1000 1001 1002 1003 1004 1005 1006 1007 1008 1009 1010 1011 1012 1013 1014 1015 1016 1017

5'  GAGGAAACGGAGGTCATCTACTACCCTGACAACGTCTCGGTTGATCAGGTTATCTTGTCAAAGAACACCA
                                                                                7210
                              BoNT/C Translocation Domain
     E   E   T   E   V   I   Y   Y   P   D   N   V   S   V   D   Q   V   I   L   S   K   N   T
    1018 1019 1020 1021 1022 1023 1024 1025 1026 1027 1028 1029 1030 1031 1032 1033 1034 1035 1036 1037 1038 1039 1040

5'  GTGAACATGGCCAACTGGACTTGCTGTACCCCTCAATTGATTCCGAGAGCGAAATCCTGCCAGGAGAGAA
                                                                                7280
                              BoNT/C Translocation Domain
     S   E   H   G   Q   L   D   L   L   Y   P   S   I   D   S   E   S   E   I   L   P   G   E   N
    1041 1042 1043 1044 1045 1046 1047 1048 1049 1050 1051 1052 1053 1054 1055 1056 1057 1058 1059 1060 1061 1062 1063 1064

    SexAI
5'  CCAGGTTTTCTACGACAACAGGACACAAAACGTGGATTACCTCAACAGCTACTACTACCTGGAGTCGCAG
                                                                                7350
                              BoNT/C Translocation Domain
     Q   V   F   Y   D   N   R   T   Q   N   V   D   Y   L   N   S   Y   Y   Y   L   E   S   Q
    1065 1066 1067 1068 1069 1070 1071 1072 1073 1074 1075 1076 1077 1078 1079 1080 1081 1082 1083 1084 1085 1086 1087
```

FIG. 55K

5' AAGCTCTCCGACAACGTCGAAGATTTCACATTTACGAGATCAATCGAGGAGGCTTTGGACAACAGTGCCA 7420
BoNT/C Translocation Domain
K L S D N V E D F T F T R S I E E A L D N S A
1088 1089 1090 1091 1092 1093 1094 1095 1096 1097 1098 1099 1100 1101 1102 1103 1104 1105 1106 1107 1108 1109 1110

5' AAGTCTACACCTACTTCCCTACTCTGGCAAACAAGGTGAACGCGGGTGTCCAAGGCGGACTCTTCTTGAT 7490
BoNT/C Translocation Domain
K V Y T Y F P T L A N K V N A G V Q G G L F L M
1111 1112 1113 1114 1115 1116 1117 1118 1119 1120 1121 1122 1123 1124 1125 1126 1127 1128 1129 1130 1131 1132 1133 1134

5' GTGGGCTAACGACGTTGTGGAAGATTTCACAACGAACATCTTGCGCAAAGACACCCTGGATAAGATCAGC 7560
BoNT/C Translocation Domain
W A N D V V E D F T T N I L R K D T L D K I S
1135 1136 1137 1138 1139 1140 1141 1142 1143 1144 1145 1146 1147 1148 1149 1150 1151 1152 1153 1154 1155 1156 1157

5' GATGTCTCTGCCATCATTCCATACATTGGCCCGGCACTGAACATCTCTAACTCAGTTCGCCGTGGCAACT 7630
BoNT/C Translocation Domain
D V S A I I P Y I G P A L N I S N S V R R G N
1158 1159 1160 1161 1162 1163 1164 1165 1166 1167 1168 1169 1170 1171 1172 1173 1174 1175 1176 1177 1178 1179 1180

PfoI
5' TCACTGAGGCATTCGCGGTCACAGGAGTTACGATCCTCTTGGAGGCTTTCCCGGAGTTCACAATCCCCGC 7700
BoNT/C Translocation Domain
F T E A F A V T G V T I L L E A F P E F T I P A
1181 1182 1183 1184 1185 1186 1187 1188 1189 1190 1191 1192 1193 1194 1195 1196 1197 1198 1199 1200 1201 1202 1203 1204

5' ACTGGGCGCGTTCGTTATCTACTCCAAAGTGCAGGAGCGCAACGAAATCATTAAGACTATCGACAACTGC 7770
BoNT/C Translocation Domain
L G A F V I Y S K V Q E R N E I I K T I D N C
1205 1206 1207 1208 1209 1210 1211 1212 1213 1214 1215 1216 1217 1218 1219 1220 1221 1222 1223 1224 1225 1226 1227

BsiWI
5' CTGGAGCAAAGGATCAAAAGATGGAAGGATTCGTACGAATGGATGATGGGTACCTGGCTCTCCCGTATCA 7840
BoNT/C Translocation Domain
L E Q R I K R W K D S Y E W M M G T W L S R I
1228 1229 1230 1231 1232 1233 1234 1235 1236 1237 1238 1239 1240 1241 1242 1243 1244 1245 1246 1247 1248 1249 1250

FIG. 55L

```
5'  TTACGCAGTTCAACAACATCAGCTACCAAATGTACGACTCTCTCAACTACCAGGCTGGTGCCATCAAGGC
                                                                              7910
                          BoNT/C Translocation Domain
     I  T  Q  F  N  N  I  S  Y  Q  M  Y  D  S  L  N  Y  Q  A  G  A  I  K  A
    1251 1252 1253 1254 1255 1256 1257 1258 1259 1260 1261 1262 1263 1264 1265 1266 1267 1268 1269 1270 1271 1272 1273 1274
```

```
            XcmI
5'  CAAAATTGACTTGGAGTACAAGAAATACAGTGGCTCGGATAAAGAGAACATCAAGAGTCAAGTCGAAAaC
                                                                              7980
                          BoNT/C Translocation Domain
     K  I  D  L  E  Y  K  K  Y  S  G  S  D  K  E  N  I  K  S  Q  V  E  N
    1275 1276 1277 1278 1279 1280 1281 1282 1283 1284 1285 1286 1287 1288 1289 1290 1291 1292 1293 1294 1295 1296 1297
```

```
5'  CTGAAAAACTCACTCGACGTTAAGATCAGTGAGGCAATGAACAACATCAACAAGTTCATTCGCGAATGTT
                                                                              8050
                          BoNT/C Translocation Domain
     L  K  N  S  L  D  V  K  I  S  E  A  M  N  N  I  N  K  F  I  R  E  C
    1298 1299 1300 1301 1302 1303 1304 1305 1306 1307 1308 1309 1310 1311 1312 1313 1314 1315 1316 1317 1318 1319 1320
```

```
5'  CCGTTACCTACCTCTTCAAAAACATGTTGCCAAAGGTCATCGACGAGCTGAACGAATTTGATCGTAACAC
                                                                              8120
                          BoNT/C Translocation Domain
     S  V  T  Y  L  F  K  N  M  L  P  K  V  I  D  E  L  N  E  F  D  R  N  T
    1321 1322 1323 1324 1325 1326 1327 1328 1329 1330 1331 1332 1333 1334 1335 1336 1337 1338 1339 1340 1341 1342 1343 1344
```

```
5'  TAAGGCGAAACTGATTAACCTCATCGACTCACACAACATCATTTTGGTGGGCGAAGTCGATAAGCTGAAA
                                                                              8190
                          BoNT/C Translocation Domain
     K  A  K  L  I  N  L  I  D  S  H  N  I  I  L  V  G  E  V  D  K  L  K
    1345 1346 1347 1348 1349 1350 1351 1352 1353 1354 1355 1356 1357 1358 1359 1360 1361 1362 1363 1364 1365 1366 1367
```

```
5'  GCCAAGGtGAACAACAGTTTCCAGAACACAATCCCTTTCAAcATTTTCTCATACACGAACAACAGTCTGC
                                                                              8260
                          BoNT/C Translocation Domain
     A  K  V  N  N  S  F  Q  N  T  I  P  F  N  I  F  S  Y  T  N  N  S  L
    1368 1369 1370 1371 1372 1373 1374 1375 1376 1377 1378 1379 1380 1381 1382 1383 1384 1385 1386 1387 1388 1389 1390
```

```
                                                                        PstI
5'  TCAAGGACATCATTAACGAGTACTTCAACAACATTAACGATAGCAAAATCCTGTCACTGCAGAACCGTAA
                                                                              8330
         BoNT/C Translocation Domain        |   BoNT/C Receptor Binding Domain
     L  K  D  I  I  N  E  Y  F  N  N  I  N  D  S  K  I  L  S  L  Q  N  R  K
    1391 1392 1393 1394 1395 1396 1397 1398 1399 1400 1401 1402 1403 1404 1405 1406 1407 1408 1409 1410 1411 1412 1413 1414
```

FIG. 55M

SpeI PvuII

5' GAACACACTGGTCGATACTAGTGGATACAACGCCGAAGTCTCTGAGGAAGGTGACGTGCAGCTGAACCCT 8400

BoNT/C Receptor Binding Domain

N T L V D T S G Y N A E V S E E G D V Q L N P 1415 1416 1417 1418 1419 1420 1421 1422 1423 1424 1425 1426 1427 1428 1429 1430 1431 1432 1433 1434 1435 1436 1437

5' ATCTTCCCCTTCGACTTCAAATTGGGCTCCAGCGGAGAGGATAGGGGCAAGGTCATCGTCACCCAGAACG 8470

BoNT/C Receptor Binding Domain

I F P F D F K L G S S G E D R G K V I V T Q N 1438 1439 1440 1441 1442 1443 1444 1445 1446 1447 1448 1449 1450 1451 1452 1453 1454 1455 1456 1457 1458 1459 1460

5' AGAACATCGTCTACAACTCAATGTACGAATCCTTCAGCATCTCTTTCTGGATCAGGATTAACAAGTGGGT 8540

BoNT/C Receptor Binding Domain

E N I V Y N S M Y E S F S I S F W I R I N K W V 1461 1462 1463 1464 1465 1466 1467 1468 1469 1470 1471 1472 1473 1474 1475 1476 1477 1478 1479 1480 1481 1482 1483 1484

BspMI

5' GAGCAACCTGCCCGGTTACACAATCATTGACTCTGTCAAGAACAACTCAGGTTGGAGTATCGGCATCATT 8610

BoNT/C Receptor Binding Domain

S N L P G Y T I I D S V K N N S G W S I G I I 1485 1486 1487 1488 1489 1490 1491 1492 1493 1494 1495 1496 1497 1498 1499 1500 1501 1502 1503 1504 1505 1506 1507

5' TCTAACTTCTTGGTCTTCACCCTGAAGCAGAACGAGGACTCGGAACAATCCATTAACTTCTCATACGATA 8680

BoNT/C Receptor Binding Domain

S N F L V F T L K Q N E D S E Q S I N F S Y D 1508 1509 1510 1511 1512 1513 1514 1515 1516 1517 1518 1519 1520 1521 1522 1523 1524 1525 1526 1527 1528 1529 1530

5' TCAGTAACAACGCTCCAGGTTACAACAAGTGGTTCTTCGTTACCGTGACTAACAACATGATGGGTAACAT 8750

BoNT/C Receptor Binding Domain

I S N N A P G Y N K W F F V T V T N N M M G N M 1531 1532 1533 1534 1535 1536 1537 1538 1539 1540 1541 1542 1543 1544 1545 1546 1547 1548 1549 1550 1551 1552 1553 1554

5' GAAAATTTACATCAACGGCAAGCTCATTGACACCATCAAAGTGAAGGAGTTGACTGGTATTAACTTCTCC 8820

BoNT/C Receptor Binding Domain

```
5'  AAAACAATCACGTTTGAAATTAaCaAGATCCCTGACACCGGCCTGATCACTTCAGACAGTGATAACATCA
                                                                              8890
                        BoNT/C Receptor Binding Domain
     K   T   I   T   F   E   I   N   K   I   P   D   T   G   L   I   T   S   D   S   D   N   I
    1578 1579 1580 1581 1582 1583 1584 1585 1586 1587 1588 1589 1590 1591 1592 1593 1594 1595 1596 1597 1598 1599 1600

                                                    EcoICRI
                                                    SacI
5'  ACATGTGGATTAGGGATTTCTACATCTTCGCCAAGGAGCTCGACGGAAAGGATATTAACATCCTCTTCAA
                                                                              8960
                        BoNT/C Receptor Binding Domain
     N   M   W   I   R   D   F   Y   I   F   A   K   E   L   D   G   K   D   I   N   I   L   F   N
    1601 1602 1603 1604 1605 1606 1607 1608 1609 1610 1611 1612 1613 1614 1615 1616 1617 1618 1619 1620 1621 1622 1623 1624

5'  CAGCTTGCAGTACACCAACGTCGTTAAAGACTACTGGGGTAACGATTTGAGATACAACAAGGAGTACTAC
                                                                              9030
                        BoNT/C Receptor Binding Domain
     S   L   Q   Y   T   N   V   V   K   D   Y   W   G   N   D   L   R   Y   N   K   E   Y   Y
    1625 1626 1627 1628 1629 1630 1631 1632 1633 1634 1635 1636 1637 1638 1639 1640 1641 1642 1643 1644 1645 1646 1647

5'  ATGGTCAACATCGACTACCTGAACAGGTACATGTACGCTAACTCCCGCCAAATCGTGTTCAACACCAGGA
                                                                              9100
                        BoNT/C Receptor Binding Domain
     M   V   N   I   D   Y   L   N   R   Y   M   Y   A   N   S   R   Q   I   V   F   N   T   R
    1648 1649 1650 1651 1652 1653 1654 1655 1656 1657 1658 1659 1660 1661 1662 1663 1664 1665 1666 1667 1668 1669 1670

5'  GAAACAACAACGACTTCAACGAGGGTTACAAAATCATTATCAAGCGCATCCGTGGCAACACCAACGATAC
                                                                              9170
                        BoNT/C Receptor Binding Domain
     R   N   N   N   D   F   N   E   G   Y   K   I   I   K   R   I   R   G   N   T   N   D   T
    1671 1672 1673 1674 1675 1676 1677 1678 1679 1680 1681 1682 1683 1684 1685 1686 1687 1688 1689 1690 1691 1692 1693 1694

5'  TAGGGTGAGAGGTGGCGACATTCTGTACTTCGATATGACTATCAACAACAAAGCCTACAACTTGTTCATG
                                                                              9240
                        BoNT/C Receptor Binding Domain
     R   V   R   G   G   D   I   L   Y   F   D   M   T   I   N   N   K   A   Y   N   L   F   M
    1695 1696 1697 1698 1699 1700 1701 1702 1703 1704 1705 1706 1707 1708 1709 1710 1711 1712 1713 1714 1715 1716 1717

5'  AAAAACGAGACAATGTACGCCGACAAcCATAGCACGGAGGATATTTACGCAATCGGACTGAGGGAACAGA
                                                                              9310
                        BoNT/C Receptor Binding Domain
     K   N   E   T   M   Y   A   D   N   H   S   T   E   D   I   Y   A   I   G   L   R   E   Q
    1718 1719 1720 1721 1722 1723 1724 1725 1726 1727 1728 1729 1730 1731 1732 1733 1734 1735 1736 1737 1738 1739 1740
```

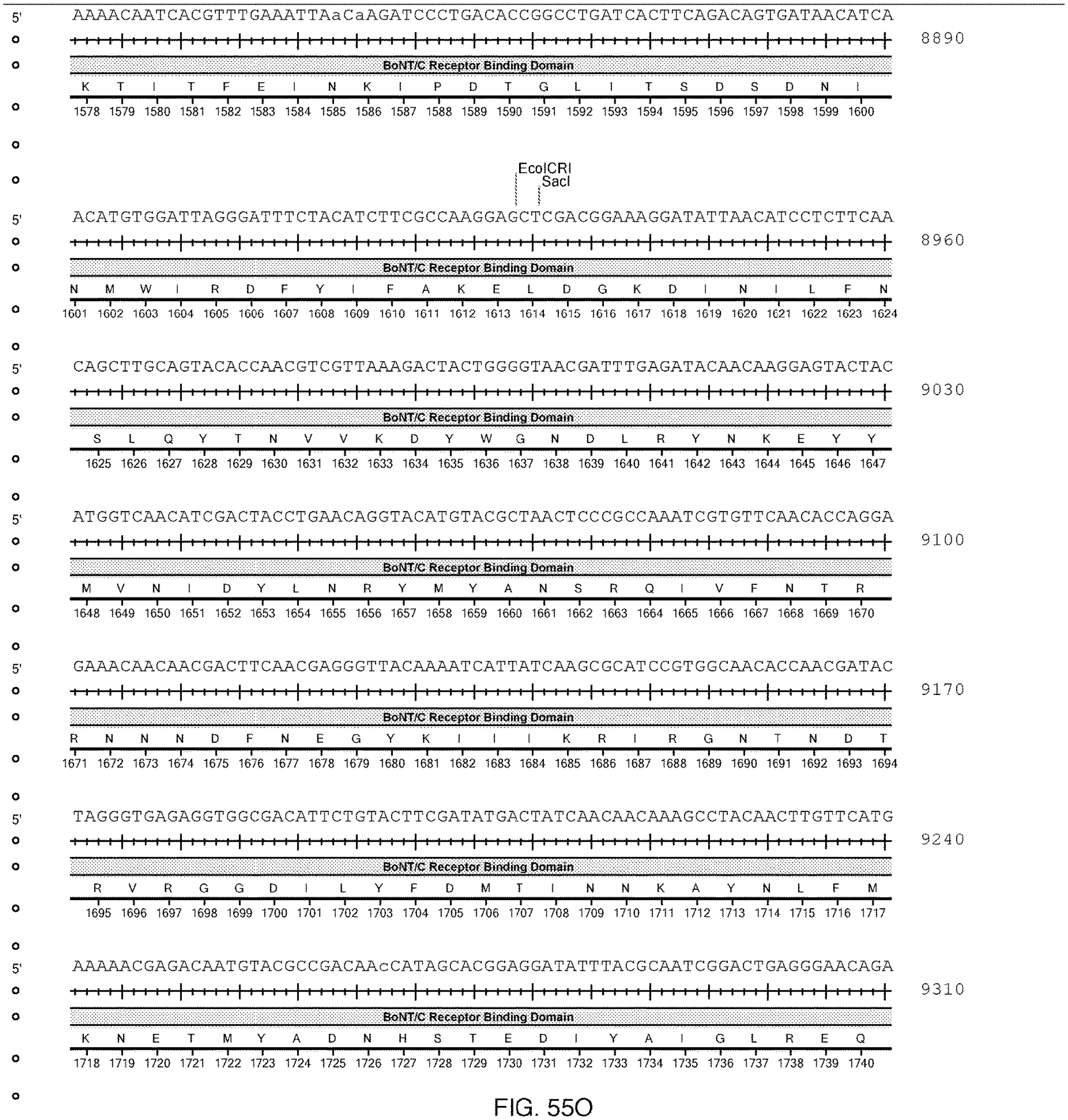

FIG. 55O

```
5'  CAAAGGACATCAACGATAACATTATCTTCCAGATCCAACCTATGAACAACACGTACTACTACGCTTCGCA
    +++++++++++++++++++++++++++++++++++++++++++++++++++++++++++++++++++++    9380
    ▓▓▓▓▓▓▓▓▓▓▓▓▓▓▓▓▓▓▓▓▓▓ BoNT/C Receptor Binding Domain ▓▓▓▓▓▓▓▓▓▓▓▓▓▓▓▓
     T   K   D   I   N   D   N   I   I   F   Q   I   Q   P   M   N   N   T   Y   Y   Y   A   S   Q
    1741 1742 1743 1744 1745 1746 1747 1748 1749 1750 1751 1752 1753 1754 1755 1756 1757 1758 1759 1760 1761 1762 1763 1764

5'  AATCTTCAAGTCCAACTTCAACGGAGAAAACATTTCGGGTATCTGTTCCATTGGCACATACCGCTTCCGT
    +++++++++++++++++++++++++++++++++++++++++++++++++++++++++++++++++++++    9450
    ▓▓▓▓▓▓▓▓▓▓▓▓▓▓▓▓▓▓▓▓▓▓ BoNT/C Receptor Binding Domain ▓▓▓▓▓▓▓▓▓▓▓▓▓▓▓▓
     I   F   K   S   N   F   N   G   E   N   I   S   G   I   C   S   I   G   T   Y   R   F   R
    1765 1766 1767 1768 1769 1770 1771 1772 1773 1774 1775 1776 1777 1778 1779 1780 1781 1782 1783 1784 1785 1786 1787

5'  CTGGGTGGTGACTGGTATCGTCACAACTACCTCGTTCCCACCGTGAAGCAGGGTAACTACGCTTCTTTGC
    +++++++++++++++++++++++++++++++++++++++++++++++++++++++++++++++++++++    9520
    ▓▓▓▓▓▓▓▓▓▓▓▓▓▓▓▓▓▓▓▓▓▓ BoNT/C Receptor Binding Domain ▓▓▓▓▓▓▓▓▓▓▓▓▓▓▓▓
     L   G   G   D   W   Y   R   H   N   Y   L   V   P   T   V   K   Q   G   N   Y   A   S   L
    1788 1789 1790 1791 1792 1793 1794 1795 1796 1797 1798 1799 1800 1801 1802 1803 1804 1805 1806 1807 1808 1809 1810

         SalI
5'  TGGAGTCGACTTCCACGCACTGGGGATTCGTTCCTGTGTCAGAGGGCGCTGGCTACCCTTACGATGTTCC
    +++++++++++++++++++++++++++++++++++++++++++++++++++++++++++++++++++++    9590
    ▓▓▓▓▓▓▓▓ BoNT/C Receptor Binding Domain ▓▓▓▓▓▓▓▓│ linker │▓▓ HA tag ▓▓
     L   E   S   T   S   T   H   W   G   F   V   P   V   S   E   G   A   G   Y   P   Y   D   V   P
    1811 1812 1813 1814 1815 1816 1817 1818 1819 1820 1821 1822 1823 1824 1825 1826 1827 1828 1829 1830 1831 1832 1833 1834

5'  CGACTACGCTGGTTGGGAACTCCAGCAAGGTGCAGGATGGTCCCACCCTCAATTCGAGAAGGGTGCCGGA
    +++++++++++++++++++++++++++++++++++++++++++++++++++++++++++++++++++++    9660
    ▓ HA tag ▓│li..r│▓ SpIE site ▓│ linker │▓▓▓▓▓ Strep tag II ▓▓▓▓▓│ linker │
     D   Y   A   G   W   E   L   Q   Q   G   A   G   W   S   H   P   Q   F   E   K   G   A   G
    1835 1836 1837 1838 1839 1840 1841 1842 1843 1844 1845 1846 1847 1848 1849 1850 1851 1852 1853 1854 1855 1856 1857

5'  TGGAGTCACCCACAGTTCGAGAAAGGCGCTGGATGGAGTCACCCACAGTTCGAGAAATAATTAGTTGATG
    +++++++++++++++++++++++++++++++++++++++++++++++++++++++++++++++++++++    9730
    ▓▓▓▓▓ Strep tag II ▓▓▓▓▓│ linker │▓▓▓▓▓ Strep tag II ▓▓▓▓▓
     W   S   H   P   Q   F   E   K   G   A   G   W   S   H   P   Q   F   E   K
    1858 1859 1860 1861 1862 1863 1864 1865 1866 1867 1868 1869 1870 1871 1872 1873 1874 1875 1876

         NsiI            XhoI                                    NsiI
5'  CATAGTTAATTAGATAGCTCGAGGCATGCGGTACCAAGATTGGATCTAGATGCATAGTTAATTAGATAGC
    +++++++++++++++++++++++++++++++++++++++++++++++++++++++++++++++++++++    9800

    XhoI
5'  TCGAGGCATGCGGTACCAAGCTTGTCGAGAAGTACTAGAGGATCATAATCAGCCATACCACATTTGTAGA
    +++++++++++++++++++++++++++++++++++++++++++++++++++++++++++++++++++++    9870
```

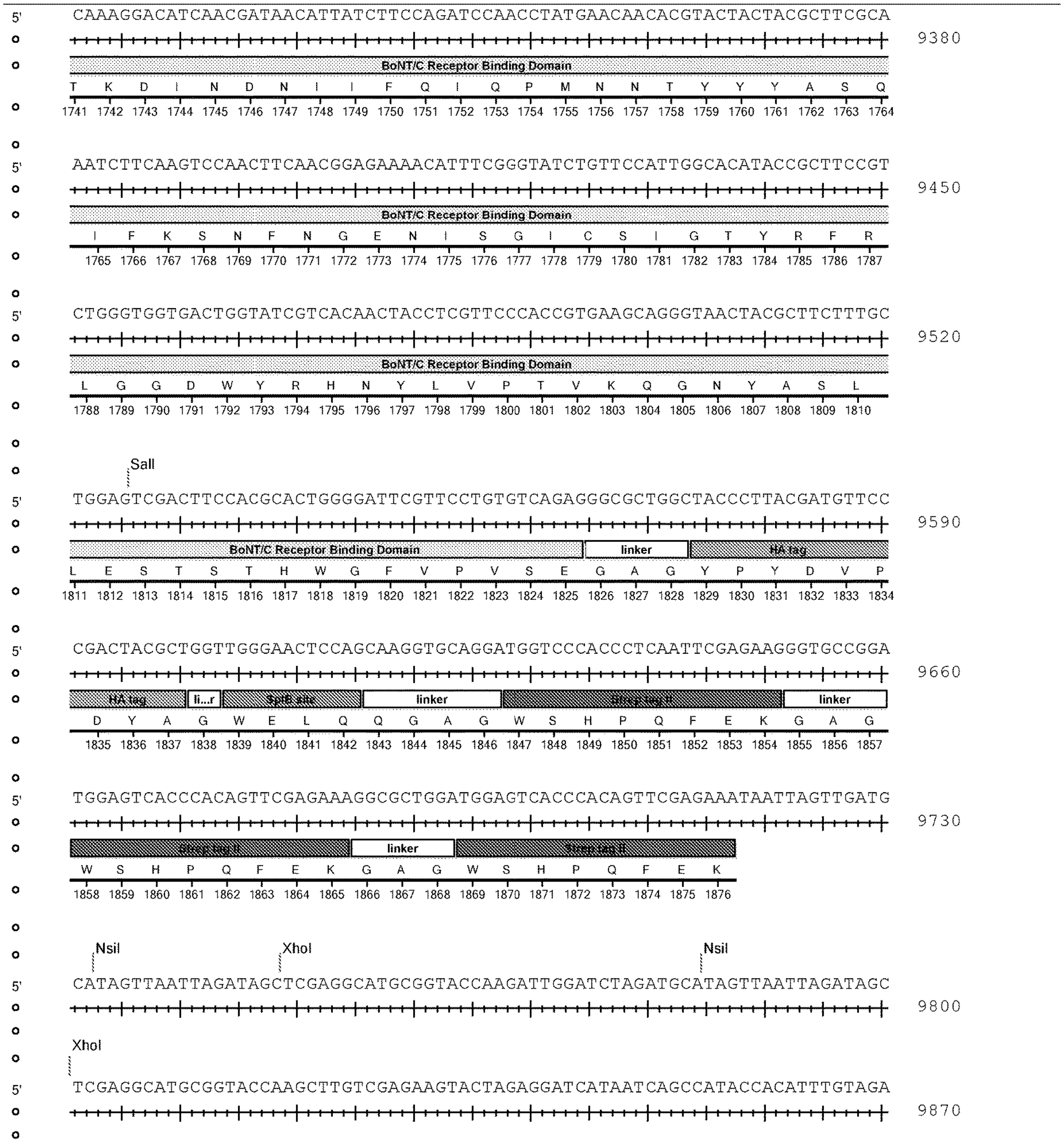

FIG. 55P

5' GGTTTTACTTGCTTTAAAAAACCTCCCACACCTCCCCCTGAACCTGAAACATAAAATGAATGCAATTGTT 9940

HpaI

5' GTTGTTAACTTGTTTATTGCAGCTTATAATGGTTACAAATAAAGCAATAGCATCACAAATTTCACAAATA 10010

5' AAGCATTTTTTTCACTGCATTCTAGTTGTGGTTTGTCCAAACTCATCAATGTATCTTATCATGTCTGGAT 10080

AvrII

5' CTGATCACTGCTTGAGCCTAGGAGATCCGAACCAGATAAGTGAAATCTAGTTCCAAACTATTTTGTCATT 10150

5' TTTAATTTTCGTATTAGCTTACGACGCTACACCCAGTTCCCATCTATTTTGTCACTCTTCCCTAAATAAT 10220

5' CCTTAAAAACTCCATTTCCACCCCTCCCAGTTCCCAACTATTTTGTCCGCCCACAGCGGGGCATTTTTCT 10290

5' TCCTGTTATGTTTTTAATCAAACATCCTGCCAACTCCATGTGACAAACCGTCATCTTCGGCTACTTTTTC 10360

5' TCTGTCACAGAATGAAAATTTTTCTGTCATCTCTTCGTTATTAATGTTTGTAATTGACTGAATATCAACG 10430

5' CTTATTTGCAGCCTGAATGGCGAATGG 10457

FIG. 55Q

PROPEPTIDE FUSION COMPRISING A MUTATED CLOSTRIDIUM BOTULINUM NEUROTOXIN AND A VHH DOMAIN

This application claims the benefit of U.S. Provisional Patent Application Serial Nos. 62/089,646, filed Dec. 9, 2014, and 62/118,970, filed Feb. 20, 2015, both of which are hereby incorporated by reference in their entirety.

This invention was made with government support under R01 A1093504 awarded by National Institutes of Health. The government has certain rights in the invention.

FIELD OF THE INVENTION

The present invention relates to Clostridial neurotoxin fusion proteins containing a single chain antibody, propeptide fusions, and methods thereof.

BACKGROUND OF THE INVENTION

Delivery of Antibodies to Intracellular Targets

Canonic antibodies are large multimeric proteins that cannot penetrate the cell membrane and, therefore, cannot directly gain access to targets inside the cytoplasmic compartment of the cell. Because many pharmaceutically important targets are exclusively exposed in the cytoplasm of cells, multiple technological approaches have been tested to deliver antibodies or antibody-derived fragments to intracellular targets. These methods are similar to those which have been used to deliver nucleic acid and other protein molecules to intracellular compartments. They include physical methods such as electroporation, sonication and microinjection, encapsulation within liposomes or polymeric shells, and formation of complexes with polymers and lipids that facilitate endocytosis and /or penetration of the plasma membrane to access the cytoplasm (Torchilin, "Multifunctional and Stimuli-Sensitive Pharmaceutical Nanocarriers," *European Journal ofPharmaceutics and Biopharmaceutics: Official Journal of Arbeitsgemeinschaft fur Pharmazeutische Verfahrenstechnik e. V* 71(3):431-444 (2009); Torchilin, "Intracellular Delivery of Protein and Peptide Therapeutics," *Drug Discovery Today: Technol.* (2009); El-Sayed et al., "Smart Polymeric Carriers for Enhanced Intracellular Delivery of Therapeutic Macromolecules," *Expert Opinion on Biological Therapy* 5(1):23-32 (2005)).

Single chain antibodies, or fragments thereof, can be delivered into the cytoplasm of cells by methods not possible for multimeric antibodies. These include: (1) transfection of the target cell with nucleic acid coding for the antibody fragment, using viral carriers or otherwise incorporating the gene into the host cell; (2) fusion of the antibody to a protein transduction domain (PTD) that allows the antibody to penetrate cell membranes (e.g., TAT fusion domains); and (3) chemical or genetic fusion of the antibody to a cell targeting protein or domain that is naturally able to translocate through cellular membranes (Marschall et al., "Targeting Antibodies to the Cytoplasm," mAbs 3(1):3-16 (2011)).

While all of these methodologies are demonstrated to be effective in vitro, they all have limitations for therapeutic application (Marschall et al., "Delivery of Antibodies to the Cytosol: Debunking the Myths," mAbs 6(4):943-956 (2014); Yin et al., "Non-Viral Vectors for Gene-Based Therapy," *Nature Reviews Genetics* 15(8):541-555 (2014)). In particular, transfection based methods have well-known limitations for use in therapeutic products, primarily due to toxicity and lack of specificity. Though viral-mediated transduction is being tested for clinical application, it is still considered to present significant risks for therapeutic intervention, and faces significant regulatory barriers. Neuron specific viral carriers are not available for clinical use. The use of protein transduction domains is not neuron-specific and likewise presents significant safety concerns. Chemical or genetic fusion of antibodies to proteins that are naturally able to translocate through cellular membranes has been extensively studied. Ribonucleases of the RNAse A superfamily have been fused to antibodies, but the purpose of the fusion was to use the antibody to target the RNAse activity to the intended cell (Schirrmann et al., "Targeted Therapeutic RNases (ImmunoRNases)," *Expert Opinion on Biological Therapy* 9(1):79-95 (2009)). Diphtheria toxin (Weaver et al., "Transferrin Receptor Ligand-Targeted Toxin Conjugate (Tf-CRM107) for Therapy of Malignant Gliomas," *Journal ofNeuro-Oncology* 65(1):3-13 (2003)) and ricin (Messmann et al., "A Phase I Study of Combination Therapy with Immunotoxins IgG-HD37-Deglycosylated Ricin A Chain (dgA) and IgG-RFB4-dgA (Combotox) in Patients with Refractory CD19(+), CD22(+) B Cell Lymphoma," *Clinical Cancer Research: An Official Journal of the American Association for Cancer Research* 6(4):1302-1313 (2000)) have likewise been fused to antibodies that enable targeted delivery of the toxin, again with the antibody being used for targeting the toxin to the cytoplasm of specific cells. In none of these cases is the toxin used to direct delivery of the antibody to neurons, and the toxins are in fact not specifically directed to neurons.

Antibody cationization has also been used to facilitate antibody delivery to cells, including to improve the delivery of single chain antibodies (Li et al., "Cell-Penetrating Anti-GFAP VHH and Corresponding Fluorescent Fusion Protein VHH-GFP Spontaneously Cross the Blood-Brain Barrier and Specifically Recognize Astrocytes: Application to Brain Imaging," *FASEB Journal: Official Publication of the Federation of American Societies for Experimental Biology* 26(10):3969-3979 (2012)). The mechanism is presumably related to the increased interaction between the cationic antibody and the negatively charged cell membrane, but again the specificity of cell binding comes solely from the antibody and not from the delivery vehicle.

Thanongsaksrikul et al., "Botulinum Neurotoxins and Botulism: A Novel Therapeutic Approach," *Toxins* 3(5):469-488 (2011), reported that a VHH (single chain antibody) that inhibited botulinum neurotoxin, serotype A enzymatic activity could be fused genetically to a cell-penetrating-peptide ("CPP"), but no data has subsequently been presented illustrating the success of this technique for delivering a functional antibody to neurons. No mechanism is suggested that would direct this postulated VHH-CPP fusion protein to the inside of neurons.

The selectivity of BoNT targeting to neurons has led several laboratories to consider using BoNT-based molecular vehicles for delivering therapeutic agents. Early work reported that the heavy chain ("HUC") and light chain ("LC") of wild-type BoNTs could be separated, and that the wild-type HC could be reconstituted in vitro with either wild-type LC or with recombinant LC, which could carry point mutations such as $His_{227}$>Tyr, which rendered the LC atoxic (Zhou et al., "Expression and Purification of the Light Chain of Botulinum Neurotoxin A: A Single Mutation Abolishes Its Cleavage of SNAP-25 and Neurotoxicity After Reconstitution With the Heavy Chain," *Biochemistry* 34(46):15175-15181 (1995); Maisey et al., "Involvement of the Constituent Chains of Botulinum Neurotoxins A and B In the Blockade of Neurotransmitter Release," *Eur. J. Biochem.* 177(3):683-691 (1988); Sathyamoorthy et al., "Separation, Purification, Partial Characterization and Comparison of the Heavy and Light Chains of Botulinum Neurotoxin Types A, B, and E," *J Biol. Chem.* 260(19):10461-10466 (1985)). The reconstituted BoNT holotoxin derivatives had a severely reduced ability to transport LC into the neuronal cytosol, probably resulting from the harsh conditions required for HC-LC separation and the difficulty of renaturing the protein and reconstituting native disulfide bonds.

Attempts have also been made to use isolated wild-type HC for targeted delivery by chemically coupling dextran to the HC to provide sites for attaching fluorescent markers or therapeutic agents (Goodnough et al., "Development of a Delivery Vehicle for Intracellular Transport of Botulinum Neurotoxin Antagonists," *FEBS Lett.* 513:163-168 (2002)). Although this "semi-synthetic" BoNT derivative was internalized by neurons, the dextran remained localized to the endosomal compartment and the specificity of the uptake was uncertain. Direct chemical or biochemical attachment of cargo molecules to the HC of BoNTs may not be sufficient for achieving cytosolic delivery, because structural features associated with the toxin LC are required for translocation to the cytosol (Baldwin et al., "The C-Terminus of Botulinum Neurotoxin Type A Light Chain Contributes to Solubility, Catalysis, and Stability," *Protein Expr. Purif* 37(1):187-195 (2004); Brunger et al., "Botulinum Neurotoxin Heavy Chain Belt as an Intramolecular Chaperone for the Light Chain," PLoSPathog. 3(9):e113 (2007)). Moreover, when chemical methods are used to attach cargo to BoNT toxoids, cargo attachment is not sufficiently selective and, consequently, produces a heterogeneous population of derivatives. These problems also limit the utility of chemically labeled BoNTs as probes for definitive demonstration of BoNT trafficking pathways.

Bade et al., "Botulinum Neurotoxin Type D Enables Cytosolic Delivery of Enzymatically Active Cargo Proteins to Neurons Via Unfolded Translocation Intermediates," *J. Neurochem.* 91(6):1461-1472 (2004), described recombinant full-length derivatives of BoNT/D as effective delivery vehicles which were expressed in *E. coli* with or without an inactivating mutation ($E_{230}$>A) to the LC protease. To evaluate the delivery of prototypic cargo proteins in neuronal cultures, green fluorescent protein ("GFP"), dihydrofolate reductase, firefly luciferase, or BoNT/A LC were fused to the amino terminus of the recombinant BoNT/D holotoxin. Delivery to the cytosol was evaluated by measuring cleavage of the BoNT/D cytoplasmic substrate, synaptobrevin. Dihydrofolate reductase and BoNT/A LC were reported to be effectively delivered. When luciferase or GFP were the cargo, delivery of the corresponding BoNT/D LC catalytic activity to the cytosol was significantly reduced, presumably due to the large size of the cargo (luciferase) or its rigidity (GFP) (Brejc et al., "Structural Basis for Dual Excitation and Photoisomerization of the *Aequorea victoria* Green Fluorescent Protein," *Proc. Natl. Acad. Sci.* (USA) 94(6):2306-1231 (1997); Palm et al., "The Structural Basis for Spectral Variations in Green Fluorescent Protein," *Nat. Struct. Biol.* 4(5):361-365 (1997)). The efficiency of light chain delivery using recombinant BoNT/D expressed in *E. coli* is not clear from the data presented, because the active light chain delivered is effective at very low concentration in the neuronal cytoplasm.

It has proven particularly difficult to successfully engineer translocation of recombinant toxin LCs from an endosomal compartment to the cytosol. This translocation requires acidification of the lumenal milieu, either to trigger a conformational change in the BoNT heterodimer or to enable its interaction with a translocation mediator (Brunger et al., "Botulinum Neurotoxin Heavy Chain Belt as an Intramolecular Chaperone for the Light Chain," *PLoS Pathog.* 3(9):e113 (2007); Kamata et al., "Involvement of Phospholipids In the Intoxication Mechanism of Botulinum Neurotoxin," *Biochim. Biophys. Acta.* 1199(1):65-68 (1994); Tortorella et al., "Immunochemical Analysis of the Structure of Diphtheria Toxin Shows all Three Domains Undergo Structural Changes at Low pH," *J. Biol. Chem.* 270(46):27439-27445 (1995); Tortorella et al., "Immunochemical Analysis Shows All Three Domains of Diphtheria Toxin Penetrate Across Model Membranes," *J. Biol. Chem.* 270(46):27446-27452 (1995)). A requirement for cooperation between the BoNT LC and the translocation domain of the HC is supported by evidence demonstrating that a decapeptide motif, common to the $HC_N$ of several BoNT serotypes as well as to diphtheria and anthrax toxins, is required for successful translocation of the LC to the cytosol (Ratts et al., "A Conserved Motif in Transmembrane Helix 1 of Diphtheria Toxin Mediates Catalytic Domain Delivery to the Cytosol," *Proc. Natl. Acad. Sci.* (USA) 102(43):15635-15640 (2005)).

Although efforts to express recombinant BoNTs have succeeded in producing effective immunogens, which in some cases are competent for epithelial transcytosis, these efforts have not produced recombinant proteins with the structural features required for targeting the neuronal cytosol with the efficiency of wild-type toxins. These limitations emphasize the importance of selecting an expression system capable of producing full-length BoNT derivatives that retain native toxin structure, disulfide bonding, and physiological trafficking. Also, work from multiple laboratories has clarified how the structural domains of wild-type *Clostridium botulinum* neurotoxin serotype A ("BoNT/A") disable neuronal exocytosis, but important questions remain unanswered.

In no case is a single chain antibody delivered using a Clostridial neurotoxin for neuronal delivery. A significant amount of work has been done on the development of single chain antibodies directed at intracellular targets in neurons, but in all cases the antibodies have been expressed by transfection as intrabodies, rather than delivered as fusion proteins. Tremblay et al., "Camelid Single Domain Antibodies (VHHs) as Neuronal Cell Intrabody Binding Agents and Inhibitors of *Clostridium botulinum* Neurotoxin (BoNT) Proteases," *Toxicon: Official Journal of the International Society on Toxinology* 56(6):990-998 (2010), reported that an anti-botulinum neurotoxin, serotype A VHH intrabody expressed in neurons by transfection was able to prevent intoxication of an immortalized neuronal cell line by wt BoNT/A. Transfection was also used to demonstrate that fusion of a proteasome-targeting sequence to an anti-botulinum neurotoxin, serotype A VHH could accelerate recovery from intoxication with wt BoNT/A (Kuo et al., "Accelerated Neuronal Cell Recovery from Botulinum Neurotoxin Intoxication by Targeted Ubiquitination," *PloS One* 6(5): e20352 (2011), which is hereby incorporated by reference in its entirety). Single chain antibodies expressed as intrabodies have also been shown to have potential for the treatment of Huntington disease, Parkinson's disease, and potentially for other protein misfolding disorders affecting neurons (Butler et al., "Engineered Antibody Therapies to Counteract Mutant Huntingtin and Related Toxic Intracellular Proteins," *Progress in Neurobiology* 97(2):190-204 (2012); Butler et al., "Bifunctional Anti-Huntingtin Proteasome- Directed Intrabodies Mediate Efficient Degradation of Mutant Huntingtin Exon 1 Protein Fragments," *PloS One* 6(12):e29199 (2011); Messer et al., "Intrabodies as Neuroprotective Therapeutics," *Neurotherapeutics: The Journal of the American Society for Experimental NeuroTherapeutics* 10(3):447-458 (2013)). None of these single chain antibodies has previously been tested after genetic fusion to a Clostridial neurotoxin for purposes of delivery.

Clostridial Neurotoxins

The *Clostridium botulinum* and *Clostridium tetani* neurotoxins are highly potent and specific poisons of neural cells (Johnson et al., "Characterization of *Clostridium botulinum* Strains Associated with an Infant Botulism Case in the United Kingdom," *J. Clin. Microbiol.* 43:2602-260 (2005); Schiavo et al., "Neurotoxins Affecting Neuroexocytosis," *Physiol. Rev.* 80:717-766 (2000); Simpson, "Identification of the Major Steps in Botulinum Toxin Action," *Annu. Rev. Pharmacol. Toxicol.* 44:167-193 (2004)). These neurotoxins are among the most lethal substances known to man. Both toxins function by inhibiting neurotransmitter release in affected neurons. The tetanus neurotoxin ("TeNT") acts mainly in interneurons, connecting the peripheral and the central nervous system, while botulinum neurotoxin ("BoNT") acts at the neuromuscular junction and other cholinergic synapses in the peripheral nervous system. Both of these neurotoxins act by inhibiting neurotransmitter release from the axon of the affected neuron into the synapse, resulting in paralysis.

There are eight currently described BoNT serotypes (A-H) and multiple sub-types, all with common structural features (Smith et al., "Sequence Variation within Botulinum Neurotoxin Serotypes Impacts Antibody Binding and Neutralization," *Infect. Immun.* 73:5450-5457 (2005); Barash et al., "A Novel Strain of *Clostridium botulinum* that Produces Type B and Type H Botulinum Toxins," J. Infect. Dis. 209:183-91 (2014); Dover et al., "Molecular Characterization of a Novel Botulinum Neurotoxin Type H Gene," *J. Infect. Dis.* 209:192-202 (2014); Hill et al., "Genetic Diversity within *Clostridium botulinum* Serotypes, Botulinum Neurotoxin Gene Clusters and Toxin Subtypes," *Curr. Top. Microbiol. Immunol.* 364:1-20 (2013)). Despite their toxicity, BoNTs have become widely used as pharmaceutical agents, because small doses can be applied to paralyze local muscle groups and thereby effect targeted therapeutic paralysis. BoNT/A, with a murine $LD_{50}$ of approximately 0.5 ng per kg, is the serotype most used in clinical medicine (e.g., Ona-, Abo-, and Incobotulinum Toxin A, sold under the trade names Botox®, Dysport®, and Xeomin®, respectively) and is approved for a wide range of indications.

BoNTs have structural and trafficking features that have ideally evolved for delivery of their metalloprotease entity (light chain (LC)) to the neuronal cytosol. They can cross epithelial barriers in the gut and lung, and pass into the circulation. From the circulation, they primarily target active neuromuscular junctions, where they block neurotransmitter release causing peripheral neuromuscular blockade (Fujinaga, "Interaction of Botulinum Toxin with the Epithelial Barrier," *J. Biomed. Biotechnol.* 2010:974943 (2010); Jahn et al., "SNAREs-Engines for Membrane Fusion," *Nat. Rev. Mol. Cell Biol.* 7:631-643 (2006); Montal, "Botulinum Neurotoxin: A Marvel of Protein Design," *Annu. Rev. Biochem.* 79:591-617 (2010)). Death results from respiratory paralysis (Schiavo et al., "Neurotoxins Affecting Neuroexocytosis," *Physiol. Rev.* 80:717-766 (2000)). All BoNT serotypes have similar structural features, and all target Soluble NSF Attachment Protein REceptor ("SNARE") components of the molecular machinery for synaptic vesicle release (Johnson, "Clostridial Toxins as Therapeutic Agents: Benefits of Nature's Most Toxic Proteins," *Annu. Rev. Microbiol.* 53:551-575 (1999)). For example, wild-type (wt) BoNT/A is synthesized as a single chain protein (Mr ~150,000), which is proteolytically activated by an endogenous clostridial protease to generate a heterodimer containing a light chain (LC, Mr ~50,000) and a heavy chain (HC, Mr ~100,000) linked by an essential disulfide bond (Schiavo et al., "Neurotoxins Affecting Neuroexocytosis," Physiol. Rev. 80:717-766 (2000); Johnson, "Clostridial Toxins as Therapeutic Agents: Benefits of Nature's Most Toxic Proteins," *Annu. Rev. Microbiol.* 53:551-575 (1999); Montecucco et al., "Mechanism of Action of Tetanus and Botulinum Neurotoxins," *Mol. Microbiol.* 13:1-8 (1994)).

The mature wild-type BoNT/A toxin is a disulfide bonded heterodimer containing three major functional domains: (1) the LC metalloprotease domain responsible for toxicity; (2) the receptor-binding domain comprising the heavy chain (HC)C-terminal region (HC); and (3) the heavy chain (HC) translocation domain comprising the HC N-terminal region (HN), which is responsible for the propulsion of the LC to the cytosol (Schiavo et al., "Neurotoxins Affecting Neuroexocytosis," *Physiol. Rev.* 80:717-766 (2000); Simpson, "Identification of the Major Steps in Botulinum Toxin Action," *Annu. Rev. Pharmacol. Toxicol.* 44:167-193 (2004); Johnson, "Clostridial Toxins as Therapeutic Agents: Benefits of Nature's Most Toxic Proteins," *Annu. Rev. Microbiol.* 53:551-575 (1999); Dong et al., "SV2 is the Protein Receptor for Botulinum Neurotoxin A," *Science* 312:592-596 (2006); Mahrhold et al., "The Synaptic Vesicle Protein 2C Mediates the Uptake of Botulinum Neurotoxin A Into Phrenic Nerves," *FEBS Lett.* 580:2011-2014 (2006)).

The same multi-step molecular mechanism is responsible for the toxicity and pharmaceutical potency of wild-type BoNT/A, which specifically targets active neurons. This specificity derives from the fact that its receptor, Synaptic Vesicle protein 2 ("SV2"), which projects into the lumen of small synaptic vesicles, is only exposed on the plasma membrane during a synaptic vesicle fusion event (Dong et al., "SV2 is the Protein Receptor for Botulinum Neurotoxin A," *Science* 312(5773):592-596 (2006)). The binding and internalization of wild-type BoNT/A also involves gangliosides (Johnson, "Clostridial Toxins as Therapeutic Agents: Benefits of Nature's Most Toxic Proteins," *Annu. Rev. Microbiol.* 53:551-575 (1999); Keller et al., "Persistence of Botulinum Neurotoxin Action in Cultured Spinal Cord Cells," *FEBS Lett.* 456:137-142 (1999)), and immediately after internalization, BoNT/A is found in an early endosome compartment (Simpson, "Identification of the Major Steps in Botulinum Toxin Action," *Annu. Rev. Pharmacol. Toxicol.* 44:167-193 (2004); Fischer et al., "Crucial Role of the Disulfide Bridge Between Botulinum Neurotoxin Light and Heavy Chains in Protease Translocation Across Membranes," *J Biol. Chem.* 282:29604-29611 (2007); Fischer et al., "Single Molecule Detection of Intermediates During Botulinum Neurotoxin Translocation Across Membranes," *Proc. Natl. Acad. Sci. USA* 104:10447-10452 (2007)), which is also associated with synaptic vesicle recycling. Upon acidification of the endosome, BoNT/A undergoes a functionally critical conformational change that enables HC-mediated translocation of the LC into the neuronal cytoplasm (Band et al., "Recombinant Derivatives of Botulinum Neurotoxin A Engineered for Trafficking Studies and Neuronal Delivery," *Protein Exp. Purif* 71:62-73 (2010); Pellett et al., "Neuronal Targeting, Internalization, and Biological Activity of a Recombinant Atoxic Derivative of Botulinum Neurotoxin A," *Biochem. Biophys. Res. Commun.* 405:673-

677 (2011)). Disruption of the early endosome acidification process by drugs such as bafilomycin or concanamycin A prevents translocation of the light chain to the neuronal cytoplasm (Simpson, "Identification of the Major Steps in Botulinum Toxin Action," *Annu. Rev. Pharmacol. Toxicol.* 44:167-193 (2004)). In the neuronal cytosol, the LC, a $Zn^{2+}$-endopeptidase, specifically cleaves Synaptosomal-Associated Protein 25 ("SNAP-25"), a SNARE protein required for synaptic vesicle exocytosis (Mahrhold et al., "The Synaptic Vesicle Protein 2C Mediates the Uptake of Botulinum Neurotoxin A Into Phrenic Nerves," *FEBS Lett.* 580:2011-2014 (2006)). Cleavage of SNAP-25 results in inhibition of neurotransmitter release, leading to peripheral neuromuscular paralysis.

A technology platform based on recombinant clostridial constructs, a baculovirus expression system, and purification methods that enable production of recombinant, full-length BoNT heterodimer derivatives has been developed (see U.S. Pat. No. 7,785,606 to Ichtchenko and Band). This platform allows the tools of modem molecular biology to be applied to bioengineering of recombinant botulinum neurotoxins that retain the structure and trafficking properties of the native toxin (Band et al., "Recombinant Derivatives of Botulinum Neurotoxin A Engineered for Trafficking Studies and Neuronal Delivery," *Protein Expr. Purif* 71:62-73 (2010)). An atoxic derivative of *Clostridium botulinum* neurotoxin, serotype A ("BoNT/A ad") is a recombinant derivative of wild-type *Clostridium botulinum* neurotoxin, serotype A (BoNT/A) produced using this platform. This derivative (i.e., BoNT/A ad) contains functional receptor binding and translocation domains, and an atoxic light chain (LC) fused to a sequence representing a cargo site (see U.S. Patent Application Publication No. 2011/0206616 to Ichtchenko and Band). In one embodiment, the BoNT/A ad LC has two mutations introduced into the enzymatic core of the protease, dramatically reducing its potent toxicity. BoNT/A ad has an $LD_{50}$ that is 100,000-fold higher than the wild-type toxin. Previous analysis demonstrated that BoNT/A ad accumulates in neuromuscular junctions of the mouse diaphragm after systemic intraperitoneal administration, and can be immunoprecipitated as a complex with SNAP-25 from neuronal cultures (Band et al., "Recombinant Derivatives of Botulinum Neurotoxin A Engineered for Trafficking Studies and Neuronal Delivery," *Protein Expr. Purif* 71:62-73 (2010); Pellett et al., "Neuronal Targeting, Internalization, and Biological Activity of a Recombinant Atoxic Derivative of Botulinum Neurotoxin A," *Biochem. Biophys. Res. Commun.* 405:673-677 (2011)), cleaves SNAP-25 at slower kinetics than wild-type BoNT/A, and accumulates at micromolar concentrations inside neurons (Vazquez-Cintron, "Atoxic Derivative of Botulinum Neurotoxin A as a Prototype Molecular Vehicle for Targeted Delivery to the Neuronal Cytoplasm," *PLoS One* 9(1):e85517 (2014)).

The present invention is directed to overcoming deficiencies in the art. This includes overcoming challenges associated with the delivery of functional single chain antibodies to targets exposed to the cytoplasm of neurons.

SUMMARY OF THE INVENTION

One aspect of the present invention relates to a fusion protein comprising a light chain region of a Clostridial neurotoxin and a heavy chain region of a Clostridial neurotoxin. The light and heavy chain regions are linked by a disulfide bond. A single chain antibody is positioned upstream of the light chain region. The single chain antibody possesses antigen-binding activity.

Another aspect of the present invention relates to a therapeutic agent comprising the fusion protein of the present invention and a pharmaceutically acceptable carrier.

A further aspect of the present invention relates to a method for treating a subject for toxic effects of a Clostridial neurotoxin. This method involves administering the therapeutic agent of the present invention to the subject under conditions effective to treat the subject for toxic effects of Clostridial neurotoxin.

Yet another aspect of the present invention relates to a treatment method. This method involves administering a fusion protein of the present invention to a subject under conditions effective to provide treatment to the subject.

Yet a further aspect of the present invention relates to a propeptide fusion. The propeptide fusion has a light chain region of a Clostridial neurotoxin and a heavy chain region of a Clostridial neurotoxin. The light and heavy chain regions are linked by a disulfide bond. An intermediate region connects the light and heavy chain regions and comprises a highly specific protease cleavage site. The highly specific protease cleavage site has three or more specific adjacent amino acid residues that are recognized by the highly specific protease to enable cleavage. A single chain antibody is positioned upstream of the light chain region. The single chain antibody possesses antigen-binding activity.

Another aspect of the present invention relates to an isolated nucleic acid molecule encoding the propeptide fusion of the present invention.

A further aspect of the present invention relates to an expression system comprising the nucleic acid molecule according to the present invention in a heterologous vector.

Still another aspect of the present invention relates to a host cell comprising the nucleic acid molecule of the present invention.

Still a further aspect of the present invention relates to a method of expressing a fusion protein. This method involves providing a nucleic acid construct comprising a nucleic acid molecule of the present invention, a heterologous promoter operably linked to the nucleic acid molecule, and a 3' regulatory region operably linked to the nucleic acid molecule. The nucleic acid construct is introduced into a host cell under conditions effective to express a propeptide of the fusion protein.

Another aspect of the present invention relates to a fusion protein produced by cleaving the propeptide fusion protein of the present invention at the highly specific protease cleavage site. The light chain region and the heavy chain region are linked by a disulfide bond.

The methods of antibody delivery discussed supra in the Background of the Invention have limitations for pharmaceutical application that the present invention is intended to overcome. Specifically, the above-described methods do not enable specific delivery of functional single chain antibodies to targets exposed to the cytoplasm of neurons. By fusing the antibody to an atoxic Clostridial neurotoxin derivative, the fusion proteins described herein are able to direct a single chain antibody to neurons, translocate the antibody from an internalized endosome into the cytoplasm, potentially deliver the antibody by retrograde transport to distant neuronal cell bodies and to other neurons, and provide a means of administering a therapeutic agent by multiple routes, including oral and inhalational.

Single chain antibodies have been developed for various purposes, including various therapeutic purposes. The present invention is specifically directed to molecules and methods of delivery of single chain antibodies to intracellular targets based on genetic fusion of the single chain antibody to a recombinant Clostridial neurotoxin derivative, so that the clostridial neurotoxin derivative can act as a molecular vehicle that can target and chaperone the transport of the antibody into the cytoplasm of neurons, and thereby allow the antibody to target specific intra-neuronal proteins. Thus, according to one embodiment of the present invention, the antibody is the drug agent, and the recombinant Clostridial neurotoxin derivative primarily serves as the delivery vehicle for the antibody.

The Examples set forth herein infra provide evidence regarding the successful delivery of single chain antibodies using atoxic derivatives of Clostridial neurotoxins. Fusion proteins of the present invention target neurons, can accumulate in the cytosolic fraction of neuronal cultures at micromolar concentrations, and are co-localized with synaptic proteins. The delivery of single chain antibodies allows the targeting and elimination of pathological proteins present in the neuronal cytoplasm, serving as a therapeutic for numerous neurological conditions.

BRIEF DESCRIPTION OF THE DRAWINGS

FIG. 1A is a schematic illustration of the full-length single chain expression product of BoNT before processing. Affinity purification tags ("APT") reside at the N- ($APT_N$) and C-terminus ($APT_C$), respectively, to be used for 2-step affinity purification. Detection tags ("DT") are placed to detect the light and heavy chains of the mature heterodimer. For example, an Ollas tag on the N-terminus of the LC and an HA tag on the C-terminus of the HC may be introduced for visualization of the protein using immunocytochemical (ICC) techniques. FIG. 1B is a schematic illustration of the disulfide-bonded LC-HC heterodimer of a BoNT produced by processing the expression product of the embodiment illustrated in FIG. 1A via cleavage with a restricted specificity protease ("RSP"), which cleaves at a restricted specificity protease (RSP) site, also referred to herein as a "highly specific protease cleavage site"), which removes the APTs and cleaves the expression product between the LC and HC.

FIG. 2 also demonstrates that even though VAMP-2 is a substrate for other BoNT serotypes, this specific derivative has no cleavage activity on VAMP-2 despite its altered primary structure.

In FIG. 3C, BoNT/A ad-1 LC does not co-localize with Early Endosome marker EEA1.

FIG. 4A is a schematic illustration showing the full-length single chain expression product before processing (propeptide fusion). Affinity purification tags (APT) are placed at the N- ($APT_N$) and C-terminus ($APT_C$), respectively, to be used for the 2-step affinity purification. The detection tag ($DT_1$) on the N-terminus of the single chain antibody (VHH) is for visualization of the protein using immunocytochemical (ICC) or other immunological techniques. A spacer sequence ("SS") is placed between the VHH and the N-terminus of the LC. FIG. 4B is a schematic illustration showing the disulfide-bonded LC-HC heterodimer produced by processing the expression product via cleavage with a restricted specificity protease (RSP), which removes the APTs and cleaves the expression product between the LC and HC. In one embodiment, this propeptide fusion and fusion protein is termed "BoNT/A ad-1 VHH."

FIGS. 9A-L provide the double-stranded DNA sequence (SEQ ID NO:1) encoding one embodiment of a propeptide fusion of the present invention and the amino acid sequence (SEQ ID NO:2) of this propeptide fusion. Text boxes are provided between the double-stranded DNA sequence to identify functional and /or structural features of the DNA sequence and /or the translated amino acid sequence.

FIGS. 10A-L provide the double-stranded DNA sequence (SEQ ID NO:3) encoding one embodiment of a propeptide fusion of the present invention and the amino acid sequence (SEQ ID NO:4) of this propeptide fusion. Text boxes are provided along the double-stranded DNA sequence to identify functional and /or structural features of the DNA sequence and /or the translated amino acid sequence.

FIGS. 11A-L provide the double-stranded DNA sequence (SEQ ID NO:5) encoding one embodiment of a propeptide fusion of the present invention and the amino acid sequence (SEQ ID NO:6) of this propeptide fusion. Text boxes are provided along the double-stranded DNA sequence to identify functional and /or structural features of the DNA sequence and /or the translated amino acid sequence.

FIGS. 12A-M provide the double-stranded DNA sequence (SEQ ID NO:7) encoding one embodiment of a propeptide fusion of the present invention and the amino acid sequence (SEQ ID NO:8) of this propeptide fusion. Text boxes are provided along the double-stranded DNA sequence to identify functional and /or structural features of the DNA sequence and /or the translated amino acid sequence.

FIG. 13A is a schematic illustration of the full-length single chain expression product (propeptide fusion) before processing. APT are placed at the N-($APT_N$) and C-terminus ($APT_C$), respectively, to be used for (2-step) affinity purification. A DT ($DT_1$) on the N-terminus of the LC is introduced for visualization of the protein using immunocytochemical (ICC) techniques. FIG. 13B is a schematic illustration of the fusion protein product of the propeptide fusion of FIG. 13A showing the disulfide-bonded LC-HC heterodimer produced by processing the expression product via cleavage with a RSP, which removes the APTs and cleaves the expression product between the LC and HC.

FIGS. 17A-L provide the double-stranded DNA sequence (SEQ ID NO:9) and amino acid sequence (SEQ ID NO:10) of an atoxic derivative of a *Clostridium botulinum* serotype C containing a single chain antibody to form a propeptide fusion and fusion protein of the present invention. Text boxes are provided along the double-stranded DNA sequence to identify functional and /or structural features of the DNA sequence and /or the translated amino acid sequence. FIGS. 17A-L illustrate one specific embodiment of the generic construct of FIG. 4A.

FIGS. 19A-L provide the double-stranded DNA sequence (SEQ ID NO:11) encoding one embodiment of a propeptide fusion of the present invention and the amino acid sequence (SEQ ID NO:12) of this propeptide fusion. Text boxes are provided along the double-stranded DNA sequence to identify functional and /or structural features of the DNA sequence and /or the translated amino acid sequence. The embodiment illustrated corresponds to the schematic illustration of FIG. 13A.

FIGS. 20A-L provide the double-stranded DNA sequence (SEQ ID NO:13) encoding one embodiment of a propeptide fusion of the present invention and the amino acid sequence (SEQ ID NO:14) of this propeptide fusion. Text boxes are provided along the sequences to identify functional and /or structural features of the DNA sequence and /or the translated amino acid sequence. The embodiment illustrated corresponds to the schematic illustration of FIG. 13A.

FIGS. 21A-C show results of BoNT/C ad propeptide purification and processing in reduced 12% SDS-PAGE stained with Coomassie BB R-250. FIG. 21A shows Ni-NTA SuperFlow chromatography purification in lanes 1 through 6, StrepTactin agarose chromatography in lanes 8 through 11, and Elution of BoNT/C ad propeptide in lane 12. FIG. 21B shows processing of BoNT/C ad propeptide to heterodimer by proteolytic cleavage with Tobacco Etch Virus (TEV). Lanes 1-5: non-reduced samples, lanes 6-10: samples reduced by addition of beta-mercaptoethanol. Lanes 1 and 6: no TEV; lanes 2-5 and 7-10 treated with TEV for the times as follows: lanes 2 and 7, 1 hour; lanes 3 and 8, 6 hours; lanes 4 and 9, 24 hours; and lanes 5 and 10, 48 hours. FIG. 21C shows removal of TEV. Lane 1: load; lanes 2-4: washes with 5 mM imidazole; Lanes 6-8: washes with 40 mM imidazole; Lanes 9-10: 250 mM elution of TEV.

FIG. 22A demonstrates that BoNT/C ad does not cleave Syntaxin-1, compared to cells treated with 0.5 nM BoNT/C as a positive control. FIG. 22B confirms that BoNT/C ad does not cleave Syntaxin-1 or SNAP-25. Detection of BoNT/C ad LC shows the presence of BoNT/C ad associated with the cortical cells. VAMP-2 serves as internal loading control.

FIGS. 23A-B demonstrate that BoNT/C ad co-localizes with pre-synaptic marker VAMP-2 in neuronal cultures. 14-DIV E19 rat hippocampal cultures were exposed to 25 nM of BoNT/C ad for 16 hours. Cells were prepared for immunocytochemistry and analyzed using confocal microscopy. FIG. 23A shows cells stained for VAMP-2 and BoNT/C ad LC. FIG. 23B shows cells stained with VAMP-2 and BoNT/C ad HC.

FIG. 25A shows a sideview of a neuromuscular junction; clockwise from bottom left: BoNT/C-HC, Syntaxin, Alpha bungarotoxin, and the composite of BoNT/C HC, Syntaxin, and Alpha bungarotoxin. Bar equals 10 microns.

FIG. 32 depicts a DNA construct with nucleotides encoding the BoNT LC and BoNT HC of any *Clostridium botulinum* serotype, separated and flanked by RSP encoding sequences, and optionally containing tag encoding sequences (tags) including, but not limited to, AFPs and DTs, and also including nucleotide spacers and /or linkers. The RSP between the LC and HC encoding sequences is optionally further separated by nucleotide spacer sequences (SS).

FIG. 35 depicts the BoNT LC of any serotype, with an upstream RSP and ADD. The RSP is selected such that after cleavage, a positively charged amino acid (-$X^+$-) is located immediately upstream (or at the N-terminus) of the ADD site.

FIGS. 36A-F provide the DNA sequence (SEQ ID NO:19) of one embodiment of a DNA construct for molecular construction of fusion proteins of the present invention and the corresponding amino acid sequence (SEQ ID NO:20) of this DNA construct. The sequences of FIGS. 36A-F are specific examples of constructs encoding/having the general structure of the construct illustrated in FIG. 35. In particular, the construct of FIGS. 36A-F encodes the BoNT/A ad-0 LC.

FIGS. 37A-E provide the DNA sequence (SEQ ID NO:21) of one embodiment of a DNA construct for molecular construction of fusion proteins of the present invention and the corresponding amino acid sequence (SEQ ID NO:22) of this DNA construct. The sequences of FIGS. 37A-E are specific examples of constructs encoding/having the general structure of the construct illustrated in FIG. 35. In particular, the construct of FIGS. 37A-E encodes the BoNT/C ad-0 LC.

FIGS. 38A-C are schematic illustrations of embodiments of DNA constructs used for molecular construction of fusion proteins of the present invention. In particular, FIGS. 38A-C depict the cloning of the construct described in FIG. 35 into the construct described in FIG. 32. FIGS. 38A-C depict the corresponding unique restriction sites ("URS," dashed lines indicate correspondence) between donor (FIG. 38B) and recipient (FIG. 38A) constructs, allowing insertion of donor DNA into recipient DNA. The resulting construct (FIG. 38C) encodes the elements of the construct described in FIG. 35, which replace the tag, RSP, and BoNT LC elements of the construct described in FIG. 32.

FIG. 41 depicts a VHH region, with an upstream RSP and optional tags, linkers, or spacers. The VHH region, denoted VHH* may be one or more VHHs, with optional spacers or linkers.

FIG. 42 provides the DNA sequence (SEQ ID NO:27) of one embodiment of a DNA construct for molecular construction of fusion proteins of the present invention and the corresponding amino acid sequence (SEQ ID NO:28) of this DNA construct. The sequences of FIG. 42 are specific examples of constructs encoding/having the general structure of the construct illustrated in FIG. 41. In particular, the construct of FIG. 42 encodes the B8 VHH against BoNT/A LC in the VHH region.

FIGS. 43A-B provide the DNA sequence (SEQ ID NO:29) of one embodiment of a DNA construct for molecular construction of fusion proteins of the present invention and the corresponding amino acid sequence (SEQ ID NO:30) of this DNA construct. The sequences of FIGS. 43A-B are specific examples of constructs encoding/having the general structure of the construct illustrated in FIG. 41. In particular, the construct of FIGS. 43A-B encodes for the JLJG3 VHH against BoNT/B LC and the B10 VHH against BoNT/B LC in the VHH region.

FIGS. 45A-B provide the DNA sequence (SEQ ID NO:33) of one embodiment of a DNA construct for molecular construction of fusion proteins of the present invention and the corresponding amino acid sequence (SEQ ID NO:34) of this DNA construct. The sequences of FIGS. 45A-B are specific examples of constructs encoding/having the general structure of the construct illustrated in FIG. 41. In particular, the construct of FIGS. 45A-B contains the EPEA alpha-synuclein VHH 1 and EPEA alpha-synuclein VHH 2 in the VHH region.

FIGS. 46A-C are schematic illustrations of embodiments of DNA constructs used for molecular construction of fusion proteins of the present invention. In particular, FIGS. 46A-C depict the cloning of the construct described in FIG. 41 into the construct described in FIG. 38C. FIGS. 46A-C depict the corresponding unique restriction sites (URS, dashed lines indicate correspondence) between donor (FIG. 46B) and recipient (FIG. 46A) constructs, allowing insertion of donor DNA into recipient DNA. The resulting construct (FIG. 46C) contains the elements of the construct described in FIG. 41, which replace the tag, RSP, and ADD elements of the construct described in FIG. 38C.

FIGS. 47A-C are schematic illustrations of embodiments of DNA constructs used for molecular construction of fusion proteins of the present invention. In particular, FIGS. 47A-C depict the cloning of the construct described in FIG. 41 into the construct described in FIG. 38C. In particular, FIGS. 47A-C depict the corresponding unique restriction sites (URS, dashed lines indicate correspondence) between donor (FIG. 47B) and recipient (FIG. 47A) constructs, allowing insertion of donor DNA into recipient DNA. The resulting construct (FIG. 47C) contains the elements of the construct described in FIG. 41, as well as those described in FIG. 38C.

DETAILED DESCRIPTION OF THE INVENTION

Figure 1A:
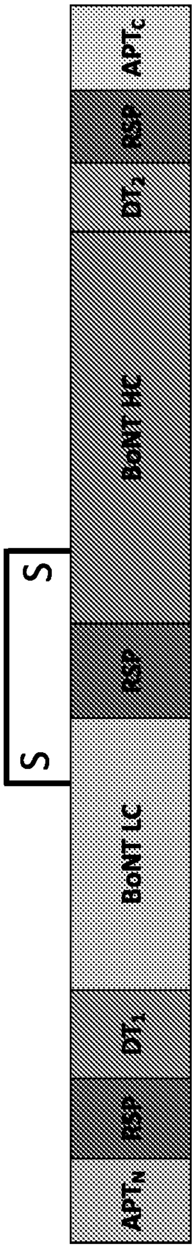
FIGS. 1A-B are schematic illustrations of a Clostridial neurotoxin (e.g., a BoNT) before (FIG. 1A) and after (FIG. 1B) processing of the full-length single chain expression product. This Clostridial neurotoxin is not a single chain antibody fusion protein, i.e., does not contain a fused single chain antibody. Specifically.

One aspect of the present invention relates to a fusion protein comprising a light chain region of a Clostridial neurotoxin and a heavy chain region of a Clostridial neurotoxin. The light and heavy chain regions are linked by a disulfide bond. A single chain antibody is positioned upstream of the light chain region. The single chain antibody possesses antigen-binding activity.

The Clostridial neurotoxins are a family of structurally similar proteins that target the neuronal machinery for synaptic vesicle exocytosis. Produced by anaerobic bacteria of the *Clostridium* genus, botulinum neurotoxins and Tetanus neurotoxins are the most poisonous substances known on a per-weight basis, with an $LD_{50}$ in the range of 0.5-2.5 ng/kg when administered by intravenous or intramuscular routes (*National Institute of Occupational Safety and Healthy*, "Registry of Toxic Effects of Chemical Substances (R-TECS)," Cincinnati, Ohio: National Institute of Occupational Safety and Health (1996), which is hereby incorporated by reference in its entirety).

Common structural features of the wild-type *Clostridium botulinum* neurotoxins are illustrated in U.S. Pat. No. 7,785,606 to Ichtchenko and Band, which is hereby incorporated by reference in its entirety. These structural features are illustrated using BoNT/A as an example, but are generalized among all BoNT serotypes.

As discussed infra, Botulinum neurotoxins are synthesized as single chain propeptides which are later activated by a specific proteolysis cleavage event, generating a dimer joined by a disulfide bond. The mature BoNT/A is composed of three functional domains of Mr ~50,000, where the catalytic function responsible for toxicity is confined to the light chain (residues 1-437), the translocation activity is associated with the N-terminal half of the heavy chain (residues 448-872), and cell binding is associated with its C-terminal half (residues 873-1,295) (Johnson, "Clostridial Toxins as Therapeutic Agents: Benefits of Nature's Most Toxic Proteins," *Annu. Rev. Microbiol.* 53:551-575 (1999); Montecucco et al., "Structure and Function of Tetanus and Botulinum Neurotoxins," *Q. Rev. Biophys.* 28:423-472 (1995), which are hereby incorporated by reference in their entirety).

Optimized expression and recovery of recombinant neurotoxins for BoNT serotypes in a native and physiologically active state is achieved by the introduction of one or more alterations to the nucleotide sequences encoding the BoNT propeptides, as discussed infra. These mutations are designed to maximize yield of recombinant Botulinum neurotoxin, while retaining the native toxins' structure and biological activity, and to render the neurotoxin atoxic, that is, with toxicity reduced by several orders of magnitude relative to wild-type BoNTs and, in some cases, devoid of any substrate cleavage activity. The fusion protein of the present invention can be isolated at a yield or concentration of at least about 0.1 mg/L, at least about 0.5 mg/L, at least about 1 mg/L, at least about 5 mg/L, at least about 10 mg/L, about 10-20 mg/L, about 20-30 mg/L, or at least about 30 mg/L. One of the particular advantages of the propeptide fusions described herein, and the method of their expression, is that the fusion proteins can be purified to a homogeneity using a two-stage, non-denaturing, and highly selective affinity purification, as described in greater detail infra.

Isolated fusion proteins of the present invention are, according to one embodiment, physiologically active. This physiological activity includes, but is not limited to, any one or more of toxin immunogenicity, trans- and intra-cellular trafficking, and cell recognition, which are properties of a wild-type Clostridial neurotoxin.

The mechanism of cellular binding and internalization of Clostridial toxins is still poorly understood. No single receptor has been unambiguously identified, and the binding constants have not been characterized. The C-terminal portion of the heavy chain of all botulinum neurotoxins binds to gangliosides (sialic acid-containing glycolipids), with a preference for gangliosides of the $G_{1b}$ series (Montecucco et al., "Structure and Function of Tetanus and Botulinum Neurotoxins," *Q. Rev. Biophys.* 28:423-472 (1995); Montecucco, "How Do Tetanus and Botulinum Toxins Bind to Neuronal Membranes?" *TIBS* 11:314-317 (1986); and Van Heyningen et al., "The Fixation of Tetanus Toxin by Ganglioside," *J. Gen. Microbiol.* 24:107-119 (1961), which are hereby incorporated by reference in their entirety). The sequence responsible for ganglioside binding has been identified for the structurally similar TeNT molecule, and is located within the 34 C-terminal amino acid residues of its heavy chain. BoNT/A, /B, /C, /E, and /F share a high degree of homology with TeNT in this region (Shapiro et al., "Identification of a Ganglioside Recognition Domain of Tetanus Toxin Using a Novel Ganglioside Photoaffinity Ligand," *J Biol. Chem.* 272:30380-30386 (1997), which is hereby incorporated by reference in its entirety). Multiple types of evidence suggest the existence of at least one additional component involved in the binding of botulinum neurotoxins to neuronal membranes (Montecucco et al., "Structure and Function of Tetanus and Botulinum Neurotoxins," *Q. Rev. Biophys.* 28:423-472 (1995); Montecucco, "How Do Tetanus and Botulinum Toxins Bind to Neuronal Membranes?" *TIBS* 11:314-317 (1986), which are hereby incorporated by reference in their entirety). In two reports (Nishiki et al., "The High-Affinity Binding of *Clostridium botulinum* Type B Neurotoxin to Synaptotagmin II Associated with Gangliosides $G_{T1b}/G_{D1a}$," FEBS Lett. 378:253-257 (1996); Dong et al., "Synaptotagmins I and II Mediate Entry of Botulinum Neurotoxin B into Cells," *J. Cell Biol.* 162:1293-1303 (2003), which are hereby incorporated by reference in their entirety), synaptotagmins were identified as possible candidates for the auxiliary BoNT/B receptor, and synaptotagmins I and II were implicated as neuronal receptors for BoNT/G (Rummel et al., "Synaptotagmins I and II Act as Nerve Cell Receptors for Botulinum Neurotoxin G," *J. Biol. Chem.* 279:30865-30870 (2004), which is hereby incorporated by reference in its entirety). However, despite the structural similarity in the putative receptor-binding domain of botulinum neurotoxins, other toxin subtypes show no affinity for synaptotagmins or synaptotagmin-related molecules. Lipid rafts (Herreros et al., "Lipid Rafts Act as Specialized Domains for Tetanus Toxin Binding and Internalization Into Neurons," *Mol. Biol. Cell* 12:2947-2960 (2001), which is hereby incorporated by reference in its entirety) have been implicated as a specialized domain involved in TeNT binding and internalization into neurons, but these domains are widely distributed on multiple cell types and, therefore, cannot simply explain the high specificity of the toxins for neurons.

Botulinum neurotoxins are internalized through the presynaptic membrane by an energy-dependent mechanism (Montecucco et al., "Structure and Function of Tetanus and Botulinum Neurotoxins," Q. Rev. Biophys. 28:423-472 (1995); Matteoli et al., "Synaptic Vesicle Endocytosis Mediates the Entry of Tetanus Neurotoxin into Hippocampal Neurons," *Proc. Natl. Acad. Sci. USA* 93:13310-13315 (1996); and Mukherjee et al., "Endocytosis," *Physiol. Rev.* 77:759-803 (1997), which are hereby incorporated by reference in their entirety), and rapidly appear in vesicles where they are at least partially protected from degradation (Dolly et al., "Acceptors for Botulinum Neurotoxin Reside on Motor Nerve Terminals and Mediate Its Internalization," *Nature* 307:457-460 (1984); Critchley et al., "Fate of Tetanus Toxin Bound to the Surface of Primary Neurons in Culture: Evidence for Rapid Internalization," *J Cell Biol.* 100:1499-1507 (1985), which are hereby incorporated by reference in their entirety). The BoNT complex of light and heavy chains interacts with the endocytic vesicle membrane in a chaperone-like way, preventing aggregation and facilitating translocation of the light chain in a fashion similar to the protein conducting/translocating channels of smooth ER, mitochondria, and chloroplasts (Koriazova et al., "Translocation of Botulinum Neurotoxin Light Chain Protease Through the Heavy Chain Channel," *Nat. Struct. Biol.* 10:13-18 (2003), which is hereby incorporated by reference in its entirety). Acidification of the endosome is believed to induce pore formation, which allows translocation of the light chain to the cytosol upon reduction of the interchain disulfide bond (Hoch et al., "Channels Formed by Botulinum, Tetanus, and Diphtheria Toxins in Planar Lipid Bilayers: Relevance to Translocation of Proteins Across Membranes," *Proc. Natl. Acad. Sci. USA* 82:1692-1696 (1985), which is hereby incorporated by reference in its entirety). Within the cytosol, the light chain displays a zinc-endopeptidase activity specific for protein components of the synaptic vesicle exocytosis apparatus. TeNT and BoNT/B, /D, /F, and /G recognize VAMP/synaptobrevin. This integral protein of the synaptic vesicle membrane is cleaved at a single peptide bond, which differs for each neurotoxin. BoNT/A, /C, and /E recognize and cleave SNAP-25, a protein of the presynaptic membrane, at two different sites within the carboxyl terminus. BoNT/C also cleaves syntaxin, another protein of the nerve plasmalemma (Montecucco et al., "Structure and Function of Tetanus and Botulinum Neurotoxins," *Q. Rev. Biophys.* 28:423-472 (1995); Sutton et al., "Crystal Structure of a SNARE Complex Involved in Synaptic Exocytosis at 2.4 Å Resolution," *Nature* 395:347-353 (1998), which are hereby incorporated by reference in their entirety). The cleavage of any component of the synaptic release machinery results in inhibition of neurotransmitter release, ultimately leading to neuromuscular paralysis.

The toxicity of botulinum neurotoxins is a result of a multi-step mechanism. BoNTs can cross epithelial barriers and they are stable in the circulation. From the circulation, BoNT primarily targets the pre-synaptic membrane of neuromuscular junctions, where it is internalized to directly exert its toxic effect on the peripheral nervous system (Dolly et al., "Acceptors for Botulinum Neurotoxin Reside on Motor Nerve Terminals and Mediate Its Internalization," *Nature* 307:457-460 (1984), which is hereby incorporated by reference in its entirety). Toxicity at the neuromuscular junction involves neuron binding; internalization into endocytic vesicles, similar to those involved in synaptic vesicle recycling; activation within an acidic compartment to allow the proteolytically active LC of the toxin to penetrate into the neuronal cytoplasm; and target recognition and catalytic cleavage of substrates in the neuronal machinery for synaptic vesicle exocytosis.

According to one embodiment, the fusion protein of the present invention has the physiological trafficking activity of a Clostridial neurotoxin, but is atoxic. In one embodiment, the fusion protein may be atoxic and still possess residual substrate cleavage activity. The retention of substrate cleavage activity has the potential to limit the ability of the fusion protein to perform as an inert drug carrier (e.g., carrier of a single chain antibody), but offers the added benefit of providing a marker for proper delivery of the single chain antibody into the cell, as discussed in the Examples infra. In another embodiment, the fusion protein is atoxic and devoid of any residual SNAP-25 cleavage activity and, therefore, performs as a more inert drug carrier. These different properties of the fusion proteins described herein can be achieved by the introduction of certain amino acid substitutions and other modifications into the propeptide fusion of the present invention, as discussed in more detail infra.

By "atoxic" it is meant that the fusion proteins have a toxicity that is reduced from a wild-type Clostridial neurotoxin by at least about 1000-fold. In certain exemplary embodiments, the $LD_{50}$ of a fusion protein of the present invention is at least 1,000; 2,000; 5,000; 7,000; 9,000; 10,000; 20,000; 30,000; 40,000; 50,000; 60,000; 70,000;

80,000; 90,000; 100,000; or 500,000-fold or more higher than the $LD_{50}$ of wild-type Clostridial neurotoxin. The particular mode of administration (discussed infra) may also affect the $LD_{50}$ of the fusion protein. Recombinant BoNT derivatives that retain the ability to deliver significant quantities of their LC to the neuronal cytoplasm may be expected to retain some level of toxicity, even if their ability to cleave substrate is eliminated by amino acid substitution. The reduced toxicity of BoNT/A ad-1 suggests that it may be more useful than BoNT/A ad-0 (a BoNT/A protein derivative comprising $E_{224}$A>A and $Y_{366}$>A mutations) as a molecular vehicle for delivering drugs to the cytoplasm. BoNT/C is significantly less toxic than BoNT/A ad-1 or ad-0.

The endopeptidase activity responsible for botulinum neurotoxin toxicity is believed to be associated with the presence of a HExxHxxH (SEQ ID NO:51) motif in the light chain, characteristic of metalloproteases. Mutagenesis of BoNT/A light chain, followed by microinjection of the corresponding mRNA into presynaptic cholinergic neurons of *Aplysia californica*, allowed the minimal essential domain responsible for toxicity to be identified (Kurazono et al., "Minimal Essential Domains Specifying Toxicity of the Light Chains of Tetanus Toxin and Botulinum Neurotoxin Type A," *J. Biol. Chem.* 267:14721-14729 (1992), which is hereby incorporated by reference in its entirety). Site-directed mutagenesis of BoNT/A light chain pinpointed the amino acid residues involved in $Zn^{2+}$coordination, and formation of the active metalloendoprotease core which cleaves SNAP-25 (Rigoni et al., "Site-Directed Mutagenesis Identifies Active-Site Residues of the Light Chain of Botulinum Neurotoxin Type A," *Biochem. Biophys. Res. Commun.* 288:1231-1237 (2001), which is hereby incorporated by reference in its entirety). The three-dimensional structures of botulinum neurotoxins and their derivatives confirmed the mutagenesis results, and detailed the spatial organization of the protein domains. For the BoNT/A holotoxin, crystal structure was obtained to a resolution of 3.3 Å (Lacy et al., "Crystal Structure of Botulinum Neurotoxin Type A and Implications for Toxicity," *Nat. Struct. Biol.* 5:898-902 (1998), which is hereby incorporated by reference in its entirety). The BoNT/B holotoxin crystal structure was determined at 1.8 and 2.6 Å resolution (Swaminathan et al., "Structural Analysis of the Catalytic and Binding Sites of *Clostridium botulinum* Neurotoxin B," *Nat. Struct. Biol.* 7:693-699 (2000), which is hereby incorporated by reference in its entirety). Recently, a crystal structure for BoNT/E catalytic domain was determined to 2.1 Å resolution (Agarwal et al., "Structural Analysis of Botulinum Neurotoxin Type E Catalytic Domain and Its Mutant $Glu_{212}$>Gln Reveals the Pivotal Role of the $Glu_{212}$ Carboxylate in the Catalytic Pathway," *Biochemistry* 43:6637-6644 (2004), which is hereby incorporated by reference in its entirety). The later study provided multiple interesting structural details, and helps explain the complete loss of metalloendoproteolytic activity in the BoNT/E LC $E_2$12>Q mutant. The availability of this detailed information on the relationship between the amino acid sequence and biological activities of Clostridial toxins enables the design of modified toxin genes with properties specifically altered for therapeutic goals.

In one embodiment of the fusion protein described herein, the Clostridial neurotoxin is *Clostridium botulinum* neurotoxin of serotype A (BoNT/A), serotype B (BoNT/B), serotype C (BoNT/C), serotype D (BoNT/D), serotype E (BoNT/E), serotype F (BoNT/F), serotype G (BoNT/G), or serotype H (BoNT/H).

In the fusion proteins described herein, the Clostridial neurotoxin of the light chain region may be the same or different from the Clostridial neurotoxin of the heavy chain region. For example, in one embodiment of the fusion protein, the Clostridial neurotoxin of the light chain region is the light chain region of BoNT/A and the Clostridial neurotoxin of the heavy chain region is the heavy chain region of BoNT/A. In another non-limiting example, the light chain region is from BoNT/A and the heavy chain region is from BoNT/E.

According to one embodiment, the light and heavy chain regions of the Clostridial neurotoxin are not truncated from their wild-type length. In other words, the light chain region and the heavy chain region are the same, or very nearly the same as the wild-type light chain region and heavy chain region in terms of overall length.

In one embodiment, the fusion protein has the following amino acid substitutions in the light chain region: $E_2$24>A and $Y_{366}$>A, and either (i) $Q_{162}$>Y, $L_{256}$>Y, $R_{257}$>E, and $L_{322}$>E or (ii) $Q_{16}$>E, $E_{263}$>L, and $L_{323}$>I. These specific mutations are with respect to the BoNT/A light chain. According to the present invention, corresponding mutations may be made in other serotypes of BoNT.

In one embodiment, the fusion protein has the following amino acid substitutions in the light chain region: $E_{446}$>A, $H_{449}$>G, $Y_{591}$>A. These specific mutations are with respect to the BoNT/C light chain. According to the present invention, corresponding mutations may be made in other serotypes of BoNT.

As used herein, the term "single chain antibody" means an immunoglobulin single chain variable domain on a single polypeptide, which is capable of specifically binding to an epitope of an antigen without pairing with an additional variable immunoglobulin domain. One example of immunoglobulin single chain variable domains includes "VHH domains" (or simply "VHHs") from camelids. Another example of immunoglobulin single variable domains includes "domain antibodies," such as the immunoglobulin single variable domains VH and VL (VH domains and VL domains, when fused together in artificial constructs).

As used herein, the term "single chain antibody" means an immunoglobulin single variable domain which is capable of specifically binding to an epitope of an antigen without pairing with an additional variable immunoglobulin domain. One example of immunoglobulin single variable domains includes "VHH domains" (or simply "VHHs") from camelids. Another example of immunoglobulin single variable domains includes "domain antibodies," such as the immunoglobulin single variable domains VH and VL (VH domains and VL domains).

Single chain antibodies or fragments thereof can be produced from multi-chain antibodies (Sheets et al., "Efficient Construction of a Large Nonimmune Phage Antibody Library: The Production of High-Affinity Human Single-Chain Antibodies to Protein Antigens," *PNAS USA* 95(11): 6157-6162 (1998), which is hereby incorporated by reference in its entirety) or can be derived from species that naturally produce single chain antibodies, such as sharks and camelids (Dumoulin et al., "Single-Domain Antibody Fragments with High Conformational Stability," *Protein Science: A Publication of the Protein Society* 11(3):500-515 (2002), which is hereby incorporated by reference in its entirety). As mentioned above, one class of single chain antibodies are referred to as VHH antibodies, which are more fully described infra.

"VHH domains," also known as VHHs, $V_{HH}$ domains, VHH antibody fragments, and VHH antibodies, have originally been described as the antigen binding immunoglobulin (variable) domain of "heavy chain antibodies" (i.e., of "antibodies devoid of light chains") (Hamers-Casterman et al., "Naturally Occurring Antibodies Devoid of Light Chains," *Nature* 363:446-448 (1993), which is hereby incorporated by reference in its entirety). The term "VHH domain" was chosen to distinguish these variable domains from the heavy chain variable domains that are present in conventional 4-chain antibodies (which are commonly referred to as "$V_H$ domains" or "VH domains") and from the light chain variable domains that are present in conventional 4-chain antibodies (which are commonly referred to as "$V_L$ domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust, and efficient antigen recognition units formed by a single immunoglobulin domain.

VHH domains have the structure: FR1-CDR1-FR2-CDR2-FR3-CDR3-FR4 and, as noted above, specifically bind to an epitope without requiring the presence of a second immunoglobulin variable domain. The amino acid residues of a VHH domain are numbered according to the general numbering for $V_H$ domains given by Kabat et al., *Sequence of Proteins of Immunological Interest*, U.S. Public Health Services, NIH Bethesda, Md., Publication No. 91, which is hereby incorporated by reference in its entirety), as applied to VHH domains from Camelids, as shown, e.g., in FIG. 2 of Riechmann et al., "Single Domain Antibodies: Comparison of Camel VH and Camelised Human VH Domains," *J. Immunol. Methods* 231:25-38 (1999), which is hereby incorporated by reference in its entirety. According to this numbering, FR1 comprises the amino acid residues at positions 1-30, CDR1 comprises the amino acid residues at positions 31-35, FR2 comprises the amino acids at positions 36-49, CDR2 comprises the amino acid residues at positions 50-65, FR3 comprises the amino acid residues at positions 66-94, CDR3 comprises the amino acid residues at positions 95-102, and FR4 comprises the amino acid residues at positions 103-113. However, as is well known in the art, for $V_H$ domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Alternative methods for numbering the amino acid residues of $V_H$ domains, which methods can also be applied in an analogous manner to VHH domains, are known in the art.

The total number of amino acid residues in a VHH domain will usually be in the range of from 110 to 120, often between 112 and 115. It should, however, be noted that smaller and longer sequences may also be suitable for the purposes described herein.

Further structural characteristics and functional properties of VHH domains and polypeptides containing the same can be summarized as follows: VHH domains (which have been "designed" by nature to functionally bind to an antigen without the presence of, and without any interaction with, a light chain variable domain) can function as a single, relatively small, functional antigen-binding structural unit, domain, or polypeptide. This distinguishes the VHH domains from the VH and VL domains of conventional 4-chain antibodies, which by themselves are generally not suited for practical application as single antigen-binding proteins or immunoglobulin single variable domains, but need to be combined in some form or another to provide a functional antigen-binding unit (as in, for example, conventional antibody fragments such as Fab fragments).

Because of these unique properties, the use of VHH domains, either alone or as part of a larger polypeptide, offers a number of significant advantages over the use of conventional VH and VL domains, scFv's, or conventional antibody fragments (such as Fab-or F(ab')2-fragments): only a single domain is required to bind an antigen with high affinity and with high selectivity, so that there is no need to have two separate domains present, nor to assure that these two domains are present in the right spacial conformation and configuration (i.e., through the use of especially designed linkers, as with scFv's); VHH domains can be expressed from a single gene and require no post-translational folding or modifications; VHH domains can easily be engineered into multivalent and multispecific formats; VHH domains are highly soluble and do not have a tendency to aggregate; VHH domains are stable to heat, pH, proteases, and other denaturing agents or conditions and, thus, may be prepared, stored or transported without the use of refrigeration equipment, conveying a cost, time, and environmental savings; and VHH domains are easy and relatively cheap to prepare, even on a scale required for production. For example, VHH domains can be produced using microbial fermentation and do not require the use of mammalian expression systems as with, for example, conventional antibody fragments; VHH domains are relatively small (approximately 15 kDa, or 10 times smaller than a conventional IgG) compared to conventional 4-chain antibodies and antigen-binding fragments thereof and, therefore, show high(er) penetration into tissues and can be administered in higher doses than such conventional 4-chain antibodies and antigen-binding fragments thereof; VHH domains can show so-called cavity-binding properties (inter alia, due to their extended CDR3 loop, compared to conventional VH domains) and can, therefore, also access targets and epitopes not accessible to conventional 4-chain antibodies and antigen-binding fragments thereof.

Methods of obtaining VHH domains binding to a specific antigen or epitope have been described earlier, e.g., in PCT Publication Nos. WO 2006/040153 and WO 2006/122786, which are hereby incorporated by reference in their entirety. As also described therein in detail, VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences and, in an even more specific embodiment, can contain human framework region sequences derived from DP-29, DP-47, DP-51, or parts thereof, optionally combined with JH sequences, such as JH5.

"Domain antibodies," also known as "Dab" s, "Domain Antibodies," and "dAbs" have been described in, e.g., Ward et al., "Binding Activities of a Repertoire of Single Immunoglobulin Variable Domains Secreted from *Escherichia coli*," Nature 341:544-546 (1989); Holt et al., "Domain Antibodies: Proteins for Therapy," *TRENDS in Biotechnol-*

*ogy* 21(11):484-490 (2003); and PCT Publication No. WO 2003/002609; all of which are hereby incorporated by reference in their entirety.

Domain antibodies essentially correspond to the VH or VL domains of non-camelid mammalians, in particular human 4-chain antibodies. To bind an epitope as a single antigen binding domain, i.e., without being paired with a VL or VH domain, respectively, specific selection for such antigen binding properties is required, e.g., by using libraries of human single VH or VL domain sequences. Domain antibodies have, like VHHs, a molecular weight of approximately 13 kDa to approximately 16 kDa and, if derived from fully human sequences, do not require humanization for, e.g., therapeutical use in humans. As in the case of VHH domains, they are well expressed also in prokaryotic expression systems, providing a significant reduction in overall manufacturing cost.

Domain antibodies, as well as VHH domains, can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules can be prepared by methods known in the art, e.g., as described by Johnson & Hawkins, *Affinity Maturation of Antibodies Using Phage Display*, Oxford University Press 1996, which is hereby incorporated by reference in its entirety.

Methods have also been developed to design bi-functional single chain antibody constructs (Yang et al., "A Novel Multivalent, Single-Domain Antibody Targeting TcdA and TcdB Prevents Fulminant *Clostridium Difficile* Infection in Mice," *J. Infect. Dis.* 210(6):964-972 (2014), which is hereby incorporated by reference in its entirety). As with all the other examples of single chain antibodies described herein, these bivalent single chain antibodies can also be used (i.e., incorporated) in the fusion proteins described herein.

Methods developed to optimize single chain antibodies by phage display or similar high throughput methodologies are also applicable to fusion proteins described herein.

Fusion of the light chain region of a Clostridial neurotoxin, a heavy chain region of a Clostridial neurotoxin, and a single chain antibody to create fusion proteins described herein can be carried out according to recombinant technology described herein infra.

In one embodiment, an amino acid spacer sequence is positioned between the light chain region and the single chain antibody.

Fusion proteins described herein have a light chain region and a heavy chain region of Clostridial neurotoxins such that the fusion protein possesses structural conformation required for (i) stability of the light and heavy chains, (ii) specific targeting of neurons by the fusion protein, and (iii) delivery of the fusion protein to neuronal cytosol. As used herein, maintaining structural conformation required for stability of the light and heavy chains means one or more of the following: no truncation of the LC or HC compared to the corresponding wild-type molecule, no exposed sites in the secondary structure for non-specific proteolysis, and minimal denaturation during purification and storage.

As used herein, maintaining structural conformation required for specific targeting of neurons by the fusion protein and maintaining structural conformation required for delivery of the fusion protein to the neuronal cytoplasm means one or more of the following: being in the form of a disulfide-bonded heterodimer, such that the $HC_C$ domain is still capable of specifically binding to neurons; having an $HC_N$ domain that is capable of forming a LC-transporting pore after endosome acidification; and the LC and its associated VHH cargo are able to pass through the $HC_N$ pore where the VHH remains active for antigen binding.

The fusion proteins described herein have a single chain antibody that possesses antigen-binding activity. As used herein, "antigen-binding activity" means that the fusion protein binds (at the single chain antibody portion) an antigen with higher affinity than other proteins or molecules. Alternatively, "antigen-binding activity" means that the fusion protein binds (at the single chain antibody portion) only a single antigen specific to the single chain antibody. "Antigen-binding activity" may also mean that the fusion protein has a functional antibody that retains its function even after it is delivered into a cell by means of the Clostridial neurotoxin light and heavy chains. In one embodiment, the antibody is determined to be functional or active by performing immunological testing following removal of the antibody from a cell after it has been delivered to the cell as cargo to the light and heavy chain regions of the Clostridial neurotoxin.

According to one embodiment, the fusion protein comprising a single chain antibody positioned upstream of the light chain region further includes a detection tag (DT) N-terminal to the single chain antibody, where the detection tag is capable of detecting delivery of the single chain antibody to neuronal cytoplasm. Suitable examples of detection tags are discussed infra. According to another embodiment, the fusion protein does not contain any detection tags.

According to another embodiment, the fusion protein comprising a single chain antibody positioned upstream of the light chain region further includes a spacer sequence (SS)C-terminal to the single chain antibody, where the spacer sequence has the properties described infra.

Another aspect of the present invention relates to a therapeutic agent comprising the fusion protein described herein. In one embodiment, the fusion protein is provided with a pharmaceutically acceptable carrier.

According to one embodiment, the single chain antibody is specific against a light chain of a wild-type *Clostridium botulinum* neurotoxin. According to this embodiment, the therapeutic agent is able to exert antidote activity after the light chain of a wild-type *Clostridium botulinum* neurotoxin has penetrated the cytoplasm of a neuron, thereby extending the time window post-exposure for exerting antidote activity. Developing these types of effective antidotes against Clostridial neurotoxins requires the preservation of structural features important to toxin trafficking. From a practical perspective, this is most easily achieved by first producing recombinant molecules that retain the structural features and toxicity of native toxin, followed by selective modification to eliminate toxicity and introduce therapeutic utility.

In one embodiment, the antidote has the physiological activity of a wild-type Clostridial neurotoxin, which activity includes, but is not limited to, trans- and intra-cellular trafficking, and cell recognition.

Atoxic neurotoxins can be tested as candidate antidotes to Clostridial neurotoxin poisoning. Fusion proteins are created using the atoxic derivatives described supra developed under the methods described herein. Parenteral routes of administration are tested first, followed by evaluation of oral and inhalational routes as applicable. Utility as an antidote can be evaluated in vitro by testing the ability of neurotoxin derivatives to prevent neuromuscular blockade in the mouse phrenic-nerve hemidiaphragm, or to inhibit cleavage in neuronal cultures of the respective serotypes' intracellular substrate. Fusion proteins created using the atoxic derivatives described supra may be superior to currently available antibody-based antidotes, because they effectively mimic native toxin absorption and trafficking pathways, and can therefore be effective after the wild-type neurotoxin is sequestered inside intoxicated neurons, where traditional antibodies cannot effectively target the toxin. Antidote effectiveness in vivo can be evaluated using multiple dosing regimens. Additional dosage and timing parameters relevant to using antidotes under crisis situations is further evaluated for neurotoxin derivatives found to be effective when administered simultaneously with toxin. Using these procedures, a series of atoxic derivatives and fusion proteins are created and their biological activities systematically catalogued. The availability of these well-characterized constructs and toxin derivatives enables the rational design of new anti-Clostridial neurotoxin therapeutics. Dose-response analyses and challenge studies against active neurotoxin provide data that allows the best candidate antidotes to be selected for further development.

A further aspect of the present invention relates to a method for treating a subject for toxic effects of a Clostridial neurotoxin. This method involves administering the therapeutic agent described herein to the subject under conditions effective to treat the subject for toxic effects of Clostridial neurotoxin.

In carrying out this and other methods described herein, administering can be carried out orally, parenterally, for example, subcutaneously, intravenously, intramuscularly, intrarticularly, intraperitoneally, by intranasal instillation, or by application to mucous membranes, such as, that of the nose, throat, and bronchial tubes. The fusion protein (or therapeutic agent) may be administered alone or with suitable pharmaceutical carriers, and can be in solid or liquid form such as, tablets, capsules, powders, solutions, suspensions, or emulsions.

The fusion protein (or therapeutic agent) may be orally administered, for example, with an inert diluent, or with an assimilable edible carrier, or may be enclosed in hard or soft shell capsules, or may be compressed into tablets, or may be incorporated directly with the food of the diet. For oral therapeutic administration, the neurotoxin (along with any cargo) may be incorporated with excipients and used in the form of tablets, capsules, elixirs, suspensions, syrups, and the like. Such compositions and preparations should contain at least 0.001% of active compound. The percentage of the compound in these compositions may, of course, be varied and may conveniently be between about 0.01% to about 10% of the weight of the unit. The amount of active compound in such therapeutically useful compositions is such that a suitable dosage will be obtained. In one embodiment, compositions are prepared so that an oral dosage unit contains between about 1 μg and 1 g of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The fusion protein (or therapeutic agent) may also be administered parenterally. Solutions or suspensions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol, hyaluronan and its derivatives, carboxymethyl cellulose and other soluble polysaccharide derivatives, or polyethylene glycol, are preferred liquid carriers, particularly for injectable solutions. Under ordinary conditions of storage and use, these preparations contain a preservative to prevent the growth of microorganisms if they are not produced aseptically.

The pharmaceutical forms suitable for injectable use include sterile aqueous solutions or dispersions and sterile powders for the extemporaneous preparation of sterile injectable solutions or dispersions. The form must be sterile and must be fluid to the extent that easy syringability exists. It must be stable under the conditions of manufacture and storage and must be protected against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The fusion protein (or therapeutic agent) may also be administered directly to the airways in the form of an aerosol. For use as aerosols, the fusion protein (or therapeutic agent) in solution or suspension may be packaged in a pressurized aerosol container together with suitable propellants, for example, hydrocarbon propellants like propane, butane, or isobutane with conventional adjuvants. The fusion protein (or therapeutic agent) also may be administered in a non-pressurized form such as in a nebulizer or atomizer.

BoNTs pass across epithelial surfaces without being destroyed or causing local toxicity. Passage across epithelia is believed to occur by specific binding and transcytosis. The ability of intact BoNT/A to pass though pulmonary epithelia and resist proteolytic inactivation was demonstrated in rat primary alveolar epithelial cells and in immortalized human pulmonary adenocarcinoma (Calu-3) cells. The rate of transport was greater in the apical-to-basolateral direction than in the basolateral-to-apical direction, and it was blocked by serotype-specific toxin antibodies (Park et al., "Inhalational Poisoning by Botulinum Toxin and Inhalation Vaccination with Its Heavy-Chain Component," *Infect. Immun.* 71:1147-1154 (2003), which is hereby incorporated by reference in its entirety).

Targeting the central nervous system ("CNS") may require intra-thecal or intra-ventricular administration. Administration may occur directly to the CNS. Alternatively, administration to the CNS may involve retrograde transport from peripheral neurons (motor neurons, nociceptors) to spinal ganglia (see Caleo et al., "A Reappraisal of the Central Effects of Botulinum Neurotoxin Type A: By What Mechanism?" *Journal of Neurochemistry* 109:15-24 (2009), which is hereby incorporated by reference in its entirety).

In one embodiment, the fusion protein (or therapeutic agent) can be used to augment the endogenous pharmaceutical activity of wild-type Clostridial neurotoxins (e.g., BOTOX®), e.g., as a combination therapy.

If BoNT/A ad-0 VHH (described infra) is used, the VHH portion of the fusion protein and the SNAP-25 cleavage activity could synergize.

Fusion proteins (or therapeutic agents) can be administered as a conjugate with a pharmaceutically acceptable water-soluble polymer moiety. By way of example, a polyethylene glycol conjugate is useful to increase the circulating half-life of the treatment compound, and to reduce the immunogenicity of the molecule. Specific PEG conjugates are described in U.S. Patent Application Publication No. 2006/0074200 to Daugs et al., which is hereby incorporated by reference in its entirety. Other materials that effect the functionality include hyaluronic acid ("HA"), as described in, e.g., U.S. Pat. No. 7,879,341 to Taylor and U.S. Patent Application Publication No. 2012/0141532 to Blanda et al., each of which is hereby incorporated by reference in its entirety. Liquid forms, including liposome-encapsulated formulations, are illustrated by injectable solutions and suspensions. Exemplary solid forms include capsules, tablets, and controlled-release forms, such as a mini-osmotic pump or an implant. Other dosage forms can be devised by those skilled in the art, as shown, for example, by Ansel & Popovich, *Pharmaceutical Dosage Forms and Drug Delivery Systems,* 5$^{th}$ Edition (Lea & Febiger 1990), Gennaro (ed.); *Remington's Pharmaceutical Sciences,* 19$^{th}$ Edition (Mack Publishing Company 1995); and Ranade & Hollinger, *Drug Delivery Systems* (CRC Press 1996), which are hereby incorporated by reference in their entirety.

In one embodiment, treating a subject further involves selecting a subject in need of treatment prior to administering.

Subjects to be treated pursuant to the methods described herein include, without limitation, human and non-human primates, or other animals such as dog, cat, horse, cow, goat, sheep, rabbit, or rodent (e.g., mouse or rat).

Single chain antibodies developed to target treatment of specific conditions are known and include, for example, those that target Huntington's Protein for treatment of Huntington's disease, synuclein for treatment of Parkinson disease, upregulated cell-division genes in malignant neurons, upregulated genes in non-malignant neuronal pathologies, genes responsible for excess accumulation of amyloid fibrils in Alzheimer's disease, dormant neurotrophic virus species, herpes virus activated during pathogenesis of shingles, prion diseases, neuropathic pain (to down-regulate pain pathways), and inducers of chronic pain. The therapeutic targets of these single chain antibodies are inside the neuron and, as noted in the Background of the Invention (supra), there has been limited success in non-viral delivery of single chain antibodies to the inside of cells in a therapeutic context. The treatment methods described herein overcome these deficiencies and provide for delivery of functional single chain antibodies to targets exposed to the cytoplasm of neurons by fusing a single chain antibody to a Clostridial neurotoxin derivative that directs single chain antibodies to neurons and translocates the antibodies from an internalized endosome into the cytoplasm.

A further aspect of the present invention relates to a propeptide fusion. The propeptide fusion has a light chain region of a Clostridial neurotoxin and a heavy chain region of a Clostridial neurotoxin. The light and heavy chain regions are linked by a disulfide bond. An intermediate region connects the light and heavy chain regions and comprises a highly specific protease cleavage site. The highly specific protease cleavage site has three or more specific adjacent amino acid residues that are recognized by the highly specific protease to enable cleavage. A single chain antibody is positioned upstream of the light chain region. The single chain antibody possesses antigen-binding activity.

BoNT/A propeptide has two chains, a light chain of Mr ~50,000 and a heavy chain of Mr ~100,000, linked by a disulfide bond between $Cys_{429}$ and $Cys_{453}$. Wild-type BoNT/A propeptide has an amino acid sequence as set forth in GenBank Accession No. ABP48106 (SEQ ID NO:52), as follows:

```
MPFVNKQFNY KDPVNGVDIA YIKIPNAGQM QPVKAFKIHN
KIWVIPERDT FTNPEEGDLN PPPEAKQVPV SYYDSTYLST
DNEKDNYLKG VTKLFERIYS TDLGRMLLTS IVRGIPFWGG
STIDTELKVI DTNCINVIQP DGSYRSEELN LVIIGPSADI
IQFECKSFGH EVLNLTRNGY GSTQYIRFSP DFTFGFEESL
EVDTNPLLGA GKFATDPAVT LAHELIHAGH RLYGIAINPN
RVFKVNTNAY YEMSGLEVSF EELRTFGGHD AKFIDSLQEN
EFRLYYYNKF KDIASTLNKA KSIVGTTASL QYMKNVFKEK
YLLSEDTSGK FSVDKLKFDK LYKMLTEIYT EDNFVKFFKV
LNRKTYLNFD KAVFKINIVP KVNYTIYDGF NLRNTNLAAN
FNGQNTEINN MNFTKLKNFT GLFEFYKLLC VRGIITSKTK
SLDKGYNKAL NDLCIKVNNW DLFFSPSEDN FTNDLNKGEE
ITSDTNIEAA EENISLDLIQ QYYLTFNFDN EPENISIENL
SSDIIGQLEL MPNIERFPNG KKYELDKYTM FHYLRAQEFE
HGKSRIALTN SVNEALLNPS RVYTFFSSDY VKKVNKATEA
AMFLGWVEQL VYDFTDETSE VSTTDKIADI TIIIPYIGPA
LNIGNMLYKD DFVGALIFSG AVILLEFIPE IAIPVLGTFA
LVSYIANKVL TVQTIDNALS KRNEKWDEVY KYIVTNWLAK
VNTQIDLIRK KMKEALENQA EATKAIINYQ YNQYTEEEKN
NINFNIDDLS SKLNESINKA MININKFLNQ CSVSYLMNSM
IPYGVKRLED FDASLKDALL KYIYDNRGTL IGQVDRLKDK
VNNTLSTDIP FQLSKYVDNQ RLLSTFTEYI KNIINTSILN
LRYESNHLID LSRYASKINI GSKVNFDPID KNQIQLFNLE
SSKIEVILKN AIVYNSMYEN FSTSFWIRIP KYFNSISLNN
EYTIINCMEN NSGWKVSLNY GEIIWTLQDT QEIKQRVVFK
YSQMINISDY INRWIFVTIT NNRLNNSKIY INGRLIDQKP
ISNLGNIHAS NNIMFKLDGC RDTHRYIWIK YFNLFDKELN
EKEIKDLYDN QSNSGILKDF WGDYLQYDKP YYMLNLYDPN
KYVDVNNVGI RGYMYLKGPR GSVMTTNIYL NSSLYRGTKF
IIKKYASGNK DNIVRNNDRV YINVVVKNKE YRLATNASQA
GVEKILSALE IPDVGNLSQV VVMKSKNDQG ITNKCKMNLQ
DNNGNDIGFI GFHQFNNIAK LVASNWYNRQ IERSSRTLGC
SWEFIPVDDG WGERPL
```

BoNT/B propeptide has an amino acid sequence as set forth in GenBank Accession No. X71343.1 (SEQ ID NO:53), as follows:

```
MPVTINNFNY NDPIDNDNII MMEPPFARGT GRYYKAFKIT
DRIWIIPERY TFGYKPEDFN KSSGIFNRDV CEYYDPDYLN
TNDKKNIFFQ TLIKLFNRIK SKPLGEKLLE MIINGIPYLG
DRRVPLEEFN TNIASVTVNK LISNPGEVER KKGIFANLII
FGPGPVLNEN ETIDIGIQNH FASREGFGGI MQMKFCPEYV
SVFNNVQENK GASIFNRRGY FSDPALILMH ELIHVLHGLY
GIKVDDLPIV PNEKKFFMQS TDTIQAEELY TFGGQDPSII
SPSTDKSIYD KVLQNFRGIV DRLNKVLVCI SDPNININIY
KNKFKDKYKF VEDSEGKYSI DVESFNKLYK SLMLGFTEIN
IAENYKIKTR ASYFSDSLPP VKIKNLLDNE IYTIEEGFNI
SDKNMGKEYR GQNKAINKQA YEEISKEHLA VYKIQMCKSV
KVPGICIDVD NENLFFIADK NSFSDDLSKN ERVEYNTQNN
YIGNDFPINE LILDTDLISK IELPSENTES LTDFNVDVPV
YEKQPAIKKV FTDENTIFQY LYSQTFPLNI RDISLTSSFD
DALLVSSKVY SFFSMDYIKT ANKVVEAGLF AGWVKQIVDD
FVIEANKSST MDKIADISLI VPYIGLALNV GDETAKGNFE
SAFEIAGSSI LLEFIPELLI PVVGVFLLES YIDNKNKIIK
TIDNALTKRV EKWIDMYGLI VAQWLSTVNT QFYTIKEGMY
KALNYQAQAL EEIIKYKYNI YSEEEKSNIN INFNDINSKL
NDGINQAMDN INDFINECSV SYLMKKMIPL AVKKLLDFDN
TLKKNLLNYI DENKLYLIGS VEDEKSKVDK YLKTIIPFDL
STYSNIEILI KIFNKYNSEI LNNIILNLRY RDNNLIDLSG
YGAKVEVYDG VKLNDKNQFK LTSSADSKIR VTQNQNIIFN
SMFLDFSVSF WIRIPKYRND DIQNYIHNEY TIINCMKNNS
GWKISIRGNR IIWTLIDING KTKSVFFEYN IREDISEYIN
RWFFVTITNN LDNAKIYING TLESNMDIKD IGEVIVNGEI
TFKLDGDVDR TQFIWMKYFS IFNTQLNQSN IKEIYKIQSY
SEYLKDFWGN PLMYNKEYYM FNAGNKNSYI KLVKDSSVGE
ILIRSKYNQN SNYINYRNLY IGEKFIIRRE SNSQSINDDI
VRKEDYIHLD LVLHHEEWRV YAYKYFKEQE EKLFLSIISD
SNEFYKTIEI KEYDEQPSYS CQLLFKKDEE STDDIGLIGI
HRFYESGVLR KKYKDYFCIS KWYLKEVKRK PYKSNLGCNW
QFIPKDEGWT E
```

BoNT/C propeptide (specifically, BoNT serotype C1, herein referred to as BoNT/C) has an amino acid sequence as set forth in GenBank Accession No. BAM65691.1 (SEQ ID NO:54), as follows:

```
MPITINNFNY SDPVDNKNIL YLDTHLNTLA NEPEKAFRIT
GNIWVIPDRF SRNSNPNLNK PPRVTSPKSG YYDPNYLSTD
```

-continued

```
SDKDTFLKEI IKLFKRINSR EIGEELIYRL STDIPFPGNN
NTPINTFDFD VDFNSVDVKT RQGNNWVKTG SINPSVIITG
PRENIIDPET STFKLINNTF AAQEGFGALS IISISPRFML
TYSNATNDVG EGRFSKSEFC MDPILILMHE LNHAMHNLYG
IAIPNDQTIS SVTSNIFYSQ YNVKLEYAEI YAFGGPTIDL
IPKSARKYFE EKALDYYRSI AKRLNSITTA NPSSFNKYIG
EYKQKLIRKY RFVVESSGEV TVNRNKFVEL YNELTQIFTE
FNYAKIYNVQ NRKIYLSNVY TPVTANILDD NVYDIQNGFN
IPKSNLNVLF MGQNLSRNPA LRKVNPENML YLFTKFCHKA
IDGRSLYNKT LDCRELLVKN TDLPFIGDIS DVKTDIFLRK
DINEETEVIY YPDNVSVDQV ILSKNTSEHG QLDLLYPSID
SESEILPGEN QVFYDNRTQN VDYLNSYYYL ESQKLSDNVE
DFTFTRSIEE ALDNSAKVYT YFPTLANKVN AGVQGGLFLM
WANDVVEDFT TNILRKDTLD KISDVSAIIP YIGPALNISN
SVRRGNFTEA FAVTGVTILL EAFPEFTIPA LGAFVIYSKV
QERNEIIKTI DNCLEQRIKR WKDSYEWMMG TWLSRIITQF
NNISYQMYDS LNYQAGAIKA KIDLEYKKYS GSDKENIKSQ
VENLKNSLDV KISEAMNNIN KFIRECSVTY LFKNMLPKVI
DELNEFDRNT KAKLINLIDS HNIILVGEVD KLKAKVNNSF
QNTIPFNIFS YTNNSLLKDI INEYFNNIND SKILSLQNRK
NTLVDTSGYN AEVSEEGDVQ LNPIFPFDFK LGSSGEDRGK
VIVTQNENIV YNSMYESFSI SFWIRINKWV SNLPGYTIID
SVKNNSGWSI GIISNFLVFT LKQNEDSEQS INFSYDISNN
APGYNKWFFV TVINNMMGNM KIYINGKLID TIKVKELTGI
NFSKTITFEI NKIPDTGLIT SDSDNINMWI RDFYIFAKEL
DGKDINILFN SLQYTNVVKD YWGNDLRYNK EYYMVNIDYL
NRYMYANSRQ IVFNTRRNNN DFNEGYKIII KRIRGNINDT
RVRGGDILYF DMTINNKAYN LFMKNETMYA DNHSTEDIYA
IGLREQTKDI NDNIIFQIQP MNNTYYYASQ IFKSNFNGEN
ISGICSIGTY RFRLGGDWYR HNYLVPTVKQ GNYASLLEST
STHWGFVPVS E
```

BoNT/D propeptide has an amino acid sequence as set forth in UniProtKB/Swiss-Prot: P19321.1 (SEQ ID NO:55), as follows:

```
MTWPVKDFNY SDPVNDNDIL YLRIPQNKLI TTPVKAFMIT
QNIWVIPERF SSDTNPSLSK PPRPTSKYQS YYDPSYLSTD
EQKDTFLKGI IKLFKRINER DIGKKLINYL VVGSPFMGDS
STPEDTFDFT RHTTNIAVEK FENGSWKVIN IITPSVLIFG
PLPNILDYTA SLTLQGQQSN PSFEGFGTLS ILKVAPEFLL
TFSDVTSNQS SAVLGKSIFC MDPVIALMHE LTHSLHQLYG
```

-continued

INIPSDKRIR PQVSEGFFSQ DGPNVQFEEL YTFGGLDVEI
IPQIERSQLR EKALGHYKDI AKRLNNINKT IPSSWISNID
KYKKIFSEKY NFDKDNTGNF VVNIDKFNSL YSDLTNVMSE
VVYSSQYNVK NRTHYFSRHY LPVFANILDD NIYTIRDGFN
LINKGFNIEN SGQNIERNPA LQKLSSESVV DLFTKVCLRL
TKNSRDDSTC IKVKNNRLPY VADKDSISQE IFENKIITDE
TNVQNYSDKF SLDESILDGQ VPINPEIVDP LLPNVNMEPL
NLPGEEIVFY DDITKYVDYL NSYYYLESQK LSNNVENITL
TTSVEEALGY SNKIYTFLPS LAEKVNKGVQ AGLFLNWANE
VVEDFTTNIM KKDTLDKISD VSVIIPYIGP ALNIGNSALR
GNFNQAFATA GVAFLLEGFP EFTIPALGVF TFYSSIQERE
KIIKTIENCL EQRVKRWKDS YQWMVSNWLS RITTQFNHIN
YQMYDSLSYQ ADAIKAKIDL EYKKYSGSDK ENIKSQVENL
KNSLDVKISE AMNNINKFIR ECSVTYLFKN MLPKVIDELN
KFDLRTKTEL INLIDSHNII LVGEVDRLKA KVNESFENTM
PFNIFSYTNN SLLKDIINEY ENSINDSKIL SLQNKKNALV
DTSGYNAEVR VGDNVQLNTI YTNDFKLSSS GDKIIVNLNN
NILYSAIYEN SSVSFWIKIS KDLTNSHNEY TIINSIEQNS
GWKLCIRNGN IEWILQDVNR KYKSLIFDYS ESLSHTGYTN
KWFFVTITNN IMGYMKLYIN GELKQSQKIE DLDEVKLDKT
IVFGIDENID ENQMLWIRDF NIFSKELSNE DINIVYEGQI
LRNVIKDYWG NPLKFDTEYY IINDNYIDRY IAPESNVLVL
VQYPDRSKLY TGNPITIKSV SDKNPYSRIL NGDNIILHML
YNSRKYMIIR DTDTIYATQG GECSQNCVYA LKLQSNLGNY
GIGIFSIKNI VSKNKYCSQI FSSFRENTML LADIYKPWRF
SFKNAYTPVA VINYETKLLS TSSFWKFISR DPGWVE

BoNT/E propeptide has an amino acid sequence as set forth in GenBank Accession No. GQ244314.1 (SEQ ID NO:56), as follows:

MPKINSFNYN DPVNDRTILY IKPGGCQEFY KSFNIMKNIW
IIPERNVIGT TPQDFHPPTS LKNGDSSYYD PNYLQSDEEK
DRFLKIVTKI FNRINNNLSG GILLEELSKA NPYLGNDNTP
DNQFHIGDAS AVEIKFSNGS QDILLPNVII MGAEPDLFET
NSSNISLRNN YMPSNHGFGS IAIVTFSPEY SFRFNDNSMN
EFIQDPALTL MHELIHSLHG LYGAKGITTK YTITQKQNPL
ITNIRGTNIE EFLTFGGTDL NIITSAQSND IYTNLLADYK
KIASKLSKVQ VSNPLLNPYK DVFEAKYGLD KDASGIYSVN
INKFNDIFKK LYSFTEFDLA TKFQVKCRQT YIGQYKYFKL
SNLLNDSIYN ISEGYNINNL KVNFRGQNAN LNPRIITPIT
GRGLVKKIIR FCKNIVSVKG IRKSICIEIN NGELFFVASE
NSYNDDNINT PKEIDDTVTS NNNYENDLDQ VILNFNSESA

-continued

PGLSDEKLNL TIQNDAYIPK YDSNGTSDIE QHDVNELNVF
FYLDAQKVPE GENNVNLTSS IDTALLEQPK IYTFFSSEFI
NNVNKPVQAA LFVSWIQQVL VDFTTEANQK STVDKIADIS
IVVPYIGLAL NIGNEAQKGN FKDALELLGA GILLEFEPEL
LIPTILVFTI KSFLGSSDNK NKVIKAINNA LKERDEKWKE
VYSFIVSNWM TKINTQFNKR KEQMYQALQN QVNAIKTIIE
SKYNSYTLEE KNELTNKYDI KQIENELNQK VSIAMNNIDR
FLTESSISYL MKLINEVKIN KLREYDENVK TYLLNYIIQH
GSILGESQQE LNSMVTDTLN NSIPFKLSSY TDDKILISYF
NKFFKRIKSS SVLNMRYKND KYVDTSGYDS NININGDVYK
YPTNKNQFGI YNDKLSEVNI SQNDYIIYDN KYKNFSISFW
VRIPNYDNKI VNVNNEYTII NCMRDNNSGW KVSLNHNEII
WTLQDNAGIN QKLAFNYGNA NGISDYINKW IFVTITNDRL
GDSKLYINGN LIDQKSILNL GNIHVSDNIL FKIVNCSYTR
YIGIRYFNIF DKELDETEIQ TLYSNEPNIN ILKDFWGNYL
LYDKEYYLLN VLKPNNFIDR RKDSTLSINN IRSTILLANR
LYSGIKVKIQ RVNNSSINDN LVRKNDQVYI NFVASKTHLF
PLYADTATTN KEKTIKISSS GNRFNQVVVM NSVGNNCTMN
FKNNNGNNIG LLGFKADTVV ASTWYYTHMR DHTNSNGCFW
NFISEEHGWQ EK

BoNT/F propeptide has an amino acid sequence as set forth in GenBank Accession No. X81714.1 (SEQ ID NO:57), as follows:

MPVVINSFNY NDPVNDDTIL YMQIPYEEKS KKYYKAFEIM
RNVWIIPERN TIGTDPSDFD PPASLENGSS AYYDPNYLTT
DAEKDRYLKT TIKLFKRINS NPAGEVLLQE ISYAKPYLGN
EHTPINEFHP VTRTTSVNIK SSTNVKSSII LNLLVLGAGP
DIFENSSYPV RKLMDSGGVY DPSNDGFGSI NIVTFSPEYE
YTFNDISGGY NSSTESFIAD PAISLAHELI HALHGLYGAR
GVTYKETIKV KQAPLMIAEK PIRLEEFLTF GGQDLNIITS
AMKEKIYNNL LANYEKIATR LSRVNSAPPE YDINEYKDYF
QWKYGLDKNA DGSYTVNENK FNEIYKKLYS FTEIDLANKF
KVKCRNTYFI KYGFLKVPNL LDDDIYTVSE GFNIGNLAVN
NRGQNIKLNP KIIDSIPDKG LVEKIVKFCK SVIPRKGTKA
PPRLCIRVNN RELFFVASES SYNENDINTP KEIDDTTNLN
NNYRNNLDEV ILDYNSETIP QISNQTLNTL VQDDSYVPRY
DSNGTSEIEE HNVVDLNVFF YLHAQKVPEG ETNISLTSSI
DTALSEESQV YTFFSSEFIN TINKPVHAAL FISWINQVIR
DFTTEATQKS TFDKIADISL VVPYVGLALN IGNEVQKENF
KEAFELLGAG ILLEFVPELL IPTILVFTIK SFIGSSENKN

-continued

```
KIIKAINNSL MERETKWKEI YSWIVSNWLT RINTQFNKRK

EQMYQALQNQ VDAIKTVIEY KYNNYTSDER NRLESEYNIN

NIREELNKKV SLAMENIERF ITESSIFYLM KLINEAKVSK

LREYDEGVKE YLLDYISEHR SILGNSVQEL NDLVTSTLNN

SIPFELSSYT NDKILILYFN KLYKKIKDNS ILDMRYENNK

FIDISGYGSN ISINGDVYIY STNRNQFGIY SSKPSEVNIA

QNNDIIYNGR YQNFSISFWV RIPKYFNKVN LNNEYTIIDC

IRNNNSGWKI SLNYNKIIWT LQDTAGNNQK LVFNYTQMIS

ISDYINKWIF VTITNNRLGN SRIYINGNLI DEKSISNLGD

IHVSDNILFK IVGCNDTRYV GIRYFKVFDT ELGKTEIETL

YSDEPDPSIL KDFWGNYLLY NKRYYLLNLL RTDKSITQNS

NFLNINQQRG VYQKPNIFSN TRLYTGVEVI IRKNGSTDIS

NTDNFVRKND LAYINVVDRD VEYRLYADIS IAKPEKIIKL

IRTSNSNNSL GQIIVMDSIG NNCTMNFQNN NGGNIGLLGF

HSNNLVASSW YYNNIRKNTS SNGCFWSFIS KEHGWQEN
```

BoNT/G propeptide has an amino acid sequence as set forth in GenBank Accession No. X74162.1 (SEQ ID NO:58), as follows:

```
MPVNIKXFNY NDPINNDDII MMEPFNDPGP GTYYKAFRII

DRIWIVPERF TYGFQPDQFN ASTGVFSKDV YEYYDPTYLK

TDAEKDKFLK TMIKLFNRIN SKPSGQRLLD MIVDAIPYLG

NASTPPDKFA ANVANVSINK KIIQPGAEDQ IKGLMTNLII

FGPGPVLSDN FTDSMIMNGH SPISEGFGAR MMIRFCPSCL

NVFNNVQENK DTSIFSRRAY FADPALTLMH ELIHVLHGLY

GIKISNLPIT PNTKEFFMQH SDPVQAEELY TFGGHDPSVI

SPSTDMNIYN KALQNFQDIA NRLNIVSSAQ GSGIDISLYK

QIYKNKYDFV EDPNGKYSVD KDKFDKLYKA LMFGFTETNL

AGEYGIKTRY SYFSEYLPPI KTEKLLDNTI YTQNEGFNIA

SKNLKTEFNG QNKAVNKEAY EEISLEHLVI YRIAMCKPVM

YKNTGKSEQC IIVNNEDLFF IANKDSFSKD LAKAETIAYN

TQNNTIENNF SIDQLILDND LSSGIDLPNE NTEPFTNFDD

IDIPVYIKQS ALKKIFVDGD SLFEYLHAQT FPSNIENLQL

TNSLNDALRN NNKVYTFFST NLVEKANTVV GASLFVNWVK

GVIDDFTSES TQKSTIDKVS DVSIIIPYIG PALNVGNETA

KENFKNAFEI GGAAILMEFI PELIVPIVGF FTLESYVGNK

GHIIMTISNA LKKRDQKWTD MYGLIVSQWL STVNTQFYTI

KERMYNALNN QSQAIEKIIE DQYNRYSEED KMNINIDFND

IDFKLNQSIN LAINNIDDFI NQCSISYLMN RMIPLAVKKL

KDFDDNLKRD LLEYIDTNEL YLLDEVNILK SKVNRHLKDS

IPFDLSLYTK DTILIQVFNN YISNISSNAI LSLSYRGGRL

IDSSGYGATM NVGSDVIFND IGNGQFKLNN SENSNITAHQ
```

-continued

```
SKFVVYDSMF DNFSINFWVR TPKYNNNDIQ TYLQNEYTII

SCIKNDSGWK VSIKGNRIIW TLIDVNAKSK SIFFEYSIKD

NISDYINKWF SITITNDRLG NANIYINGSL KKSEKILNLD

RINSSNDIDF KLINCTDTTK FVWIKDFNIF GRELNATEVS

SLYWIQSSTN TLKDFWGNPL RYDTQYYLFN QGMQNIYIKY

FSKASMGETA PRTNFNNAAI NYQNLYLGLR FIIKKASNSR

NINNDNIVRE GDYIYLNIDN ISDESYRVYV LVNSKEIQTQ

LFLAPINDDP TFYDVLQIKK YYEKTTYNCQ ILCEKDTKTF

GLFGIGKFVK DYGYVWDTYD NYFCISQWYL RRISENINKL

RLGCNWQFIP VDEGWTE
```

All propeptides of the eight BoNT serotypes have a light chain region and a heavy chain region linked by a disulfide bond. Two Cysteine (Cys) residues, one adjacent to the C-terminus of the light chain, and a second adjacent to the N-terminus of the heavy chain are present in all BoNT serotypes. These two Cys residues form the single disulfide bond holding the HC and LC polypeptides together in the mature neurotoxin. This disulfide bond enables the mature neurotoxin to accomplish its native physiological activities by permitting the HC and LC to carry out their respective biological roles in concert. The intermediate region (i.e., $Lys_{438}$-$Lys_{448}$ of BoNT/A, KTKSLDKGYNK (SEQ ID NO:59) identifies the amino acids eliminated during maturation of wild-type BoNT/A, and believed to be excised by a protease endogenous to the host microorganism. This cleavage event generates the biologically active BoNT/A HC-LC dimer.

All eight BoNT serotypes also contain Lys or Arg residues in the intermediate region, which make the propeptides susceptible to activation by trypsin. Native BoNT/A propeptide recovered from young bacterial cultures can be activated by trypsinolysis, with production of intact, S-S bound light and heavy chain. Though multiple additional trypsin-susceptible sites are present in the propeptides, they are resistant to proteolysis due to their spatial positions within the native toxin molecule (Dekleva et al., "Nicking of Single Chain *Clostridium botulinum* Type A Neurotoxin by an Endogenous Protease," *Biochem. Biophys. Res. Commun.* 162:767-772 (1989); Lacy et al., "Crystal Structure of Botulinum Neurotoxin Type A and Implications for Toxicity," *Nat. Struct. Biol.* 5:898-902 (1998), which are hereby incorporated by reference in their entirety). A second site in the native propeptide of several BoNT serotypes can be susceptible to trypsin cleavage when subjected to higher enzyme concentrations or incubation times (Chaddock et al., "Expression and Purification of Catalytically Active, Non-Toxic Endopeptidase Derivatives of *Clostridium botulinum* Toxin Type A," *Protein Expr. Purif* 25:219-228 (2002), which is hereby incorporated by reference in its entirety). This trypsin-susceptible site is located in the region adjacent to the toxin receptor-binding domain. This region of the HC peptide is found to be exposed to solvent in BoNT serotypes for which information is available on their 3-D crystal structure (Lacy et al., "Crystal Structure of Botulinum Neurotoxin Type A and Implications for Toxicity," *Nat. Struct. Biol.* 5:898-902 (1998); Swaminathan et al., "Structural Analysis of the Catalytic and Binding Sites of

*Clostridium botulinum* Neurotoxin B," Nat. Struct. Biol. 7:693-699 (2000), which are hereby incorporated by reference in their entirety).

Propeptide fusions described herein have an intermediate region connecting the light and heavy chain regions, and this intermediate region has a highly specific protease cleavage site and no low-specificity protease cleavage sites (i.e., the intermediate region has been mutated relative to the wild-type neurotoxin). For purposes of the present invention, a highly specific protease cleavage site (also referred to herein as a "restricted specificity protease" or "RSP" site) has three or more specific adjacent amino acid residues that are recognized by the highly specific protease to permit cleavage (e.g., an enterokinase cleavage site, a TEV recognition sequence, or WELQut protease recognition site). In contrast, a low-specificity protease cleavage site has two or less adjacent amino acid residues that are recognized by a protease to enable cleavage (e.g., a trypsin cleavage site). As can be appreciated by a person of ordinary skill in the art, selecting a particularly suitable highly specific protease can depend on the specific conditions under which cleavage is taking place. While one highly specific protease may be most effective under one set of conditions, another highly specific protease may be most effective under a different set of conditions.

In BoNT, the amino acid preceding the N-terminus of the heavy chain is a Lys or Arg residue which is susceptible to proteolysis with trypsin. This trypsin-susceptible site can be replaced with, e.g., a five amino acid enterokinase cleavage site (i.e., DDDDK (SEQ ID NO:60)) upstream of the heavy chain's N-terminus (see U.S. Patent Application Publication No. 2011/0206616 to Icthchenko and Band, which shows an alignment of 7 of the 8 BoNT serotypes, and which is hereby incorporated by reference in its entirety). Alternatively, the trypsin-susceptible site can be replaced with, e.g., a TEV recognition sequence (i.e., ENLYFQ (SEQ ID NO:61)) upstream of the heavy chain's N-terminus (see U.S. Patent Application Publication No. 2011/0206616 to Icthchenko and Band, which is hereby incorporated by reference in its entirety). Either of these modifications enables standardized activation with specific enzymes. In BoNT serotypes A and C, additional Lys residues within this region may be mutated to either Gln or His, thereby eliminating additional trypsin-susceptible sites which might result in undesirable non-specific activation of the toxin. Trypsin-susceptible recognition sequences also occur upstream of the heavy chain's receptor-binding domain in serotypes A, E, and F. This region's susceptibility to proteolysis is consistent with its exposure to solvent in the toxin's 3-D structure, as shown by X-ray crystallography analysis. Therefore, in serotypes A, E, and F, the susceptible residues are modified to Asn.

Propeptide fusions described herein have amino acid substitutions in the light chain region that render a mature neurotoxin of the propeptide (i.e., the fusion protein of the present invention discussed supra) atoxic. In one embodiment, the amino acid substitutions include $E_{224}$>A and $Y_{366}$>A (of BoNT/A LC), which render the fusion protein atoxic. Corresponding mutations may be made in other BoNT serotypes to likewise render them atoxic. According to another embodiment, the propeptide includes these two mutations and either (i) $Q_{162}$>Y, $L_{256}$>Y, $R_{257}$>E, and $L_{322}$>E or (ii) $Q_{16}$>E, $E_{263}$>L, and $L_{323}$>I of BoNT/A LC of SEQ ID NO:52. These additional mutations are made to BoNT/A (i.e., SEQ ID NO:52) to create BoNT/A ad-1 (defined in the paragraph below), to reduce residual SNAP-25 cleavage activity and to permit improved performance as an inert drug carrier. Corresponding amino acid substitutions may be made in the other seven BoNT serotypes. In another embodiment, amino acid substitutions include $E_{446}$>A, $H_{449}$>G, and $Y_{591}$>A (of BoNT/C LC of SEQ ID NO:54). These additional mutations are made to BoNT/C (i.e., SEQ ID NO:54) to create BoNT/C ad.

The retention of SNAP-25 cleavage activity could be viewed as limiting the use of, e.g., "BoNT/A ad" (an atoxic derivative of BoNT/A) to perform as an inert drug carrier. Therefore, according to one embodiment, to further reduce the toxicity associated with BoNT/A ad catalytic activity, a second generation of BoNT/A ad molecules were bioengineered and one embodiment is designated "BoNT/A ad-1." BoNT/A ad-1 is a recombinant botulinum neurotoxin atoxic derivative with additional amino acid substitutions in the atoxic light chain of BoNT/A (e.g., $Q_{162}$>Y, $L_{256}$>Y, $R_{257}$>E, and $L_{322}$>E of BoNT/A LC) designed to eliminate residual SNAP-25 cleavage activity and to permit BoNT/A ad-1 to perform as a more inert drug carrier. The mutations were specifically identified by computer modeling, and designed to disrupt the catalytic cleavage of SNAP-25 by the LC protease, while maintaining the conformational features required for stability of the protein (with respect to the interaction between mutated light chain and the belt region of the heavy chain pseudosubstrate) and its systemic and intra-neuronal trafficking properties.

Determining whether a BoNT molecule (or fusion protein) is devoid of substrate cleavage activity can be carried out, e.g., using Western blot analysis as described herein in the Examples.

On the other hand, it may be desirable for the fusion protein described herein to have some residual substrate cleavage activity, because this may serve as a marker for delivery of the fusion protein (and, in particular, delivery of the single chain antibody) to interior compartments of a cell. This embodiment is illustrated in Example 2, infra.

According to one embodiment, the propeptide fusions described herein have a first detection tag ($DT_1$) and a first affinity purification tag ($APT_N$) positioned upstream of the light chain region.

According to another embodiment, the propeptide fusions described herein have a second detection tag ($DT_2$) and a second affinity purification tag ($APT_C$) positioned downstream of the heavy chain.

Figures 4A, 4B:
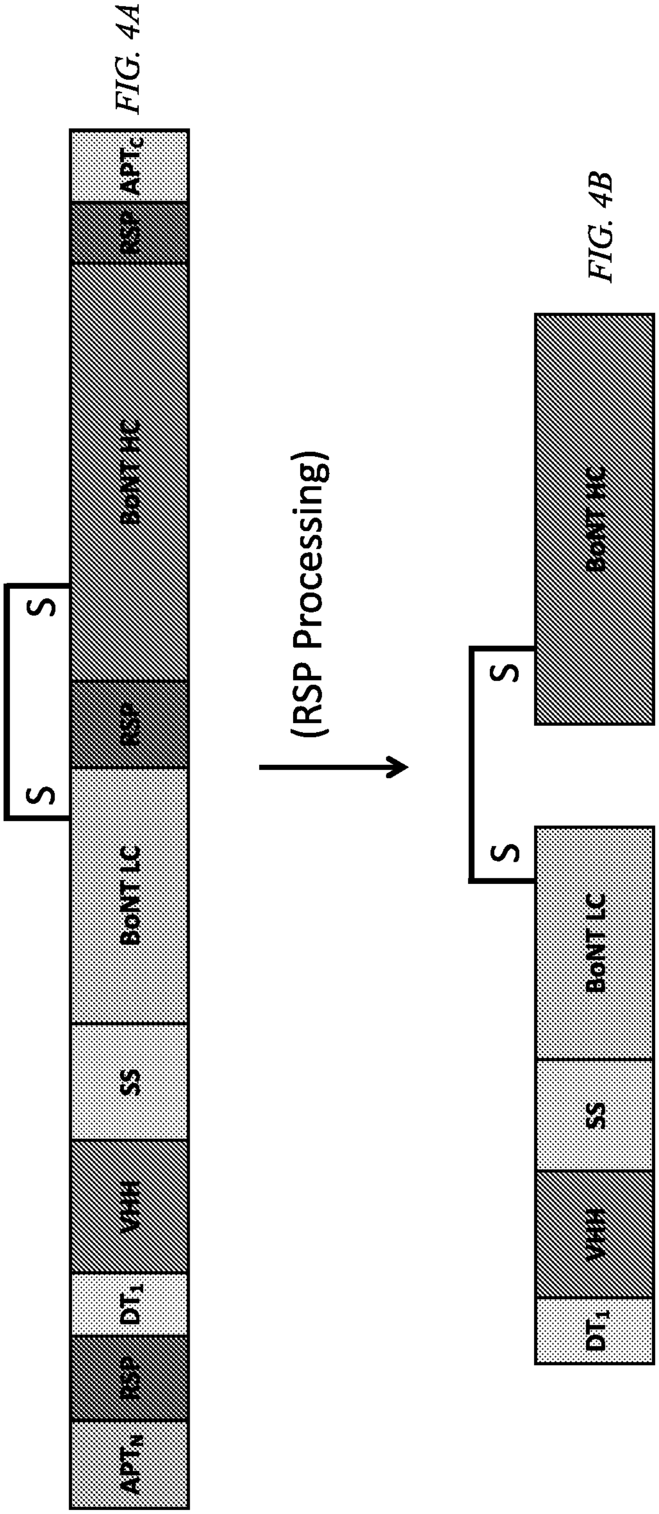
FIGS. 4A-B are schematic illustrations of one embodiment of a fusion protein of the present invention before (FIG. 4A) and after (FIG. 4B) processing of the full-length single chain expression product (i.e., propeptide fusion). In particular.

In one embodiment, the propeptide fusion includes a spacer sequence (SS) upstream of the LC, a single chain antibody (VHH) positioned upstream of the spacer sequence (SS), a detection tag (DT) positioned upstream of the single chain antibody, a restricted specificity protease (RSP) site positioned upstream of the detection tag (DT) and an affinity purification tag ($APT_N$) positioned upstream of the restricted specificity protease (RSP) site. In addition, a restriction specific (RSP) site is positioned between the LC and HC. Another restricted specificity protease (RSP) site is positioned downstream of the HC, and an affinity purification tag ($APT_C$) is positioned downstream of the restricted specificity protease (RSP) site. This embodiment is illustrated in FIG. 4A. During processing of this embodiment of the propeptide fusion, cleavage at the restricted specificity protease (RSP) sites occurs, separating the LC and HC, except for the S-S bond, and eliminates the affinity purification tags ($APT_N$ and $APT_C$), as illustrated in FIG. 4B.

Figures 8A, 8B:
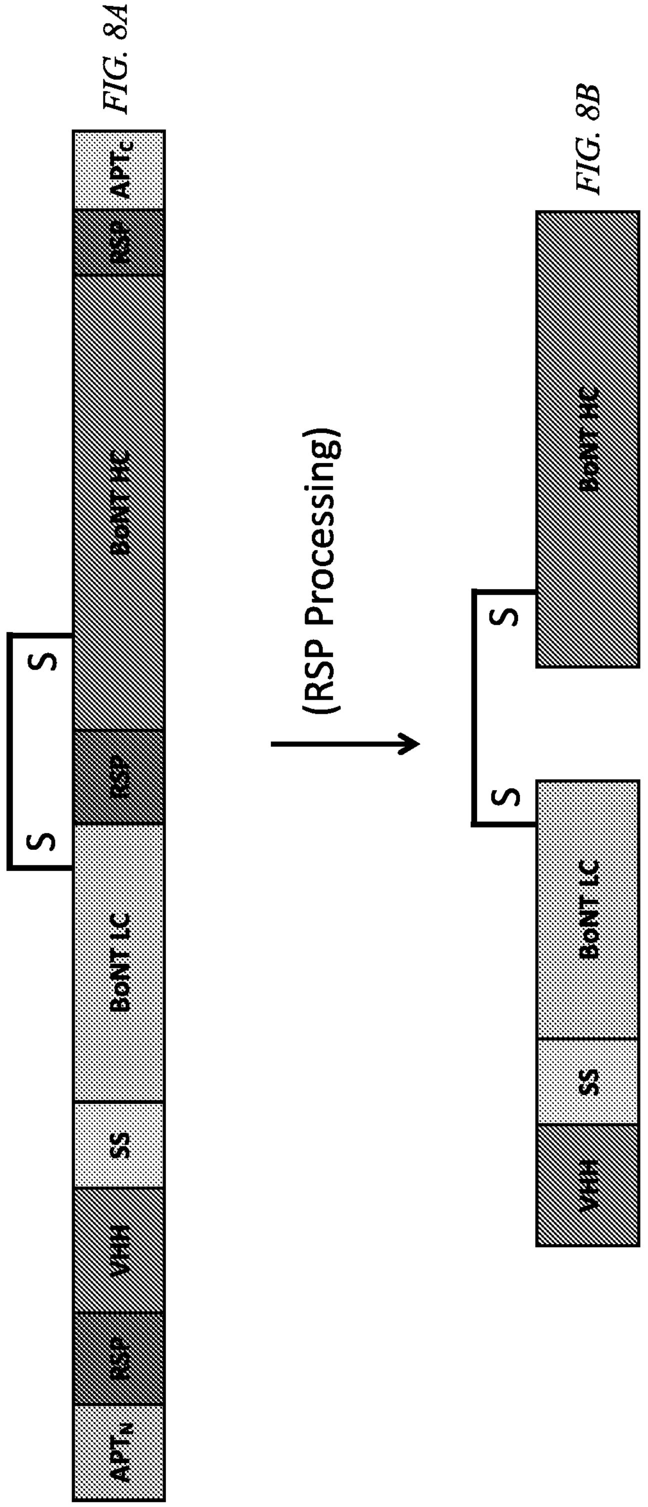
FIGS. 8A-B are schematic illustrations of a propeptide fusion (FIG. 8A) and fusion protein (FIG. 8B) according to one embodiment of the present invention shown before (FIG. 8A) and after (FIG. 8B) RSP processing. According to the embodiment illustrated here, the propeptide fusion (FIG. 8A) has the same structure of the propeptide fusion of FIG. 4A, but lacks a detection tag (DT).
Figure 9A:
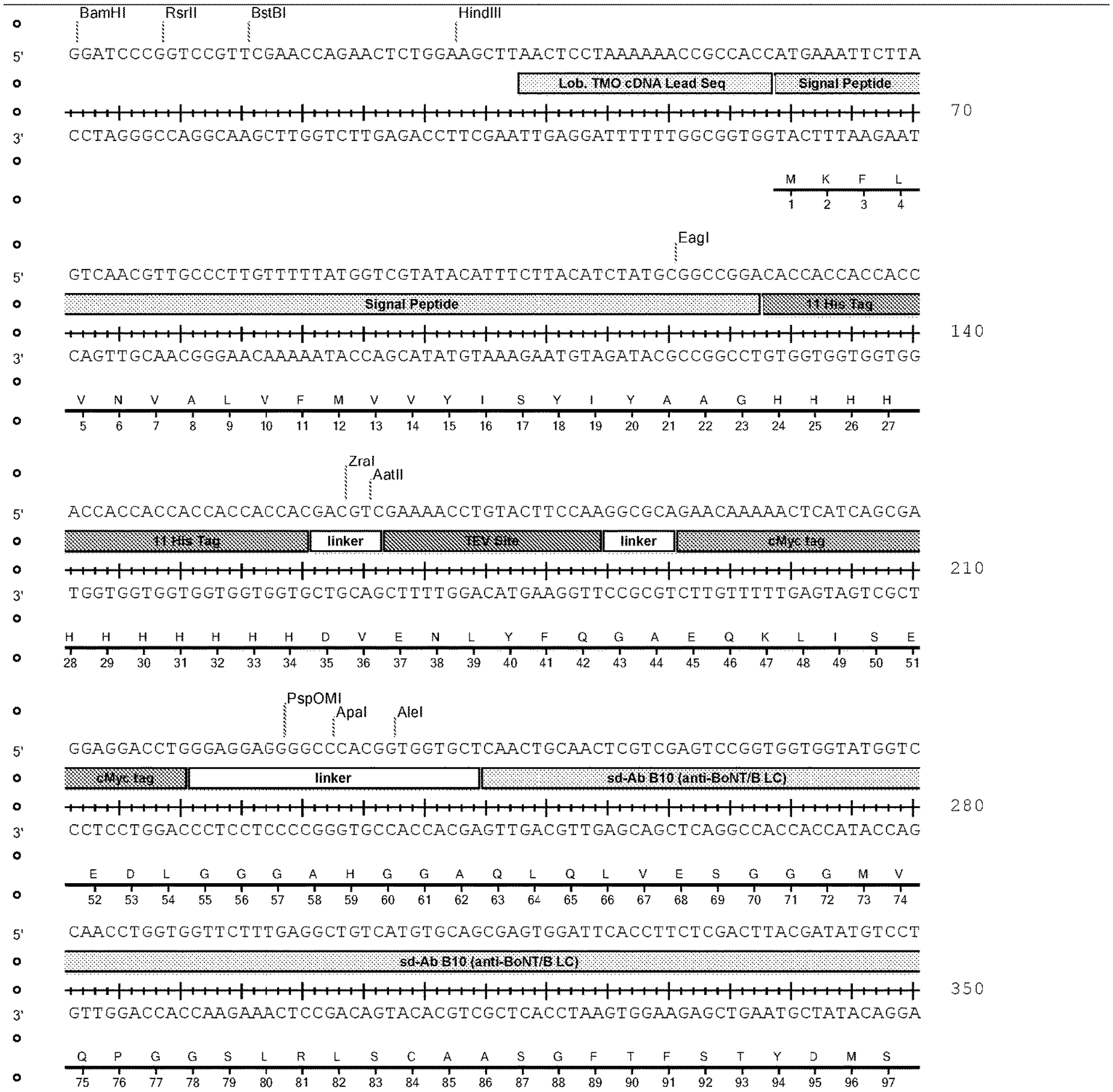
Figure 9B:
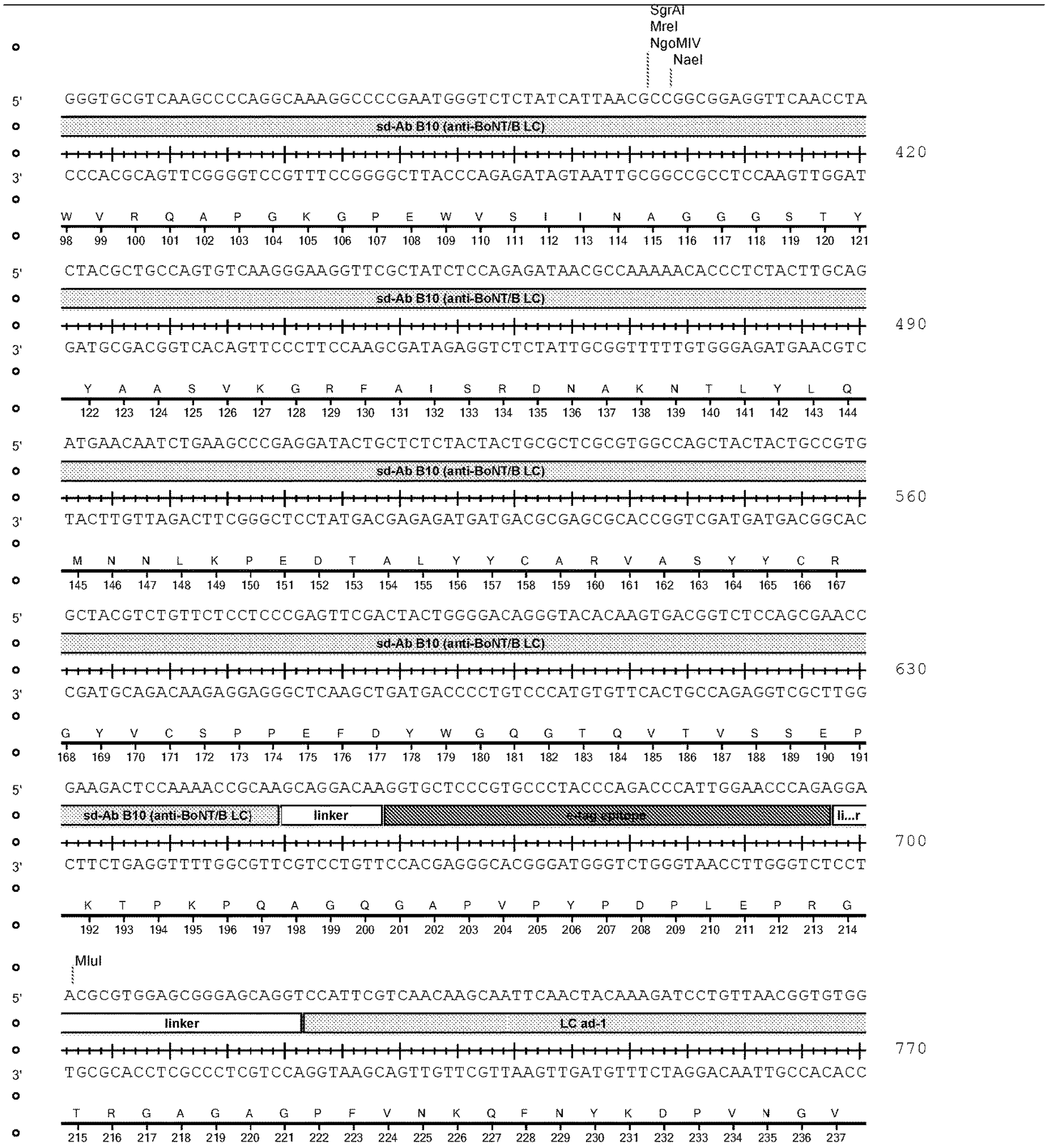
Figure 9C:
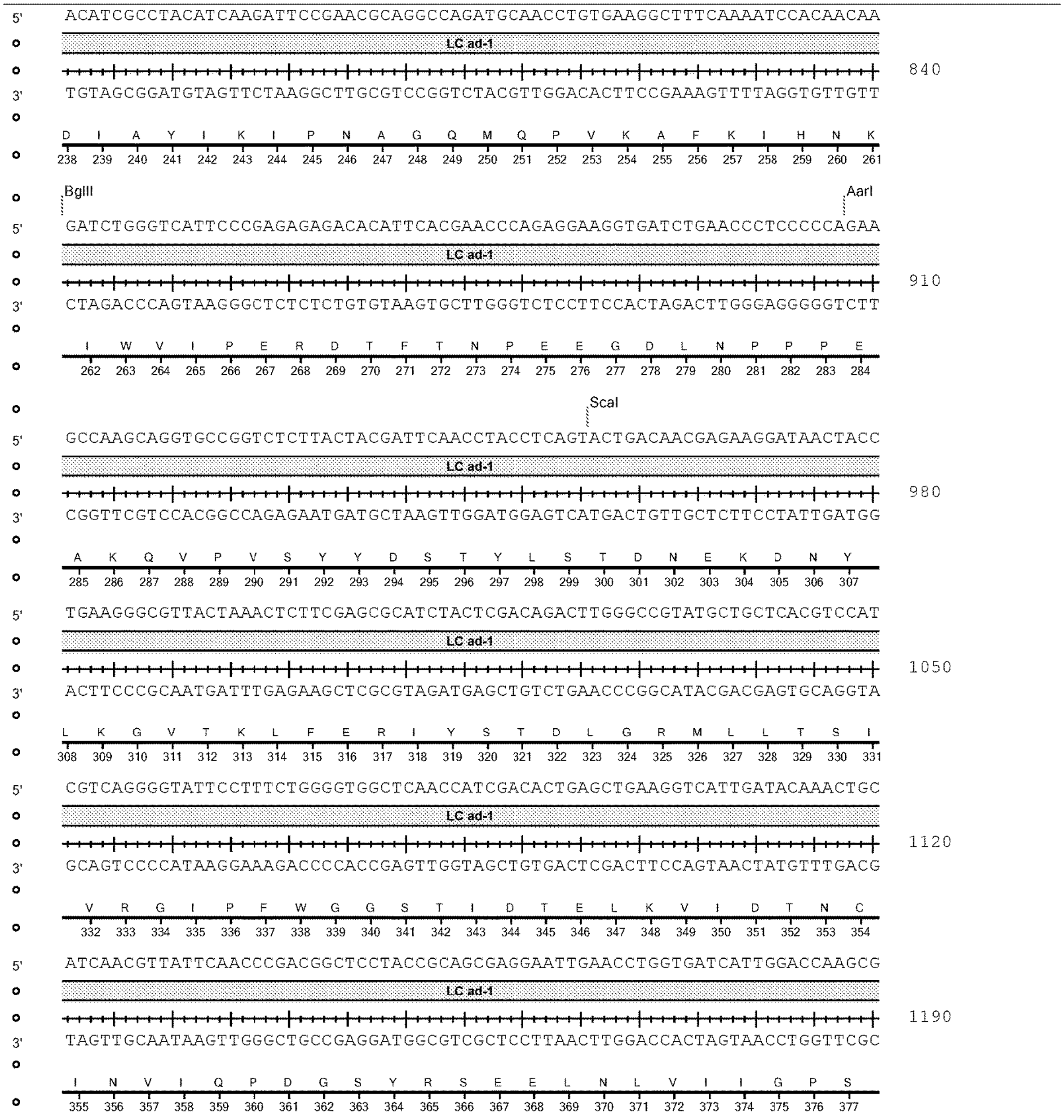
Figure 9D:
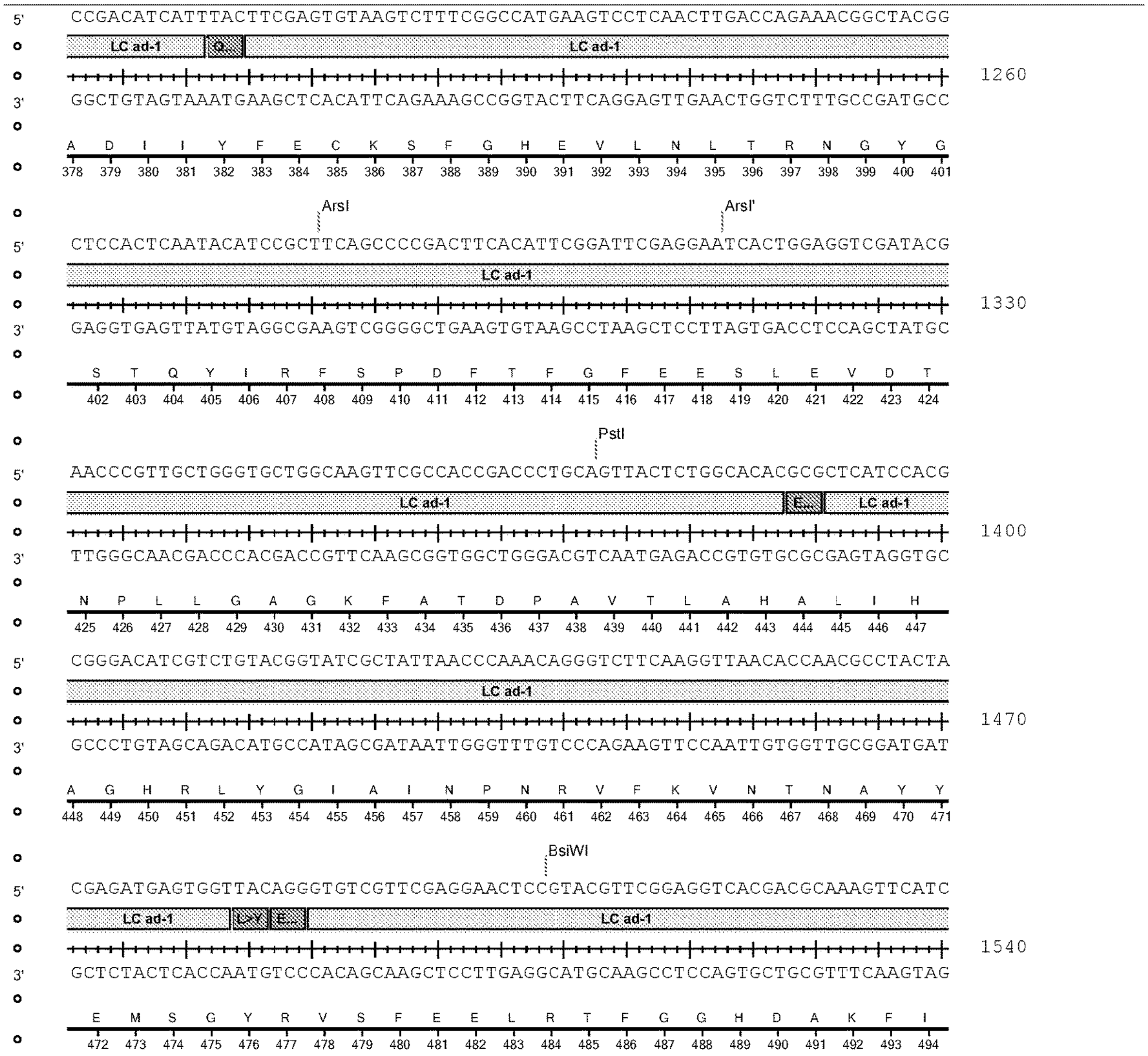
Figure 9E:
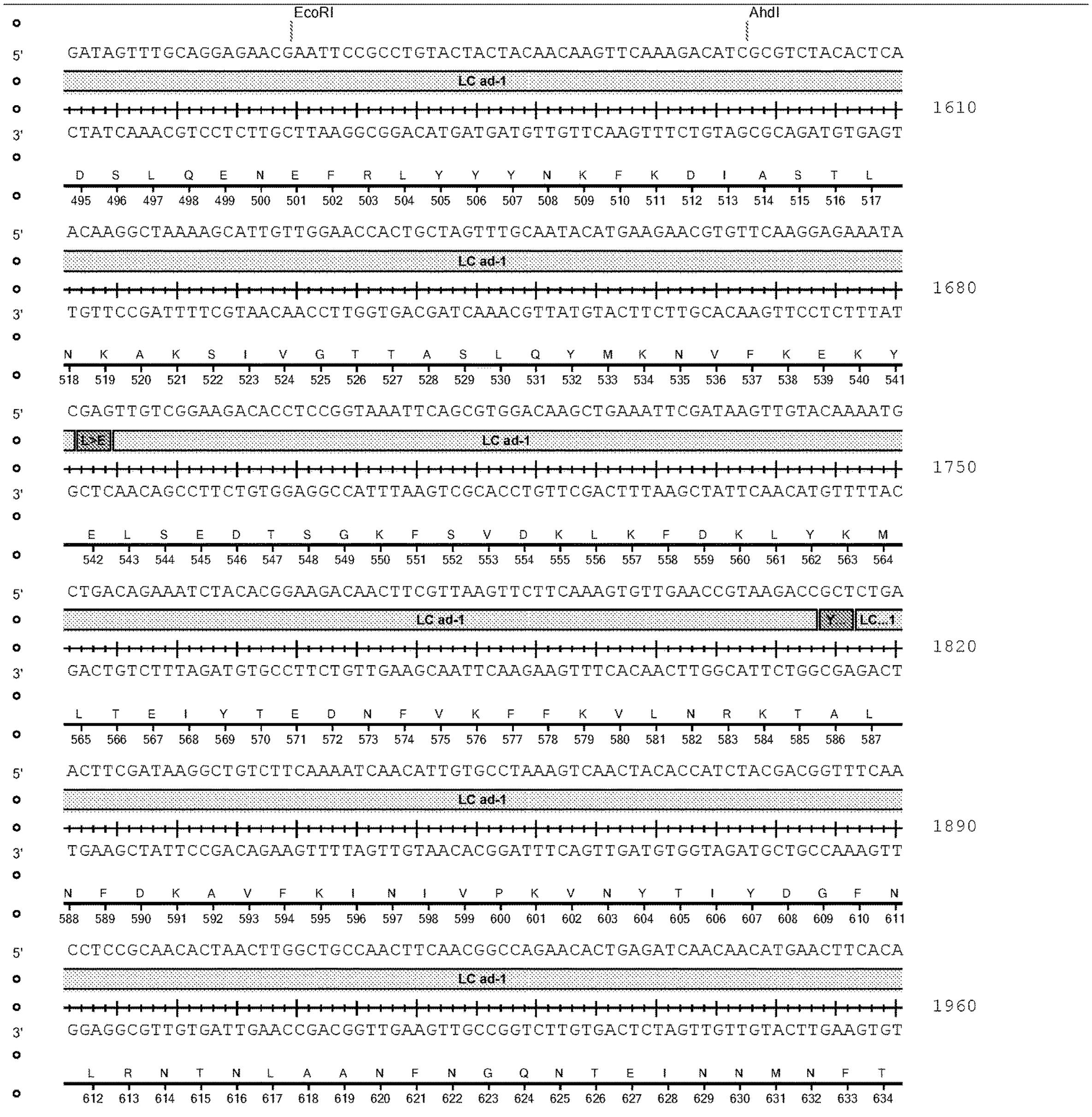
Figure 9F:
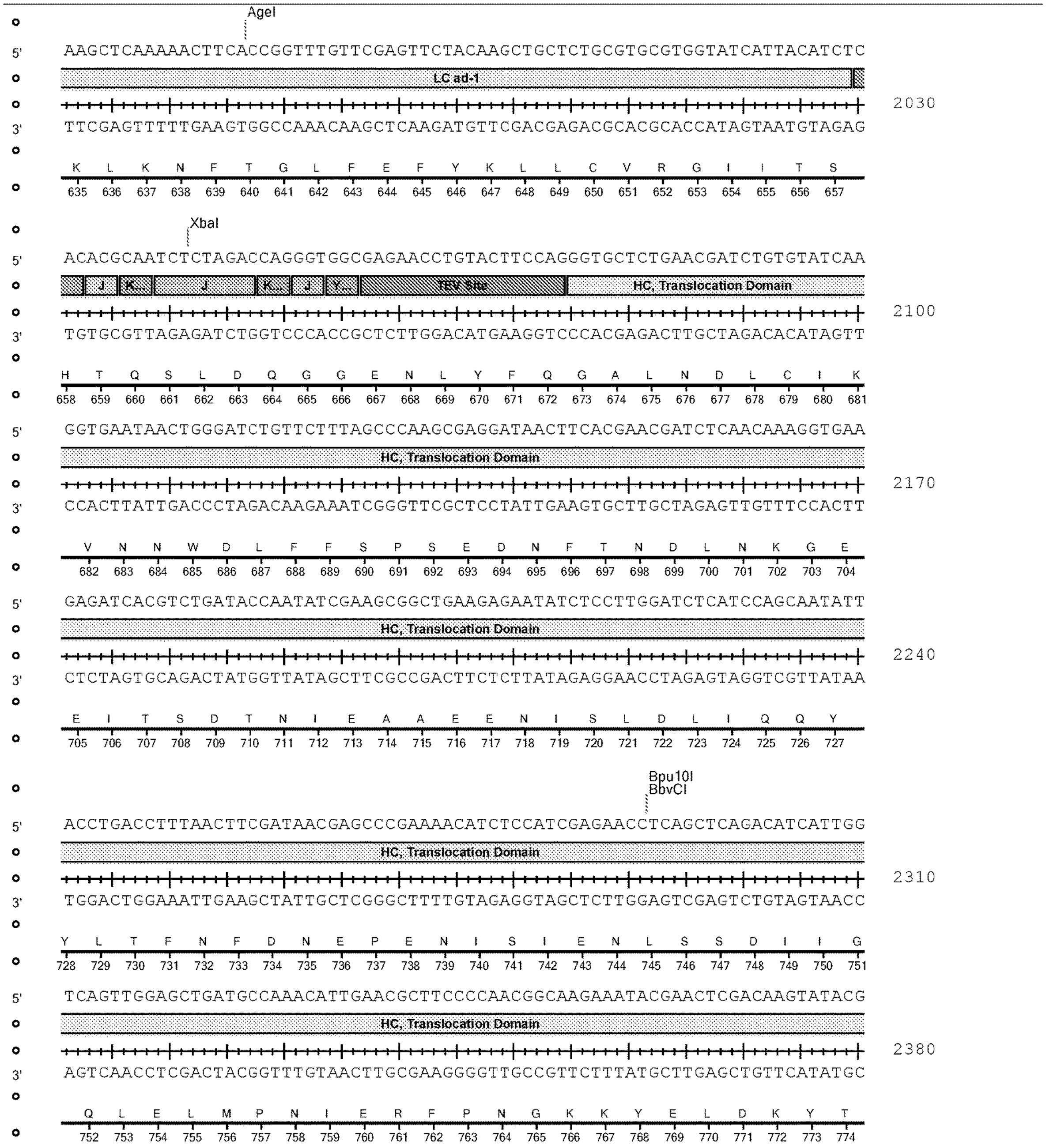
Figure 9H:
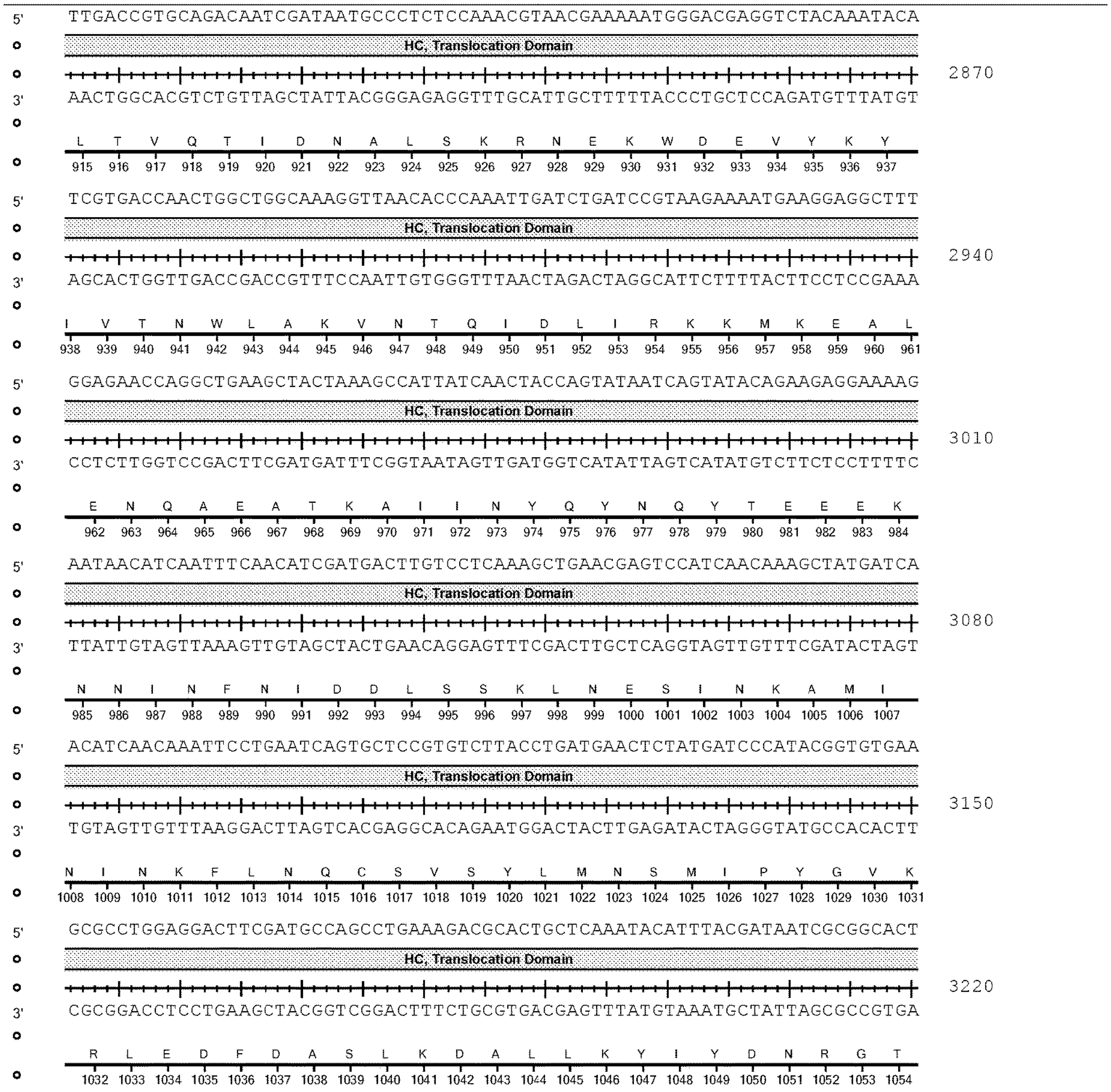
Figure 9I:
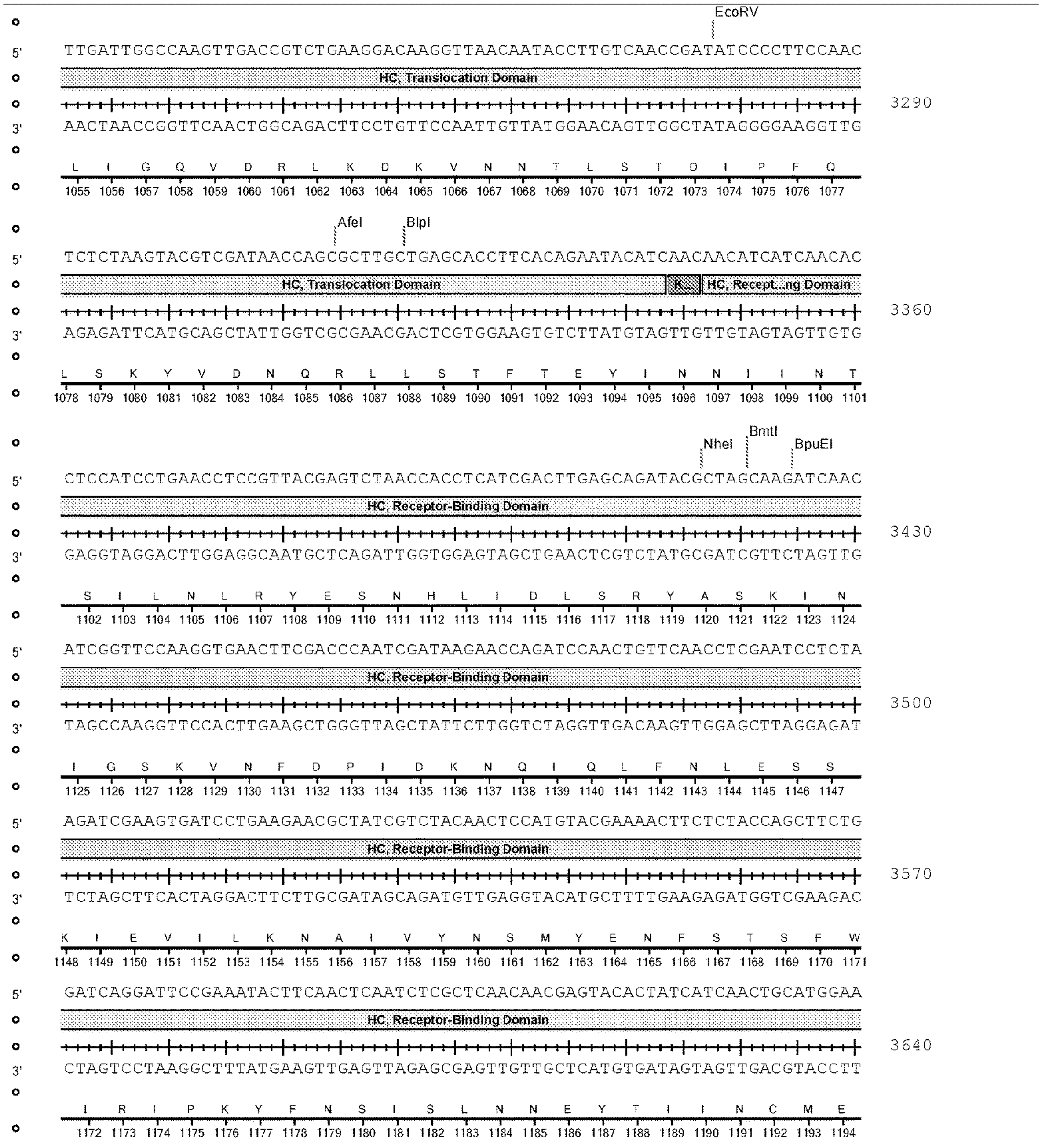
Figure 9L:
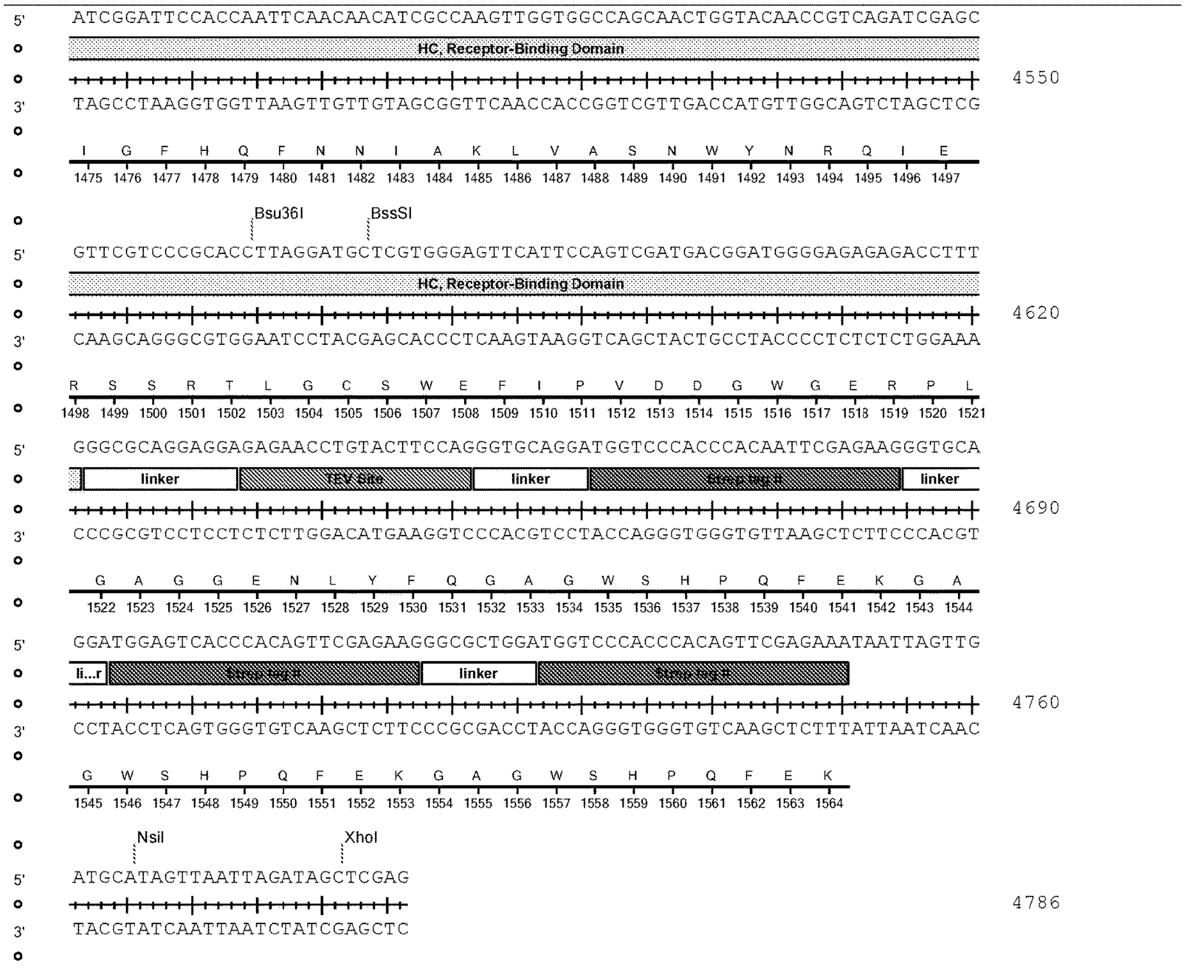
Figure 10A:
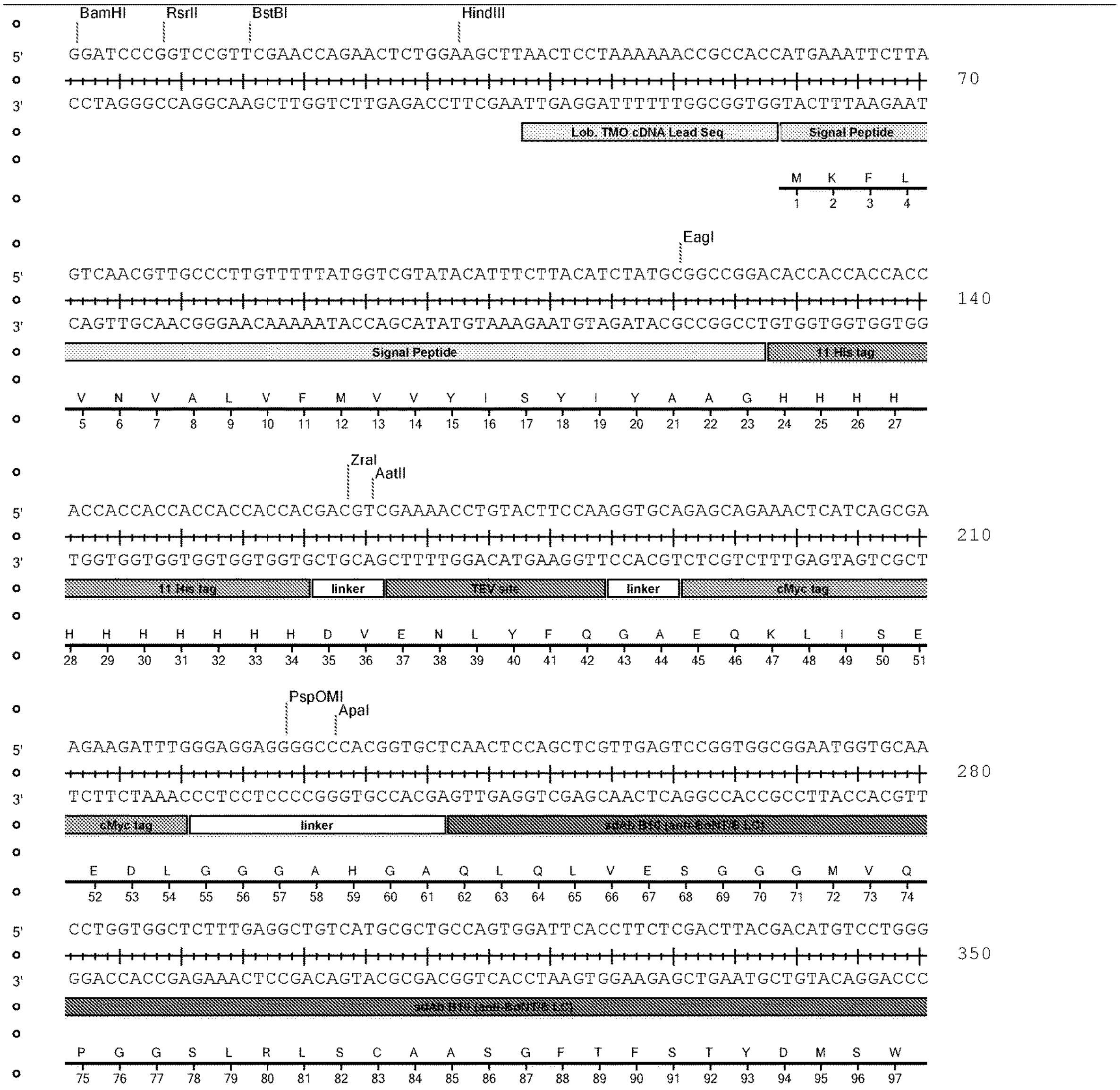
Figure 10D:
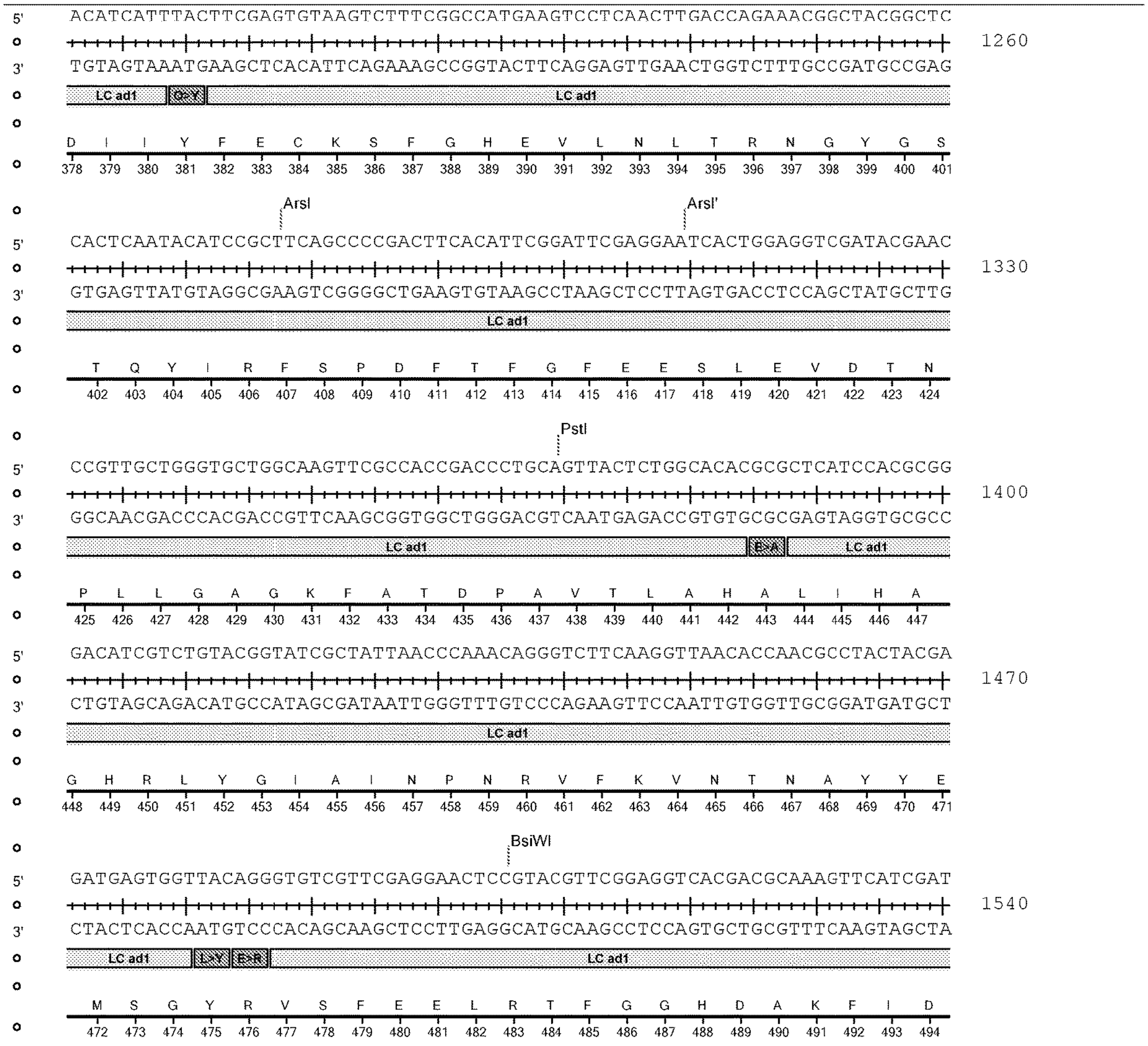
Figure 10E:
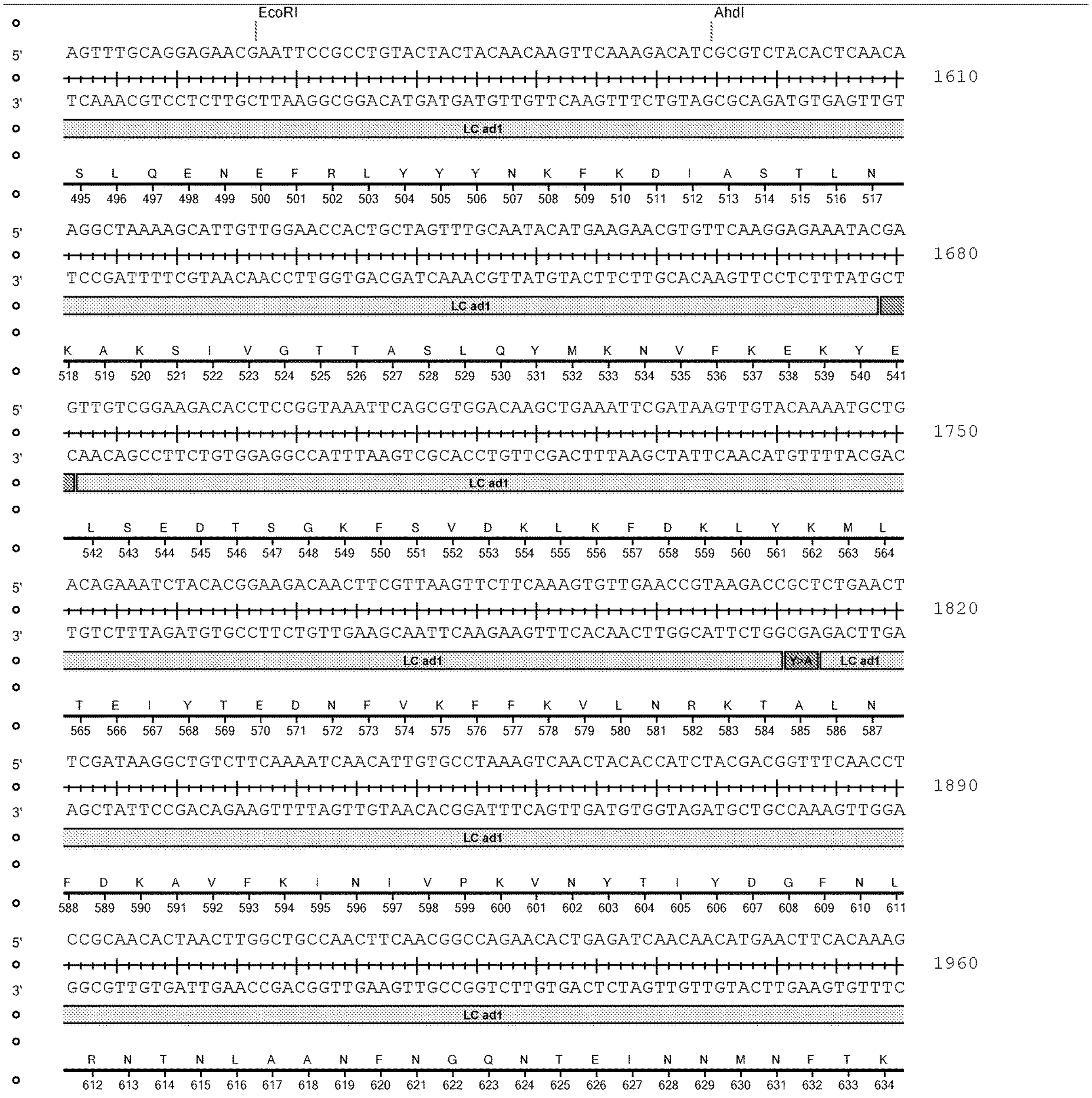
Figure 10L:
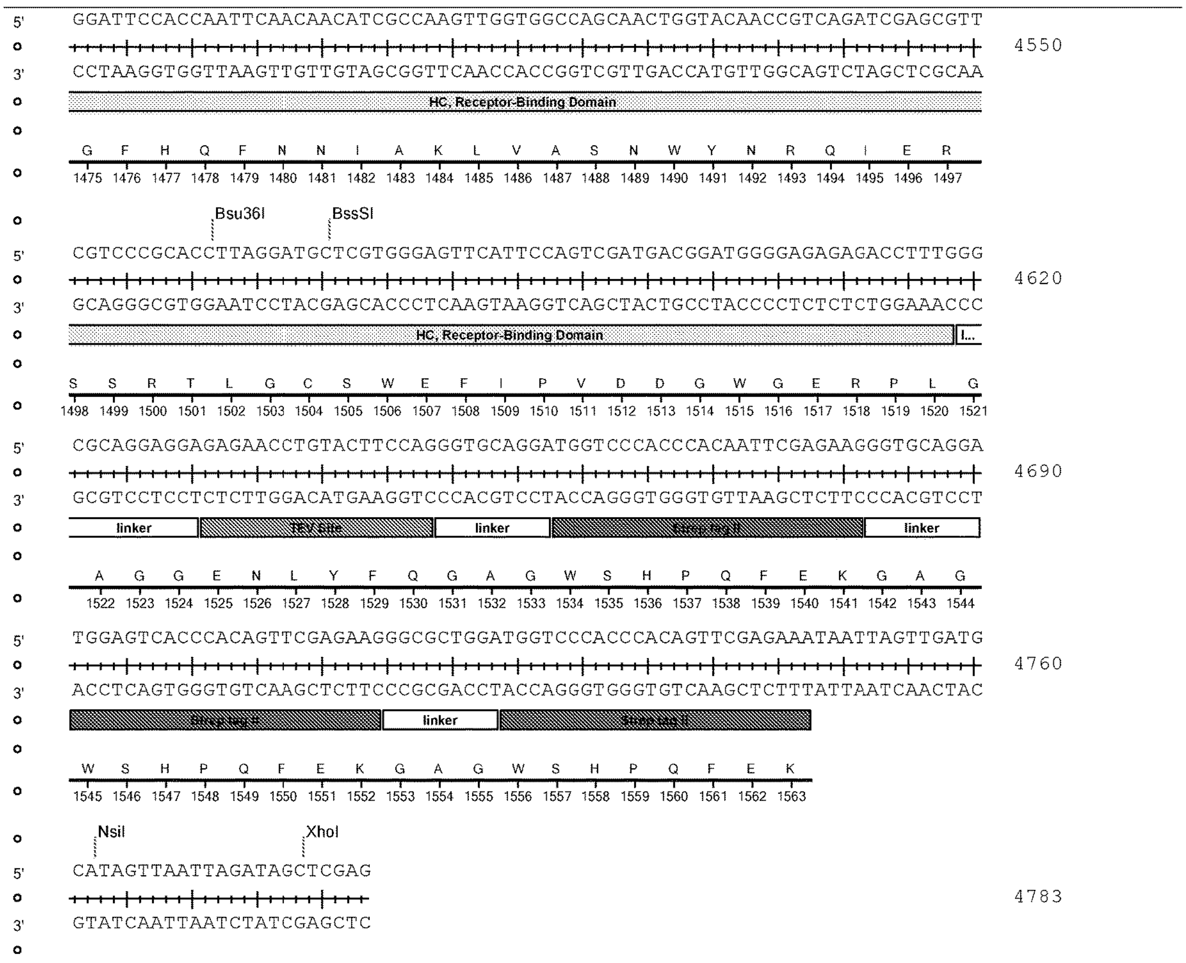
Figure 11A:
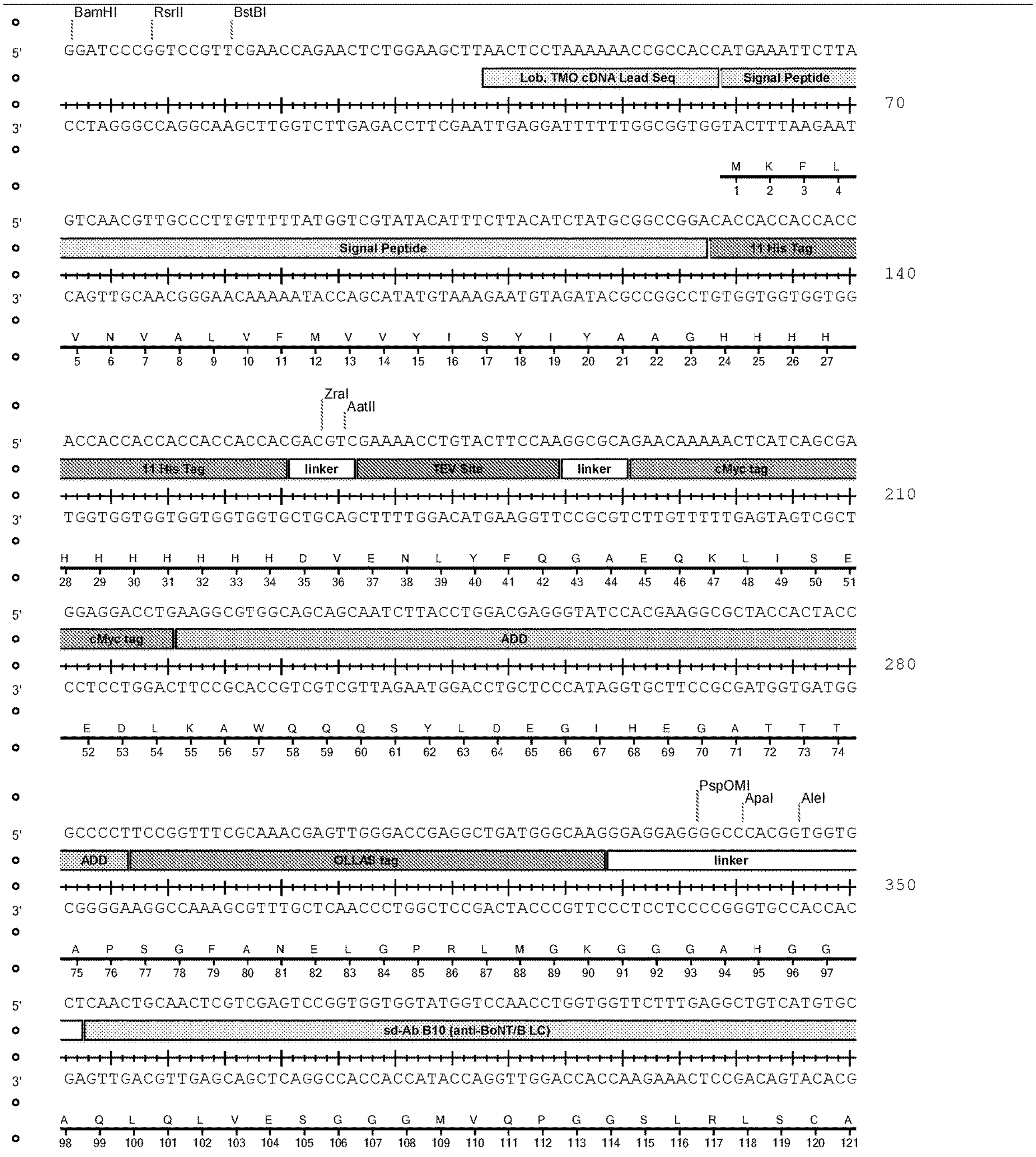
Figure 11B:
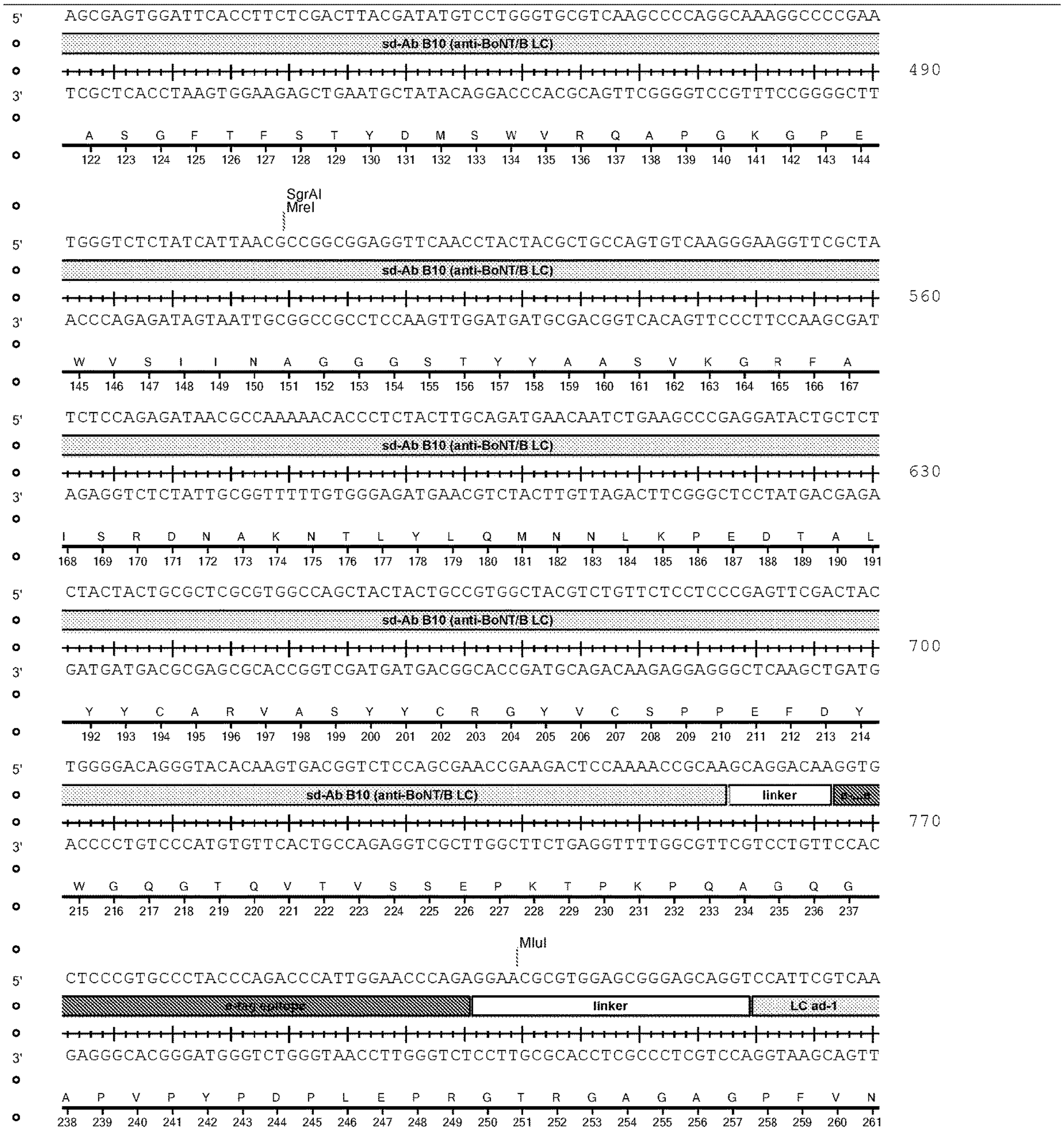
Figure 11C:
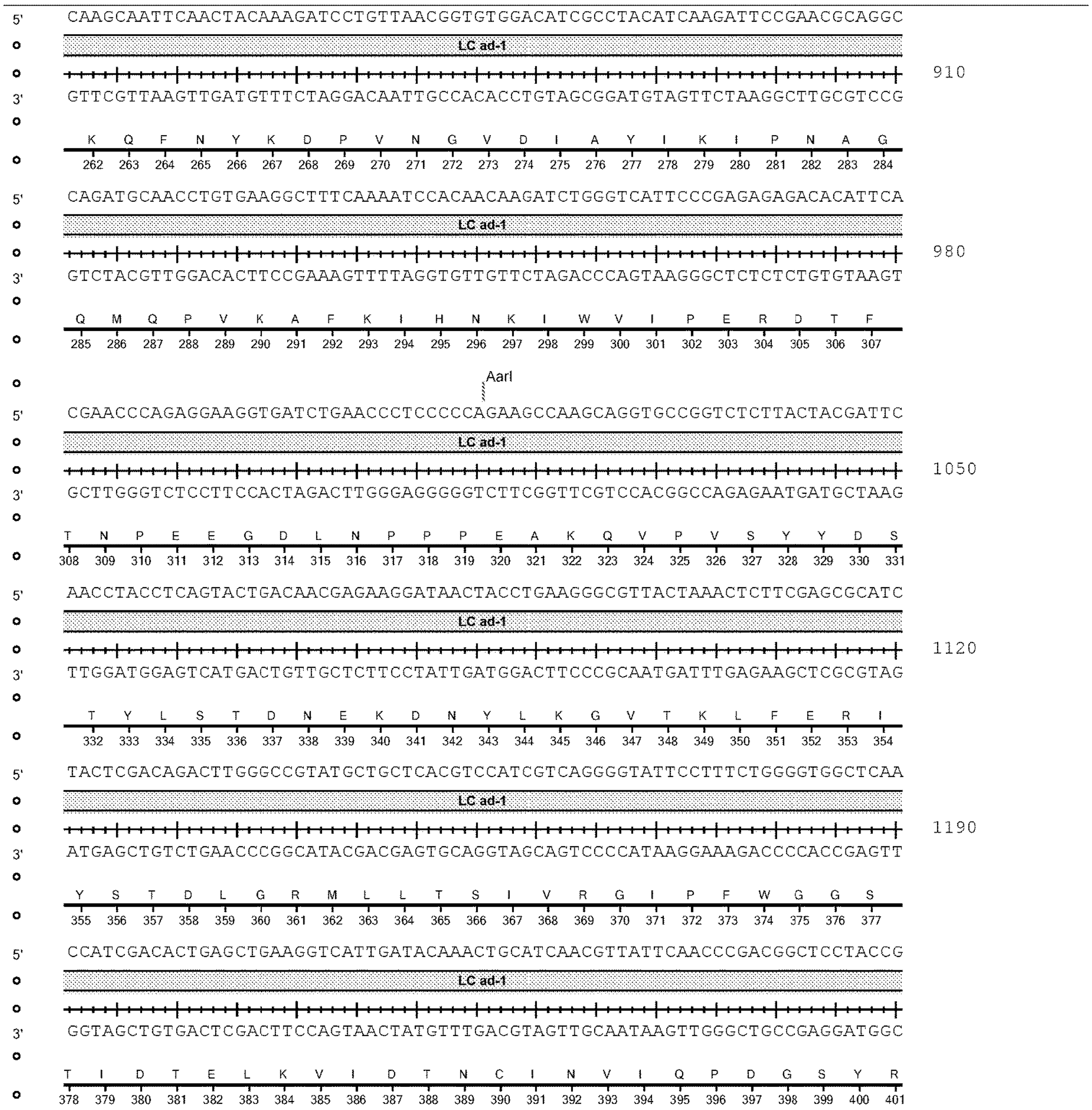
Figure 11D:
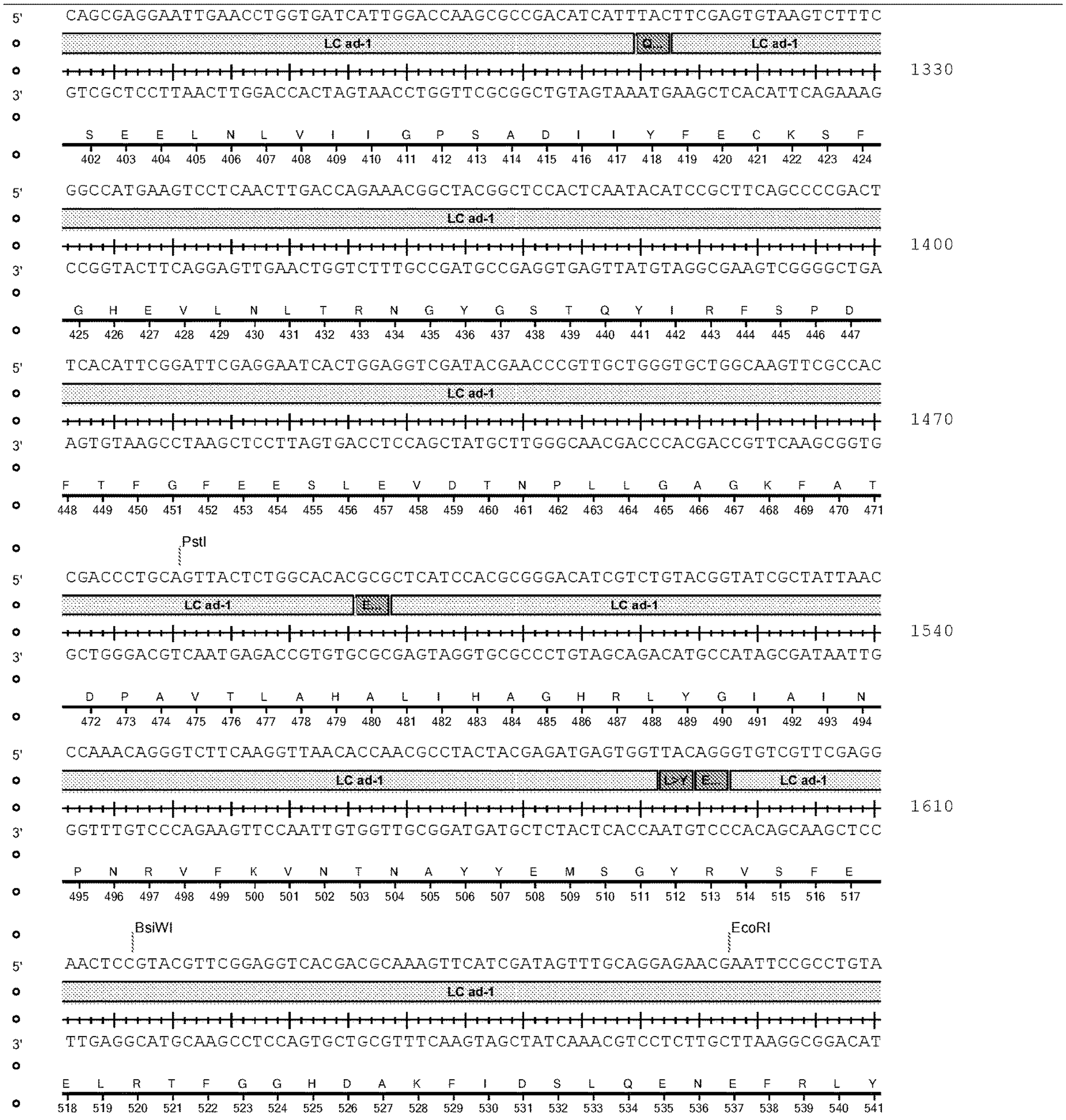
Figure 11F:
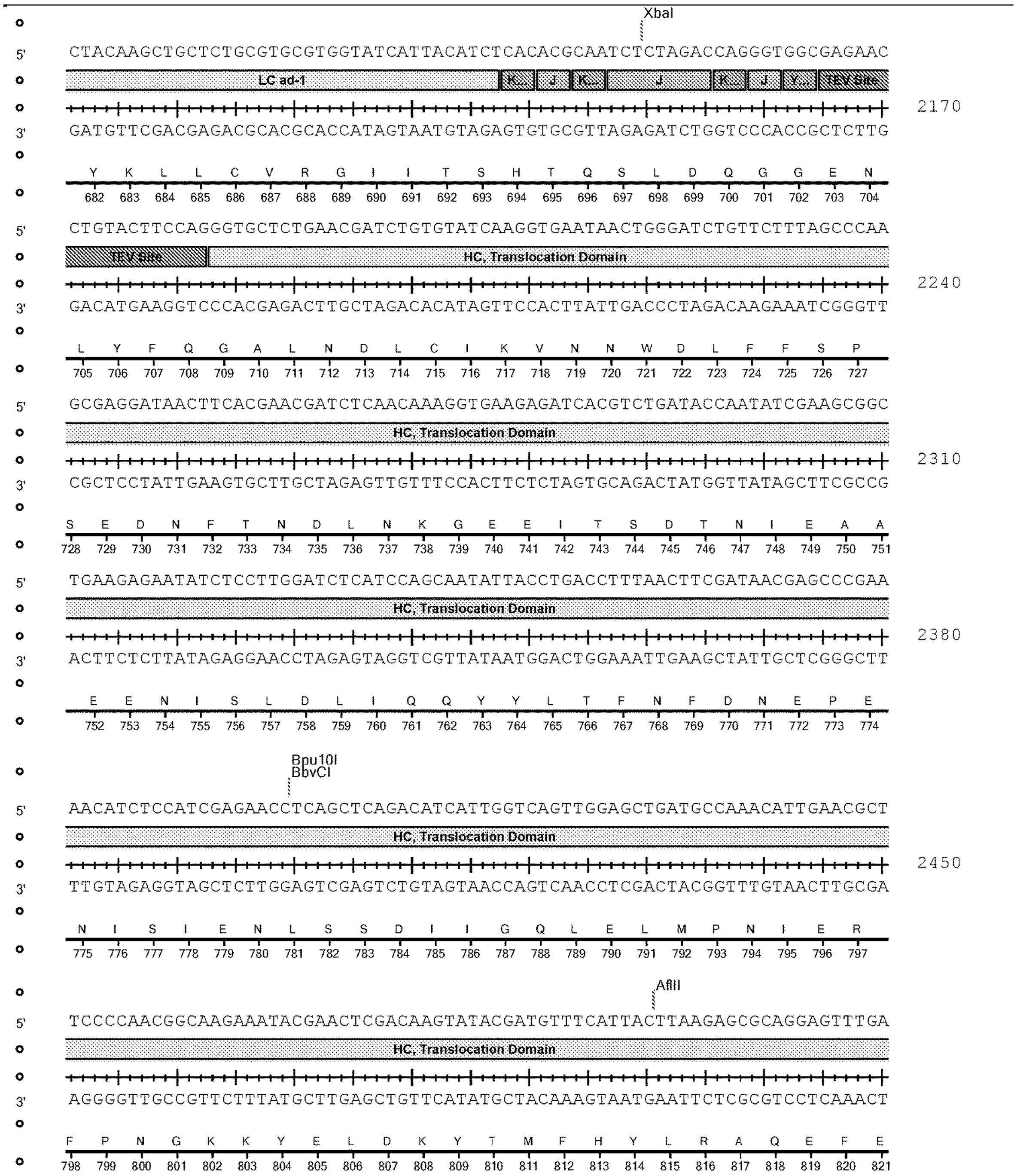
Figure 11J:
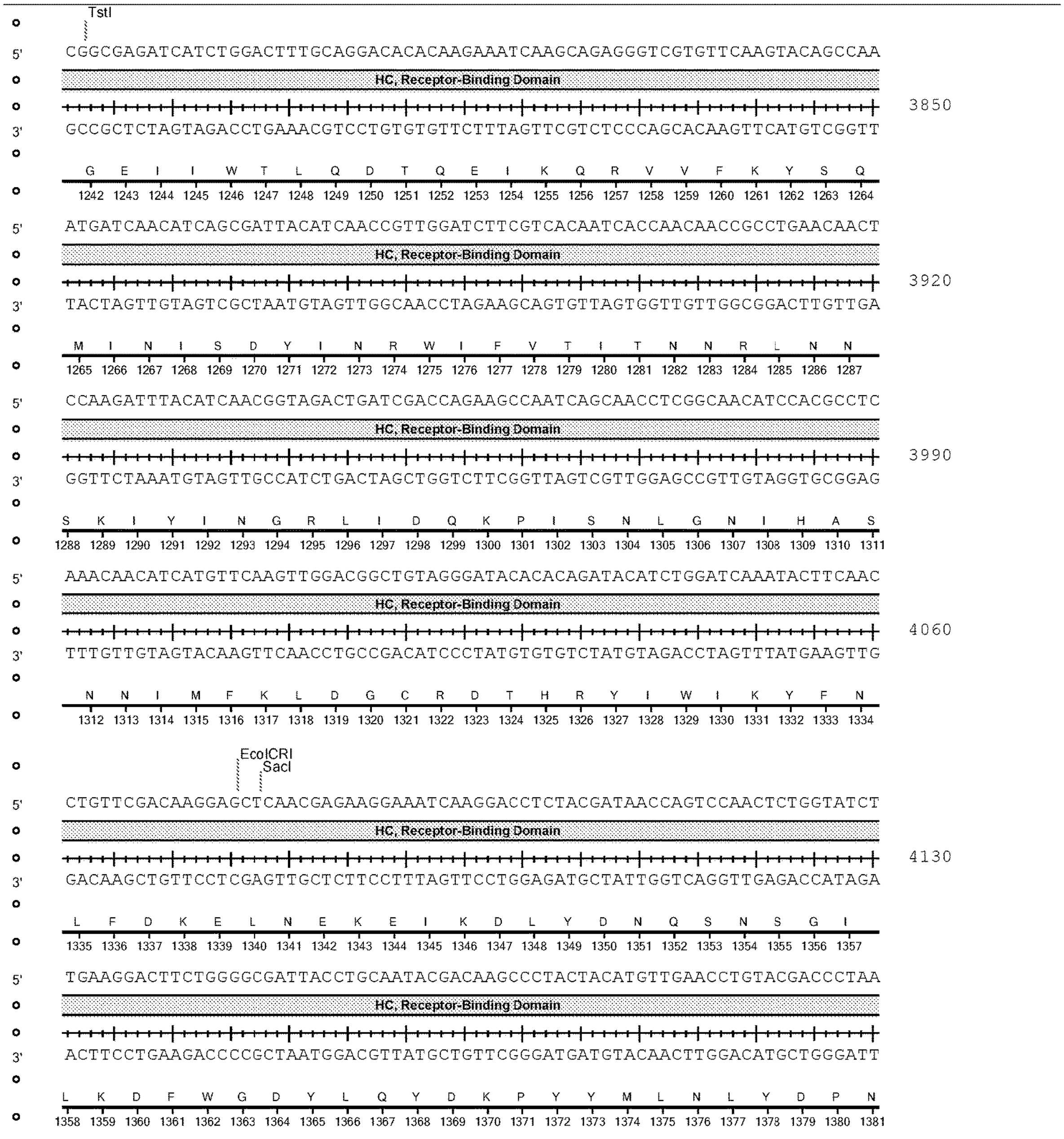
Figure 11L:
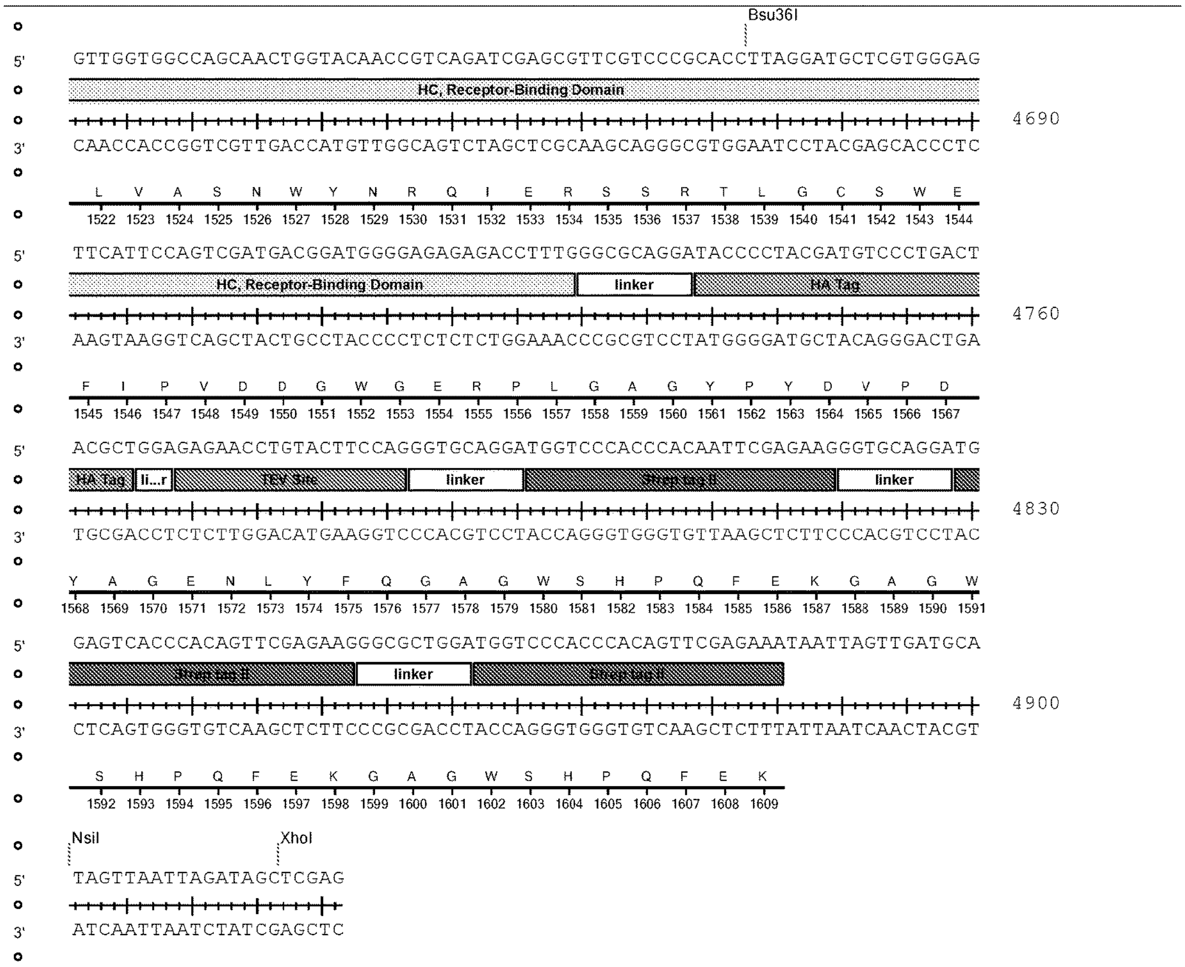
Figure 12A:
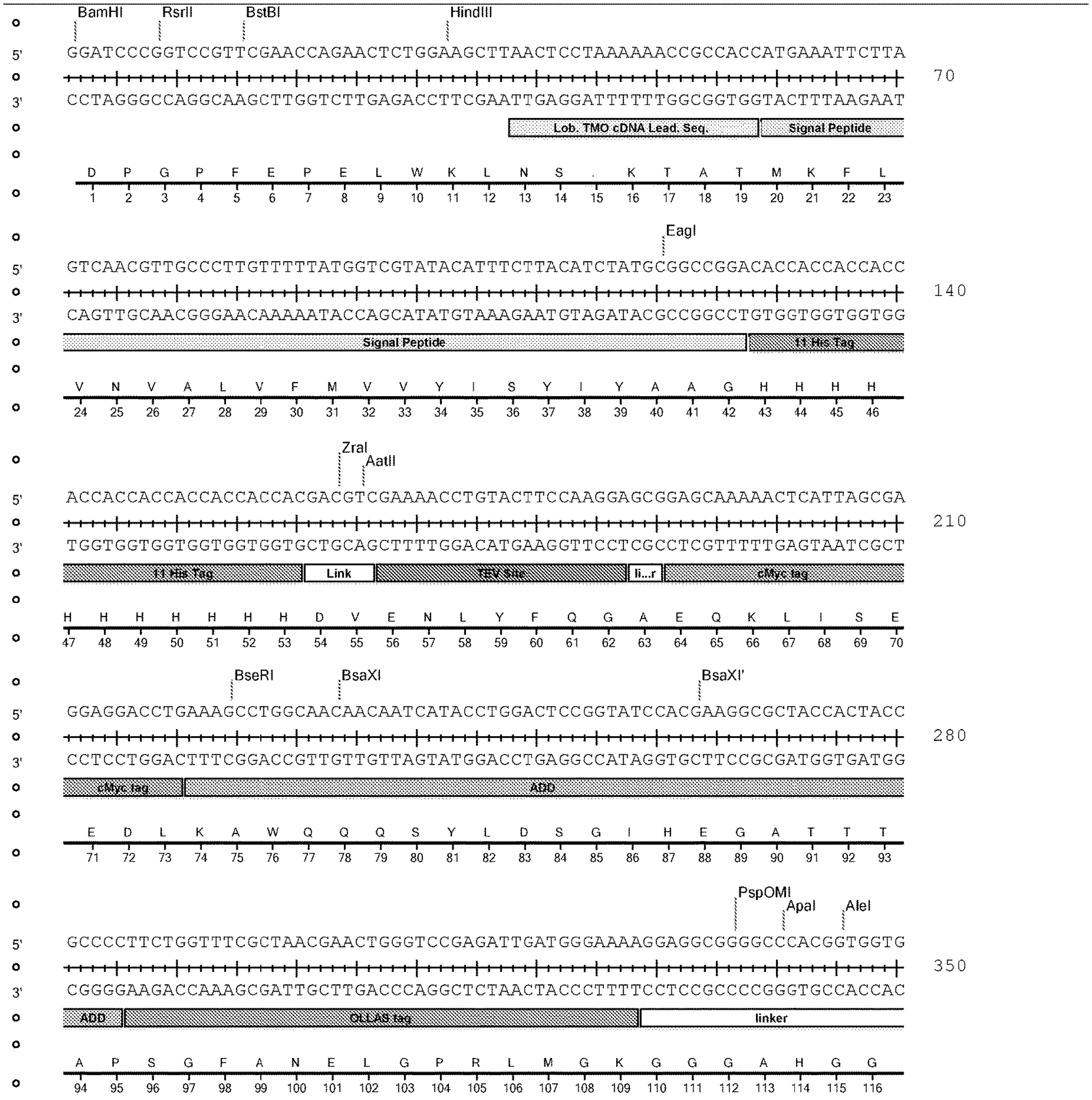
Figure 12B:
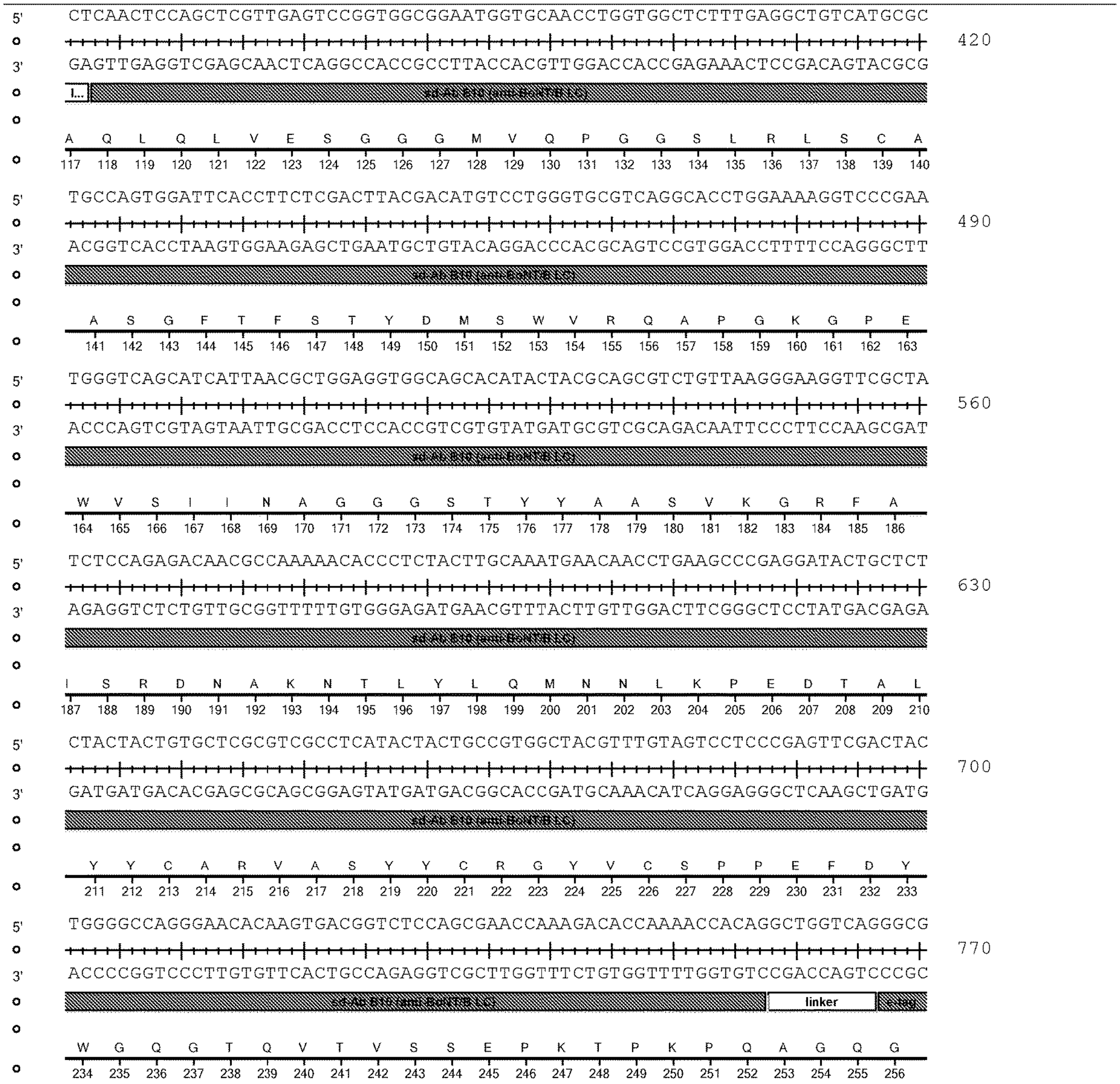
Figure 12C:
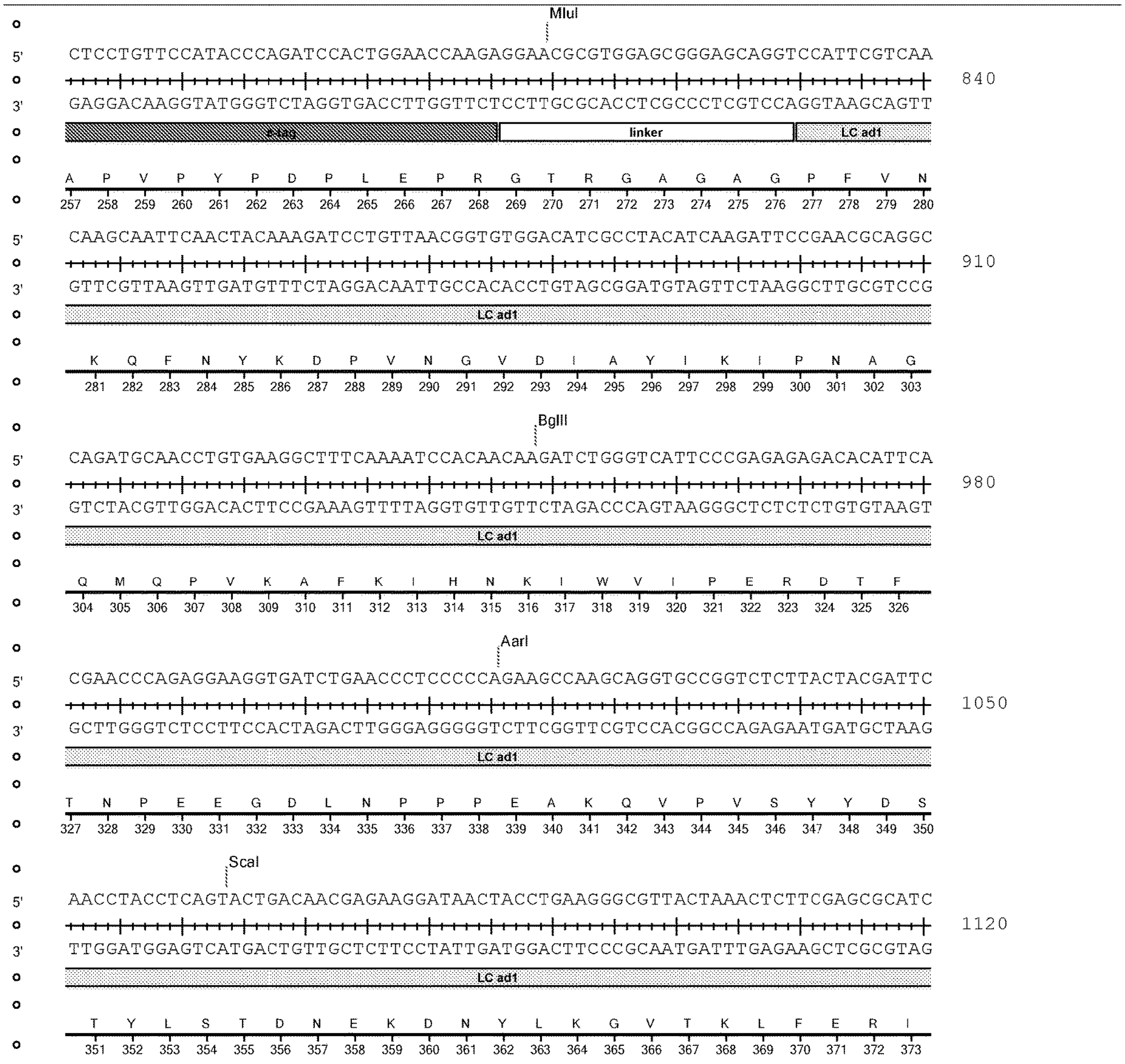
Figure 12D:
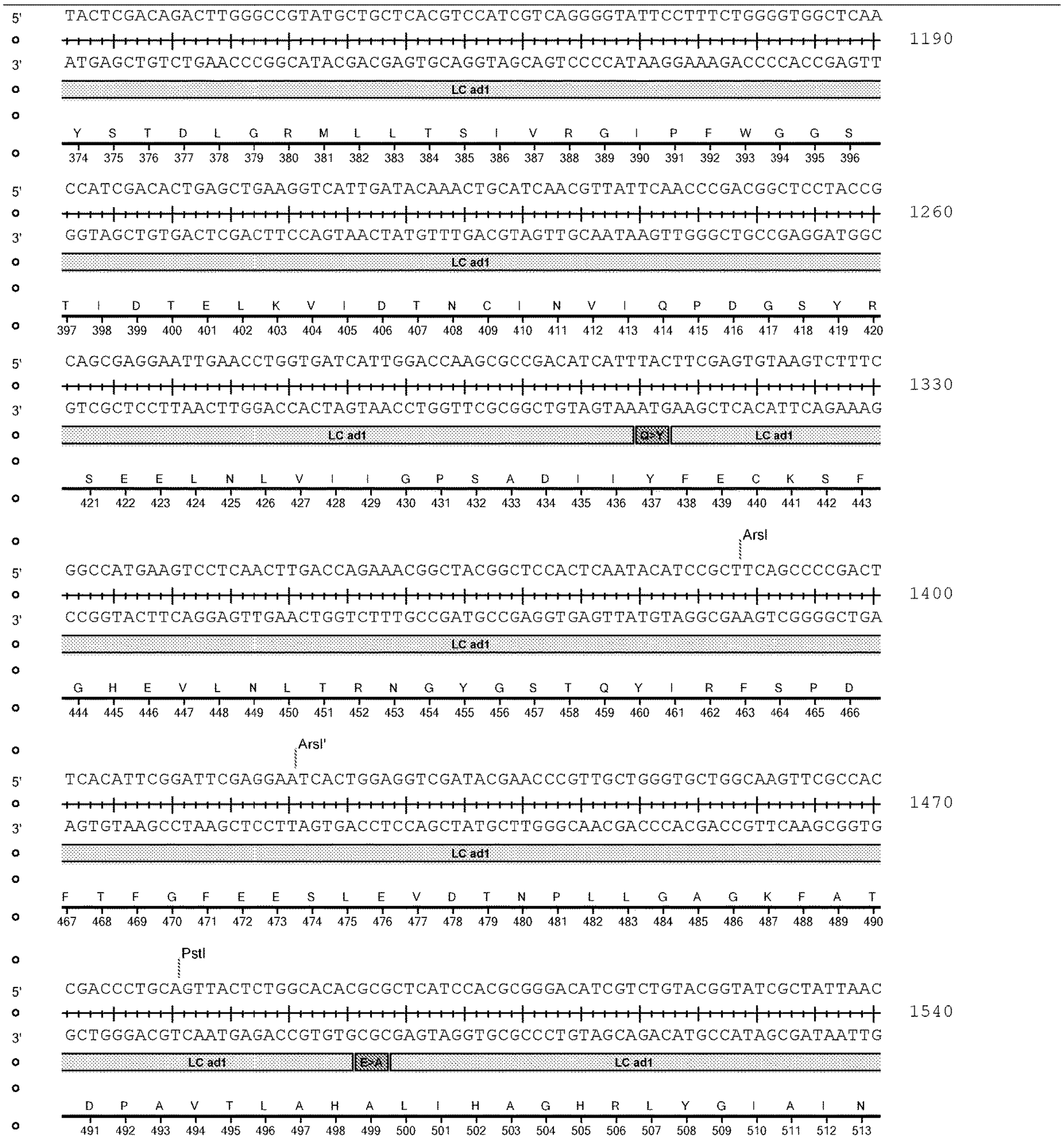
Figure 12E:
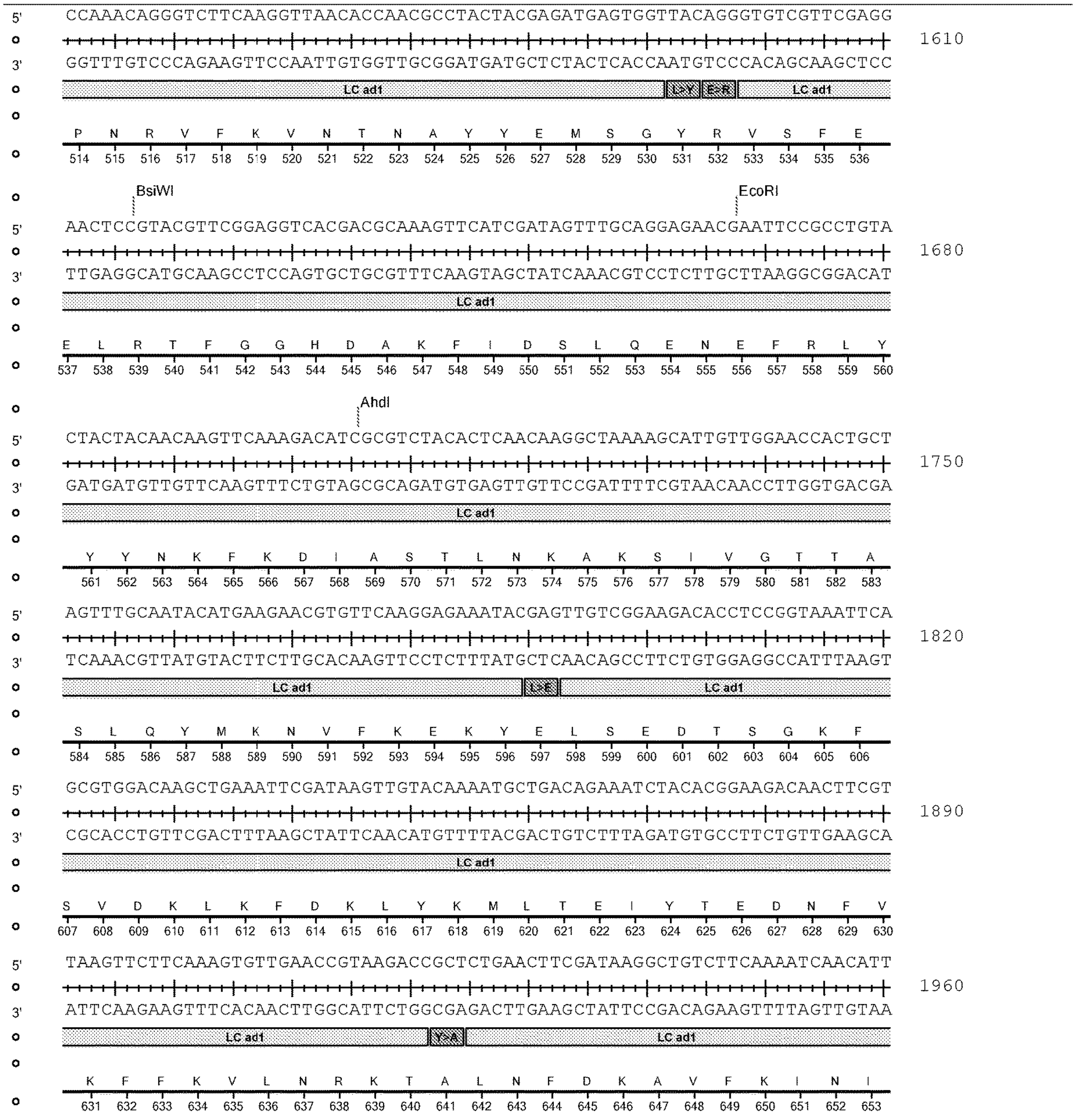
Figure 12F:
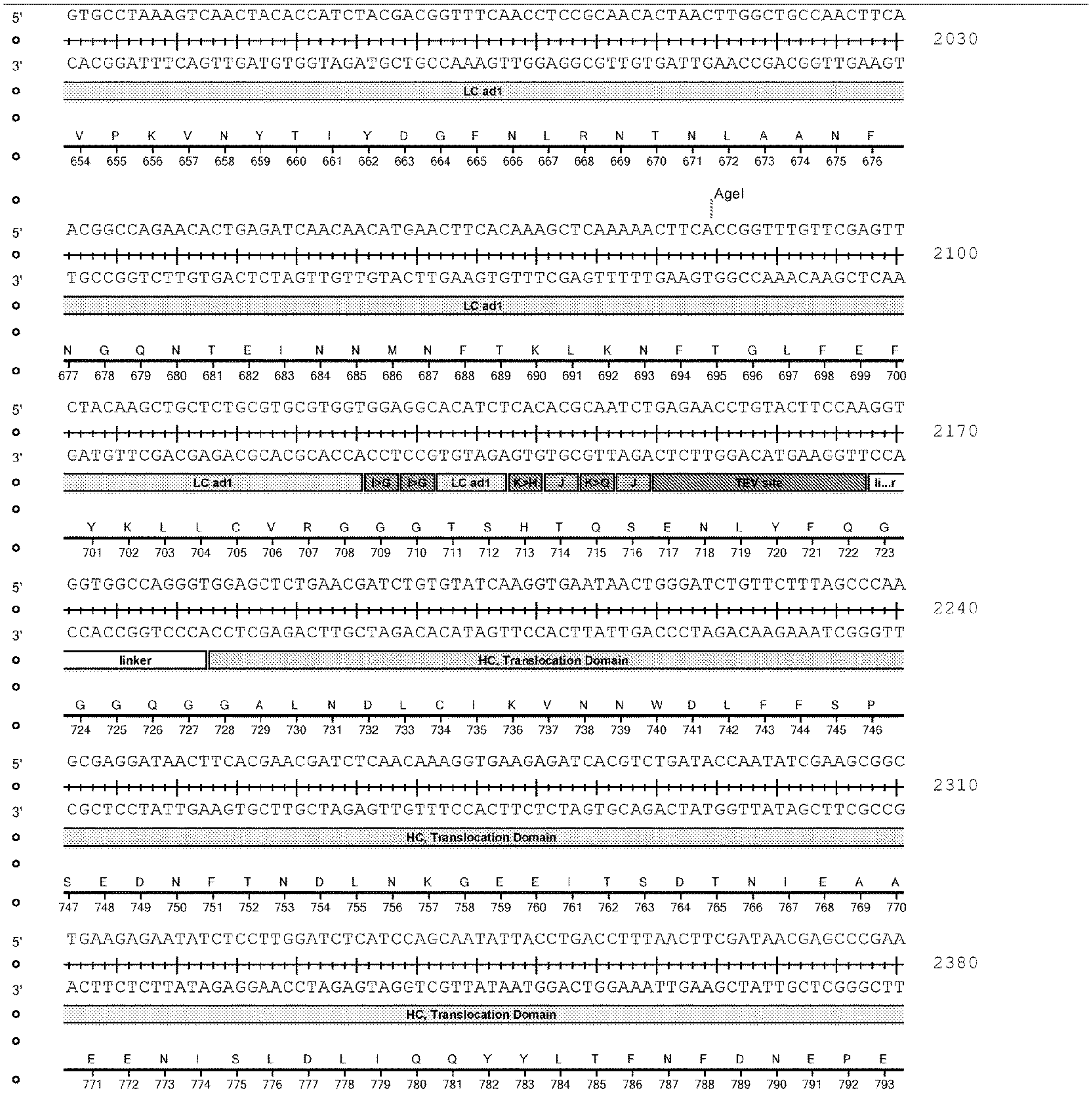

In another embodiment illustrated in FIG. 8A, the propeptide fusion has the features of the propeptide fusion illustrated in FIG. 4A, but lacks the detection tag positioned upstream of the single chain antibody. According to one embodiment, the cleavage product of the propeptide fusion of FIG. 8A (i.e., the protein of FIG. 8B) is a suitable protein for pharmaceutical applications.

Figures 6A, 6B:
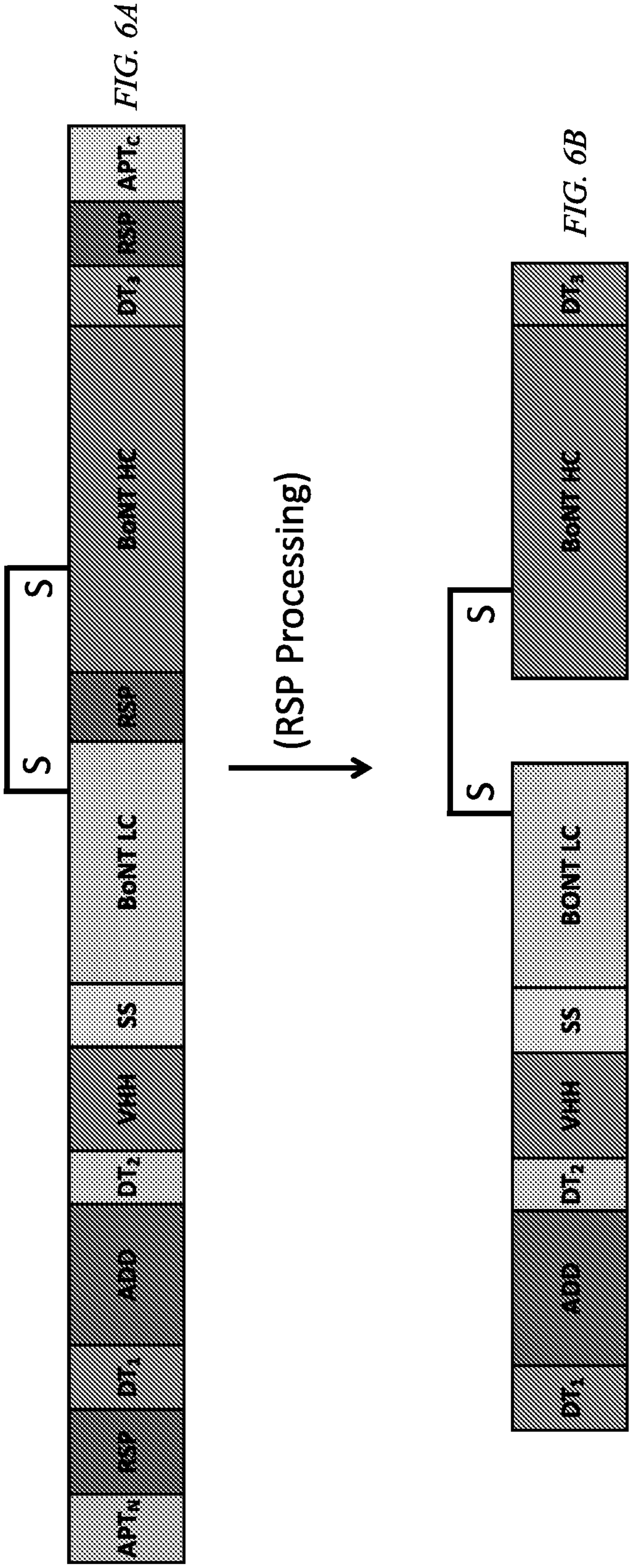
FIGS. 6A-B are schematic illustrations of a propeptide fusion (FIG. 6A) and fusion protein (FIG. 6B) according to one embodiment of the present invention containing a sequence that targets the protein for accelerated intracellular elimination, referred to as an accelerated degradation domain ("ADD"). For example, BoNT/A ad-1 with the B10-VHH that binds BoNT/B is illustrated with the added ADD signal to mark the complex for elimination by the proteasome pathway. The schematic constructs are shown before (FIG. 6A, propeptide fusion) and after (FIG. 6B, fusion protein) RSP processing.

According to yet another embodiment, the propeptide fusion further includes an accelerated degradation domain (ADD) and, optionally, another detection tag (DT) positioned upstream of the single chain antibody and downstream of the restricted specificity protease (RSP) site and the affinity purification tag ($APT_N$), as illustrated in FIG. 6A. After processing with a highly specific protease, the resulting fusion protein has the affinity purification tags removed, but still possesses the accelerated degradation domain (ADD), as illustrated in FIG. 6B.

Figures 7A, 7B:
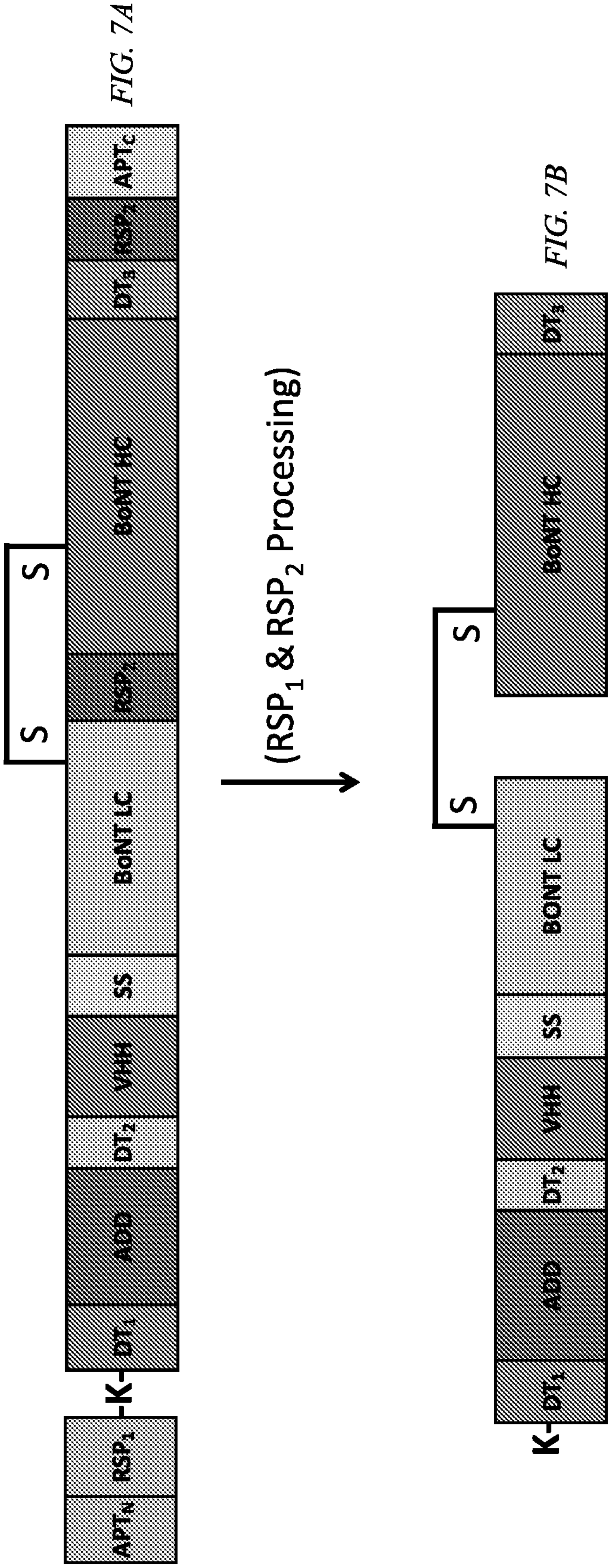
FIGS. 7A-B are schematic illustrations of a propeptide fusion (FIG. 7A) and fusion protein (FIG. 7B) according to one embodiment of the present invention in which the propeptide is designed so that the N-terminal amino acid of the mature heterodimer (FIG. 7B) is a lysine (—K—) residue to accelerate degradation by the proteasome system.

According to still another embodiment, the propeptide fusion is designed so that after removal of the N-terminal APT by the RSP, the N-terminal amino acid upstream of the ADD is a basic amino acid, such as lysine (K), or any other positively charged amino acid, to further accelerate degradation of the fusion protein and any antigens to which the fusion protein is bound. This is illustrated in FIGS. 7A and 7B, and described in the examples infra. $RSP_1$ and $RSP_2$ in FIGS. 7A and 7B (or any other propeptide fusion described herein containing more than one RSP) may or may not be the same recognition sequence. Any one or more RSP in a propeptide fusion may be concomitant or sequential.

According to one embodiment, the detection tags (DT) are capable of detecting delivery of the single chain antibody to neuronal cytoplasm. Suitable detection tags include, without limitation, c-myc, OLLAS tag, HA tag, E tag, His tag, and Strep tag. The detection tags may also serve a dual purpose by providing a means of detection and creating a spacer sequence. Likewise, spacer sequences (SS) as described herein, may also serve as detection tags. In another embodiment, detection tags (DT) are optional or are very small (i.e., short in sequence). For example, if a detection tag (DT) separates a lysine residue, or other positively charged amino acid, and an ADD site, it may be desirable to have a short detection tag (DT) for ADD to function properly.

According to one embodiment, the affinity purification tags (APT) are to enable efficient affinity purification of a recombinantly expressed protein in non-truncated form. Suitable affinity purification tags include, without limitation, His tag, Strep tag, and those mentioned supra.

In one embodiment, the restricted specificity protease (RSP) sites are selected from, e.g., an enterokinase cleavage site, a TEV recognition sequence, or a WELQut protease recognition sequence (all of which are described supra). However, these sequences, and the specific protease used to mature the propeptide fusion, do not necessarily need to be identical for all intended cleavage sites in a propeptide fusion.

Signal peptides may also be introduced into propeptide fusions described herein, as required, to enable secretion and recovery, as described, e.g., in U.S. Pat. No. 8,865,186 to Ichtchenko and Band, which is hereby incorporated by reference in its entirety. In one embodiment, a signal peptide is positioned upstream of an APT, as illustrated in FIGS. 9A-L, 11A-L, and 17A-L. According to one specific embodiment, the signal peptide is a DNA sequence coding the gp64 signal peptide and a hexahistidine affinity tag

```
                                        (SEQ ID NO: 62)
MPMLSAIVLYVLLAAAAHSAFAAMVHHHHHHSAS.
```

Propeptide fusions described herein may further include a cargo attachment peptide sequence to enable site-specific attachment of cargo (i.e., a cargo attachment peptide sequence or cargo attachment peptide). Cargo (e.g., therapeutic drug substances, lipid moieties, marker molecules, targeting agents, etc.) may be attached to the fusion proteins described herein. Such attachment is described, e.g., in U.S. Patent Application Publication No. 2011/0206616 to Ichtchenko and Band, which is hereby incorporated by reference in its entirety.

According to one embodiment, the cargo attachment peptide is positioned upstream of the light chain region (either downstream or upstream of the single chain antibody) and is separated from the N-terminus of the light chain region (or the N-terminus of the single chain antibody) by an amino acid spacer sequence. This and other amino acid spacer (or linker) sequences described herein may comprise at least 2, 3, 4, 5, 6, 7, 8, 9, 10, 11, 12, 13, 14, 15, 16, 17, 18, 19, 20, 21-25, 26-30, 31-35, or 36-40, or more, amino acid residues. The amino acid spacer (or linker) sequence may serve to preserve and protect conformational independence of the cargo attachment peptide and /or the fusion protein and to not interfere with antibody activity. An exemplary amino acid spacer (or linker) sequence is the 7 amino acid spacer ARGGASG (SEQ ID NO:63). In considering suitable sequences for linkers, it may be desirable to avoid creating any new restriction sites or other instabilities in the expression system. Suitable linkers may also be designed to keep the single chain antibody moiety independent of the rest of the polypeptide structure to enable antigen binding. Several and various specific spacers (or linkers) are illustrated in the figures.

One example of a suitable cargo attachment peptide is the S6 sequence, GDSLSWLLRLLN (SEQ ID NO:64). The S6 sequence enables site specific attachment of cargo using Sfp phosphopantetheinyl transferase from *B. subtilis*, which targets the $S_3$ amino acid of the S6 sequence as a substrate (Zhou et al., "Genetically Encoded Short Peptide Tags for Orthogonal Protein Labeling by Sfp and AcpS Phosphopantetheinyl Transferases," *ACS Chem. Biol.* 2(5):337-346 (2007), which is hereby incorporated by reference in its entirety). Other suitable cargo attachment peptides are known and can also be used.

In one embodiment, propeptide fusions described herein have light and heavy chains that are not truncated, as discussed supra.

Another aspect of the present invention relates to an isolated nucleic acid molecule encoding the propeptide fusions described herein.

The wild-type BoNT/A nucleic acid molecule has a nucleotide sequence as set forth in GenBank as Accession No. EF506573.1 (SEQ ID NO:65), as follows:

```
atgccatttg ttaataaaca atttaattat aaagatcctg taaatggtgt        50

tgatattgct tatataaaaa ttccaaatgc aggacaaatg caaccagtaa       100

aagcttttaa aattcataat aaaatatggg ttattccaga aagagataca       150

tttacaaatc ctgaagaagg agatttaaat ccaccaccag aagcaaaaca       200
```

-continued

```
agttccagtt tcatattatg attcaacata tttaagtaca gataatgaaa      250
aagataatta tttaaaggga gttacaaaat tatttgagag aatttattca      300
actgatcttg gaagaatgtt gttaacatca atagtaaggg gaataccatt      350
ttggggtgga agtacaatag atacagaatt aaaagttatt gatactaatt      400
gtattaatgt gatacaacca gatggtagtt atagatcaga agaacttaat      450
ctagtaataa taggaccctc agctgatatt atacagtttg aatgtaaaag      500
ctttggacat gaagttttga atcttacgcg aaatggttat ggctctactc      550
aatacattag atttagccca gattttacat ttggttttga ggagtcactt      600
gaagttgata caaatcctct tttaggtgca ggcaaatttg ctacagatcc      650
agcagtaaca ttagcacatg aacttataca tgctggacat agattatatg      700
gaatagcaat taatccaaat agggttttta aagtaaatac taatgcctat      750
tatgaaatga gtgggttaga agtaagcttt gaggaactta gaacatttgg      800
gggacatgat gcaaagttta tagatagttt acaggaaaac gaatttcgtc      850
tatattatta taataagttt aaagatatag caagtacact taataaagct      900
aaatcaatag taggtactac tgcttcatta cagtatatga aaaatgtttt      950
taaagagaaa tatctcctat ctgaagatac atctggaaaa ttttcggtag     1000
ataaattaaa atttgataag ttatacaaaa tgttaacaga gatttacaca     1050
gaggataatt ttgttaagtt ttttaaagta cttaacagaa aaacatattt     1100
gaattttgat aaagccgtat ttaagataaa tatagtacct aaggtaaatt     1150
acacaatata tgatggattt aatttaagaa atacaaattt agcagcaaac     1200
tttaatggtc aaaatacaga aattaataat atgaatttta ctaaactaaa     1250
aaattttact ggattgtttg aattttataa gttgctatgt gtaagaggga     1300
taataacttc taaaactaaa tcattagata aaggatacaa taaggcatta     1350
aatgatttat gtatcaaagt taataattgg gacttgtttt ttagtccttc     1400
agaagataat tttactaatg atctaaataa aggagaagaa attacatctg     1450
atactaatat agaagcagca gaagaaaata ttagtttaga tttaatacaa     1500
caatattatt taacctttaa ttttgataat gaacctgaaa atatttcaat     1550
agaaaatctt tcaagtgaca ttataggcca attagaactt atgcctaata     1600
tagaaagatt tcctaatgga aaaaagtatg agttagataa atatactatg     1650
ttccattatc ttcgtgctca agaatttgaa catggtaaat ctaggattgc     1700
tttaacaaat tctgttaacg aagcattatt aaatcctagt cgtgtttata     1750
catttttttc ttcagactat gtaaagaaag ttaataaagc tacggaggca     1800
gctatgtttt taggctgggt agaacaatta gtatatgatt ttaccgatga     1850
aactagcgaa gtaagtacta cggataaaat tgcggatata actataatta     1900
ttccatatat aggacctgct ttaaatatag gtaatatgtt atataaagat     1950
gattttgtag gtgctttaat attttcagga gctgttattc tgttagaatt     2000
tataccagag attgcaatac ctgtattagg tacttttgca cttgtatcat     2050
atattgcgaa taaggttcta accgttcaaa caatagataa tgctttaagt     2100
aaaagaaatg aaaaatggga tgaggtctat aaatatatag taacaaattg     2150
gttagcaaag gttaatacac agattgatct aataagaaaa aaaatgaaag     2200
```

-continued

```
aagctttaga aaatcaagca gaagcaacaa aggctataat aaactatcag      2250
tataatcaat atactgagga agagaaaaat aatattaatt ttaatattga      2300
tgatttaagt tcgaaactta atgagtctat aaataaagct atgattaata      2350
taaataaatt tttgaatcaa tgctctgttt catatttaat gaattctatg      2400
atcccttatg gtgttaaacg gttagaagat tttgatgcta gtcttaaaga      2450
tgcattatta aagtatatat atgataatag aggaacttta attggtcaag      2500
tagatagatt aaaagataaa gttaataata cacttagtac agatatacct      2550
tttcagcttt ccaaatacgt agataatcaa agattattat ctacatttac      2600
tgaatatatt aagaatatta ttaatacttc tatattgaat ttaagatatg      2650
aaagtaatca tttaatagac ttatctaggt atgcatcaaa aataaatatt      2700
ggtagtaaag taaattttga tccaatagat aaaaatcaaa ttcaattatt      2750
taatttagaa agtagtaaaa ttgaggtaat tttaaaaaat gctattgtat      2800
ataatagtat gtatgaaaat tttagtacta gcttttggat aagaattcct      2850
aagtatttta acagtataag tctaaataat gaatatacaa taataaattg      2900
tatggaaaat aattcaggat ggaaagtatc acttaattat ggtgaaataa      2950
tctggacttt acaggatact caggaaataa aacaaagagt agtttttaaa      3000
tacagtcaaa tgattaatat atcagattat ataaacagat ggatttttgt      3050
aactatcact aataatagat taaataactc taaaatttat ataaatggaa      3100
gattaataga tcaaaaacca atttcaaatt taggtaatat tcatgctagt      3150
aataatataa tgtttaaatt agatggttgt agagatacac atagatatat      3200
ttggataaaa tattttaatc tttttgataa ggaattaaat gaaaaagaaa      3250
tcaaagattt atatgataat caatcaaatt caggtatttt aaaagacttt      3300
tggggtgatt atttacaata tgataaacca tactatatgt taaatttata      3350
tgatccaaat aaatatgtcg atgtaaataa tgtaggtatt agaggttata      3400
tgtatcttaa agggcctaga ggtagcgtaa tgactacaaa catttattta      3450
aattcaagtt tgtatagggg gacaaaattt attataaaaa aatatgcttc      3500
tggaaataaa gataatattg ttagaaataa tgatcgtgta tatattaatg      3550
tagtagttaa aaataaagaa tataggttag ctactaatgc atcacaggca      3600
ggcgtagaaa aaatactaag tgcattagaa atacctgatg taggaaatct      3650
aagtcaagta gtagtaatga agtcaaaaaa tgatcaagga ataacaaata      3700
aatgcaaaat gaatttacaa gataataatg ggaatgatat aggctttata      3750
ggatttcatc agtttaataa tatagctaaa ctagtagcaa gtaattggta      3800
taatagacaa atagaaagat ctagtaggac tttgggttgc tcatgggaat      3850
ttattcctgt agatgatgga tggggagaaa ggccactgta a
```

In one embodiment, the isolated nucleic acid molecule of the present invention is modified from this wild-type BoNT/A nucleic acid molecule, according to the genetic code, to encode propeptide fusions described herein. Non-limiting examples of such modifications include optimization with respect to codon usage bias of the host used for production of polypeptides, exclusion of unwanted genetic features that affect transcription and translation, and introduction or exclusion of restriction sites. Thus, nucleic acid molecules of the present invention may have a nucleic acid sequence quite similar to the wild-type BoNT/A nucleic acid molecule, at least with respect to the Clostridial neurotoxin light chain region and Clostridial neurotoxin heavy chain region. For example, the combination of the Clostridial neurotoxin light chain region and the Clostridial neurotoxin heavy chain region may be at least about 80%, 81%, 82%, 83%, 84%, 85%, 86%, 87%, 88%, 89%, 90%, 91%, 92%, 93%, 94%, 95%, or more identical to the nucleic acid molecule of SEQ ID NO:65 or any other Clostridial neurotoxin molecule, including BoNT/B of GenBank Accession No. X71343.1 (SEQ ID NO:66), as follows:

gataataata atataataat gatgacaata tacctaaagc
tgcacattta tggacattaa aagggatata aacttaaaat
aaggaggaga atatttatgc cagttacaat aaataatttt
aattataatg atcctattga taatgacaat attattatga
tggaacctcc atttgcaagg ggtacgggga gatattataa
agcttttaaa atcacagatc gtatttggat aatacccgaa
agatatactt ttggatataa acctgaggat tttaataaaa
gttccggtat ttttaataga gatgtttgtg aatattatga
tccagattac ttaaatacca atgataaaaa gaatatattt
ttccaaacat tgatcaagtt atttaataga atcaaatcaa
aaccattggg tgaaaagtta ttagagatga ttataaatgg
tataccttat cttggagata gacgtgttcc actcgaagag
tttaacacaa acattgctag tgtaactgtt aataaattaa
ttagtaatcc aggagaagtg gagcgaaaaa aaggtatttt
cgcaaattta ataatatttg gacctgggcc agttttaaat
gaaaatgaga ctatagatat aggtatacaa aatcattttg
catcaaggga aggctttggg ggtataatgc aaatgaaatt
ttgtccagaa tatgtaagcg tatttaataa tgttcaagaa
aacaaaggcg caagtatatt taatagacgt ggatattttt
cagatccagc cttgatatta atgcatgaac ttatacatgt
tttgcatgga ttatatggca ttaaagtaga tgatttacca
attgtaccaa atgaaaaaaa atttttatg caatctacag
atactataca ggcagaagaa ctatatacat ttggaggaca
agatcccagc atcatatctc cttctacaga taaaagtatc
tatgataaag ttttgcaaaa ttttaggggg atagttgata
gacttaacaa ggttttagtt tgcatatcag atcctaacat
taacattaat atatataaaa ataaatttaa agataaatat
aaattcgttg aagattctga aggaaaatat agtatagatg
tagaaagttt caataaatta tataaaagct taatgttagg
ttttacagaa attaatatag cagaaaatta taaaataaaa
actagagctt cttattttag tgattcctta ccaccagtaa
aaataaaaaa tttattagat aatgaaatct atactataga
ggaagggttt aatatatctg ataaaaatat gggaaaagaa
tataggggtc agaataaagc tataaataaa caagcttatg
aagaaatcag caaggagcat ttggctgtat ataagataca
aatgtgtaaa agtgttaaag ttccaggaat atgtattgat
gtcgataatg aaaatttgtt ctttatagct gataaaaata
gtttttcaga tgatttatct aaaaatgaaa gagtagaata
taatacacag aataattata taggaaatga ctttcctata
aatgaattaa ttttagatac tgatttaata agtaaaatag
aattaccaag tgaaaataca gaatcactta ctgattttaa -continued tgtagatgtt ccagtatatg aaaaacaacc cgctataaaa
aaagtttta cagatgaaaa taccatcttt caatatttat
actctcagac atttcctcta aatataagag atataagttt
aacatcttca tttgatgatg cattattagt ttctagcaaa
gtttattcat ttttttctat ggattatatt aaaactgcta
ataaagtagt agaagcagga ttatttgcag gttgggtgaa
acagatagta gatgattttg taatcgaagc taataaaagc
agtactatgg ataaaattgc agatatatct ctaattgttc
cttatatagg attagcttta aatgtaggag atgaaacagc
taaaggaaat tttgaaagtg cttttgagat tgcaggatcc
agtattttac tagaatttat accagaactt ttaatacctg
tagttggagt ctttttatta gaatcatata ttgacaataa
aaataaaatt attaaaacaa tagataatgc tttaactaaa
agagtggaaa aatggattga tatgtacgga ttaatagtag
cgcaatggct ctcaacagtt aatactcaat tttatacaat
aaaagaggga atgtataagg ctttaaatta tcaagcacaa
gcattggaag aaataataaa atacaaatat aatatatatt
ctgaagagga aaagtcaaat attaacatca attttaatga
tataaattct aaacttaatg atggtattaa ccaagctatg
gataatataa atgattttat aaatgaatgt tctgtatcat
atttaatgaa aaaaatgatt ccattagctg taaaaaaatt
actagacttt gataatactc tcaaaaaaaa tttattaaat
tatatagatg aaaataaatt atatttaatt ggaagtgtag
aagatgaaaa atcaaaagta gataaatact tgaaaaccat
tataccattt gatctttcaa cgtattctaa tattgaaata
ctaataaaaa tatttaataa atataatagc gaaattttaa
ataatattat cttaaattta agatatagag ataataattt
aatagattta tcaggatatg gagcaaaggt agaggtatat
gatggggtca agcttaatga taaaaatcaa tttaaattaa
ctagttcagc agatagtaag attagagtca ctcaaaatca
gaatattata tttaatagta tgttccttga ttttagcgtt
agcttttgga taaggatacc taaatatagg aatgatgata
tacaaaatta tattcataat gaatatacga taattaattg
tatgaaaaat aattcaggct ggaaaatatc tattaggggt
aataggataa tatggacctt aattgatata aatggaaaaa
ccaaatcagt attttttgaa tataacataa gagaagatat
atcagagtat ataaatagat ggtttttgt aactattact
aataatttgg ataatgctaa aatttatatt aatggcacgt
tagaatcaaa tatggatatt aaagatatag gagaagttat
tgttaatggt gaaataacat ttaaattaga tggtgatgta -continued

```
gatagaacac aatttatttg gatgaaatat tttagtattt
ttaatacgca attaaatcaa tcaaatatta aagagatata
taaaattcaa tcatatagcg aatacttaaa agatttttgg
ggaaatcctt taatgtataa taaagaatat tatatgttta
atgcggggaa taaaaattca tatattaaac tagtgaaaga
ttcatctgta ggtgaaatat taatacgtag caaatataat
cagaattcca attatataaa ttatagaaat ttatatattg
gagaaaaatt tattataaga agagagtcaa attctcaatc
tataaatgat gatatagtta gaaaagaaga ttatatacat
ctagatttgg tacttcacca tgaagagtgg agagtatatg
cctataaata ttttaaggaa caggaagaaa aattgttttt
```

-continued

```
atctattata agtgattcta atgaatttta taagactata
gaaataaaag aatatgatga acagccatca tatagttgtc
agttgctttt taaaaaagat gaagaaagta ctgatgatat
aggattgatt ggtattcatc gtttctacga atctggagtt
ttacgtaaaa agtataaaga ttatttttgt ataagtaaat
ggtacttaaa agaggtaaaa aggaaaccat ataagtcaaa
tttgggatgt aattggcagt ttattcctaa agatgaaggg
tggactgaat aatataacta tatgctcagc aaacctattt
tatataagaa aagtttaagt ttataaaatc ttaagtttaa
ggatgtagct a
```

BoNT/C of GenBank Accession No. AB745658.1 (SEQ ID NO:67), as follows:

```
tatgatatgt aatgacaata acaaggtgcc taaaggtgca catttgtgga      50
tattagaaag ttaggagatg ttagtattat gccaataaca attaacaact     100
ttaattattc agatcctgtt gataataaaa atattttata tttagatact     150
catttaaata cactagctaa tgagcctgaa aaagcctttc gcattacagg     200
aaatatatgg gtaatacctg atagattttc aagaaattct aatccaaatt     250
taaataaacc tcctcgagtt acaagcccta aaagtggtta ttatgatcct     300
aattatttga gtactgattc tgacaaagat acatttttaa aagaaattat     350
aaagttattt aaaagaatta attctagaga aataggagaa gaattaatat     400
atagactttc gacagatata ccctttcctg ggaataacaa tactccaatt     450
aatacttttg attttgatgt agattttaac agtgttgatg ttaaaactag     500
acaaggtaac aactgggtta aaactggtag cataaatcct agtgttataa     550
taactggacc tagagaaaac attatagatc cagaaacttc tacgtttaaa     600
ttaactaaca atacttttgc ggcacaagaa ggatttggtg ctttatcaat     650
aatttcaata tcacctagat ttatgctaac atatagtaat gcaactaatg     700
atgtaggaga gggtagattt tctaagtctg aattttgcat ggatccaata     750
ctaattttaa tgcatgaact taatcatgca atgcataatt tatatggaat     800
agctatacca aatgatcaaa caatttcatc tgtaactagt aatatttttt     850
attctcaata taatgtgaaa ttagagtatg cagaaatata tgcatttgga     900
ggtccaacta tagaccttat tcctaaaagt gcaaggaaat attttgagga     950
aaaggcattg gattattata gatctatagc taaaagactt aatagtataa    1000
ctactgcaaa tccttcaagc tttaataaat atatagggga atataaacag    1050
aaacttatta gaaagtatag attcgtagta gaatcttcag gtgaagttac    1100
agtaaatcgt aataagtttg ttgagttata taatgaactt acacaaatat    1150
ttacagaatt taactacgct aaaatatata atgtacaaaa taggaaaata    1200
tatctttcaa atgtatatac tccggttacg gcaaatatat tagacgataa    1250
tgtttatgat atacaaaatg gatttaatat acctaaaagt aatttaaatg    1300
tactatttat gggtcaaaat ttatctcgaa atccagcatt aagaaaagtc    1350
aatcctgaaa atatgcttta tttatttaca aaattttgtc ataaagcaat    1400
```

-continued

```
agatggtaga tcattatata ataaaacatt agattgtaga gagcttttag      1450
ttaaaaatac tgacttaccc tttataggtg atattagtga tgttaaaact      1500
gatatatttt taagaaaaga tattaatgaa gaaactgaag ttatatacta      1550
tccggacaat gtttcagtag atcaagttat tctcagtaag aatacctcag      1600
aacatggaca actagattta ttatacccta gtattgacag tgagagtgaa      1650
atattaccag ggagaatca agtcttttat gataatagaa ctcaaaatgt       1700
tgattatttg aattcttatt attacctaga atctcaaaaa ctaagtgata      1750
atgttgaaga ttttactttt acgagatcaa ttgaggaggc tttggataat      1800
agtgcaaaag tatatactta ctttcctaca ctagctaata aagtaaatgc      1850
gggtgttcaa ggtggtttat ttttaatgtg ggcaaatgat gtagttgaag      1900
attttactac aaatattcta agaaaagata cattagataa aatatcagat      1950
gtatcagcta ttattcccta tataggaccc gcattaaata taagtaattc      2000
tgtaagaaga ggaaatttta ctgaagcatt tgcagttact ggtgtaacta      2050
ttttattaga agcatttcct gaatttacaa tacctgcact tggtgcattt      2100
gtgatttata gtaaggttca agaaagaaac gagattatta aaactataga      2150
taattgttta gaacaaagga ttaagagatg gaaagattca tatgaatgga      2200
tgatgggaac gtggttatcc aggattatta ctcaatttaa taatataagt      2250
tatcaaatgt atgattcttt aaattatcag gcaggtgcaa tcaaagctaa      2300
aatagattta gaatataaaa aatattcagg aagtgataaa gaaaatataa      2350
aaagtcaagt tgaaaattta aaaaatagtt tagatgtaaa aatttcggaa      2400
gcaatgaata atataaataa atttatacga gaatgttccg taacatattt      2450
atttaaaaat atgttaccta aagtaattga tgaattaaat gagtttgatc      2500
gaaatactaa agcaaaatta attaatctta tagatagtca taatattatt      2550
ctagttggtg aagtagataa attaaaagca aaagtaaata atagctttca      2600
aaatacaata ccctttaata tttttcata tactaataat tctttattaa       2650
aagatataat taatgaatat ttcaataata ttaatgattc aaaaattttg      2700
agcctacaaa acagaaaaaa tactttagtg gatacatcag gatataatgc      2750
agaagtgagt gaagaaggcg atgttcagct taatccaata tttccatttg      2800
actttaaatt aggtagttca ggggaggata gaggtaaagt tatagtaacc      2850
cagaatgaaa atattgtata taattctatg tatgaaagtt ttagcattag      2900
tttttggatt agaataaata aatgggtaag taatttacct ggatatacta      2950
taattgatag tgttaaaaat aactcaggtt ggagtatagg tattattagt      3000
aatttttag tatttacttt aaaacaaaat gaagatagtg aacaaagtat       3050
aaattttagt tatgatatat caaataatgc tcctggatac aataaatggt      3100
tttttgtaac tgttactaac aatatgatgg gaaatatgaa gatttatata      3150
aatggaaaat taatagatac tataaaagtt aaagaactaa ctggaattaa      3200
ttttagcaaa actataacat ttgaaataaa taaaattcca gataccggtt      3250
tgattacttc agattctgat aacatcaata tgtggataag agatttttat      3300
atatttgcta aagaattaga tggtaaagat attaatatat tatttaatag      3350
cttgcaatat actaatgttg taaaagatta ttggggaaat gatttaagat      3400
```

-continued

```
ataataaaga atattatatg gttaatatag attatttaaa tagatatatg       3450
tatgcgaact cacgacaaat tgtttttaat acacgtagaa ataataatga       3500
cttcaatgaa ggatataaaa ttataataaa aagaatcaga ggaaatacaa       3550
atgatactag agtacgagga ggagatattt tatattttga tatgacaatt       3600
aataacaaag catataattt gtttatgaag aatgaaacta tgtatgcaga       3650
taatcatagt actgaagata tatatgctat aggtttaaga gaacaaacaa       3700
aggatataaa tgataatatt atatttcaaa tacaaccaat gaataatact       3750
tattattacg catctcaaat atttaaatca aattttaatg gagaaaatat       3800
ttctggaata tgttcaatag gtacttatcg ttttagactt ggaggtgatt       3850
ggtatagaca caattatttg gtgcctactg tgaagcaagg aaattatgct       3900
tcattattag aatcaacatc aactcattgg ggttttgtac ctgtaagtga       3950
ataaataatg attaataata taaattatgt taaatatttt aata             3994
```

BoNT/D of GenBank Accession No. X54254.1 (SEQ ID NO: 68), as follows:

```
AAGGTGCACA CTTGTGGATA TTAGAAAGTT AGGAGATGTT AGTATTATGA         50
CATGGCCAGT AAAAGATTTT AATTATAGTG ATCCTGTTAA TGACAATGAT        100
ATATTATATT TAAGAATACC ACAAAATAAG TTAATTACTA CACCTGTAAA        150
AGCTTTTATG ATTACTCAAA ATATTTGGGT AATACCAGAA AGATTTTCAT        200
CAGATACTAA TCCAAGTTTA AGTAAACCGC CCAGACCTAC TTCAAAGTAT        250
CAAAGTTATT ATGATCCTAG TTATTTATCT ACTGATGAAC AAAAAGATAC        300
ATTTTTAAAA GGGATTATAA AATTATTTAA AAGAATTAAT GAAAGAGATA        350
TAGGAAAAAA ATTAATAAAT TATTTAGTAG TTGGTTCACC TTTTATGGGA        400
GATTCAAGTA CGCCTGAAGA TACATTTGAT TTTACACGTC ATACTACTAA        450
TATTGCAGTT GAAAAGTTTG AAAATGGTAG TTGGAAAGTA ACAAATATTA        500
TAACACCAAG TGTATTGATA TTTGGACCAC TTCCTAATAT ATTAGACTAT        550
ACAGCATCCC TTACATTGCA AGGACAACAA TCAAATCCAT CATTTGAAGG        600
GTTTGGAACA TTATCTATAC TAAAAGTAGC ACCTGAATTT TTGTTAACAT        650
TTAGTGATGT AACATCTAAT CAAAGTTCAG CTGTATTAGG CAAATCTATA        700
TTTTGTATGG ATCCAGTAAT AGCTTTAATG CATGAGTTAA CACATTCTTT        750
GCATCAATTA TATGGAATAA ATATACCATC TGATAAAAGG ATTCGTCCAC        800
AAGTTAGCGA GGGATTTTTC TCTCAAGATG GACCCAACGT ACAATTTGAG        850
GAATTATATA CATTTGGAGG ATTAGATGTT GAAATAATAC CTCAAATTGA        900
AAGATCACAA TTAAGAGAAA AAGCATTAGG TCACTATAAA GATATAGCGA        950
AAAGACTTAA TAATATTAAT AAAACTATTC CTTCTAGTTG GATTAGTAAT       1000
ATAGATAAAT ATAAAAAAAT ATTTTCTGAA AAGTATAATT TTGATAAAGA       1050
TAATACAGGA AATTTTGTTG TAAATATTGA TAAATTCAAT AGCTTATATT       1100
CAGACTTGAC TAATGTTATG TCAGAAGTTG TTTATTCTTC GCAATATAAT       1150
GTTAAAAACA GGACTCATTA TTTTTCAAGG CATTATCTAC CTGTATTTGC       1200
AAATATATTA GATGATAATA TTTATACTAT AAGAGATGGT TTTAATTTAA       1250
CAAATAAAGG TTTTAATATA GAAAATTCGG GTCAGAATAT AGAAAGGAAT       1300
```

-continued

```
CCTGCACTAC AAAAGCTTAG TTCAGAAAGT GTAGTAGATT TATTTACAAA      1350

AGTATGTTTA AGATTAACAA AAAATAGTAG AGATGATTCA ACATGTATTA      1400

AGATTAACAA TAATAGATTA CCTTATGTAG CTGATAAAGA TAGCATTTCA      1450

CAAGAAATAT TTGAAAATAA AATTATTACA GATGAGACTA ATGTACAAAA      1500

TTATTCAGAT AAATTTTCAT TAGATGAATC TATTTTAGAT GGGCAAGTTC      1550

CTATTAATCC TGAAATAGTA GATCCACTAT TACCCAATGT TAATATGGAA      1600

CCTTTAAATC TTCCAGGTGA AGAAATAGTA TTTTATGATG ATATTACTAA      1650

ATATGTTGAT TATTTAAATT CTTATTATTA TTTGGAATCT CAAAAATTAA      1700

GTAATAATGT TGAAAATATT ACTCTTACAA CTTCAGTTGA AGAAGCATTA      1750

GGTTATAGCA ATAAGATATA CACATTTTTA CCTAGCTTAG CTGAAAAAGT      1800

GAATAAAGGT GTTCAAGCAG GTTTATTCTT AAATTGGGCG AATGAAGTAG      1850

TTGAGGATTT TACTACAAAT ATTATGAAGA AAGATACATT GGATAAAATA      1900

TCAGATGTAT CAGTAATAAT TCCATATATA GGACCTGCCT TAAATATAGG      1950

AAATTCAGCA TTAAGGGGAA ATTTTAATCA AGCATTTGCA ACAGCTGGTG      2000

TAGCTTTTTT ATTAGAGGGA TTTCCAGAGT TTACTATACC TGCACTCGGT      2050

GTATTTACCT TTTATAGTTC TATTCAAGAA AGAGAGAAAA TTATTAAAAC      2100

TATAGAAAAT TGTTTGGAAC AAAGAGTTAA GAGATGGAAA GATTCATATC      2150

AATGGATGGT ATCAAATTGG TTGTCAAGAA TTACTACTCA ATTTAATCAT      2200

ATAAATTATC AAATGTATGA TTCTTTAAGT TATCAGGCAG ATGCAATCAA      2250

AGCTAAAATA GATTTAGAAT ATAAGATATA CTCAGGAAGT GATAAAGAAA      2300

ATATAAAAAG TCAAGTTGAA AATTTAAAAA ATAGTTTAGA TGTAAAAATT      2350

TCGGAAGCAA TGAATAATAT AAATAAATTT ATACGAGAAT GTTCTGTAAC      2400

ATACTTATTT AAAAATATGC TCCCTAAAGT AATTGACGAA TTAAATAAGT      2450

TTGATTTAAG AACTAAAACA GAATTAATTA ATCTTATAGA TAGTCATAAT      2500

ATTATTCTAG TTGGTGAAGT AGATAGATTA AAAGCAAAAG TAAATGAGAG      2550

TTTTGAAAAT ACAATGCCTT TTAATATTTT TTCATATACT AATAATTCTT      2600

TATTAAAAGA TATAATTAAT GAATATTTCA ATAGTATTAA TGATTCAAAA      2650

ATTTTGAGCT TACAAAACAA AAAAAATGCT TTAGTGGATA CATCAGGATA      2700

TAATGCAGAA GTGAGGGTAG GAGATAATGT TCAACTTAAT ACGATATATA      2750

CAAATGACTT TAAATTAAGT AGTTCAGGAG ATAAAATTAT AGTAAATTTA      2800

AATAATAATA TTTTATATAG CGCTATTTAT GAGAACTCTA GTGTTAGTTT      2850

TTGGATTAAG ATATCTAAAG ATTTAACTAA TTCTCATAAT GAATATACAA      2900

TAATTAACAG TATAGAACAA AATTCTGGGT GGAAATTATG TATTAGGAAT      2950

GGCAATATAG AATGGATTTT ACAAGATGTT AATAGAAAGT ATAAAAGTTT      3000

AATTTTTGAT TATAGTGAAT CATTAAGTCA TACAGGATAT ACAAATAAAT      3050

GGTTTTTTGT TACTATAACT AATAATATAA TGGGGTATAT GAAACTTTAT      3100

ATAAATGGAG AATTAAAGCA GAGTCAAAAA ATTGAAGATT TAGATGAGGT      3150

TAAGTTAGAT AAAACCATAG TATTTGGAAT AGATGAGAAT ATAGATGAGA      3200

ATCAGATGCT TTGGATTAGA GATTTTAATA TTTTTTCTAA AGAATTAAGT      3250

AATGAAGATA TTAATATTGT ATATGAGGGA CAAATATTAA GAAATGTTAT      3300
```

-continued

```
TAAAGATTAT TGGGGAAATC CTTTGAAGTT TGATACAGAA TATTATATTA      3350
TTAATGATAA TTATATAGAT AGGTATATAG CACCTGAAAG TAATGTACTT      3400
GTACTTGTTC AGTATCCAGA TAGATCTAAA TTATATACTG GAAATCCTAT      3450
TACTATTAAA TCAGTATCTG ATAAGAATCC TTATAGTAGA ATTTTAAATG      3500
GAGATAATAT AATTCTTCAT ATGTTATATA ATAGTAGGAA ATATATGATA      3550
ATAAGAGATA CTGATACAAT ATATGCAACA CAAGGAGGAG AGTGTTCACA      3600
AAATTGTGTA TATGCATTAA AATTACAGAG TAATTTAGGT AATTATGGTA      3650
TAGGTATATT TAGTATAAAA AATATTGTAT CTAAAAATAA ATATTGTAGT      3700
CAAATTTTCT CTAGTTTTAG GGAAAATACA ATGCTTCTAG CAGATATATA      3750
TAAACCTTGG AGATTTTCTT TTAAAAATGC ATACACGCCA GTTGCAGTAA      3800
CTAATTATGA AACAAAACTA TTATCAACTT CATCTTTTTG GAAATTTATT      3850
TCTAGGGATC CAGGATGGGT AGAGTAATAC AATAAAAATT TAATATAAAC      3900
TATTAAATTA TATTACAAGT TTTAGAAATT TATCGTATAA AATGTTGAAT      3950
TC                                                          3952
```

BoNT/E of GenBank Accession No. GQ244314.1 (SEQ ID NO:69), as follows:

```
ATGCCAAAAA TTAATAGTTT TAATTATAAT GATCCTGTTA ATGATAGAAC        50
AATTTTATAT ATTAAACCAG GCGGTTGTCA AGAATTTTAT AAATCATTTA       100
ATATTATGAA AAATATTTGG ATAATTCCAG AGAGAAATGT AATTGGTACA       150
ACCCCCCAAG ATTTTCATCC GCCTACTTCA TTAAAAAATG GAGATAGTAG       200
TTATTATGAC CCTAATTATT TACAAAGTGA TGAAGAAAAG GATAGATTTT       250
TAAAAATAGT CACAAAAATA TTTAATAGAA TAAATAATAA TCTTTCAGGA       300
GGGATTTTAT TAGAAGAACT GTCAAAAGCT AATCCATATT TAGGGAATGA       350
TAATACTCCA GATAATCAAT TCCATATTGG TGATGCATCA GCAGTTGAGA       400
TTAAATTCTC AAATGGTAGC CAAGACATAC TATTACCTAA TGTTATTATA       450
ATGGGAGCAG AGCCTGATTT ATTTGAAACT AACAGTTCCA ATATTTCTCT       500
AAGAAATAAT TATATGCCAA GCAATCACGG TTTTGGATCA ATAGCTATAG       550
TAACATTCTC ACCTGAATAT TCTTTTAGAT TTAATGATAA TAGTATGAAT       600
GAATTTATTC AAGATCCTGC TCTTACATTA ATGCATGAAT TAATACATTC       650
ATTACATGGA CTATATGGGG CTAAAGGGAT TACTACAAAG TATACTATAA       700
CACAAAAACA AAATCCCCTA ATAACAAATA TAAGAGGTAC AAATATTGAA       750
GAATTCTTAA CTTTTGGAGG TACTGATTTA AACATTATTA CTAGTGCTCA       800
GTCCAATGAT ATCTATACTA ATCTTCTAGC TGATTATAAA AAAATAGCGT       850
CTAAACTTAG CAAAGTACAA GTATCTAATC CACTACTTAA TCCTTATAAA       900
GATGTTTTTG AAGCAAAGTA TGGATTAGAT AAAGATGCTA GCGGAATTTA       950
TTCGGTAAAT ATAAACAAAT TTAATGATAT TTTTAAAAAA TTATACAGCT      1000
TTACGGAATT TGATTTAGCA ACTAAATTTC AAGTTAAATG TAGGCAAACT      1050
TATATTGGAC AGTATAAATA CTTCAAACTT TCAAACTTGT TAAATGATTC      1100
TATTTATAAT ATATCAGAAG GCTATAATAT AAATAATTTA AAGGTAAATT      1150
TTAGAGGACA GAATGCAAAT TTAAATCCTA GAATTATTAC ACCAATTACA      1200
```

-continued

GGTAGAGGAC TAGTAAAAAA AATCATTAGA TTTTGTAAAA ATATTGTTTC 1250

TGTAAAAGGC ATAAGGAAAT CAATATGTAT CGAAATAAAT AATGGTGAGT 1300

TATTTTTTGT GGCTTCCGAG AATAGTTATA ATGATGATAA TATAAATACT 1350

CCTAAAGAAA TTGACGATAC AGTAACTTCA AATAATAATT ATGAAAATGA 1400

TTTAGATCAG GTTATTTTAA ATTTTAATAG TGAATCAGCA CCTGGACTTT 1450

CAGATGAAAA ATTAAATTTA ACTATCCAAA ATGATGCTTA TATACCAAAA 1500

TATGATTCTA ATGGAACAAG TGATATAGAA CAACATGATG TTAATGAACT 1550

TAATGTATTT TTCTATTTAG ATGCACAGAA AGTGCCCGAA GGTGAAAATA 1600

ATGTCAATCT CACCTCTTCA ATTGATACAG CATTATTAGA ACAACCTAAA 1650

ATATATACAT TTTTTTCATC AGAATTTATT AATAATGTCA ATAAACCTGT 1700

GCAAGCAGCA TTATTTGTAA GCTGGATACA ACAAGTGTTA GTAGATTTTA 1750

CTACTGAAGC TAACCAAAAA AGTACTGTTG ATAAAATTGC AGATATTTCT 1800

ATAGTTGTTC CATATATAGG TCTTGCTTTA AATATAGGAA ATGAAGCACA 1850

AAAAGGAAAT TTTAAAGATG CACTTGAATT ATTAGGAGCA GGTATTTTAT 1900

TAGAATTTGA ACCCGAGCTT TTAATTCCTA CAATTTTAGT ATTCACGATA 1950

AAATCTTTTT TAGGTTCATC TGATAATAAA AATAAAGTTA TTAAAGCAAT 2000

AAATAATGCA TTGAAAGAAA GAGATGAAAA ATGGAAAGAA GTATATAGTT 2050

TTATAGTATC GAATTGGATG ACTAAAATTA ATACACAATT TAATAAAAGA 2100

AAAGAACAAA TGTATCAAGC TTTACAAAAT CAAGTAAATG CAATTAAAAC 2150

AATAATAGAA TCTAAGTATA ATAGTTATAC TTTAGAGGAA AAAAATGAGC 2200

TTACAAATAA ATATGATATT AAGCAAATAG AAAATGAACT TAATCAAAAG 2250

GTTTCTATAG CAATGAATAA TATAGACAGG TTCTTAACTG AAAGTTCTAT 2300

ATCCTATTTA ATGAAATTAA TAAATGAAGT AAAAATTAAT AAATTAAGAG 2350

AATATGATGA GAATGTCAAA ACGTATTTAT TGAATTATAT TATACAACAT 2400

GGATCAATCT TGGGAGAGAG TCAGCAAGAA CTAAATTCTA TGGTAACTGA 2450

TACCCTAAAT AATAGTATTC CTTTTAAGCT TTCTTCTTAT ACAGATGATA 2500

AAATTTTAAT TTCATATTTT AATAAATTCT TTAAGAGAAT TAAATGAAGT 2550

TCAGTTTTAA ATATGAGATA TAAAAATGAT AAATACGTAG ATACTTCAGG 2600

ATATGATTCA AATATAAATA TTAATGGAGA TGTATATAAA TATCCAACTA 2650

ATAAAAATCA ATTTGGAATA TATAATGATA AACTTAGTGA AGTTAATATA 2700

TCTCAAAATG ATTACATTAT ATATGATAAT AAATATAAAA ATTTTAGTAT 2750

TAGTTTTTGG GTAAGAATTC CTAACTATGA TAATAAGATA GTAAATGTTA 2800

ATAATGAATA CACTATAATA AATTGTATGA GAGATAATAA TTCAGGATGG 2850

AAAGTATCTC TTAATCATAA TGAAATAATT TGGACATTGC AAGATAATGC 2900

AGGAATTAAT CAAAAATTAG CATTTAACTA TGGTAACGCA AATGGTATTT 2950

CTGATTATAT AAATAAGTGG ATTTTTGTAA CTATAACTAA TGATAGATTA 3000

GGAGATTCTA AACTTTATAT TAATGGAAAT TTAATAGATC AAAAATCAAT 3050

TTTAAATTTA GGTAATATTC ATGTTAGTGA CAATATATTA TTTAAAATAG 3100

TTAATTGTAG TTATACAAGA TATATTGGTA TTAGATATTT TAATATTTTT 3150

GATAAAGAAT TAGATGAAAC AGAAATTCAA ACTTTATATA GCAATGAACC 3200

-continued

```
TAATACAAAT ATTTTGAAGG ATTTTTGGGG AAATTATTTG CTTTATGACA    3250
AAGAATACTA TTTATTAAAT GTGTTAAAAC CAAATAACTT TATTGATAGG    3300
AGAAAAGATT CTACTTTAAG CATTAATAAT ATAAGAAGCA CTATTCTTTT    3350
AGCTAATAGA TTATATAGTG GAATAAAAGT TAAAATACAA AGAGTTAATA    3400
ATAGTAGTAC TAACGATAAT CTTGTTAGAA AGAATGATCA GGTATATATT    3450
AATTTTGTAG CCAGCAAAAC TCACTTATTT CCATTATATG CTGATACAGC    3500
TACCACAAAT AAAGAGAAAA CAATAAAAAT ATCATCATCT GGCAATAGAT    3550
TTAATCAAGT AGTAGTTATG AATTCAGTAG GAAATAATTG TACAATGAAT    3600
TTTAAAAATA ATAATGGAAA TAATATTGGG TTGTTAGGTT TCAAGGCAGA    3650
TACTGTAGTT GCTAGTACTT GGTATTATAC ACATATGAGA GATCATACAA    3700
ACAGCAATGG ATGTTTTTGG AACTTTATTT CTGAAGAACA TGGATGGCAA    3750
GAAAAATAA                                                 3759
```

BoNT/F of GenBank Accession No. X81714.1 (SEQ ID NO: 70), as follows:

```
AAATGGCGCA AAGAAGATGA TAATTAGTAA TAATATATTT ATTTCCAATT      50
GTTTAACTCT ATCTTGTGGC GGTAAATATA TATGTTTATC TATGAAAGAT     100
GAAAACTATA ATTGGATGAT ATGTAATAAT GAAAGCAACA TACCTAAAAA     150
GGCATATTTA TGGACATTGA AAGAAGTATA GGGGGGATTT TATGCCAGTT     200
GTAATAAATA GTTTTAATTA TAATGACCCT GTTAATGATG ATACAATTTT     250
ATACATGCAG ATACCATATG AAGAAAAAAG TAAAAAATAT TATAAAGCTT     300
TTGAGATTAT GCGTAATGTT TGGATAATTC CTGAGAGAAA TACAATAGGA     350
ACGGATCCTA GTGATTTTGA TCCACCGGCT TCATTAGAGA ACGGAAGCAG     400
TGCTTATTAT GATCCTAATT ATTTAACCAC TGATGCTGAA AAAGATAGAT     450
ATTTAACCAC AACGATAAAA TTATTTAAGA GAATTAATAG TAATCCTGCA     500
GGGGAAGTTT TGTTACAAGA AATATCATAT GCTAAACCAT ATTTAGGAAA     550
TGAACACACG CCAATTAATG AATTCCATCC AGTTACTAGA ACTACAAGTG     600
TTAATATAAA ATCATCAACT AATGTTAAAA GTTCAATAAT ATTGAATCTT     650
CTTGTATTGG GAGCAGGACC TGATATATTT GAAAATTCTT CTTACCCCGT     700
TAGAAAACTA ATGGATTCAG GTGGAGTTTA TGACCCAAGT AATGATGGTT     750
TTGGATCAAT TAATATCGTG ACATTTTCAC CTGAATATGA ATATACTTTT     800
AATGATATTA GTGGAGGGTA TAACAGTAGT ACAGAATCAT TTATTGCAGA     850
TCCTGCAATT TCACTAGCTC ATGAATTGAT ACATGCACTG CATGGATTAT     900
ACGGGGCTAG GGGAGTTACT TATAAAGAGA CTATAAAAGT AAAGCAAGCA     950
CCTCTTATGA TAGCCGAAAA ACCCATAAGG CTAGAAGAAT TTTTAACCTT    1000
TGGAGGTCAG GATTTAAATA TTATTACTAG TGCTATGAAG GAAAAAATAT    1050
ATAACAATCT TTTAGCTAAC TATGAAAAAA TAGCTACTAG ACTTAGTAGA    1100
GTTAATAGTG CTCCTCCTGA ATATGATATT AATGAATATA AAGATTATTT    1150
TCAATGGAAG TATGGGCTAG ATAAAAATGC TGATGGAAGT TATACTGTAA    1200
ATGAAAATAA ATTTAATGAA ATTTATAAAA AATTATATAG CTTTACAGAG    1250
ATTGACTTAG CAAATAAATT TAAAGTAAAA TGTAGAAATA CTTATTTTAT    1300
```

-continued

```
TAAATATGGA TTTTTAAAAG TTCCAAATTT GTTAGATGAT GATATTTATA 1350
CTGTATCAGA GGGGTTTAAT ATAGGTAATT TAGCAGTAAA CAATCGCGGA 1400
CAAAATATAA AGTTAAATCC TAAAATTATT GATTCCATTC CAGATAAAGG 1450
TCTAGTGGAA AAGATCGTTA AATTTTGTAA GAGCGTTATT CCTAGAAAAG 1500
GTACAAAGGC GCCACCGCGA CTATGCATTA GAGTAAATAA TAGGGAGTTA 1550
TTTTTTGTAG CTTCAGAAAG TAGCTATAAT GAAAATGATA TTAATACACC 1600
TAAAGAAATT GACGATACAA CAAATCTAAA TAATAATTAT AGAAATAATT 1650
TAGATGAAGT TATTTTAGAT TATAATAGTG AGACAATACC TCAAATATCA 1700
AATCAAACAT TAAATACACT TGTACAAGAC GATAGTTATG TGCCAAGATA 1750
TGATTCTAAT GGAACAAGTG AAATAGAGGA ACATAATGTT GTTGACCTTA 1800
ATGTATTTTT CTATTTACAT GCACAAAAAG TACCAGAAGG TGAAACTAAT 1850
ATAAGTTTAA CTTCTTCAAT TGATACGGCA TTATCAGAAG AATCGCAAGT 1900
ATATACATTC TTTTCTTCAG AGTTTATTAA TACTATCAAT AAACCTGTAC 1950
ACGCAGCACT ATTTATAAGT TGGATAAATC AAGTAATAAG AGATTTTACT 2000
ACTGAAGCTA CACAAAAAAG TACTTTTGAT AAGATTGCAG ACATATCTTT 2050
AGTTGTACCA TATGTAGGTC TTGCTTTAAA TATAGGTAAT GAGGTACAAA 2100
AAGAAAATTT TAAGGAGGCA TTTGAATTAT TAGGAGCGGG TATTTTATTA 2150
GAATTTGTGC CAGAGCTTTT AATTCCTACA ATTTTAGTGT TTACAATAAA 2200
ATCCTTTATA GGTTCATCTG AGAATAAAAA TAAAATCATT AAAGCAATAA 2250
ATAATTCATT AATGGAAAGA GAAACAAAGT GGAAAGAAAT ATATAGTTGG 2300
ATAGTATCAA ATTGGCTTAC TAGAATTAAT ACACAATTTA ATAAAAGAAA 2350
AGAACAAATG TATCAAGCTT TGCAAAATCA AGTAGATGCA ATAAAAACAG 2400
TAATAGAATA TAAATATAAT AATTATACTT CAGATGAGAG AAATAGACTT 2450
GAATCTGAAT ATAATATCAA TAATATAAGA GAAGAATTGA ACAAAAAAGT 2500
TTCTTTAGCA ATGGAAAATA TAGAGAGATT TATAACAGAG AGTTCTATAT 2550
TTTATTTAAT GAAGTTAATA AATGAAGCCA AAGTTAGTAA ATTAAGAGAA 2600
TATGATGAAG GCGTTAAGGA ATATTTGCTA GACTATATTT CAGAACATAG 2650
ATCAATTTTA GGAAATAGTG TACAAGAATT AAATGATTTA GTGACTAGTA 2700
CTCTGAATAA TAGTATTCCA TTTGAACTTT CTTCATATAC TAATGATAAA 2750
ATTCTAATTT TATATTTTAA TAAATTATAT AAAAAAATTA AAGATAACTC 2800
TATTTTAGAT ATGCGATATG AAAATAATAA ATTTATAGAT ATCTCTGGAT 2850
ATGGTTCAAA TATAAGCATT AATGGAGATG TATATATTTA TTCAACAAAT 2900
AGAAATCAAT TTGGAATATA TAGTAGTAAG CCTAGTGAAG TTAATATAGC 2950
TCAAAATAAT GATATTATAT ACAATGGTAG ATATCAAAAT TTTAGTATTA 3000
GTTTCTGGGT AAGGATTCCT AAATACTTCA ATAAAGTGAA TCTTAATAAT 3050
GAATATACTA TAATAGATTG TATAAGGAAT AATAATTCAG GATGGAAAAT 3100
ATCACTTAAT TATAATAAAA TAATTTGGAC TTTACAAGAT ACTGCTGGAA 3150
ATAATCAAAA ACTAGTTTTT AATTATACAC AAATGATTAG TATATCTGAT 3200
TATATAAATA AATGGATTTT TGTAACTATT ACTAATAATA GATTAGGCAA 3250
TTCTAGAATT TACATCAATG GAAATTTAAT AGATGAAAAA TCAATTTCGA 3300
```

-continued

```
ATTTAGGTGA TATTCATGTT AGTGATAATA TATTATTTAA AATTGTTGGT     3350
TGTAATGATA CAAGATATGT TGGTATAAGA TATTTTAAAG TTTTTGATAC     3400
GGAATTAGGT AAAACAGAAA TTGAGACTTT ATATAGTGAT GAGCCAGATC     3450
CAAGTATCTT AAAAGACTTT TGGGGAAATT ATTTGTTATA TAATAAAAGA     3500
TATTATTTAT TGAATTTACT AAGAACAGAT AAGTCTATTA CTCAGAATTC     3550
AAACTTTCTA AATATTAATC AACAAAGAGG TGTTTATCAG AAACCAAATA     3600
TTTTTTCCAA CACTAGATTA TATACAGGAG TAGAAGTTAT TATAAGAAAA     3650
AATGGATCTA CAGATATATC TAATACAGAT AATTTTGTTA GAAAAAATGA     3700
TCTGGCATAT ATTAATGTAG TAGATCGTGA TGTAGAATAT CGGCTATATG     3750
CTGATATATC AATTGCAAAA CCAGAGAAAA TAATAAAATT AATAAGAACA     3800
TCTAATTCAA ACAATAGCTT AGGTCAAATT ATAGTTATGG ATTCAATAGG     3850
AAATAATTGC ACAATGAATT TTCAAAACAA TAATGGGGGC AATATAGGAT     3900
TACTAGGTTT TCATTCAAAT AATTTGGTTG CTAGTAGTTG GTATTATAAC     3950
AATATACGAA AAAATACTAG CAGTAATGGA TGCTTTTGGA GTTTTATTTC     4000
TAAAGAGCAT GGATGGCAAG AAAACTAATA TAATAATTCA AAAAATAGGT     4050
ATTAAAATAG AGGTAATATA TATTACCCTC TATTTTGGAA TAATTTTAAT     4100
ATATTATATG AAACATATAT AAATTTAAAG ATAATATTAA ATCAAGACAC     4150
AAATTCAAAT TAGAAATATA AAATGAAGTA AATGAAAAGT GTAAAAAGTC     4200
ATTAAATAA                                                  4209
```

BoNT/G of GenBank Accession No. X74162.1 (SEQ ID NO:71), as follows:

```
ATGCCAGTTA ATATAAAAAN CTTTAATTAT AATGACCCTA TTAATAATGA       50
TGACATTATT ATGATGGAAC CATTCAATGA CCCAGGGCCA GGAACATATT      100
ATAAAGCTTT TAGGATTATA GATCGTATTT GGATAGTACC AGAAAGGTTT      150
ACTTATGGAT TTCAACCTGA CCAATTTAAT GCCAGTACAG GAGTTTTTAG      200
TAAAGATGTC TACGAATATT ACGATCCAAC TTATTTAAAA ACCGATGCTG      250
AAAAAGATAA ATTTTTAAAA ACAATGATTA AATTATTTAA TAGAATTAAT      300
TCAAAACCAT CAGGACAGAG ATTACTGGAT ATGATAGTAG ATGCTATACC      350
TTATCTTGGA AATGCATCTA CACCGCCCGA CAAATTTGCA GCAAATGTTG      400
CAAATGTATC TATTAATAAA AAAATTATCC AACCTGGAGC TGAAGATCAA      450
ATAAAAGGTT TAATGACAAA TTTAATAATA TTTGGACCAG GACCAGTTCT      500
AAGTGATAAT TTTACTGATA GTATGATTAT GAATGGCCAT TCCCCAATAT      550
CAGAAGGATT TGGTGCAAGA ATGATGATAA GATTTTGTCC TAGTTGTTTA      600
AATGTATTTA ATAATGTTCA GGAAAATAAA GATACATCTA TATTTAGTAG      650
ACGCGCGTAT TTTGCAGATC CAGCTCTAAC GTTAATGCAT GAACTTATAC      700
ATGTGTTACA TGGATTATAT GGAATTAAGA TAAGTAATTT ACCAATTACT      750
CCAAATACAA AAGAATTTTT CATGCAACAT AGCGATCCTG TACAAGCAGA      800
AGAACTATAT ACATTCGGAG GACATGATCC TAGTGTTATA AGTCCTTCTA      850
CGGATATGAA TATTTATAAT AAAGCGTTAC ATAATGTTCA AGATATAGCT      900
AATAGGCTTA ATATTGTTTC AAGTGCCCAA GGGAGTGGAA TTGATATTTC      950
```

-continued

```
CTTATATAAA CAAATATATA AAAATAAATA TGATTTTGTT GAAGATCCTA      1000
ATGGAAAATA TAGTGTAGAT AAGGATAAGT TTGATAAATT ATATAAGGCC      1050
TTAATGTTTG GCTTTACTGA AACTAATCTA GCTGGTGAAT ATGGAATAAA      1100
AACTAGGTAT TCTTATTTTA GTGAATATTT GCCACCGATA AAAACTGAAA      1150
AATTGTTAGA CAATACAATT TATACTCAAA ATGAAGGCTT TAACATAGCT      1200
AGTAAAAATC TCAAAACGGA ATTTAATGGT CAGAATAAGG CGGTAAATAA      1250
AGAGGCTTAT GAAGAAATCA GCCTAGAACA TCTCGTTATA TATAGAATAG      1300
CAATGTGCAA GCCTGTAATG TACAAAAATA CCGGTAAATC TGAACAGTGT      1350
ATTATTGTTA ATAATGAGGA TTTATTTTTC ATAGCTAATA AAGATAGTTT      1400
TTCAAAAGAT TTAGCTAAAG CAGAAACTAT AGCATATAAT ACACAAAATA      1450
ATACTATAGA AAATAATTTT TCTATAGATC AGTTGATTTT AGATAATGAT      1500
TTAAGCAGTG GCATAGACTT ACCAAATGAA AACACAGAAC CATTTACAAA      1550
TTTTGACGAC ATAGATATCC CTGTGTATAT TAAACAATCT GCTTTAAAAA      1600
AAATTTTTGT GGATGGAGAT AGCCTTTTTG AATATTTACA TGCTCAAACA      1650
TTTCCTTCTA ATATAGAAAA TCTACAACTA ACGAATTCAT TAAATGATGC      1700
TTTAAGAAAT AATAATAAAG TCTATACTTT TTTTTCTACA AACCTTGTTG      1750
AAAAAGCTAA TACAGTTGTA GGTGCTTCAC TTTTTGTAAA CTGGGTAAAA      1800
GGAGTAATAG ATGATTTTAC ATCTGAATCC ACACAAAAAA GTACTATAGA      1850
TAAAGTTTCA GATGTATCCA TAATTATTCC CTATATAGGA CCTGCTTTGA      1900
ATGTAGGAAA TGAAACAGCT AAAGAAAATT TTAAAAATGC TTTTGAAATA      1950
GGTGGAGCCG CTATCTTAAT GGAGTTTATT CCAGAACTTA TTGTACCTAT      2000
AGTTGGATTT TTTACATTAG AATCATATGT AGGAAATAAA GGGCATATTA      2050
TTATGACGAT ATCCAATGCT TTAAAGAAAA GGGATCAAAA ATGGACAGAT      2100
ATGTATGGTT TGATAGTATC GCAGTGGCTC TCAACGGTTA ATACTCAATT      2150
TTATACAATA AAAGAAAGAA TGTACAATGC TTTAAATAAT CAATCACAAG      2200
CAATAGAAAA AATAATAGAA GATCAATATA ATAGATATAG TGAAGAAGAT      2250
AAAATGAATA TTAACATTGA TTTTAATGAT ATAGATTTTA AACTTAATCA      2300
AAGTATAAAT TTAGCAATAA ACAATATAGA TGATTTTATA AACCAATGTT      2350
CTATATCATA TCTAATGAAT AGAATGATTC CATTAGCTGT AAAAAAGTTA      2400
AAAGACTTTG ATGATAATCT TAAGAGAGAT TTATTGGAGT ATATAGATAC      2450
AAATGAACTA TATTTACTTG ATGAAGTAAA TATTCTAAAA TCAAAAGTAA      2500
ATAGACACCT AAAAGACAGT ATACCATTTG ATCTTTCACT ATATACCAAG      2550
GACACAATTT TAATACAAGT TTTTAATAAT TATATTAGTA ATATTAGTAG      2600
TAATGCTATT TTAAGTTTAA GTTATAGAGG TGGGCGTTTA ATAGATTCAT      2650
CTGGATATGG TGCAACTATG AATGTAGGTT CAGATGTTAT CTTTAATGAT      2700
ATAGGAAATG GTCAATTTAA ATTAAATAAT TCTGAAAATA GTAATATTAC      2750
GGCACATCAA AGTAAATTCG TTGTATATGA TAGTATGTTT GATAATTTTA      2800
GCATTAACTT TTGGGTAAGG ACTCCTAAAT ATAATAATAA TGATATACAA      2850
ACTTATCTTC AAAATGAGTA TACAATAATT AGTTGTATAA AAAATGACTC      2900
AGGATGGAAA GTATCTATTA AGGGAAATAG AATAATATGG ACATTAATAG      2950
```

-continued

```
ATGTTAATGC AAAATCTAAA TCAATATTTT TCGAATATAG TATAAAAGAT      3000

AATATATCAG ATTATATAAA TAAATGGTTT TCCATAACTA TTACTAATGA      3050

TAGATTAGGT AACGCAAATA TTTATATAAA TGGAAGTTTG AAAAAAAGTG      3100

AAAAAATTTT AAACTTAGAT AGAATTAATT CTAGTAATGA TATAGACTTC      3150

AAATTAATTA ATTGTACAGA TACTACTAAA TTTGTTTGGA TTAAGGATTT      3200

TAATATTTTT GGTAGAGAAT TAAATGCTAC AGAAGTATCT TCACTATATT      3250

GGATTCAATC ATCTACAAAT ACTTTAAAAG ATTTTTGGGG GAATCCTTTA      3300

AGATACGATA CACAATACTA TCTGTTTAAT CAAGGTATGC AAAATATCTA      3350

TATAAAGTAT TTTAGTAAAG CTTCTATGGG GGAAACTGCA CCACGTACAA      3400

ACTTTAATAA TGCAGCAATA AATTATCAAA ATTTATATCT TGGTTTACGA      3450

TTTATTATAA AAAAAGCATC AAATTCTCGG AATATAAATA ATGATAATAT      3500

AGTCAGAGAA GGAGATTATA TATATCTTAA TATTGATAAT ATTTCTGATG      3550

AATCTTACAG AGTATATGTT TTGGTGAATT CTAAAGAAAT TCAAACTCAA      3600

TTATTTTTAG CACCCATAAA TGATGATCCT ACGTTCTATG ATGTACTACA      3650

AAAGAAAGAA TATTATGAAA AAACAACATA TAATTGTCAG ATACTTTGCG      3700

AAAAAGATAC TAAAACATTT GGGCTGTTTG GAATTGGTAA ATTTGTTAAA      3750

GATTATGGAT ATGTTTGGGA TACCTATGAT AATTATTTTT GCATAAGTCA      3800

GTGGTATCTC AGAAGAATAT CTGAAAATAT AAATAAATTA AGGTTGGGAT      3850

GTAATTGGCA ATTCATTCCC GTGGATGAAG GATGGACAGA ATAATATAAT      3900

TAAATATTTA TTAAAGCTAC TTTGATAGGA AAATCAA                    3937
```

Isolated nucleic acid molecules that encode atoxic derivatives of a Clostridial neurotoxin that may be further modified to encode the propeptide fusions described herein are also described in U.S. Pat. No. 7,785,606 to Ichtchenko and Band, which is hereby incorporated by reference in its entirety. One specific example of a nucleic acid molecule that encodes an atoxic derivative of BoNT/C (with detection tags and affinity purification tags) that may be further modified to encode a propeptide fusion of the present invention is illustrated in FIGS. 17A-L.

The nucleic acid molecules may have other modifications which take into account codon optimization in a host, facile placement of restriction sites and absence of ambiguous sites elsewhere in the construct, and restricted specificity protease sites designed to ensure that they do not create any internal instability during expression and purification. Other modifications may include, without limitation, a mutation which renders the encoded propeptide resistant to low-specificity proteolysis, one or more silent mutations that inactivate putative internal DNA regulatory elements, and /or one or more unique restriction sites. Mature neurotoxin stability and yield may be optimized by amino acid substitution of residues within the intermediate region of the propeptide, thereby reducing susceptibility to non-specific proteolysis and poisoning of the host organism used for expression of the mature neurotoxin. Also, silent mutations are introduced into DNA regulatory elements that can affect RNA transcription or expression of the propeptide fusions in the expression system of choice.

In one embodiment, the nucleic acid molecule encodes one or more of the following mutations in the light chain region of the Clostridial neurotoxin (BoNT/A): $E_{224}$>A, $Y_{366}$>A, $K_{438}$>H, $K_{440}$>Q, $K_{444}$>Q, $K_{971}$>N, $Q_{162}$>Y, $L_{256}$>Y, $R_{257}$>E, $L_{322}$>E, $Q_{163}$>E, $E_{263}$>L, and $L_{323}$>I.

In another embodiment, the nucleic acid molecule encodes one or more of the following mutations in the light chain region of the Clostridial neurotoxin (BoNT/C, with amino acids numbered as shown in FIGS. 17A-L): $E_{446}$>A, $H_{449}$>G, $Y_{591}$>A.

Expression levels of botulinum neurotoxins may be influenced by the length and /or composition of a specific construct, including but not limited to the number, type, or spacing of VHH, RSP, DT, APT, tags, linkers, or spacers. As a specific example, when the construct includes more than one VHH domain encoding sequence, the length of the linker between the VHH domain encoding sequence may relate to expression levels.

In yet another embodiment, modular DNA constructs are designed to facilitate the creation of a diverse and wide assortment of protein fusions. These modular DNA constructs include combinations of elements or regions that can be easily exchanged through cloning by including specific restriction site recognition sequences ("RS") within the DNA constructs. Thus, according to this embodiment, modular DNA constructs are created as both "acceptor" constructs and "donor" constructs. Acceptor constructs "receive" donor constructs to alter the activity/function of the fusion protein encoded by the acceptor construct. In one embodiment, this is carried out by the incorporation, use, or placement of specific restriction sites referred to herein as unique restriction sites ("URS") not native to the DNA constructs. These restriction sites may be at or near junctions between DNA sequences encoding functional or structural elements of the encoded fusion protein (e.g., between a BoNT LC and a tag). Using restriction digestion and ligation of complementary single-stranded overhang sequences between donor and recipient constructs, the elements of these constructs may be exchanged (e.g., an acceptor construct may receive a donor construct) either fully or partially based on the position of the URSs within the constructs.

If the modular DNA constructs contain regions with BoNT sequence homology, including but not limited to BoNT LC and BoNT HC, the sequences may be derived from any BoNT serotype or mixture thereof, and may be at least about 80%, 81%, 82%, 83%, 84%, 85%, 86%, 87%, 88%, 89%, 90%, 91%, 92%, 93%, 94%, 95%, or more identical to the nucleic acid molecule of SEQ ID NO:65 or any other Clostridial neurotoxin molecule.

Although URSs may be positioned close to the junction of DNA sequences encoding elements or regions within the fusion protein the construct encodes, the exact position of the RS within the sequences may vary within the sequence encoding the element or region and may still be used to exchange that sequence encoding the element or region without loss of function, or to replace a portion of the recipient element or region encoding DNA sequence with the donor element or region encoding sequence without loss of function.

Figure 32:
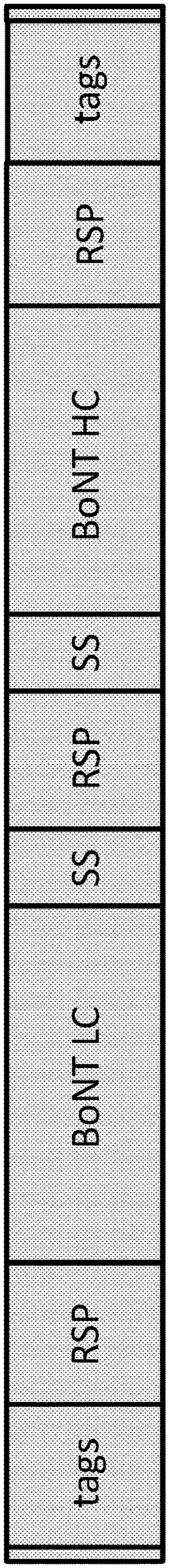
FIG. 32 is a schematic illustration of one embodiment of a DNA construct used for molecular construction of fusion proteins encoded by the DNA construct. In particular.
Figure 33F:
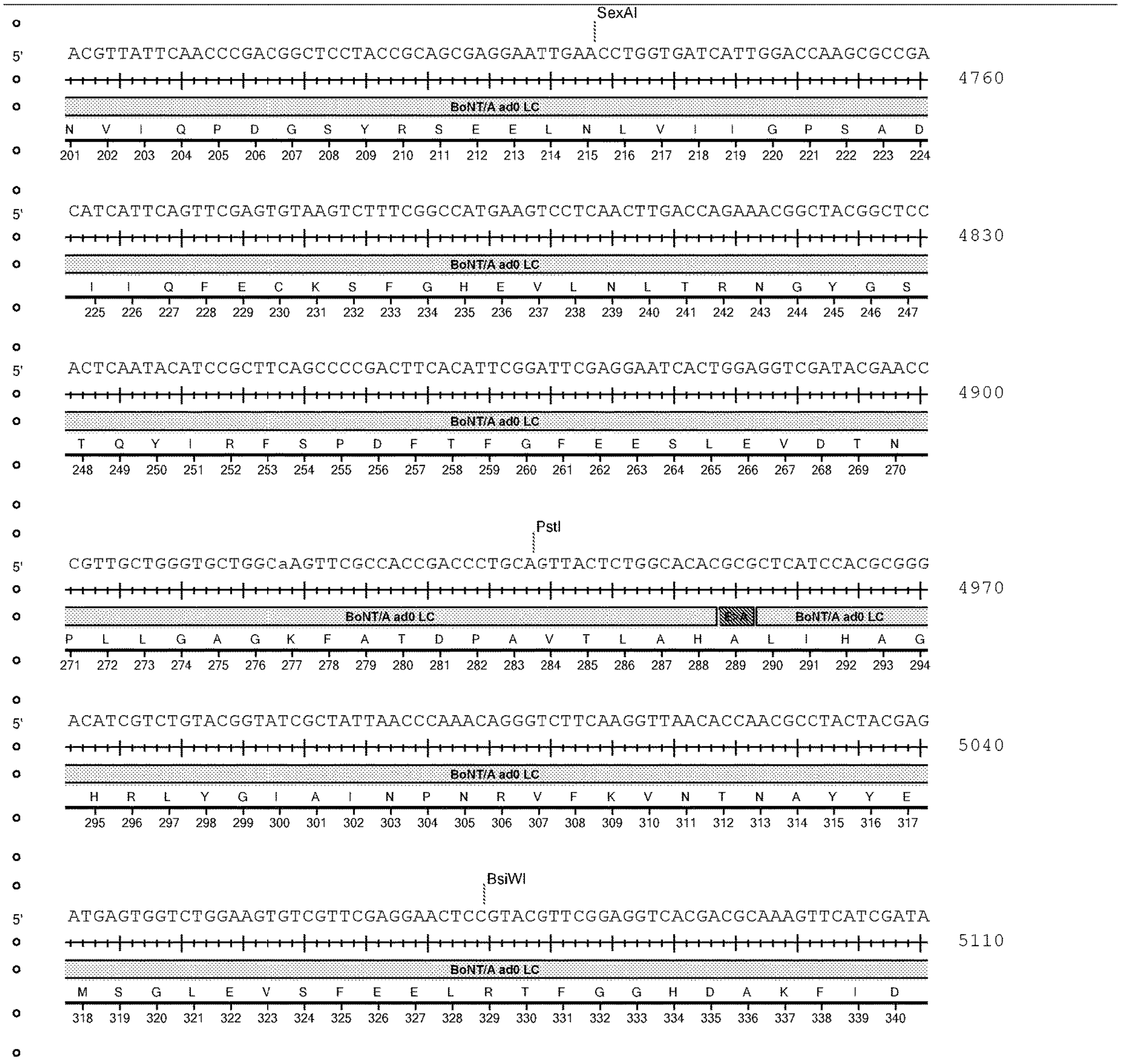
FIGS. 33A-N provide the DNA sequence (SEQ ID NO:15) of one embodiment of a DNA construct encoding fusion proteins of the present invention and the corresponding amino acid sequence (SEQ ID NO:16) of this DNA construct. The sequences of FIGS. 33A-N are specific examples of DNA constructs generally represented in FIG. 32. In particular, the construct of FIGS. 33A-N contains the BoNT/A ad-0 LC domain and BoNT/A HC domain.
Figure 33G:
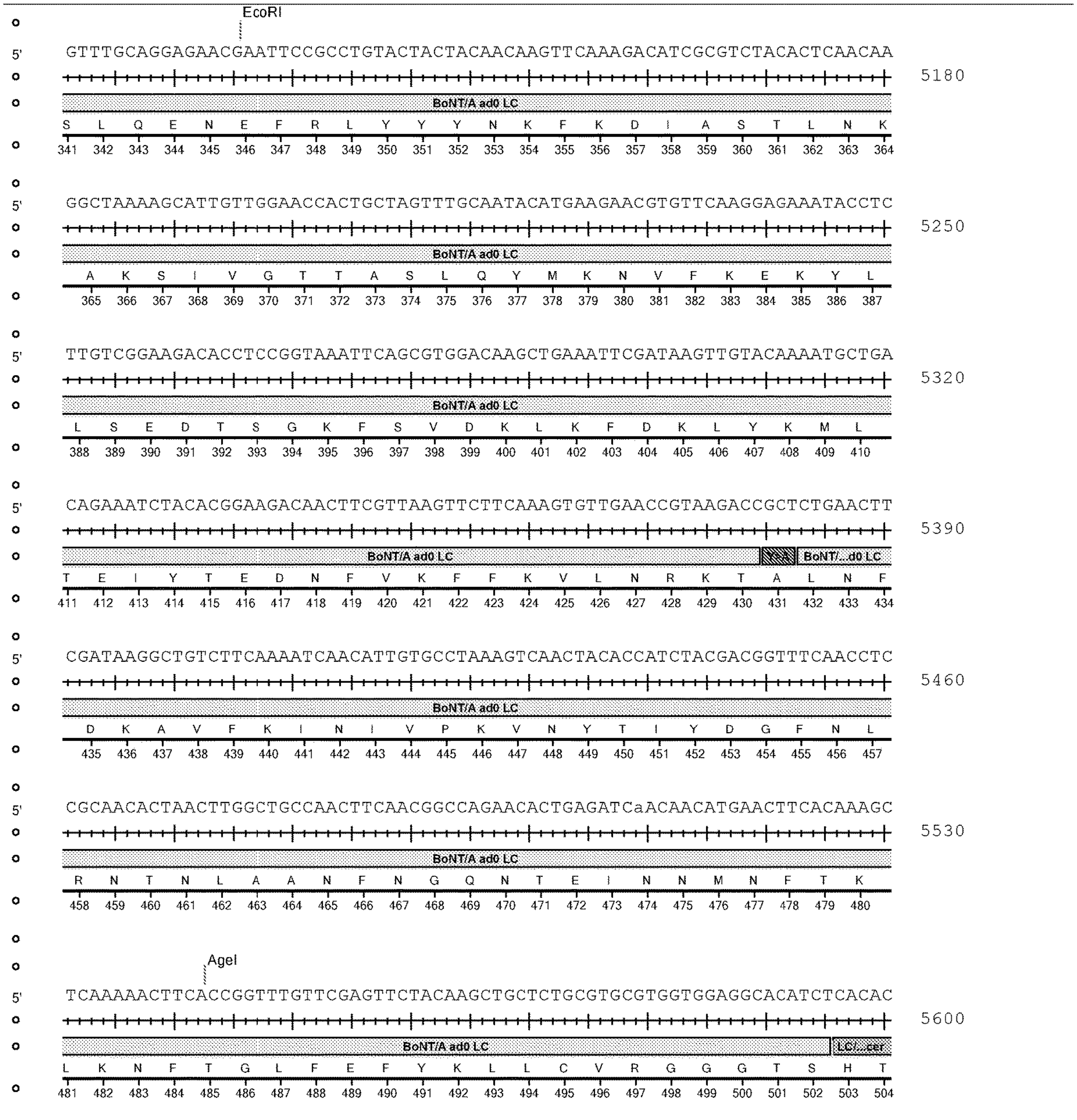
Figure 33H:
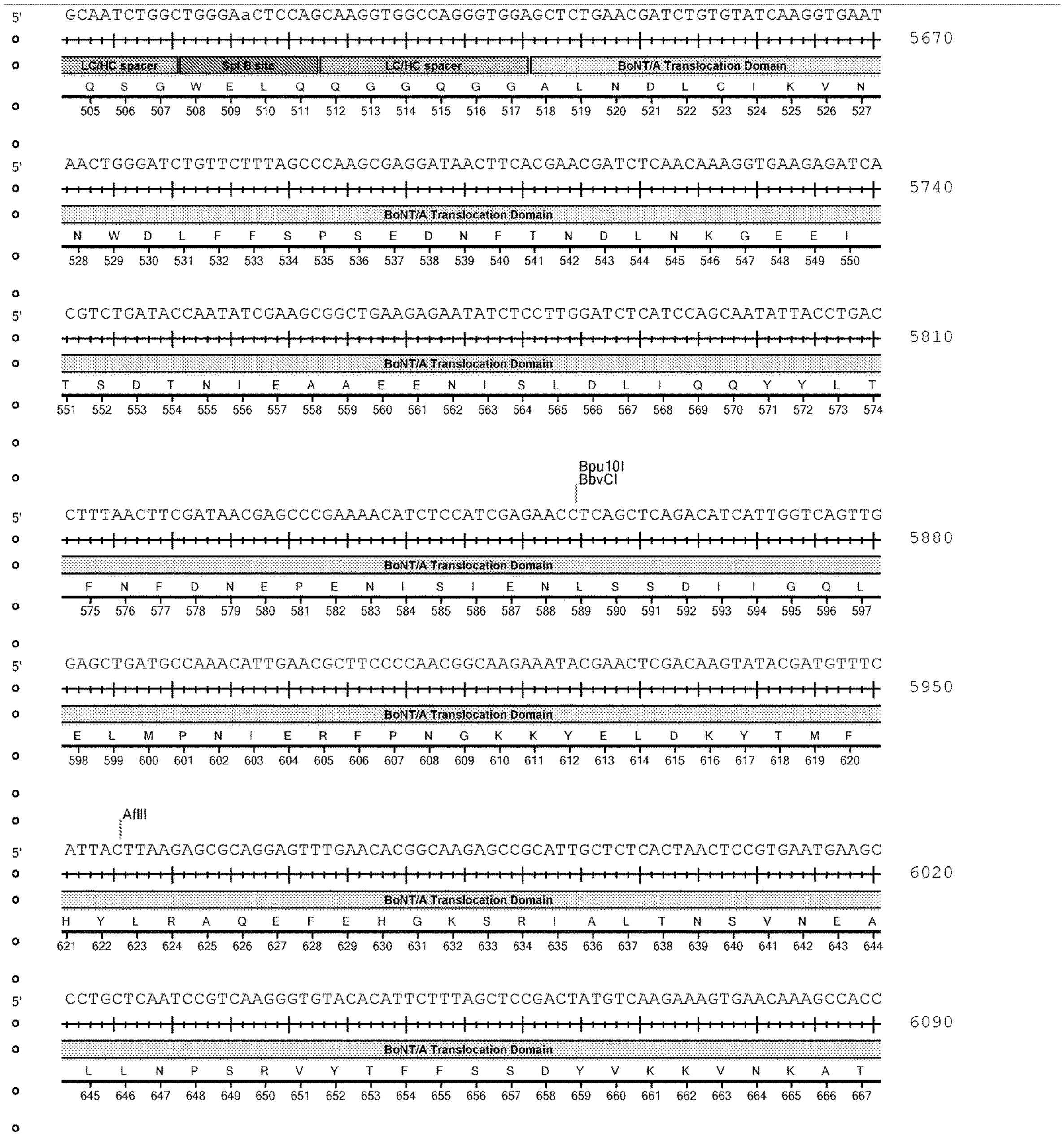
Figure 34F:
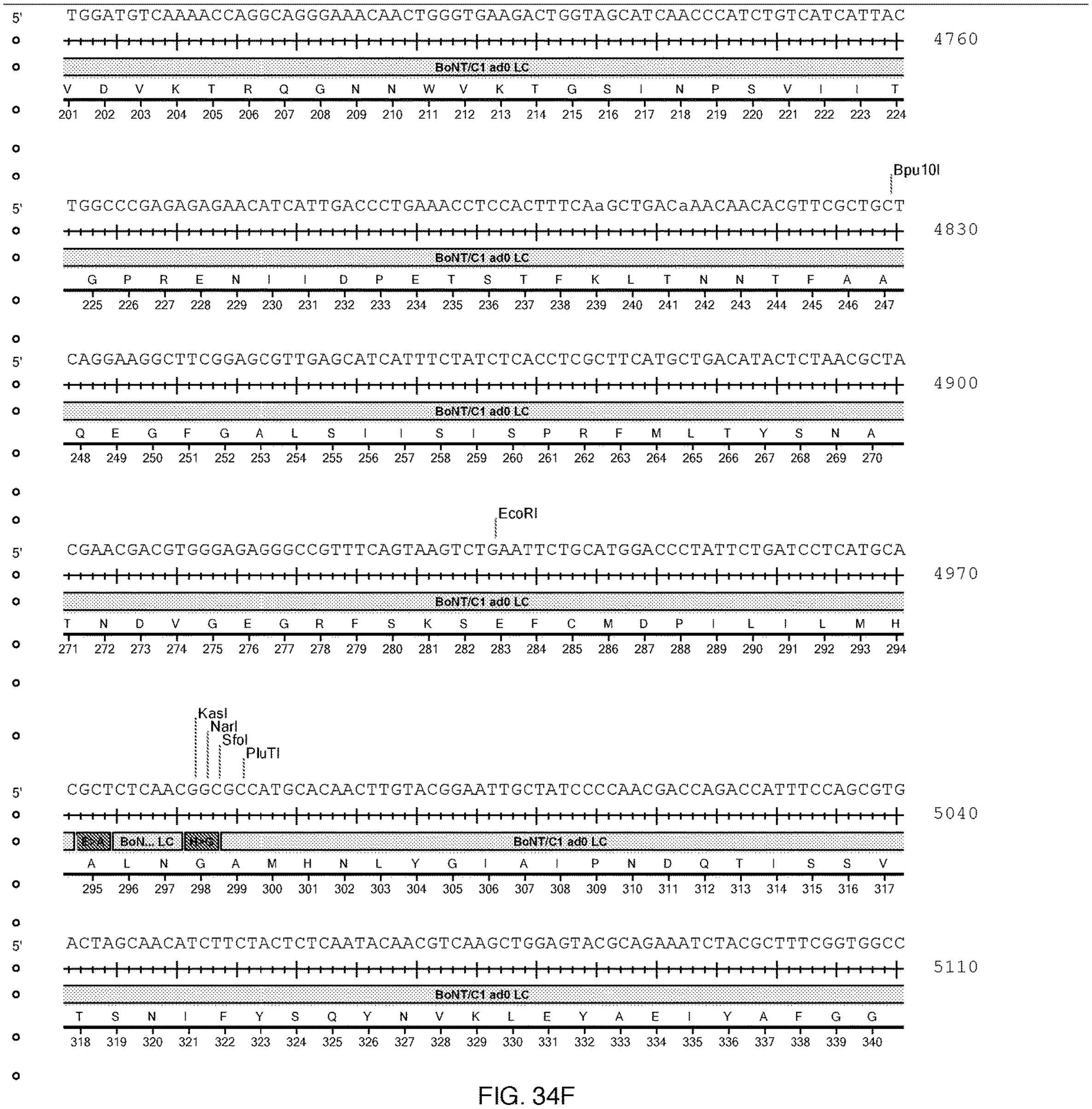
FIGS. 34A-N provide the DNA sequence (SEQ ID NO:17) of one embodiment of a DNA construct for molecular construction of fusion proteins of the present invention and the corresponding amino acid sequence (SEQ ID NO:18) of this DNA construct. The sequences of FIGS. 34A-N are specific examples of constructs encoding/having the general structure of the construct illustrated in FIG. 32. In particular, the construct of FIGS. 34A-N contains the BoNT/C ad-0 LC and BoNT/C HC.
Figure 34G:
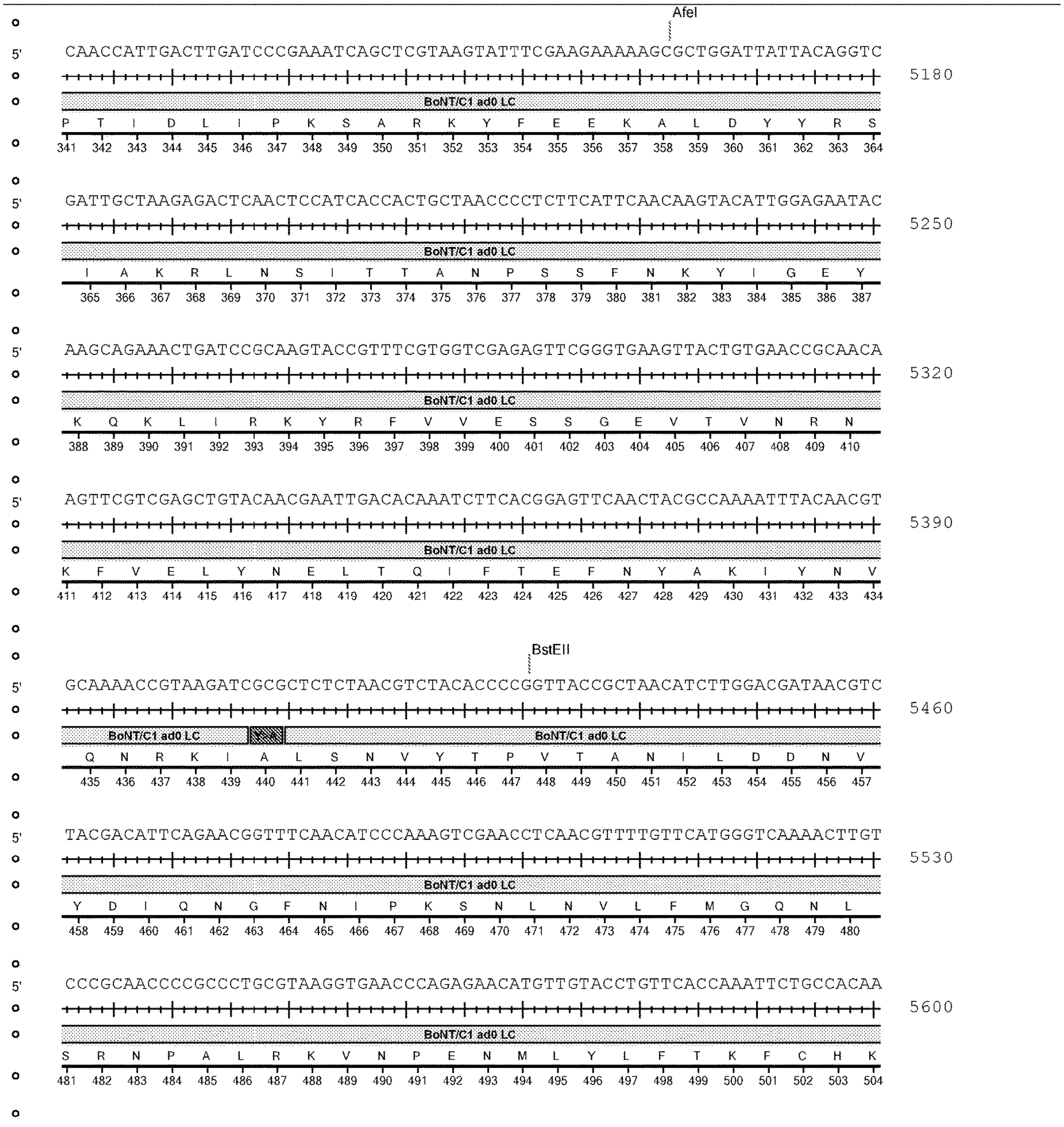

In one embodiment of modular construction of nucleotide constructs encoding fusion proteins, the construct includes RSP sites between and flanking the BoNT LC and BoNT HC. The construct optionally also includes tag sequences and spacer sequences. Tag sequences include, but are not limited to APT, DT, linkers, and spacers, as described herein. The construct may include a number of unique restriction sites (URS) that can be used to fragment the construct and easily incorporate new sequences encoding fusion protein elements through molecular cloning. This embodiment is illustrated in FIG. 32. Specific examples of this embodiment include FIG. 33 (BoNT/A) and FIG. 34 (BoNT/C), which are schematically illustrated in FIG. 32.

According to the specific embodiments illustrated in FIGS. 36A-F and FIG. 37A-E, the RSP is a protease cleavage site such as WELQut (SplB protease from *Staphylococcus aureus*) that allows for an N-terminally placed positively charged amino acid (such as lysine, arginine, or histidine, denoted by $X^+$ in FIG. 35) after the proteolytic activation of the propeptide. There may be advantages to this specific structure. In particular, the ADD encoding sequence of the specific embodiments illustrated in FIGS. 39A-O and FIGS. 37A-E create a temperature sensitive degron upstream of the VHH. The temperature sensitive degron creates a fusion protein which is stable in the cytoplasm of insect cells at 33° C., but which at the temperature of mammalian neurons (37° C.) the destabilizing N-terminal residue (such as the positively charged amino acid arginine) causes enhanced ubiquitination and degradation by the protesome machinery of the neuron, and the in vivo half-life of the protein is dramatically reduced (FIGS. 36A-F, FIGS. 37A-E).

Figure 35:
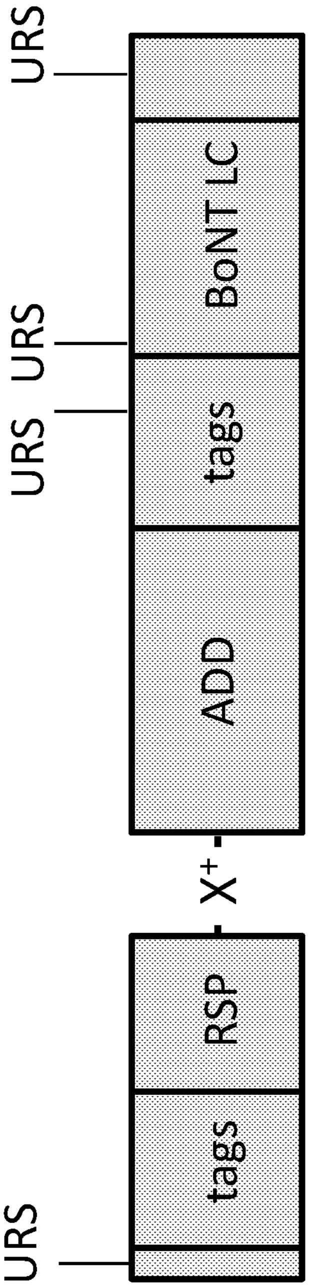
FIG. 35 is a schematic illustration of one embodiment of a DNA construct used for molecular construction of fusion proteins of the present invention. In particular.
Figure 36A:
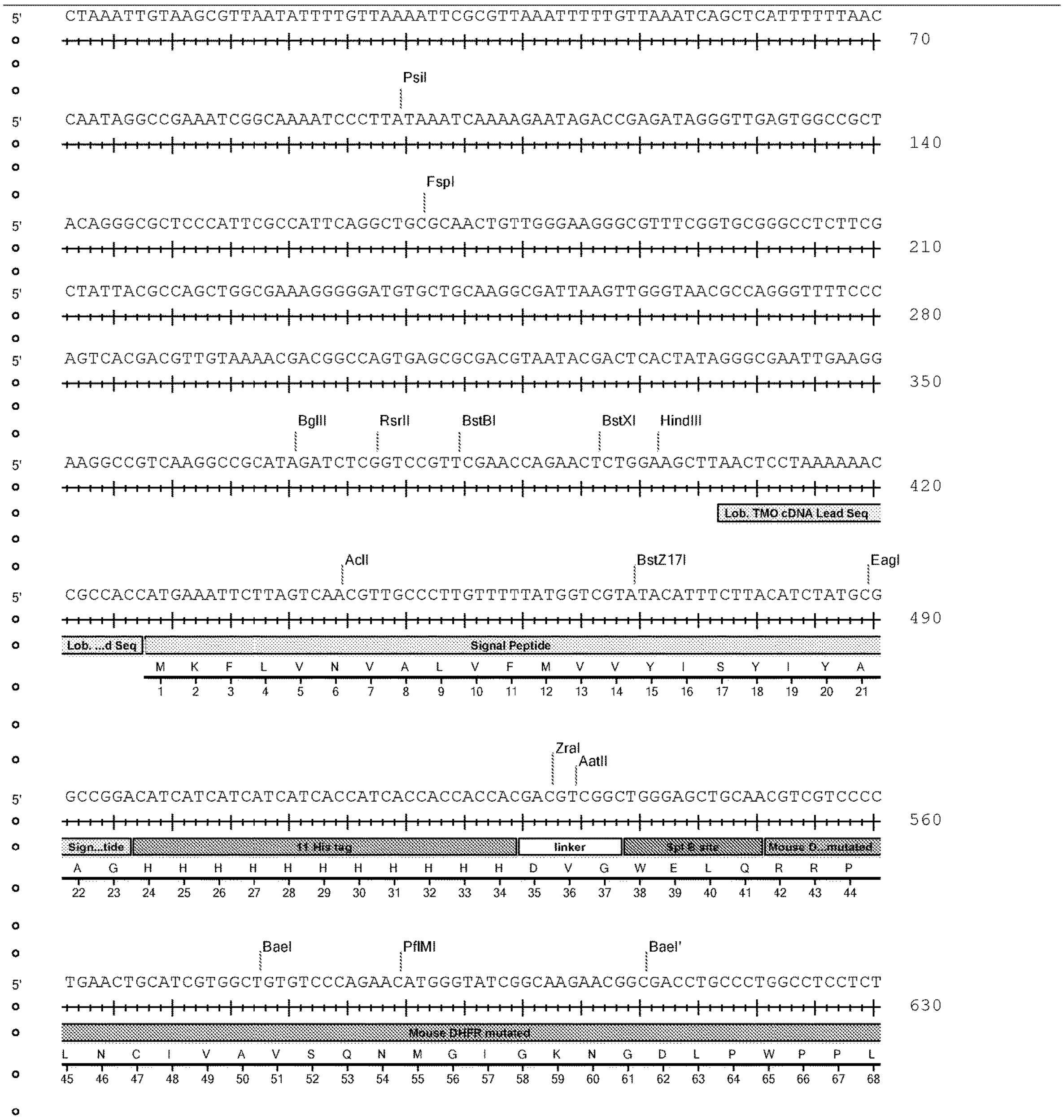
Figure 36B:
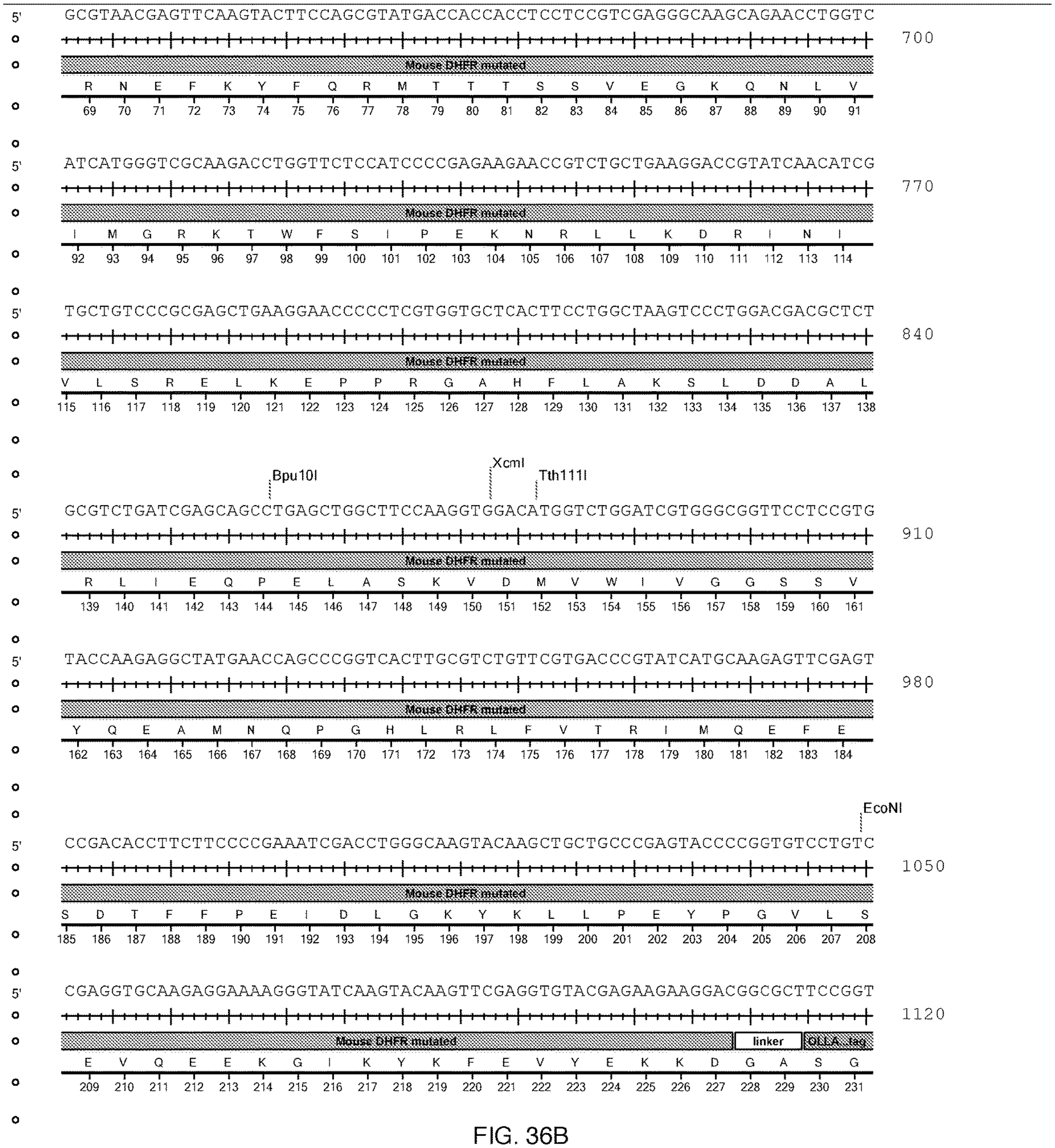
Figure 36C:
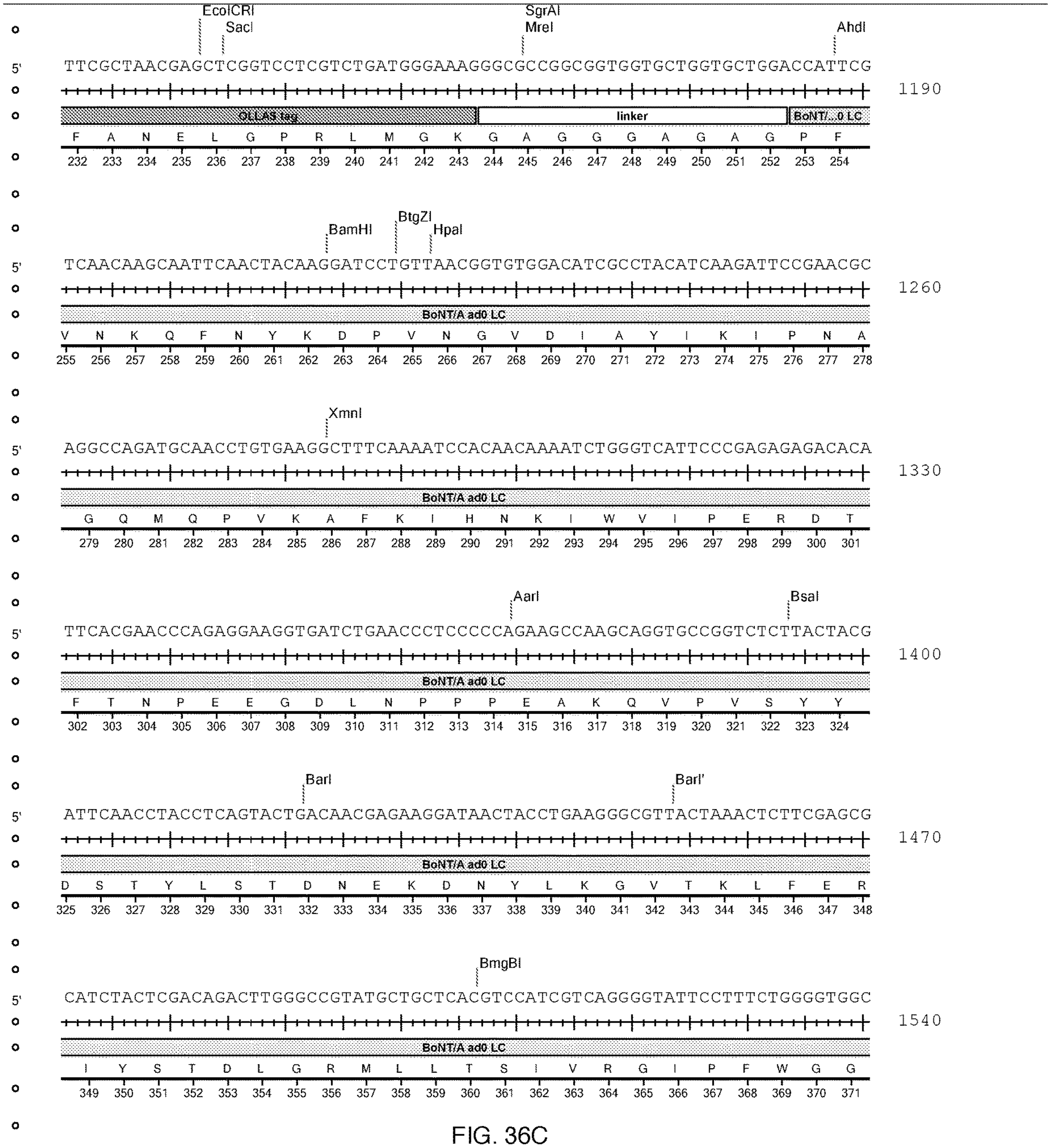
Figure 36D:
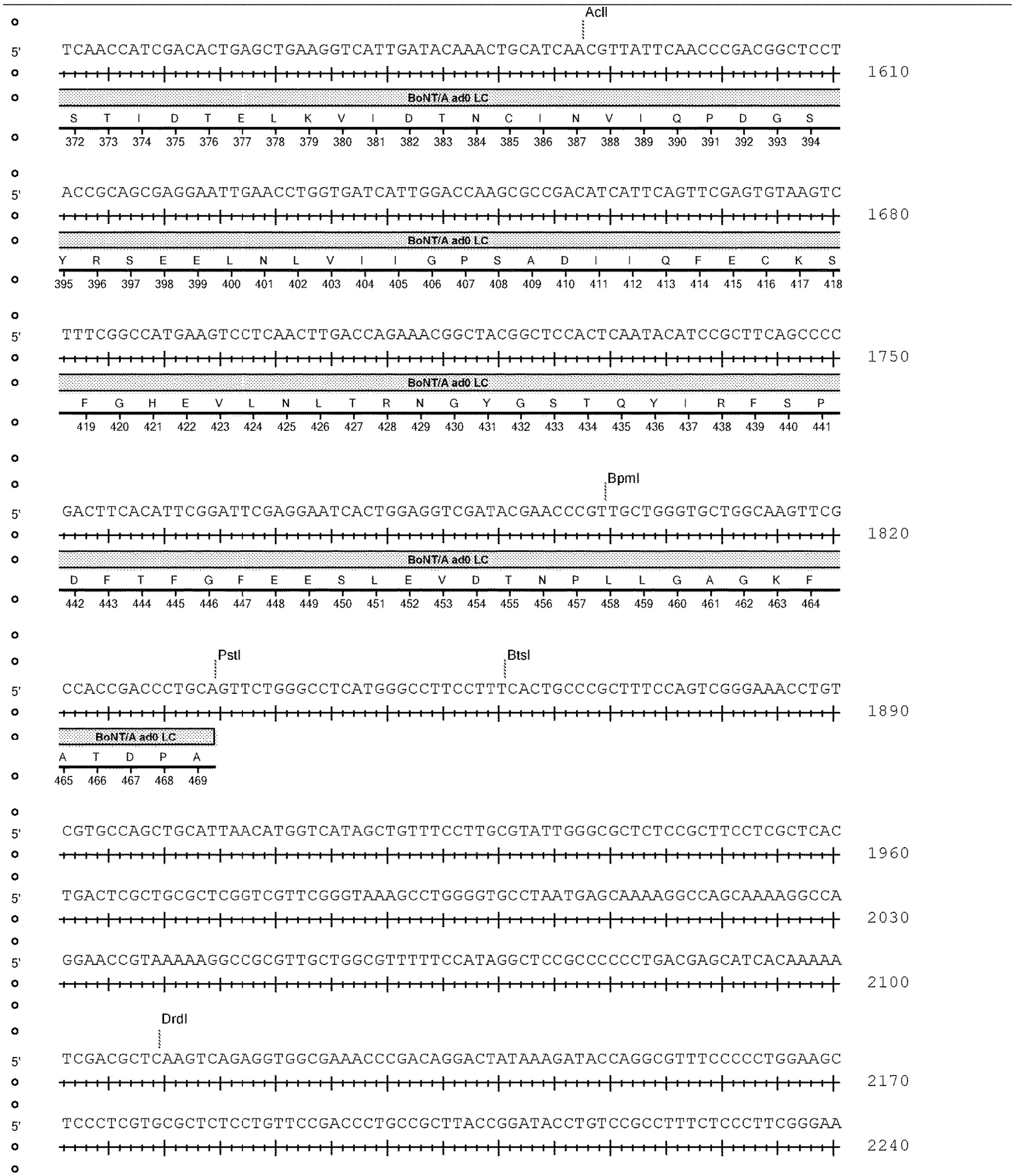
Figure 37A:
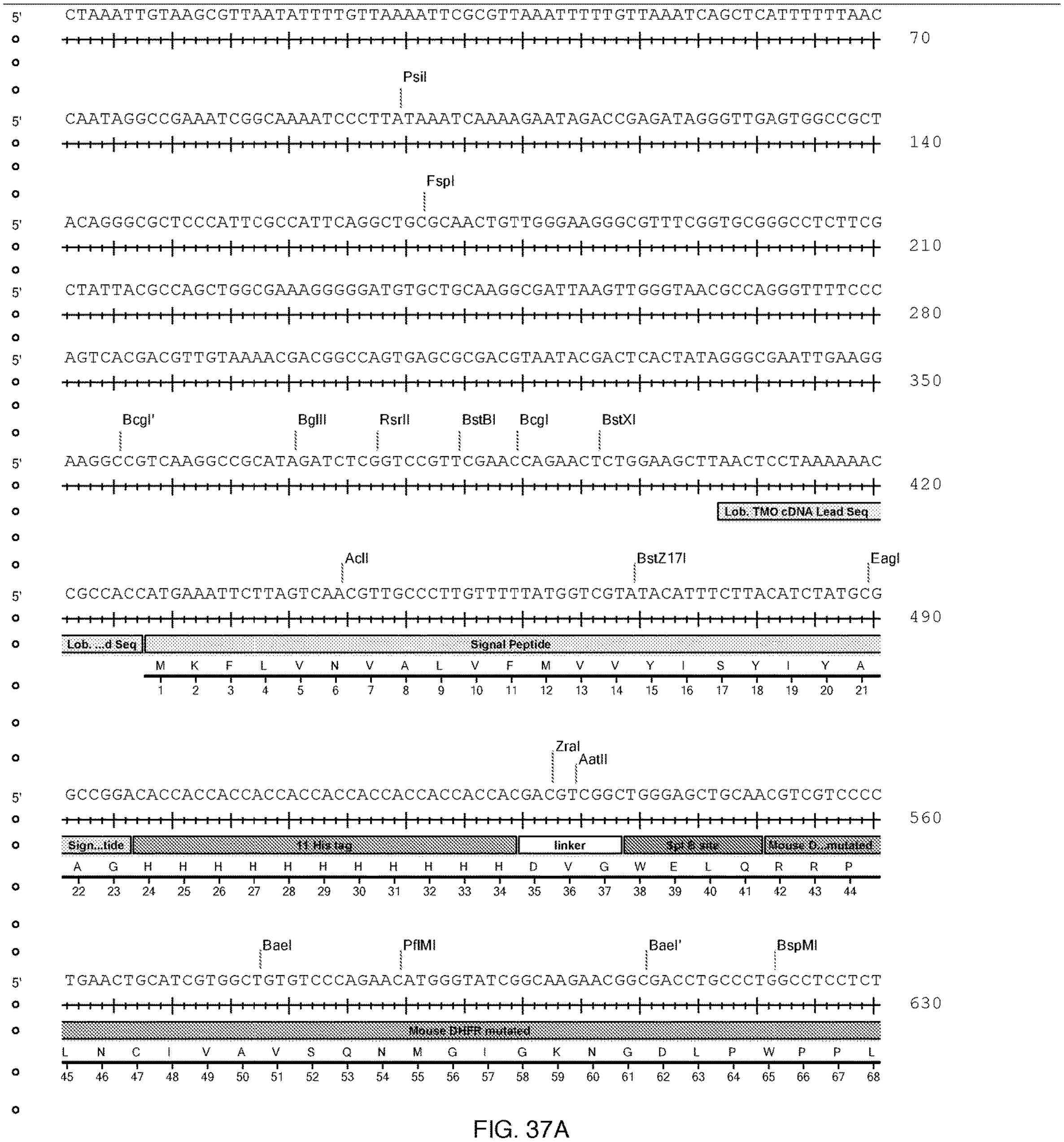
Figure 37B:
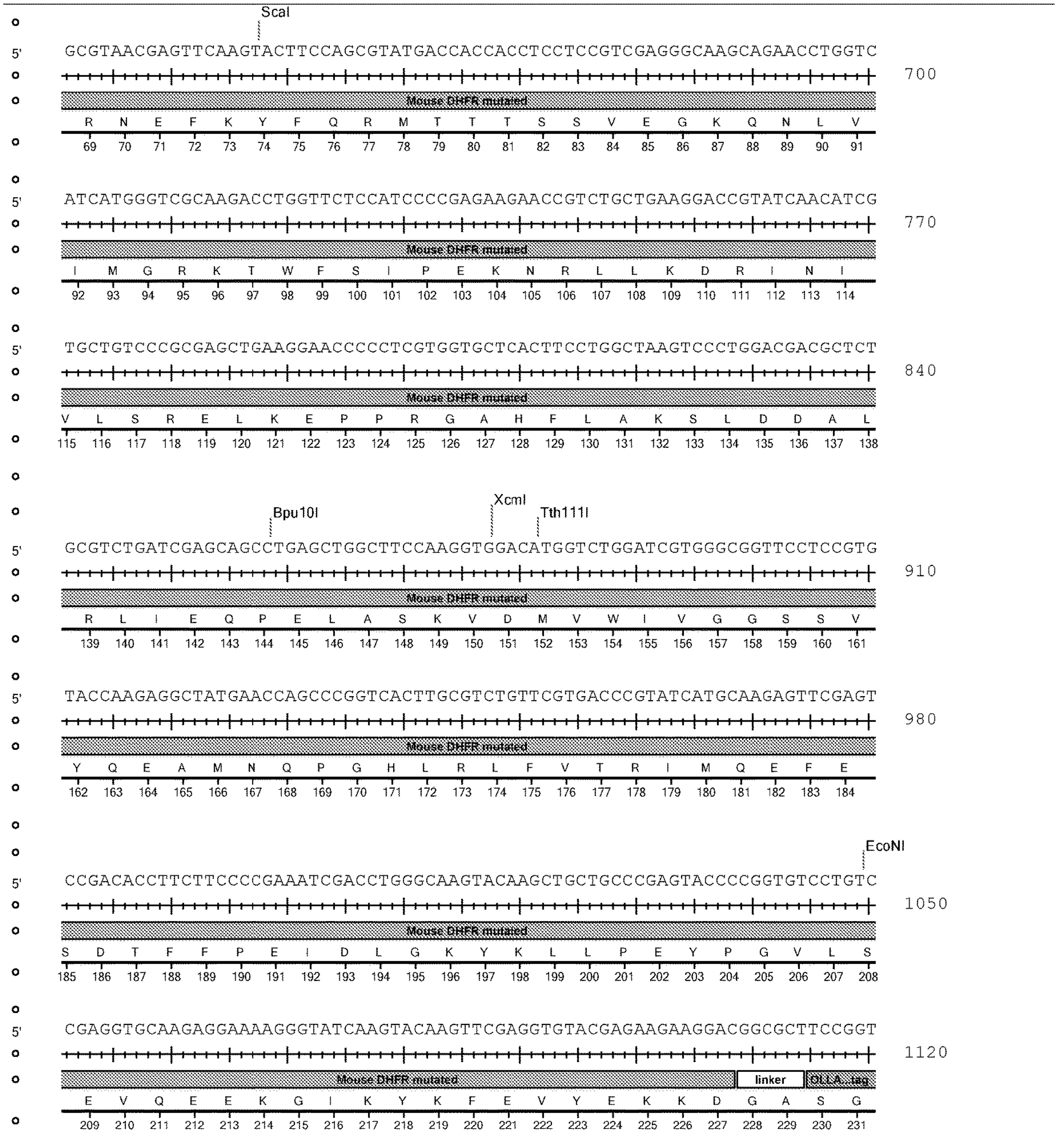
Figure 37C:
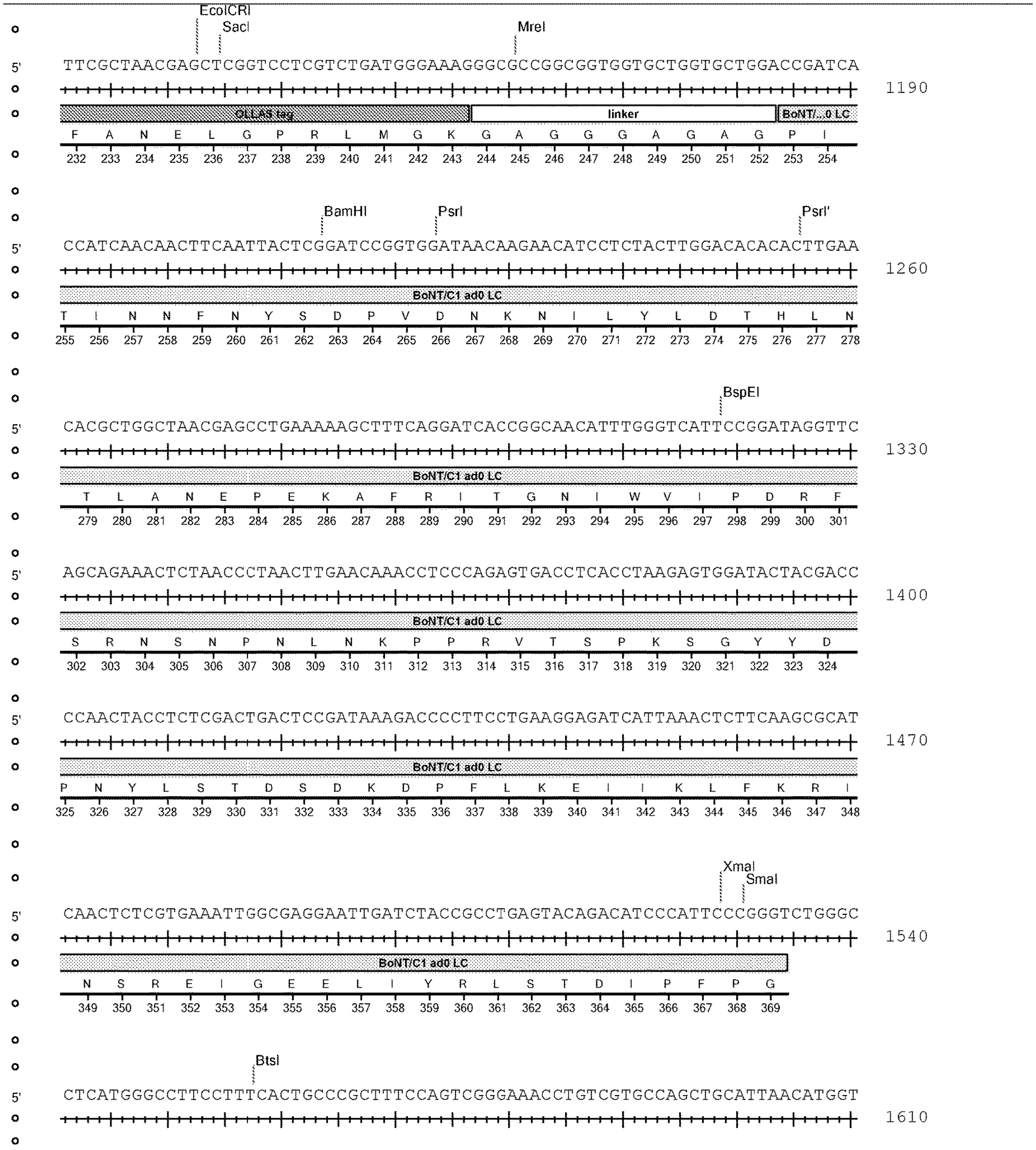
Figure 39F:
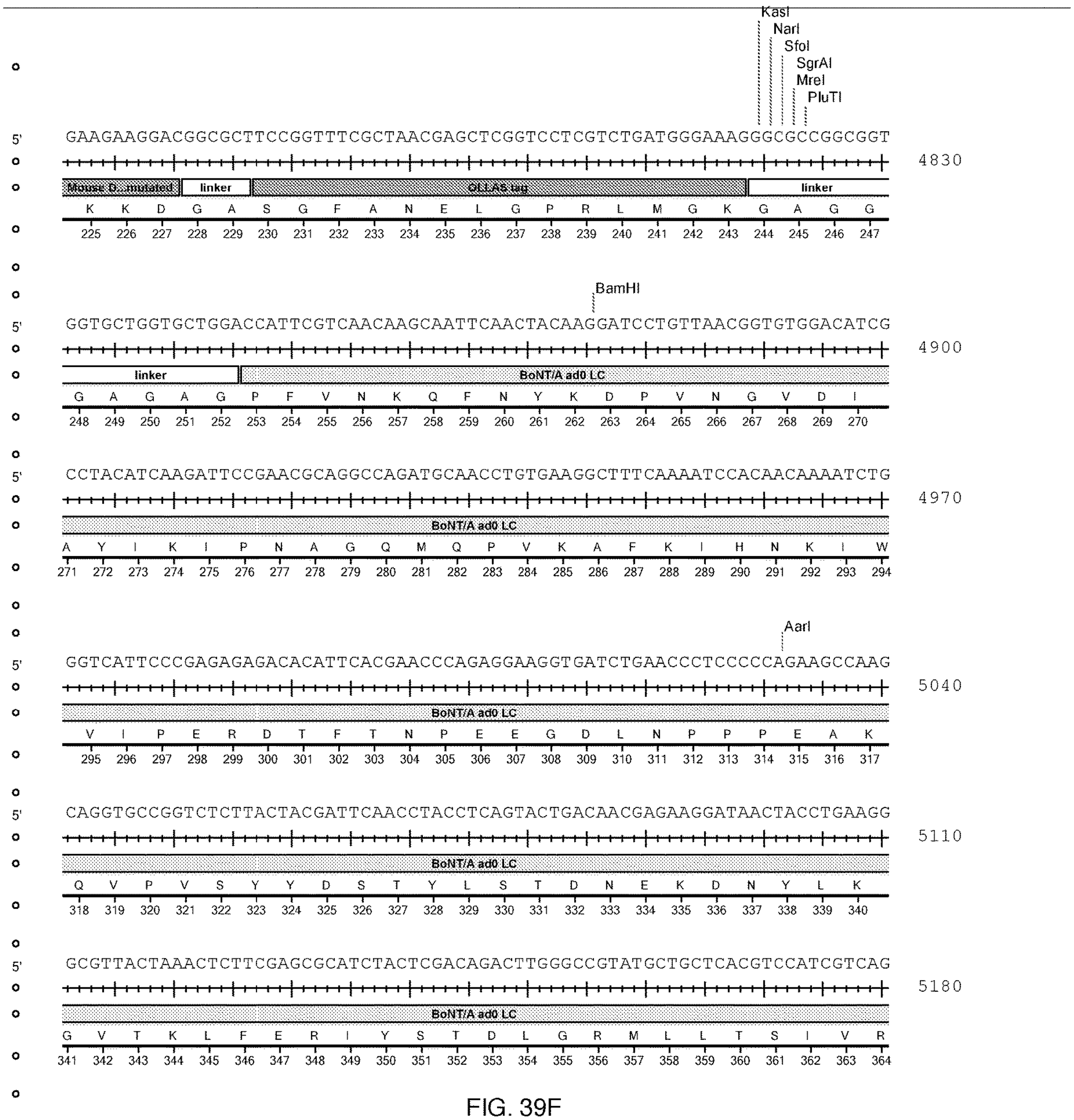
FIGS. 39A-O provide the DNA sequence (SEQ ID NO:23) of one embodiment of a DNA construct for molecular construction of fusion proteins of the present invention and the corresponding amino acid sequence (SEQ ID NO:24) of this DNA construct. The sequences of FIGS. 39A-O are specific examples of constructs encoding/having the general structure of the construct illustrated in FIG. 38C. In particular, the construct of FIGS. 39A-O encodes the BoNT/A ad-0 LC and BoNT/A HC.

In one embodiment, a modular construct includes an RSP and an ADD encoding sequence upstream of the BoNT LC encoding sequence, and optionally includes tag encoding sequences including, but not limited to APT and DT or nucleotide linkers and /or spacers. The construct includes a number of unique restriction sites (URS) that can be used to fragment the construct and easily incorporate (or accept) donor constructs encoding fusion protein elements via molecular cloning. Such an embodiment is illustrated in FIG. 35. Specific non-limiting examples of this embodiment include FIGS. 36A-F (BoNT/A) and FIGS. 37A-E (BoNT/C), which are schematically illustrated in FIG. 35.

According the specific embodiments illustrated in FIGS. 36A-F and FIGS. 37A-E, the RSP is a protease cleavage site such as WELQut (SplB protease from *Staphylococcus aureus*) that allows for an N-terminally placed positively charged amino acid (such as lysine, arginine, or histidine, denoted by $X^{'''}$ in FIG. 35). There may be advantages to this specific structure. In particular, the ADD encoding sequence of the specific embodiments illustrated in FIGS. 39A-O and FIGS. 37A-E is a temperature sensitive degron. The temperature sensitive degron is a fusion protein of ubiquitin, arginine, and dihydrofolate reductase (DHFR), a heat-labile mouse-derived enzyme that functions in the synthesis of thymine, with a destabilizing N-terminal residue (such as the positively charged amino acid arginine). At 37° C., degradation of the temperature sensitive degron by the proteasome is enhanced, and the in vivo half-life of the protein is dramatically reduced (FIGS. 36A-F, FIGS. 37A-E).

It is contemplated that the enhanced degradation at human body temperatures will enhance the in vivo therapeutic utility of propeptide fusions when said therapeutic utility results from degradation of proteins targeted by specific VHH.

Figure 40E:
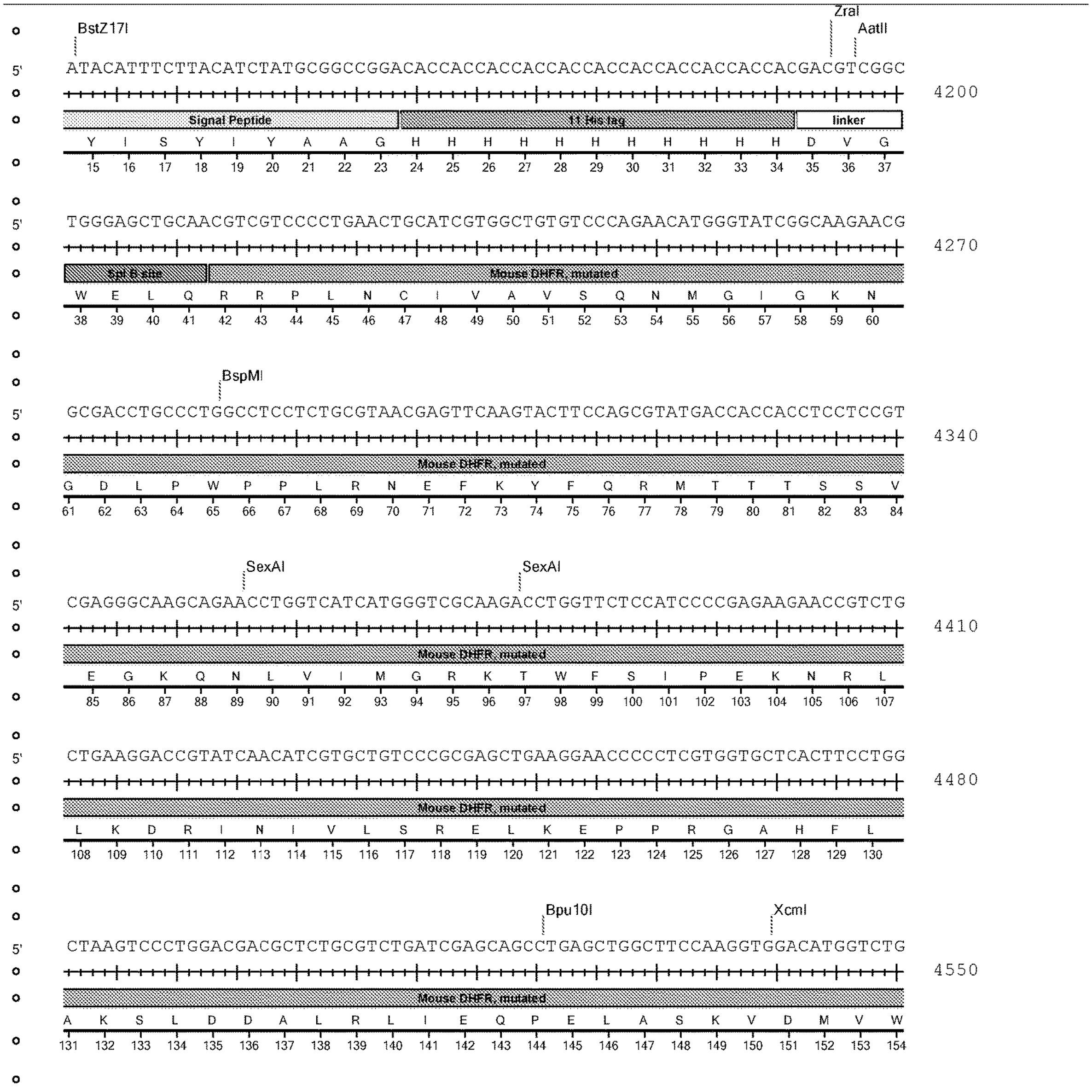
FIGS. 40A-O provide the DNA sequence (SEQ ID NO:25) of one embodiment of a DNA construct for molecular construction of fusion proteins of the present invention and the corresponding amino acid sequence (SEQ ID NO:26) of this DNA construct. The sequences of FIGS. 40A-O are specific examples of constructs encoding/having the general structure of the construct illustrated in FIG. 38C. In particular, the construct of FIGS. 40A-O encodes the BoNT/C ad-0 LC and BoNT/C HC.
Figure 40F:
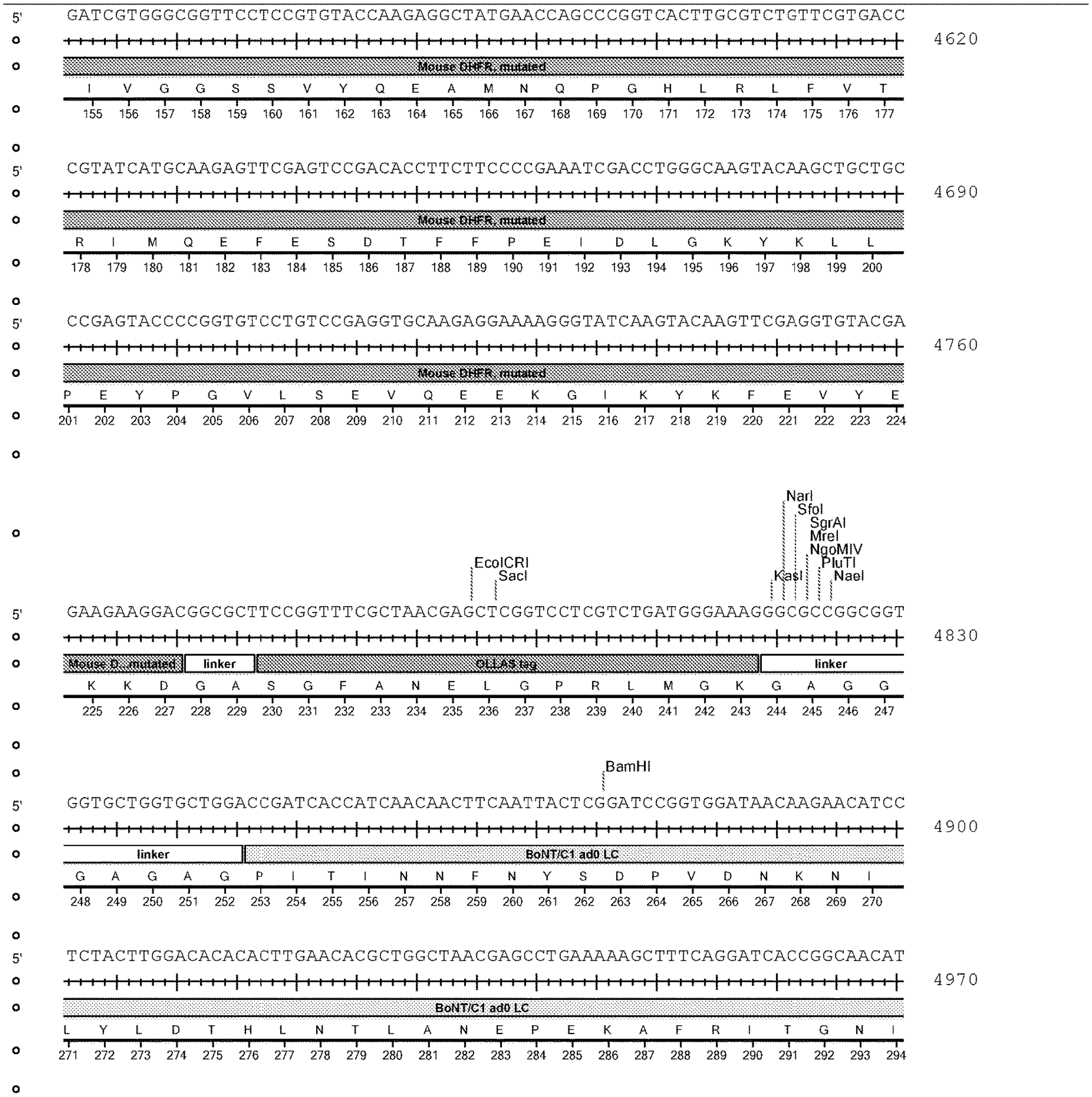
Figure 40H:
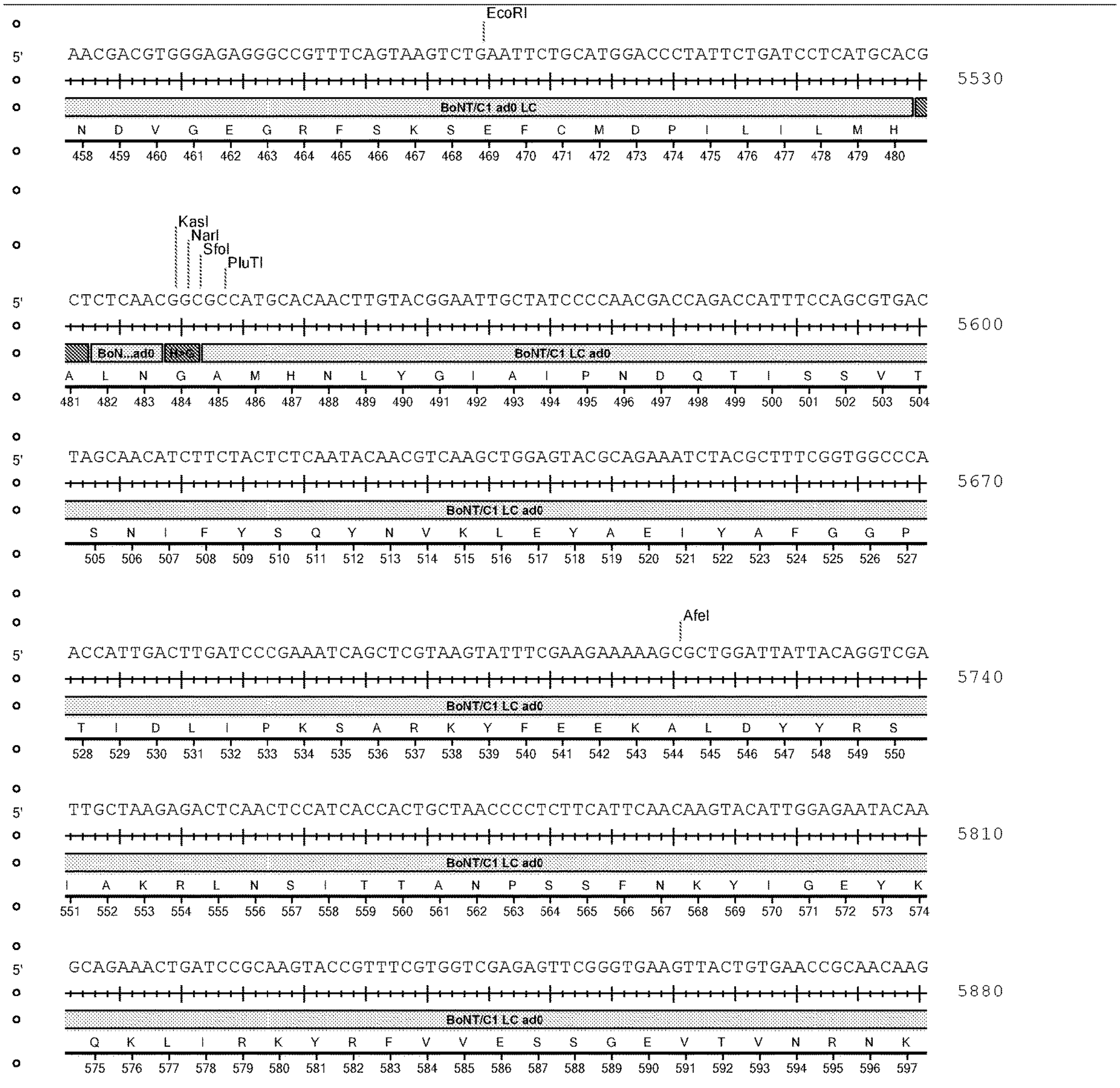

The specific embodiments illustrated in FIGS. 36A-F and FIGS. 37A-E contain two different URSs located near the N-terminal region of the BoNT LC encoding sequence. The constructs of FIG. 35 (FIGS. 36A-F, FIGS. 37A-E) can be cloned into the constructs of FIG. 32 (FIGS. 33A-N, FIGS. 34A-N), where (i) the recipient construct depicted in FIG. 38A has URSs that, when digested, produce single stranded "sticky" overhangs complementary to those produced by (ii) digestion of the donor construct depicted in FIG. 38B at corresponding URSs (dashed lines, FIG. 38A-38B), resulting in (iii) a construct with an RSP and ADD encoding sequence upstream of the BoNT LC encoding sequence, an RSP between the BoNT LC encoding sequence and BoNT HC encoding sequence, an RSP downstream of the BoNT HC encoding sequence, and optional tags and spacer sequences. Specific non-limiting examples of the embodiment illustrated in FIG. 38C include FIGS. 39A-O (BoNT/A) and FIGS. 40A-O (BoNT/C).

Figure 41:
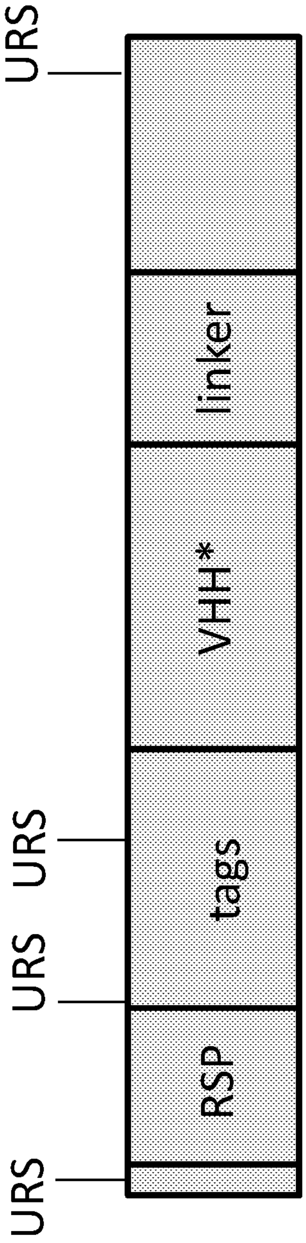
FIG. 41 is a schematic illustration of one embodiment of a DNA construct used for molecular construction of fusion proteins of the present invention. In particular.
Figure 43A:
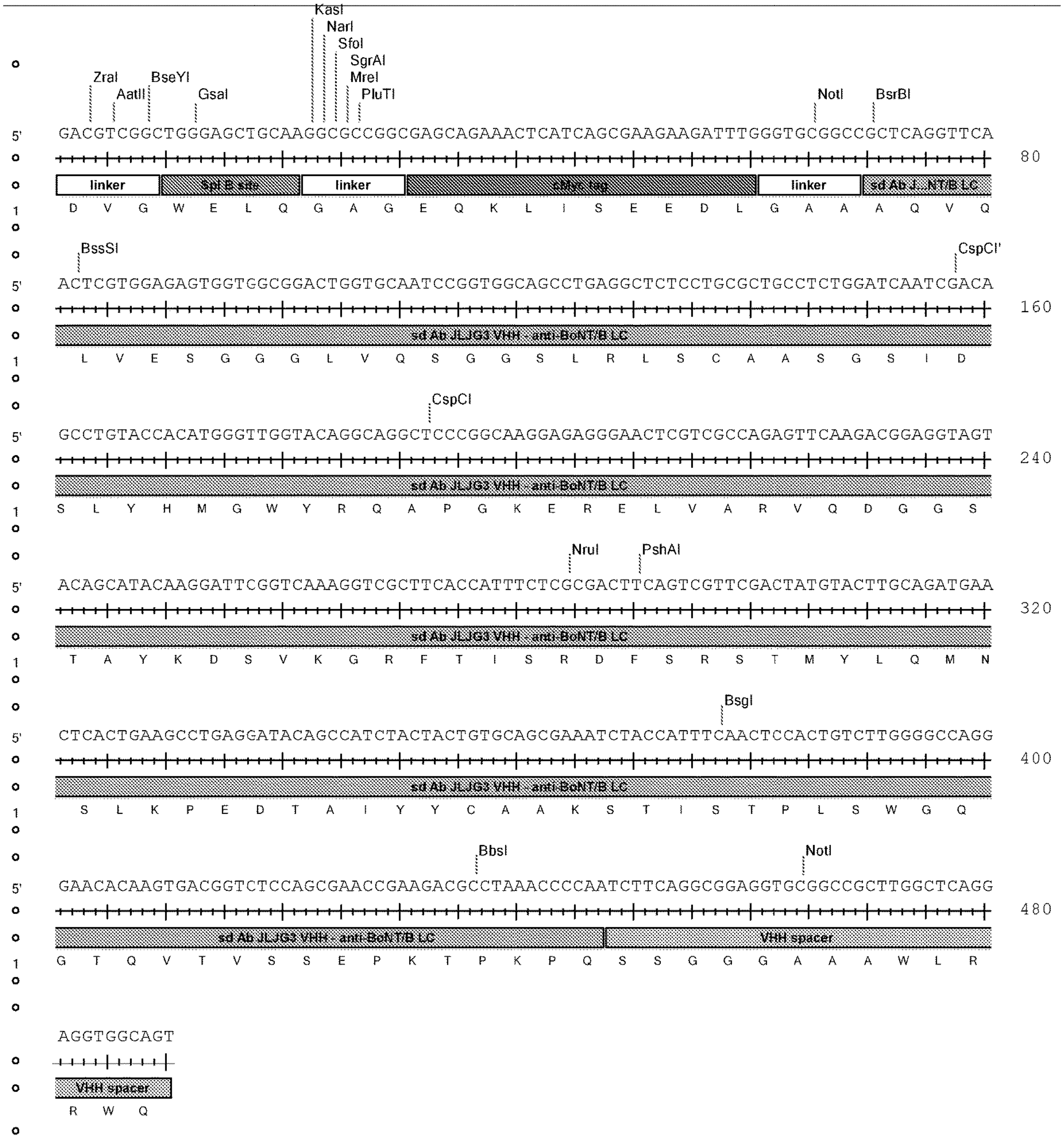
Figure 44A:
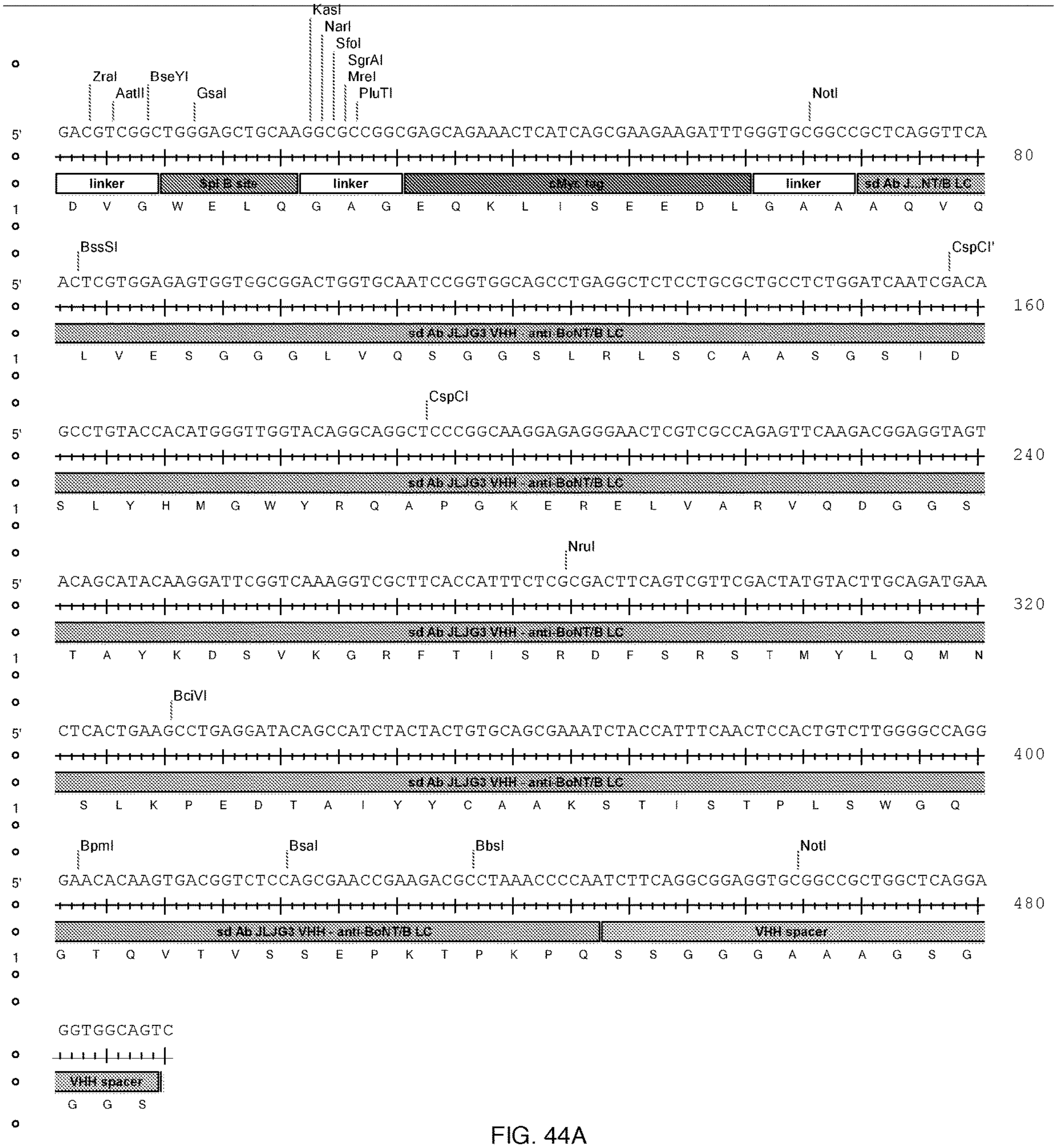
FIGS. 44A-B provide the DNA sequence (SEQ ID NO:31) of one embodiment of a DNA construct for molecular construction of fusion proteins of the present invention and the corresponding amino acid sequence (SEQ ID NO:32) of this DNA construct. The sequences of FIGS. 44A-B are specific examples of constructs encoding/having the general structure of the construct illustrated in FIG. 41. In particular, the construct of FIGS. 44A-B encodes for the JLJG3 VHH against BoNT/B LC and the JNE-B10 VHH against BoNT/B LC in the VHH region.
Figure 44B:
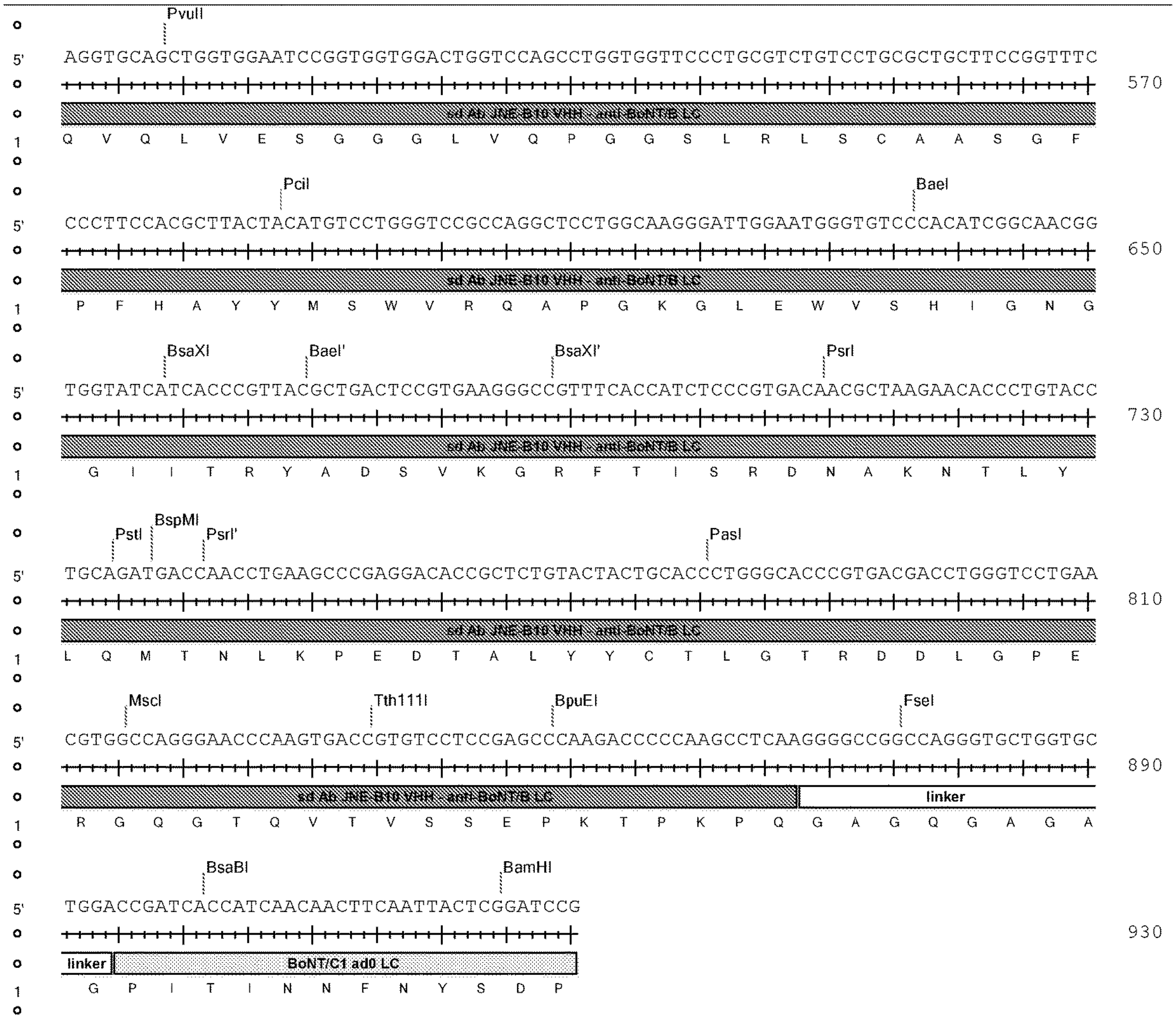
Figure 45A:
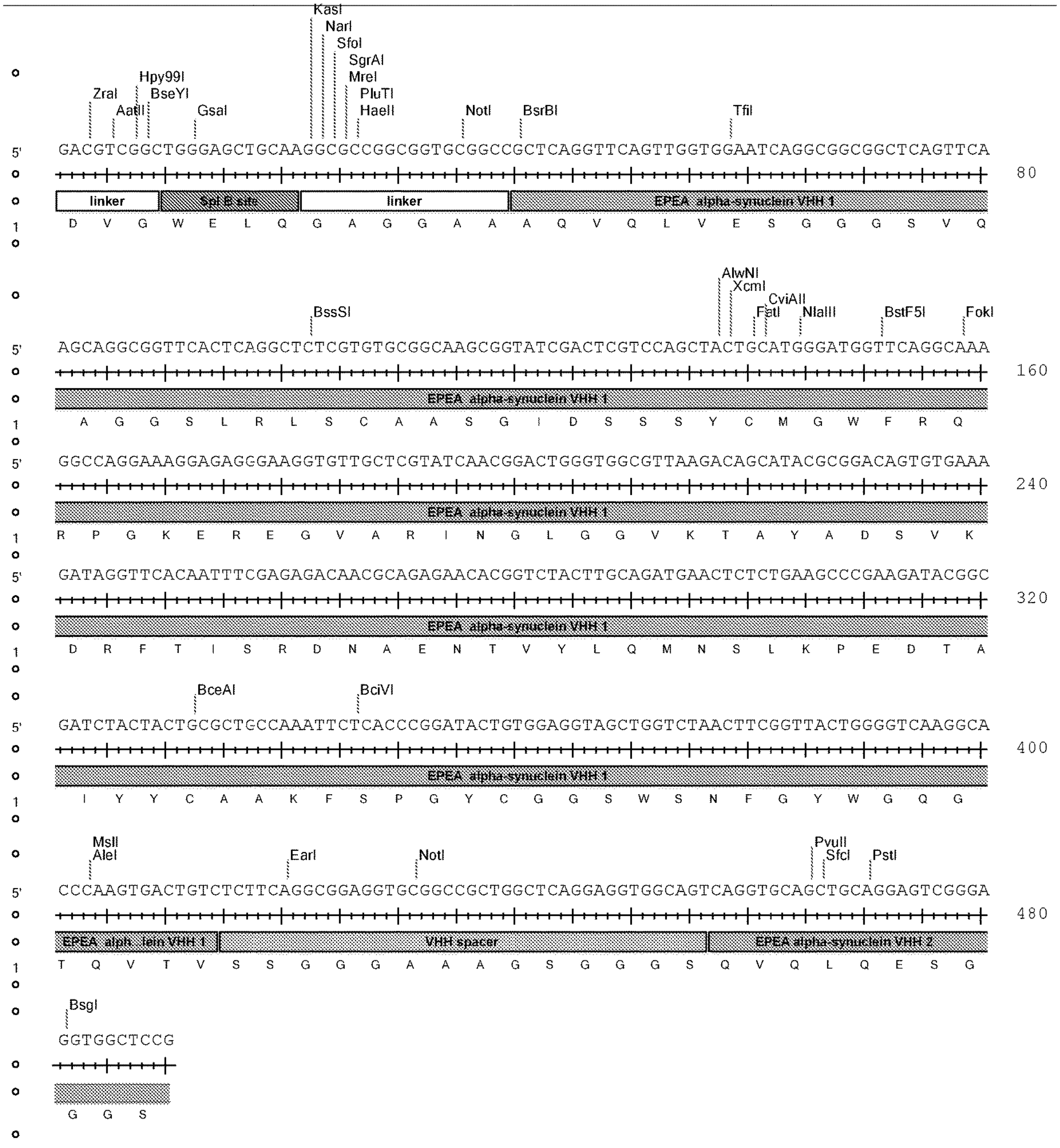
Figure 48G:
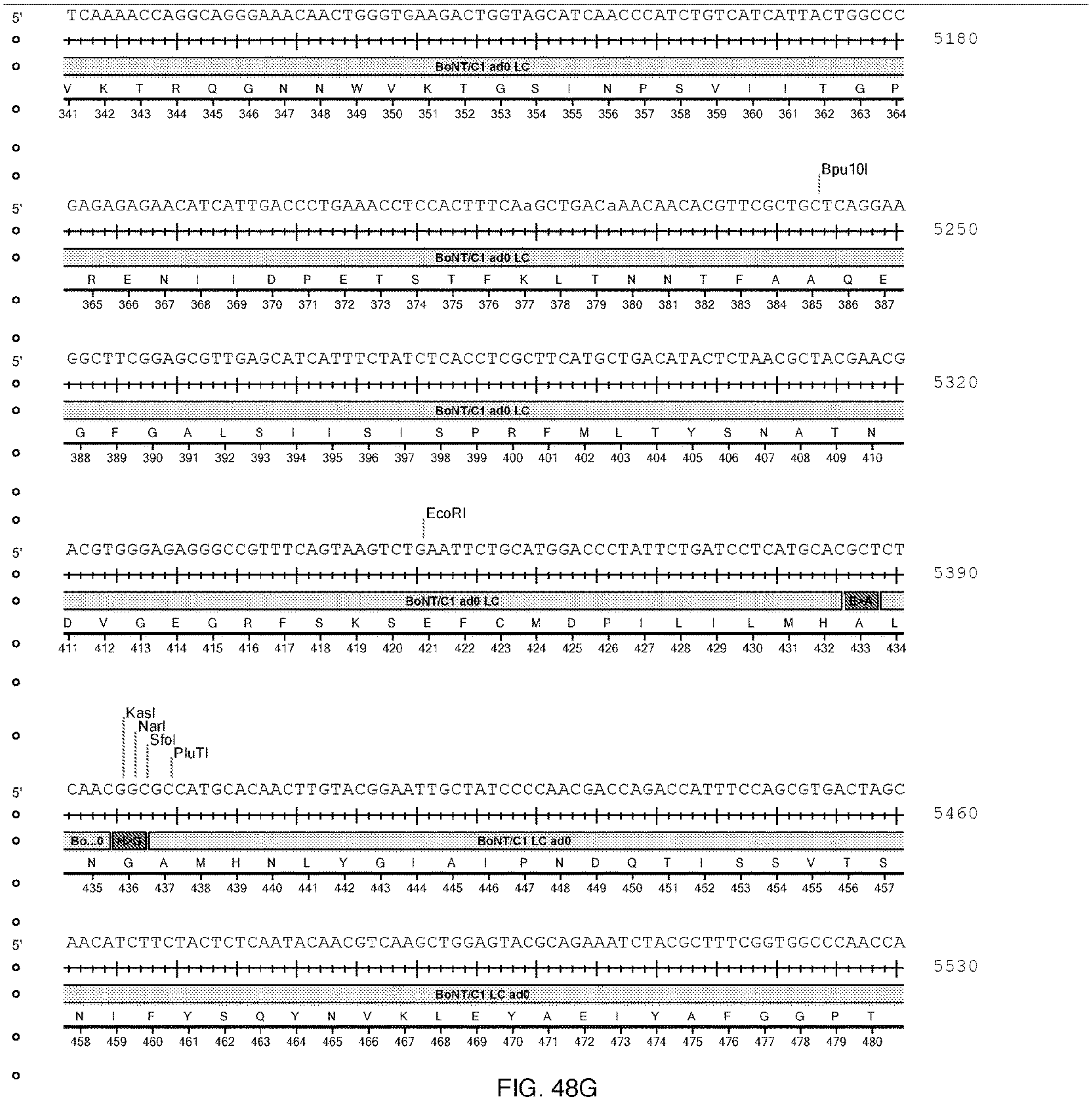
FIGS. 48A-O provide the DNA sequence (SEQ ID NO:35) of one embodiment of a DNA construct for molecular construction of fusion proteins of the present invention and the corresponding amino acid sequence (SEQ ID NO:36) of this DNA construct. The sequences of FIGS. 48A-O are specific examples of constructs encoding/having the general structure of the construct illustrated in FIG. 46C, with the construct described in FIG. 42 as the donor sequence, and the construct described in FIGS. 40A-O as the recipient sequence using URSs ZraI and BamHI.
Figure 48H:
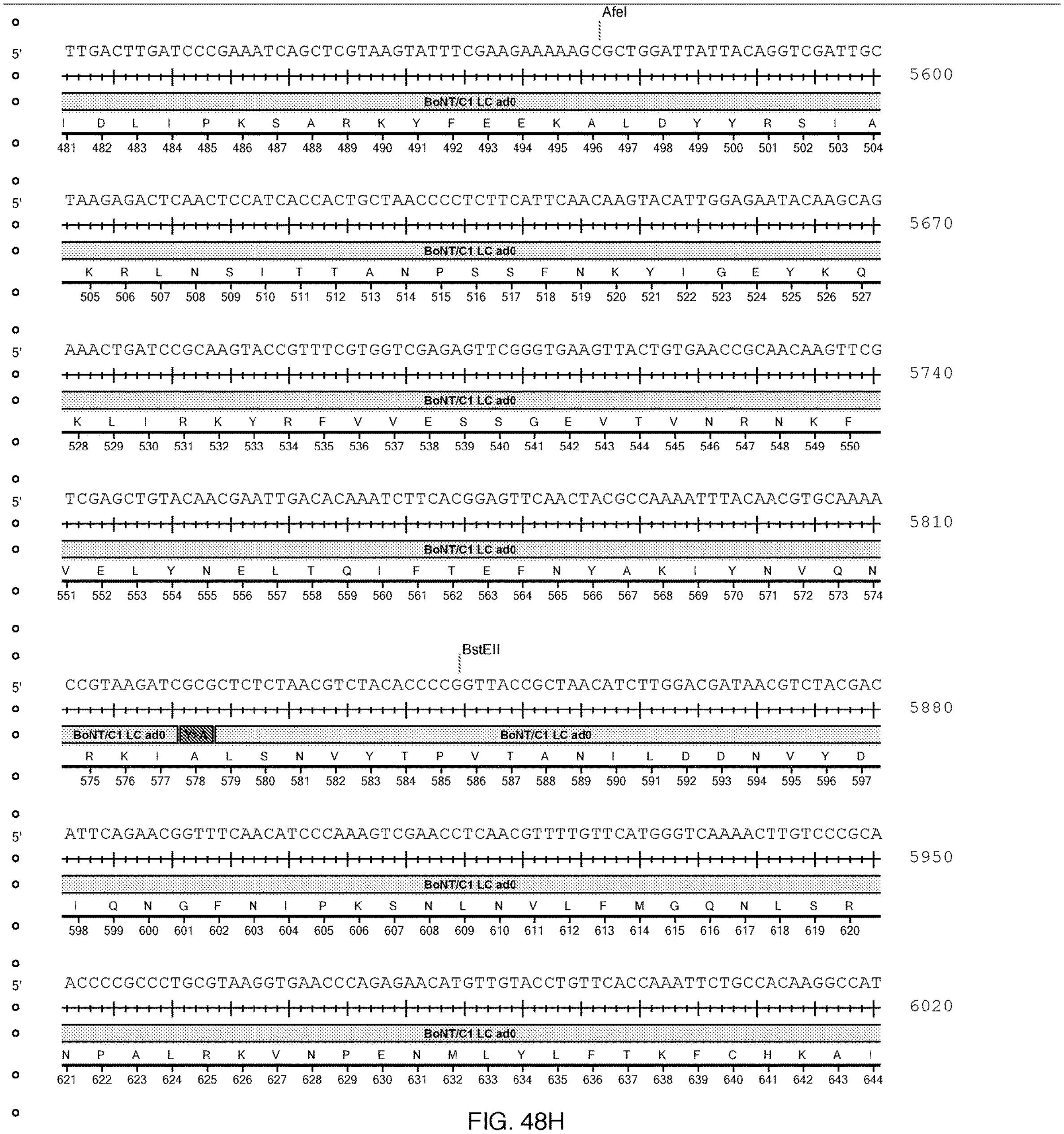
Figure 48I:
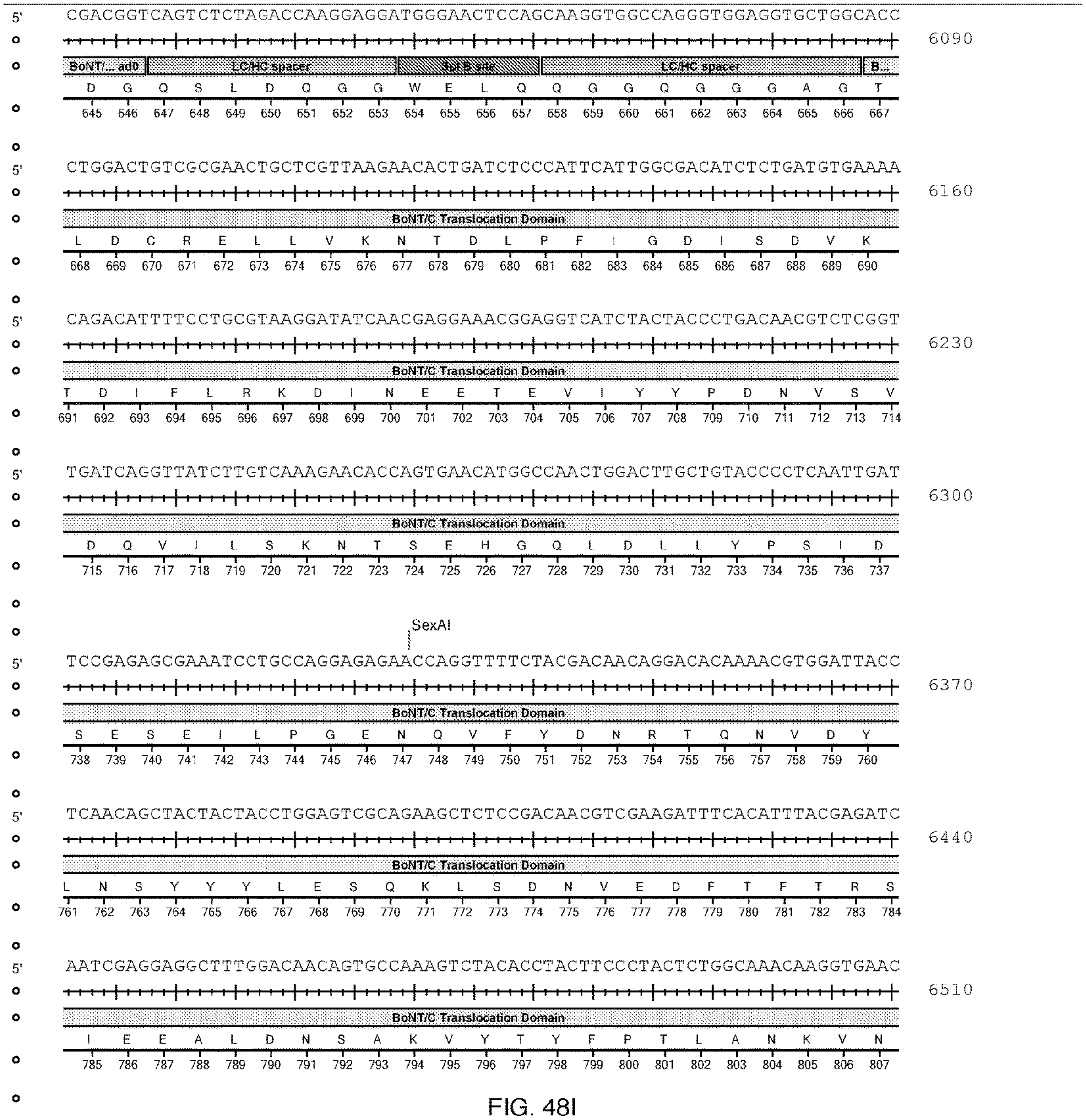
Figure 48J:
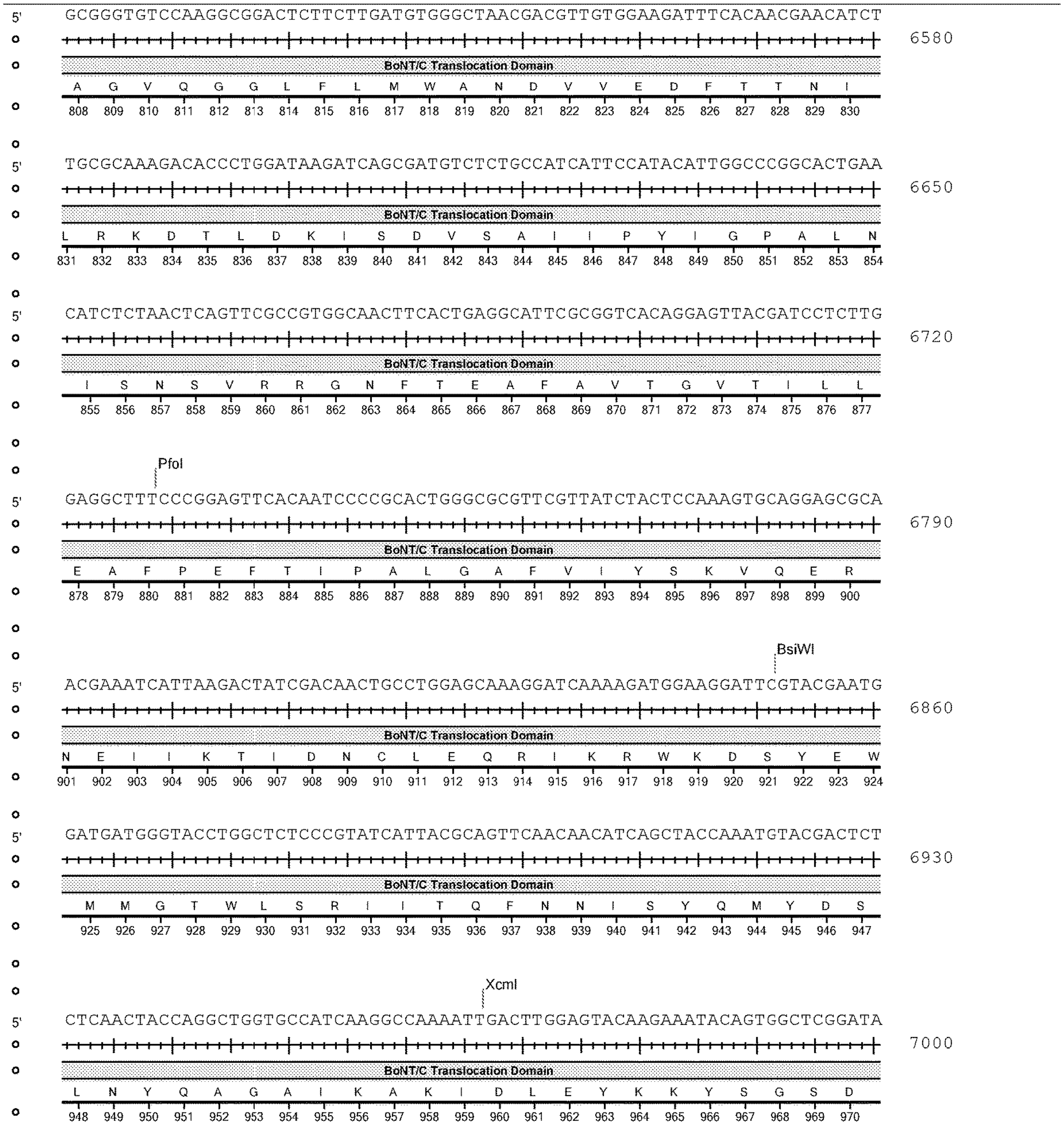
Figure 49D:
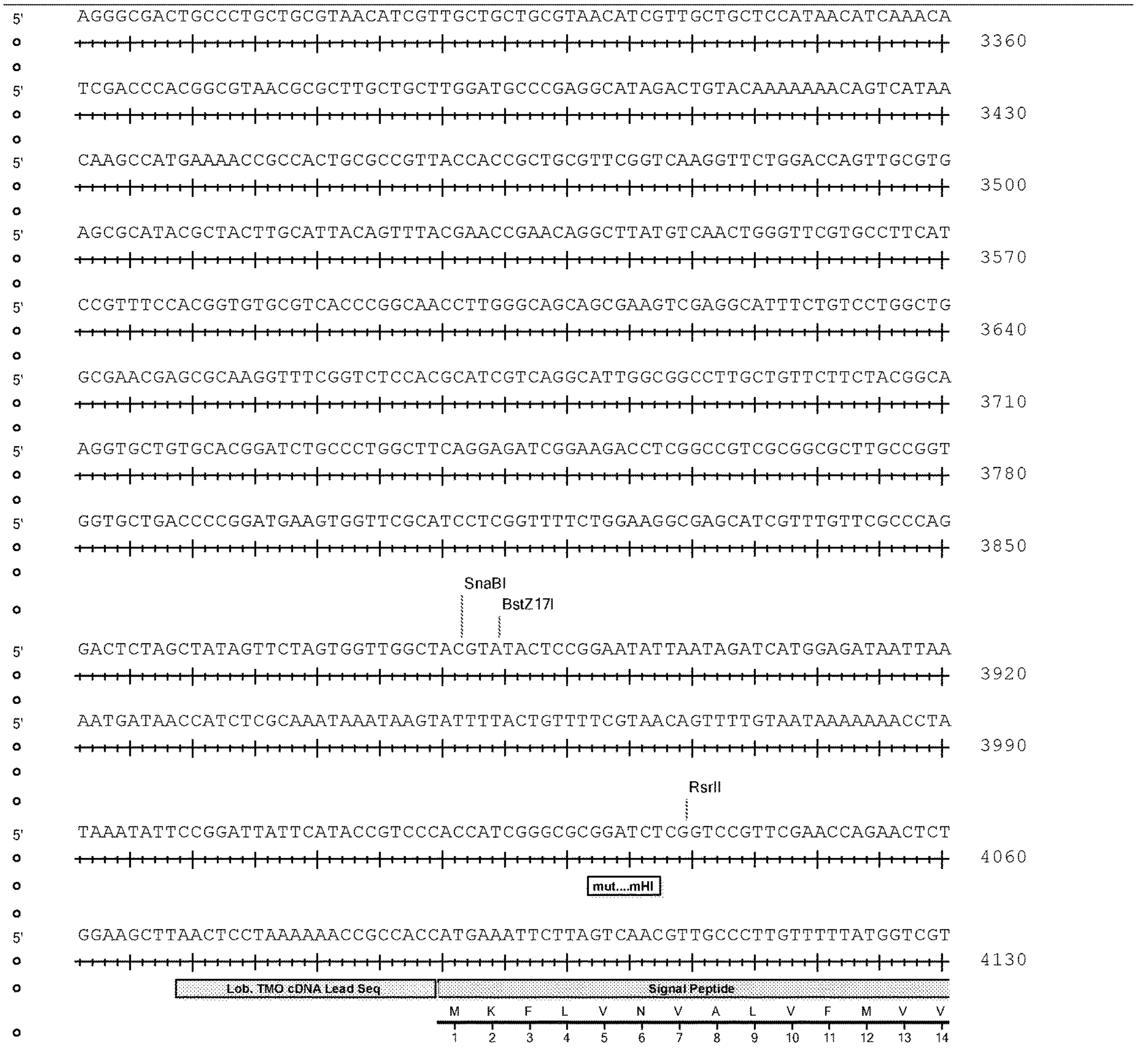
FIGS. 49A-P provide the DNA sequence (SEQ ID NO:37) of one embodiment of a DNA construct for molecular construction of fusion proteins of the present invention and the corresponding amino acid sequence (SEQ ID NO:38) of this DNA construct. The sequences of FIGS. 49A-P are specific examples of constructs encoding/having the general structure of the construct illustrated in FIG. 47C, with the sequence described in FIG. 42 as the donor sequence, and the construct described in FIGS. 40A-O as the recipient sequence using URSs SgrAI and BamHI.
Figure 49E:
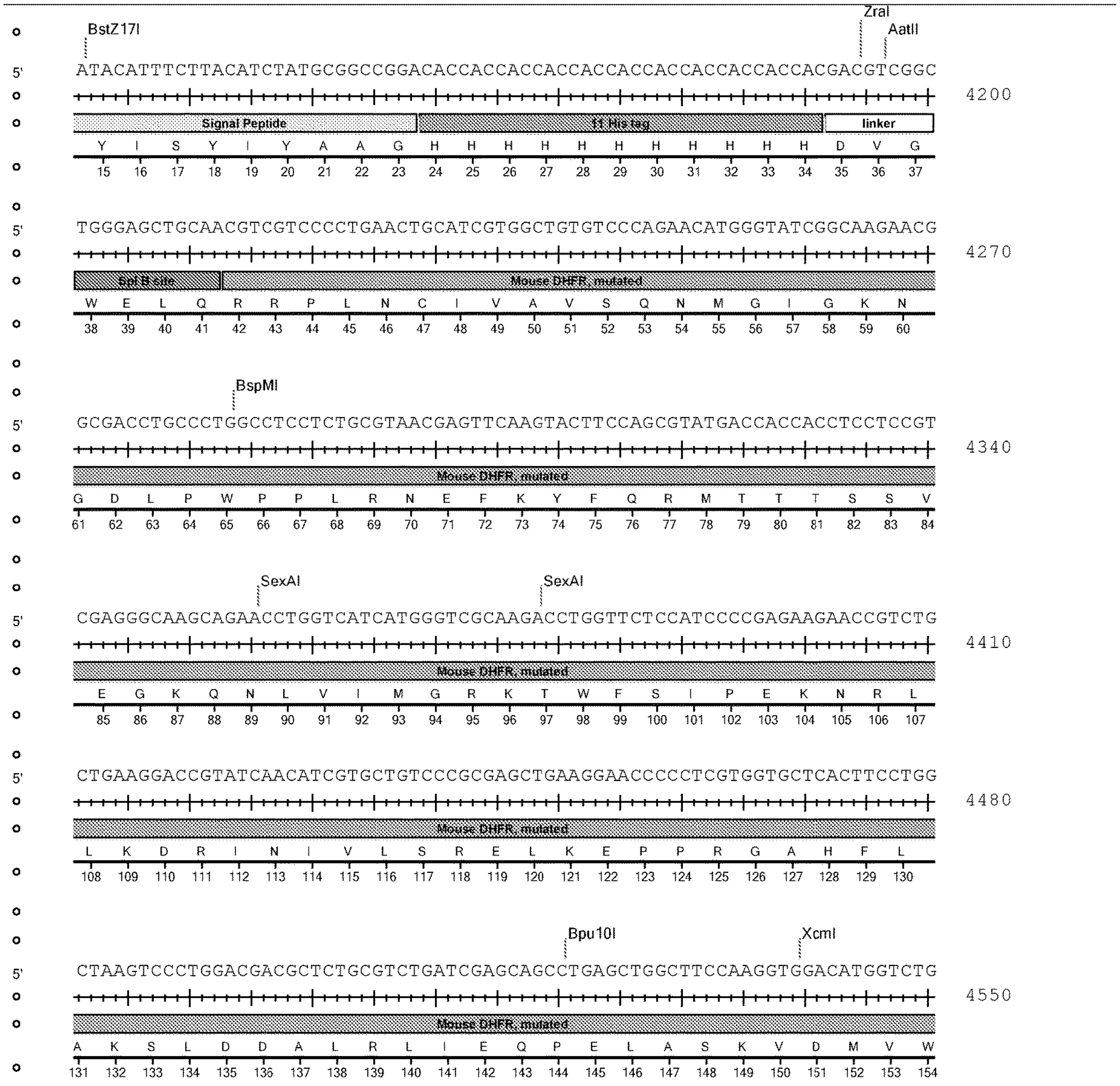
Figure 49F:
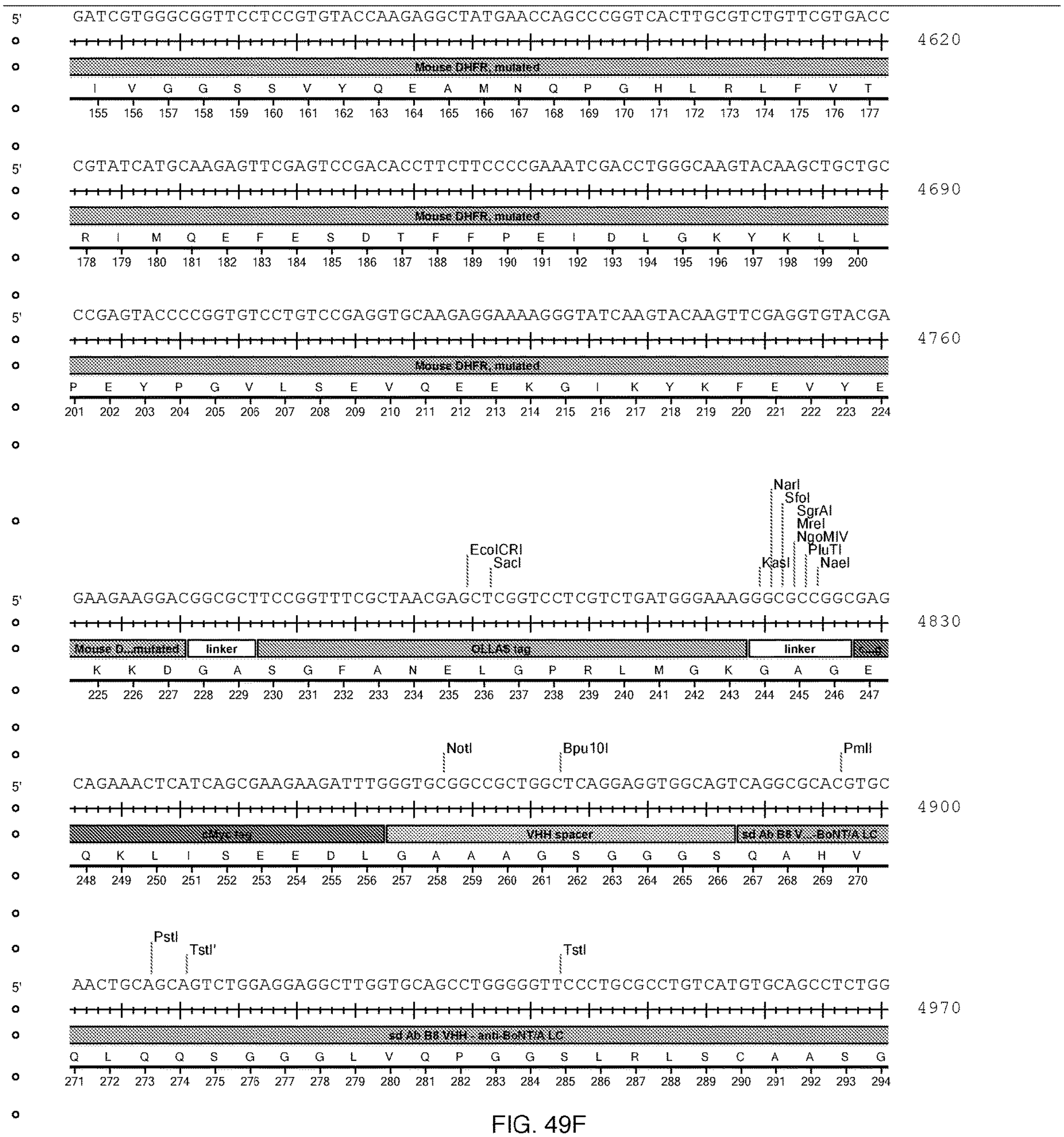
Figure 50D:
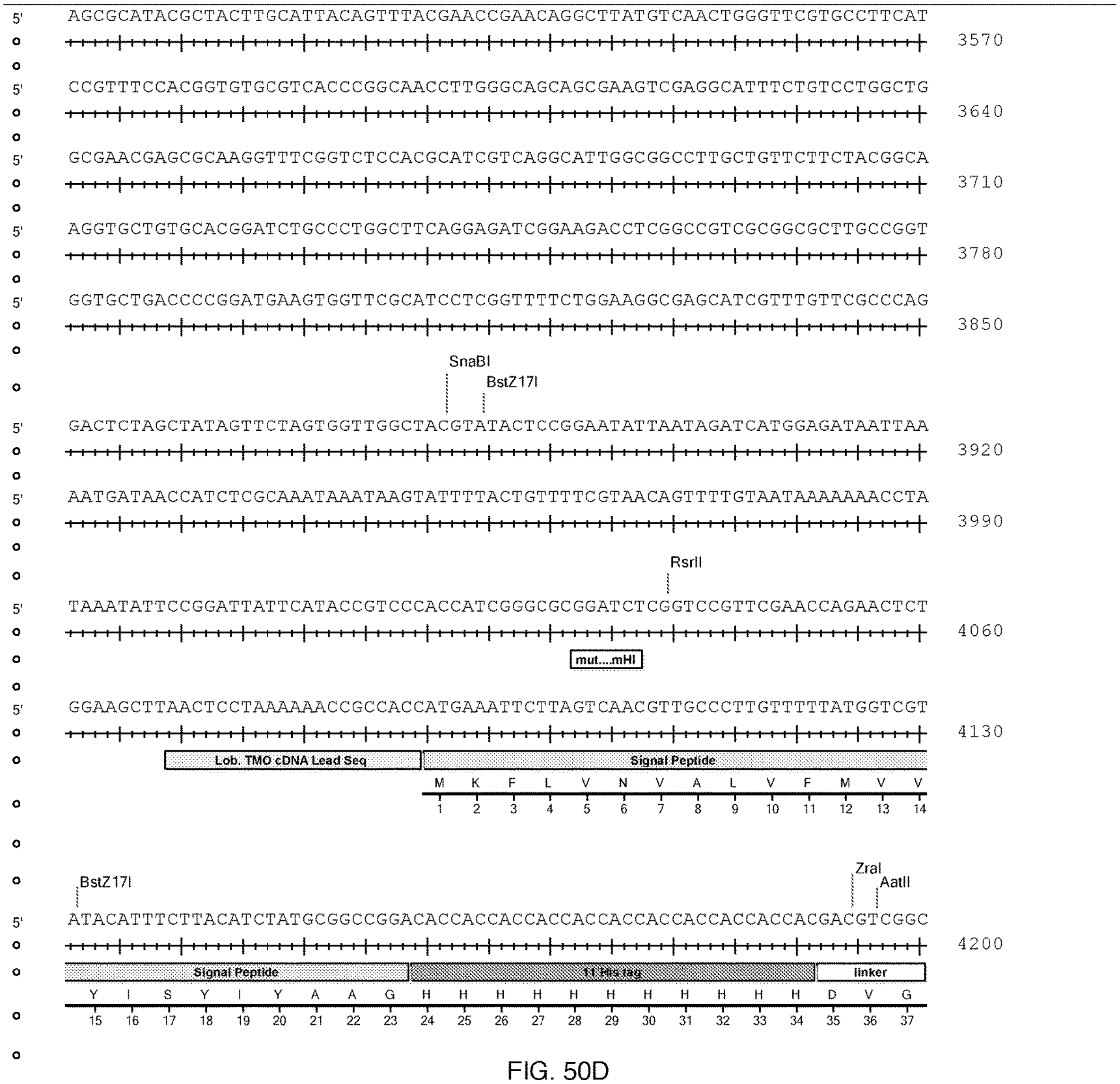
FIGS. 50A-P provide the DNA sequence (SEQ ID NO:39) of one embodiment of a DNA construct for molecular construction of fusion proteins of the present invention and the corresponding amino acid sequence (SEQ ID NO:40) of this DNA construct. The sequences of FIGS. 50A-P are specific examples of constructs encoding/having the general structure of the construct illustrated in FIG. 46C, with the sequence described in FIGS. 43A-B as the donor sequence, and the sequence described in FIGS. 40A-O as the recipient sequence using URSs ZraI and BamHI.
Figure 50E:
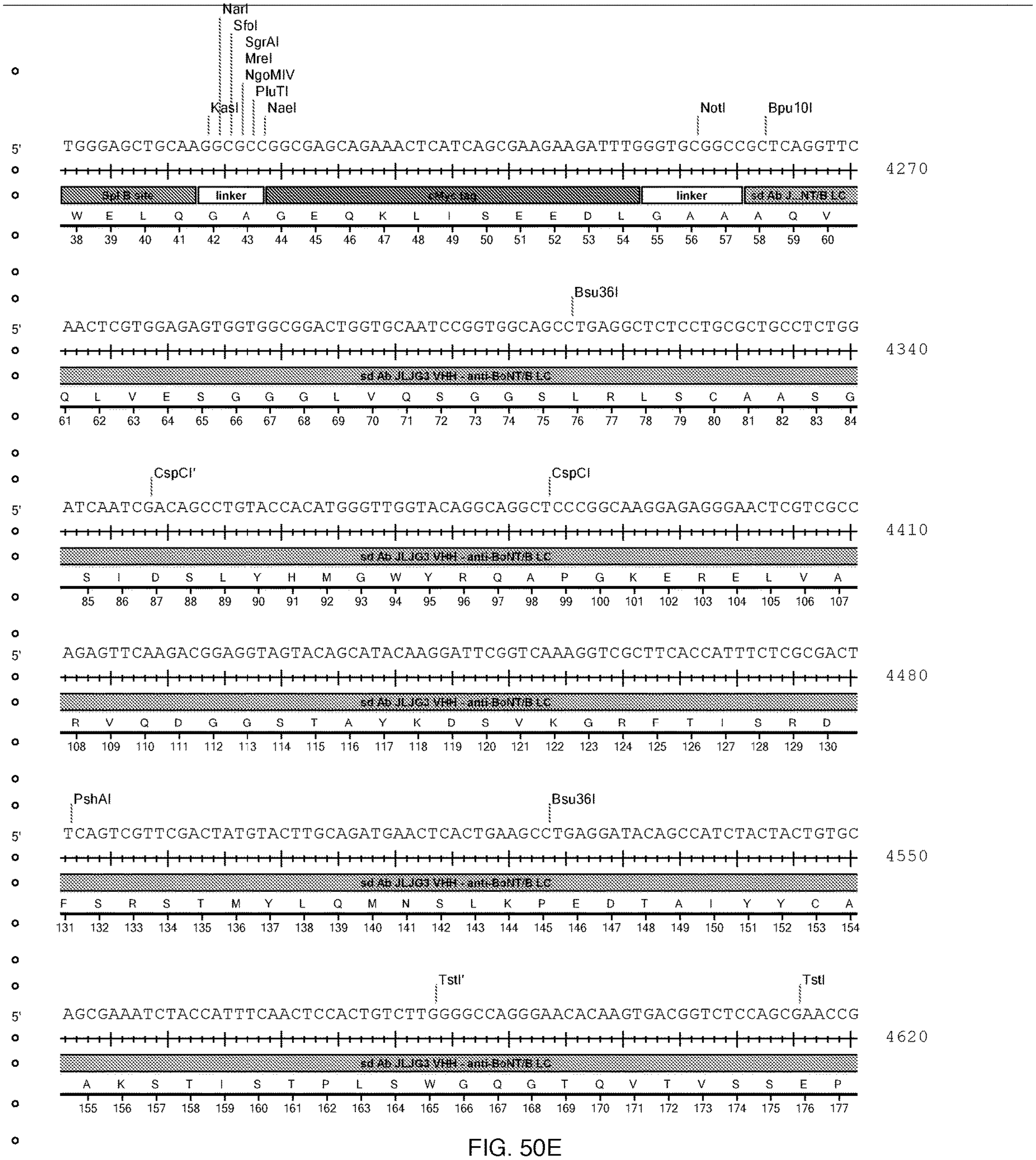
Figure 50F:
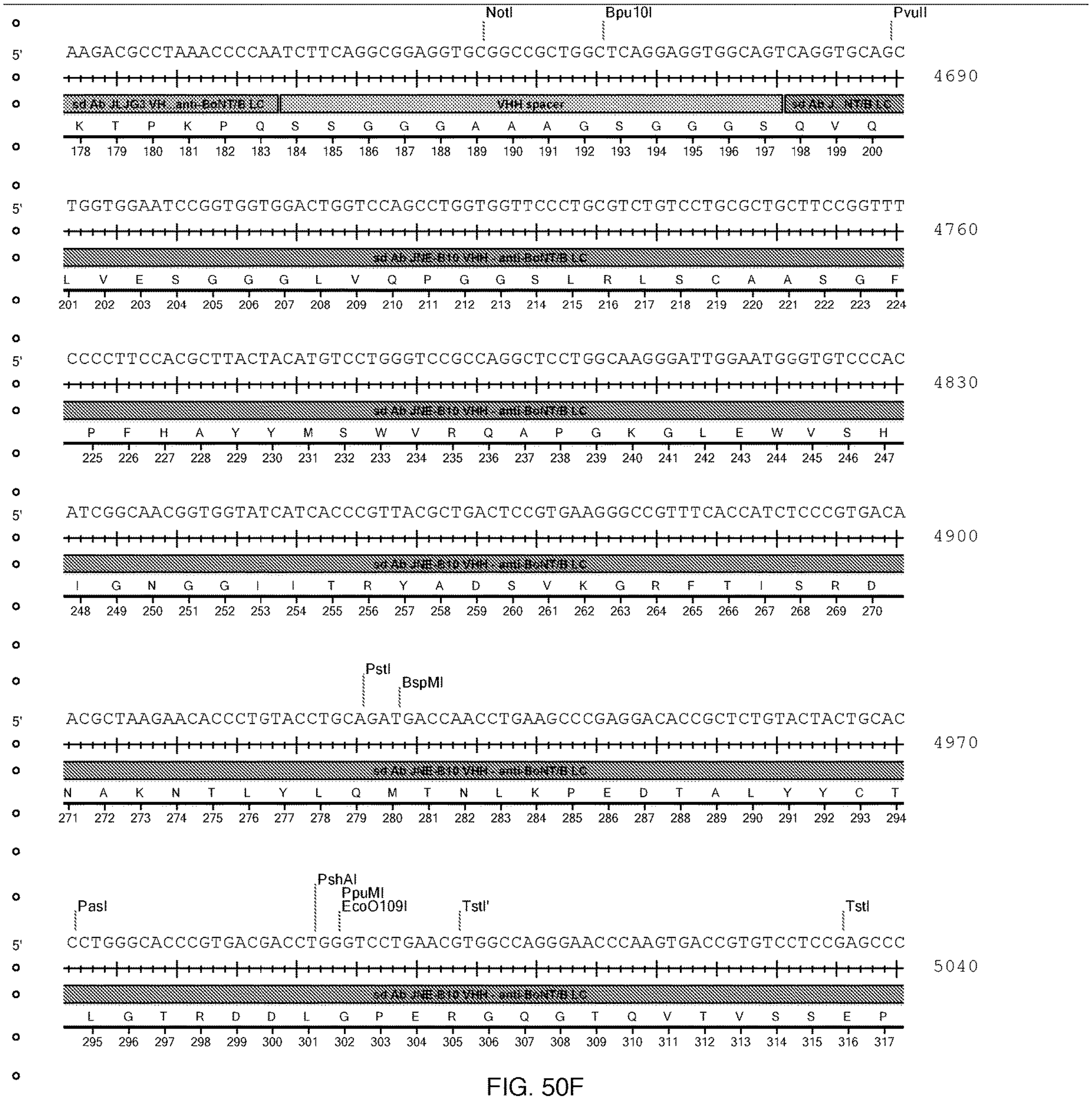
Figure 50L:
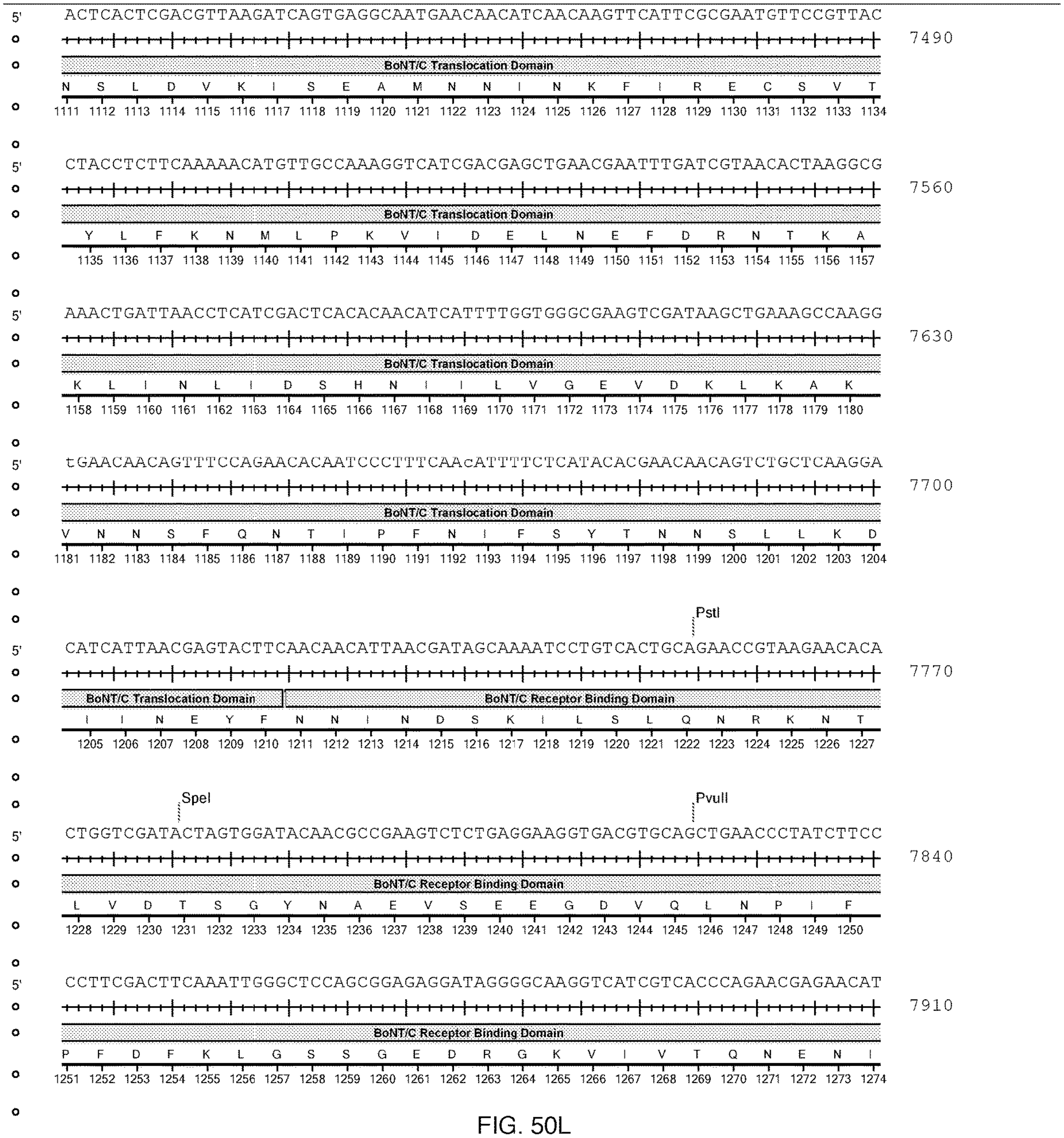
Figure 51E:
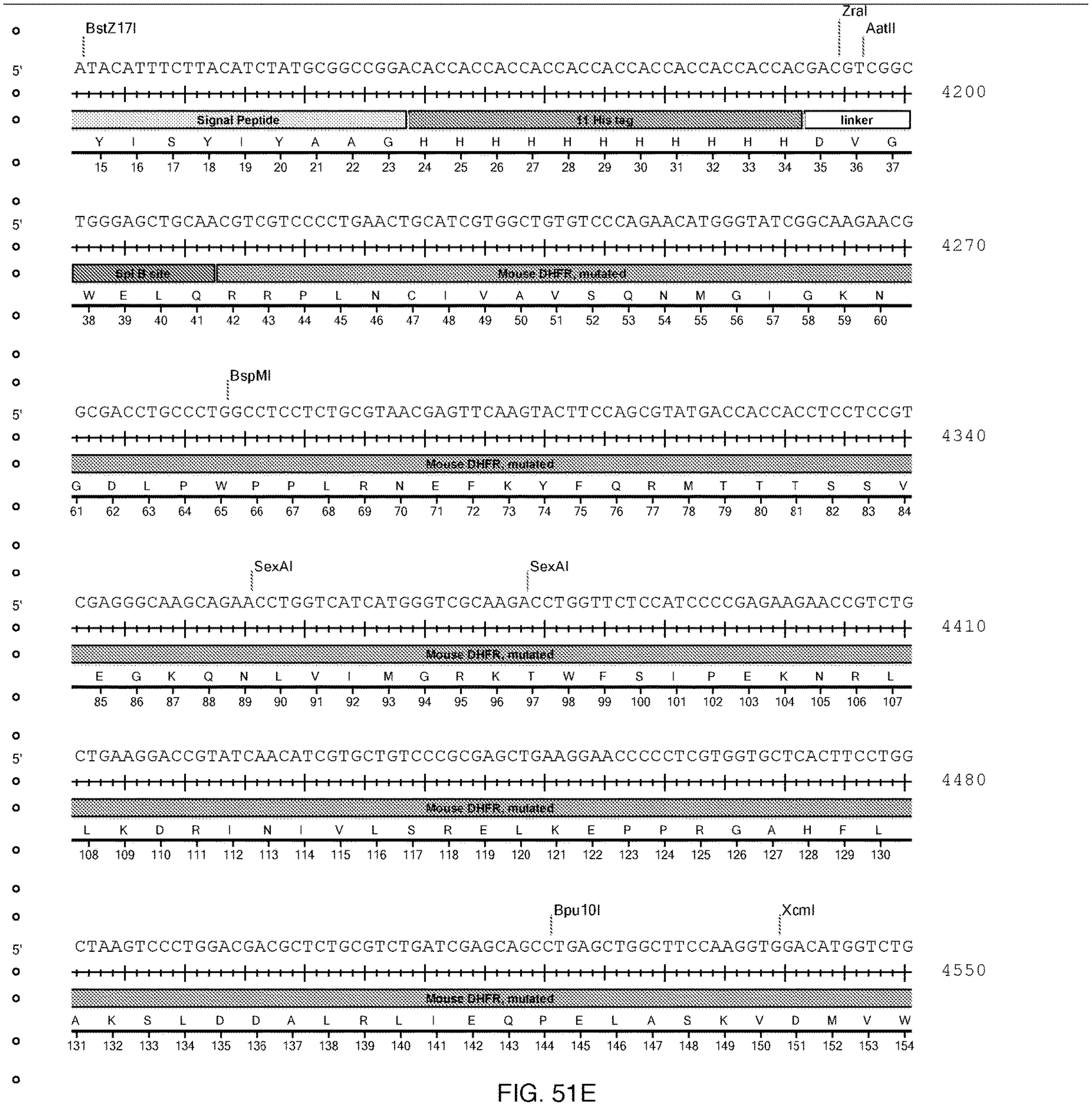
FIGS. 51A-Q provide the nucleotide sequence (SEQ ID NO:41) of one embodiment of a DNA construct for molecular construction of fusion proteins of the present invention and the corresponding amino acid sequence (SEQ ID NO:42) of this DNA construct. The sequences of FIGS. 51A-Q are specific examples of constructs encoding/having the general structure of the construct illustrated in FIG. 47C, with the sequence described in FIGS. 43A-B as the donor sequence, and the sequence described in FIGS. 40A-O as the recipient sequence using URSs SgrAI and BamHI.
Figure 51F:
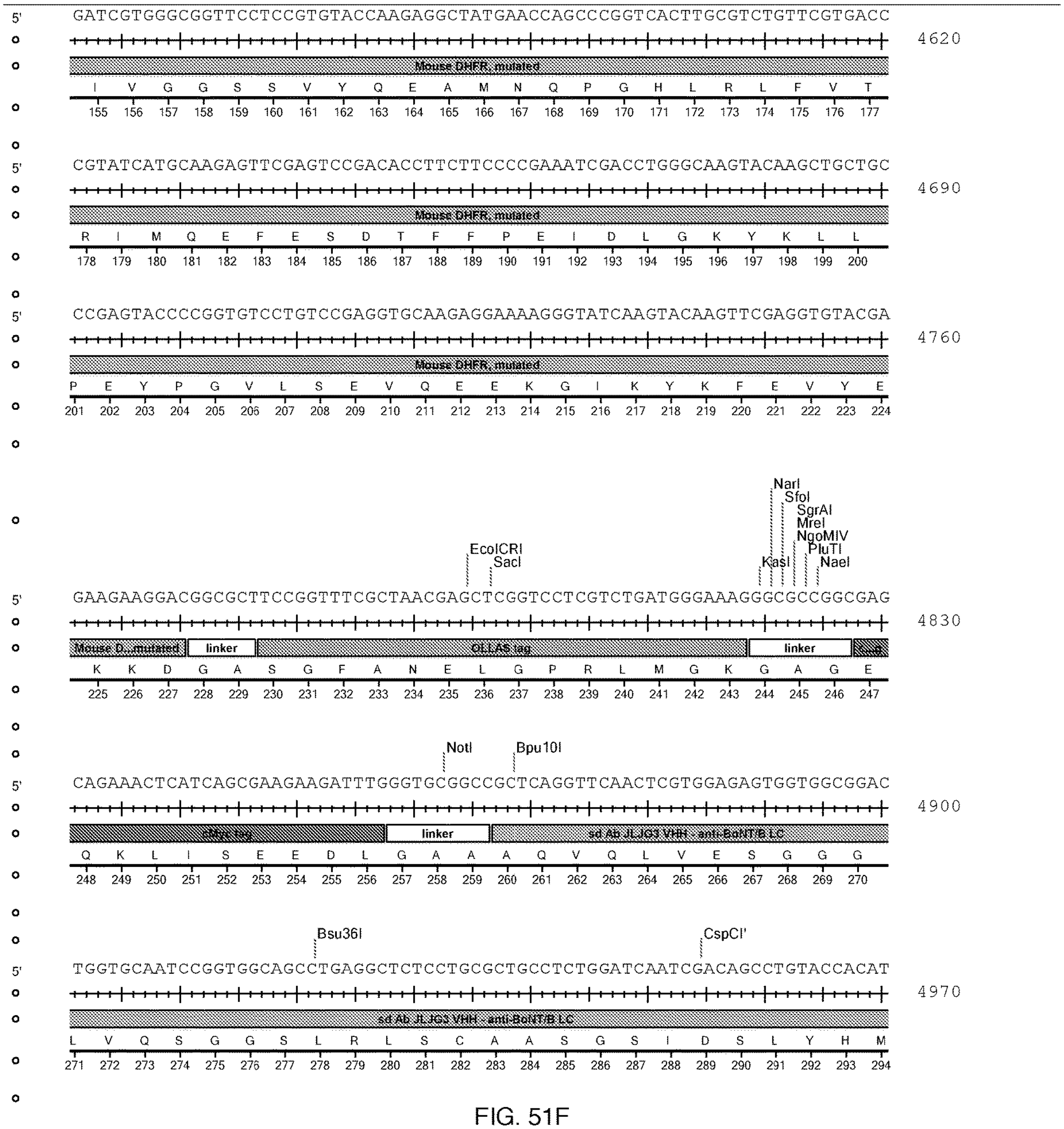
Figure 51H:
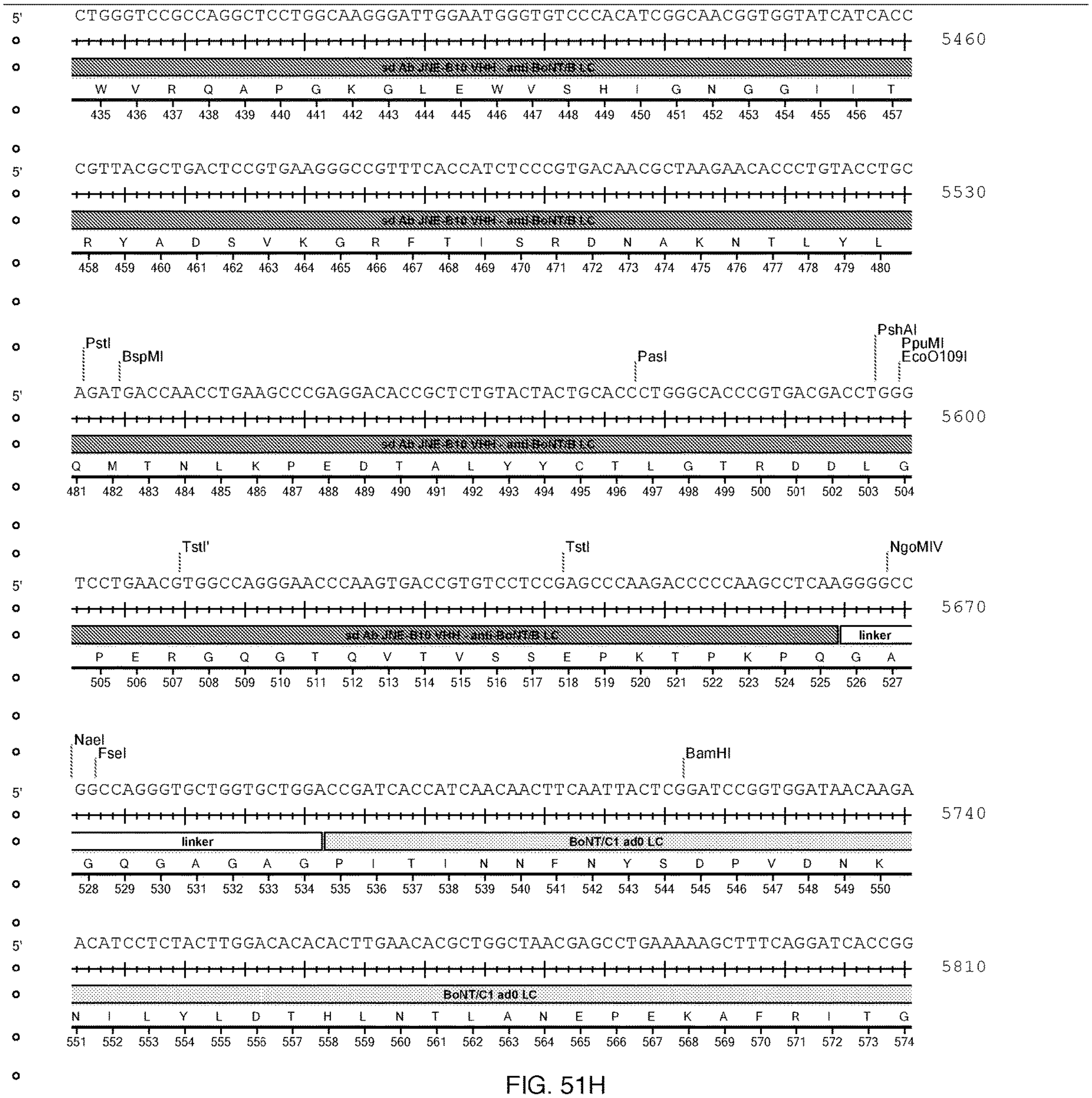
Figure 52E:
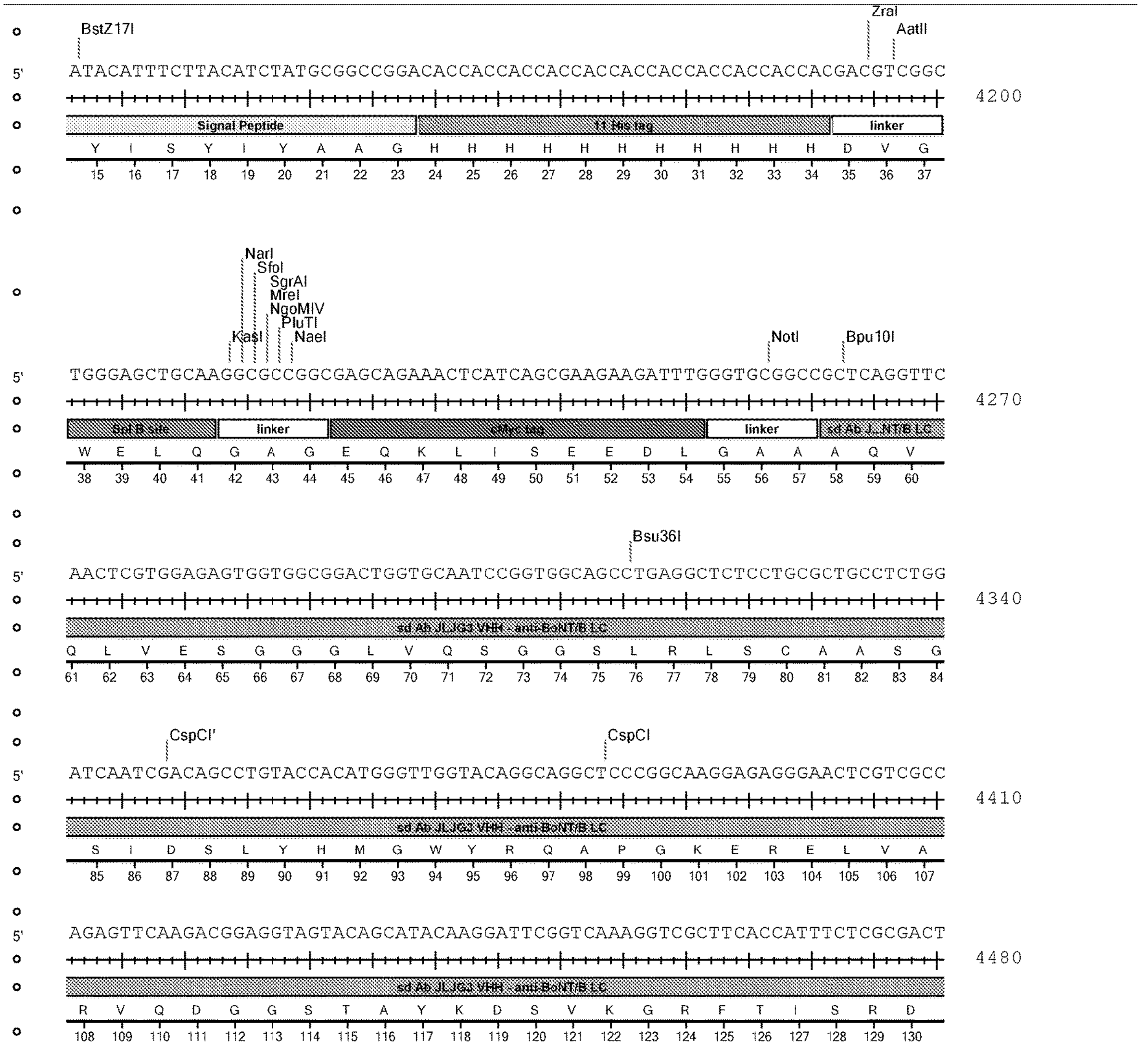
FIGS. 52A-P provide the nucleotide sequence (SEQ ID NO:43) of one embodiment of a DNA construct for molecular construction of fusion proteins of the present invention and the corresponding amino acid sequence (SEQ ID NO:44) of this DNA construct. The sequences of FIGS. 52A-P are specific examples of constructs having the general structure of the construct illustrated in FIG. 46C, with the sequence described in FIGS. 44A-B as the donor sequence, and the sequence described in FIGS. 40A-O as the recipient sequence using URSs ZraI and BamHI.
Figure 52F:
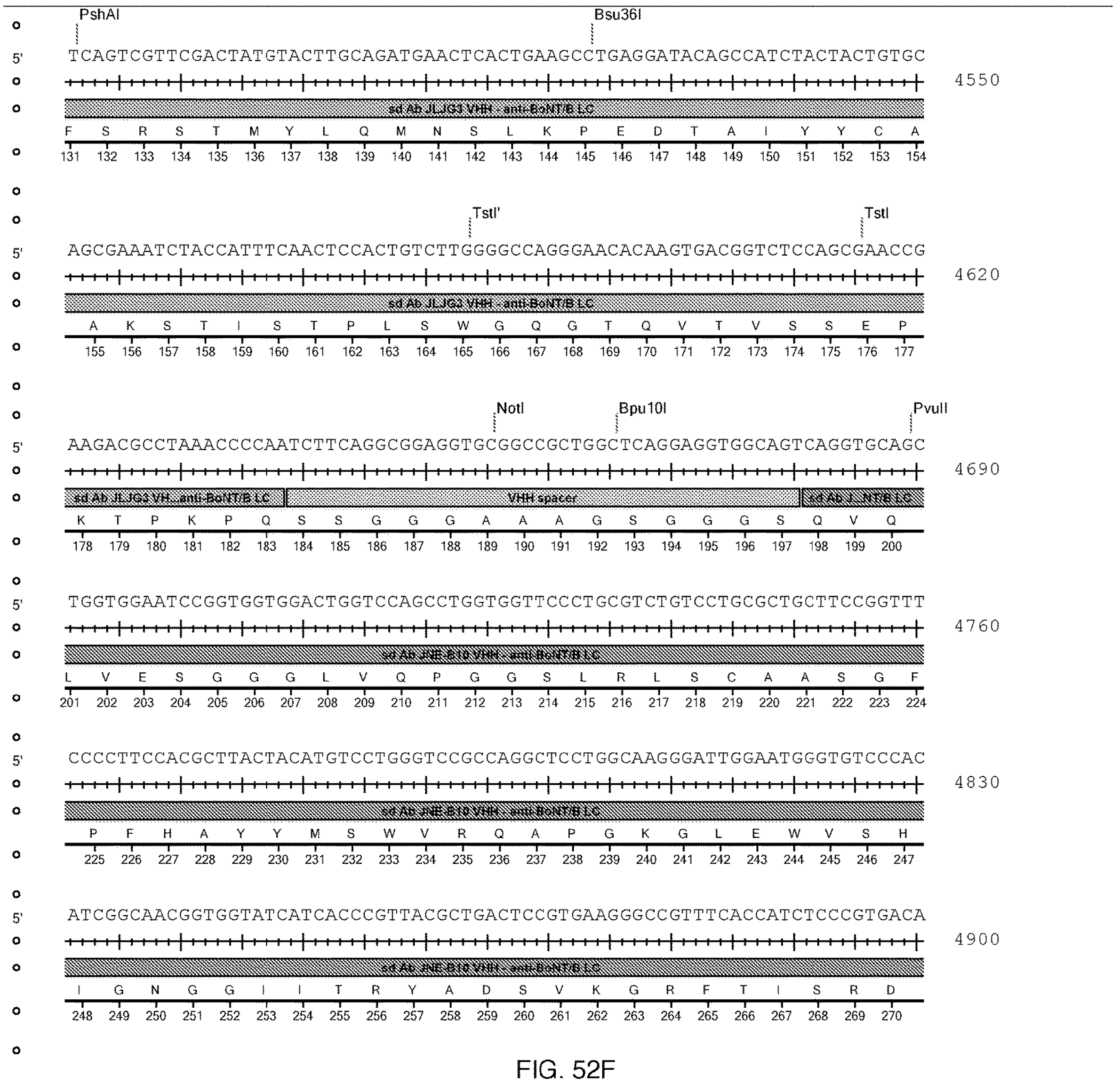
Figure 52G:
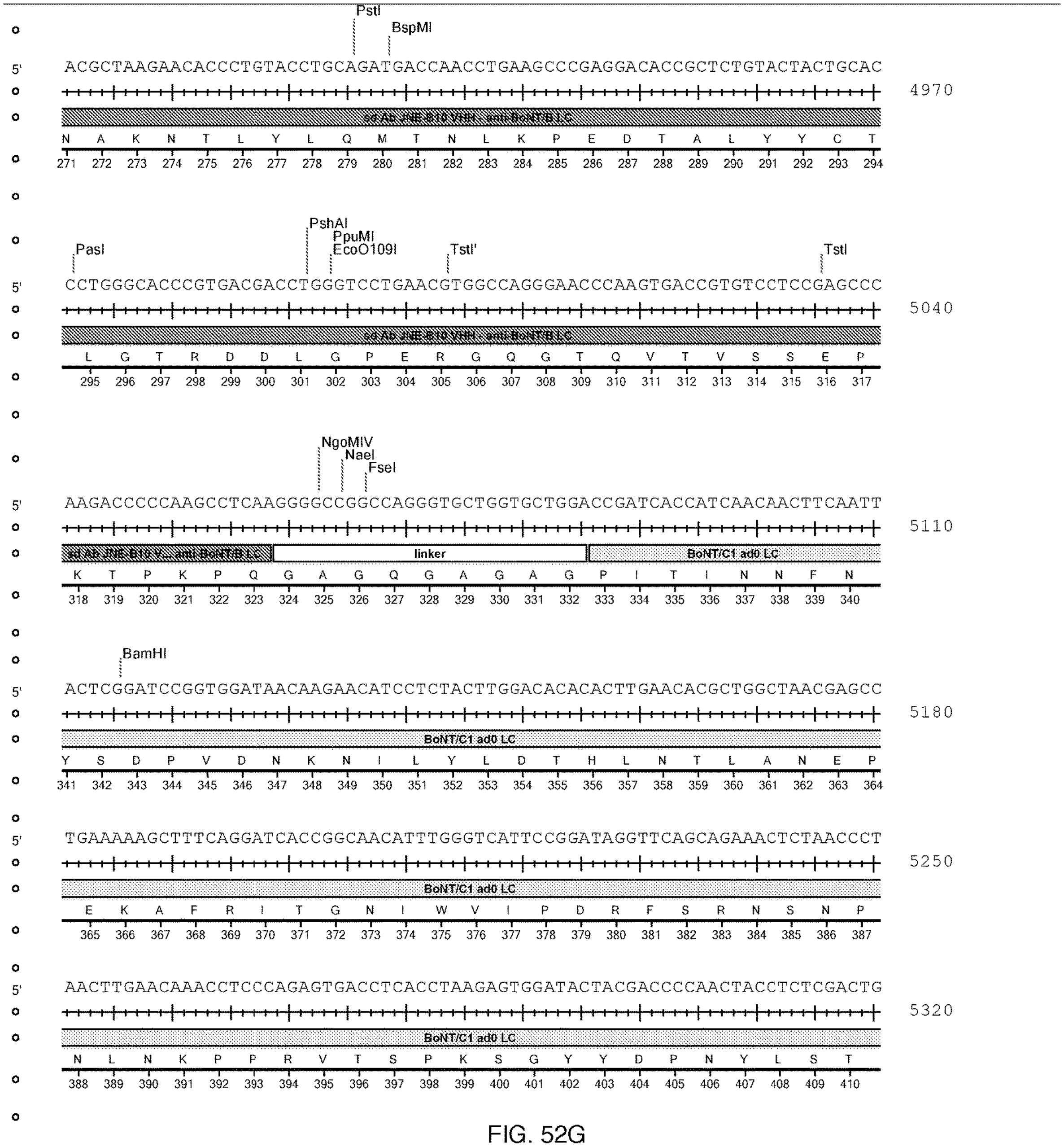
Figure 52I:
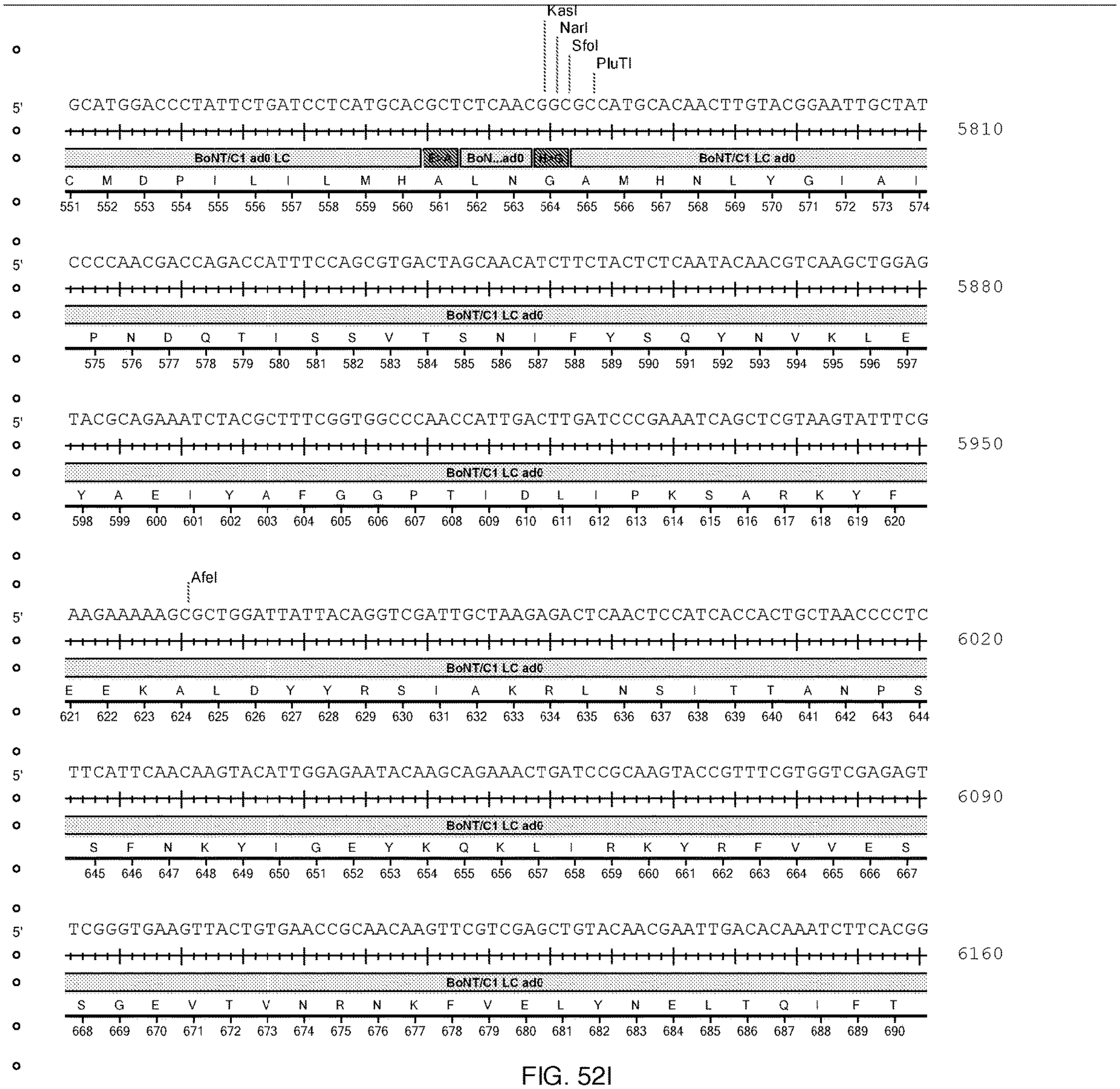
Figure 53E:
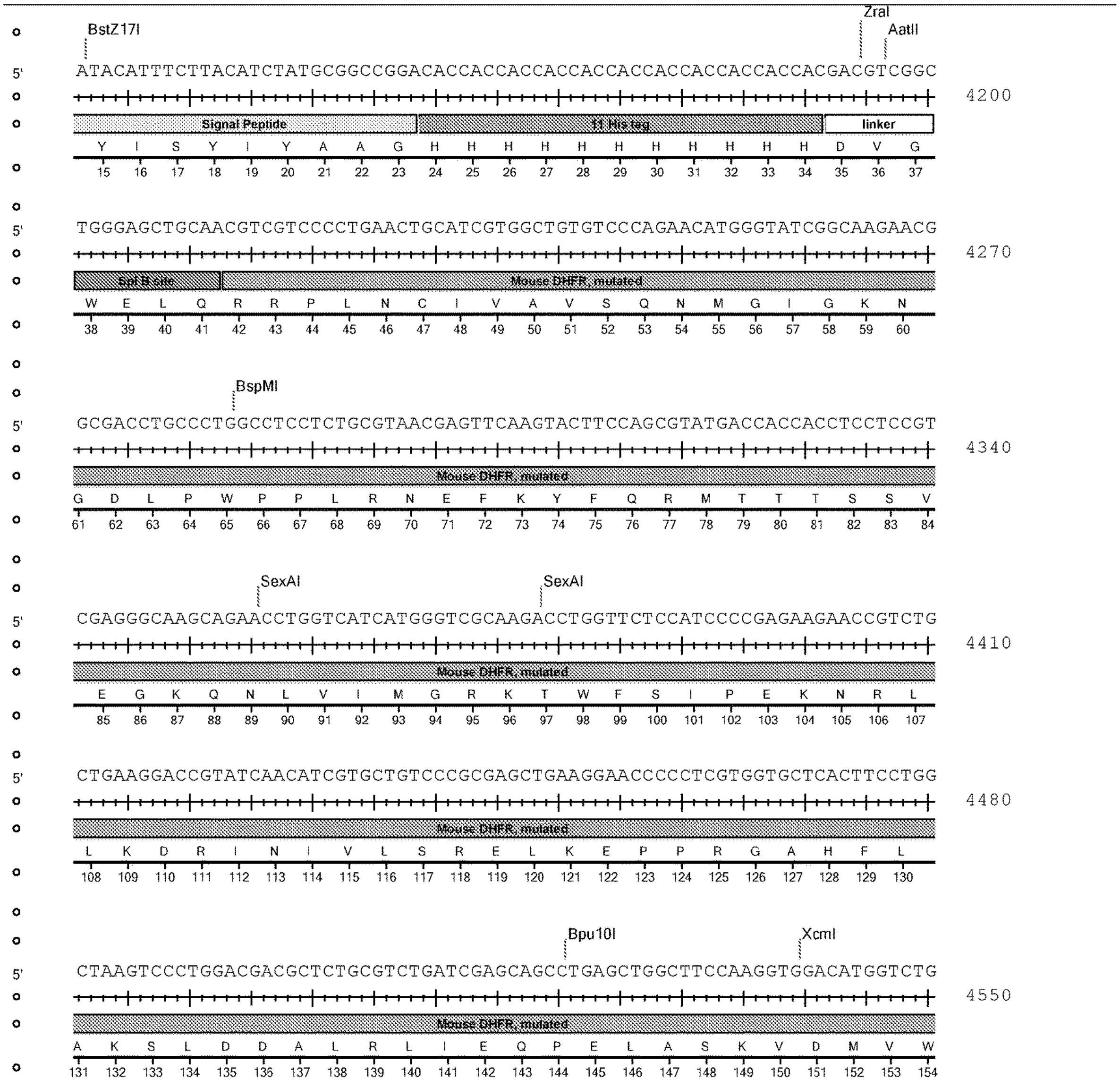
FIGS. 53A-Q provide the DNA sequence (SEQ ID NO:45) of one embodiment of a DNA construct for molecular construction of fusion proteins of the present invention and the corresponding amino acid sequence (SEQ ID NO:46) of this DNA construct. The sequences of FIGS. 53A-Q are specific examples of constructs encoding/having the general structure of the construct illustrated in FIG. 47C, with the sequence described in FIGS. 44A-B as the donor sequence, and the sequence described in FIGS. 40A-O as the recipient sequence using URSs SgrAI and BamHI.
Figure 53F:
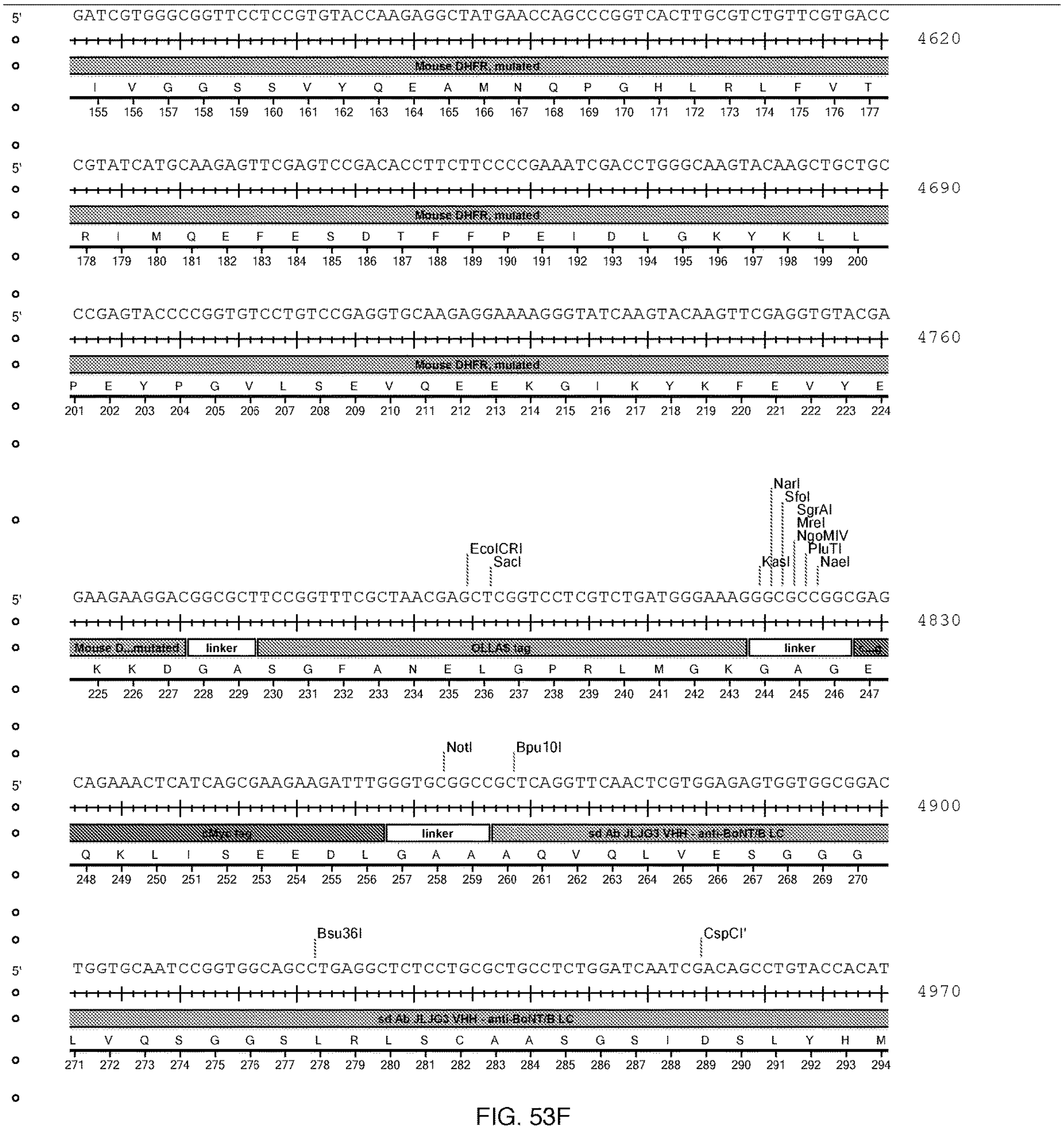
Figure 53G:
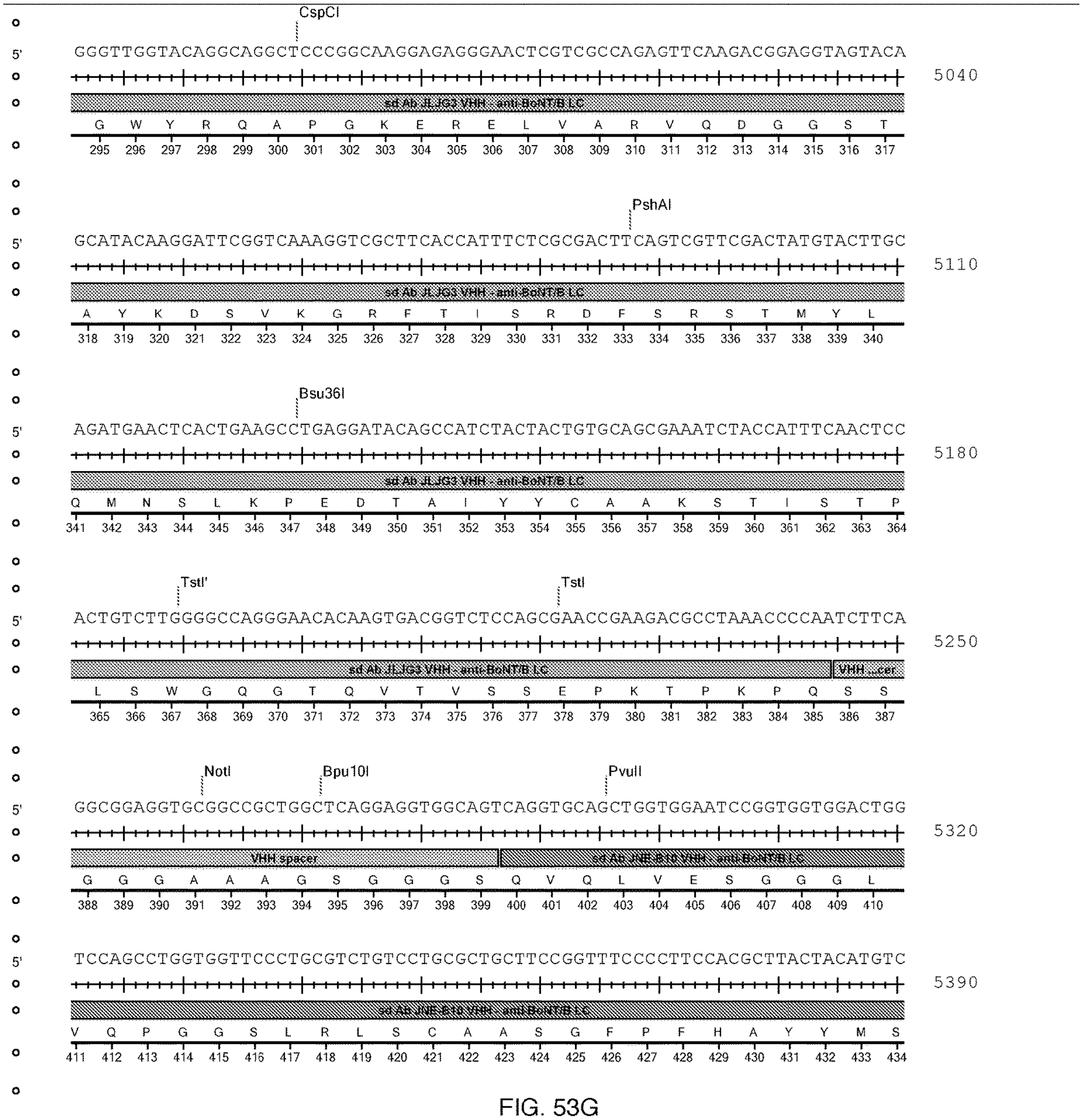
Figure 53H:
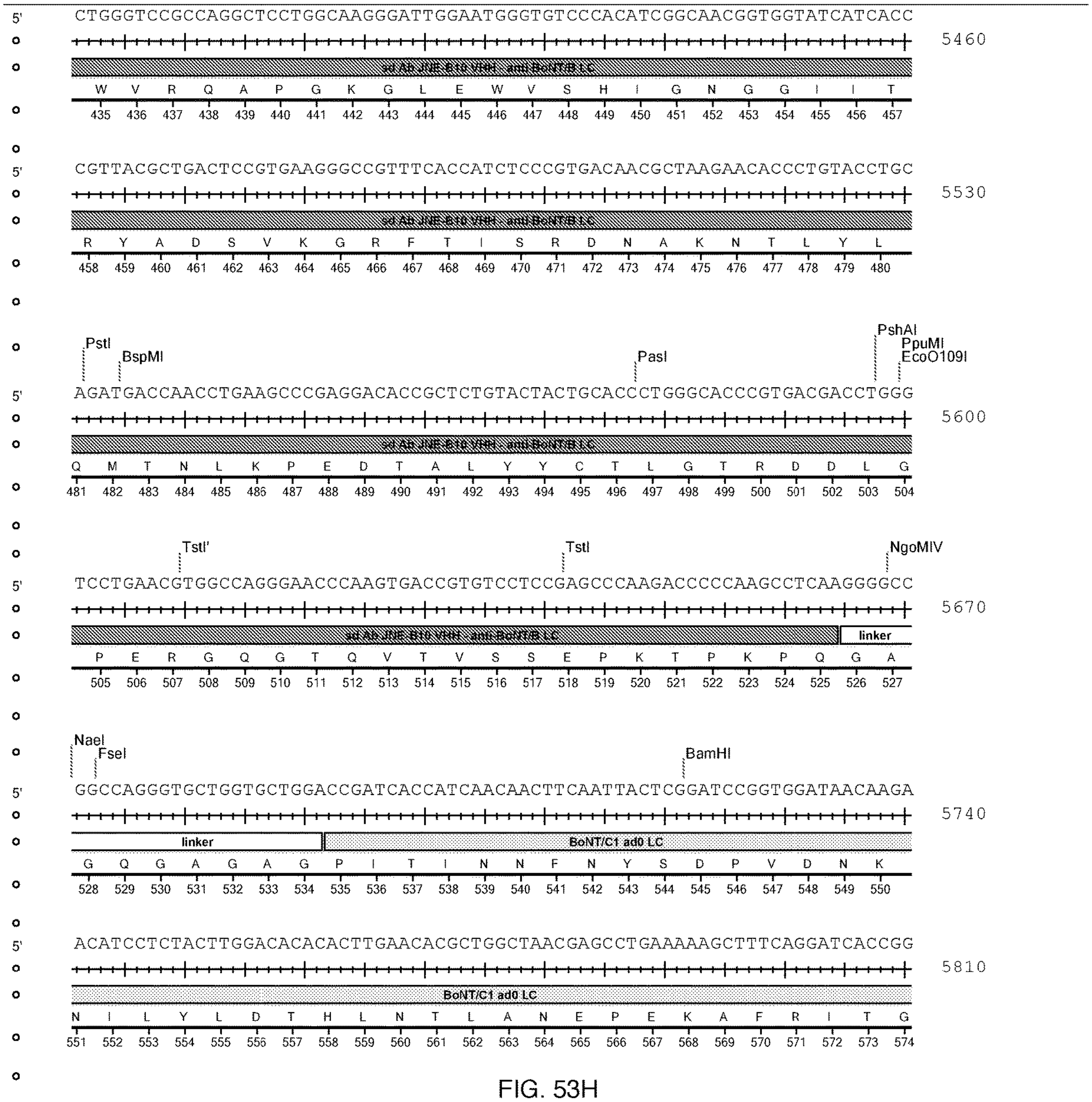
Figure 53J:
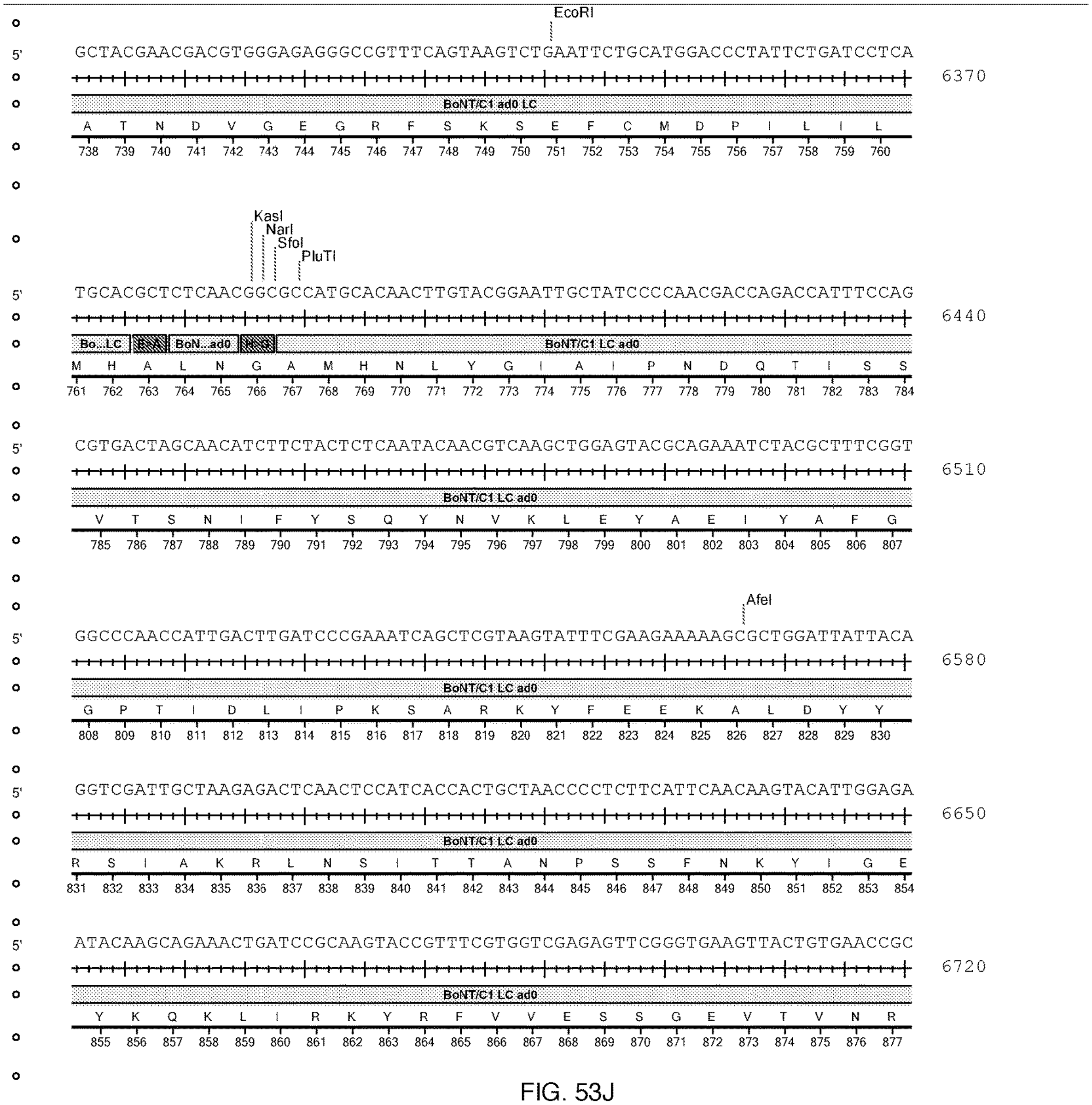
Figure 54E:
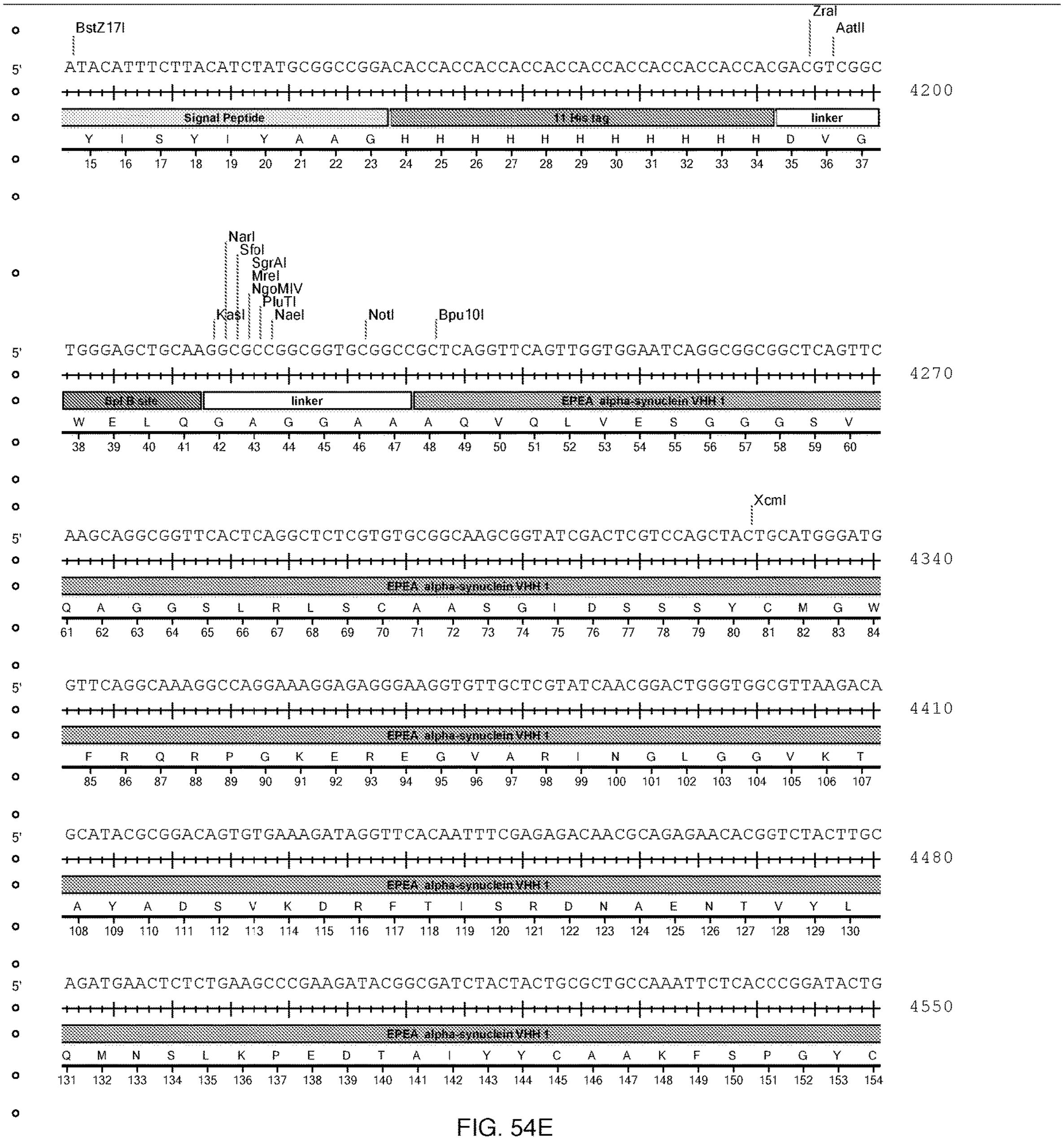
FIGS. 54A-P provide the DNA sequence (SEQ ID NO:47) of one embodiment of a DNA construct for molecular construction of fusion proteins of the present invention and the corresponding amino acid sequence (SEQ ID NO:48) of this DNA construct. The sequences of FIGS. 54A-P are specific examples of constructs encoding/having the general structure of the construct illustrated in FIG. 46C, with the sequence described in FIGS. 45A-B as the donor sequence, and the sequence described in FIGS. 40A-O as the recipient sequence using URSs ZraI and BamHI.
Figure 54H:
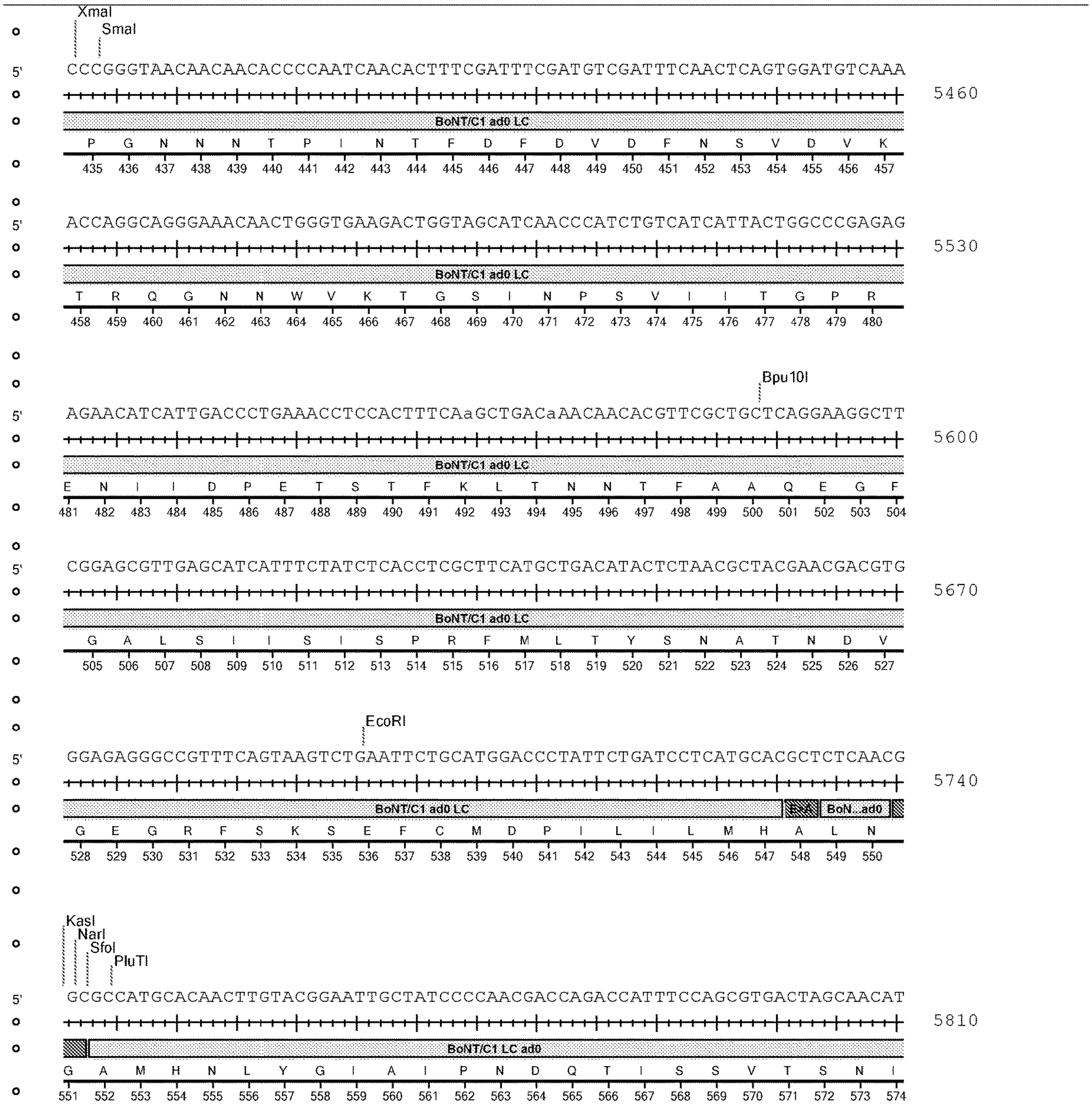
Figure 55E:
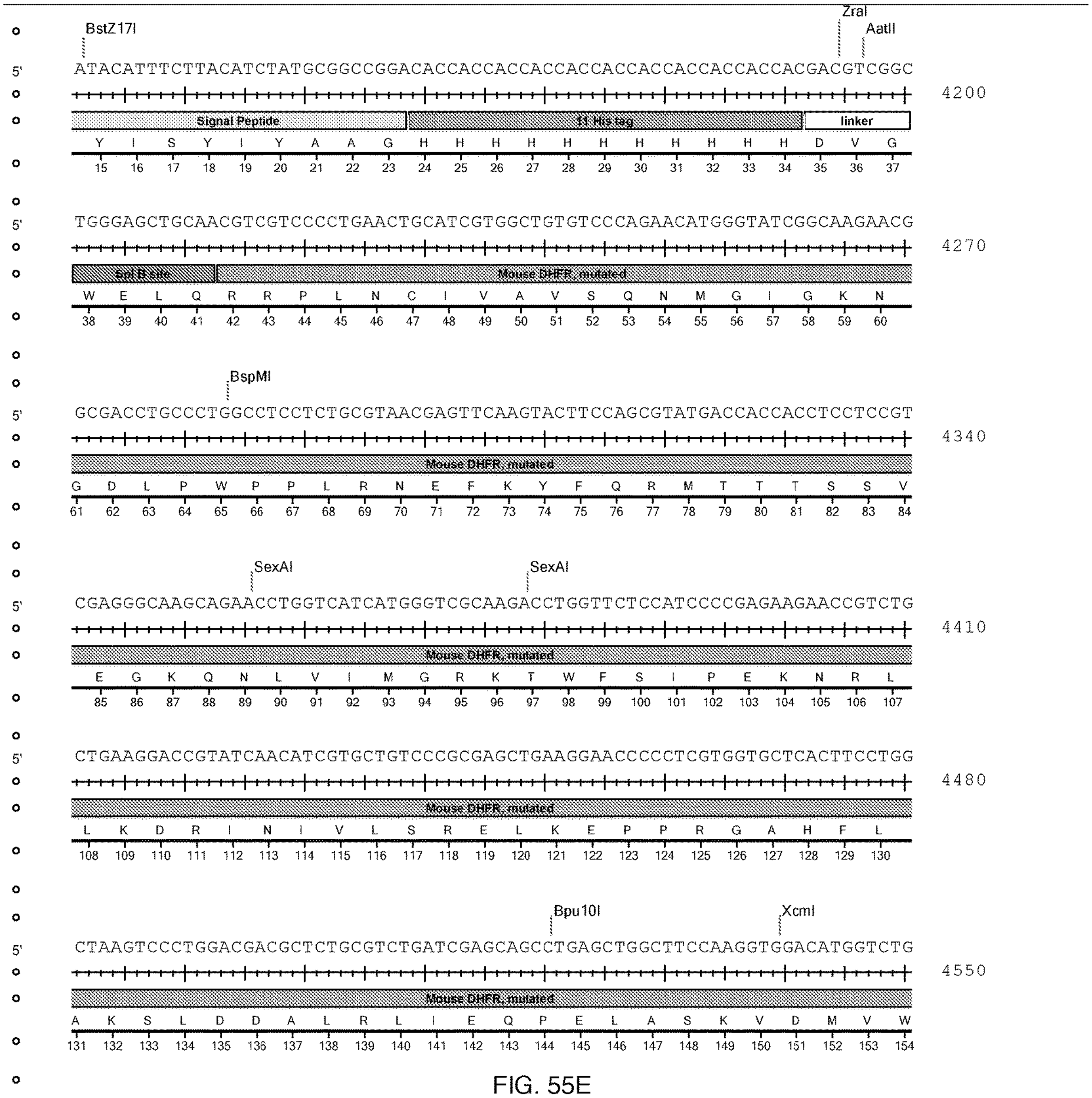
FIGS. 55A-Q provide the DNA sequence (SEQ ID NO:49) of one embodiment of a DNA construct for molecular construction of fusion proteins of the present invention and the corresponding amino acid sequence (SEQ ID NO:50) of this DNA construct. The sequences of FIGS. 55A-Q are specific examples of constructs encoding/having the general structure of the construct illustrated in FIG. 47C, with the sequence described in FIGS. 45A-B as the donor sequence, and the sequence described in FIGS. 40A-O as the recipient sequence using URSs SgrAI and BamHI.
Figure 55I:
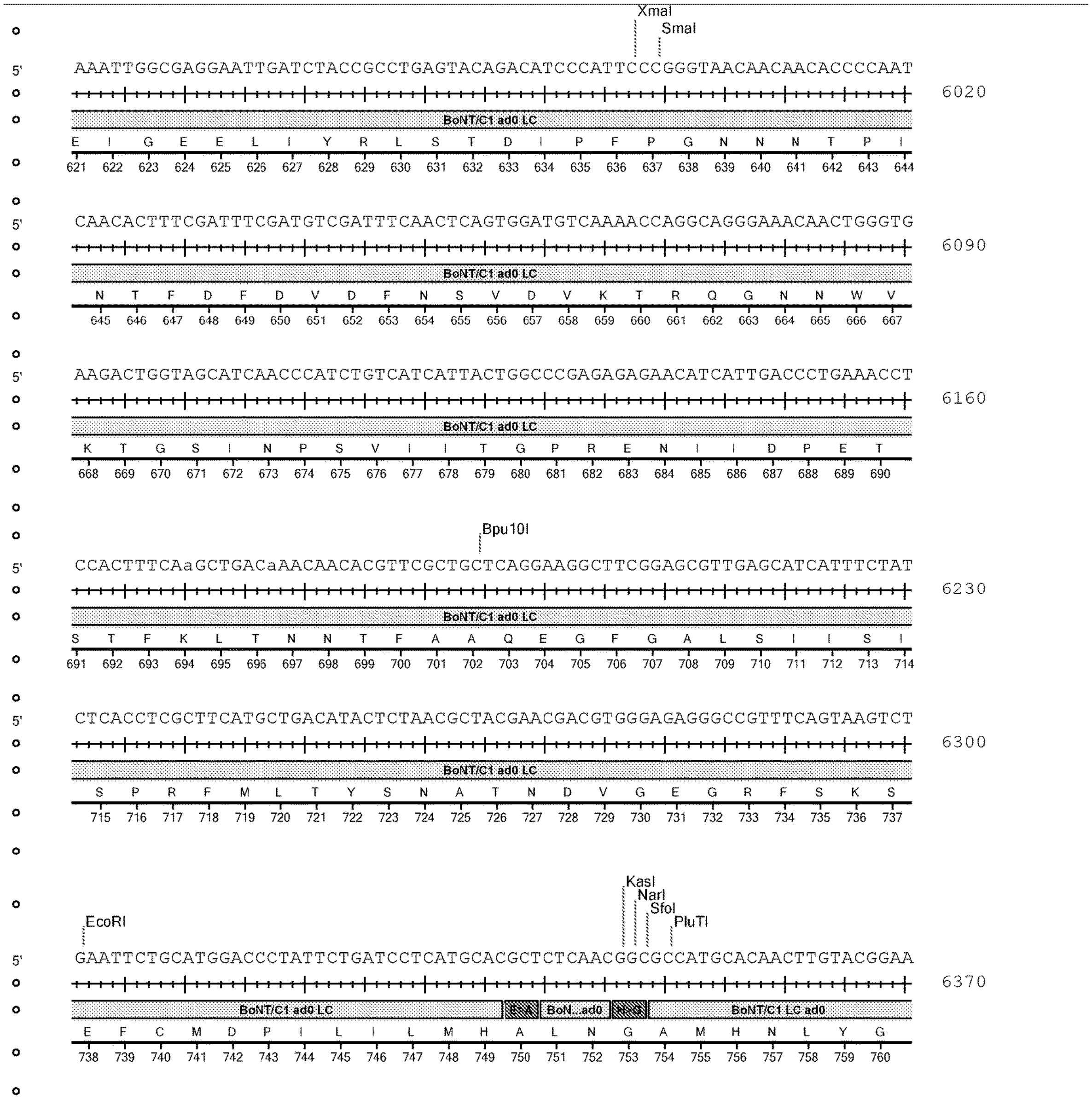
Figure 55J:
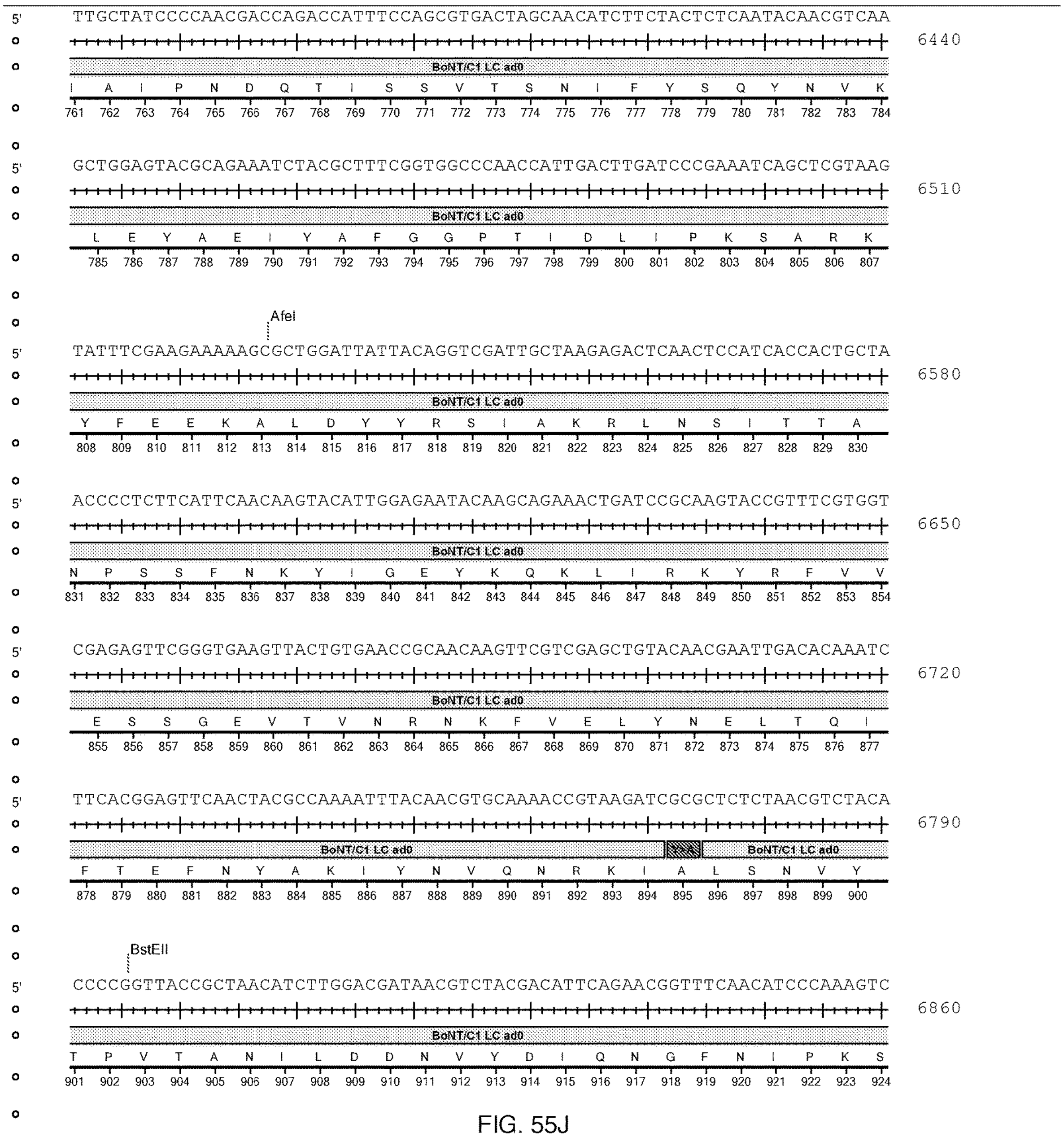

Further constructs comprising a VHH encoding sequence, or multiple VHH encoding sequences upstream of the BoNT LC encoding sequence may also be created (FIG. 41). According to this embodiment, one or more VHH domain(s) encoding sequences may be included in the construct, along with optional nucleotide linkers or spacers, or tag encoding sequences. Specific non-limiting embodiments of such a construct are illustrated in FIG. 42, FIGS. 43A-B, FIGS. 44A-B, and FIGS. 45A-B. In these specific non-limiting embodiments, an RSP element is included upstream of the VHH encoding sequence(s), and optional tag encoding sequences and nucleotide spacers or linkers between the RSP and VHH encoding sequence may also be included.

In one specific embodiment of the construct illustrated in FIG. 35, the construct includes an URS within the tag encoding sequence or nucleotide spacer sequence between the RSP and VHH encoding sequence. This URS can be used to easily introduce additional elements, including additional VHH domain encoding sequence(s), through modular construction via molecular cloning.

Specific constructs having the structure of the general construct illustrated in FIG. 41 (i.e. FIG. 42, FIGS. 43A-B, FIGS. 44A-B, and FIGS. 45A-B) can be cloned into the constructs of FIG. 38C (FIGS. 39A-O, FIGS. 40A-O), where (i) the recipient construct depicted in FIG. 46A has URSs that, when digested, produce single stranded "sticky" overhangs complementary to those produced by (ii) digestion of the donor construct depicted in FIG. 46B at corresponding URSs (dashed lines, FIG. 38A-38B), resulting in (iii) a construct where the VHH domain(s) encoding sequence(s) replaces the N-terminal RSP and ADD encoding sequences (FIG. 46C).

In another embodiment, different URSs of the constructs depicted in FIGS. 46A-C are targeted in molecular cloning to create a construct encoding a fusion protein where the VHH domain(s) are inserted downstream of the ADD and upstream of the BoNT LC (FIGS. 47A-C).

RSP cleavage activity may be affected by the length and /or composition of a specific construct, the cleavage environment, or a combination thereof. As a specific example, a reducing (or at least non-oxidizing) environment is required for cleaving using the TEV protease. However, disulfide bonds essential to the physiologic activities of the recombinant BoNT derivatives are unstable in reducing environments, necessitating modification of the redox environment during the TEV proteolysis step in ways that may not be optimal for rapid and complete proteolytic activation to be effected. Thus the conditions used for TEV proteolysis utilize a combination of glutathione and glutathione disulfide to provide a compromise between the reducing environment required for TEV action and the non-reducing environment needed to maintain essential disulfide bonds in the recombinant BoNT derivatives. Another specific example includes modification of linker length at the RSP site. It is contemplated that longer linkers at the RSP site may reduce steric hindrance and increase exposure to the protease. The effect on cleavage activity due to modification of linker length at the RSP site under non-oxidizing conditions may be more or less pronounced than in other environments. Cleavage activity could be improved by any amount. In one embodiment, cleavage is improved by about 50%. In other embodiments, cleavage is improved by about 10%, about 20%, about 30% or about 40%. Such cleavage activity may be measured by evaluating the time course of cleavage using gel electrophoresis and Western blotting under reducing and non-reducing conditions.

Destabilizing residues may be present in the constructs described herein, and in some specific embodiments, it may be beneficial to remove or replace these destabilizing residues (such as positively charged amino acids). For example, linkers associated with VHH encoding sequences with positively charged amino acids can lead to cleavage of therapeutic cargo, and it may be beneficial to eliminate such positively charged amino acids. Conversely, there may be situations where it is desirable for the region between the VHH and the LC to contain positively charged amino acids in order to effect separation of the LC from its therapeutic cargo.

The constructs exemplified in FIG. 46C and FIG. 47C provide the basis for creating propeptide fusions that can be used to deliver an antibody, but also to mark proteins for elimination. Thus, these constructs are important for both delivering and controlling the elimination of the antibody and, optionally, any proteins bound to the antibodies.

Further aspects of the present invention relate to expression systems and host cells comprising the nucleic acid molecule in a heterologous vector. The present invention also relates to a method of expressing a recombinant fusion protein described herein. This method involves providing a nucleic acid construct comprising a nucleic acid molecule described herein, a heterologous promoter operably linked to the nucleic acid molecule, and a 3' regulatory region operably linked to the nucleic acid molecule. The nucleic acid construct is introduced into a host cell under conditions effective to express the fusion protein.

Suitable expression systems and host cells for expressing the fusion protein are described in U.S. Pat. No. 7,785,606 to Ichtchenko and Band, which is hereby incorporated by reference in its entirety.

In one embodiment, the expressed neurotoxin is contacted with a highly specific protease under conditions effective to affect cleavage at the intermediate region. Preferably, the intermediate region of the propeptide fusion is not cleaved by proteases endogenous to the expression system or the host cell.

Expression of a fusion protein described herein can be carried out by introducing a nucleic acid molecule described herein into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'->3') orientation and correct reading frame. The vector contains the necessary elements for the transcription and translation of the inserted propeptide fusion-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/−or KS+/−(see "Stratagene Cloning Systems" Catalog (1993) from Stratagene, La Jolla, CA, which is hereby incorporated by reference in its entirety), pQE, pIH821, pGEX, pFastBac series (Invitrogen), pET series (Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, New York (1989), which is hereby incorporated by reference in its entirety.

A variety of host-vector systems may be utilized to express the propeptide fusion-encoding sequence in a cell.

Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and /or translation initiation signals. For instance, efficient translation in *E. coli* requires a Shine-Dalgarno (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and /or translation elements, including constitutive, inducible, and repressible promoters, as well as minimal 5' promoter elements may be used.

The propeptide fusion-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a propeptide fusion is inserted into a vector in the sense (i.e., 5'->3') direction, such that the open reading frame is properly oriented for the expression of the encoded propeptide fusion under the control of a promoter of choice. Single or multiple nucleic acids may be ligated into an appropriate vector in this way, under the control of a suitable promoter, to prepare a nucleic acid construct.

Once the isolated nucleic acid molecule encoding the propeptide fusion has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, New York (1989), which is hereby incorporated by reference in its entirety. Suitable hosts include, but are not limited to, bacteria, virus, yeast, fungi, mammalian cells, insect cells, plant cells, and the like. In one embodiment, the host cells of the present invention include, but are not limited to, *Escherichia coli*, insect cells, and *Pichia pastoris* cells.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In one embodiment, the expressed propeptide fusion is contacted with a highly specific protease (e.g., enterokinase, TEV sequence, or WELQut protease) under conditions effective to enable cleavage at the intermediate region of the propeptide fusion. By this means, the intermediate region is not cleaved by proteases endogenous to the host cell. The expressed propeptide fusion has one or more disulfide bridges.

Another aspect of the present invention relates to fusion proteins produced by cleaving the propeptide fusions described herein at the highly specific protease cleavage site, where the light chain region and the heavy chain region are linked by a disulfide bond.

Examples

The following examples are provided to illustrate embodiments of the present invention but are by no means intended to limit its scope.

Example 1—Atoxic Derivative Devoid of SNAP-25 Activity to Deliver Single Chain Antibodies into the Cytosol of Neurons Materials and Methods Expression of Botulinum Neurotoxin a Atoxic Derivatives The full-length single forms of the BoNT/A ad discussed below were bioengineered, expressed, and purified, and then converted to the di-chain by treatment with TEV protease as described before (U.S. Pat. No. 8,980,284 to Ichtchenko and Band, which is hereby incorporated by reference in its entirety).

Preparation and Maintenance of E19 Rat Hippocampal Neurons

Time pregnant Sprague-Dawley rats (Taconic) were used to isolate embryonic-day 19 ("E19") hippocampal neurons. E19 rat hippocampal neurons were prepared from hippocampi according to the protocol of Vicario-Abej6n (Vicario-Abejon, "Long-term Culture of Hippocampal Neurons," *Curr. Protoc. Neurosci*. Chapter 3: Unit 32 (2004), which is hereby incorporated by reference in its entirety). Bilateral hippocampi were dissected from fetal brain, immersed in dissection buffer (15 mM HEPES pH 7.2 (Cat. No. 15630080, Life Technologies), 0.5% glucose in DPBS without $Ca^{2+}$ and Mg+(Cat. No. 14190-250, Life Technologies)), and dissociated by incubation in 10 mL of dissection buffer supplemented with 1× Trypsin/EDTA (10× Trypsin/EDTA is 0.5% trypsin/0.2% EDTA, Cat #15400054, Life Technologies) for 15 minutes at 37° C. Tissue was triturated using a fire polished Pasteur glass pipette, and cells were counted. The single cell suspension was plated onto poly-L-lysine hydrobromide-coated plates or coverslips in plating medium (1× Minimum Essential Medium-Glutamax™ (1× MEM-Glutamax™, Cat No. 41090036, Life Technologies), 10% FBS (Fetal Bovine Serum; Cat. No. 16000044, Life Technologies), 1× Sodium pyruvate (100 mM Sodium pyruvate; Cat. No. 11360-070, Life Technologies), 1× Pen/Strep (100×Pen/Strep is 10,000 U/mL penicillin, 10 mg/mL streptomycin; Cat. No. 15240062, Life Technologies)). After two hours, plating medium was replaced with maintenance medium (1× Neurobasal medium (Cat. No. 21103049, Life Technologies), 1× B27 supplement (Cat. No. 17504044, Life Technologies), and 1× Pen/Strep). Three days after plating, 2 μg/mL cytosine P-D-arabinofuranoside (AraC, Cat. No. C1768, Sigma) was added to the maintenance medium to prevent growth of glia. Half of the medium was replaced with fresh maintenance medium every 3 days.

For experiments related to protein quantification by Western blot, 1-4×$10^6$ cells were plated in 100 mm plates in 10 mL medium. For immunocytochemical studies, 10,000-150,000 cells were plated on cover slips inserted into 6×35 mm/well plates in 3 mL medium/well.

Western Blot Analysis

BoNT/A atoxic derivatives (BoNT/A ad) were incubated with neurons for time periods as indicated in figure legends and /or results. Neurons were harvested and solubilized on ice in 300 μL lysis buffer with protease inhibitors (0.5% Triton X-100, 100 mM NaCl, 25 mM HEPES, pH 7.5, 10 mM 6-aminocaproic acid, 2 mM benzamidine, 5 mM 4-(2-aminoethyl) benzenesulfonyl fluoride hydrochloride (AEBSF), 2.5 mM EDTA, 325 μM bestatin, 35 μM E-64, 2.5 μM leupeptin, 0.75 μM aprotinin) by passing the sample several times through a 27 gauge needle. Soluble protein lysate was separated from the pellet by centrifuging the samples at 18,000 g at 4° C. for 30 minutes. After lysis, the total protein concentration in each sample was measured and sample volumes were adjusted with lysis buffer, supplemented with protease inhibitors to equalize concentration. Total protein concentration in solubilized samples was determined using a Micro BCA kit (Cat. No. 23235, Thermo Scientific) per the manufacturer's instructions. Approximately equal amounts (15 μg) of total protein were loaded per lane, separated by reduced SDS PAGE, and transferred to a 0.2 μm nitrocellulose membrane (Bio-Rad). Following transfer, membranes were blocked with 10% fat-free milk+5% NGS (Normal Goat Serum, Cat. No. 10000C, Life Technologies) in TBST (150 mM NaCl, 10 mM Tris-HCl pH 8.0, 0.1% Tween® 20) at room temperature for 1 hour. Primary and secondary antibodies were diluted in TBST containing 3% NGS. Blots were incubated with primary antibodies overnight at 4° C., and with secondary antibodies for 45 minutes at room temperature. Following incubations, blots were washed with TBST 3 times for 5 minutes. Super Signal West Pico chemiluminescent substrate (Cat. No. 34080, Thermo Scientific) was used for visualization by autoradiography. Autoradiographs of Western blots were scanned at 300 dpi on an Epson Expression 1680 scanner using Silver Fast AI v.6.4.4r7a software avoiding filter modifications. Samples of BoNT/A atoxic derivatives loaded on reduced SDS PAGE with known LC-ad content (ng/lane) were utilized to generate a standard curve.

Immunofluorescence Analysis

BoNT/A atoxic derivatives (BoNT/A ad) were incubated with neurons for 16 hours. Immediately after incubation, cells were washed three times with ice-cold DPBS, fixed with 4% formaldehyde for 15 minutes, and permeabilized with 0.1% Triton™ X-100 for 5 minutes. After fixation the permeabilized cells were washed three times with DPBS, blocked for 1 hour at room temperature with 10% BSA in DPBS, and incubated overnight at 4° C. with anti-SNAP-25 (Cat. No. 111011, Synaptic Systems, final concentration 0.1 ng/mL), anti-VAMP-2 (Cat. No. 104211, Synaptic Systems, final concentration 0.1 ng/mL), or anti-EEA1 (Cat. No. 610457, BD Biosciences, final concentration 10 ng/mL). Primary antibodies were diluted in DPBS-3% NGS. Cells were washed three times with DPBS-3% NGS and incubated with appropriate secondary antibodies diluted in DPBS-3% NGS for 45 minutes at room temperature. Cells were washed three times with DPBS, and the cover slips were mounted on slides with mounting medium. Image scanning was performed on a Nikon LSM 510 confocal microscope equipped with argon and HeNe lasers producing excitation lines of 488 and 568 nm, and images were analyzed using Zeiss LSM confocal microscopy software (v.4.2).

Results

Production of BoNT/A ad

Figure 1B:
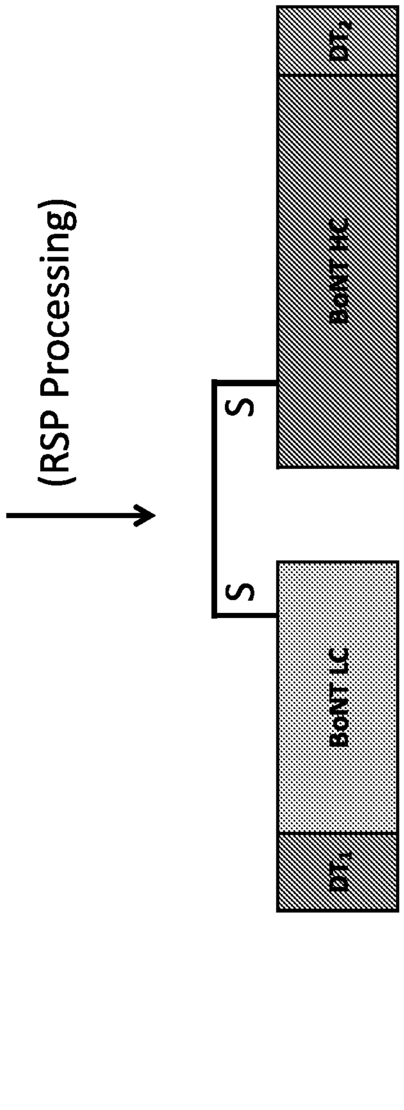

To eliminate residual activity towards SNAP-25 found for BoNT/A ad (see discussion of BoNT/A ad-0 in U.S. Patent Application Publication No. 2014/0212456 to Vazquez-Cintron et al., which is hereby incorporated by reference in its entirety), an additional 4 amino acid substitutions ($Q_{162}$>Y, $L_{256}$>Y, $R_{257}$>E, $L_{322}$>E) were made in the catalytic domain of the light chain of BoNT/A ad to make the construct BoNT/A ad-1. These substitutions were designed using computer models of the 3D crystallographic structure of BoNT/A. This example of the second generation of botulinum neurotoxin atoxic derivatives has been designated as BoNT/A ad-1. According to one embodiment, FIGS. 1A-B illustrate both the BoNT/A ad-1 full-length single chain expression product (i.e., propeptide, FIG. 1A), and the disulfide-bonded heterodimer (i.e., mature neurotoxin, FIG. 1*i*) obtained after affinity purification and processing with a restricted specificity protease. In addition to the tags ($APT_N$ and $APT_C$) built into the full-length construct for affinity purification, detection tags ($DT_1$ and $DT_2$) were built into the mature heavy and light chain regions of the construct, respectively, for detection purposes during laboratory evaluations.

BoNT/A ad-1 Light Chain Does Not Induce SNAP-25 Cleavage

Figure 2:
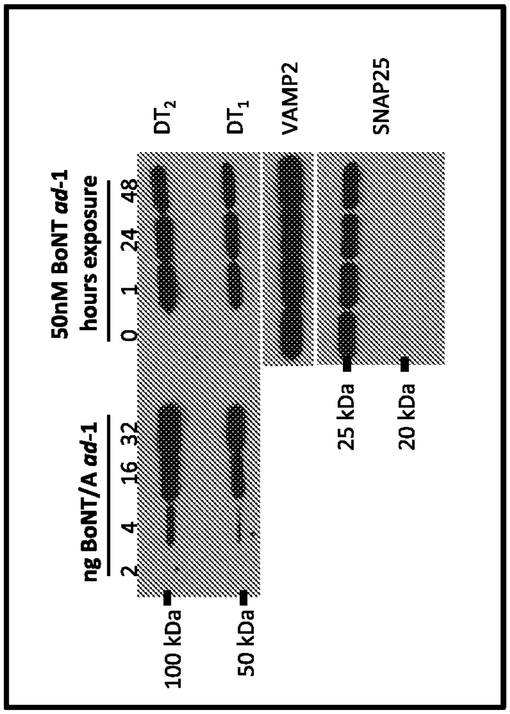
FIG. 2 is a photograph of Western blot results showing absence of SNAP-25 cleavage for one embodiment of a mature, full-length BoNT neurotoxin (i.e., BoNT/A ad-1, discussed infra) drug carrier in vitro. E19 rat hippocampal neurons were cultured for 14 days in vitro (14 DIV) and then exposed to 50 nM BoNT/A ad-1 for 0, 1, 24, or 48 hours. Western blot analysis was performed using monoclonal antibody against OLLAS tag and monoclonal antibody against HA tag to detect and measure the presence of BoNT/A ad-1 LC and HC, respectively. VAMP-2 was used as a loading control. The blot demonstrates that SNAP-25 cleavage was not detected, even though SNAP-25 is the natural substrate for BoNT/A.

BoNT/A ad-1 uptake is a cell-surface receptor mediated process that involves translocation of the BoNT/A ad-1 LC to the cytoplasm following receptor binding (Montecucco et al., "Mechanism of Action of Tetanus and Botulinum Neurotoxins," Mol. Microbiol. 13:1-8 (1994); Mahrhold et al., "The Synaptic Vesicle Protein 2C Mediates the Uptake of Botulinum Neurotoxin A into Phrenic Nerves," FEBS Lett. 580:2011-2014 (2006), which are hereby incorporated by reference in their entirety). Neuronal cultures were treated with 50 nM BoNT/A ad-1 for 1, 24, and 48 hours at 37° C. (FIG. 2). The cells were then washed with ice-cold DPBS supplemented with protease inhibitors, solubilized, and extracted with lysis buffer. Antibodies against the hemagglutinin epitope tag (HA tag) fused to the C-terminus of the BoNT/A ad-1 HC domain, and *E. coli* OmpF Linker and mouse Langerin fusion Sequence tag (OLLAS tag) fused to the N-terminus of the BoNT/A ad-1 LC ($DT_2$ and $DT_1$, respectively) were used to identify the heavy and light chain of BoNT/A ad-1.

To quantitate BoNT/A ad-1 LC accumulation, a standard curve of purified reduced BoNT/A ad-1 was generated and analyzed by Western blot. FIG. 2 shows that BoNT/A ad-1 HC and LC are internalized into the cultured neuronal cells, and are detected using $DT_1$ and $DT_2$ in an extract of the neuronal cultures produced by extraction in Triton™ X-100. Antibodies against VAMP-2 were included as an internal control to determine that intracellular SNARE proteins were intact. Antibodies against SNAP-25 show absence of SNAP-25 cleavage.

Figure 3A:
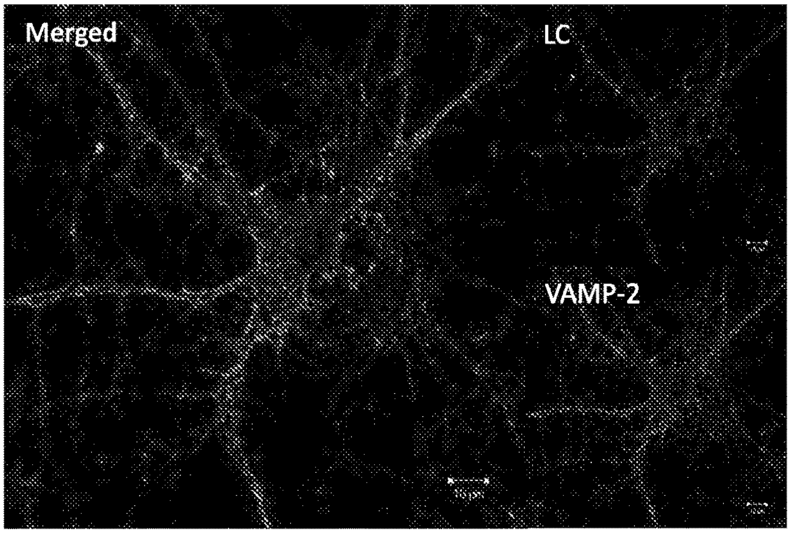
FIGS. 3A-C are photographs showing that BoNT/A ad-1 LC colocalizes with synaptic proteins exposed exclusively to the cytosol of neurons. E19 rat hippocampal neurons were cultured for 10 days in vitro and then exposed to 50 nM BoNT/A ad-1 for 16 hours. Confocal microscopy analysis shows that BoNT/A ad-1 LC colocalizes with VAMP-2 (FIG. 3A) and SNAP-25 (FIG. 3B).
Figure 3B:
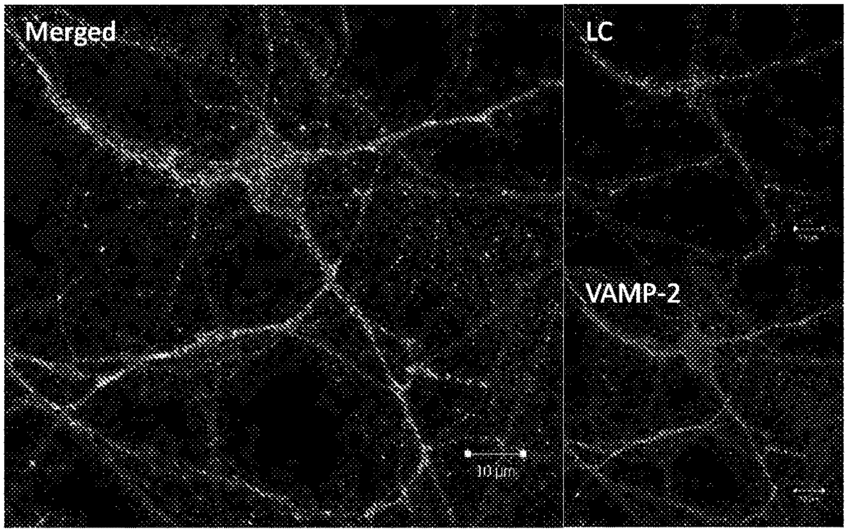
Figure 3C:
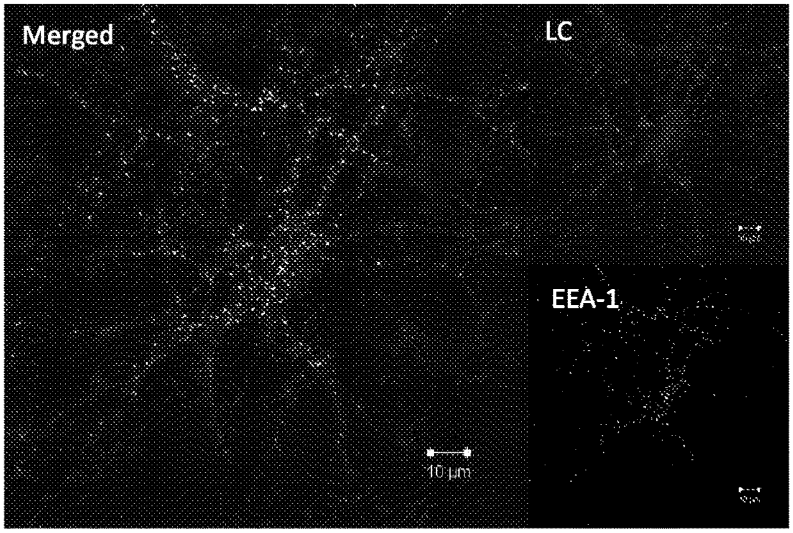

SNAP-25 and VAMP-2 are SNARE proteins that are essential components of the molecular machinery for synaptic vesicle exocytosis, and are exposed to the cytoplasmic compartment of neurons. VAMP-2 is exclusively structurally associated with small synaptic vesicles. SNAP-25 is the molecular target of the LC protease of wild-type BoNT/A (Blasi et al., "Botulinum Neurotoxin A Selectively Cleaves the Synaptic Protein SNAP-25," Nature 365:160-163 (1993), which is hereby incorporated by reference in its entirety). To determine if internalized BoNT/A ad-1 LC is similarly targeted to SNARE proteins, despite the absence of SNAP-25 cleavage, immunocytochemical analysis of BoNT/A ad-1 treated cells was performed, the results of which are shown in FIGS. 3A-C. BoNT/A ad-1 LC specifically co-localized with SNAP-25 (FIG. 3A) and with VAMP-2 (FIG. 3B). To determine if some fraction of the LC of BoNT/A ad-1 was co-localized with endosomal markers, co-immunostaining was performed with early endosome antigen 1 ("EEA1"). Few EEA1 puncta were co-localized with BoNT/A ad-1 LC (FIG. 3C). These experiments confirmed that BoNT/A ad-1 LC was indeed localized in an intracellular compartment.

BoNT/A ad-1 for Delivery of Single Chain Antibodies

Figure 5A:
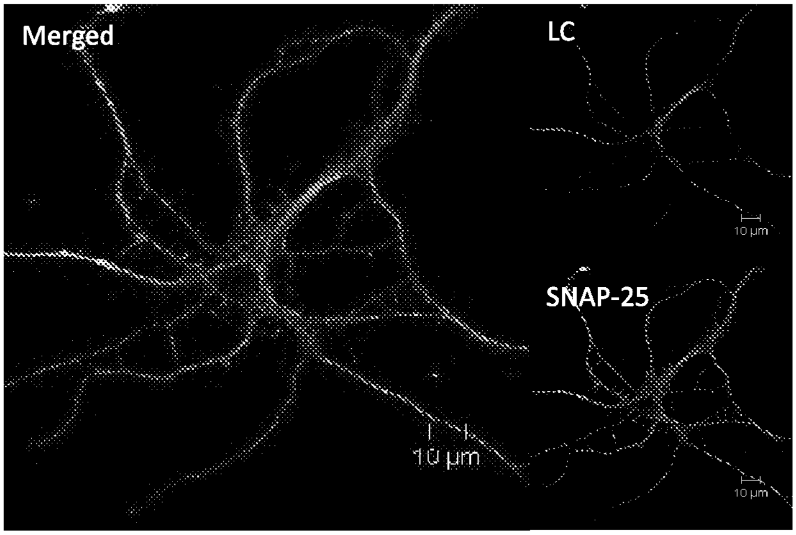
FIGS. 5A-B are photographs showing that BoNT/A ad-1 VHH (one embodiment of a fusion protein of the present invention described infra) is internalized to the cytosol of neurons. E19 rat hippocampal neurons were cultured for 10 days in vitro and then exposed to 50 nM BoNT/A ad-I VHH for 24 hours. BoNT/A ad-I VHH LC has the same pattern as BoNT/A ad molecules possessing residual SNAP-25 cleavage activity (e.g., BoNT/A ad-0), demonstrated by colocalization of BoNT/A ad-1 LC with SNAP-25 (FIG. 5A) and VAMP-2 (FIG. 5B).
Figure 5B:
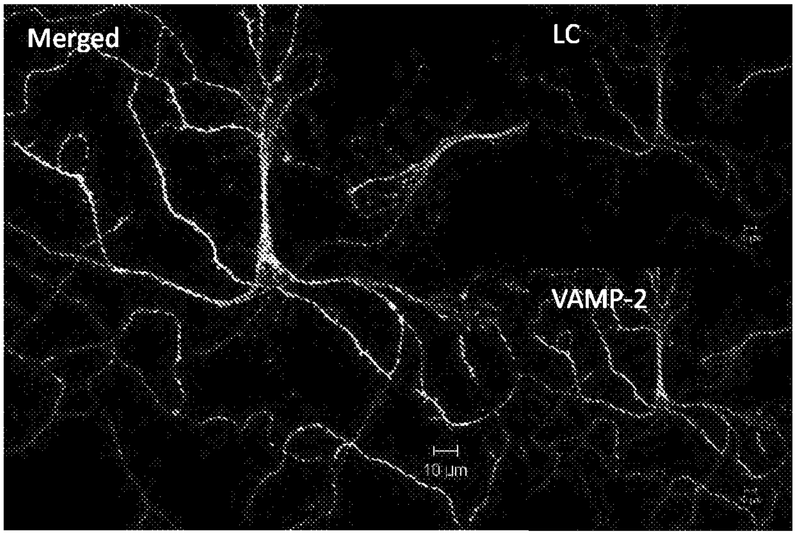

The second example of cargo delivery is the prototype BoNT/A ad-1 fusion protein containing a non-neutralizing anti-LC-BoNT/B VHH (B-10 VHH) domain inserted upstream of a spacer domain inserted at the N-terminus of BoNT/A ad-1. The VHH domain is flanked with a c-myc at its N-terminus, to detect delivery of the VHH-LC fusion protein to the neuronal cytoplasm. His and Strep tags were placed at the N- ($APT_N$) and C-terminus ($APT_C$) of the full-length expression construct, respectively, both flanked with a TEV protease cleavage site (RSP). These steps enable affinity purification of the full-length single chain expression product, and elimination of any truncated expression variants. The latter tags are removed by treatment with TEV protease during processing of the single chain expression product to form the active disulfide-bonded heterodimer suitable for pharmaceutical applications, as illustrated generically in FIGS. 4A-B. One embodiment of the nucleotide sequence (SEQ ID NO:1) and amino acid sequence (SEQ ID NO:2) of this construct, referred to as "BoNT/A ad-1 VHH" is illustrated in FIGS. 9A-L. FIGS. 5A-B demonstrate that the VHH domain fused with the N-terminus of BoNT/A ad-1 LC is internalized into hippocampal neurons and colocalizes with the SNAP-25 (FIG. 5A), as well with VAMP-2 (FIG. 5B), another component of the synaptic cycle machinery.

Use of an Accelerated Degradation Domain (ADD) to Mark VHH-Targeted Antigens for Rapid Elimination from Neurons Via Proteasomal Degradation The anti-LC-BoNT/B B-10 VHH fused to the BoNT/A ad-1 vehicle, as illustrated generically in FIGS. 4A-B and evaluated in FIGS. 5A-B (i.e., BoNT/A ad-1 VHH), is a non-neutralizing antibody. That is, the B-10 VHH binds to the LC of wild-type BoNT/B with high affinity, but it does not prevent wild-type BoNT/B from cleaving its substrate, VAMP-2. Even if a high affinity metalloprotease-neutralizing antibody were used, the time wise fate of the complex between VHH and wild-type LC does not guarantee full elimination of intracellular activity of the wild-type toxin in a timely fashion. Therefore, an additional specific sequence may be required to enable this VHH-BoNT/A ad-1 fusion protein to eliminate wild-type BoNT/LC from the cytoplasm of neurons (i.e., to function as a post-internalization antidote). This is accomplished by placing an accelerated degradation domain (ADD), N-terminal to the VHH fragment (with an optional spacer sequence or detection tag in between), as illustrated in FIGS. 6A-B. One embodiment of the nucleotide sequence (SEQ ID NO:5) and amino acid sequence (SEQ ID NO:6) of this construct, referred to as "BoNT/A ad-1 VHH Degron-1" are set forth in FIGS. 11A-L.

FIGS. 6A-B provide generic schematic illustrations of the resulting fusion protein, using a Degron-1 sequence as an example of an ADD that directs the antibody-antigen complex to proteasome degradation. This principle is general, and could be designed to eliminate any desired antigen that was bound by single chain VHH by manipulation of the proteasome degradation-signaling domain.

Use of Alternative Protease for Removal of the N-terminal Affinity Tag Used for Affinity Purification To optimize elimination by the proteasomal pathway, an N-terminal amino acid with a positively charged side chain, such as a lysine residue, can be included in the final fusion protein product to increase targeting of the VHH-antigen complex for ubiquitination and consequent degradation through the proteosomal pathway. However, natively expressed proteins with N-terminal positively charged amino acids, such as arginine or lysine are intrinsically unstable. To overcome problems related to stability of these proteins, stably expressed protein precursors (BoNT derivatives) were cleaved with built-in recognition sequence after purification with highly specific recombinant proteases, such as WELQut protease (SplB protease from *Staphylococcus aureus*). The highly specific recognition sequence WELQ allows this protease to release the N-terminus of the cleaved product (that follow this sequence), which in this case would be the fusion protein with N-terminally placed lysine residue, targeted for accelerated degradation.

The atoxic propeptide is designed so that maturation of the proprotein with the WELQut protease results in production of a mature heterodimer that contains an N-terminal lysine residue, because proteins with an N-terminal lysine residue are more rapidly degraded by the proteasome system.

Discussion

The data presented here is part of an ongoing effort to engineer recombinant Clostridial neurotoxins to deliver drugs (therapeutic agents) to the neuronal cytoplasm via the trafficking mechanism(s) of native Clostridial neurotoxins. All BoNT serotypes deliver their LC protease to the neuronal cytoplasm and target, specifically, SNARE proteins. This approach has been to develop methods to express and purify recombinant derivatives of BoNTs that retain the structure and trafficking properties of the native toxin, but which can be engineered in desirable ways using tools of modem molecular biology.

In this example, the neuronal internalization and intracellular trafficking of the prototype vehicle BoNT/A ad-1 is described. The idea is to use BoNT/A ad-1 as a "Trojan horse" to deliver therapeutic cargo, especially, single domain antibodies. This idea is exemplified using two fusion proteins, BoNT/A ad-1 VHH and BoNT/A ad-1 VHH Degron-1. These two derivatives successfully deliver single domain antibodies that target intracellular epitopes.

BoNT/A ad-1 LC and BoNT/A ad-1 VHH colocalized extensively with SNAP-25 and with VAMP-2, both cytosolic proteins and members of the SNARE complex. It is particularly noteworthy that the LCs seldom colocalized with endosomal markers, suggesting that the endosomal compartment is a transient step in internalization rather than a destination using the BoNT/A ad-1 derivatives (Montecucco et al., "Mechanism of Action of Tetanus and Botulinum Neurotoxins," *Mol. Microbiol.* 13:1-8 (1994), which is hereby incorporated by reference in its entirety). This contrasts with reports from other laboratories describing delivery vehicles based on engineered derivatives of clostridial toxins, which show endosomal localization and little or no colocalization with synaptic vesicle markers (Ho et al., "Recombinant Botulinum Neurotoxin A Heavy Chain-based Delivery Vehicles for Neuronal Cell Targeting," *Protein Eng. Des. Sel.* 24:247-253 (2011); Singh et al., "Clostridial Neurotoxins as a Drug Delivery Vehicle Targeting Nervous System," Biochimie 92:1252-1259 (2010); Zhang et al., "An Efficient Drug Delivery Vehicle for Botulism Countermeasure," *BMC Pharmacol.* 9:12 (2009); Brunger et al., "Botulinum Neurotoxin Heavy Chain Belt as an Intramolecular Chaperone for the Light Chain," PLoSPathog. 3:1191-1194 (2007); Koriazova et al., "Translocation of Botulinum Neurotoxin Light Chain Protease through the Heavy Chain Channel," *Nat. Struct. Biol.* 10:13-18 (2003), which are hereby incorporated by reference in their entirety).

In summary, the data reported here confirm previous work demonstrating that this technology platform enables the production of bioengineered recombinant botulinum neurotoxin derivatives that maintain the structure and trafficking properties of wild-type BoNT/A. This platform provides the means to generate BoNTs tailored for specific applications. In the present example, it is demonstrated that the atoxic derivative light chain is delivered to the cytosol of neurons, indicating that this fusion has the potential to be used as a "Trojan horse" to deliver drugs to the neuronal cytosol. BoNT/A ad-1 retains the ability to specifically target neurons and to translocate high levels of the LC into the neuronal cytoplasm, where the BoNT/A ad-1 LC is able to accumulate and persist without overt evidence of cytotoxicity. The BoNT/A LC-B-10 (Cyto-302) recovered from the neuronal cytoplasm still retains the ability to bind LC/B, as demonstrated by the immunoprecipitation experiments described below, and in FIG. 18. This new technology can be designed to work against all BoNT serotypes, and can be applied to bind and neutralize the function of a wide range of pathogenic proteins responsible for important neurological diseases.

Example 2—BoNT/a Ad-0 as a Delivery Vehicle to Deliver Single Chain Antibodies to the Cytoplasm of Neurons

Introduction

It has previously been shown that BoNT/A ad-0 is found at the pre-synaptic region in neuromuscular junctions after systemic administration in vivo. In vitro, BoNT/A ad-0 is internalized into the cytosol of neurons at micromolar concentrations, where the BoNT/A ad-0 light chain co-localizes with synaptic proteins. Local intramuscular administration of BoNT/A ad-0 results in muscle weakness/paralysis, a hallmark of wild-type BoNT/A, demonstrating the pharmacological properties of BoNT/A ad-0 as a neuromodulator.

In this example, empirical evidence is provided regarding the successful delivery of single chain antibodies using botulinum neurotoxin atoxic derivatives with residual SNAP-25 catalytic activity (BoNT/A ad-0). The catalytic activity of the BoNT/A ad-0 light chain towards SNAP-25 was used as a readout to measure successful delivery of the cargo material; in this example it is demonstrated that a variable domain of heavy chain antibody (VHH), fused to the ad-0 light chain, is delivered into the cytosol of neurons. The use of VHH or single chain antibodies could allow the targeting, neutralization, and elimination of pathological proteins present in the neuronal cytoplasm, serving as a therapeutic for numerous neurological conditions. In some situations, the residual SNAP-25 cleavage activity could synergize with the therapeutic activity conferred by the antibody and provide an improved therapeutic result over either activity individually.

Materials and Methods

Expression of Botulinum Neurotoxin a Atoxic Derivatives

The full-length single chain forms of BoNT/A atoxic derivatives (BoNT/A ad) discussed below were bioengineered, expressed, and purified, and then converted to the di-chain by treatment with TEV protease as described before (Band et al., "Recombinant Derivatives of Botulinum Neurotoxin A Engineered for Trafficking Studies and Neuronal Delivery," *Protein Exp. Purif* 71:62-73 (2010), which is hereby incorporated by reference in its entirety).

Preparation and Maintenance of E19 Rat Hippocampal Neurons

Time pregnant Sprague-Dawley rats (Taconic) were used to isolate embryonic-day 19 (E19) hippocampal neurons. E19 rat hippocampal neurons were prepared from hippocampi according to the protocol of Vicario-Abej6n (Vicario-Abejon, "Long-term Culture of Hippocampal Neurons," *Curr. Protoc. Neurosci*. Chapter 3: Unit 32 (2004), which is hereby incorporated by reference in its entirety). Bilateral hippocampi were dissected from fetal brain, immersed in dissection buffer (15 mM HEPES pH 7.2 (Cat. No. 15630080, Life Technologies), 0.5% glucose in DPBS without $Ca^{2+}$ and Mg+(Cat. No. 14190-250, Life Technologies)), and dissociated by incubation in 10 mL of dissection buffer supplemented with 1× Trypsin/EDTA (10× Trypsin/EDTA is 0.5% trypsin/0.2% EDTA, Cat. No. 15400054, Life Technologies) for 15 minutes at 37° C. Tissue was triturated using a fire polished Pasteur glass pipette, and cells were counted. The single cell suspension was plated onto poly-L-lysine hydrobromide-coated plates or coverslips in plating medium (1× Minimum Essential Medium-Glutamax™ (1× MEM-Glutamax™, Cat. No. 41090036, Life Technologies), 10% FBS (Fetal Bovine Serum; Cat. No. 16000044, Life Technologies), 1× Sodium pyruvate (100 mM Sodium pyruvate; Cat. No. 11360-070, Life Technologies), 1× Pen/Strep (100× Pen/Strep is 10,000 U/mL penicillin, 10 mg/mL streptomycin; Cat. No. 15240062, Life Technologies)). After two hours, plating medium was replaced with maintenance medium (1× Neurobasal medium (Cat. No. 21103049, Life Technologies), 1× B27 supplement (Cat. No. 17504044, Life Technologies), and 1×Pen/Strep). Three days after plating, 2 μg/mL cytosine P-D-arabinofuranoside (AraC, Cat. No. C1768, Sigma) was added to the maintenance medium to prevent growth of glia. Half of the medium was replaced with fresh maintenance medium every 3 days.

For experiments related to protein quantification by Western blot, 1-4×$10^6$ cells were plated in 100 mm plates in 10 mL medium. For immunocytochemical studies, 50,000-100,000 cells were plated on cover slips inserted into 6×35 mm/well plates in 3 mL medium/well.

Western Blot Studies

BoNT/A atoxic derivatives (BoNT/A ad) were incubated with neurons for time periods as indicated in figure legends and /or results. Neurons were harvested and solubilized on ice in 300 μL lysis buffer with protease inhibitors (0.5% Triton X-100, 100 mM NaCl, 25 mM HEPES, pH 7.5, 10 mM 6-aminocaproic acid, 2 mM benzamidine, 5 mM 4-(2-aminoethyl) benzenesulfonyl fluoride hydrochloride (AEBSF), 2.5 mM EDTA, 325 μM bestatin, 35 μM E-64, 2.5 μM leupeptin, 0.75 μM aprotinin) by passing the sample several times through a 27 gauge needle. Soluble protein lyzate was separated from the pellet by centrifuging the samples at 18,000 g at 4° C. for 30 minutes. After lysis, the total protein concentration in each sample was measured and sample volumes were adjusted with lysis buffer, supplemented with protease inhibitors to equalize concentration. Total protein concentration in solubilized samples was determined using a Micro BCA kit (Cat. No. 23235, Thermo Scientific) per the manufacturer's instructions. Approximately equal amounts (15 μg) of total protein were loaded per lane, separated by reduced SDS PAGE, and transferred to a 0.2 μm nitrocellulose membrane (Bio-Rad). Following transfer, membranes were blocked with 10% fat-free milk+5% NGS (Normal Goat Serum, Cat. No. 10000C, Life Technologies) in TBST (150 mM NaCl, 10 mM Tris-HCl pH 8.0, 0.1% Tween® 20) at room temperature for 1 hour. Primary and secondary antibodies were diluted in TBST containing 3% NGS. Blots were incubated with primary antibodies overnight at 4° C., and with secondary antibodies 45 minutes at room temperature. Following incubations, blots were washed with TBST 3 times for 5 minutes. Super Signal West Pico chemiluminescent substrate (Cat. No. 34080, Thermo Scientific) was used for visualization by autoradiography. Autoradiographs of Western blots were scanned at 300 dpi on an Epson Expression 1680 scanner using Silver Fast AI v.6.4.4r7a software avoiding filter modifications. Samples of BoNT/A atoxic derivatives loaded on reduced SDS PAGE with known LC-ad content (ng/lane) were utilized to generate a standard curve.

Digital Abduction Assay

A modification to the classic Digit Abduction Scoring ("DAS") Assay was used to determine local muscle weakening efficacy as described in Aoki, "Preclinical Update on BOTOX® (Botulinum Toxin Type A)-Purified Neurotoxin Complex Relative to Other Botulinum Neurotoxin Preparations," *European Journal of Neurology* (1999), which is hereby incorporated by reference in its entirety. In the DAS Assay, mice are suspended briefly to elicit a characteristic startle response in which the animal extends its hind limbs and abducts its hind digits. The mouse DAS assay is especially useful to compare muscle weakening efficacy (Aoki, "Preclinical Update on BOTOX® (Botulinum Toxin Type A)-Purified Neurotoxin Complex Relative to Other Botulinum Neurotoxin Preparations," *European Journal of Neurology* (1999) and Aoki, "A Comparison of the Safety Margins of Botulinum Neurotoxin Serotypes A, B, and F In Mice," Toxicon 39:1815-1820 (2001), which are hereby incorporated by reference in their entirety).

To evaluate digital abduction, a group of five CD-1 female (8 weeks old) mice were injected BoNT/A ad-0 VHH into the right gastrocnemius muscle in a final volume of 3 μl using a Hamilton 701 RN Syringe with 31 gauge point style custom RN needle. The digital abduction can be scored using the scoring system described in Aoki, "A Comparison of the Safety Margins of Botulinum Neurotoxin Serotypes A, B, and F In Mice," Toxicon 39:1815-1820 (2001), which is hereby incorporated by reference in its entirety. The mouse DAS assay is the most common assay used to compare the muscle weakening efficacy of botulinum neurotoxin products. Aoki, "A Comparison of the Safety Margins of Botulinum Neurotoxin Serotypes A, B, and F In Mice," *Toxicon* 39:1815-1820 (2001), which is hereby incorporated by reference in its entirety, used the mouse DAS assay to compare the dose-response efficacy of BoNT/A preparations. This test was utilized to define pharmacological activity of BoNT/A ad-0 VHH in mice. Digital Abduction was assessed at 48 hours.

Results

Pharmacologic Activity In Vitro for BoNT/A ad-0

Figure 14:
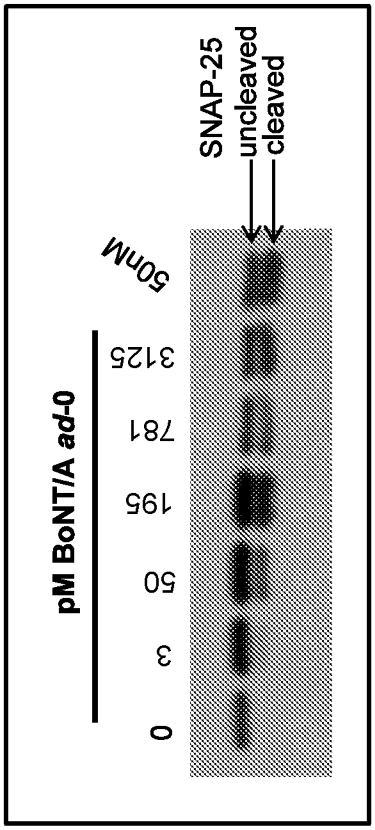
FIG. 14 shows SNAP-25 cleavage for BoNT/A ad-0 protein (i.e., a non-fusion protein insofar as it does not have a fused single chain antibody) in vitro. E19 rat hippocampal neurons were cultured for 14 days in vitro and then exposed to different concentrations of BoNT/A ad-0 for 72 hours. Western blot analysis shows cleaved and uncleaved products for SNAP-25.

To determine the residual activity towards SNAP-25, E19 Rat hippocampal neurons were cultured for 14 days and then exposed to different concentration of BoNT/A ad-0 for 72 hours. A Western blot analysis shows a concentration dependent BoNT/A ad-0 induced cleavage of SNAP-25 (FIG. 14).

Figures 13A, 13B:
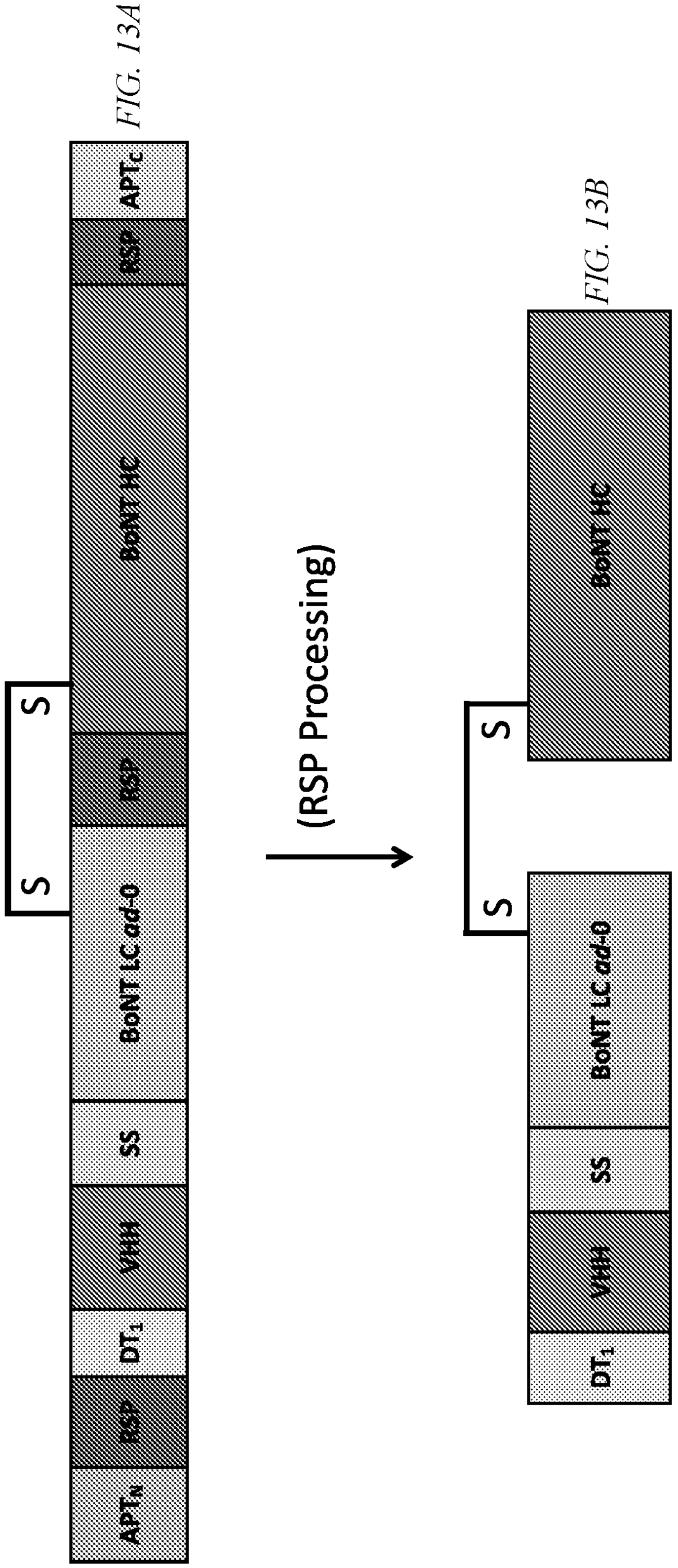
FIGS. 13A-B are schematic illustrations of a propeptide fusion (FIG. 13A) and fusion protein (FIG. 13B) according to one embodiment of the present invention, where the Clostridial neurotoxin portions of the fusion protein possess residual SNAP-25 cleavage activity (i.e., BoNT LC ad-0).
Figure 15:
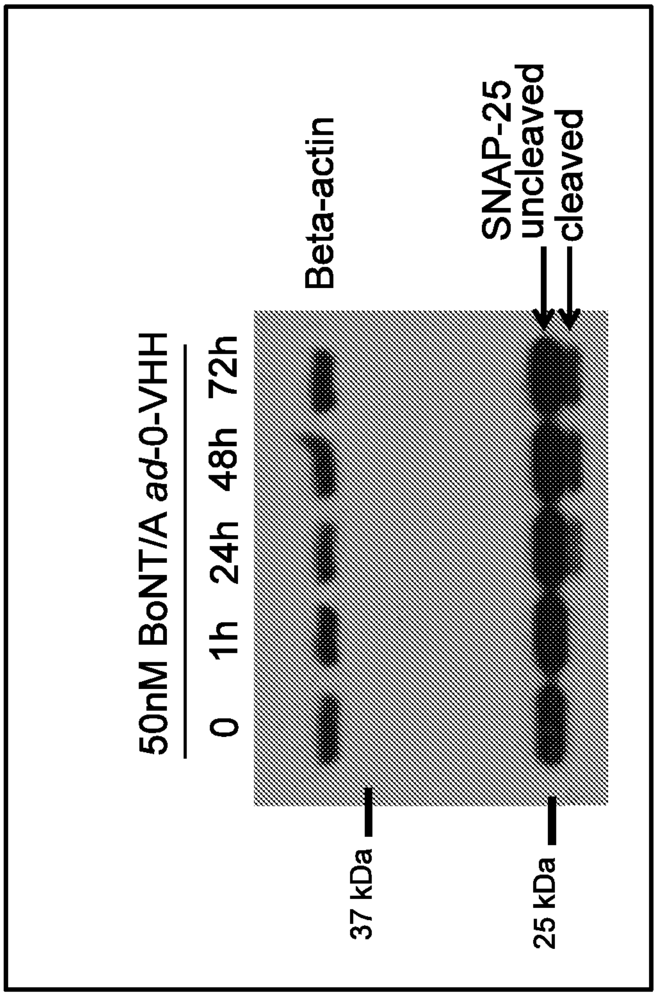
FIG. 15 shows SNAP-25 cleavage for mature full-length BoNT/A ad-0 VHH fusion protein (i.e., having the structure of the fusion protein illustrated in FIG. 13B) in E19 rat hippocampal neuronal cultures. SNAP-25 cleavage is used as a reporter for the delivery of LC and its associated VHH cargo to the cytoplasm, because LC delivery to the cytoplasm is required for access to its SNAP-25 substrate. E19 rat hippocampal neurons were cultured for 14 days in vitro and then exposed to 50 nM BoNT/A ad-0 VHH for 0, 1, 24, 48, and 72 hours. Beta actin was used as loading control.

BoNT/a Ad-0 Successfully Delivers VHH or Single Chain Antibodies into the Neuronal Cytosol The first example of cargo delivery using a prototype BoNT/A atoxic derivative (BoNT/A ad) was designed to deliver a variable domain of heavy chain antibody (VHH) or single chain antibody, raised against light chain of wild-type BoNT/B (BoNT/A ad-0 VHH). Alpaca-derived single chain VHH have a molecular weight of −11 kDa, and are able to bind to specific antigens with high affinity. The specific VHH tested was a non-neutralizing anti-LC-BoNT/B VHH (VHH B-10), the amino acid sequence of which was provided by Dr. Charles Shoemaker (Tufts University School of Veterinary Medicine) and subsequently modified pursuant to this invention to optimize its expression. Several variations for placement of the VHH domain were considered to arrive at the design illustrated in FIGS. 13A-B, which provide a schematic illustration of the BoNT/A ad-0 propeptide fusion and mature fusion protein containing a non-neutralizing anti-LC-BoNT/B VHH domain inserted at the N-terminus of BoNT/A ad-0. Since BoNT/A ad-0 retains residual SNAP-25 cleavage activity (FIG. 14), one can measure the catalytic activity of BoNT/A ad-0 light chain as a read-out for successful delivery of the light chain and the VHH into the cytosol of neurons. Thus, 14 days in vitro (14-DIV) E19 rat hippocampal neuronal cultures were exposed to 50 nM of BoNT/A ad-0 VHH for different time points. SNAP-25 cleavage is observed on cells treated with 50 nM of BoNT/A ad-0 VHH for 24, 48, and 72 hours (FIG. 15), demonstrating the successful translocation of both the LC of BoNT/A ad-0 and VHH to the cytoplasm of neurons. Beta actin was used as loading control, and to show that equal amounts of total protein were loaded per lane (FIG. 15).

Figure 16:
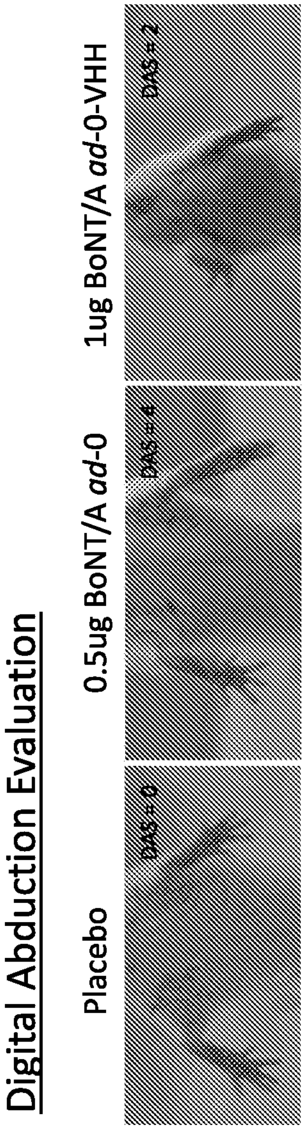
FIG. 16 are photographs showing the results of a digital abduction score (DAS) evaluation of BoNT/A ad-0 VHH, to demonstrate that placing the VHH upstream of the LC ad-0 does not abolish the paralytic activity of BoNT/A ad-0 VHH in vivo.
Figure 17A:
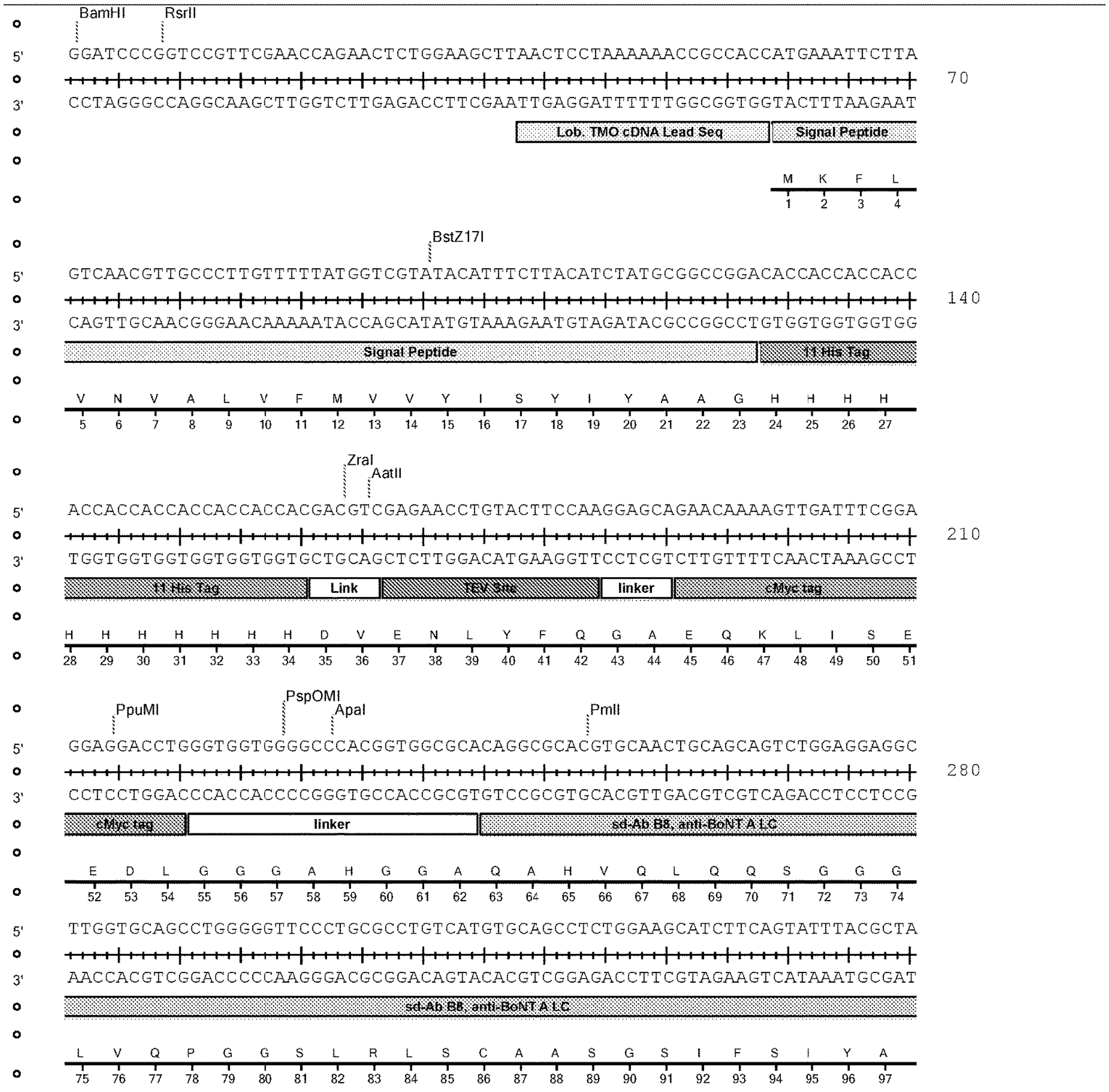
Figure 17D:
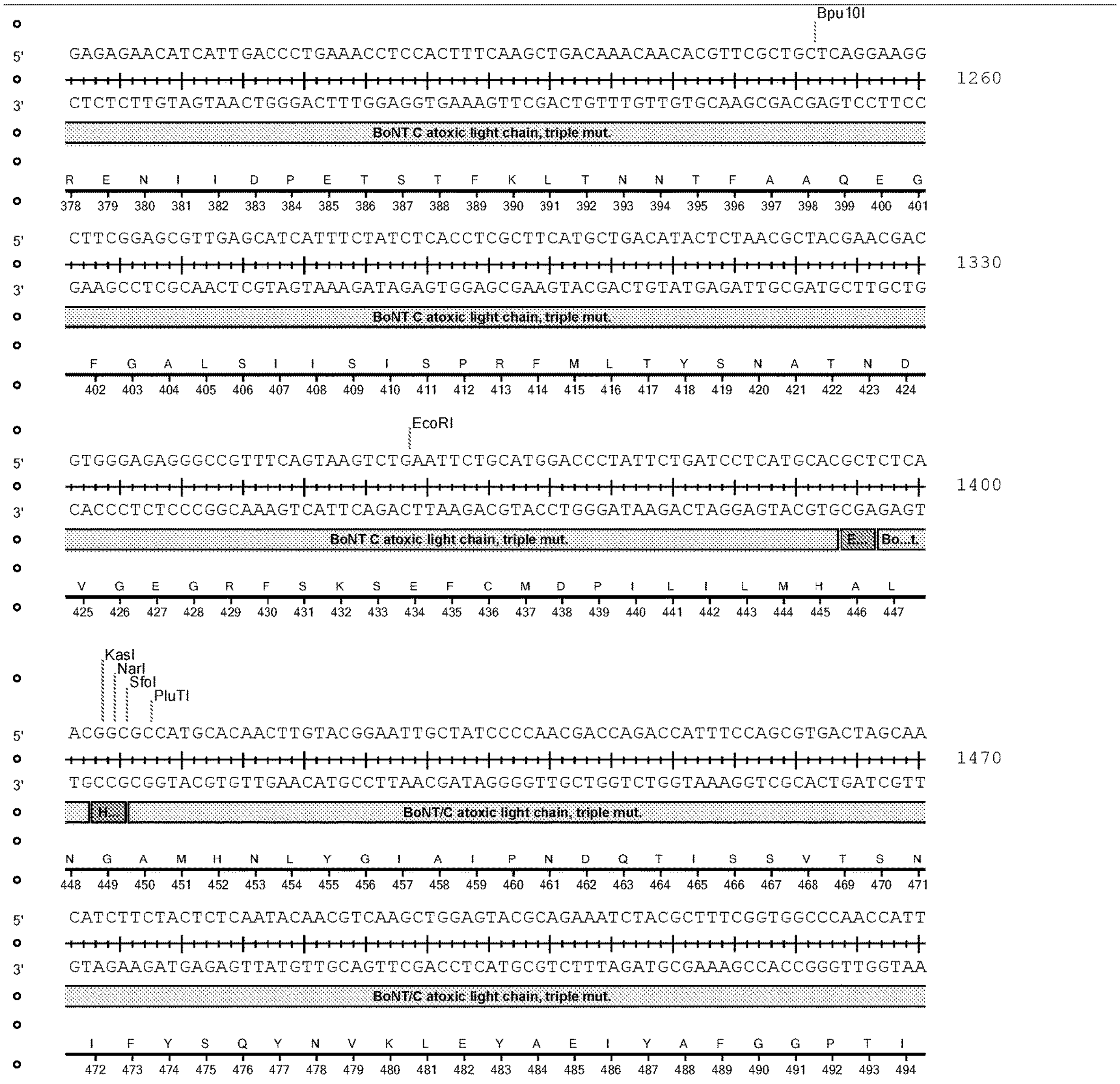
Figure 17E:
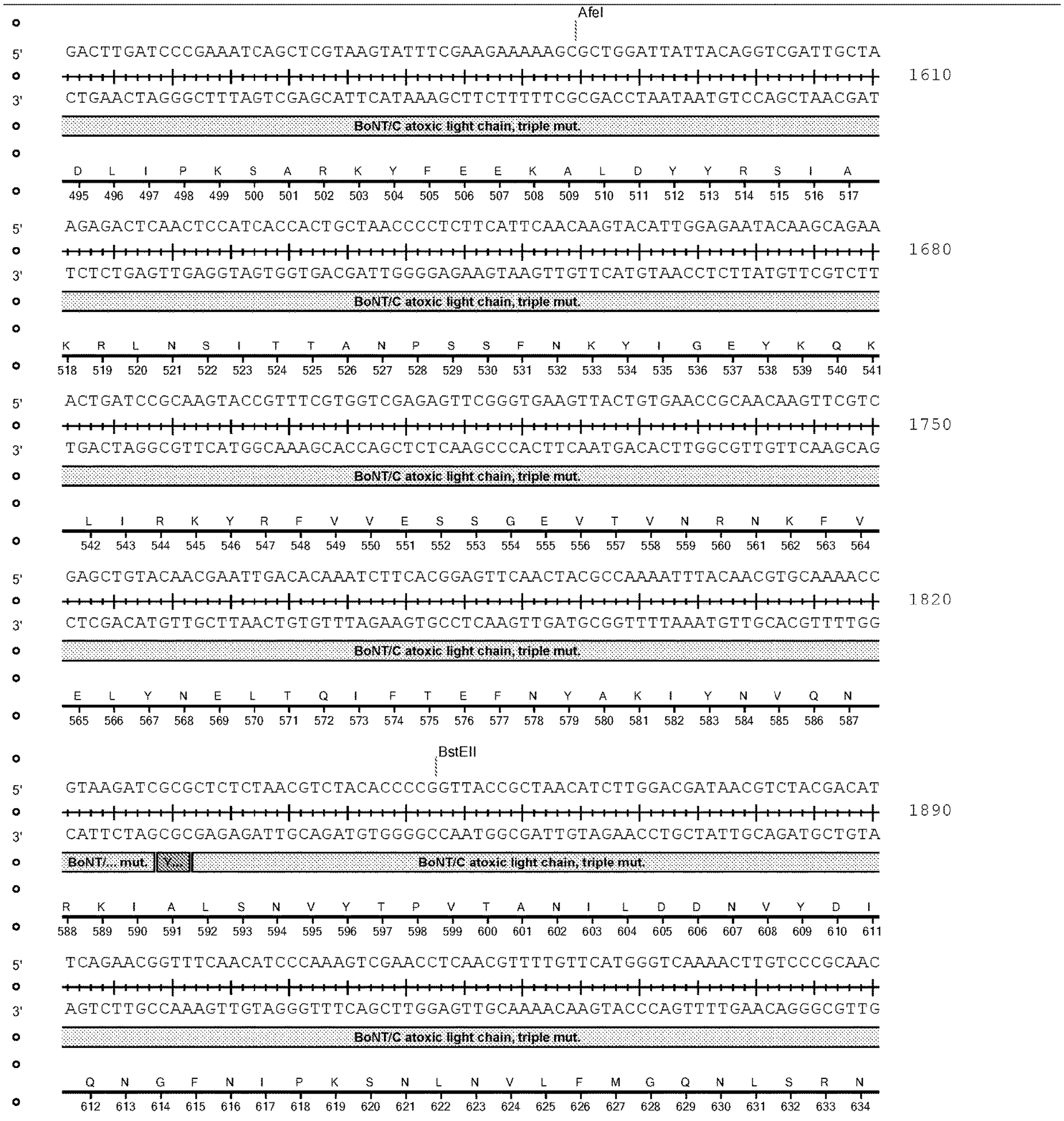

BoNT/a Ad-O-VHH Induces Localized Muscle Paralysis Indicating Successful Delivery of Cargo into the Cytosol of Neurons BoNT/A ad-0 induced muscle weakness was previously measured in vivo using the DAS assay in mice (see PCT Publication No. WO 2014/117148, which is hereby incorporated by reference in its entirety). To further validate the successful delivery of the VHH antibody to the cytosol of neurons, the DAS assay was used as an in vivo readout of successful delivery of the fusion protein. Injection of 1 μg of BoNT/A ad-0 VHH into the left gastroenemius muscle in 3 μl of saline solution resulted in definitive paralysis of the digital abduction reflex, comparable to the pharmaceutical response to BoNT/A ad-0, as seen in FIG. 16, demonstrating that the VHH fused to the light chain of BoNT/A ad-0 was successfully delivered to the cytosol compartment of motor neurons. Mice injected with BoNT/A ad-0 without VHH was used as a control.

Figure 18:
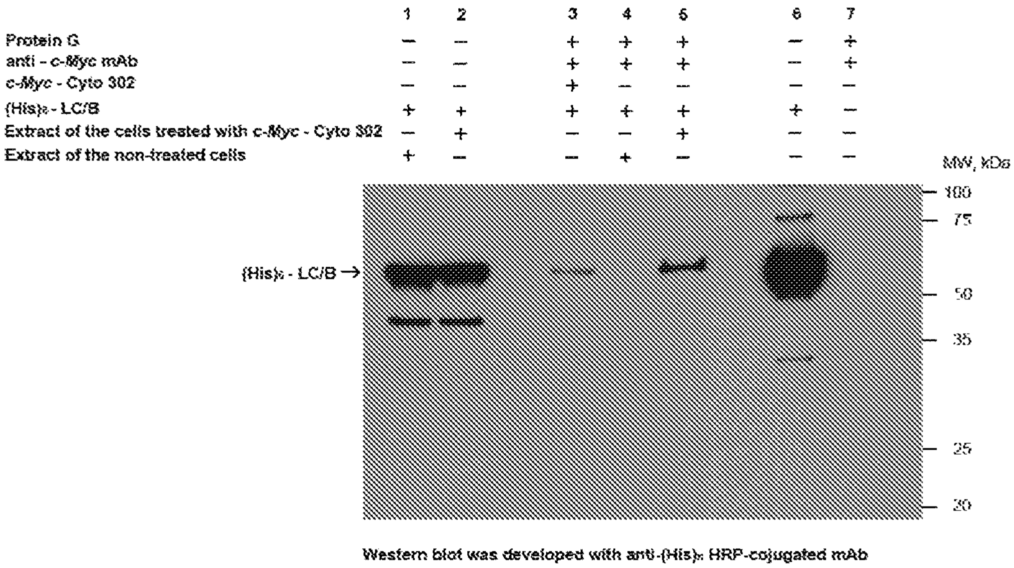
FIG. 18 demonstrates that Cyto-302 (a BoNT/A-B10 carrying BoNT/A ad-0 fusion protein, the sequences of which are shown in FIGS. 19A-L and schematically illustrated in FIG. 13A) retains its activity as a LC/B-binding single chain antibody after internalization into neurons. 14-DIV E19 rat hippocampal neurons were exposed to 50 nM Cyto-302 or buffer for 24 hours. Cells were washed and chased with 50% conditioned media for an additional 24 hours. Cells were washed and extracted with 0.5% Triton™ X 100 buffer, and BoNT/B Light Chain was added to the cytosolic extracts and incubated for 1 hour. BoNT/B LC has a 6-His tag at the C-terminus of the protein to allow simple identification. Samples were then incubated with anti-BoNT/A polyclonal antibodies for 1 hour, followed by immunoprecipitation with Protein G magnetic beads. Western blot analysis: Lane 1: input lysate of cells not treated with Cyto-302. Lane 2: input lysate cells treated Cyto-302. Lanes 3-5: samples after immunoprecipitation. Lane 3: in tube IP without lysate. Cyto-302 and LC/B were mixed in 0.5% Triton X-100 lysis buffer. Lane 4: IP of cells not treated with Cyto-302. Lane 5: IP of cells treated with Cyto-302. Lane 6: 4 ng of LC/B alone. Lane 7: Protein G alone control. Comparison of lanes 4 and 5 illustrate that the BoNT-fused VHH against LC/B can be recovered after delivery to the neuronal cytoplasm, and that the recovered VHH retains the ability to pull down LC/B in an immunoprecipitation experiment.
Figure 19A:
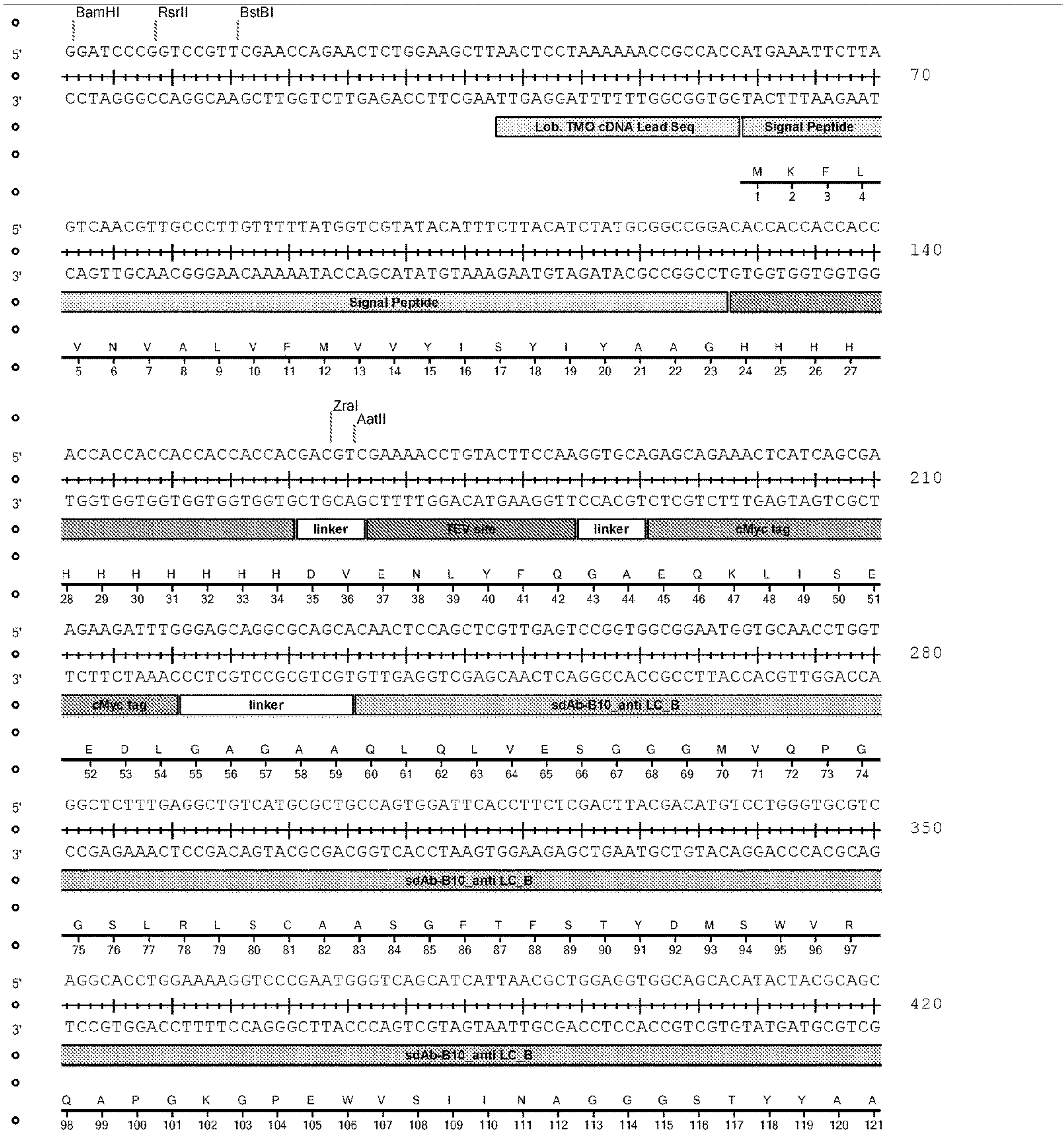
Figure 19B:
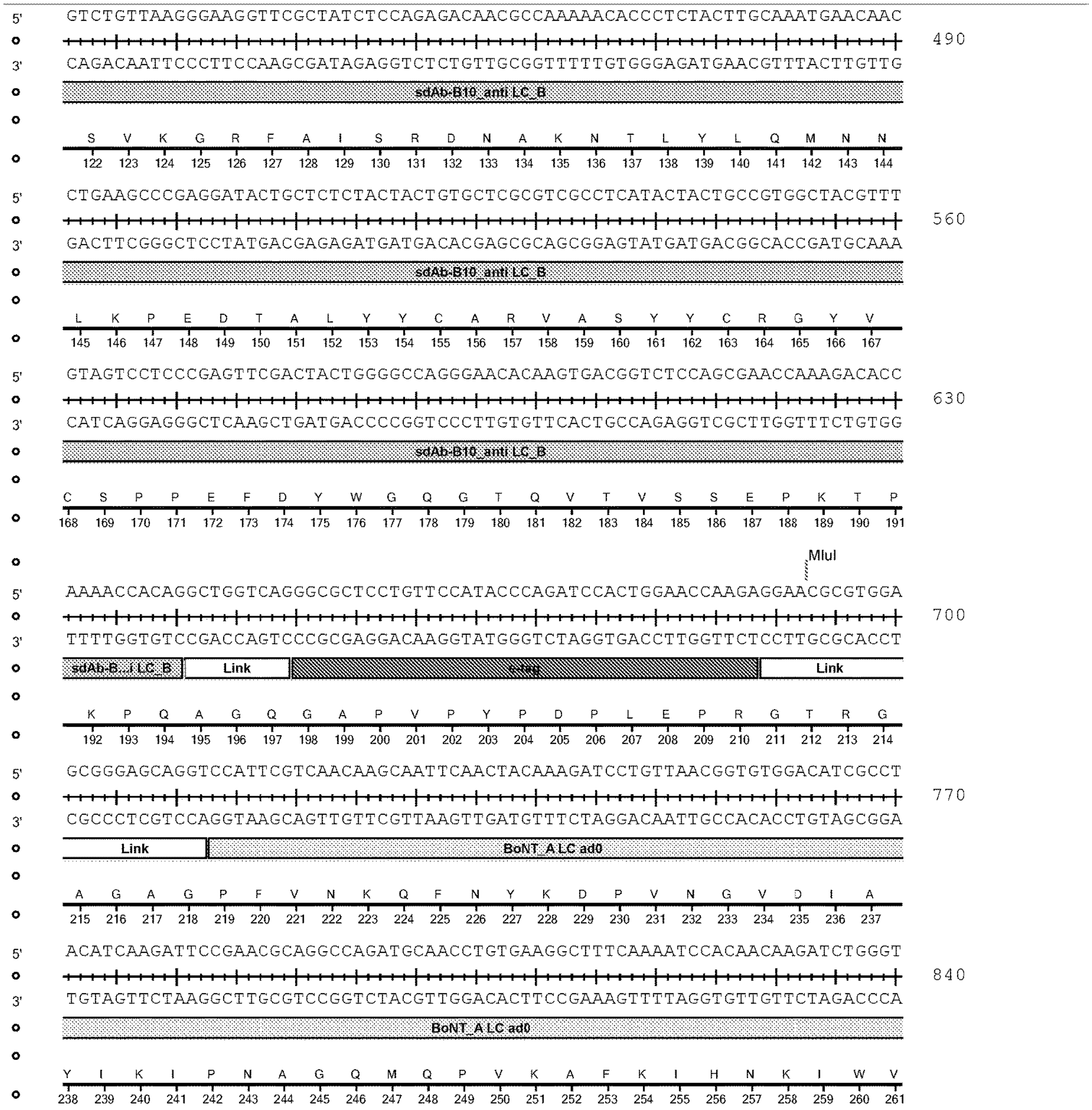
Figure 19C:
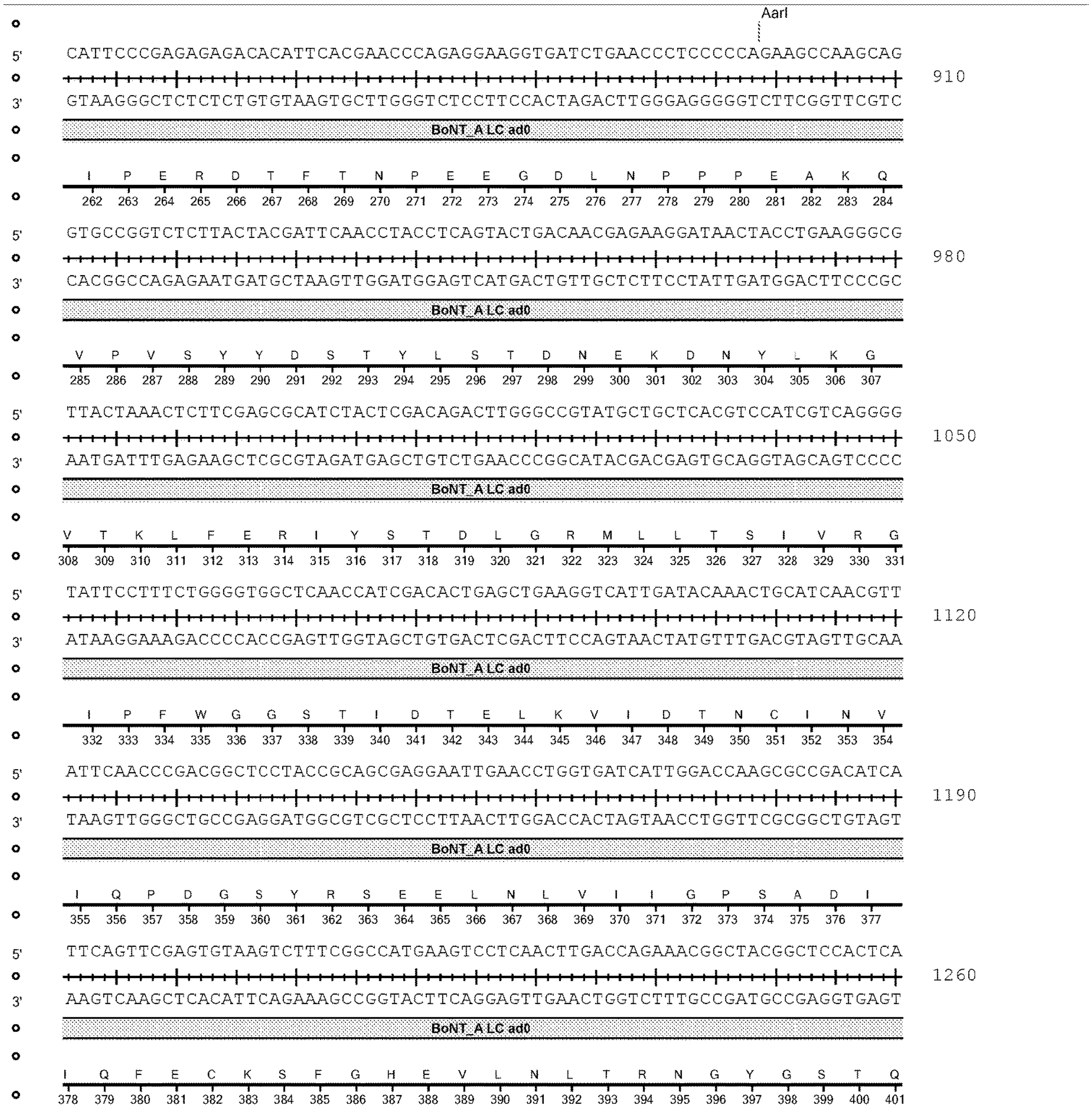
Figure 19E:
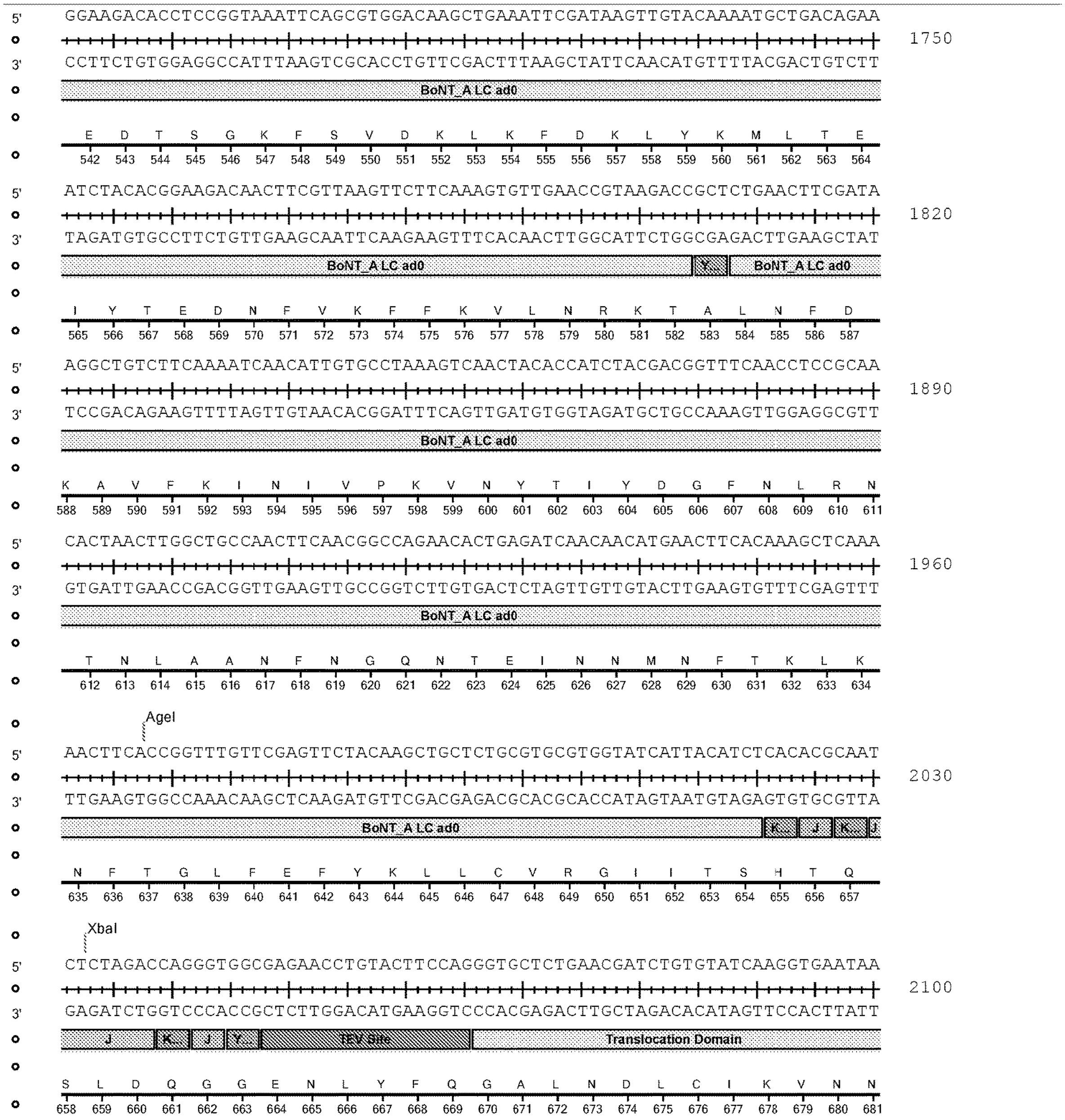
Figure 19H:
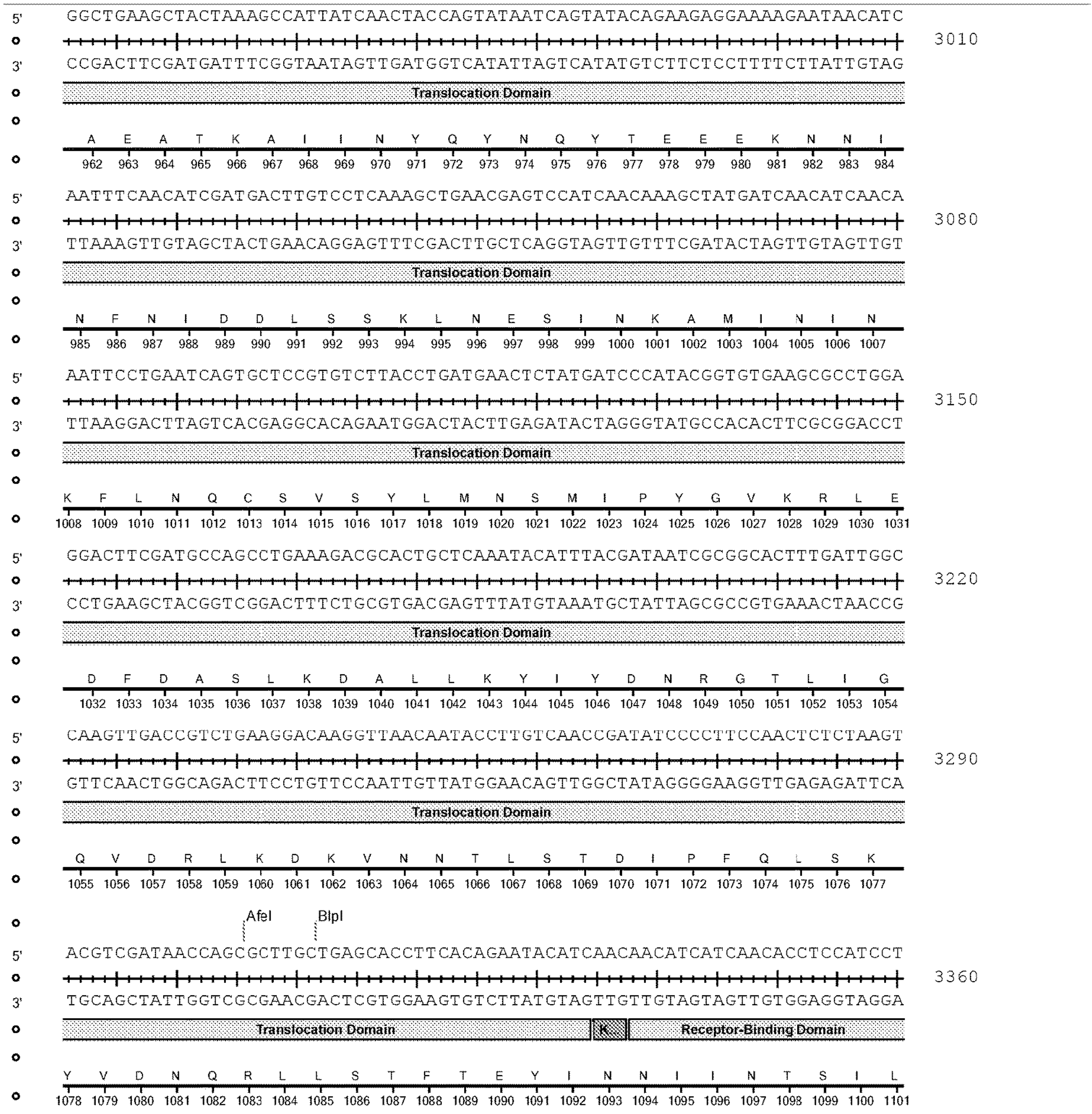
Figure 19L:
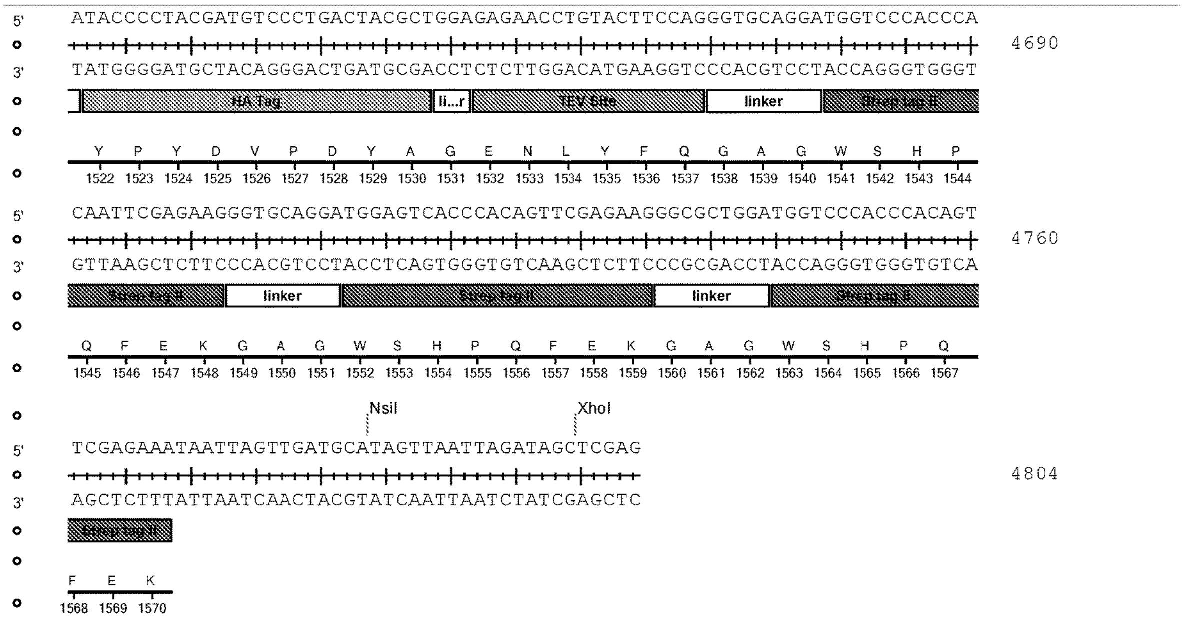
Figure 20A:
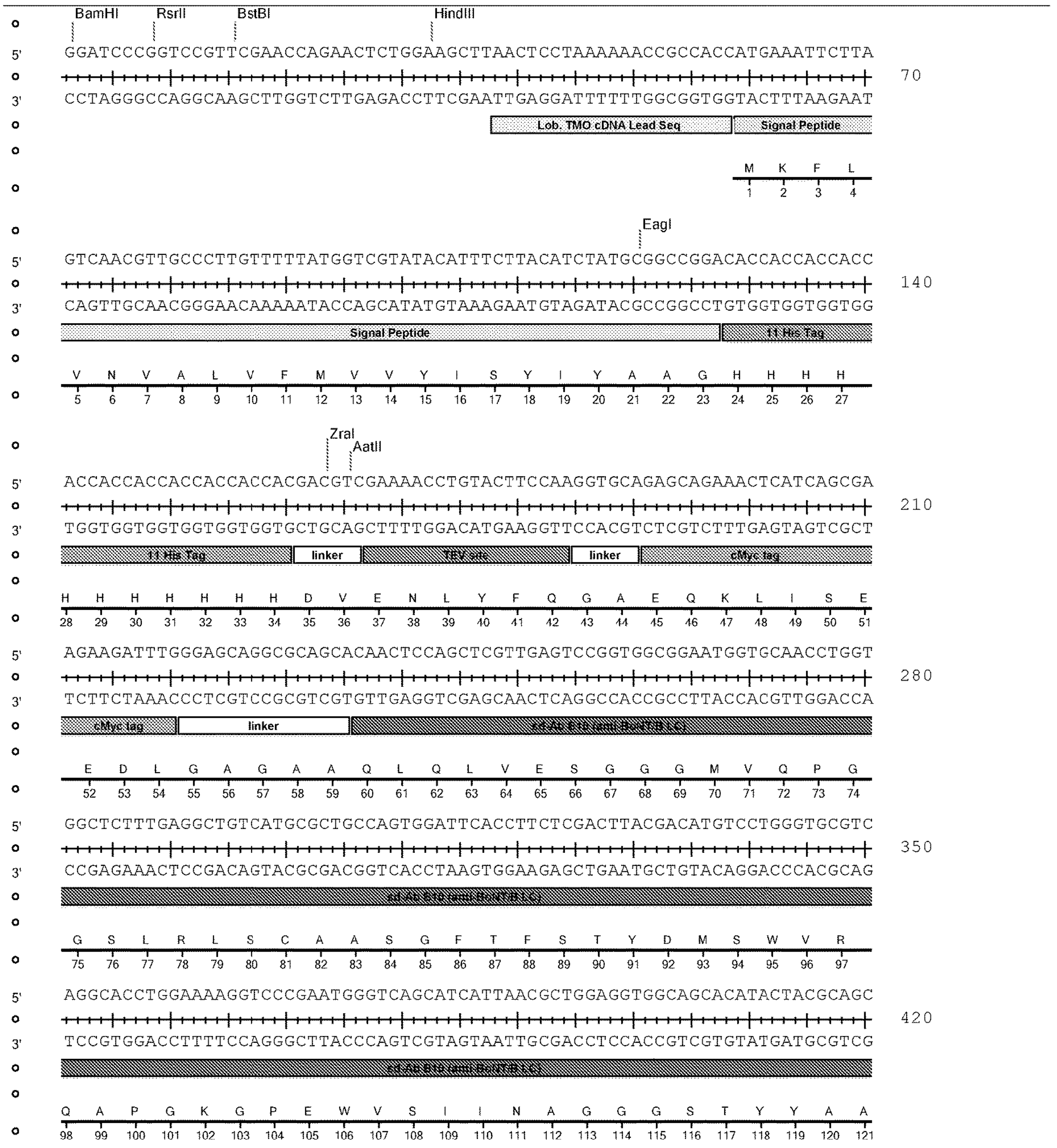
Figure 20D:
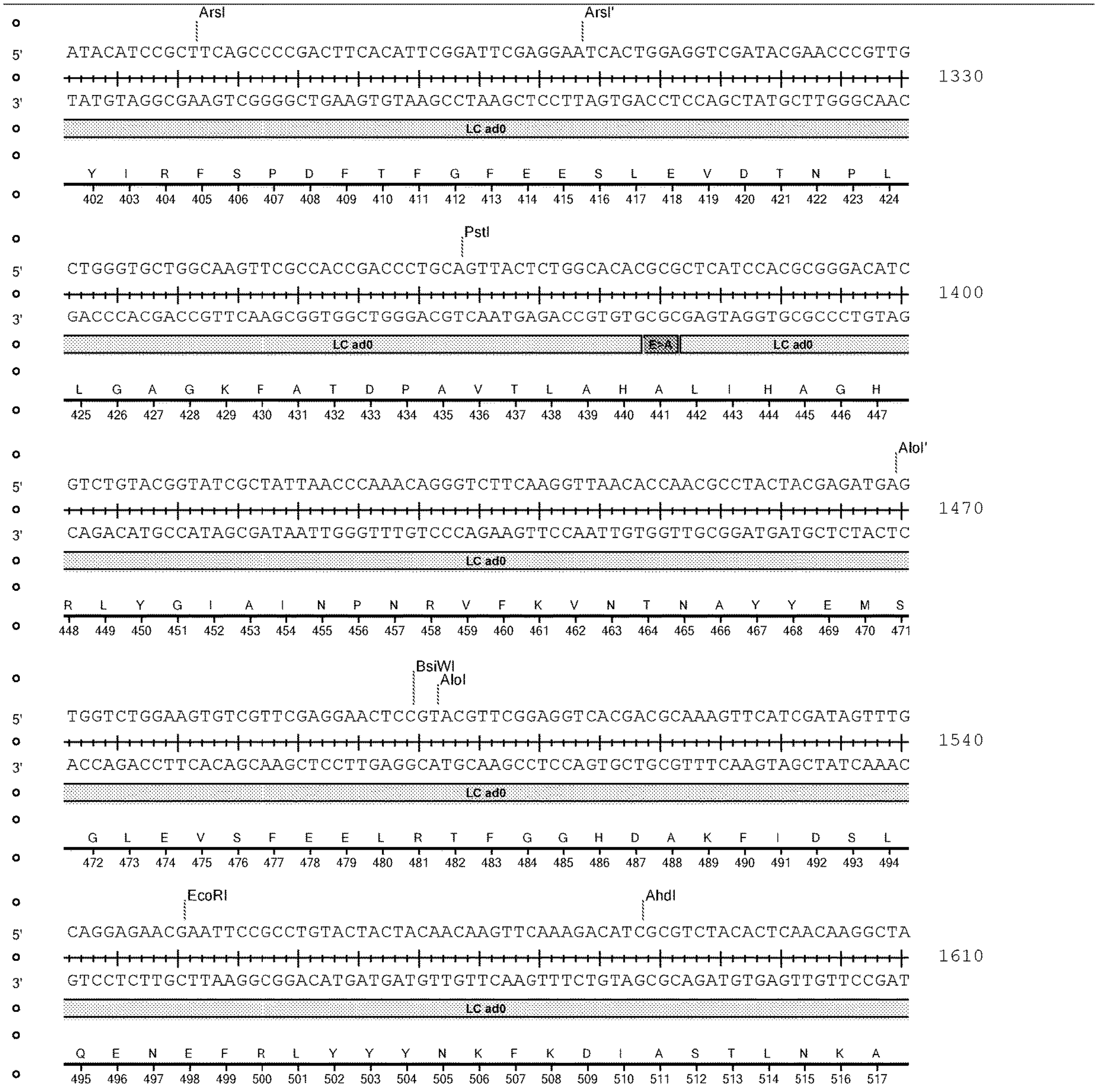
Figure 20E:
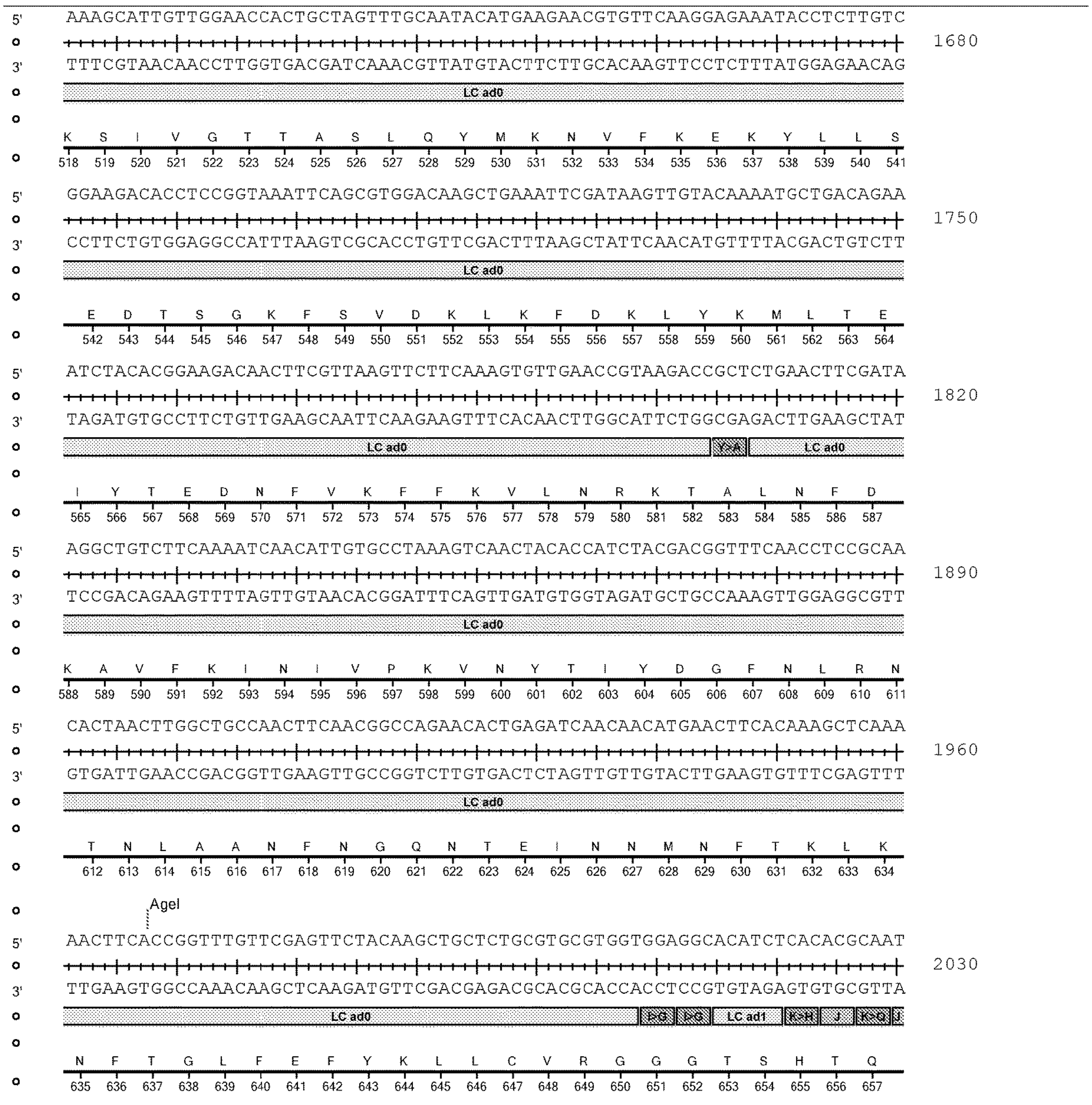
Figure 20L:
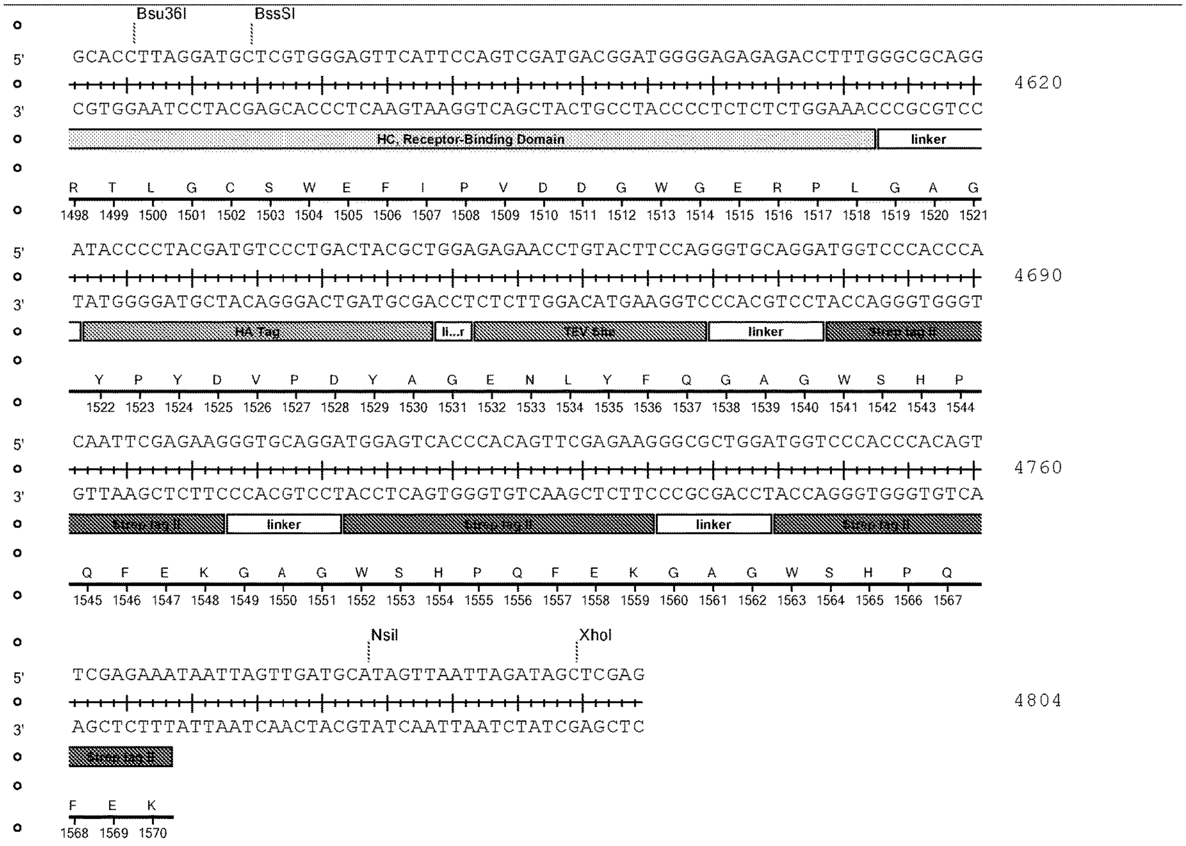

FIG. 18 describes an immunoprecipitation experiment, in which hippocampal neuron cultures are treated with the prototype BoNT/A ad-0 fusion protein containing the non-neutralizing anti-LC-BoNT/B VHH (B-10 VHH) described supra and described in FIGS. 19A-L in the form of the processed disulfide-bonded heterodimer. A comparison of lanes 4 and 5 in FIG. 18 illustrates that LC/B antigen binding activity can be recovered in a cytosolic extract from neurons treated with the BoNT-fused VHH against LC/B using the c-myc tag to immunoprecipitate the fusion protein. It also illustrates that the prototype BoNT/A ad-0 fusion recovered after delivery to the neuron has retained LC/B antigen binding activity, because the VHH recovered from the cytosolic fraction of the cells and, therefore, after translocation of the construct out of the endosome, still retains the ability to specifically pull down LC/B in the immunoprecipitation.

Discussion

In this example, the use of BoNT/A ad-0 has been described as a molecular vehicle to deliver single chain antibodies to the cytosol of neurons. The idea is to use BoNT/A ad-0 as a "Trojan horse" to target the neuronal cytosol, while using the BoNT/A ad-0 light chain catalytic activity towards SNAP-25 as a readout of therapeutic cargo delivery. The difference in the potency (dose use) between BoNT/A ad-0 and BoNT/A ad-0 VHH demonstrates that the VHH fused to the light chain of BoNT/A ad-0 diminishes the pharmacological properties of the BoNT/A ad-0 light chain. Nevertheless, the fact that SNAP-25 cleavage is detected in vitro and digital abduction is measured in vivo serves as concrete empirical evidence that the VIHH-fused to the BoNT/A ad-0 light chain is reaching the cytosolic compartment of neurons.

Example 3—Atoxic Derivative of Botulinum Neurotoxin C (BoNT/C Ad) as a Molecular Vehicle for Targeted Delivery to the Neuronal Cytoplasm Introduction Methods that enable facile production of recombinant derivatives of botulinum neurotoxins (BoNTs) have been developed, which retain the structural and trafficking properties of wild type (wt) BoNTs. Atoxic derivatives of wt BoNT/A have been described supra. Here, an atoxic derivative of BoNT/C1 with three amino acid substitutions in the catalytic domain of the light chain ($E_{446}$>A;$H_{449}$>G; $Y_{591}$>A), termed BoNT/C ad, was designed, expressed, purified, and evaluated.

Methods

The coding sequence for BoNT/C ad was designed to inactivate the light chain protease with minimal disruption of the light chain/heavy chain interactions within the protein heterodimer. Recombinant protein was secreted into culture media as a soluble propeptide. The protein was purified to homogeneity by tandem affinity chromatography and processed with TEV protease to form the disulfide-bonded heterodimer (FIGS. 21A-C), as is described in Band et al., "Recombinant Derivatives of Botulinum Neurotoxin A Engineered for Trafficking Studies and Neuronal Delivery," *Protein Exp. Purif* 71:62-73 (2010) for atoxic derivatives of BoNT/A.

Purified BoNT/C ad was studied in primary cultures of E19 embryonic rat cortical neurons to evaluate its enzymatic activity, neuronal internalization and trafficking pattern using Western blots and immunocytochemistry. The murine intraperitoneal $LD_{50}$ ($MIPLD_{50}$) of BoNT/C ad was determined by the mouse lethality assay. Targeting of BoNT/C ad to the neuromuscular junction in vivo was determined by evaluating co-localization with alpha-bungarotoxin in the murine diaphragm.

Preparation and Maintenance of E19 Rat Cortical Neurons

Time pregnant Sprague-Dawley rats (Taconic) were used to isolate embryonic-day 19 (E19) cortical neurons. Bilateral cortex were dissected from fetal brain, immersed in dissection buffer (15 mM HEPES pH 7.2 (Cat #15630080, Life Technologies), 0.5% glucose in DPBS without $Ca^{2+}$ and $Mg^{2+}$(Cat #14190-250, Life Technologies), and dissociated by incubation in 10 mL of dissection buffer supplemented with 1× Trypsin/EDTA (10× Trypsin/EDTA is 0.5% trypsin/0.2% EDTA, Cat #15400054, Life Technologies) for 10 minutes at 37° C. Tissue was triturated using a fire polished Pasteur glass pipette, and cells were counted. The single cell suspension was plated onto poly-L-lysine hydrobromide-coated plates or coverslips in plating medium (1× Minimum Essential Medium-Glutamax™ (1×MEM-Glutamax™, Cat. #41090036, Life Technologies), 10% FBS (Fetal Bovine Serum; Cat. #16000044, Life Technologies), 1×Sodium pyruvate (100 mM Sodium pyruvate; Cat. #11360-070, Life Technologies), 1×Pen/Strep (100×Pen/Strep is 10,000 U/mL penicillin, 10 mg/mL streptomycin; Cat. #15240062, LifeTechnologies). After two hours, plating medium was replaced with maintenance medium (1×Neurobasal medium (Cat. #21103049, Life Technologies), 1×B27 supplement (Cat. #17504044, Life Technologies), and 1×Pen/Strep). Three days after plating, 2 mg/mL cytosine b-D-arabinofuranoside (AraC, Cat. #C1768, Sigma) was added to the maintenance medium to prevent growth of glia. Half of the medium was replaced with fresh maintenance medium every 3 to 5 days.

Western Blot Analysis

Neurons were harvested and solubilized on ice in 200 mL lysis buffer with protease inhibitors (0.5% Triton™ X-100, 100 mM NaCl, 25 mM HEPES, pH 7.5, 10 mM 6-aminocaproic acid, 2 mM benzamidine, 5 mM 4-(2-aminoethyl) benzenesulfonyl fluoride hydrochloride (AEBSF), 2.5 mM EDTA, 325 mM bestatin, 35 mM E-64, 2.5 mM leupeptin, 0.75 mM aprotinin) by passing the sample several times through a 25 gauge needle. Soluble protein lysate was separated from the pellet by centrifuging the samples at 18,000 g at 4° C. for 20 minutes. After lysis, the total protein concentration in each sample was measured and sample volumes were adjusted with lysis buffer and supplemented with protease inhibitors to equalize concentration. Approximately 30 microgram of total protein were loaded per lane, separated by reduced SDS PAGE and transferred to a 0.2 mm nitrocellulose membrane (Bio-Rad). Following transfer, membranes were blocked in 10% fat-free milk+5% NGS (Normal Goat Serum, Cat. #10000C, Life Technologies) in TBST (150 mM NaCl, 10 mM Tris-HCl pH 8.0, 0.1% Tween® 20) at room temperature for 2 hours. Membranes were incubated with primary antibodies overnight at 4° C., and with secondary antibodies 45 minutes at room temperature. Following incubations, blots were washed with TBST 3 times for 5 minutes. Super Signal West Pico chemiluminescent substrate (Cat. #34080, Thermo Scientific) was used for visualization by autoradiography.

Immunocytochemistry Analysis

BoNT/C ad or BoNT/C ad B8 (a fusion protein with a B8 single chain antibody) was incubated with neurons for different times as indicated in figure legends. Immediately after incubation, cells were washed three times with ice-cold DPBS, fixed with 4% formaldehyde for 15 minutes, and permeabilized with 0.1% Triton™ X-100 for 5 minutes. After fixation, the permeabilized cells were washed three times with DPBS, blocked for 1 hour at room temperature with 10% BSA in DPBS, and incubated overnight at 4° C. with primary antibodies. Primary antibodies were diluted in DPBS-NGS. After primary antibody incubation, cells were washed three times with DPBS-NGS (1X DPBS with 3% NGS) and incubated with secondary antibody (in DPBS-NGS) for 45 minutes at room temperature. After secondary antibody incubation, cells were washed three times with DPBS, and the cover slips were mounted on slides with mounting medium. Image scanning was performed on a Nikon LSM 510 confocal microscope and images were analyzed using Zeiss LSM confocal microscopy software.

Detection of BoNT/C ad Catalytic Activity in a Cell-Based Assay

Figure 22A:
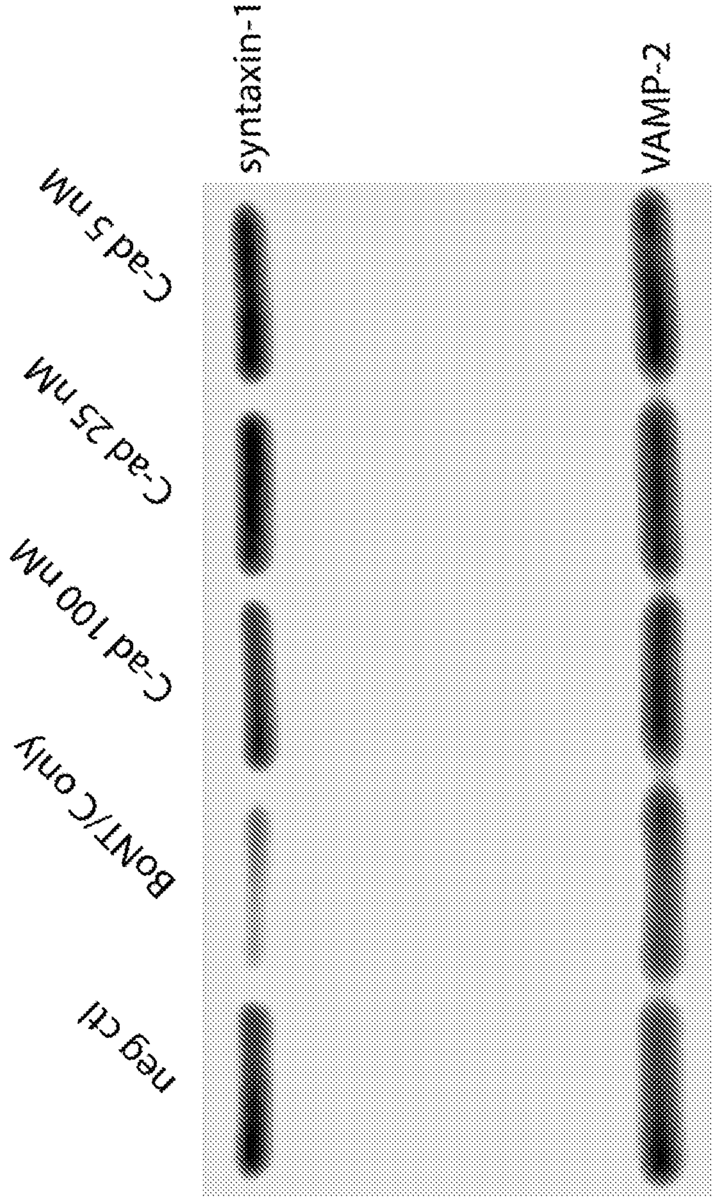
FIGS. 22A-B demonstrate BoNT/C ad is not catalytically active towards wt BoNT/C substrates in a cell-based assay. 14-DIV E19 rat cortical neurons were exposed to different concentrations of BoNT/C ad for 96 hours and analyzed by Western blot.
Figure 22B:
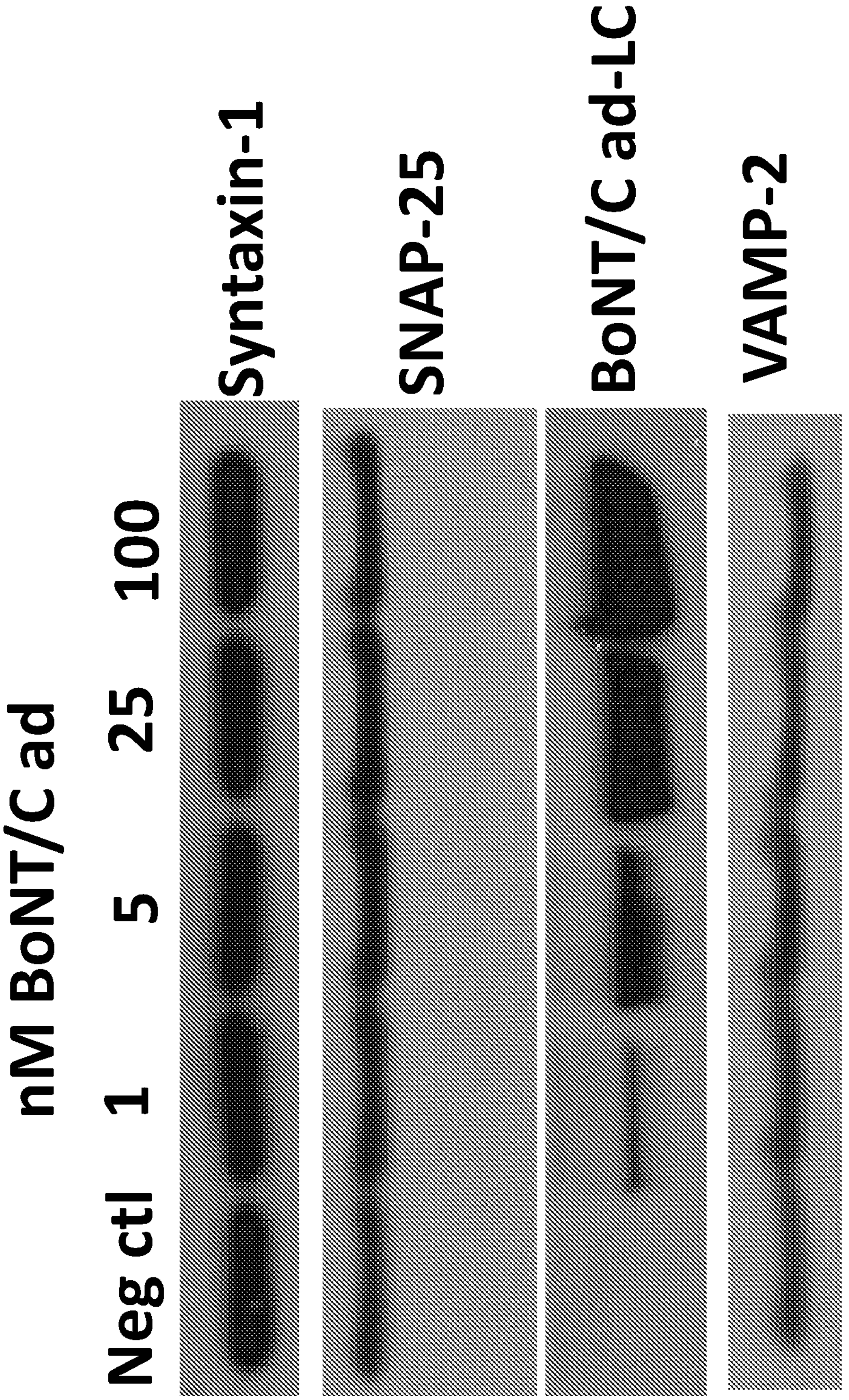

To detect if BoNT/C ad has enzymatic activity towards wt BoNT/C natural substrates Syntaxin-1 and SNAP-25, 14-DIV E19 rat cortical neurons were exposed different concentrations of BoNT/C ad for 96 hours. After the incubation time, cells were washed and prepared for Western blot analysis (FIG. 22A). Cells were exposed to media only (negative control), 0.5 nM BoNT/C (positive control), or 5, 25, or 100 nM of BoNT/C ad for 96 hours. Western blot analysis was perform to detect Syntaxin-1 and VAMP-2; VAMP-2 was used as internal loading control. In FIG. 22B, cells were exposed to 1, 5, 25, or 100 nM of of BoNT/C ad for 96 hours. Western blot analysis was performed to detect Syntaxin-1, SNAP-25, BoNT/C ad LC, and VAMP-2, respectively. VAMP-2 serves as an internal loading control.

Detection of Neuronal Internalization of BoNT/C ad

To detect neuronal internalization of BoNT/C ad, 14-DIV E19 rat hippocampal cultures were exposed to 25 nM of BoNT/C ad for 16 hours. After the incubation cells were prepared for immunocytochemistry using monoclonal antibodies to detect VAMP-2, BoNT/C ad LC, BoNT/C HC, and EEA-1, and analyzed using confocal microscopy.

Trafficking of BoNT/C to the Neuromuscular Junction

To examine trafficking patterns of BoNT/C ad, 6-week old CD-1 female mice were injected intraperitoneally with 0.4 mg/kg of BoNT/C ad. 24 hours after systemic injection, mice were euthanized and hemidiaphragm isolated and prepared for immunostaining. Hemidiaphragm was stained with monoclonal antibodies for Syntaxin, BoNT/C HC, and Alpha bungarotoxin, and analyzed by confocal microscopy.

Toxicity of BoNT/C ad in Mice

To determine the toxicity of BoNT/C in mice, survival rates of 8-week old CD-1 female mice injected intraperitoneally with 0.04, 0.2, 0.4, 2, or 4 mg/kg of BoNT/C ad were determined. BoNT/C ad was diluted in DPB-S supplemented with 0.02% gelatin. Mice were injected in the intraperitoneal cavity with a final volume of 0.250 ml.

Results

Figure 24:
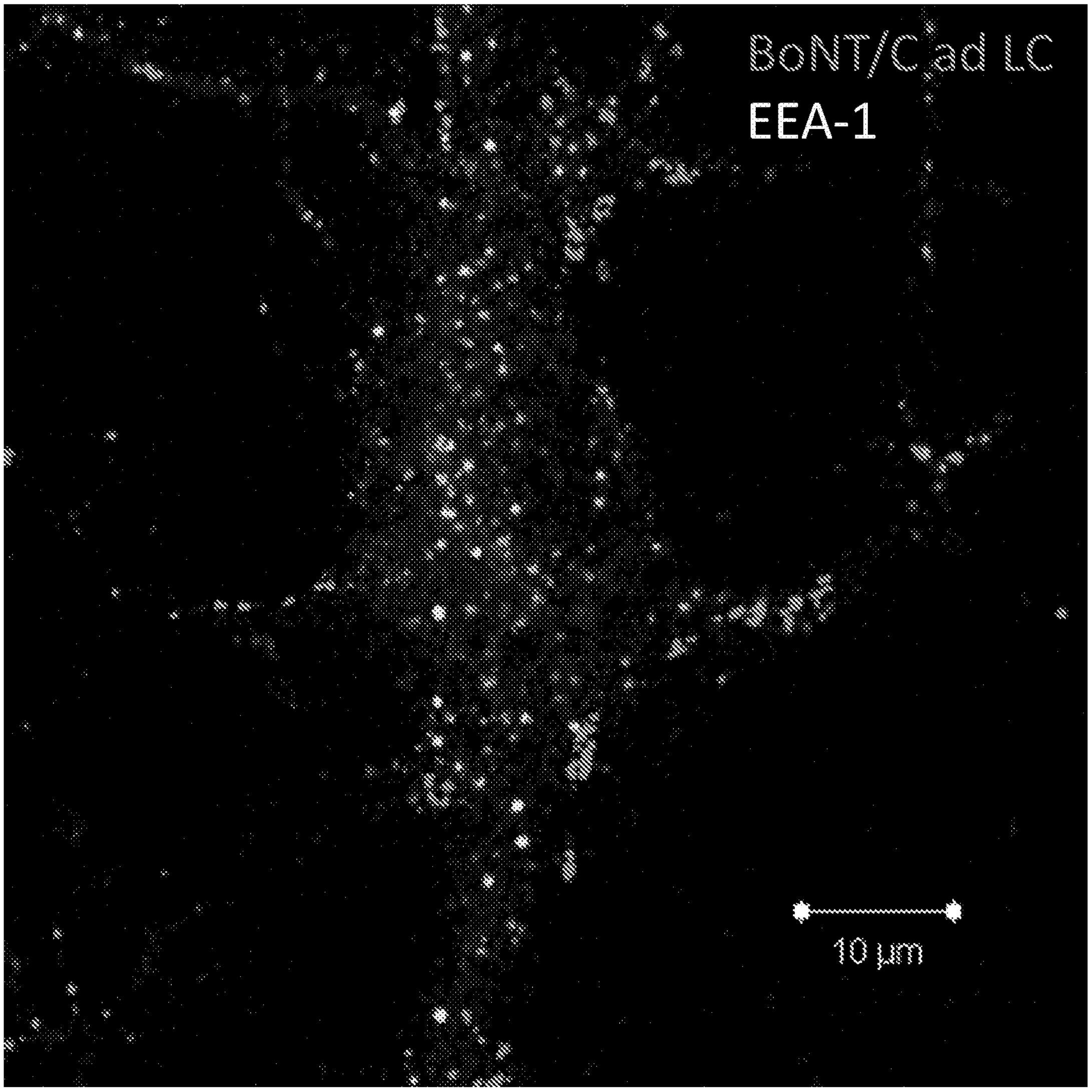
FIG. 24 demonstrates that BoNT/C LC hardly co-localizes with early endosome marker EEA-1 in neuronal cultures. 14-DIV E19 rat hippocampal cultures were treated with 25 nM of BoNT/C ad for 16 hours. Cells were prepared for immunocytochemistry and analyzed using confocal microscopy. Cells were stained for EEA-1 and BoNT/C ad LC.
Figure 25A:
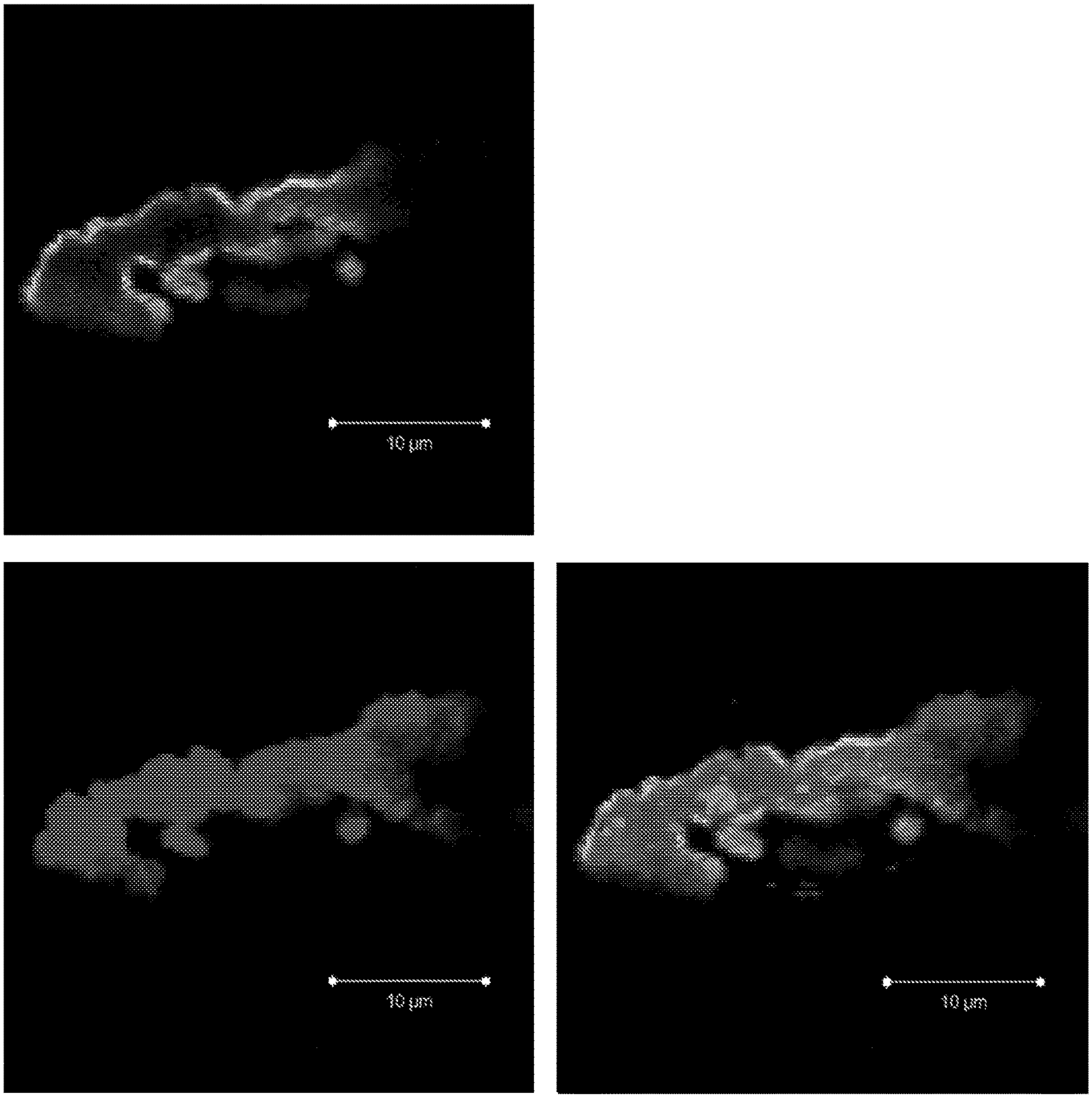
FIGS. 25A-B demonstrate that BoNT/C ad traffics to the neuromuscular junction after systemic administration. Six week old mice were injected intraperitoneally with 0.4 mg/kg of BoNT/C ad. Twenty-four hours after systemic injection, mice were euthanized and hemidiaphragm isolated and prepared for staining. Tissue was stained with Syntaxin, BoNT/C HC and Alpha bungarotoxin and analyzed by confocal microscopy.
Figure 25B:
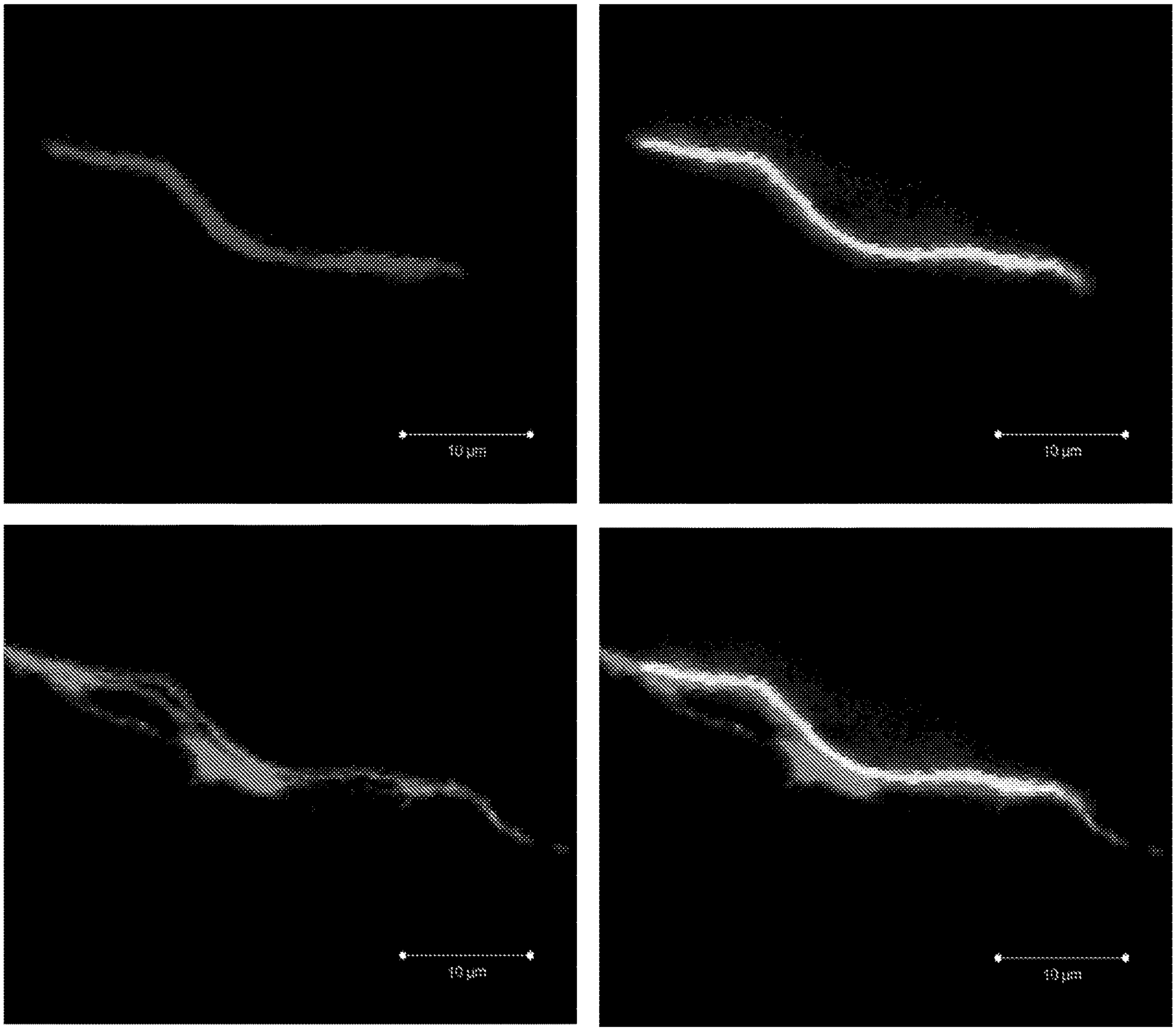

The final yield of purified protein from a 1 L culture was approximately 50 mg. BoNT/C was found to co-localize with the synaptic proteins SNAP-25 and VAMP-2 (FIGS. 23A-B); minor co-localization with early/late endosome markers was also observed (FIG. 24). Treatment of neuronal cultures with up to 100 nM BoNT/C ad for 96 hours did not result in detectable cleavage of SNARE proteins (FIGS. 22A-B). The $MIPLD_{50}$ of BoNT/C ad was determined to be greater than 4 mg/kg (Table 1). Mice injected with BoNT/C ad doses equal or higher than 2 mg/kg showed adverse clinical symptoms including waspy-like waste, generalized body weakness and difficulty breathing. BoNT/C ad traffics to the nueruomuscular junction after systemic administration evident from the heavy chain localization to alpha-bungarotoxin on the murine diaphragm after animals were injected intraperitoneally (FIGS. 25A-B).

TABLE 1

| BoNT/C ad Mouse Lethality Assay | |
|---|---|
| Dose (mg/kg) mouse | Survival (n = 10) |
| 0.04 | 100% |
| 0.2 | 100% |
| 0.4 | 100% |
| 2 | 90% |
| 4 | 70% |

Conclusion

BoNT/C maintains its natural structure shown by the ability to traffic to the neuro-muscular junction after systemic administration and co-localizes with pre-synaptic proteins. The extremely low toxicity of BoNT/C ad, absence of catalytic activity, and its neuron-targeting properties indicate its usefulness as a molecular vehicle for drug delivery to the neuronal cytoplasm.

Example 4—Post-Exposure Effectiveness of a Single Chain Antibody Against Botulinum Neurotoxin Delivered Via an Atoxic Recombinant Neurotoxin Vehicle (BoNT/C Ad)

Introduction

Current treatment for botulism rely on administration of antitoxins. These antitoxins are antibodies or antibody fragments, which are only effective against botulinum neurotoxin (BoNT) while the toxin remains in circulation. In botulism patients, prolonged mechanical ventilation is often required to prevent death, because much of the toxin has accumulated inside neurons by the time patients are diagnosed, making antitoxin treatment only partially effective. Recombinant atoxic derivatives of BoNT/C to deliver single chain antibodies directly to the presynaptic compartment of BoNT-intoxicated neurons have been developed. The single chain antibody counteracts botulism symptoms inside intoxicated neurons by blocking the light chain of BoNT/A. Here, an intracellular treatment termed C/B8 is described, comprising a single chain VHH camelid antibody (B8), delivered via an atoxic BoNT/C1 derivative (BoNT/C ad), which is designed to be effective after the toxin has already entered neurons.

The primary objective of these studies was to evaluate the efficacy of C/B8 antidote to reverse clinical respiratory symptoms associated with intoxication by BoNT/A, particularly in comparison to standard antibody-based antitoxins. In a murine model of botulism, mice were challenged with 1.2 or 4 $MIPLD_{50}$ units of BoNT/A1 by intraperitoneal (ip) injection, and then treated at various times with ip administration of C/B8 antidote or an antibody-based antitoxin.

Methods

Preparation and Maintenance of E19 Rat Cortical Neurons

Time pregnant Sprague-Dawley rats (Taconic) were used to isolate embryonic-day 19 (E19) cortical neurons. Bilateral cortex were dissected from fetal brain, immersed in dissection buffer (15 mM HEPES pH 7.2 (Cat #15630080, Life Technologies), 0.5% glucose in DPBS without $Ca^{2+}$ and $Mg^{2+}$(Cat #14190-250, Life Technologies), and dissociated by incubation in 10 mL of dissection buffer supplemented with 1×Trypsin/EDTA (10× Trypsin/EDTA is 0.5% trypsin/0.2% EDTA, Cat #15400054, Life Technologies) for 10 minutes at 37° C. Tissue was triturated using a fire polished Pasteur glass pipette, and cells were counted. The single cell suspension was plated onto poly-L-lysine hydrobromide-coated plates or coverslips in plating medium (1×Minimum Essential Medium-Glutamax™ (1×MEM-Glutamax™, Cat. #41090036, Life Technologies), 10% FBS (Fetal Bovine Serum; Cat. #16000044, Life Technologies), 1×Sodium pyruvate (100 mM Sodium pyruvate; Cat. #11360-070, Life Technologies), 1×Pen/Strep (100×Pen/Strep is 10,000 U/mL penicillin, 10 mg/mL streptomycin; Cat. #15240062, LifeTechnologies). After two hours, plating medium was replaced with maintenance medium (1×Neurobasal medium (Cat. #21103049, Life Technologies), 1×B27 supplement (Cat. #17504044, Life Technologies), and 1×Pen/Strep). Three days after plating, 2 mg/mL cytosine b-D-arabinofuranoside (AraC, Cat. #C1768, Sigma) was added to the maintenance medium to prevent growth of glia. Half of the medium was replaced with fresh maintenance medium every 3 to 5 days.

Western Blot Analysis

Neurons were harvested and solubilized on ice in 200 mL lysis buffer with protease inhibitors (0.5% Triton™ X-100, 100 mM NaCl, 25 mM HEPES, pH 7.5, 10 mM 6-aminocaproic acid, 2 mM benzamidine, 5 mM 4-(2-aminoethyl) benzenesulfonyl fluoride hydrochloride (AEBSF), 2.5 mM EDTA, 325 mM bestatin, 35 mM E-64, 2.5 mM leupeptin, 0.75 mM aprotinin) by passing the sample several times through a 25 gauge needle. Soluble protein lysate was separated from the pellet by centrifuging the samples at 18,000 g at 4° C. for 20 minutes. After lysis, the total protein concentration in each sample was measured and sample volumes were adjusted with lysis buffer and supplemented with protease inhibitors to equalize concentration. Approximately 30 microgram of total protein were loaded per lane, separated by reduced SDS PAGE and transferred to a 0.2 mm nitrocellulose membrane (Bio-Rad). Following transfer, membranes were blocked in 10% fat-free milk+5% NGS (Normal Goat Serum, Cat. #10000C, Life Technologies) in TBST (150 mM NaCl, 10 mM Tris-HCl pH 8.0, 0.1% Tween® 20) at room temperature for 2 hours. Membranes were incubated with primary antibodies overnight at 4° C., and with secondary antibodies 45 minutes at room temperature. Following incubations, blots were washed with TBST 3 times for 5 minutes. Super Signal West Pico chemiluminescent substrate (Cat. #34080, Thermo Scientific) was used for visualization by autoradiography.

Immunocytochemistry Analysis

BoNT/C ad or BoNT/C ad B8 (a fusion protein with a B8 single chain antibody) was incubated with neurons for different times as indicated in figure legends. Immediately after incubation, cells were washed three times with ice-cold DPBS, fixed with 4% formaldehyde for 15 minutes, and permeabilized with 0.1% Triton™ X-100 for 5 minutes. After fixation, the permeabilized cells were washed three times with DPBS, blocked for 1 hour at room temperature with 10% BSA in DPBS, and incubated overnight at 4° C. with primary antibodies. Primary antibodies were diluted in DPBS-NGS. After primary antibody incubation, cells were washed three times with DPBS-NGS (1X DPBS with 3% NGS) and incubated with secondary antibody (in DPBS-NGS) for 45 minutes at room temperature. After secondary antibody incubation, cells were washed three times with DPBS, and the cover slips were mounted on slides with mounting medium. Image scanning was performed on a Nikon LSM 510 confocal microscope and images were analyzed using Zeiss LSM confocal microscopy software.

Co-localization of CB8 with Synaptic Proteins

Figure 26:
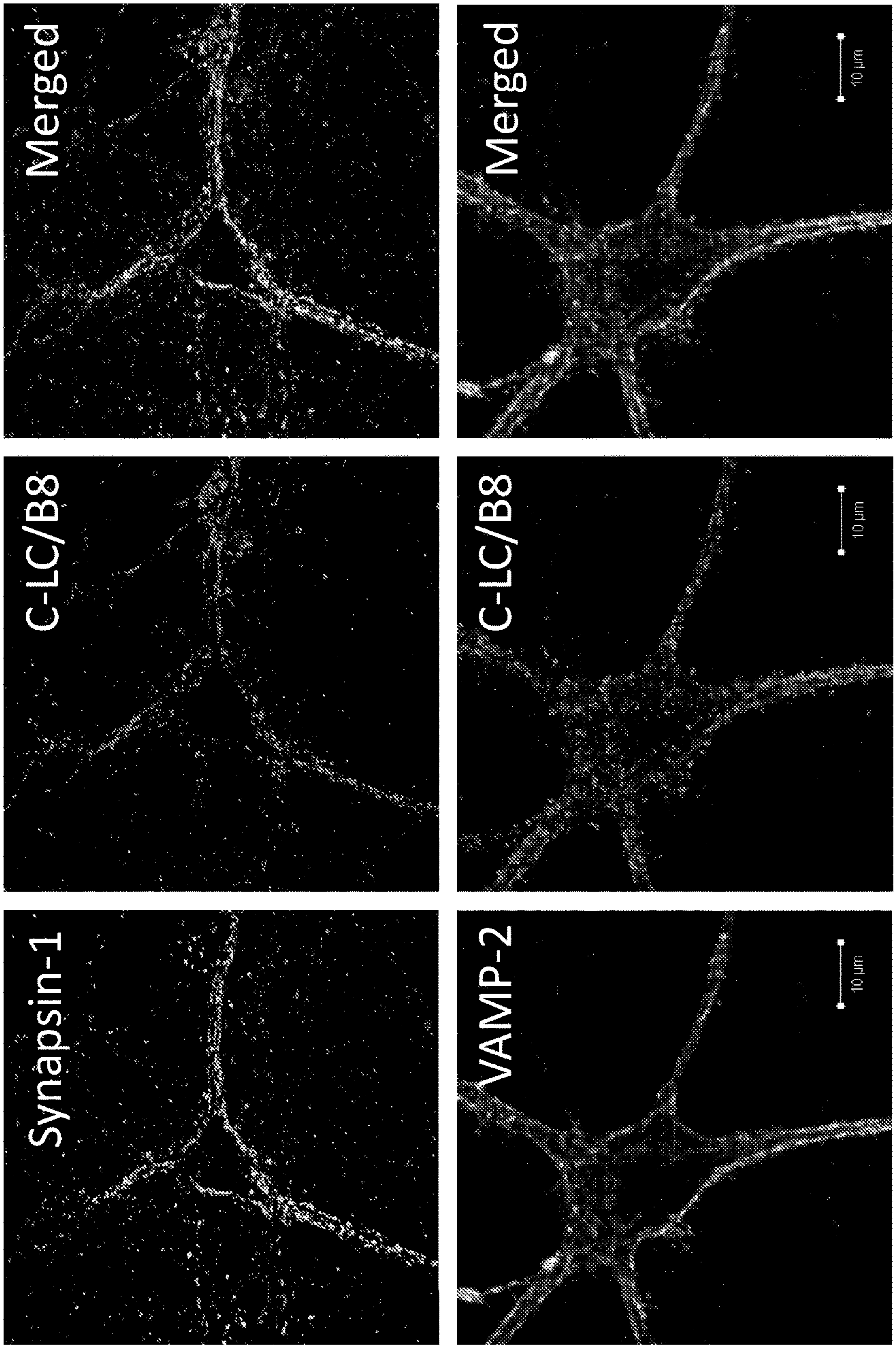
FIG. 26 is a series of photographs demonstrating that BoNT/C ad B8 ("C/B8") co-localizes with synaptic proteins in neuronal cultures. 14-DIV E19 rat hippocampal cultures were treated with 25 nM of C/B8 for 24 hours. Cells were prepared for ICC and analyzed using confocal microscopy. Upper panels: cells stained for Synapsin-1 and C-LC/B8 (using a monoclonal antibody against BoNT/C LC). Lower panel: Immunostaining for VAMP-2. Bar equals 10 microns.

To determine if C/B8 co-localizes with synaptic proteins, 14-DIV E19 rat hippocampal cultures were treated with 25 nM of C/B8 for 24 hours. Cells were then prepared for immunocytochemistry using monoclonal antibodies to detect Synapsin-1, VAMP-2, and BoNT/C LC, and analyzed using confocal microscopy (FIG. 26).

Effect of C/B8 on BoNT/A LC Activity Inside Intoxicated Neurons

Figure 27:
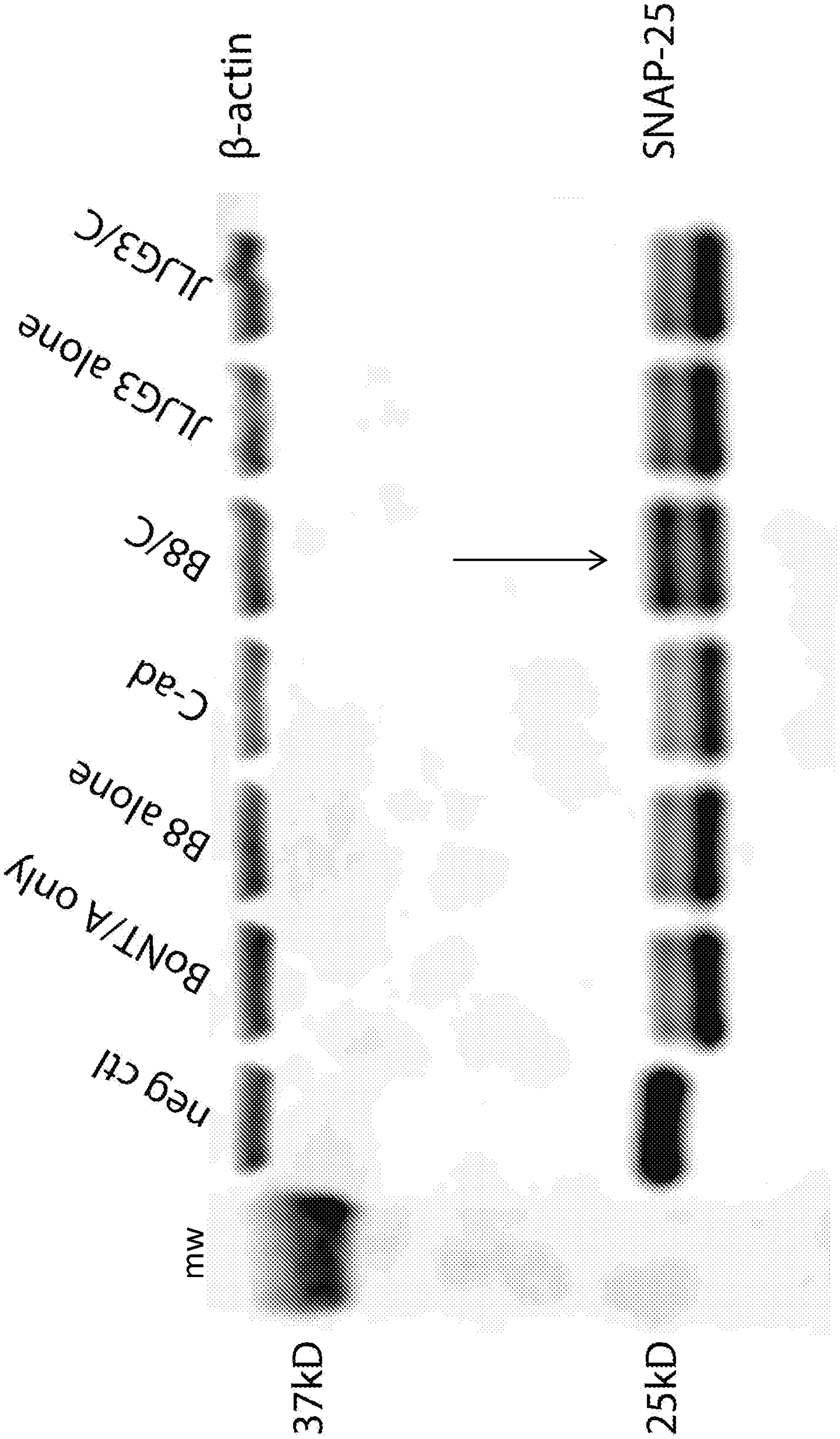
FIG. 27 demonstrates that C/B8 blocks wt BoNT/A LC activity towards SNAP-25 in a cell-based assay system. 14-DIV E19 cortical neurons were coexposed to 5 pM of wt BoNT/A and either 50 nM C/B8, 50 nM B8-alone, 50 nM BoNT/C-ad (BoNT/C molecular vehicle alone), 50 nM JLJG3-alone (VHH against BoNT/B), or 50 nM JLJG3/C (BoNT/C ad with JLJG3). Only samples co-exposed to C/B8 (shown with arrow) show partial blockage of SNAP-25 cleavage.

To investigate the effect of C/B8 on BoNT/A LC activity, 14-DIV E19 rat cortical neurons were co-exposed with 5 pM of BoNT/A and either, 50 nM C/B8, 50 nM B8 alone, 50 nM BoNT/C ad (molecular vehicle alone), 50 nM JLJG3-alone (VHH against BoNT/B), or 50 nM JLJG3/C (BoNT/C ad with JLJG3). Immediately after incubation, cells were washed with ice-cold DPBS and protein solubilized with 0.5% Triton™ X-100 buffer. Protein was analyzed by Western blot analysis using antibodies for SNAP-25 and beta-actin. (FIG. 27).

Figure 28:
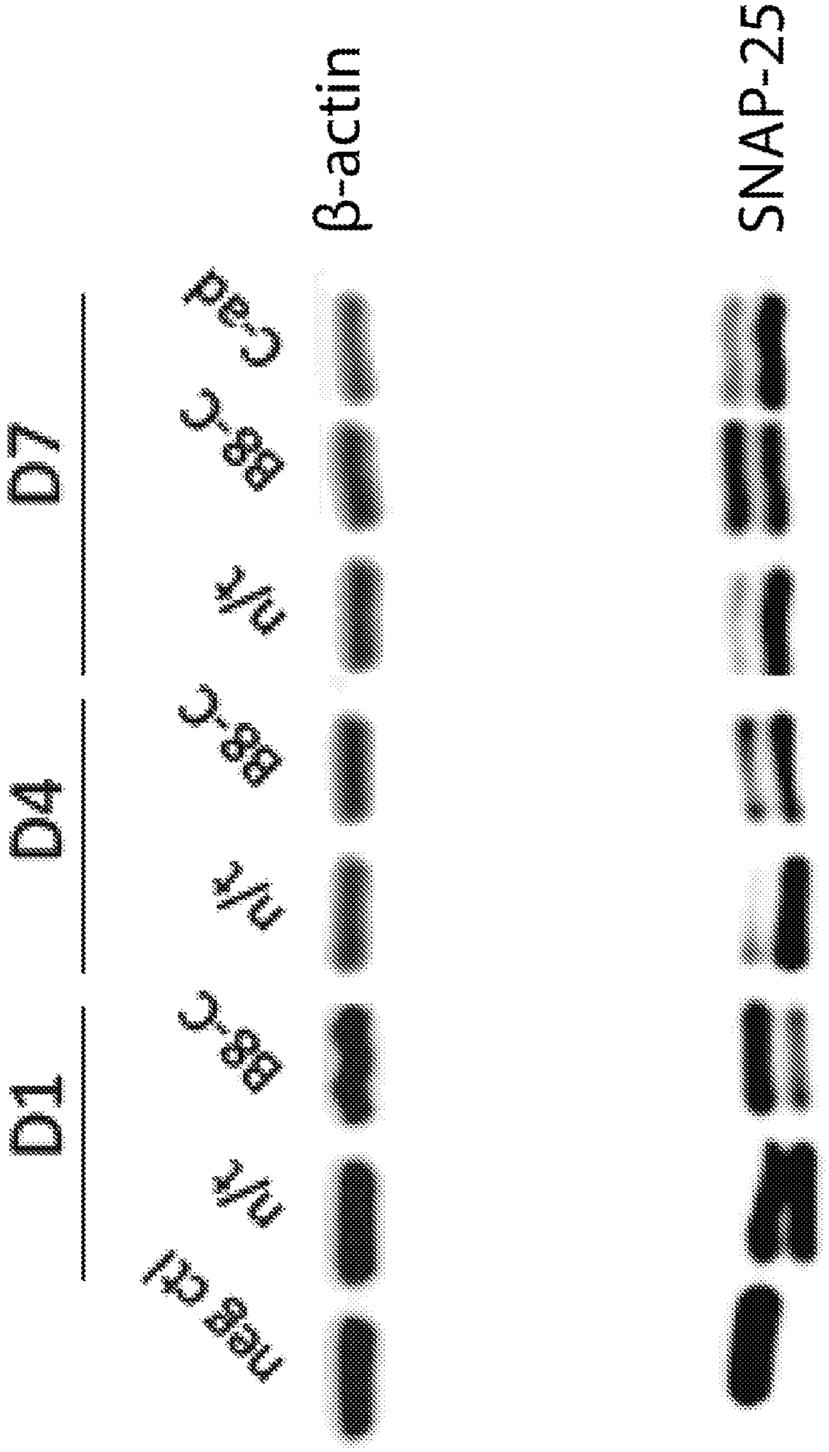
FIG. 28 demonstrates that C/B8 blocks BoNT/A LC activity and promotes SNAP-25 recovery in a cell-based system of post-exposure model of intoxication. 14-DIV E19 cortical neurons were intoxicated with 5 pM of BoNT/A for 90 minutes. Cells were washed twice with cell culture media and chased in the presence of 50 nM C/B8 and analyzed by Western blot at 1 (D1), 4 (D4), and 7 (D7) days post treatment. Cells treated with C/B8 show recovery of SNAP-25 by day 7 compared to non-treated group (n/t) or C-ad (molecular vehicle alone).

Effect of C/B8 on BoNT/A LC Activity and SNAP-25 Recovery in a Post-Exposure Model of Intoxication To investigate the effect of C/B8 on BoNT/A LC activity in a post-exposure in vitro model, 14-DIV E19 rat cortical neurons were intoxicated with 5 pM of BoNT/A for 90 minutes. Cells were washed twice with cell culture media, and chased in the presence of 50 nM C/B8 or BoNT/C ad (C-ad). Samples were analyzed by Western blot using a monoclonal antibody for SNAP-25 at different days post-treatment. (FIG. 28)

In vivo Efficacy of C/B8 Compared to Molecular Vehicle

Figure 29:
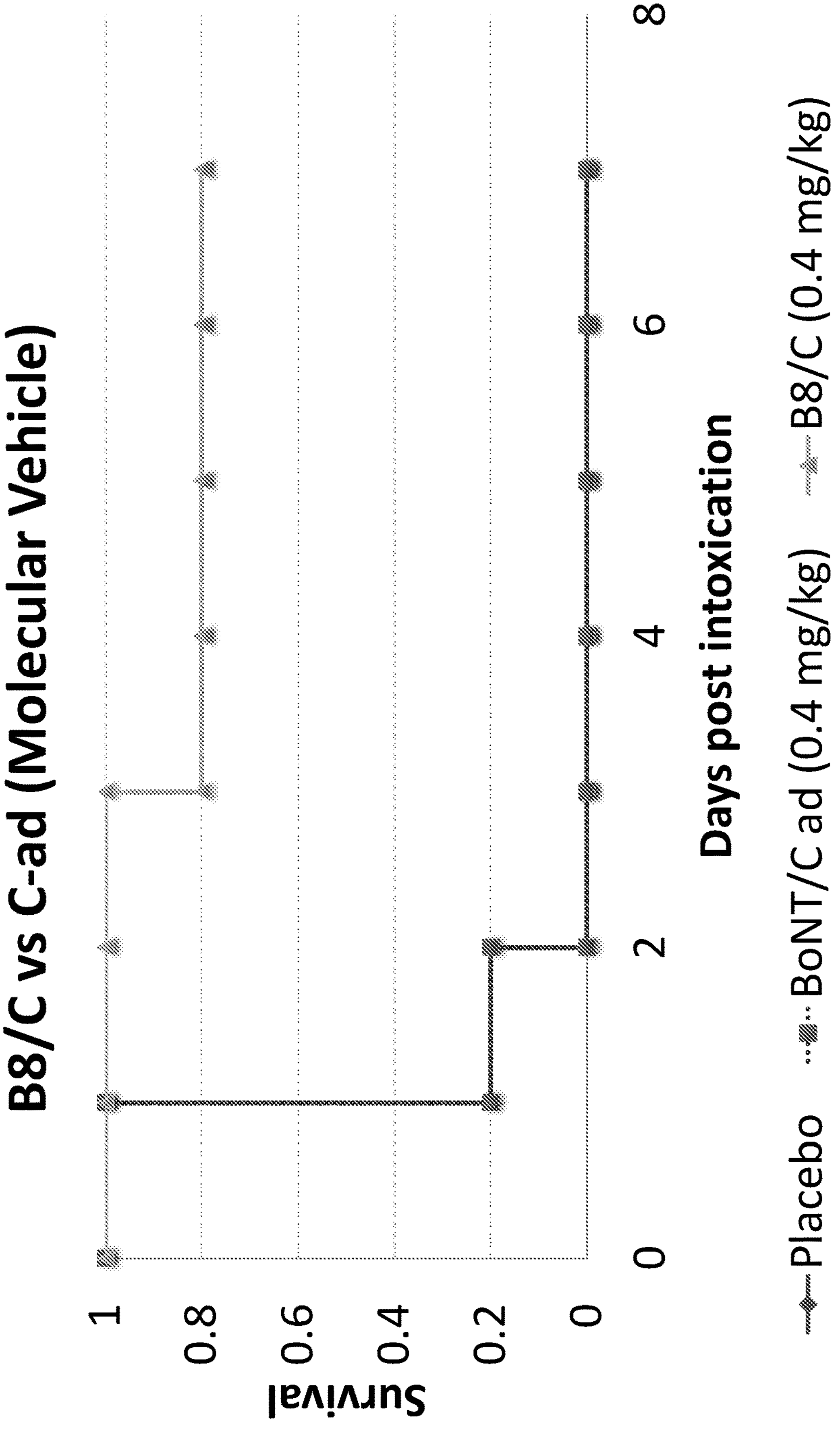
FIG. 29 shows in-vivo efficacy of C/B8 compared to the BoNT/C ad molecular vehicle. Group of 10 mice were injected ip with 2 MIPLD50 units. Three hours post intoxication, mice were injected with either placebo (buffer alone), 0.4 mg/kg of C/B8 or 0.4 mg/kg BoNT/C ad. Survival was measured daily and the living fraction was plotted against time (in days) post intoxication.

To compare the efficacy of C/B8 to its molecular vehicle (BoNT/C ad), an in vivo efficacy murine study was performed. In this blinded study, mice were challenged with 2 $MIPLD_{50}$ and treated at 3 hours post-intoxication with placebo, 0.4 mg/kg BoNT/C ad, or 0.4 mg/kg C/B8. (FIG. 29).

In vivo Effectiveness of C/B8 Versus Antitoxin at Different Times Post-Intoxication To determine the effectiveness of C/B8, mice were challenged with 1.2 or 4 $MIPLD_{50}$ units and treated with placebo, 0.4 mg/kg C/B8, or 1 U sheep polyclonal sera (antitoxin) at different hours post intoxication.

Results

In primary neuronal cultures, BoNT/C ad B8 co-localizes with synaptic proteins, Synapsin-1 and VAMP-2. In vitro efficacy studies how that C/B8 partial block of SNAP-25 cleavage. Additionally, cells treated with C/B8 showed recovery of SNAP-25 by day 7 compared to the non-treated group (n/t) or BoNT/C ad (FIG. 28).

In vivo efficacy studies show that placebo and BoNT/C ad treated animals died within 30 hours, while 80% of mice treated with C/B8 recovered, and were free of symptoms by day 10 (n=10 mice per group). This indicates that the survival benefit is attributed to the B8 VHH delivered by BoNT/C ad.

Figure 30A:
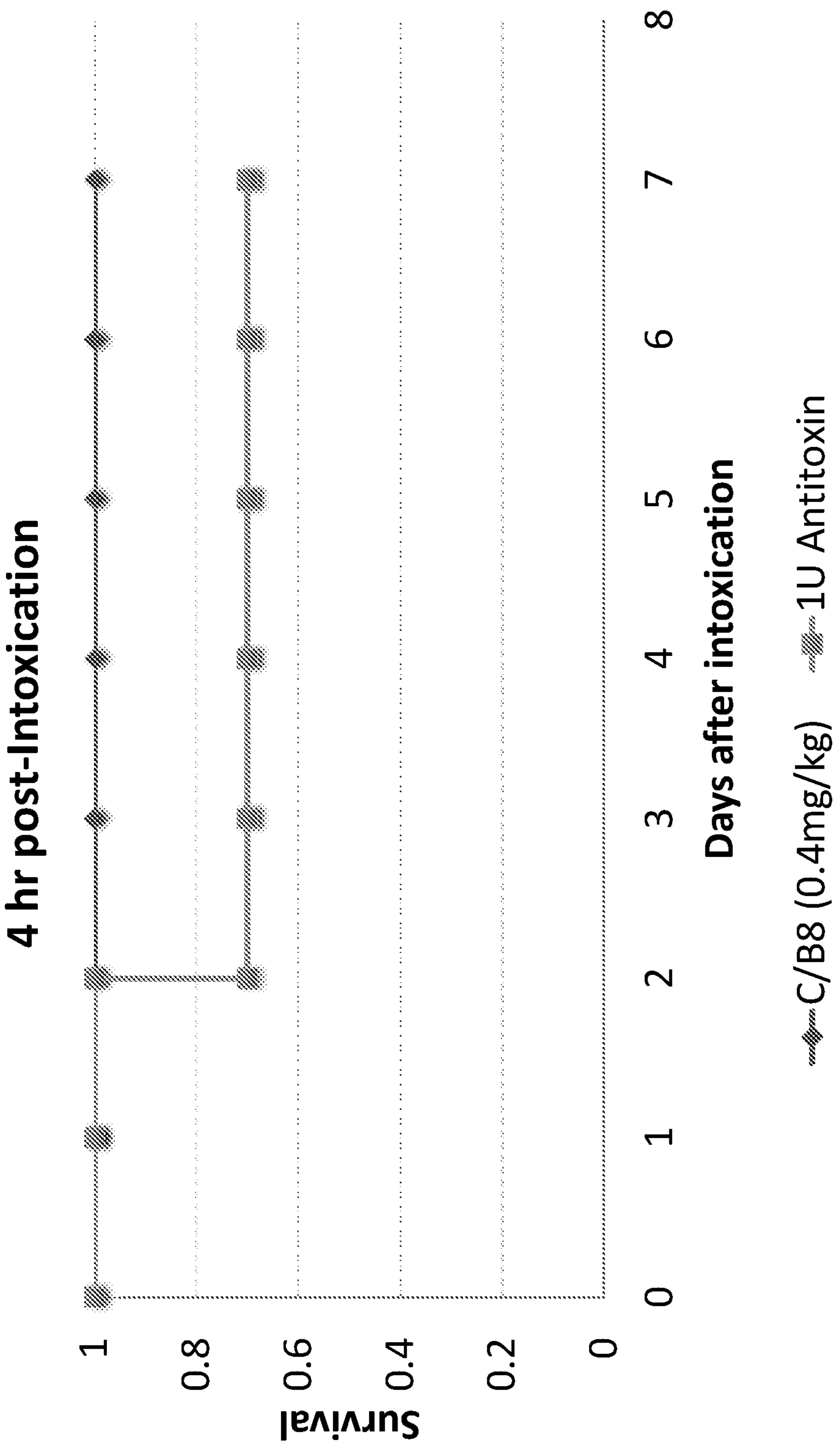
FIGS. 30A-C are graphs showing the effectiveness of C/B8 versus standard antibody-based antitoxin at different times post-intoxication. Groups of 10 mice were intoxicated ip with 1.2 MIPLD50. At 6 (FIG. 30A), 12 (FIG. 30B), or 20 (FIG. 30C) hours post intoxication, mice were injected ip with either 0.4 mg/kg C/B8 or 1 U of antitoxin. Survival was measured daily and the living fraction was plotted against time (in days) post intoxication.
Figure 30B:
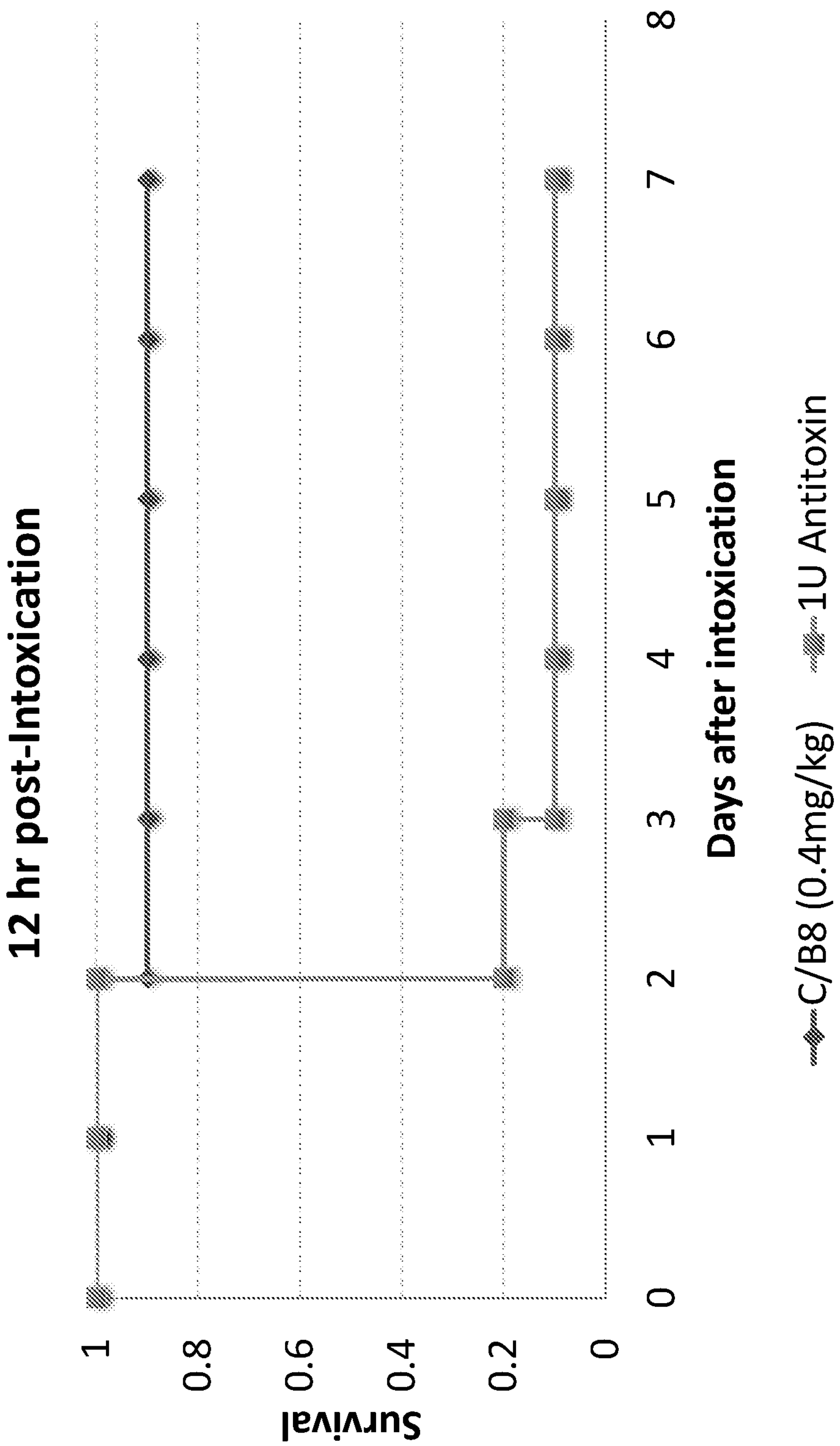
Figure 30C:
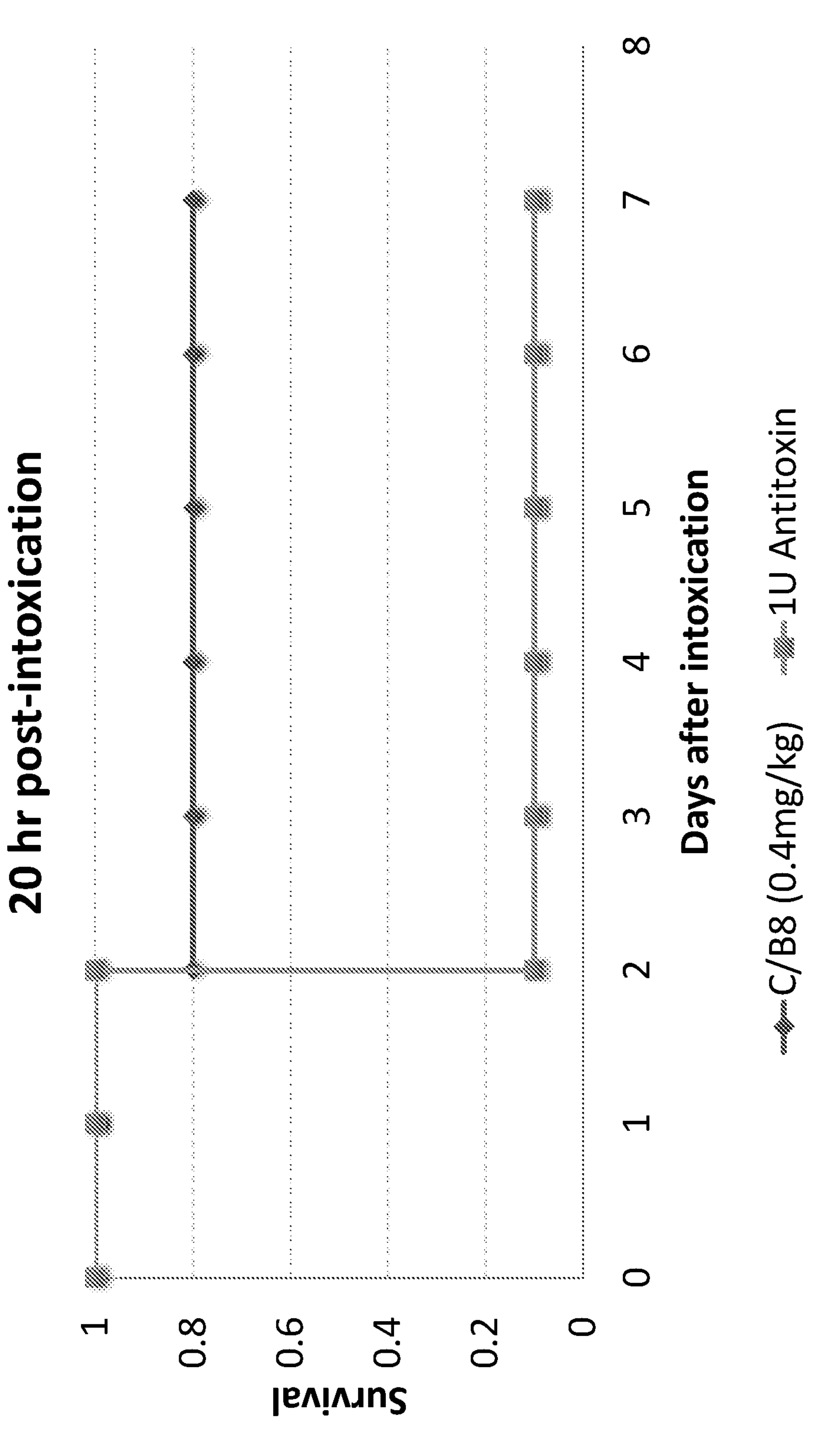

The effectiveness of C/B8 was directly compared to antibody-based antitoxin treatment. Mice were challenged ip with 1.2 $MIPLD_{50}$ units and treated with placebo, 0.4 mg/kg C/B8, or 1 U sheep polyclonal sera (antitoxin) at 4, 12, or 20 hours post-intoxication (n=10 mice per group). For the 4 hours post-intoxication treatment group, no clinical symptoms of botulism were recorded at the time of treatment intervention. For the 12 hours post-intoxication treatment group, mice displayed clinical signs of botulism toxemia, including slow respiratory patterns, wasp-like waist, and decreased mobility compared to normal mice. The 20 hours post-intoxication treatment group showed clinical signs of toxemia, including piloerection, respiratory distress accompanied by breathing noises, limb weakness, and lower mobility. Survival rate for the 4-hour treatment group was 100% for the C/B8 group and 70% for antitoxin group (FIG. 30A). Survival rate for the 12-hour treatment group was 90% for C/B8 and 10% for the antitoxin (FIG. 30B). The survival rate for the 20-hour treatment group was 80% for the C/B8 group and 10% for the antitoxin group (FIG. 30C). By day 10 on the study, surviving mice were free of clinical symptoms of botulism and weight gain was recorded. In each treatment group, mice treated with C/B8 exhibited increased survival compared to mice treated with antitoxin. This was most apparent in animals treated 20 hours post-intoxication, at which point all animals exhibited severe clinical symptoms of botulism.

Effect of Intoxication Dose on Effectiveness of C/B8 and Standard Antitoxin

Figure 31A:
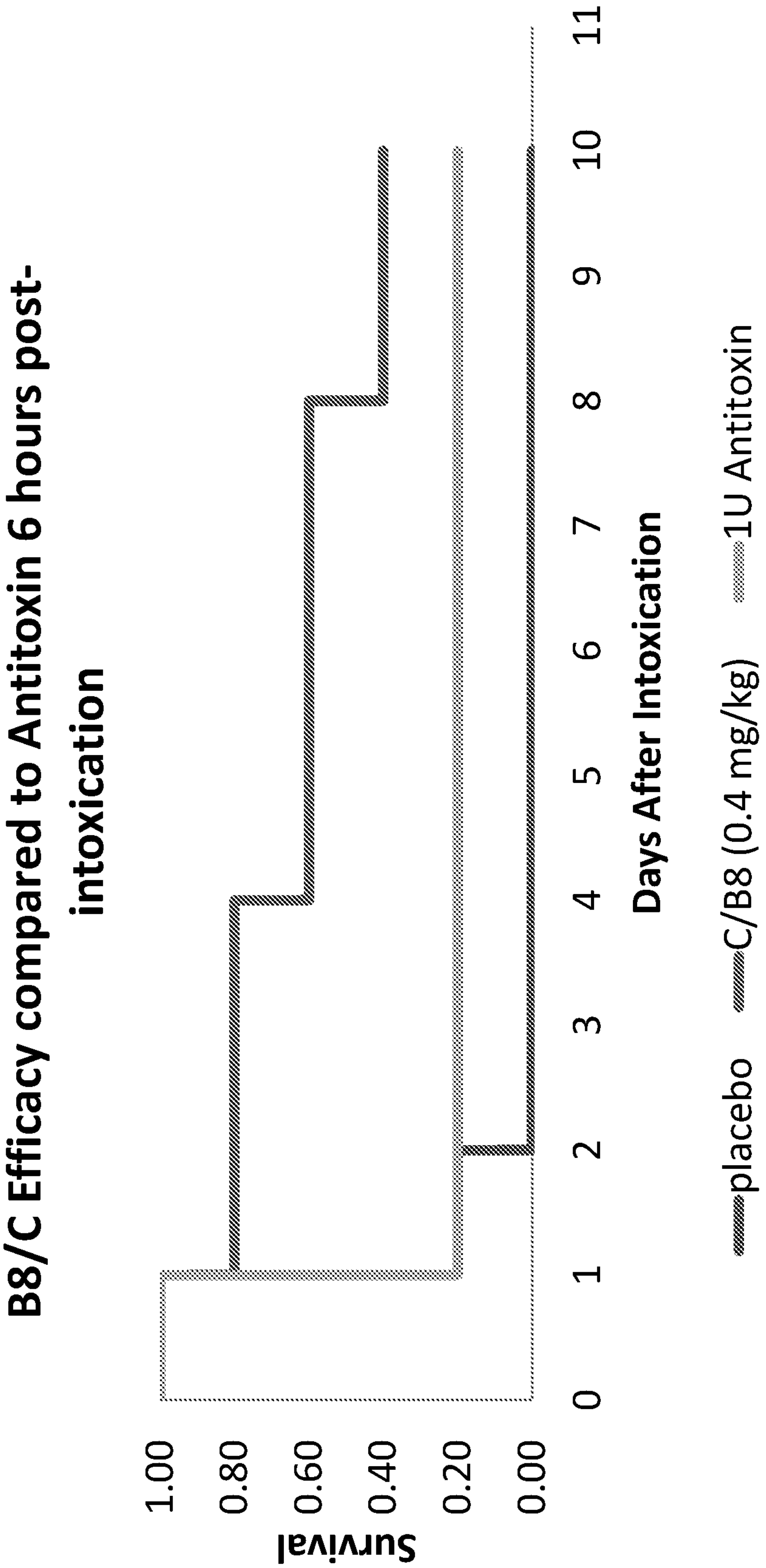
FIGS. 31A-C are graphs showing the effectiveness of C/B8 versus standard antibody-based antitoxin at different times post-intoxication. Groups of 10 mice were intoxicated ip with 4 MIPLD50. At 6 (FIG. 31A), 8 (FIG. 31B), or 10 (FIG. 31C) hours post intoxication, mice were injected ip with either 0.4 mg/kg C/B8 or 1 U of antitoxin. Survival was measured daily and the living fraction was plotted against time (in days) post intoxication.
Figure 31B:
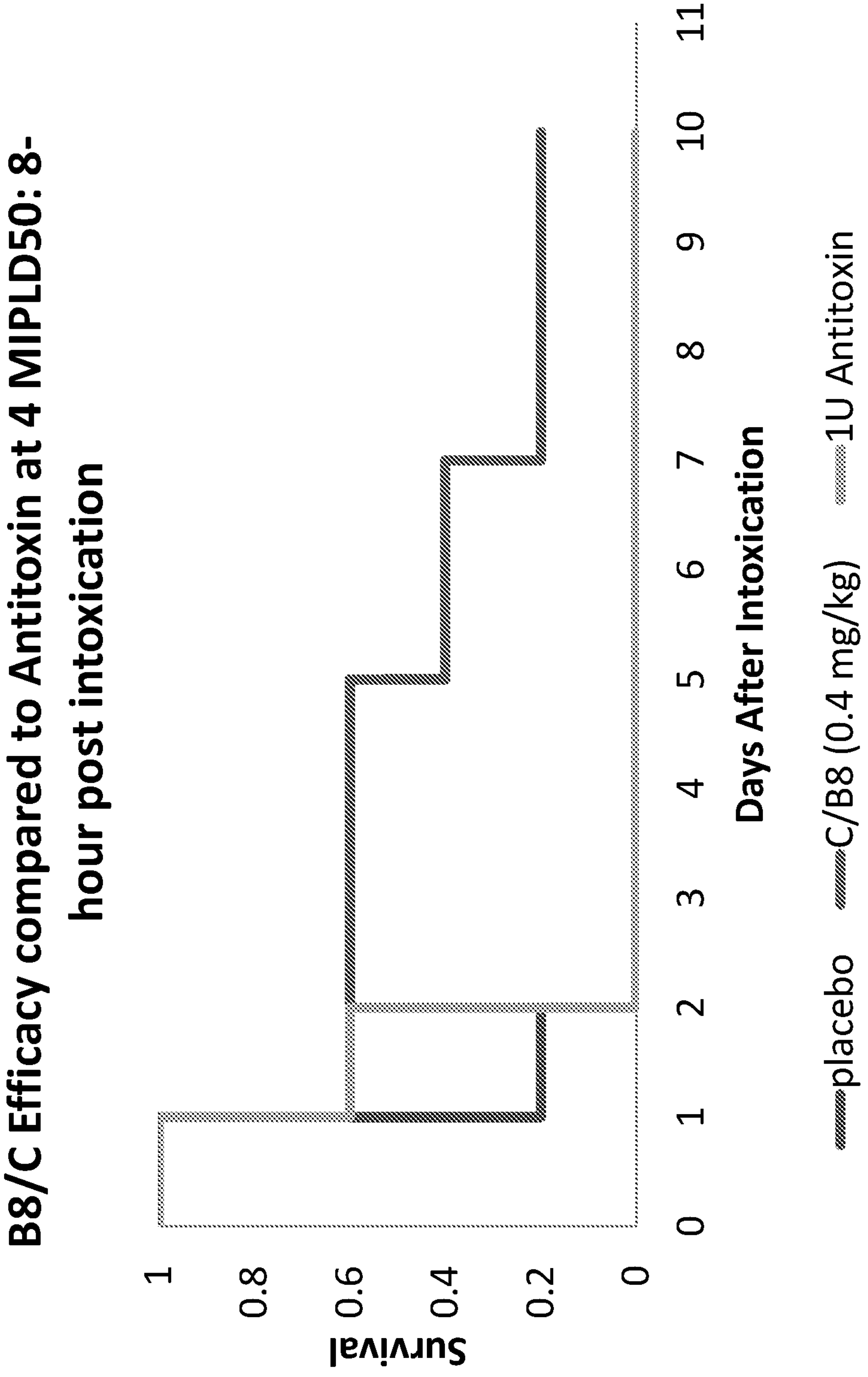
Figure 31C:
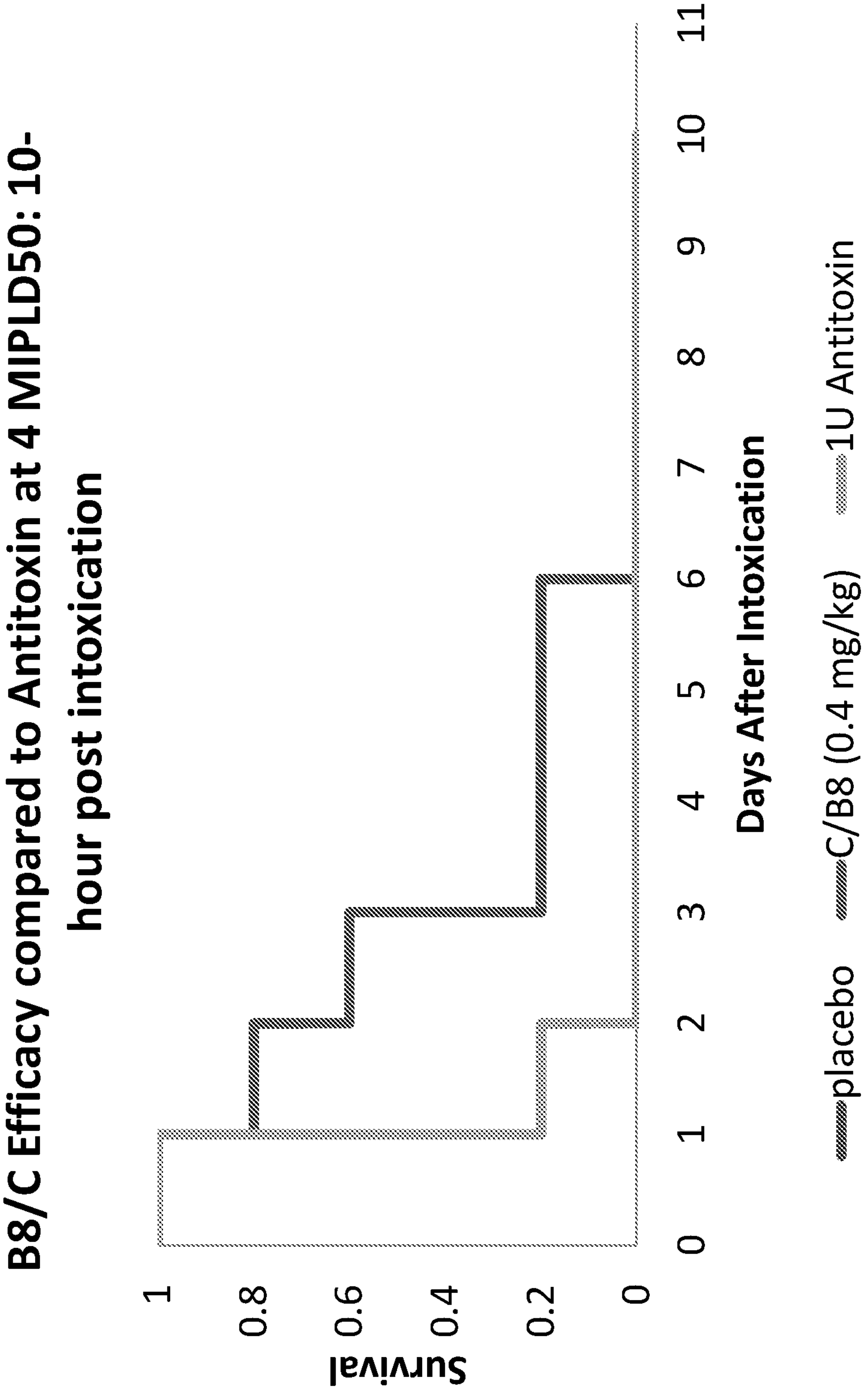

Mice were challenged with intraperitoneal injection of 4 $MIPLD_{5}o$ BoNT/A, followed by intervention with 0.4 mg/kg C/B8 or 1 U of Antitoxin (sheep polyclonal sera) at 6, 8, or 10 hours post intoxication (n=5 per group). At 6 hours post intoxication, mice showed clinical signs of botulism toxemia, including breathing changes and wasp-like waist. Survival on the 6-hour treatment group by day 10 was 40% in the C/B8 group and 20% antitoxin groups (FIG. 31A). At 8 hours post intoxication, mice showed severe clinical signs of botulism toxemia, including difficulty breathing, body weakness, and wasp-like waist. Survival on the 8-hour treatment group at day 10 was 20% in the C/B8 group and 0% in the antitoxin groups (FIG. 31B). At 10 hours post intoxication, mice showed severe clinical sigs of botulism toxemia, including difficulty breathing, body weakness and wasp-like waist. Although there was a 4-day delay on death on the C/B8 group compared to the antitoxin group, there were no survivals after day 6 of the study (FIG. 31C).

Conclusion

BoNT/C ad provides a useful molecular vehicle to deliver a therapeutic single chain antibody against BoNT/A to intoxicated neurons, enabling recovery of animals that were already exhibiting clinical symptoms of botulism.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A propeptide fusion comprising:

a light chain of a *Clostridium botulinum* neurotoxin, wherein the light chain is selected from any one of the following: (i) serotype A of SEQ ID NO:52 comprising $E_{224}$>A and $Y_{366}$>A mutations, (ii) serotype A of SEQ ID NO:52 comprising $Q_{162}$>Y, $L_{256}$>Y, $R_{257}$>E, and $L_{322}$>E mutations, (iii) serotype A of SEQ ID NO:52 comprising $Q_{163}$>E, $E_{263}$>L, and $L_{323}$>I mutations, or (iv) serotype C of SEQ ID NO:54 comprising $E_{230}$>A, $H_{233}$>G, and $Y_{375}$>A mutations;

a heavy chain of a *Closlridium botulinum* neurotoxin, wherein the light and heavy chains are linked by a disulfide bond;

an intermediate region connecting the light and heavy chain and comprising a highly specific protease cleavage site, wherein the highly specific protease cleavage site has three or more specific adjacent amino acid residues that are recognized by the highly specific protease to enable cleavage; and a VHH domain comprising FR1-CDR1-FR2-CDR2-FR3-CDR3-FR4 structures operably linked to the light chain, wherein the VHH domain possesses antigen binding activity against intra-neuronal targets after translocation into the cytoplasm;

wherein the VHH domain is positioned upstream of the light chain and the light chain is positioned upstream of the heavy chain; and wherein the propeptide fusion comprises a sequence selected from the group consisting of:

(i) the amino acid sequence comprising amino acids 63-193 of SEQ ID NO: 10 fused with amino acids 218-1517 of SEQ ID NO:10;

(ii) the amino acid sequence comprising amino acids 60-194 of SEQ ID NO: 12 fused with amino acids 219-1518 of SEQ ID NO:12;

(iii) the amino acid sequence comprising amino acids 60-194 of SEQ ID NO: 14 fused with amino acids 219-1518 of SEQ ID NO:14;

(iv) the amino acid sequence comprising amino acids 65-195 of SEQ ID NO:36 fused with amino acids 205-1508 of SEQ ID NO:36;

(v) the amino acid sequence comprising amino acids 267-397 of SEQ ID NO:38 fused with amino acids 407-1710 of SEQ ID NO:38;

(vi) the amino acid sequence comprising amino acids 58-183 of SEQ ID NO:40 fused with amino acids 198-323 of SEQ ID NO:40 fused with amino acids 333-1636 of SEQ ID NO:40;

(vii) the amino acid sequence comprising amino acids 260-385 of SEQ ID NO:42 fused with amino acids 400-525 of SEQ ID NO:42 fused with amino acids 535-1838 of SEQ ID NO:42; and (viii) the amino acid sequence comprising amino acids 58-183 of SEQ ID NO:44 fused with amino acids 198-323 of SEQ ID NO:44 fused with amino acids 333-1636 of SEQ ID NO:44.

* * * * *

SEQUENCE LISTING

```
<160> NUMBER OF SEQ ID NOS: 71

<210> SEQ ID NO 1
<211> LENGTH: 4786
<212> TYPE: DNA
<213> ORGANISM: Artificial
```

<220> FEATURE:
<223> OTHER INFORMATION: Propeptide fusion encoding sequence

<400> SEQUENCE: 1

```
ggatcccggt ccgttcgaac cagaactctg gaagcttaac tcctaaaaaa ccgccaccat     60
gaaattctta gtcaacgttg cccttgtttt tatggtcgta tacatttctt acatctatgc    120
ggccggacac caccaccacc accaccacca ccaccaccac gacgtcgaaa acctgtactt    180
ccaaggcgca gaacaaaaac tcatcagcga ggaggacctg ggaggagggg cccacggtgg    240
tgctcaactg caactcgtcg agtccggtgg tggtatggtc caacctggtg gttctttgag    300
gctgtcatgt gcagcgagtg gattcacctt ctcgacttac gatatgtcct gggtgcgtca    360
agccccaggc aaaggccccg aatgggtctc tatcattaac gccggcggag gttcaaccta    420
ctacgctgcc agtgtcaagg gaaggttcgc tatctccaga gataacgcca aaaacaccct    480
ctacttgcag atgaacaatc tgaagcccga ggatactgct ctctactact gcgctcgcgt    540
ggccagctac tactgccgtg gctacgtctg ttctcctccc gagttcgact actggggaca    600
gggtacacaa gtgacggtct ccagcgaacc gaagactcca aaaccgcaag caggacaagg    660
tgctcccgtg ccctacccag acccattgga acccagagga acgcgtggag cgggagcagg    720
tccattcgtc aacaagcaat tcaactacaa agatcctgtt aacggtgtgg acatcgccta    780
catcaagatt ccgaacgcag gccagatgca acctgtgaag gctttcaaaa tccacaacaa    840
gatctgggtc attcccgaga gagacacatt cacgaaccca gaggaaggtg atctgaaccc    900
tcccccagaa gccaagcagg tgccggtctc ttactacgat tcaacctacc tcagtactga    960
caacgagaag gataactacc tgaagggcgt tactaaactc ttcgagcgca tctactcgac   1020
agacttgggc cgtatgctgc tcacgtccat cgtcaggggt attcctttct ggggtggctc   1080
aaccatcgac actgagctga aggtcattga tacaaactgc atcaacgtta ttcaacccga   1140
cggctcctac cgcagcgagg aattgaacct ggtgatcatt ggaccaagcg ccgacatcat   1200
ttacttcgag tgtaagtctt tcggccatga agtcctcaac ttgaccagaa acggctacgg   1260
ctccactcaa tacatccgct tcagccccga cttcacattc ggattcgagg aatcactgga   1320
ggtcgatacg aacccgttgc tgggtgctgg caagttcgcc accgaccctg cagttactct   1380
ggcacacgcg ctcatccacg cgggacatcg tctgtacggt atcgctatta acccaaacag   1440
ggtcttcaag gttaacacca acgcctacta cgagatgagt ggttacaggg tgtcgttcga   1500
ggaactccgt acgttcggag gtcacgacgc aaagttcatc gatagtttgc aggagaacga   1560
attccgcctg tactactaca acaagttcaa agacatcgcg tctacactca acaaggctaa   1620
aagcattgtt ggaaccactg ctagtttgca atacatgaag aacgtgttca aggagaaata   1680
cgagttgtcg gaagacacct ccggtaaatt cagcgtggac aagctgaaat tcgataagtt   1740
gtacaaaatg ctgacagaaa tctacacgga agacaacttc gttaagttct tcaaagtgtt   1800
gaaccgtaag accgctctga acttcgataa ggctgtcttc aaaatcaaca ttgtgcctaa   1860
agtcaactac accatctacg acggtttcaa cctccgcaac actaacttgg ctgccaactt   1920
caacggccag aacactgaga tcaacaacat gaacttcaca aagctcaaaa acttcaccgg   1980
tttgttcgag ttctacaagc tgctctgcgt gcgtggtatc attacatctc acacgcaatc   2040
tctagaccag ggtggcgaga acctgtactt ccagggtgct ctgaacgatc tgtgtatcaa   2100
ggtgaataac tgggatctgt tctttagccc aagcgaggat aacttcacga acgatctcaa   2160
caaaggtgaa gagatcacgt ctgataccaa tatcgaagcg gctgaagaga atatctcctt   2220
```

-continued

```
ggatctcatc cagcaatatt acctgacctt taacttcgat aacgagcccg aaaacatctc   2280
catcgagaac ctcagctcag acatcattgg tcagttggag ctgatgccaa acattgaacg   2340
cttccccaac ggcaagaaat acgaactcga caagtatacg atgtttcatt acttaagagc   2400
gcaggagttt gaacacggca agagccgcat tgctctcact aactccgtga atgaagccct   2460
gctcaatccg tcaagggtgt acacattctt tagctccgac tatgtcaaga aagtgaacaa   2520
agccaccgaa gcggcaatgt tcctgggatg ggttgaacaa ctggtctacg acttcaccga   2580
cgagacctct gaggtgagca caacggacaa gattgctgac atcactatca ttatcccgta   2640
tattggacct gccttgaata ttggcaacat gctctacaaa gacgatttcg ttggtgccct   2700
gatcttcagc ggtgccgtga tcctgttgga gttcattcct gaaatcgcca tccctgtgct   2760
gggcacgttc gctctggtct catacattgc gaataaggtc ttgaccgtgc agacaatcga   2820
taatgccctc tccaaacgta acgaaaaatg ggacgaggtc tacaaataca tcgtgaccaa   2880
ctggctggca aaggttaaca cccaaattga tctgatccgt aagaaaatga aggaggcttt   2940
ggagaaccag gctgaagcta ctaaagccat tatcaactac cagtataatc agtatacaga   3000
agaggaaaag aataacatca atttcaacat cgatgacttg tcctcaaagc tgaacgagtc   3060
catcaacaaa gctatgatca acatcaacaa attcctgaat cagtgctccg tgtcttacct   3120
gatgaactct atgatcccat acggtgtgaa gcgcctggag gacttcgatg ccagcctgaa   3180
agacgcactg ctcaaataca tttacgataa tcgcggcact ttgattggcc aagttgaccg   3240
tctgaaggac aaggttaaca ataccttgtc aaccgatatc cccttccaac tctctaagta   3300
cgtcgataac cagcgcttgc tgagcacctt cacagaatac atcaacaaca tcatcaacac   3360
ctccatcctg aacctccgtt acgagtctaa ccacctcatc gacttgagca gatacgctag   3420
caagatcaac atcggttcca aggtgaactt cgacccaatc gataagaacc agatccaact   3480
gttcaacctc gaatcctcta agatcgaagt gatcctgaag aacgctatcg tctacaactc   3540
catgtacgaa aacttctcta ccagcttctg gatcaggatt ccgaaatact tcaactcaat   3600
ctcgctcaac aacgagtaca ctatcatcaa ctgcatggaa aacaactcgg gatggaaggt   3660
gtccctcaac tacggcgaga tcatctggac tttgcaggac acacaagaaa tcaagcagag   3720
ggtcgtgttc aagtacagcc aaatgatcaa catcagcgat tacatcaacc gttggatctt   3780
cgtcacaatc accaacaacc gcctgaacaa ctccaagatt tacatcaacg gtagactgat   3840
cgaccagaag ccaatcagca acctcggcaa catccacgcc tcaaacaaca tcatgttcaa   3900
gttggacggc tgtagggata cacacagata catctggatc aaatacttca acctgttcga   3960
caaggagctc aacgagaagg aaatcaagga cctctacgat aaccagtcca actctggtat   4020
cttgaaggac ttctggggcg attacctgca atacgacaag ccctactaca tgttgaacct   4080
gtacgaccct aacaagtacg ttgatgtgaa caacgtcggt atcaggggct acatgtacct   4140
gaagggacca cgtggttctg ttatgaccac taacatctac ctcaacagct cattgtaccg   4200
tggcacaaag ttcatcatca agaagtacgc ctccggaaac aaggacaaca tcgtccgtaa   4260
caacgatcgc gtttacatca acgttgtggt caagaacaag gagtacagac tggctaccaa   4320
cgcttcgcag gctggagttg agaagatcct gtctgctctg gaaatccctg acgtgggcaa   4380
cctctcacag gttgtggtca tgaagtcgaa gaacgatcaa ggcatcacta acaagtgcaa   4440
gatgaacttg caggacaaca acggaaacga catcggcttc atcggattcc accaattcaa   4500
caacatcgcc aagttggtgg ccagcaactg gtacaaccgt cagatcgagc gttcgtcccg   4560
caccttagga tgctcgtggg agttcattcc agtcgatgac ggatggggag agagaccttt   4620
```

gggcgcagga ggagagaacc tgtacttcca gggtgcagga tggtcccacc cacaattcga 4680
gaagggtgca ggatggagtc acccacagtt cgagaagggc gctggatggt cccacccaca 4740
gttcgagaaa taattagttg atgcatagtt aattagatag ctcgag 4786

<210> SEQ ID NO 2
<211> LENGTH: 1564
<212> TYPE: PRT
<213> ORGANISM: Artificial
<220> FEATURE:
<223> OTHER INFORMATION: Fusion protein

<400> SEQUENCE: 2

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Glu Asn Leu Tyr Phe Gln Gly Ala Glu Gln Lys Leu
35 40 45

Ile Ser Glu Glu Asp Leu Gly Gly Gly Ala His Gly Gly Ala Gln Leu
50 55 60

Gln Leu Val Glu Ser Gly Gly Gly Met Val Gln Pro Gly Gly Ser Leu
65 70 75 80

Arg Leu Ser Cys Ala Ala Ser Gly Phe Thr Phe Ser Thr Tyr Asp Met
85 90 95

Ser Trp Val Arg Gln Ala Pro Gly Lys Gly Pro Glu Trp Val Ser Ile
100 105 110

Ile Asn Ala Gly Gly Gly Ser Thr Tyr Tyr Ala Ala Ser Val Lys Gly
115 120 125

Arg Phe Ala Ile Ser Arg Asp Asn Ala Lys Asn Thr Leu Tyr Leu Gln
130 135 140

Met Asn Asn Leu Lys Pro Glu Asp Thr Ala Leu Tyr Tyr Cys Ala Arg
145 150 155 160

Val Ala Ser Tyr Tyr Cys Arg Gly Tyr Val Cys Ser Pro Pro Glu Phe
165 170 175

Asp Tyr Trp Gly Gln Gly Thr Gln Val Thr Val Ser Ser Glu Pro Lys
180 185 190

Thr Pro Lys Pro Gln Ala Gly Gln Gly Ala Pro Val Pro Tyr Pro Asp
195 200 205

Pro Leu Glu Pro Arg Gly Thr Arg Gly Ala Gly Ala Gly Pro Phe Val
210 215 220

Asn Lys Gln Phe Asn Tyr Lys Asp Pro Val Asn Gly Val Asp Ile Ala
225 230 235 240

Tyr Ile Lys Ile Pro Asn Ala Gly Gln Met Gln Pro Val Lys Ala Phe
245 250 255

Lys Ile His Asn Lys Ile Trp Val Ile Pro Glu Arg Asp Thr Phe Thr
260 265 270

Asn Pro Glu Glu Gly Asp Leu Asn Pro Pro Pro Glu Ala Lys Gln Val
275 280 285

Pro Val Ser Tyr Tyr Asp Ser Thr Tyr Leu Ser Thr Asp Asn Glu Lys
290 295 300

Asp Asn Tyr Leu Lys Gly Val Thr Lys Leu Phe Glu Arg Ile Tyr Ser
305 310 315 320

Thr Asp Leu Gly Arg Met Leu Leu Thr Ser Ile Val Arg Gly Ile Pro
325 330 335

-continued

```
Phe Trp Gly Gly Ser Thr Ile Asp Thr Glu Leu Lys Val Ile Asp Thr
            340                 345                 350

Asn Cys Ile Asn Val Ile Gln Pro Asp Gly Ser Tyr Arg Ser Glu Glu
        355                 360                 365

Leu Asn Leu Val Ile Ile Gly Pro Ser Ala Asp Ile Ile Tyr Phe Glu
    370                 375                 380

Cys Lys Ser Phe Gly His Glu Val Leu Asn Leu Thr Arg Asn Gly Tyr
385                 390                 395                 400

Gly Ser Thr Gln Tyr Ile Arg Phe Ser Pro Asp Phe Thr Phe Gly Phe
                405                 410                 415

Glu Glu Ser Leu Glu Val Asp Thr Asn Pro Leu Leu Gly Ala Gly Lys
            420                 425                 430

Phe Ala Thr Asp Pro Ala Val Thr Leu Ala His Ala Leu Ile His Ala
        435                 440                 445

Gly His Arg Leu Tyr Gly Ile Ala Ile Asn Pro Asn Arg Val Phe Lys
    450                 455                 460

Val Asn Thr Asn Ala Tyr Tyr Glu Met Ser Gly Tyr Arg Val Ser Phe
465                 470                 475                 480

Glu Glu Leu Arg Thr Phe Gly Gly His Asp Ala Lys Phe Ile Asp Ser
                485                 490                 495

Leu Gln Glu Asn Glu Phe Arg Leu Tyr Tyr Tyr Asn Lys Phe Lys Asp
            500                 505                 510

Ile Ala Ser Thr Leu Asn Lys Ala Lys Ser Ile Val Gly Thr Thr Ala
        515                 520                 525

Ser Leu Gln Tyr Met Lys Asn Val Phe Lys Glu Lys Tyr Glu Leu Ser
    530                 535                 540

Glu Asp Thr Ser Gly Lys Phe Ser Val Asp Lys Leu Lys Phe Asp Lys
545                 550                 555                 560

Leu Tyr Lys Met Leu Thr Glu Ile Tyr Thr Glu Asp Asn Phe Val Lys
                565                 570                 575

Phe Phe Lys Val Leu Asn Arg Lys Thr Ala Leu Asn Phe Asp Lys Ala
            580                 585                 590

Val Phe Lys Ile Asn Ile Val Pro Lys Val Asn Tyr Thr Ile Tyr Asp
        595                 600                 605

Gly Phe Asn Leu Arg Asn Thr Asn Leu Ala Ala Asn Phe Asn Gly Gln
    610                 615                 620

Asn Thr Glu Ile Asn Asn Met Asn Phe Thr Lys Leu Lys Asn Phe Thr
625                 630                 635                 640

Gly Leu Phe Glu Phe Tyr Lys Leu Leu Cys Val Arg Gly Ile Ile Thr
                645                 650                 655

Ser His Thr Gln Ser Leu Asp Gln Gly Gly Glu Asn Leu Tyr Phe Gln
            660                 665                 670

Gly Ala Leu Asn Asp Leu Cys Ile Lys Val Asn Asn Trp Asp Leu Phe
        675                 680                 685

Phe Ser Pro Ser Glu Asp Asn Phe Thr Asn Asp Leu Asn Lys Gly Glu
    690                 695                 700

Glu Ile Thr Ser Asp Thr Asn Ile Glu Ala Ala Glu Glu Asn Ile Ser
705                 710                 715                 720

Leu Asp Leu Ile Gln Gln Tyr Tyr Leu Thr Phe Asn Phe Asp Asn Glu
                725                 730                 735

Pro Glu Asn Ile Ser Ile Glu Asn Leu Ser Ser Asp Ile Ile Gly Gln
            740                 745                 750
```

```
Leu Glu Leu Met Pro Asn Ile Glu Arg Phe Pro Asn Gly Lys Lys Tyr
        755                 760                 765

Glu Leu Asp Lys Tyr Thr Met Phe His Tyr Leu Arg Ala Gln Glu Phe
    770                 775                 780

Glu His Gly Lys Ser Arg Ile Ala Leu Thr Asn Ser Val Asn Glu Ala
785                 790                 795                 800

Leu Leu Asn Pro Ser Arg Val Tyr Thr Phe Phe Ser Ser Asp Tyr Val
                805                 810                 815

Lys Lys Val Asn Lys Ala Thr Glu Ala Ala Met Phe Leu Gly Trp Val
            820                 825                 830

Glu Gln Leu Val Tyr Asp Phe Thr Asp Glu Thr Ser Glu Val Ser Thr
        835                 840                 845

Thr Asp Lys Ile Ala Asp Ile Thr Ile Ile Ile Pro Tyr Ile Gly Pro
    850                 855                 860

Ala Leu Asn Ile Gly Asn Met Leu Tyr Lys Asp Asp Phe Val Gly Ala
865                 870                 875                 880

Leu Ile Phe Ser Gly Ala Val Ile Leu Leu Glu Phe Ile Pro Glu Ile
                885                 890                 895

Ala Ile Pro Val Leu Gly Thr Phe Ala Leu Val Ser Tyr Ile Ala Asn
            900                 905                 910

Lys Val Leu Thr Val Gln Thr Ile Asp Asn Ala Leu Ser Lys Arg Asn
        915                 920                 925

Glu Lys Trp Asp Glu Val Tyr Lys Tyr Ile Val Thr Asn Trp Leu Ala
    930                 935                 940

Lys Val Asn Thr Gln Ile Asp Leu Ile Arg Lys Lys Met Lys Glu Ala
945                 950                 955                 960

Leu Glu Asn Gln Ala Glu Ala Thr Lys Ala Ile Ile Asn Tyr Gln Tyr
                965                 970                 975

Asn Gln Tyr Thr Glu Glu Glu Lys Asn Asn Ile Asn Phe Asn Ile Asp
            980                 985                 990

Asp Leu Ser Ser Lys Leu Asn Glu  Ser Ile Asn Lys Ala  Met Ile Asn
        995                 1000                1005

Ile Asn  Lys Phe Leu Asn Gln  Cys Ser Val Ser Tyr  Leu Met Asn
    1010                1015                1020

Ser Met  Ile Pro Tyr Gly Val  Lys Arg Leu Glu Asp  Phe Asp Ala
    1025                1030                1035

Ser Leu  Lys Asp Ala Leu Leu  Lys Tyr Ile Tyr Asp  Asn Arg Gly
    1040                1045                1050

Thr Leu  Ile Gly Gln Val Asp  Arg Leu Lys Asp Lys  Val Asn Asn
    1055                1060                1065

Thr Leu  Ser Thr Asp Ile Pro  Phe Gln Leu Ser Lys  Tyr Val Asp
    1070                1075                1080

Asn Gln  Arg Leu Leu Ser Thr  Phe Thr Glu Tyr Ile  Asn Asn Ile
    1085                1090                1095

Ile Asn  Thr Ser Ile Leu Asn  Leu Arg Tyr Glu Ser  Asn His Leu
    1100                1105                1110

Ile Asp  Leu Ser Arg Tyr Ala  Ser Lys Ile Asn Ile  Gly Ser Lys
    1115                1120                1125

Val Asn  Phe Asp Pro Ile Asp  Lys Asn Gln Ile Gln  Leu Phe Asn
    1130                1135                1140

Leu Glu  Ser Ser Lys Ile Glu  Val Ile Leu Lys Asn  Ala Ile Val
    1145                1150                1155

Tyr Asn  Ser Met Tyr Glu Asn  Phe Ser Thr Ser Phe  Trp Ile Arg
```

```
    1160                1165                1170

Ile Pro  Lys Tyr Phe Asn Ser  Ile Ser Leu Asn Asn  Glu Tyr Thr
    1175                1180                1185

Ile Ile  Asn Cys Met Glu Asn  Asn Ser Gly Trp Lys  Val Ser Leu
    1190                1195                1200

Asn Tyr  Gly Glu Ile Ile Trp  Thr Leu Gln Asp Thr  Gln Glu Ile
    1205                1210                1215

Lys Gln  Arg Val Val Phe Lys  Tyr Ser Gln Met Ile  Asn Ile Ser
    1220                1225                1230

Asp Tyr  Ile Asn Arg Trp Ile  Phe Val Thr Ile Thr  Asn Asn Arg
    1235                1240                1245

Leu Asn  Asn Ser Lys Ile Tyr  Ile Asn Gly Arg Leu  Ile Asp Gln
    1250                1255                1260

Lys Pro  Ile Ser Asn Leu Gly  Asn Ile His Ala Ser  Asn Asn Ile
    1265                1270                1275

Met Phe  Lys Leu Asp Gly Cys  Arg Asp Thr His Arg  Tyr Ile Trp
    1280                1285                1290

Ile Lys  Tyr Phe Asn Leu Phe  Asp Lys Glu Leu Asn  Glu Lys Glu
    1295                1300                1305

Ile Lys  Asp Leu Tyr Asp Asn  Gln Ser Asn Ser Gly  Ile Leu Lys
    1310                1315                1320

Asp Phe  Trp Gly Asp Tyr Leu  Gln Tyr Asp Lys Pro  Tyr Tyr Met
    1325                1330                1335

Leu Asn  Leu Tyr Asp Pro Asn  Lys Tyr Val Asp Val  Asn Asn Val
    1340                1345                1350

Gly Ile  Arg Gly Tyr Met Tyr  Leu Lys Gly Pro Arg  Gly Ser Val
    1355                1360                1365

Met Thr  Thr Asn Ile Tyr Leu  Asn Ser Ser Leu Tyr  Arg Gly Thr
    1370                1375                1380

Lys Phe  Ile Ile Lys Lys Tyr  Ala Ser Gly Asn Lys  Asp Asn Ile
    1385                1390                1395

Val Arg  Asn Asn Asp Arg Val  Tyr Ile Asn Val Val  Val Lys Asn
    1400                1405                1410

Lys Glu  Tyr Arg Leu Ala Thr  Asn Ala Ser Gln Ala  Gly Val Glu
    1415                1420                1425

Lys Ile  Leu Ser Ala Leu Glu  Ile Pro Asp Val Gly  Asn Leu Ser
    1430                1435                1440

Gln Val  Val Val Met Lys Ser  Lys Asn Asp Gln Gly  Ile Thr Asn
    1445                1450                1455

Lys Cys  Lys Met Asn Leu Gln  Asp Asn Asn Gly Asn  Asp Ile Gly
    1460                1465                1470

Phe Ile  Gly Phe His Gln Phe  Asn Asn Ile Ala Lys  Leu Val Ala
    1475                1480                1485

Ser Asn  Trp Tyr Asn Arg Gln  Ile Glu Arg Ser Ser  Arg Thr Leu
    1490                1495                1500

Gly Cys  Ser Trp Glu Phe Ile  Pro Val Asp Asp Gly  Trp Gly Glu
    1505                1510                1515

Arg Pro  Leu Gly Ala Gly Gly  Glu Asn Leu Tyr Phe  Gln Gly Ala
    1520                1525                1530

Gly Trp  Ser His Pro Gln Phe  Glu Lys Gly Ala Gly  Trp Ser His
    1535                1540                1545

Pro Gln  Phe Glu Lys Gly Ala  Gly Trp Ser His Pro  Gln Phe Glu
    1550                1555                1560
```

Lys

<210> SEQ ID NO 3
<211> LENGTH: 4783
<212> TYPE: DNA
<213> ORGANISM: Artificial
<220> FEATURE:
<223> OTHER INFORMATION: Propeptide fusion encoding sequence

<400> SEQUENCE: 3
ggatcccggt ccgttcgaac cagaactctg gaagcttaac tcctaaaaaa ccgccaccat 60
gaaattctta gtcaacgttg cccttgtttt tatggtcgta tacatttctt acatctatgc 120
ggccggacac caccaccacc accaccacca ccaccaccac gacgtcgaaa acctgtactt 180
ccaaggtgca gagcagaaac tcatcagcga agaagatttg ggaggagggg cccacggtgc 240
tcaactccag ctcgttgagt ccggtggcgg aatggtgcaa cctggtggct ctttgaggct 300
gtcatgcgct gccagtggat tcaccttctc gacttacgac atgtcctggg tgcgtcaggc 360
acctggaaaa ggtcccgaat gggtcagcat cattaacgct ggaggtggca gcacatacta 420
cgcagcgtct gttaagggaa ggttcgctat ctccagagac aacgccaaaa acaccctcta 480
cttgcaaatg aacaacctga agcccgagga tactgctctc tactactgtg ctcgcgtcgc 540
ctcatactac tgccgtggct acgtttgtag tcctcccgag ttcgactact ggggccaggg 600
aacacaagtg acggtctcca gcgaaccaaa gacaccaaaa ccacaggctg gtcagggcgc 660
tcctgttcca tacccagatc cactggaacc aagaggaacg cgtggagcgg gagcaggtcc 720
attcgtcaac aagcaattca actacaaaga tcctgttaac ggtgtggaca tcgcctacat 780
caagattccg aacgcaggcc agatgcaacc tgtgaaggct ttcaaaatcc acaacaagat 840
ctgggtcatt cccgagagag acacattcac gaacccagag gaaggtgatc tgaaccctcc 900
cccagaagcc aagcaggtgc cggtctctta ctacgattca acctacctca gtactgacaa 960
cgagaaggat aactacctga agggcgttac taaactcttc gagcgcatct actcgacaga 1020
cttgggccgt atgctgctca cgtccatcgt caggggtatt cctttctggg gtggctcaac 1080
catcgacact gagctgaagg tcattgatac aaactgcatc aacgttattc aacccgacgg 1140
ctcctaccgc agcgaggaat tgaacctggt gatcattgga ccaagcgccg acatcattta 1200
cttcgagtgt aagtctttcg gccatgaagt cctcaacttg accagaaacg gctacggctc 1260
cactcaatac atccgcttca gccccgactt cacattcgga ttcgaggaat cactggaggt 1320
cgatacgaac ccgttgctgg gtgctggcaa gttcgccacc gaccctgcag ttactctggc 1380
acacgcgctc atccacgcgg gacatcgtct gtacggtatc gctattaacc caaacagggt 1440
cttcaaggtt aacaccaacg cctactacga gatgagtggt tacagggtgt cgttcgagga 1500
actccgtacg ttcggaggtc acgacgcaaa gttcatcgat agtttgcagg agaacgaatt 1560
ccgcctgtac tactacaaca agttcaaaga catcgcgtct acactcaaca aggctaaaag 1620
cattgttgga accactgcta gtttgcaata catgaagaac gtgttcaagg agaaatacga 1680
gttgtcggaa gacacctccg gtaaattcag cgtggacaag ctgaaattcg ataagttgta 1740
caaaatgctg acagaaatct acacggaaga caacttcgtt aagttcttca aagtgttgaa 1800
ccgtaagacc gctctgaact tcgataaggc tgtcttcaaa atcaacattg tgcctaaagt 1860
caactacacc atctacgacg gtttcaacct ccgcaacact aacttggctg ccaacttcaa 1920
cggccagaac actgagatca acaacatgaa cttcacaaag ctcaaaaact tcaccggttt 1980
gttcgagttc tacaagctgc tctgcgtgcg tggtggaggc acatctcaca cgcaatctga 2040
gaacctgtac ttccaaggtg gtggccaggg tggagctctg aacgatctgt gtatcaaggt 2100
gaataactgg gatctgttct ttagcccaag cgaggataac ttcacgaacg atctcaacaa 2160
aggtgaagag atcacgtctg ataccaatat cgaagcggct gaagagaata tctccttgga 2220
tctcatccag caatattacc tgacctttaa cttcgataac gagcccgaaa acatctccat 2280
cgagaacctc agctcagaca tcattggtca gttggagctg atgccaaaca ttgaacgctt 2340
ccccaacggc aagaaatacg aactcgacaa gtatacgatg tttcattact taagagcgca 2400
ggagtttgaa cacggcaaga gccgcattgc tctcactaac tccgtgaatg aagccctgct 2460
caatccgtca agggtgtaca cattctttag ctccgactat gtcaagaaag tgaacaaagc 2520
caccgaagcg gcaatgttcc tgggatgggt tgaacaactg gtctacgact tcaccgacga 2580
gacctctgag gtgagcacaa cggacaagat tgctgacatc actatcatta tcccgtatat 2640
tggacctgcc ttgaatattg gcaacatgct ctacaaagac gatttcgttg gtgccctgat 2700
cttcagcggt gccgtgatcc tgttggagtt cattcctgaa atcgccatcc ctgtgctggg 2760
cacgttcgct ctggtctcat acattgcgaa taaggtcttg accgtgcaga caatcgataa 2820
tgccctctcc aaacgtaacg aaaaatggga cgaggtctac aaatacatcg tgaccaactg 2880
gctggcaaag gttaacaccc aaattgatct gatccgtaag aaaatgaagg aggctttgga 2940
gaaccaggct gaagctacta aagccattat caactaccag tataatcagt atacagaaga 3000
ggaaaagaat aacatcaatt tcaacatcga tgacttgtcc tcaaagctga acgagtccat 3060
caacaaagct atgatcaaca tcaacaaatt cctgaatcag tgctccgtgt cttacctgat 3120
gaactctatg atcccatacg gtgtgaagcg cctggaggac ttcgatgcca gcctgaaaga 3180
cgcactgctc aaatacattt acgataatcg cggcactttg attggccaag ttgaccgtct 3240
gaaggacaag gttaacaata ccttgtcaac cgatatcccc ttccaactct ctaagtacgt 3300
cgataaccag cgcttgctga gcaccttcac agaatacatc aacaacatca tcaacacctc 3360
catcctgaac ctccgttacg agtctaacca cctcatcgac ttgagcagat acgctagcaa 3420
gatcaacatc ggttccaagg tgaacttcga cccaatcgat aagaaccaga tccaactgtt 3480
caacctcgaa tcctctaaga tcgaagtgat cctgaagaac gctatcgtct acaactccat 3540
gtacgaaaac ttctctacca gcttctggat caggattccg aaatacttca actcaatctc 3600
gctcaacaac gagtacacta tcatcaactg catggaaaac aactcgggat ggaaggtgtc 3660
cctcaactac ggcgagatca tctggacttt gcaggacaca caagaaatca agcagagggt 3720
cgtgttcaag tacagccaaa tgatcaacat cagcgattac atcaaccgtt ggatcttcgt 3780
cacaatcacc aacaaccgcc tgaacaactc caagatttac atcaacggta gactgatcga 3840
ccagaagcca atcagcaacc tcggcaacat ccacgcctca aacaacatca tgttcaagtt 3900
ggacggctgt agggatacac acagatacat ctggatcaaa tacttcaacc tgttcgacaa 3960
ggagctcaac gagaaggaaa tcaaggacct ctacgataac cagtccaact ctggtatctt 4020
gaaggacttc tggggcgatt acctgcaata cgacaagccc tactacatgt tgaacctgta 4080
cgaccctaac aagtacgttg atgtgaacaa cgtcggtatc aggggctaca tgtacctgaa 4140
gggaccacgt ggttctgtta tgaccactaa catctacctc aacagctcat tgtaccgtgg 4200
cacaaagttc atcatcaaga agtacgcctc cggaaacaag gacaacatcg tccgtaacaa 4260
cgatcgcgtt tacatcaacg ttgtggtcaa gaacaaggag tacagactgg ctaccaacgc 4320
ttcgcaggct ggagttgaga agatcctgtc tgctctggaa atccctgacg tgggcaacct 4380
ctcacaggtt gtggtcatga agtcgaagaa cgatcaaggc atcactaaca agtgcaagat 4440
gaacttgcag gacaacaacg gaaacgacat cggcttcatc ggattccacc aattcaacaa 4500
catcgccaag ttggtggcca gcaactggta caaccgtcag atcgagcgtt cgtcccgcac 4560
cttaggatgc tcgtgggagt tcattccagt cgatgacgga tggggagaga gacctttggg 4620
cgcaggagga gagaacctgt acttccaggg tgcaggatgg tcccacccac aattcgagaa 4680
gggtgcagga tggagtcacc cacagttcga gaagggcgct ggatggtccc acccacagtt 4740
cgagaaataa ttagttgatg catagttaat tagatagctc gag 4783

<210> SEQ ID NO 4
<211> LENGTH: 1563
<212> TYPE: PRT
<213> ORGANISM: Artificial
<220> FEATURE:
<223> OTHER INFORMATION: Fusion protein

<400> SEQUENCE: 4

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Glu Asn Leu Tyr Phe Gln Gly Ala Glu Gln Lys Leu
35 40 45

Ile Ser Glu Glu Asp Leu Gly Gly Gly Ala His Gly Ala Gln Leu Gln
50 55 60

Leu Val Glu Ser Gly Gly Gly Met Val Gln Pro Gly Gly Ser Leu Arg
65 70 75 80

Leu Ser Cys Ala Ala Ser Gly Phe Thr Phe Ser Thr Tyr Asp Met Ser
85 90 95

Trp Val Arg Gln Ala Pro Gly Lys Gly Pro Glu Trp Val Ser Ile Ile
100 105 110

Asn Ala Gly Gly Gly Ser Thr Tyr Tyr Ala Ala Ser Val Lys Gly Arg
115 120 125

Phe Ala Ile Ser Arg Asp Asn Ala Lys Asn Thr Leu Tyr Leu Gln Met
130 135 140

Asn Asn Leu Lys Pro Glu Asp Thr Ala Leu Tyr Tyr Cys Ala Arg Val
145 150 155 160

Ala Ser Tyr Tyr Cys Arg Gly Tyr Val Cys Ser Pro Pro Glu Phe Asp
165 170 175

Tyr Trp Gly Gln Gly Thr Gln Val Thr Val Ser Ser Glu Pro Lys Thr
180 185 190

Pro Lys Pro Gln Ala Gly Gln Gly Ala Pro Val Pro Tyr Pro Asp Pro
195 200 205

Leu Glu Pro Arg Gly Thr Arg Gly Ala Gly Ala Gly Pro Phe Val Asn
210 215 220

Lys Gln Phe Asn Tyr Lys Asp Pro Val Asn Gly Val Asp Ile Ala Tyr
225 230 235 240

Ile Lys Ile Pro Asn Ala Gly Gln Met Gln Pro Val Lys Ala Phe Lys
245 250 255

Ile His Asn Lys Ile Trp Val Ile Pro Glu Arg Asp Thr Phe Thr Asn
260 265 270

Pro Glu Glu Gly Asp Leu Asn Pro Pro Pro Glu Ala Lys Gln Val Pro
275 280 285

```
Val Ser Tyr Tyr Asp Ser Thr Tyr Leu Ser Thr Asp Asn Glu Lys Asp
    290                 295                 300

Asn Tyr Leu Lys Gly Val Thr Lys Leu Phe Glu Arg Ile Tyr Ser Thr
305                 310                 315                 320

Asp Leu Gly Arg Met Leu Leu Thr Ser Ile Val Arg Gly Ile Pro Phe
                325                 330                 335

Trp Gly Gly Ser Thr Ile Asp Thr Glu Leu Lys Val Ile Asp Thr Asn
            340                 345                 350

Cys Ile Asn Val Ile Gln Pro Asp Gly Ser Tyr Arg Ser Glu Glu Leu
        355                 360                 365

Asn Leu Val Ile Ile Gly Pro Ser Ala Asp Ile Ile Tyr Phe Glu Cys
    370                 375                 380

Lys Ser Phe Gly His Glu Val Leu Asn Leu Thr Arg Asn Gly Tyr Gly
385                 390                 395                 400

Ser Thr Gln Tyr Ile Arg Phe Ser Pro Asp Phe Thr Phe Gly Phe Glu
                405                 410                 415

Glu Ser Leu Glu Val Asp Thr Asn Pro Leu Leu Gly Ala Gly Lys Phe
            420                 425                 430

Ala Thr Asp Pro Ala Val Thr Leu Ala His Ala Leu Ile His Ala Gly
        435                 440                 445

His Arg Leu Tyr Gly Ile Ala Ile Asn Pro Asn Arg Val Phe Lys Val
    450                 455                 460

Asn Thr Asn Ala Tyr Tyr Glu Met Ser Gly Tyr Arg Val Ser Phe Glu
465                 470                 475                 480

Glu Leu Arg Thr Phe Gly Gly His Asp Ala Lys Phe Ile Asp Ser Leu
                485                 490                 495

Gln Glu Asn Glu Phe Arg Leu Tyr Tyr Tyr Asn Lys Phe Lys Asp Ile
            500                 505                 510

Ala Ser Thr Leu Asn Lys Ala Lys Ser Ile Val Gly Thr Thr Ala Ser
        515                 520                 525

Leu Gln Tyr Met Lys Asn Val Phe Lys Glu Lys Tyr Glu Leu Ser Glu
    530                 535                 540

Asp Thr Ser Gly Lys Phe Ser Val Asp Lys Leu Lys Phe Asp Lys Leu
545                 550                 555                 560

Tyr Lys Met Leu Thr Glu Ile Tyr Thr Glu Asp Asn Phe Val Lys Phe
                565                 570                 575

Phe Lys Val Leu Asn Arg Lys Thr Ala Leu Asn Phe Asp Lys Ala Val
            580                 585                 590

Phe Lys Ile Asn Ile Val Pro Lys Val Asn Tyr Thr Ile Tyr Asp Gly
        595                 600                 605

Phe Asn Leu Arg Asn Thr Asn Leu Ala Ala Asn Phe Asn Gly Gln Asn
    610                 615                 620

Thr Glu Ile Asn Asn Met Asn Phe Thr Lys Leu Lys Asn Phe Thr Gly
625                 630                 635                 640

Leu Phe Glu Phe Tyr Lys Leu Leu Cys Val Arg Gly Gly Gly Thr Ser
                645                 650                 655

His Thr Gln Ser Glu Asn Leu Tyr Phe Gln Gly Gly Gly Gln Gly Gly
            660                 665                 670

Ala Leu Asn Asp Leu Cys Ile Lys Val Asn Asn Trp Asp Leu Phe Phe
        675                 680                 685

Ser Pro Ser Glu Asp Asn Phe Thr Asn Asp Leu Asn Lys Gly Glu Glu
    690                 695                 700

Ile Thr Ser Asp Thr Asn Ile Glu Ala Ala Glu Glu Asn Ile Ser Leu
```

-continued

```
705                 710                 715                 720

Asp Leu Ile Gln Gln Tyr Tyr Leu Thr Phe Asn Phe Asp Asn Glu Pro
                725                 730                 735

Glu Asn Ile Ser Ile Glu Asn Leu Ser Ser Asp Ile Ile Gly Gln Leu
            740                 745                 750

Glu Leu Met Pro Asn Ile Glu Arg Phe Pro Asn Gly Lys Lys Tyr Glu
        755                 760                 765

Leu Asp Lys Tyr Thr Met Phe His Tyr Leu Arg Ala Gln Glu Phe Glu
    770                 775                 780

His Gly Lys Ser Arg Ile Ala Leu Thr Asn Ser Val Asn Glu Ala Leu
785                 790                 795                 800

Leu Asn Pro Ser Arg Val Tyr Thr Phe Phe Ser Ser Asp Tyr Val Lys
                805                 810                 815

Lys Val Asn Lys Ala Thr Glu Ala Ala Met Phe Leu Gly Trp Val Glu
            820                 825                 830

Gln Leu Val Tyr Asp Phe Thr Asp Glu Thr Ser Glu Val Ser Thr Thr
        835                 840                 845

Asp Lys Ile Ala Asp Ile Thr Ile Ile Ile Pro Tyr Ile Gly Pro Ala
    850                 855                 860

Leu Asn Ile Gly Asn Met Leu Tyr Lys Asp Asp Phe Val Gly Ala Leu
865                 870                 875                 880

Ile Phe Ser Gly Ala Val Ile Leu Leu Glu Phe Ile Pro Glu Ile Ala
                885                 890                 895

Ile Pro Val Leu Gly Thr Phe Ala Leu Val Ser Tyr Ile Ala Asn Lys
            900                 905                 910

Val Leu Thr Val Gln Thr Ile Asp Asn Ala Leu Ser Lys Arg Asn Glu
        915                 920                 925

Lys Trp Asp Glu Val Tyr Lys Tyr Ile Val Thr Asn Trp Leu Ala Lys
    930                 935                 940

Val Asn Thr Gln Ile Asp Leu Ile Arg Lys Lys Met Lys Glu Ala Leu
945                 950                 955                 960

Glu Asn Gln Ala Glu Ala Thr Lys Ala Ile Ile Asn Tyr Gln Tyr Asn
                965                 970                 975

Gln Tyr Thr Glu Glu Glu Lys Asn Asn Ile Asn Phe Asn Ile Asp Asp
            980                 985                 990

Leu Ser Ser Lys Leu Asn Glu Ser  Ile Asn Lys Ala Met  Ile Asn Ile
        995                 1000                1005

Asn Lys  Phe Leu Asn Gln Cys  Ser Val Ser Tyr Leu  Met Asn Ser
    1010                1015                1020

Met Ile  Pro Tyr Gly Val Lys  Arg Leu Glu Asp Phe  Asp Ala Ser
    1025                1030                1035

Leu Lys  Asp Ala Leu Leu Lys  Tyr Ile Tyr Asp Asn  Arg Gly Thr
    1040                1045                1050

Leu Ile  Gly Gln Val Asp Arg  Leu Lys Asp Lys Val  Asn Asn Thr
    1055                1060                1065

Leu Ser  Thr Asp Ile Pro Phe  Gln Leu Ser Lys Tyr  Val Asp Asn
    1070                1075                1080

Gln Arg  Leu Leu Ser Thr Phe  Thr Glu Tyr Ile Asn  Asn Ile Ile
    1085                1090                1095

Asn Thr  Ser Ile Leu Asn Leu  Arg Tyr Glu Ser Asn  His Leu Ile
    1100                1105                1110

Asp Leu  Ser Arg Tyr Ala Ser  Lys Ile Asn Ile Gly  Ser Lys Val
    1115                1120                1125
```

```
Asn Phe  Asp Pro Ile Asp Lys  Asn Gln Ile Gln Leu  Phe Asn Leu
    1130                 1135                 1140

Glu Ser  Ser Lys Ile Glu Val  Ile Leu Lys Asn Ala  Ile Val Tyr
    1145                 1150                 1155

Asn Ser  Met Tyr Glu Asn Phe  Ser Thr Ser Phe Trp  Ile Arg Ile
    1160                 1165                 1170

Pro Lys  Tyr Phe Asn Ser Ile  Ser Leu Asn Asn Glu  Tyr Thr Ile
    1175                 1180                 1185

Ile Asn  Cys Met Glu Asn Asn  Ser Gly Trp Lys Val  Ser Leu Asn
    1190                 1195                 1200

Tyr Gly  Glu Ile Ile Trp Thr  Leu Gln Asp Thr Gln  Glu Ile Lys
    1205                 1210                 1215

Gln Arg  Val Val Phe Lys Tyr  Ser Gln Met Ile Asn  Ile Ser Asp
    1220                 1225                 1230

Tyr Ile  Asn Arg Trp Ile Phe  Val Thr Ile Thr Asn  Asn Arg Leu
    1235                 1240                 1245

Asn Asn  Ser Lys Ile Tyr Ile  Asn Gly Arg Leu Ile  Asp Gln Lys
    1250                 1255                 1260

Pro Ile  Ser Asn Leu Gly Asn  Ile His Ala Ser Asn  Asn Ile Met
    1265                 1270                 1275

Phe Lys  Leu Asp Gly Cys Arg  Asp Thr His Arg Tyr  Ile Trp Ile
    1280                 1285                 1290

Lys Tyr  Phe Asn Leu Phe Asp  Lys Glu Leu Asn Glu  Lys Glu Ile
    1295                 1300                 1305

Lys Asp  Leu Tyr Asp Asn Gln  Ser Asn Ser Gly Ile  Leu Lys Asp
    1310                 1315                 1320

Phe Trp  Gly Asp Tyr Leu Gln  Tyr Asp Lys Pro Tyr  Tyr Met Leu
    1325                 1330                 1335

Asn Leu  Tyr Asp Pro Asn Lys  Tyr Val Asp Val Asn  Asn Val Gly
    1340                 1345                 1350

Ile Arg  Gly Tyr Met Tyr Leu  Lys Gly Pro Arg Gly  Ser Val Met
    1355                 1360                 1365

Thr Thr  Asn Ile Tyr Leu Asn  Ser Ser Leu Tyr Arg  Gly Thr Lys
    1370                 1375                 1380

Phe Ile  Ile Lys Lys Tyr Ala  Ser Gly Asn Lys Asp  Asn Ile Val
    1385                 1390                 1395

Arg Asn  Asn Asp Arg Val Tyr  Ile Asn Val Val Val  Lys Asn Lys
    1400                 1405                 1410

Glu Tyr  Arg Leu Ala Thr Asn  Ala Ser Gln Ala Gly  Val Glu Lys
    1415                 1420                 1425

Ile Leu  Ser Ala Leu Glu Ile  Pro Asp Val Gly Asn  Leu Ser Gln
    1430                 1435                 1440

Val Val  Val Met Lys Ser Lys  Asn Asp Gln Gly Ile  Thr Asn Lys
    1445                 1450                 1455

Cys Lys  Met Asn Leu Gln Asp  Asn Asn Gly Asn Asp  Ile Gly Phe
    1460                 1465                 1470

Ile Gly  Phe His Gln Phe Asn  Asn Ile Ala Lys Leu  Val Ala Ser
    1475                 1480                 1485

Asn Trp  Tyr Asn Arg Gln Ile  Glu Arg Ser Ser Arg  Thr Leu Gly
    1490                 1495                 1500

Cys Ser  Trp Glu Phe Ile Pro  Val Asp Asp Gly Trp  Gly Glu Arg
    1505                 1510                 1515
```

-continued

```
Pro Leu Gly Ala Gly Gly Glu Asn Leu Tyr Phe Gln Gly Ala Gly
    1520                1525                1530

Trp Ser His Pro Gln Phe Glu Lys Gly Ala Gly Trp Ser His Pro
    1535                1540                1545

Gln Phe Glu Lys Gly Ala Gly Trp Ser His Pro Gln Phe Glu Lys
    1550                1555                1560


<210> SEQ ID NO 5
<211> LENGTH: 4921
<212> TYPE: DNA
<213> ORGANISM: Artificial
<220> FEATURE:
<223> OTHER INFORMATION: Propeptide fusion encoding sequence

<400> SEQUENCE: 5

ggatcccggt ccgttcgaac cagaactctg gaagcttaac tcctaaaaaa ccgccaccat     60

gaaattctta gtcaacgttg cccttgtttt tatggtcgta tacatttctt acatctatgc    120

ggccggacac caccaccacc accaccacca ccaccaccac gacgtcgaaa acctgtactt    180

ccaaggcgca gaacaaaaac tcatcagcga ggaggacctg aaggcgtggc agcagcaatc    240

ttacctggac gagggtatcc acgaaggcgc taccactacc gccccttccg gtttcgcaaa    300

cgagttggga ccgaggctga tgggcaaggg aggaggggcc cacggtggtg ctcaactgca    360

actcgtcgag tccggtggtg gtatggtcca acctggtggt tctttgaggc tgtcatgtgc    420

agcgagtgga ttcaccttct cgacttacga tatgtcctgg gtgcgtcaag ccccaggcaa    480

aggccccgaa tgggtctcta tcattaacgc cggcggaggt tcaacctact acgctgccag    540

tgtcaaggga aggttcgcta tctccagaga taacgccaaa aacaccctct acttgcagat    600

gaacaatctg aagcccgagg atactgctct ctactactgc gctcgcgtgg ccagctacta    660

ctgccgtggc tacgtctgtt ctcctcccga gttcgactac tggggacagg gtacacaagt    720

gacggtctcc agcgaaccga agactccaaa accgcaagca ggacaaggtg ctcccgtgcc    780

ctacccagac ccattggaac ccagaggaac gcgtggagcg ggagcaggtc cattcgtcaa    840

caagcaattc aactacaaag atcctgttaa cggtgtggac atcgcctaca tcaagattcc    900

gaacgcaggc cagatgcaac ctgtgaaggc tttcaaaatc cacaacaaga tctgggtcat    960

tcccgagaga gacacattca cgaacccaga ggaaggtgat ctgaaccctc ccccagaagc   1020

caagcaggtg ccggtctctt actacgattc aacctacctc agtactgaca acgagaagga   1080

taactacctg aagggcgtta ctaaactctt cgagcgcatc tactcgacag acttgggccg   1140

tatgctgctc acgtccatcg tcaggggtat tcctttctgg ggtggctcaa ccatcgacac   1200

tgagctgaag gtcattgata caaactgcat caacgttatt caacccgacg gctcctaccg   1260

cagcgaggaa ttgaacctgg tgatcattgg accaagcgcc gacatcattt acttcgagtg   1320

taagtctttc ggccatgaag tcctcaactt gaccagaaac ggctacggct ccactcaata   1380

catccgcttc agccccgact tcacattcgg attcgaggaa tcactggagg tcgatacgaa   1440

cccgttgctg ggtgctggca agttcgccac cgaccctgca gttactctgg cacacgcgct   1500

catccacgcg ggacatcgtc tgtacggtat cgctattaac ccaaacaggg tcttcaaggt   1560

taacaccaac gcctactacg agatgagtgg ttacagggtg tcgttcgagg aactccgtac   1620

gttcggaggt cacgacgcaa agttcatcga tagtttgcag gagaacgaat tccgcctgta   1680

ctactacaac aagttcaaag acatcgcgtc tacactcaac aaggctaaaa gcattgttgg   1740

aaccactgct agtttgcaat acatgaagaa cgtgttcaag gagaaatacg agttgtcgga   1800
```

-continued

```
agacacctcc ggtaaattca gcgtggacaa gctgaaattc gataagttgt acaaaatgct   1860
gacagaaatc tacacggaag acaacttcgt taagttcttc aaagtgttga accgtaagac   1920
cgctctgaac ttcgataagg ctgtcttcaa aatcaacatt gtgcctaaag tcaactacac   1980
catctacgac ggtttcaacc tccgcaacac taacttggct gccaacttca acggccagaa   2040
cactgagatc aacaacatga acttcacaaa gctcaaaaac ttcaccggtt tgttcgagtt   2100
ctacaagctg ctctgcgtgc gtggtatcat tacatctcac acgcaatctc tagaccaggg   2160
tggcgagaac ctgtacttcc agggtgctct gaacgatctg tgtatcaagg tgaataactg   2220
ggatctgttc tttagcccaa gcgaggataa cttcacgaac gatctcaaca aaggtgaaga   2280
gatcacgtct gataccaata tcgaagcggc tgaagagaat atctccttgg atctcatcca   2340
gcaatattac ctgaccttta acttcgataa cgagcccgaa aacatctcca tcgagaacct   2400
cagctcagac atcattggtc agttggagct gatgccaaac attgaacgct tccccaacgg   2460
caagaaatac gaactcgaca agtatacgat gtttcattac ttaagagcgc aggagtttga   2520
acacggcaag agccgcattg ctctcactaa ctccgtgaat gaagccctgc tcaatccgtc   2580
aagggtgtac acattcttta gctccgacta tgtcaagaaa gtgaacaaag ccaccgaagc   2640
ggcaatgttc ctgggatggg ttgaacaact ggtctacgac ttcaccgacg agacctctga   2700
ggtgagcaca acggacaaga ttgctgacat cactatcatt atcccgtata ttggacctgc   2760
cttgaatatt ggcaacatgc tctacaaaga cgatttcgtt ggtgccctga tcttcagcgg   2820
tgccgtgatc ctgttggagt tcattcctga aatcgccatc cctgtgctgg gcacgttcgc   2880
tctggtctca tacattgcga ataaggtctt gaccgtgcag acaatcgata atgccctctc   2940
caaacgtaac gaaaaatggg acgaggtcta caaatacatc gtgaccaact ggctggcaaa   3000
ggttaacacc caaattgatc tgatccgtaa gaaaatgaag gaggctttgg agaaccaggc   3060
tgaagctact aaagccatta tcaactacca gtataatcag tatacagaag aggaaaagaa   3120
taacatcaat ttcaacatcg atgacttgtc ctcaaagctg aacgagtcca tcaacaaagc   3180
tatgatcaac atcaacaaat tcctgaatca gtgctccgtg tcttacctga tgaactctat   3240
gatcccatac ggtgtgaagc gcctggagga cttcgatgcc agcctgaaag acgcactgct   3300
caaatacatt tacgataatc gcggcacttt gattggccaa gttgaccgtc tgaaggacaa   3360
ggttaacaat accttgtcaa ccgatatccc cttccaactc tctaagtacg tcgataacca   3420
gcgcttgctg agcaccttca cagaatacat caacaacatc atcaacacct ccatcctgaa   3480
cctccgttac gagtctaacc acctcatcga cttgagcaga tacgctagca agatcaacat   3540
cggttccaag gtgaacttcg acccaatcga taagaaccag atccaactgt tcaacctcga   3600
atcctctaag atcgaagtga tcctgaagaa cgctatcgtc tacaactcca tgtacgaaaa   3660
cttctctacc agcttctgga tcaggattcc gaaatacttc aactcaatct cgctcaacaa   3720
cgagtacact atcatcaact gcatggaaaa caactcggga tggaaggtgt ccctcaacta   3780
cggcgagatc atctggactt tgcaggacac acaagaaatc aagcagaggg tcgtgttcaa   3840
gtacagccaa atgatcaaca tcagcgatta catcaaccgt tggatcttcg tcacaatcac   3900
caacaaccgc ctgaacaact ccaagattta catcaacggt agactgatcg accagaagcc   3960
aatcagcaac ctcggcaaca tccacgcctc aaacaacatc atgttcaagt tggacggctg   4020
tagggataca cacagataca tctggatcaa atacttcaac ctgttcgaca aggagctcaa   4080
cgagaaggaa atcaaggacc tctacgataa ccagtccaac tctggtatct tgaaggactt   4140
ctggggcgat tacctgcaat acgacaagcc ctactacatg ttgaacctgt acgaccctaa   4200
```

caagtacgtt gatgtgaaca acgtcggtat caggggctac atgtacctga agggaccacg 4260
tggttctgtt atgaccacta acatctacct caacagctca ttgtaccgtg gcacaaagtt 4320
catcatcaag aagtacgcct ccggaaacaa ggacaacatc gtccgtaaca acgatcgcgt 4380
ttacatcaac gttgtggtca agaacaagga gtacagactg gctaccaacg cttcgcaggc 4440
tggagttgag aagatcctgt ctgctctgga aatccctgac gtgggcaacc tctcacaggt 4500
tgtggtcatg aagtcgaaga acgatcaagg catcactaac aagtgcaaga tgaacttgca 4560
ggacaacaac ggaaacgaca tcggcttcat cggattccac caattcaaca acatcgccaa 4620
gttggtggcc agcaactggt acaaccgtca gatcgagcgt tcgtcccgca ccttaggatg 4680
ctcgtgggag ttcattccag tcgatgacgg atggggagag agacctttgg gcgcaggata 4740
cccctacgat gtccctgact acgctggaga gaacctgtac ttccagggtg caggatggtc 4800
ccacccacaa ttcgagaagg gtgcaggatg gagtcaccca cagttcgaga agggcgctgg 4860
atggtcccac ccacagttcg agaaataatt agttgatgca tagttaatta gatagctcga 4920
g 4921

<210> SEQ ID NO 6
<211> LENGTH: 1609
<212> TYPE: PRT
<213> ORGANISM: Artificial
<220> FEATURE:
<223> OTHER INFORMATION: Fusion protein

<400> SEQUENCE: 6

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Glu Asn Leu Tyr Phe Gln Gly Ala Glu Gln Lys Leu
35 40 45

Ile Ser Glu Glu Asp Leu Lys Ala Trp Gln Gln Gln Ser Tyr Leu Asp
50 55 60

Glu Gly Ile His Glu Gly Ala Thr Thr Thr Ala Pro Ser Gly Phe Ala
65 70 75 80

Asn Glu Leu Gly Pro Arg Leu Met Gly Lys Gly Gly Gly Ala His Gly
85 90 95

Gly Ala Gln Leu Gln Leu Val Glu Ser Gly Gly Gly Met Val Gln Pro
100 105 110

Gly Gly Ser Leu Arg Leu Ser Cys Ala Ala Ser Gly Phe Thr Phe Ser
115 120 125

Thr Tyr Asp Met Ser Trp Val Arg Gln Ala Pro Gly Lys Gly Pro Glu
130 135 140

Trp Val Ser Ile Ile Asn Ala Gly Gly Gly Ser Thr Tyr Tyr Ala Ala
145 150 155 160

Ser Val Lys Gly Arg Phe Ala Ile Ser Arg Asp Asn Ala Lys Asn Thr
165 170 175

Leu Tyr Leu Gln Met Asn Asn Leu Lys Pro Glu Asp Thr Ala Leu Tyr
180 185 190

Tyr Cys Ala Arg Val Ala Ser Tyr Tyr Cys Arg Gly Tyr Val Cys Ser
195 200 205

Pro Pro Glu Phe Asp Tyr Trp Gly Gln Gly Thr Gln Val Thr Val Ser
210 215 220

-continued

```
Ser Glu Pro Lys Thr Pro Lys Pro Gln Ala Gly Gln Gly Ala Pro Val
225                 230                 235                 240

Pro Tyr Pro Asp Pro Leu Glu Pro Arg Gly Thr Arg Gly Ala Gly Ala
                245                 250                 255

Gly Pro Phe Val Asn Lys Gln Phe Asn Tyr Lys Asp Pro Val Asn Gly
            260                 265                 270

Val Asp Ile Ala Tyr Ile Lys Ile Pro Asn Ala Gly Gln Met Gln Pro
        275                 280                 285

Val Lys Ala Phe Lys Ile His Asn Lys Ile Trp Val Ile Pro Glu Arg
    290                 295                 300

Asp Thr Phe Thr Asn Pro Glu Glu Gly Asp Leu Asn Pro Pro Pro Glu
305                 310                 315                 320

Ala Lys Gln Val Pro Val Ser Tyr Tyr Asp Ser Thr Tyr Leu Ser Thr
                325                 330                 335

Asp Asn Glu Lys Asp Asn Tyr Leu Lys Gly Val Thr Lys Leu Phe Glu
            340                 345                 350

Arg Ile Tyr Ser Thr Asp Leu Gly Arg Met Leu Leu Thr Ser Ile Val
        355                 360                 365

Arg Gly Ile Pro Phe Trp Gly Gly Ser Thr Ile Asp Thr Glu Leu Lys
    370                 375                 380

Val Ile Asp Thr Asn Cys Ile Asn Val Ile Gln Pro Asp Gly Ser Tyr
385                 390                 395                 400

Arg Ser Glu Glu Leu Asn Leu Val Ile Ile Gly Pro Ser Ala Asp Ile
                405                 410                 415

Ile Tyr Phe Glu Cys Lys Ser Phe Gly His Glu Val Leu Asn Leu Thr
            420                 425                 430

Arg Asn Gly Tyr Gly Ser Thr Gln Tyr Ile Arg Phe Ser Pro Asp Phe
        435                 440                 445

Thr Phe Gly Phe Glu Glu Ser Leu Glu Val Asp Thr Asn Pro Leu Leu
    450                 455                 460

Gly Ala Gly Lys Phe Ala Thr Asp Pro Ala Val Thr Leu Ala His Ala
465                 470                 475                 480

Leu Ile His Ala Gly His Arg Leu Tyr Gly Ile Ala Ile Asn Pro Asn
                485                 490                 495

Arg Val Phe Lys Val Asn Thr Asn Ala Tyr Tyr Glu Met Ser Gly Tyr
            500                 505                 510

Arg Val Ser Phe Glu Glu Leu Arg Thr Phe Gly Gly His Asp Ala Lys
        515                 520                 525

Phe Ile Asp Ser Leu Gln Glu Asn Glu Phe Arg Leu Tyr Tyr Tyr Asn
    530                 535                 540

Lys Phe Lys Asp Ile Ala Ser Thr Leu Asn Lys Ala Lys Ser Ile Val
545                 550                 555                 560

Gly Thr Thr Ala Ser Leu Gln Tyr Met Lys Asn Val Phe Lys Glu Lys
                565                 570                 575

Tyr Glu Leu Ser Glu Asp Thr Ser Gly Lys Phe Ser Val Asp Lys Leu
            580                 585                 590

Lys Phe Asp Lys Leu Tyr Lys Met Leu Thr Glu Ile Tyr Thr Glu Asp
        595                 600                 605

Asn Phe Val Lys Phe Phe Lys Val Leu Asn Arg Lys Thr Ala Leu Asn
    610                 615                 620

Phe Asp Lys Ala Val Phe Lys Ile Asn Ile Val Pro Lys Val Asn Tyr
625                 630                 635                 640

Thr Ile Tyr Asp Gly Phe Asn Leu Arg Asn Thr Asn Leu Ala Ala Asn
```

```
                645                 650                 655

Phe Asn Gly Gln Asn Thr Glu Ile Asn Asn Met Asn Phe Thr Lys Leu
            660                 665                 670

Lys Asn Phe Thr Gly Leu Phe Glu Phe Tyr Lys Leu Leu Cys Val Arg
        675                 680                 685

Gly Ile Ile Thr Ser His Thr Gln Ser Leu Asp Gln Gly Gly Glu Asn
    690                 695                 700

Leu Tyr Phe Gln Gly Ala Leu Asn Asp Leu Cys Ile Lys Val Asn Asn
705                 710                 715                 720

Trp Asp Leu Phe Phe Ser Pro Ser Glu Asp Asn Phe Thr Asn Asp Leu
                725                 730                 735

Asn Lys Gly Glu Glu Ile Thr Ser Asp Thr Asn Ile Glu Ala Ala Glu
            740                 745                 750

Glu Asn Ile Ser Leu Asp Leu Ile Gln Gln Tyr Tyr Leu Thr Phe Asn
        755                 760                 765

Phe Asp Asn Glu Pro Glu Asn Ile Ser Ile Glu Asn Leu Ser Ser Asp
    770                 775                 780

Ile Ile Gly Gln Leu Glu Leu Met Pro Asn Ile Glu Arg Phe Pro Asn
785                 790                 795                 800

Gly Lys Lys Tyr Glu Leu Asp Lys Tyr Thr Met Phe His Tyr Leu Arg
                805                 810                 815

Ala Gln Glu Phe Glu His Gly Lys Ser Arg Ile Ala Leu Thr Asn Ser
            820                 825                 830

Val Asn Glu Ala Leu Leu Asn Pro Ser Arg Val Tyr Thr Phe Phe Ser
        835                 840                 845

Ser Asp Tyr Val Lys Lys Val Asn Lys Ala Thr Glu Ala Ala Met Phe
    850                 855                 860

Leu Gly Trp Val Glu Gln Leu Val Tyr Asp Phe Thr Asp Glu Thr Ser
865                 870                 875                 880

Glu Val Ser Thr Thr Asp Lys Ile Ala Asp Ile Thr Ile Ile Ile Pro
                885                 890                 895

Tyr Ile Gly Pro Ala Leu Asn Ile Gly Asn Met Leu Tyr Lys Asp Asp
            900                 905                 910

Phe Val Gly Ala Leu Ile Phe Ser Gly Ala Val Ile Leu Leu Glu Phe
        915                 920                 925

Ile Pro Glu Ile Ala Ile Pro Val Leu Gly Thr Phe Ala Leu Val Ser
    930                 935                 940

Tyr Ile Ala Asn Lys Val Leu Thr Val Gln Thr Ile Asp Asn Ala Leu
945                 950                 955                 960

Ser Lys Arg Asn Glu Lys Trp Asp Glu Val Tyr Lys Tyr Ile Val Thr
                965                 970                 975

Asn Trp Leu Ala Lys Val Asn Thr Gln Ile Asp Leu Ile Arg Lys Lys
            980                 985                 990

Met Lys Glu Ala Leu Glu Asn Gln  Ala Glu Ala Thr Lys  Ala Ile Ile
        995                 1000                1005

Asn Tyr  Gln Tyr Asn Gln Tyr  Thr Glu Glu Glu Lys  Asn Asn Ile
    1010                1015                1020

Asn Phe  Asn Ile Asp Asp Leu  Ser Ser Lys Leu Asn  Glu Ser Ile
    1025                1030                1035

Asn Lys  Ala Met Ile Asn Ile  Asn Lys Phe Leu Asn  Gln Cys Ser
    1040                1045                1050

Val Ser  Tyr Leu Met Asn Ser  Met Ile Pro Tyr Gly  Val Lys Arg
    1055                1060                1065
```

Leu Glu Asp Phe Asp Ala Ser Leu Lys Asp Ala Leu Leu Lys Tyr
1070 1075 1080

Ile Tyr Asp Asn Arg Gly Thr Leu Ile Gly Gln Val Asp Arg Leu
1085 1090 1095

Lys Asp Lys Val Asn Asn Thr Leu Ser Thr Asp Ile Pro Phe Gln
1100 1105 1110

Leu Ser Lys Tyr Val Asp Asn Gln Arg Leu Leu Ser Thr Phe Thr
1115 1120 1125

Glu Tyr Ile Asn Asn Ile Ile Asn Thr Ser Ile Leu Asn Leu Arg
1130 1135 1140

Tyr Glu Ser Asn His Leu Ile Asp Leu Ser Arg Tyr Ala Ser Lys
1145 1150 1155

Ile Asn Ile Gly Ser Lys Val Asn Phe Asp Pro Ile Asp Lys Asn
1160 1165 1170

Gln Ile Gln Leu Phe Asn Leu Glu Ser Ser Lys Ile Glu Val Ile
1175 1180 1185

Leu Lys Asn Ala Ile Val Tyr Asn Ser Met Tyr Glu Asn Phe Ser
1190 1195 1200

Thr Ser Phe Trp Ile Arg Ile Pro Lys Tyr Phe Asn Ser Ile Ser
1205 1210 1215

Leu Asn Asn Glu Tyr Thr Ile Ile Asn Cys Met Glu Asn Asn Ser
1220 1225 1230

Gly Trp Lys Val Ser Leu Asn Tyr Gly Glu Ile Ile Trp Thr Leu
1235 1240 1245

Gln Asp Thr Gln Glu Ile Lys Gln Arg Val Val Phe Lys Tyr Ser
1250 1255 1260

Gln Met Ile Asn Ile Ser Asp Tyr Ile Asn Arg Trp Ile Phe Val
1265 1270 1275

Thr Ile Thr Asn Asn Arg Leu Asn Asn Ser Lys Ile Tyr Ile Asn
1280 1285 1290

Gly Arg Leu Ile Asp Gln Lys Pro Ile Ser Asn Leu Gly Asn Ile
1295 1300 1305

His Ala Ser Asn Asn Ile Met Phe Lys Leu Asp Gly Cys Arg Asp
1310 1315 1320

Thr His Arg Tyr Ile Trp Ile Lys Tyr Phe Asn Leu Phe Asp Lys
1325 1330 1335

Glu Leu Asn Glu Lys Glu Ile Lys Asp Leu Tyr Asp Asn Gln Ser
1340 1345 1350

Asn Ser Gly Ile Leu Lys Asp Phe Trp Gly Asp Tyr Leu Gln Tyr
1355 1360 1365

Asp Lys Pro Tyr Tyr Met Leu Asn Leu Tyr Asp Pro Asn Lys Tyr
1370 1375 1380

Val Asp Val Asn Asn Val Gly Ile Arg Gly Tyr Met Tyr Leu Lys
1385 1390 1395

Gly Pro Arg Gly Ser Val Met Thr Thr Asn Ile Tyr Leu Asn Ser
1400 1405 1410

Ser Leu Tyr Arg Gly Thr Lys Phe Ile Ile Lys Lys Tyr Ala Ser
1415 1420 1425

Gly Asn Lys Asp Asn Ile Val Arg Asn Asn Asp Arg Val Tyr Ile
1430 1435 1440

Asn Val Val Val Lys Asn Lys Glu Tyr Arg Leu Ala Thr Asn Ala
1445 1450 1455

Ser Gln Ala Gly Val Glu Lys Ile Leu Ser Ala Leu Glu Ile Pro
1460 1465 1470

Asp Val Gly Asn Leu Ser Gln Val Val Val Met Lys Ser Lys Asn
1475 1480 1485

Asp Gln Gly Ile Thr Asn Lys Cys Lys Met Asn Leu Gln Asp Asn
1490 1495 1500

Asn Gly Asn Asp Ile Gly Phe Ile Gly Phe His Gln Phe Asn Asn
1505 1510 1515

Ile Ala Lys Leu Val Ala Ser Asn Trp Tyr Asn Arg Gln Ile Glu
1520 1525 1530

Arg Ser Ser Arg Thr Leu Gly Cys Ser Trp Glu Phe Ile Pro Val
1535 1540 1545

Asp Asp Gly Trp Gly Glu Arg Pro Leu Gly Ala Gly Tyr Pro Tyr
1550 1555 1560

Asp Val Pro Asp Tyr Ala Gly Glu Asn Leu Tyr Phe Gln Gly Ala
1565 1570 1575

Gly Trp Ser His Pro Gln Phe Glu Lys Gly Ala Gly Trp Ser His
1580 1585 1590

Pro Gln Phe Glu Lys Gly Ala Gly Trp Ser His Pro Gln Phe Glu
1595 1600 1605

Lys

<210> SEQ ID NO 7
<211> LENGTH: 4921
<212> TYPE: DNA
<213> ORGANISM: Artificial
<220> FEATURE:
<223> OTHER INFORMATION: Propeptide fusion encoding sequence

<400> SEQUENCE: 7
ggatcccggt ccgttcgaac cagaactctg gaagcttaac tcctaaaaaa ccgccaccat 60
gaaattctta gtcaacgttg cccttgtttt tatggtcgta tacatttctt acatctatgc 120
ggccggacac caccaccacc accaccacca ccaccaccac gacgtcgaaa acctgtactt 180
ccaaggagcg gagcaaaaac tcattagcga ggaggacctg aaagcctggc aacaacaatc 240
atacctggac tccggtatcc acgaaggcgc taccactacc gccccttctg gtttcgctaa 300
cgaactgggt ccgagattga tgggaaaagg aggcggggcc cacggtggtg ctcaactcca 360
gctcgttgag tccggtggcg gaatggtgca acctggtggc tctttgaggc tgtcatgcgc 420
tgccagtgga ttcaccttct cgacttacga catgtcctgg gtgcgtcagg cacctggaaa 480
aggtcccgaa tgggtcagca tcattaacgc tggaggtggc agcacatact acgcagcgtc 540
tgttaaggga aggttcgcta tctccagaga caacgccaaa aacaccctct acttgcaaat 600
gaacaacctg aagcccgagg atactgctct ctactactgt gctcgcgtcg cctcatacta 660
ctgccgtggc tacgtttgta gtcctcccga gttcgactac tggggccagg gaacacaagt 720
gacggtctcc agcgaaccaa agacaccaaa accacaggct ggtcagggcg ctcctgttcc 780
atacccagat ccactggaac caagaggaac gcgtggagcg ggagcaggtc cattcgtcaa 840
caagcaattc aactacaaag atcctgttaa cggtgtggac atcgcctaca tcaagattcc 900
gaacgcaggc cagatgcaac ctgtgaaggc tttcaaaatc cacaacaaga tctgggtcat 960
tcccgagaga gacacattca cgaacccaga ggaaggtgat ctgaaccctc ccccagaagc 1020
caagcaggtg ccggtctctt actacgattc aacctacctc agtactgaca acgagaagga 1080
taactacctg aagggcgtta ctaaactctt cgagcgcatc tactcgacag acttgggccg 1140

```
tatgctgctc acgtccatcg tcaggggtat tcctttctgg ggtggctcaa ccatcgacac   1200
tgagctgaag gtcattgata caaactgcat caacgttatt caacccgacg gctcctaccg   1260
cagcgaggaa ttgaacctgg tgatcattgg accaagcgcc gacatcattt acttcgagtg   1320
taagtctttc ggccatgaag tcctcaactt gaccagaaac ggctacggct ccactcaata   1380
catccgcttc agccccgact tcacattcgg attcgaggaa tcactggagg tcgatacgaa   1440
cccgttgctg ggtgctggca agttcgccac cgaccctgca gttactctgg cacacgcgct   1500
catccacgcg ggacatcgtc tgtacggtat cgctattaac ccaaacaggg tcttcaaggt   1560
taacaccaac gcctactacg agatgagtgg ttacagggtg tcgttcgagg aactccgtac   1620
gttcggaggt cacgacgcaa agttcatcga tagtttgcag gagaacgaat tccgcctgta   1680
ctactacaac aagttcaaag acatcgcgtc tacactcaac aaggctaaaa gcattgttgg   1740
aaccactgct agtttgcaat acatgaagaa cgtgttcaag gagaaatacg agttgtcgga   1800
agacacctcc ggtaaattca gcgtggacaa gctgaaattc gataagttgt acaaaatgct   1860
gacagaaatc tacacggaag acaacttcgt taagttcttc aaagtgttga accgtaagac   1920
cgctctgaac ttcgataagg ctgtcttcaa aatcaacatt gtgcctaaag tcaactacac   1980
catctacgac ggtttcaacc tccgcaacac taacttggct gccaacttca acggccagaa   2040
cactgagatc aacaacatga acttcacaaa gctcaaaaac ttcaccggtt tgttcgagtt   2100
ctacaagctg ctctgcgtgc gtggtggagg cacatctcac acgcaatctg agaacctgta   2160
cttccaaggt ggtggccagg gtggagctct gaacgatctg tgtatcaagg tgaataactg   2220
ggatctgttc tttagcccaa gcgaggataa cttcacgaac gatctcaaca aaggtgaaga   2280
gatcacgtct gataccaata tcgaagcggc tgaagagaat atctccttgg atctcatcca   2340
gcaatattac ctgaccttta acttcgataa cgagcccgaa aacatctcca tcgagaacct   2400
cagctcagac atcattggtc agttggagct gatgccaaac attgaacgct tccccaacgg   2460
caagaaatac gaactcgaca agtatacgat gtttcattac ttaagagcgc aggagtttga   2520
acacggcaag agccgcattg ctctcactaa ctccgtgaat gaagccctgc tcaatccgtc   2580
aagggtgtac acattcttta gctccgacta tgtcaagaaa gtgaacaaag ccaccgaagc   2640
ggcaatgttc ctgggatggg ttgaacaact ggtctacgac ttcaccgacg agacctctga   2700
ggtgagcaca acggacaaga ttgctgacat cactatcatt atcccgtata ttggacctgc   2760
cttgaatatt ggcaacatgc tctacaaaga cgatttcgtt ggtgccctga tcttcagcgg   2820
tgccgtgatc ctgttggagt tcattcctga aatcgccatc cctgtgctgg gcacgttcgc   2880
tctggtctca tacattgcga ataaggtctt gaccgtgcag acaatcgata atgccctctc   2940
caaacgtaac gaaaaatggg acgaggtcta caaatacatc gtgaccaact ggctggcaaa   3000
ggttaacacc caaattgatc tgatccgtaa gaaaatgaag gaggctttgg agaaccaggc   3060
tgaagctact aaagccatta tcaactacca gtataatcag tatacagaag aggaaaagaa   3120
taacatcaat ttcaacatcg atgacttgtc ctcaaagctg aacgagtcca tcaacaaagc   3180
tatgatcaac atcaacaaat tcctgaatca gtgctccgtg tcttacctga tgaactctat   3240
gatcccatac ggtgtgaagc gcctggagga cttcgatgcc agcctgaaag acgcactgct   3300
caaatacatt tacgataatc gcggcacttt gattggccaa gttgaccgtc tgaaggacaa   3360
ggttaacaat accttgtcaa ccgatatccc cttccaactc tctaagtacg tcgataacca   3420
gcgcttgctg agcaccttca cagaatacat caacaacatc atcaacacct ccatcctgaa   3480
```

-continued

```
cctccgttac gagtctaacc acctcatcga cttgagcaga tacgctagca agatcaacat   3540
cggttccaag gtgaacttcg acccaatcga taagaaccag atccaactgt tcaacctcga   3600
atcctctaag atcgaagtga tcctgaagaa cgctatcgtc tacaactcca tgtacgaaaa   3660
cttctctacc agcttctgga tcaggattcc gaaatacttc aactcaatct cgctcaacaa   3720
cgagtacact atcatcaact gcatggaaaa caactcggga tggaaggtgt ccctcaacta   3780
cggcgagatc atctggactt tgcaggacac acaagaaatc aagcagaggg tcgtgttcaa   3840
gtacagccaa atgatcaaca tcagcgatta catcaaccgt tggatcttcg tcacaatcac   3900
caacaaccgc ctgaacaact ccaagattta catcaacggt agactgatcg accagaagcc   3960
aatcagcaac ctcggcaaca tccacgcctc aaacaacatc atgttcaagt tggacggctg   4020
tagggataca cacagataca tctggatcaa atacttcaac ctgttcgaca aggagctcaa   4080
cgagaaggaa atcaaggacc tctacgataa ccagtccaac tctggtatct tgaaggactt   4140
ctggggcgat tacctgcaat acgacaagcc ctactacatg ttgaacctgt acgaccctaa   4200
caagtacgtt gatgtgaaca acgtcggtat caggggctac atgtacctga agggaccacg   4260
tggttctgtt atgaccacta acatctacct caacagctca ttgtaccgtg gcacaaagtt   4320
catcatcaag aagtacgcct ccggaaacaa ggacaacatc gtccgtaaca acgatcgcgt   4380
ttacatcaac gttgtggtca agaacaagga gtacagactg gctaccaacg cttcgcaggc   4440
tggagttgag aagatcctgt ctgctctgga aatccctgac gtgggcaacc tctcacaggt   4500
tgtggtcatg aagtcgaaga acgatcaagg catcactaac aagtgcaaga tgaacttgca   4560
ggacaacaac ggaaacgaca tcggcttcat cggattccac caattcaaca acatcgccaa   4620
gttggtggcc agcaactggt acaaccgtca gatcgagcgt tcgtcccgca ccttaggatg   4680
ctcgtgggag ttcattccag tcgatgacgg atggggagag agacctttgg gcgcaggata   4740
cccctacgat gtccctgact acgctggaga gaacctgtac ttccagggtg caggatggtc   4800
ccacccacaa ttcgagaagg gtgcaggatg gagtcaccca cagttcgaga agggcgctgg   4860
atggtcccac ccacagttcg agaaataatt agttgatgca tagttaatta gatagctcga   4920
g                                                                   4921
```

<210> SEQ ID NO 8
<211> LENGTH: 1627
<212> TYPE: PRT
<213> ORGANISM: Artificial
<220> FEATURE:
<223> OTHER INFORMATION: Fusion protein

<400> SEQUENCE: 8

```
Asp Pro Gly Pro Phe Glu Pro Glu Leu Trp Lys Leu Asn Ser Lys Thr
1               5                   10                  15

Ala Thr Met Lys Phe Leu Val Asn Val Ala Leu Val Phe Met Val Val
            20                  25                  30

Tyr Ile Ser Tyr Ile Tyr Ala Ala Gly His His His His His His His
        35                  40                  45

His His His His Asp Val Glu Asn Leu Tyr Phe Gln Gly Ala Glu Gln
    50                  55                  60

Lys Leu Ile Ser Glu Glu Asp Leu Lys Ala Trp Gln Gln Gln Ser Tyr
65                  70                  75                  80

Leu Asp Ser Gly Ile His Glu Gly Ala Thr Thr Thr Ala Pro Ser Gly
                85                  90                  95

Phe Ala Asn Glu Leu Gly Pro Arg Leu Met Gly Lys Gly Gly Gly Ala
```

```
            100                 105                 110

His Gly Gly Ala Gln Leu Gln Leu Val Glu Ser Gly Gly Gly Met Val
        115                 120                 125

Gln Pro Gly Gly Ser Leu Arg Leu Ser Cys Ala Ala Ser Gly Phe Thr
    130                 135                 140

Phe Ser Thr Tyr Asp Met Ser Trp Val Arg Gln Ala Pro Gly Lys Gly
145                 150                 155                 160

Pro Glu Trp Val Ser Ile Ile Asn Ala Gly Gly Gly Ser Thr Tyr Tyr
                165                 170                 175

Ala Ala Ser Val Lys Gly Arg Phe Ala Ile Ser Arg Asp Asn Ala Lys
            180                 185                 190

Asn Thr Leu Tyr Leu Gln Met Asn Asn Leu Lys Pro Glu Asp Thr Ala
        195                 200                 205

Leu Tyr Tyr Cys Ala Arg Val Ala Ser Tyr Tyr Cys Arg Gly Tyr Val
    210                 215                 220

Cys Ser Pro Pro Glu Phe Asp Tyr Trp Gly Gln Gly Thr Gln Val Thr
225                 230                 235                 240

Val Ser Ser Glu Pro Lys Thr Pro Lys Pro Gln Ala Gly Gln Gly Ala
                245                 250                 255

Pro Val Pro Tyr Pro Asp Pro Leu Glu Pro Arg Gly Thr Arg Gly Ala
            260                 265                 270

Gly Ala Gly Pro Phe Val Asn Lys Gln Phe Asn Tyr Lys Asp Pro Val
        275                 280                 285

Asn Gly Val Asp Ile Ala Tyr Ile Lys Ile Pro Asn Ala Gly Gln Met
    290                 295                 300

Gln Pro Val Lys Ala Phe Lys Ile His Asn Lys Ile Trp Val Ile Pro
305                 310                 315                 320

Glu Arg Asp Thr Phe Thr Asn Pro Glu Glu Gly Asp Leu Asn Pro Pro
                325                 330                 335

Pro Glu Ala Lys Gln Val Pro Val Ser Tyr Tyr Asp Ser Thr Tyr Leu
            340                 345                 350

Ser Thr Asp Asn Glu Lys Asp Asn Tyr Leu Lys Gly Val Thr Lys Leu
        355                 360                 365

Phe Glu Arg Ile Tyr Ser Thr Asp Leu Gly Arg Met Leu Leu Thr Ser
    370                 375                 380

Ile Val Arg Gly Ile Pro Phe Trp Gly Gly Ser Thr Ile Asp Thr Glu
385                 390                 395                 400

Leu Lys Val Ile Asp Thr Asn Cys Ile Asn Val Ile Gln Pro Asp Gly
                405                 410                 415

Ser Tyr Arg Ser Glu Glu Leu Asn Leu Val Ile Ile Gly Pro Ser Ala
            420                 425                 430

Asp Ile Ile Tyr Phe Glu Cys Lys Ser Phe Gly His Glu Val Leu Asn
        435                 440                 445

Leu Thr Arg Asn Gly Tyr Gly Ser Thr Gln Tyr Ile Arg Phe Ser Pro
    450                 455                 460

Asp Phe Thr Phe Gly Phe Glu Glu Ser Leu Glu Val Asp Thr Asn Pro
465                 470                 475                 480

Leu Leu Gly Ala Gly Lys Phe Ala Thr Asp Pro Ala Val Thr Leu Ala
                485                 490                 495

His Ala Leu Ile His Ala Gly His Arg Leu Tyr Gly Ile Ala Ile Asn
            500                 505                 510

Pro Asn Arg Val Phe Lys Val Asn Thr Asn Ala Tyr Tyr Glu Met Ser
        515                 520                 525
```

```
Gly Tyr Arg Val Ser Phe Glu Glu Leu Arg Thr Phe Gly Gly His Asp
    530                 535                 540

Ala Lys Phe Ile Asp Ser Leu Gln Glu Asn Glu Phe Arg Leu Tyr Tyr
545                 550                 555                 560

Tyr Asn Lys Phe Lys Asp Ile Ala Ser Thr Leu Asn Lys Ala Lys Ser
                565                 570                 575

Ile Val Gly Thr Thr Ala Ser Leu Gln Tyr Met Lys Asn Val Phe Lys
            580                 585                 590

Glu Lys Tyr Glu Leu Ser Glu Asp Thr Ser Gly Lys Phe Ser Val Asp
        595                 600                 605

Lys Leu Lys Phe Asp Lys Leu Tyr Lys Met Leu Thr Glu Ile Tyr Thr
    610                 615                 620

Glu Asp Asn Phe Val Lys Phe Phe Lys Val Leu Asn Arg Lys Thr Ala
625                 630                 635                 640

Leu Asn Phe Asp Lys Ala Val Phe Lys Ile Asn Ile Val Pro Lys Val
                645                 650                 655

Asn Tyr Thr Ile Tyr Asp Gly Phe Asn Leu Arg Asn Thr Asn Leu Ala
            660                 665                 670

Ala Asn Phe Asn Gly Gln Asn Thr Glu Ile Asn Asn Met Asn Phe Thr
        675                 680                 685

Lys Leu Lys Asn Phe Thr Gly Leu Phe Glu Phe Tyr Lys Leu Leu Cys
    690                 695                 700

Val Arg Gly Gly Gly Thr Ser His Thr Gln Ser Glu Asn Leu Tyr Phe
705                 710                 715                 720

Gln Gly Gly Gly Gln Gly Gly Ala Leu Asn Asp Leu Cys Ile Lys Val
                725                 730                 735

Asn Asn Trp Asp Leu Phe Phe Ser Pro Ser Glu Asp Asn Phe Thr Asn
            740                 745                 750

Asp Leu Asn Lys Gly Glu Glu Ile Thr Ser Asp Thr Asn Ile Glu Ala
        755                 760                 765

Ala Glu Glu Asn Ile Ser Leu Asp Leu Ile Gln Gln Tyr Tyr Leu Thr
    770                 775                 780

Phe Asn Phe Asp Asn Glu Pro Glu Asn Ile Ser Ile Glu Asn Leu Ser
785                 790                 795                 800

Ser Asp Ile Ile Gly Gln Leu Glu Leu Met Pro Asn Ile Glu Arg Phe
                805                 810                 815

Pro Asn Gly Lys Lys Tyr Glu Leu Asp Lys Tyr Thr Met Phe His Tyr
            820                 825                 830

Leu Arg Ala Gln Glu Phe Glu His Gly Lys Ser Arg Ile Ala Leu Thr
        835                 840                 845

Asn Ser Val Asn Glu Ala Leu Leu Asn Pro Ser Arg Val Tyr Thr Phe
    850                 855                 860

Phe Ser Ser Asp Tyr Val Lys Lys Val Asn Lys Ala Thr Glu Ala Ala
865                 870                 875                 880

Met Phe Leu Gly Trp Val Glu Gln Leu Val Tyr Asp Phe Thr Asp Glu
                885                 890                 895

Thr Ser Glu Val Ser Thr Thr Asp Lys Ile Ala Asp Ile Thr Ile Ile
            900                 905                 910

Ile Pro Tyr Ile Gly Pro Ala Leu Asn Ile Gly Asn Met Leu Tyr Lys
        915                 920                 925

Asp Asp Phe Val Gly Ala Leu Ile Phe Ser Gly Ala Val Ile Leu Leu
    930                 935                 940
```

```
Glu Phe Ile Pro Glu Ile Ala Ile Pro Val Leu Gly Thr Phe Ala Leu
945                 950                 955                 960

Val Ser Tyr Ile Ala Asn Lys Val Leu Thr Val Gln Thr Ile Asp Asn
                965                 970                 975

Ala Leu Ser Lys Arg Asn Glu Lys Trp Asp Glu Val Tyr Lys Tyr Ile
            980                 985                 990

Val Thr Asn Trp Leu Ala Lys Val  Asn Thr Gln Ile Asp  Leu Ile Arg
        995                 1000                 1005

Lys Lys  Met Lys Glu Ala Leu  Glu Asn Gln Ala Glu  Ala Thr Lys
    1010                 1015                 1020

Ala Ile  Ile Asn Tyr Gln Tyr  Asn Gln Tyr Thr Glu  Glu Glu Lys
    1025                 1030                 1035

Asn Asn  Ile Asn Phe Asn Ile  Asp Asp Leu Ser Ser  Lys Leu Asn
    1040                 1045                 1050

Glu Ser  Ile Asn Lys Ala Met  Ile Asn Ile Asn Lys  Phe Leu Asn
    1055                 1060                 1065

Gln Cys  Ser Val Ser Tyr Leu  Met Asn Ser Met Ile  Pro Tyr Gly
    1070                 1075                 1080

Val Lys  Arg Leu Glu Asp Phe  Asp Ala Ser Leu Lys  Asp Ala Leu
    1085                 1090                 1095

Leu Lys  Tyr Ile Tyr Asp Asn  Arg Gly Thr Leu Ile  Gly Gln Val
    1100                 1105                 1110

Asp Arg  Leu Lys Asp Lys Val  Asn Asn Thr Leu Ser  Thr Asp Ile
    1115                 1120                 1125

Pro Phe  Gln Leu Ser Lys Tyr  Val Asp Asn Gln Arg  Leu Leu Ser
    1130                 1135                 1140

Thr Phe  Thr Glu Tyr Ile Asn  Asn Ile Ile Asn Thr  Ser Ile Leu
    1145                 1150                 1155

Asn Leu  Arg Tyr Glu Ser Asn  His Leu Ile Asp Leu  Ser Arg Tyr
    1160                 1165                 1170

Ala Ser  Lys Ile Asn Ile Gly  Ser Lys Val Asn Phe  Asp Pro Ile
    1175                 1180                 1185

Asp Lys  Asn Gln Ile Gln Leu  Phe Asn Leu Glu Ser  Ser Lys Ile
    1190                 1195                 1200

Glu Val  Ile Leu Lys Asn Ala  Ile Val Tyr Asn Ser  Met Tyr Glu
    1205                 1210                 1215

Asn Phe  Ser Thr Ser Phe Trp  Ile Arg Ile Pro Lys  Tyr Phe Asn
    1220                 1225                 1230

Ser Ile  Ser Leu Asn Asn Glu  Tyr Thr Ile Ile Asn  Cys Met Glu
    1235                 1240                 1245

Asn Asn  Ser Gly Trp Lys Val  Ser Leu Asn Tyr Gly  Glu Ile Ile
    1250                 1255                 1260

Trp Thr  Leu Gln Asp Thr Gln  Glu Ile Lys Gln Arg  Val Val Phe
    1265                 1270                 1275

Lys Tyr  Ser Gln Met Ile Asn  Ile Ser Asp Tyr Ile  Asn Arg Trp
    1280                 1285                 1290

Ile Phe  Val Thr Ile Thr Asn  Asn Arg Leu Asn Asn  Ser Lys Ile
    1295                 1300                 1305

Tyr Ile  Asn Gly Arg Leu Ile  Asp Gln Lys Pro Ile  Ser Asn Leu
    1310                 1315                 1320

Gly Asn  Ile His Ala Ser Asn  Asn Ile Met Phe Lys  Leu Asp Gly
    1325                 1330                 1335

Cys Arg  Asp Thr His Arg Tyr  Ile Trp Ile Lys Tyr  Phe Asn Leu
```

1340 1345 1350

Phe Asp Lys Glu Leu Asn Glu Lys Glu Ile Lys Asp Leu Tyr Asp
1355 1360 1365

Asn Gln Ser Asn Ser Gly Ile Leu Lys Asp Phe Trp Gly Asp Tyr
1370 1375 1380

Leu Gln Tyr Asp Lys Pro Tyr Tyr Met Leu Asn Leu Tyr Asp Pro
1385 1390 1395

Asn Lys Tyr Val Asp Val Asn Asn Val Gly Ile Arg Gly Tyr Met
1400 1405 1410

Tyr Leu Lys Gly Pro Arg Gly Ser Val Met Thr Thr Asn Ile Tyr
1415 1420 1425

Leu Asn Ser Ser Leu Tyr Arg Gly Thr Lys Phe Ile Ile Lys Lys
1430 1435 1440

Tyr Ala Ser Gly Asn Lys Asp Asn Ile Val Arg Asn Asn Asp Arg
1445 1450 1455

Val Tyr Ile Asn Val Val Val Lys Asn Lys Glu Tyr Arg Leu Ala
1460 1465 1470

Thr Asn Ala Ser Gln Ala Gly Val Glu Lys Ile Leu Ser Ala Leu
1475 1480 1485

Glu Ile Pro Asp Val Gly Asn Leu Ser Gln Val Val Val Met Lys
1490 1495 1500

Ser Lys Asn Asp Gln Gly Ile Thr Asn Lys Cys Lys Met Asn Leu
1505 1510 1515

Gln Asp Asn Asn Gly Asn Asp Ile Gly Phe Ile Gly Phe His Gln
1520 1525 1530

Phe Asn Asn Ile Ala Lys Leu Val Ala Ser Asn Trp Tyr Asn Arg
1535 1540 1545

Gln Ile Glu Arg Ser Ser Arg Thr Leu Gly Cys Ser Trp Glu Phe
1550 1555 1560

Ile Pro Val Asp Asp Gly Trp Gly Glu Arg Pro Leu Gly Ala Gly
1565 1570 1575

Tyr Pro Tyr Asp Val Pro Asp Tyr Ala Gly Glu Asn Leu Tyr Phe
1580 1585 1590

Gln Gly Ala Gly Trp Ser His Pro Gln Phe Glu Lys Gly Ala Gly
1595 1600 1605

Trp Ser His Pro Gln Phe Glu Lys Gly Ala Gly Trp Ser His Pro
1610 1615 1620

Gln Phe Glu Lys
1625

<210> SEQ ID NO 9
<211> LENGTH: 4801
<212> TYPE: DNA
<213> ORGANISM: Artificial
<220> FEATURE:
<223> OTHER INFORMATION: Propeptide fusion encoding sequence

<400> SEQUENCE: 9
ggatcccggt ccgttcgaac cagaactctg gaagcttaac tcctaaaaaa ccgccaccat 60
gaaattctta gtcaacgttg cccttgtttt tatggtcgta tacatttctt acatctatgc 120
ggccggacac caccaccacc accaccacca ccaccaccac gacgtcgaga acctgtactt 180
ccaaggagca gaacaaaagt tgatttcgga ggaggacctg ggtggtgggg cccacggtgg 240
cgcacaggcg cacgtgcaac tgcagcagtc tggaggaggc ttggtgcagc ctgggggttc 300

-continued

```
cctgcgcctg tcatgtgcag cctctggaag catcttcagt atttacgcta tgggctggta    360
caggcaggct cctggcaagc aacgtgaact ggttgctgcc atctccagct acggtagtac    420
caactacgct gattcggtca agggcaggtt caccatctcc cgcgacaatg ccaagaatac    480
cgtctatttg caaatgaact ctctgaaacc tgaggatacg gccgtctact actgcaacgc    540
tgacattgct actatgaccg cggtaggcgg attcgactac tggggacagg gaactcaggt    600
gacggtctct tccgaaccta agacccctaa accccaagcg ggccaaggcg ctccagtccc    660
atacccagac ccactcgaac ccaggggcac gcgtggagcg ggagctggac cgatcaccat    720
caacaacttc aattacagcg acccggtgga taacaagaac atcctctact tggacacaca    780
cttgaacacg ctggctaacg agcctgaaaa agctttcagg atcaccggca acatttgggt    840
cattccggat aggttcagca gaaactctaa ccctaacttg aacaaacctc ccagagtgac    900
ctcacctaag agtggatact acgaccccaa ctacctctcg actgactccg ataaagaccc    960
cttcctgaag gagatcatta aactcttcaa gcgcatcaac tctcgtgaaa ttggcgagga   1020
attgatctac cgcctgagta cagacatccc attcccgggt aacaacaaca ccccaatcaa   1080
cactttcgat ttcgatgtcg atttcaactc agtggatgtc aaaaccaggc agggaaacaa   1140
ctgggtgaag actggtagca tcaacccatc tgtcatcatt actggcccga gagagaacat   1200
cattgaccct gaaacctcca ctttcaagct gacaaacaac acgttcgctg ctcaggaagg   1260
cttcggagcg ttgagcatca tttctatctc acctcgcttc atgctgacat actctaacgc   1320
tacgaacgac gtgggagagg gccgtttcag taagtctgaa ttctgcatgg accctattct   1380
gatcctcatg cacgctctca acggcgccat gcacaacttg tacggaattg ctatccccaa   1440
cgaccagacc atttccagcg tgactagcaa catcttctac tctcaataca acgtcaagct   1500
ggagtacgca gaaatctacg ctttcggtgg cccaaccatt gacttgatcc cgaaatcagc   1560
tcgtaagtat ttcgaagaaa aagcgctgga ttattacagg tcgattgcta agagactcaa   1620
ctccatcacc actgctaacc cctcttcatt caacaagtac attggagaat acaagcagaa   1680
actgatccgc aagtaccgtt tcgtggtcga gagttcgggt gaagttactg tgaaccgcaa   1740
caagttcgtc gagctgtaca acgaattgac acaaatcttc acggagttca actacgccaa   1800
aatttacaac gtgcaaaacc gtaagatcgc gctctctaac gtctacaccc cggttaccgc   1860
taacatcttg gacgataacg tctacgacat tcagaacggt ttcaacatcc caaagtcgaa   1920
cctcaacgtt ttgttcatgg gtcaaaactt gtcccgcaac cccgccctgc gtaaggtgaa   1980
cccagagaac atgttgtacc tgttcaccaa attctgccac aaggccatcg acggtcagtc   2040
tctagaccaa ggaggagaga acctctactt ccaaggtgct ggcaccctgg actgtcgcga   2100
actgctcgtt aagaacactg atctcccatt cattggcgac atctctgatg tgaaaacaga   2160
cattttcctg cgtaaggata tcaacgagga aacggaggtc atctactacc ctgacaacgt   2220
ctcggttgat caggttatct tgtcaaagaa caccagtgaa catggccaac tggacttgct   2280
gtacccctca attgattccg agagcgaaat cctgccagga gagaaccagg ttttctacga   2340
caacaggaca caaaacgtgg attacctcaa cagctactac tacctggagt cgcagaagct   2400
ctccgacaac gtcgaagatt tcacatttac gagatcaatc gaggaggctt tggacaacag   2460
tgccaaagtc tacacctact tccctactct ggcaaacaag gtgaacgcgg gtgtccaagg   2520
cggactcttc ttgatgtggg ctaacgacgt tgtggaagat ttcacaacga acatcttgcg   2580
caaagacacc ctggataaga tcagcgatgt ctctgccatc attccataca ttggcccggc   2640
actgaacatc tctaactcag ttcgccgtgg caacttcact gaggcattcg cggtcacagg   2700
```

```
agttacgatc ctcttggagg ctttcccgga gttcacaatc cccgcactgg gcgcgttcgt   2760
tatctactcc aaagtgcagg agcgcaacga aatcattaag actatcgaca actgcctgga   2820
gcaaaggatc aaaagatgga aggattcgta cgaatggatg atgggtacct ggctctcccg   2880
tatcattacg cagttcaaca acatcagcta ccaaatgtac gactctctca actaccaggc   2940
tggtgccatc aaggccaaaa ttgacttgga gtacaagaaa tacagtggct cggataaaga   3000
gaacatcaag agtcaagtcg aaaacctgaa aaactcactc gacgttaaga tcagtgaggc   3060
aatgaacaac atcaacaagt tcattcgcga atgttccgtt acctacctct tcaaaaacat   3120
gttgccaaag gtcatcgacg agctgaacga atttgatcgt aacactaagg cgaaactgat   3180
taacctcatc gactcacaca acatcatttt ggtgggcgaa gtcgataagc tgaaagccaa   3240
ggtgaacaac agtttccaga acacaatccc tttcaacatt ttctcataca cgaacaacag   3300
tctgctcaag gacatcatta acgagtactt caacaacatt aacgatagca aaatcctgtc   3360
actgcagaac cgtaagaaca cactggtcga tactagtgga tacaacgccg aagtctctga   3420
ggaaggtgac gtgcagctga accctatctt ccccttcgac ttcaaattgg gctccagcgg   3480
agaggatagg ggcaaggtca tcgtcaccca gaacgagaac atcgtctaca actcaatgta   3540
cgaatccttc agcatctctt tctggatcag gattaacaag tgggtgagca acctgcccgg   3600
ttacacaatc attgactctg tcaagaacaa ctcaggttgg agtatcggca tcatttctaa   3660
cttcttggtc ttcaccctga agcagaacga ggactcggaa caatccatta acttctcata   3720
cgatatcagt aacaacgctc caggttacaa caagtggttc ttcgttaccg tgactaacaa   3780
catgatgggt aacatgaaaa tttacatcaa cggcaagctc attgacacca tcaaagtgaa   3840
ggagttgact ggtattaact tctccaaaac aatcacgttt gaaattaaca agatccctga   3900
caccggcctg atcacttcag acagtgataa catcaacatg tggattaggg atttctacat   3960
cttcgccaag gagctcgacg gaaaggatat taacatcctc ttcaacagct tgcagtacac   4020
caacgtcgtt aaagactact ggggtaacga tttgagatac aacaaggagt actacatggt   4080
caacatcgac tacctgaaca ggtacatgta cgctaactcc cgccaaatcg tgttcaacac   4140
caggagaaac aacaacgact tcaacgaggg ttacaaaatc attatcaagc gcatccgtgg   4200
caacaccaac gatactaggg tgagaggtgg cgacattctg tacttcgata tgactatcaa   4260
caacaaagcc tacaacttgt tcatgaaaaa cgagacaatg tacgccgaca accatagcac   4320
ggaggatatt tacgcaatcg gactgaggga acagacaaag gacatcaacg ataacattat   4380
cttccagatc caacctatga acaacacgta ctactacgct tcgcaaatct tcaagtccaa   4440
cttcaacgga gaaaacattt cgggtatctg ttccattggc acataccgct tccgtctggg   4500
tggtgactgg tatcgtcaca actacctcgt tcccaccgtg aagcagggta actacgcttc   4560
tttgctggag tcgacctcca ctcattgggg attcgttcca gtttcagaag gagcgggata   4620
cccatacgac gtgcccgact atgctggtga gaacctgtac ttccagggcg ctggttggtc   4680
ccaccctcag ttcgagaagg gagcgggatg gtcacacccg cagtttgaga aaggcgcagg   4740
ttggtcacat ccccagttcg agaagtaatt agttgatgca tagttaatta gatagctcga   4800
g                                                                   4801
```

<210> SEQ ID NO 10
<211> LENGTH: 1569
<212> TYPE: PRT
<213> ORGANISM: Artificial
<220> FEATURE:

<223> OTHER INFORMATION: Fusion protein

<400> SEQUENCE: 10

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Glu Asn Leu Tyr Phe Gln Gly Ala Glu Gln Lys Leu
        35                  40                  45

Ile Ser Glu Glu Asp Leu Gly Gly Gly Ala His Gly Gly Ala Gln Ala
    50                  55                  60

His Val Gln Leu Gln Gln Ser Gly Gly Gly Leu Val Gln Pro Gly Gly
65                  70                  75                  80

Ser Leu Arg Leu Ser Cys Ala Ala Ser Gly Ser Ile Phe Ser Ile Tyr
                85                  90                  95

Ala Met Gly Trp Tyr Arg Gln Ala Pro Gly Lys Gln Arg Glu Leu Val
            100                 105                 110

Ala Ala Ile Ser Ser Tyr Gly Ser Thr Asn Tyr Ala Asp Ser Val Lys
        115                 120                 125

Gly Arg Phe Thr Ile Ser Arg Asp Asn Ala Lys Asn Thr Val Tyr Leu
    130                 135                 140

Gln Met Asn Ser Leu Lys Pro Glu Asp Thr Ala Val Tyr Tyr Cys Asn
145                 150                 155                 160

Ala Asp Ile Ala Thr Met Thr Ala Val Gly Gly Phe Asp Tyr Trp Gly
                165                 170                 175

Gln Gly Thr Gln Val Thr Val Ser Ser Glu Pro Lys Thr Pro Lys Pro
            180                 185                 190

Gln Ala Gly Gln Gly Ala Pro Val Pro Tyr Pro Asp Pro Leu Glu Pro
        195                 200                 205

Arg Gly Thr Arg Gly Ala Gly Ala Gly Pro Ile Thr Ile Asn Asn Phe
    210                 215                 220

Asn Tyr Ser Asp Pro Val Asp Asn Lys Asn Ile Leu Tyr Leu Asp Thr
225                 230                 235                 240

His Leu Asn Thr Leu Ala Asn Glu Pro Glu Lys Ala Phe Arg Ile Thr
                245                 250                 255

Gly Asn Ile Trp Val Ile Pro Asp Arg Phe Ser Arg Asn Ser Asn Pro
            260                 265                 270

Asn Leu Asn Lys Pro Pro Arg Val Thr Ser Pro Lys Ser Gly Tyr Tyr
        275                 280                 285

Asp Pro Asn Tyr Leu Ser Thr Asp Ser Asp Lys Asp Pro Phe Leu Lys
    290                 295                 300

Glu Ile Ile Lys Leu Phe Lys Arg Ile Asn Ser Arg Glu Ile Gly Glu
305                 310                 315                 320

Glu Leu Ile Tyr Arg Leu Ser Thr Asp Ile Pro Phe Pro Gly Asn Asn
                325                 330                 335

Asn Thr Pro Ile Asn Thr Phe Asp Phe Asp Val Asp Phe Asn Ser Val
            340                 345                 350

Asp Val Lys Thr Arg Gln Gly Asn Asn Trp Val Lys Thr Gly Ser Ile
        355                 360                 365

Asn Pro Ser Val Ile Ile Thr Gly Pro Arg Glu Asn Ile Ile Asp Pro
    370                 375                 380

Glu Thr Ser Thr Phe Lys Leu Thr Asn Asn Thr Phe Ala Ala Gln Glu
385                 390                 395                 400
```

```
Gly Phe Gly Ala Leu Ser Ile Ile Ser Ile Ser Pro Arg Phe Met Leu
                405                 410                 415

Thr Tyr Ser Asn Ala Thr Asn Asp Val Gly Glu Gly Arg Phe Ser Lys
            420                 425                 430

Ser Glu Phe Cys Met Asp Pro Ile Leu Ile Leu Met His Ala Leu Asn
        435                 440                 445

Gly Ala Met His Asn Leu Tyr Gly Ile Ala Ile Pro Asn Asp Gln Thr
    450                 455                 460

Ile Ser Ser Val Thr Ser Asn Ile Phe Tyr Ser Gln Tyr Asn Val Lys
465                 470                 475                 480

Leu Glu Tyr Ala Glu Ile Tyr Ala Phe Gly Gly Pro Thr Ile Asp Leu
                485                 490                 495

Ile Pro Lys Ser Ala Arg Lys Tyr Phe Glu Glu Lys Ala Leu Asp Tyr
            500                 505                 510

Tyr Arg Ser Ile Ala Lys Arg Leu Asn Ser Ile Thr Thr Ala Asn Pro
        515                 520                 525

Ser Ser Phe Asn Lys Tyr Ile Gly Glu Tyr Lys Gln Lys Leu Ile Arg
    530                 535                 540

Lys Tyr Arg Phe Val Val Glu Ser Ser Gly Glu Val Thr Val Asn Arg
545                 550                 555                 560

Asn Lys Phe Val Glu Leu Tyr Asn Glu Leu Thr Gln Ile Phe Thr Glu
                565                 570                 575

Phe Asn Tyr Ala Lys Ile Tyr Asn Val Gln Asn Arg Lys Ile Ala Leu
            580                 585                 590

Ser Asn Val Tyr Thr Pro Val Thr Ala Asn Ile Leu Asp Asp Asn Val
        595                 600                 605

Tyr Asp Ile Gln Asn Gly Phe Asn Ile Pro Lys Ser Asn Leu Asn Val
    610                 615                 620

Leu Phe Met Gly Gln Asn Leu Ser Arg Asn Pro Ala Leu Arg Lys Val
625                 630                 635                 640

Asn Pro Glu Asn Met Leu Tyr Leu Phe Thr Lys Phe Cys His Lys Ala
                645                 650                 655

Ile Asp Gly Gln Ser Leu Asp Gln Gly Gly Glu Asn Leu Tyr Phe Gln
            660                 665                 670

Gly Ala Gly Thr Leu Asp Cys Arg Glu Leu Leu Val Lys Asn Thr Asp
        675                 680                 685

Leu Pro Phe Ile Gly Asp Ile Ser Asp Val Lys Thr Asp Ile Phe Leu
    690                 695                 700

Arg Lys Asp Ile Asn Glu Glu Thr Glu Val Ile Tyr Tyr Pro Asp Asn
705                 710                 715                 720

Val Ser Val Asp Gln Val Ile Leu Ser Lys Asn Thr Ser Glu His Gly
                725                 730                 735

Gln Leu Asp Leu Leu Tyr Pro Ser Ile Asp Ser Glu Ser Glu Ile Leu
            740                 745                 750

Pro Gly Glu Asn Gln Val Phe Tyr Asp Asn Arg Thr Gln Asn Val Asp
        755                 760                 765

Tyr Leu Asn Ser Tyr Tyr Tyr Leu Glu Ser Gln Lys Leu Ser Asp Asn
    770                 775                 780

Val Glu Asp Phe Thr Phe Thr Arg Ser Ile Glu Glu Ala Leu Asp Asn
785                 790                 795                 800

Ser Ala Lys Val Tyr Thr Tyr Phe Pro Thr Leu Ala Asn Lys Val Asn
                805                 810                 815

Ala Gly Val Gln Gly Gly Leu Phe Leu Met Trp Ala Asn Asp Val Val
```

```
            820                 825                 830

Glu Asp Phe Thr Thr Asn Ile Leu Arg Lys Asp Thr Leu Asp Lys Ile
        835                 840                 845

Ser Asp Val Ser Ala Ile Ile Pro Tyr Ile Gly Pro Ala Leu Asn Ile
    850                 855                 860

Ser Asn Ser Val Arg Arg Gly Asn Phe Thr Glu Ala Phe Ala Val Thr
865                 870                 875                 880

Gly Val Thr Ile Leu Leu Glu Ala Phe Pro Glu Phe Thr Ile Pro Ala
                885                 890                 895

Leu Gly Ala Phe Val Ile Tyr Ser Lys Val Gln Glu Arg Asn Glu Ile
            900                 905                 910

Ile Lys Thr Ile Asp Asn Cys Leu Glu Gln Arg Ile Lys Arg Trp Lys
        915                 920                 925

Asp Ser Tyr Glu Trp Met Met Gly Thr Trp Leu Ser Arg Ile Ile Thr
    930                 935                 940

Gln Phe Asn Asn Ile Ser Tyr Gln Met Tyr Asp Ser Leu Asn Tyr Gln
945                 950                 955                 960

Ala Gly Ala Ile Lys Ala Lys Ile Asp Leu Glu Tyr Lys Lys Tyr Ser
                965                 970                 975

Gly Ser Asp Lys Glu Asn Ile Lys Ser Gln Val Glu Asn Leu Lys Asn
            980                 985                 990

Ser Leu Asp Val Lys Ile Ser Glu  Ala Met Asn Asn Ile  Asn Lys Phe
        995                 1000                1005

Ile Arg  Glu Cys Ser Val Thr  Tyr Leu Phe Lys Asn  Met Leu Pro
    1010                1015                1020

Lys Val  Ile Asp Glu Leu Asn  Glu Phe Asp Arg Asn  Thr Lys Ala
    1025                1030                1035

Lys Leu  Ile Asn Leu Ile Asp  Ser His Asn Ile Ile  Leu Val Gly
    1040                1045                1050

Glu Val  Asp Lys Leu Lys Ala  Lys Val Asn Asn Ser  Phe Gln Asn
    1055                1060                1065

Thr Ile  Pro Phe Asn Ile Phe  Ser Tyr Thr Asn Asn  Ser Leu Leu
    1070                1075                1080

Lys Asp  Ile Ile Asn Glu Tyr  Phe Asn Asn Ile Asn  Asp Ser Lys
    1085                1090                1095

Ile Leu  Ser Leu Gln Asn Arg  Lys Asn Thr Leu Val  Asp Thr Ser
    1100                1105                1110

Gly Tyr  Asn Ala Glu Val Ser  Glu Glu Gly Asp Val  Gln Leu Asn
    1115                1120                1125

Pro Ile  Phe Pro Phe Asp Phe  Lys Leu Gly Ser Ser  Gly Glu Asp
    1130                1135                1140

Arg Gly  Lys Val Ile Val Thr  Gln Asn Glu Asn Ile  Val Tyr Asn
    1145                1150                1155

Ser Met  Tyr Glu Ser Phe Ser  Ile Ser Phe Trp Ile  Arg Ile Asn
    1160                1165                1170

Lys Trp  Val Ser Asn Leu Pro  Gly Tyr Thr Ile Ile  Asp Ser Val
    1175                1180                1185

Lys Asn  Asn Ser Gly Trp Ser  Ile Gly Ile Ile Ser  Asn Phe Leu
    1190                1195                1200

Val Phe  Thr Leu Lys Gln Asn  Glu Asp Ser Glu Gln  Ser Ile Asn
    1205                1210                1215

Phe Ser  Tyr Asp Ile Ser Asn  Asn Ala Pro Gly Tyr  Asn Lys Trp
    1220                1225                1230
```

Phe Phe Val Thr Val Thr Asn Asn Met Met Gly Asn Met Lys Ile
1235 1240 1245

Tyr Ile Asn Gly Lys Leu Ile Asp Thr Ile Lys Val Lys Glu Leu
1250 1255 1260

Thr Gly Ile Asn Phe Ser Lys Thr Ile Thr Phe Glu Ile Asn Lys
1265 1270 1275

Ile Pro Asp Thr Gly Leu Ile Thr Ser Asp Ser Asp Asn Ile Asn
1280 1285 1290

Met Trp Ile Arg Asp Phe Tyr Ile Phe Ala Lys Glu Leu Asp Gly
1295 1300 1305

Lys Asp Ile Asn Ile Leu Phe Asn Ser Leu Gln Tyr Thr Asn Val
1310 1315 1320

Val Lys Asp Tyr Trp Gly Asn Asp Leu Arg Tyr Asn Lys Glu Tyr
1325 1330 1335

Tyr Met Val Asn Ile Asp Tyr Leu Asn Arg Tyr Met Tyr Ala Asn
1340 1345 1350

Ser Arg Gln Ile Val Phe Asn Thr Arg Arg Asn Asn Asn Asp Phe
1355 1360 1365

Asn Glu Gly Tyr Lys Ile Ile Ile Lys Arg Ile Arg Gly Asn Thr
1370 1375 1380

Asn Asp Thr Arg Val Arg Gly Gly Asp Ile Leu Tyr Phe Asp Met
1385 1390 1395

Thr Ile Asn Asn Lys Ala Tyr Asn Leu Phe Met Lys Asn Glu Thr
1400 1405 1410

Met Tyr Ala Asp Asn His Ser Thr Glu Asp Ile Tyr Ala Ile Gly
1415 1420 1425

Leu Arg Glu Gln Thr Lys Asp Ile Asn Asp Asn Ile Ile Phe Gln
1430 1435 1440

Ile Gln Pro Met Asn Asn Thr Tyr Tyr Tyr Ala Ser Gln Ile Phe
1445 1450 1455

Lys Ser Asn Phe Asn Gly Glu Asn Ile Ser Gly Ile Cys Ser Ile
1460 1465 1470

Gly Thr Tyr Arg Phe Arg Leu Gly Gly Asp Trp Tyr Arg His Asn
1475 1480 1485

Tyr Leu Val Pro Thr Val Lys Gln Gly Asn Tyr Ala Ser Leu Leu
1490 1495 1500

Glu Ser Thr Ser Thr His Trp Gly Phe Val Pro Val Ser Glu Gly
1505 1510 1515

Ala Gly Tyr Pro Tyr Asp Val Pro Asp Tyr Ala Gly Glu Asn Leu
1520 1525 1530

Tyr Phe Gln Gly Ala Gly Trp Ser His Pro Gln Phe Glu Lys Gly
1535 1540 1545

Ala Gly Trp Ser His Pro Gln Phe Glu Lys Gly Ala Gly Trp Ser
1550 1555 1560

His Pro Gln Phe Glu Lys
1565

<210> SEQ ID NO 11
<211> LENGTH: 4804
<212> TYPE: DNA
<213> ORGANISM: Artificial
<220> FEATURE:
<223> OTHER INFORMATION: Propeptide fusion encoding sequence

<400> SEQUENCE: 11

```
ggatcccggt ccgttcgaac cagaactctg gaagcttaac tcctaaaaaa ccgccaccat     60
gaaattctta gtcaacgttg cccttgtttt tatggtcgta tacatttctt acatctatgc    120
ggccggacac caccaccacc accaccacca ccaccaccac gacgtcgaaa acctgtactt    180
ccaaggtgca gagcagaaac tcatcagcga agaagatttg ggagcaggcg cagcacaact    240
ccagctcgtt gagtccggtg gcggaatggt gcaacctggt ggctctttga ggctgtcatg    300
cgctgccagt ggattcacct tctcgactta cgacatgtcc tgggtgcgtc aggcacctgg    360
aaaaggtccc gaatgggtca gcatcattaa cgctggaggt ggcagcacat actacgcagc    420
gtctgttaag ggaaggttcg ctatctccag agacaacgcc aaaaacaccc tctacttgca    480
aatgaacaac ctgaagcccg aggatactgc tctctactac tgtgctcgcg tcgcctcata    540
ctactgccgt ggctacgttt gtagtcctcc cgagttcgac tactggggcc agggaacaca    600
agtgacggtc tccagcgaac caaagacacc aaaaccacag gctggtcagg gcgctcctgt    660
tccataccca gatccactgg aaccaagagg aacgcgtgga gcgggagcag gtccattcgt    720
caacaagcaa ttcaactaca aagatcctgt taacggtgtg gacatcgcct acatcaagat    780
tccgaacgca ggccagatgc aacctgtgaa ggctttcaaa atccacaaca agatctgggt    840
cattcccgag agagacacat tcacgaaccc agaggaaggt gatctgaacc ctcccccaga    900
agccaagcag gtgccggtct cttactacga ttcaacctac ctcagtactg acaacgagaa    960
ggataactac ctgaagggcg ttactaaact cttcgagcgc atctactcga cagacttggg   1020
ccgtatgctg ctcacgtcca tcgtcagggg tattcctttc tggggtggct caaccatcga   1080
cactgagctg aaggtcattg atacaaactg catcaacgtt attcaacccg acggctccta   1140
ccgcagcgag gaattgaacc tggtgatcat tggaccaagc gccgacatca ttcagttcga   1200
gtgtaagtct ttcggccatg aagtcctcaa cttgaccaga aacggctacg gctccactca   1260
atacatccgc ttcagccccg acttcacatt cggattcgag gaatcactgg aggtcgatac   1320
gaacccgttg ctgggtgctg gcaagttcgc caccgaccct gcagttactc tggcacacgc   1380
gctcatccac gcgggacatc gtctgtacgg tatcgctatt aacccaaaca gggtcttcaa   1440
ggttaacacc aacgcctact acgagatgag tggtctggaa gtgtcgttcg aggaactccg   1500
tacgttcgga ggtcacgacg caaagttcat cgatagtttg caggagaacg aattccgcct   1560
gtactactac aacaagttca aagacatcgc gtctacactc aacaaggcta aaagcattgt   1620
tggaaccact gctagtttgc aatacatgaa gaacgtgttc aaggagaaat acctcttgtc   1680
ggaagacacc tccggtaaat tcagcgtgga caagctgaaa ttcgataagt tgtacaaaat   1740
gctgacagaa atctacacgg aagacaactt cgttaagttc ttcaaagtgt tgaaccgtaa   1800
gaccgctctg aacttcgata aggctgtctt caaaatcaac attgtgccta aagtcaacta   1860
caccatctac gacggtttca acctccgcaa cactaacttg gctgccaact tcaacggcca   1920
gaacactgag atcaacaaca tgaacttcac aaagctcaaa aacttcaccg gtttgttcga   1980
gttctacaag ctgctctgcg tgcgtggtat cattacatct cacacgcaat ctctagacca   2040
gggtggcgag aacctgtact tccagggtgc tctgaacgat ctgtgtatca aggtgaataa   2100
ctgggatctg ttctttagcc caagcgagga taacttcacg aacgatctca acaaaggtga   2160
agagatcacg tctgatacca atatcgaagc ggctgaagag aatatctcct tggatctcat   2220
ccagcaatat tacctgacct ttaacttcga taacgagccc gaaaacatct ccatcgagaa   2280
cctcagctca gacatcattg gtcagttgga gctgatgcca aacattgaac gcttccccaa   2340
```

```
cggcaagaaa tacgaactcg acaagtatac gatgtttcat tacttaagag cgcaggagtt   2400
tgaacacggc aagagccgca ttgctctcac taactccgtg aatgaagccc tgctcaatcc   2460
gtcaagggtg tacacattct ttagctccga ctatgtcaag aaagtgaaca aagccaccga   2520
agcggcaatg ttcctgggat gggttgaaca actggtctac gacttcaccg acgagacctc   2580
tgaggtgagc acaacggaca agattgctga catcactatc attatcccgt atattggacc   2640
tgccttgaat attggcaaca tgctctacaa agacgatttc gttggtgccc tgatcttcag   2700
cggtgccgtg atcctgttgg agttcattcc tgaaatcgcc atccctgtgc tgggcacgtt   2760
cgctctggtc tcatacattg cgaataaggt cttgaccgtg cagacaatcg ataatgccct   2820
ctccaaacgt aacgaaaaat gggacgaggt ctacaaatac atcgtgacca actggctggc   2880
aaaggttaac acccaaattg atctgatccg taagaaaatg aaggaggctt tggagaacca   2940
ggctgaagct actaaagcca ttatcaacta ccagtataat cagtatacag aagaggaaaa   3000
gaataacatc aatttcaaca tcgatgactt gtcctcaaag ctgaacgagt ccatcaacaa   3060
agctatgatc aacatcaaca aattcctgaa tcagtgctcc gtgtcttacc tgatgaactc   3120
tatgatccca tacggtgtga agcgcctgga ggacttcgat gccagcctga aagacgcact   3180
gctcaaatac atttacgata atcgcggcac tttgattggc caagttgacc gtctgaagga   3240
caaggttaac aataccttgt caaccgatat ccccttccaa ctctctaagt acgtcgataa   3300
ccagcgcttg ctgagcacct tcacagaata catcaacaac atcatcaaca cctccatcct   3360
gaacctccgt tacgagtcta accacctcat cgacttgagc agatacgcta gcaagatcaa   3420
catcggttcc aaggtgaact tcgacccaat cgataagaac cagatccaac tgttcaacct   3480
cgaatcctct aagatcgaag tgatcctgaa gaacgctatc gtctacaact ccatgtacga   3540
aaacttctct accagcttct ggatcaggat tccgaaatac ttcaactcaa tctcgctcaa   3600
caacgagtac actatcatca actgcatgga aaacaactcg ggatggaagg tgtccctcaa   3660
ctacggcgag atcatctgga ctttgcagga cacacaagaa atcaagcaga gggtcgtgtt   3720
caagtacagc caaatgatca acatcagcga ttacatcaac cgttggatct tcgtcacaat   3780
caccaacaac cgcctgaaca actccaagat ttacatcaac ggtagactga tcgaccagaa   3840
gccaatcagc aacctcggca acatccacgc ctcaaacaac atcatgttca agttggacgg   3900
ctgtagggat acacacagat acatctggat caaatacttc aacctgttcg acaaggagct   3960
caacgagaag gaaatcaagg acctctacga taaccagtcc aactctggta tcttgaagga   4020
cttctggggc gattacctgc aatacgacaa gccctactac atgttgaacc tgtacgaccc   4080
taacaagtac gttgatgtga acaacgtcgg tatcaggggc tacatgtacc tgaagggacc   4140
acgtggttct gttatgacca ctaacatcta cctcaacagc tcattgtacc gtggcacaaa   4200
gttcatcatc aagaagtacg cctccggaaa caaggacaac atcgtccgta acaacgatcg   4260
cgtttacatc aacgttgtgg tcaagaacaa ggagtacaga ctggctacca acgcttcgca   4320
ggctggagtt gagaagatcc tgtctgctct ggaaatccct gacgtgggca acctctcaca   4380
ggttgtggtc atgaagtcga agaacgatca aggcatcact aacaagtgca agatgaactt   4440
gcaggacaac aacggaaacg acatcggctt catcggattc caccaattca acaacatcgc   4500
caagttggtg gccagcaact ggtacaaccg tcagatcgag cgttcgtccc gcaccttagg   4560
atgctcgtgg gagttcattc cagtcgatga cggatgggga gagagacctt tgggcgcagg   4620
atacccctac gatgtccctg actacgctgg agagaacctg tacttccagg gtgcaggatg   4680
gtcccaccca caattcgaga agggtgcagg atggagtcac ccacagttcg agaagggcgc   4740
```

tggatggtcc cacccacagt tcgagaaata attagttgat gcatagttaa ttagatagct 4800
cgag 4804

<210> SEQ ID NO 12
<211> LENGTH: 1570
<212> TYPE: PRT
<213> ORGANISM: Artificial
<220> FEATURE:
<223> OTHER INFORMATION: Fusion protein

<400> SEQUENCE: 12

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Glu Asn Leu Tyr Phe Gln Gly Ala Glu Gln Lys Leu
35 40 45

Ile Ser Glu Glu Asp Leu Gly Ala Gly Ala Ala Gln Leu Gln Leu Val
50 55 60

Glu Ser Gly Gly Gly Met Val Gln Pro Gly Gly Ser Leu Arg Leu Ser
65 70 75 80

Cys Ala Ala Ser Gly Phe Thr Phe Ser Thr Tyr Asp Met Ser Trp Val
85 90 95

Arg Gln Ala Pro Gly Lys Gly Pro Glu Trp Val Ser Ile Ile Asn Ala
100 105 110

Gly Gly Gly Ser Thr Tyr Tyr Ala Ala Ser Val Lys Gly Arg Phe Ala
115 120 125

Ile Ser Arg Asp Asn Ala Lys Asn Thr Leu Tyr Leu Gln Met Asn Asn
130 135 140

Leu Lys Pro Glu Asp Thr Ala Leu Tyr Tyr Cys Ala Arg Val Ala Ser
145 150 155 160

Tyr Tyr Cys Arg Gly Tyr Val Cys Ser Pro Pro Glu Phe Asp Tyr Trp
165 170 175

Gly Gln Gly Thr Gln Val Thr Val Ser Ser Glu Pro Lys Thr Pro Lys
180 185 190

Pro Gln Ala Gly Gln Gly Ala Pro Val Pro Tyr Pro Asp Pro Leu Glu
195 200 205

Pro Arg Gly Thr Arg Gly Ala Gly Ala Gly Pro Phe Val Asn Lys Gln
210 215 220

Phe Asn Tyr Lys Asp Pro Val Asn Gly Val Asp Ile Ala Tyr Ile Lys
225 230 235 240

Ile Pro Asn Ala Gly Gln Met Gln Pro Val Lys Ala Phe Lys Ile His
245 250 255

Asn Lys Ile Trp Val Ile Pro Glu Arg Asp Thr Phe Thr Asn Pro Glu
260 265 270

Glu Gly Asp Leu Asn Pro Pro Pro Glu Ala Lys Gln Val Pro Val Ser
275 280 285

Tyr Tyr Asp Ser Thr Tyr Leu Ser Thr Asp Asn Glu Lys Asp Asn Tyr
290 295 300

Leu Lys Gly Val Thr Lys Leu Phe Glu Arg Ile Tyr Ser Thr Asp Leu
305 310 315 320

Gly Arg Met Leu Leu Thr Ser Ile Val Arg Gly Ile Pro Phe Trp Gly
325 330 335

Gly Ser Thr Ile Asp Thr Glu Leu Lys Val Ile Asp Thr Asn Cys Ile

```
            340                 345                 350

Asn Val Ile Gln Pro Asp Gly Ser Tyr Arg Ser Glu Glu Leu Asn Leu
        355                 360                 365

Val Ile Ile Gly Pro Ser Ala Asp Ile Ile Gln Phe Glu Cys Lys Ser
    370                 375                 380

Phe Gly His Glu Val Leu Asn Leu Thr Arg Asn Gly Tyr Gly Ser Thr
385                 390                 395                 400

Gln Tyr Ile Arg Phe Ser Pro Asp Phe Thr Phe Gly Phe Glu Glu Ser
                405                 410                 415

Leu Glu Val Asp Thr Asn Pro Leu Leu Gly Ala Gly Lys Phe Ala Thr
            420                 425                 430

Asp Pro Ala Val Thr Leu Ala His Ala Leu Ile His Ala Gly His Arg
        435                 440                 445

Leu Tyr Gly Ile Ala Ile Asn Pro Asn Arg Val Phe Lys Val Asn Thr
    450                 455                 460

Asn Ala Tyr Tyr Glu Met Ser Gly Leu Glu Val Ser Phe Glu Glu Leu
465                 470                 475                 480

Arg Thr Phe Gly Gly His Asp Ala Lys Phe Ile Asp Ser Leu Gln Glu
                485                 490                 495

Asn Glu Phe Arg Leu Tyr Tyr Tyr Asn Lys Phe Lys Asp Ile Ala Ser
            500                 505                 510

Thr Leu Asn Lys Ala Lys Ser Ile Val Gly Thr Thr Ala Ser Leu Gln
        515                 520                 525

Tyr Met Lys Asn Val Phe Lys Glu Lys Tyr Leu Leu Ser Glu Asp Thr
    530                 535                 540

Ser Gly Lys Phe Ser Val Asp Lys Leu Lys Phe Asp Lys Leu Tyr Lys
545                 550                 555                 560

Met Leu Thr Glu Ile Tyr Thr Glu Asp Asn Phe Val Lys Phe Phe Lys
                565                 570                 575

Val Leu Asn Arg Lys Thr Ala Leu Asn Phe Asp Lys Ala Val Phe Lys
            580                 585                 590

Ile Asn Ile Val Pro Lys Val Asn Tyr Thr Ile Tyr Asp Gly Phe Asn
        595                 600                 605

Leu Arg Asn Thr Asn Leu Ala Ala Asn Phe Asn Gly Gln Asn Thr Glu
    610                 615                 620

Ile Asn Asn Met Asn Phe Thr Lys Leu Lys Asn Phe Thr Gly Leu Phe
625                 630                 635                 640

Glu Phe Tyr Lys Leu Leu Cys Val Arg Gly Ile Ile Thr Ser His Thr
                645                 650                 655

Gln Ser Leu Asp Gln Gly Gly Glu Asn Leu Tyr Phe Gln Gly Ala Leu
            660                 665                 670

Asn Asp Leu Cys Ile Lys Val Asn Asn Trp Asp Leu Phe Phe Ser Pro
        675                 680                 685

Ser Glu Asp Asn Phe Thr Asn Asp Leu Asn Lys Gly Glu Glu Ile Thr
    690                 695                 700

Ser Asp Thr Asn Ile Glu Ala Ala Glu Glu Asn Ile Ser Leu Asp Leu
705                 710                 715                 720

Ile Gln Gln Tyr Tyr Leu Thr Phe Asn Phe Asp Asn Glu Pro Glu Asn
                725                 730                 735

Ile Ser Ile Glu Asn Leu Ser Ser Asp Ile Ile Gly Gln Leu Glu Leu
            740                 745                 750

Met Pro Asn Ile Glu Arg Phe Pro Asn Gly Lys Lys Tyr Glu Leu Asp
        755                 760                 765
```

-continued

```
Lys Tyr Thr Met Phe His Tyr Leu Arg Ala Gln Glu Phe Glu His Gly
    770                 775                 780

Lys Ser Arg Ile Ala Leu Thr Asn Ser Val Asn Glu Ala Leu Leu Asn
785                 790                 795                 800

Pro Ser Arg Val Tyr Thr Phe Phe Ser Ser Asp Tyr Val Lys Lys Val
                805                 810                 815

Asn Lys Ala Thr Glu Ala Ala Met Phe Leu Gly Trp Val Glu Gln Leu
            820                 825                 830

Val Tyr Asp Phe Thr Asp Glu Thr Ser Glu Val Ser Thr Thr Asp Lys
        835                 840                 845

Ile Ala Asp Ile Thr Ile Ile Ile Pro Tyr Ile Gly Pro Ala Leu Asn
    850                 855                 860

Ile Gly Asn Met Leu Tyr Lys Asp Asp Phe Val Gly Ala Leu Ile Phe
865                 870                 875                 880

Ser Gly Ala Val Ile Leu Leu Glu Phe Ile Pro Glu Ile Ala Ile Pro
                885                 890                 895

Val Leu Gly Thr Phe Ala Leu Val Ser Tyr Ile Ala Asn Lys Val Leu
            900                 905                 910

Thr Val Gln Thr Ile Asp Asn Ala Leu Ser Lys Arg Asn Glu Lys Trp
        915                 920                 925

Asp Glu Val Tyr Lys Tyr Ile Val Thr Asn Trp Leu Ala Lys Val Asn
    930                 935                 940

Thr Gln Ile Asp Leu Ile Arg Lys Lys Met Lys Glu Ala Leu Glu Asn
945                 950                 955                 960

Gln Ala Glu Ala Thr Lys Ala Ile Ile Asn Tyr Gln Tyr Asn Gln Tyr
                965                 970                 975

Thr Glu Glu Glu Lys Asn Asn Ile Asn Phe Asn Ile Asp Asp Leu Ser
            980                 985                 990

Ser Lys Leu Asn Glu Ser Ile Asn  Lys Ala Met Ile Asn  Ile Asn Lys
        995                 1000                1005

Phe Leu  Asn Gln Cys Ser Val  Ser Tyr Leu Met Asn  Ser Met Ile
    1010                1015                1020

Pro Tyr  Gly Val Lys Arg Leu  Glu Asp Phe Asp Ala  Ser Leu Lys
    1025                1030                1035

Asp Ala  Leu Leu Lys Tyr Ile  Tyr Asp Asn Arg Gly  Thr Leu Ile
    1040                1045                1050

Gly Gln  Val Asp Arg Leu Lys  Asp Lys Val Asn Asn  Thr Leu Ser
    1055                1060                1065

Thr Asp  Ile Pro Phe Gln Leu  Ser Lys Tyr Val Asp  Asn Gln Arg
    1070                1075                1080

Leu Leu  Ser Thr Phe Thr Glu  Tyr Ile Asn Asn Ile  Ile Asn Thr
    1085                1090                1095

Ser Ile  Leu Asn Leu Arg Tyr  Glu Ser Asn His Leu  Ile Asp Leu
    1100                1105                1110

Ser Arg  Tyr Ala Ser Lys Ile  Asn Ile Gly Ser Lys  Val Asn Phe
    1115                1120                1125

Asp Pro  Ile Asp Lys Asn Gln  Ile Gln Leu Phe Asn  Leu Glu Ser
    1130                1135                1140

Ser Lys  Ile Glu Val Ile Leu  Lys Asn Ala Ile Val  Tyr Asn Ser
    1145                1150                1155

Met Tyr  Glu Asn Phe Ser Thr  Ser Phe Trp Ile Arg  Ile Pro Lys
    1160                1165                1170
```

```
Tyr Phe  Asn Ser Ile Ser Leu  Asn Asn Glu Tyr Thr  Ile Ile Asn
    1175                 1180                 1185

Cys Met  Glu Asn Asn Ser Gly  Trp Lys Val Ser Leu  Asn Tyr Gly
    1190                 1195                 1200

Glu Ile  Ile Trp Thr Leu Gln  Asp Thr Gln Glu Ile  Lys Gln Arg
    1205                 1210                 1215

Val Val  Phe Lys Tyr Ser Gln  Met Ile Asn Ile Ser  Asp Tyr Ile
    1220                 1225                 1230

Asn Arg  Trp Ile Phe Val Thr  Ile Thr Asn Asn Arg  Leu Asn Asn
    1235                 1240                 1245

Ser Lys  Ile Tyr Ile Asn Gly  Arg Leu Ile Asp Gln  Lys Pro Ile
    1250                 1255                 1260

Ser Asn  Leu Gly Asn Ile His  Ala Ser Asn Asn Ile  Met Phe Lys
    1265                 1270                 1275

Leu Asp  Gly Cys Arg Asp Thr  His Arg Tyr Ile Trp  Ile Lys Tyr
    1280                 1285                 1290

Phe Asn  Leu Phe Asp Lys Glu  Leu Asn Glu Lys Glu  Ile Lys Asp
    1295                 1300                 1305

Leu Tyr  Asp Asn Gln Ser Asn  Ser Gly Ile Leu Lys  Asp Phe Trp
    1310                 1315                 1320

Gly Asp  Tyr Leu Gln Tyr Asp  Lys Pro Tyr Tyr Met  Leu Asn Leu
    1325                 1330                 1335

Tyr Asp  Pro Asn Lys Tyr Val  Asp Val Asn Asn Val  Gly Ile Arg
    1340                 1345                 1350

Gly Tyr  Met Tyr Leu Lys Gly  Pro Arg Gly Ser Val  Met Thr Thr
    1355                 1360                 1365

Asn Ile  Tyr Leu Asn Ser Ser  Leu Tyr Arg Gly Thr  Lys Phe Ile
    1370                 1375                 1380

Ile Lys  Lys Tyr Ala Ser Gly  Asn Lys Asp Asn Ile  Val Arg Asn
    1385                 1390                 1395

Asn Asp  Arg Val Tyr Ile Asn  Val Val Val Lys Asn  Lys Glu Tyr
    1400                 1405                 1410

Arg Leu  Ala Thr Asn Ala Ser  Gln Ala Gly Val Glu  Lys Ile Leu
    1415                 1420                 1425

Ser Ala  Leu Glu Ile Pro Asp  Val Gly Asn Leu Ser  Gln Val Val
    1430                 1435                 1440

Val Met  Lys Ser Lys Asn Asp  Gln Gly Ile Thr Asn  Lys Cys Lys
    1445                 1450                 1455

Met Asn  Leu Gln Asp Asn Asn  Gly Asn Asp Ile Gly  Phe Ile Gly
    1460                 1465                 1470

Phe His  Gln Phe Asn Asn Ile  Ala Lys Leu Val Ala  Ser Asn Trp
    1475                 1480                 1485

Tyr Asn  Arg Gln Ile Glu Arg  Ser Ser Arg Thr Leu  Gly Cys Ser
    1490                 1495                 1500

Trp Glu  Phe Ile Pro Val Asp  Asp Gly Trp Gly Glu  Arg Pro Leu
    1505                 1510                 1515

Gly Ala  Gly Tyr Pro Tyr Asp  Val Pro Asp Tyr Ala  Gly Glu Asn
    1520                 1525                 1530

Leu Tyr  Phe Gln Gly Ala Gly  Trp Ser His Pro Gln  Phe Glu Lys
    1535                 1540                 1545

Gly Ala  Gly Trp Ser His Pro  Gln Phe Glu Lys Gly  Ala Gly Trp
    1550                 1555                 1560

Ser His  Pro Gln Phe Glu Lys
```

1565 1570

<210> SEQ ID NO 13
<211> LENGTH: 4804
<212> TYPE: DNA
<213> ORGANISM: Artificial
<220> FEATURE:
<223> OTHER INFORMATION: Propeptide fusion encoding sequence

<400> SEQUENCE: 13
ggatcccggt ccgttcgaac cagaactctg gaagcttaac tcctaaaaaa ccgccaccat 60
gaaattctta gtcaacgttg cccttgtttt tatggtcgta tacatttctt acatctatgc 120
ggccggacac caccaccacc accaccacca ccaccaccac gacgtcgaaa acctgtactt 180
ccaaggtgca gagcagaaac tcatcagcga agaagatttg ggagcaggcg cagcacaact 240
ccagctcgtt gagtccggtg gcggaatggt gcaacctggt ggctctttga ggctgtcatg 300
cgctgccagt ggattcacct tctcgactta cgacatgtcc tgggtgcgtc aggcacctgg 360
aaaaggtccc gaatgggtca gcatcattaa cgctggaggt ggcagcacat actacgcagc 420
gtctgttaag ggaaggttcg ctatctccag agacaacgcc aaaaacaccc tctacttgca 480
aatgaacaac ctgaagcccg aggatactgc tctctactac tgtgctcgcg tcgcctcata 540
ctactgccgt ggctacgttt gtagtcctcc cgagttcgac tactggggcc agggaacaca 600
agtgacggtc tccagcgaac caaagacacc aaaaccacag gctggtcagg gcgctcctgt 660
tccataccca gatccactgg aaccaagagg aacgcgtgga gcgggagcag gtccattcgt 720
caacaagcaa ttcaactaca aagatcctgt taacggtgtg gacatcgcct acatcaagat 780
tccgaacgca ggccagatgc aacctgtgaa ggctttcaaa atccacaaca agatctgggt 840
cattcccgag agagacacat tcacgaaccc agaggaaggt gatctgaacc ctcccccaga 900
agccaagcag gtgccggtct cttactacga ttcaacctac ctcagtactg acaacgagaa 960
ggataactac ctgaagggcg ttactaaact cttcgagcgc atctactcga cagacttggg 1020
ccgtatgctg ctcacgtcca tcgtcagggg tattcctttc tggggtggct caaccatcga 1080
cactgagctg aaggtcattg atacaaactg catcaacgtt attcaacccg acggctccta 1140
ccgcagcgag gaattgaacc tggtgatcat tggaccaagc gccgacatca ttcagttcga 1200
gtgtaagtct ttcggccatg aagtcctcaa cttgaccaga aacggctacg gctccactca 1260
atacatccgc ttcagccccg acttcacatt cggattcgag gaatcactgg aggtcgatac 1320
gaacccgttg ctgggtgctg gcaagttcgc caccgaccct gcagttactc tggcacacgc 1380
gctcatccac gcgggacatc gtctgtacgg tatcgctatt aacccaaaca gggtcttcaa 1440
ggttaacacc aacgcctact acgagatgag tggtctggaa gtgtcgttcg aggaactccg 1500
tacgttcgga ggtcacgacg caaagttcat cgatagtttg caggagaacg aattccgcct 1560
gtactactac aacaagttca aagacatcgc gtctacactc aacaaggcta aaagcattgt 1620
tggaaccact gctagtttgc aatacatgaa gaacgtgttc aaggagaaat acctcttgtc 1680
ggaagacacc tccggtaaat tcagcgtgga caagctgaaa ttcgataagt tgtacaaaat 1740
gctgacagaa atctacacgg aagacaactt cgttaagttc ttcaaagtgt tgaaccgtaa 1800
gaccgctctg aacttcgata aggctgtctt caaaatcaac attgtgccta aagtcaacta 1860
caccatctac gacggtttca acctccgcaa cactaacttg gctgccaact tcaacggcca 1920
gaacactgag atcaacaaca tgaacttcac aaagctcaaa aacttcaccg gtttgttcga 1980
gttctacaag ctgctctgcg tgcgtggtgg aggcacatct cacacgcaat ctgagaacct 2040
gtacttccaa ggtggtggcc agggtggagc tctgaacgat ctgtgtatca aggtgaataa 2100
ctgggatctg ttctttagcc caagcgagga taacttcacg aacgatctca acaaaggtga 2160
agagatcacg tctgatacca atatcgaagc ggctgaagag aatatctcct tggatctcat 2220
ccagcaatat tacctgacct ttaacttcga taacgagccc gaaaacatct ccatcgagaa 2280
cctcagctca gacatcattg gtcagttgga gctgatgcca aacattgaac gcttccccaa 2340
cggcaagaaa tacgaactcg acaagtatac gatgtttcat tacttaagag cgcaggagtt 2400
tgaacacggc aagagccgca ttgctctcac taactccgtg aatgaagccc tgctcaatcc 2460
gtcaagggtg tacacattct ttagctccga ctatgtcaag aaagtgaaca aagccaccga 2520
agcggcaatg ttcctgggat gggttgaaca actggtctac gacttcaccg acgagacctc 2580
tgaggtgagc acaacggaca agattgctga catcactatc attatcccgt atattggacc 2640
tgccttgaat attggcaaca tgctctacaa agacgatttc gttggtgccc tgatcttcag 2700
cggtgccgtg atcctgttgg agttcattcc tgaaatcgcc atccctgtgc tgggcacgtt 2760
cgctctggtc tcatacattg cgaataaggt cttgaccgtg cagacaatcg ataatgccct 2820
ctccaaacgt aacgaaaaat gggacgaggt ctacaaatac atcgtgacca actggctggc 2880
aaaggttaac acccaaattg atctgatccg taagaaaatg aaggaggctt tggagaacca 2940
ggctgaagct actaaagcca ttatcaacta ccagtataat cagtatacag aagaggaaaa 3000
gaataacatc aatttcaaca tcgatgactt gtcctcaaag ctgaacgagt ccatcaacaa 3060
agctatgatc aacatcaaca aattcctgaa tcagtgctcc gtgtcttacc tgatgaactc 3120
tatgatccca tacggtgtga agcgcctgga ggacttcgat gccagcctga aagacgcact 3180
gctcaaatac atttacgata atcgcggcac tttgattggc caagttgacc gtctgaagga 3240
caaggttaac aataccttgt caaccgatat ccccttccaa ctctctaagt acgtcgataa 3300
ccagcgcttg ctgagcacct tcacagaata catcaacaac atcatcaaca cctccatcct 3360
gaacctccgt tacgagtcta accacctcat cgacttgagc agatacgcta gcaagatcaa 3420
catcggttcc aaggtgaact tcgacccaat cgataagaac cagatccaac tgttcaacct 3480
cgaatcctct aagatcgaag tgatcctgaa gaacgctatc gtctacaact ccatgtacga 3540
aaacttctct accagcttct ggatcaggat tccgaaatac ttcaactcaa tctcgctcaa 3600
caacgagtac actatcatca actgcatgga aaacaactcg ggatggaagg tgtccctcaa 3660
ctacggcgag atcatctgga ctttgcagga cacacaagaa atcaagcaga gggtcgtgtt 3720
caagtacagc caaatgatca acatcagcga ttacatcaac cgttggatct tcgtcacaat 3780
caccaacaac cgcctgaaca actccaagat ttacatcaac ggtagactga tcgaccagaa 3840
gccaatcagc aacctcggca acatccacgc ctcaaacaac atcatgttca agttggacgg 3900
ctgtagggat acacacagat acatctggat caaatacttc aacctgttcg acaaggagct 3960
caacgagaag gaaatcaagg acctctacga taaccagtcc aactctggta tcttgaagga 4020
cttctggggc gattacctgc aatacgacaa gccctactac atgttgaacc tgtacgaccc 4080
taacaagtac gttgatgtga acaacgtcgg tatcaggggc tacatgtacc tgaagggacc 4140
acgtggttct gttatgacca ctaacatcta cctcaacagc tcattgtacc gtggcacaaa 4200
gttcatcatc aagaagtacg cctccggaaa caaggacaac atcgtccgta acaacgatcg 4260
cgtttacatc aacgttgtgg tcaagaacaa ggagtacaga ctggctacca acgcttcgca 4320
ggctggagtt gagaagatcc tgtctgctct ggaaatccct gacgtgggca acctctcaca 4380

```
ggttgtggtc atgaagtcga agaacgatca aggcatcact aacaagtgca agatgaactt   4440

gcaggacaac aacggaaacg acatcggctt catcggattc caccaattca acaacatcgc   4500

caagttggtg gccagcaact ggtacaaccg tcagatcgag cgttcgtccc gcaccttagg   4560

atgctcgtgg gagttcattc cagtcgatga cggatgggga gagagacctt tgggcgcagg   4620

atacccctac gatgtccctg actacgctgg agagaacctg tacttccagg gtgcaggatg   4680

gtcccaccca caattcgaga agggtgcagg atggagtcac ccacagttcg agaagggcgc   4740

tggatggtcc cacccacagt tcgagaaata attagttgat gcatagttaa ttagatagct   4800

cgag                                                                4804
```

<210> SEQ ID NO 14
<211> LENGTH: 1570
<212> TYPE: PRT
<213> ORGANISM: Artificial
<220> FEATURE:
<223> OTHER INFORMATION: Fusion protein

<400> SEQUENCE: 14

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Glu Asn Leu Tyr Phe Gln Gly Ala Glu Gln Lys Leu
        35                  40                  45

Ile Ser Glu Glu Asp Leu Gly Ala Gly Ala Ala Gln Leu Gln Leu Val
    50                  55                  60

Glu Ser Gly Gly Gly Met Val Gln Pro Gly Gly Ser Leu Arg Leu Ser
65                  70                  75                  80

Cys Ala Ala Ser Gly Phe Thr Phe Ser Thr Tyr Asp Met Ser Trp Val
                85                  90                  95

Arg Gln Ala Pro Gly Lys Gly Pro Glu Trp Val Ser Ile Ile Asn Ala
            100                 105                 110

Gly Gly Gly Ser Thr Tyr Tyr Ala Ala Ser Val Lys Gly Arg Phe Ala
        115                 120                 125

Ile Ser Arg Asp Asn Ala Lys Asn Thr Leu Tyr Leu Gln Met Asn Asn
    130                 135                 140

Leu Lys Pro Glu Asp Thr Ala Leu Tyr Tyr Cys Ala Arg Val Ala Ser
145                 150                 155                 160

Tyr Tyr Cys Arg Gly Tyr Val Cys Ser Pro Pro Glu Phe Asp Tyr Trp
                165                 170                 175

Gly Gln Gly Thr Gln Val Thr Val Ser Ser Glu Pro Lys Thr Pro Lys
            180                 185                 190

Pro Gln Ala Gly Gln Gly Ala Pro Val Pro Tyr Pro Asp Pro Leu Glu
        195                 200                 205

Pro Arg Gly Thr Arg Gly Ala Gly Ala Gly Pro Phe Val Asn Lys Gln
    210                 215                 220

Phe Asn Tyr Lys Asp Pro Val Asn Gly Val Asp Ile Ala Tyr Ile Lys
225                 230                 235                 240

Ile Pro Asn Ala Gly Gln Met Gln Pro Val Lys Ala Phe Lys Ile His
                245                 250                 255

Asn Lys Ile Trp Val Ile Pro Glu Arg Asp Thr Phe Thr Asn Pro Glu
            260                 265                 270

Glu Gly Asp Leu Asn Pro Pro Pro Glu Ala Lys Gln Val Pro Val Ser
        275                 280                 285
```

```
Tyr Tyr Asp Ser Thr Tyr Leu Ser Thr Asp Asn Glu Lys Asp Asn Tyr
    290                 295                 300

Leu Lys Gly Val Thr Lys Leu Phe Glu Arg Ile Tyr Ser Thr Asp Leu
305                 310                 315                 320

Gly Arg Met Leu Leu Thr Ser Ile Val Arg Gly Ile Pro Phe Trp Gly
                325                 330                 335

Gly Ser Thr Ile Asp Thr Glu Leu Lys Val Ile Asp Thr Asn Cys Ile
            340                 345                 350

Asn Val Ile Gln Pro Asp Gly Ser Tyr Arg Ser Glu Glu Leu Asn Leu
        355                 360                 365

Val Ile Ile Gly Pro Ser Ala Asp Ile Ile Gln Phe Glu Cys Lys Ser
    370                 375                 380

Phe Gly His Glu Val Leu Asn Leu Thr Arg Asn Gly Tyr Gly Ser Thr
385                 390                 395                 400

Gln Tyr Ile Arg Phe Ser Pro Asp Phe Thr Phe Gly Phe Glu Glu Ser
                405                 410                 415

Leu Glu Val Asp Thr Asn Pro Leu Leu Gly Ala Gly Lys Phe Ala Thr
            420                 425                 430

Asp Pro Ala Val Thr Leu Ala His Ala Leu Ile His Ala Gly His Arg
        435                 440                 445

Leu Tyr Gly Ile Ala Ile Asn Pro Asn Arg Val Phe Lys Val Asn Thr
    450                 455                 460

Asn Ala Tyr Tyr Glu Met Ser Gly Leu Glu Val Ser Phe Glu Glu Leu
465                 470                 475                 480

Arg Thr Phe Gly Gly His Asp Ala Lys Phe Ile Asp Ser Leu Gln Glu
                485                 490                 495

Asn Glu Phe Arg Leu Tyr Tyr Tyr Asn Lys Phe Lys Asp Ile Ala Ser
            500                 505                 510

Thr Leu Asn Lys Ala Lys Ser Ile Val Gly Thr Thr Ala Ser Leu Gln
        515                 520                 525

Tyr Met Lys Asn Val Phe Lys Glu Lys Tyr Leu Leu Ser Glu Asp Thr
    530                 535                 540

Ser Gly Lys Phe Ser Val Asp Lys Leu Lys Phe Asp Lys Leu Tyr Lys
545                 550                 555                 560

Met Leu Thr Glu Ile Tyr Thr Glu Asp Asn Phe Val Lys Phe Phe Lys
                565                 570                 575

Val Leu Asn Arg Lys Thr Ala Leu Asn Phe Asp Lys Ala Val Phe Lys
            580                 585                 590

Ile Asn Ile Val Pro Lys Val Asn Tyr Thr Ile Tyr Asp Gly Phe Asn
        595                 600                 605

Leu Arg Asn Thr Asn Leu Ala Ala Asn Phe Asn Gly Gln Asn Thr Glu
    610                 615                 620

Ile Asn Asn Met Asn Phe Thr Lys Leu Lys Asn Phe Thr Gly Leu Phe
625                 630                 635                 640

Glu Phe Tyr Lys Leu Leu Cys Val Arg Gly Gly Gly Thr Ser His Thr
                645                 650                 655

Gln Ser Glu Asn Leu Tyr Phe Gln Gly Gly Gly Gln Gly Gly Ala Leu
            660                 665                 670

Asn Asp Leu Cys Ile Lys Val Asn Asn Trp Asp Leu Phe Phe Ser Pro
        675                 680                 685

Ser Glu Asp Asn Phe Thr Asn Asp Leu Asn Lys Gly Glu Glu Ile Thr
    690                 695                 700
```

```
Ser Asp Thr Asn Ile Glu Ala Ala Glu Glu Asn Ile Ser Leu Asp Leu
705                 710                 715                 720

Ile Gln Gln Tyr Tyr Leu Thr Phe Asn Phe Asp Asn Glu Pro Glu Asn
                725                 730                 735

Ile Ser Ile Glu Asn Leu Ser Ser Asp Ile Ile Gly Gln Leu Glu Leu
            740                 745                 750

Met Pro Asn Ile Glu Arg Phe Pro Asn Gly Lys Lys Tyr Glu Leu Asp
        755                 760                 765

Lys Tyr Thr Met Phe His Tyr Leu Arg Ala Gln Glu Phe Glu His Gly
    770                 775                 780

Lys Ser Arg Ile Ala Leu Thr Asn Ser Val Asn Glu Ala Leu Leu Asn
785                 790                 795                 800

Pro Ser Arg Val Tyr Thr Phe Phe Ser Ser Asp Tyr Val Lys Lys Val
                805                 810                 815

Asn Lys Ala Thr Glu Ala Ala Met Phe Leu Gly Trp Val Glu Gln Leu
            820                 825                 830

Val Tyr Asp Phe Thr Asp Glu Thr Ser Glu Val Ser Thr Thr Asp Lys
        835                 840                 845

Ile Ala Asp Ile Thr Ile Ile Ile Pro Tyr Ile Gly Pro Ala Leu Asn
    850                 855                 860

Ile Gly Asn Met Leu Tyr Lys Asp Asp Phe Val Gly Ala Leu Ile Phe
865                 870                 875                 880

Ser Gly Ala Val Ile Leu Leu Glu Phe Ile Pro Glu Ile Ala Ile Pro
                885                 890                 895

Val Leu Gly Thr Phe Ala Leu Val Ser Tyr Ile Ala Asn Lys Val Leu
            900                 905                 910

Thr Val Gln Thr Ile Asp Asn Ala Leu Ser Lys Arg Asn Glu Lys Trp
        915                 920                 925

Asp Glu Val Tyr Lys Tyr Ile Val Thr Asn Trp Leu Ala Lys Val Asn
    930                 935                 940

Thr Gln Ile Asp Leu Ile Arg Lys Lys Met Lys Glu Ala Leu Glu Asn
945                 950                 955                 960

Gln Ala Glu Ala Thr Lys Ala Ile Ile Asn Tyr Gln Tyr Asn Gln Tyr
                965                 970                 975

Thr Glu Glu Glu Lys Asn Asn Ile Asn Phe Asn Ile Asp Asp Leu Ser
            980                 985                 990

Ser Lys Leu Asn Glu Ser Ile Asn  Lys Ala Met Ile Asn  Ile Asn Lys
        995                 1000                1005

Phe Leu  Asn Gln Cys Ser Val  Ser Tyr Leu Met Asn  Ser Met Ile
    1010                1015                1020

Pro Tyr  Gly Val Lys Arg Leu  Glu Asp Phe Asp Ala  Ser Leu Lys
    1025                1030                1035

Asp Ala  Leu Leu Lys Tyr Ile  Tyr Asp Asn Arg Gly  Thr Leu Ile
    1040                1045                1050

Gly Gln  Val Asp Arg Leu Lys  Asp Lys Val Asn Asn  Thr Leu Ser
    1055                1060                1065

Thr Asp  Ile Pro Phe Gln Leu  Ser Lys Tyr Val Asp  Asn Gln Arg
    1070                1075                1080

Leu Leu  Ser Thr Phe Thr Glu  Tyr Ile Asn Asn Ile  Ile Asn Thr
    1085                1090                1095

Ser Ile  Leu Asn Leu Arg Tyr  Glu Ser Asn His Leu  Ile Asp Leu
    1100                1105                1110

Ser Arg  Tyr Ala Ser Lys Ile  Asn Ile Gly Ser Lys  Val Asn Phe
```

```
    1115                1120                1125

Asp Pro  Ile Asp Lys Asn Gln  Ile Gln Leu Phe Asn  Leu Glu Ser
    1130                1135                1140

Ser Lys  Ile Glu Val Ile Leu  Lys Asn Ala Ile Val  Tyr Asn Ser
    1145                1150                1155

Met Tyr  Glu Asn Phe Ser Thr  Ser Phe Trp Ile Arg  Ile Pro Lys
    1160                1165                1170

Tyr Phe  Asn Ser Ile Ser Leu  Asn Asn Glu Tyr Thr  Ile Ile Asn
    1175                1180                1185

Cys Met  Glu Asn Asn Ser Gly  Trp Lys Val Ser Leu  Asn Tyr Gly
    1190                1195                1200

Glu Ile  Ile Trp Thr Leu Gln  Asp Thr Gln Glu Ile  Lys Gln Arg
    1205                1210                1215

Val Val  Phe Lys Tyr Ser Gln  Met Ile Asn Ile Ser  Asp Tyr Ile
    1220                1225                1230

Asn Arg  Trp Ile Phe Val Thr  Ile Thr Asn Asn Arg  Leu Asn Asn
    1235                1240                1245

Ser Lys  Ile Tyr Ile Asn Gly  Arg Leu Ile Asp Gln  Lys Pro Ile
    1250                1255                1260

Ser Asn  Leu Gly Asn Ile His  Ala Ser Asn Asn Ile  Met Phe Lys
    1265                1270                1275

Leu Asp  Gly Cys Arg Asp Thr  His Arg Tyr Ile Trp  Ile Lys Tyr
    1280                1285                1290

Phe Asn  Leu Phe Asp Lys Glu  Leu Asn Glu Lys Glu  Ile Lys Asp
    1295                1300                1305

Leu Tyr  Asp Asn Gln Ser Asn  Ser Gly Ile Leu Lys  Asp Phe Trp
    1310                1315                1320

Gly Asp  Tyr Leu Gln Tyr Asp  Lys Pro Tyr Tyr Met  Leu Asn Leu
    1325                1330                1335

Tyr Asp  Pro Asn Lys Tyr Val  Asp Val Asn Asn Val  Gly Ile Arg
    1340                1345                1350

Gly Tyr  Met Tyr Leu Lys Gly  Pro Arg Gly Ser Val  Met Thr Thr
    1355                1360                1365

Asn Ile  Tyr Leu Asn Ser Ser  Leu Tyr Arg Gly Thr  Lys Phe Ile
    1370                1375                1380

Ile Lys  Lys Tyr Ala Ser Gly  Asn Lys Asp Asn Ile  Val Arg Asn
    1385                1390                1395

Asn Asp  Arg Val Tyr Ile Asn  Val Val Val Lys Asn  Lys Glu Tyr
    1400                1405                1410

Arg Leu  Ala Thr Asn Ala Ser  Gln Ala Gly Val Glu  Lys Ile Leu
    1415                1420                1425

Ser Ala  Leu Glu Ile Pro Asp  Val Gly Asn Leu Ser  Gln Val Val
    1430                1435                1440

Val Met  Lys Ser Lys Asn Asp  Gln Gly Ile Thr Asn  Lys Cys Lys
    1445                1450                1455

Met Asn  Leu Gln Asp Asn Asn  Gly Asn Asp Ile Gly  Phe Ile Gly
    1460                1465                1470

Phe His  Gln Phe Asn Asn Ile  Ala Lys Leu Val Ala  Ser Asn Trp
    1475                1480                1485

Tyr Asn  Arg Gln Ile Glu Arg  Ser Ser Arg Thr Leu  Gly Cys Ser
    1490                1495                1500

Trp Glu  Phe Ile Pro Val Asp  Asp Gly Trp Gly Glu  Arg Pro Leu
    1505                1510                1515
```

```
Gly Ala  Gly Tyr Pro Tyr Asp  Val Pro Asp Tyr Ala  Gly Glu Asn
    1520                1525                1530

Leu Tyr  Phe Gln Gly Ala Gly  Trp Ser His Pro Gln  Phe Glu Lys
    1535                1540                1545

Gly Ala  Gly Trp Ser His Pro  Gln Phe Glu Lys Gly  Ala Gly Trp
    1550                1555                1560

Ser His  Pro Gln Phe Glu Lys
    1565                1570
```

<210> SEQ ID NO 15
<211> LENGTH: 9028
<212> TYPE: DNA
<213> ORGANISM: Artificial
<220> FEATURE:
<223> OTHER INFORMATION: Propeptide fusion encoding sequence

<400> SEQUENCE: 15

```
gacgcgccct gtagcggcgc attaagcgcg gcgggtgtgg tggttacgcg cagcgtgacc     60
gctacacttg ccagcgccct agcgcccgct cctttcgctt tcttcccttc ctttctcgcc    120
acgttcgccg gctttccccg tcaagctcta aatcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
```

-continued gcggtggttt gtttgccgga tcaagagcta ccaactcttt ttccgaaggt aactggcttc 1740
agcagagcgc agataccaaa tactgtcctt ctagtgtagc cgtagttagg ccaccacttc 1800
aagaactctg tagcaccgcc tacatacctc gctctgctaa tcctgttacc agtggctgct 1860
gccagtggcg ataagtcgtg tcttaccggg ttggactcaa gacgatagtt accggataag 1920
gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400
cggtattttc tccttacgca tctgtgcggt atttcacacc gcagaccagc cgcgtaacct 2460
ggcaaaatcg gttacggttg agtaataaat ggatgccctg cgtaagcggg tgtgggcgga 2520
caataaagtc ttaaactgaa caaaatagat ctaaactatg acaataaagt cttaaactag 2580
acagaatagt tgtaaactga aatcagtcca gttatgctgt gaaaaagcat actggacttt 2640
tgttatggct aaagcaaact cttcattttc tgaagtgcaa attgcccgtc gtattaaaga 2700
ggggcgtggc caagggcatg gtaaagacta tattcgcggc gttgtgacaa tttaccgaac 2760
aactccgcgg ccgggaagcc gatctcggct tgaacgaatt gttaggtggc ggtacttggg 2820
tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatcccgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtctcg 4200
ggcttcgcta acgagctggg accacgcctg atgggaaaag gtgcaggatg ggaactccag 4260
caagccacgc gtggagcggg agcaggtcca ttcgtcaaca agcaattcaa ctacaaagat 4320
cctgttaacg gtgtggacat cgcctacatc aagattccga acgcaggcca gatgcaacct 4380
gtgaaggctt tcaaaatcca caacaagatc tgggtcattc ccgagagaga cacattcacg 4440
aacccagagg aaggtgatct gaaccctccc ccagaagcca agcaggtgcc ggtctcttac 4500
tacgattcaa cctacctcag tactgacaac gagaaggata actacctgaa gggcgttact 4560
aaactcttcg agcgcatcta ctcgacagac ttgggccgta tgctgctcac gtccatcgtc 4620
aggggtattc ctttctgggg tggctcaacc atcgacactg agctgaaggt cattgataca 4680
aactgcatca acgttattca acccgacggc tcctaccgca gcgaggaatt gaacctggtg 4740
atcattggac caagcgccga catcattcag ttcgagtgta agtctttcgg ccatgaagtc 4800
ctcaacttga ccagaaacgg ctacggctcc actcaataca tccgcttcag ccccgacttc 4860
acattcggat tcgaggaatc actggaggtc gatacgaacc cgttgctggg tgctggcaag 4920
ttcgccaccg accctgcagt tactctggca cacgcgctca tccacgcggg acatcgtctg 4980
tacggtatcg ctattaaccc aaacagggtc ttcaaggtta acaccaacgc ctactacgag 5040
atgagtggtc tggaagtgtc gttcgaggaa ctccgtacgt tcggaggtca cgacgcaaag 5100
ttcatcgata gtttgcagga gaacgaattc cgcctgtact actacaacaa gttcaaagac 5160
atcgcgtcta cactcaacaa ggctaaaagc attgttggaa ccactgctag tttgcaatac 5220
atgaagaacg tgttcaagga gaaatacctc ttgtcggaag acacctccgg taaattcagc 5280
gtggacaagc tgaaattcga taagttgtac aaaatgctga cagaaatcta cacggaagac 5340
aacttcgtta agttcttcaa agtgttgaac cgtaagaccg ctctgaactt cgataaggct 5400
gtcttcaaaa tcaacattgt gcctaaagtc aactacacca tctacgacgg tttcaacctc 5460
cgcaacacta acttggctgc caacttcaac ggccagaaca ctgagatcaa caacatgaac 5520
ttcacaaagc tcaaaaactt caccggtttg ttcgagttct acaagctgct ctgcgtgcgt 5580
ggtggaggca catctcacac gcaatctggc tgggaactcc agcaaggtgg ccagggtgga 5640
gctctgaacg atctgtgtat caaggtgaat aactgggatc tgttctttag cccaagcgag 5700
gataacttca cgaacgatct caacaaaggt gaagagatca cgtctgatac caatatcgaa 5760
gcggctgaag agaatatctc cttggatctc atccagcaat attacctgac ctttaacttc 5820
gataacgagc ccgaaaacat ctccatcgag aacctcagct cagacatcat tggtcagttg 5880
gagctgatgc caaacattga acgcttcccc aacggcaaga aatacgaact cgacaagtat 5940
acgatgtttc attacttaag agcgcaggag tttgaacacg gcaagagccg cattgctctc 6000
actaactccg tgaatgaagc cctgctcaat ccgtcaaggg tgtacacatt ctttagctcc 6060
gactatgtca agaaagtgaa caaagccacc gaagcggcaa tgttcctggg atgggttgaa 6120
caactggtct acgacttcac cgacgagacc tctgaggtga gcacaacgga caagattgct 6180
gacatcacta tcattatccc gtatattgga cctgccttga atattggcaa catgctctac 6240
aaagacgatt tcgttggtgc cctgatcttc agcggtgccg tgatcctgtt ggagttcatt 6300
cctgaaatcg ccatccctgt gctgggcacg ttcgctctgg tctcatacat tgcgaataar 6360
gtcttgaccg tgcagacaat cgataatgcc ctctccaaac gtaacgaaaa atgggacgag 6420

-continued

```
gtctacaaat acatcgtgac caactggctg gcaaaggtta acacccaaat tgatctgatc   6480
cgtaagaaaa tgaaggaggc tttggagaac caggctgaag ctactaaagc cattatcaac   6540
taccagtata atcagtatac agaagaggaa aagaataaca tcaatttcaa catcgatgac   6600
ttgtcctcaa agctgaacga gtccatcaac aaagctatga tcaacatcaa caaattcctg   6660
aatcagtgct ccgtgtctta cctgatgaac tctatgatcc catacggtgt gaagcgcctg   6720
gaggacttcg atgccagcct gaaagacgca ctgctcaaat acatttacga taatcgcggc   6780
actttgattg gccaagttga ccgtctgaag gacaaggtta acaatacctt gtcaaccgat   6840
atccccttcc aactctctaa gtacgtcgat aaccagcgct tgctgagcac cttcacagaa   6900
tacatcaaca acatcatcaa cacctccatc ctgaacctcc gttacgagtc taaccacctc   6960
atcgacttga gcagatacgc tagcaagatc aacatcggtt ccaaggtgaa cttcgaccca   7020
atcgataaga accagatcca actgttcaac ctcgaatcct ctaagatcga agtgatcctg   7080
aagaacgcta tcgtctacaa ctccatgtac gaaaacttct ctaccagctt ctggatcagg   7140
attccgaaat acttcaactc aatctcgctc aacaacgagt acactatcat caactgcatg   7200
gaaaacaact cgggatggaa ggtgtccctc aactacggcg agatcatctg gactttgcag   7260
gacacacaag aaatcaagca gagggtcgtg ttcaagtaca gccaaatgat caacatcagc   7320
gattacatca accgttggat cttcgtcaca atcaccaaca accgcctgaa caactccaag   7380
atttacatca acggtagact gatcgaccag aagccaatca gcaacctcgg caacatccac   7440
gcctcaaaca acatcatgtt caagttggac ggctgtaggg atacacacag atacatctgg   7500
atcaaatact tcaacctgtt cgacaaggag ctcaacgaga aggaaatcaa ggacctctac   7560
gataaccagt ccaactctgg tatcttgaag gacttctggg gcgattacct gcaatacgac   7620
aagccctact acatgttgaa cctgtacgac cctaacaagt acgttgatgt gaacaacgtc   7680
ggtatcaggg gctacatgta cctgaaggga ccacgtggtt ctgttatgac cactaacatc   7740
tacctcaaca gctcattgta ccgtggcaca aagttcatca tcaagaagta cgcctccgga   7800
aacaaggaca acatcgtccg taacaacgat cgcgtttaca tcaacgttgt ggtcaagaac   7860
aaggagtaca gactggctac caacgcttcg caggctggag ttgagaagat cctgtctgct   7920
ctggaaatcc ctgacgtggg caacctctca caggttgtgg tcatgaagtc gaagaacgat   7980
caaggcatca ctaacaagtg caagatgaac ttgcaggaca acaacggaaa cgacatcggc   8040
ttcatcggat tccaccaatt caacaacatc gccaagttgg tggccagcaa ctggtacaac   8100
cgtcagatcg agcgttcgtc ccgcacctta ggatgctcgt gggagttcat tccagtcgat   8160
gacggatggg gagagagacc tttgggcgca ggaggatggg aactccagca aggttacccc   8220
tacgatgtcc ctgactacgc tggtgcagga tggtcccacc cacaattcga gaagggtgca   8280
ggatggagtc acccacagtt cgagaagggc gctggatggt cccacccaca gttcgagaaa   8340
taattagttg atgcatagtt aattagatag ctcgaggcat gcggtaccaa gcttgtcgag   8400
aagtactaga ggatcataat cagccatacc acatttgtag aggttttact tgctttaaaa   8460
aacctcccac acctccccct gaacctgaaa cataaaatga atgcaattgt tgttgttaac   8520
ttgtttattg cagcttataa tggttacaaa taaagcaata gcatcacaaa tttcacaaat   8580
aaagcatttt tttcactgca ttctagttgt ggtttgtcca aactcatcaa tgtatcttat   8640
catgtctgga tctgatcact gcttgagcct aggagatccg aaccagataa gtgaaatcta   8700
gttccaaact attttgtcat ttttaatttt cgtattagct tacgacgcta cacccagttc   8760
ccatctattt tgtcactctt ccctaaataa tccttaaaaa ctccatttcc acccctccca   8820
```

gttcccaact attttgtccg cccacagcgg ggcatttttc ttcctgttat gtttttaatc 8880
aaacatcctg ccaactccat gtgacaaacc gtcatcttcg gctacttttt ctctgtcaca 8940
gaatgaaaat tttctgtca tctcttcgtt attaatgttt gtaattgact gaatatcaac 9000
gcttatttgc agcctgaatg gcgaatgg 9028

<210> SEQ ID NO 16
<211> LENGTH: 1417
<212> TYPE: PRT
<213> ORGANISM: Artificial
<220> FEATURE:
<223> OTHER INFORMATION: Fusion protein

<400> SEQUENCE: 16

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Ser Gly Phe Ala Asn Glu Leu Gly Pro Arg Leu Met
35 40 45

Gly Lys Gly Ala Gly Trp Glu Leu Gln Gln Ala Thr Arg Gly Ala Gly
50 55 60

Ala Gly Pro Phe Val Asn Lys Gln Phe Asn Tyr Lys Asp Pro Val Asn
65 70 75 80

Gly Val Asp Ile Ala Tyr Ile Lys Ile Pro Asn Ala Gly Gln Met Gln
85 90 95

Pro Val Lys Ala Phe Lys Ile His Asn Lys Ile Trp Val Ile Pro Glu
100 105 110

Arg Asp Thr Phe Thr Asn Pro Glu Glu Gly Asp Leu Asn Pro Pro Pro
115 120 125

Glu Ala Lys Gln Val Pro Val Ser Tyr Tyr Asp Ser Thr Tyr Leu Ser
130 135 140

Thr Asp Asn Glu Lys Asp Asn Tyr Leu Lys Gly Val Thr Lys Leu Phe
145 150 155 160

Glu Arg Ile Tyr Ser Thr Asp Leu Gly Arg Met Leu Leu Thr Ser Ile
165 170 175

Val Arg Gly Ile Pro Phe Trp Gly Gly Ser Thr Ile Asp Thr Glu Leu
180 185 190

Lys Val Ile Asp Thr Asn Cys Ile Asn Val Ile Gln Pro Asp Gly Ser
195 200 205

Tyr Arg Ser Glu Glu Leu Asn Leu Val Ile Ile Gly Pro Ser Ala Asp
210 215 220

Ile Ile Gln Phe Glu Cys Lys Ser Phe Gly His Glu Val Leu Asn Leu
225 230 235 240

Thr Arg Asn Gly Tyr Gly Ser Thr Gln Tyr Ile Arg Phe Ser Pro Asp
245 250 255

Phe Thr Phe Gly Phe Glu Glu Ser Leu Glu Val Asp Thr Asn Pro Leu
260 265 270

Leu Gly Ala Gly Lys Phe Ala Thr Asp Pro Ala Val Thr Leu Ala His
275 280 285

Ala Leu Ile His Ala Gly His Arg Leu Tyr Gly Ile Ala Ile Asn Pro
290 295 300

Asn Arg Val Phe Lys Val Asn Thr Asn Ala Tyr Tyr Glu Met Ser Gly
305 310 315 320

-continued

```
Leu Glu Val Ser Phe Glu Glu Leu Arg Thr Phe Gly Gly His Asp Ala
            325                 330                 335

Lys Phe Ile Asp Ser Leu Gln Glu Asn Glu Phe Arg Leu Tyr Tyr Tyr
        340                 345                 350

Asn Lys Phe Lys Asp Ile Ala Ser Thr Leu Asn Lys Ala Lys Ser Ile
    355                 360                 365

Val Gly Thr Thr Ala Ser Leu Gln Tyr Met Lys Asn Val Phe Lys Glu
370                 375                 380

Lys Tyr Leu Leu Ser Glu Asp Thr Ser Gly Lys Phe Ser Val Asp Lys
385                 390                 395                 400

Leu Lys Phe Asp Lys Leu Tyr Lys Met Leu Thr Glu Ile Tyr Thr Glu
                405                 410                 415

Asp Asn Phe Val Lys Phe Phe Lys Val Leu Asn Arg Lys Thr Ala Leu
            420                 425                 430

Asn Phe Asp Lys Ala Val Phe Lys Ile Asn Ile Val Pro Lys Val Asn
        435                 440                 445

Tyr Thr Ile Tyr Asp Gly Phe Asn Leu Arg Asn Thr Asn Leu Ala Ala
    450                 455                 460

Asn Phe Asn Gly Gln Asn Thr Glu Ile Asn Asn Met Asn Phe Thr Lys
465                 470                 475                 480

Leu Lys Asn Phe Thr Gly Leu Phe Glu Phe Tyr Lys Leu Leu Cys Val
                485                 490                 495

Arg Gly Gly Gly Thr Ser His Thr Gln Ser Gly Trp Glu Leu Gln Gln
            500                 505                 510

Gly Gly Gln Gly Gly Ala Leu Asn Asp Leu Cys Ile Lys Val Asn Asn
        515                 520                 525

Trp Asp Leu Phe Phe Ser Pro Ser Glu Asp Asn Phe Thr Asn Asp Leu
    530                 535                 540

Asn Lys Gly Glu Glu Ile Thr Ser Asp Thr Asn Ile Glu Ala Ala Glu
545                 550                 555                 560

Glu Asn Ile Ser Leu Asp Leu Ile Gln Gln Tyr Tyr Leu Thr Phe Asn
                565                 570                 575

Phe Asp Asn Glu Pro Glu Asn Ile Ser Ile Glu Asn Leu Ser Ser Asp
            580                 585                 590

Ile Ile Gly Gln Leu Glu Leu Met Pro Asn Ile Glu Arg Phe Pro Asn
        595                 600                 605

Gly Lys Lys Tyr Glu Leu Asp Lys Tyr Thr Met Phe His Tyr Leu Arg
    610                 615                 620

Ala Gln Glu Phe Glu His Gly Lys Ser Arg Ile Ala Leu Thr Asn Ser
625                 630                 635                 640

Val Asn Glu Ala Leu Leu Asn Pro Ser Arg Val Tyr Thr Phe Phe Ser
                645                 650                 655

Ser Asp Tyr Val Lys Lys Val Asn Lys Ala Thr Glu Ala Ala Met Phe
            660                 665                 670

Leu Gly Trp Val Glu Gln Leu Val Tyr Asp Phe Thr Asp Glu Thr Ser
        675                 680                 685

Glu Val Ser Thr Thr Asp Lys Ile Ala Asp Ile Thr Ile Ile Ile Pro
    690                 695                 700

Tyr Ile Gly Pro Ala Leu Asn Ile Gly Asn Met Leu Tyr Lys Asp Asp
705                 710                 715                 720

Phe Val Gly Ala Leu Ile Phe Ser Gly Ala Val Ile Leu Leu Glu Phe
                725                 730                 735

Ile Pro Glu Ile Ala Ile Pro Val Leu Gly Thr Phe Ala Leu Val Ser
```

-continued

```
            740                 745                 750

Tyr Ile Ala Asn Lys Val Leu Thr Val Gln Thr Ile Asp Asn Ala Leu
        755                 760                 765

Ser Lys Arg Asn Glu Lys Trp Asp Glu Val Tyr Lys Tyr Ile Val Thr
    770                 775                 780

Asn Trp Leu Ala Lys Val Asn Thr Gln Ile Asp Leu Ile Arg Lys Lys
785                 790                 795                 800

Met Lys Glu Ala Leu Glu Asn Gln Ala Glu Ala Thr Lys Ala Ile Ile
                805                 810                 815

Asn Tyr Gln Tyr Asn Gln Tyr Thr Glu Glu Glu Lys Asn Asn Ile Asn
            820                 825                 830

Phe Asn Ile Asp Asp Leu Ser Ser Lys Leu Asn Glu Ser Ile Asn Lys
        835                 840                 845

Ala Met Ile Asn Ile Asn Lys Phe Leu Asn Gln Cys Ser Val Ser Tyr
    850                 855                 860

Leu Met Asn Ser Met Ile Pro Tyr Gly Val Lys Arg Leu Glu Asp Phe
865                 870                 875                 880

Asp Ala Ser Leu Lys Asp Ala Leu Leu Lys Tyr Ile Tyr Asp Asn Arg
                885                 890                 895

Gly Thr Leu Ile Gly Gln Val Asp Arg Leu Lys Asp Lys Val Asn Asn
            900                 905                 910

Thr Leu Ser Thr Asp Ile Pro Phe Gln Leu Ser Lys Tyr Val Asp Asn
        915                 920                 925

Gln Arg Leu Leu Ser Thr Phe Thr Glu Tyr Ile Asn Asn Ile Ile Asn
    930                 935                 940

Thr Ser Ile Leu Asn Leu Arg Tyr Glu Ser Asn His Leu Ile Asp Leu
945                 950                 955                 960

Ser Arg Tyr Ala Ser Lys Ile Asn Ile Gly Ser Lys Val Asn Phe Asp
                965                 970                 975

Pro Ile Asp Lys Asn Gln Ile Gln Leu Phe Asn Leu Glu Ser Ser Lys
            980                 985                 990

Ile Glu Val Ile Leu Lys Asn Ala  Ile Val Tyr Asn Ser  Met Tyr Glu
        995                 1000                1005

Asn Phe  Ser Thr Ser Phe Trp  Ile Arg Ile Pro Lys  Tyr Phe Asn
    1010                1015                1020

Ser Ile  Ser Leu Asn Asn Glu  Tyr Thr Ile Ile Asn  Cys Met Glu
    1025                1030                1035

Asn Asn  Ser Gly Trp Lys Val  Ser Leu Asn Tyr Gly  Glu Ile Ile
    1040                1045                1050

Trp Thr  Leu Gln Asp Thr Gln  Glu Ile Lys Gln Arg  Val Val Phe
    1055                1060                1065

Lys Tyr  Ser Gln Met Ile Asn  Ile Ser Asp Tyr Ile  Asn Arg Trp
    1070                1075                1080

Ile Phe  Val Thr Ile Thr Asn  Asn Arg Leu Asn Asn  Ser Lys Ile
    1085                1090                1095

Tyr Ile  Asn Gly Arg Leu Ile  Asp Gln Lys Pro Ile  Ser Asn Leu
    1100                1105                1110

Gly Asn  Ile His Ala Ser Asn  Asn Ile Met Phe Lys  Leu Asp Gly
    1115                1120                1125

Cys Arg  Asp Thr His Arg Tyr  Ile Trp Ile Lys Tyr  Phe Asn Leu
    1130                1135                1140

Phe Asp  Lys Glu Leu Asn Glu  Lys Glu Ile Lys Asp  Leu Tyr Asp
    1145                1150                1155
```

```
Asn Gln  Ser Asn Ser Gly Ile  Leu Lys Asp Phe Trp  Gly Asp Tyr
    1160                 1165                 1170

Leu Gln  Tyr Asp Lys Pro Tyr  Tyr Met Leu Asn Leu  Tyr Asp Pro
    1175                 1180                 1185

Asn Lys  Tyr Val Asp Val Asn  Asn Val Gly Ile Arg  Gly Tyr Met
    1190                 1195                 1200

Tyr Leu  Lys Gly Pro Arg Gly  Ser Val Met Thr Thr  Asn Ile Tyr
    1205                 1210                 1215

Leu Asn  Ser Ser Leu Tyr Arg  Gly Thr Lys Phe Ile  Ile Lys Lys
    1220                 1225                 1230

Tyr Ala  Ser Gly Asn Lys Asp  Asn Ile Val Arg Asn  Asn Asp Arg
    1235                 1240                 1245

Val Tyr  Ile Asn Val Val Val  Lys Asn Lys Glu Tyr  Arg Leu Ala
    1250                 1255                 1260

Thr Asn  Ala Ser Gln Ala Gly  Val Glu Lys Ile Leu  Ser Ala Leu
    1265                 1270                 1275

Glu Ile  Pro Asp Val Gly Asn  Leu Ser Gln Val Val  Val Met Lys
    1280                 1285                 1290

Ser Lys  Asn Asp Gln Gly Ile  Thr Asn Lys Cys Lys  Met Asn Leu
    1295                 1300                 1305

Gln Asp  Asn Asn Gly Asn Asp  Ile Gly Phe Ile Gly  Phe His Gln
    1310                 1315                 1320

Phe Asn  Asn Ile Ala Lys Leu  Val Ala Ser Asn Trp  Tyr Asn Arg
    1325                 1330                 1335

Gln Ile  Glu Arg Ser Ser Arg  Thr Leu Gly Cys Ser  Trp Glu Phe
    1340                 1345                 1350

Ile Pro  Val Asp Asp Gly Trp  Gly Glu Arg Pro Leu  Gly Ala Gly
    1355                 1360                 1365

Gly Trp  Glu Leu Gln Gln Gly  Tyr Pro Tyr Asp Val  Pro Asp Tyr
    1370                 1375                 1380

Ala Gly  Ala Gly Trp Ser His  Pro Gln Phe Glu Lys  Gly Ala Gly
    1385                 1390                 1395

Trp Ser  His Pro Gln Phe Glu  Lys Gly Ala Gly Trp  Ser His Pro
    1400                 1405                 1410

Gln Phe  Glu Lys
    1415
```

<210> SEQ ID NO 17
<211> LENGTH: 9092
<212> TYPE: DNA
<213> ORGANISM: Artificial
<220> FEATURE:
<223> OTHER INFORMATION: Propeptide fusion encoding sequence

<400> SEQUENCE: 17

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420
```

-continued

```
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
```

tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatcccgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtctcg 4200
ggcttcgcta acgagctggg accacgcctg atgggaaaag gtgcaggatg ggaactccag 4260
caagccacgc gtggagcggg agctggaccg atcaccatca acaacttcaa ttacagcgac 4320
ccggtggata acaagaacat cctctacttg gacacacact tgaacacgct ggctaacgag 4380
cctgaaaaag ctttcaggat caccggcaac atttgggtca ttccggatag gttcagcaga 4440
aactctaacc ctaacttgaa caaacctccc agagtgacct cacctaagag tggatactac 4500
gaccccaact acctctcgac tgactccgat aaagacccct tcctgaagga gatcattaaa 4560
ctcttcaagc gcatcaactc tcgtgaaatt ggcgaggaat tgatctaccg cctgagtaca 4620
gacatcccat tcccgggtaa caacaacacc ccaatcaaca ctttcgattt cgatgtcgat 4680
ttcaactcag tggatgtcaa aaccaggcag ggaaacaact gggtgaagac tggtagcatc 4740
aacccatctg tcatcattac tggcccgaga gagaacatca ttgaccctga aacctccact 4800
ttcaagctga caaacaacac gttcgctgct caggaaggct tcggagcgtt gagcatcatt 4860
tctatctcac ctcgcttcat gctgacatac tctaacgcta cgaacgacgt gggagagggc 4920
cgtttcagta agtctgaatt ctgcatggac cctattctga tcctcatgca cgctctcaac 4980
ggcgccatgc acaacttgta cggaattgct atccccaacg accagaccat ttccagcgtg 5040
actagcaaca tcttctactc tcaatacaac gtcaagctgg agtacgcaga aatctacgct 5100
ttcggtggcc caaccattga cttgatcccg aaatcagctc gtaagtattt cgaagaaaaa 5160

```
gcgctggatt attacaggtc gattgctaag agactcaact ccatcaccac tgctaacccc   5220
tcttcattca acaagtacat tggagaatac aagcagaaac tgatccgcaa gtaccgtttc   5280
gtggtcgaga gttcgggtga agttactgtg aaccgcaaca agttcgtcga gctgtacaac   5340
gaattgacac aaatcttcac ggagttcaac tacgccaaaa tttacaacgt gcaaaaccgt   5400
aagatcgcgc tctctaacgt ctacaccccg gttaccgcta acatcttgga cgataacgtc   5460
tacgacattc agaacggttt caacatccca aagtcgaacc tcaacgtttt gttcatgggt   5520
caaaacttgt cccgcaaccc cgccctgcgt aaggtgaacc cagagaacat gttgtacctg   5580
ttcaccaaat tctgccacaa ggccatcgac ggtcagtctc tagaccaagg aggatgggaa   5640
ctccagcaag gtggccaggg tggaggtgct ggcaccctgg actgtcgcga actgctcgtt   5700
aagaacactg atctcccatt cattggcgac atctctgatg tgaaaacaga cattttcctg   5760
cgtaaggata tcaacgagga aacggaggtc atctactacc ctgacaacgt ctcggttgat   5820
caggttatct tgtcaaagaa caccagtgaa catggccaac tggacttgct gtacccctca   5880
attgattccg agagcgaaat cctgccagga gagaaccagg ttttctacga caacaggaca   5940
caaaacgtgg attacctcaa cagctactac tacctggagt cgcagaagct ctccgacaac   6000
gtcgaagatt tcacatttac gagatcaatc gaggaggctt tggacaacag tgccaaagtc   6060
tacacctact tccctactct ggcaaacaag gtgaacgcgg gtgtccaagg cggactcttc   6120
ttgatgtggg ctaacgacgt tgtggaagat ttcacaacga acatcttgcg caaagacacc   6180
ctggataaga tcagcgatgt ctctgccatc attccataca ttggcccggc actgaacatc   6240
tctaactcag ttcgccgtgg caacttcact gaggcattcg cggtcacagg agttacgatc   6300
ctcttggagg ctttcccgga gttcacaatc cccgcactgg gcgcgttcgt tatctactcc   6360
aaagtgcagg agcgcaacga aatcattaag actatcgaca actgcctgga gcaaaggatc   6420
aaaagatgga aggattcgta cgaatggatg atgggtacct ggctctcccg tatcattacg   6480
cagttcaaca acatcagcta ccaaatgtac gactctctca actaccaggc tggtgccatc   6540
aaggccaaaa ttgacttgga gtacaagaaa tacagtggct cggataaaga gaacatcaag   6600
agtcaagtcg aaaacctgaa aaactcactc gacgttaaga tcagtgaggc aatgaacaac   6660
atcaacaagt tcattcgcga atgttccgtt acctacctct tcaaaaacat gttgccaaag   6720
gtcatcgacg agctgaacga atttgatcgt aacactaagg cgaaactgat taacctcatc   6780
gactcacaca acatcatttt ggtgggcgaa gtcgataagc tgaaagccaa ggtgaacaac   6840
agtttccaga acacaatccc tttcaacatt ttctcataca cgaacaacag tctgctcaag   6900
gacatcatta acgagtactt caacaacatt aacgatagca aaatcctgtc actgcagaac   6960
cgtaagaaca cactggtcga tactagtgga tacaacgccg aagtctctga ggaaggtgac   7020
gtgcagctga accctatctt cccctttcgac ttcaaattgg gctccagcgg agaggatagg   7080
ggcaaggtca tcgtcaccca gaacgagaac atcgtctaca actcaatgta cgaatccttc   7140
agcatctctt tctggatcag gattaacaag tgggtgagca acctgcccgg ttacacaatc   7200
attgactctg tcaagaacaa ctcaggttgg agtatcggca tcatttctaa cttcttggtc   7260
ttcaccctga agcagaacga ggactcggaa caatccatta acttctcata cgatatcagt   7320
aacaacgctc caggttacaa caagtggttc ttcgttaccg tgactaacaa catgatgggt   7380
aacatgaaaa tttacatcaa cggcaagctc attgacacca tcaaagtgaa ggagttgact   7440
ggtattaact tctccaaaac aatcacgttt gaaattaaca agatccctga caccggcctg   7500
atcacttcag acagtgataa catcaacatg tggattaggg atttctacat cttcgccaag   7560
```

```
gagctcgacg gaaaggatat taacatcctc ttcaacagct tgcagtacac caacgtcgtt   7620
aaagactact ggggtaacga tttgagatac aacaaggagt actacatggt caacatcgac   7680
tacctgaaca ggtacatgta cgctaactcc cgccaaatcg tgttcaacac caggagaaac   7740
aacaacgact tcaacgaggg ttacaaaatc attatcaagc gcatccgtgg caacaccaac   7800
gatactaggg tgagaggtgg cgacattctg tacttcgata tgactatcaa caacaaagcc   7860
tacaacttgt tcatgaaaaa cgagacaatg tacgccgaca accatagcac ggaggatatt   7920
tacgcaatcg gactgaggga acagacaaag gacatcaacg ataacattat cttccagatc   7980
caacctatga acaacacgta ctactacgct tcgcaaatct tcaagtccaa cttcaacgga   8040
gaaaacattt cgggtatctg ttccattggc acataccgct tccgtctggg tggtgactgg   8100
tatcgtcaca actacctcgt tcccaccgtg aagcagggta actacgcttc tttgctggag   8160
tcgacttcca cgcactgggg attcgttcct gtgtcagagg gcgctggcta cccttacgat   8220
gttcccgact acgctggttg ggaactccag caaggtgcag gatggtccca ccctcaattc   8280
gagaagggtg ccggatggag tcacccacag ttcgagaaag gcgctggatg gagtcaccca   8340
cagttcgaga aataattagt tgatgcatag ttaattagat agctcgaggc atgcggtacc   8400
aagattggat ctagatgcat agttaattag atagctcgag gcatgcggta ccaagcttgt   8460
cgagaagtac tagaggatca taatcagcca taccacattt gtagaggttt tacttgcttt   8520
aaaaaacctc ccacacctcc ccctgaacct gaaacataaa atgaatgcaa ttgttgttgt   8580
taacttgttt attgcagctt ataatggtta caaataaagc aatagcatca caaatttcac   8640
aaataaagca tttttttcac tgcattctag ttgtggtttg tccaaactca tcaatgtatc   8700
ttatcatgtc tggatctgat cactgcttga gcctaggaga tccgaaccag ataagtgaaa   8760
tctagttcca aactattttg tcatttttaa ttttcgtatt agcttacgac gctacaccca   8820
gttcccatct attttgtcac tcttccctaa ataatcctta aaaactccat ttccacccct   8880
cccagttccc aactattttg tccgcccaca gcggggcatt tttcttcctg ttatgttttt   8940
aatcaaacat cctgccaact ccatgtgaca aaccgtcatc ttcggctact tttctctgt    9000
cacagaatga aaatttttct gtcatctctt cgttattaat gtttgtaatt gactgaatat   9060
caacgcttat ttgcagcctg aatggcgaat gg                                 9092
```

<210> SEQ ID NO 18
<211> LENGTH: 1421
<212> TYPE: PRT
<213> ORGANISM: Artificial
<220> FEATURE:
<223> OTHER INFORMATION: Fusion protein

<400> SEQUENCE: 18

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Ser Gly Phe Ala Asn Glu Leu Gly Pro Arg Leu Met
        35                  40                  45

Gly Lys Gly Ala Gly Trp Glu Leu Gln Gln Ala Thr Arg Gly Ala Gly
    50                  55                  60

Ala Gly Pro Ile Thr Ile Asn Asn Phe Asn Tyr Ser Asp Pro Val Asp
65                  70                  75                  80

Asn Lys Asn Ile Leu Tyr Leu Asp Thr His Leu Asn Thr Leu Ala Asn
```

-continued

```
                85                  90                  95

Glu Pro Glu Lys Ala Phe Arg Ile Thr Gly Asn Ile Trp Val Ile Pro
            100                 105                 110

Asp Arg Phe Ser Arg Asn Ser Asn Pro Asn Leu Asn Lys Pro Pro Arg
        115                 120                 125

Val Thr Ser Pro Lys Ser Gly Tyr Tyr Asp Pro Asn Tyr Leu Ser Thr
    130                 135                 140

Asp Ser Asp Lys Asp Pro Phe Leu Lys Glu Ile Ile Lys Leu Phe Lys
145                 150                 155                 160

Arg Ile Asn Ser Arg Glu Ile Gly Glu Glu Leu Ile Tyr Arg Leu Ser
                165                 170                 175

Thr Asp Ile Pro Phe Pro Gly Asn Asn Asn Thr Pro Ile Asn Thr Phe
            180                 185                 190

Asp Phe Asp Val Asp Phe Asn Ser Val Asp Val Lys Thr Arg Gln Gly
        195                 200                 205

Asn Asn Trp Val Lys Thr Gly Ser Ile Asn Pro Ser Val Ile Ile Thr
    210                 215                 220

Gly Pro Arg Glu Asn Ile Ile Asp Pro Glu Thr Ser Thr Phe Lys Leu
225                 230                 235                 240

Thr Asn Asn Thr Phe Ala Ala Gln Glu Gly Phe Gly Ala Leu Ser Ile
                245                 250                 255

Ile Ser Ile Ser Pro Arg Phe Met Leu Thr Tyr Ser Asn Ala Thr Asn
            260                 265                 270

Asp Val Gly Glu Gly Arg Phe Ser Lys Ser Glu Phe Cys Met Asp Pro
        275                 280                 285

Ile Leu Ile Leu Met His Ala Leu Asn Gly Ala Met His Asn Leu Tyr
    290                 295                 300

Gly Ile Ala Ile Pro Asn Asp Gln Thr Ile Ser Ser Val Thr Ser Asn
305                 310                 315                 320

Ile Phe Tyr Ser Gln Tyr Asn Val Lys Leu Glu Tyr Ala Glu Ile Tyr
                325                 330                 335

Ala Phe Gly Gly Pro Thr Ile Asp Leu Ile Pro Lys Ser Ala Arg Lys
            340                 345                 350

Tyr Phe Glu Glu Lys Ala Leu Asp Tyr Tyr Arg Ser Ile Ala Lys Arg
        355                 360                 365

Leu Asn Ser Ile Thr Thr Ala Asn Pro Ser Ser Phe Asn Lys Tyr Ile
    370                 375                 380

Gly Glu Tyr Lys Gln Lys Leu Ile Arg Lys Tyr Arg Phe Val Val Glu
385                 390                 395                 400

Ser Ser Gly Glu Val Thr Val Asn Arg Asn Lys Phe Val Glu Leu Tyr
                405                 410                 415

Asn Glu Leu Thr Gln Ile Phe Thr Glu Phe Asn Tyr Ala Lys Ile Tyr
            420                 425                 430

Asn Val Gln Asn Arg Lys Ile Ala Leu Ser Asn Val Tyr Thr Pro Val
        435                 440                 445

Thr Ala Asn Ile Leu Asp Asp Asn Val Tyr Asp Ile Gln Asn Gly Phe
    450                 455                 460

Asn Ile Pro Lys Ser Asn Leu Asn Val Leu Phe Met Gly Gln Asn Leu
465                 470                 475                 480

Ser Arg Asn Pro Ala Leu Arg Lys Val Asn Pro Glu Asn Met Leu Tyr
                485                 490                 495

Leu Phe Thr Lys Phe Cys His Lys Ala Ile Asp Gly Gln Ser Leu Asp
            500                 505                 510
```

```
Gln Gly Gly Trp Glu Leu Gln Gln Gly Gly Gln Gly Gly Gly Ala Gly
        515                 520                 525

Thr Leu Asp Cys Arg Glu Leu Leu Val Lys Asn Thr Asp Leu Pro Phe
    530                 535                 540

Ile Gly Asp Ile Ser Asp Val Lys Thr Asp Ile Phe Leu Arg Lys Asp
545                 550                 555                 560

Ile Asn Glu Glu Thr Glu Val Ile Tyr Tyr Pro Asp Asn Val Ser Val
                565                 570                 575

Asp Gln Val Ile Leu Ser Lys Asn Thr Ser Glu His Gly Gln Leu Asp
            580                 585                 590

Leu Leu Tyr Pro Ser Ile Asp Ser Glu Ser Glu Ile Leu Pro Gly Glu
        595                 600                 605

Asn Gln Val Phe Tyr Asp Asn Arg Thr Gln Asn Val Asp Tyr Leu Asn
    610                 615                 620

Ser Tyr Tyr Tyr Leu Glu Ser Gln Lys Leu Ser Asp Asn Val Glu Asp
625                 630                 635                 640

Phe Thr Phe Thr Arg Ser Ile Glu Glu Ala Leu Asp Asn Ser Ala Lys
                645                 650                 655

Val Tyr Thr Tyr Phe Pro Thr Leu Ala Asn Lys Val Asn Ala Gly Val
            660                 665                 670

Gln Gly Gly Leu Phe Leu Met Trp Ala Asn Asp Val Val Glu Asp Phe
        675                 680                 685

Thr Thr Asn Ile Leu Arg Lys Asp Thr Leu Asp Lys Ile Ser Asp Val
    690                 695                 700

Ser Ala Ile Ile Pro Tyr Ile Gly Pro Ala Leu Asn Ile Ser Asn Ser
705                 710                 715                 720

Val Arg Arg Gly Asn Phe Thr Glu Ala Phe Ala Val Thr Gly Val Thr
                725                 730                 735

Ile Leu Leu Glu Ala Phe Pro Glu Phe Thr Ile Pro Ala Leu Gly Ala
            740                 745                 750

Phe Val Ile Tyr Ser Lys Val Gln Glu Arg Asn Glu Ile Ile Lys Thr
        755                 760                 765

Ile Asp Asn Cys Leu Glu Gln Arg Ile Lys Arg Trp Lys Asp Ser Tyr
    770                 775                 780

Glu Trp Met Met Gly Thr Trp Leu Ser Arg Ile Ile Thr Gln Phe Asn
785                 790                 795                 800

Asn Ile Ser Tyr Gln Met Tyr Asp Ser Leu Asn Tyr Gln Ala Gly Ala
                805                 810                 815

Ile Lys Ala Lys Ile Asp Leu Glu Tyr Lys Lys Tyr Ser Gly Ser Asp
            820                 825                 830

Lys Glu Asn Ile Lys Ser Gln Val Glu Asn Leu Lys Asn Ser Leu Asp
        835                 840                 845

Val Lys Ile Ser Glu Ala Met Asn Asn Ile Asn Lys Phe Ile Arg Glu
    850                 855                 860

Cys Ser Val Thr Tyr Leu Phe Lys Asn Met Leu Pro Lys Val Ile Asp
865                 870                 875                 880

Glu Leu Asn Glu Phe Asp Arg Asn Thr Lys Ala Lys Leu Ile Asn Leu
                885                 890                 895

Ile Asp Ser His Asn Ile Ile Leu Val Gly Glu Val Asp Lys Leu Lys
            900                 905                 910

Ala Lys Val Asn Asn Ser Phe Gln Asn Thr Ile Pro Phe Asn Ile Phe
        915                 920                 925
```

```
Ser Tyr Thr Asn Asn Ser Leu Leu Lys Asp Ile Ile Asn Glu Tyr Phe
    930                 935                 940

Asn Asn Ile Asn Asp Ser Lys Ile Leu Ser Leu Gln Asn Arg Lys Asn
945                 950                 955                 960

Thr Leu Val Asp Thr Ser Gly Tyr Asn Ala Glu Val Ser Glu Glu Gly
                965                 970                 975

Asp Val Gln Leu Asn Pro Ile Phe Pro Phe Asp Phe Lys Leu Gly Ser
            980                 985                 990

Ser Gly Glu Asp Arg Gly Lys Val  Ile Val Thr Gln Asn  Glu Asn Ile
        995                 1000                1005

Val Tyr  Asn Ser Met Tyr Glu  Ser Phe Ser Ile Ser  Phe Trp Ile
    1010                 1015                1020

Arg Ile  Asn Lys Trp Val Ser  Asn Leu Pro Gly Tyr  Thr Ile Ile
    1025                 1030                1035

Asp Ser  Val Lys Asn Asn Ser  Gly Trp Ser Ile Gly  Ile Ile Ser
    1040                 1045                1050

Asn Phe  Leu Val Phe Thr Leu  Lys Gln Asn Glu Asp  Ser Glu Gln
    1055                 1060                1065

Ser Ile  Asn Phe Ser Tyr Asp  Ile Ser Asn Asn Ala  Pro Gly Tyr
    1070                 1075                1080

Asn Lys  Trp Phe Phe Val Thr  Val Thr Asn Asn Met  Met Gly Asn
    1085                 1090                1095

Met Lys  Ile Tyr Ile Asn Gly  Lys Leu Ile Asp Thr  Ile Lys Val
    1100                 1105                1110

Lys Glu  Leu Thr Gly Ile Asn  Phe Ser Lys Thr Ile  Thr Phe Glu
    1115                 1120                1125

Ile Asn  Lys Ile Pro Asp Thr  Gly Leu Ile Thr Ser  Asp Ser Asp
    1130                 1135                1140

Asn Ile  Asn Met Trp Ile Arg  Asp Phe Tyr Ile Phe  Ala Lys Glu
    1145                 1150                1155

Leu Asp  Gly Lys Asp Ile Asn  Ile Leu Phe Asn Ser  Leu Gln Tyr
    1160                 1165                1170

Thr Asn  Val Val Lys Asp Tyr  Trp Gly Asn Asp Leu  Arg Tyr Asn
    1175                 1180                1185

Lys Glu  Tyr Tyr Met Val Asn  Ile Asp Tyr Leu Asn  Arg Tyr Met
    1190                 1195                1200

Tyr Ala  Asn Ser Arg Gln Ile  Val Phe Asn Thr Arg  Arg Asn Asn
    1205                 1210                1215

Asn Asp  Phe Asn Glu Gly Tyr  Lys Ile Ile Ile Lys  Arg Ile Arg
    1220                 1225                1230

Gly Asn  Thr Asn Asp Thr Arg  Val Arg Gly Gly Asp  Ile Leu Tyr
    1235                 1240                1245

Phe Asp  Met Thr Ile Asn Asn  Lys Ala Tyr Asn Leu  Phe Met Lys
    1250                 1255                1260

Asn Glu  Thr Met Tyr Ala Asp  Asn His Ser Thr Glu  Asp Ile Tyr
    1265                 1270                1275

Ala Ile  Gly Leu Arg Glu Gln  Thr Lys Asp Ile Asn  Asp Asn Ile
    1280                 1285                1290

Ile Phe  Gln Ile Gln Pro Met  Asn Asn Thr Tyr Tyr  Tyr Ala Ser
    1295                 1300                1305

Gln Ile  Phe Lys Ser Asn Phe  Asn Gly Glu Asn Ile  Ser Gly Ile
    1310                 1315                1320

Cys Ser  Ile Gly Thr Tyr Arg  Phe Arg Leu Gly Gly  Asp Trp Tyr
```

```
    1325                1330                1335

Arg His  Asn Tyr Leu Val Pro  Thr Val Lys Gln Gly  Asn Tyr Ala
    1340                1345                1350

Ser Leu  Leu Glu Ser Thr Ser  Thr His Trp Gly Phe  Val Pro Val
    1355                1360                1365

Ser Glu  Gly Ala Gly Tyr Pro  Tyr Asp Val Pro Asp  Tyr Ala Gly
    1370                1375                1380

Trp Glu  Leu Gln Gln Gly Ala  Gly Trp Ser His Pro  Gln Phe Glu
    1385                1390                1395

Lys Gly  Ala Gly Trp Ser His  Pro Gln Phe Glu Lys  Gly Ala Gly
    1400                1405                1410

Trp Ser  His Pro Gln Phe Glu  Lys
    1415                1420
```

<210> SEQ ID NO 19
<211> LENGTH: 3746
<212> TYPE: DNA
<213> ORGANISM: Artificial
<220> FEATURE:
<223> OTHER INFORMATION: Propeptide fusion encoding sequence

<400> SEQUENCE: 19

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcata gatctcggtc cgttcgaacc agaactctgg aagcttaact cctaaaaaac    420
cgccaccatg aaattcttag tcaacgttgc ccttgttttt atggtcgtat acatttctta    480
catctatgcg gccggacatc atcatcatca tcaccatcac caccaccacg acgtcggctg    540
ggagctgcaa cgtcgtcccc tgaactgcat cgtggctgtg tcccagaaca tgggtatcgg    600
caagaacggc gacctgccct ggcctcctct gcgtaacgag ttcaagtact tccagcgtat    660
gaccaccacc tcctccgtcg agggcaagca gaacctggtc atcatgggtc gcaagacctg    720
gttctccatc cccgagaaga accgtctgct gaaggaccgt atcaacatcg tgctgtcccg    780
cgagctgaag gaacccccctc gtggtgctca cttcctggct aagtccctgg acgacgctct    840
gcgtctgatc gagcagcctg agctggcttc caaggtggac atggtctgga tcgtgggcgg    900
ttcctccgtg taccaagagg ctatgaacca gcccggtcac ttgcgtctgt tcgtgacccg    960
tatcatgcaa gagttcgagt ccgacacctt cttccccgaa atcgacctgg gcaagtacaa   1020
gctgctgccc gagtaccccg gtgtcctgtc cgaggtgcaa gaggaaaagg gtatcaagta   1080
caagttcgag gtgtacgaga agaaggacgg cgcttccggt ttcgctaacg agctcggtcc   1140
tcgtctgatg ggaaagggcg ccggcggtgg tgctggtgct ggaccattcg tcaacaagca   1200
attcaactac aaggatcctg ttaacggtgt ggacatcgcc tacatcaaga ttccgaacgc   1260
aggccagatg caacctgtga aggctttcaa aatccacaac aaaatctggg tcattcccga   1320
gagagacaca ttcacgaacc cagaggaagg tgatctgaac cctcccccag aagccaagca   1380
ggtgccggtc tcttactacg attcaaccta cctcagtact gacaacgaga aggataacta   1440
cctgaagggc gttactaaac tcttcgagcg catctactcg acagacttgg gccgtatgct   1500
```

gctcacgtcc atcgtcaggg gtattccttt ctggggtggc tcaaccatcg acactgagct 1560
gaaggtcatt gatacaaact gcatcaacgt tattcaaccc gacggctcct accgcagcga 1620
ggaattgaac ctggtgatca ttggaccaag cgccgacatc attcagttcg agtgtaagtc 1680
tttcggccat gaagtcctca acttgaccag aaacggctac ggctccactc aatacatccg 1740
cttcagcccc gacttcacat tcggattcga ggaatcactg gaggtcgata cgaacccgtt 1800
gctgggtgct ggcaagttcg ccaccgaccc tgcagttctg ggcctcatgg gccttccttt 1860
cactgcccgc tttccagtcg ggaaacctgt cgtgccagct gcattaacat ggtcatagct 1920
gtttccttgc gtattgggcg ctctccgctt cctcgctcac tgactcgctg cgctcggtcg 1980
ttcgggtaaa gcctggggtg cctaatgagc aaaaggccag caaaaggcca ggaaccgtaa 2040
aaaggccgcg ttgctggcgt ttttccatag gctccgcccc cctgacgagc atcacaaaaa 2100
tcgacgctca agtcagaggt ggcgaaaccc gacaggacta taaagatacc aggcgtttcc 2160
ccctggaagc tccctcgtgc gctctcctgt tccgaccctg ccgcttaccg gatacctgtc 2220
cgcctttctc ccttcgggaa gcgtggcgct ttctcatagc tcacgctgta ggtatctcag 2280
ttcggtgtag gtcgttcgct ccaagctggg ctgtgtgcac gaaccccccg ttcagcccga 2340
ccgctgcgcc ttatccggta actatcgtct tgagtccaac ccggtaagac acgacttatc 2400
gccactggca gcagccactg gtaacaggat tagcagagcg aggtatgtag gcggtgctac 2460
agagttcttg aagtggtggc ctaactacgg ctacactaga agaacagtat ttggtatctg 2520
cgctctgctg aagccagtta ccttcggaaa aagagttggt agctcttgat ccggcaaaca 2580
aaccaccgct ggtagcggtg gtttttttgt ttgcaagcag cagattacgc gcagaaaaaa 2640
aggatctcaa gaagatcctt tgatcttttc tacggggtct gacgctcagt ggaacgaaaa 2700
ctcacgttaa gggattttgg tcatgagatt atcaaaaagg atcttcacct agatcctttt 2760
aaattaaaaa tgaagtttta aatcaatcta aagtatatat gagtaaactt ggtctgacag 2820
ttattagaaa aattcatcca gcagacgata aaacgcaata cgctggctat ccggtgccgc 2880
aatgccatac agcaccagaa aacgatccgc ccattcgccg cccagttctt ccgcaatatc 2940
acgggtggcc agcgcaatat cctgataacg atccgccacg cccagacggc cgcaatcaat 3000
aaagccgcta aaacggccat tttccaccat aatgttcggc aggcacgcat caccatgggt 3060
caccaccaga tcttcgccat ccggcatgct cgctttcaga cgcgcaaaca gctctgccgg 3120
tgccaggccc tgatgttctt catccagatc atcctgatcc accaggcccg cttccatacg 3180
ggtacgcgca cgttcaatac gatgtttcgc ctgatgatca aacggacagg tcgccgggtc 3240
cagggtatgc agacgacgca tggcatccgc cataatgctc acttttctg ccggcgccag 3300
atggctagac agcagatcct gacccggcac ttcgcccagc agcagccaat cacggcccgc 3360
ttcggtcacc acatccagca ccgccgcaca cggaacaccg gtggtggcca gccagctcag 3420
acgcgccgct tcatcctgca gctcgttcag cgcaccgctc agatcggttt tcacaaacag 3480
caccggacga ccctgcgcgc tcagacgaaa caccgccgca tcagagcagc caatggtctg 3540
ctgcgcccaa tcatagccaa acagacgttc cacccacgct gccgggctac ccgcatgcag 3600
gccatcctgt tcaatcatac tcttcctttt tcaatattat tgaagcattt atcagggtta 3660
ttgtctcatg agcggataca tatttgaatg tatttagaaa aataaacaaa taggggttcc 3720
gcgcacattt ccccgaaaag tgccac 3746

<210> SEQ ID NO 20

-continued

<211> LENGTH: 469
<212> TYPE: PRT
<213> ORGANISM: Artificial
<220> FEATURE:
<223> OTHER INFORMATION: Fusion protein

<400> SEQUENCE: 20

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140

Glu Leu Ala Ser Lys Val Asp Met Val Trp Ile Val Gly Gly Ser Ser
145                 150                 155                 160

Val Tyr Gln Glu Ala Met Asn Gln Pro Gly His Leu Arg Leu Phe Val
                165                 170                 175

Thr Arg Ile Met Gln Glu Phe Glu Ser Asp Thr Phe Phe Pro Glu Ile
            180                 185                 190

Asp Leu Gly Lys Tyr Lys Leu Leu Pro Glu Tyr Pro Gly Val Leu Ser
        195                 200                 205

Glu Val Gln Glu Glu Lys Gly Ile Lys Tyr Lys Phe Glu Val Tyr Glu
    210                 215                 220

Lys Lys Asp Gly Ala Ser Gly Phe Ala Asn Glu Leu Gly Pro Arg Leu
225                 230                 235                 240

Met Gly Lys Gly Ala Gly Gly Gly Ala Gly Ala Gly Pro Phe Val Asn
                245                 250                 255

Lys Gln Phe Asn Tyr Lys Asp Pro Val Asn Gly Val Asp Ile Ala Tyr
            260                 265                 270

Ile Lys Ile Pro Asn Ala Gly Gln Met Gln Pro Val Lys Ala Phe Lys
        275                 280                 285

Ile His Asn Lys Ile Trp Val Ile Pro Glu Arg Asp Thr Phe Thr Asn
    290                 295                 300

Pro Glu Glu Gly Asp Leu Asn Pro Pro Pro Glu Ala Lys Gln Val Pro
305                 310                 315                 320

Val Ser Tyr Tyr Asp Ser Thr Tyr Leu Ser Thr Asp Asn Glu Lys Asp
                325                 330                 335

Asn Tyr Leu Lys Gly Val Thr Lys Leu Phe Glu Arg Ile Tyr Ser Thr
            340                 345                 350

Asp Leu Gly Arg Met Leu Leu Thr Ser Ile Val Arg Gly Ile Pro Phe
        355                 360                 365

Trp Gly Gly Ser Thr Ile Asp Thr Glu Leu Lys Val Ile Asp Thr Asn
    370                 375                 380
```

Cys Ile Asn Val Ile Gln Pro Asp Gly Ser Tyr Arg Ser Glu Glu Leu
385 390 395 400

Asn Leu Val Ile Ile Gly Pro Ser Ala Asp Ile Ile Gln Phe Glu Cys
405 410 415

Lys Ser Phe Gly His Glu Val Leu Asn Leu Thr Arg Asn Gly Tyr Gly
420 425 430

Ser Thr Gln Tyr Ile Arg Phe Ser Pro Asp Phe Thr Phe Gly Phe Glu
435 440 445

Glu Ser Leu Glu Val Asp Thr Asn Pro Leu Leu Gly Ala Gly Lys Phe
450 455 460

Ala Thr Asp Pro Ala
465

<210> SEQ ID NO 21
<211> LENGTH: 3443
<212> TYPE: DNA
<213> ORGANISM: Artificial
<220> FEATURE:
<223> OTHER INFORMATION: Propeptide fusion encoding sequence

<400> SEQUENCE: 21
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtggccgct acagggcgct cccattcgcc attcaggctg cgcaactgtt 180
gggaagggcg tttcggtgcg ggcctcttcg ctattacgcc agctggcgaa agggggatgt 240
gctgcaaggc gattaagttg ggtaacgcca gggttttccc agtcacgacg ttgtaaaacg 300
acggccagtg agcgcgacgt aatacgactc actatagggc gaattgaagg aaggccgtca 360
aggccgcata gatctcggtc cgttcgaacc agaactctgg aagcttaact cctaaaaaac 420
cgccaccatg aaattcttag tcaacgttgc ccttgttttt atggtcgtat acatttctta 480
catctatgcg gccggacacc accaccacca ccaccaccac caccaccacg acgtcggctg 540
ggagctgcaa cgtcgtcccc tgaactgcat cgtggctgtg tcccagaaca tgggtatcgg 600
caagaacggc gacctgccct ggcctcctct gcgtaacgag ttcaagtact tccagcgtat 660
gaccaccacc tcctccgtcg agggcaagca gaacctggtc atcatgggtc gcaagacctg 720
gttctccatc cccgagaaga accgtctgct gaaggaccgt atcaacatcg tgctgtcccg 780
cgagctgaag gaacccccctc gtggtgctca cttcctggct aagtccctgg acgacgctct 840
gcgtctgatc gagcagcctg agctggcttc caaggtggac atggtctgga tcgtgggcgg 900
ttcctccgtg taccaagagg ctatgaacca gcccggtcac ttgcgtctgt tcgtgacccg 960
tatcatgcaa gagttcgagt ccgacacctt cttccccgaa atcgacctgg gcaagtacaa 1020
gctgctgccc gagtaccccg gtgtcctgtc cgaggtgcaa gaggaaaagg gtatcaagta 1080
caagttcgag gtgtacgaga agaaggacgg cgcttccggt ttcgctaacg agctcggtcc 1140
tcgtctgatg ggaaagggcg ccggcggtgg tgctggtgct ggaccgatca ccatcaacaa 1200
cttcaattac tcggatccgg tggataacaa gaacatcctc tacttggaca cacacttgaa 1260
cacgctggct aacgagcctg aaaaagcttt caggatcacc ggcaacattt gggtcattcc 1320
ggataggttc agcagaaact ctaaccctaa cttgaacaaa cctcccagag tgacctcacc 1380
taagagtgga tactacgacc ccaactacct ctcgactgac tccgataaag accccttcct 1440
gaaggagatc attaaactct tcaagcgcat caactctcgt gaaattggcg aggaattgat 1500

```
ctaccgcctg agtacagaca tcccattccc gggtctgggc ctcatgggcc ttcctttcac   1560
tgcccgcttt ccagtcggga aacctgtcgt gccagctgca ttaacatggt catagctgtt   1620
tccttgcgta ttgggcgctc tccgcttcct cgctcactga ctcgctgcgc tcggtcgttc   1680
gggtaaagcc tggggtgcct aatgagcaaa aggccagcaa aaggccagga accgtaaaaa   1740
ggccgcgttg ctggcgtttt tccataggct ccgcccccct gacgagcatc acaaaaatcg   1800
acgctcaagt cagaggtggc gaaacccgac aggactataa agataccagg cgtttccccc   1860
tggaagctcc ctcgtgcgct ctcctgttcc gaccctgccg cttaccggat acctgtccgc   1920
ctttctccct tcgggaagcg tggcgctttc tcatagctca cgctgtaggt atctcagttc   1980
ggtgtaggtc gttcgctcca agctgggctg tgtgcacgaa ccccccgttc agcccgaccg   2040
ctgcgcctta tccggtaact atcgtcttga gtccaacccg gtaagacacg acttatcgcc   2100
actggcagca gccactggta acaggattag cagagcgagg tatgtaggcg gtgctacaga   2160
gttcttgaag tggtggccta actacggcta cactagaaga acagtatttg gtatctgcgc   2220
tctgctgaag ccagttacct tcggaaaaag agttggtagc tcttgatccg gcaaacaaac   2280
caccgctggt agcggtggtt tttttgtttg caagcagcag attacgcgca gaaaaaaagg   2340
atctcaagaa gatcctttga tcttttctac ggggtctgac gctcagtgga acgaaaactc   2400
acgttaaggg attttggtca tgagattatc aaaaaggatc ttcacctaga tccttttaaa   2460
ttaaaaatga agttttaaat caatctaaag tatatatgag taaacttggt ctgacagtta   2520
ttagaaaaat tcatccagca gacgataaaa cgcaatacgc tggctatccg gtgccgcaat   2580
gccatacagc accagaaaac gatccgccca ttcgccgccc agttcttccg caatatcacg   2640
ggtggccagc gcaatatcct gataacgatc cgccacgccc agacggccgc aatcaataaa   2700
gccgctaaaa cggccatttt ccaccataat gttcggcagg cacgcatcac catgggtcac   2760
caccagatct tcgccatccg gcatgctcgc tttcagacgc gcaaacagct ctgccggtgc   2820
caggccctga tgttcttcat ccagatcatc ctgatccacc aggcccgctt ccatacgggt   2880
acgcgcacgt tcaatacgat gtttcgcctg atgatcaaac ggacaggtcg ccgggtccag   2940
ggtatgcaga cgacgcatgg catccgccat aatgctcact ttttctgccg gcgccagatg   3000
gctagacagc agatcctgac ccggcacttc gcccagcagc agccaatcac ggcccgcttc   3060
ggtcaccaca tccagcaccg ccgcacacgg aacaccggtg gtggccagcc agctcagacg   3120
cgccgcttca tcctgcagct cgttcagcgc accgctcaga tcggttttca caaacagcac   3180
cggacgaccc tgcgcgctca gacgaaacac cgccgcatca gagcagccaa tggtctgctg   3240
cgcccaatca tagccaaaca gacgttccac ccacgctgcc gggctacccg catgcaggcc   3300
atcctgttca atcatactct tcctttttca atattattga agcatttatc agggttattg   3360
tctcatgagc ggatacatat ttgaatgtat ttagaaaaat aaacaaatag gggttccgcg   3420
cacatttccc cgaaaagtgc cac                                           3443
```

<210> SEQ ID NO 22
<211> LENGTH: 369
<212> TYPE: PRT
<213> ORGANISM: Artificial
<220> FEATURE:
<223> OTHER INFORMATION: Fusion protein

<400> SEQUENCE: 22

```
Met Lys Phe Leu Val Asn Val Ala Leu Val Phe Met Val Val Tyr Ile
1               5                   10                  15
```

```
Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140

Glu Leu Ala Ser Lys Val Asp Met Val Trp Ile Val Gly Gly Ser Ser
145                 150                 155                 160

Val Tyr Gln Glu Ala Met Asn Gln Pro Gly His Leu Arg Leu Phe Val
                165                 170                 175

Thr Arg Ile Met Gln Glu Phe Glu Ser Asp Thr Phe Phe Pro Glu Ile
            180                 185                 190

Asp Leu Gly Lys Tyr Lys Leu Leu Pro Glu Tyr Pro Gly Val Leu Ser
        195                 200                 205

Glu Val Gln Glu Glu Lys Gly Ile Lys Tyr Lys Phe Glu Val Tyr Glu
    210                 215                 220

Lys Lys Asp Gly Ala Ser Gly Phe Ala Asn Glu Leu Gly Pro Arg Leu
225                 230                 235                 240

Met Gly Lys Gly Ala Gly Gly Gly Ala Gly Ala Gly Pro Ile Thr Ile
                245                 250                 255

Asn Asn Phe Asn Tyr Ser Asp Pro Val Asp Asn Lys Asn Ile Leu Tyr
            260                 265                 270

Leu Asp Thr His Leu Asn Thr Leu Ala Asn Glu Pro Glu Lys Ala Phe
        275                 280                 285

Arg Ile Thr Gly Asn Ile Trp Val Ile Pro Asp Arg Phe Ser Arg Asn
    290                 295                 300

Ser Asn Pro Asn Leu Asn Lys Pro Pro Arg Val Thr Ser Pro Lys Ser
305                 310                 315                 320

Gly Tyr Tyr Asp Pro Asn Tyr Leu Ser Thr Asp Ser Asp Lys Asp Pro
                325                 330                 335

Phe Leu Lys Glu Ile Ile Lys Leu Phe Lys Arg Ile Asn Ser Arg Glu
            340                 345                 350

Ile Gly Glu Glu Leu Ile Tyr Arg Leu Ser Thr Asp Ile Pro Phe Pro
        355                 360                 365

Gly
```

<210> SEQ ID NO 23
<211> LENGTH: 9586
<212> TYPE: DNA
<213> ORGANISM: Artificial
<220> FEATURE:
<223> OTHER INFORMATION: Propeptide fusion encoding sequence

<400> SEQUENCE: 23

```
gacgcgccct gtagcggcgc attaagcgcg gcgggtgtgg tggttacgcg cagcgtgacc     60
```

gctacacttg ccagcgccct agcgcccgct cctttcgctt tcttcccttc ctttctcgcc 120
acgttcgccg gctttccccg tcaagctcta aatcgggggc tccctttagg gttccgattt 180
agtgctttac ggcacctcga ccccaaaaaa cttgattagg gtgatggttc acgtagtggg 240
ccatcgccct gatagacggt ttttcgccct ttgacgttgg agtccacgtt ctttaatagt 300
ggactcttgt tccaaactgg aacaacactc aaccctatct cggtctattc ttttgattta 360
taagggattt tgccgatttc ggcctattgg ttaaaaaatg agctgattta acaaaaattt 420
aacgcgaatt ttaacaaaat attaacgttt acaatttcag gtggcacttt tcggggaaat 480
gtgcgcggaa cccctatttg tttatttttc taaatacatt caaatatgta tccgctcatg 540
agacaataac cctgataaat gcttcaataa tattgaaaaa ggaagagtat gagtattcaa 600
catttccgtg tcgcccttat tccctttttt gcggcatttt gccttcctgt ttttgctcac 660
ccagaaacgc tggtgaaagt aaaagatgct gaagatcagt tgggtgcacg agtgggttac 720
atcgaactgg atctcaacag cggtaagatc cttgagagtt ttcgccccga agaacgtttt 780
ccaatgatga gcacttttaa agttctgcta tgtggcgcgg tattatcccg tattgacgcc 840
gggcaagagc aactcggtcg ccgcatacac tattctcaga atgacttggt tgagtactca 900
ccagtcacag aaaagcatct tacggatggc atgacagtaa gagaattatg cagtgctgcc 960
ataaccatga gtgataacac tgcggccaac ttacttctga caacgatcgg aggaccgaag 1020
gagctaaccg cttttttgca caacatgggg gatcatgtaa ctcgccttga tcgttgggaa 1080
ccggagctga atgaagccat accaaacgac gagcgtgaca ccacgatgcc tgtagcaatg 1140
gcaacaacgt tgcgcaaact attaactggc gaactactta ctctagcttc ccggcaacaa 1200
ttaatagact ggatggaggc ggataaagtt gcaggaccac ttctgcgctc ggcccttccg 1260
gctggctggt ttattgctga taaatctgga gccggtgagc gtgggtctcg cggtatcatt 1320
gcagcactgg ggccagatgg taagccctcc cgtatcgtag ttatctacac gacggggagt 1380
caggcaacta tggatgaacg aaatagacag atcgctgaga taggtgcctc actgattaag 1440
cattggtaac tgtcagacca agtttactca tatatacttt agattgattt aaaacttcat 1500
ttttaattta aaaggatcta ggtgaagatc ctttttgata atctcatgac caaaatccct 1560
taacgtgagt tttcgttcca ctgagcgtca gaccccgtag aaaagatcaa aggatcttct 1620
tgagatcctt tttttctgcg cgtaatctgc tgcttgcaaa caaaaaaacc accgctacca 1680
gcggtggttt gtttgccgga tcaagagcta ccaactcttt ttccgaaggt aactggcttc 1740
agcagagcgc agataccaaa tactgtcctt ctagtgtagc cgtagttagg ccaccacttc 1800
aagaactctg tagcaccgcc tacatacctc gctctgctaa tcctgttacc agtggctgct 1860
gccagtggcg ataagtcgtg tcttaccggg ttggactcaa gacgatagtt accggataag 1920
gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400

-continued

```
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca tcatcatcat catcaccatc accaccacca cgacgtcggc   4200
tgggagctgc aacgtcgtcc cctgaactgc atcgtggctg tgtcccagaa catgggtatc   4260
ggcaagaacg gcgacctgcc ctggcctcct ctgcgtaacg agttcaagta cttccagcgt   4320
atgaccacca cctcctccgt cgagggcaag cagaacctgg tcatcatggg tcgcaagacc   4380
tggttctcca tccccgagaa gaaccgtctg ctgaaggacc gtatcaacat cgtgctgtcc   4440
cgcgagctga aggaaccccc tcgtggtgct cacttcctgg ctaagtccct ggacgacgct   4500
ctgcgtctga tcgagcagcc tgagctggct tccaaggtgg acatggtctg gatcgtgggc   4560
ggttcctccg tgtaccaaga ggctatgaac cagcccggtc acttgcgtct gttcgtgacc   4620
cgtatcatgc aagagttcga gtccgacacc ttcttccccg aaatcgacct gggcaagtac   4680
aagctgctgc ccgagtaccc cggtgtcctg tccgaggtgc aagaggaaaa gggtatcaag   4740
tacaagttcg aggtgtacga gaagaaggac ggcgcttccg gtttcgctaa cgagctcggt   4800
```

cctcgtctga tgggaaaggg cgccggcggt ggtgctggtg ctggaccatt cgtcaacaag 4860
caattcaact acaaggatcc tgttaacggt gtggacatcg cctacatcaa gattccgaac 4920
gcaggccaga tgcaacctgt gaaggctttc aaaatccaca acaaaatctg ggtcattccc 4980
gagagagaca cattcacgaa cccagaggaa ggtgatctga accctccccc agaagccaag 5040
caggtgccgg tctcttacta cgattcaacc tacctcagta ctgacaacga gaaggataac 5100
tacctgaagg gcgttactaa actcttcgag cgcatctact cgacagactt gggccgtatg 5160
ctgctcacgt ccatcgtcag ggtattcct ttctggggtg gctcaaccat cgacactgag 5220
ctgaaggtca ttgatacaaa ctgcatcaac gttattcaac ccgacggctc ctaccgcagc 5280
gaggaattga acctggtgat cattggacca agcgccgaca tcattcagtt cgagtgtaag 5340
tctttcggcc atgaagtcct caacttgacc agaaacggct acggctccac tcaatacatc 5400
cgcttcagcc ccgacttcac attcggattc gaggaatcac tggaggtcga tacgaacccg 5460
ttgctgggtg ctggcaagtt cgccaccgac cctgcagtta ctctggcaca cgcgctcatc 5520
cacgcgggac atcgtctgta cggtatcgct attaacccaa acagggtctt caaggttaac 5580
accaacgcct actacgagat gagtggtctg gaagtgtcgt tcgaggaact ccgtacgttc 5640
ggaggtcacg acgcaaagtt catcgatagt ttgcaggaga acgaattccg cctgtactac 5700
tacaacaagt tcaaagacat cgcgtctaca ctcaacaagg ctaaaagcat tgttggaacc 5760
actgctagtt tgcaatacat gaagaacgtg ttcaaggaga aatacctctt gtcggaagac 5820
acctccggta aattcagcgt ggacaagctg aaattcgata agttgtacaa aatgctgaca 5880
gaaatctaca cggaagacaa cttcgttaag ttcttcaaag tgttgaaccg taagaccgct 5940
ctgaacttcg ataaggctgt cttcaaaatc aacattgtgc ctaaagtcaa ctacaccatc 6000
tacgacggtt tcaacctccg caacactaac ttggctgcca acttcaacgg ccagaacact 6060
gagatcaaca acatgaactt cacaaagctc aaaaacttca ccggtttgtt cgagttctac 6120
aagctgctct gcgtgcgtgg tggaggcaca tctcacacgc aatctggctg ggaactccag 6180
caaggtggcc agggtggagc tctgaacgat ctgtgtatca aggtgaataa ctgggatctg 6240
ttctttagcc caagcgagga taacttcacg aacgatctca acaaaggtga agagatcacg 6300
tctgatacca atatcgaagc ggctgaagag aatatctcct tggatctcat ccagcaatat 6360
tacctgacct ttaacttcga taacgagccc gaaaacatct ccatcgagaa cctcagctca 6420
gacatcattg gtcagttgga gctgatgcca aacattgaac gcttccccaa cggcaagaaa 6480
tacgaactcg acaagtatac gatgtttcat tacttaagag cgcaggagtt tgaacacggc 6540
aagagccgca ttgctctcac taactccgtg aatgaagccc tgctcaatcc gtcaagggtg 6600
tacacattct ttagctccga ctatgtcaag aaagtgaaca aagccaccga agcggcaatg 6660
ttcctgggat gggttgaaca actggtctac gacttcaccg acgagacctc tgaggtgagc 6720
acaacggaca agattgctga catcactatc attatcccgt atattggacc tgccttgaat 6780
attggcaaca tgctctacaa agacgatttc gttggtgccc tgatcttcag cggtgccgtg 6840
atcctgttgg agttcattcc tgaaatcgcc atccctgtgc tgggcacgtt cgctctggtc 6900
tcatacattg cgaataargt cttgaccgtg cagacaatcg ataatgccct ctccaaacgt 6960
aacgaaaaat gggacgaggt ctacaaatac atcgtgacca actggctggc aaaggttaac 7020
acccaaattg atctgatccg taagaaaatg aaggaggctt tggagaacca ggctgaagct 7080
actaaagcca ttatcaacta ccagtataat cagtatacag aagaggaaaa gaataacatc 7140

```
aatttcaaca tcgatgactt gtcctcaaag ctgaacgagt ccatcaacaa agctatgatc   7200
aacatcaaca aattcctgaa tcagtgctcc gtgtcttacc tgatgaactc tatgatccca   7260
tacggtgtga agcgcctgga ggacttcgat gccagcctga aagacgcact gctcaaatac   7320
atttacgata atcgcggcac tttgattggc caagttgacc gtctgaagga caaggttaac   7380
aataccttgt caaccgatat ccccttccaa ctctctaagt acgtcgataa ccagcgcttg   7440
ctgagcacct tcacagaata catcaacaac atcatcaaca cctccatcct gaacctccgt   7500
tacgagtcta accacctcat cgacttgagc agatacgcta gcaagatcaa catcggttcc   7560
aaggtgaact tcgacccaat cgataagaac cagatccaac tgttcaacct cgaatcctct   7620
aagatcgaag tgatcctgaa gaacgctatc gtctacaact ccatgtacga aaacttctct   7680
accagcttct ggatcaggat tccgaaatac ttcaactcaa tctcgctcaa caacgagtac   7740
actatcatca actgcatgga aaacaactcg ggatggaagg tgtccctcaa ctacggcgag   7800
atcatctgga ctttgcagga cacacaagaa atcaagcaga gggtcgtgtt caagtacagc   7860
caaatgatca acatcagcga ttacatcaac cgttggatct tcgtcacaat caccaacaac   7920
cgcctgaaca actccaagat ttacatcaac ggtagactga tcgaccagaa gccaatcagc   7980
aacctcggca acatccacgc ctcaaacaac atcatgttca agttggacgg ctgtagggat   8040
acacacagat acatctggat caaatacttc aacctgttcg acaaggagct caacgagaag   8100
gaaatcaagg acctctacga taaccagtcc aactctggta tcttgaagga cttctggggc   8160
gattacctgc aatacgacaa gccctactac atgttgaacc tgtacgaccc taacaagtac   8220
gttgatgtga acaacgtcgg tatcaggggc tacatgtacc tgaagggacc acgtggttct   8280
gttatgacca ctaacatcta cctcaacagc tcattgtacc gtggcacaaa gttcatcatc   8340
aagaagtacg cctccggaaa caaggacaac atcgtccgta acaacgatcg cgtttacatc   8400
aacgttgtgg tcaagaacaa ggagtacaga ctggctacca acgcttcgca ggctggagtt   8460
gagaagatcc tgtctgctct ggaaatccct gacgtgggca acctctcaca ggttgtggtc   8520
atgaagtcga agaacgatca aggcatcact aacaagtgca agatgaactt gcaggacaac   8580
aacggaaacg acatcggctt catcggattc caccaattca acaacatcgc caagttggtg   8640
gccagcaact ggtacaaccg tcagatcgag cgttcgtccc gcaccttagg atgctcgtgg   8700
gagttcattc cagtcgatga cggatgggga gagagacctt tgggcgcagg aggatgggaa   8760
ctccagcaag gttacccccta cgatgtccct gactacgctg gtgcaggatg gtcccaccca   8820
caattcgaga agggtgcagg atggagtcac ccacagttcg agaagggcgc tggatggtcc   8880
cacccacagt tcgagaaata attagttgat gcatagttaa ttagatagct cgaggcatgc   8940
ggtaccaagc ttgtcgagaa gtactagagg atcataatca gccataccac atttgtagag   9000
gttttacttg ctttaaaaaa cctcccacac ctccccctga acctgaaaca taaaatgaat   9060
gcaattgttg ttgttaactt gtttattgca gcttataatg gttacaaata aagcaatagc   9120
atcacaaatt tcacaaataa agcatttttt tcactgcatt ctagttgtgg tttgtccaaa   9180
ctcatcaatg tatcttatca tgtctggatc tgatcactgc ttgagcctag gagatccgaa   9240
ccagataagt gaaatctagt tccaaactat tttgtcattt ttaattttcg tattagctta   9300
cgacgctaca cccagttccc atctattttg tcactcttcc ctaaataatc cttaaaaact   9360
ccatttccac ccctcccagt tcccaactat tttgtccgcc cacagcgggg catttttctt   9420
cctgttatgt ttttaatcaa acatcctgcc aactccatgt gacaaaccgt catcttcggc   9480
tactttttct ctgtcacaga atgaaaattt ttctgtcatc tcttcgttat taatgtttgt   9540
```

aattgactga atatcaacgc ttatttgcag cctgaatggc gaatgg 9586

<210> SEQ ID NO 24
<211> LENGTH: 1603
<212> TYPE: PRT
<213> ORGANISM: Artificial
<220> FEATURE:
<223> OTHER INFORMATION: Fusion protein

<400> SEQUENCE: 24

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Gly Trp Glu Leu Gln Arg Arg Pro Leu Asn Cys Ile
35 40 45

Val Ala Val Ser Gln Asn Met Gly Ile Gly Lys Asn Gly Asp Leu Pro
50 55 60

Trp Pro Pro Leu Arg Asn Glu Phe Lys Tyr Phe Gln Arg Met Thr Thr
65 70 75 80

Thr Ser Ser Val Glu Gly Lys Gln Asn Leu Val Ile Met Gly Arg Lys
85 90 95

Thr Trp Phe Ser Ile Pro Glu Lys Asn Arg Leu Leu Lys Asp Arg Ile
100 105 110

Asn Ile Val Leu Ser Arg Glu Leu Lys Glu Pro Pro Arg Gly Ala His
115 120 125

Phe Leu Ala Lys Ser Leu Asp Asp Ala Leu Arg Leu Ile Glu Gln Pro
130 135 140

Glu Leu Ala Ser Lys Val Asp Met Val Trp Ile Val Gly Gly Ser Ser
145 150 155 160

Val Tyr Gln Glu Ala Met Asn Gln Pro Gly His Leu Arg Leu Phe Val
165 170 175

Thr Arg Ile Met Gln Glu Phe Glu Ser Asp Thr Phe Phe Pro Glu Ile
180 185 190

Asp Leu Gly Lys Tyr Lys Leu Leu Pro Glu Tyr Pro Gly Val Leu Ser
195 200 205

Glu Val Gln Glu Glu Lys Gly Ile Lys Tyr Lys Phe Glu Val Tyr Glu
210 215 220

Lys Lys Asp Gly Ala Ser Gly Phe Ala Asn Glu Leu Gly Pro Arg Leu
225 230 235 240

Met Gly Lys Gly Ala Gly Gly Gly Ala Gly Ala Gly Pro Phe Val Asn
245 250 255

Lys Gln Phe Asn Tyr Lys Asp Pro Val Asn Gly Val Asp Ile Ala Tyr
260 265 270

Ile Lys Ile Pro Asn Ala Gly Gln Met Gln Pro Val Lys Ala Phe Lys
275 280 285

Ile His Asn Lys Ile Trp Val Ile Pro Glu Arg Asp Thr Phe Thr Asn
290 295 300

Pro Glu Glu Gly Asp Leu Asn Pro Pro Pro Glu Ala Lys Gln Val Pro
305 310 315 320

Val Ser Tyr Tyr Asp Ser Thr Tyr Leu Ser Thr Asp Asn Glu Lys Asp
325 330 335

Asn Tyr Leu Lys Gly Val Thr Lys Leu Phe Glu Arg Ile Tyr Ser Thr
340 345 350

```
Asp Leu Gly Arg Met Leu Leu Thr Ser Ile Val Arg Gly Ile Pro Phe
        355                 360                 365

Trp Gly Gly Ser Thr Ile Asp Thr Glu Leu Lys Val Ile Asp Thr Asn
    370                 375                 380

Cys Ile Asn Val Ile Gln Pro Asp Gly Ser Tyr Arg Ser Glu Glu Leu
385                 390                 395                 400

Asn Leu Val Ile Ile Gly Pro Ser Ala Asp Ile Ile Gln Phe Glu Cys
                405                 410                 415

Lys Ser Phe Gly His Glu Val Leu Asn Leu Thr Arg Asn Gly Tyr Gly
            420                 425                 430

Ser Thr Gln Tyr Ile Arg Phe Ser Pro Asp Phe Thr Phe Gly Phe Glu
        435                 440                 445

Glu Ser Leu Glu Val Asp Thr Asn Pro Leu Leu Gly Ala Gly Lys Phe
    450                 455                 460

Ala Thr Asp Pro Ala Val Thr Leu Ala His Ala Leu Ile His Ala Gly
465                 470                 475                 480

His Arg Leu Tyr Gly Ile Ala Ile Asn Pro Asn Arg Val Phe Lys Val
                485                 490                 495

Asn Thr Asn Ala Tyr Tyr Glu Met Ser Gly Leu Glu Val Ser Phe Glu
            500                 505                 510

Glu Leu Arg Thr Phe Gly Gly His Asp Ala Lys Phe Ile Asp Ser Leu
        515                 520                 525

Gln Glu Asn Glu Phe Arg Leu Tyr Tyr Tyr Asn Lys Phe Lys Asp Ile
    530                 535                 540

Ala Ser Thr Leu Asn Lys Ala Lys Ser Ile Val Gly Thr Thr Ala Ser
545                 550                 555                 560

Leu Gln Tyr Met Lys Asn Val Phe Lys Glu Lys Tyr Leu Leu Ser Glu
                565                 570                 575

Asp Thr Ser Gly Lys Phe Ser Val Asp Lys Leu Lys Phe Asp Lys Leu
            580                 585                 590

Tyr Lys Met Leu Thr Glu Ile Tyr Thr Glu Asp Asn Phe Val Lys Phe
        595                 600                 605

Phe Lys Val Leu Asn Arg Lys Thr Ala Leu Asn Phe Asp Lys Ala Val
    610                 615                 620

Phe Lys Ile Asn Ile Val Pro Lys Val Asn Tyr Thr Ile Tyr Asp Gly
625                 630                 635                 640

Phe Asn Leu Arg Asn Thr Asn Leu Ala Ala Asn Phe Asn Gly Gln Asn
                645                 650                 655

Thr Glu Ile Asn Asn Met Asn Phe Thr Lys Leu Lys Asn Phe Thr Gly
            660                 665                 670

Leu Phe Glu Phe Tyr Lys Leu Leu Cys Val Arg Gly Gly Gly Thr Ser
        675                 680                 685

His Thr Gln Ser Gly Trp Glu Leu Gln Gln Gly Gly Gln Gly Gly Ala
    690                 695                 700

Leu Asn Asp Leu Cys Ile Lys Val Asn Asn Trp Asp Leu Phe Phe Ser
705                 710                 715                 720

Pro Ser Glu Asp Asn Phe Thr Asn Asp Leu Asn Lys Gly Glu Glu Ile
                725                 730                 735

Thr Ser Asp Thr Asn Ile Glu Ala Ala Glu Glu Asn Ile Ser Leu Asp
            740                 745                 750

Leu Ile Gln Gln Tyr Tyr Leu Thr Phe Asn Phe Asp Asn Glu Pro Glu
        755                 760                 765

Asn Ile Ser Ile Glu Asn Leu Ser Ser Asp Ile Ile Gly Gln Leu Glu
```

```
    770                 775                 780

Leu Met Pro Asn Ile Glu Arg Phe Pro Asn Gly Lys Lys Tyr Glu Leu
785                 790                 795                 800

Asp Lys Tyr Thr Met Phe His Tyr Leu Arg Ala Gln Glu Phe Glu His
                805                 810                 815

Gly Lys Ser Arg Ile Ala Leu Thr Asn Ser Val Asn Glu Ala Leu Leu
            820                 825                 830

Asn Pro Ser Arg Val Tyr Thr Phe Phe Ser Ser Asp Tyr Val Lys Lys
        835                 840                 845

Val Asn Lys Ala Thr Glu Ala Ala Met Phe Leu Gly Trp Val Glu Gln
    850                 855                 860

Leu Val Tyr Asp Phe Thr Asp Glu Thr Ser Glu Val Ser Thr Thr Asp
865                 870                 875                 880

Lys Ile Ala Asp Ile Thr Ile Ile Ile Pro Tyr Ile Gly Pro Ala Leu
                885                 890                 895

Asn Ile Gly Asn Met Leu Tyr Lys Asp Asp Phe Val Gly Ala Leu Ile
            900                 905                 910

Phe Ser Gly Ala Val Ile Leu Leu Glu Phe Ile Pro Glu Ile Ala Ile
        915                 920                 925

Pro Val Leu Gly Thr Phe Ala Leu Val Ser Tyr Ile Ala Asn Lys Val
    930                 935                 940

Leu Thr Val Gln Thr Ile Asp Asn Ala Leu Ser Lys Arg Asn Glu Lys
945                 950                 955                 960

Trp Asp Glu Val Tyr Lys Tyr Ile Val Thr Asn Trp Leu Ala Lys Val
                965                 970                 975

Asn Thr Gln Ile Asp Leu Ile Arg Lys Lys Met Lys Glu Ala Leu Glu
            980                 985                 990

Asn Gln Ala Glu Ala Thr Lys Ala  Ile Ile Asn Tyr Gln  Tyr Asn Gln
        995                 1000                1005

Tyr Thr  Glu Glu Glu Lys Asn  Asn Ile Asn Phe Asn  Ile Asp Asp
    1010                1015                1020

Leu Ser  Ser Lys Leu Asn Glu  Ser Ile Asn Lys Ala  Met Ile Asn
    1025                1030                1035

Ile Asn  Lys Phe Leu Asn Gln  Cys Ser Val Ser Tyr  Leu Met Asn
    1040                1045                1050

Ser Met  Ile Pro Tyr Gly Val  Lys Arg Leu Glu Asp  Phe Asp Ala
    1055                1060                1065

Ser Leu  Lys Asp Ala Leu Leu  Lys Tyr Ile Tyr Asp  Asn Arg Gly
    1070                1075                1080

Thr Leu  Ile Gly Gln Val Asp  Arg Leu Lys Asp Lys  Val Asn Asn
    1085                1090                1095

Thr Leu  Ser Thr Asp Ile Pro  Phe Gln Leu Ser Lys  Tyr Val Asp
    1100                1105                1110

Asn Gln  Arg Leu Leu Ser Thr  Phe Thr Glu Tyr Ile  Asn Asn Ile
    1115                1120                1125

Ile Asn  Thr Ser Ile Leu Asn  Leu Arg Tyr Glu Ser  Asn His Leu
    1130                1135                1140

Ile Asp  Leu Ser Arg Tyr Ala  Ser Lys Ile Asn Ile  Gly Ser Lys
    1145                1150                1155

Val Asn  Phe Asp Pro Ile Asp  Lys Asn Gln Ile Gln  Leu Phe Asn
    1160                1165                1170

Leu Glu  Ser Ser Lys Ile Glu  Val Ile Leu Lys Asn  Ala Ile Val
    1175                1180                1185
```

-continued

Tyr Asn Ser Met Tyr Glu Asn Phe Ser Thr Ser Phe Trp Ile Arg
1190 1195 1200

Ile Pro Lys Tyr Phe Asn Ser Ile Ser Leu Asn Asn Glu Tyr Thr
1205 1210 1215

Ile Ile Asn Cys Met Glu Asn Asn Ser Gly Trp Lys Val Ser Leu
1220 1225 1230

Asn Tyr Gly Glu Ile Ile Trp Thr Leu Gln Asp Thr Gln Glu Ile
1235 1240 1245

Lys Gln Arg Val Val Phe Lys Tyr Ser Gln Met Ile Asn Ile Ser
1250 1255 1260

Asp Tyr Ile Asn Arg Trp Ile Phe Val Thr Ile Thr Asn Asn Arg
1265 1270 1275

Leu Asn Asn Ser Lys Ile Tyr Ile Asn Gly Arg Leu Ile Asp Gln
1280 1285 1290

Lys Pro Ile Ser Asn Leu Gly Asn Ile His Ala Ser Asn Asn Ile
1295 1300 1305

Met Phe Lys Leu Asp Gly Cys Arg Asp Thr His Arg Tyr Ile Trp
1310 1315 1320

Ile Lys Tyr Phe Asn Leu Phe Asp Lys Glu Leu Asn Glu Lys Glu
1325 1330 1335

Ile Lys Asp Leu Tyr Asp Asn Gln Ser Asn Ser Gly Ile Leu Lys
1340 1345 1350

Asp Phe Trp Gly Asp Tyr Leu Gln Tyr Asp Lys Pro Tyr Tyr Met
1355 1360 1365

Leu Asn Leu Tyr Asp Pro Asn Lys Tyr Val Asp Val Asn Asn Val
1370 1375 1380

Gly Ile Arg Gly Tyr Met Tyr Leu Lys Gly Pro Arg Gly Ser Val
1385 1390 1395

Met Thr Thr Asn Ile Tyr Leu Asn Ser Ser Leu Tyr Arg Gly Thr
1400 1405 1410

Lys Phe Ile Ile Lys Lys Tyr Ala Ser Gly Asn Lys Asp Asn Ile
1415 1420 1425

Val Arg Asn Asn Asp Arg Val Tyr Ile Asn Val Val Val Lys Asn
1430 1435 1440

Lys Glu Tyr Arg Leu Ala Thr Asn Ala Ser Gln Ala Gly Val Glu
1445 1450 1455

Lys Ile Leu Ser Ala Leu Glu Ile Pro Asp Val Gly Asn Leu Ser
1460 1465 1470

Gln Val Val Val Met Lys Ser Lys Asn Asp Gln Gly Ile Thr Asn
1475 1480 1485

Lys Cys Lys Met Asn Leu Gln Asp Asn Asn Gly Asn Asp Ile Gly
1490 1495 1500

Phe Ile Gly Phe His Gln Phe Asn Asn Ile Ala Lys Leu Val Ala
1505 1510 1515

Ser Asn Trp Tyr Asn Arg Gln Ile Glu Arg Ser Ser Arg Thr Leu
1520 1525 1530

Gly Cys Ser Trp Glu Phe Ile Pro Val Asp Asp Gly Trp Gly Glu
1535 1540 1545

Arg Pro Leu Gly Ala Gly Gly Trp Glu Leu Gln Gln Gly Tyr Pro
1550 1555 1560

Tyr Asp Val Pro Asp Tyr Ala Gly Ala Gly Trp Ser His Pro Gln
1565 1570 1575

-continued

```
Phe Glu  Lys Gly Ala Gly Trp  Ser His Pro Gln Phe  Glu Lys Gly
    1580                1585                1590

Ala Gly  Trp Ser His Pro Gln  Phe Glu Lys
    1595                1600


<210> SEQ ID NO 25
<211> LENGTH: 9650
<212> TYPE: DNA
<213> ORGANISM: Artificial
<220> FEATURE:
<223> OTHER INFORMATION: Propeptide fusion encoding sequence

<400> SEQUENCE: 25

gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440

cattggtaac tgtcagacca agtttactca tatatacttt agattgattt aaaacttcat   1500

ttttaattta aaaggatcta ggtgaagatc ctttttgata atctcatgac caaaatccct   1560

taacgtgagt tttcgttcca ctgagcgtca gaccccgtag aaaagatcaa aggatcttct   1620

tgagatcctt tttttctgcg cgtaatctgc tgcttgcaaa caaaaaaacc accgctacca   1680

gcggtggttt gtttgccgga tcaagagcta ccaactcttt ttccgaaggt aactggcttc   1740

agcagagcgc agataccaaa tactgtcctt ctagtgtagc cgtagttagg ccaccacttc   1800

aagaactctg tagcaccgcc tacatacctc gctctgctaa tcctgttacc agtggctgct   1860

gccagtggcg ataagtcgtg tcttaccggg ttggactcaa gacgatagtt accggataag   1920
```

-continued

```
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca ccaccaccac caccaccacc accaccacca cgacgtcggc   4200
tgggagctgc aacgtcgtcc cctgaactgc atcgtggctg tgtcccagaa catgggtatc   4260
```

ggcaagaacg gcgacctgcc ctggcctcct ctgcgtaacg agttcaagta cttccagcgt 4320
atgaccacca cctcctccgt cgagggcaag cagaacctgg tcatcatggg tcgcaagacc 4380
tggttctcca tccccgagaa gaaccgtctg ctgaaggacc gtatcaacat cgtgctgtcc 4440
cgcgagctga aggaaccccc tcgtggtgct cacttcctgg ctaagtccct ggacgacgct 4500
ctgcgtctga tcgagcagcc tgagctggct tccaaggtgg acatggtctg gatcgtgggc 4560
ggttcctccg tgtaccaaga ggctatgaac cagcccggtc acttgcgtct gttcgtgacc 4620
cgtatcatgc aagagttcga gtccgacacc ttcttccccg aaatcgacct gggcaagtac 4680
aagctgctgc ccgagtaccc cggtgtcctg tccgaggtgc aagaggaaaa gggtatcaag 4740
tacaagttcg aggtgtacga gaagaaggac ggcgcttccg gtttcgctaa cgagctcggt 4800
cctcgtctga tgggaaaggg cgccggcggt ggtgctggtg ctggaccgat caccatcaac 4860
aacttcaatt actcggatcc ggtggataac aagaacatcc tctacttgga cacacacttg 4920
aacacgctgg ctaacgagcc tgaaaaagct ttcaggatca ccggcaacat ttgggtcatt 4980
ccggataggt tcagcagaaa ctctaaccct aacttgaaca aacctcccag agtgacctca 5040
cctaagagtg gatactacga ccccaactac ctctcgactg actccgataa agacccccttc 5100
ctgaaggaga tcattaaact cttcaagcgc atcaactctc gtgaaattgg cgaggaattg 5160
atctaccgcc tgagtacaga catcccattc ccgggtaaca acaacacccc aatcaacact 5220
ttcgatttcg atgtcgattt caactcagtg gatgtcaaaa ccaggcaggg aaacaactgg 5280
gtgaagactg gtagcatcaa cccatctgtc atcattactg gcccgagaga gaacatcatt 5340
gaccctgaaa cctccacttt caagctgaca aacaacacgt tcgctgctca ggaaggcttc 5400
ggagcgttga gcatcatttc tatctcacct cgcttcatgc tgacatactc taacgctacg 5460
aacgacgtgg gagagggccg tttcagtaag tctgaattct gcatggaccc tattctgatc 5520
ctcatgcacg ctctcaacgg cgccatgcac aacttgtacg gaattgctat ccccaacgac 5580
cagaccattt ccagcgtgac tagcaacatc ttctactctc aatacaacgt caagctggag 5640
tacgcagaaa tctacgcttt cggtggccca accattgact tgatcccgaa atcagctcgt 5700
aagtatttcg aagaaaaagc gctggattat tacaggtcga ttgctaagag actcaactcc 5760
atcaccactg ctaacccctc ttcattcaac aagtacattg gagaatacaa gcagaaactg 5820
atccgcaagt accgtttcgt ggtcgagagt tcgggtgaag ttactgtgaa ccgcaacaag 5880
ttcgtcgagc tgtacaacga attgacacaa atcttcacgg agttcaacta cgccaaaatt 5940
tacaacgtgc aaaaccgtaa gatcgcgctc tctaacgtct acaccccggt taccgctaac 6000
atcttggacg ataacgtcta cgacattcag aacggtttca acatcccaaa gtcgaacctc 6060
aacgttttgt tcatgggtca aaacttgtcc cgcaaccccg ccctgcgtaa ggtgaaccca 6120
gagaacatgt tgtacctgtt caccaaattc tgccacaagg ccatcgacgg tcagtctcta 6180
gaccaaggag gatgggaact ccagcaaggt ggccagggtg gaggtgctgg caccctggac 6240
tgtcgcgaac tgctcgttaa gaacactgat ctcccattca ttggcgacat ctctgatgtg 6300
aaaacagaca ttttcctgcg taaggatatc aacgaggaaa cggaggtcat ctactaccct 6360
gacaacgtct cggttgatca ggttatcttg tcaaagaaca ccagtgaaca tggccaactg 6420
gacttgctgt accccctcaat tgattccgag agcgaaatcc tgccaggaga gaaccaggtt 6480
ttctacgaca acaggacaca aaacgtggat tacctcaaca gctactacta cctggagtcg 6540
cagaagctct ccgacaacgt cgaagatttc acatttacga gatcaatcga ggaggctttg 6600
gacaacagtg ccaaagtcta cacctacttc cctactctgg caaacaaggt gaacgcgggt 6660
gtccaaggcg gactcttctt gatgtgggct aacgacgttg tggaagattt cacaacgaac 6720
atcttgcgca aagacaccct ggataagatc agcgatgtct ctgccatcat tccatacatt 6780
ggcccggcac tgaacatctc taactcagtt cgccgtggca acttcactga ggcattcgcg 6840
gtcacaggag ttacgatcct cttggaggct ttcccggagt tcacaatccc cgcactgggc 6900
gcgttcgtta tctactccaa agtgcaggag cgcaacgaaa tcattaagac tatcgacaac 6960
tgcctggagc aaaggatcaa aagatggaag gattcgtacg aatggatgat gggtacctgg 7020
ctctcccgta tcattacgca gttcaacaac atcagctacc aaatgtacga ctctctcaac 7080
taccaggctg gtgccatcaa ggccaaaatt gacttggagt acaagaaata cagtggctcg 7140
gataaagaga acatcaagag tcaagtcgaa aacctgaaaa actcactcga cgttaagatc 7200
agtgaggcaa tgaacaacat caacaagttc attcgcgaat gttccgttac ctacctcttc 7260
aaaaacatgt tgccaaaggt catcgacgag ctgaacgaat ttgatcgtaa cactaaggcg 7320
aaactgatta acctcatcga ctcacacaac atcattttgg tgggcgaagt cgataagctg 7380
aaagccaagg tgaacaacag tttccagaac acaatccctt tcaacatttt ctcatacacg 7440
aacaacagtc tgctcaagga catcattaac gagtacttca acaacattaa cgatagcaaa 7500
atcctgtcac tgcagaaccg taagaacaca ctggtcgata ctagtggata caacgccgaa 7560
gtctctgagg aaggtgacgt gcagctgaac cctatcttcc ccttcgactt caaattgggc 7620
tccagcggag aggatagggg caaggtcatc gtcacccaga acgagaacat cgtctacaac 7680
tcaatgtacg aatccttcag catctctttc tggatcagga ttaacaagtg ggtgagcaac 7740
ctgcccggtt acacaatcat tgactctgtc aagaacaact caggttggag tatcggcatc 7800
atttctaact tcttggtctt caccctgaag cagaacgagg actcggaaca atccattaac 7860
ttctcatacg atatcagtaa caacgctcca ggttacaaca agtggttctt cgttaccgtg 7920
actaacaaca tgatgggtaa catgaaaatt tacatcaacg gcaagctcat tgacaccatc 7980
aaagtgaagg agttgactgg tattaacttc tccaaaacaa tcacgtttga aattaacaag 8040
atccctgaca ccggcctgat cacttcagac agtgataaca tcaacatgtg gattagggat 8100
ttctacatct tcgccaagga gctcgacgga aaggatatta acatcctctt caacagcttg 8160
cagtacacca acgtcgttaa agactactgg ggtaacgatt tgagatacaa caaggagtac 8220
tacatggtca acatcgacta cctgaacagg tacatgtacg ctaactcccg ccaaatcgtg 8280
ttcaacacca ggagaaacaa caacgacttc aacgagggtt acaaaatcat tatcaagcgc 8340
atccgtggca acaccaacga tactagggtg agaggtggcg acattctgta cttcgatatg 8400
actatcaaca acaaagccta caacttgttc atgaaaaacg agacaatgta cgccgacaac 8460
catagcacgg aggatattta cgcaatcgga ctgagggaac agacaaagga catcaacgat 8520
aacattatct tccagatcca acctatgaac aacacgtact actacgcttc gcaaatcttc 8580
aagtccaact tcaacggaga aaacatttcg ggtatctgtt ccattggcac ataccgcttc 8640
cgtctgggtg gtgactggta tcgtcacaac tacctcgttc ccaccgtgaa gcagggtaac 8700
tacgcttctt tgctggagtc gacttccacg cactggggat tcgttcctgt gtcagagggc 8760
gctggctacc cttacgatgt tcccgactac gctggttggg aactccagca aggtgcagga 8820
tggtcccacc ctcaattcga gaagggtgcc ggatggagtc acccacagtt cgagaaaggc 8880
gctggatgga gtcacccaca gttcgagaaa taattagttg atgcatagtt aattagatag 8940
ctcgaggcat gcggtaccaa gattggatct agatgcatag ttaattagat agctcgaggc 9000

```
atgcggtacc aagcttgtcg agaagtacta gaggatcata atcagccata ccacatttgt   9060

agaggtttta cttgctttaa aaaacctccc acacctcccc ctgaacctga aacataaaat   9120

gaatgcaatt gttgttgtta acttgtttat tgcagcttat aatggttaca aataaagcaa   9180

tagcatcaca aatttcacaa ataaagcatt tttttcactg cattctagtt gtggtttgtc   9240

caaactcatc aatgtatctt atcatgtctg gatctgatca ctgcttgagc ctaggagatc   9300

cgaaccagat aagtgaaatc tagttccaaa ctattttgtc atttttaatt ttcgtattag   9360

cttacgacgc tacacccagt tcccatctat tttgtcactc ttccctaaat aatccttaaa   9420

aactccattt ccacccctcc cagttcccaa ctattttgtc cgcccacagc ggggcatttt   9480

tcttcctgtt atgtttttaa tcaaacatcc tgccaactcc atgtgacaaa ccgtcatctt   9540

cggctacttt ttctctgtca cagaatgaaa atttttctgt catctcttcg ttattaatgt   9600

ttgtaattga ctgaatatca acgcttattt gcagcctgaa tggcgaatgg              9650
```

<210> SEQ ID NO 26
<211> LENGTH: 1607
<212> TYPE: PRT
<213> ORGANISM: Artificial
<220> FEATURE:
<223> OTHER INFORMATION: Fusion protein

<400> SEQUENCE: 26

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140

Glu Leu Ala Ser Lys Val Asp Met Val Trp Ile Val Gly Gly Ser Ser
145                 150                 155                 160

Val Tyr Gln Glu Ala Met Asn Gln Pro Gly His Leu Arg Leu Phe Val
                165                 170                 175

Thr Arg Ile Met Gln Glu Phe Glu Ser Asp Thr Phe Phe Pro Glu Ile
            180                 185                 190

Asp Leu Gly Lys Tyr Lys Leu Leu Pro Glu Tyr Pro Gly Val Leu Ser
        195                 200                 205

Glu Val Gln Glu Glu Lys Gly Ile Lys Tyr Lys Phe Glu Val Tyr Glu
    210                 215                 220

Lys Lys Asp Gly Ala Ser Gly Phe Ala Asn Glu Leu Gly Pro Arg Leu
225                 230                 235                 240

Met Gly Lys Gly Ala Gly Gly Gly Ala Gly Ala Gly Pro Ile Thr Ile
                245                 250                 255
```

```
Asn Asn Phe Asn Tyr Ser Asp Pro Val Asp Asn Lys Asn Ile Leu Tyr
            260                 265                 270

Leu Asp Thr His Leu Asn Thr Leu Ala Asn Glu Pro Glu Lys Ala Phe
        275                 280                 285

Arg Ile Thr Gly Asn Ile Trp Val Ile Pro Asp Arg Phe Ser Arg Asn
    290                 295                 300

Ser Asn Pro Asn Leu Asn Lys Pro Pro Arg Val Thr Ser Pro Lys Ser
305                 310                 315                 320

Gly Tyr Tyr Asp Pro Asn Tyr Leu Ser Thr Asp Ser Asp Lys Asp Pro
                325                 330                 335

Phe Leu Lys Glu Ile Ile Lys Leu Phe Lys Arg Ile Asn Ser Arg Glu
            340                 345                 350

Ile Gly Glu Glu Leu Ile Tyr Arg Leu Ser Thr Asp Ile Pro Phe Pro
        355                 360                 365

Gly Asn Asn Asn Thr Pro Ile Asn Thr Phe Asp Phe Asp Val Asp Phe
    370                 375                 380

Asn Ser Val Asp Val Lys Thr Arg Gln Gly Asn Asn Trp Val Lys Thr
385                 390                 395                 400

Gly Ser Ile Asn Pro Ser Val Ile Ile Thr Gly Pro Arg Glu Asn Ile
                405                 410                 415

Ile Asp Pro Glu Thr Ser Thr Phe Lys Leu Thr Asn Asn Thr Phe Ala
            420                 425                 430

Ala Gln Glu Gly Phe Gly Ala Leu Ser Ile Ile Ser Ile Ser Pro Arg
        435                 440                 445

Phe Met Leu Thr Tyr Ser Asn Ala Thr Asn Asp Val Gly Glu Gly Arg
    450                 455                 460

Phe Ser Lys Ser Glu Phe Cys Met Asp Pro Ile Leu Ile Leu Met His
465                 470                 475                 480

Ala Leu Asn Gly Ala Met His Asn Leu Tyr Gly Ile Ala Ile Pro Asn
                485                 490                 495

Asp Gln Thr Ile Ser Ser Val Thr Ser Asn Ile Phe Tyr Ser Gln Tyr
            500                 505                 510

Asn Val Lys Leu Glu Tyr Ala Glu Ile Tyr Ala Phe Gly Gly Pro Thr
        515                 520                 525

Ile Asp Leu Ile Pro Lys Ser Ala Arg Lys Tyr Phe Glu Glu Lys Ala
    530                 535                 540

Leu Asp Tyr Tyr Arg Ser Ile Ala Lys Arg Leu Asn Ser Ile Thr Thr
545                 550                 555                 560

Ala Asn Pro Ser Ser Phe Asn Lys Tyr Ile Gly Glu Tyr Lys Gln Lys
                565                 570                 575

Leu Ile Arg Lys Tyr Arg Phe Val Val Glu Ser Ser Gly Glu Val Thr
            580                 585                 590

Val Asn Arg Asn Lys Phe Val Glu Leu Tyr Asn Glu Leu Thr Gln Ile
        595                 600                 605

Phe Thr Glu Phe Asn Tyr Ala Lys Ile Tyr Asn Val Gln Asn Arg Lys
    610                 615                 620

Ile Ala Leu Ser Asn Val Tyr Thr Pro Val Thr Ala Asn Ile Leu Asp
625                 630                 635                 640

Asp Asn Val Tyr Asp Ile Gln Asn Gly Phe Asn Ile Pro Lys Ser Asn
                645                 650                 655

Leu Asn Val Leu Phe Met Gly Gln Asn Leu Ser Arg Asn Pro Ala Leu
            660                 665                 670
```

-continued

```
Arg Lys Val Asn Pro Glu Asn Met Leu Tyr Leu Phe Thr Lys Phe Cys
        675                 680                 685

His Lys Ala Ile Asp Gly Gln Ser Leu Asp Gln Gly Gly Trp Glu Leu
    690                 695                 700

Gln Gln Gly Gly Gln Gly Gly Gly Ala Gly Thr Leu Asp Cys Arg Glu
705                 710                 715                 720

Leu Leu Val Lys Asn Thr Asp Leu Pro Phe Ile Gly Asp Ile Ser Asp
                725                 730                 735

Val Lys Thr Asp Ile Phe Leu Arg Lys Asp Ile Asn Glu Glu Thr Glu
            740                 745                 750

Val Ile Tyr Tyr Pro Asp Asn Val Ser Val Asp Gln Val Ile Leu Ser
        755                 760                 765

Lys Asn Thr Ser Glu His Gly Gln Leu Asp Leu Leu Tyr Pro Ser Ile
    770                 775                 780

Asp Ser Glu Ser Glu Ile Leu Pro Gly Glu Asn Gln Val Phe Tyr Asp
785                 790                 795                 800

Asn Arg Thr Gln Asn Val Asp Tyr Leu Asn Ser Tyr Tyr Tyr Leu Glu
                805                 810                 815

Ser Gln Lys Leu Ser Asp Asn Val Glu Asp Phe Thr Phe Thr Arg Ser
            820                 825                 830

Ile Glu Glu Ala Leu Asp Asn Ser Ala Lys Val Tyr Thr Tyr Phe Pro
        835                 840                 845

Thr Leu Ala Asn Lys Val Asn Ala Gly Val Gln Gly Gly Leu Phe Leu
    850                 855                 860

Met Trp Ala Asn Asp Val Val Glu Asp Phe Thr Thr Asn Ile Leu Arg
865                 870                 875                 880

Lys Asp Thr Leu Asp Lys Ile Ser Asp Val Ser Ala Ile Ile Pro Tyr
                885                 890                 895

Ile Gly Pro Ala Leu Asn Ile Ser Asn Ser Val Arg Arg Gly Asn Phe
            900                 905                 910

Thr Glu Ala Phe Ala Val Thr Gly Val Thr Ile Leu Leu Glu Ala Phe
        915                 920                 925

Pro Glu Phe Thr Ile Pro Ala Leu Gly Ala Phe Val Ile Tyr Ser Lys
    930                 935                 940

Val Gln Glu Arg Asn Glu Ile Ile Lys Thr Ile Asp Asn Cys Leu Glu
945                 950                 955                 960

Gln Arg Ile Lys Arg Trp Lys Asp Ser Tyr Glu Trp Met Met Gly Thr
                965                 970                 975

Trp Leu Ser Arg Ile Ile Thr Gln Phe Asn Asn Ile Ser Tyr Gln Met
            980                 985                 990

Tyr Asp Ser Leu Asn Tyr Gln Ala  Gly Ala Ile Lys Ala  Lys Ile Asp
        995                 1000                 1005

Leu Glu  Tyr Lys Lys Tyr Ser  Gly Ser Asp Lys Glu  Asn Ile Lys
    1010                 1015                 1020

Ser Gln  Val Glu Asn Leu Lys  Asn Ser Leu Asp Val  Lys Ile Ser
    1025                 1030                 1035

Glu Ala  Met Asn Asn Ile Asn  Lys Phe Ile Arg Glu  Cys Ser Val
    1040                 1045                 1050

Thr Tyr  Leu Phe Lys Asn Met  Leu Pro Lys Val Ile  Asp Glu Leu
    1055                 1060                 1065

Asn Glu  Phe Asp Arg Asn Thr  Lys Ala Lys Leu Ile  Asn Leu Ile
    1070                 1075                 1080

Asp Ser  His Asn Ile Ile Leu  Val Gly Glu Val Asp  Lys Leu Lys
```

-continued

```
    1085                1090                1095

Ala Lys  Val Asn Asn Ser Phe  Gln Asn Thr Ile Pro  Phe Asn Ile
    1100                1105                1110

Phe Ser  Tyr Thr Asn Asn Ser  Leu Leu Lys Asp Ile  Ile Asn Glu
    1115                1120                1125

Tyr Phe  Asn Asn Ile Asn Asp  Ser Lys Ile Leu Ser  Leu Gln Asn
    1130                1135                1140

Arg Lys  Asn Thr Leu Val Asp  Thr Ser Gly Tyr Asn  Ala Glu Val
    1145                1150                1155

Ser Glu  Glu Gly Asp Val Gln  Leu Asn Pro Ile Phe  Pro Phe Asp
    1160                1165                1170

Phe Lys  Leu Gly Ser Ser Gly  Glu Asp Arg Gly Lys  Val Ile Val
    1175                1180                1185

Thr Gln  Asn Glu Asn Ile Val  Tyr Asn Ser Met Tyr  Glu Ser Phe
    1190                1195                1200

Ser Ile  Ser Phe Trp Ile Arg  Ile Asn Lys Trp Val  Ser Asn Leu
    1205                1210                1215

Pro Gly  Tyr Thr Ile Ile Asp  Ser Val Lys Asn Asn  Ser Gly Trp
    1220                1225                1230

Ser Ile  Gly Ile Ile Ser Asn  Phe Leu Val Phe Thr  Leu Lys Gln
    1235                1240                1245

Asn Glu  Asp Ser Glu Gln Ser  Ile Asn Phe Ser Tyr  Asp Ile Ser
    1250                1255                1260

Asn Asn  Ala Pro Gly Tyr Asn  Lys Trp Phe Phe Val  Thr Val Thr
    1265                1270                1275

Asn Asn  Met Met Gly Asn Met  Lys Ile Tyr Ile Asn  Gly Lys Leu
    1280                1285                1290

Ile Asp  Thr Ile Lys Val Lys  Glu Leu Thr Gly Ile  Asn Phe Ser
    1295                1300                1305

Lys Thr  Ile Thr Phe Glu Ile  Asn Lys Ile Pro Asp  Thr Gly Leu
    1310                1315                1320

Ile Thr  Ser Asp Ser Asp Asn  Ile Asn Met Trp Ile  Arg Asp Phe
    1325                1330                1335

Tyr Ile  Phe Ala Lys Glu Leu  Asp Gly Lys Asp Ile  Asn Ile Leu
    1340                1345                1350

Phe Asn  Ser Leu Gln Tyr Thr  Asn Val Val Lys Asp  Tyr Trp Gly
    1355                1360                1365

Asn Asp  Leu Arg Tyr Asn Lys  Glu Tyr Tyr Met Val  Asn Ile Asp
    1370                1375                1380

Tyr Leu  Asn Arg Tyr Met Tyr  Ala Asn Ser Arg Gln  Ile Val Phe
    1385                1390                1395

Asn Thr  Arg Arg Asn Asn Asn  Asp Phe Asn Glu Gly  Tyr Lys Ile
    1400                1405                1410

Ile Ile  Lys Arg Ile Arg Gly  Asn Thr Asn Asp Thr  Arg Val Arg
    1415                1420                1425

Gly Gly  Asp Ile Leu Tyr Phe  Asp Met Thr Ile Asn  Asn Lys Ala
    1430                1435                1440

Tyr Asn  Leu Phe Met Lys Asn  Glu Thr Met Tyr Ala  Asp Asn His
    1445                1450                1455

Ser Thr  Glu Asp Ile Tyr Ala  Ile Gly Leu Arg Glu  Gln Thr Lys
    1460                1465                1470

Asp Ile  Asn Asp Asn Ile Ile  Phe Gln Ile Gln Pro  Met Asn Asn
    1475                1480                1485
```

Thr Tyr Tyr Tyr Ala Ser Gln Ile Phe Lys Ser Asn Phe Asn Gly
1490 1495 1500

Glu Asn Ile Ser Gly Ile Cys Ser Ile Gly Thr Tyr Arg Phe Arg
1505 1510 1515

Leu Gly Gly Asp Trp Tyr Arg His Asn Tyr Leu Val Pro Thr Val
1520 1525 1530

Lys Gln Gly Asn Tyr Ala Ser Leu Leu Glu Ser Thr Ser Thr His
1535 1540 1545

Trp Gly Phe Val Pro Val Ser Glu Gly Ala Gly Tyr Pro Tyr Asp
1550 1555 1560

Val Pro Asp Tyr Ala Gly Trp Glu Leu Gln Gln Gly Ala Gly Trp
1565 1570 1575

Ser His Pro Gln Phe Glu Lys Gly Ala Gly Trp Ser His Pro Gln
1580 1585 1590

Phe Glu Lys Gly Ala Gly Trp Ser His Pro Gln Phe Glu Lys
1595 1600 1605

<210> SEQ ID NO 27
<211> LENGTH: 546
<212> TYPE: DNA
<213> ORGANISM: Artificial
<220> FEATURE:
<223> OTHER INFORMATION: DNA construct for molecular construction of fusion proteins

<400> SEQUENCE: 27
gacgtcggct gggagctgca aggcgccggc gagcagaaac tcatcagcga agaagatttg 60
ggtgcggccg ctggctcagg aggtggcagt caggcgcacg tgcaactgca gcagtctgga 120
ggaggcttgg tgcagcctgg gggttccctg cgcctgtcat gtgcagcctc tggaagcatc 180
ttcagtattt acgctatggg ctggtacagg caggctcctg gcaagcaacg tgaactggtt 240
gctgccatct ccagctacgg tagtaccaac tacgctgatt cggtcaaggg caggttcacc 300
atctcccgcg acaatgccaa gaataccgtc tatttgcaaa tgaactctct gaaacctgag 360
gatacggccg tctactactg caacgctgac attgctacta tgaccgcggt aggcggattc 420
gactactggg gacagggaac tcaggtgacg gtctcttccg aacctaagac ccctaaaccc 480
caaggggccg gccagggtgc tggtgctgga ccgatcacca tcaacaactt caattactcg 540
gatccg 546

<210> SEQ ID NO 28
<211> LENGTH: 182
<212> TYPE: PRT
<213> ORGANISM: Artificial
<220> FEATURE:
<223> OTHER INFORMATION: Fusion protein construct

<400> SEQUENCE: 28

Asp Val Gly Trp Glu Leu Gln Gly Ala Gly Glu Gln Lys Leu Ile Ser
1 5 10 15

Glu Glu Asp Leu Gly Ala Ala Ala Gly Ser Gly Gly Gly Ser Gln Ala
20 25 30

His Val Gln Leu Gln Gln Ser Gly Gly Gly Leu Val Gln Pro Gly Gly
35 40 45

Ser Leu Arg Leu Ser Cys Ala Ala Ser Gly Ser Ile Phe Ser Ile Tyr
50 55 60

Ala Met Gly Trp Tyr Arg Gln Ala Pro Gly Lys Gln Arg Glu Leu Val

```
65                  70                  75                  80

Ala Ala Ile Ser Ser Tyr Gly Ser Thr Asn Tyr Ala Asp Ser Val Lys
                85                  90                  95

Gly Arg Phe Thr Ile Ser Arg Asp Asn Ala Lys Asn Thr Val Tyr Leu
            100                 105                 110

Gln Met Asn Ser Leu Lys Pro Glu Asp Thr Ala Val Tyr Tyr Cys Asn
        115                 120                 125

Ala Asp Ile Ala Thr Met Thr Ala Val Gly Gly Phe Asp Tyr Trp Gly
    130                 135                 140

Gln Gly Thr Gln Val Thr Val Ser Ser Glu Pro Lys Thr Pro Lys Pro
145                 150                 155                 160

Gln Gly Ala Gly Gln Gly Ala Gly Ala Gly Pro Ile Thr Ile Asn Asn
                165                 170                 175

Phe Asn Tyr Ser Asp Pro
            180
```

<210> SEQ ID NO 29
<211> LENGTH: 957
<212> TYPE: DNA
<213> ORGANISM: Artificial
<220> FEATURE:
<223> OTHER INFORMATION: DNA construct for molecular construction of fusion proteins

<400> SEQUENCE: 29

```
gacgtcggct gggagctgca aggcgccggc gagcagaaac tcatcagcga agaagatttg     60

ggtgcggccg ctcaggttca actcgtggag agtggtggcg gactggtgca atccggtggc    120

agcctgaggc tctcctgcgc tgcctctgga tcaatcgaca gcctgtacca catgggttgg    180

tacaggcagg ctcccggcaa ggagagggaa ctcgtcgcca gagttcaaga cggaggtagt    240

acagcataca aggattcggt caaaggtcgc ttcaccattt ctcgcgactt cagtcgttcg    300

actatgtact tgcagatgaa ctcactgaag cctgaggata cagccatcta ctactgtgca    360

gcgaaatcta ccatttcaac tccactgtct tggggccagg gaacacaagt gacggtctcc    420

agcgaaccga agacgcctaa accccaatct tcaggcggag gtgcggccgc ttggctcagg    480

aggtggcagt caactccagc tcgttgagtc cggtggcgga atggtgcaac ctggtggctc    540

tttgaggctg tcatgcgctg cagtggattc accttctcga cttacgacat gtcctgggtg    600

cgtcaggcac ctggaaaagg tcccgaatgg gtcagcatca ttaacgctgg aggtggcagc    660

acatactacg cagcgtctgt taagggaagg ttcgctatct ccagagacaa cgccaaaaac    720

accctctact tgcaaatgaa caacctgaag cccgaggata ctgctctcta ctactgtgct    780

cgcgtcgcct catactactg ccgtggctac gtttgtagtc ctcccgagtt cgactactgg    840

ggccagggaa cacaagtgac ggtctccagc gaaccaaaga caccaaaacc acagggggcc    900

ggccagggtg ctggtgctgg accgatcacc atcaacaact tcaattactc ggatccg       957
```

<210> SEQ ID NO 30
<211> LENGTH: 315
<212> TYPE: PRT
<213> ORGANISM: Artificial
<220> FEATURE:
<223> OTHER INFORMATION: Fusion protein construct

<400> SEQUENCE: 30

```
Asp Val Gly Trp Glu Leu Gln Gly Ala Gly Glu Gln Lys Leu Ile Ser
1               5                   10                  15
```

-continued

```
Glu Glu Asp Leu Gly Ala Ala Ala Gln Val Gln Leu Val Glu Ser Gly
            20                  25                  30

Gly Gly Leu Val Gln Ser Gly Gly Ser Leu Arg Leu Ser Cys Ala Ala
        35                  40                  45

Ser Gly Ser Ile Asp Ser Leu Tyr His Met Gly Trp Tyr Arg Gln Ala
    50                  55                  60

Pro Gly Lys Glu Arg Glu Leu Val Ala Arg Val Gln Asp Gly Gly Ser
65                  70                  75                  80

Thr Ala Tyr Lys Asp Ser Val Lys Gly Arg Phe Thr Ile Ser Arg Asp
                85                  90                  95

Phe Ser Arg Ser Thr Met Tyr Leu Gln Met Asn Ser Leu Lys Pro Glu
            100                 105                 110

Asp Thr Ala Ile Tyr Tyr Cys Ala Ala Lys Ser Thr Ile Ser Thr Pro
        115                 120                 125

Leu Ser Trp Gly Gln Gly Thr Gln Val Thr Val Ser Ser Glu Pro Lys
    130                 135                 140

Thr Pro Lys Pro Gln Ser Ser Gly Gly Gly Ala Ala Ala Trp Leu Arg
145                 150                 155                 160

Arg Trp Gln Ser Thr Pro Ala Arg Val Arg Trp Arg Asn Gly Ala Thr
                165                 170                 175

Trp Trp Leu Phe Glu Ala Val Met Arg Cys Gln Trp Ile His Leu Leu
            180                 185                 190

Asp Leu Arg His Val Leu Gly Ala Ser Gly Thr Trp Lys Arg Ser Arg
        195                 200                 205

Met Gly Gln His His Arg Trp Arg Trp Gln His Ile Leu Arg Ser Val
    210                 215                 220

Cys Gly Lys Val Arg Tyr Leu Gln Arg Gln Arg Gln Lys His Pro Leu
225                 230                 235                 240

Leu Ala Asn Glu Gln Pro Glu Ala Arg Gly Tyr Cys Ser Leu Leu Leu
                245                 250                 255

Cys Ser Arg Arg Leu Ile Leu Leu Pro Trp Leu Arg Leu Ser Ser Arg
            260                 265                 270

Val Arg Leu Leu Gly Pro Gly Asn Thr Ser Asp Gly Leu Gln Arg Thr
        275                 280                 285

Lys Asp Thr Lys Thr Thr Gly Gly Arg Pro Gly Cys Trp Cys Trp Thr
    290                 295                 300

Asp His His Gln Gln Leu Gln Leu Leu Gly Ser
305                 310                 315
```

<210> SEQ ID NO 31
<211> LENGTH: 930
<212> TYPE: DNA
<213> ORGANISM: Artificial
<220> FEATURE:
<223> OTHER INFORMATION: DNA construct for molecular construction of fusion proteins

<400> SEQUENCE: 31

```
gacgtcggct gggagctgca aggcgccggc gagcagaaac tcatcagcga agaagatttg      60

ggtgcggccg ctcaggttca actcgtggag agtggtggcg gactggtgca atccggtggc     120

agcctgaggc tctcctgcgc tgcctctgga tcaatcgaca gcctgtacca catgggttgg     180

tacaggcagg ctcccggcaa ggagagggaa ctcgtcgcca gagttcaaga cggaggtagt     240

acagcataca aggattcggt caaaggtcgc ttcaccattt ctcgcgactt cagtcgttcg     300

actatgtact tgcagatgaa ctcactgaag cctgaggata cagccatcta ctactgtgca     360
```

gcgaaatcta ccatttcaac tccactgtct tggggccagg gaacacaagt gacggtctcc 420
agcgaaccga agacgcctaa accccaatct tcaggcggag gtgcggccgc tggctcagga 480
ggtggcagtc aggtgcagct ggtggaatcc ggtggtggac tggtccagcc tggtggttcc 540
ctgcgtctgt cctgcgctgc ttccggtttc cccttccacg cttactacat gtcctgggtc 600
cgccaggctc ctggcaaggg attggaatgg gtgtcccaca tcggcaacgg tggtatcatc 660
acccgttacg ctgactccgt gaagggccgt ttcaccatct cccgtgacaa cgctaagaac 720
accctgtacc tgcagatgac caacctgaag cccgaggaca ccgctctgta ctactgcacc 780
ctgggcaccc gtgacgacct gggtcctgaa cgtggccagg gaacccaagt gaccgtgtcc 840
tccgagccca agacccccaa gcctcaaggg gccggccagg gtgctggtgc tggaccgatc 900
accatcaaca acttcaatta ctcggatccg 930

<210> SEQ ID NO 32
<211> LENGTH: 310
<212> TYPE: PRT
<213> ORGANISM: Artificial
<220> FEATURE:
<223> OTHER INFORMATION: Fusion protein construct

<400> SEQUENCE: 32

Asp Val Gly Trp Glu Leu Gln Gly Ala Gly Glu Gln Lys Leu Ile Ser
1 5 10 15

Glu Glu Asp Leu Gly Ala Ala Ala Gln Val Gln Leu Val Glu Ser Gly
20 25 30

Gly Gly Leu Val Gln Ser Gly Gly Ser Leu Arg Leu Ser Cys Ala Ala
35 40 45

Ser Gly Ser Ile Asp Ser Leu Tyr His Met Gly Trp Tyr Arg Gln Ala
50 55 60

Pro Gly Lys Glu Arg Glu Leu Val Ala Arg Val Gln Asp Gly Gly Ser
65 70 75 80

Thr Ala Tyr Lys Asp Ser Val Lys Gly Arg Phe Thr Ile Ser Arg Asp
85 90 95

Phe Ser Arg Ser Thr Met Tyr Leu Gln Met Asn Ser Leu Lys Pro Glu
100 105 110

Asp Thr Ala Ile Tyr Tyr Cys Ala Ala Lys Ser Thr Ile Ser Thr Pro
115 120 125

Leu Ser Trp Gly Gln Gly Thr Gln Val Thr Val Ser Ser Glu Pro Lys
130 135 140

Thr Pro Lys Pro Gln Ser Ser Gly Gly Gly Ala Ala Ala Gly Ser Gly
145 150 155 160

Gly Gly Ser Gln Val Gln Leu Val Glu Ser Gly Gly Gly Leu Val Gln
165 170 175

Pro Gly Gly Ser Leu Arg Leu Ser Cys Ala Ala Ser Gly Phe Pro Phe
180 185 190

His Ala Tyr Tyr Met Ser Trp Val Arg Gln Ala Pro Gly Lys Gly Leu
195 200 205

Glu Trp Val Ser His Ile Gly Asn Gly Gly Ile Ile Thr Arg Tyr Ala
210 215 220

Asp Ser Val Lys Gly Arg Phe Thr Ile Ser Arg Asp Asn Ala Lys Asn
225 230 235 240

Thr Leu Tyr Leu Gln Met Thr Asn Leu Lys Pro Glu Asp Thr Ala Leu
245 250 255

-continued

```
Tyr Tyr Cys Thr Leu Gly Thr Arg Asp Asp Leu Gly Pro Glu Arg Gly
            260                 265                 270

Gln Gly Thr Gln Val Thr Val Ser Ser Glu Pro Lys Thr Pro Lys Pro
        275                 280                 285

Gln Gly Ala Gly Gln Gly Ala Gly Ala Gly Pro Ile Thr Ile Asn Asn
    290                 295                 300

Phe Asn Tyr Ser Asp Pro
305                 310
```

<210> SEQ ID NO 33
<211> LENGTH: 891
<212> TYPE: DNA
<213> ORGANISM: Artificial
<220> FEATURE:
<223> OTHER INFORMATION: DNA construct for molecular construction of fusion proteins

<400> SEQUENCE: 33

```
gacgtcggct gggagctgca aggcgccggc ggtgcggccg ctcaggttca gttggtggaa     60

tcaggcggcg gctcagttca agcaggcggt tcactcaggc tctcgtgtgc ggcaagcggt    120

atcgactcgt ccagctactg catgggatgg ttcaggcaaa ggccaggaaa ggagagggaa    180

ggtgttgctc gtatcaacgg actgggtggc gttaagacag catacgcgga cagtgtgaaa    240

gataggttca caatttcgag agacaacgca gagaacacgg tctacttgca gatgaactct    300

ctgaagcccg aagatacggc gatctactac tgcgctgcca aattctcacc cggatactgt    360

ggaggtagct ggtctaactt cggttactgg ggtcaaggca cccaagtgac tgtctcttca    420

ggcggaggtg cggccgctgg ctcaggaggt ggcagtcagg tgcagctgca ggagtcggga    480

ggtggctccg tccaagcagg aggtagcctg cgcctctctt gcgcagcgtc aggtatcgac    540

agttcgtcct actgtatggg ctggttcagg cagcgtcctg gcaaggagag ggaaggagtg    600

gcacgtatca acggtctcgg cggagtcaag acagcttacg ccgactccgt taaagatagg    660

ttcaccatta gccgcgacaa cgctgagaac actgtctacc tccaaatgaa cagtttgaag    720

ccggaagata ctgccattta ctactgtgct gccaaattct caccgggcta ctgtggagga    780

agctggtcta acttcggcta ctggggacaa ggaactcaag tcaccgttgg ggccggccag    840

ggtgctggtg ctggaccgat caccatcaac aacttcaatt actcggatcc g             891
```

<210> SEQ ID NO 34
<211> LENGTH: 297
<212> TYPE: PRT
<213> ORGANISM: Artificial
<220> FEATURE:
<223> OTHER INFORMATION: Fusion protein construct

<400> SEQUENCE: 34

```
Asp Val Gly Trp Glu Leu Gln Gly Ala Gly Gly Ala Ala Ala Gln Val
1               5                   10                  15

Gln Leu Val Glu Ser Gly Gly Gly Ser Val Gln Ala Gly Gly Ser Leu
            20                  25                  30

Arg Leu Ser Cys Ala Ala Ser Gly Ile Asp Ser Ser Ser Tyr Cys Met
        35                  40                  45

Gly Trp Phe Arg Gln Arg Pro Gly Lys Glu Arg Glu Gly Val Ala Arg
    50                  55                  60

Ile Asn Gly Leu Gly Gly Val Lys Thr Ala Tyr Ala Asp Ser Val Lys
65                  70                  75                  80

Asp Arg Phe Thr Ile Ser Arg Asp Asn Ala Glu Asn Thr Val Tyr Leu
```

```
                85                  90                  95

Gln Met Asn Ser Leu Lys Pro Glu Asp Thr Ala Ile Tyr Tyr Cys Ala
            100                 105                 110

Ala Lys Phe Ser Pro Gly Tyr Cys Gly Gly Ser Trp Ser Asn Phe Gly
        115                 120                 125

Tyr Trp Gly Gln Gly Thr Gln Val Thr Val Ser Ser Gly Gly Gly Ala
    130                 135                 140

Ala Ala Gly Ser Gly Gly Gly Ser Gln Val Gln Leu Gln Glu Ser Gly
145                 150                 155                 160

Gly Gly Ser Val Gln Ala Gly Gly Ser Leu Arg Leu Ser Cys Ala Ala
                165                 170                 175

Ser Gly Ile Asp Ser Ser Ser Tyr Cys Met Gly Trp Phe Arg Gln Arg
            180                 185                 190

Pro Gly Lys Glu Arg Glu Gly Val Ala Arg Ile Asn Gly Leu Gly Gly
        195                 200                 205

Val Lys Thr Ala Tyr Ala Asp Ser Val Lys Asp Arg Phe Thr Ile Ser
    210                 215                 220

Arg Asp Asn Ala Glu Asn Thr Val Tyr Leu Gln Met Asn Ser Leu Lys
225                 230                 235                 240

Pro Glu Asp Thr Ala Ile Tyr Tyr Cys Ala Ala Lys Phe Ser Pro Gly
                245                 250                 255

Tyr Cys Gly Gly Ser Trp Ser Asn Phe Gly Tyr Trp Gly Gln Gly Thr
            260                 265                 270

Gln Val Thr Val Gly Ala Gly Gln Gly Ala Gly Ala Gly Pro Ile Thr
        275                 280                 285

Ile Asn Asn Phe Asn Tyr Ser Asp Pro
    290                 295
```

<210> SEQ ID NO 35
<211> LENGTH: 9506
<212> TYPE: DNA
<213> ORGANISM: Artificial
<220> FEATURE:
<223> OTHER INFORMATION: DNA construct for molecular construction of fusion proteins

<400> SEQUENCE: 35

```
gacgcgccct gtagcggcgc attaagcgcg gcgggtgtgg tggttacgcg cagcgtgacc      60

gctacacttg ccagcgccct agcgcccgct cctttcgctt tcttcccttc ctttctcgcc     120

acgttcgccg gctttccccg tcaagctcta aatcgggggc tccctttagg gttccgattt     180

agtgctttac ggcacctcga ccccaaaaaa cttgattagg gtgatggttc acgtagtggg     240

ccatcgccct gatagacggt ttttcgccct ttgacgttgg agtccacgtt ctttaatagt     300

ggactcttgt tccaaactgg aacaacactc aaccctatct cggtctattc ttttgattta     360

taagggattt tgccgatttc ggcctattgg ttaaaaaatg agctgattta acaaaaattt     420

aacgcgaatt ttaacaaaat attaacgttt acaatttcag gtggcacttt tcggggaaat     480

gtgcgcggaa cccctatttg tttatttttc taaatacatt caaatatgta tccgctcatg     540

agacaataac cctgataaat gcttcaataa tattgaaaaa ggaagagtat gagtattcaa     600

catttccgtg tcgcccttat tccctttttt gcggcatttt gccttcctgt ttttgctcac     660

ccagaaacgc tggtgaaagt aaaagatgct gaagatcagt tgggtgcacg agtgggttac     720

atcgaactgg atctcaacag cggtaagatc cttgagagtt ttcgccccga agaacgtttt     780

ccaatgatga gcacttttaa agttctgcta tgtggcgcgg tattatcccg tattgacgcc     840
```

-continued

```
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
```

ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatctcgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtcggc 4200
tgggagctgc aaggcgccgg cgagcagaaa ctcatcagcg aagaagattt gggtgcggcc 4260
gctggctcag gaggtggcag tcaggcgcac gtgcaactgc agcagtctgg aggaggcttg 4320
gtgcagcctg gggggttccct gcgcctgtca tgtgcagcct ctggaagcat cttcagtatt 4380
tacgctatgg gctggtacag gcaggctcct ggcaagcaac gtgaactggt tgctgccatc 4440
tccagctacg gtagtaccaa ctacgctgat tcggtcaagg gcaggttcac catctcccgc 4500
gacaatgcca agaataccgt ctatttgcaa atgaactctc tgaaacctga ggatacggcc 4560
gtctactact gcaacgctga cattgctact atgaccgcgg taggcggatt cgactactgg 4620
ggacagggaa ctcaggtgac ggtctcttcc gaacctaaga cccctaaacc ccaaggggcc 4680
ggccagggtg ctggtgctgg accgatcacc atcaacaact tcaattactc ggatccggtg 4740
gataacaaga acatcctcta cttggacaca cacttgaaca cgctggctaa cgagcctgaa 4800
aaagctttca ggatcaccgg caacatttgg gtcattccgg ataggttcag cagaaactct 4860
aaccctaact tgaacaaacc tcccagagtg acctcaccta agagtggata ctacgacccc 4920
aactacctct cgactgactc cgataaagac cccttcctga aggagatcat taaactcttc 4980
aagcgcatca actctcgtga aattggcgag gaattgatct accgcctgag tacagacatc 5040
ccattcccgg gtaacaacaa caccccaatc aacactttcg atttcgatgt cgatttcaac 5100
tcagtggatg tcaaaaccag gcagggaaac aactgggtga agactggtag catcaaccca 5160
tctgtcatca ttactggccc gagagagaac atcattgacc ctgaaacctc cactttcaag 5220
ctgacaaaca acacgttcgc tgctcaggaa ggcttcggag cgttgagcat catttctatc 5280
tcacctcgct tcatgctgac atactctaac gctacgaacg acgtgggaga gggccgtttc 5340
agtaagtctg aattctgcat ggaccctatt ctgatcctca tgcacgctct caacggcgcc 5400
atgcacaact tgtacggaat tgctatcccc aacgaccaga ccatttccag cgtgactagc 5460
aacatcttct actctcaata caacgtcaag ctggagtacg cagaaatcta cgctttcggt 5520
ggcccaacca ttgacttgat cccgaaatca gctcgtaagt atttcgaaga aaaagcgctg 5580

```
gattattaca ggtcgattgc taagagactc aactccatca ccactgctaa cccctcttca   5640
ttcaacaagt acattggaga atacaagcag aaactgatcc gcaagtaccg tttcgtggtc   5700
gagagttcgg gtgaagttac tgtgaaccgc aacaagttcg tcgagctgta caacgaattg   5760
acacaaatct tcacggagtt caactacgcc aaaatttaca acgtgcaaaa ccgtaagatc   5820
gcgctctcta acgtctacac cccggttacc gctaacatct tggacgataa cgtctacgac   5880
attcagaacg gtttcaacat cccaaagtcg aacctcaacg ttttgttcat gggtcaaaac   5940
ttgtcccgca accccgccct gcgtaaggtg aacccagaga acatgttgta cctgttcacc   6000
aaattctgcc acaaggccat cgacggtcag tctctagacc aaggaggatg ggaactccag   6060
caaggtggcc agggtggagg tgctggcacc ctggactgtc gcgaactgct cgttaagaac   6120
actgatctcc cattcattgg cgacatctct gatgtgaaaa cagacatttt cctgcgtaag   6180
gatatcaacg aggaaacgga ggtcatctac taccctgaca acgtctcggt tgatcaggtt   6240
atcttgtcaa agaacaccag tgaacatggc caactggact tgctgtaccc ctcaattgat   6300
tccgagagcg aaatcctgcc aggagagaac caggttttct acgacaacag gacacaaaac   6360
gtggattacc tcaacagcta ctactacctg gagtcgcaga agctctccga caacgtcgaa   6420
gatttcacat ttacgagatc aatcgaggag gctttggaca acagtgccaa agtctacacc   6480
tacttcccta ctctggcaaa caaggtgaac gcgggtgtcc aaggcggact cttcttgatg   6540
tgggctaacg acgttgtgga agatttcaca acgaacatct tgcgcaaaga caccctggat   6600
aagatcagcg atgtctctgc catcattcca tacattggcc cggcactgaa catctctaac   6660
tcagttcgcc gtggcaactt cactgaggca ttcgcggtca caggagttac gatcctcttg   6720
gaggctttcc cggagttcac aatccccgca ctgggcgcgt tcgttatcta ctccaaagtg   6780
caggagcgca acgaaatcat taagactatc gacaactgcc tggagcaaag gatcaaaaga   6840
tggaaggatt cgtacgaatg gatgatgggt acctggctct cccgtatcat tacgcagttc   6900
aacaacatca gctaccaaat gtacgactct ctcaactacc aggctggtgc catcaaggcc   6960
aaaattgact tggagtacaa gaaatacagt ggctcggata aagagaacat caagagtcaa   7020
gtcgaaaacc tgaaaaactc actcgacgtt aagatcagtg aggcaatgaa caacatcaac   7080
aagttcattc gcgaatgttc cgttacctac ctcttcaaaa acatgttgcc aaaggtcatc   7140
gacgagctga acgaatttga tcgtaacact aaggcgaaac tgattaacct catcgactca   7200
cacaacatca ttttggtggg cgaagtcgat aagctgaaag ccaaggtgaa caacagtttc   7260
cagaacacaa tccctttcaa cattttctca tacacgaaca acagtctgct caaggacatc   7320
attaacgagt acttcaacaa cattaacgat agcaaaatcc tgtcactgca gaaccgtaag   7380
aacacactgg tcgatactag tggatacaac gccgaagtct ctgaggaagg tgacgtgcag   7440
ctgaacccta tcttcccctt cgacttcaaa ttgggctcca gcggagagga taggggcaag   7500
gtcatcgtca cccagaacga gaacatcgtc tacaactcaa tgtacgaatc cttcagcatc   7560
tctttctgga tcaggattaa caagtgggtg agcaacctgc ccggttacac aatcattgac   7620
tctgtcaaga acaactcagg ttggagtatc ggcatcattt ctaacttctt ggtcttcacc   7680
ctgaagcaga acgaggactc ggaacaatcc attaacttct catacgatat cagtaacaac   7740
gctccaggtt acaacaagtg gttcttcgtt accgtgacta acaacatgat gggtaacatg   7800
aaaatttaca tcaacggcaa gctcattgac accatcaaag tgaaggagtt gactggtatt   7860
aacttctcca aaacaatcac gtttgaaatt aacaagatcc ctgacaccgg cctgatcact   7920
```

```
tcagacagtg ataacatcaa catgtggatt agggatttct acatcttcgc caaggagctc   7980

gacggaaagg atattaacat cctcttcaac agcttgcagt acaccaacgt cgttaaagac   8040

tactggggta acgatttgag atacaacaag gagtactaca tggtcaacat cgactacctg   8100

aacaggtaca tgtacgctaa ctcccgccaa atcgtgttca acaccaggag aaacaacaac   8160

gacttcaacg agggttacaa aatcattatc aagcgcatcc gtggcaacac caacgatact   8220

agggtgagag gtggcgacat tctgtacttc gatatgacta tcaacaacaa agcctacaac   8280

ttgttcatga aaaacgagac aatgtacgcc gacaaccata gcacggagga tatttacgca   8340

atcggactga gggaacagac aaaggacatc aacgataaca ttatcttcca gatccaacct   8400

atgaacaaca cgtactacta cgcttcgcaa atcttcaagt ccaacttcaa cggagaaaac   8460

atttcgggta tctgttccat tggcacatac cgcttccgtc tgggtggtga ctggtatcgt   8520

cacaactacc tcgttcccac cgtgaagcag ggtaactacg cttctttgct ggagtcgact   8580

tccacgcact ggggattcgt tcctgtgtca gagggcgctg gctaccctta cgatgttccc   8640

gactacgctg gttgggaact ccagcaaggt gcaggatggt cccaccctca attcgagaag   8700

ggtgccggat ggagtcaccc acagttcgag aaaggcgctg gatggagtca cccacagttc   8760

gagaaataat tagttgatgc atagttaatt agatagctcg aggcatgcgg taccaagatt   8820

ggatctagat gcatagttaa ttagatagct cgaggcatgc ggtaccaagc ttgtcgagaa   8880

gtactagagg atcataatca gccataccac atttgtagag gttttacttg ctttaaaaaa   8940

cctcccacac ctccccctga acctgaaaca taaaatgaat gcaattgttg ttgttaactt   9000

gtttattgca gcttataatg gttacaaata aagcaatagc atcacaaatt tcacaaataa   9060

agcatttttt tcactgcatt ctagttgtgg tttgtccaaa ctcatcaatg tatcttatca   9120

tgtctggatc tgatcactgc ttgagcctag gagatccgaa ccagataagt gaaatctagt   9180

tccaaactat tttgtcattt ttaattttcg tattagctta cgacgctaca cccagttccc   9240

atctattttg tcactcttcc ctaaataatc cttaaaaact ccatttccac ccctcccagt   9300

tcccaactat tttgtccgcc cacagcgggg catttttctt cctgttatgt ttttaatcaa   9360

acatcctgcc aactccatgt gacaaaccgt catcttcggc tacttttttct ctgtcacaga   9420

atgaaaattt ttctgtcatc tcttcgttat taatgtttgt aattgactga atatcaacgc   9480

ttatttgcag cctgaatggc gaatgg                                        9506
```

<210> SEQ ID NO 36
<211> LENGTH: 1559
<212> TYPE: PRT
<213> ORGANISM: Artificial
<220> FEATURE:
<223> OTHER INFORMATION: Fusion protein construct

<400> SEQUENCE: 36

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Gly Ala Gly Glu Gln Lys Leu
        35                  40                  45

Ile Ser Glu Glu Asp Leu Gly Ala Ala Ala Gly Ser Gly Gly Gly Ser
    50                  55                  60

Gln Ala His Val Gln Leu Gln Gln Ser Gly Gly Gly Leu Val Gln Pro
65                  70                  75                  80
```

```
Gly Gly Ser Leu Arg Leu Ser Cys Ala Ala Ser Gly Ser Ile Phe Ser
                85                  90                  95

Ile Tyr Ala Met Gly Trp Tyr Arg Gln Ala Pro Gly Lys Gln Arg Glu
            100                 105                 110

Leu Val Ala Ala Ile Ser Ser Tyr Gly Ser Thr Asn Tyr Ala Asp Ser
        115                 120                 125

Val Lys Gly Arg Phe Thr Ile Ser Arg Asp Asn Ala Lys Asn Thr Val
    130                 135                 140

Tyr Leu Gln Met Asn Ser Leu Lys Pro Glu Asp Thr Ala Val Tyr Tyr
145                 150                 155                 160

Cys Asn Ala Asp Ile Ala Thr Met Thr Ala Val Gly Gly Phe Asp Tyr
                165                 170                 175

Trp Gly Gln Gly Thr Gln Val Thr Val Ser Ser Glu Pro Lys Thr Pro
            180                 185                 190

Lys Pro Gln Gly Ala Gly Gln Gly Ala Gly Ala Gly Pro Ile Thr Ile
        195                 200                 205

Asn Asn Phe Asn Tyr Ser Asp Pro Val Asp Asn Lys Asn Ile Leu Tyr
    210                 215                 220

Leu Asp Thr His Leu Asn Thr Leu Ala Asn Glu Pro Glu Lys Ala Phe
225                 230                 235                 240

Arg Ile Thr Gly Asn Ile Trp Val Ile Pro Asp Arg Phe Ser Arg Asn
                245                 250                 255

Ser Asn Pro Asn Leu Asn Lys Pro Pro Arg Val Thr Ser Pro Lys Ser
            260                 265                 270

Gly Tyr Tyr Asp Pro Asn Tyr Leu Ser Thr Asp Ser Asp Lys Asp Pro
        275                 280                 285

Phe Leu Lys Glu Ile Ile Lys Leu Phe Lys Arg Ile Asn Ser Arg Glu
    290                 295                 300

Ile Gly Glu Glu Leu Ile Tyr Arg Leu Ser Thr Asp Ile Pro Phe Pro
305                 310                 315                 320

Gly Asn Asn Asn Thr Pro Ile Asn Thr Phe Asp Phe Asp Val Asp Phe
                325                 330                 335

Asn Ser Val Asp Val Lys Thr Arg Gln Gly Asn Asn Trp Val Lys Thr
            340                 345                 350

Gly Ser Ile Asn Pro Ser Val Ile Ile Thr Gly Pro Arg Glu Asn Ile
        355                 360                 365

Ile Asp Pro Glu Thr Ser Thr Phe Lys Leu Thr Asn Asn Thr Phe Ala
    370                 375                 380

Ala Gln Glu Gly Phe Gly Ala Leu Ser Ile Ile Ser Ile Ser Pro Arg
385                 390                 395                 400

Phe Met Leu Thr Tyr Ser Asn Ala Thr Asn Asp Val Gly Glu Gly Arg
                405                 410                 415

Phe Ser Lys Ser Glu Phe Cys Met Asp Pro Ile Leu Ile Leu Met His
            420                 425                 430

Ala Leu Asn Gly Ala Met His Asn Leu Tyr Gly Ile Ala Ile Pro Asn
        435                 440                 445

Asp Gln Thr Ile Ser Ser Val Thr Ser Asn Ile Phe Tyr Ser Gln Tyr
    450                 455                 460

Asn Val Lys Leu Glu Tyr Ala Glu Ile Tyr Ala Phe Gly Gly Pro Thr
465                 470                 475                 480

Ile Asp Leu Ile Pro Lys Ser Ala Arg Lys Tyr Phe Glu Glu Lys Ala
                485                 490                 495

Leu Asp Tyr Tyr Arg Ser Ile Ala Lys Arg Leu Asn Ser Ile Thr Thr
```

```
            500                 505                 510

Ala Asn Pro Ser Ser Phe Asn Lys Tyr Ile Gly Glu Tyr Lys Gln Lys
        515                 520                 525

Leu Ile Arg Lys Tyr Arg Phe Val Val Glu Ser Ser Gly Glu Val Thr
    530                 535                 540

Val Asn Arg Asn Lys Phe Val Glu Leu Tyr Asn Glu Leu Thr Gln Ile
545                 550                 555                 560

Phe Thr Glu Phe Asn Tyr Ala Lys Ile Tyr Asn Val Gln Asn Arg Lys
                565                 570                 575

Ile Ala Leu Ser Asn Val Tyr Thr Pro Val Thr Ala Asn Ile Leu Asp
            580                 585                 590

Asp Asn Val Tyr Asp Ile Gln Asn Gly Phe Asn Ile Pro Lys Ser Asn
        595                 600                 605

Leu Asn Val Leu Phe Met Gly Gln Asn Leu Ser Arg Asn Pro Ala Leu
    610                 615                 620

Arg Lys Val Asn Pro Glu Asn Met Leu Tyr Leu Phe Thr Lys Phe Cys
625                 630                 635                 640

His Lys Ala Ile Asp Gly Gln Ser Leu Asp Gln Gly Gly Trp Glu Leu
                645                 650                 655

Gln Gln Gly Gly Gln Gly Gly Gly Ala Gly Thr Leu Asp Cys Arg Glu
            660                 665                 670

Leu Leu Val Lys Asn Thr Asp Leu Pro Phe Ile Gly Asp Ile Ser Asp
        675                 680                 685

Val Lys Thr Asp Ile Phe Leu Arg Lys Asp Ile Asn Glu Glu Thr Glu
    690                 695                 700

Val Ile Tyr Tyr Pro Asp Asn Val Ser Val Asp Gln Val Ile Leu Ser
705                 710                 715                 720

Lys Asn Thr Ser Glu His Gly Gln Leu Asp Leu Leu Tyr Pro Ser Ile
                725                 730                 735

Asp Ser Glu Ser Glu Ile Leu Pro Gly Glu Asn Gln Val Phe Tyr Asp
            740                 745                 750

Asn Arg Thr Gln Asn Val Asp Tyr Leu Asn Ser Tyr Tyr Tyr Leu Glu
        755                 760                 765

Ser Gln Lys Leu Ser Asp Asn Val Glu Asp Phe Thr Phe Thr Arg Ser
    770                 775                 780

Ile Glu Glu Ala Leu Asp Asn Ser Ala Lys Val Tyr Thr Tyr Phe Pro
785                 790                 795                 800

Thr Leu Ala Asn Lys Val Asn Ala Gly Val Gln Gly Gly Leu Phe Leu
                805                 810                 815

Met Trp Ala Asn Asp Val Val Glu Asp Phe Thr Thr Asn Ile Leu Arg
            820                 825                 830

Lys Asp Thr Leu Asp Lys Ile Ser Asp Val Ser Ala Ile Ile Pro Tyr
        835                 840                 845

Ile Gly Pro Ala Leu Asn Ile Ser Asn Ser Val Arg Arg Gly Asn Phe
    850                 855                 860

Thr Glu Ala Phe Ala Val Thr Gly Val Thr Ile Leu Leu Glu Ala Phe
865                 870                 875                 880

Pro Glu Phe Thr Ile Pro Ala Leu Gly Ala Phe Val Ile Tyr Ser Lys
                885                 890                 895

Val Gln Glu Arg Asn Glu Ile Ile Lys Thr Ile Asp Asn Cys Leu Glu
            900                 905                 910

Gln Arg Ile Lys Arg Trp Lys Asp Ser Tyr Glu Trp Met Met Gly Thr
        915                 920                 925
```

-continued

```
Trp Leu Ser Arg Ile Ile Thr Gln Phe Asn Asn Ile Ser Tyr Gln Met
    930                 935                 940

Tyr Asp Ser Leu Asn Tyr Gln Ala Gly Ala Ile Lys Ala Lys Ile Asp
945                 950                 955                 960

Leu Glu Tyr Lys Lys Tyr Ser Gly Ser Asp Lys Glu Asn Ile Lys Ser
                965                 970                 975

Gln Val Glu Asn Leu Lys Asn Ser Leu Asp Val Lys Ile Ser Glu Ala
            980                 985                 990

Met Asn Asn Ile Asn Lys Phe Ile  Arg Glu Cys Ser Val  Thr Tyr Leu
        995                 1000                1005

Phe Lys  Asn Met Leu Pro Lys  Val Ile Asp Glu Leu  Asn Glu Phe
    1010                 1015                1020

Asp Arg  Asn Thr Lys Ala Lys  Leu Ile Asn Leu Ile  Asp Ser His
    1025                 1030                1035

Asn Ile  Ile Leu Val Gly Glu  Val Asp Lys Leu Lys  Ala Lys Val
    1040                 1045                1050

Asn Asn  Ser Phe Gln Asn Thr  Ile Pro Phe Asn Ile  Phe Ser Tyr
    1055                 1060                1065

Thr Asn  Asn Ser Leu Leu Lys  Asp Ile Ile Asn Glu  Tyr Phe Asn
    1070                 1075                1080

Asn Ile  Asn Asp Ser Lys Ile  Leu Ser Leu Gln Asn  Arg Lys Asn
    1085                 1090                1095

Thr Leu  Val Asp Thr Ser Gly  Tyr Asn Ala Glu Val  Ser Glu Glu
    1100                 1105                1110

Gly Asp  Val Gln Leu Asn Pro  Ile Phe Pro Phe Asp  Phe Lys Leu
    1115                 1120                1125

Gly Ser  Ser Gly Glu Asp Arg  Gly Lys Val Ile Val  Thr Gln Asn
    1130                 1135                1140

Glu Asn  Ile Val Tyr Asn Ser  Met Tyr Glu Ser Phe  Ser Ile Ser
    1145                 1150                1155

Phe Trp  Ile Arg Ile Asn Lys  Trp Val Ser Asn Leu  Pro Gly Tyr
    1160                 1165                1170

Thr Ile  Ile Asp Ser Val Lys  Asn Asn Ser Gly Trp  Ser Ile Gly
    1175                 1180                1185

Ile Ile  Ser Asn Phe Leu Val  Phe Thr Leu Lys Gln  Asn Glu Asp
    1190                 1195                1200

Ser Glu  Gln Ser Ile Asn Phe  Ser Tyr Asp Ile Ser  Asn Asn Ala
    1205                 1210                1215

Pro Gly  Tyr Asn Lys Trp Phe  Phe Val Thr Val Thr  Asn Asn Met
    1220                 1225                1230

Met Gly  Asn Met Lys Ile Tyr  Ile Asn Gly Lys Leu  Ile Asp Thr
    1235                 1240                1245

Ile Lys  Val Lys Glu Leu Thr  Gly Ile Asn Phe Ser  Lys Thr Ile
    1250                 1255                1260

Thr Phe  Glu Ile Asn Lys Ile  Pro Asp Thr Gly Leu  Ile Thr Ser
    1265                 1270                1275

Asp Ser  Asp Asn Ile Asn Met  Trp Ile Arg Asp Phe  Tyr Ile Phe
    1280                 1285                1290

Ala Lys  Glu Leu Asp Gly Lys  Asp Ile Asn Ile Leu  Phe Asn Ser
    1295                 1300                1305

Leu Gln  Tyr Thr Asn Val Val  Lys Asp Tyr Trp Gly  Asn Asp Leu
    1310                 1315                1320
```

-continued

```
Arg Tyr  Asn Lys Glu Tyr Tyr  Met Val Asn Ile Asp  Tyr Leu Asn
    1325                 1330                 1335

Arg Tyr  Met Tyr Ala Asn Ser  Arg Gln Ile Val Phe  Asn Thr Arg
    1340                 1345                 1350

Arg Asn  Asn Asn Asp Phe Asn  Glu Gly Tyr Lys Ile  Ile Ile Lys
    1355                 1360                 1365

Arg Ile  Arg Gly Asn Thr Asn  Asp Thr Arg Val Arg  Gly Gly Asp
    1370                 1375                 1380

Ile Leu  Tyr Phe Asp Met Thr  Ile Asn Asn Lys Ala  Tyr Asn Leu
    1385                 1390                 1395

Phe Met  Lys Asn Glu Thr Met  Tyr Ala Asp Asn His  Ser Thr Glu
    1400                 1405                 1410

Asp Ile  Tyr Ala Ile Gly Leu  Arg Glu Gln Thr Lys  Asp Ile Asn
    1415                 1420                 1425

Asp Asn  Ile Ile Phe Gln Ile  Gln Pro Met Asn Asn  Thr Tyr Tyr
    1430                 1435                 1440

Tyr Ala  Ser Gln Ile Phe Lys  Ser Asn Phe Asn Gly  Glu Asn Ile
    1445                 1450                 1455

Ser Gly  Ile Cys Ser Ile Gly  Thr Tyr Arg Phe Arg  Leu Gly Gly
    1460                 1465                 1470

Asp Trp  Tyr Arg His Asn Tyr  Leu Val Pro Thr Val  Lys Gln Gly
    1475                 1480                 1485

Asn Tyr  Ala Ser Leu Leu Glu  Ser Thr Ser Thr His  Trp Gly Phe
    1490                 1495                 1500

Val Pro  Val Ser Glu Gly Ala  Gly Tyr Pro Tyr Asp  Val Pro Asp
    1505                 1510                 1515

Tyr Ala  Gly Trp Glu Leu Gln  Gln Gly Ala Gly Trp  Ser His Pro
    1520                 1525                 1530

Gln Phe  Glu Lys Gly Ala Gly  Trp Ser His Pro Gln  Phe Glu Lys
    1535                 1540                 1545

Gly Ala  Gly Trp Ser His Pro  Gln Phe Glu Lys
    1550                 1555
```

<210> SEQ ID NO 37
<211> LENGTH: 10112
<212> TYPE: DNA
<213> ORGANISM: Artificial
<220> FEATURE:
<223> OTHER INFORMATION: DNA construct for molecular construction of
      fusion proteins

<400> SEQUENCE: 37

```
gacgcgccct gtagcggcgc attaagcgcg gcgggtgtgg tggttacgcg cagcgtgacc      60

gctacacttg ccagcgccct agcgcccgct cctttcgctt tcttcccttc ctttctcgcc     120

acgttcgccg gctttccccg tcaagctcta aatcgggggc tccctttagg gttccgattt     180

agtgctttac ggcacctcga ccccaaaaaa cttgattagg gtgatggttc acgtagtggg     240

ccatcgccct gatagacggt ttttcgccct ttgacgttgg agtccacgtt ctttaatagt     300

ggactcttgt tccaaactgg aacaacactc aaccctatct cggtctattc ttttgattta     360

taagggattt tgccgatttc ggcctattgg ttaaaaaatg agctgattta acaaaaattt     420

aacgcgaatt ttaacaaaat attaacgttt acaatttcag gtggcacttt tcggggaaat     480

gtgcgcggaa cccctatttg tttatttttc taaatacatt caaatatgta tccgctcatg     540

agacaataac cctgataaat gcttcaataa tattgaaaaa ggaagagtat gagtattcaa     600
```

-continued

```
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
```

-continued

```
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca ccaccaccac caccaccacc accaccacca cgacgtcggc   4200
tgggagctgc aacgtcgtcc cctgaactgc atcgtggctg tgtcccagaa catgggtatc   4260
ggcaagaacg gcgacctgcc ctggcctcct ctgcgtaacg agttcaagta cttccagcgt   4320
atgaccacca cctcctccgt cgagggcaag cagaacctgg tcatcatggg tcgcaagacc   4380
tggttctcca tccccgagaa gaaccgtctg ctgaaggacc gtatcaacat cgtgctgtcc   4440
cgcgagctga aggaaccccc tcgtggtgct cacttcctgg ctaagtccct ggacgacgct   4500
ctgcgtctga tcgagcagcc tgagctggct tccaaggtgg acatggtctg gatcgtgggc   4560
ggttcctccg tgtaccaaga ggctatgaac cagcccggtc acttgcgtct gttcgtgacc   4620
cgtatcatgc aagagttcga gtccgacacc ttcttccccg aaatcgacct gggcaagtac   4680
aagctgctgc ccgagtaccc cggtgtcctg tccgaggtgc aagaggaaaa gggtatcaag   4740
tacaagttcg aggtgtacga gaagaaggac ggcgcttccg gtttcgctaa cgagctcggt   4800
cctcgtctga tgggaaaggg cgccggcgag cagaaactca tcagcgaaga agatttgggt   4860
gcggccgctg gctcaggagg tggcagtcag gcgcacgtgc aactgcagca gtctggagga   4920
ggcttggtgc agcctggggg ttccctgcgc ctgtcatgtg cagcctctgg aagcatcttc   4980
agtatttacg ctatgggctg gtacaggcag gctcctggca agcaacgtga actggttgct   5040
gccatctcca gctacggtag taccaactac gctgattcgg tcaagggcag gttcaccatc   5100
tcccgcgaca atgccaagaa taccgtctat ttgcaaatga actctctgaa acctgaggat   5160
acggccgtct actactgcaa cgctgacatt gctactatga ccgcggtagg cggattcgac   5220
tactggggac agggaactca ggtgacggtc tcttccgaac ctaagacccc taaaccccaa   5280
ggggccggcc agggtgctgg tgctggaccg atcaccatca acaacttcaa ttactcggat   5340
```

-continued

```
ccggtggata acaagaacat cctctacttg gacacacact tgaacacgct ggctaacgag   5400
cctgaaaaag ctttcaggat caccggcaac atttgggtca ttccggatag gttcagcaga   5460
aactctaacc ctaacttgaa caaacctccc agagtgacct cacctaagag tggatactac   5520
gaccccaact acctctcgac tgactccgat aaagacccct tcctgaagga gatcattaaa   5580
ctcttcaagc gcatcaactc tcgtgaaatt ggcgaggaat tgatctaccg cctgagtaca   5640
gacatcccat tcccgggtaa caacaacacc ccaatcaaca ctttcgattt cgatgtcgat   5700
ttcaactcag tggatgtcaa aaccaggcag ggaaacaact gggtgaagac tggtagcatc   5760
aacccatctg tcatcattac tggcccgaga gagaacatca ttgaccctga aacctccact   5820
ttcaagctga caaacaacac gttcgctgct caggaaggct tcggagcgtt gagcatcatt   5880
tctatctcac ctcgcttcat gctgacatac tctaacgcta cgaacgacgt gggagagggc   5940
cgtttcagta agtctgaatt ctgcatggac cctattctga tcctcatgca cgctctcaac   6000
ggcgccatgc acaacttgta cggaattgct atccccaacg accagaccat ttccagcgtg   6060
actagcaaca tcttctactc tcaatacaac gtcaagctgg agtacgcaga aatctacgct   6120
ttcggtggcc caaccattga cttgatcccg aaatcagctc gtaagtattt cgaagaaaaa   6180
gcgctggatt attacaggtc gattgctaag agactcaact ccatcaccac tgctaacccc   6240
tcttcattca acaagtacat tggagaatac aagcagaaac tgatccgcaa gtaccgtttc   6300
gtggtcgaga gttcgggtga agttactgtg aaccgcaaca agttcgtcga gctgtacaac   6360
gaattgacac aaatcttcac ggagttcaac tacgccaaaa tttacaacgt gcaaaaccgt   6420
aagatcgcgc tctctaacgt ctacaccccg gttaccgcta acatcttgga cgataacgtc   6480
tacgacattc agaacggttt caacatccca aagtcgaacc tcaacgtttt gttcatgggt   6540
caaaacttgt cccgcaaccc cgccctgcgt aaggtgaacc cagagaacat gttgtacctg   6600
ttcaccaaat tctgccacaa ggccatcgac ggtcagtctc tagaccaagg aggatgggaa   6660
ctccagcaag gtggccaggg tggaggtgct ggcaccctgg actgtcgcga actgctcgtt   6720
aagaacactg atctcccatt cattggcgac atctctgatg tgaaaacaga cattttcctg   6780
cgtaaggata tcaacgagga aacggaggtc atctactacc ctgacaacgt ctcggttgat   6840
caggttatct tgtcaaagaa caccagtgaa catggccaac tggacttgct gtacccctca   6900
attgattccg agagcgaaat cctgccagga gagaaccagg ttttctacga caacaggaca   6960
caaaacgtgg attacctcaa cagctactac tacctggagt cgcagaagct ctccgacaac   7020
gtcgaagatt tcacatttac gagatcaatc gaggaggctt tggacaacag tgccaaagtc   7080
tacacctact tccctactct ggcaaacaag gtgaacgcgg gtgtccaagg cggactcttc   7140
ttgatgtggg ctaacgacgt tgtggaagat ttcacaacga acatcttgcg caaagacacc   7200
ctggataaga tcagcgatgt ctctgccatc attccataca ttggcccggc actgaacatc   7260
tctaactcag ttcgccgtgg caacttcact gaggcattcg cggtcacagg agttacgatc   7320
ctcttggagg ctttcccgga gttcacaatc cccgcactgg gcgcgttcgt tatctactcc   7380
aaagtgcagg agcgcaacga aatcattaag actatcgaca actgcctgga gcaaaggatc   7440
aaaagatgga aggattcgta cgaatggatg atgggtacct ggctctcccg tatcattacg   7500
cagttcaaca acatcagcta ccaaatgtac gactctctca actaccaggc tggtgccatc   7560
aaggccaaaa ttgacttgga gtacaagaaa tacagtggct cggataaaga gaacatcaag   7620
agtcaagtcg aaaacctgaa aaactcactc gacgttaaga tcagtgaggc aatgaacaac   7680
atcaacaagt tcattcgcga atgttccgtt acctacctct tcaaaaacat gttgccaaag   7740
```

gtcatcgacg agctgaacga atttgatcgt aacactaagg cgaaactgat taacctcatc 7800
gactcacaca acatcatttt ggtgggcgaa gtcgataagc tgaaagccaa ggtgaacaac 7860
agtttccaga acacaatccc tttcaacatt ttctcataca cgaacaacag tctgctcaag 7920
gacatcatta acgagtactt caacaacatt aacgatagca aaatcctgtc actgcagaac 7980
cgtaagaaca cactggtcga tactagtgga tacaacgccg aagtctctga ggaaggtgac 8040
gtgcagctga accctatctt ccccttcgac ttcaaattgg gctccagcgg agaggatagg 8100
ggcaaggtca tcgtcaccca gaacgagaac atcgtctaca actcaatgta cgaatccttc 8160
agcatctctt tctggatcag gattaacaag tgggtgagca acctgcccgg ttacacaatc 8220
attgactctg tcaagaacaa ctcaggttgg agtatcggca tcatttctaa cttcttggtc 8280
ttcaccctga agcagaacga ggactcggaa caatccatta acttctcata cgatatcagt 8340
aacaacgctc caggttacaa caagtggttc ttcgttaccg tgactaacaa catgatgggt 8400
aacatgaaaa tttacatcaa cggcaagctc attgacacca tcaaagtgaa ggagttgact 8460
ggtattaact tctccaaaac aatcacgttt gaaattaaca agatccctga caccggcctg 8520
atcacttcag acagtgataa catcaacatg tggattaggg atttctacat cttcgccaag 8580
gagctcgacg gaaaggatat taacatcctc ttcaacagct tgcagtacac caacgtcgtt 8640
aaagactact ggggtaacga tttgagatac aacaaggagt actacatggt caacatcgac 8700
tacctgaaca ggtacatgta cgctaactcc cgccaaatcg tgttcaacac caggagaaac 8760
aacaacgact tcaacgaggg ttacaaaatc attatcaagc gcatccgtgg caacaccaac 8820
gatactaggg tgagaggtgg cgacattctg tacttcgata tgactatcaa caacaaagcc 8880
tacaacttgt tcatgaaaaa cgagacaatg tacgccgaca accatagcac ggaggatatt 8940
tacgcaatcg gactgaggga acagacaaag gacatcaacg ataacattat cttccagatc 9000
caacctatga acaacacgta ctactacgct tcgcaaatct tcaagtccaa cttcaacgga 9060
gaaaacattt cgggtatctg ttccattggc acataccgct tccgtctggg tggtgactgg 9120
tatcgtcaca actacctcgt tcccaccgtg aagcagggta actacgcttc tttgctggag 9180
tcgacttcca cgcactgggg attcgttcct gtgtcagagg gcgctggcta cccttacgat 9240
gttcccgact acgctggttg ggaactccag caaggtgcag gatggtccca ccctcaattc 9300
gagaagggtg ccggatggag tcacccacag ttcgagaaag gcgctggatg gagtcaccca 9360
cagttcgaga aataattagt tgatgcatag ttaattagat agctcgaggc atgcggtacc 9420
aagattggat ctagatgcat agttaattag atagctcgag gcatgcggta ccaagcttgt 9480
cgagaagtac tagaggatca taatcagcca taccacattt gtagaggttt tacttgcttt 9540
aaaaaacctc ccacacctcc ccctgaacct gaaacataaa atgaatgcaa ttgttgttgt 9600
taacttgttt attgcagctt ataatggtta caaataaagc aatagcatca caaatttcac 9660
aaataaagca tttttttcac tgcattctag ttgtggtttg tccaaactca tcaatgtatc 9720
ttatcatgtc tggatctgat cactgcttga gcctaggaga tccgaaccag ataagtgaaa 9780
tctagttcca aactattttg tcatttttaa ttttcgtatt agcttacgac gctacaccca 9840
gttcccatct attttgtcac tcttccctaa ataatcctta aaaactccat ttccacccct 9900
cccagttccc aactattttg tccgcccaca gcggggcatt tttcttcctg ttatgttttt 9960
aatcaaacat cctgccaact ccatgtgaca aaccgtcatc ttcggctact ttttctctgt 10020
cacagaatga aaatttttct gtcatctctt cgttattaat gtttgtaatt gactgaatat 10080
caacgcttat ttgcagcctg aatggcgaat gg 10112

<210> SEQ ID NO 38
<211> LENGTH: 1761
<212> TYPE: PRT
<213> ORGANISM: Artificial
<220> FEATURE:
<223> OTHER INFORMATION: Fusion protein construct

<400> SEQUENCE: 38

Met Lys Phe Leu Val Asn Val Ala Leu Val Phe Met Val Val Tyr Ile
1 5 10 15

Ser Tyr Ile Tyr Ala Ala Gly His His His His His His His His His
20 25 30

His His Asp Val Gly Trp Glu Leu Gln Arg Arg Pro Leu Asn Cys Ile
35 40 45

Val Ala Val Ser Gln Asn Met Gly Ile Gly Lys Asn Gly Asp Leu Pro
50 55 60

Trp Pro Pro Leu Arg Asn Glu Phe Lys Tyr Phe Gln Arg Met Thr Thr
65 70 75 80

Thr Ser Ser Val Glu Gly Lys Gln Asn Leu Val Ile Met Gly Arg Lys
85 90 95

Thr Trp Phe Ser Ile Pro Glu Lys Asn Arg Leu Leu Lys Asp Arg Ile
100 105 110

Asn Ile Val Leu Ser Arg Glu Leu Lys Glu Pro Pro Arg Gly Ala His
115 120 125

Phe Leu Ala Lys Ser Leu Asp Asp Ala Leu Arg Leu Ile Glu Gln Pro
130 135 140

Glu Leu Ala Ser Lys Val Asp Met Val Trp Ile Val Gly Gly Ser Ser
145 150 155 160

Val Tyr Gln Glu Ala Met Asn Gln Pro Gly His Leu Arg Leu Phe Val
165 170 175

Thr Arg Ile Met Gln Glu Phe Glu Ser Asp Thr Phe Phe Pro Glu Ile
180 185 190

Asp Leu Gly Lys Tyr Lys Leu Leu Pro Glu Tyr Pro Gly Val Leu Ser
195 200 205

Glu Val Gln Glu Glu Lys Gly Ile Lys Tyr Lys Phe Glu Val Tyr Glu
210 215 220

Lys Lys Asp Gly Ala Ser Gly Phe Ala Asn Glu Leu Gly Pro Arg Leu
225 230 235 240

Met Gly Lys Gly Ala Gly Glu Gln Lys Leu Ile Ser Glu Glu Asp Leu
245 250 255

Gly Ala Ala Ala Gly Ser Gly Gly Gly Ser Gln Ala His Val Gln Leu
260 265 270

Gln Gln Ser Gly Gly Gly Leu Val Gln Pro Gly Gly Ser Leu Arg Leu
275 280 285

Ser Cys Ala Ala Ser Gly Ser Ile Phe Ser Ile Tyr Ala Met Gly Trp
290 295 300

Tyr Arg Gln Ala Pro Gly Lys Gln Arg Glu Leu Val Ala Ala Ile Ser
305 310 315 320

Ser Tyr Gly Ser Thr Asn Tyr Ala Asp Ser Val Lys Gly Arg Phe Thr
325 330 335

Ile Ser Arg Asp Asn Ala Lys Asn Thr Val Tyr Leu Gln Met Asn Ser
340 345 350

Leu Lys Pro Glu Asp Thr Ala Val Tyr Tyr Cys Asn Ala Asp Ile Ala

```
        355                 360                 365

Thr Met Thr Ala Val Gly Gly Phe Asp Tyr Trp Gly Gln Gly Thr Gln
    370                 375                 380

Val Thr Val Ser Ser Glu Pro Lys Thr Pro Lys Pro Gln Gly Ala Gly
385                 390                 395                 400

Gln Gly Ala Gly Ala Gly Pro Ile Thr Ile Asn Asn Phe Asn Tyr Ser
                405                 410                 415

Asp Pro Val Asp Asn Lys Asn Ile Leu Tyr Leu Asp Thr His Leu Asn
            420                 425                 430

Thr Leu Ala Asn Glu Pro Glu Lys Ala Phe Arg Ile Thr Gly Asn Ile
        435                 440                 445

Trp Val Ile Pro Asp Arg Phe Ser Arg Asn Ser Asn Pro Asn Leu Asn
    450                 455                 460

Lys Pro Pro Arg Val Thr Ser Pro Lys Ser Gly Tyr Tyr Asp Pro Asn
465                 470                 475                 480

Tyr Leu Ser Thr Asp Ser Asp Lys Asp Pro Phe Leu Lys Glu Ile Ile
                485                 490                 495

Lys Leu Phe Lys Arg Ile Asn Ser Arg Glu Ile Gly Glu Glu Leu Ile
            500                 505                 510

Tyr Arg Leu Ser Thr Asp Ile Pro Phe Pro Gly Asn Asn Asn Thr Pro
        515                 520                 525

Ile Asn Thr Phe Asp Phe Asp Val Asp Phe Asn Ser Val Asp Val Lys
    530                 535                 540

Thr Arg Gln Gly Asn Asn Trp Val Lys Thr Gly Ser Ile Asn Pro Ser
545                 550                 555                 560

Val Ile Ile Thr Gly Pro Arg Glu Asn Ile Ile Asp Pro Glu Thr Ser
                565                 570                 575

Thr Phe Lys Leu Thr Asn Asn Thr Phe Ala Ala Gln Glu Gly Phe Gly
            580                 585                 590

Ala Leu Ser Ile Ile Ser Ile Ser Pro Arg Phe Met Leu Thr Tyr Ser
        595                 600                 605

Asn Ala Thr Asn Asp Val Gly Glu Gly Arg Phe Ser Lys Ser Glu Phe
    610                 615                 620

Cys Met Asp Pro Ile Leu Ile Leu Met His Ala Leu Asn Gly Ala Met
625                 630                 635                 640

His Asn Leu Tyr Gly Ile Ala Ile Pro Asn Asp Gln Thr Ile Ser Ser
                645                 650                 655

Val Thr Ser Asn Ile Phe Tyr Ser Gln Tyr Asn Val Lys Leu Glu Tyr
            660                 665                 670

Ala Glu Ile Tyr Ala Phe Gly Gly Pro Thr Ile Asp Leu Ile Pro Lys
        675                 680                 685

Ser Ala Arg Lys Tyr Phe Glu Glu Lys Ala Leu Asp Tyr Tyr Arg Ser
    690                 695                 700

Ile Ala Lys Arg Leu Asn Ser Ile Thr Thr Ala Asn Pro Ser Ser Phe
705                 710                 715                 720

Asn Lys Tyr Ile Gly Glu Tyr Lys Gln Lys Leu Ile Arg Lys Tyr Arg
                725                 730                 735

Phe Val Val Glu Ser Ser Gly Glu Val Thr Val Asn Arg Asn Lys Phe
            740                 745                 750

Val Glu Leu Tyr Asn Glu Leu Thr Gln Ile Phe Thr Glu Phe Asn Tyr
        755                 760                 765

Ala Lys Ile Tyr Asn Val Gln Asn Arg Lys Ile Ala Leu Ser Asn Val
    770                 775                 780
```

Tyr Thr Pro Val Thr Ala Asn Ile Leu Asp Asp Asn Val Tyr Asp Ile
785 790 795 800

Gln Asn Gly Phe Asn Ile Pro Lys Ser Asn Leu Asn Val Leu Phe Met
805 810 815

Gly Gln Asn Leu Ser Arg Asn Pro Ala Leu Arg Lys Val Asn Pro Glu
820 825 830

Asn Met Leu Tyr Leu Phe Thr Lys Phe Cys His Lys Ala Ile Asp Gly
835 840 845

Gln Ser Leu Asp Gln Gly Gly Trp Glu Leu Gln Gln Gly Gly Gln Gly
850 855 860

Gly Gly Ala Gly Thr Leu Asp Cys Arg Glu Leu Leu Val Lys Asn Thr
865 870 875 880

Asp Leu Pro Phe Ile Gly Asp Ile Ser Asp Val Lys Thr Asp Ile Phe
885 890 895

Leu Arg Lys Asp Ile Asn Glu Glu Thr Glu Val Ile Tyr Tyr Pro Asp
900 905 910

Asn Val Ser Val Asp Gln Val Ile Leu Ser Lys Asn Thr Ser Glu His
915 920 925

Gly Gln Leu Asp Leu Leu Tyr Pro Ser Ile Asp Ser Glu Ser Glu Ile
930 935 940

Leu Pro Gly Glu Asn Gln Val Phe Tyr Asp Asn Arg Thr Gln Asn Val
945 950 955 960

Asp Tyr Leu Asn Ser Tyr Tyr Tyr Leu Glu Ser Gln Lys Leu Ser Asp
965 970 975

Asn Val Glu Asp Phe Thr Phe Thr Arg Ser Ile Glu Glu Ala Leu Asp
980 985 990

Asn Ser Ala Lys Val Tyr Thr Tyr Phe Pro Thr Leu Ala Asn Lys Val
995 1000 1005

Asn Ala Gly Val Gln Gly Gly Leu Phe Leu Met Trp Ala Asn Asp
1010 1015 1020

Val Val Glu Asp Phe Thr Thr Asn Ile Leu Arg Lys Asp Thr Leu
1025 1030 1035

Asp Lys Ile Ser Asp Val Ser Ala Ile Ile Pro Tyr Ile Gly Pro
1040 1045 1050

Ala Leu Asn Ile Ser Asn Ser Val Arg Arg Gly Asn Phe Thr Glu
1055 1060 1065

Ala Phe Ala Val Thr Gly Val Thr Ile Leu Leu Glu Ala Phe Pro
1070 1075 1080

Glu Phe Thr Ile Pro Ala Leu Gly Ala Phe Val Ile Tyr Ser Lys
1085 1090 1095

Val Gln Glu Arg Asn Glu Ile Ile Lys Thr Ile Asp Asn Cys Leu
1100 1105 1110

Glu Gln Arg Ile Lys Arg Trp Lys Asp Ser Tyr Glu Trp Met Met
1115 1120 1125

Gly Thr Trp Leu Ser Arg Ile Ile Thr Gln Phe Asn Asn Ile Ser
1130 1135 1140

Tyr Gln Met Tyr Asp Ser Leu Asn Tyr Gln Ala Gly Ala Ile Lys
1145 1150 1155

Ala Lys Ile Asp Leu Glu Tyr Lys Lys Tyr Ser Gly Ser Asp Lys
1160 1165 1170

Glu Asn Ile Lys Ser Gln Val Glu Asn Leu Lys Asn Ser Leu Asp
1175 1180 1185

Val Lys Ile Ser Glu Ala Met Asn Asn Ile Asn Lys Phe Ile Arg
1190 1195 1200

Glu Cys Ser Val Thr Tyr Leu Phe Lys Asn Met Leu Pro Lys Val
1205 1210 1215

Ile Asp Glu Leu Asn Glu Phe Asp Arg Asn Thr Lys Ala Lys Leu
1220 1225 1230

Ile Asn Leu Ile Asp Ser His Asn Ile Ile Leu Val Gly Glu Val
1235 1240 1245

Asp Lys Leu Lys Ala Lys Val Asn Asn Ser Phe Gln Asn Thr Ile
1250 1255 1260

Pro Phe Asn Ile Phe Ser Tyr Thr Asn Asn Ser Leu Leu Lys Asp
1265 1270 1275

Ile Ile Asn Glu Tyr Phe Asn Asn Ile Asn Asp Ser Lys Ile Leu
1280 1285 1290

Ser Leu Gln Asn Arg Lys Asn Thr Leu Val Asp Thr Ser Gly Tyr
1295 1300 1305

Asn Ala Glu Val Ser Glu Glu Gly Asp Val Gln Leu Asn Pro Ile
1310 1315 1320

Phe Pro Phe Asp Phe Lys Leu Gly Ser Ser Gly Glu Asp Arg Gly
1325 1330 1335

Lys Val Ile Val Thr Gln Asn Glu Asn Ile Val Tyr Asn Ser Met
1340 1345 1350

Tyr Glu Ser Phe Ser Ile Ser Phe Trp Ile Arg Ile Asn Lys Trp
1355 1360 1365

Val Ser Asn Leu Pro Gly Tyr Thr Ile Ile Asp Ser Val Lys Asn
1370 1375 1380

Asn Ser Gly Trp Ser Ile Gly Ile Ile Ser Asn Phe Leu Val Phe
1385 1390 1395

Thr Leu Lys Gln Asn Glu Asp Ser Glu Gln Ser Ile Asn Phe Ser
1400 1405 1410

Tyr Asp Ile Ser Asn Asn Ala Pro Gly Tyr Asn Lys Trp Phe Phe
1415 1420 1425

Val Thr Val Thr Asn Asn Met Met Gly Asn Met Lys Ile Tyr Ile
1430 1435 1440

Asn Gly Lys Leu Ile Asp Thr Ile Lys Val Lys Glu Leu Thr Gly
1445 1450 1455

Ile Asn Phe Ser Lys Thr Ile Thr Phe Glu Ile Asn Lys Ile Pro
1460 1465 1470

Asp Thr Gly Leu Ile Thr Ser Asp Ser Asp Asn Ile Asn Met Trp
1475 1480 1485

Ile Arg Asp Phe Tyr Ile Phe Ala Lys Glu Leu Asp Gly Lys Asp
1490 1495 1500

Ile Asn Ile Leu Phe Asn Ser Leu Gln Tyr Thr Asn Val Val Lys
1505 1510 1515

Asp Tyr Trp Gly Asn Asp Leu Arg Tyr Asn Lys Glu Tyr Tyr Met
1520 1525 1530

Val Asn Ile Asp Tyr Leu Asn Arg Tyr Met Tyr Ala Asn Ser Arg
1535 1540 1545

Gln Ile Val Phe Asn Thr Arg Arg Asn Asn Asn Asp Phe Asn Glu
1550 1555 1560

Gly Tyr Lys Ile Ile Ile Lys Arg Ile Arg Gly Asn Thr Asn Asp
1565 1570 1575

Thr Arg Val Arg Gly Gly Asp Ile Leu Tyr Phe Asp Met Thr Ile

```
    1580                 1585                 1590

Asn Asn  Lys Ala Tyr Asn Leu  Phe Met Lys Asn Glu  Thr Met Tyr
    1595                 1600                 1605

Ala Asp  Asn His Ser Thr Glu  Asp Ile Tyr Ala Ile  Gly Leu Arg
    1610                 1615                 1620

Glu Gln  Thr Lys Asp Ile Asn  Asp Asn Ile Ile Phe  Gln Ile Gln
    1625                 1630                 1635

Pro Met  Asn Asn Thr Tyr Tyr  Tyr Ala Ser Gln Ile  Phe Lys Ser
    1640                 1645                 1650

Asn Phe  Asn Gly Glu Asn Ile  Ser Gly Ile Cys Ser  Ile Gly Thr
    1655                 1660                 1665

Tyr Arg  Phe Arg Leu Gly Gly  Asp Trp Tyr Arg His  Asn Tyr Leu
    1670                 1675                 1680

Val Pro  Thr Val Lys Gln Gly  Asn Tyr Ala Ser Leu  Leu Glu Ser
    1685                 1690                 1695

Thr Ser  Thr His Trp Gly Phe  Val Pro Val Ser Glu  Gly Ala Gly
    1700                 1705                 1710

Tyr Pro  Tyr Asp Val Pro Asp  Tyr Ala Gly Trp Glu  Leu Gln Gln
    1715                 1720                 1725

Gly Ala  Gly Trp Ser His Pro  Gln Phe Glu Lys Gly  Ala Gly Trp
    1730                 1735                 1740

Ser His  Pro Gln Phe Glu Lys  Gly Ala Gly Trp Ser  His Pro Gln
    1745                 1750                 1755

Phe Glu  Lys
    1760


<210> SEQ ID NO 39
<211> LENGTH: 9890
<212> TYPE: DNA
<213> ORGANISM: Artificial
<220> FEATURE:
<223> OTHER INFORMATION: DNA construct for molecular construction of
      fusion proteins

<400> SEQUENCE: 39

gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900
```

-continued

```
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
```

ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatctcgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtcggc 4200
tgggagctgc aaggcgccgg cgagcagaaa ctcatcagcg aagaagattt gggtgcggcc 4260
gctcaggttc aactcgtgga gagtggtggc ggactggtgc aatccggtgg cagcctgagg 4320
ctctcctgcg ctgcctctgg atcaatcgac agcctgtacc acatgggttg gtacaggcag 4380
gctcccggca aggagaggga actcgtcgcc agagttcaag acggaggtag tacagcatac 4440
aaggattcgg tcaaaggtcg cttcaccatt tctcgcgact tcagtcgttc gactatgtac 4500
ttgcagatga actcactgaa gcctgaggat acagccatct actactgtgc agcgaaatct 4560
accatttcaa ctccactgtc ttggggccag ggaacacaag tgacggtctc cagcgaaccg 4620
aagacgccta aaccccaatc ttcaggcgga ggtgcggccg ctggctcagg aggtggcagt 4680
caggtgcagc tggtggaatc cggtggtgga ctggtccagc ctggtggttc cctgcgtctg 4740
tcctgcgctg cttccggttt ccccttccac gcttactaca tgtcctgggt ccgccaggct 4800
cctggcaagg gattggaatg ggtgtcccac atcggcaacg gtggtatcat cacccgttac 4860
gctgactccg tgaagggccg tttcaccatc tcccgtgaca acgctaagaa caccctgtac 4920
ctgcagatga ccaacctgaa gcccgaggac accgctctgt actactgcac cctgggcacc 4980
cgtgacgacc tgggtcctga acgtggccag ggaacccaag tgaccgtgtc ctccgagccc 5040
aagaccccca agcctcaagg ggccggccag ggtgctggtg ctggaccgat caccatcaac 5100
aacttcaatt actcggatcc ggtggataac aagaacatcc tctacttgga cacacacttg 5160
aacacgctgg ctaacgagcc tgaaaaagct ttcaggatca ccggcaacat ttgggtcatt 5220
ccggataggt tcagcagaaa ctctaaccct aacttgaaca aacctcccag agtgacctca 5280
cctaagagtg gatactacga ccccaactac ctctcgactg actccgataa agaccccttc 5340
ctgaaggaga tcattaaact cttcaagcgc atcaactctc gtgaaattgg cgaggaattg 5400
atctaccgcc tgagtacaga catcccattc ccgggtaaca acaacacccc aatcaacact 5460
ttcgatttcg atgtcgattt caactcagtg gatgtcaaaa ccaggcaggg aaacaactgg 5520
gtgaagactg gtagcatcaa cccatctgtc atcattactg gcccgagaga gaacatcatt 5580
gaccctgaaa cctccacttt caagctgaca aacaacacgt tcgctgctca ggaaggcttc 5640

-continued ggagcgttga gcatcatttc tatctcacct cgcttcatgc tgacatactc taacgctacg 5700
aacgacgtgg gagagggccg tttcagtaag tctgaattct gcatggaccc tattctgatc 5760
ctcatgcacg ctctcaacgg cgccatgcac aacttgtacg gaattgctat ccccaacgac 5820
cagaccattt ccagcgtgac tagcaacatc ttctactctc aatacaacgt caagctggag 5880
tacgcagaaa tctacgcttt cggtggccca accattgact tgatcccgaa atcagctcgt 5940
aagtatttcg aagaaaaagc gctggattat tacaggtcga ttgctaagag actcaactcc 6000
atcaccactg ctaacccctc ttcattcaac aagtacattg gagaatacaa gcagaaactg 6060
atccgcaagt accgtttcgt ggtcgagagt tcgggtgaag ttactgtgaa ccgcaacaag 6120
ttcgtcgagc tgtacaacga attgacacaa atcttcacgg agttcaacta cgccaaaatt 6180
tacaacgtgc aaaaccgtaa gatcgcgctc tctaacgtct acaccccggt taccgctaac 6240
atcttggacg ataacgtcta cgacattcag aacggtttca acatcccaaa gtcgaacctc 6300
aacgttttgt tcatgggtca aaacttgtcc cgcaaccccg ccctgcgtaa ggtgaaccca 6360
gagaacatgt tgtacctgtt caccaaattc tgccacaagg ccatcgacgg tcagtctcta 6420
gaccaaggag gatgggaact ccagcaaggt ggccagggtg gaggtgctgg caccctggac 6480
tgtcgcgaac tgctcgttaa gaacactgat ctcccattca ttggcgacat ctctgatgtg 6540
aaaacagaca ttttcctgcg taaggatatc aacgaggaaa cggaggtcat ctactaccct 6600
gacaacgtct cggttgatca ggttatcttg tcaaagaaca ccagtgaaca tggccaactg 6660
gacttgctgt acccctcaat tgattccgag agcgaaatcc tgccaggaga gaaccaggtt 6720
ttctacgaca acaggacaca aaacgtggat tacctcaaca gctactacta cctggagtcg 6780
cagaagctct ccgacaacgt cgaagatttc acatttacga gatcaatcga ggaggctttg 6840
gacaacagtg ccaaagtcta cacctacttc cctactctgg caaacaaggt gaacgcgggt 6900
gtccaaggcg gactcttctt gatgtgggct aacgacgttg tggaagattt cacaacgaac 6960
atcttgcgca aagacaccct ggataagatc agcgatgtct ctgccatcat tccatacatt 7020
ggcccggcac tgaacatctc taactcagtt cgccgtggca acttcactga ggcattcgcg 7080
gtcacaggag ttacgatcct cttggaggct ttcccggagt tcacaatccc cgcactgggc 7140
gcgttcgtta tctactccaa agtgcaggag cgcaacgaaa tcattaagac tatcgacaac 7200
tgcctggagc aaaggatcaa aagatggaag gattcgtacg aatggatgat gggtacctgg 7260
ctctcccgta tcattacgca gttcaacaac atcagctacc aaatgtacga ctctctcaac 7320
taccaggctg gtgccatcaa ggccaaaatt gacttggagt acaagaaata cagtggctcg 7380
gataaagaga acatcaagag tcaagtcgaa aacctgaaaa actcactcga cgttaagatc 7440
agtgaggcaa tgaacaacat caacaagttc attcgcgaat gttccgttac ctacctcttc 7500
aaaaacatgt tgccaaaggt catcgacgag ctgaacgaat ttgatcgtaa cactaaggcg 7560
aaactgatta acctcatcga ctcacacaac atcattttgg tgggcgaagt cgataagctg 7620
aaagccaagg tgaacaacag tttccagaac acaatccctt tcaacatttt ctcatacacg 7680
aacaacagtc tgctcaagga catcattaac gagtacttca acaacattaa cgatagcaaa 7740
atcctgtcac tgcagaaccg taagaacaca ctggtcgata ctagtggata caacgccgaa 7800
gtctctgagg aaggtgacgt gcagctgaac cctatcttcc ccttcgactt caaattgggc 7860
tccagcggag aggatagggg caaggtcatc gtcacccaga acgagaacat cgtctacaac 7920
tcaatgtacg aatccttcag catctctttc tggatcagga ttaacaagtg ggtgagcaac 7980
ctgcccggtt acacaatcat tgactctgtc aagaacaact caggttggag tatcggcatc 8040

```
atttctaact tcttggtctt caccctgaag cagaacgagg actcggaaca atccattaac   8100
ttctcatacg atatcagtaa caacgctcca ggttacaaca agtggttctt cgttaccgtg   8160
actaacaaca tgatgggtaa catgaaaatt tacatcaacg gcaagctcat tgacaccatc   8220
aaagtgaagg agttgactgg tattaacttc tccaaaacaa tcacgtttga aattaacaag   8280
atccctgaca ccggcctgat cacttcagac agtgataaca tcaacatgtg gattagggat   8340
ttctacatct tcgccaagga gctcgacgga aaggatatta acatcctctt caacagcttg   8400
cagtacacca acgtcgttaa agactactgg ggtaacgatt tgagatacaa caaggagtac   8460
tacatggtca acatcgacta cctgaacagg tacatgtacg ctaactcccg ccaaatcgtg   8520
ttcaacacca ggagaaacaa caacgacttc aacgagggtt acaaaatcat tatcaagcgc   8580
atccgtggca acaccaacga tactagggtg agaggtggcg acattctgta cttcgatatg   8640
actatcaaca acaaagccta caacttgttc atgaaaaacg agacaatgta cgccgacaac   8700
catagcacgg aggatattta cgcaatcgga ctgagggaac agacaaagga catcaacgat   8760
aacattatct tccagatcca acctatgaac aacacgtact actacgcttc gcaaatcttc   8820
aagtccaact tcaacggaga aaacatttcg ggtatctgtt ccattggcac ataccgcttc   8880
cgtctgggtg gtgactggta tcgtcacaac tacctcgttc ccaccgtgaa gcagggtaac   8940
tacgcttctt tgctggagtc gacttccacg cactggggat tcgttcctgt gtcagagggc   9000
gctggctacc cttacgatgt tcccgactac gctggttggg aactccagca aggtgcagga   9060
tggtcccacc ctcaattcga gaagggtgcc ggatggagtc acccacagtt cgagaaaggc   9120
gctggatgga gtcacccaca gttcgagaaa taattagttg atgcatagtt aattagatag   9180
ctcgaggcat gcggtaccaa gattggatct agatgcatag ttaattagat agctcgaggc   9240
atgcggtacc aagcttgtcg agaagtacta gaggatcata atcagccata ccacatttgt   9300
agaggtttta cttgctttaa aaaacctccc acacctcccc ctgaacctga aacataaaat   9360
gaatgcaatt gttgttgtta acttgtttat tgcagcttat aatggttaca aataaagcaa   9420
tagcatcaca aatttcacaa ataaagcatt tttttcactg cattctagtt gtggtttgtc   9480
caaactcatc aatgtatctt atcatgtctg gatctgatca ctgcttgagc ctaggagatc   9540
cgaaccagat aagtgaaatc tagttccaaa ctattttgtc atttttaatt ttcgtattag   9600
cttacgacgc tacacccagt tcccatctat tttgtcactc ttccctaaat aatccttaaa   9660
aactccattt ccacccctcc cagttcccaa ctattttgtc cgcccacagc ggggcatttt   9720
tcttcctgtt atgtttttaa tcaaacatcc tgccaactcc atgtgacaaa ccgtcatctt   9780
cggctacttt ttctctgtca cagaatgaaa atttttctgt catctcttcg ttattaatgt   9840
ttgtaattga ctgaatatca acgcttattt gcagcctgaa tggcgaatgg              9890
```

<210> SEQ ID NO 40
<211> LENGTH: 1687
<212> TYPE: PRT
<213> ORGANISM: Artificial
<220> FEATURE:
<223> OTHER INFORMATION: Fusion protein construct

<400> SEQUENCE: 40

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30
```

```
His His Asp Val Gly Trp Glu Leu Gln Gly Ala Gly Glu Gln Lys Leu
        35                  40                  45

Ile Ser Glu Glu Asp Leu Gly Ala Ala Ala Gln Val Gln Leu Val Glu
    50                  55                  60

Ser Gly Gly Gly Leu Val Gln Ser Gly Gly Ser Leu Arg Leu Ser Cys
65                  70                  75                  80

Ala Ala Ser Gly Ser Ile Asp Ser Leu Tyr His Met Gly Trp Tyr Arg
                85                  90                  95

Gln Ala Pro Gly Lys Glu Arg Glu Leu Val Ala Arg Val Gln Asp Gly
            100                 105                 110

Gly Ser Thr Ala Tyr Lys Asp Ser Val Lys Gly Arg Phe Thr Ile Ser
        115                 120                 125

Arg Asp Phe Ser Arg Ser Thr Met Tyr Leu Gln Met Asn Ser Leu Lys
    130                 135                 140

Pro Glu Asp Thr Ala Ile Tyr Tyr Cys Ala Ala Lys Ser Thr Ile Ser
145                 150                 155                 160

Thr Pro Leu Ser Trp Gly Gln Gly Thr Gln Val Thr Val Ser Ser Glu
                165                 170                 175

Pro Lys Thr Pro Lys Pro Gln Ser Ser Gly Gly Gly Ala Ala Ala Gly
            180                 185                 190

Ser Gly Gly Gly Ser Gln Val Gln Leu Val Glu Ser Gly Gly Gly Leu
        195                 200                 205

Val Gln Pro Gly Gly Ser Leu Arg Leu Ser Cys Ala Ala Ser Gly Phe
    210                 215                 220

Pro Phe His Ala Tyr Tyr Met Ser Trp Val Arg Gln Ala Pro Gly Lys
225                 230                 235                 240

Gly Leu Glu Trp Val Ser His Ile Gly Asn Gly Gly Ile Ile Thr Arg
                245                 250                 255

Tyr Ala Asp Ser Val Lys Gly Arg Phe Thr Ile Ser Arg Asp Asn Ala
            260                 265                 270

Lys Asn Thr Leu Tyr Leu Gln Met Thr Asn Leu Lys Pro Glu Asp Thr
        275                 280                 285

Ala Leu Tyr Tyr Cys Thr Leu Gly Thr Arg Asp Asp Leu Gly Pro Glu
    290                 295                 300

Arg Gly Gln Gly Thr Gln Val Thr Val Ser Ser Glu Pro Lys Thr Pro
305                 310                 315                 320

Lys Pro Gln Gly Ala Gly Gln Gly Ala Gly Ala Gly Pro Ile Thr Ile
                325                 330                 335

Asn Asn Phe Asn Tyr Ser Asp Pro Val Asp Asn Lys Asn Ile Leu Tyr
            340                 345                 350

Leu Asp Thr His Leu Asn Thr Leu Ala Asn Glu Pro Glu Lys Ala Phe
        355                 360                 365

Arg Ile Thr Gly Asn Ile Trp Val Ile Pro Asp Arg Phe Ser Arg Asn
    370                 375                 380

Ser Asn Pro Asn Leu Asn Lys Pro Pro Arg Val Thr Ser Pro Lys Ser
385                 390                 395                 400

Gly Tyr Tyr Asp Pro Asn Tyr Leu Ser Thr Asp Ser Asp Lys Asp Pro
                405                 410                 415

Phe Leu Lys Glu Ile Ile Lys Leu Phe Lys Arg Ile Asn Ser Arg Glu
            420                 425                 430

Ile Gly Glu Glu Leu Ile Tyr Arg Leu Ser Thr Asp Ile Pro Phe Pro
        435                 440                 445

Gly Asn Asn Asn Thr Pro Ile Asn Thr Phe Asp Phe Asp Val Asp Phe
```

```
    450                 455                 460

Asn Ser Val Asp Val Lys Thr Arg Gln Gly Asn Asn Trp Val Lys Thr
465                 470                 475                 480

Gly Ser Ile Asn Pro Ser Val Ile Ile Thr Gly Pro Arg Glu Asn Ile
                485                 490                 495

Ile Asp Pro Glu Thr Ser Thr Phe Lys Leu Thr Asn Asn Thr Phe Ala
            500                 505                 510

Ala Gln Glu Gly Phe Gly Ala Leu Ser Ile Ile Ser Ile Ser Pro Arg
        515                 520                 525

Phe Met Leu Thr Tyr Ser Asn Ala Thr Asn Asp Val Gly Glu Gly Arg
    530                 535                 540

Phe Ser Lys Ser Glu Phe Cys Met Asp Pro Ile Leu Ile Leu Met His
545                 550                 555                 560

Ala Leu Asn Gly Ala Met His Asn Leu Tyr Gly Ile Ala Ile Pro Asn
                565                 570                 575

Asp Gln Thr Ile Ser Ser Val Thr Ser Asn Ile Phe Tyr Ser Gln Tyr
            580                 585                 590

Asn Val Lys Leu Glu Tyr Ala Glu Ile Tyr Ala Phe Gly Gly Pro Thr
        595                 600                 605

Ile Asp Leu Ile Pro Lys Ser Ala Arg Lys Tyr Phe Glu Glu Lys Ala
    610                 615                 620

Leu Asp Tyr Tyr Arg Ser Ile Ala Lys Arg Leu Asn Ser Ile Thr Thr
625                 630                 635                 640

Ala Asn Pro Ser Ser Phe Asn Lys Tyr Ile Gly Glu Tyr Lys Gln Lys
                645                 650                 655

Leu Ile Arg Lys Tyr Arg Phe Val Val Glu Ser Ser Gly Glu Val Thr
            660                 665                 670

Val Asn Arg Asn Lys Phe Val Glu Leu Tyr Asn Glu Leu Thr Gln Ile
        675                 680                 685

Phe Thr Glu Phe Asn Tyr Ala Lys Ile Tyr Asn Val Gln Asn Arg Lys
    690                 695                 700

Ile Ala Leu Ser Asn Val Tyr Thr Pro Val Thr Ala Asn Ile Leu Asp
705                 710                 715                 720

Asp Asn Val Tyr Asp Ile Gln Asn Gly Phe Asn Ile Pro Lys Ser Asn
                725                 730                 735

Leu Asn Val Leu Phe Met Gly Gln Asn Leu Ser Arg Asn Pro Ala Leu
            740                 745                 750

Arg Lys Val Asn Pro Glu Asn Met Leu Tyr Leu Phe Thr Lys Phe Cys
        755                 760                 765

His Lys Ala Ile Asp Gly Gln Ser Leu Asp Gln Gly Gly Trp Glu Leu
    770                 775                 780

Gln Gln Gly Gly Gln Gly Gly Gly Ala Gly Thr Leu Asp Cys Arg Glu
785                 790                 795                 800

Leu Leu Val Lys Asn Thr Asp Leu Pro Phe Ile Gly Asp Ile Ser Asp
                805                 810                 815

Val Lys Thr Asp Ile Phe Leu Arg Lys Asp Ile Asn Glu Glu Thr Glu
            820                 825                 830

Val Ile Tyr Tyr Pro Asp Asn Val Ser Val Asp Gln Val Ile Leu Ser
        835                 840                 845

Lys Asn Thr Ser Glu His Gly Gln Leu Asp Leu Leu Tyr Pro Ser Ile
    850                 855                 860

Asp Ser Glu Ser Glu Ile Leu Pro Gly Glu Asn Gln Val Phe Tyr Asp
865                 870                 875                 880
```

```
Asn Arg Thr Gln Asn Val Asp Tyr Leu Asn Ser Tyr Tyr Tyr Leu Glu
                885                 890                 895

Ser Gln Lys Leu Ser Asp Asn Val Glu Asp Phe Thr Phe Thr Arg Ser
            900                 905                 910

Ile Glu Glu Ala Leu Asp Asn Ser Ala Lys Val Tyr Thr Tyr Phe Pro
        915                 920                 925

Thr Leu Ala Asn Lys Val Asn Ala Gly Val Gln Gly Gly Leu Phe Leu
    930                 935                 940

Met Trp Ala Asn Asp Val Val Glu Asp Phe Thr Thr Asn Ile Leu Arg
945                 950                 955                 960

Lys Asp Thr Leu Asp Lys Ile Ser Asp Val Ser Ala Ile Ile Pro Tyr
                965                 970                 975

Ile Gly Pro Ala Leu Asn Ile Ser Asn Ser Val Arg Arg Gly Asn Phe
            980                 985                 990

Thr Glu Ala Phe Ala Val Thr Gly  Val Thr Ile Leu Leu  Glu Ala Phe
        995                 1000                1005

Pro Glu  Phe Thr Ile Pro Ala  Leu Gly Ala Phe Val  Ile Tyr Ser
    1010                1015                1020

Lys Val  Gln Glu Arg Asn Glu  Ile Ile Lys Thr Ile  Asp Asn Cys
    1025                1030                1035

Leu Glu  Gln Arg Ile Lys Arg  Trp Lys Asp Ser Tyr  Glu Trp Met
    1040                1045                1050

Met Gly  Thr Trp Leu Ser Arg  Ile Ile Thr Gln Phe  Asn Asn Ile
    1055                1060                1065

Ser Tyr  Gln Met Tyr Asp Ser  Leu Asn Tyr Gln Ala  Gly Ala Ile
    1070                1075                1080

Lys Ala  Lys Ile Asp Leu Glu  Tyr Lys Lys Tyr Ser  Gly Ser Asp
    1085                1090                1095

Lys Glu  Asn Ile Lys Ser Gln  Val Glu Asn Leu Lys  Asn Ser Leu
    1100                1105                1110

Asp Val  Lys Ile Ser Glu Ala  Met Asn Asn Ile Asn  Lys Phe Ile
    1115                1120                1125

Arg Glu  Cys Ser Val Thr Tyr  Leu Phe Lys Asn Met  Leu Pro Lys
    1130                1135                1140

Val Ile  Asp Glu Leu Asn Glu  Phe Asp Arg Asn Thr  Lys Ala Lys
    1145                1150                1155

Leu Ile  Asn Leu Ile Asp Ser  His Asn Ile Ile Leu  Val Gly Glu
    1160                1165                1170

Val Asp  Lys Leu Lys Ala Lys  Val Asn Asn Ser Phe  Gln Asn Thr
    1175                1180                1185

Ile Pro  Phe Asn Ile Phe Ser  Tyr Thr Asn Asn Ser  Leu Leu Lys
    1190                1195                1200

Asp Ile  Ile Asn Glu Tyr Phe  Asn Asn Ile Asn Asp  Ser Lys Ile
    1205                1210                1215

Leu Ser  Leu Gln Asn Arg Lys  Asn Thr Leu Val Asp  Thr Ser Gly
    1220                1225                1230

Tyr Asn  Ala Glu Val Ser Glu  Glu Gly Asp Val Gln  Leu Asn Pro
    1235                1240                1245

Ile Phe  Pro Phe Asp Phe Lys  Leu Gly Ser Ser Gly  Glu Asp Arg
    1250                1255                1260

Gly Lys  Val Ile Val Thr Gln  Asn Glu Asn Ile Val  Tyr Asn Ser
    1265                1270                1275
```

-continued

```
Met Tyr  Glu Ser Phe Ser Ile  Ser Phe Trp Ile Arg  Ile Asn Lys
    1280                 1285                 1290

Trp Val  Ser Asn Leu Pro Gly  Tyr Thr Ile Ile Asp  Ser Val Lys
    1295                 1300                 1305

Asn Asn  Ser Gly Trp Ser Ile  Gly Ile Ile Ser Asn  Phe Leu Val
    1310                 1315                 1320

Phe Thr  Leu Lys Gln Asn Glu  Asp Ser Glu Gln Ser  Ile Asn Phe
    1325                 1330                 1335

Ser Tyr  Asp Ile Ser Asn Asn  Ala Pro Gly Tyr Asn  Lys Trp Phe
    1340                 1345                 1350

Phe Val  Thr Val Thr Asn Asn  Met Met Gly Asn Met  Lys Ile Tyr
    1355                 1360                 1365

Ile Asn  Gly Lys Leu Ile Asp  Thr Ile Lys Val Lys  Glu Leu Thr
    1370                 1375                 1380

Gly Ile  Asn Phe Ser Lys Thr  Ile Thr Phe Glu Ile  Asn Lys Ile
    1385                 1390                 1395

Pro Asp  Thr Gly Leu Ile Thr  Ser Asp Ser Asp Asn  Ile Asn Met
    1400                 1405                 1410

Trp Ile  Arg Asp Phe Tyr Ile  Phe Ala Lys Glu Leu  Asp Gly Lys
    1415                 1420                 1425

Asp Ile  Asn Ile Leu Phe Asn  Ser Leu Gln Tyr Thr  Asn Val Val
    1430                 1435                 1440

Lys Asp  Tyr Trp Gly Asn Asp  Leu Arg Tyr Asn Lys  Glu Tyr Tyr
    1445                 1450                 1455

Met Val  Asn Ile Asp Tyr Leu  Asn Arg Tyr Met Tyr  Ala Asn Ser
    1460                 1465                 1470

Arg Gln  Ile Val Phe Asn Thr  Arg Arg Asn Asn Asn  Asp Phe Asn
    1475                 1480                 1485

Glu Gly  Tyr Lys Ile Ile Ile  Lys Arg Ile Arg Gly  Asn Thr Asn
    1490                 1495                 1500

Asp Thr  Arg Val Arg Gly Gly  Asp Ile Leu Tyr Phe  Asp Met Thr
    1505                 1510                 1515

Ile Asn  Asn Lys Ala Tyr Asn  Leu Phe Met Lys Asn  Glu Thr Met
    1520                 1525                 1530

Tyr Ala  Asp Asn His Ser Thr  Glu Asp Ile Tyr Ala  Ile Gly Leu
    1535                 1540                 1545

Arg Glu  Gln Thr Lys Asp Ile  Asn Asp Asn Ile Ile  Phe Gln Ile
    1550                 1555                 1560

Gln Pro  Met Asn Asn Thr Tyr  Tyr Tyr Ala Ser Gln  Ile Phe Lys
    1565                 1570                 1575

Ser Asn  Phe Asn Gly Glu Asn  Ile Ser Gly Ile Cys  Ser Ile Gly
    1580                 1585                 1590

Thr Tyr  Arg Phe Arg Leu Gly  Gly Asp Trp Tyr Arg  His Asn Tyr
    1595                 1600                 1605

Leu Val  Pro Thr Val Lys Gln  Gly Asn Tyr Ala Ser  Leu Leu Glu
    1610                 1615                 1620

Ser Thr  Ser Thr His Trp Gly  Phe Val Pro Val Ser  Glu Gly Ala
    1625                 1630                 1635

Gly Tyr  Pro Tyr Asp Val Pro  Asp Tyr Ala Gly Trp  Glu Leu Gln
    1640                 1645                 1650

Gln Gly  Ala Gly Trp Ser His  Pro Gln Phe Glu Lys  Gly Ala Gly
    1655                 1660                 1665

Trp Ser  His Pro Gln Phe Glu  Lys Gly Ala Gly Trp  Ser His Pro
```

```
    1670                1675                1680

Gln Phe  Glu Lys
    1685


<210> SEQ ID NO 41
<211> LENGTH: 10496
<212> TYPE: DNA
<213> ORGANISM: Artificial
<220> FEATURE:
<223> OTHER INFORMATION: DNA construct for molecular construction of
      fusion proteins

<400> SEQUENCE: 41

gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320

gcagcactgg ggccagatgg taagccctcc cgtatcgtag ttatctacac gacggggagt   1380

caggcaacta tggatgaacg aaatagacag atcgctgaga taggtgcctc actgattaag   1440

cattggtaac tgtcagacca agtttactca tatatacttt agattgattt aaaacttcat   1500

ttttaattta aaaggatcta ggtgaagatc ctttttgata atctcatgac caaaatccct   1560

taacgtgagt tttcgttcca ctgagcgtca gaccccgtag aaaagatcaa aggatcttct   1620

tgagatcctt tttttctgcg cgtaatctgc tgcttgcaaa caaaaaaacc accgctacca   1680

gcggtggttt gtttgccgga tcaagagcta ccaactcttt ttccgaaggt aactggcttc   1740

agcagagcgc agataccaaa tactgtcctt ctagtgtagc cgtagttagg ccaccacttc   1800

aagaactctg tagcaccgcc tacatacctc gctctgctaa tcctgttacc agtggctgct   1860

gccagtggcg ataagtcgtg tcttaccggg ttggactcaa gacgatagtt accggataag   1920
```

gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400
cggtattttc tccttacgca tctgtgcggt atttcacacc gcagaccagc cgcgtaacct 2460
ggcaaaatcg gttacggttg agtaataaat ggatgccctg cgtaagcggg tgtgggcgga 2520
caataaagtc ttaaactgaa caaaatagat ctaaactatg acaataaagt cttaaactag 2580
acagaatagt tgtaaactga aatcagtcca gttatgctgt gaaaaagcat actggacttt 2640
tgttatggct aaagcaaact cttcattttc tgaagtgcaa attgcccgtc gtattaaaga 2700
ggggcgtggc caagggcatg gtaaagacta tattcgcggc gttgtgacaa tttaccgaac 2760
aactccgcgg ccgggaagcc gatctcggct tgaacgaatt gttaggtggc ggtacttggg 2820
tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatctcgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtcggc 4200
tgggagctgc aacgtcgtcc cctgaactgc atcgtggctg tgtcccagaa catgggtatc 4260

-continued

```
ggcaagaacg gcgacctgcc ctggcctcct ctgcgtaacg agttcaagta cttccagcgt   4320
atgaccacca cctcctccgt cgagggcaag cagaacctgg tcatcatggg tcgcaagacc   4380
tggttctcca tccccgagaa gaaccgtctg ctgaaggacc gtatcaacat cgtgctgtcc   4440
cgcgagctga aggaaccccc tcgtggtgct cacttcctgg ctaagtccct ggacgacgct   4500
ctgcgtctga tcgagcagcc tgagctggct tccaaggtgg acatggtctg gatcgtgggc   4560
ggttcctccg tgtaccaaga ggctatgaac cagcccggtc acttgcgtct gttcgtgacc   4620
cgtatcatgc aagagttcga gtccgacacc ttcttccccg aaatcgacct gggcaagtac   4680
aagctgctgc ccgagtaccc cggtgtcctg tccgaggtgc aagaggaaaa gggtatcaag   4740
tacaagttcg aggtgtacga gaagaaggac ggcgcttccg gtttcgctaa cgagctcggt   4800
cctcgtctga tgggaaaggg cgccggcgag cagaaactca tcagcgaaga agatttgggt   4860
gcggccgctc aggttcaact cgtggagagt ggtggcggac tggtgcaatc cggtggcagc   4920
ctgaggctct cctgcgctgc ctctggatca atcgacagcc tgtaccacat gggttggtac   4980
aggcaggctc ccggcaagga gagggaactc gtcgccagag ttcaagacgg aggtagtaca   5040
gcatacaagg attcggtcaa aggtcgcttc accatttctc gcgacttcag tcgttcgact   5100
atgtacttgc agatgaactc actgaagcct gaggatacag ccatctacta ctgtgcagcg   5160
aaatctacca tttcaactcc actgtcttgg ggccagggaa cacaagtgac ggtctccagc   5220
gaaccgaaga cgcctaaacc ccaatcttca ggcggaggtg cggccgctgg ctcaggaggt   5280
ggcagtcagg tgcagctggt ggaatccggt ggtggactgg tccagcctgg tggttccctg   5340
cgtctgtcct gcgctgcttc cggtttcccc ttccacgctt actacatgtc ctgggtccgc   5400
caggctcctg gcaagggatt ggaatgggtg tcccacatcg gcaacggtgg tatcatcacc   5460
cgttacgctg actccgtgaa gggccgtttc accatctccc gtgacaacgc taagaacacc   5520
ctgtacctgc agatgaccaa cctgaagccc gaggacaccg ctctgtacta ctgcaccctg   5580
ggcacccgtg acgacctggg tcctgaacgt ggccagggaa cccaagtgac cgtgtcctcc   5640
gagcccaaga cccccaagcc tcaaggggcc ggccagggtg ctggtgctgg accgatcacc   5700
atcaacaact tcaattactc ggatccggtg gataacaaga acatcctcta cttggacaca   5760
cacttgaaca cgctggctaa cgagcctgaa aaagctttca ggatcaccgg caacatttgg   5820
gtcattccgg ataggttcag cagaaactct aaccctaact tgaacaaacc tcccagagtg   5880
acctcaccta agagtggata ctacgacccc aactacctct cgactgactc cgataaagac   5940
cccttcctga aggagatcat taaactcttc aagcgcatca actctcgtga aattggcgag   6000
gaattgatct accgcctgag tacagacatc ccattcccgg gtaacaacaa caccccaatc   6060
aacactttcg atttcgatgt cgatttcaac tcagtggatg tcaaaaccag gcagggaaac   6120
aactgggtga agactggtag catcaaccca tctgtcatca ttactggccc gagagagaac   6180
atcattgacc ctgaaacctc cactttcaag ctgacaaaca acacgttcgc tgctcaggaa   6240
ggcttcggag cgttgagcat catttctatc tcacctcgct tcatgctgac atactctaac   6300
gctacgaacg acgtgggaga gggccgtttc agtaagtctg aattctgcat ggaccctatt   6360
ctgatcctca tgcacgctct caacggcgcc atgcacaact tgtacggaat tgctatcccc   6420
aacgaccaga ccatttccag cgtgactagc aacatcttct actctcaata caacgtcaag   6480
ctggagtacg cagaaatcta cgctttcggt ggcccaacca ttgacttgat cccgaaatca   6540
gctcgtaagt atttcgaaga aaaagcgctg gattattaca ggtcgattgc taagagactc   6600
aactccatca ccactgctaa cccctcttca ttcaacaagt acattggaga atacaagcag   6660
```

aaactgatcc gcaagtaccg tttcgtggtc gagagttcgg gtgaagttac tgtgaaccgc 6720
aacaagttcg tcgagctgta caacgaattg acacaaatct tcacggagtt caactacgcc 6780
aaaatttaca acgtgcaaaa ccgtaagatc gcgctctcta acgtctacac cccggttacc 6840
gctaacatct tggacgataa cgtctacgac attcagaacg gtttcaacat cccaaagtcg 6900
aacctcaacg ttttgttcat gggtcaaaac ttgtcccgca accccgccct gcgtaaggtg 6960
aacccagaga acatgttgta cctgttcacc aaattctgcc acaaggccat cgacggtcag 7020
tctctagacc aaggaggatg ggaactccag caaggtggcc agggtggagg tgctggcacc 7080
ctggactgtc gcgaactgct cgttaagaac actgatctcc cattcattgg cgacatctct 7140
gatgtgaaaa cagacatttt cctgcgtaag gatatcaacg aggaaacgga ggtcatctac 7200
taccctgaca acgtctcggt tgatcaggtt atcttgtcaa agaacaccag tgaacatggc 7260
caactggact tgctgtaccc ctcaattgat tccgagagcg aaatcctgcc aggagagaac 7320
caggttttct acgacaacag gacacaaaac gtggattacc tcaacagcta ctactacctg 7380
gagtcgcaga agctctccga caacgtcgaa gatttcacat ttacgagatc aatcgaggag 7440
gctttggaca acagtgccaa agtctacacc tacttcccta ctctggcaaa caaggtgaac 7500
gcgggtgtcc aaggcggact cttcttgatg tgggctaacg acgttgtgga agatttcaca 7560
acgaacatct tgcgcaaaga caccctggat aagatcagcg atgtctctgc catcattcca 7620
tacattggcc cggcactgaa catctctaac tcagttcgcc gtggcaactt cactgaggca 7680
ttcgcggtca caggagttac gatcctcttg gaggctttcc cggagttcac aatccccgca 7740
ctgggcgcgt tcgttatcta ctccaaagtg caggagcgca acgaaatcat taagactatc 7800
gacaactgcc tggagcaaag gatcaaaaga tggaaggatt cgtacgaatg gatgatgggt 7860
acctggctct cccgtatcat tacgcagttc aacaacatca gctaccaaat gtacgactct 7920
ctcaactacc aggctggtgc catcaaggcc aaaattgact tggagtacaa gaaatacagt 7980
ggctcggata aagagaacat caagagtcaa gtcgaaaacc tgaaaaactc actcgacgtt 8040
aagatcagtg aggcaatgaa caacatcaac aagttcattc gcgaatgttc cgttacctac 8100
ctcttcaaaa acatgttgcc aaaggtcatc gacgagctga acgaatttga tcgtaacact 8160
aaggcgaaac tgattaacct catcgactca cacaacatca ttttggtggg cgaagtcgat 8220
aagctgaaag ccaaggtgaa caacagtttc cagaacacaa tccctttcaa cattttctca 8280
tacacgaaca acagtctgct caaggacatc attaacgagt acttcaacaa cattaacgat 8340
agcaaaatcc tgtcactgca gaaccgtaag aacacactgg tcgatactag tggatacaac 8400
gccgaagtct ctgaggaagg tgacgtgcag ctgaacccta tcttcccctt cgacttcaaa 8460
ttgggctcca gcggagagga taggggcaag gtcatcgtca cccagaacga gaacatcgtc 8520
tacaactcaa tgtacgaatc cttcagcatc tctttctgga tcaggattaa caagtgggtg 8580
agcaacctgc ccggttacac aatcattgac tctgtcaaga acaactcagg ttggagtatc 8640
ggcatcattt ctaacttctt ggtcttcacc ctgaagcaga acgaggactc ggaacaatcc 8700
attaacttct catacgatat cagtaacaac gctccaggtt acaacaagtg gttcttcgtt 8760
accgtgacta acaacatgat gggtaacatg aaaatttaca tcaacggcaa gctcattgac 8820
accatcaaag tgaaggagtt gactggtatt aacttctcca aaacaatcac gtttgaaatt 8880
aacaagatcc ctgacaccgg cctgatcact tcagacagtg ataacatcaa catgtggatt 8940
agggatttct acatcttcgc caaggagctc gacggaaagg atattaacat cctcttcaac 9000

-continued

```
agcttgcagt acaccaacgt cgttaaagac tactggggta acgatttgag atacaacaag   9060
gagtactaca tggtcaacat cgactacctg aacaggtaca tgtacgctaa ctcccgccaa   9120
atcgtgttca acaccaggag aaacaacaac gacttcaacg agggttacaa aatcattatc   9180
aagcgcatcc gtggcaacac caacgatact agggtgagag gtggcgacat tctgtacttc   9240
gatatgacta tcaacaacaa agcctacaac ttgttcatga aaaacgagac aatgtacgcc   9300
gacaaccata gcacggagga tatttacgca atcggactga gggaacagac aaaggacatc   9360
aacgataaca ttatcttcca gatccaacct atgaacaaca cgtactacta cgcttcgcaa   9420
atcttcaagt ccaacttcaa cggagaaaac atttcgggta tctgttccat tggcacatac   9480
cgcttccgtc tgggtggtga ctggtatcgt cacaactacc tcgttcccac cgtgaagcag   9540
ggtaactacg cttctttgct ggagtcgact tccacgcact ggggattcgt tcctgtgtca   9600
gagggcgctg gctaccctta cgatgttccc gactacgctg gttgggaact ccagcaaggt   9660
gcaggatggt cccaccctca attcgagaag ggtgccggat ggagtcaccc acagttcgag   9720
aaaggcgctg gatggagtca cccacagttc gagaaataat tagttgatgc atagttaatt   9780
agatagctcg aggcatgcgg taccaagatt ggatctagat gcatagttaa ttagatagct   9840
cgaggcatgc ggtaccaagc ttgtcgagaa gtactagagg atcataatca gccataccac   9900
atttgtagag gttttacttg ctttaaaaaa cctcccacac ctccccctga acctgaaaca   9960
taaaatgaat gcaattgttg ttgttaactt gtttattgca gcttataatg gttacaaata  10020
aagcaatagc atcacaaatt tcacaaataa agcatttttt tcactgcatt ctagttgtgg  10080
tttgtccaaa ctcatcaatg tatcttatca tgtctggatc tgatcactgc ttgagcctag  10140
gagatccgaa ccagataagt gaaatctagt tccaaactat tttgtcattt ttaattttcg  10200
tattagctta cgacgctaca cccagttccc atctattttg tcactcttcc ctaaataatc  10260
cttaaaaact ccatttccac ccctcccagt tcccaactat tttgtccgcc cacagcgggg  10320
catttttctt cctgttatgt ttttaatcaa acatcctgcc aactccatgt gacaaaccgt  10380
catcttcggc tactttttct ctgtcacaga atgaaaattt ttctgtcatc tcttcgttat  10440
taatgtttgt aattgactga atatcaacgc ttatttgcag cctgaatggc gaatgg       10496
```

<210> SEQ ID NO 42
<211> LENGTH: 1889
<212> TYPE: PRT
<213> ORGANISM: Artificial
<220> FEATURE:
<223> OTHER INFORMATION: Fusion protein construct

<400> SEQUENCE: 42

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
```

```
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140

Glu Leu Ala Ser Lys Val Asp Met Val Trp Ile Val Gly Gly Ser Ser
145                 150                 155                 160

Val Tyr Gln Glu Ala Met Asn Gln Pro Gly His Leu Arg Leu Phe Val
                165                 170                 175

Thr Arg Ile Met Gln Glu Phe Glu Ser Asp Thr Phe Phe Pro Glu Ile
            180                 185                 190

Asp Leu Gly Lys Tyr Lys Leu Leu Pro Glu Tyr Pro Gly Val Leu Ser
        195                 200                 205

Glu Val Gln Glu Glu Lys Gly Ile Lys Tyr Lys Phe Glu Val Tyr Glu
    210                 215                 220

Lys Lys Asp Gly Ala Ser Gly Phe Ala Asn Glu Leu Gly Pro Arg Leu
225                 230                 235                 240

Met Gly Lys Gly Ala Gly Glu Gln Lys Leu Ile Ser Glu Glu Asp Leu
                245                 250                 255

Gly Ala Ala Ala Gln Val Gln Leu Val Glu Ser Gly Gly Gly Leu Val
            260                 265                 270

Gln Ser Gly Gly Ser Leu Arg Leu Ser Cys Ala Ala Ser Gly Ser Ile
        275                 280                 285

Asp Ser Leu Tyr His Met Gly Trp Tyr Arg Gln Ala Pro Gly Lys Glu
    290                 295                 300

Arg Glu Leu Val Ala Arg Val Gln Asp Gly Gly Ser Thr Ala Tyr Lys
305                 310                 315                 320

Asp Ser Val Lys Gly Arg Phe Thr Ile Ser Arg Asp Phe Ser Arg Ser
                325                 330                 335

Thr Met Tyr Leu Gln Met Asn Ser Leu Lys Pro Glu Asp Thr Ala Ile
            340                 345                 350

Tyr Tyr Cys Ala Ala Lys Ser Thr Ile Ser Thr Pro Leu Ser Trp Gly
        355                 360                 365

Gln Gly Thr Gln Val Thr Val Ser Ser Glu Pro Lys Thr Pro Lys Pro
    370                 375                 380

Gln Ser Ser Gly Gly Gly Ala Ala Ala Gly Ser Gly Gly Gly Ser Gln
385                 390                 395                 400

Val Gln Leu Val Glu Ser Gly Gly Gly Leu Val Gln Pro Gly Gly Ser
                405                 410                 415

Leu Arg Leu Ser Cys Ala Ala Ser Gly Phe Pro Phe His Ala Tyr Tyr
            420                 425                 430

Met Ser Trp Val Arg Gln Ala Pro Gly Lys Gly Leu Glu Trp Val Ser
        435                 440                 445

His Ile Gly Asn Gly Gly Ile Ile Thr Arg Tyr Ala Asp Ser Val Lys
    450                 455                 460

Gly Arg Phe Thr Ile Ser Arg Asp Asn Ala Lys Asn Thr Leu Tyr Leu
465                 470                 475                 480

Gln Met Thr Asn Leu Lys Pro Glu Asp Thr Ala Leu Tyr Tyr Cys Thr
                485                 490                 495

Leu Gly Thr Arg Asp Asp Leu Gly Pro Glu Arg Gly Gln Gly Thr Gln
            500                 505                 510

Val Thr Val Ser Ser Glu Pro Lys Thr Pro Lys Pro Gln Gly Ala Gly
        515                 520                 525
```

```
Gln Gly Ala Gly Ala Gly Pro Ile Thr Ile Asn Asn Phe Asn Tyr Ser
    530                 535                 540

Asp Pro Val Asp Asn Lys Asn Ile Leu Tyr Leu Asp Thr His Leu Asn
545                 550                 555                 560

Thr Leu Ala Asn Glu Pro Glu Lys Ala Phe Arg Ile Thr Gly Asn Ile
                565                 570                 575

Trp Val Ile Pro Asp Arg Phe Ser Arg Asn Ser Asn Pro Asn Leu Asn
            580                 585                 590

Lys Pro Pro Arg Val Thr Ser Pro Lys Ser Gly Tyr Tyr Asp Pro Asn
        595                 600                 605

Tyr Leu Ser Thr Asp Ser Asp Lys Asp Pro Phe Leu Lys Glu Ile Ile
    610                 615                 620

Lys Leu Phe Lys Arg Ile Asn Ser Arg Glu Ile Gly Glu Glu Leu Ile
625                 630                 635                 640

Tyr Arg Leu Ser Thr Asp Ile Pro Phe Pro Gly Asn Asn Asn Thr Pro
                645                 650                 655

Ile Asn Thr Phe Asp Phe Asp Val Asp Phe Asn Ser Val Asp Val Lys
            660                 665                 670

Thr Arg Gln Gly Asn Asn Trp Val Lys Thr Gly Ser Ile Asn Pro Ser
        675                 680                 685

Val Ile Ile Thr Gly Pro Arg Glu Asn Ile Ile Asp Pro Glu Thr Ser
    690                 695                 700

Thr Phe Lys Leu Thr Asn Asn Thr Phe Ala Ala Gln Glu Gly Phe Gly
705                 710                 715                 720

Ala Leu Ser Ile Ile Ser Ile Ser Pro Arg Phe Met Leu Thr Tyr Ser
                725                 730                 735

Asn Ala Thr Asn Asp Val Gly Glu Gly Arg Phe Ser Lys Ser Glu Phe
            740                 745                 750

Cys Met Asp Pro Ile Leu Ile Leu Met His Ala Leu Asn Gly Ala Met
        755                 760                 765

His Asn Leu Tyr Gly Ile Ala Ile Pro Asn Asp Gln Thr Ile Ser Ser
    770                 775                 780

Val Thr Ser Asn Ile Phe Tyr Ser Gln Tyr Asn Val Lys Leu Glu Tyr
785                 790                 795                 800

Ala Glu Ile Tyr Ala Phe Gly Gly Pro Thr Ile Asp Leu Ile Pro Lys
                805                 810                 815

Ser Ala Arg Lys Tyr Phe Glu Glu Lys Ala Leu Asp Tyr Tyr Arg Ser
            820                 825                 830

Ile Ala Lys Arg Leu Asn Ser Ile Thr Thr Ala Asn Pro Ser Ser Phe
        835                 840                 845

Asn Lys Tyr Ile Gly Glu Tyr Lys Gln Lys Leu Ile Arg Lys Tyr Arg
    850                 855                 860

Phe Val Val Glu Ser Ser Gly Glu Val Thr Val Asn Arg Asn Lys Phe
865                 870                 875                 880

Val Glu Leu Tyr Asn Glu Leu Thr Gln Ile Phe Thr Glu Phe Asn Tyr
                885                 890                 895

Ala Lys Ile Tyr Asn Val Gln Asn Arg Lys Ile Ala Leu Ser Asn Val
            900                 905                 910

Tyr Thr Pro Val Thr Ala Asn Ile Leu Asp Asp Asn Val Tyr Asp Ile
        915                 920                 925

Gln Asn Gly Phe Asn Ile Pro Lys Ser Asn Leu Asn Val Leu Phe Met
    930                 935                 940
```

```
Gly Gln Asn Leu Ser Arg Asn Pro Ala Leu Arg Lys Val Asn Pro Glu
945                 950                 955                 960

Asn Met Leu Tyr Leu Phe Thr Lys Phe Cys His Lys Ala Ile Asp Gly
                965                 970                 975

Gln Ser Leu Asp Gln Gly Gly Trp Glu Leu Gln Gln Gly Gly Gln Gly
            980                 985                 990

Gly Gly Ala Gly Thr Leu Asp Cys  Arg Glu Leu Leu Val  Lys Asn Thr
        995                 1000                 1005

Asp Leu  Pro Phe Ile Gly Asp  Ile Ser Asp Val Lys  Thr Asp Ile
    1010                 1015                 1020

Phe Leu  Arg Lys Asp Ile Asn  Glu Glu Thr Glu Val  Ile Tyr Tyr
    1025                 1030                 1035

Pro Asp  Asn Val Ser Val Asp  Gln Val Ile Leu Ser  Lys Asn Thr
    1040                 1045                 1050

Ser Glu  His Gly Gln Leu Asp  Leu Leu Tyr Pro Ser  Ile Asp Ser
    1055                 1060                 1065

Glu Ser  Glu Ile Leu Pro Gly  Glu Asn Gln Val Phe  Tyr Asp Asn
    1070                 1075                 1080

Arg Thr  Gln Asn Val Asp Tyr  Leu Asn Ser Tyr Tyr  Tyr Leu Glu
    1085                 1090                 1095

Ser Gln  Lys Leu Ser Asp Asn  Val Glu Asp Phe Thr  Phe Thr Arg
    1100                 1105                 1110

Ser Ile  Glu Glu Ala Leu Asp  Asn Ser Ala Lys Val  Tyr Thr Tyr
    1115                 1120                 1125

Phe Pro  Thr Leu Ala Asn Lys  Val Asn Ala Gly Val  Gln Gly Gly
    1130                 1135                 1140

Leu Phe  Leu Met Trp Ala Asn  Asp Val Val Glu Asp  Phe Thr Thr
    1145                 1150                 1155

Asn Ile  Leu Arg Lys Asp Thr  Leu Asp Lys Ile Ser  Asp Val Ser
    1160                 1165                 1170

Ala Ile  Ile Pro Tyr Ile Gly  Pro Ala Leu Asn Ile  Ser Asn Ser
    1175                 1180                 1185

Val Arg  Arg Gly Asn Phe Thr  Glu Ala Phe Ala Val  Thr Gly Val
    1190                 1195                 1200

Thr Ile  Leu Leu Glu Ala Phe  Pro Glu Phe Thr Ile  Pro Ala Leu
    1205                 1210                 1215

Gly Ala  Phe Val Ile Tyr Ser  Lys Val Gln Glu Arg  Asn Glu Ile
    1220                 1225                 1230

Ile Lys  Thr Ile Asp Asn Cys  Leu Glu Gln Arg Ile  Lys Arg Trp
    1235                 1240                 1245

Lys Asp  Ser Tyr Glu Trp Met  Met Gly Thr Trp Leu  Ser Arg Ile
    1250                 1255                 1260

Ile Thr  Gln Phe Asn Asn Ile  Ser Tyr Gln Met Tyr  Asp Ser Leu
    1265                 1270                 1275

Asn Tyr  Gln Ala Gly Ala Ile  Lys Ala Lys Ile Asp  Leu Glu Tyr
    1280                 1285                 1290

Lys Lys  Tyr Ser Gly Ser Asp  Lys Glu Asn Ile Lys  Ser Gln Val
    1295                 1300                 1305

Glu Asn  Leu Lys Asn Ser Leu  Asp Val Lys Ile Ser  Glu Ala Met
    1310                 1315                 1320

Asn Asn  Ile Asn Lys Phe Ile  Arg Glu Cys Ser Val  Thr Tyr Leu
    1325                 1330                 1335

Phe Lys  Asn Met Leu Pro Lys  Val Ile Asp Glu Leu  Asn Glu Phe
```

1340 1345 1350

Asp Arg Asn Thr Lys Ala Lys Leu Ile Asn Leu Ile Asp Ser His
1355 1360 1365

Asn Ile Ile Leu Val Gly Glu Val Asp Lys Leu Lys Ala Lys Val
1370 1375 1380

Asn Asn Ser Phe Gln Asn Thr Ile Pro Phe Asn Ile Phe Ser Tyr
1385 1390 1395

Thr Asn Asn Ser Leu Leu Lys Asp Ile Ile Asn Glu Tyr Phe Asn
1400 1405 1410

Asn Ile Asn Asp Ser Lys Ile Leu Ser Leu Gln Asn Arg Lys Asn
1415 1420 1425

Thr Leu Val Asp Thr Ser Gly Tyr Asn Ala Glu Val Ser Glu Glu
1430 1435 1440

Gly Asp Val Gln Leu Asn Pro Ile Phe Pro Phe Asp Phe Lys Leu
1445 1450 1455

Gly Ser Ser Gly Glu Asp Arg Gly Lys Val Ile Val Thr Gln Asn
1460 1465 1470

Glu Asn Ile Val Tyr Asn Ser Met Tyr Glu Ser Phe Ser Ile Ser
1475 1480 1485

Phe Trp Ile Arg Ile Asn Lys Trp Val Ser Asn Leu Pro Gly Tyr
1490 1495 1500

Thr Ile Ile Asp Ser Val Lys Asn Asn Ser Gly Trp Ser Ile Gly
1505 1510 1515

Ile Ile Ser Asn Phe Leu Val Phe Thr Leu Lys Gln Asn Glu Asp
1520 1525 1530

Ser Glu Gln Ser Ile Asn Phe Ser Tyr Asp Ile Ser Asn Asn Ala
1535 1540 1545

Pro Gly Tyr Asn Lys Trp Phe Phe Val Thr Val Thr Asn Asn Met
1550 1555 1560

Met Gly Asn Met Lys Ile Tyr Ile Asn Gly Lys Leu Ile Asp Thr
1565 1570 1575

Ile Lys Val Lys Glu Leu Thr Gly Ile Asn Phe Ser Lys Thr Ile
1580 1585 1590

Thr Phe Glu Ile Asn Lys Ile Pro Asp Thr Gly Leu Ile Thr Ser
1595 1600 1605

Asp Ser Asp Asn Ile Asn Met Trp Ile Arg Asp Phe Tyr Ile Phe
1610 1615 1620

Ala Lys Glu Leu Asp Gly Lys Asp Ile Asn Ile Leu Phe Asn Ser
1625 1630 1635

Leu Gln Tyr Thr Asn Val Val Lys Asp Tyr Trp Gly Asn Asp Leu
1640 1645 1650

Arg Tyr Asn Lys Glu Tyr Tyr Met Val Asn Ile Asp Tyr Leu Asn
1655 1660 1665

Arg Tyr Met Tyr Ala Asn Ser Arg Gln Ile Val Phe Asn Thr Arg
1670 1675 1680

Arg Asn Asn Asn Asp Phe Asn Glu Gly Tyr Lys Ile Ile Ile Lys
1685 1690 1695

Arg Ile Arg Gly Asn Thr Asn Asp Thr Arg Val Arg Gly Gly Asp
1700 1705 1710

Ile Leu Tyr Phe Asp Met Thr Ile Asn Asn Lys Ala Tyr Asn Leu
1715 1720 1725

Phe Met Lys Asn Glu Thr Met Tyr Ala Asp Asn His Ser Thr Glu
1730 1735 1740

```
Asp Ile  Tyr Ala Ile Gly Leu  Arg Glu Gln Thr Lys  Asp Ile Asn
    1745                 1750                 1755

Asp Asn  Ile Ile Phe Gln Ile  Gln Pro Met Asn Asn  Thr Tyr Tyr
    1760                 1765                 1770

Tyr Ala  Ser Gln Ile Phe Lys  Ser Asn Phe Asn Gly  Glu Asn Ile
    1775                 1780                 1785

Ser Gly  Ile Cys Ser Ile Gly  Thr Tyr Arg Phe Arg  Leu Gly Gly
    1790                 1795                 1800

Asp Trp  Tyr Arg His Asn Tyr  Leu Val Pro Thr Val  Lys Gln Gly
    1805                 1810                 1815

Asn Tyr  Ala Ser Leu Leu Glu  Ser Thr Ser Thr His  Trp Gly Phe
    1820                 1825                 1830

Val Pro  Val Ser Glu Gly Ala  Gly Tyr Pro Tyr Asp  Val Pro Asp
    1835                 1840                 1845

Tyr Ala  Gly Trp Glu Leu Gln  Gln Gly Ala Gly Trp  Ser His Pro
    1850                 1855                 1860

Gln Phe  Glu Lys Gly Ala Gly  Trp Ser His Pro Gln  Phe Glu Lys
    1865                 1870                 1875

Gly Ala  Gly Trp Ser His Pro  Gln Phe Glu Lys
    1880                 1885
```

<210> SEQ ID NO 43
<211> LENGTH: 9890
<212> TYPE: DNA
<213> ORGANISM: Artificial
<220> FEATURE:
<223> OTHER INFORMATION: DNA construct for molecular construction of fusion proteins

<400> SEQUENCE: 43

```
gacgcgccct gtagcggcgc attaagcgcg gcgggtgtgg tggttacgcg cagcgtgacc     60
gctacacttg ccagcgccct agcgcccgct cctttcgctt tcttcccttc ctttctcgcc    120
acgttcgccg gctttccccg tcaagctcta aatcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
```

gcaacaacgt tgcgcaaact attaactggc gaactactta ctctagcttc ccggcaacaa 1200
ttaatagact ggatggaggc ggataaagtt gcaggaccac ttctgcgctc ggcccttccg 1260
gctggctggt ttattgctga taaatctgga gccggtgagc gtgggtctcg cggtatcatt 1320
gcagcactgg ggccagatgg taagccctcc cgtatcgtag ttatctacac gacggggagt 1380
caggcaacta tggatgaacg aaatagacag atcgctgaga taggtgcctc actgattaag 1440
cattggtaac tgtcagacca agtttactca tatatacttt agattgattt aaaacttcat 1500
ttttaattta aaaggatcta ggtgaagatc ctttttgata atctcatgac caaaatccct 1560
taacgtgagt tttcgttcca ctgagcgtca gaccccgtag aaaagatcaa aggatcttct 1620
tgagatcctt tttttctgcg cgtaatctgc tgcttgcaaa caaaaaaacc accgctacca 1680
gcggtggttt gtttgccgga tcaagagcta ccaactcttt ttccgaaggt aactggcttc 1740
agcagagcgc agataccaaa tactgtcctt ctagtgtagc cgtagttagg ccaccacttc 1800
aagaactctg tagcaccgcc tacatacctc gctctgctaa tcctgttacc agtggctgct 1860
gccagtggcg ataagtcgtg tcttaccggg ttggactcaa gacgatagtt accggataag 1920
gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400
cggtattttc tccttacgca tctgtgcggt atttcacacc gcagaccagc cgcgtaacct 2460
ggcaaaatcg gttacggttg agtaataaat ggatgccctg cgtaagcggg tgtgggcgga 2520
caataaagtc ttaaactgaa caaaatagat ctaaactatg acaataaagt cttaaactag 2580
acagaatagt tgtaaactga aatcagtcca gttatgctgt gaaaaagcat actggacttt 2640
tgttatggct aaagcaaact cttcattttc tgaagtgcaa attgcccgtc gtattaaaga 2700
ggggcgtggc caagggcatg gtaaagacta tattcgcggc gttgtgacaa tttaccgaac 2760
aactccgcgg ccgggaagcc gatctcggct tgaacgaatt gttaggtggc ggtacttggg 2820
tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480

```
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca ccaccaccac caccaccacc accaccacca cgacgtcggc   4200
tgggagctgc aaggcgccgg cgagcagaaa ctcatcagcg aagaagattt gggtgcggcc   4260
gctcaggttc aactcgtgga gagtggtggc ggactggtgc aatccggtgg cagcctgagg   4320
ctctcctgcg ctgcctctgg atcaatcgac agcctgtacc acatgggttg gtacaggcag   4380
gctcccggca aggagaggga actcgtcgcc agagttcaag acggaggtag tacagcatac   4440
aaggattcgg tcaaaggtcg cttcaccatt tctcgcgact tcagtcgttc gactatgtac   4500
ttgcagatga actcactgaa gcctgaggat acagccatct actactgtgc agcgaaatct   4560
accatttcaa ctccactgtc ttggggccag ggaacacaag tgacggtctc cagcgaaccg   4620
aagacgccta aaccccaatc ttcaggcgga ggtgcggccg ctggctcagg aggtggcagt   4680
caggtgcagc tggtggaatc cggtggtgga ctggtccagc ctggtggttc cctgcgtctg   4740
tcctgcgctg cttccggttt ccccttccac gcttactaca tgtcctgggt ccgccaggct   4800
cctggcaagg gattggaatg ggtgtcccac atcggcaacg gtggtatcat cacccgttac   4860
gctgactccg tgaagggccg tttcaccatc tcccgtgaca acgctaagaa caccctgtac   4920
ctgcagatga ccaacctgaa gcccgaggac accgctctgt actactgcac cctgggcacc   4980
cgtgacgacc tgggtcctga acgtggccag ggaacccaag tgaccgtgtc ctccgagccc   5040
aagaccccca agcctcaagg ggccggccag ggtgctggtg ctggaccgat caccatcaac   5100
aacttcaatt actcggatcc ggtggataac aagaacatcc tctacttgga cacacacttg   5160
aacacgctgg ctaacgagcc tgaaaaagct ttcaggatca ccggcaacat ttgggtcatt   5220
ccggataggt tcagcagaaa ctctaaccct aacttgaaca aacctcccag agtgacctca   5280
cctaagagtg gatactacga ccccaactac ctctcgactg actccgataa agaccccttc   5340
ctgaaggaga tcattaaact cttcaagcgc atcaactctc gtgaaattgg cgaggaattg   5400
atctaccgcc tgagtacaga catcccattc ccgggtaaca acaacacccc aatcaacact   5460
ttcgatttcg atgtcgattt caactcagtg gatgtcaaaa ccaggcaggg aaacaactgg   5520
gtgaagactg gtagcatcaa cccatctgtc atcattactg gcccgagaga gaacatcatt   5580
gaccctgaaa cctccacttt caagctgaca aacaacacgt tcgctgctca ggaaggcttc   5640
ggagcgttga gcatcatttc tatctcacct cgcttcatgc tgacatactc taacgctacg   5700
aacgacgtgg gagagggccg tttcagtaag tctgaattct gcatggaccc tattctgatc   5760
ctcatgcacg ctctcaacgg cgccatgcac aacttgtacg gaattgctat ccccaacgac   5820
cagaccattt ccagcgtgac tagcaacatc ttctactctc aatacaacgt caagctggag   5880
```

```
tacgcagaaa tctacgcttt cggtggccca accattgact tgatcccgaa atcagctcgt   5940
aagtatttcg aagaaaaagc gctggattat tacaggtcga ttgctaagag actcaactcc   6000
atcaccactg ctaacccctc ttcattcaac aagtacattg gagaatacaa gcagaaactg   6060
atccgcaagt accgtttcgt ggtcgagagt tcgggtgaag ttactgtgaa ccgcaacaag   6120
ttcgtcgagc tgtacaacga attgacacaa atcttcacgg agttcaacta cgccaaaatt   6180
tacaacgtgc aaaaccgtaa gatcgcgctc tctaacgtct acaccccggt taccgctaac   6240
atcttggacg ataacgtcta cgacattcag aacggtttca acatcccaaa gtcgaacctc   6300
aacgttttgt tcatgggtca aaacttgtcc cgcaaccccg ccctgcgtaa ggtgaaccca   6360
gagaacatgt tgtacctgtt caccaaattc tgccacaagg ccatcgacgg tcagtctcta   6420
gaccaaggag gatgggaact ccagcaaggt ggccagggtg gaggtgctgg caccctggac   6480
tgtcgcgaac tgctcgttaa gaacactgat ctcccattca ttggcgacat ctctgatgtg   6540
aaaacagaca ttttcctgcg taaggatatc aacgaggaaa cggaggtcat ctactaccct   6600
gacaacgtct cggttgatca ggttatcttg tcaaagaaca ccagtgaaca tggccaactg   6660
gacttgctgt accccctcaat tgattccgag agcgaaatcc tgccaggaga gaaccaggtt   6720
ttctacgaca acaggacaca aaacgtggat tacctcaaca gctactacta cctggagtcg   6780
cagaagctct ccgacaacgt cgaagatttc acatttacga gatcaatcga ggaggctttg   6840
gacaacagtg ccaaagtcta cacctacttc cctactctgg caaacaaggt gaacgcgggt   6900
gtccaaggcg gactcttctt gatgtgggct aacgacgttg tggaagattt cacaacgaac   6960
atcttgcgca aagacaccct ggataagatc agcgatgtct ctgccatcat tccatacatt   7020
ggcccggcac tgaacatctc taactcagtt cgccgtggca acttcactga ggcattcgcg   7080
gtcacaggag ttacgatcct cttggaggct ttcccggagt tcacaatccc cgcactgggc   7140
gcgttcgtta tctactccaa agtgcaggag cgcaacgaaa tcattaagac tatcgacaac   7200
tgcctggagc aaaggatcaa aagatggaag gattcgtacg aatggatgat gggtacctgg   7260
ctctcccgta tcattacgca gttcaacaac atcagctacc aaatgtacga ctctctcaac   7320
taccaggctg gtgccatcaa ggccaaaatt gacttggagt acaagaaata cagtggctcg   7380
gataaagaga acatcaagag tcaagtcgaa aacctgaaaa actcactcga cgttaagatc   7440
agtgaggcaa tgaacaacat caacaagttc attcgcgaat gttccgttac ctacctcttc   7500
aaaaacatgt tgccaaaggt catcgacgag ctgaacgaat ttgatcgtaa cactaaggcg   7560
aaactgatta acctcatcga ctcacacaac atcattttgg tgggcgaagt cgataagctg   7620
aaagccaagg tgaacaacag tttccagaac acaatccctt tcaacatttt ctcatacacg   7680
aacaacagtc tgctcaagga catcattaac gagtacttca acaacattaa cgatagcaaa   7740
atcctgtcac tgcagaaccg taagaacaca ctggtcgata ctagtggata caacgccgaa   7800
gtctctgagg aaggtgacgt gcagctgaac cctatcttcc ccttcgactt caaattgggc   7860
tccagcggag aggatagggg caaggtcatc gtcacccaga acgagaacat cgtctacaac   7920
tcaatgtacg aatccttcag catctctttc tggatcagga ttaacaagtg ggtgagcaac   7980
ctgcccggtt acacaatcat tgactctgtc aagaacaact caggttggag tatcggcatc   8040
atttctaact tcttggtctt caccctgaag cagaacgagg actcggaaca atccattaac   8100
ttctcatacg atatcagtaa caacgctcca ggttacaaca agtggttctt cgttaccgtg   8160
actaacaaca tgatgggtaa catgaaaatt tacatcaacg gcaagctcat tgacaccatc   8220
```

```
aaagtgaagg agttgactgg tattaacttc tccaaaacaa tcacgtttga aattaacaag   8280

atccctgaca ccggcctgat cacttcagac agtgataaca tcaacatgtg gattagggat   8340

ttctacatct tcgccaagga gctcgacgga aaggatatta acatcctctt caacagcttg   8400

cagtacacca acgtcgttaa agactactgg ggtaacgatt tgagatacaa caaggagtac   8460

tacatggtca acatcgacta cctgaacagg tacatgtacg ctaactcccg ccaaatcgtg   8520

ttcaacacca ggagaaacaa caacgacttc aacgagggtt acaaaatcat tatcaagcgc   8580

atccgtggca acaccaacga tactagggtg agaggtggcg acattctgta cttcgatatg   8640

actatcaaca acaaagccta caacttgttc atgaaaaacg agacaatgta cgccgacaac   8700

catagcacgg aggatattta cgcaatcgga ctgagggaac agacaaagga catcaacgat   8760

aacattatct tccagatcca acctatgaac aacacgtact actacgcttc gcaaatcttc   8820

aagtccaact tcaacggaga aaacatttcg ggtatctgtt ccattggcac ataccgcttc   8880

cgtctgggtg gtgactggta tcgtcacaac tacctcgttc ccaccgtgaa gcagggtaac   8940

tacgcttctt tgctggagtc gacttccacg cactggggat tcgttcctgt gtcagagggc   9000

gctggctacc cttacgatgt tcccgactac gctggttggg aactccagca aggtgcagga   9060

tggtcccacc ctcaattcga gaagggtgcc ggatggagtc acccacagtt cgagaaaggc   9120

gctggatgga gtcacccaca gttcgagaaa taattagttg atgcatagtt aattagatag   9180

ctcgaggcat gcggtaccaa gattggatct agatgcatag ttaattagat agctcgaggc   9240

atgcggtacc aagcttgtcg agaagtacta gaggatcata atcagccata ccacatttgt   9300

agaggtttta cttgctttaa aaaacctccc acacctcccc ctgaacctga aacataaaat   9360

gaatgcaatt gttgttgtta acttgtttat tgcagcttat aatggttaca aataaagcaa   9420

tagcatcaca aatttcacaa ataaagcatt tttttcactg cattctagtt gtggtttgtc   9480

caaactcatc aatgtatctt atcatgtctg gatctgatca ctgcttgagc ctaggagatc   9540

cgaaccagat aagtgaaatc tagttccaaa ctattttgtc atttttaatt ttcgtattag   9600

cttacgacgc tacacccagt tcccatctat tttgtcactc ttccctaaat aatccttaaa   9660

aactccattt ccacccctcc cagttcccaa ctattttgtc cgcccacagc ggggcatttt   9720

tcttcctgtt atgtttttaa tcaaacatcc tgccaactcc atgtgacaaa ccgtcatctt   9780

cggctacttt ttctctgtca cagaatgaaa atttttctgt catctcttcg ttattaatgt   9840

ttgtaattga ctgaatatca acgcttattt gcagcctgaa tggcgaatgg              9890
```

<210> SEQ ID NO 44
<211> LENGTH: 1687
<212> TYPE: PRT
<213> ORGANISM: Artificial
<220> FEATURE:
<223> OTHER INFORMATION: Fusion protein construct

<400> SEQUENCE: 44

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Gly Ala Gly Glu Gln Lys Leu
        35                  40                  45

Ile Ser Glu Glu Asp Leu Gly Ala Ala Ala Gln Val Gln Leu Val Glu
    50                  55                  60

Ser Gly Gly Gly Leu Val Gln Ser Gly Gly Ser Leu Arg Leu Ser Cys
```

-continued

```
65                  70                  75                  80

Ala Ala Ser Gly Ser Ile Asp Ser Leu Tyr His Met Gly Trp Tyr Arg
                85                  90                  95

Gln Ala Pro Gly Lys Glu Arg Glu Leu Val Ala Arg Val Gln Asp Gly
            100                 105                 110

Gly Ser Thr Ala Tyr Lys Asp Ser Val Lys Gly Arg Phe Thr Ile Ser
        115                 120                 125

Arg Asp Phe Ser Arg Ser Thr Met Tyr Leu Gln Met Asn Ser Leu Lys
    130                 135                 140

Pro Glu Asp Thr Ala Ile Tyr Tyr Cys Ala Ala Lys Ser Thr Ile Ser
145                 150                 155                 160

Thr Pro Leu Ser Trp Gly Gln Gly Thr Gln Val Thr Val Ser Ser Glu
                165                 170                 175

Pro Lys Thr Pro Lys Pro Gln Ser Ser Gly Gly Gly Ala Ala Ala Gly
            180                 185                 190

Ser Gly Gly Gly Ser Gln Val Gln Leu Val Glu Ser Gly Gly Gly Leu
        195                 200                 205

Val Gln Pro Gly Gly Ser Leu Arg Leu Ser Cys Ala Ala Ser Gly Phe
    210                 215                 220

Pro Phe His Ala Tyr Tyr Met Ser Trp Val Arg Gln Ala Pro Gly Lys
225                 230                 235                 240

Gly Leu Glu Trp Val Ser His Ile Gly Asn Gly Gly Ile Ile Thr Arg
                245                 250                 255

Tyr Ala Asp Ser Val Lys Gly Arg Phe Thr Ile Ser Arg Asp Asn Ala
            260                 265                 270

Lys Asn Thr Leu Tyr Leu Gln Met Thr Asn Leu Lys Pro Glu Asp Thr
        275                 280                 285

Ala Leu Tyr Tyr Cys Thr Leu Gly Thr Arg Asp Asp Leu Gly Pro Glu
    290                 295                 300

Arg Gly Gln Gly Thr Gln Val Thr Val Ser Ser Glu Pro Lys Thr Pro
305                 310                 315                 320

Lys Pro Gln Gly Ala Gly Gln Gly Ala Gly Ala Gly Pro Ile Thr Ile
                325                 330                 335

Asn Asn Phe Asn Tyr Ser Asp Pro Val Asp Asn Lys Asn Ile Leu Tyr
            340                 345                 350

Leu Asp Thr His Leu Asn Thr Leu Ala Asn Glu Pro Glu Lys Ala Phe
        355                 360                 365

Arg Ile Thr Gly Asn Ile Trp Val Ile Pro Asp Arg Phe Ser Arg Asn
    370                 375                 380

Ser Asn Pro Asn Leu Asn Lys Pro Pro Arg Val Thr Ser Pro Lys Ser
385                 390                 395                 400

Gly Tyr Tyr Asp Pro Asn Tyr Leu Ser Thr Asp Ser Asp Lys Asp Pro
                405                 410                 415

Phe Leu Lys Glu Ile Ile Lys Leu Phe Lys Arg Ile Asn Ser Arg Glu
            420                 425                 430

Ile Gly Glu Glu Leu Ile Tyr Arg Leu Ser Thr Asp Ile Pro Phe Pro
        435                 440                 445

Gly Asn Asn Asn Thr Pro Ile Asn Thr Phe Asp Phe Asp Val Asp Phe
    450                 455                 460

Asn Ser Val Asp Val Lys Thr Arg Gln Gly Asn Asn Trp Val Lys Thr
465                 470                 475                 480

Gly Ser Ile Asn Pro Ser Val Ile Ile Thr Gly Pro Arg Glu Asn Ile
                485                 490                 495
```

```
Ile Asp Pro Glu Thr Ser Thr Phe Lys Leu Thr Asn Asn Thr Phe Ala
            500                 505                 510

Ala Gln Glu Gly Phe Gly Ala Leu Ser Ile Ile Ser Ile Ser Pro Arg
        515                 520                 525

Phe Met Leu Thr Tyr Ser Asn Ala Thr Asn Asp Val Gly Glu Gly Arg
    530                 535                 540

Phe Ser Lys Ser Glu Phe Cys Met Asp Pro Ile Leu Ile Leu Met His
545                 550                 555                 560

Ala Leu Asn Gly Ala Met His Asn Leu Tyr Gly Ile Ala Ile Pro Asn
                565                 570                 575

Asp Gln Thr Ile Ser Ser Val Thr Ser Asn Ile Phe Tyr Ser Gln Tyr
            580                 585                 590

Asn Val Lys Leu Glu Tyr Ala Glu Ile Tyr Ala Phe Gly Gly Pro Thr
        595                 600                 605

Ile Asp Leu Ile Pro Lys Ser Ala Arg Lys Tyr Phe Glu Glu Lys Ala
    610                 615                 620

Leu Asp Tyr Tyr Arg Ser Ile Ala Lys Arg Leu Asn Ser Ile Thr Thr
625                 630                 635                 640

Ala Asn Pro Ser Ser Phe Asn Lys Tyr Ile Gly Glu Tyr Lys Gln Lys
                645                 650                 655

Leu Ile Arg Lys Tyr Arg Phe Val Val Glu Ser Ser Gly Glu Val Thr
            660                 665                 670

Val Asn Arg Asn Lys Phe Val Glu Leu Tyr Asn Glu Leu Thr Gln Ile
        675                 680                 685

Phe Thr Glu Phe Asn Tyr Ala Lys Ile Tyr Asn Val Gln Asn Arg Lys
    690                 695                 700

Ile Ala Leu Ser Asn Val Tyr Thr Pro Val Thr Ala Asn Ile Leu Asp
705                 710                 715                 720

Asp Asn Val Tyr Asp Ile Gln Asn Gly Phe Asn Ile Pro Lys Ser Asn
                725                 730                 735

Leu Asn Val Leu Phe Met Gly Gln Asn Leu Ser Arg Asn Pro Ala Leu
            740                 745                 750

Arg Lys Val Asn Pro Glu Asn Met Leu Tyr Leu Phe Thr Lys Phe Cys
        755                 760                 765

His Lys Ala Ile Asp Gly Gln Ser Leu Asp Gln Gly Gly Trp Glu Leu
    770                 775                 780

Gln Gln Gly Gly Gln Gly Gly Gly Ala Gly Thr Leu Asp Cys Arg Glu
785                 790                 795                 800

Leu Leu Val Lys Asn Thr Asp Leu Pro Phe Ile Gly Asp Ile Ser Asp
                805                 810                 815

Val Lys Thr Asp Ile Phe Leu Arg Lys Asp Ile Asn Glu Glu Thr Glu
            820                 825                 830

Val Ile Tyr Tyr Pro Asp Asn Val Ser Val Asp Gln Val Ile Leu Ser
        835                 840                 845

Lys Asn Thr Ser Glu His Gly Gln Leu Asp Leu Leu Tyr Pro Ser Ile
    850                 855                 860

Asp Ser Glu Ser Glu Ile Leu Pro Gly Glu Asn Gln Val Phe Tyr Asp
865                 870                 875                 880

Asn Arg Thr Gln Asn Val Asp Tyr Leu Asn Ser Tyr Tyr Tyr Leu Glu
                885                 890                 895

Ser Gln Lys Leu Ser Asp Asn Val Glu Asp Phe Thr Phe Thr Arg Ser
            900                 905                 910
```

```
Ile Glu Glu Ala Leu Asp Asn Ser Ala Lys Val Tyr Thr Tyr Phe Pro
        915                 920                 925

Thr Leu Ala Asn Lys Val Asn Ala Gly Val Gln Gly Gly Leu Phe Leu
    930                 935                 940

Met Trp Ala Asn Asp Val Val Glu Asp Phe Thr Thr Asn Ile Leu Arg
945                 950                 955                 960

Lys Asp Thr Leu Asp Lys Ile Ser Asp Val Ser Ala Ile Ile Pro Tyr
                965                 970                 975

Ile Gly Pro Ala Leu Asn Ile Ser Asn Ser Val Arg Arg Gly Asn Phe
            980                 985                 990

Thr Glu Ala Phe Ala Val Thr Gly  Val Thr Ile Leu Leu  Glu Ala Phe
        995                 1000                 1005

Pro Glu  Phe Thr Ile Pro Ala  Leu Gly Ala Phe Val  Ile Tyr Ser
    1010                 1015                 1020

Lys Val  Gln Glu Arg Asn Glu  Ile Ile Lys Thr Ile  Asp Asn Cys
    1025                 1030                 1035

Leu Glu  Gln Arg Ile Lys Arg  Trp Lys Asp Ser Tyr  Glu Trp Met
    1040                 1045                 1050

Met Gly  Thr Trp Leu Ser Arg  Ile Ile Thr Gln Phe  Asn Asn Ile
    1055                 1060                 1065

Ser Tyr  Gln Met Tyr Asp Ser  Leu Asn Tyr Gln Ala  Gly Ala Ile
    1070                 1075                 1080

Lys Ala  Lys Ile Asp Leu Glu  Tyr Lys Lys Tyr Ser  Gly Ser Asp
    1085                 1090                 1095

Lys Glu  Asn Ile Lys Ser Gln  Val Glu Asn Leu Lys  Asn Ser Leu
    1100                 1105                 1110

Asp Val  Lys Ile Ser Glu Ala  Met Asn Asn Ile Asn  Lys Phe Ile
    1115                 1120                 1125

Arg Glu  Cys Ser Val Thr Tyr  Leu Phe Lys Asn Met  Leu Pro Lys
    1130                 1135                 1140

Val Ile  Asp Glu Leu Asn Glu  Phe Asp Arg Asn Thr  Lys Ala Lys
    1145                 1150                 1155

Leu Ile  Asn Leu Ile Asp Ser  His Asn Ile Ile Leu  Val Gly Glu
    1160                 1165                 1170

Val Asp  Lys Leu Lys Ala Lys  Val Asn Asn Ser Phe  Gln Asn Thr
    1175                 1180                 1185

Ile Pro  Phe Asn Ile Phe Ser  Tyr Thr Asn Asn Ser  Leu Leu Lys
    1190                 1195                 1200

Asp Ile  Ile Asn Glu Tyr Phe  Asn Asn Ile Asn Asp  Ser Lys Ile
    1205                 1210                 1215

Leu Ser  Leu Gln Asn Arg Lys  Asn Thr Leu Val Asp  Thr Ser Gly
    1220                 1225                 1230

Tyr Asn  Ala Glu Val Ser Glu  Glu Gly Asp Val Gln  Leu Asn Pro
    1235                 1240                 1245

Ile Phe  Pro Phe Asp Phe Lys  Leu Gly Ser Ser Gly  Glu Asp Arg
    1250                 1255                 1260

Gly Lys  Val Ile Val Thr Gln  Asn Glu Asn Ile Val  Tyr Asn Ser
    1265                 1270                 1275

Met Tyr  Glu Ser Phe Ser Ile  Ser Phe Trp Ile Arg  Ile Asn Lys
    1280                 1285                 1290

Trp Val  Ser Asn Leu Pro Gly  Tyr Thr Ile Ile Asp  Ser Val Lys
    1295                 1300                 1305

Asn Asn  Ser Gly Trp Ser Ile  Gly Ile Ile Ser Asn  Phe Leu Val
```

```
    1310                1315                1320

Phe Thr  Leu Lys Gln Asn Glu  Asp Ser Glu Gln Ser  Ile Asn Phe
    1325                1330                1335

Ser Tyr  Asp Ile Ser Asn Asn  Ala Pro Gly Tyr Asn  Lys Trp Phe
    1340                1345                1350

Phe Val  Thr Val Thr Asn Asn  Met Met Gly Asn Met  Lys Ile Tyr
    1355                1360                1365

Ile Asn  Gly Lys Leu Ile Asp  Thr Ile Lys Val Lys  Glu Leu Thr
    1370                1375                1380

Gly Ile  Asn Phe Ser Lys Thr  Ile Thr Phe Glu Ile  Asn Lys Ile
    1385                1390                1395

Pro Asp  Thr Gly Leu Ile Thr  Ser Asp Ser Asp Asn  Ile Asn Met
    1400                1405                1410

Trp Ile  Arg Asp Phe Tyr Ile  Phe Ala Lys Glu Leu  Asp Gly Lys
    1415                1420                1425

Asp Ile  Asn Ile Leu Phe Asn  Ser Leu Gln Tyr Thr  Asn Val Val
    1430                1435                1440

Lys Asp  Tyr Trp Gly Asn Asp  Leu Arg Tyr Asn Lys  Glu Tyr Tyr
    1445                1450                1455

Met Val  Asn Ile Asp Tyr Leu  Asn Arg Tyr Met Tyr  Ala Asn Ser
    1460                1465                1470

Arg Gln  Ile Val Phe Asn Thr  Arg Arg Asn Asn Asn  Asp Phe Asn
    1475                1480                1485

Glu Gly  Tyr Lys Ile Ile Ile  Lys Arg Ile Arg Gly  Asn Thr Asn
    1490                1495                1500

Asp Thr  Arg Val Arg Gly Gly  Asp Ile Leu Tyr Phe  Asp Met Thr
    1505                1510                1515

Ile Asn  Asn Lys Ala Tyr Asn  Leu Phe Met Lys Asn  Glu Thr Met
    1520                1525                1530

Tyr Ala  Asp Asn His Ser Thr  Glu Asp Ile Tyr Ala  Ile Gly Leu
    1535                1540                1545

Arg Glu  Gln Thr Lys Asp Ile  Asn Asp Asn Ile Ile  Phe Gln Ile
    1550                1555                1560

Gln Pro  Met Asn Asn Thr Tyr  Tyr Tyr Ala Ser Gln  Ile Phe Lys
    1565                1570                1575

Ser Asn  Phe Asn Gly Glu Asn  Ile Ser Gly Ile Cys  Ser Ile Gly
    1580                1585                1590

Thr Tyr  Arg Phe Arg Leu Gly  Gly Asp Trp Tyr Arg  His Asn Tyr
    1595                1600                1605

Leu Val  Pro Thr Val Lys Gln  Gly Asn Tyr Ala Ser  Leu Leu Glu
    1610                1615                1620

Ser Thr  Ser Thr His Trp Gly  Phe Val Pro Val Ser  Glu Gly Ala
    1625                1630                1635

Gly Tyr  Pro Tyr Asp Val Pro  Asp Tyr Ala Gly Trp  Glu Leu Gln
    1640                1645                1650

Gln Gly  Ala Gly Trp Ser His  Pro Gln Phe Glu Lys  Gly Ala Gly
    1655                1660                1665

Trp Ser  His Pro Gln Phe Glu  Lys Gly Ala Gly Trp  Ser His Pro
    1670                1675                1680

Gln Phe  Glu Lys
    1685
```

<210> SEQ ID NO 45

<211> LENGTH: 10496
<212> TYPE: DNA
<213> ORGANISM: Artificial
<220> FEATURE:
<223> OTHER INFORMATION: DNA construct for molecular construction of fusion proteins

<400> SEQUENCE: 45
gacgcgccct gtagcggcgc attaagcgcg gcgggtgtgg tggttacgcg cagcgtgacc 60
gctacacttg ccagcgccct agcgcccgct cctttcgctt tcttcccttc ctttctcgcc 120
acgttcgccg gctttccccg tcaagctcta aatcgggggc tccctttagg gttccgattt 180
agtgctttac ggcacctcga ccccaaaaaa cttgattagg gtgatggttc acgtagtggg 240
ccatcgccct gatagacggt ttttcgccct ttgacgttgg agtccacgtt ctttaatagt 300
ggactcttgt tccaaactgg aacaacactc aaccctatct cggtctattc ttttgattta 360
taagggattt tgccgatttc ggcctattgg ttaaaaaatg agctgattta acaaaaattt 420
aacgcgaatt ttaacaaaat attaacgttt acaatttcag gtggcacttt tcggggaaat 480
gtgcgcggaa cccctatttg tttatttttc taaatacatt caaatatgta tccgctcatg 540
agacaataac cctgataaat gcttcaataa tattgaaaaa ggaagagtat gagtattcaa 600
catttccgtg tcgcccttat tccctttttt gcggcatttt gccttcctgt ttttgctcac 660
ccagaaacgc tggtgaaagt aaaagatgct gaagatcagt tgggtgcacg agtgggttac 720
atcgaactgg atctcaacag cggtaagatc cttgagagtt ttcgccccga agaacgtttt 780
ccaatgatga gcacttttaa agttctgcta tgtggcgcgg tattatcccg tattgacgcc 840
gggcaagagc aactcggtcg ccgcatacac tattctcaga atgacttggt tgagtactca 900
ccagtcacag aaaagcatct tacggatggc atgacagtaa gagaattatg cagtgctgcc 960
ataaccatga gtgataacac tgcggccaac ttacttctga caacgatcgg aggaccgaag 1020
gagctaaccg cttttttgca caacatgggg gatcatgtaa ctcgccttga tcgttgggaa 1080
ccggagctga atgaagccat accaaacgac gagcgtgaca ccacgatgcc tgtagcaatg 1140
gcaacaacgt tgcgcaaact attaactggc gaactactta ctctagcttc ccggcaacaa 1200
ttaatagact ggatggaggc ggataaagtt gcaggaccac ttctgcgctc ggcccttccg 1260
gctggctggt ttattgctga taaatctgga gccggtgagc gtgggtctcg cggtatcatt 1320
gcagcactgg ggccagatgg taagccctcc cgtatcgtag ttatctacac gacggggagt 1380
caggcaacta tggatgaacg aaatagacag atcgctgaga taggtgcctc actgattaag 1440
cattggtaac tgtcagacca agtttactca tatatacttt agattgattt aaaacttcat 1500
ttttaattta aaaggatcta ggtgaagatc ctttttgata atctcatgac caaaatccct 1560
taacgtgagt tttcgttcca ctgagcgtca gaccccgtag aaaagatcaa aggatcttct 1620
tgagatcctt tttttctgcg cgtaatctgc tgcttgcaaa caaaaaaacc accgctacca 1680
gcggtggttt gtttgccgga tcaagagcta ccaactcttt ttccgaaggt aactggcttc 1740
agcagagcgc agataccaaa tactgtcctt ctagtgtagc cgtagttagg ccaccacttc 1800
aagaactctg tagcaccgcc tacatacctc gctctgctaa tcctgttacc agtggctgct 1860
gccagtggcg ataagtcgtg tcttaccggg ttggactcaa gacgatagtt accggataag 1920
gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400
cggtattttc tccttacgca tctgtgcggt atttcacacc gcagaccagc cgcgtaacct 2460
ggcaaaatcg gttacggttg agtaataaat ggatgccctg cgtaagcggg tgtgggcgga 2520
caataaagtc ttaaactgaa caaaatagat ctaaactatg acaataaagt cttaaactag 2580
acagaatagt tgtaaactga aatcagtcca gttatgctgt gaaaaagcat actggacttt 2640
tgttatggct aaagcaaact cttcattttc tgaagtgcaa attgcccgtc gtattaaaga 2700
ggggcgtggc caagggcatg gtaaagacta tattcgcggc gttgtgacaa tttaccgaac 2760
aactccgcgg ccgggaagcc gatctcggct tgaacgaatt gttaggtggc ggtacttggg 2820
tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720
cacggatctg ccctggcttc aggagatcgg aagacctcgg ccgtcgcggc gcttgccggt 3780
ggtgctgacc ccggatgaag tggttcgcat cctcggtttt ctggaaggcg agcatcgttt 3840
gttcgcccag gactctagct atagttctag tggttggcta cgtatactcc ggaatattaa 3900
tagatcatgg agataattaa aatgataacc atctcgcaaa taaataagta ttttactgtt 3960
ttcgtaacag ttttgtaata aaaaaaccta taaatattcc ggattattca taccgtccca 4020
ccatcgggcg cggatctcgg tccgttcgaa ccagaactct ggaagcttaa ctcctaaaaa 4080
accgccacca tgaaattctt agtcaacgtt gcccttgttt ttatggtcgt atacatttct 4140
tacatctatg cggccggaca ccaccaccac caccaccacc accaccacca cgacgtcggc 4200
tgggagctgc aacgtcgtcc cctgaactgc atcgtggctg tgtcccagaa catgggtatc 4260
ggcaagaacg gcgacctgcc ctggcctcct ctgcgtaacg agttcaagta cttccagcgt 4320
atgaccacca cctcctccgt cgagggcaag cagaacctgg tcatcatggg tcgcaagacc 4380
tggttctcca tccccgagaa gaaccgtctg ctgaaggacc gtatcaacat cgtgctgtcc 4440
cgcgagctga aggaaccccc tcgtggtgct cacttcctgg ctaagtccct ggacgacgct 4500
ctgcgtctga tcgagcagcc tgagctggct tccaaggtgg acatggtctg gatcgtgggc 4560
ggttcctccg tgtaccaaga ggctatgaac cagcccggtc acttgcgtct gttcgtgacc 4620
cgtatcatgc aagagttcga gtccgacacc ttcttccccg aaatcgacct gggcaagtac 4680
aagctgctgc ccgagtaccc cggtgtcctg tccgaggtgc aagaggaaaa gggtatcaag 4740
tacaagttcg aggtgtacga gaagaaggac ggcgcttccg gtttcgctaa cgagctcggt 4800
cctcgtctga tgggaaaggg cgccggcgag cagaaactca tcagcgaaga agatttgggt 4860
gcggccgctc aggttcaact cgtggagagt ggtggcggac tggtgcaatc cggtggcagc 4920
ctgaggctct cctgcgctgc ctctggatca atcgacagcc tgtaccacat gggttggtac 4980
aggcaggctc ccggcaagga gagggaactc gtcgccagag ttcaagacgg aggtagtaca 5040
gcatacaagg attcggtcaa aggtcgcttc accatttctc gcgacttcag tcgttcgact 5100
atgtacttgc agatgaactc actgaagcct gaggatacag ccatctacta ctgtgcagcg 5160
aaatctacca tttcaactcc actgtcttgg ggccagggaa cacaagtgac ggtctccagc 5220
gaaccgaaga cgcctaaacc ccaatcttca ggcggaggtg cggccgctgg ctcaggaggt 5280
ggcagtcagg tgcagctggt ggaatccggt ggtggactgg tccagcctgg tggttccctg 5340
cgtctgtcct gcgctgcttc cggtttcccc ttccacgctt actacatgtc ctgggtccgc 5400
caggctcctg gcaagggatt ggaatgggtg tcccacatcg gcaacggtgg tatcatcacc 5460
cgttacgctg actccgtgaa gggccgtttc accatctccc gtgacaacgc taagaacacc 5520
ctgtacctgc agatgaccaa cctgaagccc gaggacaccg ctctgtacta ctgcaccctg 5580
ggcacccgtg acgacctggg tcctgaacgt ggccagggaa cccaagtgac cgtgtcctcc 5640
gagcccaaga cccccaagcc tcaaggggcc ggccagggtg ctggtgctgg accgatcacc 5700
atcaacaact tcaattactc ggatccggtg gataacaaga acatcctcta cttggacaca 5760
cacttgaaca cgctggctaa cgagcctgaa aaagctttca ggatcaccgg caacatttgg 5820
gtcattccgg ataggttcag cagaaactct aaccctaact tgaacaaacc tcccagagtg 5880
acctcaccta agagtggata ctacgacccc aactacctct cgactgactc cgataaagac 5940
cccttcctga aggagatcat taaactcttc aagcgcatca actctcgtga aattggcgag 6000
gaattgatct accgcctgag tacagacatc ccattcccgg gtaacaacaa caccccaatc 6060
aacactttcg atttcgatgt cgatttcaac tcagtggatg tcaaaaccag gcagggaaac 6120
aactgggtga agactggtag catcaaccca tctgtcatca ttactggccc gagagagaac 6180
atcattgacc ctgaaacctc cactttcaag ctgacaaaca acacgttcgc tgctcaggaa 6240
ggcttcggag cgttgagcat catttctatc tcacctcgct tcatgctgac atactctaac 6300
gctacgaacg acgtgggaga gggccgtttc agtaagtctg aattctgcat ggaccctatt 6360
ctgatcctca tgcacgctct caacggcgcc atgcacaact tgtacggaat tgctatcccc 6420
aacgaccaga ccatttccag cgtgactagc aacatcttct actctcaata caacgtcaag 6480
ctggagtacg cagaaatcta cgctttcggt ggcccaacca ttgacttgat cccgaaatca 6540
gctcgtaagt atttcgaaga aaaagcgctg gattattaca ggtcgattgc taagagactc 6600
aactccatca ccactgctaa cccctcttca ttcaacaagt acattggaga atacaagcag 6660
aaactgatcc gcaagtaccg tttcgtggtc gagagttcgg gtgaagttac tgtgaaccgc 6720
aacaagttcg tcgagctgta caacgaattg acacaaatct tcacggagtt caactacgcc 6780
aaaatttaca acgtgcaaaa ccgtaagatc gcgctctcta acgtctacac cccggttacc 6840
gctaacatct tggacgataa cgtctacgac attcagaacg gtttcaacat cccaaagtcg 6900
aacctcaacg ttttgttcat gggtcaaaac ttgtcccgca accccgccct gcgtaaggtg 6960
aacccagaga acatgttgta cctgttcacc aaattctgcc acaaggccat cgacggtcag 7020
tctctagacc aaggaggatg ggaactccag caaggtggcc agggtggagg tgctggcacc 7080
ctggactgtc gcgaactgct cgttaagaac actgatctcc cattcattgg cgacatctct 7140
gatgtgaaaa cagacatttt cctgcgtaag gatatcaacg aggaaacgga ggtcatctac 7200
taccctgaca acgtctcggt tgatcaggtt atcttgtcaa agaacaccag tgaacatggc 7260
caactggact tgctgtaccc ctcaattgat tccgagagcg aaatcctgcc aggagagaac 7320
caggttttct acgacaacag gacacaaaac gtggattacc tcaacagcta ctactacctg 7380
gagtcgcaga agctctccga caacgtcgaa gatttcacat ttacgagatc aatcgaggag 7440
gctttggaca acagtgccaa agtctacacc tacttcccta ctctggcaaa caaggtgaac 7500
gcgggtgtcc aaggcggact cttcttgatg tgggctaacg acgttgtgga agatttcaca 7560
acgaacatct tgcgcaaaga caccctggat aagatcagcg atgtctctgc catcattcca 7620
tacattggcc cggcactgaa catctctaac tcagttcgcc gtggcaactt cactgaggca 7680
ttcgcggtca caggagttac gatcctcttg gaggctttcc cggagttcac aatccccgca 7740
ctgggcgcgt tcgttatcta ctccaaagtg caggagcgca acgaaatcat taagactatc 7800
gacaactgcc tggagcaaag gatcaaaaga tggaaggatt cgtacgaatg gatgatgggt 7860
acctggctct cccgtatcat tacgcagttc aacaacatca gctaccaaat gtacgactct 7920
ctcaactacc aggctggtgc catcaaggcc aaaattgact tggagtacaa gaaatacagt 7980
ggctcggata aagagaacat caagagtcaa gtcgaaaacc tgaaaaactc actcgacgtt 8040
aagatcagtg aggcaatgaa caacatcaac aagttcattc gcgaatgttc cgttacctac 8100
ctcttcaaaa acatgttgcc aaaggtcatc gacgagctga acgaatttga tcgtaacact 8160
aaggcgaaac tgattaacct catcgactca cacaacatca ttttggtggg cgaagtcgat 8220
aagctgaaag ccaaggtgaa caacagtttc cagaacacaa tccctttcaa cattttctca 8280
tacacgaaca acagtctgct caaggacatc attaacgagt acttcaacaa cattaacgat 8340
agcaaaatcc tgtcactgca gaaccgtaag aacacactgg tcgatactag tggatacaac 8400
gccgaagtct ctgaggaagg tgacgtgcag ctgaacccta tcttcccctt cgacttcaaa 8460
ttgggctcca gcggagagga taggggcaag gtcatcgtca cccagaacga gaacatcgtc 8520
tacaactcaa tgtacgaatc cttcagcatc tctttctgga tcaggattaa caagtgggtg 8580
agcaacctgc ccggttacac aatcattgac tctgtcaaga acaactcagg ttggagtatc 8640
ggcatcattt ctaacttctt ggtcttcacc ctgaagcaga acgaggactc ggaacaatcc 8700
attaacttct catacgatat cagtaacaac gctccaggtt acaacaagtg gttcttcgtt 8760
accgtgacta acaacatgat gggtaacatg aaaatttaca tcaacggcaa gctcattgac 8820
accatcaaag tgaaggagtt gactggtatt aacttctcca aaacaatcac gtttgaaatt 8880
aacaagatcc ctgacaccgg cctgatcact tcagacagtg ataacatcaa catgtggatt 8940
agggatttct acatcttcgc caaggagctc gacggaaagg atattaacat cctcttcaac 9000
agcttgcagt acaccaacgt cgttaaagac tactggggta acgatttgag atacaacaag 9060
gagtactaca tggtcaacat cgactacctg aacaggtaca tgtacgctaa ctcccgccaa 9120
atcgtgttca acaccaggag aaacaacaac gacttcaacg agggttacaa aatcattatc 9180
aagcgcatcc gtggcaacac caacgatact agggtgagag gtggcgacat tctgtacttc 9240

```
gatatgacta tcaacaacaa agcctacaac ttgttcatga aaaacgagac aatgtacgcc   9300
gacaaccata gcacggagga tatttacgca atcggactga gggaacagac aaaggacatc   9360
aacgataaca ttatcttcca gatccaacct atgaacaaca cgtactacta cgcttcgcaa   9420
atcttcaagt ccaacttcaa cggagaaaac atttcgggta tctgttccat tggcacatac   9480
cgcttccgtc tgggtggtga ctggtatcgt cacaactacc tcgttcccac cgtgaagcag   9540
ggtaactacg cttctttgct ggagtcgact tccacgcact ggggattcgt tcctgtgtca   9600
gagggcgctg gctaccctta cgatgttccc gactacgctg gttgggaact ccagcaaggt   9660
gcaggatggt cccaccctca attcgagaag ggtgccggat ggagtcaccc acagttcgag   9720
aaaggcgctg gatggagtca cccacagttc gagaaataat tagttgatgc atagttaatt   9780
agatagctcg aggcatgcgg taccaagatt ggatctagat gcatagttaa ttagatagct   9840
cgaggcatgc ggtaccaagc ttgtcgagaa gtactagagg atcataatca gccataccac   9900
atttgtagag gttttacttg ctttaaaaaa cctcccacac ctccccctga acctgaaaca   9960
taaaatgaat gcaattgttg ttgttaactt gtttattgca gcttataatg gttacaaata  10020
aagcaatagc atcacaaatt tcacaaataa agcatttttt tcactgcatt ctagttgtgg  10080
tttgtccaaa ctcatcaatg tatcttatca tgtctggatc tgatcactgc ttgagcctag  10140
gagatccgaa ccagataagt gaaatctagt tccaaactat tttgtcattt ttaattttcg  10200
tattagctta cgacgctaca cccagttccc atctattttg tcactcttcc ctaaataatc  10260
cttaaaaact ccatttccac ccctcccagt tcccaactat tttgtccgcc cacagcgggg  10320
catttttctt cctgttatgt ttttaatcaa acatcctgcc aactccatgt gacaaaccgt  10380
catcttcggc tacttttct ctgtcacaga atgaaaattt ttctgtcatc tcttcgttat  10440
taatgtttgt aattgactga atatcaacgc ttatttgcag cctgaatggc gaatgg      10496
```

<210> SEQ ID NO 46
<211> LENGTH: 1889
<212> TYPE: PRT
<213> ORGANISM: Artificial
<220> FEATURE:
<223> OTHER INFORMATION: Fusion protein construct

<400> SEQUENCE: 46

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140
```

Glu Leu Ala Ser Lys Val Asp Met Val Trp Ile Val Gly Gly Ser Ser
145 150 155 160

Val Tyr Gln Glu Ala Met Asn Gln Pro Gly His Leu Arg Leu Phe Val
165 170 175

Thr Arg Ile Met Gln Glu Phe Glu Ser Asp Thr Phe Phe Pro Glu Ile
180 185 190

Asp Leu Gly Lys Tyr Lys Leu Leu Pro Glu Tyr Pro Gly Val Leu Ser
195 200 205

Glu Val Gln Glu Glu Lys Gly Ile Lys Tyr Lys Phe Glu Val Tyr Glu
210 215 220

Lys Lys Asp Gly Ala Ser Gly Phe Ala Asn Glu Leu Gly Pro Arg Leu
225 230 235 240

Met Gly Lys Gly Ala Gly Glu Gln Lys Leu Ile Ser Glu Glu Asp Leu
245 250 255

Gly Ala Ala Ala Gln Val Gln Leu Val Glu Ser Gly Gly Gly Leu Val
260 265 270

Gln Ser Gly Gly Ser Leu Arg Leu Ser Cys Ala Ala Ser Gly Ser Ile
275 280 285

Asp Ser Leu Tyr His Met Gly Trp Tyr Arg Gln Ala Pro Gly Lys Glu
290 295 300

Arg Glu Leu Val Ala Arg Val Gln Asp Gly Gly Ser Thr Ala Tyr Lys
305 310 315 320

Asp Ser Val Lys Gly Arg Phe Thr Ile Ser Arg Asp Phe Ser Arg Ser
325 330 335

Thr Met Tyr Leu Gln Met Asn Ser Leu Lys Pro Glu Asp Thr Ala Ile
340 345 350

Tyr Tyr Cys Ala Ala Lys Ser Thr Ile Ser Thr Pro Leu Ser Trp Gly
355 360 365

Gln Gly Thr Gln Val Thr Val Ser Ser Glu Pro Lys Thr Pro Lys Pro
370 375 380

Gln Ser Ser Gly Gly Gly Ala Ala Ala Gly Ser Gly Gly Gly Ser Gln
385 390 395 400

Val Gln Leu Val Glu Ser Gly Gly Gly Leu Val Gln Pro Gly Gly Ser
405 410 415

Leu Arg Leu Ser Cys Ala Ala Ser Gly Phe Pro Phe His Ala Tyr Tyr
420 425 430

Met Ser Trp Val Arg Gln Ala Pro Gly Lys Gly Leu Glu Trp Val Ser
435 440 445

His Ile Gly Asn Gly Gly Ile Ile Thr Arg Tyr Ala Asp Ser Val Lys
450 455 460

Gly Arg Phe Thr Ile Ser Arg Asp Asn Ala Lys Asn Thr Leu Tyr Leu
465 470 475 480

Gln Met Thr Asn Leu Lys Pro Glu Asp Thr Ala Leu Tyr Tyr Cys Thr
485 490 495

Leu Gly Thr Arg Asp Asp Leu Gly Pro Glu Arg Gly Gln Gly Thr Gln
500 505 510

Val Thr Val Ser Ser Glu Pro Lys Thr Pro Lys Pro Gln Gly Ala Gly
515 520 525

Gln Gly Ala Gly Ala Gly Pro Ile Thr Ile Asn Asn Phe Asn Tyr Ser
530 535 540

Asp Pro Val Asp Asn Lys Asn Ile Leu Tyr Leu Asp Thr His Leu Asn
545 550 555 560

```
Thr Leu Ala Asn Glu Pro Glu Lys Ala Phe Arg Ile Thr Gly Asn Ile
                565                 570                 575

Trp Val Ile Pro Asp Arg Phe Ser Arg Asn Ser Asn Pro Asn Leu Asn
            580                 585                 590

Lys Pro Pro Arg Val Thr Ser Pro Lys Ser Gly Tyr Tyr Asp Pro Asn
        595                 600                 605

Tyr Leu Ser Thr Asp Ser Asp Lys Asp Pro Phe Leu Lys Glu Ile Ile
    610                 615                 620

Lys Leu Phe Lys Arg Ile Asn Ser Arg Glu Ile Gly Glu Glu Leu Ile
625                 630                 635                 640

Tyr Arg Leu Ser Thr Asp Ile Pro Phe Pro Gly Asn Asn Asn Thr Pro
                645                 650                 655

Ile Asn Thr Phe Asp Phe Asp Val Asp Phe Asn Ser Val Asp Val Lys
            660                 665                 670

Thr Arg Gln Gly Asn Asn Trp Val Lys Thr Gly Ser Ile Asn Pro Ser
        675                 680                 685

Val Ile Ile Thr Gly Pro Arg Glu Asn Ile Ile Asp Pro Glu Thr Ser
    690                 695                 700

Thr Phe Lys Leu Thr Asn Asn Thr Phe Ala Ala Gln Glu Gly Phe Gly
705                 710                 715                 720

Ala Leu Ser Ile Ile Ser Ile Ser Pro Arg Phe Met Leu Thr Tyr Ser
                725                 730                 735

Asn Ala Thr Asn Asp Val Gly Glu Gly Arg Phe Ser Lys Ser Glu Phe
            740                 745                 750

Cys Met Asp Pro Ile Leu Ile Leu Met His Ala Leu Asn Gly Ala Met
        755                 760                 765

His Asn Leu Tyr Gly Ile Ala Ile Pro Asn Asp Gln Thr Ile Ser Ser
    770                 775                 780

Val Thr Ser Asn Ile Phe Tyr Ser Gln Tyr Asn Val Lys Leu Glu Tyr
785                 790                 795                 800

Ala Glu Ile Tyr Ala Phe Gly Gly Pro Thr Ile Asp Leu Ile Pro Lys
                805                 810                 815

Ser Ala Arg Lys Tyr Phe Glu Glu Lys Ala Leu Asp Tyr Tyr Arg Ser
            820                 825                 830

Ile Ala Lys Arg Leu Asn Ser Ile Thr Thr Ala Asn Pro Ser Ser Phe
        835                 840                 845

Asn Lys Tyr Ile Gly Glu Tyr Lys Gln Lys Leu Ile Arg Lys Tyr Arg
    850                 855                 860

Phe Val Val Glu Ser Ser Gly Glu Val Thr Val Asn Arg Asn Lys Phe
865                 870                 875                 880

Val Glu Leu Tyr Asn Glu Leu Thr Gln Ile Phe Thr Glu Phe Asn Tyr
                885                 890                 895

Ala Lys Ile Tyr Asn Val Gln Asn Arg Lys Ile Ala Leu Ser Asn Val
            900                 905                 910

Tyr Thr Pro Val Thr Ala Asn Ile Leu Asp Asp Asn Val Tyr Asp Ile
        915                 920                 925

Gln Asn Gly Phe Asn Ile Pro Lys Ser Asn Leu Asn Val Leu Phe Met
    930                 935                 940

Gly Gln Asn Leu Ser Arg Asn Pro Ala Leu Arg Lys Val Asn Pro Glu
945                 950                 955                 960

Asn Met Leu Tyr Leu Phe Thr Lys Phe Cys His Lys Ala Ile Asp Gly
                965                 970                 975

Gln Ser Leu Asp Gln Gly Gly Trp Glu Leu Gln Gln Gly Gly Gln Gly
```

```
            980                 985                 990

Gly Gly Ala Gly Thr Leu Asp Cys  Arg Glu Leu Leu Val  Lys Asn Thr
        995                 1000                1005

Asp Leu  Pro Phe Ile Gly Asp  Ile Ser Asp Val Lys  Thr Asp Ile
    1010                 1015                 1020

Phe Leu  Arg Lys Asp Ile Asn  Glu Glu Thr Glu Val  Ile Tyr Tyr
    1025                 1030                 1035

Pro Asp  Asn Val Ser Val Asp  Gln Val Ile Leu Ser  Lys Asn Thr
    1040                 1045                 1050

Ser Glu  His Gly Gln Leu Asp  Leu Leu Tyr Pro Ser  Ile Asp Ser
    1055                 1060                 1065

Glu Ser  Glu Ile Leu Pro Gly  Glu Asn Gln Val Phe  Tyr Asp Asn
    1070                 1075                 1080

Arg Thr  Gln Asn Val Asp Tyr  Leu Asn Ser Tyr Tyr  Tyr Leu Glu
    1085                 1090                 1095

Ser Gln  Lys Leu Ser Asp Asn  Val Glu Asp Phe Thr  Phe Thr Arg
    1100                 1105                 1110

Ser Ile  Glu Glu Ala Leu Asp  Asn Ser Ala Lys Val  Tyr Thr Tyr
    1115                 1120                 1125

Phe Pro  Thr Leu Ala Asn Lys  Val Asn Ala Gly Val  Gln Gly Gly
    1130                 1135                 1140

Leu Phe  Leu Met Trp Ala Asn  Asp Val Val Glu Asp  Phe Thr Thr
    1145                 1150                 1155

Asn Ile  Leu Arg Lys Asp Thr  Leu Asp Lys Ile Ser  Asp Val Ser
    1160                 1165                 1170

Ala Ile  Ile Pro Tyr Ile Gly  Pro Ala Leu Asn Ile  Ser Asn Ser
    1175                 1180                 1185

Val Arg  Arg Gly Asn Phe Thr  Glu Ala Phe Ala Val  Thr Gly Val
    1190                 1195                 1200

Thr Ile  Leu Leu Glu Ala Phe  Pro Glu Phe Thr Ile  Pro Ala Leu
    1205                 1210                 1215

Gly Ala  Phe Val Ile Tyr Ser  Lys Val Gln Glu Arg  Asn Glu Ile
    1220                 1225                 1230

Ile Lys  Thr Ile Asp Asn Cys  Leu Glu Gln Arg Ile  Lys Arg Trp
    1235                 1240                 1245

Lys Asp  Ser Tyr Glu Trp Met  Met Gly Thr Trp Leu  Ser Arg Ile
    1250                 1255                 1260

Ile Thr  Gln Phe Asn Asn Ile  Ser Tyr Gln Met Tyr  Asp Ser Leu
    1265                 1270                 1275

Asn Tyr  Gln Ala Gly Ala Ile  Lys Ala Lys Ile Asp  Leu Glu Tyr
    1280                 1285                 1290

Lys Lys  Tyr Ser Gly Ser Asp  Lys Glu Asn Ile Lys  Ser Gln Val
    1295                 1300                 1305

Glu Asn  Leu Lys Asn Ser Leu  Asp Val Lys Ile Ser  Glu Ala Met
    1310                 1315                 1320

Asn Asn  Ile Asn Lys Phe Ile  Arg Glu Cys Ser Val  Thr Tyr Leu
    1325                 1330                 1335

Phe Lys  Asn Met Leu Pro Lys  Val Ile Asp Glu Leu  Asn Glu Phe
    1340                 1345                 1350

Asp Arg  Asn Thr Lys Ala Lys  Leu Ile Asn Leu Ile  Asp Ser His
    1355                 1360                 1365

Asn Ile  Ile Leu Val Gly Glu  Val Asp Lys Leu Lys  Ala Lys Val
    1370                 1375                 1380
```

Asn Asn Ser Phe Gln Asn Thr Ile Pro Phe Asn Ile Phe Ser Tyr
1385 1390 1395

Thr Asn Asn Ser Leu Leu Lys Asp Ile Ile Asn Glu Tyr Phe Asn
1400 1405 1410

Asn Ile Asn Asp Ser Lys Ile Leu Ser Leu Gln Asn Arg Lys Asn
1415 1420 1425

Thr Leu Val Asp Thr Ser Gly Tyr Asn Ala Glu Val Ser Glu Glu
1430 1435 1440

Gly Asp Val Gln Leu Asn Pro Ile Phe Pro Phe Asp Phe Lys Leu
1445 1450 1455

Gly Ser Ser Gly Glu Asp Arg Gly Lys Val Ile Val Thr Gln Asn
1460 1465 1470

Glu Asn Ile Val Tyr Asn Ser Met Tyr Glu Ser Phe Ser Ile Ser
1475 1480 1485

Phe Trp Ile Arg Ile Asn Lys Trp Val Ser Asn Leu Pro Gly Tyr
1490 1495 1500

Thr Ile Ile Asp Ser Val Lys Asn Asn Ser Gly Trp Ser Ile Gly
1505 1510 1515

Ile Ile Ser Asn Phe Leu Val Phe Thr Leu Lys Gln Asn Glu Asp
1520 1525 1530

Ser Glu Gln Ser Ile Asn Phe Ser Tyr Asp Ile Ser Asn Asn Ala
1535 1540 1545

Pro Gly Tyr Asn Lys Trp Phe Phe Val Thr Val Thr Asn Asn Met
1550 1555 1560

Met Gly Asn Met Lys Ile Tyr Ile Asn Gly Lys Leu Ile Asp Thr
1565 1570 1575

Ile Lys Val Lys Glu Leu Thr Gly Ile Asn Phe Ser Lys Thr Ile
1580 1585 1590

Thr Phe Glu Ile Asn Lys Ile Pro Asp Thr Gly Leu Ile Thr Ser
1595 1600 1605

Asp Ser Asp Asn Ile Asn Met Trp Ile Arg Asp Phe Tyr Ile Phe
1610 1615 1620

Ala Lys Glu Leu Asp Gly Lys Asp Ile Asn Ile Leu Phe Asn Ser
1625 1630 1635

Leu Gln Tyr Thr Asn Val Val Lys Asp Tyr Trp Gly Asn Asp Leu
1640 1645 1650

Arg Tyr Asn Lys Glu Tyr Tyr Met Val Asn Ile Asp Tyr Leu Asn
1655 1660 1665

Arg Tyr Met Tyr Ala Asn Ser Arg Gln Ile Val Phe Asn Thr Arg
1670 1675 1680

Arg Asn Asn Asn Asp Phe Asn Glu Gly Tyr Lys Ile Ile Ile Lys
1685 1690 1695

Arg Ile Arg Gly Asn Thr Asn Asp Thr Arg Val Arg Gly Gly Asp
1700 1705 1710

Ile Leu Tyr Phe Asp Met Thr Ile Asn Asn Lys Ala Tyr Asn Leu
1715 1720 1725

Phe Met Lys Asn Glu Thr Met Tyr Ala Asp Asn His Ser Thr Glu
1730 1735 1740

Asp Ile Tyr Ala Ile Gly Leu Arg Glu Gln Thr Lys Asp Ile Asn
1745 1750 1755

Asp Asn Ile Ile Phe Gln Ile Gln Pro Met Asn Asn Thr Tyr Tyr
1760 1765 1770

-continued

```
Tyr Ala  Ser Gln Ile Phe Lys  Ser Asn Phe Asn Gly  Glu Asn Ile
    1775                 1780                 1785

Ser Gly  Ile Cys Ser Ile Gly  Thr Tyr Arg Phe Arg  Leu Gly Gly
    1790                 1795                 1800

Asp Trp  Tyr Arg His Asn Tyr  Leu Val Pro Thr Val  Lys Gln Gly
    1805                 1810                 1815

Asn Tyr  Ala Ser Leu Leu Glu  Ser Thr Ser Thr His  Trp Gly Phe
    1820                 1825                 1830

Val Pro  Val Ser Glu Gly Ala  Gly Tyr Pro Tyr Asp  Val Pro Asp
    1835                 1840                 1845

Tyr Ala  Gly Trp Glu Leu Gln  Gln Gly Ala Gly Trp  Ser His Pro
    1850                 1855                 1860

Gln Phe  Glu Lys Gly Ala Gly  Trp Ser His Pro Gln  Phe Glu Lys
    1865                 1870                 1875

Gly Ala  Gly Trp Ser His Pro  Gln Phe Glu Lys
    1880                 1885
```

<210> SEQ ID NO 47
<211> LENGTH: 9851
<212> TYPE: DNA
<213> ORGANISM: Artificial
<220> FEATURE:
<223> OTHER INFORMATION: DNA construct for molecular construction of fusion proteins

<400> SEQUENCE: 47

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgttt acaatttcag gtggcacttt tcggggaaat    480

gtgcgcggaa cccctatttg tttatttttc taaatacatt caaatatgta tccgctcatg    540

agacaataac cctgataaat gcttcaataa tattgaaaaa ggaagagtat gagtattcaa    600

catttccgtg tcgcccttat tccctttttt gcggcatttt gccttcctgt ttttgctcac    660

ccagaaacgc tggtgaaagt aaaagatgct gaagatcagt tgggtgcacg agtgggttac    720

atcgaactgg atctcaacag cggtaagatc cttgagagtt ttcgccccga agaacgtttt    780

ccaatgatga gcacttttaa agttctgcta tgtggcgcgg tattatcccg tattgacgcc    840

gggcaagagc aactcggtcg ccgcatacac tattctcaga atgacttggt tgagtactca    900

ccagtcacag aaaagcatct tacggatggc atgacagtaa gagaattatg cagtgctgcc    960

ataaccatga gtgataacac tgcggccaac ttacttctga caacgatcgg aggaccgaag   1020

gagctaaccg cttttttgca caacatgggg gatcatgtaa ctcgccttga tcgttgggaa   1080

ccggagctga atgaagccat accaaacgac gagcgtgaca ccacgatgcc tgtagcaatg   1140

gcaacaacgt tgcgcaaact attaactggc gaactactta ctctagcttc ccggcaacaa   1200

ttaatagact ggatggaggc ggataaagtt gcaggaccac ttctgcgctc ggcccttccg   1260

gctggctggt ttattgctga taaatctgga gccggtgagc gtgggtctcg cggtatcatt   1320
```

gcagcactgg ggccagatgg taagccctcc cgtatcgtag ttatctacac gacggggagt 1380
caggcaacta tggatgaacg aaatagacag atcgctgaga taggtgcctc actgattaag 1440
cattggtaac tgtcagacca agtttactca tatatacttt agattgattt aaaacttcat 1500
ttttaattta aaaggatcta ggtgaagatc ctttttgata atctcatgac caaaatccct 1560
taacgtgagt tttcgttcca ctgagcgtca gaccccgtag aaaagatcaa aggatcttct 1620
tgagatcctt tttttctgcg cgtaatctgc tgcttgcaaa caaaaaaacc accgctacca 1680
gcggtggttt gtttgccgga tcaagagcta ccaactcttt ttccgaaggt aactggcttc 1740
agcagagcgc agataccaaa tactgtcctt ctagtgtagc cgtagttagg ccaccacttc 1800
aagaactctg tagcaccgcc tacatacctc gctctgctaa tcctgttacc agtggctgct 1860
gccagtggcg ataagtcgtg tcttaccggg ttggactcaa gacgatagtt accggataag 1920
gcgcagcggt cgggctgaac ggggggttcg tgcacacagc ccagcttgga gcgaacgacc 1980
tacaccgaac tgagatacct acagcgtgag cattgagaaa gcgccacgct tcccgaaggg 2040
agaaaggcgg acaggtatcc ggtaagcggc agggtcggaa caggagagcg cacgagggag 2100
cttccagggg gaaacgcctg gtatctttat agtcctgtcg ggtttcgcca cctctgactt 2160
gagcgtcgat ttttgtgatg ctcgtcaggg gggcggagcc tatggaaaaa cgccagcaac 2220
gcggcctttt tacggttcct ggccttttgc tggccttttg ctcacatgtt ctttcctgcg 2280
ttatcccctg attctgtgga taaccgtatt accgcctttg agtgagctga taccgctcgc 2340
cgcagccgaa cgaccgagcg cagcgagtca gtgagcgagg aagcggaaga gcgcctgatg 2400
cggtattttc tccttacgca tctgtgcggt atttcacacc gcagaccagc cgcgtaacct 2460
ggcaaaatcg gttacggttg agtaataaat ggatgccctg cgtaagcggg tgtgggcgga 2520
caataaagtc ttaaactgaa caaaatagat ctaaactatg acaataaagt cttaaactag 2580
acagaatagt tgtaaactga aatcagtcca gttatgctgt gaaaaagcat actggacttt 2640
tgttatggct aaagcaaact cttcattttc tgaagtgcaa attgcccgtc gtattaaaga 2700
ggggcgtggc caagggcatg gtaaagacta tattcgcggc gttgtgacaa tttaccgaac 2760
aactccgcgg ccgggaagcc gatctcggct tgaacgaatt gttaggtggc ggtacttggg 2820
tcgatatcaa agtgcatcac ttcttcccgt atgcccaact ttgtatagag agccactgcg 2880
ggatcgtcac cgtaatctgc ttgcacgtag atcacataag caccaagcgc gttggcctca 2940
tgcttgagga gattgatgag cgcggtggca atgccctgcc tccggtgctc gccggagact 3000
gcgagatcat agatatagat ctcactacgc ggctgctcaa acctgggcag aacgtaagcc 3060
gcgagagcgc caacaaccgc ttcttggtcg aaggcagcaa gcgcgatgaa tgtcttacta 3120
cggagcaagt tcccgaggta atcggagtcc ggctgatgtt gggagtaggt ggctacgtct 3180
ccgaactcac gaccgaaaag atcaagagca gcccgcatgg atttgacttg gtcagggccg 3240
agcctacatg tgcgaatgat gcccatactt gagccaccta actttgtttt agggcgactg 3300
ccctgctgcg taacatcgtt gctgctgcgt aacatcgttg ctgctccata acatcaaaca 3360
tcgacccacg gcgtaacgcg cttgctgctt ggatgcccga ggcatagact gtacaaaaaa 3420
acagtcataa caagccatga aaaccgccac tgcgccgtta ccaccgctgc gttcggtcaa 3480
ggttctggac cagttgcgtg agcgcatacg ctacttgcat tacagtttac gaaccgaaca 3540
ggcttatgtc aactgggttc gtgccttcat ccgtttccac ggtgtgcgtc acccggcaac 3600
cttgggcagc agcgaagtcg aggcatttct gtcctggctg gcgaacgagc gcaaggtttc 3660
ggtctccacg catcgtcagg cattggcggc cttgctgttc ttctacggca aggtgctgtg 3720

```
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca ccaccaccac caccaccacc accaccacca cgacgtcggc   4200
tgggagctgc aaggcgccgg cggtgcggcc gctcaggttc agttggtgga atcaggcggc   4260
ggctcagttc aagcaggcgg ttcactcagg ctctcgtgtg cggcaagcgg tatcgactcg   4320
tccagctact gcatgggatg gttcaggcaa aggccaggaa aggagaggga aggtgttgct   4380
cgtatcaacg gactgggtgg cgttaagaca gcatacgcgg acagtgtgaa agataggttc   4440
acaatttcga gagacaacgc agagaacacg gtctacttgc agatgaactc tctgaagccc   4500
gaagatacgg cgatctacta ctgcgctgcc aaattctcac ccggatactg tggaggtagc   4560
tggtctaact tcggttactg gggtcaaggc acccaagtga ctgtctcttc aggcggaggt   4620
gcggccgctg gctcaggagg tggcagtcag gtgcagctgc aggagtcggg aggtggctcc   4680
gtccaagcag gaggtagcct gcgcctctct tgcgcagcgt caggtatcga cagttcgtcc   4740
tactgtatgg gctggttcag gcagcgtcct ggcaaggaga gggaaggagt ggcacgtatc   4800
aacggtctcg gcggagtcaa gacagcttac gccgactccg ttaaagatag gttcaccatt   4860
agccgcgaca acgctgagaa cactgtctac ctccaaatga acagtttgaa gccggaagat   4920
actgccattt actactgtgc tgccaaattc tcaccgggct actgtggagg aagctggtct   4980
aacttcggct actggggaca aggaactcaa gtcaccgttg gggccggcca gggtgctggt   5040
gctggaccga tcaccatcaa caacttcaat tactcggatc cggtggataa caagaacatc   5100
ctctacttgg acacacactt gaacacgctg gctaacgagc ctgaaaaagc tttcaggatc   5160
accggcaaca tttgggtcat tccggatagg ttcagcagaa actctaaccc taacttgaac   5220
aaacctccca gagtgacctc acctaagagt ggatactacg accccaacta cctctcgact   5280
gactccgata aagacccctt cctgaaggag atcattaaac tcttcaagcg catcaactct   5340
cgtgaaattg gcgaggaatt gatctaccgc ctgagtacag acatcccatt cccgggtaac   5400
aacaacaccc caatcaacac tttcgatttc gatgtcgatt tcaactcagt ggatgtcaaa   5460
accaggcagg gaaacaactg ggtgaagact ggtagcatca acccatctgt catcattact   5520
ggcccgagag agaacatcat tgaccctgaa acctccactt tcaagctgac aaacaacacg   5580
ttcgctgctc aggaaggctt cggagcgttg agcatcattt ctatctcacc tcgcttcatg   5640
ctgacatact ctaacgctac gaacgacgtg ggagagggcc gtttcagtaa gtctgaattc   5700
tgcatggacc ctattctgat cctcatgcac gctctcaacg gcgccatgca caacttgtac   5760
ggaattgcta tccccaacga ccagaccatt tccagcgtga ctagcaacat cttctactct   5820
caatacaacg tcaagctgga gtacgcagaa atctacgctt tcggtggccc aaccattgac   5880
ttgatcccga aatcagctcg taagtatttc gaagaaaaag cgctggatta ttacaggtcg   5940
attgctaaga gactcaactc catcaccact gctaacccct cttcattcaa caagtacatt   6000
ggagaataca agcagaaact gatccgcaag taccgtttcg tggtcgagag ttcgggtgaa   6060
```

gttactgtga accgcaacaa gttcgtcgag ctgtacaacg aattgacaca aatcttcacg 6120
gagttcaact acgccaaaat ttacaacgtg caaaaccgta agatcgcgct ctctaacgtc 6180
tacaccccgg ttaccgctaa catcttggac gataacgtct acgacattca gaacggtttc 6240
aacatcccaa agtcgaacct caacgttttg ttcatgggtc aaaacttgtc ccgcaacccc 6300
gccctgcgta aggtgaaccc agagaacatg ttgtacctgt tcaccaaatt ctgccacaag 6360
gccatcgacg gtcagtctct agaccaagga ggatgggaac tccagcaagg tggccagggt 6420
ggaggtgctg gcaccctgga ctgtcgcgaa ctgctcgtta agaacactga tctcccattc 6480
attggcgaca tctctgatgt gaaaaacagac attttcctgc gtaaggatat caacgaggaa 6540
acggaggtca tctactaccc tgacaacgtc tcggttgatc aggttatctt gtcaaagaac 6600
accagtgaac atggccaact ggacttgctg taccccctcaa ttgattccga gagcgaaatc 6660
ctgccaggag agaaccaggt tttctacgac aacaggacac aaaacgtgga ttacctcaac 6720
agctactact acctggagtc gcagaagctc tccgacaacg tcgaagattt cacatttacg 6780
agatcaatcg aggaggcttt ggacaacagt gccaaagtct acacctactt ccctactctg 6840
gcaaacaagg tgaacgcggg tgtccaaggc ggactcttct tgatgtgggc taacgacgtt 6900
gtggaagatt tcacaacgaa catcttgcgc aaagacaccc tggataagat cagcgatgtc 6960
tctgccatca ttccatacat tggcccggca ctgaacatct ctaactcagt tcgccgtggc 7020
aacttcactg aggcattcgc ggtcacagga gttacgatcc tcttggaggc tttcccggag 7080
ttcacaatcc ccgcactggg cgcgttcgtt atctactcca aagtgcagga gcgcaacgaa 7140
atcattaaga ctatcgacaa ctgcctggag caaaggatca aaagatggaa ggattcgtac 7200
gaatggatga tgggtacctg gctctcccgt atcattacgc agttcaacaa catcagctac 7260
caaatgtacg actctctcaa ctaccaggct ggtgccatca aggccaaaat tgacttggag 7320
tacaagaaat acagtggctc ggataaagag aacatcaaga gtcaagtcga aaacctgaaa 7380
aactcactcg acgttaagat cagtgaggca atgaacaaca tcaacaagtt cattcgcgaa 7440
tgttccgtta cctacctctt caaaaacatg ttgccaaagg tcatcgacga gctgaacgaa 7500
tttgatcgta acactaaggc gaaactgatt aacctcatcg actcacacaa catcattttg 7560
gtgggcgaag tcgataagct gaaagccaag gtgaacaaca gtttccagaa cacaatccct 7620
ttcaacattt tctcatacac gaacaacagt ctgctcaagg acatcattaa cgagtacttc 7680
aacaacatta acgatagcaa aatcctgtca ctgcagaacc gtaagaacac actggtcgat 7740
actagtggat acaacgccga agtctctgag gaaggtgacg tgcagctgaa ccctatcttc 7800
cccttcgact tcaaattggg ctccagcgga gaggataggg gcaaggtcat cgtcacccag 7860
aacgagaaca tcgtctacaa ctcaatgtac gaatccttca gcatctcttt ctggatcagg 7920
attaacaagt gggtgagcaa cctgcccggt tacacaatca ttgactctgt caagaacaac 7980
tcaggttgga gtatcggcat catttctaac ttcttggtct tcaccctgaa gcagaacgag 8040
gactcggaac aatccattaa cttctcatac gatatcagta acaacgctcc aggttacaac 8100
aagtggttct tcgttaccgt gactaacaac atgatgggta acatgaaaat ttacatcaac 8160
ggcaagctca ttgacaccat caaagtgaag gagttgactg gtattaactt ctccaaaaca 8220
atcacgtttg aaattaacaa gatccctgac accggcctga tcacttcaga cagtgataac 8280
atcaacatgt ggattaggga tttctacatc ttcgccaagg agctcgacgg aaaggatatt 8340
aacatcctct tcaacagctt gcagtacacc aacgtcgtta aagactactg ggtaacgat 8400
ttgagataca acaaggagta ctacatggtc aacatcgact acctgaacag gtacatgtac 8460
gctaactccc gccaaatcgt gttcaacacc aggagaaaca acaacgactt caacgagggt 8520
tacaaaatca ttatcaagcg catccgtggc aacaccaacg atactagggt gagaggtggc 8580
gacattctgt acttcgatat gactatcaac aacaaagcct acaacttgtt catgaaaaac 8640
gagacaatgt acgccgacaa ccatagcacg gaggatattt acgcaatcgg actgagggaa 8700
cagacaaagg acatcaacga taacattatc ttccagatcc aacctatgaa caacacgtac 8760
tactacgctt cgcaaatctt caagtccaac ttcaacggag aaaacatttc gggtatctgt 8820
tccattggca cataccgctt ccgtctgggt ggtgactggt atcgtcacaa ctacctcgtt 8880
cccaccgtga agcagggtaa ctacgcttct ttgctggagt cgacttccac gcactgggga 8940
ttcgttcctg tgtcagaggg cgctggctac ccttacgatg ttcccgacta cgctggttgg 9000
gaactccagc aaggtgcagg atggtcccac cctcaattcg agaagggtgc cggatggagt 9060
cacccacagt tcgagaaagg cgctggatgg agtcacccac agttcgagaa ataattagtt 9120
gatgcatagt taattagata gctcgaggca tgcggtacca agattggatc tagatgcata 9180
gttaattaga tagctcgagg catgcggtac caagcttgtc gagaagtact agaggatcat 9240
aatcagccat accacatttg tagaggtttt acttgcttta aaaaacctcc cacacctccc 9300
cctgaacctg aaacataaaa tgaatgcaat tgttgttgtt aacttgttta ttgcagctta 9360
taatggttac aaataaagca atagcatcac aaatttcaca aataaagcat ttttttcact 9420
gcattctagt tgtggtttgt ccaaactcat caatgtatct tatcatgtct ggatctgatc 9480
actgcttgag cctaggagat ccgaaccaga taagtgaaat ctagttccaa actattttgt 9540
catttttaat tttcgtatta gcttacgacg ctacacccag ttcccatcta ttttgtcact 9600
cttccctaaa taatccttaa aaactccatt tccacccctc ccagttccca actattttgt 9660
ccgcccacag cggggcattt ttcttcctgt tatgttttta atcaaacatc ctgccaactc 9720
catgtgacaa accgtcatct tcggctactt tttctctgtc acagaatgaa aatttttctg 9780
tcatctcttc gttattaatg tttgtaattg actgaatatc aacgcttatt tgcagcctga 9840
atggcgaatg g 9851

<210> SEQ ID NO 48
<211> LENGTH: 1674
<212> TYPE: PRT
<213> ORGANISM: Artificial
<220> FEATURE:
<223> OTHER INFORMATION: Fusion protein construct

<400> SEQUENCE: 48

Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Gly Ala Gly Gly Ala Ala Ala
        35                  40                  45

Gln Val Gln Leu Val Glu Ser Gly Gly Gly Ser Val Gln Ala Gly Gly
    50                  55                  60

Ser Leu Arg Leu Ser Cys Ala Ala Ser Gly Ile Asp Ser Ser Ser Tyr
65                  70                  75                  80

Cys Met Gly Trp Phe Arg Gln Arg Pro Gly Lys Glu Arg Glu Gly Val
                85                  90                  95

Ala Arg Ile Asn Gly Leu Gly Gly Val Lys Thr Ala Tyr Ala Asp Ser
            100                 105                 110

```
Val Lys Asp Arg Phe Thr Ile Ser Arg Asp Asn Ala Glu Asn Thr Val
        115                 120                 125

Tyr Leu Gln Met Asn Ser Leu Lys Pro Glu Asp Thr Ala Ile Tyr Tyr
    130                 135                 140

Cys Ala Ala Lys Phe Ser Pro Gly Tyr Cys Gly Gly Ser Trp Ser Asn
145                 150                 155                 160

Phe Gly Tyr Trp Gly Gln Gly Thr Gln Val Thr Val Ser Ser Gly Gly
                165                 170                 175

Gly Ala Ala Ala Gly Ser Gly Gly Gly Ser Gln Val Gln Leu Gln Glu
            180                 185                 190

Ser Gly Gly Gly Ser Val Gln Ala Gly Gly Ser Leu Arg Leu Ser Cys
        195                 200                 205

Ala Ala Ser Gly Ile Asp Ser Ser Ser Tyr Cys Met Gly Trp Phe Arg
    210                 215                 220

Gln Arg Pro Gly Lys Glu Arg Glu Gly Val Ala Arg Ile Asn Gly Leu
225                 230                 235                 240

Gly Gly Val Lys Thr Ala Tyr Ala Asp Ser Val Lys Asp Arg Phe Thr
                245                 250                 255

Ile Ser Arg Asp Asn Ala Glu Asn Thr Val Tyr Leu Gln Met Asn Ser
            260                 265                 270

Leu Lys Pro Glu Asp Thr Ala Ile Tyr Tyr Cys Ala Ala Lys Phe Ser
        275                 280                 285

Pro Gly Tyr Cys Gly Gly Ser Trp Ser Asn Phe Gly Tyr Trp Gly Gln
    290                 295                 300

Gly Thr Gln Val Thr Val Gly Ala Gly Gln Gly Ala Gly Ala Gly Pro
305                 310                 315                 320

Ile Thr Ile Asn Asn Phe Asn Tyr Ser Asp Pro Val Asp Asn Lys Asn
                325                 330                 335

Ile Leu Tyr Leu Asp Thr His Leu Asn Thr Leu Ala Asn Glu Pro Glu
            340                 345                 350

Lys Ala Phe Arg Ile Thr Gly Asn Ile Trp Val Ile Pro Asp Arg Phe
        355                 360                 365

Ser Arg Asn Ser Asn Pro Asn Leu Asn Lys Pro Pro Arg Val Thr Ser
    370                 375                 380

Pro Lys Ser Gly Tyr Tyr Asp Pro Asn Tyr Leu Ser Thr Asp Ser Asp
385                 390                 395                 400

Lys Asp Pro Phe Leu Lys Glu Ile Ile Lys Leu Phe Lys Arg Ile Asn
                405                 410                 415

Ser Arg Glu Ile Gly Glu Glu Leu Ile Tyr Arg Leu Ser Thr Asp Ile
            420                 425                 430

Pro Phe Pro Gly Asn Asn Asn Thr Pro Ile Asn Thr Phe Asp Phe Asp
        435                 440                 445

Val Asp Phe Asn Ser Val Asp Val Lys Thr Arg Gln Gly Asn Asn Trp
    450                 455                 460

Val Lys Thr Gly Ser Ile Asn Pro Ser Val Ile Ile Thr Gly Pro Arg
465                 470                 475                 480

Glu Asn Ile Ile Asp Pro Glu Thr Ser Thr Phe Lys Leu Thr Asn Asn
                485                 490                 495

Thr Phe Ala Ala Gln Glu Gly Phe Gly Ala Leu Ser Ile Ile Ser Ile
            500                 505                 510

Ser Pro Arg Phe Met Leu Thr Tyr Ser Asn Ala Thr Asn Asp Val Gly
        515                 520                 525
```

```
Glu Gly Arg Phe Ser Lys Ser Glu Phe Cys Met Asp Pro Ile Leu Ile
    530                 535                 540

Leu Met His Ala Leu Asn Gly Ala Met His Asn Leu Tyr Gly Ile Ala
545                 550                 555                 560

Ile Pro Asn Asp Gln Thr Ile Ser Ser Val Thr Ser Asn Ile Phe Tyr
                565                 570                 575

Ser Gln Tyr Asn Val Lys Leu Glu Tyr Ala Glu Ile Tyr Ala Phe Gly
            580                 585                 590

Gly Pro Thr Ile Asp Leu Ile Pro Lys Ser Ala Arg Lys Tyr Phe Glu
        595                 600                 605

Glu Lys Ala Leu Asp Tyr Tyr Arg Ser Ile Ala Lys Arg Leu Asn Ser
    610                 615                 620

Ile Thr Thr Ala Asn Pro Ser Ser Phe Asn Lys Tyr Ile Gly Glu Tyr
625                 630                 635                 640

Lys Gln Lys Leu Ile Arg Lys Tyr Arg Phe Val Val Glu Ser Ser Gly
                645                 650                 655

Glu Val Thr Val Asn Arg Asn Lys Phe Val Glu Leu Tyr Asn Glu Leu
            660                 665                 670

Thr Gln Ile Phe Thr Glu Phe Asn Tyr Ala Lys Ile Tyr Asn Val Gln
        675                 680                 685

Asn Arg Lys Ile Ala Leu Ser Asn Val Tyr Thr Pro Val Thr Ala Asn
    690                 695                 700

Ile Leu Asp Asp Asn Val Tyr Asp Ile Gln Asn Gly Phe Asn Ile Pro
705                 710                 715                 720

Lys Ser Asn Leu Asn Val Leu Phe Met Gly Gln Asn Leu Ser Arg Asn
                725                 730                 735

Pro Ala Leu Arg Lys Val Asn Pro Glu Asn Met Leu Tyr Leu Phe Thr
            740                 745                 750

Lys Phe Cys His Lys Ala Ile Asp Gly Gln Ser Leu Asp Gln Gly Gly
        755                 760                 765

Trp Glu Leu Gln Gln Gly Gly Gln Gly Gly Gly Ala Gly Thr Leu Asp
    770                 775                 780

Cys Arg Glu Leu Leu Val Lys Asn Thr Asp Leu Pro Phe Ile Gly Asp
785                 790                 795                 800

Ile Ser Asp Val Lys Thr Asp Ile Phe Leu Arg Lys Asp Ile Asn Glu
                805                 810                 815

Glu Thr Glu Val Ile Tyr Tyr Pro Asp Asn Val Ser Val Asp Gln Val
            820                 825                 830

Ile Leu Ser Lys Asn Thr Ser Glu His Gly Gln Leu Asp Leu Leu Tyr
        835                 840                 845

Pro Ser Ile Asp Ser Glu Ser Glu Ile Leu Pro Gly Glu Asn Gln Val
    850                 855                 860

Phe Tyr Asp Asn Arg Thr Gln Asn Val Asp Tyr Leu Asn Ser Tyr Tyr
865                 870                 875                 880

Tyr Leu Glu Ser Gln Lys Leu Ser Asp Asn Val Glu Asp Phe Thr Phe
                885                 890                 895

Thr Arg Ser Ile Glu Glu Ala Leu Asp Asn Ser Ala Lys Val Tyr Thr
            900                 905                 910

Tyr Phe Pro Thr Leu Ala Asn Lys Val Asn Ala Gly Val Gln Gly Gly
        915                 920                 925

Leu Phe Leu Met Trp Ala Asn Asp Val Val Glu Asp Phe Thr Thr Asn
    930                 935                 940

Ile Leu Arg Lys Asp Thr Leu Asp Lys Ile Ser Asp Val Ser Ala Ile
```

-continued

```
945                 950                 955                 960

Ile Pro Tyr Ile Gly Pro Ala Leu Asn Ile Ser Asn Ser Val Arg Arg
                965                 970                 975

Gly Asn Phe Thr Glu Ala Phe Ala Val Thr Gly Val Thr Ile Leu Leu
            980                 985                 990

Glu Ala Phe Pro Glu Phe Thr Ile  Pro Ala Leu Gly Ala  Phe Val Ile
        995                 1000                1005

Tyr Ser  Lys Val Gln Glu Arg  Asn Glu Ile Ile Lys  Thr Ile Asp
    1010                 1015                 1020

Asn Cys  Leu Glu Gln Arg Ile  Lys Arg Trp Lys Asp  Ser Tyr Glu
    1025                 1030                 1035

Trp Met  Met Gly Thr Trp Leu  Ser Arg Ile Ile Thr  Gln Phe Asn
    1040                 1045                 1050

Asn Ile  Ser Tyr Gln Met Tyr  Asp Ser Leu Asn Tyr  Gln Ala Gly
    1055                 1060                 1065

Ala Ile  Lys Ala Lys Ile Asp  Leu Glu Tyr Lys Lys  Tyr Ser Gly
    1070                 1075                 1080

Ser Asp  Lys Glu Asn Ile Lys  Ser Gln Val Glu Asn  Leu Lys Asn
    1085                 1090                 1095

Ser Leu  Asp Val Lys Ile Ser  Glu Ala Met Asn Asn  Ile Asn Lys
    1100                 1105                 1110

Phe Ile  Arg Glu Cys Ser Val  Thr Tyr Leu Phe Lys  Asn Met Leu
    1115                 1120                 1125

Pro Lys  Val Ile Asp Glu Leu  Asn Glu Phe Asp Arg  Asn Thr Lys
    1130                 1135                 1140

Ala Lys  Leu Ile Asn Leu Ile  Asp Ser His Asn Ile  Ile Leu Val
    1145                 1150                 1155

Gly Glu  Val Asp Lys Leu Lys  Ala Lys Val Asn Asn  Ser Phe Gln
    1160                 1165                 1170

Asn Thr  Ile Pro Phe Asn Ile  Phe Ser Tyr Thr Asn  Asn Ser Leu
    1175                 1180                 1185

Leu Lys  Asp Ile Ile Asn Glu  Tyr Phe Asn Asn Ile  Asn Asp Ser
    1190                 1195                 1200

Lys Ile  Leu Ser Leu Gln Asn  Arg Lys Asn Thr Leu  Val Asp Thr
    1205                 1210                 1215

Ser Gly  Tyr Asn Ala Glu Val  Ser Glu Glu Gly Asp  Val Gln Leu
    1220                 1225                 1230

Asn Pro  Ile Phe Pro Phe Asp  Phe Lys Leu Gly Ser  Ser Gly Glu
    1235                 1240                 1245

Asp Arg  Gly Lys Val Ile Val  Thr Gln Asn Glu Asn  Ile Val Tyr
    1250                 1255                 1260

Asn Ser  Met Tyr Glu Ser Phe  Ser Ile Ser Phe Trp  Ile Arg Ile
    1265                 1270                 1275

Asn Lys  Trp Val Ser Asn Leu  Pro Gly Tyr Thr Ile  Ile Asp Ser
    1280                 1285                 1290

Val Lys  Asn Asn Ser Gly Trp  Ser Ile Gly Ile Ile  Ser Asn Phe
    1295                 1300                 1305

Leu Val  Phe Thr Leu Lys Gln  Asn Glu Asp Ser Glu  Gln Ser Ile
    1310                 1315                 1320

Asn Phe  Ser Tyr Asp Ile Ser  Asn Asn Ala Pro Gly  Tyr Asn Lys
    1325                 1330                 1335

Trp Phe  Phe Val Thr Val Thr  Asn Asn Met Met Gly  Asn Met Lys
    1340                 1345                 1350
```

```
Ile Tyr  Ile Asn Gly Lys Leu  Ile Asp Thr Ile Lys  Val Lys Glu
    1355                 1360                 1365

Leu Thr  Gly Ile Asn Phe Ser  Lys Thr Ile Thr Phe  Glu Ile Asn
    1370                 1375                 1380

Lys Ile  Pro Asp Thr Gly Leu  Ile Thr Ser Asp Ser  Asp Asn Ile
    1385                 1390                 1395

Asn Met  Trp Ile Arg Asp Phe  Tyr Ile Phe Ala Lys  Glu Leu Asp
    1400                 1405                 1410

Gly Lys  Asp Ile Asn Ile Leu  Phe Asn Ser Leu Gln  Tyr Thr Asn
    1415                 1420                 1425

Val Val  Lys Asp Tyr Trp Gly  Asn Asp Leu Arg Tyr  Asn Lys Glu
    1430                 1435                 1440

Tyr Tyr  Met Val Asn Ile Asp  Tyr Leu Asn Arg Tyr  Met Tyr Ala
    1445                 1450                 1455

Asn Ser  Arg Gln Ile Val Phe  Asn Thr Arg Arg Asn  Asn Asn Asp
    1460                 1465                 1470

Phe Asn  Glu Gly Tyr Lys Ile  Ile Ile Lys Arg Ile  Arg Gly Asn
    1475                 1480                 1485

Thr Asn  Asp Thr Arg Val Arg  Gly Gly Asp Ile Leu  Tyr Phe Asp
    1490                 1495                 1500

Met Thr  Ile Asn Asn Lys Ala  Tyr Asn Leu Phe Met  Lys Asn Glu
    1505                 1510                 1515

Thr Met  Tyr Ala Asp Asn His  Ser Thr Glu Asp Ile  Tyr Ala Ile
    1520                 1525                 1530

Gly Leu  Arg Glu Gln Thr Lys  Asp Ile Asn Asp Asn  Ile Ile Phe
    1535                 1540                 1545

Gln Ile  Gln Pro Met Asn Asn  Thr Tyr Tyr Tyr Ala  Ser Gln Ile
    1550                 1555                 1560

Phe Lys  Ser Asn Phe Asn Gly  Glu Asn Ile Ser Gly  Ile Cys Ser
    1565                 1570                 1575

Ile Gly  Thr Tyr Arg Phe Arg  Leu Gly Gly Asp Trp  Tyr Arg His
    1580                 1585                 1590

Asn Tyr  Leu Val Pro Thr Val  Lys Gln Gly Asn Tyr  Ala Ser Leu
    1595                 1600                 1605

Leu Glu  Ser Thr Ser Thr His  Trp Gly Phe Val Pro  Val Ser Glu
    1610                 1615                 1620

Gly Ala  Gly Tyr Pro Tyr Asp  Val Pro Asp Tyr Ala  Gly Trp Glu
    1625                 1630                 1635

Leu Gln  Gln Gly Ala Gly Trp  Ser His Pro Gln Phe  Glu Lys Gly
    1640                 1645                 1650

Ala Gly  Trp Ser His Pro Gln  Phe Glu Lys Gly Ala  Gly Trp Ser
    1655                 1660                 1665

His Pro  Gln Phe Glu Lys
    1670
```

<210> SEQ ID NO 49
<211> LENGTH: 10457
<212> TYPE: DNA
<213> ORGANISM: Artificial
<220> FEATURE:
<223> OTHER INFORMATION: DNA construct for molecular construction of fusion proteins

<400> SEQUENCE: 49

```
gacgcgccct gtagcggcgc attaagcgcg gcgggtgtgg tggttacgcg cagcgtgacc     60
```

```
gctacacttg ccagcgccct agcgcccgct cctttcgctt tcttcccttc ctttctcgcc    120
acgttcgccg gctttccccg tcaagctcta aatcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat tccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca caacatgggg gatcatgtaa ctcgccttga tcgttgggaa   1080
ccggagctga atgaagccat accaaacgac gagcgtgaca ccacgatgcc tgtagcaatg   1140
gcaacaacgt tgcgcaaact attaactggc gaactactta ctctagcttc ccggcaacaa   1200
ttaatagact ggatggaggc ggataaagtt gcaggaccac ttctgcgctc ggcccttccg   1260
gctggctggt ttattgctga taaatctgga gccggtgagc gtgggtctcg cggtatcatt   1320
gcagcactgg ggccagatgg taagccctcc cgtatcgtag ttatctacac gacggggagt   1380
caggcaacta tggatgaacg aaatagacag atcgctgaga taggtgcctc actgattaag   1440
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
```

-continued

```
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatgg agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatctcgg tccgttcgaa ccagaactct ggaagcttaa ctcctaaaaa   4080
accgccacca tgaaattctt agtcaacgtt gcccttgttt ttatggtcgt atacatttct   4140
tacatctatg cggccggaca ccaccaccac caccaccacc accaccacca cgacgtcggc   4200
tgggagctgc aacgtcgtcc cctgaactgc atcgtggctg tgtcccagaa catgggtatc   4260
ggcaagaacg gcgacctgcc ctggcctcct ctgcgtaacg agttcaagta cttccagcgt   4320
atgaccacca cctcctccgt cgagggcaag cagaacctgg tcatcatggg tcgcaagacc   4380
tggttctcca tccccgagaa gaaccgtctg ctgaaggacc gtatcaacat cgtgctgtcc   4440
cgcgagctga aggaaccccc tcgtggtgct cacttcctgg ctaagtccct ggacgacgct   4500
ctgcgtctga tcgagcagcc tgagctggct tccaaggtgg acatggtctg gatcgtgggc   4560
ggttcctccg tgtaccaaga ggctatgaac cagcccggtc acttgcgtct gttcgtgacc   4620
cgtatcatgc aagagttcga gtccgacacc ttcttccccg aaatcgacct gggcaagtac   4680
aagctgctgc ccgagtaccc cggtgtcctg tccgaggtgc aagaggaaaa gggtatcaag   4740
tacaagttcg aggtgtacga gaagaaggac ggcgcttccg gtttcgctaa cgagctcggt   4800
```

```
cctcgtctga tgggaaaggg cgccggcggt gcggccgctc aggttcagtt ggtggaatca   4860
ggcggcggct cagttcaagc aggcggttca ctcaggctct cgtgtgcggc aagcggtatc   4920
gactcgtcca gctactgcat gggatggttc aggcaaaggc caggaaagga gagggaaggt   4980
gttgctcgta tcaacggact gggtggcgtt aagacagcat acgcggacag tgtgaaagat   5040
aggttcacaa tttcgagaga caacgcagag aacacggtct acttgcagat gaactctctg   5100
aagcccgaag atacggcgat ctactactgc gctgccaaat tctcacccgg atactgtgga   5160
ggtagctggt ctaacttcgg ttactggggt caaggcaccc aagtgactgt ctcttcaggc   5220
ggaggtgcgg ccgctggctc aggaggtggc agtcaggtgc agctgcagga gtcgggaggt   5280
ggctccgtcc aagcaggagg tagcctgcgc ctctcttgcg cagcgtcagg tatcgacagt   5340
tcgtcctact gtatgggctg gttcaggcag cgtcctggca aggagaggga aggagtggca   5400
cgtatcaacg gtctcggcgg agtcaagaca gcttacgccg actccgttaa agataggttc   5460
accattagcc gcgacaacgc tgagaacact gtctacctcc aaatgaacag tttgaagccg   5520
gaagatactg ccatttacta ctgtgctgcc aaattctcac cgggctactg tggaggaagc   5580
tggtctaact tcggctactg gggacaagga actcaagtca ccgttggggc cggccagggt   5640
gctggtgctg gaccgatcac catcaacaac ttcaattact cggatccggt ggataacaag   5700
aacatcctct acttggacac acacttgaac acgctggcta acgagcctga aaaagctttc   5760
aggatcaccg gcaacatttg ggtcattccg gataggttca gcagaaactc taaccctaac   5820
ttgaacaaac ctcccagagt gacctcacct aagagtggat actacgaccc caactacctc   5880
tcgactgact ccgataaaga ccccttcctg aaggagatca ttaaactctt caagcgcatc   5940
aactctcgtg aaattggcga ggaattgatc taccgcctga gtacagacat cccattcccg   6000
ggtaacaaca acaccccaat caacactttc gatttcgatg tcgatttcaa ctcagtggat   6060
gtcaaaacca ggcagggaaa caactgggtg aagactggta gcatcaaccc atctgtcatc   6120
attactggcc cgagagagaa catcattgac cctgaaacct ccactttcaa gctgacaaac   6180
aacacgttcg ctgctcagga aggcttcgga gcgttgagca tcatttctat ctcacctcgc   6240
ttcatgctga catactctaa cgctacgaac gacgtgggag agggccgttt cagtaagtct   6300
gaattctgca tggaccctat tctgatcctc atgcacgctc tcaacggcgc catgcacaac   6360
ttgtacggaa ttgctatccc caacgaccag accatttcca gcgtgactag caacatcttc   6420
tactctcaat acaacgtcaa gctggagtac gcagaaatct acgctttcgg tggcccaacc   6480
attgacttga tcccgaaatc agctcgtaag tatttcgaag aaaaagcgct ggattattac   6540
aggtcgattg ctaagagact caactccatc accactgcta acccctcttc attcaacaag   6600
tacattggag aatacaagca gaaactgatc cgcaagtacc gtttcgtggt cgagagttcg   6660
ggtgaagtta ctgtgaaccg caacaagttc gtcgagctgt acaacgaatt gacacaaatc   6720
ttcacggagt tcaactacgc caaaatttac aacgtgcaaa accgtaagat cgcgctctct   6780
aacgtctaca ccccggttac cgctaacatc ttggacgata acgtctacga cattcagaac   6840
ggtttcaaca tcccaaagtc gaacctcaac gttttgttca tgggtcaaaa cttgtcccgc   6900
aaccccgccc tgcgtaaggt gaacccagag aacatgttgt acctgttcac caaattctgc   6960
cacaaggcca tcgacggtca gtctctagac caaggaggat gggaactcca gcaaggtggc   7020
cagggtggag gtgctggcac cctggactgt cgcgaactgc tcgttaagaa cactgatctc   7080
ccattcattg gcgacatctc tgatgtgaaa acagacattt tcctgcgtaa ggatatcaac   7140
```

-continued

```
gaggaaacgg aggtcatcta ctaccctgac aacgtctcgg ttgatcaggt tatcttgtca   7200
aagaacacca gtgaacatgg ccaactggac ttgctgtacc cctcaattga ttccgagagc   7260
gaaatcctgc caggagagaa ccaggttttc tacgacaaca ggacacaaaa cgtggattac   7320
ctcaacagct actactacct ggagtcgcag aagctctccg acaacgtcga agatttcaca   7380
tttacgagat caatcgagga ggctttggac aacagtgcca aagtctacac ctacttccct   7440
actctggcaa acaaggtgaa cgcgggtgtc caaggcggac tcttcttgat gtgggctaac   7500
gacgttgtgg aagatttcac aacgaacatc ttgcgcaaag acaccctgga taagatcagc   7560
gatgtctctg ccatcattcc atacattggc ccggcactga acatctctaa ctcagttcgc   7620
cgtggcaact tcactgaggc attcgcggtc acaggagtta cgatcctctt ggaggctttc   7680
ccggagttca caatccccgc actgggcgcg ttcgttatct actccaaagt gcaggagcgc   7740
aacgaaatca ttaagactat cgacaactgc ctggagcaaa ggatcaaaag atggaaggat   7800
tcgtacgaat ggatgatggg tacctggctc tcccgtatca ttacgcagtt caacaacatc   7860
agctaccaaa tgtacgactc tctcaactac caggctggtg ccatcaaggc caaaattgac   7920
ttggagtaca agaaatacag tggctcggat aaagagaaca tcaagagtca agtcgaaaac   7980
ctgaaaaact cactcgacgt taagatcagt gaggcaatga acaacatcaa caagttcatt   8040
cgcgaatgtt ccgttaccta cctcttcaaa aacatgttgc caaaggtcat cgacgagctg   8100
aacgaatttg atcgtaacac taaggcgaaa ctgattaacc tcatcgactc acacaacatc   8160
attttggtgg gcgaagtcga taagctgaaa gccaaggtga acaacagttt ccagaacaca   8220
atccctttca acattttctc atacacgaac aacagtctgc tcaaggacat cattaacgag   8280
tacttcaaca acattaacga tagcaaaatc ctgtcactgc agaaccgtaa gaacacactg   8340
gtcgatacta gtggatacaa cgccgaagtc tctgaggaag gtgacgtgca gctgaaccct   8400
atcttcccct tcgacttcaa attgggctcc agcggagagg ataggggcaa ggtcatcgtc   8460
acccagaacg agaacatcgt ctacaactca atgtacgaat ccttcagcat ctctttctgg   8520
atcaggatta acaagtgggt gagcaacctg cccggttaca caatcattga ctctgtcaag   8580
aacaactcag gttggagtat cggcatcatt tctaacttct tggtcttcac cctgaagcag   8640
aacgaggact cggaacaatc cattaacttc tcatacgata tcagtaacaa cgctccaggt   8700
tacaacaagt ggttcttcgt taccgtgact aacaacatga tgggtaacat gaaaatttac   8760
atcaacggca agctcattga caccatcaaa gtgaaggagt tgactggtat taacttctcc   8820
aaaacaatca cgtttgaaat taacaagatc cctgacaccg gcctgatcac ttcagacagt   8880
gataacatca acatgtggat tagggatttc tacatcttcg ccaaggagct cgacggaaag   8940
gatattaaca tcctcttcaa cagcttgcag tacaccaacg tcgttaaaga ctactggggt   9000
aacgatttga gatacaacaa ggagtactac atggtcaaca tcgactacct gaacaggtac   9060
atgtacgcta actcccgcca aatcgtgttc aacaccagga gaaacaacaa cgacttcaac   9120
gagggttaca aaatcattat caagcgcatc cgtggcaaca ccaacgatac tagggtgaga   9180
ggtggcgaca ttctgtactt cgatatgact atcaacaaca aagcctacaa cttgttcatg   9240
aaaaacgaga caatgtacgc cgacaaccat agcacggagg atatttacgc aatcggactg   9300
agggaacaga caaaggacat caacgataac attatcttcc agatccaacc tatgaacaac   9360
acgtactact acgcttcgca aatcttcaag tccaacttca acggagaaaa catttcgggt   9420
atctgttcca ttggcacata ccgcttccgt ctgggtggtg actggtatcg tcacaactac   9480
ctcgttccca ccgtgaagca gggtaactac gcttctttgc tggagtcgac ttccacgcac   9540
```

-continued

```
tggggattcg ttcctgtgtc agagggcgct ggctaccctt acgatgttcc cgactacgct   9600

ggttgggaac tccagcaagg tgcaggatgg tcccaccctc aattcgagaa gggtgccgga   9660

tggagtcacc cacagttcga gaaaggcgct ggatggagtc acccacagtt cgagaaataa   9720

ttagttgatg catagttaat tagatagctc gaggcatgcg gtaccaagat tggatctaga   9780

tgcatagtta attagatagc tcgaggcatg cggtaccaag cttgtcgaga agtactagag   9840

gatcataatc agccatacca catttgtaga ggttttactt gctttaaaaa acctcccaca   9900

cctccccctg aacctgaaac ataaaatgaa tgcaattgtt gttgttaact tgtttattgc   9960

agcttataat ggttacaaat aaagcaatag catcacaaat ttcacaaata aagcattttt  10020

ttcactgcat tctagttgtg gtttgtccaa actcatcaat gtatcttatc atgtctggat  10080

ctgatcactg cttgagccta ggagatccga accagataag tgaaatctag ttccaaacta  10140

ttttgtcatt tttaatttc gtattagctt acgacgctac acccagttcc catctatttt  10200

gtcactcttc cctaaataat ccttaaaaac tccatttcca cccctcccag ttcccaacta  10260

ttttgtccgc ccacagcggg gcatttttct tcctgttatg tttttaatca aacatcctgc  10320

caactccatg tgacaaaccg tcatcttcgg ctactttttc tctgtcacag aatgaaaatt  10380

tttctgtcat ctcttcgtta ttaatgtttg taattgactg aatatcaacg cttatttgca  10440

gcctgaatgg cgaatgg                                                 10457
```

<210> SEQ ID NO 50
<211> LENGTH: 1876
<212> TYPE: PRT
<213> ORGANISM: Artificial
<220> FEATURE:
<223> OTHER INFORMATION: Fusion protein construct

<400> SEQUENCE: 50

```
Met Lys Phe Leu Val Asn Val Ala Leu Val Phe Met Val Val Tyr Ile
1               5                   10                  15

Ser Tyr Ile Tyr Ala Ala Gly His His His His His His His His His
            20                  25                  30

His His Asp Val Gly Trp Glu Leu Gln Arg Arg Pro Leu Asn Cys Ile
        35                  40                  45

Val Ala Val Ser Gln Asn Met Gly Ile Gly Lys Asn Gly Asp Leu Pro
    50                  55                  60

Trp Pro Pro Leu Arg Asn Glu Phe Lys Tyr Phe Gln Arg Met Thr Thr
65                  70                  75                  80

Thr Ser Ser Val Glu Gly Lys Gln Asn Leu Val Ile Met Gly Arg Lys
                85                  90                  95

Thr Trp Phe Ser Ile Pro Glu Lys Asn Arg Leu Leu Lys Asp Arg Ile
            100                 105                 110

Asn Ile Val Leu Ser Arg Glu Leu Lys Glu Pro Pro Arg Gly Ala His
        115                 120                 125

Phe Leu Ala Lys Ser Leu Asp Asp Ala Leu Arg Leu Ile Glu Gln Pro
    130                 135                 140

Glu Leu Ala Ser Lys Val Asp Met Val Trp Ile Val Gly Gly Ser Ser
145                 150                 155                 160

Val Tyr Gln Glu Ala Met Asn Gln Pro Gly His Leu Arg Leu Phe Val
                165                 170                 175

Thr Arg Ile Met Gln Glu Phe Glu Ser Asp Thr Phe Phe Pro Glu Ile
            180                 185                 190
```

```
Asp Leu Gly Lys Tyr Lys Leu Leu Pro Glu Tyr Pro Gly Val Leu Ser
        195                 200                 205

Glu Val Gln Glu Glu Lys Gly Ile Lys Tyr Lys Phe Glu Val Tyr Glu
    210                 215                 220

Lys Lys Asp Gly Ala Ser Gly Phe Ala Asn Glu Leu Gly Pro Arg Leu
225                 230                 235                 240

Met Gly Lys Gly Ala Gly Gly Ala Ala Ala Gln Val Gln Leu Val Glu
                245                 250                 255

Ser Gly Gly Gly Ser Val Gln Ala Gly Gly Ser Leu Arg Leu Ser Cys
            260                 265                 270

Ala Ala Ser Gly Ile Asp Ser Ser Ser Tyr Cys Met Gly Trp Phe Arg
        275                 280                 285

Gln Arg Pro Gly Lys Glu Arg Glu Gly Val Ala Arg Ile Asn Gly Leu
    290                 295                 300

Gly Gly Val Lys Thr Ala Tyr Ala Asp Ser Val Lys Asp Arg Phe Thr
305                 310                 315                 320

Ile Ser Arg Asp Asn Ala Glu Asn Thr Val Tyr Leu Gln Met Asn Ser
                325                 330                 335

Leu Lys Pro Glu Asp Thr Ala Ile Tyr Tyr Cys Ala Ala Lys Phe Ser
            340                 345                 350

Pro Gly Tyr Cys Gly Gly Ser Trp Ser Asn Phe Gly Tyr Trp Gly Gln
        355                 360                 365

Gly Thr Gln Val Thr Val Ser Ser Gly Gly Gly Ala Ala Ala Gly Ser
    370                 375                 380

Gly Gly Gly Ser Gln Val Gln Leu Gln Glu Ser Gly Gly Gly Ser Val
385                 390                 395                 400

Gln Ala Gly Gly Ser Leu Arg Leu Ser Cys Ala Ala Ser Gly Ile Asp
                405                 410                 415

Ser Ser Ser Tyr Cys Met Gly Trp Phe Arg Gln Arg Pro Gly Lys Glu
            420                 425                 430

Arg Glu Gly Val Ala Arg Ile Asn Gly Leu Gly Gly Val Lys Thr Ala
        435                 440                 445

Tyr Ala Asp Ser Val Lys Asp Arg Phe Thr Ile Ser Arg Asp Asn Ala
    450                 455                 460

Glu Asn Thr Val Tyr Leu Gln Met Asn Ser Leu Lys Pro Glu Asp Thr
465                 470                 475                 480

Ala Ile Tyr Tyr Cys Ala Ala Lys Phe Ser Pro Gly Tyr Cys Gly Gly
                485                 490                 495

Ser Trp Ser Asn Phe Gly Tyr Trp Gly Gln Gly Thr Gln Val Thr Val
            500                 505                 510

Gly Ala Gly Gln Gly Ala Gly Ala Gly Pro Ile Thr Ile Asn Asn Phe
        515                 520                 525

Asn Tyr Ser Asp Pro Val Asp Asn Lys Asn Ile Leu Tyr Leu Asp Thr
    530                 535                 540

His Leu Asn Thr Leu Ala Asn Glu Pro Glu Lys Ala Phe Arg Ile Thr
545                 550                 555                 560

Gly Asn Ile Trp Val Ile Pro Asp Arg Phe Ser Arg Asn Ser Asn Pro
                565                 570                 575

Asn Leu Asn Lys Pro Pro Arg Val Thr Ser Pro Lys Ser Gly Tyr Tyr
            580                 585                 590

Asp Pro Asn Tyr Leu Ser Thr Asp Ser Asp Lys Asp Pro Phe Leu Lys
        595                 600                 605

Glu Ile Ile Lys Leu Phe Lys Arg Ile Asn Ser Arg Glu Ile Gly Glu
```

```
    610                 615                 620

Glu Leu Ile Tyr Arg Leu Ser Thr Asp Ile Pro Phe Pro Gly Asn Asn
625                 630                 635                 640

Asn Thr Pro Ile Asn Thr Phe Asp Phe Asp Val Asp Phe Asn Ser Val
                645                 650                 655

Asp Val Lys Thr Arg Gln Gly Asn Asn Trp Val Lys Thr Gly Ser Ile
            660                 665                 670

Asn Pro Ser Val Ile Ile Thr Gly Pro Arg Glu Asn Ile Ile Asp Pro
        675                 680                 685

Glu Thr Ser Thr Phe Lys Leu Thr Asn Asn Thr Phe Ala Ala Gln Glu
    690                 695                 700

Gly Phe Gly Ala Leu Ser Ile Ile Ser Ile Ser Pro Arg Phe Met Leu
705                 710                 715                 720

Thr Tyr Ser Asn Ala Thr Asn Asp Val Gly Glu Gly Arg Phe Ser Lys
                725                 730                 735

Ser Glu Phe Cys Met Asp Pro Ile Leu Ile Leu Met His Ala Leu Asn
            740                 745                 750

Gly Ala Met His Asn Leu Tyr Gly Ile Ala Ile Pro Asn Asp Gln Thr
        755                 760                 765

Ile Ser Ser Val Thr Ser Asn Ile Phe Tyr Ser Gln Tyr Asn Val Lys
    770                 775                 780

Leu Glu Tyr Ala Glu Ile Tyr Ala Phe Gly Gly Pro Thr Ile Asp Leu
785                 790                 795                 800

Ile Pro Lys Ser Ala Arg Lys Tyr Phe Glu Glu Lys Ala Leu Asp Tyr
                805                 810                 815

Tyr Arg Ser Ile Ala Lys Arg Leu Asn Ser Ile Thr Thr Ala Asn Pro
            820                 825                 830

Ser Ser Phe Asn Lys Tyr Ile Gly Glu Tyr Lys Gln Lys Leu Ile Arg
        835                 840                 845

Lys Tyr Arg Phe Val Val Glu Ser Ser Gly Glu Val Thr Val Asn Arg
    850                 855                 860

Asn Lys Phe Val Glu Leu Tyr Asn Glu Leu Thr Gln Ile Phe Thr Glu
865                 870                 875                 880

Phe Asn Tyr Ala Lys Ile Tyr Asn Val Gln Asn Arg Lys Ile Ala Leu
                885                 890                 895

Ser Asn Val Tyr Thr Pro Val Thr Ala Asn Ile Leu Asp Asp Asn Val
            900                 905                 910

Tyr Asp Ile Gln Asn Gly Phe Asn Ile Pro Lys Ser Asn Leu Asn Val
        915                 920                 925

Leu Phe Met Gly Gln Asn Leu Ser Arg Asn Pro Ala Leu Arg Lys Val
    930                 935                 940

Asn Pro Glu Asn Met Leu Tyr Leu Phe Thr Lys Phe Cys His Lys Ala
945                 950                 955                 960

Ile Asp Gly Gln Ser Leu Asp Gln Gly Gly Trp Glu Leu Gln Gln Gly
                965                 970                 975

Gly Gln Gly Gly Gly Ala Gly Thr Leu Asp Cys Arg Glu Leu Leu Val
            980                 985                 990

Lys Asn Thr Asp Leu Pro Phe Ile  Gly Asp Ile Ser Asp  Val Lys Thr
        995                 1000                 1005

Asp Ile  Phe Leu Arg Lys Asp  Ile Asn Glu Glu Thr  Glu Val Ile
    1010                 1015                 1020

Tyr Tyr  Pro Asp Asn Val Ser  Val Asp Gln Val Ile  Leu Ser Lys
    1025                 1030                 1035
```

Asn Thr Ser Glu His Gly Gln Leu Asp Leu Leu Tyr Pro Ser Ile
1040 1045 1050

Asp Ser Glu Ser Glu Ile Leu Pro Gly Glu Asn Gln Val Phe Tyr
1055 1060 1065

Asp Asn Arg Thr Gln Asn Val Asp Tyr Leu Asn Ser Tyr Tyr Tyr
1070 1075 1080

Leu Glu Ser Gln Lys Leu Ser Asp Asn Val Glu Asp Phe Thr Phe
1085 1090 1095

Thr Arg Ser Ile Glu Glu Ala Leu Asp Asn Ser Ala Lys Val Tyr
1100 1105 1110

Thr Tyr Phe Pro Thr Leu Ala Asn Lys Val Asn Ala Gly Val Gln
1115 1120 1125

Gly Gly Leu Phe Leu Met Trp Ala Asn Asp Val Val Glu Asp Phe
1130 1135 1140

Thr Thr Asn Ile Leu Arg Lys Asp Thr Leu Asp Lys Ile Ser Asp
1145 1150 1155

Val Ser Ala Ile Ile Pro Tyr Ile Gly Pro Ala Leu Asn Ile Ser
1160 1165 1170

Asn Ser Val Arg Arg Gly Asn Phe Thr Glu Ala Phe Ala Val Thr
1175 1180 1185

Gly Val Thr Ile Leu Leu Glu Ala Phe Pro Glu Phe Thr Ile Pro
1190 1195 1200

Ala Leu Gly Ala Phe Val Ile Tyr Ser Lys Val Gln Glu Arg Asn
1205 1210 1215

Glu Ile Ile Lys Thr Ile Asp Asn Cys Leu Glu Gln Arg Ile Lys
1220 1225 1230

Arg Trp Lys Asp Ser Tyr Glu Trp Met Met Gly Thr Trp Leu Ser
1235 1240 1245

Arg Ile Ile Thr Gln Phe Asn Asn Ile Ser Tyr Gln Met Tyr Asp
1250 1255 1260

Ser Leu Asn Tyr Gln Ala Gly Ala Ile Lys Ala Lys Ile Asp Leu
1265 1270 1275

Glu Tyr Lys Lys Tyr Ser Gly Ser Asp Lys Glu Asn Ile Lys Ser
1280 1285 1290

Gln Val Glu Asn Leu Lys Asn Ser Leu Asp Val Lys Ile Ser Glu
1295 1300 1305

Ala Met Asn Asn Ile Asn Lys Phe Ile Arg Glu Cys Ser Val Thr
1310 1315 1320

Tyr Leu Phe Lys Asn Met Leu Pro Lys Val Ile Asp Glu Leu Asn
1325 1330 1335

Glu Phe Asp Arg Asn Thr Lys Ala Lys Leu Ile Asn Leu Ile Asp
1340 1345 1350

Ser His Asn Ile Ile Leu Val Gly Glu Val Asp Lys Leu Lys Ala
1355 1360 1365

Lys Val Asn Asn Ser Phe Gln Asn Thr Ile Pro Phe Asn Ile Phe
1370 1375 1380

Ser Tyr Thr Asn Asn Ser Leu Leu Lys Asp Ile Ile Asn Glu Tyr
1385 1390 1395

Phe Asn Asn Ile Asn Asp Ser Lys Ile Leu Ser Leu Gln Asn Arg
1400 1405 1410

Lys Asn Thr Leu Val Asp Thr Ser Gly Tyr Asn Ala Glu Val Ser
1415 1420 1425

```
Glu Glu  Gly Asp Val Gln Leu  Asn Pro Ile Phe Pro  Phe Asp Phe
    1430                 1435                 1440

Lys Leu  Gly Ser Ser Gly Glu  Asp Arg Gly Lys Val  Ile Val Thr
    1445                 1450                 1455

Gln Asn  Glu Asn Ile Val Tyr  Asn Ser Met Tyr Glu  Ser Phe Ser
    1460                 1465                 1470

Ile Ser  Phe Trp Ile Arg Ile  Asn Lys Trp Val Ser  Asn Leu Pro
    1475                 1480                 1485

Gly Tyr  Thr Ile Ile Asp Ser  Val Lys Asn Asn Ser  Gly Trp Ser
    1490                 1495                 1500

Ile Gly  Ile Ile Ser Asn Phe  Leu Val Phe Thr Leu  Lys Gln Asn
    1505                 1510                 1515

Glu Asp  Ser Glu Gln Ser Ile  Asn Phe Ser Tyr Asp  Ile Ser Asn
    1520                 1525                 1530

Asn Ala  Pro Gly Tyr Asn Lys  Trp Phe Phe Val Thr  Val Thr Asn
    1535                 1540                 1545

Asn Met  Met Gly Asn Met Lys  Ile Tyr Ile Asn Gly  Lys Leu Ile
    1550                 1555                 1560

Asp Thr  Ile Lys Val Lys Glu  Leu Thr Gly Ile Asn  Phe Ser Lys
    1565                 1570                 1575

Thr Ile  Thr Phe Glu Ile Asn  Lys Ile Pro Asp Thr  Gly Leu Ile
    1580                 1585                 1590

Thr Ser  Asp Ser Asp Asn Ile  Asn Met Trp Ile Arg  Asp Phe Tyr
    1595                 1600                 1605

Ile Phe  Ala Lys Glu Leu Asp  Gly Lys Asp Ile Asn  Ile Leu Phe
    1610                 1615                 1620

Asn Ser  Leu Gln Tyr Thr Asn  Val Val Lys Asp Tyr  Trp Gly Asn
    1625                 1630                 1635

Asp Leu  Arg Tyr Asn Lys Glu  Tyr Tyr Met Val Asn  Ile Asp Tyr
    1640                 1645                 1650

Leu Asn  Arg Tyr Met Tyr Ala  Asn Ser Arg Gln Ile  Val Phe Asn
    1655                 1660                 1665

Thr Arg  Arg Asn Asn Asn Asp  Phe Asn Glu Gly Tyr  Lys Ile Ile
    1670                 1675                 1680

Ile Lys  Arg Ile Arg Gly Asn  Thr Asn Asp Thr Arg  Val Arg Gly
    1685                 1690                 1695

Gly Asp  Ile Leu Tyr Phe Asp  Met Thr Ile Asn Asn  Lys Ala Tyr
    1700                 1705                 1710

Asn Leu  Phe Met Lys Asn Glu  Thr Met Tyr Ala Asp  Asn His Ser
    1715                 1720                 1725

Thr Glu  Asp Ile Tyr Ala Ile  Gly Leu Arg Glu Gln  Thr Lys Asp
    1730                 1735                 1740

Ile Asn  Asp Asn Ile Ile Phe  Gln Ile Gln Pro Met  Asn Asn Thr
    1745                 1750                 1755

Tyr Tyr  Tyr Ala Ser Gln Ile  Phe Lys Ser Asn Phe  Asn Gly Glu
    1760                 1765                 1770

Asn Ile  Ser Gly Ile Cys Ser  Ile Gly Thr Tyr Arg  Phe Arg Leu
    1775                 1780                 1785

Gly Gly  Asp Trp Tyr Arg His  Asn Tyr Leu Val Pro  Thr Val Lys
    1790                 1795                 1800

Gln Gly  Asn Tyr Ala Ser Leu  Leu Glu Ser Thr Ser  Thr His Trp
    1805                 1810                 1815

Gly Phe  Val Pro Val Ser Glu  Gly Ala Gly Tyr Pro  Tyr Asp Val
```

1820 1825 1830

Pro Asp Tyr Ala Gly Trp Glu Leu Gln Gln Gly Ala Gly Trp Ser
1835 1840 1845

His Pro Gln Phe Glu Lys Gly Ala Gly Trp Ser His Pro Gln Phe
1850 1855 1860

Glu Lys Gly Ala Gly Trp Ser His Pro Gln Phe Glu Lys
1865 1870 1875

<210> SEQ ID NO 51
<211> LENGTH: 8
<212> TYPE: PRT
<213> ORGANISM: Clostridium botulinum
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 51

His Glu Xaa Xaa His Xaa Xaa His
1 5

<210> SEQ ID NO 52
<211> LENGTH: 1296
<212> TYPE: PRT
<213> ORGANISM: Clostridium botulinum

<400> SEQUENCE: 52

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

```
Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640
```

```
Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                1015                1020

Leu Asn  Asn Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Asn Ile
    1040                1045                1050

Met Phe  Lys Leu Asp Gly Cys  Arg Asp Thr His Arg  Tyr Ile Trp
```

```
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Gln Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290

Arg Pro  Leu
    1295


<210> SEQ ID NO 53
<211> LENGTH: 1291
<212> TYPE: PRT
<213> ORGANISM: Clostridium botulinum

<400> SEQUENCE: 53

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Phe Gln Thr Leu Ile Lys Leu Phe
                85                  90                  95

Asn Arg Ile Lys Ser Lys Pro Leu Gly Glu Lys Leu Leu Glu Met Ile
            100                 105                 110
```

```
Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Leu Gly Phe Thr Glu Ile Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
        435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Val Phe Thr Asp Glu Asn Thr Ile Phe Gln Tyr Leu Tyr Ser Gln
```

```
    530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655

Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Glu Lys Ser Asn Ile Asn Ile Asn
            740                 745                 750

Phe Asn Asp Ile Asn Ser Lys Leu Asn Asp Gly Ile Asn Gln Ala Met
        755                 760                 765

Asp Asn Ile Asn Asp Phe Ile Asn Glu Cys Ser Val Ser Tyr Leu Met
    770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Ser Asn Ile Glu Ile
        835                 840                 845

Leu Ile Lys Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Arg Asn Asp Asp Ile Gln Asn
    930                 935                 940

Tyr Ile His Asn Glu Tyr Thr Ile Ile Asn Cys Met Lys Asn Asn Ser
945                 950                 955                 960
```

Gly Trp Lys Ile Ser Ile Arg Gly Asn Arg Ile Ile Trp Thr Leu Ile
965 970 975

Asp Ile Asn Gly Lys Thr Lys Ser Val Phe Phe Glu Tyr Asn Ile Arg
980 985 990

Glu Asp Ile Ser Glu Tyr Ile Asn Arg Trp Phe Phe Val Thr Ile Thr
995 1000 1005

Asn Asn Leu Asp Asn Ala Lys Ile Tyr Ile Asn Gly Thr Leu Glu
1010 1015 1020

Ser Asn Met Asp Ile Lys Asp Ile Gly Glu Val Ile Val Asn Gly
1025 1030 1035

Glu Ile Thr Phe Lys Leu Asp Gly Asp Val Asp Arg Thr Gln Phe
1040 1045 1050

Ile Trp Met Lys Tyr Phe Ser Ile Phe Asn Thr Gln Leu Asn Gln
1055 1060 1065

Ser Asn Ile Lys Glu Ile Tyr Lys Ile Gln Ser Tyr Ser Glu Tyr
1070 1075 1080

Leu Lys Asp Phe Trp Gly Asn Pro Leu Met Tyr Asn Lys Glu Tyr
1085 1090 1095

Tyr Met Phe Asn Ala Gly Asn Lys Asn Ser Tyr Ile Lys Leu Val
1100 1105 1110

Lys Asp Ser Ser Val Gly Glu Ile Leu Ile Arg Ser Lys Tyr Asn
1115 1120 1125

Gln Asn Ser Asn Tyr Ile Asn Tyr Arg Asn Leu Tyr Ile Gly Glu
1130 1135 1140

Lys Phe Ile Ile Arg Arg Glu Ser Asn Ser Gln Ser Ile Asn Asp
1145 1150 1155

Asp Ile Val Arg Lys Glu Asp Tyr Ile His Leu Asp Leu Val Leu
1160 1165 1170

His His Glu Glu Trp Arg Val Tyr Ala Tyr Lys Tyr Phe Lys Glu
1175 1180 1185

Gln Glu Glu Lys Leu Phe Leu Ser Ile Ile Ser Asp Ser Asn Glu
1190 1195 1200

Phe Tyr Lys Thr Ile Glu Ile Lys Glu Tyr Asp Glu Gln Pro Ser
1205 1210 1215

Tyr Ser Cys Gln Leu Leu Phe Lys Lys Asp Glu Glu Ser Thr Asp
1220 1225 1230

Asp Ile Gly Leu Ile Gly Ile His Arg Phe Tyr Glu Ser Gly Val
1235 1240 1245

Leu Arg Lys Lys Tyr Lys Asp Tyr Phe Cys Ile Ser Lys Trp Tyr
1250 1255 1260

Leu Lys Glu Val Lys Arg Lys Pro Tyr Lys Ser Asn Leu Gly Cys
1265 1270 1275

Asn Trp Gln Phe Ile Pro Lys Asp Glu Gly Trp Thr Glu
1280 1285 1290

<210> SEQ ID NO 54
<211> LENGTH: 1291
<212> TYPE: PRT
<213> ORGANISM: Clostridium botulinum

<400> SEQUENCE: 54

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu

```
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445
```

```
Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860
```

Phe Asn Asn Ile Asn Asp Ser Lys Ile Leu Ser Leu Gln Asn Arg Lys
865 870 875 880

Asn Thr Leu Val Asp Thr Ser Gly Tyr Asn Ala Glu Val Ser Glu Glu
885 890 895

Gly Asp Val Gln Leu Asn Pro Ile Phe Pro Phe Asp Phe Lys Leu Gly
900 905 910

Ser Ser Gly Glu Asp Arg Gly Lys Val Ile Val Thr Gln Asn Glu Asn
915 920 925

Ile Val Tyr Asn Ser Met Tyr Glu Ser Phe Ser Ile Ser Phe Trp Ile
930 935 940

Arg Ile Asn Lys Trp Val Ser Asn Leu Pro Gly Tyr Thr Ile Ile Asp
945 950 955 960

Ser Val Lys Asn Asn Ser Gly Trp Ser Ile Gly Ile Ile Ser Asn Phe
965 970 975

Leu Val Phe Thr Leu Lys Gln Asn Glu Asp Ser Glu Gln Ser Ile Asn
980 985 990

Phe Ser Tyr Asp Ile Ser Asn Asn Ala Pro Gly Tyr Asn Lys Trp Phe
995 1000 1005

Phe Val Thr Val Thr Asn Asn Met Met Gly Asn Met Lys Ile Tyr
1010 1015 1020

Ile Asn Gly Lys Leu Ile Asp Thr Ile Lys Val Lys Glu Leu Thr
1025 1030 1035

Gly Ile Asn Phe Ser Lys Thr Ile Thr Phe Glu Ile Asn Lys Ile
1040 1045 1050

Pro Asp Thr Gly Leu Ile Thr Ser Asp Ser Asp Asn Ile Asn Met
1055 1060 1065

Trp Ile Arg Asp Phe Tyr Ile Phe Ala Lys Glu Leu Asp Gly Lys
1070 1075 1080

Asp Ile Asn Ile Leu Phe Asn Ser Leu Gln Tyr Thr Asn Val Val
1085 1090 1095

Lys Asp Tyr Trp Gly Asn Asp Leu Arg Tyr Asn Lys Glu Tyr Tyr
1100 1105 1110

Met Val Asn Ile Asp Tyr Leu Asn Arg Tyr Met Tyr Ala Asn Ser
1115 1120 1125

Arg Gln Ile Val Phe Asn Thr Arg Arg Asn Asn Asn Asp Phe Asn
1130 1135 1140

Glu Gly Tyr Lys Ile Ile Ile Lys Arg Ile Arg Gly Asn Thr Asn
1145 1150 1155

Asp Thr Arg Val Arg Gly Gly Asp Ile Leu Tyr Phe Asp Met Thr
1160 1165 1170

Ile Asn Asn Lys Ala Tyr Asn Leu Phe Met Lys Asn Glu Thr Met
1175 1180 1185

Tyr Ala Asp Asn His Ser Thr Glu Asp Ile Tyr Ala Ile Gly Leu
1190 1195 1200

Arg Glu Gln Thr Lys Asp Ile Asn Asp Asn Ile Ile Phe Gln Ile
1205 1210 1215

Gln Pro Met Asn Asn Thr Tyr Tyr Tyr Ala Ser Gln Ile Phe Lys
1220 1225 1230

Ser Asn Phe Asn Gly Glu Asn Ile Ser Gly Ile Cys Ser Ile Gly
1235 1240 1245

Thr Tyr Arg Phe Arg Leu Gly Gly Asp Trp Tyr Arg His Asn Tyr
1250 1255 1260

Leu Val Pro Thr Val Lys Gln Gly Asn Tyr Ala Ser Leu Leu Glu

```
    1265                1270                1275

Ser Thr  Ser Thr His Trp Gly  Phe Val Pro Val Ser  Glu
    1280                1285                1290


<210> SEQ ID NO 55
<211> LENGTH: 1276
<212> TYPE: PRT
<213> ORGANISM: Clostridium botulinum

<400> SEQUENCE: 55

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350
```

```
Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
```

```
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn  Lys Trp Phe Phe Val  Thr Ile Thr
        995                 1000                1005

Asn Asn  Ile Met Gly Tyr Met  Lys Leu Tyr Ile Asn  Gly Glu Leu
    1010                1015                1020

Lys Gln  Ser Gln Lys Ile Glu  Asp Leu Asp Glu Val  Lys Leu Asp
    1025                1030                1035

Lys Thr  Ile Val Phe Gly Ile  Asp Glu Asn Ile Asp  Glu Asn Gln
    1040                1045                1050

Met Leu  Trp Ile Arg Asp Phe  Asn Ile Phe Ser Lys  Glu Leu Ser
    1055                1060                1065

Asn Glu  Asp Ile Asn Ile Val  Tyr Glu Gly Gln Ile  Leu Arg Asn
    1070                1075                1080

Val Ile  Lys Asp Tyr Trp Gly  Asn Pro Leu Lys Phe  Asp Thr Glu
    1085                1090                1095

Tyr Tyr  Ile Ile Asn Asp Asn  Tyr Ile Asp Arg Tyr  Ile Ala Pro
    1100                1105                1110

Glu Ser  Asn Val Leu Val Leu  Val Gln Tyr Pro Asp  Arg Ser Lys
    1115                1120                1125

Leu Tyr  Thr Gly Asn Pro Ile  Thr Ile Lys Ser Val  Ser Asp Lys
    1130                1135                1140

Asn Pro  Tyr Ser Arg Ile Leu  Asn Gly Asp Asn Ile  Ile Leu His
    1145                1150                1155

Met Leu  Tyr Asn Ser Arg Lys  Tyr Met Ile Ile Arg  Asp Thr Asp
    1160                1165                1170

Thr Ile  Tyr Ala Thr Gln Gly  Gly Glu Cys Ser Gln  Asn Cys Val
    1175                1180                1185
```

```
Tyr Ala  Leu Lys Leu Gln Ser  Asn Leu Gly Asn Tyr  Gly Ile Gly
    1190                 1195                 1200

Ile Phe  Ser Ile Lys Asn Ile  Val Ser Lys Asn Lys  Tyr Cys Ser
    1205                 1210                 1215

Gln Ile  Phe Ser Ser Phe Arg  Glu Asn Thr Met Leu  Leu Ala Asp
    1220                 1225                 1230

Ile Tyr  Lys Pro Trp Arg Phe  Ser Phe Lys Asn Ala  Tyr Thr Pro
    1235                 1240                 1245

Val Ala  Val Thr Asn Tyr Glu  Thr Lys Leu Leu Ser  Thr Ser Ser
    1250                 1255                 1260

Phe Trp  Lys Phe Ile Ser Arg  Asp Pro Gly Trp Val  Glu
    1265                 1270                 1275


<210> SEQ ID NO 56
<211> LENGTH: 1252
<212> TYPE: PRT
<213> ORGANISM: Clostridium botulinum

<400> SEQUENCE: 56

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
```

-continued

```
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700
```

```
Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                 1015                 1020

His Val  Ser Asp Asn Ile Leu  Phe Lys Ile Val Asn  Cys Ser Tyr
    1025                 1030                 1035

Thr Arg  Tyr Ile Gly Ile Arg  Tyr Phe Asn Ile Phe  Asp Lys Glu
    1040                 1045                 1050

Leu Asp  Glu Thr Glu Ile Gln  Thr Leu Tyr Ser Asn  Glu Pro Asn
    1055                 1060                 1065

Thr Asn  Ile Leu Lys Asp Phe  Trp Gly Asn Tyr Leu  Leu Tyr Asp
    1070                 1075                 1080

Lys Glu  Tyr Tyr Leu Leu Asn  Val Leu Lys Pro Asn  Asn Phe Ile
    1085                 1090                 1095

Asp Arg  Arg Lys Asp Ser Thr  Leu Ser Ile Asn Asn  Ile Arg Ser
    1100                 1105                 1110
```

```
Thr Ile  Leu Leu Ala Asn Arg  Leu Tyr Ser Gly Ile  Lys Val Lys
    1115                 1120                 1125

Ile Gln  Arg Val Asn Asn Ser  Ser Thr Asn Asp Asn  Leu Val Arg
    1130                 1135                 1140

Lys Asn  Asp Gln Val Tyr Ile  Asn Phe Val Ala Ser  Lys Thr His
    1145                 1150                 1155

Leu Phe  Pro Leu Tyr Ala Asp  Thr Ala Thr Thr Asn  Lys Glu Lys
    1160                 1165                 1170

Thr Ile  Lys Ile Ser Ser Ser  Gly Asn Arg Phe Asn  Gln Val Val
    1175                 1180                 1185

Val Met  Asn Ser Val Gly Asn  Asn Cys Thr Met Asn  Phe Lys Asn
    1190                 1195                 1200

Asn Asn  Gly Asn Asn Ile Gly  Leu Leu Gly Phe Lys  Ala Asp Thr
    1205                 1210                 1215

Val Val  Ala Ser Thr Trp Tyr  Tyr Thr His Met Arg  Asp His Thr
    1220                 1225                 1230

Asn Ser  Asn Gly Cys Phe Trp  Asn Phe Ile Ser Glu  Glu His Gly
    1235                 1240                 1245

Trp Gln  Glu Lys
    1250


<210> SEQ ID NO 57
<211> LENGTH: 1278
<212> TYPE: PRT
<213> ORGANISM: Clostridium botulinum

<400> SEQUENCE: 57

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220
```

```
Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Arg Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
        595                 600                 605

Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640
```

```
Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
            660                 665                 670

Ile Gly Ser Ser Glu Asn Lys Asn Lys Ile Ile Lys Ala Ile Asn Asn
        675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
            740                 745                 750

Leu Glu Ser Glu Tyr Asn Ile Asn Asn Ile Arg Glu Glu Leu Asn Lys
        755                 760                 765

Lys Val Ser Leu Ala Met Glu Asn Ile Glu Arg Phe Ile Thr Glu Ser
    770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
        835                 840                 845

Tyr Thr Asn Asp Lys Ile Leu Ile Leu Tyr Phe Asn Lys Leu Tyr Lys
    850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
        915                 920                 925

Gly Arg Tyr Gln Asn Phe Ser Ile Ser Phe Trp Val Arg Ile Pro Lys
    930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
            980                 985                 990

Phe Asn Tyr Thr Gln Met Ile Ser  Ile Ser Asp Tyr Ile  Asn Lys Trp
        995                 1000                1005

Ile Phe  Val Thr Ile Thr Asn  Asn Arg Leu Gly Asn  Ser Arg Ile
    1010                1015                1020

Tyr Ile  Asn Gly Asn Leu Ile  Asp Glu Lys Ser Ile  Ser Asn Leu
    1025                1030                1035

Gly Asp  Ile His Val Ser Asp  Asn Ile Leu Phe Lys  Ile Val Gly
    1040                1045                1050

Cys Asn  Asp Thr Arg Tyr Val  Gly Ile Arg Tyr Phe  Lys Val Phe
```

1055 1060 1065

Asp Thr Glu Leu Gly Lys Thr Glu Ile Glu Thr Leu Tyr Ser Asp
1070 1075 1080

Glu Pro Asp Pro Ser Ile Leu Lys Asp Phe Trp Gly Asn Tyr Leu
1085 1090 1095

Leu Tyr Asn Lys Arg Tyr Tyr Leu Leu Asn Leu Leu Arg Thr Asp
1100 1105 1110

Lys Ser Ile Thr Gln Asn Ser Asn Phe Leu Asn Ile Asn Gln Gln
1115 1120 1125

Arg Gly Val Tyr Gln Lys Pro Asn Ile Phe Ser Asn Thr Arg Leu
1130 1135 1140

Tyr Thr Gly Val Glu Val Ile Ile Arg Lys Asn Gly Ser Thr Asp
1145 1150 1155

Ile Ser Asn Thr Asp Asn Phe Val Arg Lys Asn Asp Leu Ala Tyr
1160 1165 1170

Ile Asn Val Val Asp Arg Asp Val Glu Tyr Arg Leu Tyr Ala Asp
1175 1180 1185

Ile Ser Ile Ala Lys Pro Glu Lys Ile Ile Lys Leu Ile Arg Thr
1190 1195 1200

Ser Asn Ser Asn Asn Ser Leu Gly Gln Ile Ile Val Met Asp Ser
1205 1210 1215

Ile Gly Asn Asn Cys Thr Met Asn Phe Gln Asn Asn Asn Gly Gly
1220 1225 1230

Asn Ile Gly Leu Leu Gly Phe His Ser Asn Asn Leu Val Ala Ser
1235 1240 1245

Ser Trp Tyr Tyr Asn Asn Ile Arg Lys Asn Thr Ser Ser Asn Gly
1250 1255 1260

Cys Phe Trp Ser Phe Ile Ser Lys Glu His Gly Trp Gln Glu Asn
1265 1270 1275

<210> SEQ ID NO 58
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 58

Met Pro Val Asn Ile Lys Xaa Phe Asn Tyr Asn Asp Pro Ile Asn Asn
1 5 10 15

Asp Asp Ile Ile Met Met Glu Pro Phe Asn Asp Pro Gly Pro Gly Thr
20 25 30

Tyr Tyr Lys Ala Phe Arg Ile Ile Asp Arg Ile Trp Ile Val Pro Glu
35 40 45

Arg Phe Thr Tyr Gly Phe Gln Pro Asp Gln Phe Asn Ala Ser Thr Gly
50 55 60

Val Phe Ser Lys Asp Val Tyr Glu Tyr Tyr Asp Pro Thr Tyr Leu Lys
65 70 75 80

Thr Asp Ala Glu Lys Asp Lys Phe Leu Lys Thr Met Ile Lys Leu Phe
85 90 95

Asn Arg Ile Asn Ser Lys Pro Ser Gly Gln Arg Leu Leu Asp Met Ile
100 105 110

Val Asp Ala Ile Pro Tyr Leu Gly Asn Ala Ser Thr Pro Pro Asp Lys
115 120 125

```
Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540
```

```
Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
```

965 970 975

Arg Ile Ile Trp Thr Leu Ile Asp Val Asn Ala Lys Ser Lys Ser Ile
980 985 990

Phe Phe Glu Tyr Ser Ile Lys Asp Asn Ile Ser Asp Tyr Ile Asn Lys
995 1000 1005

Trp Phe Ser Ile Thr Ile Thr Asn Asp Arg Leu Gly Asn Ala Asn
1010 1015 1020

Ile Tyr Ile Asn Gly Ser Leu Lys Lys Ser Glu Lys Ile Leu Asn
1025 1030 1035

Leu Asp Arg Ile Asn Ser Ser Asn Asp Ile Asp Phe Lys Leu Ile
1040 1045 1050

Asn Cys Thr Asp Thr Thr Lys Phe Val Trp Ile Lys Asp Phe Asn
1055 1060 1065

Ile Phe Gly Arg Glu Leu Asn Ala Thr Glu Val Ser Ser Leu Tyr
1070 1075 1080

Trp Ile Gln Ser Ser Thr Asn Thr Leu Lys Asp Phe Trp Gly Asn
1085 1090 1095

Pro Leu Arg Tyr Asp Thr Gln Tyr Tyr Leu Phe Asn Gln Gly Met
1100 1105 1110

Gln Asn Ile Tyr Ile Lys Tyr Phe Ser Lys Ala Ser Met Gly Glu
1115 1120 1125

Thr Ala Pro Arg Thr Asn Phe Asn Asn Ala Ala Ile Asn Tyr Gln
1130 1135 1140

Asn Leu Tyr Leu Gly Leu Arg Phe Ile Ile Lys Lys Ala Ser Asn
1145 1150 1155

Ser Arg Asn Ile Asn Asn Asp Asn Ile Val Arg Glu Gly Asp Tyr
1160 1165 1170

Ile Tyr Leu Asn Ile Asp Asn Ile Ser Asp Glu Ser Tyr Arg Val
1175 1180 1185

Tyr Val Leu Val Asn Ser Lys Glu Ile Gln Thr Gln Leu Phe Leu
1190 1195 1200

Ala Pro Ile Asn Asp Asp Pro Thr Phe Tyr Asp Val Leu Gln Ile
1205 1210 1215

Lys Lys Tyr Tyr Glu Lys Thr Thr Tyr Asn Cys Gln Ile Leu Cys
1220 1225 1230

Glu Lys Asp Thr Lys Thr Phe Gly Leu Phe Gly Ile Gly Lys Phe
1235 1240 1245

Val Lys Asp Tyr Gly Tyr Val Trp Asp Thr Tyr Asp Asn Tyr Phe
1250 1255 1260

Cys Ile Ser Gln Trp Tyr Leu Arg Arg Ile Ser Glu Asn Ile Asn
1265 1270 1275

Lys Leu Arg Leu Gly Cys Asn Trp Gln Phe Ile Pro Val Asp Glu
1280 1285 1290

Gly Trp Thr Glu
1295

<210> SEQ ID NO 59
<211> LENGTH: 11
<212> TYPE: PRT
<213> ORGANISM: Clostridium botulinum

<400> SEQUENCE: 59

Lys Thr Lys Ser Leu Asp Lys Gly Tyr Asn Lys
1 5 10

<210> SEQ ID NO 60
<211> LENGTH: 5
<212> TYPE: PRT
<213> ORGANISM: Artificial
<220> FEATURE:
<223> OTHER INFORMATION: Enterokinase cleavage site

<400> SEQUENCE: 60

Asp Asp Asp Asp Lys
1               5

<210> SEQ ID NO 61
<211> LENGTH: 6
<212> TYPE: PRT
<213> ORGANISM: Artificial
<220> FEATURE:
<223> OTHER INFORMATION: TEV recognition sequence

<400> SEQUENCE: 61

Glu Asn Leu Tyr Phe Gln
1               5

<210> SEQ ID NO 62
<211> LENGTH: 34
<212> TYPE: PRT
<213> ORGANISM: Artificial
<220> FEATURE:
<223> OTHER INFORMATION: Signal peptide

<400> SEQUENCE: 62

Met Pro Met Leu Ser Ala Ile Val Leu Tyr Val Leu Leu Ala Ala Ala
1               5                   10                  15

Ala His Ser Ala Phe Ala Ala Met Val His His His His His His Ser
            20                  25                  30

Ala Ser

<210> SEQ ID NO 63
<211> LENGTH: 7
<212> TYPE: PRT
<213> ORGANISM: Artificial
<220> FEATURE:
<223> OTHER INFORMATION: Spacer

<400> SEQUENCE: 63

Ala Arg Gly Gly Ala Ser Gly
1               5

<210> SEQ ID NO 64
<211> LENGTH: 12
<212> TYPE: PRT
<213> ORGANISM: Artificial
<220> FEATURE:
<223> OTHER INFORMATION: Cargo attachment peptide

<400> SEQUENCE: 64

Gly Asp Ser Leu Ser Trp Leu Leu Arg Leu Leu Asn
1               5                   10

<210> SEQ ID NO 65
<211> LENGTH: 3891
<212> TYPE: DNA
<213> ORGANISM: Clostridium botulinum

<400> SEQUENCE: 65
atgccatttg ttaataaaca atttaattat aaagatcctg taaatggtgt tgatattgct     60

```
tatataaaaa ttccaaatgc aggacaaatg caaccagtaa aagcttttaa aattcataat    120
aaaatatggg ttattccaga aagagataca tttacaaatc ctgaagaagg agatttaaat    180
ccaccaccag aagcaaaaca agttccagtt tcatattatg attcaacata tttaagtaca    240
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaatttta ctaaactaaa aaattttact   1260
ggattgtttg aattttataa gttgctatgt gtaagaggga taataacttc taaaactaaa   1320
tcattagata aaggatacaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata catttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
```

```
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatatacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agtttttaaa   3000
tacagtcaaa tgattaatat atcagattat ataaacagat ggatttttgt aactatcact   3060
aataatagat taaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc tttttgataa ggaattaaat   3240
gaaaaagaaa tcaaagattt atatgataat caatcaaatt caggtatttt aaaagacttt   3300
tggggtgatt atttacaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttattta aattcaagtt tgtatagggg gacaaaattt   3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaatttacaa   3720
gataataatg ggaatgatat aggctttata ggatttcatc agtttaataa tatagctaaa   3780
ctagtagcaa gtaattggta taatagacaa atagaaagat ctagtaggac tttgggttgc   3840
tcatgggaat ttattcctgt agatgatgga tggggagaaa ggccactgta a            3891
```

```
<210> SEQ ID NO 66
<211> LENGTH: 4051
<212> TYPE: DNA
<213> ORGANISM: Clostridium botulinum

<400> SEQUENCE: 66

gataataata atataataat gatgacaata tacctaaagc tgcacattta tggacattaa     60
aagggatata aacttaaaat aaggaggaga atatttatgc cagttacaat aaataatttt    120
aattataatg atcctattga taatgacaat attattatga tggaacctcc atttgcaagg    180
ggtacgggga gatattataa agcttttaaa atcacagatc gtatttggat aatacccgaa    240
agatatactt ttggatataa acctgaggat tttaataaaa gttccggtat ttttaataga    300
gatgtttgtg aatattatga tccagattac ttaaatacca atgataaaaa gaatatattt    360
ttccaaacat tgatcaagtt atttaataga atcaaatcaa aaccattggg tgaaaagtta    420
ttagagatga ttataaatgg tataccttat cttggagata gacgtgttcc actcgaagag    480
tttaacacaa acattgctag tgtaactgtt aataaattaa ttagtaatcc aggagaagtg    540
gagcgaaaaa aaggtatttt cgcaaattta ataatatttg gacctgggcc agttttaaat    600
gaaaatgaga ctatagatat aggtatacaa aatcattttg catcaaggga aggctttggg    660
```

```
ggtataatgc aaatgaaatt ttgtccagaa tatgtaagcg tatttaataa tgttcaagaa    720
aacaaaggcg caagtatatt taatagacgt ggatattttt cagatccagc cttgatatta    780
atgcatgaac ttatacatgt tttgcatgga ttatatggca ttaaagtaga tgatttacca    840
attgtaccaa atgaaaaaaa attttttatg caatctacag atactataca ggcagaagaa    900
ctatatacat ttggaggaca agatcccagc atcatatctc cttctacaga taaaagtatc    960
tatgataaag ttttgcaaaa ttttaggggg atagttgata gacttaacaa ggttttagtt   1020
tgcatatcag atcctaacat taacattaat atatataaaa ataaatttaa agataaatat   1080
aaattcgttg aagattctga aggaaaatat agtatagatg tagaaagttt caataaatta   1140
tataaaagct taatgttagg ttttacagaa attaatatag cagaaaatta taaaataaaa   1200
actagagctt cttattttag tgattcctta ccaccagtaa aaataaaaaa tttattagat   1260
aatgaaatct atactataga ggaagggttt aatatatctg ataaaaatat gggaaaagaa   1320
tataggggtc agaataaagc tataaataaa caagcttatg aagaaatcag caaggagcat   1380
ttggctgtat ataagataca aatgtgtaaa agtgttaaag ttccaggaat atgtattgat   1440
gtcgataatg aaaatttgtt ctttatagct gataaaaata gtttttcaga tgatttatct   1500
aaaaatgaaa gagtagaata taatacacag aataattata taggaaatga ctttcctata   1560
aatgaattaa ttttagatac tgatttaata agtaaaatag aattaccaag tgaaaataca   1620
gaatcactta ctgattttaa tgtagatgtt ccagtatatg aaaaacaacc cgctataaaa   1680
aaagttttta cagatgaaaa taccatcttt caatatttat actctcagac atttcctcta   1740
aatataagag atataagttt aacatcttca tttgatgatg cattattagt ttctagcaaa   1800
gtttattcat ttttttctat ggattatatt aaaactgcta ataaagtagt agaagcagga   1860
ttatttgcag gttgggtgaa acagatagta gatgattttg taatcgaagc taataaaagc   1920
agtactatgg ataaaattgc agatatatct ctaattgttc cttatatagg attagcttta   1980
aatgtaggag atgaaacagc taaaggaaat tttgaaagtg cttttgagat tgcaggatcc   2040
agtattttac tagaatttat accagaactt ttaatacctg tagttggagt ctttttatta   2100
gaatcatata ttgacaataa aaataaaatt attaaaacaa tagataatgc tttaactaaa   2160
agagtggaaa aatggattga tatgtacgga ttaatagtag cgcaatggct ctcaacagtt   2220
aatactcaat tttatacaat aaaagaggga atgtataagg ctttaaatta tcaagcacaa   2280
gcattggaag aaataataaa atacaaatat aatatatatt ctgaagagga aaagtcaaat   2340
attaacatca attttaatga tataaattct aaacttaatg atggtattaa ccaagctatg   2400
gataatataa atgattttat aaatgaatgt tctgtatcat atttaatgaa aaaaatgatt   2460
ccattagctg taaaaaaatt actagacttt gataatactc tcaaaaaaaa tttattaaat   2520
tatatagatg aaaataaatt atatttaatt ggaagtgtag aagatgaaaa atcaaaagta   2580
gataaatact tgaaaaccat tataccattt gatctttcaa cgtattctaa tattgaaata   2640
ctaataaaaa tatttaataa atataatagc gaaattttaa ataatattat cttaaattta   2700
agatatagag ataataattt aatagattta tcaggatatg gagcaaaggt agaggtatat   2760
gatggggtca agcttaatga taaaaatcaa tttaaattaa ctagttcagc agatagtaag   2820
attagagtca ctcaaaatca gaatattata tttaatagta tgttccttga ttttagcgtt   2880
agcttttgga taaggatacc taaatatagg aatgatgata tacaaaatta tattcataat   2940
gaatatacga taattaattg tatgaaaaat aattcaggct ggaaaatatc tattaggggt   3000
```

```
aataggataa tatggacctt aattgatata aatggaaaaa ccaaatcagt attttttgaa   3060
tataacataa gagaagatat atcagagtat ataaatagat ggttttttgt aactattact   3120
aataatttgg ataatgctaa aatttatatt aatggcacgt tagaatcaaa tatggatatt   3180
aaagatatag gagaagttat tgttaatggt gaaataacat ttaaattaga tggtgatgta   3240
gatagaacac aatttatttg gatgaaatat tttagtattt ttaatacgca attaaatcaa   3300
tcaaatatta aagagatata taaaattcaa tcatatagcg aatacttaaa agatttttgg   3360
ggaaatcctt taatgtataa taaagaatat tatatgttta atgcggggaa taaaaattca   3420
tatattaaac tagtgaaaga ttcatctgta ggtgaaatat taatacgtag caaatataat   3480
cagaattcca attatataaa ttatagaaat ttatatattg gagaaaaatt tattataaga   3540
agagagtcaa attctcaatc tataaatgat gatatagtta gaaaagaaga ttatatacat   3600
ctagatttgg tacttcacca tgaagagtgg agagtatatg cctataaata ttttaaggaa   3660
caggaagaaa aattgttttt atctattata agtgattcta atgaatttta taagactata   3720
gaaataaaag aatatgatga acagccatca tatagttgtc agttgctttt taaaaaagat   3780
gaagaaagta ctgatgatat aggattgatt ggtattcatc gtttctacga atctggagtt   3840
ttacgtaaaa agtataaaga ttatttttgt ataagtaaat ggtacttaaa agaggtaaaa   3900
aggaaaccat ataagtcaaa tttgggatgt aattggcagt ttattcctaa agatgaaggg   3960
tggactgaat aatataacta tatgctcagc aaacctattt tatataagaa aagtttaagt   4020
ttataaaatc ttaagtttaa ggatgtagct a                                  4051
```

<210> SEQ ID NO 67
<211> LENGTH: 3994
<212> TYPE: DNA
<213> ORGANISM: Clostridium botulinum

<400> SEQUENCE: 67

```
tatgatatgt aatgacaata acaaggtgcc taaaggtgca catttgtgga tattagaaag     60
ttaggagatg ttagtattat gccaataaca attaacaact ttaattattc agatcctgtt    120
gataataaaa atattttata tttagatact catttaaata cactagctaa tgagcctgaa    180
aaagcctttc gcattacagg aaatatatgg gtaatacctg atagattttc aagaaattct    240
aatccaaatt taaataaacc tcctcgagtt acaagcccta aaagtggtta ttatgatcct    300
aattatttga gtactgattc tgacaaagat acatttttaa aagaaattat aaagttattt    360
aaaagaatta attctagaga aataggagaa gaattaaatat atagactttc gacagatata    420
ccctttcctg ggaataacaa tactccaatt aatacttttg attttgatgt agattttaac    480
agtgttgatg ttaaaactag acaaggtaac aactgggtta aaactggtag cataaatcct    540
agtgttataa taactggacc tagagaaaac attatagatc cagaaacttc tacgtttaaa    600
ttaactaaca atactttgc ggcacaagaa ggatttggtg ctttatcaat aatttcaata    660
tcacctagat ttatgctaac atatagtaat gcaactaatg atgtaggaga gggtagattt    720
tctaagtctg aattttgcat ggatccaata ctaattttaa tgcatgaact taatcatgca    780
atgcataatt tatatggaat agctatacca aatgatcaaa caatttcatc tgtaactagt    840
aatatttttt attctcaata taatgtgaaa ttagagtatg cagaaatata tgcatttgga    900
ggtccaacta tagaccttat tcctaaaagt gcaaggaaat attttgagga aaaggcattg    960
gattattata gatctatagc taaaagactt aatagtataa ctactgcaaa tccttcaagc   1020
tttaataaat atataggga atataaacag aaacttatta gaaagtatag attcgtagta   1080
```

gaatcttcag gtgaagttac agtaaatcgt aataagtttg ttgagttata taatgaactt 1140
acacaaatat ttacagaatt taactacgct aaaatatata atgtacaaaa taggaaaata 1200
tatctttcaa atgtatatac tccggttacg gcaaatatat tagacgataa tgtttatgat 1260
atacaaaatg gatttaatat acctaaaagt aatttaaatg tactatttat gggtcaaaat 1320
ttatctcgaa atccagcatt aagaaaagtc aatcctgaaa atatgcttta tttatttaca 1380
aaattttgtc ataaagcaat agatggtaga tcattatata ataaaacatt agattgtaga 1440
gagcttttag ttaaaaatac tgacttaccc tttataggtg atattagtga tgttaaaact 1500
gatatatttt taagaaaaga tattaatgaa gaaactgaag ttatatacta tccggacaat 1560
gtttcagtag atcaagttat tctcagtaag aatacctcag aacatggaca actagattta 1620
ttataccta gtattgacag tgagagtgaa atattaccag gggagaatca agtcttttat 1680
gataatagaa ctcaaaatgt tgattatttg aattcttatt attacctaga atctcaaaaa 1740
ctaagtgata atgttgaaga ttttactttt acgagatcaa ttgaggaggc tttggataat 1800
agtgcaaaag tatatactta ctttcctaca ctagctaata aagtaaatgc gggtgttcaa 1860
ggtggtttat ttttaatgtg ggcaaatgat gtagttgaag attttactac aaatattcta 1920
agaaaagata cattagataa aatatcagat gtatcagcta ttattcccta tataggaccc 1980
gcattaaata taagtaattc tgtaagaaga ggaaatttta ctgaagcatt tgcagttact 2040
ggtgtaacta ttttattaga agcatttcct gaatttacaa tacctgcact tggtgcattt 2100
gtgatttata gtaaggttca agaaagaaac gagattatta aaactataga taattgttta 2160
gaacaaagga ttaagagatg gaaagattca tatgaatgga tgatgggaac gtggttatcc 2220
aggattatta ctcaatttaa taatataagt tatcaaatgt atgattcttt aaattatcag 2280
gcaggtgcaa tcaaagctaa aatagattta gaatataaaa aatattcagg aagtgataaa 2340
gaaaatataa aaagtcaagt tgaaaattta aaaaatagtt tagatgtaaa aatttcggaa 2400
gcaatgaata atataaataa atttatacga gaatgttccg taacatattt atttaaaaat 2460
atgttaccta aagtaattga tgaattaaat gagtttgatc gaaatactaa agcaaaatta 2520
attaatctta tagatagtca taatattatt ctagttggtg aagtagataa attaaaagca 2580
aaagtaaata atagctttca aaatacaata ccctttaata ttttttcata tactaataat 2640
tctttattaa aagatataat taatgaatat ttcaataata ttaatgattc aaaaattttg 2700
agcctacaaa acagaaaaaa tactttagtg gatacatcag gatataatgc agaagtgagt 2760
gaagaaggcg atgttcagct taatccaata tttccatttg actttaaatt aggtagttca 2820
ggggaggata gaggtaaagt tatagtaacc cagaatgaaa atattgtata taattctatg 2880
tatgaaagtt ttagcattag tttttggatt agaataaata aatgggtaag taatttacct 2940
ggatatacta taattgatag tgttaaaaat aactcaggtt ggagtatagg tattattagt 3000
aatttttag tatttacttt aaaacaaaat gaagatagtg aacaaagtat aaattttagt 3060
tatgatatat caaataatgc tcctggatac aataaatggt tttttgtaac tgttactaac 3120
aatatgatgg gaaatatgaa gatttatata aatggaaaat taatagatac tataaaagtt 3180
aaagaactaa ctggaattaa ttttagcaaa actataacat ttgaaataaa taaaattcca 3240
gataccggtt tgattacttc agattctgat aacatcaata tgtggataag agatttttat 3300
atatttgcta aagaattaga tggtaaagat attaatatat tatttaatag cttgcaatat 3360
actaatgttg taaaagatta ttggggaaat gatttaagat ataataaaga atattatatg 3420

```
gttaatatag attatttaaa tagatatatg tatgcgaact cacgacaaat tgtttttaat   3480

acacgtagaa ataataatga cttcaatgaa ggatataaaa ttataataaa aagaatcaga   3540

ggaaatacaa atgatactag agtacgagga ggagatattt tatattttga tatgacaatt   3600

aataacaaag catataattt gtttatgaag aatgaaacta tgtatgcaga taatcatagt   3660

actgaagata tatatgctat aggtttaaga gaacaaacaa aggatataaa tgataatatt   3720

atatttcaaa tacaaccaat gaataatact tattattacg catctcaaat atttaaatca   3780

aattttaatg gagaaaatat ttctggaata tgttcaatag gtacttatcg ttttagactt   3840

ggaggtgatt ggtatagaca caattatttg gtgcctactg tgaagcaagg aaattatgct   3900

tcattattag aatcaacatc aactcattgg ggttttgtac ctgtaagtga ataaataatg   3960

attaataata taaattatgt taaatatttt aata                              3994


<210> SEQ ID NO 68
<211> LENGTH: 3952
<212> TYPE: DNA
<213> ORGANISM: Clostridium botulinum

<400> SEQUENCE: 68

aaggtgcaca cttgtggata ttagaaagtt aggagatgtt agtattatga catggccagt     60

aaaagatttt aattatagtg atcctgttaa tgacaatgat atattatatt taagaatacc    120

acaaaataag ttaattacta cacctgtaaa agcttttatg attactcaaa atatttgggt    180

aataccagaa agattttcat cagatactaa tccaagttta agtaaaccgc ccagacctac    240

ttcaaagtat caaagttatt atgatcctag ttatttatct actgatgaac aaaaagatac    300

atttttaaaa ggattataaa aattatttaa aagaattaat gaaagagata taggaaaaaa    360

attaataaat tatttagtag ttggttcacc ttttatggga gattcaagta cgcctgaaga    420

tacatttgat tttacacgtc atactactaa tattgcagtt gaaaagtttg aaaatggtag    480

ttggaaagta acaaatatta taacaccaag tgtattgata tttggaccac ttcctaatat    540

attagactat acagcatccc ttacattgca aggacaacaa tcaaatccat catttgaagg    600

gtttggaaca ttatctatac taaaagtagc acctgaattt ttgttaacat ttagtgatgt    660

aacatctaat caaagttcag ctgtattagg caaatctata ttttgtatgg atccagtaat    720

agctttaatg catgagttaa cacattcttt gcatcaatta tatggaataa atataccatc    780

tgataaaagg attcgtccac aagttagcga gggatttttc tctcaagatg gacccaacgt    840

acaatttgag gaattatata catttggagg attagatgtt gaaataatac ctcaaattga    900

aagatcacaa ttaagagaaa aagcattagg tcactataaa gatatagcga aaagacttaa    960

taatattaat aaaactattc cttctagttg gattagtaat atagataaat ataaaaaaat   1020

attttctgaa aagtataatt ttgataaaga taatacagga aattttgttg taaatattga   1080

taaattcaat agcttatatt cagacttgac taatgttatg tcagaagttg tttattcttc   1140

gcaatataat gttaaaaaca ggactcatta tttttcaagg cattatctac ctgtatttgc   1200

aaatatatta gatgataata tttatactat aagagatggt tttaatttaa caaataaagg   1260

ttttaatata gaaaattcgg gtcagaatat agaaaggaat cctgcactac aaaagcttag   1320

ttcagaaagt gtagtagatt tatttacaaa agtatgttta agattaacaa aaaatagtag   1380

agatgattca acatgtatta aagttaaaaa taatagatta ccttatgtag ctgataaaga   1440

tagcatttca caagaaatat ttgaaaataa aattattaca gatgagacta atgtacaaaa   1500

ttattcagat aaattttcat tagatgaatc tattttagat gggcaagttc ctattaatcc   1560
```

tgaaatagta gatccactat tacccaatgt taatatggaa cctttaaatc ttccaggtga 1620
agaaatagta ttttatgatg atattactaa atatgttgat tatttaaatt cttattatta 1680
tttggaatct caaaaattaa gtaataatgt tgaaaatatt actcttacaa cttcagttga 1740
agaagcatta ggttatagca ataagatata cacattttta cctagcttag ctgaaaaagt 1800
gaataaaggt gttcaagcag gtttattctt aaattgggcg aatgaagtag ttgaggattt 1860
tactacaaat attatgaaga aagatacatt ggataaaata tcagatgtat cagtaataat 1920
tccatatata ggacctgcct taaatatagg aaattcagca ttaaggggaa attttaatca 1980
agcatttgca acagctggtg tagctttttt attagaggga tttccagagt ttactatacc 2040
tgcactcggt gtatttacct tttatagttc tattcaagaa agagagaaaa ttattaaaac 2100
tatagaaaat tgtttggaac aaagagttaa gagatggaaa gattcatatc aatggatggt 2160
atcaaattgg ttgtcaagaa ttactactca atttaatcat ataaattatc aaatgtatga 2220
ttctttaagt tatcaggcag atgcaatcaa agctaaaata gatttagaat ataaaaaata 2280
ctcaggaagt gataaagaaa atataaaaag tcaagttgaa aatttaaaaa atagtttaga 2340
tgtaaaaatt tcggaagcaa tgaataatat aaataaattt atacgagaat gttctgtaac 2400
atacttattt aaaaatatgc tccctaaagt aattgacgaa ttaaataagt ttgatttaag 2460
aactaaaaca gaattaatta atcttataga tagtcataat attattctag ttggtgaagt 2520
agatagatta aaagcaaaag taaatgagag ttttgaaaat acaatgcctt ttaatatttt 2580
ttcatatact aataattctt tattaaaaga tataattaat gaatatttca atagtattaa 2640
tgattcaaaa attttgagct tacaaaacaa aaaaaatgct ttagtggata catcaggata 2700
taatgcagaa gtgagggtag gagataatgt tcaacttaat acgatatata caaatgactt 2760
taaattaagt agttcaggag ataaaattat agtaaattta aataataata ttttatatag 2820
cgctatttat gagaactcta gtgttagttt ttggattaag atatctaaag atttaactaa 2880
ttctcataat gaatatacaa taattaacag tatagaacaa aattctgggt ggaaattatg 2940
tattaggaat ggcaatatag aatggatttt acaagatgtt aatagaaagt ataaaagttt 3000
aatttttgat tatagtgaat cattaagtca tacaggatat acaaataaat ggtttttgt 3060
tactataact aataatataa tggggtatat gaaactttat ataaatggag aattaaagca 3120
gagtcaaaaa attgaagatt tagatgaggt taagttagat aaaaccatag tatttggaat 3180
agatgagaat atagatgaga atcagatgct ttggattaga gattttaata tttttctaa 3240
agaattaagt aatgaagata ttaatattgt atatgaggga caaatattaa gaaatgttat 3300
taaagattat tggggaaatc ctttgaagtt tgatacagaa tattatatta ttaatgataa 3360
ttatatagat aggtatatag cacctgaaag taatgtactt gtacttgttc agtatccaga 3420
tagatctaaa ttatatactg gaaatcctat tactattaaa tcagtatctg ataagaatcc 3480
ttatagtaga attttaaatg gagataatat aattcttcat atgttatata atagtaggaa 3540
atatatgata ataagagata ctgatacaat atatgcaaca caaggaggag agtgttcaca 3600
aaattgtgta tatgcattaa aattacagag taatttaggt aattatggta taggtatatt 3660
tagtataaaa aatattgtat ctaaaaataa atattgtagt caaattttct ctagttttag 3720
ggaaaataca atgcttctag cagatatata taaaccttgg agattttctt ttaaaaatgc 3780
atacacgcca gttgcagtaa ctaattatga aacaaaacta ttatcaactt catctttttg 3840
gaaatttatt tctagggatc caggatgggt agagtaatac aataaaaatt taatataaac 3900

-continued tattaaatta tattacaagt tttagaaatt tatcgtataa aatgttgaat tc 3952

<210> SEQ ID NO 69
<211> LENGTH: 3759
<212> TYPE: DNA
<213> ORGANISM: Clostridium botulinum

<400> SEQUENCE: 69
atgccaaaaa ttaatagttt taattataat gatcctgtta atgatagaac aattttatat 60
attaaaccag gcggttgtca agaattttat aaatcattta atattatgaa aaatatttgg 120
ataattccag agagaaatgt aattggtaca acccccccaag attttcatcc gcctacttca 180
ttaaaaaatg gagatagtag ttattatgac cctaattatt tacaaagtga tgaagaaaag 240
gatagatttt taaaaatagt cacaaaaata tttaatagaa taaataataa tctttcagga 300
gggattttat tagaagaact gtcaaaagct aatccatatt tagggaatga taatactcca 360
gataatcaat tccatattgg tgatgcatca gcagttgaga ttaaattctc aaatggtagc 420
caagacatac tattacctaa tgttattata atgggagcag agcctgattt atttgaaact 480
aacagttcca atatttctct aagaaataat tatatgccaa gcaatcacgg ttttggatca 540
atagctatag taacattctc acctgaatat tcttttagat ttaatgataa tagtatgaat 600
gaatttattc aagatcctgc tcttacatta atgcatgaat taatacattc attacatgga 660
ctatatgggg ctaaagggat tactacaaag tatactataa cacaaaaaca aaatccccta 720
ataacaaata taagaggtac aaatattgaa gaattcttaa cttttggagg tactgattta 780
aacattatta ctagtgctca gtccaatgat atctatacta atcttctagc tgattataaa 840
aaaatagcgt ctaaacttag caaagtacaa gtatctaatc cactacttaa tccttataaa 900
gatgtttttg aagcaaagta tggattagat aaagatgcta gcggaattta ttcggtaaat 960
ataaacaaat ttaatgatat ttttaaaaaa ttatacagct ttacggaatt tgatttagca 1020
actaaatttc aagttaaatg taggcaaact tatattggac agtataaata cttcaaactt 1080
tcaaacttgt taaatgattc tatttataat atatcagaag gctataatat aaataattta 1140
aaggtaaatt ttagaggaca gaatgcaaat ttaaatccta gaattattac accaattaca 1200
ggtagaggac tagtaaaaaa aatcattaga ttttgtaaaa atattgtttc tgtaaaaggc 1260
ataaggaaat caatatgtat cgaaataaat aatggtgagt tattttttgt ggcttccgag 1320
aatagttata atgatgataa tataaatact cctaaagaaa ttgacgatac agtaacttca 1380
aataataatt atgaaaatga tttagatcag gttattttaa attttaatag tgaatcagca 1440
cctggacttt cagatgaaaa attaaattta actatccaaa atgatgctta tataccaaaa 1500
tatgattcta atggaacaag tgatatagaa caacatgatg ttaatgaact taatgtattt 1560
ttctatttag atgcacagaa agtgcccgaa ggtgaaaata atgtcaatct cacctcttca 1620
attgatacag cattattaga acaacctaaa atatatacat ttttttcatc agaatttatt 1680
aataatgtca ataaacctgt gcaagcagca ttatttgtaa gctggataca acaagtgtta 1740
gtagatttta ctactgaagc taaccaaaaa agtactgttg ataaaattgc agatatttct 1800
atagttgttc catatatagg tcttgcttta aatataggaa atgaagcaca aaaaggaaat 1860
tttaaagatg cacttgaatt attaggagca ggtattttat tagaatttga acccgagctt 1920
ttaattccta caattttagt attcacgata aaatcttttt taggttcatc tgataataaa 1980
aataaagtta ttaaagcaat aaataatgca ttgaaagaaa gagatgaaaa atggaaagaa 2040
gtatatagtt ttatagtatc gaattggatg actaaaatta atacacaatt taataaaaga 2100

```
aaagaacaaa tgtatcaagc tttacaaaat caagtaaatg caattaaaac aataatagaa   2160

tctaagtata atagttatac tttagaggaa aaaaatgagc ttacaaataa atatgatatt   2220

aagcaaatag aaaatgaact taatcaaaag gtttctatag caatgaataa tatagacagg   2280

ttcttaactg aaagttctat atcctattta atgaaattaa taaatgaagt aaaaattaat   2340

aaattaagag aatatgatga gaatgtcaaa acgtatttat tgaattatat tatacaacat   2400

ggatcaatct tgggagagag tcagcaagaa ctaaattcta tggtaactga taccctaaat   2460

aatagtattc cttttaagct ttcttcttat acagatgata aaattttaat ttcatatttt   2520

aataaattct ttaagagaat taaaagtagt tcagttttaa atatgagata taaaaatgat   2580

aaatacgtag atacttcagg atatgattca aatataaata ttaatggaga tgtatataaa   2640

tatccaacta ataaaaatca atttggaata tataatgata aacttagtga agttaatata   2700

tctcaaaatg attacattat atatgataat aaatataaaa attttagtat tagtttttgg   2760

gtaagaattc ctaactatga taataagata gtaaatgtta ataatgaata cactataaata   2820

aattgtatga gagataataa ttcaggatgg aaagtatctc ttaatcataa tgaaataatt   2880

tggacattgc aagataatgc aggaattaat caaaaattag catttaacta tggtaacgca   2940

aatggtattt ctgattatat aaataagtgg attttgtaa ctataactaa tgatagatta   3000

ggagattcta aactttatat taatggaaat ttaatagatc aaaaatcaat tttaaattta   3060

ggtaatattc atgttagtga caatatatta tttaaaatag ttaattgtag ttatacaaga   3120

tatattggta ttagatattt taatattttt gataaagaat tagatgaaac agaaattcaa   3180

actttatata gcaatgaacc taatacaaat attttgaagg atttttgggg aaattatttg   3240

ctttatgaca aagaatacta tttattaaat gtgttaaaac caaataactt tattgatagg   3300

agaaaagatt ctactttaag cattaataat ataagaagca ctattctttt agctaataga   3360

ttatatagtg gaataaaagt taaaatacaa agagttaata atagtagtac taacgataat   3420

cttgttagaa agaatgatca ggtatatatt aattttgtag ccagcaaaac tcacttattt   3480

ccattatatg ctgatacagc taccacaaat aaagagaaaa caataaaaat atcatcatct   3540

ggcaatagat ttaatcaagt agtagttatg aattcagtag gaaataattg tacaatgaat   3600

tttaaaaata ataatggaaa taatattggg ttgttaggtt tcaaggcaga tactgtagtt   3660

gctagtactt ggtattatac acatatgaga gatcatacaa acagcaatgg atgtttttgg   3720

aactttattt ctgaagaaca tggatggcaa gaaaaataa                          3759
```

<210> SEQ ID NO 70
<211> LENGTH: 4209
<212> TYPE: DNA
<213> ORGANISM: Clostridium botulinum

<400> SEQUENCE: 70

```
aaatggcgca aagaagatga taattagtaa taatatattt atttccaatt gtttaactct     60

atcttgtggc ggtaaatata tatgtttatc tatgaaagat gaaaactata attggatgat    120

atgtaataat gaaagcaaca tacctaaaaa ggcatattta tggacattga aagaagtata    180

gggggattt tatgccagtt gtaataaata gttttaatta taatgaccct gttaatgatg    240

atacaatttt atacatgcag ataccatatg aagaaaaaag taaaaaatat tataaagctt    300

ttgagattat gcgtaatgtt tggataattc ctgagagaaa tacaatagga acggatccta    360

gtgattttga tccaccggct tcattagaga acggaagcag tgcttattat gatcctaatt    420
```

```
atttaaccac tgatgctgaa aaagatagat atttaaaaac aacgataaaa ttatttaaga    480
gaattaatag taatcctgca ggggaagttt tgttacaaga aatatcatat gctaaaccat    540
atttaggaaa tgaacacacg ccaattaatg aattccatcc agttactaga actacaagtg    600
ttaatataaa atcatcaact aatgttaaaa gttcaataat attgaatctt cttgtattgg    660
gagcaggacc tgatatattt gaaaattctt cttaccccgt tagaaaacta atggattcag    720
gtggagttta tgacccaagt aatgatggtt ttggatcaat taatatcgtg acattttcac    780
ctgaatatga atatactttt aatgatatta gtggagggta taacagtagt acagaatcat    840
ttattgcaga tcctgcaatt tcactagctc atgaattgat acatgcactg catggattat    900
acggggctag gggagttact tataaagaga ctataaaagt aaagcaagca cctcttatga    960
tagccgaaaa acccataagg ctagaagaat tttaaacctt tggaggtcag gatttaaata   1020
ttattactag tgctatgaag gaaaaaatat ataacaatct tttagctaac tatgaaaaaa   1080
tagctactag acttagtaga gttaatagtg ctcctcctga atatgatatt aatgaatata   1140
aagattattt tcaatggaag tatgggctag ataaaaatgc tgatggaagt tatactgtaa   1200
atgaaaataa atttaatgaa atttataaaa aattatatag ctttacagag attgacttag   1260
caaataaatt taaagtaaaa tgtagaaata cttattttat taaatatgga tttttaaaag   1320
ttccaaattt gttagatgat gatatttata ctgtatcaga ggggtttaat ataggtaatt   1380
tagcagtaaa caatcgcgga caaaatataa agttaaatcc taaaattatt gattccattc   1440
cagataaagg tctagtggaa aagatcgtta aattttgtaa gagcgttatt cctagaaaag   1500
gtacaaaggc gccaccgcga ctatgcatta gagtaaataa tagggagtta tttttgtag   1560
cttcagaaag tagctataat gaaaatgata ttaatacacc taaagaaatt gacgatacaa   1620
caaatctaaa taataattat agaaataatt tagatgaagt tattttagat tataatagtg   1680
agacaatacc tcaaatatca aatcaaacat taaatacact tgtacaagac gatagttatg   1740
tgccaagata tgattctaat ggaacaagtg aaatagagga acataatgtt gttgacctta   1800
atgtattttt ctatttacat gcacaaaaag taccagaagg tgaaactaat ataagtttaa   1860
cttcttcaat tgatacggca ttatcagaag aatcgcaagt atatacattc ttttcttcag   1920
agtttattaa tactatcaat aaacctgtac acgcagcact atttataagt tggataaatc   1980
aagtaataag agattttact actgaagcta cacaaaaaag tacttttgat aagattgcag   2040
acatatcttt agttgtacca tatgtaggtc ttgctttaaa tataggtaat gaggtacaaa   2100
aagaaaattt taaggaggca tttgaattat taggagcggg tattttatta gaatttgtgc   2160
cagagctttt aattcctaca attttagtgt ttacaataaa atcctttata ggttcatctg   2220
agaataaaaa taaaatcatt aaagcaataa ataattcatt aatggaaaga gaaacaaagt   2280
ggaaagaaat atatagttgg atagtatcaa attggcttac tagaattaat acacaattta   2340
ataaaagaaa agaacaaatg tatcaagctt tgcaaaatca agtagatgca ataaaaacag   2400
taatagaata taaatataat aattatactt cagatgagag aaatagactt gaatctgaat   2460
ataatatcaa taatataaga gaagaattga acaaaaaagt ttctttagca atggaaaata   2520
tagagagatt tataacagag agttctatat tttatttaat gaagttaata aatgaagcca   2580
aagttagtaa attaagagaa tatgatgaag gcgttaagga atatttgcta gactatattt   2640
cagaacatag atcaatttta ggaaatagtg tacaagaatt aaatgattta gtgactagta   2700
ctctgaataa tagtattcca tttgaacttt cttcatatac taatgataaa attctaattt   2760
tatattttaa taaattatat aaaaaaatta aagataactc tattttagat atgcgatatg   2820
```

```
aaaataataa atttatagat atctctggat atggttcaaa tataagcatt aatggagatg   2880

tatatattta ttcaacaaat agaaatcaat ttggaatata tagtagtaag cctagtgaag   2940

ttaatatagc tcaaaataat gatattatat acaatggtag atatcaaaat tttagtatta   3000

gtttctgggt aaggattcct aaatacttca ataaagtgaa tcttaataat gaatatacta   3060

taatagattg tataaggaat aataattcag gatggaaaat atcacttaat tataataaaa   3120

taatttggac tttacaagat actgctggaa ataatcaaaa actagttttt aattatacac   3180

aaatgattag tatatctgat tatataaata aatggatttt tgtaactatt actaataaata   3240

gattaggcaa ttctagaatt tacatcaatg gaaatttaat agatgaaaaa tcaatttcga   3300

atttaggtga tattcatgtt agtgataata tattatttaa aattgttggt tgtaatgata   3360

caagatatgt tggtataaga tattttaaag tttttgatac ggaattaggt aaaacagaaa   3420

ttgagacttt atatagtgat gagccagatc caagtatctt aaaagacttt tggggaaatt   3480

atttgttata taataaaaga tattatttat tgaatttact aagaacagat aagtctatta   3540

ctcagaattc aaactttcta aatattaatc aacaaagagg tgtttatcag aaaccaaata   3600

tttttccaa cactagatta tatacaggag tagaagttat tataagaaaa aatggatcta   3660

cagatatatc taatacagat aattttgtta gaaaaaatga tctggcatat attaatgtag   3720

tagatcgtga tgtagaatat cggctatatg ctgatatatc aattgcaaaa ccagagaaaa   3780

taataaaatt aataagaaca tctaattcaa acaatagctt aggtcaaatt atagttatgg   3840

attcaatagg aaataattgc acaatgaatt ttcaaaacaa taatgggggc aatataggat   3900

tactaggttt tcattcaaat aatttggttg ctagtagttg gtattataac aatatacgaa   3960

aaaatactag cagtaatgga tgcttttgga gttttatttc taaagagcat ggatggcaag   4020

aaaactaata taataattca aaaaataggt attaaaatag aggtaatata tattaccctc   4080

tattttggaa taattttaat atattatatg aaacatatat aaatttaaag ataatattaa   4140

atcaagacac aaattcaaat tagaaatata aaatgaagta aatgaaaagt gtaaaaagtc   4200

attaaataa                                                           4209
```

<210> SEQ ID NO 71
<211> LENGTH: 3937
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 71

```
atgccagtta atataaaaan ctttaattat aatgacccta ttaataatga tgacattatt     60

atgatggaac cattcaatga cccagggcca ggaacatatt ataaagcttt taggattata    120

gatcgtattt ggatagtacc agaaaggttt acttatggat ttcaacctga ccaatttaat    180

gccagtacag gagtttttag taaagatgtc tacgaatatt acgatccaac ttatttaaaa    240

accgatgctg aaaaagataa atttttaaaa acaatgatta aattatttaa tagaattaat    300

tcaaaaccat caggacagag attactggat atgatagtag atgctatacc ttatcttgga    360

aatgcatcta caccgcccga caaatttgca gcaaatgttg caaatgtatc tattaataaa    420

aaaattatcc aacctggagc tgaagatcaa ataaaaggtt taatgacaaa tttaataata    480

tttggaccag gaccagttct aagtgataat tttactgata gtatgattat gaatggccat    540
```

```
tccccaatat cagaaggatt tggtgcaaga atgatgataa gattttgtcc tagttgttta    600
aatgtattta ataatgttca ggaaaataaa gatacatcta tatttagtag acgcgcgtat    660
tttgcagatc cagctctaac gttaatgcat gaacttatac atgtgttaca tggattatat    720
ggaattaaga taagtaattt accaattact ccaaatacaa aagaattttt catgcaacat    780
agcgatcctg tacaagcaga agaactatat acattcggag gacatgatcc tagtgttata    840
agtccttcta cggatatgaa tatttataat aaagcgttac aaaattttca agatatagct    900
aataggctta atattgtttc aagtgcccaa gggagtggaa ttgatatttc cttatataaa    960
caaatatata aaaataaata tgattttgtt gaagatccta atggaaaata tagtgtagat   1020
aaggataagt ttgataaatt atataaggcc ttaatgtttg gctttactga aactaatcta   1080
gctggtgaat atggaataaa aactaggtat tcttatttta gtgaatattt gccaccgata   1140
aaaactgaaa aattgttaga caatacaatt tatactcaaa atgaaggctt taacatagct   1200
agtaaaaatc tcaaaacgga atttaatggt cagaataagg cggtaaataa agaggcttat   1260
gaagaaatca gcctagaaca tctcgttata tatagaatag caatgtgcaa gcctgtaatg   1320
tacaaaaata ccggtaaatc tgaacagtgt attattgtta ataatgagga tttatttttc   1380
atagctaata aagatagttt ttcaaaagat ttagctaaag cagaaactat agcatataat   1440
acacaaaata atactataga aaataatttt tctatagatc agttgatttt agataatgat   1500
ttaagcagtg gcatagactt accaaatgaa aacacagaac catttacaaa ttttgacgac   1560
atagatatcc ctgtgtatat taaacaatct gctttaaaaa aaatttttgt ggatggagat   1620
agccttttttg aatatttaca tgctcaaaca tttccttcta atatagaaaa tctacaacta   1680
acgaattcat taaatgatgc tttaagaaat aataataaag tctatacttt tttttctaca   1740
aaccttgttg aaaaagctaa tacagttgta ggtgcttcac tttttgtaaa ctgggtaaaa   1800
ggagtaatag atgattttac atctgaatcc acacaaaaaa gtactataga taaagtttca   1860
gatgtatcca taattattcc ctatatagga cctgctttga atgtaggaaa tgaaacagct   1920
aaagaaaatt ttaaaaatgc ttttgaaata ggtggagccg ctatcttaat ggagtttatt   1980
ccagaactta ttgtacctat agttggattt tttacattag aatcatatgt aggaaataaa   2040
gggcatatta ttatgacgat atccaatgct ttaaagaaaa gggatcaaaa atggacagat   2100
atgtatggtt tgatagtatc gcagtggctc tcaacggtta atactcaatt ttatacaata   2160
aaagaaagaa tgtacaatgc tttaaataat caatcacaag caatagaaaa aataatagaa   2220
gatcaatata atagatatag tgaagaagat aaaatgaata ttaacattga ttttaatgat   2280
atagatttta aacttaatca aagtataaat ttagcaataa acaatataga tgattttata   2340
aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaaagtaa atagacacct aaaagacagt   2520
ataccatttg atctttcact atataccaag gacacaattt taatacaagt ttttaataat   2580
tatattagta atattagtag taatgctatt ttaagtttaa gttatagagg tgggcgttta   2640
atagattcat ctggatatgg tgcaactatg aatgtaggtt cagatgttat ctttaatgat   2700
ataggaaatg gtcaatttaa attaaataat tctgaaaata gtaatattac ggcacatcaa   2760
agtaaattcg ttgtatatga tagtatgttt gataatttta gcattaactt ttgggtaagg   2820
actcctaaat ataataataa tgatatacaa acttatcttc aaaatgagta tacaataatt   2880
agttgtataa aaaatgactc aggatggaaa gtatctatta agggaaatag aataatatgg   2940
```

-continued

```
acattaatag atgttaatgc aaaatctaaa tcaatatttt tcgaatatag tataaaagat   3000

aatatatcag attatataaa taaatggttt tccataacta ttactaatga tagattaggt   3060

aacgcaaata tttatataaa tggaagtttg aaaaaaagtg aaaaaatttt aaacttagat   3120

agaattaatt ctagtaatga tatagacttc aaattaatta attgtacaga tactactaaa   3180

tttgtttgga ttaaggattt taatattttt ggtagagaat taaatgctac agaagtatct   3240

tcactatatt ggattcaatc atctacaaat actttaaaag atttttgggg gaatccttta   3300

agatacgata cacaatacta tctgtttaat caaggtatgc aaaatatcta tataaagtat   3360

tttagtaaag cttctatggg ggaaactgca ccacgtacaa actttaataa tgcagcaata   3420

aattatcaaa atttatatct tggtttacga tttattataa aaaaagcatc aaattctcgg   3480

aatataaata atgataatat agtcagagaa ggagattata tatatcttaa tattgataat   3540

atttctgatg aatcttacag agtatatgtt ttggtgaatt ctaaagaaat tcaaactcaa   3600

ttatttttag cacccataaa tgatgatcct acgttctatg atgtactaca aataaaaaaa   3660

tattatgaaa aaacaacata taattgtcag atactttgcg aaaaagatac taaaacattt   3720

gggctgtttg gaattggtaa atttgttaaa gattatggat atgtttggga tacctatgat   3780

aattattttt gcataagtca gtggtatctc agaagaatat ctgaaaatat aaataaatta   3840

aggttgggat gtaattggca attcattccc gtggatgaag gatggacaga ataatataat   3900

taaatattta ttaaagctac tttgatagga aaatcaa                            3937
```